United States Patent
Chen et al.

(10) Patent No.: US 11,046,680 B1
(45) Date of Patent: Jun. 29, 2021

(54) HETEROARYL-SUBSTITUTED TRIAZOLES AS APJ RECEPTOR AGONISTS

(71) Applicant: AMGEN INC., Thousand Oaks, CA (US)

(72) Inventors: Ning Chen, Thousand Oaks, CA (US); Xiaoqi Chen, Palo Alto, CA (US); Yinhong Chen, Hayward, CA (US); Alan C. Cheng, San Francisco, CA (US); Richard V. Connors, Mesa, AZ (US); Jeffrey Deignan, San Francisco, CA (US); Paul John Dransfield, Arlington, MA (US); Xiaohui Du, Belmont, CA (US); Zice Fu, Foster City, CA (US); James S. Harvey, Arlington, MA (US); Julie Anne Heath, Chico, CA (US); Lars V. Heumann, Redwood City, CA (US); Daniel B. Horne, Natick, MA (US); Jonathan Houze, Cambridge, MA (US); Matthew R. Kaller, Ventura, CA (US); Frank Kayser, San Francisco, CA (US); Aarif Yusuf Khakoo, Woodside, CA (US); David J. Kopecky, Washington D.C., DC (US); Su-Jen Lai, Cambridge, MA (US); Zhihua Ma, Lexington, MA (US); Julio C. Medina, San Carlos, CA (US); Jeffrey T. Mihalic, San Francisco, CA (US); Nobuko Nishimura, West Hills, CA (US); Steven H. Olson, Millbrae, CA (US); Vatee Pattaropong, Bedford, MA (US); Gayathri Swaminath, Brisbane, CA (US); Xiaodong Wang, Johns Creek, GA (US); Malgorzata Wanska, Camarillo, CA (US); Kevin Yang, San Gabriel, CA (US); Wen-Chen Yeh, Belmont, CA (US)

(73) Assignee: AMGEN INC., Thousand Oaks, CA (US)

( * ) Notice: Subject to any disclaimer, the term of this patent is extended or adjusted under 35 U.S.C. 154(b) by 78 days.

(21) Appl. No.: 16/347,910
(22) PCT Filed: Nov. 3, 2017
(86) PCT No.: PCT/US2017/059824
  § 371 (c)(1),
  (2) Date: May 7, 2019
(87) PCT Pub. No.: WO2018/097945
  PCT Pub. Date: May 31, 2018

Related U.S. Application Data

(60) Provisional application No. 62/422,652, filed on Nov. 16, 2016.

(51) Int. Cl.
  *C07D 417/14* (2006.01)
  *A61P 9/00* (2006.01)
  *C07D 401/14* (2006.01)
  *C07D 403/14* (2006.01)
  *C07D 409/04* (2006.01)
  *C07D 413/04* (2006.01)
  *C07D 413/14* (2006.01)
  *C07D 417/04* (2006.01)

(52) U.S. Cl.
  CPC .............. *C07D 417/14* (2013.01); *A61P 9/00* (2018.01); *C07D 401/14* (2013.01); *C07D 403/14* (2013.01); *C07D 409/04* (2013.01); *C07D 413/04* (2013.01); *C07D 413/14* (2013.01); *C07D 417/04* (2013.01)

(58) Field of Classification Search
  CPC .. C07D 417/14; C07D 401/14; C07D 403/14; C07D 409/04; C07D 413/04; C07D 413/14; C07D 417/04; A61P 9/00
  USPC ........................................................ 514/256
  See application file for complete search history.

(56) References Cited

U.S. PATENT DOCUMENTS

| | | |
|---|---|---|
| 4,844,730 A | 7/1989 | Moriya et al. |
| 4,941,912 A | 7/1990 | Kirsten et al. |
| 5,302,718 A | 4/1994 | Agback et al. |
| 5,328,803 A | 7/1994 | Fujikura et al. |
| 5,411,839 A | 5/1995 | Harder et al. |
| 5,451,588 A | 9/1995 | Baker et al. |
| 5,510,362 A | 4/1996 | Matassa et al. |
| 5,563,026 A | 10/1996 | Singer |
| 5,910,504 A | 6/1999 | Hutchinson |
| 6,069,141 A | 5/2000 | Barbachyn et al. |
| 6,194,090 B1 | 2/2001 | Okada |
| 6,555,693 B2 | 4/2003 | Ge et al. |
| 6,586,423 B2 | 7/2003 | Bilodeau et al. |
| 6,727,364 B2 | 4/2004 | Tullis et al. |
| 6,787,555 B2 | 9/2004 | Tullis et al. |
| 6,790,846 B2 | 9/2004 | Clark et al. |

(Continued)

FOREIGN PATENT DOCUMENTS

| | | |
|---|---|---|
| AU | 199886243 B2 | 4/1999 |
| AU | 2012200157 A1 | 9/2012 |
| DE | 3928605 A1 | 3/1991 |
| DE | 4035141 A1 | 5/1992 |
| EP | 0121082 B1 | 10/1984 |

(Continued)

OTHER PUBLICATIONS

SciFinder Structure Search with Substances Performed May 20, 2016.

(Continued)

*Primary Examiner* — Kristin A Vajda
(74) *Attorney, Agent, or Firm* — Bernard P. Friedrichsen

(57) ABSTRACT

Compounds of Formula (I) and Formula (II), pharmaceutically acceptable salt thereof, stereoisomers of any of the foregoing, or mixtures thereof are agonists of the APJ Receptor and may have use in treating cardiovascular and other conditions. Compounds of Formula I and Formula II have the following structures: where the definitions of the variables are provided herein.

33 Claims, 3 Drawing Sheets

(56) References Cited

U.S. PATENT DOCUMENTS

| | | |
|---|---|---|
| 7,084,145 B2 | 8/2006 | Armour et al. |
| 7,084,164 B2 | 8/2006 | Tobe et al. |
| 7,169,797 B2 | 1/2007 | Xin et al. |
| 7,297,168 B2 | 11/2007 | Murphy et al. |
| 7,361,669 B2 | 4/2008 | Scarborough et al. |
| 7,371,757 B2 | 5/2008 | Morningstar et al. |
| 7,615,569 B2 | 11/2009 | Fulp et al. |
| 7,635,751 B2 | 12/2009 | Kitada et al. |
| 7,638,541 B2 | 12/2009 | Chen et al. |
| 7,718,683 B2 | 5/2010 | Charvat et al. |
| 7,776,897 B2 | 8/2010 | Murakami et al. |
| 7,820,665 B2 | 10/2010 | Booker et al. |
| 8,034,834 B2 | 10/2011 | Du et al. |
| 8,053,456 B2 | 11/2011 | Sun et al. |
| 8,063,083 B2 | 11/2011 | Foley |
| 8,076,486 B2 | 12/2011 | Goutopoulos et al. |
| 8,101,618 B2 | 1/2012 | Kawamoto et al. |
| 8,252,822 B2 | 8/2012 | An et al. |
| 8,299,107 B2 | 10/2012 | Chimmanamada et al. |
| 8,318,790 B2 | 11/2012 | Ying et al. |
| 8,399,464 B2 | 3/2013 | Kuramochi et al. |
| 8,415,377 B2 | 4/2013 | Sun et al. |
| 8,426,602 B2 | 4/2013 | Meibom et al. |
| 8,431,604 B2 | 4/2013 | Netz et al. |
| 8,445,518 B2 | 5/2013 | Charvat et al. |
| 8,466,170 B2 | 6/2013 | Klein |
| 8,492,427 B2 | 7/2013 | Gancia et al. |
| 8,563,741 B2 | 10/2013 | Qian et al. |
| 8,648,104 B2 | 2/2014 | Du et al. |
| 8,673,848 B2 | 3/2014 | Zecri et al. |
| 8,742,133 B2 | 6/2014 | Ying et al. |
| 8,778,977 B2 | 7/2014 | Lind et al. |
| 8,835,464 B2 | 9/2014 | Sun et al. |
| 8,883,827 B2 | 11/2014 | Holsworth et al. |
| 9,156,796 B2 | 10/2015 | Hachtel et al. |
| 9,573,936 B2 | 2/2017 | Chen et al. |
| 9,656,997 B2 | 5/2017 | Chen et al. |
| 9,656,998 B2 | 5/2017 | Chen et al. |
| 9,745,286 B2 | 8/2017 | Chen et al. |
| 9,751,864 B2 | 9/2017 | Chen et al. |
| 9,845,310 B2 | 12/2017 | Chen et al. |
| 9,868,721 B2 | 1/2018 | Chen et al. |
| 9,988,369 B2 | 6/2018 | Chen et al. |
| 10,058,550 B2 | 8/2018 | Chen et al. |
| 10,100,059 B2 | 10/2018 | Runyon et al. |
| 10,150,760 B2 | 12/2018 | Chen et al. |
| 10,221,162 B2 | 3/2019 | Chen et al. |
| 2002/0107245 A1 | 8/2002 | Wagle et al. |
| 2004/0167188 A1 | 8/2004 | Xin et al. |
| 2005/0075275 A1 | 4/2005 | Albrecht et al. |
| 2005/0165015 A1 | 7/2005 | Ncube |
| 2005/0170431 A1 | 8/2005 | Ibrahim et al. |
| 2005/0288347 A1 | 12/2005 | Hodge et al. |
| 2006/0156480 A1 | 7/2006 | Lim |
| 2006/0281749 A1 | 12/2006 | Wagle et al. |
| 2008/0153869 A1 | 6/2008 | Bressi et al. |
| 2008/0249131 A1 | 10/2008 | Girardet et al. |
| 2009/0318438 A1 | 12/2009 | Chen et al. |
| 2010/0130472 A1 | 5/2010 | Young et al. |
| 2010/0249185 A1 | 9/2010 | Du et al. |
| 2010/0280032 A1 | 11/2010 | Zhou et al. |
| 2011/0046125 A1 | 2/2011 | Ying |
| 2011/0158940 A1 | 6/2011 | Byrd et al. |
| 2011/0190257 A1 | 8/2011 | Heald et al. |
| 2011/0207788 A1 | 8/2011 | Amberg et al. |
| 2011/0265691 A1 | 11/2011 | Orth et al. |
| 2012/0094837 A1 | 4/2012 | Muhlthau et al. |
| 2012/0208828 A1 | 8/2012 | Holsworth et al. |
| 2012/0238576 A1 | 9/2012 | Tao et al. |
| 2013/0034536 A1 | 2/2013 | Gedulin |
| 2013/0040950 A1 | 2/2013 | Short et al. |
| 2013/0059807 A1 | 3/2013 | Gedulin et al. |
| 2013/0059845 A1 | 3/2013 | Song et al. |
| 2013/0108573 A1 | 5/2013 | Gedulin et al. |
| 2013/0109671 A1 | 5/2013 | Gedulin et al. |
| 2013/0150385 A1 | 6/2013 | Blackman et al. |
| 2013/0156755 A1 | 6/2013 | Blackman et al. |
| 2013/0266636 A1 | 10/2013 | Cheresh et al. |
| 2013/0303505 A1 | 11/2013 | Bollu et al. |
| 2014/0005181 A1 | 1/2014 | Smith et al. |
| 2016/0058705 A1 | 3/2016 | Rajadas et al. |
| 2016/0060349 A1 | 3/2016 | Van Schravendijk et al. |
| 2016/0340336 A1 | 11/2016 | Chen et al. |
| 2016/0355507 A1 | 12/2016 | Johnson et al. |
| 2017/0035744 A1 | 2/2017 | Chen et al. |
| 2017/0037026 A1 | 2/2017 | Chen et al. |
| 2017/0042871 A1 | 2/2017 | Chen et al. |
| 2017/0042872 A1 | 2/2017 | Chen et al. |
| 2017/0042897 A1 | 2/2017 | Chen et al. |
| 2017/0044131 A1 | 2/2017 | Chen et al. |
| 2017/0281625 A1 | 10/2017 | Chen et al. |
| 2017/0320860 A1 | 11/2017 | Chen et al. |
| 2017/0355734 A1 | 12/2017 | Llorens-Cortes et al. |
| 2018/0118698 A1 | 5/2018 | Smith et al. |
| 2019/0100510 A1 | 4/2019 | Dransfield et al. |

FOREIGN PATENT DOCUMENTS

| | | |
|---|---|---|
| EP | 0330959 A2 | 2/1989 |
| EP | 0409332 A2 | 1/1991 |
| EP | 0484750 A1 | 10/1991 |
| JP | 2003-5356 A | 8/2003 |
| JP | 2003-321456 A | 11/2003 |
| JP | 2005-170939 A | 6/2005 |
| WO | 91/11909 A1 | 8/1991 |
| WO | 99/43671 A1 | 9/1999 |
| WO | 01/87855 A1 | 11/2001 |
| WO | 2005/039569 A1 | 5/2005 |
| WO | 2006/026488 A1 | 3/2006 |
| WO | 2006/055760 A1 | 5/2006 |
| WO | 2006/080533 A1 | 8/2006 |
| WO | 2006/095783 A1 | 9/2006 |
| WO | 2006/100588 A1 | 9/2006 |
| WO | 2006/109817 A1 | 10/2006 |
| WO | 2007/007688 A1 | 1/2007 |
| WO | 2007/139952 A2 | 12/2007 |
| WO | 2007/139967 A2 | 12/2007 |
| WO | 2008/008375 A2 | 1/2008 |
| WO | 2008/021364 A2 | 2/2008 |
| WO | 2008/103352 A1 | 8/2008 |
| WO | 2009/075890 A2 | 6/2009 |
| WO | 2009/115503 A1 | 9/2009 |
| WO | 2010/017545 A2 | 2/2010 |
| WO | 2011/146801 A1 | 11/2011 |
| WO | 2012/076898 A1 | 6/2012 |
| WO | 2012/116247 A1 | 8/2012 |
| WO | 2013/067162 A1 | 5/2013 |
| WO | 2013/067165 A1 | 5/2013 |
| WO | 2013/074594 A1 | 5/2013 |
| WO | 2013/106437 A1 | 7/2013 |
| WO | 2013/106614 A1 | 7/2013 |
| WO | 2013/111110 A2 | 8/2013 |
| WO | 2013-148857 A1 | 10/2013 |
| WO | 2013/184755 A2 | 12/2013 |
| WO | 2014/044738 A1 | 3/2014 |
| WO | 2014/099984 A1 | 6/2014 |
| WO | 2014/150326 A1 | 9/2014 |
| WO | 2014/194270 A1 | 12/2014 |
| WO | 2015/140296 A2 | 9/2015 |
| WO | 2015/163818 A1 | 10/2015 |
| WO | 2015/184011 A2 | 12/2015 |
| WO | 2015/188073 A1 | 12/2015 |
| WO | 2016/151018 A1 | 9/2016 |
| WO | 2016/196771 A1 | 12/2016 |
| WO | 2017/066402 | 4/2017 |
| WO | 2017/091513 A1 | 6/2017 |
| WO | 2017/096130 A1 | 6/2017 |
| WO | 2017/100558 A1 | 6/2017 |
| WO | 2017/106396 A1 | 6/2017 |
| WO | 2017/165640 A1 | 9/2017 |
| WO | 2017/174758 A1 | 10/2017 |
| WO | 2017/218617 A1 | 12/2017 |
| WO | 2017/218633 A1 | 12/2017 |
| WO | 2018/071526 A1 | 4/2018 |

(56) References Cited

FOREIGN PATENT DOCUMENTS

| WO | 2018/071622 A1 | 4/2018 |
|---|---|---|
| WO | 2018/093576 A1 | 5/2018 |
| WO | 2018/093577 A1 | 5/2018 |
| WO | 2018/093579 A1 | 5/2018 |
| WO | 2018/093580 A1 | 5/2018 |
| WO | 2018/097944 A1 | 5/2018 |

OTHER PUBLICATIONS

SciFinder Structure Search with References Performed May 20, 2016.
SciFinder Structure Search Sulfonamide Tail with Substance Performed May 12, 2016.
Berry, M. F. et al., "Apelin Has In Vivo Inotropic Effects on Normal and Failing Hearts," Circulation 110, pp. II187-II193, (2004).
Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett. 6b00038; lccn:2009200243; oclcnum:455500725; serissn:1948-5875; itc:84452717; itcp:10547084 (2016).
Chun, H. et al., "Apelin Signaling Antagonizes ANG II Effects in Mouse Models of Atherosclerosis," J. Clin. Invest. 118(10), pp. 3343-3354 (2008).
Japp, A. G. et al., "Acute Cardiovascular Effects of Apelin in Humans," Circulation 121, pp. 1818-1827 (2010).
Modzelewska-Banachiewicz et al., "Synthesis and Biological Action of 3-4-Disubstituted 5-Arylsulphonylamino-1,2,4-triazoles," Pharmazie 54, pp. 588-589 (1999).
Pauli, A. et al., "Toddler: An Embryonic Signal That Promotes Cell Movement via Apelin Receptors," Science 343, pp. 1248636-0-1248636-8 (2014).
Siddiquee, K. et al., "The Apelin receptor Inhibits the Angiotensin II Type 1 Receptor Via Allosteric Trans-Inhibition," Br. J. Pharmacol. 168, pp. 1104-1117 (2013).
Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).
Tatemoto, K. et al., "Isolation and Characterization of a Novel Endogenous Peptide Ligand for the Human APJ Receptor," Bioch. Biophys. Res. Comm., 251, pp. 471-476 (1998).
Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).
Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).
Barnes, G. et al., "Translational Promise of the Apelin-APJ System," Heart 96(13), pp. 1011-1016 (2010).
Kawamata, Y. et al., "Molecular Properties of Apelin: Tissue Distribution and Receptor Binding," Biochemica et Biophysica Acta 1538(2-3), pp. 162-171 (2001).
Nishizawa, N. et al., "High Potency Analog of Apelin, A Ligand of Orphan GPCT APJ," T Shiori (ed.) Petptide Science 2000: Proceedings of the 37$^{th}$ Japanese Peptide Symposium, pp. 151-154 (2000).
Medhurst, A. D. et al., "Pharmacological and Immunohistochemical Characteization of the APJ Receptor and its Endogenous Ligand Apelin," J. Neurochem. 84(5), pp. 1162-1172 (2003).
Hamada, J. et al., "Evaluation of Novel Cyclic Analogoues of Apelin," Int. J. Mol. Med. 22, pp. 547-552 (2008).
Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).
Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).
Thomas, J.B. et al., "Identification of N-[5-{[(4-Methylphenyl)sulfonyl]amino}-3-(trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).
Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett. 25, pp. 2060-2064 (2015).
Thompson, M. E. "α,N-Alkanesulfonamide Dianions: Formation and Chemoselective C-Alkylation," J. Org. Chem. 49, pp. 1700-1703 (1984).
Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).
Singh, O. M. et al., "A Facile One-Pot Synthetic Method for 1,2,4-Triazoles and 1,3-Disubstituted Thioureas," J. Chem. Res. pp. 483-485 (2006).
Carlsen, P.J.J. et al., "Synthesis of Unsymmetrically Substituted 4H-1,2,4-Triazoles," J. Heterocyclic Chem. 31, pp. 805-807 (1994).
Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).
Hassan, A. A. et al., "Thiosemicarbazides in Heterocyclization," J. Heterocyclic Chem. 48, pp. 495-516 (2011).
Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).
Ivanova, N. V. et al., "A Convenient Synthesis of 4,5-Disubstituted 1,2,4-Triazoles Functionalized in Position 3," Synthesis 1, pp. 156-160 (2005).
Modzelewska-Banaschiewicz, B et al., "Antiviral Activity of the Products of Cyclization of Dimethyl 2-[1-arylamino-1-arylmethylideine)hydrazono]succinate," Eur. J. Med. Chem. 36, pp. 93-99 (2001).
SciFinder Structure Search with Substances Performed Sep. 1, 2016.
SciFinder Structure Search with References Performed Sep. 1, 2016.
Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).
Johnson, M. G. et al., "Convenient Route to Secondary Sulfinates: Application to the Stereospecific Synthesis of α-C-Chiral Sulfonamides," Organic Letters 16(23), pp. 6248-6251 (2014).
Enders, D. et al., "Asymmetric Synthesis of α-Substituted N-Methylsulfonamides," Helvetica Chimica Acta, 85, pp. 3657-3677 (2002).
Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).
Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).
Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).
International Search Report and Written Opinion for analogous PCT Application No. PCT/US2017/059824, dated May 3, 2018.

HETEROARYL-SUBSTITUTED TRIAZOLES AS APJ RECEPTOR AGONISTS

CROSS REFERENCES TO RELATED APPLICATIONS

This application claims the benefit of U.S. Provisional Application No. 62/422,652, filed on Nov. 16, 2016, which is hereby incorporated by reference in its entirety and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77—also referred to as Apelin-36) and a smaller 13 residue polypeptide (Apelin 65-77—also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at sub-nanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275:21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin-13. Nishizawa et al., in: T. Shioiri (ed.), Peptide Science 2000: Proceedings of the 37$^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule, but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. ChemMedChem 7:318-325, 2012. Additionally, PCT/US2013/075773 describes a group of modifications, including substitution of non-canonical amino acids and changes at the N- and C-terminal of the apelin molecule that can affect, inter alia, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336, WO 2016/187308, WO 2015/184011, and WO 2015/188073.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

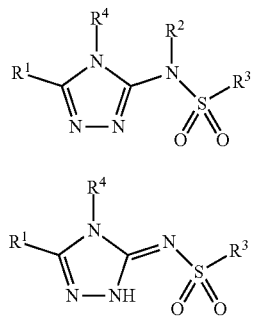

I

II or a pharmaceutically acceptable salt thereof, a tautomer thereof, a pharmaceutically acceptable salt of the tautomer, a stereoisomer of any of the foregoing, or a mixture thereof, wherein:

$R^1$ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl $R^1$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O) OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—

($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or SO$_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

wherein if $R^1$ is a substituted or unsubstituted pyrimidine and $R^4$ is a substituted or unsubstituted alkyl and $R^3$ is -Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S;

wherein if $R^1$ is a substituted or unsubstituted pyrimidine and $R^4$ is a substituted or unsubstituted alkyl and $R^3$ is —CH$_2$-Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S;

and further wherein if $R^1$ is a substituted or unsubstituted pyrimidine and $R^3$ is -Q and Q is an unsubstituted or substituted phenyl, then $R^4$ is selected from an unsubstituted or substituted monocyclic or bicyclic $C_6$-$C_{10}$ aryl group, an unsubstituted or substituted monocyclic or bicyclic heteroaryl group with 5 to 10 ring members containing 1, 2, or 3 heteroatoms independently selected from N, O, or S, an unsubstituted or substituted monocyclic or bicyclic heterocyclyl group with 5 to 10 ring members containing 1, 2, 3, or 4 heteroatoms independently selected from N, O, or S, or an unsubstituted or substituted monocyclic 3-6 membered cycloalkyl group.

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy or chronic kidney disease.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy.

Other objects, features and advantages of the invention will become apparent to those skilled in the art from the following description and claims.

DETAILED DESCRIPTION OF THE INVENTION

Figure 1:
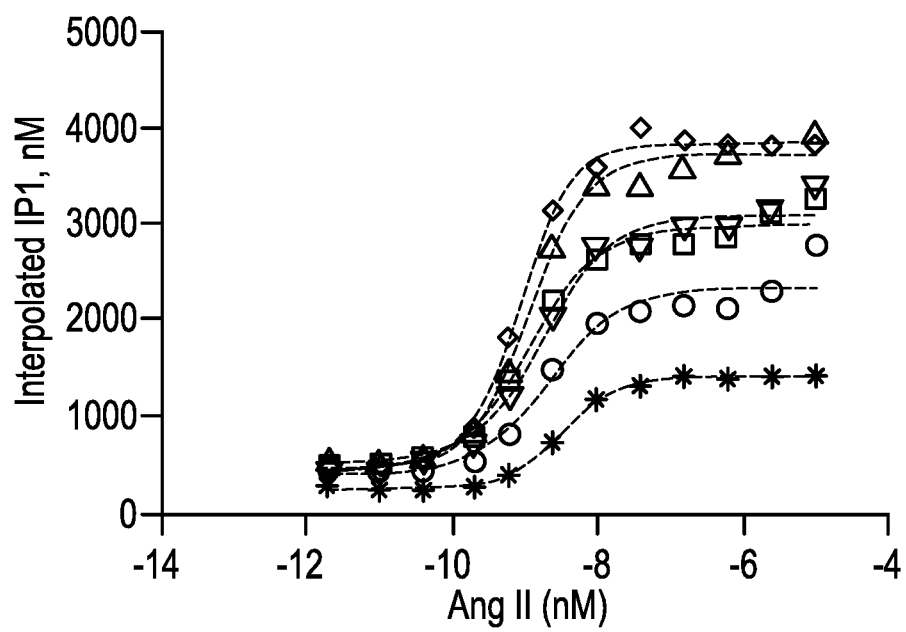
FIG. 1 is a graph plotting different concentrations of angiotensin (AngII) with fixed concentration of pyr apelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyr apelin-13 induces the positive cooperativity on the AT1R upon activation by APJ receptor.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where $R^2$ is H. These forms are illustrated below as Tautomer A and Tautomer B:

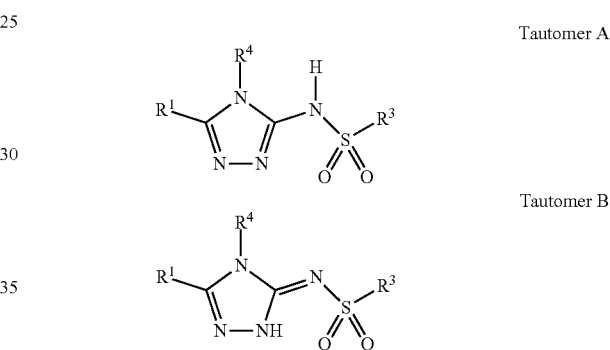

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

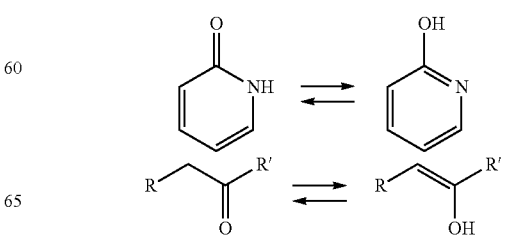

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as $(C_1-C_4)$alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a $(C_1-C_6)$alkyl group and an alkyl group having 1 to 4 carbon atoms may be referred to as a $(C_1-C_4)$alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—$(C_1-C_6$ alkyl)-OH will be recognized as a group where an —O atom is bonded to a $C_1-C_6$ alkyl group and one of the H atoms bonded to a C atom of the $C_1-C_6$ alkyl group is replaced with a bond to the O atom of an —OH group. As another example, a group —O—$(C_1-C_6$ alkyl)-O—$(C_1-C_6$ alkyl) will be recognized as a group where an —O atom is bonded to a first $C_1-C_6$ alkyl group and one of the H atoms bonded to a C atom of the first $C_1-C_6$ alkyl group is replaced with a bond to a second O atom that is bonded to a second $C_1-C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a $(C_2-C_6)$alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —$(C_2-C_6)$alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—$(C_1-C_6)$ alkyl or as —O—$(C_1-C_6$ alkyl) groups. In some embodiments, an alkoxy group may include 1 to 4 carbon atoms and may be designated as —O—$(C_1-C_4)$ alkyl or as —O—$(C_1-C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6-C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a $(C_3-C_8)$cycloalkyl, a cycloalkyl group having 3 to 7 ring members may be referred to as a $(C_3-C_7)$cycloalkyl and a cycloalkyl group having 4 to 7 ring members may be referred to as a $(C_4-C_7)$cycloalkyl. In certain embodiments, the cycloalkyl group can be a $(C_3-C_{10})$cycloalkyl, a $(C_3-C_8)$cycloalkyl, a $(C_3-C_7)$cycloalkyl, a $(C_3-C_6)$cycloalkyl, or a $(C_4-C_7)$cycloalkyl group and these may be referred to as $C_3-C_{10}$ cycloalkyl, $C_3-C_8$ cycloalkyl, $C_3-C_7$ cycloalkyl, $C_3-C_6$ cycloalkyl, or $C_4-C_7$ cycloalkyl groups using alternative language.

"Heterocyclyl" refers to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

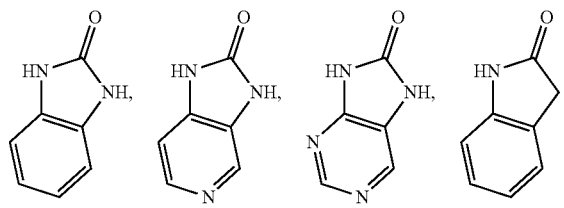 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O—) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, antiadherants, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize. this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments

The embodiments listed below are presented in numbered form for convenience and in ease and clarity of reference in referring back to multiple embodiments.

In a first embodiment, the invention provides a compound of Formula I or Formula II:

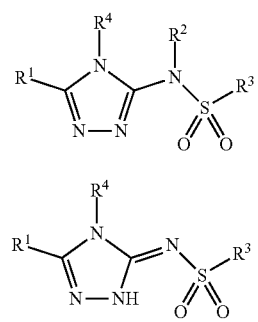

or a pharmaceutically acceptable salt thereof, a tautomer thereof, a pharmaceutically acceptable salt of the tautomer, a stereoisomer of any of the foregoing, or a mixture thereof, wherein:

$R^1$ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl $R^1$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —(C$R^{3b}R^{3c}$)-Q, a group of formula —(C$R^{3d}R^{3e}$)—(C$R^{3f}R^{3g}$)-Q, a group of formula —(C$R^{3d}R^{3e}$)—(C$R^{3f}R^{3g}$)—C(=O)-Q, a group of formula —(C$R^{3d}R^{3e}$)—(C$R^{3f}R^{3g}$)—CH(OH)-Q, a group of formula —(C$R^{3d}R^{3e}$)—(C$R^{3f}R^{3g}$)—(C$R^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or SO$_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

wherein if $R^1$ is a substituted or unsubstituted pyrimidine and $R^4$ is a substituted or unsubstituted alkyl and $R^3$ is -Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S;

wherein if $R^1$ is a substituted or unsubstituted pyrimidine and $R^4$ is a substituted or unsubstituted alkyl and $R^3$ is —CH$_2$-Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S;

and further wherein if $R^1$ is a substituted or unsubstituted pyrimidine and $R^3$ is -Q and Q is an unsubstituted or substituted phenyl, then $R^4$ is selected from an unsubstituted or substituted monocyclic or bicyclic $C_6$-$C_{10}$ aryl group, an unsubstituted or substituted monocyclic or bicyclic heteroaryl group with 5 to 10 ring members containing 1, 2, or 3 heteroatoms independently selected from N, O, or S, an unsubstituted or substituted monocyclic or bicyclic heterocyclyl group with 5 to 10 ring members containing 1, 2, 3, or 4 heteroatoms independently selected from N, O, or S, or an unsubstituted or substituted monocyclic 3-6 membered cycloalkyl group.

In some embodiments, if $R^1$ is a substituted or unsubstituted pyrimidine and $R^4$ is an unsubstituted alkyl, then $R^3$ is selected from a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, or a group of formula -(heterocyclyl)-Q.

In some embodiments, if $R^1$ is a substituted or unsubstituted pyrimidine and $R^4$ is an unsubstituted alkyl, then $R^3$ is selected from a group of formula —($CR^{3d}R^{3e}$)—($CR^{3f}R^{3g}$)-Q or a group of formula -(heterocyclyl)-Q. In some such embodiments, if $R^1$ is a substituted or unsubstituted pyrimidine and $R^4$ is an unsubstituted alkyl, then $R^3$ is a group of formula —($CR^{3d}R^{3e}$)—($CR^{3f}R^{3g}$)-Q whereas in other such embodiments, if $R^1$ is a substituted or unsubstituted pyrimidine and $R^4$ is an unsubstituted alkyl, then $R^3$ is a group of formula -(heterocyclyl)-Q.

In some embodiments, if $R^1$ is a substituted or unsubstituted pyrimidine, then $R^3$ is selected from a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, or a group of formula -(heterocyclyl)-Q; Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S; and $R^4$ is selected from an unsubstituted or substituted monocyclic or bicyclic $C_6$-$C_{10}$ aryl group, an unsubstituted or substituted monocyclic or bicyclic heteroaryl group with 5 to 10 ring members containing 1, 2, or 3 heteroatoms independently selected from N, O, or S, an unsubstituted or substituted monocyclic or bicyclic heterocyclyl group with 5 to 10 ring members containing 1, 2, 3, or 4 heteroatoms independently selected from N, O, or S, or an unsubstituted or substituted monocyclic 3-6 membered cycloalkyl group.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrazolyl, thiazolyl, imidazolyl, thienyl, pyrrolyl, 1,2,4-triazolyl, 1,2,3-triazolyl, oxazolyl, isoxazolyl, 1,3,4-oxadiazolyl, 1,3,4-thiadiazolyl, pyrazinyl, pyrimidinyl, or pyridazinyl any of which may unsubstituted or substituted with 1, 2, or 3 independently selected $R^{1a}$ substituents.

3. The compound of embodiment 2 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrazolyl, thiazolyl, imidazolyl, thienyl, pyrrolyl, 1,2,4-triazolyl, 1,2,3-triazolyl, oxazolyl, isoxazolyl, 1,3,4-oxadiazolyl, or 1,3,4-thiadiazolyl any of which may unsubstituted or substituted with 1, 2, or 3 independently selected $R^{1a}$ substituents.

4. The compound of embodiment 4 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrazinyl, pyrimidinyl, or pyridazinyl any of which may unsubstituted or substituted with 1, 2, or 3 independently selected $R^{1a}$ substituents.

5. The compound of any one of embodiment 1-4 or the pharmaceutically acceptable salt thereof, the tautomer thereof, the pharmaceutically acceptable salt of the tautomer, the stereoisomer of any of the foregoing, or the mixture thereof, wherein $R^1$ is unsubstituted or is substituted with 1 or 2 $R^{1a}$ substituents independently selected from —F, —Cl, —Br, —$C_1$-$C_6$ alkyl, —$C_1$-$C_6$ haloalkyl, —$C_1$-$C_6$ perhaloalkyl, —O—($C_1$-$C_6$ alkyl), $C_3$-$C_8$ cycloalkyl, or —($C_1$-$C_6$ alkyl)-O—($C_1$-$C_6$ alkyl), or —C(=O)NH($C_1$-$C_6$ alkyl).

6. The compound of embodiment 1 or the pharmaceutically acceptable salt thereof, the tautomer thereof, the pharmaceutically acceptable salt of the tautomer, the stereoisomer of any of the foregoing, or the mixture thereof, wherein R is selected from

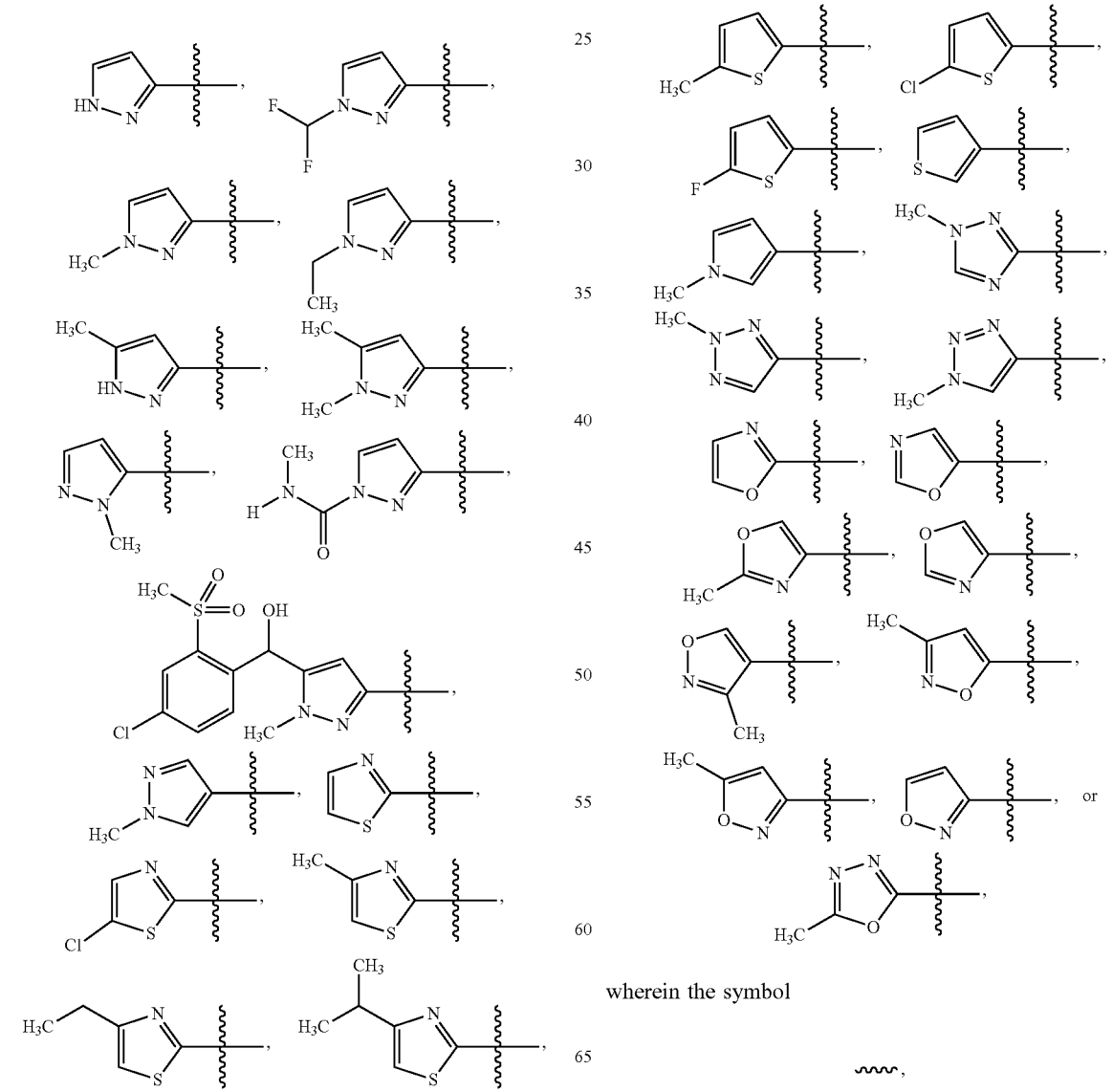

wherein the symbol when drawn across a bond, indicates the point of attachment to the rest of the molecule. In some such embodiments, R¹ is selected from

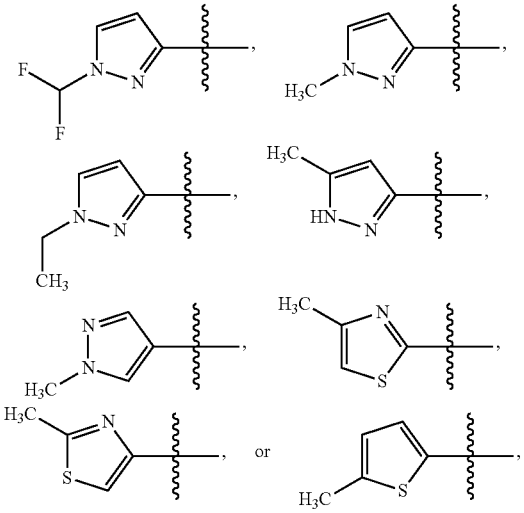

wherein the symbol

∿, when drawn across a bond, indicates the point of attachment to the rest of the molecule. In some such embodiments, R¹ is

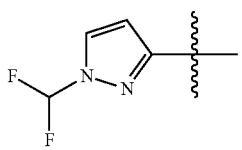 [SMILES: *c1ccn(C(F)F)n1]

wherein the symbol

∿, when drawn across a bond, indicates the point of attachment to the rest of the molecule. In some such embodiments, R¹ is

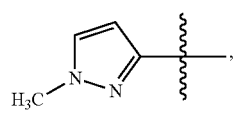

wherein the symbol

∿, when drawn across a bond, indicates the point of attachment to the rest of the molecule. In some such embodiments, R¹ is

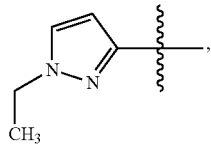

wherein the symbol

∿, when drawn across a bond, indicates the point of attachment to the rest of the molecule. In some such embodiments, R¹ is

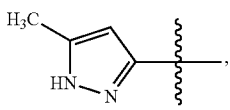

wherein the symbol

∿, when drawn across a bond, indicates the point of attachment to the rest of the molecule. In some such embodiments, R¹ is

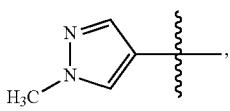

wherein the symbol

∿, when drawn across a bond, indicates the point of attachment to the rest of the molecule. In some such embodiments, R¹ is

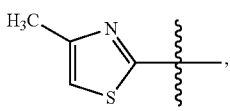 [SMILES: *c1nc(C)cs1]

wherein the symbol

∿, when drawn across a bond, indicates the point of attachment to the rest of the molecule. In some such embodiments, R¹ is,

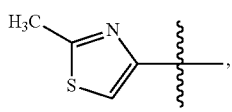

wherein the symbol

∼∼∼, when drawn across a bond, indicates the point of attachment to the rest of the molecule. In some such embodiments, $R^1$ is

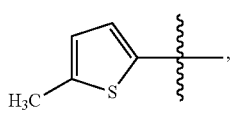

wherein the symbol

∼∼∼, when drawn across a bond, indicates the point of attachment to the rest of the molecule.

6. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

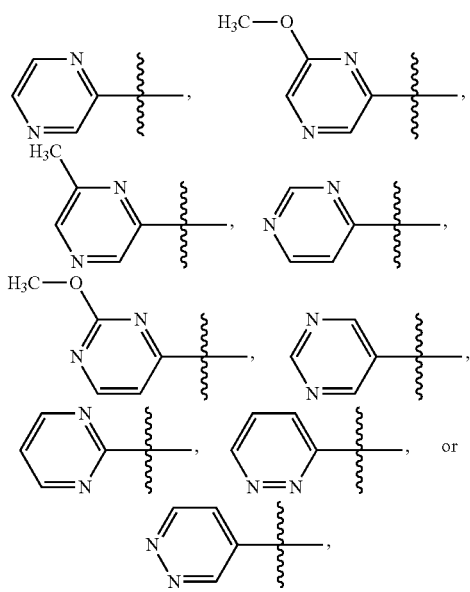

wherein the symbol

∼∼∼, when drawn across a bond, indicates the point of attachment to the rest of the molecule. In some such embodiments, $R^1$ is

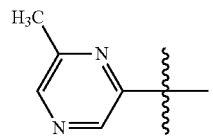 [SMILES: *c1cncc(C)n1]

wherein the symbol

∼∼∼, when drawn across a bond, indicates the point of attachment to the rest of the molecule.

7. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrrolo[2,3-b]pyrazinyl, 5,6-dihydro-4H-pyrrolo[1,2-b]pyrazolyl, 4,5,6,7-tetrahydro-1H-indazolyl, or indolyl any of which may unsubstituted or substituted with 1, 2, or 3 independently selected $R^{1a'}$ substituents.

8. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

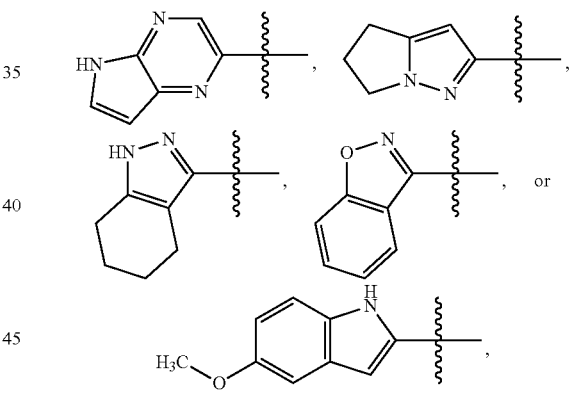

wherein the symbol

∼∼∼, when drawn across a bond, indicates the point of attachment to the rest of the molecule. In some such embodiments, $R^1$ is

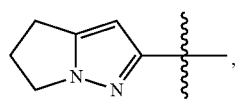 [SMILES: *c1cc2n(n1)CCC2]

wherein the symbol

∼∼∼, when drawn across a bond, indicates the point of attachment to the rest of the molecule. In some such embodiments, $R^1$ is

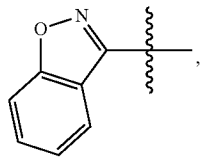 [SMILES: *c1noc2ccccc12]

wherein the symbol

when drawn across a bond, indicates the point of attachment to the rest of the molecule 9. The compound of any one of embodiments 1-8 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

10. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, 3, or 4 $R^{4a}$ substituents.

11. The compound of any one of embodiments 1-10 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, NH($C_1$-$C_6$ alkyl-OH), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), or heterocyclyl, wherein the heterocyclyl of the heterocyclyl $R^{4a}$ group is a 3-6 membered ring comprising 1 or 2 heteroatoms independently selected from N, O, or S and may be optionally substituted with 1 or 2 oxo groups.

12. The compound of embodiment 11 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Cl, —Br, —CN, —$CF_3$, —$OCH_3$, —$OCHF_2$, —C(=O)OH, —C(=O)—O—$CH_2CH_3$, —S(=O)$_2$—$CH_3$, or —N($CH_3$)$_2$.

13. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic or bicyclic $C_6$-$C_{10}$ aryl group that is unsubstituted or is substituted with 1, 2, or 3 $R^{4a}$ substituents.

14. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic or bicyclic heteroaryl group with 5 to 10 ring members containing 1, 2, or 3 heteroatoms independently selected from N, O, or S, wherein the heteroaryl $R^4$ group is unsubstituted or is substituted with 1, 2, or 3 $R^{4a}$ substituents.

15. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic 3-6 membered cycloalkyl group that is unsubstituted or is substituted with 1, 2, or 3 $R^{4a}$ substituents.

16. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a straight or branched chain $C_1$-$C_6$ alkyl group that is unsubstituted or is substituted with 1, 2, or 3 $R^{4b}$ substituents.

17. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is selected from

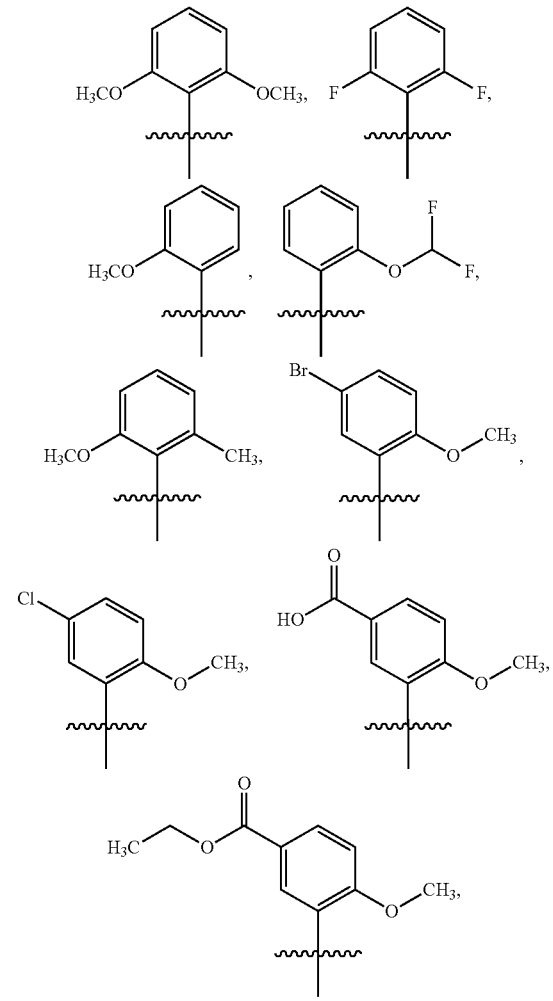

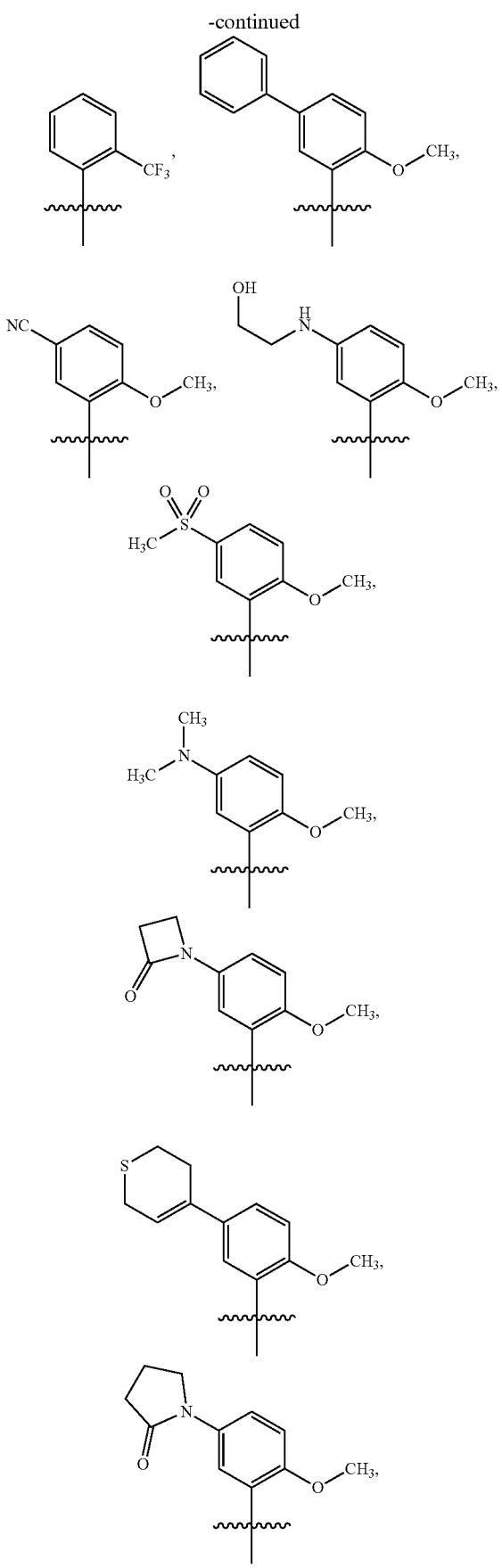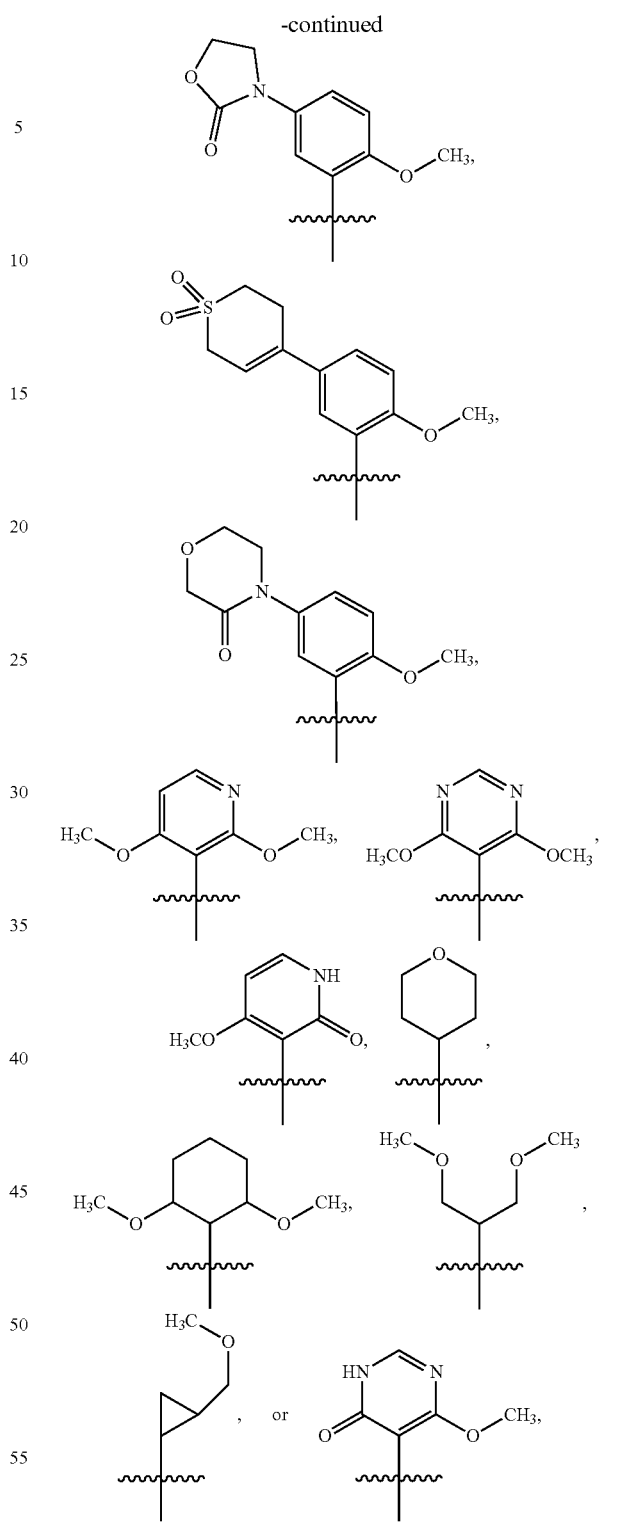
wherein the symbol
~~~
when drawn across a bond, indicates the point of attachment to the rest of the molecule.

18. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is selected from

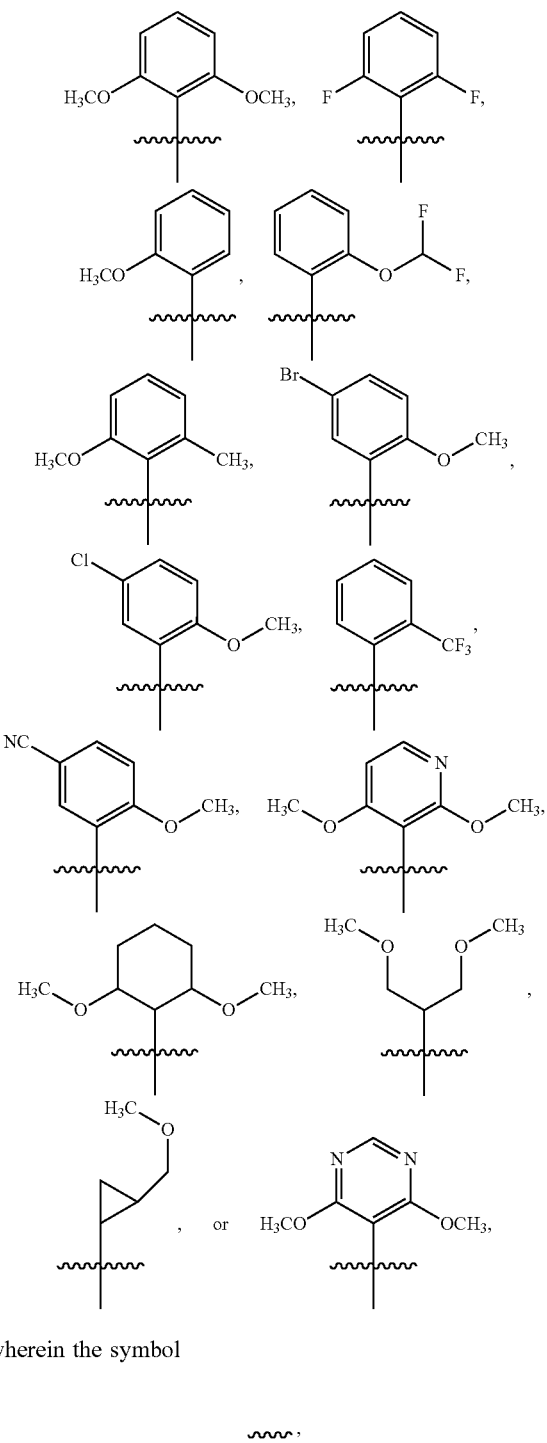

wherein the symbol

when drawn across a bond, indicates the point of attachment to the rest of the molecule.

19. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents.

20. The compound of embodiment 19 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

21. The compound of embodiment 19 or the pharmaceutically acceptable salt thereof, the tautomer thereof, the pharmaceutically acceptable salt of the tautomer, the stereoisomer of any of the foregoing, or the mixture thereof, wherein $R^4$ is

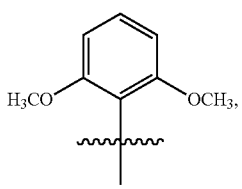

wherein the symbol when drawn across a bond, indicates the point of attachment to the rest of the molecule.

22. The compound of any one of embodiments 1-21 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyrazine-1-oxide, pyradizinyl, pyridinyl, phenyl, oxazolyl, thiazolyl, imidazolyl, pyrazolyl, piperidinyl, piperidin-2-onyl, tetrahydropyrimidin-2(1H)-onyl, 1,3-oxazinan-2-onyl, pyrrolidin-2-onyl, pyrrolidinyl, cyclopentyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1 or 2 $R^Q$ substituents.

23. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyrazine-1-oxide, pyridinyl, phenyl, thiazolyl, piperidinyl, piperidin-2-onyl, tetrahydropyrimidin-2(1H)-onyl, pyrrolidinyl, cyclopentyl, or imidazo[1,2-a]pyridinyl, any of which may be unsubstituted or substituted with 1 or 2 $R^Q$ substituents.

24. The compound of embodiment 22 or the pharmaceutically acceptable salt thereof, the tautomer thereof, the pharmaceutically acceptable salt of the tautomer, the stereoisomer of any of the foregoing, or the mixture thereof, wherein Q is an unsubstituted phenyl or is a phenyl substituted with 1 or 2 $R^Q$ substituents.

25. The compound of any one of embodiments 1-21 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

26. The compound of embodiment 25 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl pyridinyl, or pyrazinyl group and Q is unsubstituted or is substituted with 1 or 2 $R^Q$ substituents.

27. The compound of any one of embodiments 1-26 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), or —S(=O)$_2$—($C_1$-$C_6$ alkyl).

28. The compound of any one of embodiments 1-21 or the pharmaceutically acceptable salt thereof, the tautomer thereof, the pharmaceutically acceptable salt of the tautomer, the stereoisomer of any of the foregoing, or the mixture thereof, wherein Q is selected from

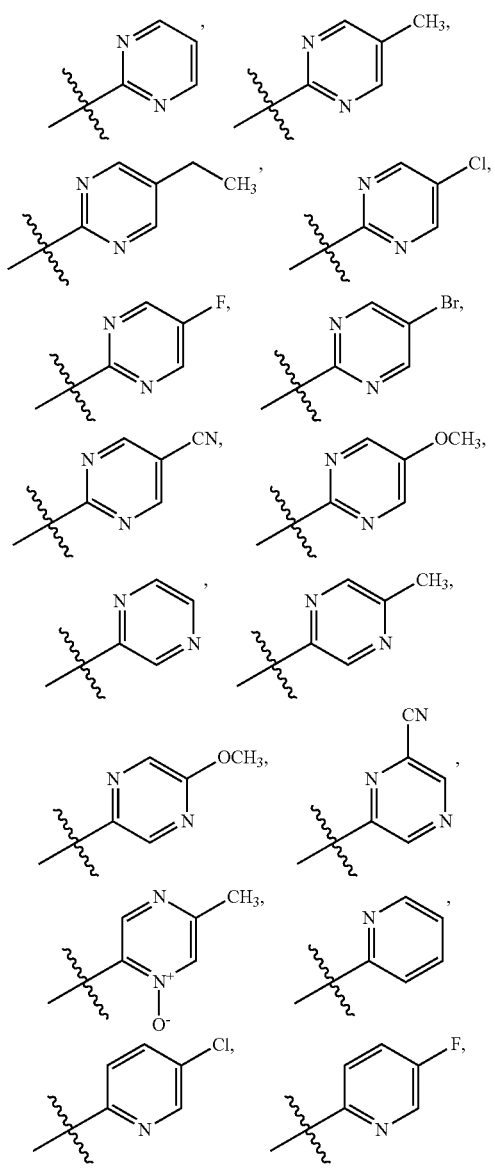

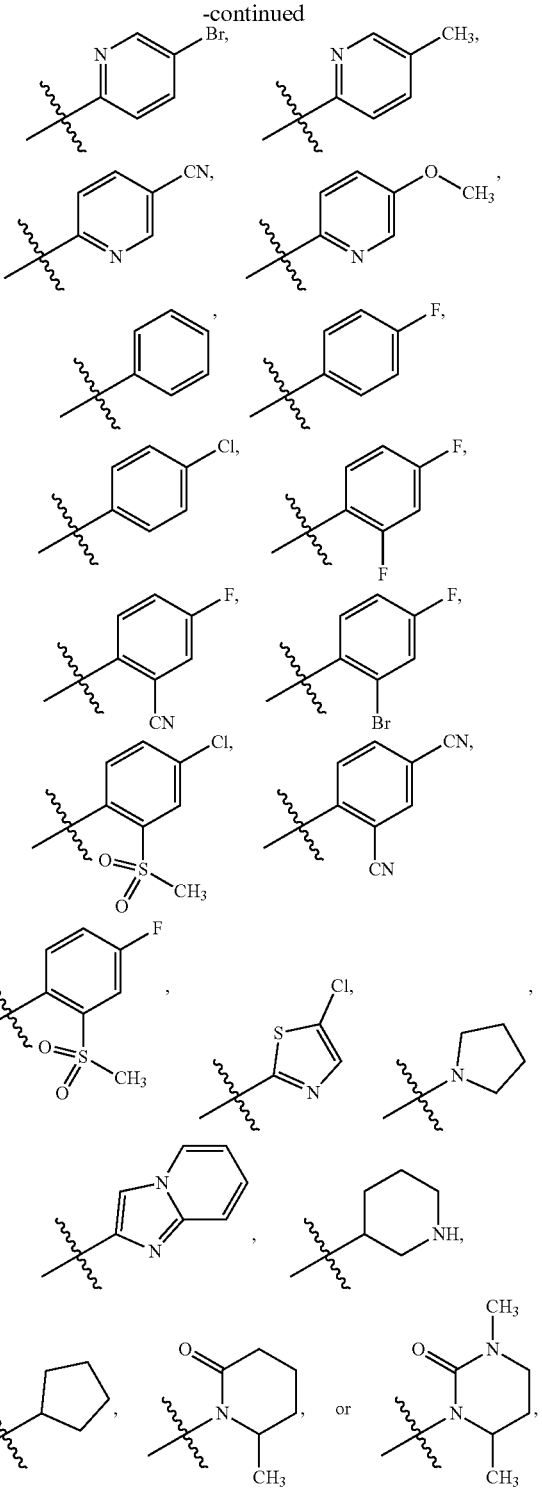

wherein the symbol when drawn across a bond, indicates the point of attachment to the rest of the molecule.

29. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is selected from

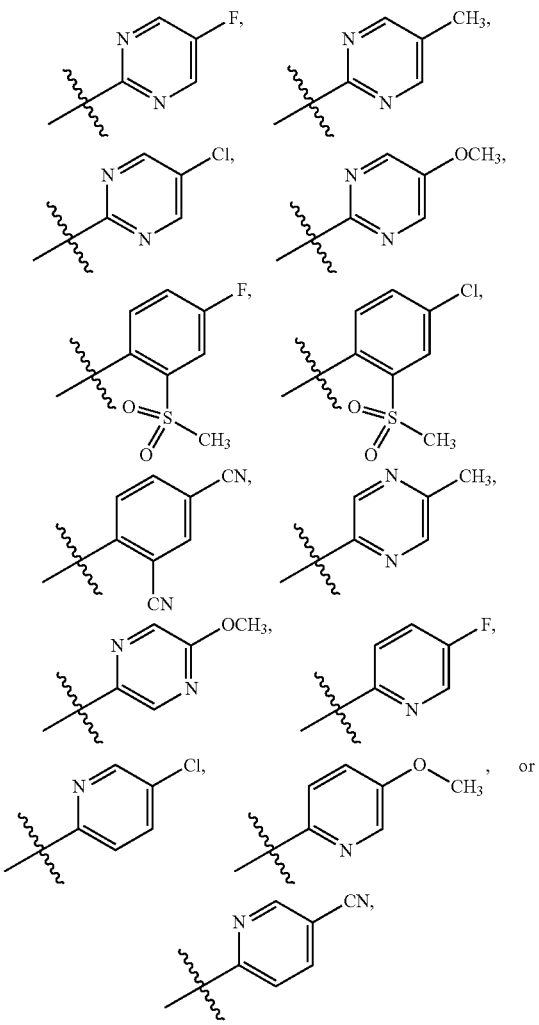

wherein the symbol

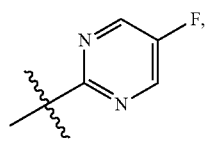 [SMILES: *c1ncc(F)cn1]

when drawn across a bond, indicates the point of attachment to the rest of the molecule.

30. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

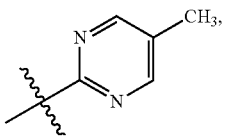 [SMILES: *c1ncc(C)cn1]

wherein the symbol when drawn across a bond, indicates the point of attachment to the rest of the molecule.

31. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

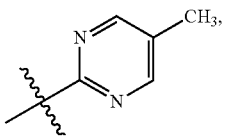 [SMILES: *c1ncc(C)cn1]

wherein the symbol when drawn across a bond, indicates the point of attachment to the rest of the molecule.

32. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

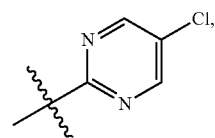

wherein the symbol when drawn across a bond, indicates the point of attachment to the rest of the molecule.

33. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

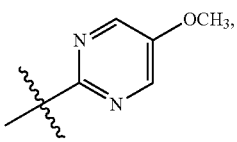 [SMILES: *c1ncc(OC)cn1]

wherein the symbol when drawn across a bond, indicates the point of attachment to the rest of the molecule.

34. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

37

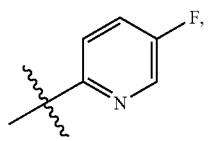 [SMILES: *c1ccc(F)cn1]

wherein the symbol

∿∿∿, when drawn across a bond, indicates the point of attachment to the rest of the molecule.

35. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

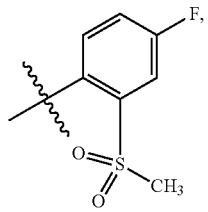 [SMILES: *c1ccc(F)cc1S(C)(=O)=O]

wherein the symbol

∿∿∿, when drawn across a bond, indicates the point of attachment to the rest of the molecule.

36. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

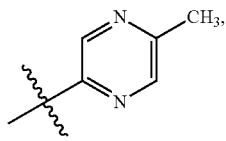 [SMILES: *c1cnc(C)cn1]

wherein the symbol

∿∿∿, when drawn across a bond, indicates the point of attachment to the rest of the molecule.

37. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

38

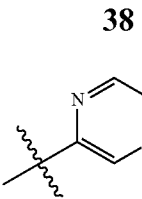

wherein the symbol

∿∿∿, when drawn across a bond, indicates the point of attachment to the rest of the molecule.

38. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

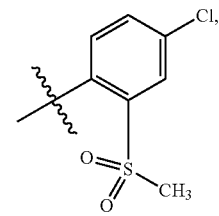 [SMILES: *c1ccc(Cl)cc1S(C)(=O)=O]

wherein the symbol

∿∿∿, when drawn across a bond, indicates the point of attachment to the rest of the molecule.

39. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

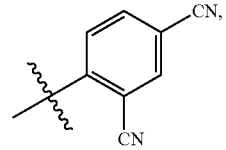 [SMILES: *c1ccc(C#N)cc1C#N]

wherein the symbol

∿∿∿, when drawn across a bond, indicates the point of attachment to the rest of the molecule.

40. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

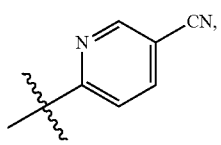 [SMILES: *c1ccc(C#N)cn1]

wherein the symbol

∿∿∿, when drawn across a bond, indicates the point of attachment to the rest of the molecule.

41. The compound of embodiment 28 or the pharmaceutically acceptable salt thereof, the tautomer thereof, the pharmaceutically acceptable salt of the tautomer, the stereoisomer of any of the foregoing, or the mixture thereof, wherein Q is

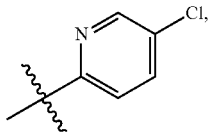 [SMILES: *c1ccc(Cl)cn1]

wherein the symbol

∿∿∿, when drawn across a bond, indicates the point of attachment to the rest of the molecule.

42. The compound of any one of embodiments 1-41 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —$(CR^{3b}R^{3c})$-Q, a group of formula —$(CR^{3d}R^{3e})$—$(CR^{3f}R^{3g})$-Q, a group of formula —$(CR^{3d}R^{3e})$—$(CR^{3f}R^{3g})$—C(=O)-Q, a group of formula —$(CR^{3d}R^{3e})$—$(CR^{3f}R^{3g})$—CH(OH)-Q, a group of formula —$(C_3$-$C_8$ cycloalkyl)-Q, a group of formula -(heterocyclyl)-Q, or -Q.

43. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —$(CR^{3d}R^{3e})$—$(CR^{3f}R^{3g})$-Q, a group of formula —$(C_3$-$C_8$ cycloalkyl)-Q, or a group of formula -(heterocyclyl)-Q.

44. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

45. The compound of embodiment 44 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, —$C_1$-$C_6$ alkyl, —$(C_1$-$C_6$ alkyl)-OH, —$(C_1$-$C_6$ alkyl)-O—$(C_1$-$C_6$ alkyl), or —$(C_1$-$C_6$ alkyl)-O—$(C_1$-$C_6$ alkyl)-phenyl; and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—$(C_1$-$C_6$ alkyl), —O—$(C_1$-$C_6$ haloalkyl), —O—$(C_1$-$C_6$ perhaloalkyl), or —O—$(C_2$-$C_6$ alkenyl).

46. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(C_3$-$C_8$ cycloalkyl)-Q.

47. The compound of embodiment 46 or the pharmaceutically acceptable salt thereof, the tautomer thereof, the pharmaceutically acceptable salt of the tautomer, the stereoisomer of any of the foregoing, or the mixture thereof, wherein the $C_3$-$C_8$ cycloalkyl of the —$(C_3$-$C_8$ cycloalkyl)-Q $R^3$ group is a cyclopropyl, cyclobutyl, cyclopentyl, or cyclohexyl that is unsubstituted or is substituted with 1 $R^{3h}$ substituent.

48. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q.

49. The compound of embodiment 48 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a piperidinyl that is unsubstituted or is substituted with 1 or 2 $R^{3h}$ substituent.

50. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3b}R^{3c})$-Q.

51. The compound of embodiment 50 or the pharmaceutically acceptable salt thereof, the tautomer thereof, the pharmaceutically acceptable salt of the tautomer, the stereoisomer of any of the foregoing, or the mixture thereof, wherein $R^{3b}$ and $R^{3c}$ are independently selected from —H or —$C_1$-$C_6$ alkyl.

52. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$—C(=O)-Q.

53. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$—CH(OH)-Q.

54. The compound of embodiment 42 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -Q.

55. The compound of any one of embodiments 1-41 or the pharmaceutically acceptable salt thereof, the tautomer thereof, the pharmaceutically acceptable salt of the tautomer, the stereoisomer of any of the foregoing, or the mixture thereof, wherein $R^3$ is selected from

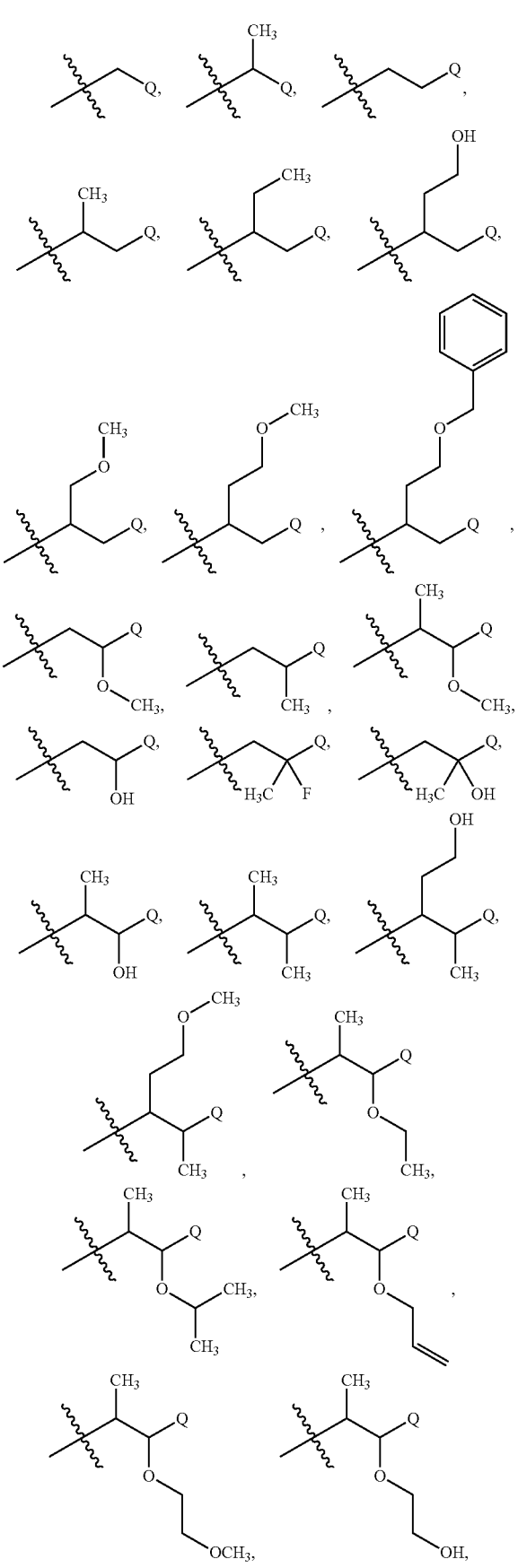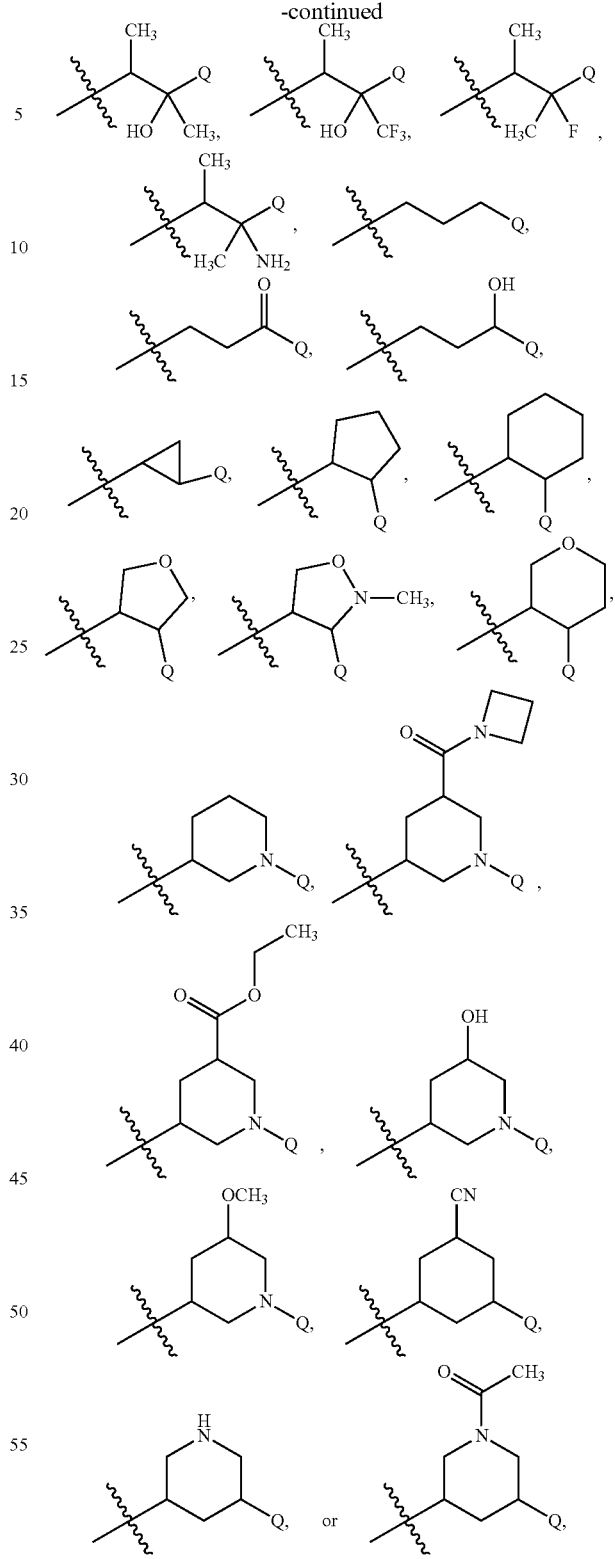
wherein the symbol
when drawn across a bond, indicates the point of attachment to the rest of the molecule.

56. The compound of any one of embodiments 1-41 or the pharmaceutically acceptable salt thereof, the tautomer thereof, the pharmaceutically acceptable salt of the tautomer, the stereoisomer of any of the foregoing, or the mixture thereof, wherein R³ is selected from

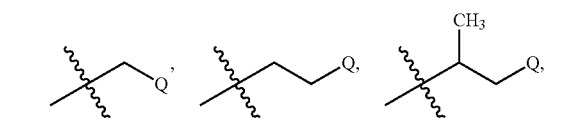
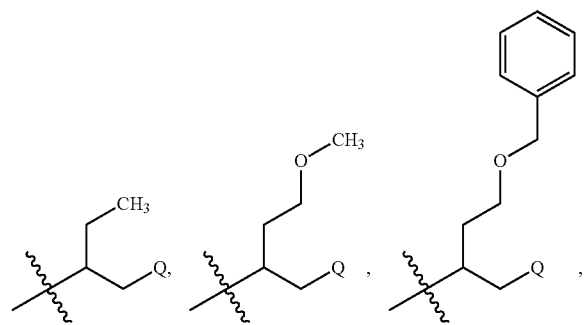
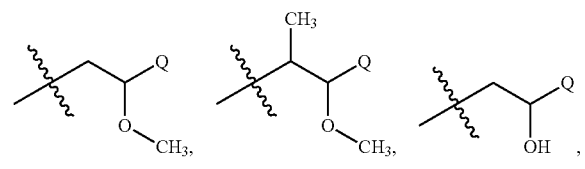
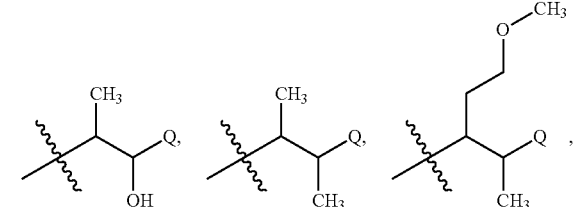
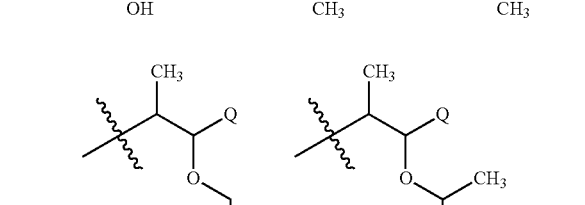
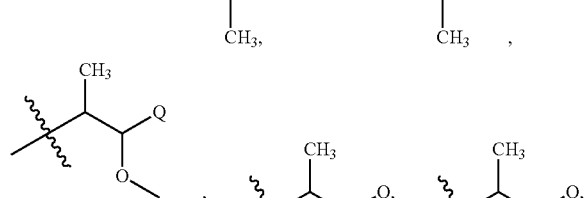
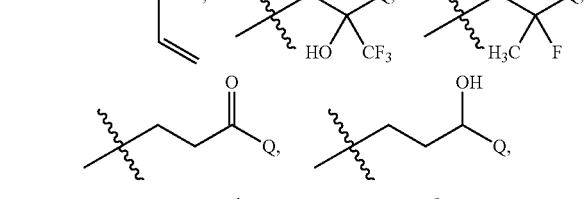
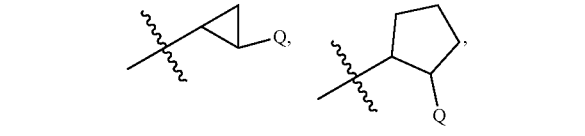

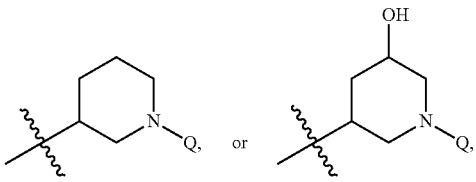

wherein the symbol

~~~, when drawn across a bond, indicates the point of attachment to the rest of the molecule.

57. The compound of any one of embodiments 1-41 or the pharmaceutically acceptable salt thereof, the tautomer thereof, the pharmaceutically acceptable salt of the tautomer, the stereoisomer of any of the foregoing, or the mixture thereof, wherein R³ is selected from

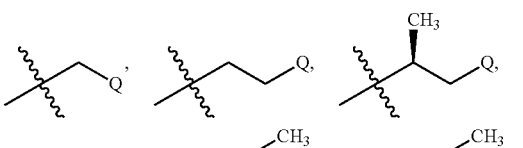
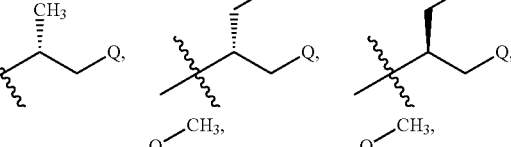
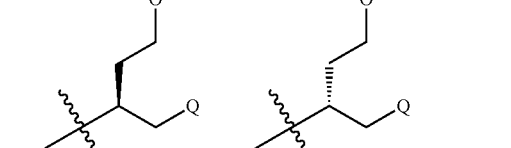
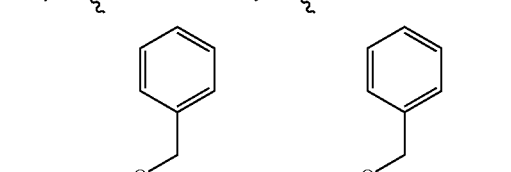
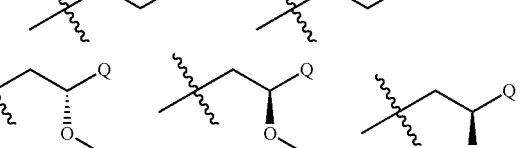
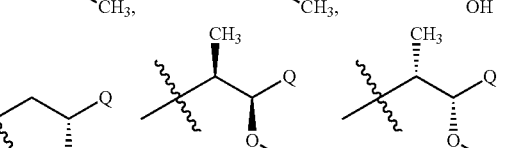

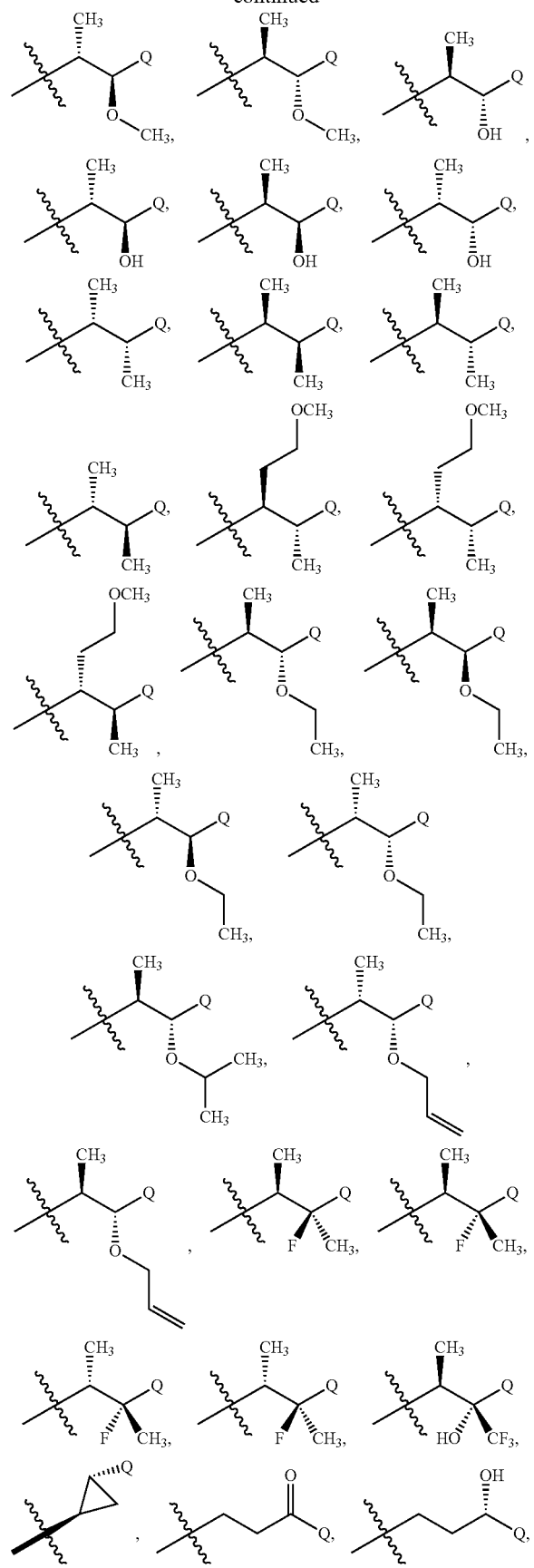
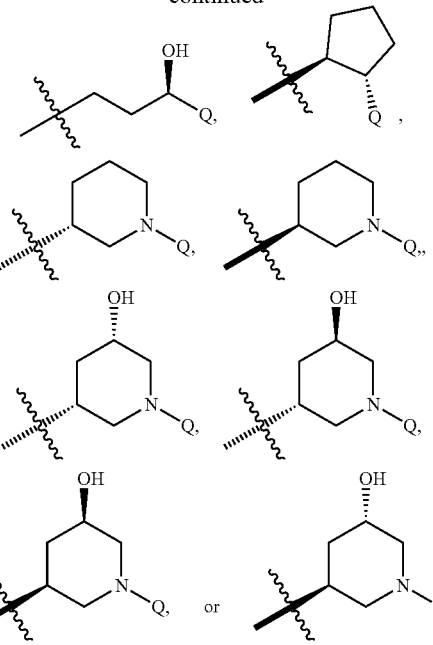
wherein the symbol
~~~
when drawn across a bond, indicates the point of attachment to the rest of the molecule.
58. The compound of embodiment 57 or the pharmaceutically acceptable salt thereof, the tautomer thereof, the pharmaceutically acceptable salt of the tautomer, the stereoisomer of any of the foregoing, or the mixture thereof, wherein $R^3$ is selected from
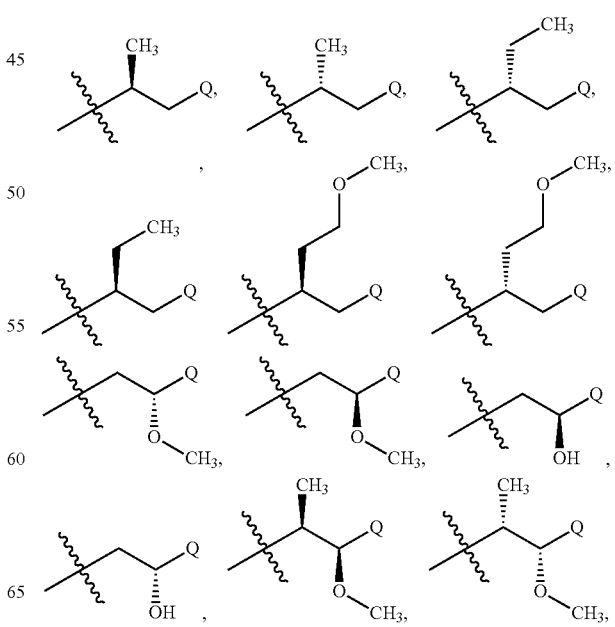

-continued

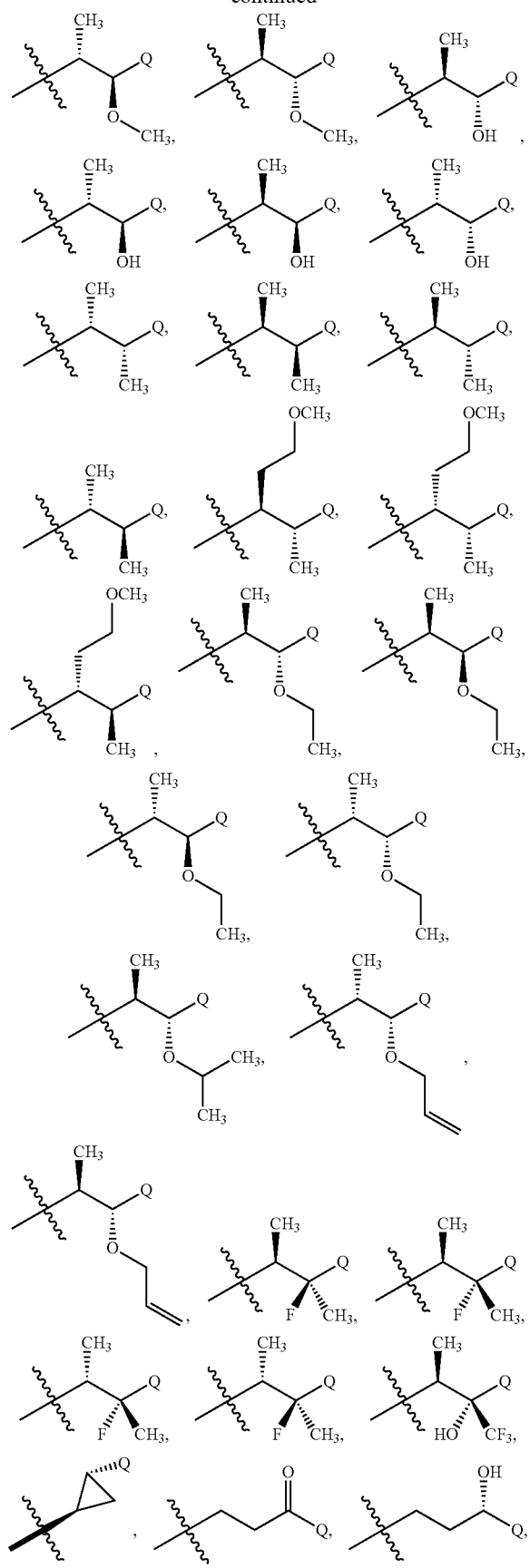

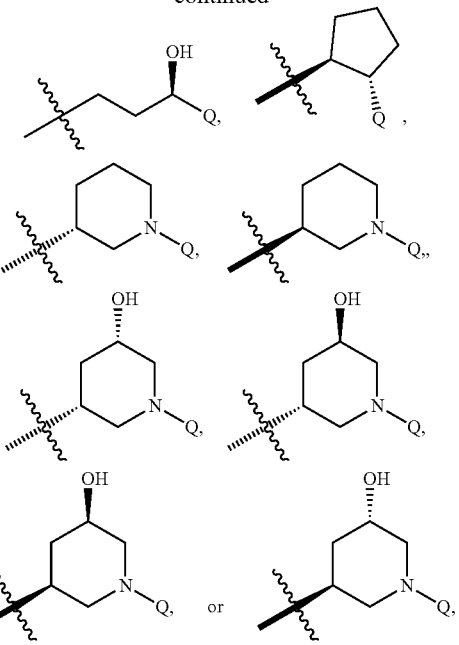

wherein the symbol

∼∼∼ , when drawn across a bond, indicates the point of attachment to the rest of the molecule.

59. The compound of any one of embodiments 1-21 or the pharmaceutically acceptable salt thereof, the tautomer thereof, the pharmaceutically acceptable salt of the tautomer, the stereoisomer of any of the foregoing, or the mixture thereof, wherein $R^3$ is selected from an unsubstituted $C_1$-$C_3$ alkyl, or a $C_1$-$C_3$ alkyl substituted with 1 2, or 3 independently selected $R^{3a}$ substituents.

60. The compound of any one of embodiments 1-21 or the pharmaceutically acceptable salt thereof, the tautomer thereof, the pharmaceutically acceptable salt of the tautomer, the stereoisomer of any of the foregoing, or the mixture thereof, wherein $R^3$ is selected from

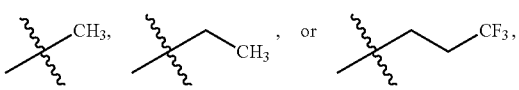

wherein the symbol

∼∼∼ , when drawn across a bond, indicates the point of attachment to the rest of the molecule.

61. The compound of embodiment 1, wherein the compound is selected from
1-(4-chlorophenyl)-N-(4-(2-methoxyphenyl)-5-(2-thiophenyl)-4H-1,2,4-triazol-3-yl)methanesulfonamide;
1-(4-chlorophenyl)-N-(5-(5-fluoro-2-thiophenyl)-4-(2-methoxyphenyl)-4H-1,2,4-triazol-3-yl)methanesulfonamide;

2-(4-chlorophenyl)-N-(4-(2-methoxyphenyl)-5-(2-thiophenyl)-4H-1,2,4-triazol-3-yl)ethanesulfonamide;
1-(4-chlorophenyl)-N-(4-(2-(difluoromethoxy)phenyl)-5-(2-thiophenyl)-4H-1,2,4-triazol-3-yl)methanesulfonamide;
N-(4-(5-bromo-2-methoxyphenyl)-5-(2-thiophenyl)-4H-1,2,4-triazol-3-yl)-1-(4-chlorophenyl)methanesulfonamide;
N-(4-(5-bromo-2-methoxyphenyl)-5-(2-thiophenyl)-4H-1,2,4-triazol-3-yl)-2-(4-chlorophenyl)ethanesulfonamide;
3-(3-(((4-chlorobenzyl)sulfonyl)amino)-5-(2-thiophenyl)-4H-1,2,4-triazol-4-yl)-4-methoxybenzoic acid;
ethyl 3-(3-(((2-(4-chlorophenyl)ethyl)sulfonyl)amino)-5-(2-thiophenyl)-4H-1,2,4-triazol-4-yl)-4-methoxybenzoate;
N-(4-(2-methoxyphenyl)-5-(2-thiophenyl)-4H-1,2,4-triazol-3-yl)-2-phenylethanesulfonamide;
2-(4-chlorophenyl)-N-(5-(5-fluoro-2-thiophenyl)-4-(2-methoxyphenyl)-4H-1,2,4-triazol-3-yl)ethanesulfonamide;
2-(4-chlorophenyl)-N-(4-(2-(difluoromethoxy)phenyl)-5-(2-thiophenyl)-4H-1,2,4-triazol-3-yl)ethanesulfonamide;
N-(4-(5-bromo-2-methoxyphenyl)-5-(2-thiophenyl)-4H-1,2,4-triazol-3-yl)-2-(4-chlorophenyl)-N-methylethanesulfonamide;
1-(4-chlorophenyl)-N-(4-(2-methoxyphenyl)-5-(2-thiophenyl)-4H-1,2,4-triazol-3-yl)-N-methylmethanesulfonamide;
1-(4-chlorophenyl)-N-(5-(2-thiophenyl)-4-(2-(trifluoromethyl)phenyl)-4H-1,2,4-triazol-3-yl)methanesulfonamide;
2-(4-chlorophenyl)-N-(5-(2-thiophenyl)-4-(2-(trifluoromethyl)phenyl)-4H-1,2,4-triazol-3-yl)ethanesulfonamide;
(1R,2S)-2-(4-chlorophenyl)-N-(4-(2-methoxyphenyl)-5-(2-thiophenyl)-4H-1,2,4-triazol-3-yl)cyclopropanesulfonamide;
(1S,2R)-2-(4-chlorophenyl)-N-(4-(2-methoxyphenyl)-5-(2-thiophenyl)-4H-1,2,4-triazol-3-yl)cyclopropanesulfonamide;
(1R,2S)-N-(4-(5-bromo-2-methoxyphenyl)-5-(2-thiophenyl)-4H-1,2,4-triazol-3-yl)-2-(4-chlorophenyl)cyclopropanesulfonamide;
(1S,2R)-N-(4-(5-bromo-2-methoxyphenyl)-5-(2-thiophenyl)-4H-1,2,4-triazol-3-yl)-2-(4-chlorophenyl)cyclopropanesulfonamide;
2-(4-chlorophenyl)-N-(4-(2-(difluoromethoxy)phenyl)-5-(5-fluoro-2-thiophenyl)-4H-1,2,4-triazol-3-yl)ethanesulfonamide;
3-(3-(((2-(4-chlorophenyl)ethyl)sulfonyl)amino)-5-(2-thiophenyl)-4H-1,2,4-triazol-4-yl)-4-methoxybenzoic acid;
N-(4-(2-(difluoromethoxy)phenyl)-5-(5-fluoro-2-thiophenyl)-4H-1,2,4-triazol-3-yl)-2-phenylethanesulfonamide;
2-(4-chlorophenyl)-N-(4-(4-methoxy-3-biphenylyl)-5-(2-thiophenyl)-4H-1,2,4-triazol-3-yl)ethanesulfonamide;
2-(4-chlorophenyl)-N-(4-(5-cyano-2-methoxyphenyl)-5-(2-thiophenyl)-4H-1,2,4-triazol-3-yl)ethanesulfonamide;
N-(4-(5-bromo-2-methoxyphenyl)-5-(2-thiophenyl)-4H-1,2,4-triazol-3-yl)-2-(4-fluorophenyl)ethanesulfonamide;
2-(4-chlorophenyl)-N-(4-(2,6-dimethoxyphenyl)-5-(2-thiophenyl)-4H-1,2,4-triazol-3-yl)ethanesulfonamide;
2-(4-chlorophenyl)-N-(4-(2-methoxy-5-(methylsulfonyl)phenyl)-5-(2-thiophenyl)-4H-1,2,4-triazol-3-yl)ethanesulfonamide;
3,3,3-trifluoro-N-(4-(2-methoxyphenyl)-5-(2-thiophenyl)-4H-1,2,4-triazol-3-yl)-1-propanesulfonamide;
2-(4-fluorophenyl)-N-(4-(2-methoxy-5-(methylsulfonyl)phenyl)-5-(2-thiophenyl)-4H-1,2,4-triazol-3-yl)ethanesulfonamide;
N-(4-(5-(dimethylamino)-2-methoxyphenyl)-5-(2-thiophenyl)-4H-1,2,4-triazol-3-yl)-2-(4-fluorophenyl)ethanesulfonamide;
2-(4-fluorophenyl)-N-(4-(2-methoxyphenyl)-5-(2-thiophenyl)-4H-1,2,4-triazol-3-yl)ethanesulfonamide;
2-(4-chlorophenyl)-N-(4-(2-methoxy-6-methylphenyl)-5-(2-thiophenyl)-4H-1,2,4-triazol-3-yl)ethanesulfonamide;
2-(4-chlorophenyl)-N-(4-(5-(3,6-dihydro-2H-thiopyran-4-yl)-2-methoxyphenyl)-5-(2-thiophenyl)-4H-1,2,4-triazol-3-yl)ethanesulfonamide;
2-(4-chlorophenyl)-N-(4-(2-methoxy-5-(2-oxo-1-pyrrolidinyl)phenyl)-5-(2-thiophenyl)-4H-1,2,4-triazol-3-yl)ethanesulfonamide;
2-(4-chlorophenyl)-N-(4-(2-methoxy-5-(2-oxo-1-azetidinyl)phenyl)-5-(2-thiophenyl)-4H-1,2,4-triazol-3-yl)ethanesulfonamide;
2-(4-chlorophenyl)-N-(4-(2-methoxy-5-(2-oxo-1,3-oxazolidin-3-yl)phenyl)-5-(2-thiophenyl)-4H-1,2,4-triazol-3-yl)ethanesulfonamide;
2-(4-chlorophenyl)-N-(4-(5-(1,1-dioxido-3,6-dihydro-2H-thiopyran-4-yl)-2-methoxyphenyl)-5-(2-thiophenyl)-4H-1,2,4-triazol-3-yl)ethanesulfonamide;
2-(4-chlorophenyl)-N-(4-(2-methoxy-5-(3-oxo-4-morpholinyl)phenyl)-5-(2-thiophenyl)-4H-1,2,4-triazol-3-yl)ethanesulfonamide;
2-(4-chlorophenyl)-N-(4-(2-methoxy-6-methylphenyl)-5-(2-thiophenyl)-4H-1,2,4-triazol-3-yl)ethanesulfonamide;
2-(4-chlorophenyl)-N-(4-(2-methoxy-6-methylphenyl)-5-(2-thiophenyl)-4H-1,2,4-triazol-3-yl)ethanesulfonamide;
N-(4-(5-chloro-2-methoxyphenyl)-5-(2-thiophenyl)-4H-1,2,4-triazol-3-yl)-2-(4-fluorophenyl)ethanesulfonamide;
2-(4-chlorophenyl)-N-(4-(5-((2-hydroxyethyl)amino)-2-methoxyphenyl)-5-(2-thiophenyl)-4H-1,2,4-triazol-3-yl)ethanesulfonamide;
2-(4-chlorophenyl)-N-(4-(5-(dimethylamino)-2-methoxyphenyl)-5-(2-thiophenyl)-4H-1,2,4-triazol-3-yl)ethanesulfonamide;
2-(4-chlorophenyl)-N-(4-(2,6-dimethoxyphenyl)-5-(1,3-thiazol-2-yl)-4H-1,2,4-triazol-3-yl)ethanesulfonamide;
2-(4-chlorophenyl)-N-(4-(2,6-dimethoxyphenyl)-5-(1,3-thiazol-5-yl)-4H-1,2,4-triazol-3-yl)ethanesulfonamide;
2-(4-fluorophenyl)-N-(4-(2-methoxy-5-(2-oxo-1-azetidinyl)phenyl)-5-(2-thiophenyl)-4H-1,2,4-triazol-3-yl)ethanesulfonamide;
2-(2-bromo-4-fluorophenyl)-N-(4-(2-methoxy-5-(2-oxo-1-azetidinyl)phenyl)-5-(2-thiophenyl)-4H-1,2,4-triazol-3-yl)ethanesulfonamide;
2-(4-chlorophenyl)-N-(4-(2,6-dimethoxyphenyl)-5-(1,3-oxazol-5-yl)-4H-1,2,4-triazol-3-yl)ethanesulfonamide;
2-(2-cyano-4-fluorophenyl)-N-(4-(2-methoxy-5-(2-oxo-1-azetidinyl)phenyl)-5-(2-thiophenyl)-4H-1,2,4-triazol-3-yl)ethanesulfonamide;
2-(4-chlorophenyl)-N-(4-(2,6-dimethoxyphenyl)-5-(1,3-thiazol-4-yl)-4H-1,2,4-triazol-3-yl)ethanesulfonamide;
2-(4-chlorophenyl)-N-(4-(2,6-dimethoxyphenyl)-5-(1,3-oxazol-4-yl)-4H-1,2,4-triazol-3-yl)ethanesulfonamide;
2-(2-bromo-4-fluorophenyl)-N-(4-(2,6-dimethoxyphenyl)-5-(1,3-thiazol-2-yl)-4H-1,2,4-triazol-3-yl)ethanesulfonamide;
2-(4-chlorophenyl)-N-(4-(2,6-dimethoxyphenyl)-5-(3-thiophenyl)-4H-1,2,4-triazol-3-yl)ethanesulfonamide;
2-(4-chlorophenyl)-N-(4-(2,6-dimethoxyphenyl)-5-(1,3-oxazol-2-yl)-4H-1,2,4-triazol-3-yl)ethanesulfonamide;
2-(4-chlorophenyl)-N-(4-(2,6-dimethoxyphenyl)-5-(4-methyl-1,3-thiazol-2-yl)-4H-1,2,4-triazol-3-yl)ethanesulfonamide;

2-(4-chlorophenyl)-N-(4-(2,6-dimethoxyphenyl)-5-(5-methyl-1,3-thiazol-2-yl)-4H-1,2,4-triazol-3-yl)ethanesulfonamide;

2-(4-chlorophenyl)-N-(4-(2,6-dimethoxyphenyl)-5-(1-methyl-1H-imidazol-5-yl)-4H-1,2,4-triazol-3-yl)ethanesulfonamide;

2-(4-chlorophenyl)-N-(5-(5-chloro-1,3-thiazol-2-yl)-4-(2,6-dimethoxyphenyl)-4H-1,2,4-triazol-3-yl)ethanesulfonamide;

2-(4-chlorophenyl)-N-(4-(2,6-dimethoxyphenyl)-5-(5-methyl-3-isoxazolyl)-4H-1,2,4-triazol-3-yl)ethanesulfonamide;

2-(4-chlorophenyl)-N-(4-(2,6-dimethoxyphenyl)-5-(2-(methoxymethyl)-1,3-thiazol-4-yl)-4H-1,2,4-triazol-3-yl)ethanesulfonamide;

N-(4-(2,6-dimethoxyphenyl)-5-(2-thiophenyl)-4H-1,2,4-triazol-3-yl)-3-oxo-3-(1-pyrrolidinyl)-1-propanesulfonamide;

(3R)-3-cyclopentyl-N-(4-(2,6-dimethoxyphenyl)-5-(2-thiophenyl)-4H-1,2,4-triazol-3-yl)-3-hydroxy-1-propanesulfonamide;

(3S)-3-cyclopentyl-N-(4-(2,6-dimethoxyphenyl)-5-(2-thiophenyl)-4H-1,2,4-triazol-3-yl)-3-hydroxy-1-propanesulfonamide;

2-(2-cyano-4-fluorophenyl)-N-(4-(2,6-dimethoxyphenyl)-5-(4-methyl-1,3-thiazol-2-yl)-4H-1,2,4-triazol-3-yl)ethanesulfonamide;

N-(4-(2,6-dimethoxyphenyl)-5-(4-methyl-1,3-thiazol-2-yl)-4H-1,2,4-triazol-3-yl)-2-(5-fluoro-2-pyrimidinyl)ethanesulfonamide;

2-(2-cyano-4-fluorophenyl)-N-(4-(2,6-dimethoxyphenyl)-5-(2-methyl-1,3-thiazol-4-yl)-4H-1,2,4-triazol-3-yl)ethanesulfonamide;

2-(4-chlorophenyl)-N-(4-(2,6-dimethoxyphenyl)-5-(2-methyl-1,3-thiazol-4-yl)-4H-1,2,4-triazol-3-yl)ethanesulfonamide;

2-(4-chlorophenyl)-N-(4-(2,6-dimethoxyphenyl)-5-(4-(1-methylethyl)-1,3-thiazol-2-yl)-4H-1,2,4-triazol-3-yl)ethanesulfonamide;

2-(2-cyano-4-fluorophenyl)-N-(4-(2,6-dimethoxyphenyl)-5-(4-(1-methylethyl)-1,3-thiazol-2-yl)-4H-1,2,4-triazol-3-yl)ethanesulfonamide;

2-(4-chlorophenyl)-N-(4-(2,6-dimethoxyphenyl)-5-(4-ethyl-1,3-thiazol-2-yl)-4H-1,2,4-triazol-3-yl)ethanesulfonamide;

2-(2-cyano-4-fluorophenyl)-N-(4-(2,6-dimethoxyphenyl)-5-(4-ethyl-1,3-thiazol-2-yl)-4H-1,2,4-triazol-3-yl)ethanesulfonamide;

N-(4-(2,6-dimethoxyphenyl)-5-(4-methyl-1,3-thiazol-2-yl)-4H-1,2,4-triazol-3-yl)-2-((2R)-2-methyl-6-oxo-1-piperidinyl)ethanesulfonamide;

N-(4-(2,6-dimethoxyphenyl)-5-(4-methyl-1,3-thiazol-2-yl)-4H-1,2,4-triazol-3-yl)-2-((2S)-2-methyl-6-oxo-1-piperidinyl)ethanesulfonamide;

N-(4-(2,6-dimethoxyphenyl)-5-(4-(1-methylethyl)-1,3-thiazol-2-yl)-4H-1,2,4-triazol-3-yl)-2-(5-fluoro-2-pyrimidinyl)ethanesulfonamide;

2-(2-cyano-4-fluorophenyl)-N-(4-(2,6-dimethoxyphenyl)-5-(2-ethyl-1,3-thiazol-4-yl)-4H-1,2,4-triazol-3-yl)ethanesulfonamide;

N-(4-(2,6-dimethoxyphenyl)-5-(4-ethyl-1,3-thiazol-2-yl)-4H-1,2,4-triazol-3-yl)-2-(5-fluoro-2-pyrimidinyl)ethanesulfonamide;

(3R)-3-cyclopentyl-N-(4-(2,6-dimethoxyphenyl)-5-(4-methyl-1,3-thiazol-2-yl)-4H-1,2,4-triazol-3-yl)-3-hydroxy-1-propanesulfonamide;

(3S)-3-cyclopentyl-N-(4-(2,6-dimethoxyphenyl)-5-(4-methyl-1,3-thiazol-2-yl)-4H-1,2,4-triazol-3-yl)-3-hydroxy-1-propanesulfonamide;

N-(4-(2,6-dimethoxyphenyl)-5-(2-ethyl-1,3-thiazol-4-yl)-4H-1,2,4-triazol-3-yl)-2-(5-fluoro-2-pyrimidinyl)ethanesulfonamide;

(2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-2-propanesulfonamide;

(2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-2-propanesulfonamide;

(2R)-N-(4-(2,6-dimethoxyphenyl)-5-(4-ethyl-1,3-thiazol-2-yl)-4H-1,2,4-triazol-3-yl)-1-(5-fluoro-2-pyrimidinyl)-2-propanesulfonamide;

(2S)-N-(4-(2,6-dimethoxyphenyl)-5-(4-ethyl-1,3-thiazol-2-yl)-4H-1,2,4-triazol-3-yl)-1-(5-fluoro-2-pyrimidinyl)-2-propanesulfonamide;

2-(2-cyano-4-fluorophenyl)-N-(5-(4-cyclopropyl-1,3-thiazol-2-yl)-4-(2,6-dimethoxyphenyl)-4H-1,2,4-triazol-3-yl)ethanesulfonamide;

(2R)-N-(5-(4-cyclopropyl-1,3-thiazol-2-yl)-4-(2,6-dimethoxyphenyl)-4H-1,2,4-triazol-3-yl)-1-(5-fluoro-2-pyrimidinyl)-2-propanesulfonamide;

(2S)-N-(5-(4-cyclopropyl-1,3-thiazol-2-yl)-4-(2,6-dimethoxyphenyl)-4H-1,2,4-triazol-3-yl)-1-(5-fluoro-2-pyrimidinyl)-2-propanesulfonamide;

(2R)-N-(4-(2,6-dimethoxyphenyl)-5-(4-(1-methylethyl)-1,3-thiazol-2-yl)-4H-1,2,4-triazol-3-yl)-1-(5-fluoro-2-pyrimidinyl)-2-propanesulfonamide;

(2S)-N-(4-(2,6-dimethoxyphenyl)-5-(4-(1-methylethyl)-1,3-thiazol-2-yl)-4H-1,2,4-triazol-3-yl)-1-(5-fluoro-2-pyrimidinyl)-2-propanesulfonamide;

(2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-2-butanesulfonamide;

(2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-2-butanesulfonamide;

(2R,3R)-N-(4-(2,6-dimethoxyphenyl)-5-(4-methyl-1,3-thiazol-2-yl)-4H-1,2,4-triazol-3-yl)-3-(5-fluoro-2-pyrimidinyl)-2-butanesulfonamide;

(2R,3S)-N-(4-(2,6-dimethoxyphenyl)-5-(4-methyl-1,3-thiazol-2-yl)-4H-1,2,4-triazol-3-yl)-3-(5-fluoro-2-pyrimidinyl)-2-butanesulfonamide;

(2S,3R)-N-(4-(2,6-dimethoxyphenyl)-5-(4-methyl-1,3-thiazol-2-yl)-4H-1,2,4-triazol-3-yl)-3-(5-fluoro-2-pyrimidinyl)-2-butanesulfonamide;

(2S,3S)-N-(4-(2,6-dimethoxyphenyl)-5-(4-methyl-1,3-thiazol-2-yl)-4H-1,2,4-triazol-3-yl)-3-(5-fluoro-2-pyrimidinyl)-2-butanesulfonamide;

(1R,2S)-N-(4-(2,6-dimethoxyphenyl)-5-(4-methyl-1,3-thiazol-2-yl)-4H-1,2,4-triazol-3-yl)-2-(5-fluoro-2-pyrimidinyl)cyclopentanesulfonamide;

(1S,2R)-N-(4-(2,6-dimethoxyphenyl)-5-(4-methyl-1,3-thiazol-2-yl)-4H-1,2,4-triazol-3-yl)-2-(5-fluoro-2-pyrimidinyl)cyclopentanesulfonamide;

(2R)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide;

(2S)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide;

N-(4-(2,6-dimethoxyphenyl)-5-(4-methyl-1,3-thiazol-2-yl)-4H-1,2,4-triazol-3-yl)-2-(5-methyl-2-pyrimidinyl)ethanesulfonamide;

(2R)-1-(5-cyano-2-pyridinyl)-N-(4-(2,6-dimethoxyphenyl)-5-(4-methyl-1,3-thiazol-2-yl)-4H-1,2,4-triazol-3-yl)-2-propanesulfonamide;

(3R,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide;

(3R,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide;

(3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide;

(3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide;

(2S)-1-(5-cyano-2-pyridinyl)-N-(4-(2,6-dimethoxyphenyl)-5-(4-methyl-1,3-thiazol-2-yl)-4H-1,2,4-triazol-3-yl)-2-propanesulfonamide;

(2R)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide;

(2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide;

(3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide;

(3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide;

(3S,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide;

(3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide;

(2R)-N-(4-(2,6-dimethoxyphenyl)-5-(4-pyrimidinyl)-4H-1,2,4-triazol-3-yl)-1-(5-fluoro-2-pyrimidinyl)-2-propanesulfonamide;

(2S)-N-(4-(2,6-dimethoxyphenyl)-5-(4-pyrimidinyl)-4H-1,2,4-triazol-3-yl)-1-(5-fluoro-2-pyrimidinyl)-2-propanesulfonamide;

(2S)-N-(4-(2,6-dimethoxyphenyl)-5-(3-pyridazinyl)-4H-1,2,4-triazol-3-yl)-1-(5-fluoro-2-pyrimidinyl)-2-propanesulfonamide;

(2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide;

(2S)-N-(4-(2,6-dimethoxyphenyl)-5-(1-methyl-1H-pyrrol-3-yl)-4H-1,2,4-triazol-3-yl)-1-(5-fluoro-2-pyrimidinyl)-2-propanesulfonamide;

(2R)-N-(4-(4,6-dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide;

(2S)-N-(4-(4,6-dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide;

(2R)-N-(4-(2,6-dimethoxyphenyl)-5-(1-methyl-1H-pyrrol-3-yl)-4H-1,2,4-triazol-3-yl)-1-(5-fluoro-2-pyrimidinyl)-2-propanesulfonamide;

(2R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-2-propanesulfonamide;

(2R)-1-(5-fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide;

(2S)-1-(5-fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide;

(2R)-4-(benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide;

(2S)-4-(benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide;

(2S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-2-propanesulfonamide;

(2R)-N-(4-(2,6-dimethoxyphenyl)-5-(1-methyl-1H-pyrazol-4-yl)-4H-1,2,4-triazol-3-yl)-1-(5-fluoro-2-pyrimidinyl)-2-propanesulfonamide;

(2S)-N-(4-(2,6-dimethoxyphenyl)-5-(1-methyl-1H-pyrazol-4-yl)-4H-1,2,4-triazol-3-yl)-1-(5-fluoro-2-pyrimidinyl)-2-propanesulfonamide;

(2R)-N-(4-(2,6-dimethoxyphenyl)-5-(5-methyl-1,3,4-oxadiazol-2-yl)-4H-1,2,4-triazol-3-yl)-1-(5-fluoro-2-pyrimidinyl)-2-propanesulfonamide;

(2S)-N-(4-(2,6-dimethoxyphenyl)-5-(5-methyl-1,3,4-oxadiazol-2-yl)-4H-1,2,4-triazol-3-yl)-1-(5-fluoro-2-pyrimidinyl)-2-propanesulfonamide;

(2R)-N-(4-(2,6-dimethoxyphenyl)-5-(5-pyrimidinyl)-4H-1,2,4-triazol-3-yl)-1-(5-fluoro-2-pyrimidinyl)-2-propanesulfonamide;

(2S)-N-(4-(2,6-dimethoxyphenyl)-5-(5-pyrimidinyl)-4H-1,2,4-triazol-3-yl)-1-(5-fluoro-2-pyrimidinyl)-2-propanesulfonamide;

(2R)-N-(4-(2,6-dimethoxyphenyl)-5-(4-pyridazinyl)-4H-1,2,4-triazol-3-yl)-1-(5-fluoro-2-pyrimidinyl)-2-propanesulfonamide;

(2S)-N-(4-(2,6-dimethoxyphenyl)-5-(4-pyridazinyl)-4H-1,2,4-triazol-3-yl)-1-(5-fluoro-2-pyrimidinyl)-2-propanesulfonamide;

(2R)-N-(4-(2,6-dimethoxyphenyl)-5-(1,5-dimethyl-1H-pyrazol-3-yl)-4H-1,2,4-triazol-3-yl)-1-(5-fluoro-2-pyrimidinyl)-2-propanesulfonamide;

(2S)-N-(4-(2,6-dimethoxyphenyl)-5-(1,5-dimethyl-1H-pyrazol-3-yl)-4H-1,2,4-triazol-3-yl)-1-(5-fluoro-2-pyrimidinyl)-2-propanesulfonamide;

(2R)-N-(4-(2,6-dimethoxyphenyl)-5-(1-methyl-1H-1,2,3-triazol-4-yl)-4H-1,2,4-triazol-3-yl)-1-(5-fluoro-2-pyrimidinyl)-2-propanesulfonamide;

(2S)-N-(4-(2,6-dimethoxyphenyl)-5-(1-methyl-1H-1,2,3-triazol-4-yl)-4H-1,2,4-triazol-3-yl)-1-(5-fluoro-2-pyrimidinyl)-2-propanesulfonamide;

(2R)-N-(4-(2,6-dimethoxyphenyl)-5-(2-pyrimidinyl)-4H-1,2,4-triazol-3-yl)-1-(5-fluoro-2-pyrimidinyl)-2-propanesulfonamide;

(2S)-N-(4-(2,6-dimethoxyphenyl)-5-(2-pyrimidinyl)-4H-1,2,4-triazol-3-yl)-1-(5-fluoro-2-pyrimidinyl)-2-propanesulfonamide;

(2R)-N-(4-(2,6-dimethoxyphenyl)-5-(3-methyl-5-isoxazolyl)-4H-1,2,4-triazol-3-yl)-1-(5-fluoro-2-pyrimidinyl)-2-propanesulfonamide;

(2S)-N-(4-(2,6-dimethoxyphenyl)-5-(3-methyl-5-isoxazolyl)-4H-1,2,4-triazol-3-yl)-1-(5-fluoro-2-pyrimidinyl)-2-propanesulfonamide;

(1R,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-hydroxy-2-propanesulfonamide;

(1S,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-hydroxy-2-propanesulfonamide;

(1R,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-hydroxy-2-propanesulfonamide;

(1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-hydroxy-2-propanesulfonamide;

(2S)-N-(4-(2,6-dimethoxyphenyl)-5-(3-methyl-4-isoxazolyl)-4H-1,2,4-triazol-3-yl)-1-(5-fluoro-2-pyrimidinyl)-2-propanesulfonamide;

(2R)-N-(4-(2,6-dimethoxyphenyl)-5-(3-methyl-4-isoxazolyl)-4H-1,2,4-triazol-3-yl)-1-(5-fluoro-2-pyrimidinyl)-2-propanesulfonamide;

(1S,2S)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide;

(1R,2R)-N-(4-(2,6-dimethoxyphenyl)-5-(4-methyl-1,3-thiazol-2-yl)-4H-1,2,4-triazol-3-yl)-1-hydroxy-1-(5-methyl-2-pyrimidinyl)-2-propanesulfonamide;

(1S,2S)-N-(4-(2,6-dimethoxyphenyl)-5-(4-methyl-1,3-thiazol-2-yl)-4H-1,2,4-triazol-3-yl)-1-hydroxy-1-(5-methyl-2-pyrimidinyl)-2-propanesulfonamide;

(1R,2S)-N-(4-(2,6-dimethoxyphenyl)-5-(4-methyl-1,3-thiazol-2-yl)-4H-1,2,4-triazol-3-yl)-1-hydroxy-1-(5-methyl-2-pyrimidinyl)-2-propanesulfonamide;

(1S,2R)-N-(4-(2,6-dimethoxyphenyl)-5-(4-methyl-1,3-thiazol-2-yl)-4H-1,2,4-triazol-3-yl)-1-hydroxy-1-(5-methyl-2-pyrimidinyl)-2-propanesulfonamide;

(1S,2R)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide;

(2R,3S)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide;

(2S,3R)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide;

(2S,3S)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide;

(2R,3R)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide;

N-(4-(2,6-dimethoxyphenyl)-5-(4-methyl-1,3-thiazol-2-yl)-4H-1,2,4-triazol-3-yl)-2-((6S)-3,6-dimethyl-2-oxotetrahydro-1(2H)-pyrimidinyl)ethanesulfonamide;

(2R)-N-(4-(2,6-dimethoxyphenyl)-5-(1-ethyl-1H-pyrazol-3-yl)-4H-1,2,4-triazol-3-yl)-1-(5-fluoro-2-pyrimidinyl)-2-propanesulfonamide;

(2S)-N-(4-(2,6-dimethoxyphenyl)-5-(1-ethyl-1H-pyrazol-3-yl)-4H-1,2,4-triazol-3-yl)-1-(5-fluoro-2-pyrimidinyl)-2-propanesulfonamide;

(1S,2R)-N-(4-(2,6-dimethoxyphenyl)-5-(4-methyl-1,3-thiazol-2-yl)-4H-1,2,4-triazol-3-yl)-1-methoxy-2-propanesulfonamide;

(1R,2S)-N-(4-(2,6-dimethoxyphenyl)-5-(4-methyl-1,3-thiazol-2-yl)-4H-1,2,4-triazol-3-yl)-1-methoxy-2-propanesulfonamide;

(2R)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide;

(2S)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide;

(2R,3S)-N-(4-(2,6-dimethoxyphenyl)-5-(1-methyl-1H-pyrazol-3-yl)-4H-1,2,4-triazol-3-yl)-3-(5-fluoro-2-pyrimidinyl)-2-butanesulfonamide;

(2S,3R)-N-(4-(2,6-dimethoxyphenyl)-5-(1-methyl-1H-pyrazol-3-yl)-4H-1,2,4-triazol-3-yl)-3-(5-fluoro-2-pyrimidinyl)-2-butanesulfonamide;

(3R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide;

(3S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide;

(2R)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide;

(2S)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide;

(1S,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-(2-propen-1-yloxy)-2-propanesulfonamide;

(1R,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-(2-propen-1-yloxy)-2-propanesulfonamide;

(1R,2S)-N-(4-(2,6-dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide;

(1S,2R)-N-(4-(2,6-dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide;

(2R)-N-(4-(2,6-dimethoxyphenyl)-5-(5-methyl-1H-pyrazol-3-yl)-4H-1,2,4-triazol-3-yl)-1-(5-fluoro-2-pyrimidinyl)-2-propanesulfonamide;

(2S)-N-(4-(2,6-dimethoxyphenyl)-5-(5-methyl-1H-pyrazol-3-yl)-4H-1,2,4-triazol-3-yl)-1-(5-fluoro-2-pyrimidinyl)-2-propanesulfonamide;

(3R,5S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide;

(3S,5R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide;

(1R,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide;

(1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide;

(2R)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide;

(2S)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide;

(1R,2S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide;

(1S,2R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide;

N-(4-(2,6-dimethoxyphenyl)-5-(1-methyl-1H-pyrazol-3-yl)-4H-1,2,4-triazol-3-yl)methanesulfonamide;

(2R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide;

(2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide;

(2R)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide;

(2S)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide;

(2R)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide;

(2S)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide;

(2R)-N-(4-(2,6-dimethoxyphenyl)-5-(2-pyrazinyl)-4H-1,2,4-triazol-3-yl)-1-(5-fluoro-2-pyrimidinyl)-2-propanesulfonamide;

(2S)-N-(4-(2,6-dimethoxyphenyl)-5-(2-pyrazinyl)-4H-1,2,4-triazol-3-yl)-1-(5-fluoro-2-pyrimidinyl)-2-propanesulfonamide;

(3R)-N-(4-(2,6-dimethoxyphenyl)-5-(1-methyl-1H-pyrazol-3-yl)-4H-1,2,4-triazol-3-yl)-3-piperidinesulfonamide;

(3S)-N-(4-(2,6-dimethoxyphenyl)-5-(1-methyl-1H-pyrazol-3-yl)-4H-1,2,4-triazol-3-yl)-3-piperidinesulfonamide;

(2R)-2-(5-chloro-2-pyridinyl)-N-(4-(2,6-dimethoxyphenyl)-5-(1-methyl-1H-pyrazol-3-yl)-4H-1,2,4-triazol-3-yl)-2-hydroxyethanesulfonamide;

(2S)-2-(5-chloro-2-pyridinyl)-N-(4-(2,6-dimethoxyphenyl)-5-(1-methyl-1H-pyrazol-3-yl)-4H-1,2,4-triazol-3-yl)-2-hydroxyethanesulfonamide;

(2R)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide;

(2S)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide;

(2R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide;

(2S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide;

(2R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide;

(2S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide;

(1R,2S)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1S,2R)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide;

(2R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide;

(2S)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide;

(2R)-2-(5-chloro-2-pyridinyl)-N-(4-(2,6-dimethoxyphenyl)-5-(1-methyl-1H-pyrazol-3-yl)-4H-1,2,4-triazol-3-yl)-2-methoxyethanesulfonamide;

(2S)-2-(5-chloro-2-pyridinyl)-N-(4-(2,6-dimethoxyphenyl)-5-(1-methyl-1H-pyrazol-3-yl)-4H-1,2,4-triazol-3-yl)-2-methoxyethanesulfonamide;

(2R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide;

(2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide;

(2R)-N-(4-(2,6-dimethoxyphenyl)-5-(1H-pyrazol-3-yl)-4H-1,2,4-triazol-3-yl)-1-(5-fluoro-2-pyrimidinyl)-2-propanesulfonamide;

(2S)-N-(4-(2,6-dimethoxyphenyl)-5-(1H-pyrazol-3-yl)-4H-1,2,4-triazol-3-yl)-1-(5-fluoro-2-pyrimidinyl)-2-propanesulfonamide;

3-(4-(2,6-dimethoxyphenyl)-5-(((((1R)-2-(5-fluoro-2-pyrimidinyl)-1-methylethyl)sulfonyl)amino)-4H-1,2,4-triazol-3-yl)-N-methyl-1H-pyrazole-1-carboxamide;

3-(4-(2,6-dimethoxyphenyl)-5-(((((1S)-2-(5-fluoro-2-pyrimidinyl)-1-methylethyl)sulfonyl)amino)-4H-1,2,4-triazol-3-yl)-N-methyl-1H-pyrazole-1-carboxamide;

N-(4-(2,6-dimethoxyphenyl)-5-(1-methyl-1H-pyrazol-3-yl)-4H-1,2,4-triazol-3-yl)ethanesulfonamide;

(2S,3R)-N-(4-(2,6-dimethoxyphenyl)-5-(1-ethyl-1H-pyrazol-3-yl)-4H-1,2,4-triazol-3-yl)-3-(5-fluoro-2-pyrimidinyl)-2-butanesulfonamide;

(2S,3R)-N-(5-(1-(difluoromethyl)-1H-pyrazol-3-yl)-4-(2,6-dimethoxyphenyl)-4H-1,2,4-triazol-3-yl)-3-(5-fluoro-2-pyrimidinyl)-2-butanesulfonamide;

(1R,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide;

(1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide;

(1R,2S)-N-(4-(2,6-dimethoxyphenyl)-5-(1-ethyl-1H-pyrazol-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1-ethyl-1H-pyrazol-3-yl)-4H-1,2,4-triazol-3-yl)-1-hydroxy-1-(5-methyl-2-pyrimidinyl)-2-propanesulfonamide;

(1R,2S)-N-(4-(2,6-dimethoxyphenyl)-5-(5-methyl-1,3-thiazol-2-yl)-4H-1,2,4-triazol-3-yl)-1-methoxy-1-(5-methyl-2-pyrimidinyl)-2-propanesulfonamide;

(2S,3R)-N-(4-(2,6-dimethoxyphenyl)-5-(4-methyl-1,3-thiazol-2-yl)-4H-1,2,4-triazol-3-yl)-3-(5-methyl-2-pyrimidinyl)-2-butanesulfonamide;

(2S,3R)-N-(4-(2,6-dimethoxyphenyl)-5-(1-ethyl-1H-pyrazol-3-yl)-4H-1,2,4-triazol-3-yl)-3-(5-methyl-2-pyrimidinyl)-2-butanesulfonamide;

(1R,2S)-N-(4-(2,6-dimethoxyphenyl)-5-(5-methyl-2-thiophenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methyl-1H-pyrazol-3-yl)-4H-1,2,4-triazol-3-yl)-1-methoxy-1-(5-methyl-2-pyrimidinyl)-2-propanesulfonamide;

(1R,2S)-N-(5-(5-chloro-2-thiophenyl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(4,5,6,7-tetrahydro-1H-indazol-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methoxy-1H-indol-2-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(2-pyrazinyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(2-methyl-1,3-thiazol-4-yl)-4H-1,2,4-triazol-3-yl)-1-methoxy-1-(5-methyl-2-pyrimidinyl)-2-propanesulfonamide;

N-(5-(5-((R)-(4-chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)ethanesulfonamide;

N-(5-(5-((S)-(4-chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)ethanesulfonamide;

(1R,2S)-N-(4-(2,6-dimethoxyphenyl)-5-(2-methyl-1,3-oxazol-4-yl)-4H-1,2,4-triazol-3-yl)-1-methoxy-1-(5-methyl-2-pyrimidinyl)-2-propanesulfonamide;

(1R,2S)-N-(5-(4-cyclopropyl-1,3-thiazol-2-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1,3-thiazol-2-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1,3-thiazol-4-yl)-4H-1,2,4-triazol-3-yl)-1-methoxy-1-(5-methyl-2-pyrimidinyl)-2-propanesulfonamide;

(2S,3R)-N-(4-(2,6-dimethoxyphenyl)-5-(2-methoxy-4-pyrimidinyl)-4H-1,2,4-triazol-3-yl)-3-(5-fluoro-2-pyrimidinyl)-2-butanesulfonamide;

(1R,2S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-methoxy-2-propanesulfonamide;

(1S,2R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-methoxy-2-propanesulfonamide;

(2S,3R)-N-(4-(2,6-dimethoxyphenyl)-5-(1-ethyl-1H-pyrazol-3-yl)-4H-1,2,4-triazol-3-yl)-4,4,4-trifluoro-3-hydroxy-3-(5-methyl-2-pyrimidinyl)-2-butanesulfonamide;

(2S,3S)-N-(4-(2,6-dimethoxyphenyl)-5-(1-ethyl-1H-pyrazol-3-yl)-4H-1,2,4-triazol-3-yl)-4,4,4-trifluoro-3-hydroxy-3-(5-methyl-2-pyrimidinyl)-2-butanesulfonamide;

(2S,3R)-N-(4-(2,6-dimethoxyphenyl)-5-(2-methyl-1,3-thiazol-4-yl)-4H-1,2,4-triazol-3-yl)-3-(5-methyl-2-pyrimidinyl)-2-butanesulfonamide;

(2S,3R)-N-(5-(1-(difluoromethyl)-1H-pyrazol-3-yl)-4-(2,6-dimethoxyphenyl)-4H-1,2,4-triazol-3-yl)-3-(5-methyl-2-pyrimidinyl)-2-butanesulfonamide;

(1R,2S)-N-(5-(1-(difluoromethyl)-1H-pyrazol-3-yl)-4-(2,6-dimethoxyphenyl)-4H-1,2,4-triazol-3-yl)-1-ethoxy-1-(5-methyl-2-pyrimidinyl)-2-propanesulfonamide;

(1R,2S)-1-(5-chloro-2-pyrimidinyl)-N-(4-(2,6-dimethoxyphenyl)-5-(1-ethyl-1H-pyrazol-3-yl)-4H-1,2,4-triazol-3-yl)-1-methoxy-2-propanesulfonamide;

(1S,2R)-1-(5-chloro-2-pyrimidinyl)-N-(4-(2,6-dimethoxyphenyl)-5-(1-ethyl-1H-pyrazol-3-yl)-4H-1,2,4-triazol-3-yl)-1-methoxy-2-propanesulfonamide;

(1R,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-methoxy-2-propanesulfonamide;

(1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-methoxy-2-propanesulfonamide;

(2S,3R)-N-(4-(4,6-dimethoxy-5-pyrimidinyl)-5-(4-methyl-1,3-thiazol-2-yl)-4H-1,2,4-triazol-3-yl)-3-(5-methyl-2-pyrimidinyl)-2-butanesulfonamide;

(1R,2S)-N-(4-(2,6-dimethoxyphenyl)-5-(1-methyl-1H-pyrazol-3-yl)-4H-1,2,4-triazol-3-yl)-1-methoxy-1-(5-methyl-2-pyrazinyl)-2-propanesulfonamide;

(2R)-2-(2,4-difluorophenyl)-N-(4-(2,6-dimethoxyphenyl)-5-(1-methyl-1H-pyrazol-3-yl)-4H-1,2,4-triazol-3-yl)-2-hydroxyethanesulfonamide;

(2S)-2-(2,4-difluorophenyl)-N-(4-(2,6-dimethoxyphenyl)-5-(1-methyl-1H-pyrazol-3-yl)-4H-1,2,4-triazol-3-yl)-2-hydroxyethanesulfonamide;

(1S,2R)-N-(4-(2,6-dimethoxyphenyl)-5-(4-methyl-1,3-thiazol-2-yl)-4H-1,2,4-triazol-3-yl)-1-ethoxy-1-(5-methyl-2-pyrimidinyl)-2-propanesulfonamide;

(1R,2S)-N-(4-(2,6-dimethoxyphenyl)-5-(4-methyl-1,3-thiazol-2-yl)-4H-1,2,4-triazol-3-yl)-1-ethoxy-1-(5-methyl-2-pyrimidinyl)-2-propanesulfonamide;

(1R,2S)-N-(4-(2,6-dimethoxyphenyl)-5-(1-ethyl-1H-pyrazol-3-yl)-4H-1,2,4-triazol-3-yl)-1-(5-fluoro-2-pyrimidinyl)-1-methoxy-2-propanesulfonamide;

(1S,2R)-N-(4-(2,6-dimethoxyphenyl)-5-(1-methyl-1H-pyrazol-3-yl)-4H-1,2,4-triazol-3-yl)-1-ethoxy-1-(5-methyl-2-pyrimidinyl)-2-propanesulfonamide;

(1R,2S)-N-(4-(2,6-dimethoxyphenyl)-5-(1-methyl-1H-pyrazol-3-yl)-4H-1,2,4-triazol-3-yl)-1-ethoxy-1-(5-methyl-2-pyrimidinyl)-2-propanesulfonamide;

(1R,2S)-N-(4-(2,6-dimethoxyphenyl)-5-(1-methyl-1H-pyrazol-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(6-methoxy-2-pyrazinyl)-4H-1,2,4-triazol-3-yl)-1-methoxy-1-(5-methyl-2-pyrimidinyl)-2-propanesulfonamide;

(1S,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1S,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1R,2S)-N-(4-(2,6-dimethoxyphenyl)-5-(6-methoxy-2-pyrazinyl)-4H-1,2,4-triazol-3-yl)-1-methoxy-1-(5-methyl-2-pyrazinyl)-2-propanesulfonamide;

(1R,2S)-N-(4-(2,6-dimethoxyphenyl)-5-(1-ethyl-H-pyrazol-3-yl)-4H-1,2,4-triazol-3-yl)-1-methoxy-1-(5-methyl-2-pyrazinyl)-2-propanesulfonamide;

(2S,3R)-N-(4-(2,6-dimethoxyphenyl)-5-(1-methyl-1H-pyrazol-3-yl)-4H-1,2,4-triazol-3-yl)-3-(5-methyl-2-pyrimidinyl)-2-butanesulfonamide;

(2S,3R)-N-(4-(2,6-dimethoxyphenyl)-5-(6-methoxy-2-pyrazinyl)-4H-1,2,4-triazol-3-yl)-3-(5-methyl-2-pyrimidinyl)-2-butanesulfonamide;

(1R,2S)-N-(5-(4-cyclopropyl-1,3-thiazol-2-yl)-4-(4,6-dimethoxy-5-pyrimidinyl)-4H-1,2,4-triazol-3-yl)-1-methoxy-1-(5-methyl-2-pyrimidinyl)-2-propanesulfonamide;

(1R,2S)-N-(4-(4,6-dimethoxy-5-pyrimidinyl)-5-(2-methyl-1,3-thiazol-4-yl)-4H-1,2,4-triazol-3-yl)-1-methoxy-1-(5-methyl-2-pyrimidinyl)-2-propanesulfonamide;

(1R,2S)-1-(5-chloro-2-pyrimidinyl)-N-(4-(2,6-dimethoxyphenyl)-5-(5-methyl-1H-pyrazol-3-yl)-4H-1,2,4-triazol-3-yl)-1-methoxy-2-propanesulfonamide;

(1R,2S)-N-(4-(2,6-dimethoxyphenyl)-5-(1-methyl-1H-pyrazol-3-yl)-4H-1,2,4-triazol-3-yl)-1-ethoxy-1-(5-fluoro-2-pyrimidinyl)-2-propanesulfonamide;

(1R,2S)-1-(5-chloro-2-pyrimidinyl)-N-(4-(2,6-dimethoxyphenyl)-5-(5-methyl-1H-pyrazol-3-yl)-4H-1,2,4-triazol-3-yl)-1-ethoxy-2-propanesulfonamide;

(1R,2S)-1-(5-chloro-2-pyrimidinyl)-N-(4-(2,6-dimethoxyphenyl)-5-(1-ethyl-1H-pyrazol-3-yl)-4H-1,2,4-triazol-3-yl)-1-ethoxy-2-propanesulfonamide;

(1R,2S)-N-(4-(2,6-dimethoxyphenyl)-5-(5-methyl-1H-pyrazol-3-yl)-4H-1,2,4-triazol-3-yl)-1-(5-fluoro-2-pyrimidinyl)-1-methoxy-2-propanesulfonamide;

(1R,2S)-N-(5-(1-(difluoromethyl)-1H-pyrazol-3-yl)-4-(2,6-dimethoxyphenyl)-4H-1,2,4-triazol-3-yl)-1-methoxy-1-(5-methyl-2-pyrimidinyl)-2-propanesulfonamide;

(2S,3R)-N-(4-(2,6-dimethoxyphenyl)-5-(5-methyl-1H-pyrazol-3-yl)-4H-1,2,4-triazol-3-yl)-3-(5-fluoro-2-pyrimidinyl)-2-butanesulfonamide;

(2S,3R)-3-(5-fluoro-2-pyrimidinyl)-N-(4-(2-methoxyphenyl)-5-(1-methyl-1H-pyrazol-3-yl)-4H-1,2,4-triazol-3-yl)-2-butanesulfonamide;

(1R,2S)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide;

(1S,2R)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide;

(1R,2S)-N-(4'-(2,6-dimethoxyphenyl)-1-methyl-1H,4'H-3,3'-bi-1,2,4-triazol-5'-yl)-1-methoxy-1-(5-methyl-2-pyrimidinyl)-2-propanesulfonamide;

(1R,2S)-1-(5-chloro-2-pyridinyl)-N-(4-(2,6-dimethoxyphenyl)-5-(5-methyl-1H-pyrazol-3-yl)-4H-1,2,4-triazol-3-yl)-1-methoxy-2-propanesulfonamide;

(1S,2R)-1-(5-chloro-2-pyridinyl)-N-(4-(2,6-dimethoxyphenyl)-5-(5-methyl-1H-pyrazol-3-yl)-4H-1,2,4-triazol-3-yl)-1-methoxy-2-propanesulfonamide;

(1R,2S)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1S,2R)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(2S,3R)-N-(4-(2,6-dimethoxyphenyl)-5-(5-methyl-1H-pyrazol-3-yl)-4H-1,2,4-triazol-3-yl)-3-(5-methyl-2-pyrimidinyl)-2-butanesulfonamide;

(1R,2R)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide;

(1S,2S)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide;

(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methyl-1H-pyrazol-3-yl)-4H-1,2,4-triazol-3-yl)-1-hydroxy-1-(5-methyl-2-pyrimidinyl)-2-propanesulfonamide;

(1R,2S)-N-(4-(2,6-dimethoxyphenyl)-5-(5-methyl-1H-pyrazol-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methyl-1H-pyrazol-3-yl)-4H-1,2,4-triazol-3-yl)-1-hydroxy-1-(5-methyl-2-pyrimidinyl)-2-propanesulfonamide;

(1R,2S)-N-(4-(2,6-dimethoxyphenyl)-5-(5H-pyrrolo[2,3-b]pyrazin-2-yl)-4H-1,2,4-triazol-3-yl)-1-methoxy-1-(5-methyl-2-pyrimidinyl)-2-propanesulfonamide;

(2R,3S)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide;

(2S,3R)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide;

(2R,3S)-N-(4-(2,6-dimethoxyphenyl)-5-(1-methyl-1H-pyrazol-3-yl)-4H-1,2,4-triazol-3-yl)-3-(5-methyl-1-oxido-2-pyrazinyl)-2-butanesulfonamide;

(2S,3R)-N-(4-(2,6-dimethoxyphenyl)-5-(1-methyl-1H-pyrazol-3-yl)-4H-1,2,4-triazol-3-yl)-3-(5-methyl-1-oxido-2-pyrazinyl)-2-butanesulfonamide;

(1R,2S)-1-(5-chloro-2-pyrimidinyl)-N-(5-(1-(difluoromethyl)-1H-pyrazol-3-yl)-4-(2,6-dimethoxyphenyl)-4H-1,2,4-triazol-3-yl)-1-methoxy-2-propanesulfonamide;

(2S,3R)-N-(5-(5,6-dihydro-4H-pyrrolo[1,2-b]pyrazol-2-yl)-4-(2,6-dimethoxyphenyl)-4H-1,2,4-triazol-3-yl)-3-(5-fluoro-2-pyrimidinyl)-2-butanesulfonamide;

(2S,3R)-N-(4-(2,6-dimethoxyphenyl)-5-(6-methyl-2-pyrazinyl)-4H-1,2,4-triazol-3-yl)-3-(5-fluoro-2-pyrimidinyl)-2-butanesulfonamide;

(1R,2S)-1-(5-chloro-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-2-propanesulfonamide;

(2S,3R)-N-(4-(2,6-dimethoxyphenyl)-5-(1-methyl-1H-pyrazol-5-yl)-4H-1,2,4-triazol-3-yl)-3-(5-fluoro-2-pyrimidinyl)-2-butanesulfonamide;

(2S,3R)-N-(4-(2,6-dimethoxyphenyl)-5-(1-methyl-1H-pyrazol-4-yl)-4H-1,2,4-triazol-3-yl)-3-(5-fluoro-2-pyrimidinyl)-2-butanesulfonamide;

(1S,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide;

(1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide;

(1S,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide;

(1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide;

(1R,2S)-1-(5-cyano-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(6-methyl-2-pyrazinyl)-4H-1,2,4-triazol-3-yl)-1-methoxy-2-propanesulfonamide;

(1R,2S)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide;

(1S,2R)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide;

(2S,3R)-N-(4-(2,6-dimethoxyphenyl)-5-(1-methyl-1H-pyrazol-4-yl)-4H-1,2,4-triazol-3-yl)-3-(5-methyl-2-pyrimidinyl)-2-butanesulfonamide;

(2S,3R)-3-(5-chloro-2-pyrimidinyl)-N-(4-(4-methoxy-2-oxo-1,2-dihydro-3-pyridinyl)-5-(1-methyl-1H-pyrazol-3-yl)-4H-1,2,4-triazol-3-yl)-2-butanesulfonamide;

(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-1-(5-methyl-2-pyrazinyl)-2-propanesulfonamide;

(2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide;

(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-ethoxy-1-(5-methyl-2-pyrimidinyl)-2-propanesulfonamide;

(1R,2S)-N-(5-(1-(difluoromethyl)-1H-pyrazol-3-yl)-4-(2,6-dimethoxyphenyl)-4H-1,2,4-triazol-3-yl)-1-hydroxy-1-(5-methyl-2-pyrimidinyl)-2-propanesulfonamide;

(2S,3R)-N-(5-(5,6-dihydro-4H-pyrrolo[1,2-b]pyrazol-2-yl)-4-(2,6-dimethoxyphenyl)-4H-1,2,4-triazol-3-yl)-3-(5-methyl-2-pyrimidinyl)-2-butanesulfonamide;

(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-hydroxy-1-(5-methyl-2-pyrimidinyl)-2-propanesulfonamide;

(2S,3R)-N-(4-(2,6-dimethoxyphenyl)-5-(1-methyl-H-pyrazol-3-yl)-4H-1,2,4-triazol-3-yl)-3-(5-methoxy-2-pyrazinyl)-2-butanesulfonamide;

(2S,3R)-3-(5-chloro-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-2-butanesulfonamide;

(2S,3R)-3-(5-chloro-2-pyrimidinyl)-N-(5-(1-(difluoromethyl)-1H-pyrazol-3-yl)-4-(2,6-dimethoxyphenyl)-4H-1,2,4-triazol-3-yl)-2-butanesulfonamide;

(1R,2S)-N-(5-(1-(difluoromethyl)-1H-pyrazol-3-yl)-4-(2,6-dimethoxyphenyl)-4H-1,2,4-triazol-3-yl)-1-methoxy-1-(5-methyl-2-pyrazinyl)-2-propanesulfonamide;

(2S,3R)-3-(5-cyano-2-pyrimidinyl)-N-(5-(1-(difluoromethyl)-1H-pyrazol-3-yl)-4-(2,6-dimethoxyphenyl)-4H-1,2,4-triazol-3-yl)-2-butanesulfonamide;

(2S,3R)-3-(5-cyano-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-2-butanesulfonamide;

(1R,2S)-1-(5-chloro-2-pyridinyl)-N-(4-(4,6-dimethoxy-5-pyrimidinyl)-5-(1-methyl-1H-pyrazol-3-yl)-4H-1,2,4-triazol-3-yl)-1-methoxy-2-propanesulfonamide;

(2R,3S)-3-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-2-butanesulfonamide;

(1S,2S)-N-(4-(2,6-dimethoxyphenyl)-5-(1-methyl-1H-pyrazol-3-yl)-4H-1,2,4-triazol-3-yl)-1-(1-methylethoxy)-1-(5-methyl-2-pyrimidinyl)-2-propanesulfonamide;

(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyrazinyl)-2-butanesulfonamide;

(2S,3R)-N-(4-(4-methoxy-6-oxo-1,6-dihydro-5-pyrimidinyl)-5-(1-methyl-1H-pyrazol-3-yl)-4H-1,2,4-triazol-3-yl)-3-(5-methoxy-2-pyrazinyl)-2-butanesulfonamide;

(2S,3R)-N-(4-(2,6-dimethoxyphenyl)-5-(1-methyl-1H-pyrazol-3-yl)-4H-1,2,4-triazol-3-yl)-3-(5-methoxy-2-pyrimidinyl)-2-butanesulfonamide;

(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyrimidinyl)-2-butanesulfonamide;

(1S,2R)-1-(5-chloropyridin-2-yl)-N-(4-(2,6-dimethoxyphenyl)-5-(5-methyl-1H-pyrazol-3-yl)-4H-1,2,4-triazol-3-yl)-1-methoxypropane-2-sulfonamide;

(1R,2S)-1-(5-chloropyridin-2-yl)-N-(4-(2,6-dimethoxyphenyl)-5-(5-methyl-1H-pyrazol-3-yl)-4H-1,2,4-triazol-3-yl)-1-methoxypropane-2-sulfonamide;

(2S,3R)-N-(4-(2,6-difluorophenyl)-5-(1-methyl-1H-pyrazol-3-yl)-4H-1,2,4-triazol-3-yl)-3-(5-methyl-2-pyrimidinyl)-2-butanesulfonamide;

(3R,5S)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide;

(3S,5R)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide;

(2S,3R)-N-(5-(1,2-benzisoxazol-3-yl)-4-(2,6-dimethoxyphenyl)-4H-1,2,4-triazol-3-yl)-3-(5-methyl-2-pyrimidinyl)-2-butanesulfonamide;

(1S,2S)-N-(4-(2,6-difluorophenyl)-5-(1-methyl-1H-pyrazol-3-yl)-4H-1,2,4-triazol-3-yl)-1-(1-methylethoxy)-1-(5-methyl-2-pyrimidinyl)-2-propanesulfonamide;

(2S,3R)-3-(5-chloro-2-pyrimidinyl)-N-(4-(2,6-difluorophenyl)-5-(1-methyl-1H-pyrazol-3-yl)-4H-1,2,4-triazol-3-yl)-2-butanesulfonamide;

(1R,2S)-1-(5-chloro-2-pyrimidinyl)-N-(4-(2,6-difluorophenyl)-5-(1-methyl-1H-pyrazol-3-yl)-4H-1,2,4-triazol-3-yl)-1-methoxy-2-propanesulfonamide;

(2S,3R)-N-(4-(2,6-difluorophenyl)-5-(1-methyl-1H-pyrazol-3-yl)-4H-1,2,4-triazol-3-yl)-3-(5-methoxy-2-pyrazinyl)-2-butanesulfonamide;

(2S,3R)-N-(4-(2,6-difluorophenyl)-5-(1-methyl-1H-pyrazol-3-yl)-4H-1,2,4-triazol-3-yl)-3-(5-methyl-2-pyrazinyl)-2-butanesulfonamide;

(1R,2S)-N-(4-(2,6-difluorophenyl)-5-(1-methyl-1H-pyrazol-3-yl)-4H-1,2,4-triazol-3-yl)-1-methoxy-1-(5-methyl-2-pyrazinyl)-2-propanesulfonamide;

(1R,2S)-N-(4-(2,6-difluorophenyl)-5-(1-methyl-1H-pyrazol-3-yl)-4H-1,2,4-triazol-3-yl)-1-methoxy-1-(5-methyl-2-pyrimidinyl)-2-propanesulfonamide;

(2R,3S)-N-(4-(2,6-dimethoxyphenyl)-5-(1-methyl-1H-pyrazol-3-yl)-4H-1,2,4-triazol-3-yl)-3-(5-methoxy-2-pyrazinyl)-2-butanesulfonamide;

(1R,2S)-N-(5-(1,2-benzisoxazol-3-yl)-4-(2,6-dimethoxyphenyl)-4H-1,2,4-triazol-3-yl)-1-(5-chloro-2-pyrimidinyl)-1-methoxy-2-propanesulfonamide;

(2S,3R)-N-(5-(1,2-benzisoxazol-3-yl)-4-(tetrahydro-2H-pyran-4-yl)-4H-1,2,4-triazol-3-yl)-3-(5-methyl-2-pyrimidinyl)-2-butanesulfonamide;

(1R,2S)-N-(5-(1,2-benzisoxazol-3-yl)-4-(2,6-dimethoxyphenyl)-4H-1,2,4-triazol-3-yl)-1-methoxy-1-(5-methyl-2-pyrimidinyl)-2-propanesulfonamide;

(2S,3R)-N-(5-(1,2-benzisoxazol-3-yl)-4-(4,6-dimethoxy-5-pyrimidinyl)-4H-1,2,4-triazol-3-yl)-3-(5-methyl-2-pyrimidinyl)-2-butanesulfonamide;

(1R,2S)-N-(4-(2,6-dimethoxyphenyl)-5-(3-isoxazolyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(2-methylimidazo[1,2-a]pyridin-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1H-indazol-3-yl)-4H-1,2,4-triazol-3-yl)-1-methoxy-1-(5-methyl-2-pyrimidinyl)-2-propanesulfonamide;

(1R,2S)-N-(5-(5-chloro-1H-indazol-3-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1H-pyrrolo[2,3-b]pyridin-3-yl)-4H-1,2,4-triazol-3-yl)-1-methoxy-1-(5-methyl-2-pyrimidinyl)-2-propanesulfonamide;

(1R,2S)-N-(5-(5-bromo-1,2-benzisoxazol-3-yl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-pyrazolo[1,5-a]pyridin-3-yl-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methylpyrazolo[1,5-a]pyridin-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(4-quinolinyl)-4H-1,2,4-triazol-3-yl)-1-methoxy-1-(5-methyl-2-pyrimidinyl)-2-propanesulfonamide;

(1R,2S)-1-(5-chloro-2-pyrimidinyl)-N-(4-(2,6-dimethoxyphenyl)-5-(5-methyl-1H-indazol-3-yl)-4H-1,2,4-triazol-3-yl)-1-methoxy-2-propanesulfonamide;

(1R,2S)-1-(5-chloro-2-pyrimidinyl)-N-(4-(2,6-dimethoxy-phenyl)-5-(1H-pyrrolo[2,3-b]pyridin-3-yl)-4H-1,2,4-triazol-3-yl)-1-methoxy-2-propanesulfonamide;

(1R,2S)-N-(5-(1,2-benzisoxazol-3-yl)-4-(4,6-dimethoxy-5-pyrimidinyl)-4H-1,2,4-triazol-3-yl)-1-(5-chloro-2-pyrimidinyl)-1-methoxy-2-propanesulfonamide;

(1R,2S)-1-(5-chloro-2-pyrimidinyl)-N-(4-(2,6-dimethoxy-phenyl)-5-(1H-indazol-3-yl)-4H-1,2,4-triazol-3-yl)-1-methoxy-2-propanesulfonamide;

(1R,2S)-N-(5-(5-chloro-1H-indazol-3-yl)-4-(2,6-dimethoxyphenyl)-4H-1,2,4-triazol-3-yl)-1-(5-chloro-2-pyrimidinyl)-1-methoxy-2-propanesulfonamide;

(1R,2S)-1-(5-chloro-2-pyrimidinyl)-N-(4-(2,6-dimethoxy-phenyl)-5-pyrazolo[1,5-a]pyridin-3-yl-4H-1,2,4-triazol-3-yl)-1-methoxy-2-propanesulfonamide;

(1R,2S)-N-(5-(5-cyclopropyl-3-isoxazolyl)-4-(2,6-dimethoxyphenyl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-methyl-3-isoxazolyl)-4H-1,2,4-triazol-3-yl)-1-methoxy-1-(5-methyl-2-pyrimidinyl)-2-propanesulfonamide;

(2S,3R)-3-(5-chloro-2-pyrimidinyl)-N-(4-(4,6-dimethoxy-5-pyrimidinyl)-5-(1H-indazol-3-yl)-4H-1,2,4-triazol-3-yl)-2-butanesulfonamide;

(2S,3R)-N-(4-(4,6-dimethoxy-5-pyrimidinyl)-5-(1H-indazol-3-yl)-4H-1,2,4-triazol-3-yl)-3-(5-methyl-2-pyrimidinyl)-2-butanesulfonamide;

(1R,2S)-1-(5-chloro-2-pyrimidinyl)-N-(4-(2,6-dimethoxy-phenyl)-5-(2-methylimidazo[1,2-a]pyridin-3-yl)-4H-1,2,4-triazol-3-yl)-1-methoxy-2-propanesulfonamide;

(2S,3R)-3-(5-chloro-2-pyrimidinyl)-N-(4-(2,6-dimethoxy-phenyl)-5-(1H-indazol-3-yl)-4H-1,2,4-triazol-3-yl)-2-butanesulfonamide;

(2R,3S)-3-(5-chloro-2-pyrimidinyl)-N-(4-(2,6-dimethoxy-phenyl)-5-(1H-indazol-3-yl)-4H-1,2,4-triazol-3-yl)-2-butanesulfonamide;

(2R,3S)-N-(4-(2,6-dimethoxyphenyl)-5-(1H-indazol-3-yl)-4H-1,2,4-triazol-3-yl)-3-(5-methyl-2-pyrimidinyl)-2-butanesulfonamide;

(2S,3R)-3-(5-chloro-2-pyrimidinyl)-N-(4-(2,6-dimethoxy-phenyl)-5-(1,5-dimethyl-1H-indazol-3-yl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-(1,5-dimethyl-1H-indazol-3-yl)-4H-1,2,4-triazol-3-yl)-2-butanesulfonamide;

(1R,2S)-1-(5-chloro-2-pyrimidinyl)-N-(4-(2,6-dimethoxy-phenyl)-5-(5H-pyrrolo[3,2-d]pyrimidin-4-yl)-4H-1,2,4-triazol-3-yl)-1-methoxy-2-propanesulfonamide;

(1R,2S)-N-(4-(2,6-dimethoxyphenyl)-5-(5H-pyrrolo[3,2-d]pyrimidin-4-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(1-methyl-1H-indazol-3-yl)-4H-1,2,4-triazol-3-yl)-1-methoxy-1-(5-methyl-2-pyrimidinyl)-2-propanesulfonamide;

(1R,2S)-N-(4-(2,6-dimethoxyphenyl)-5-(5-fluoro-1H-indazol-3-yl)-4H-1,2,4-triazol-3-yl)-1-methoxy-1-(5-methyl-2-pyrimidinyl)-2-propanesulfonamide;

(2S,3R)-3-(5-chloro-2-pyrimidinyl)-N-(4-(2,6-dimethoxy-phenyl)-5-(4,5,6,7-tetrahydro-1H-indazol-3-yl)-4H-1,2,4-triazol-3-yl)-2-butanesulfonamide;

(1R,2S)-1-(5-chloro-2-pyrimidinyl)-N-(4-(4,6-dimethoxy-5-pyrimidinyl)-5-pyrazolo[1,5-a]pyridin-3-yl-4H-1,2,4-triazol-3-yl)-1-methoxy-2-propanesulfonamide;

(2S,3R)-3-(5-chloro-2-pyrimidinyl)-N-(4-(4,6-dimethoxy-5-pyrimidinyl)-5-(pyrazolo[1,5-a]pyridin-3-yl)-4H-1,2,4-triazol-3-yl)-2-butanesulfonamide;

(2S,3R)-3-(5-chloro-2-pyrimidinyl)-N-(4-(2,6-dimethoxy-phenyl)-5-(4,5,6,7-tetrahydro-1,2-benzoxazol-3-yl)-4H-1,2,4-triazol-3-yl)-2-butanesulfonamide;

(2S,3R)-3-(5-chloro-2-pyrimidinyl)-N-(4-((1r,2R,6S)-2,6-dimethoxycyclohexyl)-5-(pyrazolo[1,5-a]pyridin-3-yl)-4H-1,2,4-triazol-3-yl)-2-butanesulfonamide;

(2R,3S)-3-(5-chloro-2-pyrimidinyl)-N-(4-(2,6-dimethoxy-phenyl)-5-(1-methyl-1H-pyrazol-3-yl)-4H-1,2,4-triazol-3-yl)-2-butanesulfonamide;

(1R,2S)-N-(5-(5,6-dihydro-4H-pyrrolo[1,2-b]pyrazol-3-yl)-4-(2,6-dimethoxyphenyl)-4H-1,2,4-triazol-3-yl)-1-methoxy-1-(5-methyl-2-pyrimidinyl)-2-propanesulfonamide;

(2S,3R)-3-(5-chloro-2-pyrimidinyl)-N-(5-(5,6-dihydro-4H-pyrrolo[1,2-b]pyrazol-3-yl)-4-(2,6-dimethoxyphenyl)-4H-1,2,4-triazol-3-yl)-2-butanesulfonamide;

(1S,2S)-N-(5-(5,6-dihydro-4H-pyrrolo[1,2-b]pyrazol-3-yl)-4-(2,6-dimethoxyphenyl)-4H-1,2,4-triazol-3-yl)-1-(5-methyl-2-pyrimidinyl)-1-(2-propanyloxy)-2-propanesulfonamide;

(1S,2S)-1-(5-chloro-2-pyrimidinyl)-N-(5-(5,6-dihydro-4H-pyrrolo[1,2-b]pyrazol-3-yl)-4-(2,6-dimethoxyphenyl)-4H-1,2,4-triazol-3-yl)-1-(2-propanyloxy)-2-propanesulfonamide;

(2S,3R)-3-(5-chloro-2-pyrimidinyl)-N-(4-(1,3-dimethoxy-2-propanyl)-5-(1,5-dimethyl-1H-indazol-3-yl)-4H-1,2,4-triazol-3-yl)-2-butanesulfonamide;

(2S,3R)-3-(5-chloro-2-pyrimidinyl)-N-(4-(1,3-dimethoxy-2-propanyl)-5-(1-methyl-1H-indazol-3-yl)-4H-1,2,4-triazol-3-yl)-2-butanesulfonamide;

(1R,2S)-1-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclopropyl)-5-(1-methyl-1H-pyrazol-3-yl)-4H-1,2,4-triazol-3-yl)-2-propanesulfonamide;

(2S,3R)-N-(4-(1,3-dimethoxy-2-propanyl)-5-(1-methyl-H-pyrazol-3-yl)-4H-1,2,4-triazol-3-yl)-3-(5-methyl-2-pyrazinyl)-2-butanesulfonamide;

(2S,3R)-N-(4-(1,3-dimethoxy-2-propanyl)-5-(1-methyl-H-pyrazol-3-yl)-4H-1,2,4-triazol-3-yl)-3-(5-methoxy-2-pyrazinyl)-2-butanesulfonamide;

(2S,3R)-N-(4-(1-(methoxymethyl)cyclopropyl)-5-(1-methyl-1H-pyrazol-3-yl)-4H-1,2,4-triazol-3-yl)-3-(5-methoxy-2-pyrazinyl)-2-butanesulfonamide;

(1R,2S)-N-(4-(4,6-dimethoxy-5-pyrimidinyl)-5-(1-methyl-1H-pyrazol-3-yl)-4H-1,2,4-triazol-3-yl)-1-methoxy-1-(5-methoxy-2-pyridinyl)-2-propanesulfonamide;

(1S,2S)-1-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-1-(1-methylethoxy)-2-propanesulfonamide;

(2R,3S)-N-(4-(2,6-dimethoxyphenyl)-5-(1-methyl-1H-pyrazol-3-yl)-4H-1,2,4-triazol-3-yl)-3-(5-methoxy-2-pyrimidinyl)-2-butanesulfonamide;

(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyridinyl)-2-butanesulfonamide;

(2S,3R)-N-(4-(2,6-dimethoxyphenyl)-5-(1-methyl-1H-pyrazol-3-yl)-4H-1,2,4-triazol-3-yl)-3-(5-methoxy-2-pyridinyl)-2-butanesulfonamide;

(1R,2S)-N-(4-(4,6-dimethoxy-5-pyrimidinyl)-5-(1-methyl-1H-pyrazol-3-yl)-4H-1,2,4-triazol-3-yl)-1-methoxy-1-(5-methoxy-2-pyrazinyl)-2-propanesulfonamide;

(1S,2S)-N-(4-(4,6-dimethoxy-5-pyrimidinyl)-5-(1-methyl-1H-pyrazol-3-yl)-4H-1,2,4-triazol-3-yl)-1-(5-methyl-2-pyrazinyl)-1-(2-propanyloxy)-2-propanesulfonamide;

(1S,2S)-N-(4-(1-(methoxymethyl)cyclopropyl)-5-(1-methyl-H-pyrazol-3-yl)-4H-1,2,4-triazol-3-yl)-1-(5-methyl-2-pyrimidinyl)-1-(2-propanyloxy)-2-propanesulfonamide; or (1R,2S)-1-(5-chloro-2-pyrimidinyl)-N-(4-(1,3-dimethoxy-2-propanyl)-5-(1-methyl-1H-pyrazol-3-yl)-4H-1,2,4-triazol-3-yl)-1-methoxy-2-propanesulfonamide; or the pharmaceutically acceptable salt thereof, the tautomer thereof, the pharmaceutically acceptable salt of the tautomer, the stereoisomer of any of the foregoing, or the mixture thereof. In some such embodiments, the compound may be any one of these presented above. In some such embodiments, the embodiment provides any of the compounds shown above or a pharmaceutically acceptable salt thereof. In still other such embodiments, the embodiment provides any of the compounds shown above, or a pharmaceutically acceptable salt thereof, or a mixture thereof.

62. The compound of claim 1, wherein the compound is selected from

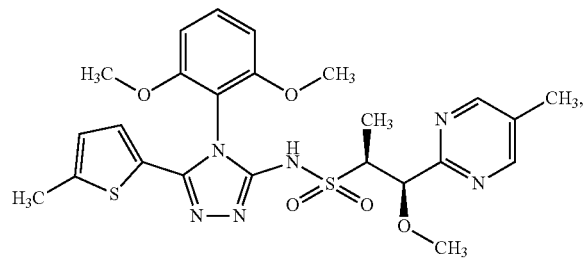

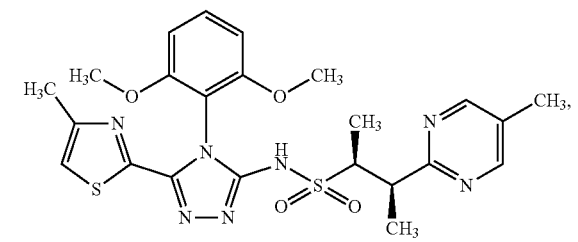

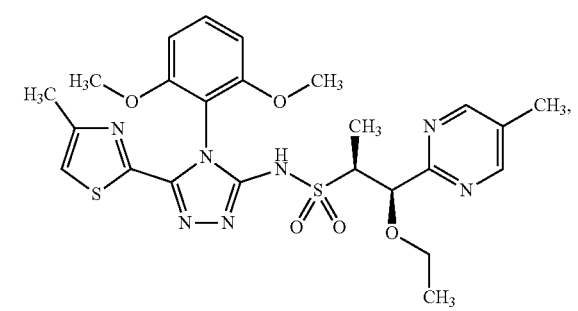

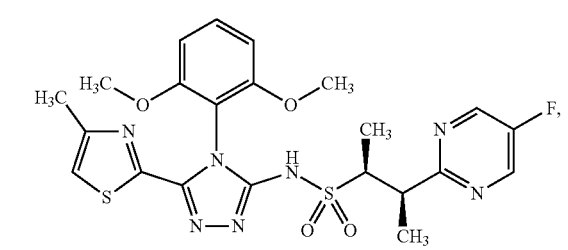

-continued

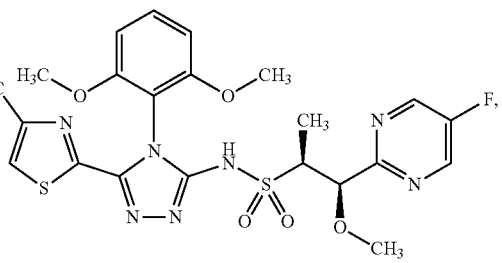

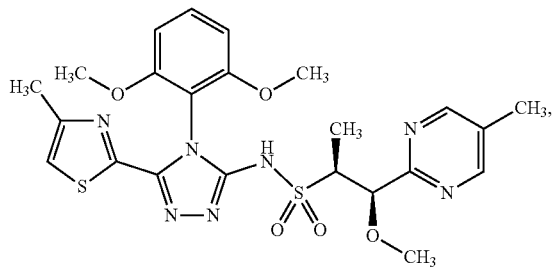

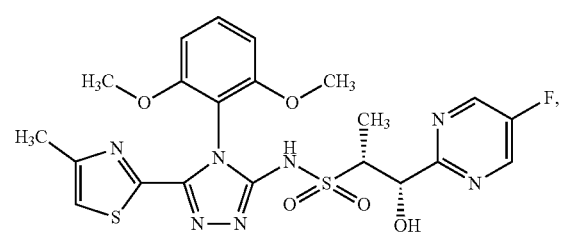

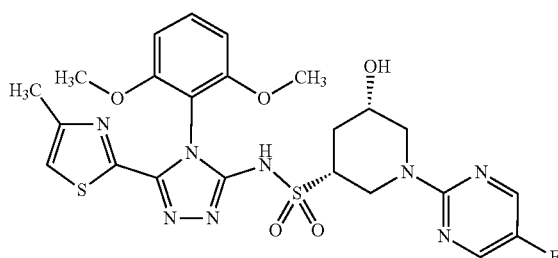

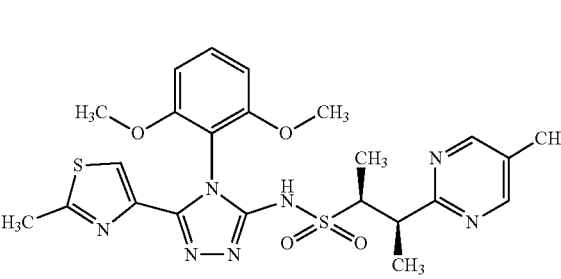

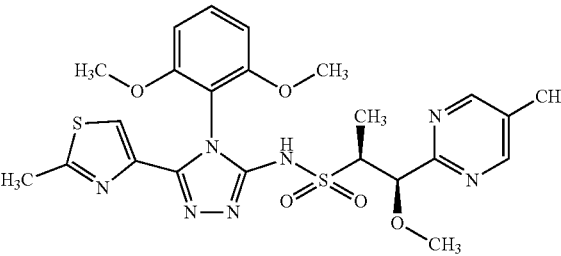

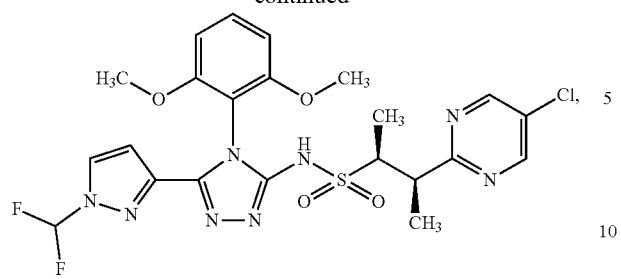
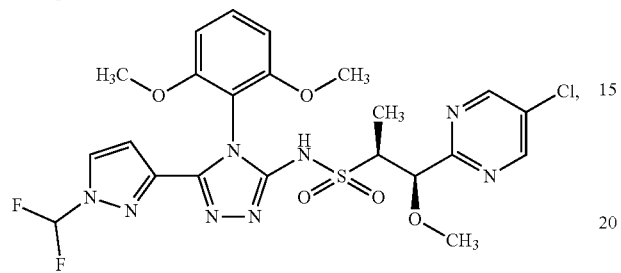
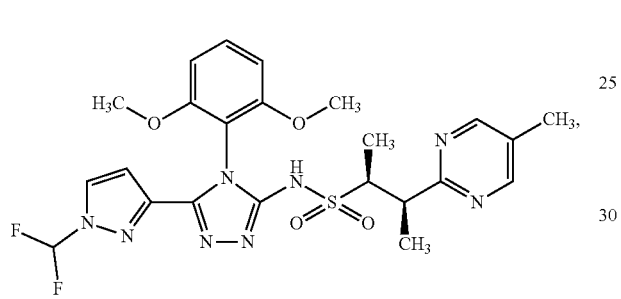
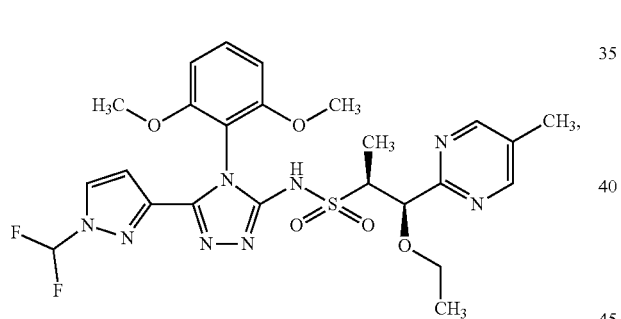
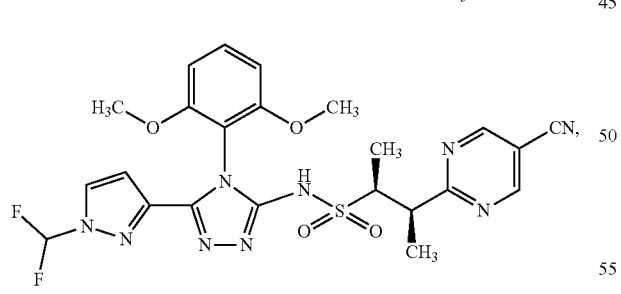
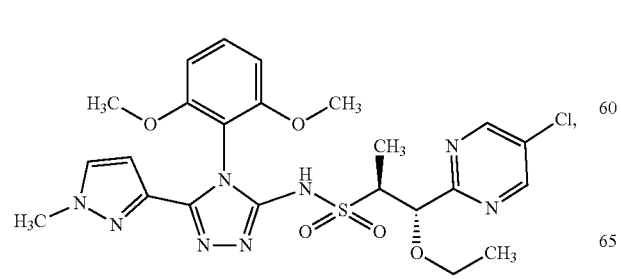
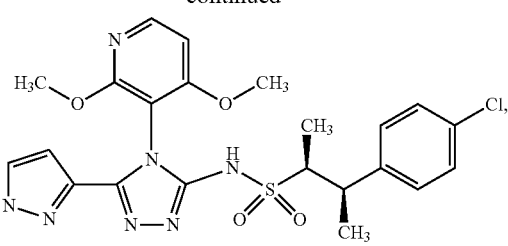
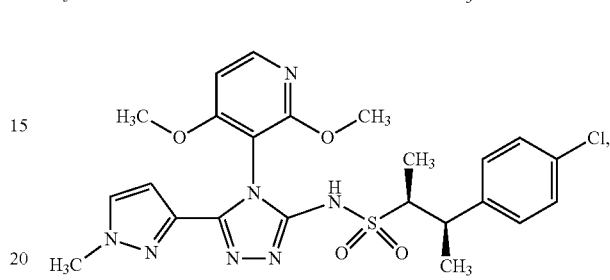
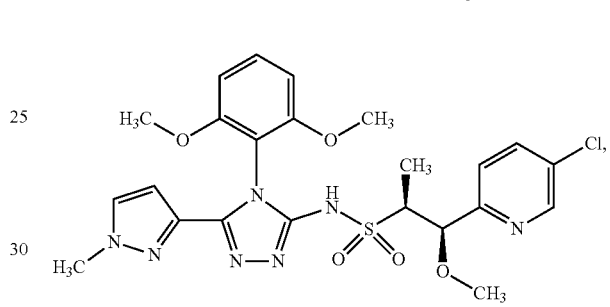
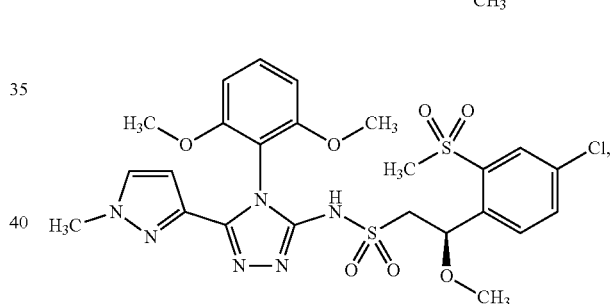
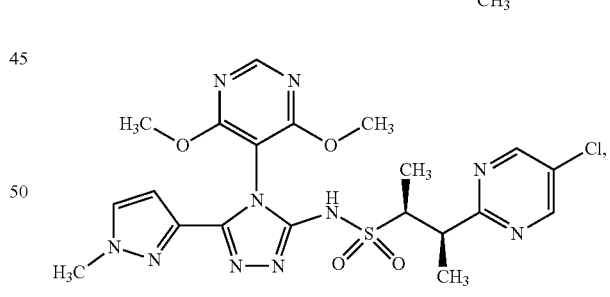
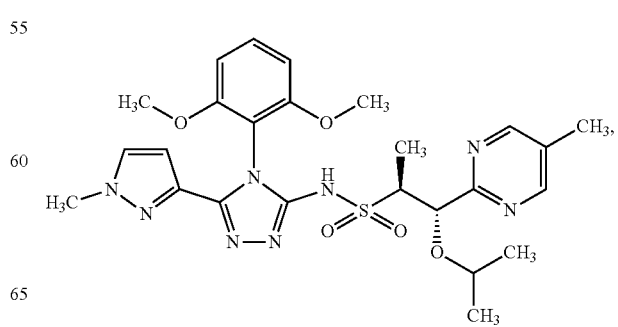

-continued
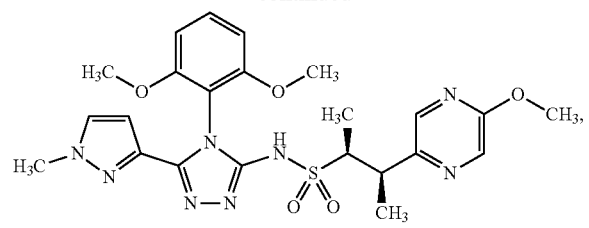
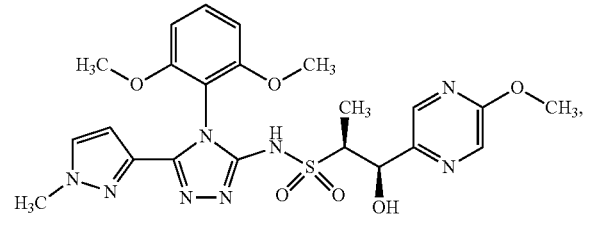
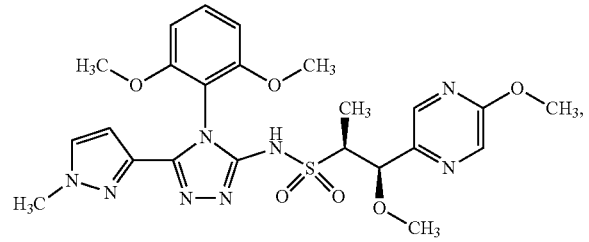
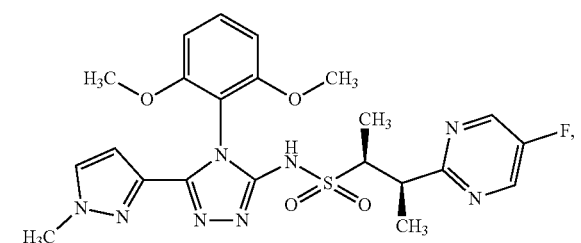
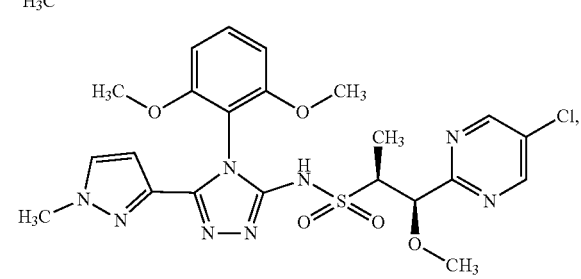
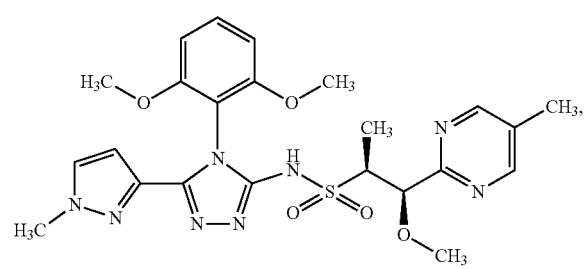
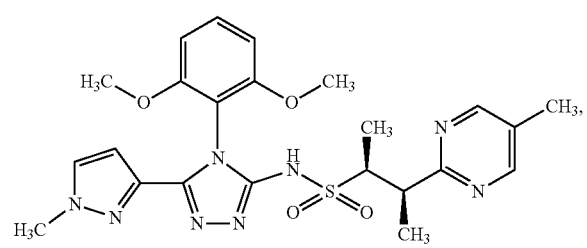
-continued
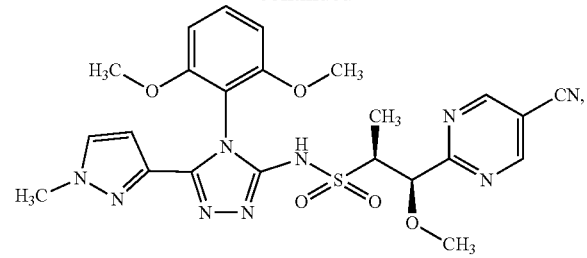
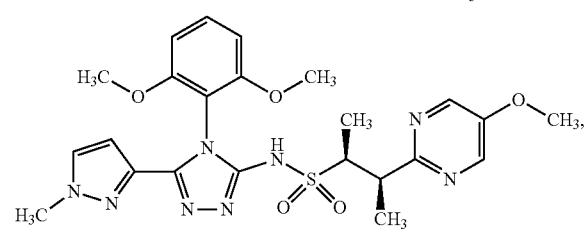
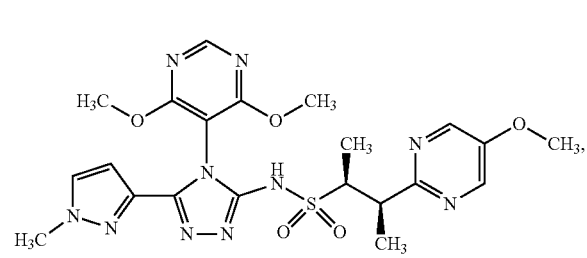
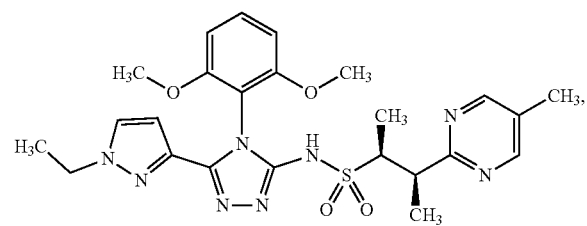
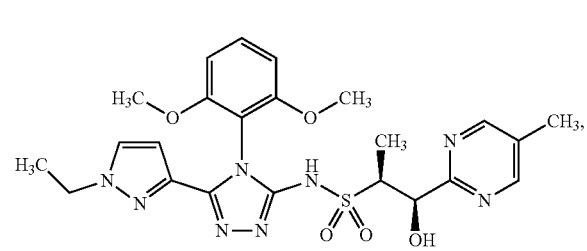
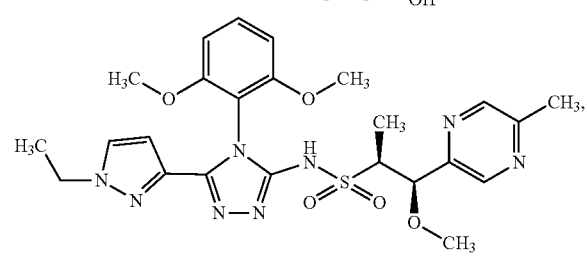
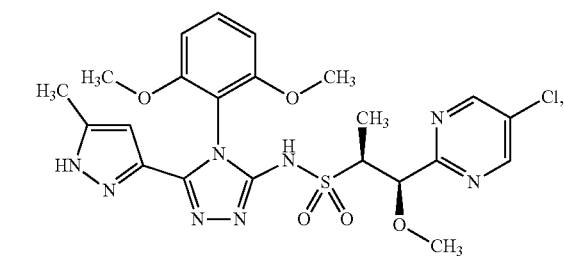

-continued

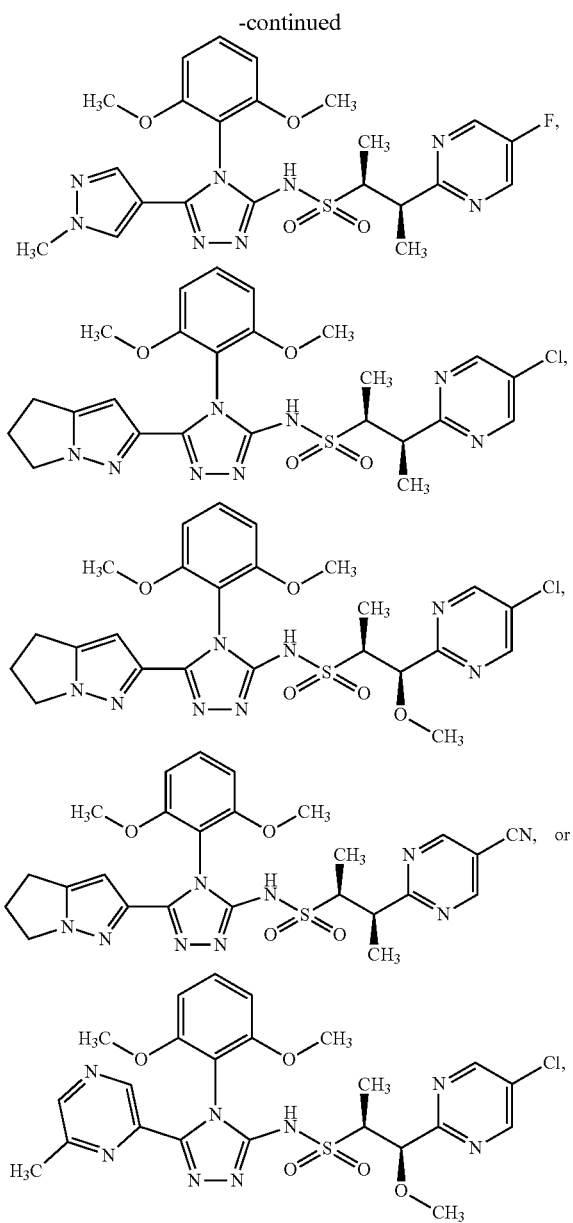

or the pharmaceutically acceptable salt thereof, the tautomer thereof, the pharmaceutically acceptable salt of the tautomer, or the mixture thereof. In some such embodiments, the compound may be any one of these presented above. In some such embodiments, the embodiment provides any of the compounds shown above or a pharmaceutically acceptable salt thereof. In still other such embodiments, the embodiment provides any of the compounds shown above, or a pharmaceutically acceptable salt thereof, or a mixture thereof.

62. The compound of claim 1, wherein the compound is selected from (1R,2S)-1-(5-chloro-2-pyrimidinyl)-N-(4-cyclopropyl-5-(5,6-dihydro-4H-pyrrolo[1,2-b]pyrazol-3-yl)-4H-1,2,4-triazol-3-yl)-1-methoxy-2-propanesulfonamide;

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-fluoro-2-pyrimidinyl)-2-butanesulfonamide;

(2S,3R)-N-(5-(5,6-dihydro-4H-pyrrolo[1,2-b]pyrazol-3-yl)-4-(4,6-dimethoxy-5-pyrimidinyl)-4H-1,2,4-triazol-3-yl)-3-(5-fluoro-2-pyrimidinyl)-2-butanesulfonamide;

(1R,2S)-1-(5-chloro-2-pyrimidinyl)-N-(5-(5,6-dihydro-4H-pyrrolo[1,2-b]pyrazol-3-yl)-4-(1,3-dimethoxy-2-propanyl)-4H-1,2,4-triazol-3-yl)-1-methoxy-2-propanesulfonamide;

(1S,2S)-N-(5-(5,6-dihydro-4H-pyrrolo[1,2-b]pyrazol-3-yl)-4-(2,6-dimethoxyphenyl)-4H-1,2,4-triazol-3-yl)-1-(5-fluoro-2-pyrimidinyl)-1-(2-propanyloxy)-2-propanesulfonamide;

(2S,3R)-N-(4-(2,6-difluorophenyl)-5-(5,6-dihydro-4H-pyrrolo[1,2-b]pyrazol-3-yl)-4H-1,2,4-triazol-3-yl)-3-(5-methyl-2-pyrimidinyl)-2-butanesulfonamide;

(1S,2S)-N-(4-(2,6-difluorophenyl)-5-(5,6-dihydro-4H-pyrrolo[1,2-b]pyrazol-3-yl)-4H-1,2,4-triazol-3-yl)-1-(5-methyl-2-pyrazinyl)-1-(2-propanyloxy)-2-propanesulfonamide;

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methoxy-2-pyrimidinyl)-2-butanesulfonamide;

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methoxy-2-pyrazinyl)-2-butanesulfonamide;

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methyl-2-pyrimidinyl)-2-butanesulfonamide;

(1R,2S)-1-(5-chloro-2-pyrimidinyl)-N-(5-(5,6-dihydro-4H-pyrrolo[1,2-b]pyrazol-3-yl)-4-(2,6-dimethoxyphenyl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclobutyl)-5-(1,4,5,6-tetrahydrocyclopenta[c]pyrazol-3-yl)-4H-1,2,4-triazol-3-yl)-2-propanesulfonamide;

(1R,2S)-1-(5-chloro-2-pyrimidinyl)-1-methoxy-N-(4-(1-methylcyclopropyl)-5-(1,4,5,6-tetrahydrocyclopenta[c]pyrazol-3-yl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(4,5,6,7-tetrahydro-1H-indazol-3-yl)-4H-1,2,4-triazol-3-yl)-2-propanesulfonamide;

(1R,2S)-1-(5-chloro-2-pyrimidinyl)-1-methoxy-N-(4-(1-methylcyclobutyl)-5-(1,4,5,6-tetrahydrocyclopenta[c]pyrazol-3-yl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(5-methyl-1H-indazol-3-yl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(1-methyl-1H-indazol-3-yl)-4H-1,2,4-triazol-3-yl)-2-propanesulfonamide;

(1R,2S)-1-(5-chloro-2-pyrimidinyl)-N-(5-(1H-indazol-3-yl)-4-(1-(methoxymethyl)cyclopropyl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(5-methyl-1,2-oxazol-3-yl)-4H-1,2,4-triazol-3-yl)-1-methoxy-2-propanesulfonamide;

(1S,2S)-N-(4-(2,6-dimethoxyphenyl)-5-(5-methyl-1,2-oxazol-3-yl)-4H-1,2,4-triazol-3-yl)-1-(5-methyl-2-pyrazinyl)-1-(2-propanyloxy)-2-propanesulfonamide;

(2S,3R)-3-(5-chloro-2-pyrimidinyl)-N-(4-(2,6-dimethoxyphenyl)-5-(5-methyl-1,2-oxazol-3-yl)-4H-1,2,4-triazol-3-yl)-2-butanesulfonamide;

(1R,2S)-1-(5-chloro-2-pyrimidinyl)-N-(4-(2,6-dimethoxyphenyl)-5-(1,5-dimethyl-1H-pyrazol-4-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(1-methyl-5-(2-propanyl)-1H-pyrazol-4-yl)-4H-1,2,4-triazol-3-yl)-1-methoxy-2-propanesulfonamide;

(1R,2S)-N-(5-(1,2-benzoxazol-3-yl)-4-(1-(methoxymethyl)cyclopropyl)-4H-1,2,4-triazol-3-yl)-1-(5-chloro-2-pyrimidinyl)-1-methoxy-2-propanesulfonamide;

(1R,2S)-N-(5-(1,2-benzoxazol-3-yl)-4-cyclopropyl-4H-1,2,4-triazol-3-yl)-1-(5-chloro-2-pyrimidinyl)-1-methoxy-2-propanesulfonamide;

(1R,2S)-1-(5-chloro-2-pyrimidinyl)-N-(4-cyclopropyl-5-(pyrazolo[1,5-a]pyridin-3-yl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclobutyl)-5-(pyrazolo[1,5-a]pyridin-3-yl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(pyrazolo[1,5-a]pyridin-3-yl)-4H-1,2,4-triazol-3-yl)-2-propanesulfonamide;

(1R,2S)-N-(5-(1,2-benzoxazol-3-yl)-4-(2-propanyl)-4H-1,2,4-triazol-3-yl)-1-(5-chloro-2-pyrimidinyl)-1-methoxy-2-propanesulfonamide;

(1R,2S)-1-(5-chloro-2-pyrimidinyl)-1-methoxy-N-(5-(1-methyl-4,5,6,7-tetrahydro-1H-indazol-3-yl)-4-(2-propanyl)-4H-1,2,4-triazol-3-yl)-2-propanesulfonamide;

(1R,2S)-1-(5-chloro-2-pyrimidinyl)-1-methoxy-N-(4-(1-(methoxymethyl)cyclopropyl)-5-(1-methyl-4,5,6,7-tetrahydro-1H-indazol-3-yl)-4H-1,2,4-triazol-3-yl)-2-propanesulfonamide;

(1R,2S)-1-(5-chloro-2-pyrimidinyl)-N-(4-cyclopropyl-5-(1-methyl-4,5,6,7-tetrahydro-1H-indazol-3-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(4,5-dimethyl-1,2-oxazol-3-yl)-4H-1,2,4-triazol-3-yl)-1-methoxy-2-propanesulfonamide;

(1R,2S)-N-(4-(2,6-dimethoxyphenyl)-5-(4,5-dimethyl-1,2-oxazol-3-yl)-4H-1,2,4-triazol-3-yl)-1-methoxy-1-(5-methyl-2-pyrimidinyl)-2-propanesulfonamide;

(1S,2S)-N-(4-(2,6-dimethoxyphenyl)-5-(4,5-dimethyl-1,2-oxazol-3-yl)-4H-1,2,4-triazol-3-yl)-1-(5-methyl-2-pyrimidinyl)-1-(2-propanyloxy)-2-propanesulfonamide;

(1R,2S)-1-(5-chloro-2-pyrimidinyl)-1-methoxy-N-(4-(1-(methoxymethyl)cyclobutyl)-5-(1-methyl-4,5,6,7-tetrahydro-1H-indazol-3-yl)-4H-1,2,4-triazol-3-yl)-2-propanesulfonamide;

(1R,2S)-1-(5-chloro-2-pyrimidinyl)-N-(4-(2,6-dimethoxyphenyl)-5-(5-ethyl-4-methyl-1,2-oxazol-3-yl)-4H-1,2,4-triazol-3-yl)-1-methoxy-2-propanesulfonamide;

(1R,2S)-1-(5-chloro-2-pyrimidinyl)-N-(4-(2,6-dimethoxyphenyl)-5-(1H-imidazol-4-yl)-4H-1,2,4-triazol-3-yl)-1-methoxy-2-propanesulfonamide;

(1R,2S)-1-(5-chloro-2-pyrimidinyl)-1-methoxy-N-(4-((2R)-1-methoxy-2-propanyl)-5-(1-methyl-1H-pyrazol-3-yl)-4H-1,2,4-triazol-3-yl)-2-propanesulfonamide;

(1S,2S)-1-(5-chloro-2-pyrimidinyl)-N-(4-cyclopropyl-5-(1-methyl-H-pyrazol-3-yl)-4H-1,2,4-triazol-3-yl)-1-(2-propanyloxy)-2-propanesulfonamide;

(2S,3R)-3-(5-chloro-2-pyrimidinyl)-N-(4-((2S)-1-methoxy-2-propanyl)-5-(1-methyl-1H-pyrazol-3-yl)-4H-1,2,4-triazol-3-yl)-2-butanesulfonamide;

(2S,3R)-3-(5-chloro-2-pyridinyl)-N-(4-(4,6-dimethoxy-5-pyrimidinyl)-5-(1-methyl-1H-pyrazol-3-yl)-4H-1,2,4-triazol-3-yl)-2-butanesulfonamide;

(2S,3R)-3-(5-chloro-2-pyridinyl)-N-(4-(4,6-dimethoxy-5-pyrimidinyl)-5-(1-methyl-1H-pyrazol-4-yl)-4H-1,2,4-triazol-3-yl)-2-butanesulfonamide;

(1S,2S)-1-(5-chloro-2-pyrimidinyl)-N-(4-cyclopropyl-5-(1-methyl-1H-pyrazol-4-yl)-4H-1,2,4-triazol-3-yl)-1-(2-propanyloxy)-2-propanesulfonamide;

(1S,2S)-1-(5-chloro-2-pyrimidinyl)-N-(5-(1-methyl-1H-pyrazol-3-yl)-4-(2-propanyl)-4H-1,2,4-triazol-3-yl)-1-(2-propanyloxy)-2-propanesulfonamide; or (1S,2S)-1-(5-chloro-2-pyrimidinyl)-N-(4-(1-methylcyclopropyl)-5-(1-methyl-1H-pyrazol-3-yl)-4H-1,2,4-triazol-3-yl)-1-(2-propanyloxy)-2-propanesulfonamide; or the pharmaceutically acceptable salt thereof, the tautomer thereof, the pharmaceutically acceptable salt of the tautomer, or the mixture thereof. In some such embodiments, the compound may be any one of these presented above. In some such embodiments, the embodiment provides any of the compounds shown above or a pharmaceutically acceptable salt thereof. In still other such embodiments, the embodiment provides any of the compounds shown above, or a pharmaceutically acceptable salt thereof, or a mixture thereof.

64. The compound of embodiment 1, wherein the compound has the formula IA

IA or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in embodiment 1;

X is selected from CH or N;

Z is selected from CH or N;

$R^{3d}$ and $R^{3e}$ are independently selected from —H, —$C_1$-$C_3$ alkyl, or —($C_1$-$C_3$ alkyl)-O—($C_1$-$C_3$ alkyl);

$R^{3f}$ and $R^{3g}$ are independently selected from —H, —F, —$CF_3$, —$C_1$-$C_3$ alkyl, —OH, —O—($C_1$-$C_4$ alkyl), or —O—($C_2$-$C_4$ alkenyl);

Q is a phenyl group or a monocyclic heteroaryl group with 6 ring members containing 1 or 2 N heteroatoms, wherein the phenyl and the monocyclic heteroaryl Q groups are unsubstituted or are substituted with 1 or 2 $R^Q$ substituent; and $R^Q$ is independently selected from —F, —Cl, —Br, —CN, —$C_1$-$C_6$ alkyl, —O—($C_1$-$C_6$ alkyl), or —S(=O)$_2$—($C_1$-$C_6$ alkyl).

65. The compound of embodiment 64 or the pharmaceutically acceptable salt thereof, the tautomer thereof, the pharmaceutically acceptable salt of the tautomer, the stereoisomer of any of the foregoing, or the mixture thereof, wherein:

X is CH;

Z is CH $R^{3d}$ and $R^{3e}$ are independently selected from —H, —$CH_3$, —$CH_2CH_3$, or —$CH_2CH_2OCH_3$;

$R^{3f}$ and $R^{3g}$ are independently selected from —H, —F, —$CF_3$, —$CH_3$, —OH, —$OCH_3$, —$OCH_2CH_3$, —$OCH(CH_3)_2$, or —$OCH_2C(H)=CH_2$;

Q is a phenyl, a pyrimidinyl, a pyridinyl, or a pyrazinyl any of which are unsubstituted or are substituted with 1 or 2 $R^Q$ substituent; and $R^Q$ is independently selected from —F, —Cl, —Br, —CN, —CH$_3$, —OCH$_3$, or —S(=O)$_2$—CH$_3$.

66. The compound of embodiment 64 or 65 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrazolyl, thiazolyl, imidazolyl, thienyl, pyrrolyl, 1,2,4-triazolyl, 1,2,3-triazolyl, oxazolyl, isoxazolyl, 1,3,4-oxadiazolyl, or 1,3,4-thiadiazolyl any of which may unsubstituted or substituted with 1, 2, or 3 independently selected $R^{1a}$ substituents.

67. The compound of embodiment 64 or 65 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrazinyl, pyrimidinyl, or pyridazinyl any of which may unsubstituted or substituted with 1, 2, or 3 independently selected $R^{1a}$ substitutents.

68. The compound of embodiment 66 or 67 or the pharmaceutically acceptable salt thereof, the tautomer thereof, the pharmaceutically acceptable salt of the tautomer, the stereoisomer of any of the foregoing, or the mixture thereof, wherein $R^1$ is unsubstituted or is substituted with 1 or 2 $R^{1a}$ substituents independently selected from —F, —Cl, —Br, —C$_1$-C$_6$ alkyl, —C$_1$-C$_6$ haloalkyl, —C$_1$-C$_6$ perhaloalkyl, —O—(C$_1$-C$_6$ alkyl), C$_3$-C$_8$ cycloalkyl, or —(C$_1$-C$_6$ alkyl)-O—(C$_1$-C$_6$ alkyl), or —C(=O)NH(C$_1$-C$_6$ alkyl).

69. A pharmaceutical composition, comprising the compound of any one of embodiments 1-68 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

70. A pharmaceutical composition, comprising the compound of any one of embodiments 1-68 or the pharmaceutically acceptable salt thereof and at least one pharmaceutically acceptable excipient.

71. A pharmaceutical composition, comprising the compound of any one of embodiments 1-68 and at least one pharmaceutically acceptable excipient.

72. A pharmaceutical composition, comprising the pharmaceutically acceptable salt of the compound of any one of embodiments 1-68 and at least one pharmaceutically acceptable excipient.

73. The pharmaceutical composition of embodiment 69, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

74. The pharmaceutical composition of embodiment 69, further comprising a therapeutic agent selected from an angiotensin converting enzyme (ACE) inhibitor or an angiotensin-receptor blocker (ARB).

75. A method of treating a cardiovascular condition, the method comprising: administering to a subject an effective amount of the compound of any one of embodiments 1-68 or the pharmaceutically acceptable salt thereof, the stereoisomer of any of the foregoing, or the mixture thereof, or the pharmaceutical composition of any one of embodiments 69-74.

76. The method of embodiment 75, wherein the cardiovascular condition is heart failure.

77. The method of embodiment 75, wherein the cardiovascular condition is heart failure with reduced ejection fraction.

78. The method of embodiment 75, wherein the cardiovascular condition is heart failure with preserved ejection fraction.

79. The method of embodiment 75, wherein the cardiovascular condition is chronic systolic heart failure or chronic diastolic heart failure.

80. The method of embodiment 75, wherein the cardiovascular condition is acute heart failure.

81. The method of embodiment 75, wherein the cardiovascular condition is hypertension.

82. A method of improving cardiac contractility in a subject suffering from a cardiovascular condition, the method comprising: administering to the subject an effective amount of the compound of any one of embodiments 1-68 or the pharmaceutically acceptable salt thereof, the stereoisomer of any of the foregoing, or the mixture thereof, or the pharmaceutical composition of any one of embodiments 69-74, wherein cardiac contractility is improved in the subject after administration.

83. A method of increasing ejection fraction in a subject suffering from a cardiovascular condition, the method comprising: administering to the subject an effective amount of the compound of any one of embodiments 1-68 or the pharmaceutically acceptable salt thereof, the stereoisomer of any of the foregoing, or the mixture thereof, or the pharmaceutical composition of any one of embodiments 69-74, wherein the ejection fraction is increased in the subject after administration.

84. A method of treating a condition in a subject where it is desired to activate the APJ Receptor, the method comprising: administering to the subject an effective amount of the compound of any one of embodiments 1-68 or the pharmaceutically acceptable salt thereof, the stereoisomer of any of the foregoing, or the mixture thereof or the pharmaceutical composition of any one of embodiments 69-74.

85. The method of embodiment 84, wherein the condition is obesity or diabetes.

86. The method of embodiment 84, wherein the condition is diabetic nephropathy or chronic kidney disease.

87. The method of any one of embodiments 75-86, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

88. The method of any one of embodiments 75-86, wherein the method includes administering at least one additional therapeutic agent to the subject, wherein the additional therapeutic agent is selected from an angiotensin converting enzyme (ACE) inhibitor or an angiotensin-receptor blocker (ARB).

89. A compound of any one of embodiments 1-68 or the pharmaceutically acceptable salt thereof, the stereoisomer of any of the foregoing, or the mixture thereof, or the pharmaceutical composition of any one of embodiments 69-74 for use in treating a cardiovascular condition.

90. The compound of embodiment 89, wherein the cardiovascular condition is heart failure.

91. The compound of embodiment 89, wherein the cardiovascular condition is heart failure with reduced ejection fraction.

92. The compound of embodiment 89, wherein the cardiovascular condition is heart failure with preserved ejection fraction.

93. The compound of embodiment 89, wherein the cardiovascular condition is chronic systolic heart failure or chronic diastolic heart failure.

94. The compound of embodiment 89, wherein the cardiovascular condition is acute heart failure.

95. The compound of embodiment 89, wherein the cardiovascular condition is hypertension.

96. A compound of any one of embodiments 1-68 or the pharmaceutically acceptable salt thereof, the stereoisomer of any of the foregoing, or the mixture thereof, or the pharmaceutical composition of any one of embodiments 69-74 for use in activating the APJ Receptor or for treating a condition where it is desirable to activate the APJ Receptor.

97. The compound of embodiment 96, wherein the condition is obesity or diabetes.

98. The compound of embodiment 96, wherein the condition is diabetic nephropathy or chronic kidney disease.

99. A use of the compound of any one of embodiments 1-68 or the pharmaceutically acceptable salt thereof, the stereoisomer of any of the foregoing, or the mixture thereof in the preparation of a medicament for treating a cardiovascular condition.

100. The use of embodiment 99, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

101. The use of embodiment 99, further comprising a therapeutic agent selected from an angiotensin converting enzyme (ACE) inhibitor or an angiotensin-receptor blocker (ARB).

102. The use of the compound of embodiment 99, wherein the cardiovascular condition is heart failure.

103. The use of the compound of embodiment 99, wherein the cardiovascular condition is heart failure with reduced ejection fraction.

104. The use of the compound of embodiment 99, wherein the cardiovascular condition is heart failure with preserved ejection fraction.

105. The use of the compound of embodiment 99, wherein the cardiovascular condition is chronic systolic heart failure or chronic diastolic heart failure.

106. The use of the compound of embodiment 99, wherein the cardiovascular condition is acute heart failure.

107. The use of the compound of embodiment 99, wherein the cardiovascular condition is hypertension.

108. A use of the compound of any one of embodiments 1-68 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

109. The use of embodiment 108, wherein the condition is obesity or diabetes.

110. The use of embodiment 108, wherein the condition is diabetic nephropathy or chronic kidney disease.

111. A treatment regimen for a cardiovascular disease, the regimen comprising: the compound of any one of embodiments 1-68 or the pharmaceutically acceptable salt thereof, the stereoisomer of any of the foregoing, or the mixture thereof.

112. The treatment regimen of embodiment 111, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

113. The treatment regimen of embodiment 111, wherein the regimen further comprises a therapeutic agent selected from an angiotensin converting enzyme (ACE) inhibitor or an angiotensin-receptor blocker (ARB).

114. A kit, the kit comprising: the compound of any one of embodiments 1-68 or the pharmaceutically acceptable salt thereof, the stereoisomer of any of the foregoing, or the mixture thereof.

115. The kit of embodiment 114, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

116. The kit of embodiment 114, wherein the kit further comprises a therapeutic agent selected from an angiotensin converting enzyme (ACE) inhibitor or an angiotensin-receptor blocker (ARB).

117. In one embodiment, the invention provides a compound of Formula V, a salt thereof, a tautomer thereof, or a salt of the tautomer:

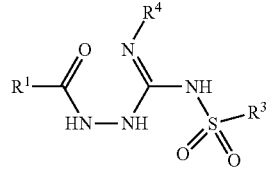

V wherein:

$R^1$ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl $R^1$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR_3R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl R⁴ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH₂, —NH($C_1$-$C_6$ alkyl), —N($C_1$-$C_6$ alkyl)₂, NH($C_1$-$C_6$ alkyl-OH), —N($C_1$-$C_6$ alkyl-OH)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, phenyl, —S(=O)₂—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or SO₂ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH₂, —NH($C_1$-$C_6$ alkyl), —N($C_1$-$C_6$ alkyl)₂, NH($C_1$-$C_6$ alkyl-OH), —N($C_1$-$C_6$ alkyl-OH)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, or —S(=O)₂—($C_1$-$C_6$ alkyl).

118. The compound of embodiment 117, the salt thereof, the tautomer thereof, or the salt of the tautomer, wherein the compound has any of the $R^1$, $R^{1a}$, $R^{1a'}$, $R^{1b'}$, $R^3$, $R^{3d}$, $R^{3e}$, $R^{3f}$, $R^{3g}$, $R^{3h}$, $R^4$, $R^{4a}$, $R^{4b}$, Q, or $R^Q$, values or combinations of values of any one of embodiments 2-60.

119. In another embodiment, the invention provides a method for preparing a compound of Formula VI, a salt thereof, a tautomer thereof, or a salt of the tautomer:

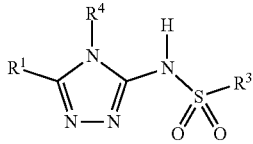

VI the method comprising:

a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

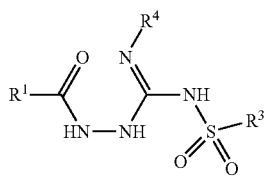

V wherein:

$R^1$ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, —S(=O)₂—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl $R^1$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂ or —S(=O)₂—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH₂, —NH($C_1$-$C_6$ alkyl), —N($C_1$-$C_6$ alkyl)₂, —C(=O)—($C_1$-$C_6$ alkyl), —C(=O)OH, —C(=O)—O—($C_1$-$C_6$ alkyl), —C(=O)NH₂, —C(=O)NH($C_1$-$C_6$ alkyl), —C(=O)N($C_1$-$C_6$ alkyl)₂, or —S(=O)₂—($C_1$-$C_6$ alkyl);

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^3$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or $SO_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl).

120. The method of embodiment 119, wherein $R^1$, $R^{1a}$, $R^{1a'}$, $R^{1b'}$, $R^3$, $R^{3d}$, $R^{3e}$, $R^{3f}$, $R^{3g}$, $R^{3h}$, $R^{4a}$, $R^{4b}$, Q, or $R^Q$, have any of the values or combination of values of any one of embodiments 2-60.

121. The method of embodiment 119 or embodiment 120, wherein cyclizing further comprises heating the compound of Formula V, the salt thereof, the tautomer thereof, or the salt of the tautomer in the presence of the acid or the base.

122. The method of embodiment 121, wherein heating the compound of Formula V, the salt thereof, the tautomer thereof, or the salt of the tautomer comprises heating the compound to a temperature of from 50° C. to 100° C.

123. The method of embodiment 121, wherein heating the compound of Formula V, the salt thereof, the tautomer thereof, or the salt of the tautomer comprises heating the compound to a temperature of from 60° C. to 85° C.

124. The method of any one of embodiments 119-123, wherein the cyclizing of the compound of Formula V, the salt thereof, the tautomer thereof, or the salt of the tautomer is performed in the presence of the base.

125. The method of any one of embodiments 119-124, wherein the base is a metal hydroxide.

126. The method of embodiment 125, wherein the metal hydroxide is selected from NaOH or LiOH.

127. The method of any one of embodiments 124-126, wherein the cyclizing is carried out in an alcohol solvent.

128. The method of embodiment 127, wherein the alcohol is isopropanol.

129. The method of any one of embodiments 119-123, wherein cyclizing further comprises heating the compound of Formula V, the salt thereof, the tautomer thereof, or the salt of the tautomer in the presence of the acid.

130. The method of embodiment 129, wherein the acid is selected from a sulfonic acid, a carboxylic acid, polyphosphoric acid, phosphoric acid, sulfuric acid, or hydrochloric acid.

131. The method of embodiment 130, wherein the sulfonic acid is methanesulfonic acid.

132. The method of embodiment 130, wherein the acid is trifluoroacetic acid, acetic acid, or trichloroacetic acid.

133. The method of any one of embodiments 129-132, wherein the cyclizing is carried out in a cyclic ether, an acyclic ether, N,N-dimethylformamide, or acetonitrile.

134. The method of embodiment 133, wherein the cyclizing is carried out in a cyclic ether.

135. The method of embodiment 134, wherein the cyclic ether is selected from tetrahydrofuran, tetrahydropyran, or 1,4-dioxane.

136. The method of embodiment 134, wherein the cyclic ether is 1,4-dioxane.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet where the effective amount of the active ingredient ranges from 5 mg to 60 mg, from 6 mg to 58 mg, from 10 mg to 40 mg, from 15 mg to 30 mg, from 16 mg to 25 mg, or from 17 mg to 20 mg. In some such compositions, the amount of active ingredient is 17 mg.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts.

Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 μL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^3$, $R^4$, and Q groups taught in WO 2016/187308 and U.S. Pat. Appl. Pub. No. US 2016/0340336.

The following Abbreviations are used to refer to various reagents and solvents:
ACN Acetonitrile
AcOH Acetic Acid
d day or days
CV Column volume
CDI 1,1'-Carbonyldiimidazole
DAST Diethylaminosulfur trifluoride
DCM Dichloromethane
DEA Diethylamine
DMF N,N-Dimethylformamide
DMA Dimethylacetamide
DMSO Dimethylsulfoxide
EtOAc Ethyl Acetate
EtOH Ethanol
EtOTf Ethyl trifluoromethanesulfonate
h hour or hours
HATU 1-[Bis(dimethylamino)methylene]-1H-1,2,3-triazolo[4,5-b]pyridinium 3-oxid hexafluorophosphate
HMDS Hexamethyldisilazane
HOBt Hydroxybenzotriazole
IPA Isopropanol
LAH Lithium aluminum hydride
KHMDS Potassium bis(trimethylsilyl)amide
MeOH Methanol
MeOTf Methyl trifluoromethanesulfonate
min minute or minutes
MS Mass spectrum
MSA Methane sulfonic acid
NaHMDS Sodium bis(trimethylsilyl)amide
RBF Round bottom flask
RT Room temperature
SFC Supercritical fluid chromatography
TASF Tris(dimethylamino)sulfonium difluorotrimethylsilicate
TBAF Tetrabutylammonium fluoride
TBS t-Butyldimethylsilane
TBSOTf t-Butyldimethylsilyl trifluoromethanesulfonate
TEA Triethylamine
TFA Trifluoroacetic acid
THF Tetrahydrofuran
TLC Thin Layer Chromatography The following compounds were synthesized using the intermediates described, following the procedure described within Example 14.0.

TABLE 1

| Example | Reagents | Structure, Name and and Data |
|---|---|---|
| 1.0 | 4-methyl-1,3-thiazole-2-carbohydrazide (commercially available from Allichem), 2-isothiocyanato-1,3-dimethoxybenzene (Example 465.0), and (2S,3R)-3-(5-methylpyrimidin-2-yl)butane-2-sulfonamide (Example 464.0). | 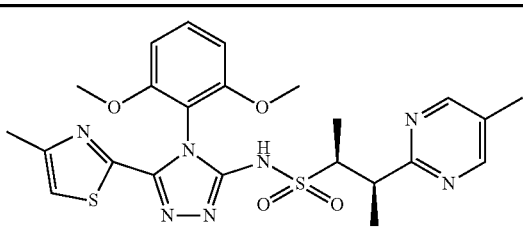<br>(2R,3 S)-N-(4-(2,6-dimethoxyphenyl)-5-(4-methylthiazol-2-yl)-4H-1,2,4-triazol-3-yl)-3-(5-methylpyrimidin-2-yl)butane-2-sulfonamide.<br>$^1$H NMR (400 MHz, CDCl$_3$) δ 1.37 (m, δ H) 2.29 (s, 3 H) 2.40 (s, 3 H) 3.66-3.81 (m, 7 H) 3.89 (t, J = 6.65 Hz, 1 H) 6.64 (dd, J = 8.41, 5.09 Hz, 2 H) 6.90 (s, 1 H) 7.45 (t, J = 8.51 Hz, 1 H) 8.52 (s, 2H) 11.51 (br. s, 1 H). LCMS (pos.) m/z: 530.2 (M + H)$^+$. |

TABLE 1-continued

| Example | Reagents | Structure, Name and and Data |
|---|---|---|
| 2.0 | 2-methyl-1,3-thiazole-4-carbohydrazine (commercially available from Oakwood Products), 2-isothiocyanato-1,3-dimethoxybenzene (Example 465.0), and (2S,3R)-3-(5-methylpyrimidin-2-yl)butane-2-sulfonamide (Example 464.0). | 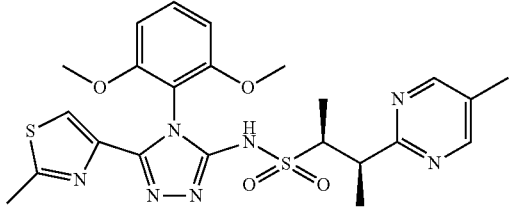<br>(2R,3S)-N-(4-(2,6-dimethoxyphenyl)-5-(2-methylthiazol-4-yl)-4H-1,2,4-triazol-3-yl)-3-(5-methylpyrimidin-2-yl)butane-2-sulfonamide.<br>$^1$H NMR (300 MHz, CDCl$_3$) δ 1.37 (m, 6 H) 2.29 (s, 3 H) 2.72 (s, 3 H) 3.75 (s, 3 H) 3.75 (s, 3 H) 3.76-3.83 (m, 1 H) 3.83-3.99 (m, 1 H) 6.67 (dd, J = 8.48, 3.07 Hz, 2 H) 6.76 (s, 1 H) 7.46 (t, J = 8.48 Hz, 1 H) 8.53 (s, 2 H) 11.35 (br. s, 1 H).LCMS (pos.) m/z: 529.9 (M + H)$^+$. |
| 3.0 | 4-methyl-1,3-thiazole-2-carbohydrazide (commercially available from Allichem), 5-isothiocyanato-4,6-dimethoxypyrimidine, Example 465.1, and (2S,3R)-3-(5-methylpyrimidin-2-yl)butane-2-sulfonamide (Example 464.0). | 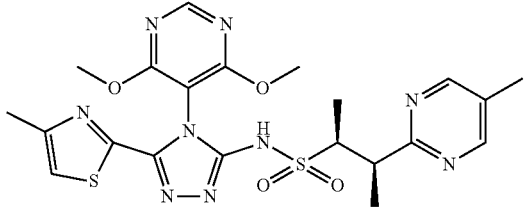<br>(2S,3R)-N-(4-(4,6-dimethoxypyrimidin-5-yl)-5-(4-methylthiazol-2-yl)-4H-1,2,4-triazol-3-yl)-3-(5-methylpyrimidin-2-yl)butane-2-sulfonamide.<br>$^1$H NMR (CDCl$_3$) δ: 8.53 (d, J = 3.9 Hz, 3H), 6.98 (d, J = 0.9 Hz, 1H), 3.84-3.96 (m, 7H), 3.67-3.77 (m, 1H), 2.24-2.34 (m, 6H), 1.40 (m, 6H), 1.34-1.45 (m, 6H). LCMS (pos.) m/z: 532.0 (M + H)$^+$. |
| 4.0 | 4-cyclopropylthiazole-2-carbohydrazide (commercially available from FSSI), 5-isothiocyanato-4,6-dimethoxypyrimidine Example 465.1, and (1R,2S)-1-methoxy-1-(5-methylpyrimidin-2-yl)propane-2-sulfonamide (Example 466.0). | 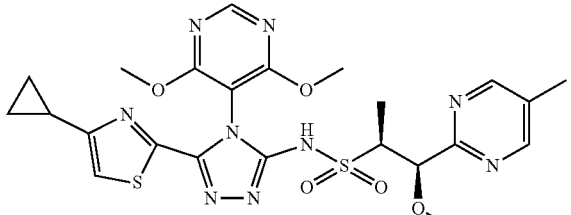<br>(1R,2S)-N-(5-(4-cyclopropylthiazol-2-yl)-4-(4,6-dimethoxypyrimidin-5-yl)-4H-1,2,4-triazol-3-yl)-1-methoxy-1-(5-methylpyrimidin-2-yl)propane-2-sulfonamide.<br>$^1$H NMR (400 MHz, CDCl$_3$) δ 0.34-0.45 (m, 2 H) 0.81 (dd, J = 8.02, 2.35 Hz, 2 H) 1.28-1.28(m, 1 H) 1.38 (d, J = 7.04 Hz, 3 H) 2.36 (s, 3 H) 3.33 (s, 3 H) 3.69-3.82 (m, 1 H) 3.93 (s, 3 H) 3.93 (s, 3 H) 4.97 (d, J = 4.50 Hz, 1 H) 6.99 (s, 1 H) 8.53 (s, 1 H) 8.67 (s, 2 H). LCMS (pos.) m/z: 574.1 (M + H)$^+$. |

TABLE 1-continued

| Example | Reagents | Structure, Name and and Data |
|---|---|---|
| 5.0 | 2-methyl-1,3-thiazole-4-carbohydrazine (commercially available from Allichem), 5-isothiocyanato-4,6-dimethoxypyrimidine, Example 465.1, and (1R,2S)-1-methoxy-1-(5-methylpyrimidin-2-yl)propane-2-sulfonamide (Example 466.0). | 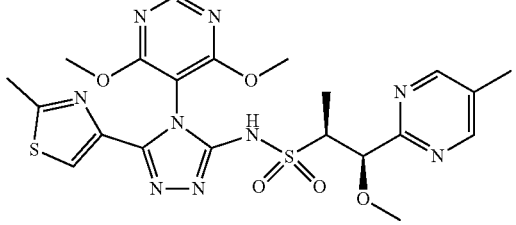(1R,2S)-N-(4-(4,6-dimethoxypyrimidin-5-yl)-5-(2-methylthiazol-4-yl)-4H-1,2,4-triazol-3-yl)-1-methoxy-1-(5-methylpyrimidin-2-yl)propane-2-sulfonamide. $^1$H NMR (400 MHz, CDCl$_3$) δ 1.38 (d, J = 7.04 Hz, 3 H) 2.36 (s, 3 H) 2.57 (s, 3 H) 3.33 (s, 3 H) 3.74 (dd, J = 7.04, 4.69 Hz, 1 H) 3.93 (s, 3 H) 3.93 (s, 3 H) 4.98 (d, J = 4.69 Hz, 1 H) 7.54 (s, 1 H) 8.51 (s, 1 H) 8.67 (s, 2 H). LCMS (pos.) m/z: 548.0 (M + H)$^+$. |

Example 6.0. Preparation of (2R)-N-(4-(4,6-dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide and (2S)-N-(4-(4,6-dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide 6.0

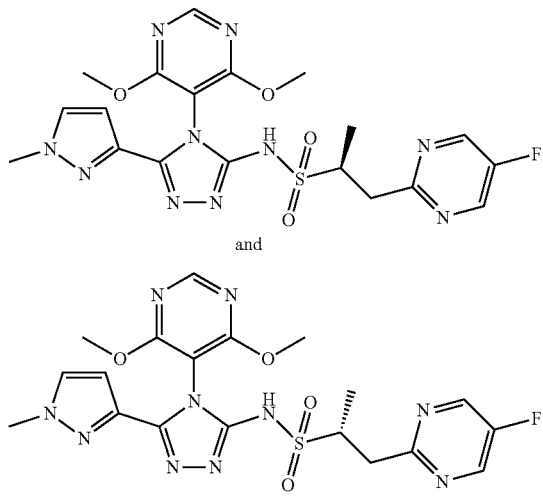

and (2R)-N-(4-(4,6-Dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide and (2S)-N-(4-(4,6-dimethoxy-5-pyrimidinyl)-5-(1-methyl-1H-pyrazol-3-yl)-4H-1,2,4-triazol-3-yl)-1-(5-fluoro-2-pyrimidinyl)-2-propanesulfonamide, Example 6.0. To a 50 mL RBF was added 5-isothiocyanato-4,6-dimethoxypyrimidine (Example 465.1, 138 mg, 0.701 mmol) in DMF (3 mL), followed by cesium carbonate (60.7 µL, 0.759 mmol) and (S)-1-(5-fluoropyrimidin-2-yl)propane-2-sulfonamide and (R)-1-(5-fluoropyrimidin-2-yl)propane-2-sulfonamide, Example 402.0 (128 mg, 0.584 mmol) at RT. The reaction was stirred overnight. To the reaction mixture was then added 1-methyl-1H-pyrazole-3-carbohydrazide (Example 395.13, 82 mg, 0.584 mmol), silver nitrate (45.6 µL, 1.168 mmol) and AcOH, (143 µL, 2.481 mmol). The reaction mixture was stirred for 1 h. EtOAc was then added and the reaction was filtered to remove the solids. The solvent was concentrated in vacuo. TFA (195 µL, 2.63 mmol) was added to the residue and the mixture was heated at 100° C. overnight. The reaction was concentrated in vacuo and purified by reverse-phase preparative HPLC using a Phenomenex Luna column, 5 micron, C8(2), 100 Å, 150×21.2 mm, 0.1% TFA in ACN/H$_2$O, gradient 0% to 90% to provide Example 6.0 (78 mg, 0.155 mmol, 27%). $^1$H NMR (400 MHz, CDCl$_3$) δ 1.35 (d, J=6.65 Hz, 3H) 3.13 (dd, J=14.67, 9.78 Hz, 1H) 3.69-3.88 (m, 5H) 3.94 (s, 3H) 3.96 (s, 3H) 6.58 (d, J=2.35 Hz, 1H) 7.35 (d, J=2.35 Hz, 1H) 8.53 (s, 1H) 8.56 (s, 2H). LCMS ESI (pos.) m/z: 505.1 (M+H)$^+$.

Example 7.0. Preparation of (2R)-1-(5-fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide and (2S)-1-(5-fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide 7.0

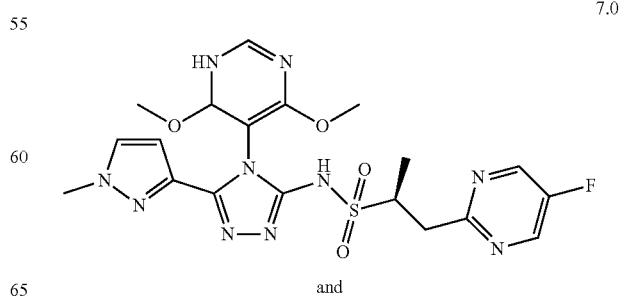

and

-continued

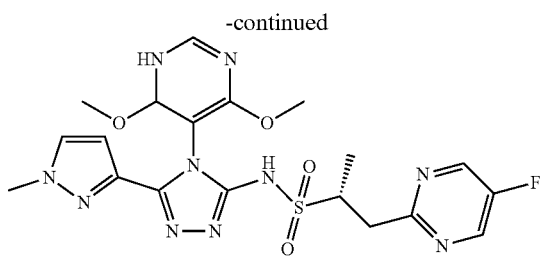

(2R)-1-(5-Fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide and (2S)-1-(5-fluoro-2-pyrimidinyl)-N-(4-(4-methoxy-6-oxo-1,6-dihydro-5-pyrimidinyl)-5-(1-methyl-1H-pyrazol-3-yl)-4H-1,2,4-triazol-3-yl)-2-propanesulfonamide, Example 7.0. Further elution under the conditions described in Example 6.0 delivered Example 7.0 (20 mg, 0.041 mmol, 7% yield) as a white solid. $^1$H NMR (400 MHz, CDCl$_3$) δ 1.33 (dd, J=6.85, 2.54 Hz, 3H) 3.03-3.24 (m, 1H) 3.70 (td, J=9.44, 4.60 Hz, 1H) 3.77-3.83 (m, 4H) 3.91 (d, J=3.52 Hz, 3H) 6.61 (d, J=2.35 Hz, 1H) 7.34 (d, J=2.35 Hz, 1H) 8.13 (d, J=1.56 Hz, 1H) 8.54 (s, 2H). LCMS ESI (pos.) m/z: 491.1 (M+H)$^+$.

Example 8.0. Preparation of (2S)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide or (2R)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide 8.0

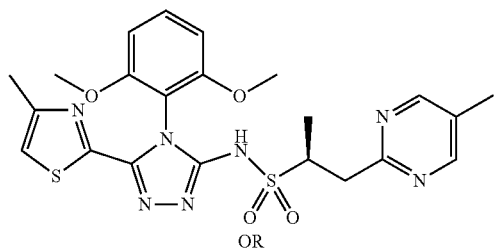

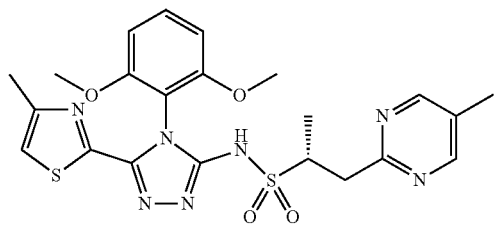

(2S)-N-(4-(2,6-Dimethoxyphenyl)-5-(4-methyl-1,3-thiazol-2-yl)-4H-1,2,4-triazol-3-yl)-1-(5-methyl-2-pyrimidinyl)-2-propanesulfonamide or (2R)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide, Example 8.0. The title compound was prepared in an analogous fashion to that described in Example 10.0 employing Example 397.4 and employing 1-(5-methylpyrimidin-2-yl)propane-2-sulfonyl chloride prepared following the general procedure described in Example 402.0 using 2-chloro-5-methylpyrimidine. Purification of initial material by SFC [20×150 mm AD-H column with 20% MeOH (neat) in CO$_2$ at 100 bar] afforded two enantiomers. The title compound was the first isomer to elute under these conditions. $^1$H NMR (500 MHz, CDCl$_3$) δ 11.51 (br. s, 1H) 8.54 (br. s, 2H) 7.47 (t, J=8.56 Hz, 1H) 6.93 (s, 1H) 6.67 (dd, J=8.56, 2.69 Hz, 2H) 3.83-3.94 (m, 1H) 3.76 (s, 3H) 3.76 (s, 3H) 3.67 (dd, J=14.79, 4.77 Hz, 1H) 3.09 (dd, J=14.67, 9.29 Hz, 1H) 2.42 (s, 3H) 2.32 (s, 3H) 1.36 (d, J=6.85 Hz, 3H). LCMS-ESI (pos.) m/z: 516.0 (M+H)$^+$.

Example 9.0. Preparation of (2S)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide or (2R)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide 9.0

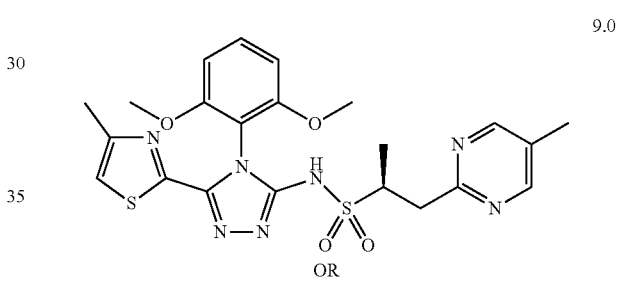

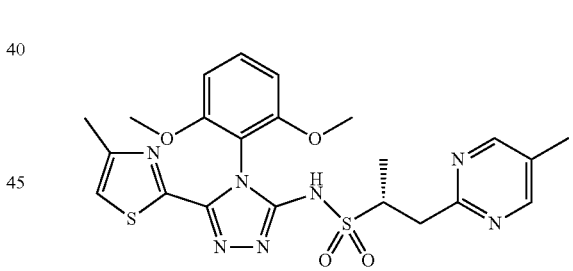

(2S)-N-(4-(2,6-Dimethoxyphenyl)-5-(4-methyl-1,3-thiazol-2-yl)-4H-1,2,4-triazol-3-yl)-1-(5-methyl-2-pyrimidinyl)-2-propanesulfonamide or (2R)-N-(4-(2,6-dimethoxyphenyl)-5-(4-methyl-1,3-thiazol-2-yl)-4H-1,2,4-triazol-3-yl)-1-(5-methyl-2-pyrimidinyl)-2-propanesulfonamide, Example 9.0. Example 9.0 is the enantiomer of Example 8.0. Further elution under the conditions described in Example 8.0, delivered the title compound as the second isomer. $^1$H NMR (500 MHz, CDCl$_3$) δ 11.50 (br. s, 1H) 8.52 (br. s, 2H) 7.45 (t, J=8.56 Hz, 1H) 6.91 (s, 1H) 6.65 (dd, J=8.44, 2.32 Hz, 2H) 3.83-3.92 (m, 1H) 3.74 (s, 3H) 3.74 (s, 3H) 3.65 (dd, J=14.55, 4.52 Hz, 1H) 3.07 (dd, J=14.67, 9.05 Hz, 1H) 2.40 (s, 3H) 2.30 (s, 3H) 1.34 (d, J=6.85 Hz, 3H). LCMS-ESI (pos.) m/z: 516.0 (M+H)$^+$.

Example 10.0. Preparation of N-(4-(2,6-dimethoxyphenyl)-5-(4-methyl-1,3-thiazol-2-yl)-4H-1,2,4-triazol-3-yl)-2-(5-methyl-2-pyrimidinyl)ethanesulfonamide

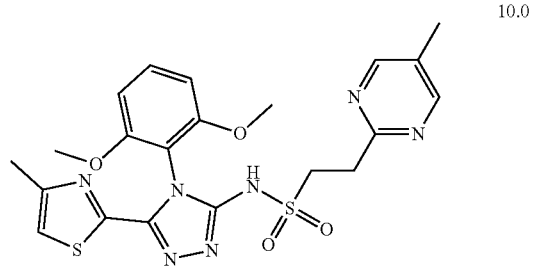

10.0

N-(4-(2,6-Dimethoxyphenyl)-5-(4-methyl-1,3-thiazol-2-yl)-4H-1,2,4-triazol-3-yl)-2-(5-methyl-2-pyrimidinyl)ethanesulfonamide, Example 10.0. To a suspension of 2-(5-methylpyrimidin-2-yl)ethanesulfonic acid (394 mg, 1.948 mmol) in DCM (10 mL) at 0° C. was added oxalyl chloride (215 μL, 2.46 mmol, 1.26 eq) followed by DMF (1 drop). The reaction was stirred for 2 h. The reaction was concentrated to dryness, azeotroped with benzene twice and then dried on HVAC. To a 0° C. suspension of Example 397.4 (123 mg, 0.388 mmol) in THF (5 mL) was added potassium bis(trimethylsilyl)amide (1.0 M solution in THF, 1.2 mL, 1.20 mmol). The reaction was stirred at 0° C. for 2 h. The amino triazole solution was added to a 0° C. suspension of the 2-(5-methylpyrimidin-2-yl)ethanesulfonyl chloride (prepared in an analogous fashion as described in Example 402.0 employing 5-methyl-2-vinylpyrimidine) in THF (5 mL), in one portion. Once the addition was complete, the cooling bath was removed and the yellow mixture was warmed to RT and stirred overnight. The reaction was quenched with water (0.5 mL), then concentrated in vacuo, and redissolved using water and MeOH. The material was purified by reverse-phase preparative HPLC using an Agilent SB C8 column, 0.1% TFA in ACN/H₂O, gradient 10% to 50% over 25 min. The desired fraction was lyophilized over the weekend to give Example 10.0 (37.0 mg, 0.074 mmol, 19.03% yield). ¹H NMR (500 MHz, CDCl₃) δ 2.36 (s, 3H) 2.40 (d, J=0.73 Hz, 3H) 3.46-3.51 (m, 2H) 3.62-3.67 (m, 2H) 3.74 (s, 3H) 3.74 (s, 3H) 6.66 (d, J=8.56 Hz, 2H) 6.92 (d, J=0.73 Hz, 1H) 7.46 (t, J=8.44 Hz, 1H) 8.64 (s, 2H). LCMS ESI (pos.) m/z: 502.1 (M+H)⁺.

Example 11.0. Preparation of (2R)-1-(5-cyano-2-pyridinyl)-N-(4-(2,6-dimethoxyphenyl)-5-(4-methyl-1,3-thiazol-2-yl)-4H-1,2,4-triazol-3-yl)-2-propanesulfonamide or (2S)-1-(5-cyano-2-pyridinyl)-N-(4-(2,6-dimethoxyphenyl)-5-(4-methyl-1,3-thiazol-2-yl)-4H-1,2,4-triazol-3-yl)-2-propanesulfonamide

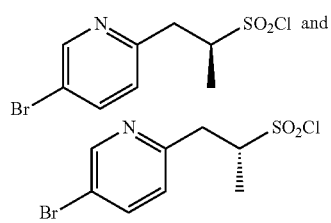

11.1

(S)-1-(5-Bromopyridin-2-yl)propane-2-sulfonyl chloride and (R)-1-(5-bromopyridin-2-yl)propane-2-sulfonyl chloride, Example 11.1. The title compound was prepared employing 2,5-dibromopyridine (commercially available from Frontier Scientific Services, Newark, Del., USA) and the procedures described for the synthesis of Example 402.0. LCMS-ESI (pos.) m/z: 296.9 (M+H)⁺.

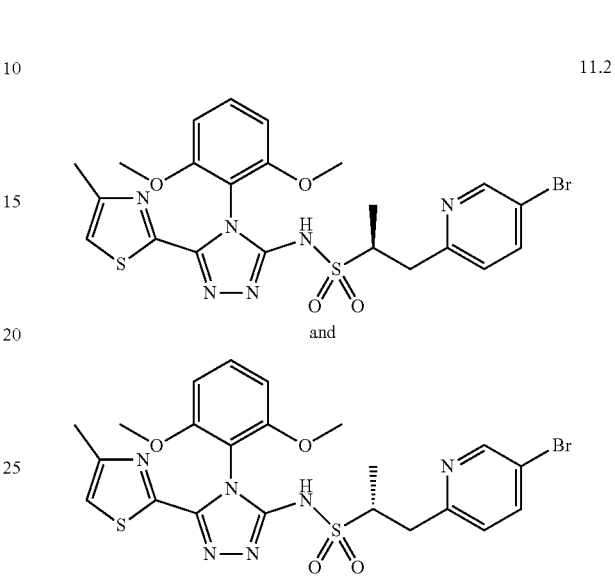

11.2

(R)-1-(5-Bromopyridin-2-yl)-N-(4-(2,6-dimethoxyphenyl)-5-(4-methylthiazol-2-yl)-4H-1,2,4-triazol-3-yl)propane-2-sulfonamide and (S)-1-(5-bromopyridin-2-yl)-N-(4-(2,6-dimethoxyphenyl)-5-(4-methylthiazol-2-yl)-4H-1,2,4-triazol-3-yl)propane-2-sulfonamide, Example 11.2. The title compound was prepared employing Example 397.4 and Example 11.1 following the procedure described for the synthesis of Example 10.0. LCMS-ESI (pos.) m/z: 578.9 (M+H)⁺.

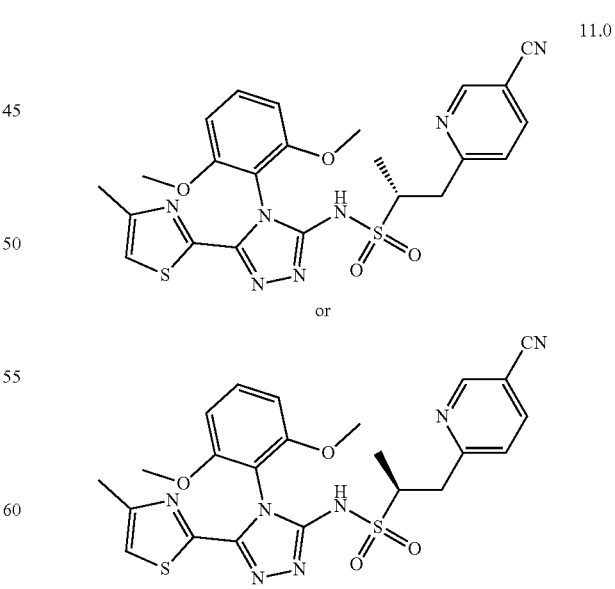

11.0

(2R)-1-(5-Cyano-2-pyridinyl)-N-(4-(2,6-dimethoxyphenyl)-5-(4-methyl-1,3-thiazol-2-yl)-4H-1,2,4-triazol-3-yl)-2-propanesulfonamide or (2S)-1-(5-cyano-2-pyridinyl)-N-(4-

(2,6-dimethoxyphenyl)-5-(4-methyl-1,3-thiazol-2-yl)-4H-1,2,4-triazol-3-yl)-2-propanesulfonamide, Example 11.0. To a solution of Example 11.2 (99 mg, 0.143 mmol) in DMF (1.0 mL) was added tetrakis(triphenylphosphine)palladium(0) (55 mg, 0.048 mmol) and zinc cyanide (31 mg, 0.264 mmol). Argon was then sparged through the mixture for one min before the microwave vial was sealed. The resulting mixture was heated in a microwave for 1 h at 120° C. under argon. The reaction mixture was filtered through a syringe filter, rinsed with MeOH and DCM and then concentrated in vacuo. The material was purified by reverse-phase preparative HPLC using an Agilent SB C8 column, 0.1% TFA in ACN/H$_2$O, gradient 10% to 80% over 25 min to give the title product for chiral separation. Chiral separation was performed with an IA column eluting with 28% MeOH/CO$_2$, 100 bar, 60 mL/min. The first peak to elute on the IA column was Example 11.0 (11.2 mg, 0.021 mmol, 15%). $^1$H NMR (500 MHz, CDCl$_3$) δ 1.30 (d, J=6.85 Hz, 3H) 2.39 (d, J=0.73 Hz, 3H) 2.97 (dd, J=14.18, 9.05 Hz, 1H) 3.60 (dd, J=14.18, 4.65 Hz, 1H) 3.66 (m, J=2.20 Hz, 1H) 3.72 (s, 3H) 3.72 (s, 3H) 6.66 (d, J=8.56 Hz, 2H) 6.92 (d, J=0.98 Hz, 1H) 7.30 (d, J=8.07 Hz, 1H) 7.47 (t, J=8.56 Hz, 1H) 7.85 (dd, J=8.19, 2.08 Hz, 1H) 8.79 (d, J=1.47 Hz, 1H) 11.10 (br. s, 1H). LCMS ESI (pos.) m/z: 526.1 (M+H)$^+$.

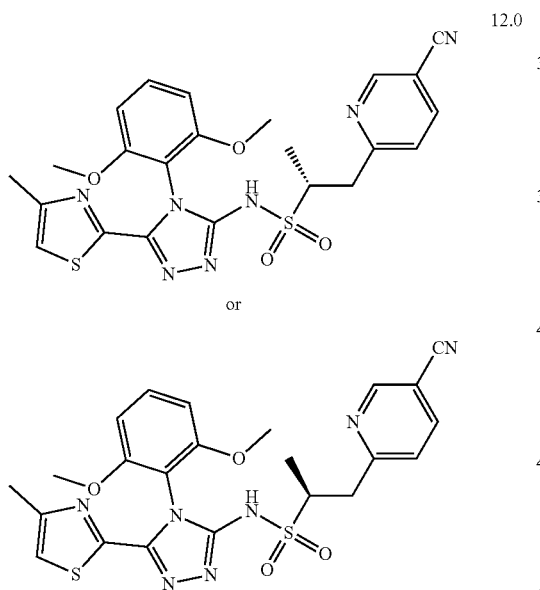

(2R)-1-(5-Cyano-2-pyridinyl)-N-(4-(2,6-dimethoxyphenyl)-5-(4-methyl-1,3-thiazol-2-yl)-4H-1,2,4-triazol-3-yl)-2-propanesulfonamide or (2S)-1-(5-cyano-2-pyridinyl)-N-(4-(2,6-dimethoxyphenyl)-5-(4-methyl-1,3-thiazol-2-yl)-4H-1,2,4-triazol-3-yl)-2-propanesulfonamide, Example 12.0. Further elution under the conditions described in Example 11.0 delivered the second peak to elute on the IA column as Example 12.0 (11.6 mg, 0.022 mmol, 16%). $^1$H NMR (500 MHz, CDCl$_3$) δ 1.30 (d, J=6.85 Hz, 3H) 2.39 (s, 3H) 2.97 (dd, J=14.18, 9.29 Hz, 1H) 3.60 (dd, J=14.18, 4.40 Hz, 1H) 3.66 (ddd, J=9.17, 6.72, 4.65 Hz, 1H) 3.72 (s, 3H) 3.72 (s, 3H) 6.66 (d, J=8.56 Hz, 2H) 6.92 (s, 1H) 7.31 (d, J=8.07 Hz, 1H) 7.47 (t, J=8.56 Hz, 1H) 7.85 (dd, J=8.07, 2.20 Hz, 1H) 8.79 (d, J=1.71 Hz, 1H) 11.11 (br. s, 1H), LCMS ESI (pos.) m/z: 526.1 (M+H)$^+$.

Example 13.0. Preparation of N-(4-(2,6-dimethoxyphenyl)-5-(4-methyl-1,3-thiazol-2-yl)-4H-1,2,4-triazol-3-yl)-2-((6S)-3,6-dimethyl-2-oxotetrahydro-1 (2H)-pyrimidinyl)ethanesulfonamide

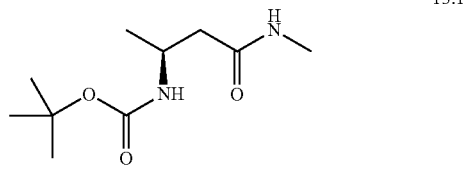

(S)-tert-Butyl (4-(methylamino)-4-oxobutan-2-yl)carbamate, Example 13.1. A 100 mL flask was charged with Boc-L-β-homoalanine (223 mg, 1.1 mmol), 1-(3-dimethylaminopropyl)-n'-ethylcarbodiimide hydrochloride (316 mg, 1.65 mmol), HOBt, hydrate (74.1 mg, 0.55 mmol). DCM (9 mL) was added followed by methylamine (2.0 M solution in THF, 2.19 mL, 4.39 mmol). The reaction was stirred overnight. After which 15% IPA/CHCl$_3$ and water were added and the aqueous layer was extracted. The organics were concentrated in vacuo, the initial material was purified on silica gel using 15-80% EtOAc/hexanes gradient with ELS detector, to delivered the title compound.

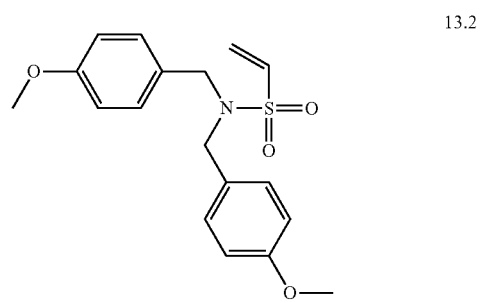

N,N-Bis(4-methoxybenzyl)ethenesulfonamide, Example 13.2. To a solution of bis(4-methoxybenzyl)amine (Example 406.1, 5.11 g, 19.86 mmol) and TEA (8.30 mL, 59.6 mmol) in DCM (99 mL) at RT was added 2-chloroethanesulfonyl chloride (2.51 mL, 23.83 mmol) in DCM (25 mL) dropwise. The reaction was stirred at RT overnight. The reaction was diluted with a saturated NaCl solution and extracted with DCM, dried over MgSO$_4$, filtered, and evaporated onto silica gel. Purification of the residue by flash silica gel chromatography on a 220 g Redisep Gold pre-packed spherical silica gel column (eluent: 0-30% EtOAc/hexanes, gradient elution) provided the title product as a white solid (5.15 g, 75% yield).

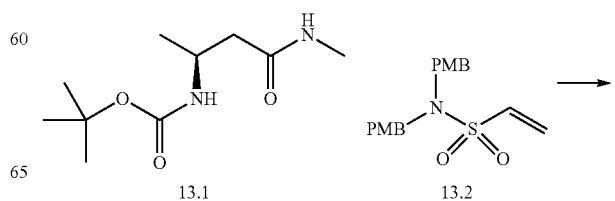

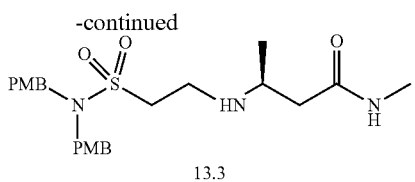

13.3

(S)-3-((2-(N,N-Bis(4-methoxybenzyl)sulfamoyl)ethyl)amino)-N-methylbutanamide, Example 13.3. Example 13.1 (130 mg, 0.60 mmol) was dissolved in DCM (7 mL) and HCl (4.0 M in dioxane, 0.751 mL, 3.01 mmol) was added. The reaction was then stirred for 4 h. Next, the reaction was concentrated in vacuo and redissolved in MeOH (3 mL). TEA (0.503 mL, 3.61 mmol) was then added, followed by Example 13.2 (209 mg, 0.601 mmol). The reaction was heated at 60° C. overnight and then concentrated in vacuo. Purification on silica gel eluting with 0-8% MeOH/DCM gradient provided the title compound (220 mg, 70% yield for 2 steps). LCMS ESI (pos.) m/z: 464.1 (M+H)+.

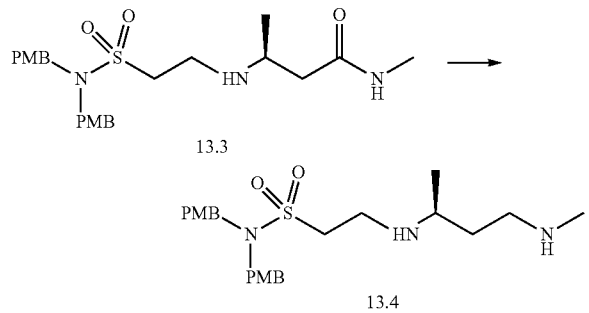

13.3

13.4

(S)-N,N-Bis(4-methoxybenzyl)-2-((4-(methylamino)butan-2-yl)amino)ethanesulfonamide, Example 13.4. (S)-3-((2-(N,N-Bis(4-methoxybenzyl)sulfamoyl)ethyl)amino)-N-methylbutanamide (200 mg, 0.431 mmol) was azeotroped with toluene. THF (4 mL) was added, followed by borane-methyl sulfide complex (0.102 mL, 1.08 mmol). The reaction was heated at 65° C. for 3 h. MeOH was then added to quench the excess borane and the reaction was concentrated in vacuo. The reaction mixture was dissolved in a mixture of MeOH (3 mL) and HCl (3 N, 4.5 mL). The mixture was stirred for 30 min, and then 3N NaOH was added to give a basic solution that was further stirred for 30 min. The mixture was extracted with IPA and CHCl₃ and concentrated in vacuo. The material was purified on silica gel eluting with 0.5% NH₄OH in DCM and MeOH to give the title compound (98.0 mg, 51%). LCMS ESI (pos.) m/z: 450.1 (M+H)+.

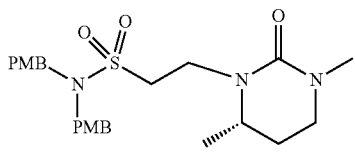

13.5

(S)-2-(3,6-Dimethyl-2-oxotetrahydropyrimidin-1(2H)-yl)-N,N-bis(4-methoxybenzyl)ethanesulfonamide, Example 13.5. Example 13.4 (98 mg, 0.218 mmol) was azeotroped with toluene. DCM (3 mL) was added, followed by TEA (0.061 mL, 0.44 mmol) followed by CDI (36.4 mg, 0.225 mmol). The reaction was stirred at RT for 2 h, followed by heating to 40° C. and continued stirring overnight. A further aliquot of CDI (18 mg), TEA (30 L) and DCM (1.5 mL) were added to the reaction mixture and heating continued for 2 d. The mixture was concentrated in vacuo and purified on silica gel combiflash eluting with 0-7% MeOH in DCM to yield the intermediate, which was dissolved in dioxane (3 mL) and Hunig's base (0.076 mL, 0.44 mmol) and heated to 100° C., stirring continued overnight. After which, the reaction was concentrated in vacuo and purified on silica gel eluting with 0-7% MeOH/DCM, to give the title product (79.0 mg, 76%). LCMS ESI (pos.) m/z: 476.1 (M+H)+.

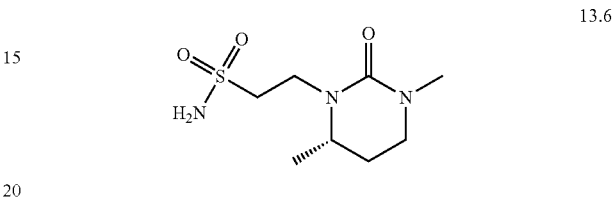

13.6

(S)-2-(3,6-Dimethyl-2-oxotetrahydropyrimidin-1(2H)-yl)ethanesulfonamide, Example 13.6. (S)-2-(3,6-Dimethyl-2-oxotetrahydropyrimidin-1(2H)-yl)-N,N-bis(4-methoxybenzyl)ethanesulfonamide (77 mg, 0.162 mmol) was azeotroped with toluene. TFA (1619 μL) was added, followed by anisole (70.7 μL, 0.648 mmol) and the reaction was stirred overnight. The reaction mixture was concentrated in vacuo and the initial material was purified on silica gel eluting with 0-10% MeOH/DCM using an ELSD detector to give the title compound (32.0 mg, 84%).

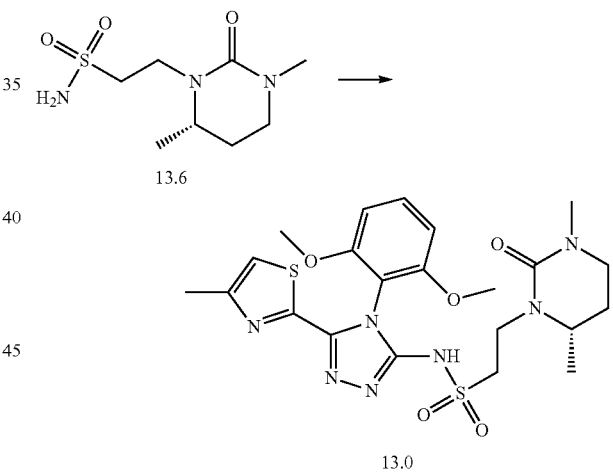

13.6

13.0

N-(4-(2,6-Dimethoxyphenyl)-5-(4-methyl-1,3-thiazol-2-yl)-4H-1,2,4-triazol-3-yl)-2-((6S)-3,6-dimethyl-2-oxotetrahydro-1(2H)-pyrimidinyl)ethanesulfonamide, Example 13.0. To a solution of 2-isothiocyanato-1,3-dimethoxybenzene (Example 465.0, 0.043 g, 0.220 mmol) and (S)-2-(3,6-dimethyl-2-oxotetrahydropyrimidin-1(2H)-yl)ethanesulfonamide (Example 13.6, 0.047 g, 0.200 mmol) in ACN (0.4 mL) was added cesium carbonate (0.085 g, 0.260 mmol). The reaction was stirred at RT for 16 h. To the reaction mixture was then added silver(I) nitrate (0.068 g, 0.399 mmol), 4-methylthiazole-2-carbohydrazide (0.031 g, 0.200 mmol), and the reaction was further stirred for 10 min at RT. The reaction was then filtered through a plug of silica gel and concentrated in vacuo. To a solution of (S,Z)-N'-(2,6-dimethoxyphenyl)-N-((2-(3,6-dimethyl-2-oxotetrahydropyrimidin-1(2H)-yl)ethyl)sulfonyl)-2-(4-methylthiazole-2-carbonyl)hydrazinecarboximidamide (0.111 g, 0.200 mmol)

in 1,4-dioxane (2.0 mL) was added TFA (0.093 mL, 1.20 mmol). The reaction was stirred at 90° C. for 48h. The mixture was then concentrated in vacuo and a saturated solution of sodium hydrogen carbonate was added. The mixture was extracted with DCM and concentrated in vacuo. The material was purified on silica gel eluting with 0-80% hexanes in EtOAc/EtOH (3/1) to give the title compound (0.0337 g, 31% yield). $^1$H NMR (400 MHz, CD$_2$Cl$_2$) δ 7.49 (t, J=8.5 Hz, 1H), 6.96 (s, 1H), 6.70 (d, J=8.6 Hz, 2H), 4.00-3.88 (m, 1H), 3.75 (s, 3H), 3.75 (s, 3H), 3.66 (q, J=7.0 Hz, 1H), 3.55 (dd, J=4.2, 10.5 Hz, 1H), 3.44-3.17 (m, 4H), 3.15-3.06 (m, 1H), 2.89 (s, 3H), 2.31 (s, 3H), 2.11-1.98 (m, 1H), 1.64 (qd, J=3.8, 13.3 Hz, 1H), 1.19 (t, J=7.0 Hz, 2H), 1.14 (d, J=6.7 Hz, 3H). LCMS-ESI (pos.) m/z: 536.3 (M+H)$^+$.

Example 14.0. Preparation of (1S,2R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide and (1R,2S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide

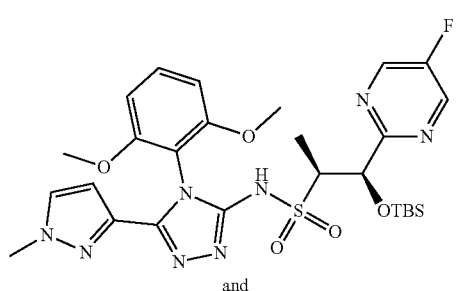

14.1

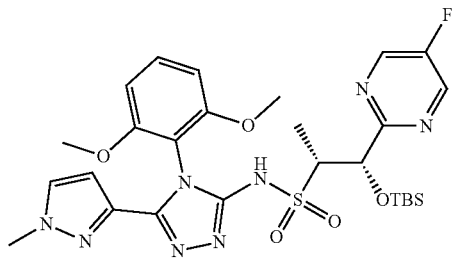

(1R,2S)-1-((tert-Butyldimethylsilyl)oxy)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide and (1S,2R)-1-((tert-butyldimethylsilyl)oxy)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide, Example 14.1. To a solution of Example 465.0 (0.031 g, 0.16 mmol) and (1S,2R)-1-((tert-butyldimethylsilyl)oxy)-1-(5-fluoropyrimidin-2-yl)propane-2-sulfonamide and (1R,2S)-1-((tert-butyldimethylsilyl)oxy)-1-(5-fluoropyrimidin-2-yl)propane-2-sulfonamide (prepared in an anlogous fashion to that of Example 466.6, 0.05 g, 0.143 mmol) in ACN (1.43 mL) was added cesium carbonate (0.061 g, 0.19 mmol). The reaction was stirred at RT for 16 h. To the reaction mixture was then added silver(I) nitrate (0.049 g, 0.29 mmol) and 1-methyl-1H-pyrazole-3-carbohydrazide (0.020 g, 0.143 mmol) and stirring was continued for 10 min at RT. After which, the reaction was filtered through a plug of silica gel and concentrated in vacuo. The initial product was dissolved in 1,4-dioxane (1.43 mL) and TFA (0.066 mL, 0.86 mmol) was added. The reaction was stirred at 90° C. for 16 h. The reaction was then concentrated in vacuo to give Example 14.1. LCMS-ESI (pos.) m/z: 633.3 (M+H)$^+$.

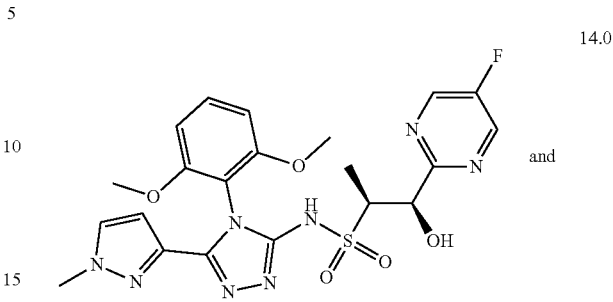

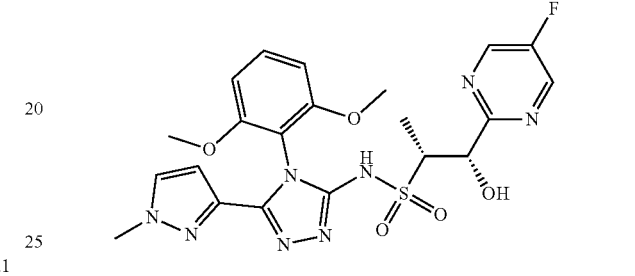

(1S,2R)-N-(4-(2,6-Dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide and (1R,2S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-1-hydroxy-2-propanesulfonamide, Example 14.0. To a solution of Example 14.1 (0.09 g, 0.142 mmol) in EtOH (1 mL) was added HCl (4.32 µL, 0.142 mmol). The reaction was stirred at RT for 16 h. The reaction was then concentrated in vacuo and the pH was adjusted to pH 7. The material was extracted with EtOAc and the organics were concentrated in vacuo. The initial material was purified on silica gel eluting with 0-80% EtOAc/EtOH (3/1) in hexanes to give Example 14.0 (0.005 g, 7% yield). $^1$H NMR (400 MHz, CD$_2$Cl$_2$) δ 11.11-10.66 (m, 1H), 8.61 (s, 2H), 7.48 (t, J=8.5 Hz, 1H), 7.28 (d, J=2.3 Hz, 1H), 6.73-6.70 (m, 1H), 6.70-6.68 (m, 1H), 6.09 (d, J=2.3 Hz, 1H), 5.47 (s, 1H), 3.92 (br. s, 1H), 3.80 (s, 3H), 3.75 (m, 6H), 3.68 (dq, J=1.9, 7.0 Hz, 1H), 1.13 (d, J=7.0 Hz, 3H). LCMS-ESI (pos.) m/z: 519.2 (M+H)$^+$.

Example 15.0. Preparation of (2R)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide and (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide

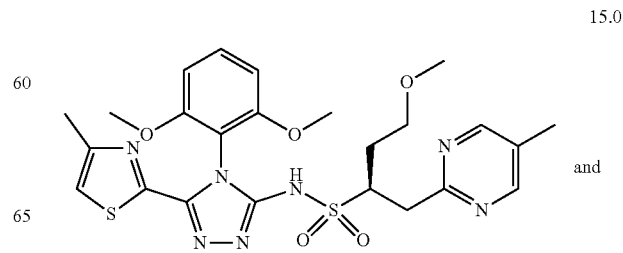

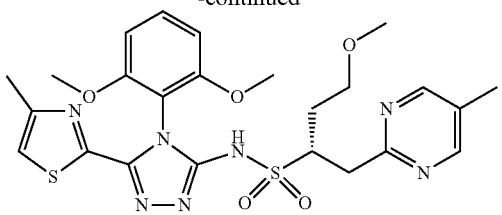

(2R)-N-(4-(2,6-Dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide and (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide, Example 15.0. The title compound was prepared following the procedures described in Example 10.0 employing Example 397.4 and 4-methoxy-1-(5-methylpyrimidin-2-yl)butane-2-sulfonic acid (prepared in an anlogous manner to the procedures described in Example 22.0 employing trans-4-(tert-butyldimethylsiloxy)-1-buten-1-ylboronic acid pinacol ester and 2-bromo-5-methylpyrimidine and reactions described therein. $^1$H NMR (400 MHz, CD$_3$OD) δ 8.60 (s, 2H) 7.52 (t, J=8.61 Hz, 1H) 7.23 (s, 1H) 6.80 (d, J=8.61 Hz, 2H) 3.79-3.87 (m, 1H) 3.75 (s, 3H) 3.74 (s, 3H) 3.56 (dd, J=15.06, 4.89 Hz, 1H) 3.33-3.43 (m, 2H) 3.06-3.15 (m, 4H) 2.33 (s, 3H) 2.30 (d, J=0.98 Hz, 3H) 2.18 (m, J=14.48, 5.87 Hz, 1H) 1.74-1.86 (m, 1H). LCMS-ESI (pos.) m/z: 560.0 (M+H)$^+$.

Example 16.0. Preparation of (3S,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide

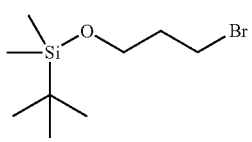

16.1

(3-Bromopropoxy)(tert-butyl)dimethylsilane, Example 16.1. A flask was charged with 3-bromopropan-1-ol (3.25 mL, 36.0 mmol), 1H-imidazole (4.90 g, 71.9 mmol) and tert-butylchlorodimethylsilane (5.69 g, 37.8 mmol). DCM (100 mL) was added and the reaction was stirred overnight. Water and EtOAc were added to the reaction mixture. The EtOAc layer was dried, and then concentrated in vacuo and purified by silica gel to give the title compound.

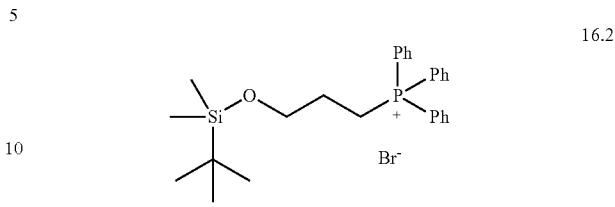

16.2

(3-((tert-Butyldimethylsilyl)oxy)propyl)triphenylphosphonium bromide, Example 16.2. A flask was charged with (3-bromopropoxy)(tert-butyl)dimethylsilane (Example 16.1, 6.40 g, 25.3 mmol) which was azeotroped with toluene. Triphenylphosphine (4.51 mL, 19.44 mmol) was added and the flask was flushed with nitrogen. Benzene (5 mL) was added and the reaction was heated at 90° C. overnight. After overnight refluxing and upon cooling, a solid precipitated. The reaction mixture was diluted with hexanes and filtered to yield the title product (7.69 g) as a white solid which was directly used in the next step.

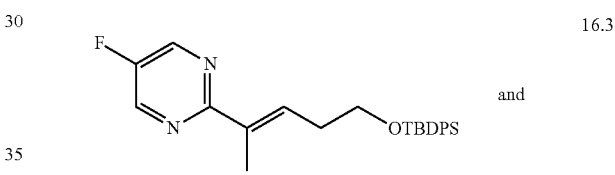

16.3 and

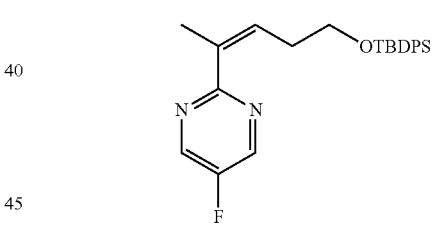

(E)-2-(5-((tert-Butyldiphenylsilyl)oxy)pent-2-en-2-yl)-5-fluoropyrimidine and (Z)-2-(5-((tert-butyldiphenylsilyl)oxy)pent-2-en-2-yl)-5-fluoropyrimidine, Example 16.3. (3-((tert-Butyldiphenylsilyl)oxy)propyl)triphenylphosphonium bromide (Example 16.2, 8.47 g, 13.25 mmol) was azeotroped with toluene and dried on a high vacuum pump overnight. The material was suspended in THF (65 mL) under nitrogen. The suspension was cooled in an ice-bath. NaHMDS (1.0 M in THF, 14.17 mL, 14.17 mmol) was added dropwise. Then after 30 min, 1-(5-fluoropyrimidin-2-yl)ethanone (Bellen Chem, 1.16 g, 8.28 mmol) in THF (2 mL) was added, and the resulting mixture was stirred overnight. A saturated solution of NH$_4$Cl was added followed by EtOAc. The organic extracts were concentrated in vacuo and purified on silica gel eluting with 0-10% EtOAc/hexanes to obtain the title compound (2.16 g).

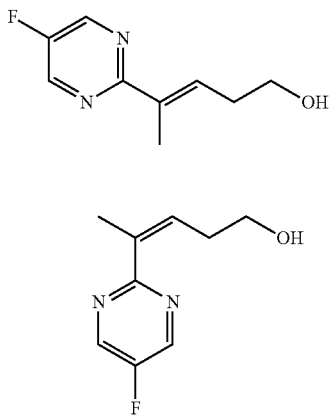

16.4 and (E)-4-(5-Fluoropyrimidin-2-yl)pent-3-en-1-ol and (Z)-4-(5-fluoropyrimidin-2-yl)pent-3-en-1-ol, Example 16.4. A flask containing Example 16.3 (2.16 g, 5.14 mmol) was azeotroped with toluene. THF (15 mL) was added, followed by TBAF (1.0 M, 2.57 mL, 2.57 mmol). The reaction mixture was stirred at RT for 75 min. The reaction mixture was then concentrated in vacuo and purified on silica gel to give the title compound (0.96 g). LCMS-ESI (pos.) m/z: 183.0 (M+H)$^+$.

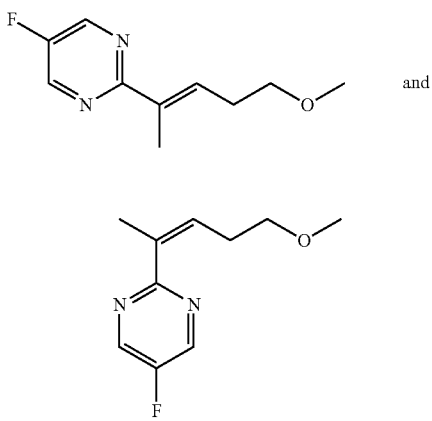

16.5 and (E)-5-Fluoro-2-(5-methoxypent-2-en-2-yl)pyrimidine and (Z)-5-fluoro-2-(5-methoxypent-2-en-2-yl)pyrimidine, Example 16.5. Example 16.4 (790 mg, 4.34 mmol) was azeotroped with toluene. DMF (14 mL) was added, and the mixture was cooled to 0° C. NaH (191 mg, 4.77 mmol) was added and the mixture was stirred for 10 min. Methyl iodide (0.542 mL, 8.67 mmol) was then added and the reaction was allowed to stir at 0° C. for 5-10 min and then the temperature was raised to RT. The reaction was further stirred for 5 h. A saturated solution of NH$_4$Cl was then added to the reaction, the reaction was extracted with EtOAc, and the organics were concentrated in vacuo. Purification on silica gel eluting with 0-70% EtOAc/hexanes afforded the title compound (522 mg).

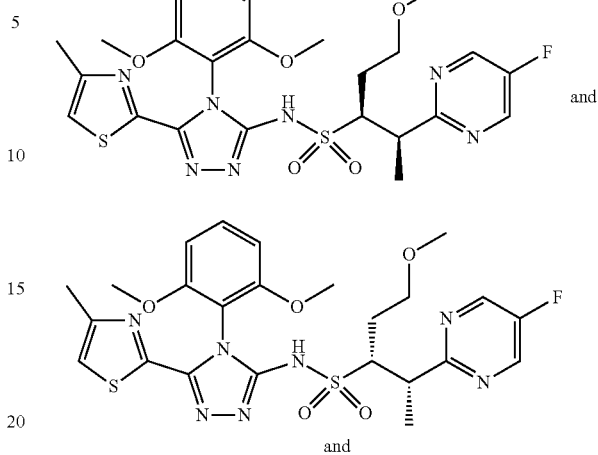

16.0 and and and

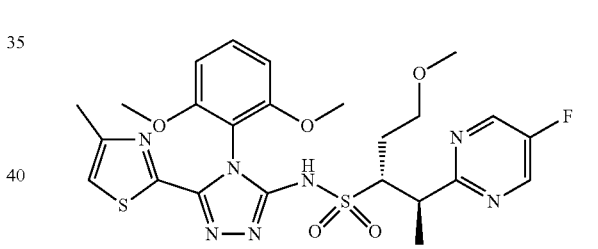

(3S,4R)-N-(4-(2,6-Dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide and (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide, Example 16.0. The title compound was prepared following the same procedure as Example 10.0 employing Example 397.4 and 4-(5-fluoropyrimidin-2-yl)-1-methoxypentane-3-sulfonic acid (prepared in an anlogous manner to the procedures described in Example 22.0 employing Example 16.5 and reactions described therein. $^1$H NMR (400 MHz, CD$_3$OD) δ 8.65 (s, 1H), 8.60 (s, 1H), 7.52 (td, J=8.51, 3.72 Hz, 1H), 7.23 (t, J=0.98 Hz, 1H), 6.80 (m, 2H), 3.88 (m, 1H), 3.77 (s, 3H), 3.73 (m, 3H), 3.64 (m, 1H), 3.44 (t, J=6.85 Hz, 1H), 3.28 (m, 1H), 3.12 (m, 3H), 2.31 (d, J=0.78 Hz, 3H), 2.01 (m, 2H), 1.40 (m, 3H). LCMS-ESI (pos.) m/z: 578.0 (M+H)+.

Example 17.0. Preparation of (2R)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide or (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide 17.0

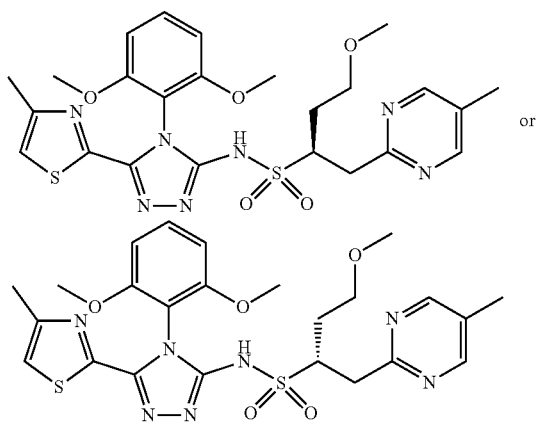

(2R)-N-(4-(2,6-Dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide or (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide, Example 17.0. Example 15.0 was separated by SFC (AD-H (2×25 cm) 20% MeOH/CO2, 100 bar, 70 mL/min, 220 nm, inj vol.: 1.5 mL, 8 mg/mL MeOH) to give the first peak (faster-eluting) from chiral separation as the title compound. 1H NMR (400 MHz, CD3OD) δ 8.56 (s, 2H) 7.51 (t, J=8.51 Hz, 1H) 7.22 (s, 1H) 6.79 (d, J=8.61 Hz, 2H) 3.79-3.89 (m, 1H) 3.74 (s, 3H) 3.73 (s, 3H) 3.54-3.62 (m, 1H) 3.32-3.42 (m, 2H) 3.02-3.13 (m, 4H) 2.30 (m, 6H) 2.11-2.23 (m, 1H) 1.74-1.87 (m, 1H). LCMS-ESI (pos.) m/z: 560.0 (M+H)+.

Example 18.0. Preparation of (2R)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide or (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide 18.0

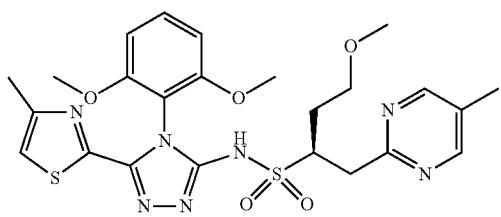

-continued

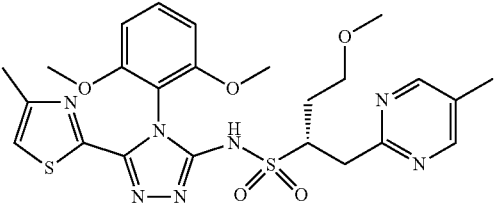

(2R)-N-(4-(2,6-Dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide or (2S)-N-(4-(2,6-dimethoxyphenyl)-5-(4-methyl-1,3-thiazol-2-yl)-4H-1,2,4-triazol-3-yl)-4-methoxy-1-(5-methyl-2-pyrimidinyl)-2-butanesulfonamide, Example 17.0. Example 18.0 is the enantiomer of Example 17.0. Further elution under the conditions described in Example 17.0 delivered the second peak to elute on subjecting Example 15.0 to the SFC conditions described. 1H NMR (400 MHz, CD3OD) δ 8.56 (s, 2H) 7.52 (t, J=8.51 Hz, 1H) 7.23 (s, 1H) 6.79 (d, J=8.41 Hz, 2H) 3.78-3.87 (m, 1H) 3.75 (s, 3H) 3.73 (s, 3H) 3.57 (dd, J=14.77, 4.40 Hz, 1H) 3.32-3.41 (m, 2H) 3.02-3.13 (m, 4H) 2.29-2.32 (m, 6H) 2.12-2.22 (m, 1H) 1.74-1.85 (m, 1H). LCMS-ESI (pos.) m/z: 560.0 (M+H)+.

Example 19.0. Preparation of (3S,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide 19.0

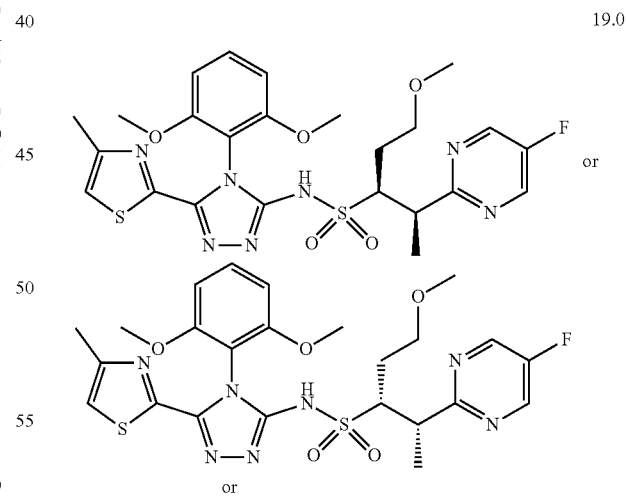

or

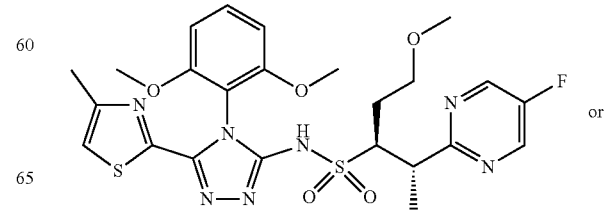

or

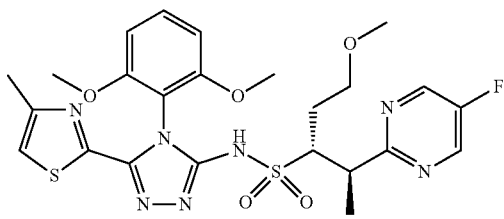

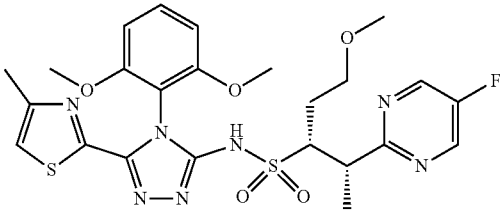

(3S,4R)-N-(4-(2,6-Dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide, Example 19.0. Example 16.0 was purified by SFC using the following conditions: Preparative SFC: 1st Purification: AS-H (5 m, 21 mm×25 cm, S/N=1071) with 13% organic modifier modifier: 87% carbon dioxide; Organic modifier: EtOH no additive. F=70 mL/min, T=40° C., BPR=100 bar, P=179 bar, 220 nm. The sample (~150 mg) was dissolved in 10 mL MeOH. ~15 mg/mL, 0.3 mL per injection (~5 mg per injection). Second stage purification: Preparative SFC: OZ-H (5 um, 21 mm×25 cm, S/N=1221) with 50% organic modifier modifier: 50% carbon dioxide; Organic modifier: EtOH no additive. F=50 mL/min, T=40° C., BPR=100 bar, P=227 bar, 220 nm. The sample dissolved in 4 mL MeOH. 1.2 mL per injection. Four isomers were isolated. Example 19.0 was the third peak off the column. $^1$H NMR (400 MHz, CD$_3$OD) δ 8.65 (s, 2H), 7.52 (t, J=8.51 Hz, 1H), 7.23 (d, J=0.78 Hz, 1H), 6.79 (dd, J=8.51, 2.84 Hz, 2H), 3.93 (m, 1H), 3.78 (m, 1H), 3.73 (s, 3H), 3.73 (s, 3H), 3.29 (m, 2H), 3.03 (s, 3H), 2.30 (d, J=0.78 Hz, 3H), 2.10 (m, 1H), 1.89 (m, 1H), 1.37 (d, J=7.24 Hz, 3H). LCMS-ESI (pos.) m/z: 578.0 (M+H)$^+$.

Example 20.0. Preparation of (3S,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide 20.0

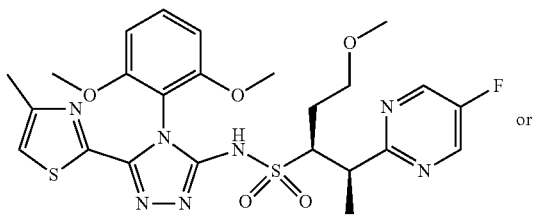

or

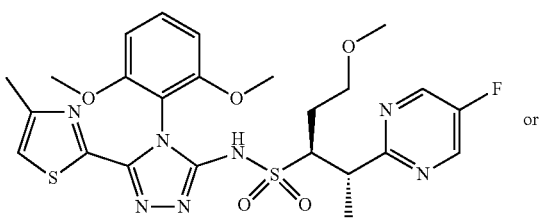

or

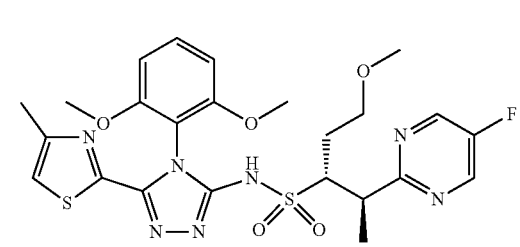

(3S,4R)-N-(4-(2,6-Dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide, Example 20.0. Example 20.0 was the fourth peak off the column, following the conditions described in Example 19.0. $^1$H NMR (400 MHz, CD$_3$OD) δ 8.65 (s, 2H), 7.52 (t, J=8.51 Hz, 1H), 7.23 (s, 1H), 6.79 (dd, J=8.41, 2.93 Hz, 2H), 3.93 (m, 1H), 3.79 (m, 1H), 3.73 (s, 3H), 3.73 (s, 3H), 3.29 (m, 2H), 3.03 (s, 3H), 2.30 (s, 3H), 2.11 (m, 1H), 1.90 (m, 1H), 1.37 (d, J=7.24 Hz, 3H). LCMS-ESI (pos.) m/z: 578.0 (M+H)$^+$.

Example 21.0. Preparation of (3S,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide

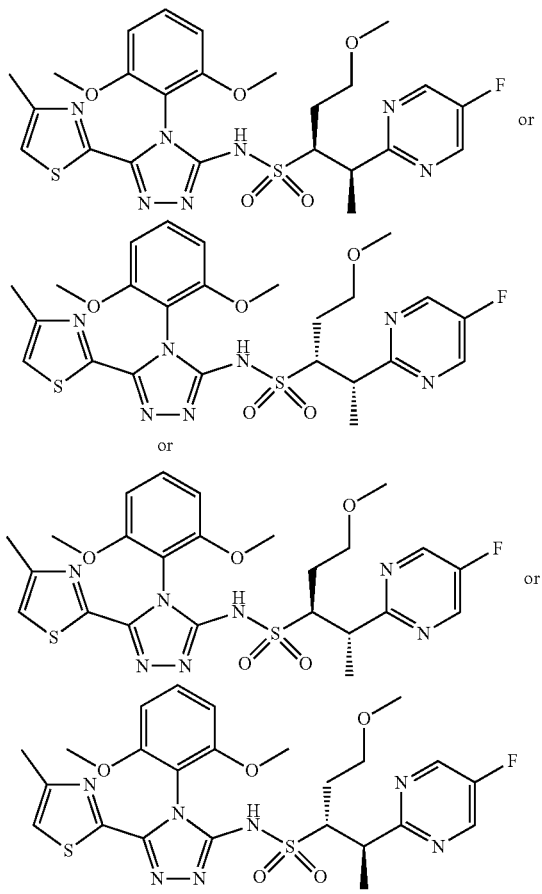

21.0

(3S,4R)-N-(4-(2,6-Dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3S,4S)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide or (3R,4R)-N-(4-(2,6-dimethoxyphenyl)-5-(4-methyl-1,3-thiazol-2-yl)-4H-1,2,4-triazol-3-yl)-4-(5-fluoro-2-pyrimidinyl)-1-methoxy-3-pentanesulfonamide, Example 21.0. Example 21.0 was the second peak off the column. $^1$H NMR (400 MHz, CD$_3$OD) δ 8.65 (s, 2H), 7.52 (t, J=8.51 Hz, 1H), 7.23 (s, 1H), 6.79 (dd, J=8.41, 2.93 Hz, 2H), 3.93 (m, 1H), 3.78 (m, 1H), 3.73 (s, 3H), 3.73 (s, 3H), 3.28 (m, 2H), 3.03 (s, 3H), 2.30 (s, 3H), 2.11 (m, 1H), 1.89 (m, 1H), 1.37 (d, J=7.24 Hz, 3H). LCMS-ESI (pos.) m/z: 578.0 (M+H)$^+$.

Example 22.0. Preparation of (2R)-4-(benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide and (2S)-4-(benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide

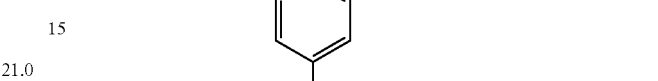

22.1

((But-3-yn-1-yloxy)methyl)benzene, Example 22.1. To a cooled (0° C.) 250 mL RBF containing 3-butyn-1-ol (10.00 mL, 143 mmol) in THF (100 mL) was added NaH (60% dispersion in mineral oil, 3.60 mL, 171 mmol) portionwise. To the reaction mixture was added benzyl bromide (17.43 mL, 143 mmol, Alfa Aesar) and the reaction was cooled in an ice bath. The reaction was stirred at RT overnight. The reaction mixture was then diluted with a saturated solution of NaHCO$_3$ and extracted with EtOAc. The organic extract was washed with a saturated solution of NaCl and dried over Na$_2$SO$_4$. The solution was filtered and concentrated in vacuo to give the initial material as an oil. The initial material was distilled under vacuum to provide Example 22.1 (22.1 g, 138 mmol, 97% yield) as an oil.

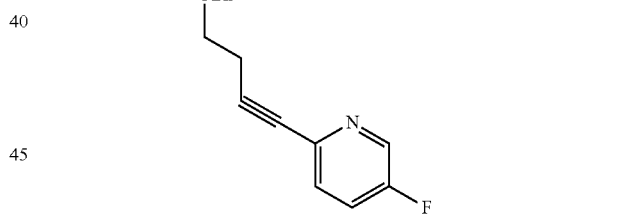

22.2

2-(4-(Benzyloxy)but-1-yn-1-yl)-5-fluoropyridine, Example 22.2. To a 100 mL RBF was added ((but-3-yn-1-yloxy)methyl)benzene (1.514 g, 9.45 mmol), TEA (5.97 mL, 43.0 mmol) and 2-chloro-5-fluoropyridine (0.87 mL, 8.59 mmol) in THF under Ar. To the reaction mixture was added bis(triphenylphosphine)palladium(II) dichloride (0.301 g, 0.43 mmol, Strem Chemicals Inc.) followed by copper(I) iodide (0.029 mL, 0.86 mmol, Strem Chemicals Inc.). The reaction mixture was stirred at 70° C. for 3 h. The reaction mixture was then diluted with 1N HCl and extracted with EtOAc. The organic extract was washed with a saturated solution of NaCl and dried over Na$_2$SO$_4$. The solution was filtered and concentrated in vacuo to give the initial material as an oil. The initial material was absorbed onto a plug of silica gel and purified by chromatography through a Redi-Sep pre-packed gold silica gel column (12 g), eluting with a gradient of 0% to 100% EtOAc in hexanes, to provide 2-(4-(benzyloxy)but-1-yn-1-yl)-5-fluoropyridine (410 mg, 1.61 mmol, 19% yield) as a white solid. LCMS-ESI (pos.) m/z: 256.2 (M+H)$^+$.

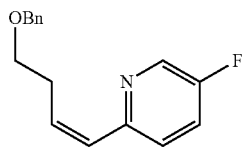

22.3

(Z)-2-(4-(Benzyloxy)but-1-en-1-yl)-5-fluoropyridine, Example 22.3. To a 25 mL RBF was added 2-(4-(benzyloxy)but-1-yn-1-yl)-5-fluoropyridine (1.0 g, 3.92 mmol) and quinoline (0.460 mL, 3.92 mmol) and palladium on calcium carbonate, lead poisoned (0.208 mL, 0.098 mmol) in MeOH under $H_2$. The reaction mixture was stirred overnight. The solvent was removed under vacuum. The initial material was absorbed onto a plug of silica gel and purified by chromatography through a Redi-Sep pre-packed gold silica gel column (12 g), eluting with a gradient of 0% to 60% EtOAc in hexanes, to provide (Z)-2-(4-(benzyloxy)but-1-en-1-yl)-5-fluoropyridine (780 mg, 77% yield) as an yellow oil. LCMS-ESI (pos.) m/z: 258.0 (M+H)$^+$.

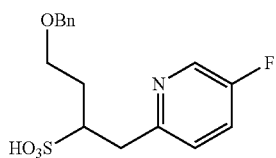

22.4

4-(Benzyloxy)-1-(5-fluoropyridin-2-yl)butane-2-sulfonic acid, Example 22.4. To a suspension of (Z)-2-(4-(benzyloxy)but-1-en-1-yl)-5-fluoropyridine (800 mg, 3.11 mmol) in water (0.8 mL) and THF (0.2 mL) was added sodium hydrogensulfite (425 mg, 4.08 mmol, 1.3 eq). The resulting bi-phasic mixture was stirred at 50° C. over the weekend. EtOH (0.5 mL) was added and the reaction was further heated at 50° C. overnight. Tetrabutylammonium bromide (218 mg, 0.676 mmol) was added and heating continued at 50° C. overnight. Sodium hydrogensulfite (1.1 g, 10.57 mmol, 3.4 eq) and water (0.2 mL) were added and heating continued at 60° C. overnight. Water (1.0 mL) was added and the reaction was heated at 80° C. over the weekend and then heated at 90° C. for a week. LCMS showed 95% conversion to the product. The reaction was cooled to RT. The reaction mixture was then acidified to pH 2 using concentrated HCl, the reaction was concentrated in vacuo to remove all solvents and water, and then it was dried on HVAC. The material was purified by reverse-phase preparative HPLC in 2 injections using a Phenomenex Gemini 10 uM C18, 250×50 mm column; the mobile phase was 0.1% TFA in ACN/$H_2O$; the method was 2.5% isocratic for 5 min, then grading to 70% over 10 min, then 95% isocratic for 3 min (collected the peaks that were visible at 220 nm). The title fractions were lyophilized to give 4-(benzyloxy)-1-(5-fluoropyridin-2-yl)butane-2-sulfonic acid (612 mg, 58.0% yield). LCMS-ESI (pos.) m/z: 340.0 (M+H)$^+$.

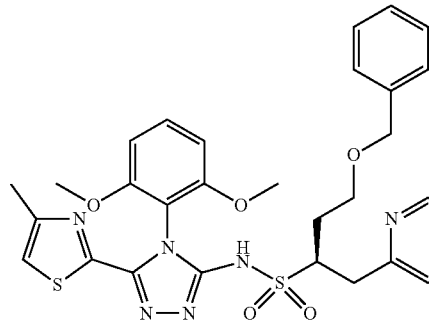

22.0 and

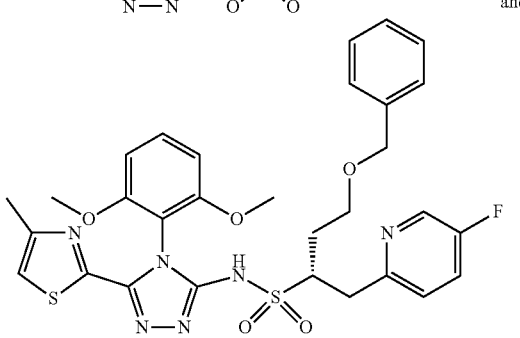

(2R)-4-(Benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide and (2S)-4-(benzyloxy)-N-(4-(2,6-dimethoxyphenyl)-5-(4-methyl-1,3-thiazol-2-yl)-4H-1,2,4-triazol-3-yl)-1-(5-fluoro-2-pyridinyl)-2-butanesulfonamide, Example 22.0. Following the procedure described in Example 10.0 employing Example 397.4 and Example 22.4, delivered the title compound. $^1$H NMR (400 MHz, CD$_3$OD) δ 8.34 (d, J=2.9 Hz, 1H) 7.46-7.56 (m, 2H) 7.21-7.36 (m, 5H) 7.13-7.20 (m, 2H) 6.79 (d, J=8.0 Hz, 2H) 4.27 (q, J=11.5 Hz, 2H) 3.73 (s, 3H) 3.70 (s, 3H) 3.62-3.68 (m, 1H) 3.39-3.55 (m, 3H) 2.95-3.05 (m, 1H) 2.30 (d, J=1.0 Hz, 3H) 2.16-2.27 (m, 1H) 1.79-1.88 (m, 1H). LCMS-ESI (pos.) m/z: 639.0 (M+H)$^+$.

Example 23.0. Preparation of (1R,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide or (1S,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1R,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide

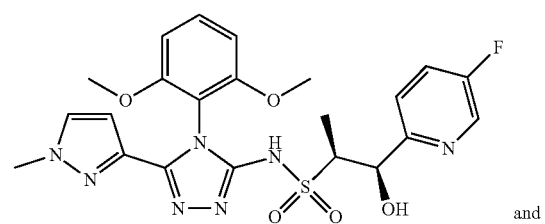

23.0 and

-continued

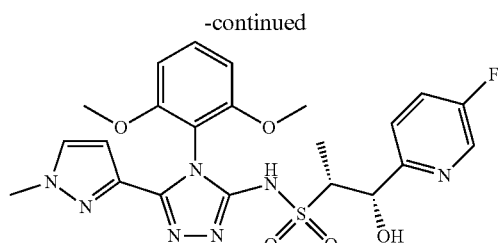

or

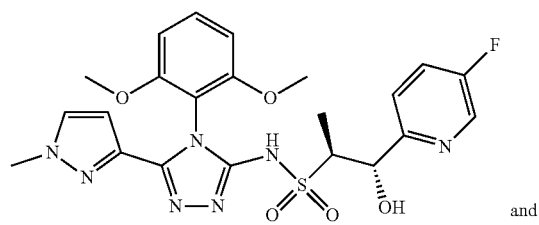

and

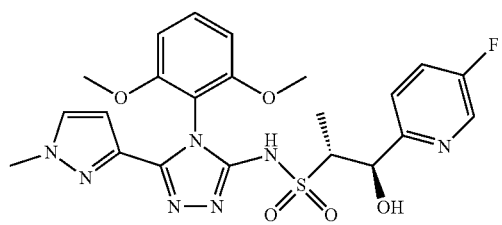

(1R,2S)-N-(4-(2,6-Dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide or (1S,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1R,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide, Example 23.0. The title compound was prepared according to the procedure described in Example 14.0, employing (1S,2R)-1-((tert-butyldimethylsilyl)oxy)-1-(5-fluoropyridin-2-yl)propane-2-sulfonamide and (1R,2S)-1-((tert-butyldimethylsilyl)oxy)-1-(5-fluoropyridin-2-yl)propane-2-sulfonamide or (1R,2R)-1-((tert-butyldimethylsilyl)oxy)-1-(5-fluoropyridin-2-yl)propane-2-sulfonamide and (1S,2S)-1-((tert-butyldimethylsilyl)oxy)-1-(5-fluoropyridin-2-yl)propane-2-sulfonamide (prepared in an anlogous fashion to that of Example 466.6, employing 5-fluoropicolinaldehyde and Example 467.0). $^1$H NMR (400 MHz, CD$_3$OD) δ 8.42 (d, J=2.70 Hz, 1H) 7.57-7.67 (m, 2H) 7.46-7.54 (m, 2H) 6.79 (dd, J=8.50, 3.11 Hz, 2H) 6.08 (d, J=2.49 Hz, 1H) 5.37 (br. s, 1H) 3.81 (s, 3H) 3.75-3.77 (m, 3H) 3.73 (s, 3H) 3.60 (qd, J=7.08, 2.18 Hz, 1H) 1.11 (d, J=6.84 Hz, 3H). LCMS-ESI (pos.) m/z: 518.0 (M+H)$^+$.

Example 24.0. Preparation of (1R,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide 24.0

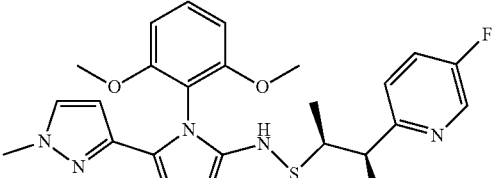

or

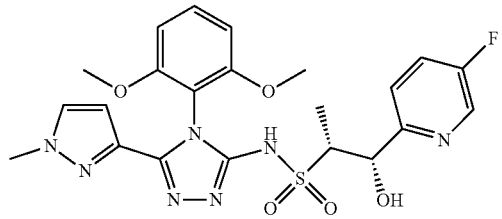

(1R,2S)-N-(4-(2,6-Dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide, Example 24.0. Example 23.0 was purified on an IA column (2×15 cm) using 30% MeOH/CO$_2$, 100 bar at 65 mL/min, 220 nm, with an injection volume of 0.5 mL, 8 mg/mL MeOH. To give peak one as the title compound (52 mg, >99% ee) as a white solid. $^1$H NMR (500 MHz, CD$_3$OD) δ 8.39-8.41 (m, 1H) 7.58-7.61 (m, 2H) 7.48-7.53 (m, 2H) 6.78-6.82 (m, 2H) 6.07 (d, J=2.45 Hz, 1H), 5.37-5.39 (m, 1H) 3.81 (s, 3H) 3.75 (s, 3H) 3.73 (s, 3H) 3.57-3.65 (m, 1H) 1.07-1.10 (m, 3H). LCMS-ESI (pos.) m/z: 518.2 (M+H)$^+$.

Example 25.0. Preparation of (1R,2S)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide 25.0

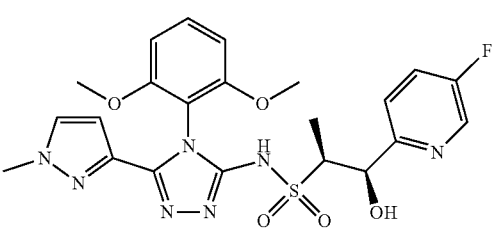

or

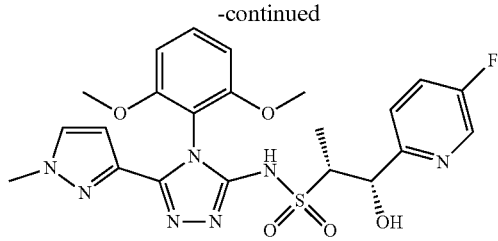

(1R,2S)-N-(4-(2,6-Dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide and (1S,2R)-N-(4-(2,6-dimethoxyphenyl)-5-(1-methyl-1H-pyrazol-3-yl)-4H-1,2,4-triazol-3-yl)-1-(5-fluoro-2-pyridinyl)-1-hydroxy-2-propanesulfonamide, Example 25.0. Further elution under the conditions described in Example 24.0 delivered peak 2 (57 mg, 98% ee). ¹H NMR (500 MHz, CD₃OD) δ 8.39-8.41 (m, 1H) 7.58-7.61 (m, 2H) 7.48-7.53 (m, 2H) 6.77-6.82 (m, 2H) 6.07 (d, J=2.20 Hz, 1H) 5.37-5.39 (m, 1H) 3.81 (s, 3H) 3.75 (s, 3H) 3.73 (s, 3H) 3.58-3.64 (m, 1H) 1.09 (d, J=6.85 Hz, 3H). LCMS-ESI (pos.) m/z: 518.2 (M+H)⁺.

Example 26.0. Preparation of (1R,2S)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide and (1S,2R)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide

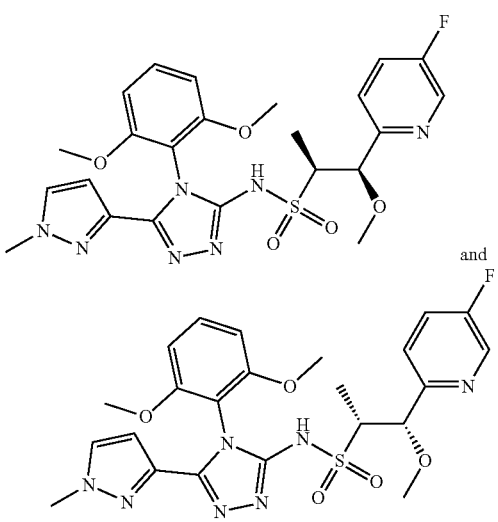

(1R,2S)-N-(4-(2,6-Dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide and (1S,2R)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide, Example 26.0. The title compound was prepared according to the procedure described in Example 14.0 employing (1R,2S)-1-(5-fluoropyridin-2-yl)-1-methoxypropane-2-sulfonamide and (1S,2R)-1-(5-fluoropyridin-2-yl)-1-methoxypropane-2-sulfonamide (prepared in an anlogous fashion to that of Example 466.0, employing 5-fluoropicolinaldehyde and Example 467.0 and isolating the major diasteromers) to give the title compound (270 mg) as an off white solid. LCMS-ESI (pos.) m/z: 532.0 (M+H)⁺.

Example 27.0. Preparation of (1R,2S)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide or (1S,2R)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide

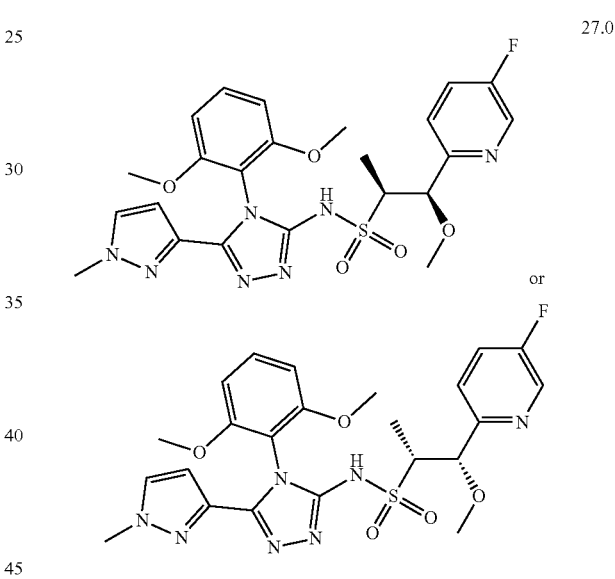

(1R,2S)-N-(4-(2,6-Dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide or (1S,2R)-N-(4-(2,6-dimethoxyphenyl)-5-(1-methyl-1H-pyrazol-3-yl)-4H-1,2,4-triazol-3-yl)-1-(5-fluoropyridin-2-yl)-1-methoxypropane-2-sulfonamide, Example 27.0. Example 26.0 was purified by SFC (250×30 mm on an AD-H column on Thar 350 with 50 mL/min IPA+100 g/min CO₂. Outlet pressure=100 bar; temperature=19° C.; wavelength=253 nm; injection volume=2.0 mL of 267 mg/15 mL (17.8 mg/mL) sample solution in MeOH:DCM (2:1). Two enantiomers were obtained. To give peak 2 as the title compound. ¹H NMR (500 MHz, CD₃OD) δ 1.14-1.17 (s, 3H), 3.23-3.30 (s, 3H), 3.37-3.45 (m, 1H), 3.72-3.80 (m, 6H), 3.82-3.86 (s, 3H), 4.98-5.07 (m, 1H), 6.03-6.08 (m, 1H), 6.75-6.85 (m, 2H), 7.45-7.56 (m, 3H), 7.60-7.68 (m, 1H), 8.43-8.50 (m, 1H). LCMS-ESI (pos.) m/z: 532.0 (M+H)⁺.

Example 28.0. Preparation of Ethyl 3-(3-(2-(4-chlorophenyl)ethylsulfonamido)-5-(thiophen-2-yl)-4H-1,2,4-triazol-4-yl)-4-methoxybenzoate

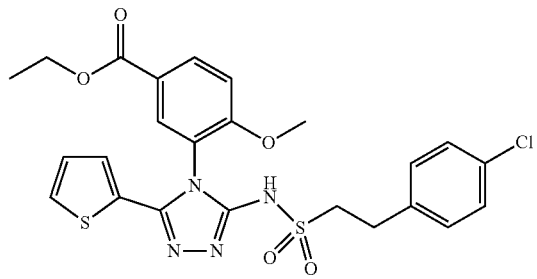

28.0

Ethyl 3-(3-(2-(4-chlorophenyl)ethylsulfonamido)-5-(thiophen-2-yl)-4H-1,2,4-triazol-4-yl)-4-methoxybenzoate, Example 28.0. A mixture of Example 133.0 (115 mg, 0.208 mmol), TEA (57.8 µL, 0.415 mmol), and 1,1'-bis(diphenylphosphino)ferrocene-palladium dichloride (16.96 mg, 0.021 mmol) in N-methyl-2-pyrrolidinone (2 mL) and EtOH (2 mL) were combined in a 50 mL RBF. The flask was evacuated with stirring and placed under an atmosphere of CO. The mixture was heated at 80° C. overnight. The mixture was partitioned between EtOAc and water, resulting in an emulsion. The emulsion layer was removed and filtered through a coarse fritted funnel. The organic layers were combined, washed with brine and evaporated to give a black solid. The material thus obtained was absorbed onto a plug of silica gel and purified by chromatography through a Redi-Sep pre-packed silica gel column (12 g), eluting with a gradient of 60% to 100% EtOAc in DCM, to provide the title compound (88 mg, 0.16 mmol, 77% yield) as a white solid. $^1$H NMR (400 MHz, CDCl$_3$) δ 10.79 (s, 1H), 8.19 (d, J=8.3 Hz, 1H), 7.93 (d, J=2.2 Hz, 1H), 7.29 (dd, J=7.3 Hz, 1H), 7.16-7.18 (m, 1H), 7.14-7.21 (m, 2H), 6.97-7.08 (m, 3H), 6.84-6.91 (m, 2H), 4.30 (q, J=7.1 Hz, 2H), 3.69 (s, 3H), 3.16-3.26 (m, 2H), 2.94-3.05 (m, 2H), 1.31 (t, J=7.1 Hz, 3H). LCMS-ESI (pos.), m/z: 547.0 (M+H)$^+$.

Example 32.0. Preparation of (2S)-N-(4-(2,6-dimethoxyphenyl)-5-(3-pyridazinyl)-4H-1,2,4-triazol-3-yl)-1-(5-fluoro-2-pyrimidinyl)-2-propanesulfonamide or (2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide

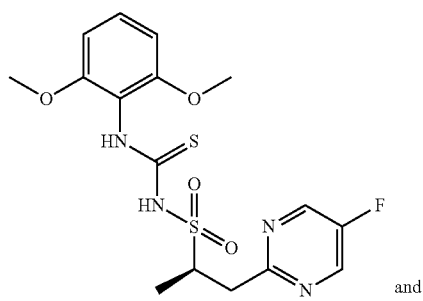

32.1 and

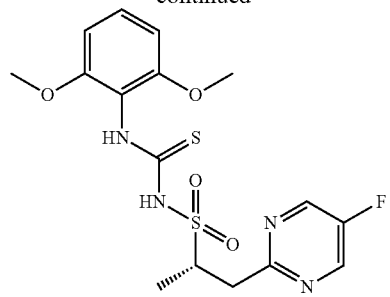

28.0

(S)-N-((2,6-Dimethoxyphenyl)carbamothioyl)-1-(5-fluoropyrimidin-2-yl)propane-2-sulfonamide and (R)-N-((2,6-dimethoxyphenyl)carbamothioyl)-1-(5-fluoropyrimidin-2-yl)propane-2-sulfonamide, Example 32.1. To a solution of (S)-1-(5-fluoropyrimidin-2-yl)propane-2-sulfonamide and (R)-1-(5-fluoropyrimidin-2-yl)propane-2-sulfonamide (Example 402.0, 1.8 g, 8.21 mmol) in DMF (10 mL) was added cesium carbonate (0.99 mL, 12.3 mmol) in portions. The mixture was stirred at RT for 5 min before 2-isothiocyanato-1,3-dimethoxybenzene (Example 465.0, 1.68 g, 8.62 mmol) was added in portions. The resulting mixture was allowed to stir at RT and was monitored by LCMS. Upon completion, 20 mL of water was added and the mixture was acidified by addition of aqueous HCl solution (2.0N, 6.16 mL, 12.32 mmol) to pH 5. The precipitate was collected and washed with water three times and then dried under vacuum to give Example 32.1 (3.37 g, 8.13 mmol, 99% yield). LCMS-ESI (pos.) m/z: 415.1 (M+H)$^+$.

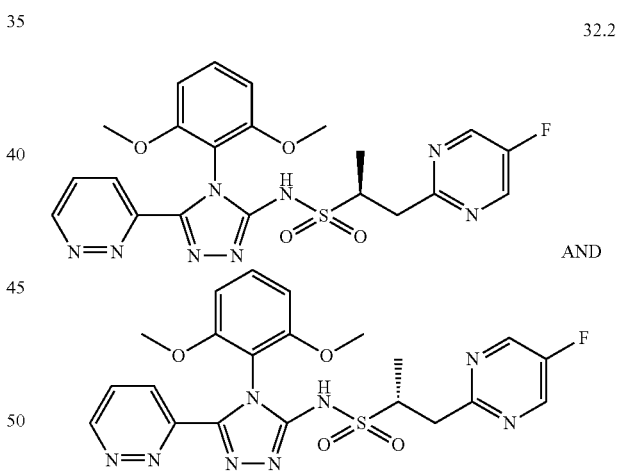

32.2

(2S)-N-(4-(2,6-Dimethoxyphenyl)-5-(3-pyridazinyl)-4H-1,2,4-triazol-3-yl)-1-(5-fluoro-2-pyrimidinyl)-2-propanesulfonamide and (2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide, Example 32.2. To a mixture of Example 32.1 (0.150 g, 0.362 mmol) and pyridazine-3-carbohydrazide Example 395.10 (0.250 g, 1.810 mmol) in DMF (1.8 mL) was added mercuric acetate (0.121 g, 0.380 mmol) in portions. The resulting mixture was allowed to stir at RT. After 1 h, TFA (0.167 mL, 2.171 mmol) was added and the resulting mixture was allowed to stir at 105° C. for 18 h. AcOH (0.209 mL, 3.62 mmol) was then added, and the resulting mixture was stirred at 110° C. for 2 d. The mixture was cooled to RT and directly absorbed onto a plug of silica gel and purified by chromatography through a Redi-Sep pre-packed silica gel column (24 g), eluting with a gradient of 0% to 10% MeOH in DCM, to give the title product which was further purified by RP-HPLC to give Example 32.2 (68 mg, 0.13 mmol, 38% yield). LCMS-ESI (pos.): 501.1 (M+H)⁺.

Example 33.0. Preparation of (2S)-N-(4-(2,6-dimethoxyphenyl)-5-(3-pyridazinyl)-4H-1,2,4-triazol-3-yl)-1-(5-fluoro-2-pyrimidinyl)-2-propanesulfonamide or (2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide

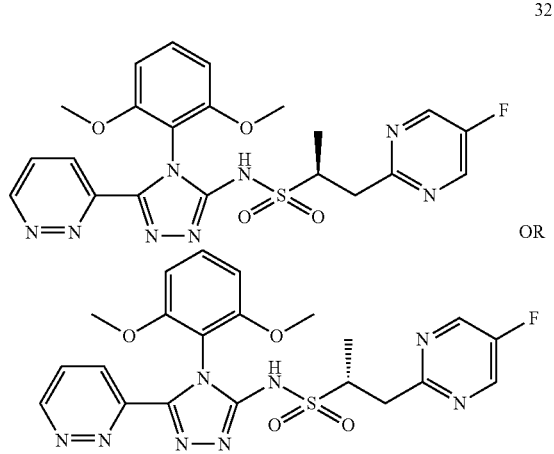

(2S)-N-(4-(2,6-Dimethoxyphenyl)-5-(3-pyridazinyl)-4H-1,2,4-triazol-3-yl)-1-(5-fluoro-2-pyrimidinyl)-2-propanesulfonamide or (2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide, Example 32.0. The racemic compound (Example 32.2) was separated by SFC (150×30 mm OJ-H column on Thar 350 with 20 mL/min MeOH (+20 mM NH₃)+68 g/min CO₂. Outlet pressure=100 bar; temperature=18° C.; wavelength=214 nm; injection volume=1.0 mL of 68 mg/14 mL (4.9 mg/mL) sample solution in MeOH:DCM (1:1). Two enantiomers were obtained. The title compound (Example 32.0) was the first isomer to elute under these conditions. ¹H NMR (400 MHz, CDCl₃) δ 11.31 (br. s, 1H), 9.12 (dd, J=5.0, 1.7 Hz, 1H), 8.54 (s, 2H), 8.06 (dd, J=8.6, 1.8 Hz, 1H), 7.54 (dd, J=8.6, 4.9 Hz, 1H), 7.37 (dd, J=8.4, 8.4 Hz, 1H), 6.61 (dd, J=8.5, 1.2 Hz, 2H), 3.79-3.85 (m, 1H), 3.72 (dd, J=14.9, 10 Hz, 1H), 3.71 (s, 3H), 3.69 (s, 3H), 3.12 (dd, J=14.9, 10 Hz, 1H), 1.34 (d, J=6.7 Hz, 3H). LCMS-ESI (pos.) m/z: 501.1 (M+H)⁺.

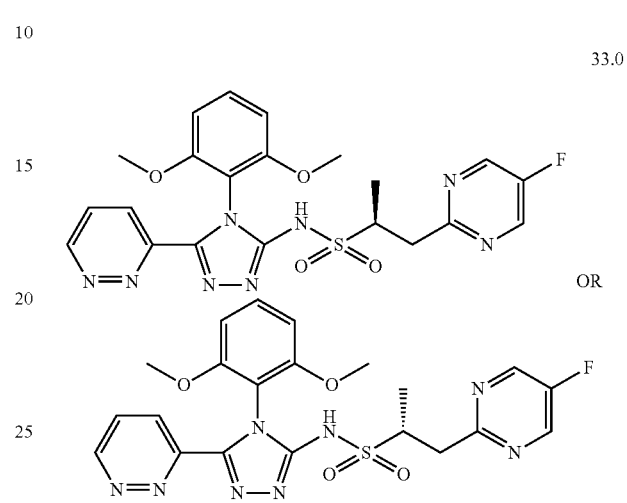

(2S)-N-(4-(2,6-Dimethoxyphenyl)-5-(3-pyridazinyl)-4H-1,2,4-triazol-3-yl)-1-(5-fluoro-2-pyrimidinyl)-2-propanesulfonamide or (2R)-N-(4-(2,6-dimethoxyphenyl)-5-(3-pyridazinyl)-4H-1,2,4-triazol-3-yl)-1-(5-fluoro-2-pyrimidinyl)-2-propanesulfonamide, Example 33.0. Example 33.0 is the enantiomer of Example 32.0. The title compound was the second isomer to elute on subjecting Example 32.2 to the SFC conditions described in Example 32.0. ¹H NMR (400 MHz, CDCl₃) δ 11.32 (br. s, 1H), 9.12 (dd, J=5.0, 1.7 Hz, 1H), 8.54 (s, 2H), 8.06 (dd, J=8.5, 1.7 Hz, 1H), 7.54 (dd, J=8.6, 5.1 Hz, 1H), 7.37 (dd, J=8.5, 8.5 Hz, 1H), 6.61 (dd, J=8.6, 1.2 Hz, 2H), 3.79-3.87 (m, 1H), 3.75 (dd, J=14.9, 9.8 Hz, 1H), 3.71 (s, 3H), 3.69 (s, 3H), 3.12 (dd, J=14.9, 9.8 Hz, 1H), 1.34 (d, J=6.8 Hz, 3H). LCMS-ESI (pos.) m/z: 501.1 (M+H)⁺.

The following compounds were synthesized using the intermediates described, following the procedure described within Example 32.0.

TABLE 2

| Example | Reagents | Structure, Name and and Data |
|---|---|---|
| 29.1 | N-((2,6-dimethoxyphenyl)carbamothioyl)-1-(5-fluoropyrimidin-2-yl)propane-2-sulfonamide Example 32.1, and pyrazine-2-carbohydrazide (Example 395.11). | and |

TABLE 2-continued

| Example | Reagents | Structure, Name and and Data |
|---|---|---|
| | | (R)-N-(4-(2,6-dimethoxyphenyl)-5-(pyrazin-2-yl)-4H-1,2,4-triazol-3-yl)-1-(5-fluoropyrimidin-2-yl)propane-2-sulfonamide and (S)-N-(4-(2,6-dimethoxyphenyl)-5-(pyrazin-2-yl)-4H-1,2,4-triazol-3-yl)-1-(5-fluoropyrimidin-2-yl)propane-2-sulfonamide. LCMS-ESI (pos.) m/z = 501.0 (M + H)+. |
| 29.0 | The racemic compound (Example 29.1) was separated by SFC (250 × 30 mm AD-H column with 32 g/min MeOH (+20 mM NH$_3$) + 68 g/min CO$_2$. Outlet pressure = 100 bar; wavelength = 214 nm; injection volume = 0.18 mL of 5 mL in MeOH (20% DCM). Two enantiomers were obtained. The title compound was the first isomer to elute under these conditions. | or<br><br>(R)-N-(4-(2,6-dimethoxyphenyl)-5-(pyrazin-2-yl)-4H-1,2,4-triazol-3-yl)-1-(5-fluoropyrimidin-2-yl)propane-2-sulfonamide or (S)-N-(4-(2,6-dimethoxyphenyl)-5-(pyrazin-2-yl)-4H-1,2,4-triazol-3-yl)-1-(5-fluoropyrimidin-2-yl)propane-2-sulfonamide. <sup>1</sup>H NMR (400 MHz, CDCl$_3$) δ 11.30 (br s, 1H), 9.06 (br s, 1H), 8.54 (s, 2H), 8.35 (br s, 1H), 7.38 (dd, J = 8.5, 8.5 Hz, 1H), 6.60 (d, J = 8.5 Hz, 2H), 3.78-3.85 (m, 1H), 3.72 (s, 3H), 3.71 (oscured dd, J = 14.7, 9.8 Hz, 1H), 3.70 (s, 3H), 3.11 (dd, J = 14.8, 9.9 Hz, 1H), 1.33 (d, J = 6.8 Hz, 3H). MS ESI (pos.) m/z = 501.0 [M + H]. |
| 30.0 | The title compound was the second isomer to elute on subjecting Example 29.1 to the SFC conditions described in Example 29.0. | 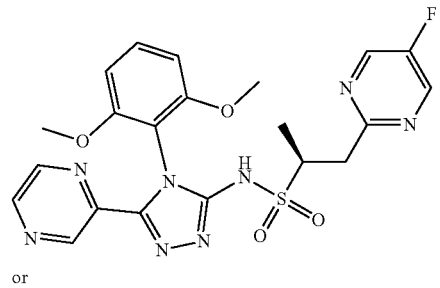<br>or |

TABLE 2-continued

| Example | Reagents | Structure, Name and and Data |
|---|---|---|
| | | 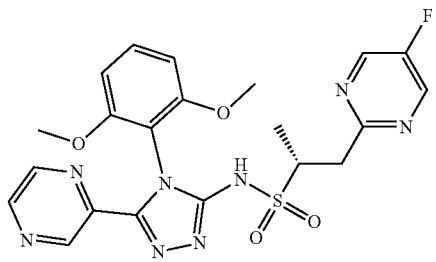<br>(R)-N-(4-(2,6-dimethoxyphenyl)-5-(pyrazin-2-yl)-4H-1,2,4-triazol-3-yl)-1-(5-fluoropyrimidin-2-yl)propane-2-sulfonamide or (S)-N-(4-(2,6-dimethoxyphenyl)-5-(pyrazin-2-yl)-4H-1,2,4-triazol-3-yl)-1-(5-fluoropyrimidin-2-yl)propane-2-sulfonamide.<br>$^1$H NMR (400 MHz, CDCl$_3$) δ 11.30 (br s, 1H), 9.06 (br s, 1H), 8.54 (s, 2H), 8.35 (br s, 1H), 7.38 (dd, J = 8.5, 8.5 Hz, 1H), 6.60 (d, J = 8.5 Hz, 2H), 3.78-3.85 (m, 1H), 3.72 (s, 3H), 3.71 (oscured dd, J = 14.7, 9.8 Hz, 1H), 3.70 (s, 3H), 3.11 (dd, J = 14.8, 9.9 Hz, 1H), 1.33 (d, J = 6.8 Hz, 3H). MS ESI (pos.) m/z = 501.0 [M + H]. |
| 34.1 | N-((2,6-dimethoxyphenyl)carbamothioyl)-1-(5-fluoropyrimidin-2-yl)propane-2-sulfonamide Example 32.1, and 1-methyl-1H-pyrrole-3-carbohydrazide (1-methyl-1H-pyrrole-3-carbohydrazide (395.4). | 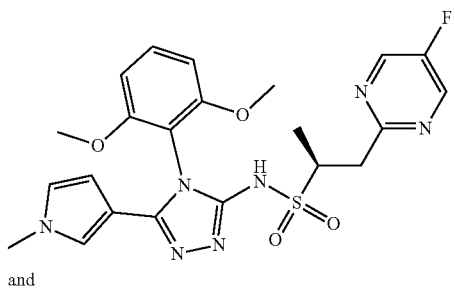<br>and<br>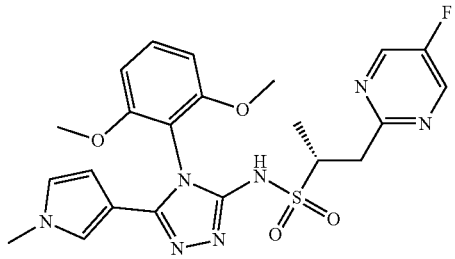<br>(R)-N-(4-(2,6-dimethoxyphenyl)-5-(1-methyl-1H-pyrrol-3-yl)-4H-1,2,4-triazol-3-yl)-1-(5-fluoropyrimidin-2-yl)propane-2-sulfonamide and (S)-N-(4-(2,6-dimethoxyphenyl)-5-(1-methyl-1H-pyrr01-3-yl)-4H-1,2,4-triazol-3-yl)-1-(5-fluoropyrimidin-2-yl)propane-2-sulfonamide.<br>LCMS-ESI (pos.): m/z = 502.1 (M + H)$^+$. |
| 34.0 | The racemic compound (Example 34.1) was separated by SFC (150 × 30 mm IA column on Thar 200 with 27 g/min MeOH (+20 mM NH$_3$) + 63 g/min CO$_2$. Outlet pressure = 100 bar; temperature = 23° C.; wavelength = 225 nm; injection volume = 0.5 mL of 87 mg/9 mL sample solution in ACN). Two enantiomers were obtained. The title compound was the first isomer to elute under these conditions. | 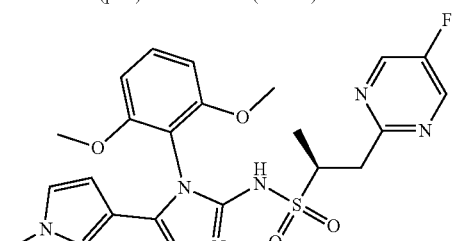<br>or |

| Example | Reagents | Structure, Name and and Data |
|---|---|---|
|  |  | 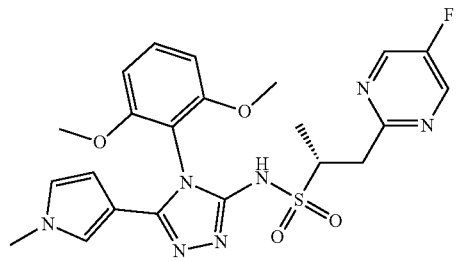<br>(R)-N-(4-(2,6-dimethoxyphenyl)-5-(1-methyl-1H-pyrrol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-pyrrol-3-yl)-4H-1,2,4-triazol-3-yl)-1-(5-fluoropyrimidin-2-yl)propane-2-sulfonamide.<br>$^1$H NMR (400 MHz, CDCl$_3$) δ 8.51 (s, 2H), 7.43 (dd, J = 8.5, 8.5 Hz, 1H), 6.65 (dd, J = 8.6, 2.0 Hz, 2H), 6.50 (br s, 1H), 6.45 (br s, 1H), 6.07 (br s, 1H), 3.67-3.80 (m, 2H), 3.74 (s, 3H), 3.72 (s, 3H), 3.54 (s, 3H), 3.07 (dd, J = 14.5, 10 1H), 1.28 (d, J = 6.7 Hz, 3H). MS ESI (pos.) m/z = 502.1 [M + H]. |
| 35.0 | The title compound was the second isomer to elute on subjecting Example 34.1 to the SFC conditions described in Example 34.0. | 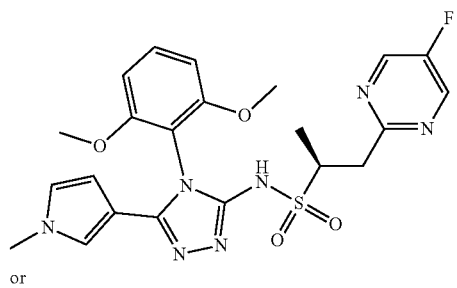<br>or<br>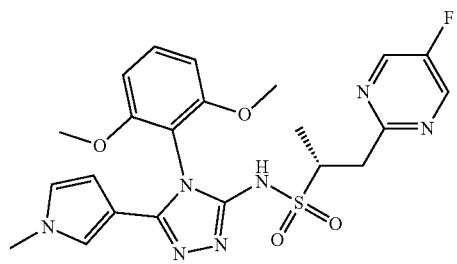<br>(R)-N-(4-(2,6-dimethoxyphenyl)-5-(1-methyl-1H-pyrrol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-pyrrol-3-yl)-4H-1,2,4-triazol-3-yl)-1-(5-fluoropyrimidin-2-yl)propane-2-sulfonamide.<br>$^1$H NMR (400 MHz, CDCl$_3$) δ 10.84 (br s, 1H), 8.53 (s, 2H), 7.44 (dd, J = 8.4, 8.4 Hz, 1H), 6.64-6.67 (m, 2H), 6.46-6.50 (m, 2H), 6.07-7.09 (m, 1H), 3.73-3.80 (m, 1H), 3.75 (s, 3H), 3.73 (s, 3H), 3.54 (s, 3H), 3.07 (dd, J = 14.7, 10 Hz, 1H), 1.28 (d, J = 6.7 Hz, 3H). MS ESI (pos.) m/z = 502.1 [M + H]. |
| 36.1 | N-((2,6-dimethoxyphenyl)carbamothioyl)-1-(5-fluoropyrimidin-2-yl)propane-2-sulfonamide, Example 32.1, and1-methyl-1H-pyrazole-3-carbohydrazide(Example 395.13). | 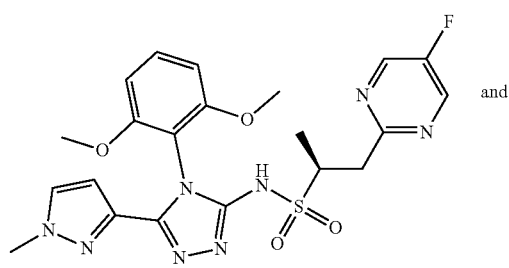 and |

| Example | Reagents | Structure, Name and and Data |
|---|---|---|
| | | 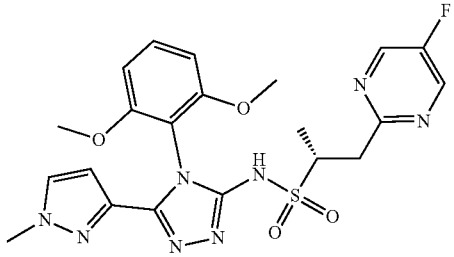<br>(R)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide.<br>LCMS-ESI (pos.): 503.1 (M + H)⁺ |
| 37.0 | Example 36.1 was separated by SFC (2 × 15 cm AD-H column with 70 mL/min 15% MeOH (0.1% NH₄OH)/CO₂. Outlet pressure = 100 bar; wavelength = 220 nm; injection volume = 1 mL, 9 mg/mL MeOH:DCM). Two enantiomers were obtained. The title compound was the first isomer to elute under these conditions. | 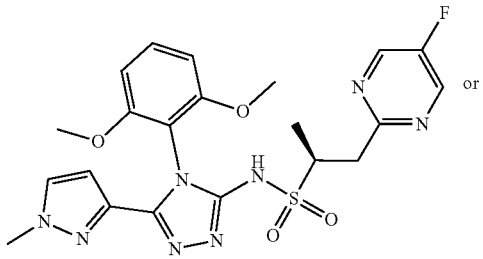<br>(R)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide.<br>¹H NMR (400 MHz, CDCl₃) δ 11.05 ( br s, 1H), 8.52 (s, 2H), 7.42 (dd, J = 8.5, 8.5 Hz, 1H), 7.22 (d, J = 2.3 Hz, 1H), 6.64 (dd, J = 8.4, 2.3 Hz, 2H), 5.91 (d, J = 2.3 Hz, 1H), 3.87 (s, 3H), 3.77-3.81 (m, 1H), 3.74 (s, 3H), 3.73 (s, 3H), 3.72 (m, 1H), 3.08 (dd, J = 14.7, 10 Hz, 1H), 1.29 (d, J = 6.7 Hz, 3H). MS ESI (pos.) m/z = 503.1 [M + H]. |
| 36.0 | The title compound was the second isomer to elute on subjecting Example 36.1 to the SFC conditions described in Example 37.0. | 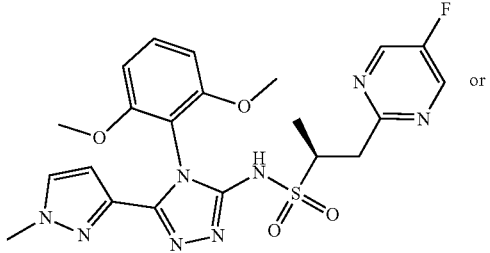 |

TABLE 2-continued

| Example | Reagents | Structure, Name and and Data |
|---|---|---|
| | | (R)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-pyrazol-3-yl)-4H-1,2,4-triazol-3-yl)-1-(5-fluoropyrimidin-2-yl)propane-2-sulfonamide. $^1$H NMR (400 MHz, CDCl$_3$) δ: 11.07 ( br s, 1H), 8.51 (s, 2H), 7.42 (dd, J = 8.3, 8.3 Hz, 1H), 7.22 (d, J = 2.3 Hz, 1H), 6.64 (dd, J = 8.4, 2.3 Hz, 2H), 5.88 (d, J = 2.3 Hz, 1H), 3.85 (s, 3H), 3.75-3.81 (m, 1H), 3.72 (s, 3H), 3.71 (s, 3H), 3.68 (m, 1H), 3.07 (dd, J = 14.7, 10 Hz, 1H), 1.29 (d, J = 6.7 Hz, 3H). MS ESI (pos.) m/z = 503.1 [M + H]. |
| 31.0 | N-((2,6-dimethoxyphenyl)carbamothioyl)-1-(5-fluoropyrimidin-2-yl)propane-2-sulfonamide, Example 32.1. pyrimidine-4-carbohydrazide (Example 395.14). | (R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide and (R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide. LCMS-ESI (pos.): 501.2 (M + H)$^+$. |
| 38.0 | Example 31.0 was separated by SFC (450 × 30 mm IA-H column on Thar 80 with 28 g/min MeOH (NH$_3$) + 52 g/min CO$_2$, 35% co-solvent at 80 g/min. Outlet pressure = 100 bar; wavelength = 215 nm; injection volume = 0.5 mL of a solution from 24 mg sample dissolved in 4 mL of MeOH:DCM 3:1). Two enantiomers were obtained. The title compound was the first isomer to elute under these conditions. | |

TABLE 2-continued

| Example | Reagents | Structure, Name and and Data |
|---|---|---|
| | | 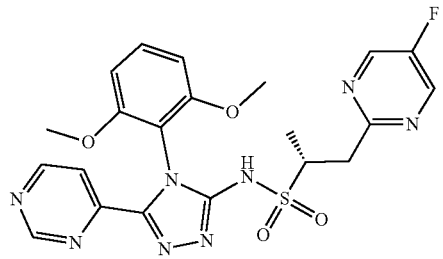<br>(R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide or (R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.97 (d, J = 1.2 Hz, 1H), 8.8 (d, J = 5.3 Hz, 1H), 8.53 (s, 2H), 7.8 (dd, J = 5.1, 1.2 Hz, 1H), 7.4 (dd, J = 8.5, 8.5 Hz, 1H), 6.62 (dd, J = 8.5, 1.3 Hz, 2H), 3.78-3.86 (m, 1H), 3.72 (s, 3H), 3.70 (s, 3H), 3.69 (dd, J = 14.9, 10 Hz, 1H), 3.1 (dd, J = 14.9, 10 Hz, 1H), 1.33 (d, J = 6.7 Hz, 3H). MS ESI (pos.) m/z = 501.2 [M + H]. |
| 39.0 | The title compound was the second isomer to elute on subjecting Example 31.0 to the SFC conditions described in Example 38.0. | 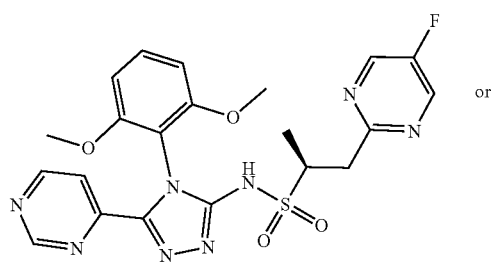 or<br>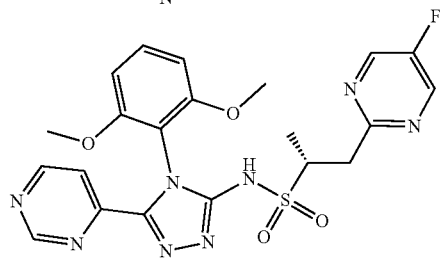<br>(R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide or (R)-N-(4-(2,6-dimethoxyphenyl)-5-(pyrimidin-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.97 (br s, 1H), 8.8 (d, J = 5.3 Hz, 1H), 8.53 (s, 2H), 7.79-7.81 (m, 1H), 7.4 (dd, J = 8.5, 8.5 Hz, 1H), 6.62 (dd, J = 8.5, 1.3 Hz, 2H), 3.78-3.85 (m, 1H), 3.72 (s, 3H), 3.70 (s, 3H), 3.69 (obcured dd, J = 14.8, 9.9 Hz, 1H), 3.1 (dd, J = 14.8, 9.9 Hz, 1H), 1.33 (d, J = 6.7 Hz, 3H). MS ESI (pos.) m/z = 501.2 [M + H]. |
| 40.0 | [N-((2,6-dimethoxyphenyl)carbamothioyl)-1-(5-fluoropyrimidin-2-yl)propane-2-sulfonamide, Example 32.1, and 1-methyl-1H-pyrazole-4-carbohydrazide (Example 395.15). | 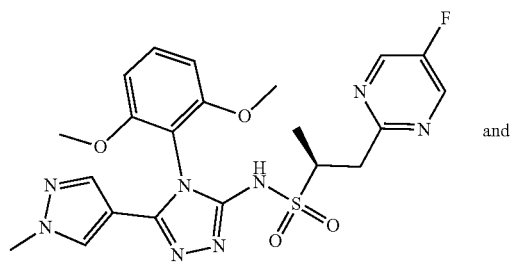 and |

TABLE 2-continued

| Example | Reagents | Structure, Name and and Data |
|---|---|---|
| | | 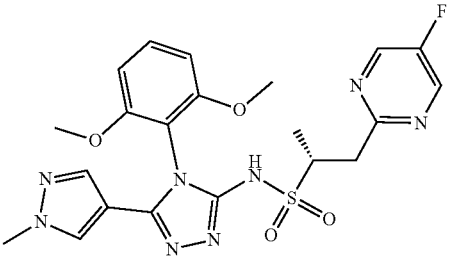<br>(R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide and (R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide.<br>MS ESI (pos.) m/z = 503.1 [M + H]. |
| 44.0 | The racemic compound (Example 40.0) was separated by SFC (2 × 15 cm IA column with 60 mL/min 20% MeOH (0.1%NH$_3$)/CO$_2$. Outlet pressure = 100 bar; wavelength = 220 mn; injection volume = 2 mL, δ mg/mL 2:1 MeOH:DCM). Two enantiomers were obtained. The title compound was the first isomer to elute under these conditions. | 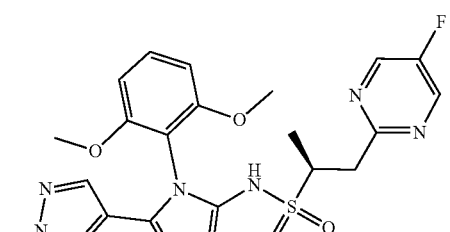 or 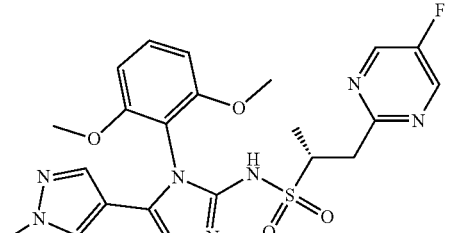<br>(R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide and (R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.52 (s, 2H), 7.43-7.48 (m, 2H), 7.25 (s, 1H), 6.67 (d, J = 8.7 Hz, 2H), 3.84 (s, 3H), 3.75-3.80 (m, 1H), 3.76 (s, 3H), 3.74 (s, 3H), 3.67-3.72 (m, 1H), 3.08 (dd, J = 14.8, 9.9 Hz, 1H), 1.30 (d, J = 6.8 Hz, 3H). MS ESI (pos.) m/z = 502.9 [M + H]. |
| 45.0 | The title compound was the second isomer to elute on subjecting Example 40.0 to the SFC conditions described in Example 44.0. | 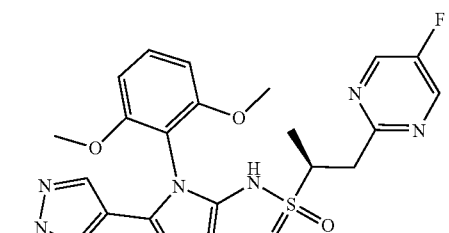 or  |

TABLE 2-continued

| Example | Reagents | Structure, Name and Data |
|---|---|---|
| | | 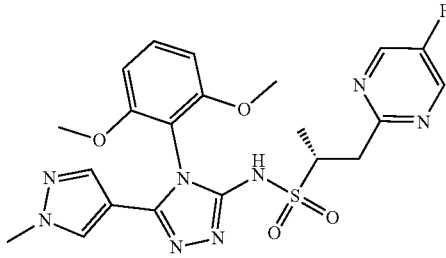(R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide and (R)-N-(4-(2,6-dimethoxyphenyl)-5-(1-methyl-1H-pyrazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.52 (s, 2H), 7.42-7.48 (m, 2H), 7.25 (s, 1H), 6.67 (d, J = 8.7 Hz, 2H), 3.84 (s, 3H), 3.75-3.81 (m, 1H), 3.76 (s, 3H), 3.74 (s, 3H), 3.67-3.72 (m, 1H), 3.08 (dd, J = 14.8, 10 Hz, 1H), 1.30 (d, J = 6.8 Hz, 3H). MS ESI (pos.) m/z = 502.9 [M + H]. |
| 42.0 | [N-((2,6-dimethoxyphenyl)carbamothioyl)-1-(5-fluoropyrimidin-2-yl)propane-2-sulfonamide, Example 32.1. pyrimidine-5-carbohydrazide (Example 395.16). | 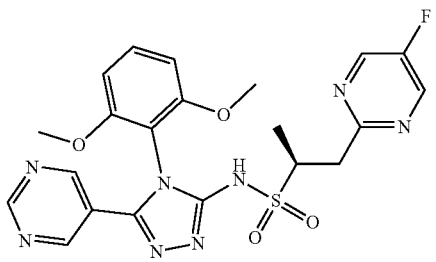(R)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide and (S)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide.<br>MS ESI (pos.) m/z = 500.9 [M + H]. |
| 47.0 | The racemic compound (Example 42.0) was separated by SFC (2 × 15 cm 1A column with 60 mL/min 20% MeOH (0.1% NH$_4$OH)/CO$_2$. Outlet pressure = 100 bar; wavelength = 220 nm; injection volume = 0.5 mL, 10 mg/mL 3:1 MeOH:DCM). Two enantiomers were obtained. The title compound was the first isomer to elute under these conditions. | 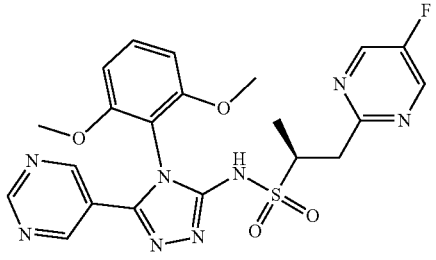 |

| Example | Reagents | Structure, Name and and Data |
|---|---|---|
| | | 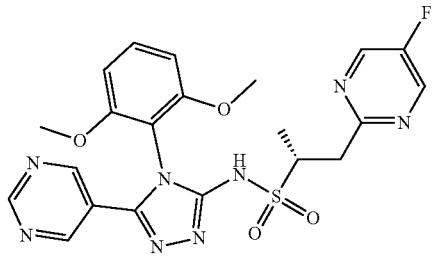(R)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide and (S)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide. $^1$H NMR (400 MHz, CDCl$_3$) δ 9.23 (br s, 1H), 8.78 (br s, 2H), 8.54 (s, 2H), 7.42 (dd, J = 8.5, 8.5 Hz, 1H), 6.63 (d, J = 8.4 Hz, 2H), 3.67-3.85 (m, 2H), 3.76 (s, 3H), 3.74 (s, 3H), 3.09 (dd, J = 14.8, 9.9 Hz, 1H), 1.31 (d, J = 6.7 Hz, H). MS ESI (pos.) m/z = 500.9 [M + H]. |
| 48.0 | The title compound was the second isomer to elute on subjecting Example 42.0 to the SFC conditions described in Example 47.0. | 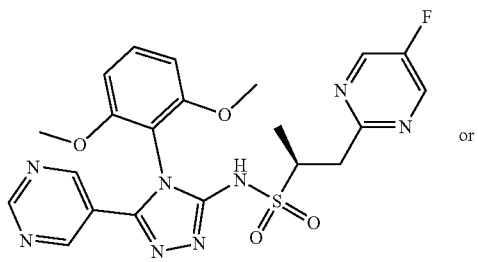or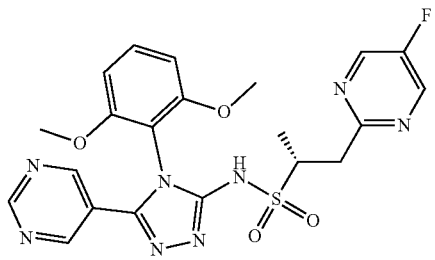(R)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide and (S)-N-(4-(2,6-dimethoxyphenyl)-5-(pyrimidin-5-yl)-4H-1,2,4-triazol-3-yl)-1-(5-fluoropyrimidin-2-yl)propane-2-sulfonamide. $^1$H NMR (400 MHz, CDCl$_3$) δ 9.22 (br s, 1H), 8.78 (br s, 2H), 8.53 (s, 2H), 7.42 (dd, J = 8.5, 8.5 Hz, 1H), 6.63 (d, J = 8.6 Hz, 2H), 3.67-3.85 (m, 2H), 3.76 (s, 3H), 3.74 (s, 3H), 3.09 (dd, J = 14.6, 9.9 Hz, 1H), 1.31 (d, J = 6.7 Hz, H). MS ESI (pos.) m/z = 500.9 [M + H]. |
| 41.0 | [[N-((2,6-dimethoxyphenyl)carbamothioyl)-1-(5-fluoropyrimidin-2-yl)propane-2-sulfonamide, Example 32.1, and 5-methyl-1,3,4-oxadiazole-2-carbohydrazide (Example 395.17). | 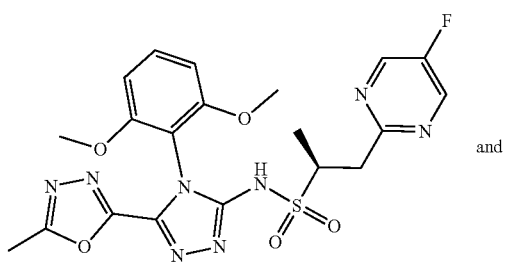and |

TABLE 2-continued

| Example | Reagents | Structure, Name and and Data |
|---|---|---|
| | | 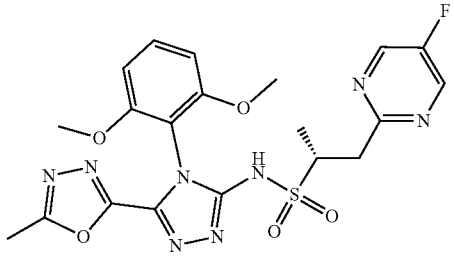<br>(R)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide and (S)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide.<br>MS ESI (pos.) m/z = 505.9 [M + H]. |
| 49.0 | The racemic compound (Example 41.0) was separated by SFC (250 × 30 mm 1A column on Thar 80 with 21 g/min MeOH (NH$_3$)/+49 g/min CO$_2$, 30% co-solvent at 70 g/min. Outlet pressure = 100 bar; temperature = 23° C.; wavelength = 265 nm; injection volume = 0.3 mL of a solution from 29 mg sample dissolved in 3.5 mL of MeOH:DCM 3:1). Two enantiomers were obtained. The title compound was the first isomer to elute under these conditions. | 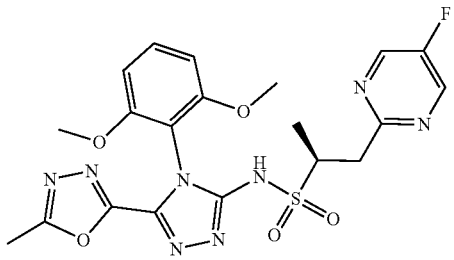<br>(R)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide.<br>$^1$H NMR (400 MHz, CDCl$_3$) δ 8.52 (s, 2H), 7.41 (dd, J = 8.4, 8.4 Hz, 1H), 6.64 (d, J = 8.6 Hz, 2H), 3.78-3.85 (m, 1H), 3.75 (s, 3H), 3.72 (s, 3H), 3.66-3.70 (m, 1H), 3.06-3.13 (m, 1H), 2.59 (S, 3H), 1.31 (d, J = 6.8 Hz, 3H). MS ESI (pos.) m/z = 505.9 [M + H]. |
| 50.0 | The title compound was the second isomer to elute on subjecting Example 41.0 to the SFC conditions described in Example 49.0. | 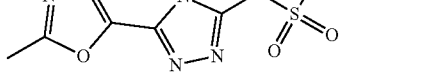 or |

TABLE 2-continued

| Example | Reagents | Structure, Name and and Data |
|---|---|---|
| | | 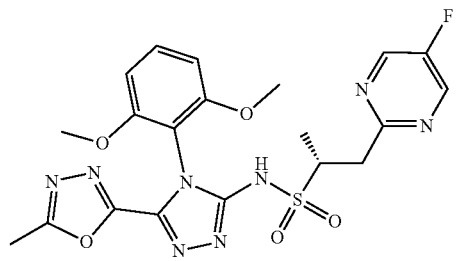<br>(R)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(5-methyl-1,3,4-oxadiazol-2-yl)-4H-1,2,4-triazol-3-yl)-1-(5-fluoropyrimidin-2-yl)propane-2-sulfonamide.<br>$^1$H NMR (400 MHz, CDCl$_3$) δ: 8.53 (s, 2H), 7.43 (dd, J = 8.5, 8.5 Hz, 1H), 6.65 (dd, J = 8.5, 1.1 Hz, 2H), 3.79-3.85 (m, 1H), 3.76 (s, 3H), 3.74 (s, 3H), 3.66-3.72 (m, 1H), 3.10 (dd, J = 14.8, 9.7 Hz, 1H), 2.59 (S, 3H), 1.31 (d, J = 6.7 Hz, 3H). MS ESI (pos.) m/z = 505.9 [M + H]. |
| 43.0 | [[N-((2,6-dimethoxyphenyl)carbamothioyl)-1-(5-fluoropyrimidin-2-yl)propane-2-sulfonamide (Example 32.1), and pyridazine-4-carbohydrazide (395.18). | 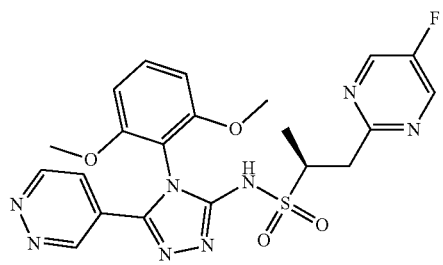<br>and<br>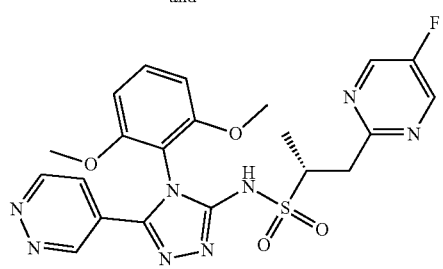<br>(R)-N-(4-(2,6-dimethoxyphenyl)-5-(pyridazin-4-yl)-4H-1,2,4-triazol-3-yl)-1-(5-fluoropyrimidin-2-yl)propane-2-sulfonamide and (S)-N-(4-(2,6-dimethoxyphenyl)-5-(pyridazin-4-yl)-4H-1,2,4-triazol-3-yl)-1-(5-fluoropyrimidin-2-yl)propane-2-sulfonamide.<br>MS ESI (pos.) m/z = 501.8 [M + H]. |
| 51.0 | The racemic compound (Example 43.0) was separated by SFC (2 × 15 cm IA column with 60 mL/min 25% MeOH (0.1% NH$_4$OH)/CO$_2$. Outlet pressure = 100 bar; wavelength = 220 nm; injection volume = 0.5 mL, 10 mg/mL 2:1 MeOH:DCM). Two enantiomers were obtained. The title compound was the first isomer to elute under these conditions. | 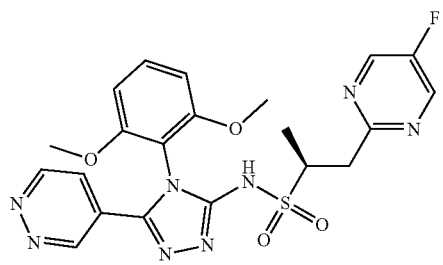<br>or |

TABLE 2-continued

| Example | Reagents | Structure, Name and and Data |
|---|---|---|
| | | 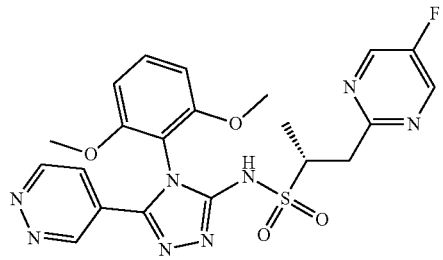 (R)-N-(4-(2,6-dimethoxyphenyl)-5-(pyridazin-4-yl)-4H-1,2,4-triazol-3-yl)-1-(5-fluoropyrimidin-2-yl)propane-2-sulfonamide or (S)-N-(4-(2,6-dimethoxyphenyl)-5-(pyridazin-4-yl)-4H-1,2,4-triazol-3-yl)-1-(5-fluoropyrimidin-2-yl)propane-2-sulfonamide. $^1$H NMR (400 MHz, CDCl$_3$) δ: 9.26 (br s, 2H), 8.53 (s, 2H), 7.4-7.6 (m, 2H), 6.67 (d, J = 8.4 Hz, 2H), 3.78-3.85 (m, 1H), 3.76 (s, 3H), 3.73 (s, 3H), 3.66-3.73 (m, 1H, 3.09 (dd, J = 14.8, 9.9 Hz, 1H), 1.31 (d, J = 6.7 Hz, 3H). MS ESI (pos.) m/z = 501.9 [M + H]. |
| 52.0 | The title compound was the second isomer to elute on subjecting Example 43.0 to the SFC conditions described in Example 51.0. | 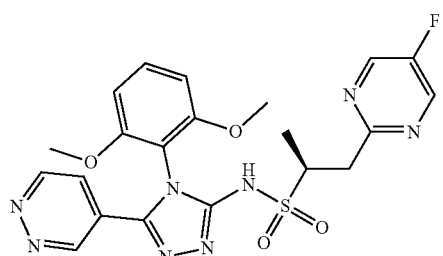 or 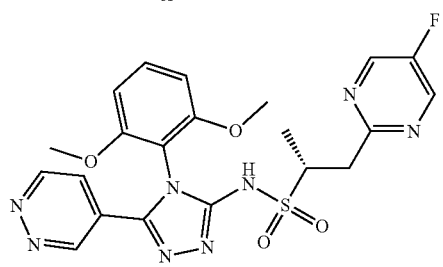 (R)-N-(4-(2,6-dimethoxyphenyl)-5-(pyridazin-4-yl)-4H-1,2,4-triazol-3-yl)-1-(5-fluoropyrimidin-2-yl)propane-2-sulfonamide or (S)-N-(4-(2,6-dimethoxyphenyl)-5-(pyridazin-4-yl)-4H-1,2,4-triazol-3-yl)-1-(5-fluoropyrimidin-2-yl)propane-2-sulfonamide. $^1$H NMR (400 MHz, CDCl$_3$) δ 9.27 (br s, 2H), 8.53 (s, 2H), 7.2-7.50 (m, 2H), 6.66 (d, J = 8.6 Hz, 2H), 3.78-3.85 (m, 1H), 3.76 (s, 3H), 3.73 (s, 3H), 3.66-3.73 (m, 1H), 3.09 (dd, J = 14.8, 10 Hz, 1H), 1.30 (d, J = 6.7 Hz, 3H).. MS ESI (pos.) m/z = 501.2 [M + H]. |
| 46.0 | [N-((2,6-dimethoxyphenyl)carbamothioyl)-1-(5-fluoropyrimidin-2-yl)propane-2-sulfonamide, Example 32.1, and 1,5-dimethyl-1H-pyrazole-3-carbohydrazide (Example 395.19). | 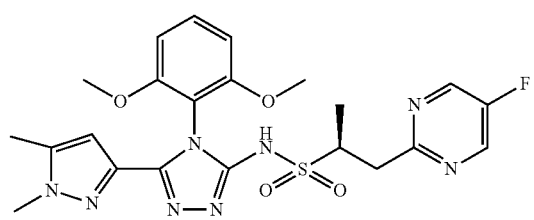 and |

TABLE 2-continued

| Example | Reagents | Structure, Name and and Data |
|---|---|---|
| | | 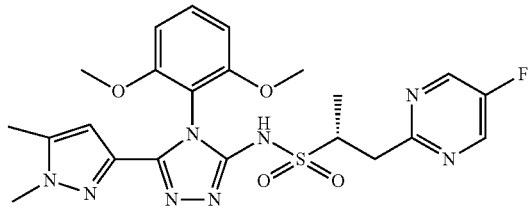 (R)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide. MS ESI (pos.) m/z = 517.0 [M + H]. |
| 53.0 | The racemic compound (Example 46.0) was separated by SFC (2 × 15 cm AD-H column with 60 mL/min 25% MeOH/CO$_2$. Outlet pressure = 100 bar; wavelength = 220 nm; injection volume = 0.7 mL, 3 mg/mL 1:1 MeOH:DCM). Two enantiomers were obtained. The title compound was the first isomer to elute under these conditions. | 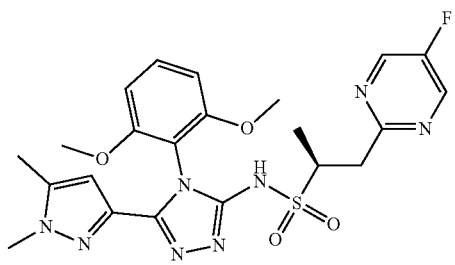 or 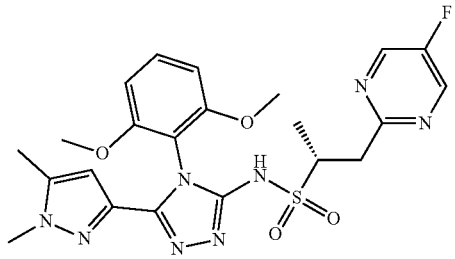 (R)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide. $^1$H NMR (400 MHz, CDCl$_3$) δ 11.01 (br s, 1H), 8.52 (s, 2H), 7.42 (dd, J = 8.4, 8.4 Hz, 1H), 6.64 (dd, J = 8.5, 2.6 Hz, 2H), 5.64 (s, 1H), 3.65-3.84 (m, 11H), 3.07 (dd, J = 14.7, 9.8 Hz, 1H), 2.17 (s, 3H), 1.30 (d, J = 6.7 Hz, 3H). MS ESI (pos.) m/z = 517.3 [M + H]. |
| 54.0 | The title compound was the second isomer to elute on subjecting Example 46.0 to the SFC conditions described in Example 53.0. | 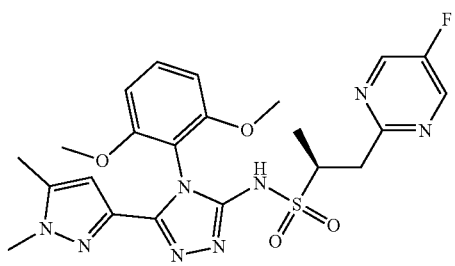 or |

| Example | Reagents | Structure, Name and and Data |
|---|---|---|
| | | 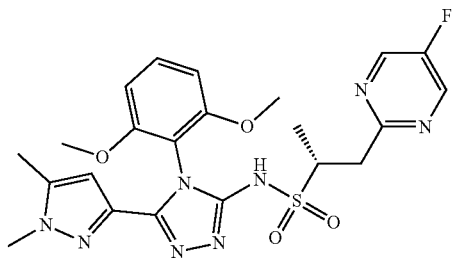 (R)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1,5-dimethyl-1H-pyrazol-3-yl)-4H-1,2,4-triazol-3-yl)-1-(5-fluoropyrimidin-2-yl)propane-2-sulfonamide. $^1$H NMR (400 MHz, CDCl$_3$) δ 11.01 (br s, 1H), 8.52 (s, 2H), 7.42 (dd, J = 8.4, 8.4 Hz, 1H), 6.64 (dd, J = 8.5, 2.6 Hz, 2H), 5.64 (s, 1H), 3.65-3.84 (m, 11H), 3.07 (dd, J = 14.7, 9.8 Hz, 1H), 2.17 (s, 3H), 1.30 (d, J = 6.7 Hz, 3H). MS ESI (pos.) m/z = 517.3 [M + H]. |
| 56.0 | N-((2,6-dimethoxyphenyl)carbamothioyl)-1-(5-fluoropyrimidin-2-yl)propane-2-sulfonamide, Example 32.1, and pyrimidine-2-carbohydrazide (Example 395.20). | 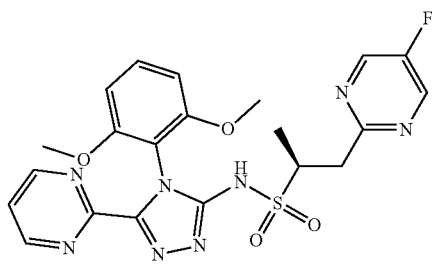 and 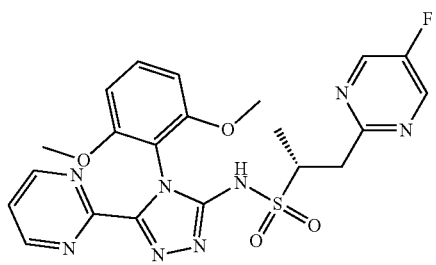 (R)-N-(4-(2,6-dimethoxyphenyl)-5-(pyrimidin-2-yl)-4H-1,2,4-triazol-3-yl)-1-(5-fluoropyrimidin-2-yl)propane-2-sulfonamide and (S)-N-(4-(2,6-dimethoxyphenyl)-5-(pyrimidin-2-yl)-4H-1,2,4-triazol-3-yl)-1-(5-fluoropyrimidin-2-yl)propane-2-sulfonamide. MS ESI (pos.) m/z = 501.9 [M + H]. |
| 58.0 | The racemic compound (Example 56.0) was separated by SFC (150 × 30 mm AD-H column on Thar 350 with 42 mL/min EtOH + (20 mM NH$_3$) + 78 g/min CO$_2$. Outlet pressure = 100 bar; temperature = 19° C.; wavelength = 215 nm; injection volume = 0.8 mL of 90 mg/10 mL in MeOH). Two enantiomers were obtained. The title compound was the first isomer to elute under these conditions. | 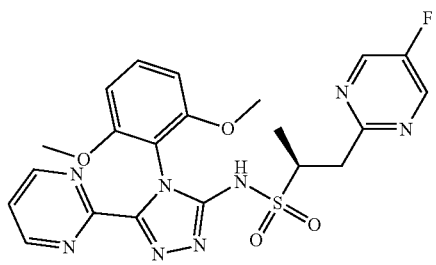 or |

TABLE 2-continued

| Example | Reagents | Structure, Name and and Data |
|---|---|---|

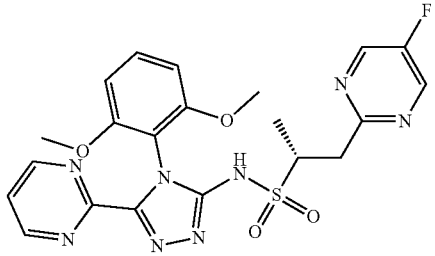

(R)-N-(4-(2,6-dimethoxyphenyl)-5-(pyrimidin-
2-yl)-4H-1,2,4-triazol-3-yl)-1-(5-
fluoropyrimidin-2-yl)propane-2-sulfonamide or
(S)-N-(4-(2,6-dimethoxyphenyl)-5-(pyrimidin-
2-yl)-4H-1,2,4-triazol-3-yl)-1-(5-
fluoropyrimidin-2-yl)propane-2-sulfonamide.
$^1$H NMR (400 MHz, CDCl$_3$) δ 8.66 (d, J = 4.9
Hz, 2H), 8.53 (s, 2H), 7.36 (dd, J = 8.5, 8.5 Hz,
1H), 7.26 (dd, J = 4.9, 4.9 Hz, 1H), 6.60 (d, J =
7.9 Hz, 2H), 3.79-3.85 (m, 1H), 3.67-3.73 (m,
1H), 3.70 (s, 3H), 3.69 (s, 3H), 3.11 (dd, J =
14.8, 9.7 Hz, 1H), 1.33 (d, J = 6.8 Hz, 3H).
MS ESI (pos.) m/z = 501.1 [M + H].

59.0 The title compound was the second isomer to elute on subjecting Example 56.0 to the SFC conditions described in Example 58.0.

or (R)-N-(4-(2,6-dimethoxyphenyl)-5-(pyrimidin-
2-yl)-4H-1,2,4-triazol-3-yl)-1-(5-
fluoropyrimidin-2-yl)propane-2-sulfonamide or
(S)-N-(4-(2,6-dimethoxyphenyl)-5-(pyrimidin-
2-yl)-4H-1,2,4-triazol-3-yl)-1-(5-
fluoropyrimidin-2-yl)propane-2-sulfonamide.
$^1$H NMR (400 MHz, CDCl$_3$) δ 8.66 (d, J = 4.9
Hz, 2H), 8.53 (s, 2H), 7.37 (dd, J = 8.4, 8.4 Hz,
1H), 7.26 (dd, J = 4.9, 4.9 Hz, 1H), 6.60 (dd, J =
8.5, 2.2 Hz, 2H), 3.79-3.85 (m, 1H), 3.67-3.74
(m, 1H), 3.71 (s, 3H), 3.69 (s, 3H), 3.11 (dd, J =
14.8, 9.7 Hz, 1H), 1.33 (d, J = 6.8 Hz, 3H).
MS ESI (pos.) m/z = 501.1 [M + H].

TABLE 2-continued

| Example | Reagents | Structure, Name and and Data |
|---|---|---|
| 55.0 | N-((2,6-dimethoxyphenyl)carbamothioyl)-1-(5-fluoropyrimidin-2-yl)propane-2-sulfonamide (Example 32.1), and 1-methyl-1H-1,2,3-triazole-4-carbohydrazide (Example 395.21). | 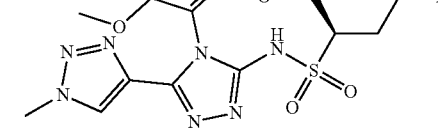<br>and<br>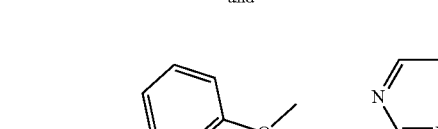<br>(R)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide and (S)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide.<br>MS ESI (pos.) m/z = 504.2 [M + H]. |
| 60.0 | The racemic compound (Example 55.0) was separated by SFC (2 × 15 cm IA column with 60 mL/min 30% MeOH (0.1%NH$_3$)/CO$_2$. Outlet pressure = 100 bar; wavelength = 220 nm; injection volume = 0.75 mL, 3 mg/mL 1:1 MeOH:DCM). Two enantiomers were obtained. The title compound was the first isomer to elute under these conditions. | 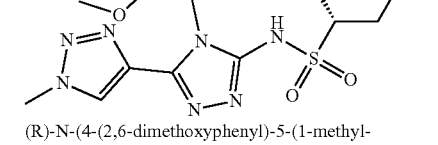<br>or<br>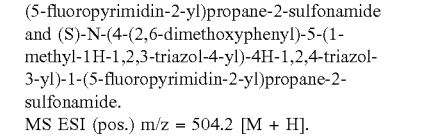<br>(R)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.53 (s, 2H), 7.48 (s, 1H), 7.43 (dd, J = 8.4, 8.4 Hz, 1H), 6.66 (d, J = 8.4 Hz, 2H), 4.06 (s, 3H), 3.78-3.84 (m, 1H), 3.76 (s, 3H), 3.74 (s, 3H), 3.67-3.72 (m, 1H), 3.09 (dd, J = 14.8, 9.9 Hz, 1H), 1.31 (d, J = 6.7 Hz, 3H). MS ESI (pos.) m/z = 504.2 [M + H]. |

TABLE 2-continued

| Example | Reagents | Structure, Name and and Data |
|---|---|---|
| 61.0 | The title compound was the second isomer to elute on subjecting Example 55.0 to the SFC conditions described in Example 60.0. | 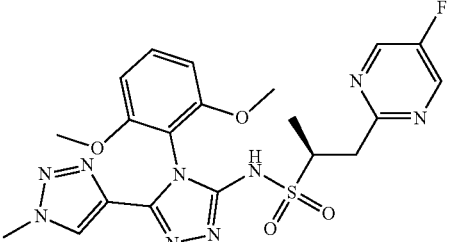<br>or<br>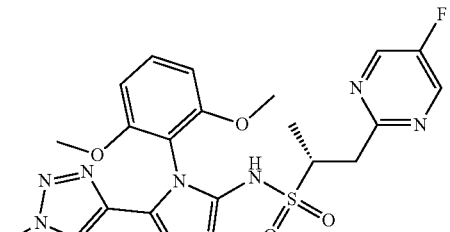<br>(R)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide or (S)-N-(4-(2,6-dimethoxyphenyl)-5-(1-methyl-1H-1,2,3-triazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.53 (s, 2H), 7.48 (s, 1H), 7.43 (dd, J = 8.4, 8.4 Hz, 1H), 6.66 (d, J = 8.4 Hz, 2H), 4.06 (s, 3H), 3.78-3.84 (m, 1H), 3.76 (s, 3H), 3.74 (s, 3H), 3.67-3.72 (m, 1H), 3.09 (dd, J = 14.8, 9.9 Hz, 1H), 1.31 (d, J 6.7 Hz, 3H). MS ESI (pos.) m/z = 504.2 [M + H]. |
| 57.0 | N-((2,6-dimethoxyphenyl)carbamothioyl)-1-(5-fluoropyrimidin-2-yl)propane-2-sulfonamide, Example 32.1 and 3-methylisoxazole-5-carbohydrazide (Example 395.22). | 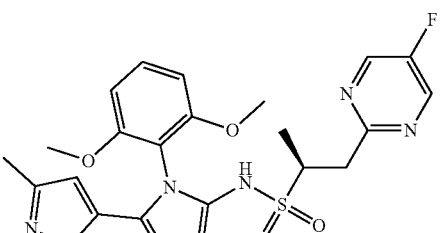<br>and<br>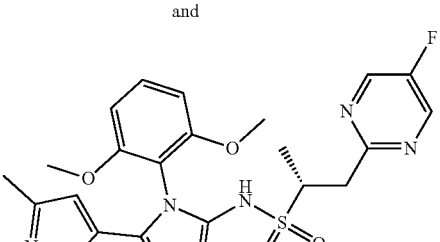<br>(R)-N-(4-(2,6-dimethoxyphenyl)-5-(3-methylisoxazol-5-yl)-4H-1,2,4-triazol-3-yl)-1-(5-fluoropyrimidin-2-yl)propane-2-sulfonamide and (R)-N-(4-(2,6-dimethoxyphenyl)-5-(3-methylisoxazol-5-yl)-4H-1,2,4-triazol-3-yl)-1-(5-fluoropyrimidin-2-yl)propane-2-sulfonamide.<br>MS ESI (pos.) m/z = 503.9 [M + H]. |

TABLE 2-continued

| Example | Reagents | Structure, Name and and Data |
|---|---|---|
| 62.0 | The racemic compound (Example 57.0) was separated by SFC (2 × 15 cm AD-H column with 60 mL/min 20% MeOH (0.1%NH$_3$)/CO$_2$. Outlet pressure = 100 bar; wavelength = 220 nm; injection volume = 0.7 mL, 9 mg/mL 1:1 MeOH:DCM). Two enantiomers were obtained. The title compound was the first isomer to elute under these conditions. | 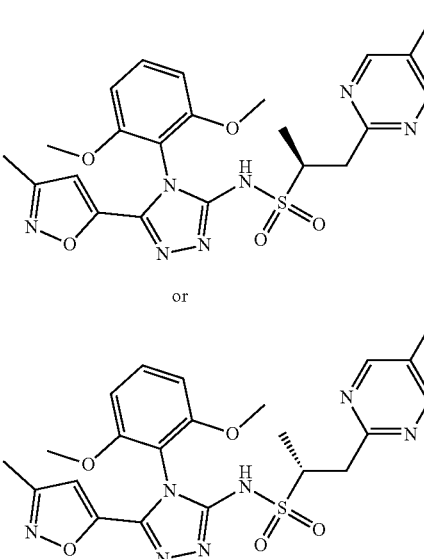<br>or<br><br>((R)-N-(4-(2,6-dimethoxyphenyl)-5-(3-methylisoxazol-5-yl)-4H-1,2,4-triazol-3-yl)-1-(5-fluoropyrimidin-2-yl)propane-2-sulfonamide (or (R)-N-(4-(2,6-dimethoxyphenyl)-5-(3-methylisoxazol-5-yl)-4H-1,2,4-triazol-3-yl)-1-(5-fluoropyrimidin-2-yl)propane-2-(sulfonamide.<br>$^1$H NMR (400 MHz, CDCl$_3$) δ 8.53 (s, 2H), 7.46 (dd, J = 8.5, 8.5 HZ, 1H), 6.68 (dd, J = (8.6, 1.4 Hz, 2H), 6.00 (s, 1H), 3.78-3.85 (m, 1H), 3.77 (s, 3H), 3.75 (s, 3H), 3.68 (dd, J = 14.8, 4.2 Hz, 1H), 3.08 (dd, J = 14.7, 9.8 Hz, 1H), 2.27 (s, 3H), 1.31 (d, J = 6.8 HZ, 3H). MS ESI (pos.) m/z = 504.2 [M + H]. |
| 63.0 | The title compound was the second isomer to elute on subjecting Example 57.0 to the SFC conditions described in Example 62.0. | 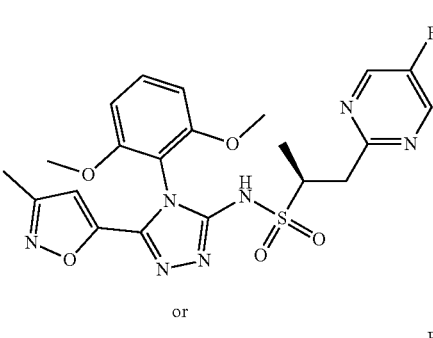<br>or<br><br>(R)-N-(4-(2,6-dimethoxyphenyl)-5-(3-methylisoxazol-5-yl)-4H-1,2,4-triazol-3-yl)-1-(5-fluoropyrimidin-2-yl)propane-2-sulfonamide or (R)-N-(4-(2,6-dimethoxyphenyl)-5-(3-methylisoxazol-5-yl)-4H-1,2,4-triazol-3-yl)-1-(5-fluoropyrimidin-2-yl)propane-2-sulfonamide. |

TABLE 2-continued

| Example | Reagents | Structure, Name and and Data |
|---|---|---|
| | | $^1$H NMR (400 MHz, CDCl$_3$) δ 8.53 (s, 2H), 7.46 (dd, J = 8.5, 8.5 HZ, 1H), 6.67 (d, J = 8.5Hz, 2H), 6.00 (s, 1H), 3.78-3.85 (m, 1H), 3.77 (s, 3H), 3.75 (s, 3H), 3.65-3.70 (m, 1H), 3.08 (dd, J = 14.9, 9.8 Hz, 1H), 2.27 (s, 3H), 1.31 (d, J = 6.7 HZ, 3H). MS ESI (pos.) m/z = 504.1 [M + H]. |
| 64.1 | [N-((2,6-dimethoxyphenyl)carbamothioyl)-1-(5-fluoropyrimidin-2-yl)propane-2-sulfonamide Example 32.1, and 3-methylisoxazole-4-carbohydrazide (Example 395.23). | 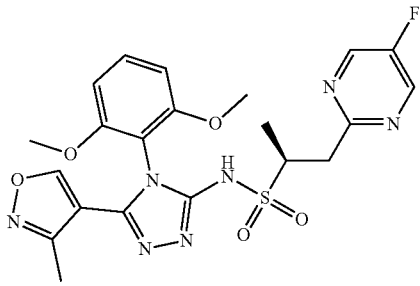<br>and<br>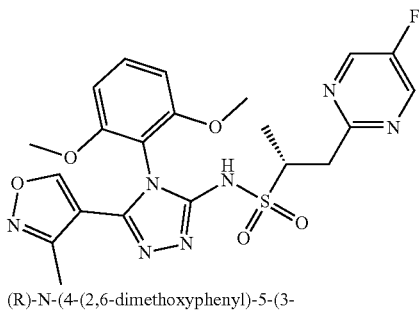<br>(R)-N-(4-(2,6-dimethoxyphenyl)-5-(3-methylisoxazol-4-yl)-4H-1,2,4-triazol-3-yl)-1-(5-fluoropyrimidin-2-yl)propane-2-sulfonamide and (R)-N-(4-(2,6-dimethoxyphenyl)-5-(3-methylisoxazol-4-yl)-4H-1,2,4-triazol-3-yl)-1-(5-fluoropyrimidin-2-yl)propane-2-sulfonamide.<br>LCMS-ESI (pos.) 504.2 (M + H)$^+$. |
| 64.0 | The racemic compound Example 64.1 was separated by SFC (Chiralpak 250 × 20 mm IA column with 70 mL/min, 5 uM, 15% MeOH (+20 mM NH$_3$). Wavelength = 220 nm). Two enantiomers were 64.0 obtained. The title compound was the first isomer to elute under these conditions. | 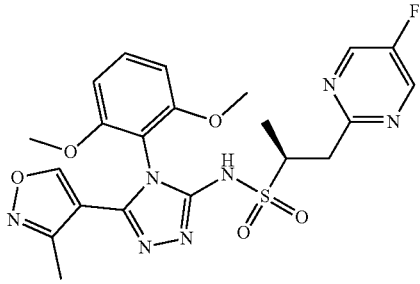<br>or<br>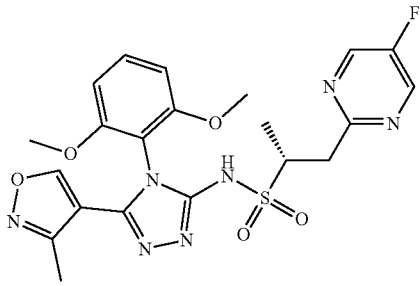<br>(R)-N-(4-(2,6-dimethoxyphenyl)-5-(3-methylisoxazol-4-yl)-4H-1,2,4-triazol-3-yl)-1-(5-fluoropyrimidin-2-yl)propane-2-sulfonamide or (S)-N-(4-(2,6-dimethoxyphenyl)-5-(3- |

TABLE 2-continued

| Example | Reagents | Structure, Name and and Data |
|---|---|---|
| | | methylisoxazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.53 (s, 2H), 7.69 (s, 1H), 7.47 (dd, J = 8.3, 8.3 Hz, 1H), 6.68 (d, J = 8.6 Hz, 2H), 3.77-3.84 (m, 1H), 3.76 (s, 3H), 3.75 (s, 3H), 3.66-3.71 (m, 1H), 3.08 (dd, J = 14.8, 10.1 Hz, 1H), 2.54 (s, 3H), 1.30 (d, J = 6.7 Hz, 3H). MS ESI (pos.) m/z = 504.1 [M + H]. |
| 65.0 | The title compound was the second isomer to elute on subjecting Example 64.1 to the SFC conditions described in Example 64.0. | 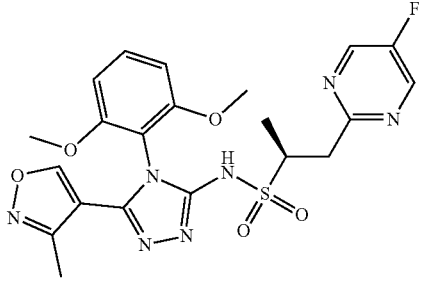<br>or<br>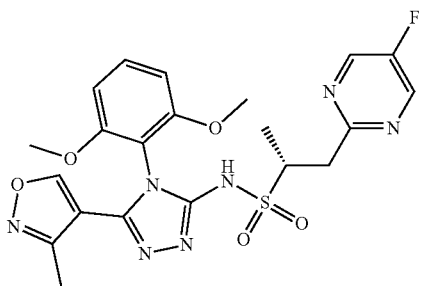<br>(R)-N-(4-(2,6-dimethoxyphenyl)-5-(3-methylisoxazol-4-yl)-4H-1,2,4-triazol-3-yl)-1-(5-fluoropyrimidin-2-yl)propane-2-sulfonamide or (S)-N-(4-(2,6-dimethoxyphenyl)-5-(3-methylisoxazol-4-yl)-4H-1,2,4-triazol-3-yl)-1-(5-fluoropyrimidin-2-yl)propane-2-sulfonamide.<br>$^1$H NMR (400 MHz, CDCl$_3$) δ 8.53 (s, 2H), 7.69 (s, 1H), 7.47 (dd, J = 8.3, 8.3 Hz, 1H), 6.69 (d, J = 8.3 Hz, 2H), 3.77-3.84 (m, 1H), 3.78 (s, 3H), 3.76 (s, 3H), 3.66-3.71 (m, 1H), 3.08 (dd, J = 14.9, 10 Hz, 1H), 2.55 (s, 3H), 1.30 (d, J = 6.8 Hz, 3H). MS ESI (pos.) m/z = 504.1 [M + H]. |
| 66.0 | [N-((2,6-dimethoxyphenyl)carbamothioyl)-1-(5-fluoropyrimidin-2-yl)propane-2-sulfonamide, Example 32.1, and 1-ethyl-1H-pyrazole-3-carbohydrazide (ChemBridge). | 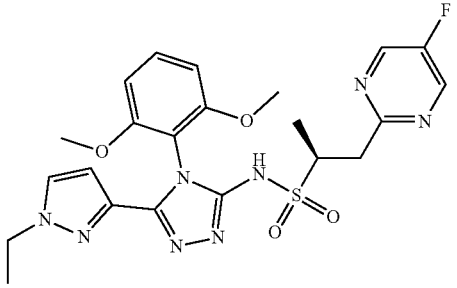<br>and |

TABLE 2-continued

| Example | Reagents | Structure, Name and Data |
|---|---|---|
| | | 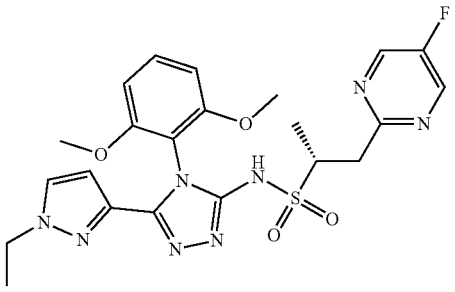
(R)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide.
MS ESI (pos.) m/z = 517.1 [M + H]. |
| 69.0 | The racemic compound (Example 66.0) was separated by SFC (2 × 15 cm AD-H column with 65 mL/min 20% 1:1 ACN:MeOH (0.1% NH$_4$OH)/CO$_2$. Outlet pressure = 100 bar; wavelength = 254 nm; injection volume = 1 mL, 9 mg/mL 1:2 DCM:MeOH). Two enantiomers were obtained. The title compound was the first isomer to elute under these conditions. | 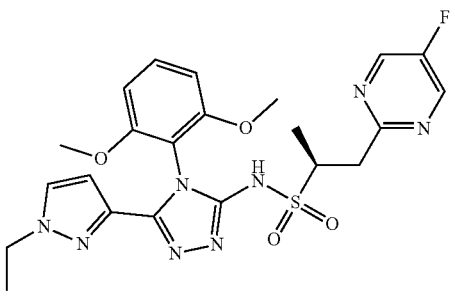
and
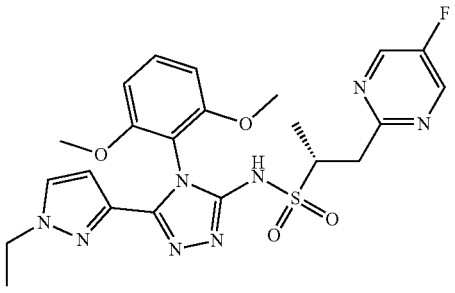
(R)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide.
$^1$H NMR (400 MHz, CDCl$_3$) δ 8.52 (s, 2H), 7.41 (t, J = 8.51 Hz, 1H), 7.26 (d, J = 2.35 Hz, 1H), 6.63 (dd, J = 2.25, 8.51 Hz, 2H), 5.98 (d, J = 2.35 Hz, 1H), 4.11 (q, J = 7.24 Hz, 2H), 3.76-3.85 (m, 1H) 3.74 (s, 3H), 3.72 (s, 3H), 3.66-3.73 (obscured m, 1H), 3.08 (dd, J = 14.67, 9.78 Hz, 1H), 1.39 (t, J = 7.34 Hz, 3H), 1.30 (d, J = 6.85 Hz, 3H). MS ESI (pos.) m/z = 517.1 [M + H]. |

| Example | Reagents | Structure, Name and and Data |
|---|---|---|
| 70.0 | The title compound was the second isomer to elute on subjecting Example 66.0 to the SFC conditions described in Example 69.0. | 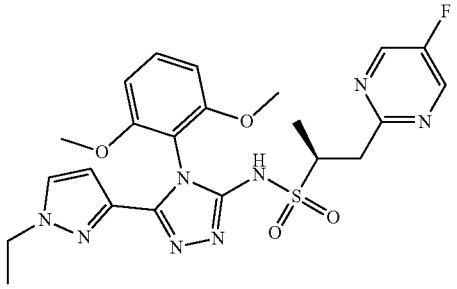<br>or<br>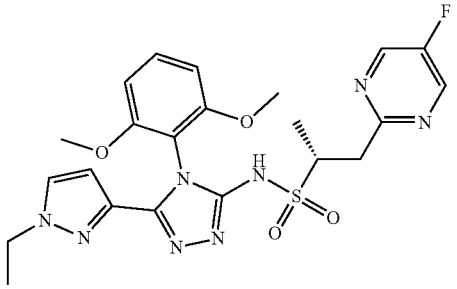<br>(R)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1-ethyl-1H-pyrazol-3-yl)-4H-1,2,4-triazol-3-yl)-1-(5-fluoropyrimidin-2-yl)propane-2-sulfonamide.<br>$^1$H NMR (400 MHz, CDCl$_3$) δ 8.52 (s, 2H), 7.41 (t, J = 8.51 Hz, 1H), 7.26 (d, J = 2.35 Hz, 1H), 6.63 (dd, J = 2.25, 8.51 Hz, 2H), 5.98 (d, J = 2.35 Hz, 1H), 4.11 (q, J = 7.24 Hz, 2H), 3.76-3.85 (m, 1H) 3.74 (s, 3H), 3.72 (s, 3H), 3.66-3.73 (obscured m, 1H), 3.08 (dd, J = 14.67, 9.78 Hz, 1H), 1.39 (t, J = 7.34 Hz, 3H), 1.30 (d, J = 6.85 Hz, 3H). MS ESI (pos.) m/z = 517.1 [M + H]. |
| 72.0 | [[N-((2,6-dimethoxyphenyl)carbamothioyl)-1-(5-fluoropyrimidin-2-yl)propane-2-sulfonamide, Example 32.1, and 3-(hydrazinecarbonyl)-N-methyl-1H-pyrazole-1-carboxamide (Example 395.2). | 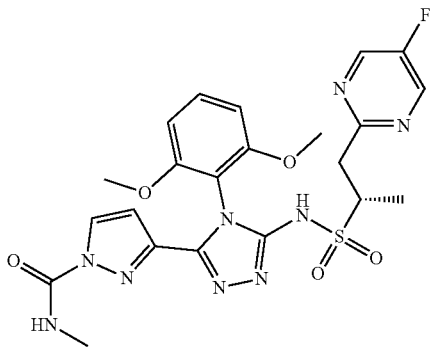<br>and |

| Example | Reagents | Structure, Name and and Data |
|---|---|---|
| | | 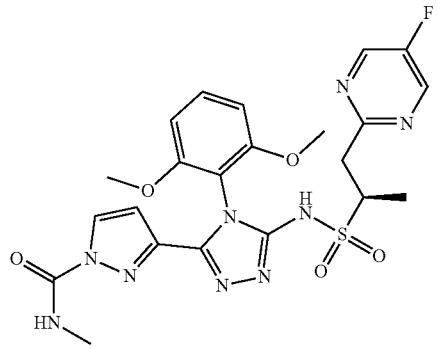<br>(R)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide (S)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide.<br>LCMS-ESI (pos.): 546.2 (M + H)$^+$ |
| 73.0 | Example 72.0 was separated by SFC (2 × 15 cm AS-H column with 65 mL/min 30% MeOH (0.1% NH$_4$OH)/CO$_2$. Outlet pressure = 100 bar; wavelength = 220 nm; injection volume = 0.75 mL, 3 mg/mL 1:5 DCM:MeOH). Two enantiomers were obtained. The title compound was the first isomer to elute under these conditions. | 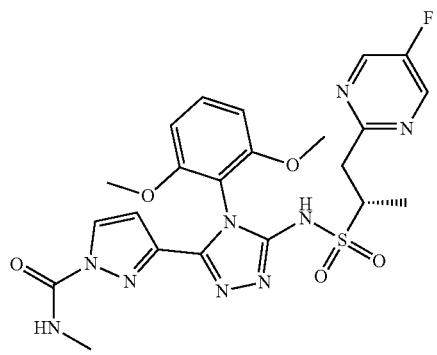<br>or<br>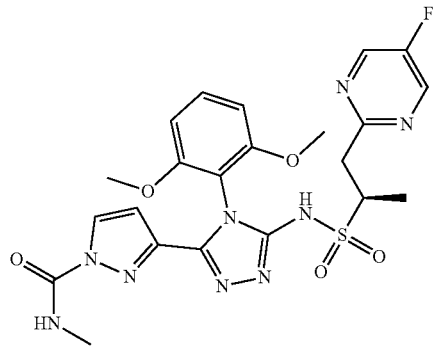<br>(R)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide or (S)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide.<br>$^1$H NMR (400 MHz, CDCl$_3$) δ 8.52 (s, 2 H), 8.11 (d, J = 2.74 Hz, 1 H), 7.46 (t, J = 8.41 Hz, 1 H), 6.66 (dd, J = 8.51, 1.27 Hz, 2 H), 6.62 (d, J = 4.69 Hz, 1 H), 6.43 (d, J = 2.93 Hz, 1 H), 3.78-3.87 (m, 1 H), 3.75 (s, 3 H), 3.73 (s, 3 H), 3.66-3.72 (m, 1 H), 3.10 (dd, J = 14.67, 9.78 Hz, 1 H), 2.91 (d, J = 4.89 Hz, 3 H), 1.32 (d, J = 6.65 Hz, 3 H). LCMS-ESI (pos.): 546.2 (M + H)$^+$ |

TABLE 2-continued

| Example | Reagents | Structure, Name and and Data |
|---|---|---|
| 74.0 | The title compound was the second isomer to elute on subjecting Example 72.0 to the SFC conditions described in Example 73.0. | 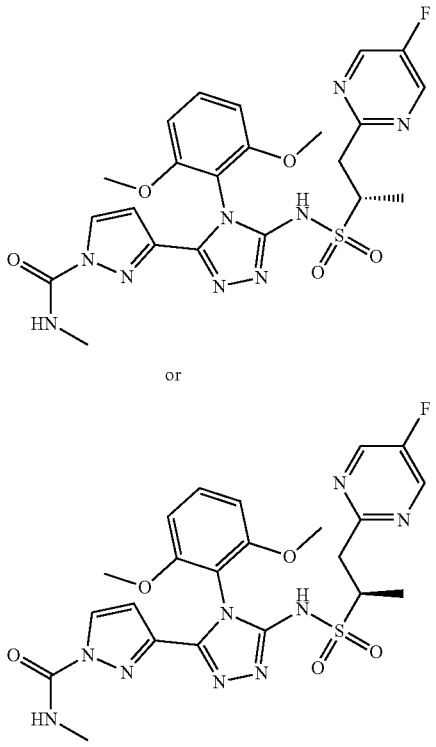<br>or<br><br>(R)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide (S)-3-(4-(2,6-dimethoxyphenyl)-5-(2-(5-fluoropyrimidin-2-yl)-1-methylethylsulfonamido)-4H-1,2,4-triazol-3-yl)-N-methyl-1H-pyrazole-1-carboxamide.<br>$^1$H NMR (400 MHz, CDCl$_3$) δ 8.52 (s, 2 H), 8.11 (d, J = 2.93 Hz, 1 H), 7.45 (t, J = 8.41 Hz, 1 H), 6.66 (dd, J = 8.51, 1.66 Hz, 3 H), 6.41 (br. s, 1 H), 3.78-3.87 (m, 1 H), 3.75 (s, 3 H), 3.73 (s, 3 H), 3.66-3.72 (m, 1 H), 3.10 (dd, J = 14.67, 9.78 Hz, 1 H), 2.91 (d, J = 5.09 Hz, 3 H), 1.32 (d, J = 6.85 Hz, 3 H). LCMS-ESI (pos.): 546.2 (M + H)$^+$ |
| 71.0 | N-((2,6-dimethoxyphenyl)carbamothioyl)-1-(5-fluoropyrimidin-2-yl)propane-2-sulfonamide, Example 32.1, and 3-(hydrazinecarbonyl)-N-methyl-1H-pyrazole-1-carboxamide (Example 395.2). | 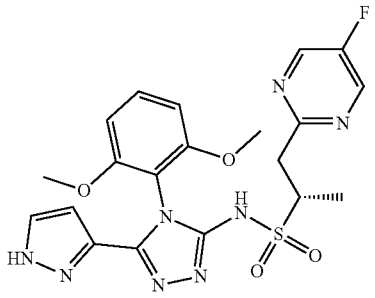<br>and |

TABLE 2-continued

| Example | Reagents | Structure, Name and and Data |
|---|---|---|
| | | 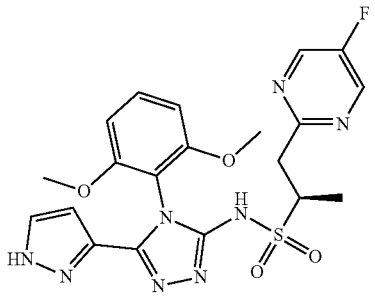<br>(R)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide and (S)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide. LCMS-ESI (pos.): 489.1 (M + H)$^+$ |
| 75.0 | Example 71.0 was separated by SFC (250 × 21 mm IC column on Thar 80 with 29.4 g/min MeOH + 20 mM NH$_3$ + 41g/min CO$_2$, 42% co-solvent at 70 g/min. Outlet pressure = 100 bar; temperature = 24° C.; wavelength = 220 nm; injection volume = 2 mL, 4 mg/mL 2:1 MeOH:DCM). Two enantiomers were obtained. The title compound was the first isomer to elute under these conditions. | 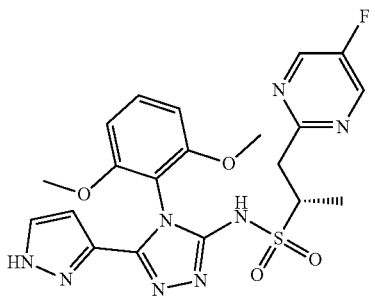<br>or<br>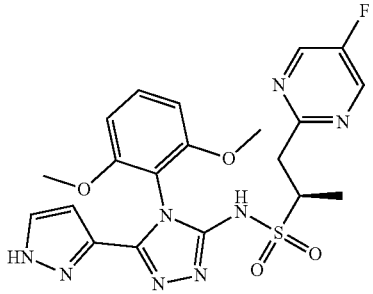<br>(R)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide. $^1$H NMR (400 MHz, Solvent) δ 8.66 (s, 2 H), 7.59 (br. s, 1 H), 7.48 (t, J = 8.12 Hz, 1 H), 6.78 (d, J = 7.24 Hz, 2 H), 6.14 (br. s, 1 H), 3.74 (m, 6 H), 3.70-3.72 (m, 1 H), 3.62 (d, J = 14.48 Hz, 1 H), 3.00 (dd, J = 14.57, 10.27 Hz, 1 H), 1.24 (d, J = 6.85 Hz, 3 H). LCMS-ESI (pos.): 489.2 (M + H)$^+$. |

TABLE 2-continued

| Example | Reagents | Structure, Name and and Data |
|---|---|---|
| 76.0 | The title compound was the second isomer to elute on subjecting Example 71.0 to the SFC conditions described in Example 75.0. | 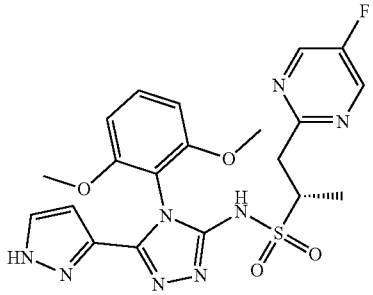<br>or<br>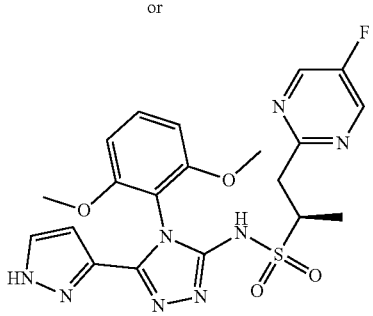<br>(R)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide or (S)-N-(4-(2,6-dimethoxyphenyl)-5-(1H-pyrazol-3-yl)-4H-1,2,4-triazol-3-yl)-1-(5-fluoropyrimidin-2-yl)propane-2-sulfonamide.<br>$^1$H NMR (400 MHz, CD$_3$OD) δ 8.66 (s, 2 H), 7.58 (br. s, 1 H), 7.48 (t, J = 8.12 Hz, 1 H), 6.78 (d, J = 7.83 Hz, 2 H), 6.14 (br. s, 1 H), 3.74 (m, 6 H), 3.68-3.72 (m, 1 H), 3.61 (dd, J = 14.57, 3.42 Hz, 1 H), 3.00 (dd, J = 14.57, 10.27 Hz, 1 H), 1.24 (d, J = 6.65 Hz, 3 H). LCMS-ESI (pos.) 489.2 (M + H)$^+$. |
| 67.1 | (2S,3R)-3-(5-fluoropyrimidin-2-yl)butane-2-sulfonamide and (2R,3S)-3-(5-fluoropyrimidin-2-yl)butane-2-sulfonamide (Example 403.0), 1-methyl-1H-pyrazole-3-carbohydrazide (Example 395.13), and 2-isothiocyanato-1,3-dimethoxybenzene Example 465.0. | 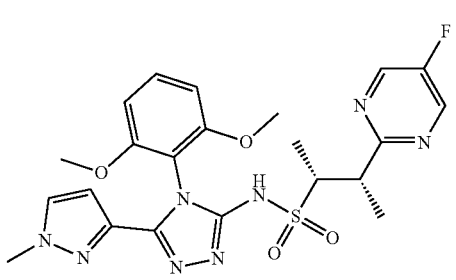<br>and<br>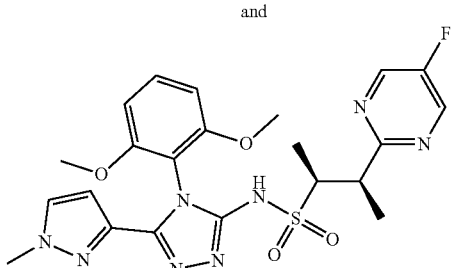<br>(2S,3R)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide and (2R,3S)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide.<br>LCMS-ESI (pos.): 517.8 (M + H)$^+$ |

TABLE 2-continued

| Example | Reagents | Structure, Name and and Data |
|---|---|---|
| 68.0 | Example 67.1 was separated by SFC (2.1 × 25 cm AS column with 70 mL/min 20% MeOH (20 mM NH$_3$)/CO$_2$. Outlet pressure = 100 bar; temperature = 40° C.; wavelength = 220 nm; injection volume = 1.0 mL, 17 mg/ mL 1:1 DCM:MeOH). Two enantiomers were obtained. The title compound was the first isomer to elute under these conditions. | 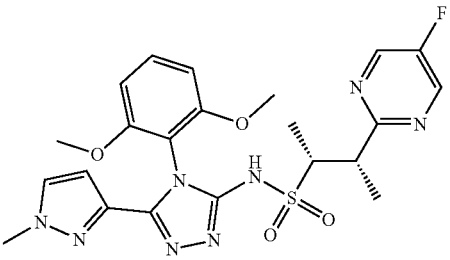<br><br>or<br><br>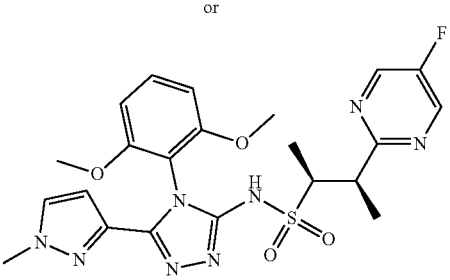<br><br>((2S,3R)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide or (2R,3S)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide.<br>$^1$H NMR (400 MHz, CDCl$_3$) δ 8.52 (s, 2H), 7.41 (dd, J = 8.4, 8.4 Hz, 1H), 7.22 (d, J = 2.2 Hz, 1H), 6.63 (dd, J = 8.z, 4.5 Hz, 2H), 5.09 (d, J = 2.3 Hz, 1H), 3.84 (s, 3H), 3.79-3.85 (m, 2H), 3.72 (s, 3H), 3.71 (s, 3H), 1.36 (d, J = 6.8 Hz, 3H), 1.34 (d, J = 6.8 Hz, 3H). MS ESI (pos.) m/z = 517.8 [M + H]. |
| 67.0 | The racemic compound was separated by SFC (2.1 × 25 cm AS column with 70 mL/min 20% MeOH (20 mM NH$_3$)/CO$_2$. Outlet pressure = 100 bar; temperature = 40°+0C.; wavelength = 220 nm; injection volume = 1.0 mL, 17 mg/mL 1:1 DCM:MeOH). Two enantiomers were obtained. The title compound was the first isomer to elute under these conditions. | 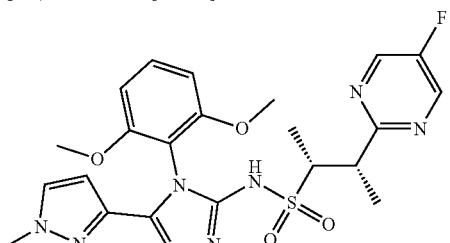<br><br>or<br><br>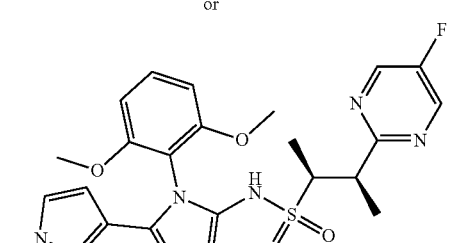<br><br>(2S,3R)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide or (2R,3S)-N-(4-(2,6-dimethoxyphenyl)-5-(1-methyl-1H-pyrazol-3-yl)-4H-1,2,4-triazol-3-yl)-3-(5-fluoropyrimidin-2-yl)butane-2-sulfonamide. |

TABLE 2-continued

| Example | Reagents | Structure, Name and and Data |
|---|---|---|
| | | $^1$H NMR (400 MHz, CDCl$_3$) δ: 8.52 (s, 2H), 7.41 (dd, J = 8.4, 8.4 Hz, 1H), 7.22 (d, J = 2.2 Hz, 1H), 6.63 (dd, J = 8.4, 4.5 Hz, 2H), 5.09 (d, J = 2.3 Hz, 1H), 3.84 (s, 3H), 3.79-3.85 (m, 2H), 3.72 (s, 3H), 3.71 (s, 3H), 1.36 (d, J = 6.8 Hz, 3H), 1.34 (d, J = 6.8 Hz, 3H). MS ESI (pos.) m/z = 517.8 [M + H]. |

Example 77.1. Preparation of benzo[d]isoxazole-3-carbohydrazide

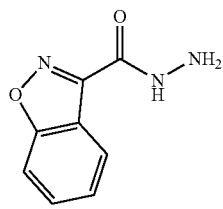

77.1

Benzo[d]isoxazole-3-carbohydrazide, Example 77.1. To a solution of 1,2-benzisoxazole-3-carboxylic acid ethyl ester (commercially available from AstaTech, Inc., 1.0 g, 5.23 mmol) in EtOH (7.93 mL) was added hydrazine, monohydrate (0.78 mL, 10.46 mmol), and the reaction was heated to reflux. After 3 d, the reaction showed 80% conversion to product by LCMS. A further 2 equiv. of hydrazine was added and the reaction stirred at 60° C. After a further day, the reaction was judged complete by LCMS. The reaction was then cooled to RT, EtOAc was added, and the mixture was stirred for 30 min. The mixture was then concentrated in vacuo to yield benzo[d]isoxazole-3-carbohydrazide (1.1 g), the material was carried forward without purification. LCMS-ESI (pos.) m/z: 178.1 (M+H)$^+$.

The compounds set forth in the following table were synthesized following the procedures in Example 77.1 using the known starting material as described.

TABLE 3

| Example | Reagents | Structure, Name and Data |
|---|---|---|
| 77.3 | 2-methyl-2H-indazole-7-carboxylic acid methyl ester (commercially available from Synthonix Inc.). | 2-methyl-2H-indazole-7-carbohydrazide. LCMS-ESI (pos.) m/z: 191.2 (M + H)$^+$. |
| 77.4 | 2-methyl-2H-indazole-4-carboxylic acid methyl ester (commercially available from AstaTech, Inc.). | 2-methyl-2H-indazole-4-carbohydrazide. LCMS-ESI (pos.) m/z: 191.2 (M + H)$^+$. |
| 77.5 | methyl 2-oxoindoline-7-carboxylate (commercially available from Accela ChemBio Inc.). | 2-oxoindoline-7-carbohydrazide. LCMS-ESI (pos.) m/z: 192.2 (M + H)$^+$. |

Example 77.0. Preparation of (2S,3R)-N-(5-(benzo[d]isoxazol-3-yl)-4-(2,6-dimethoxyphenyl)-4H-1,2,4-triazol-3-yl)-3-(5-methylpyrimidin-2-yl)butane-2-sulfonamide

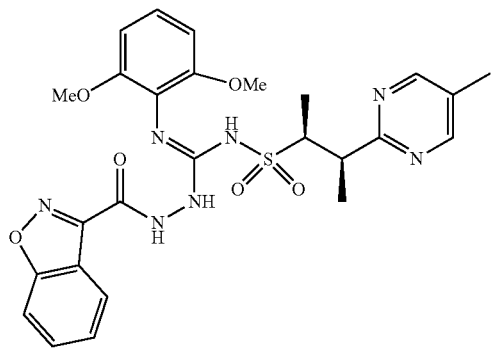

77.01

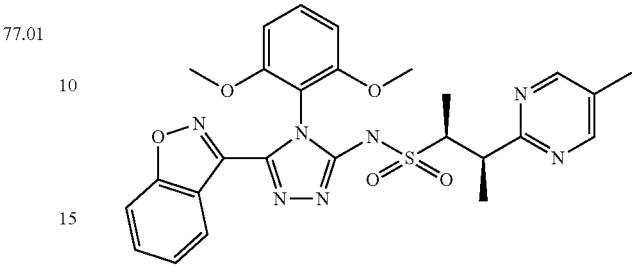

77.0

((Z)-2-(Benzo[d]isoxazole-3-carbonyl)-N'-(2,6-dimethoxyphenyl)-N-(((2S,3R)-3-(5-methylpyrimidin-2-yl)butan-2-yl)sulfonyl)hydrazinecarboximidamide, Example 77.01. To a solution of (2S,3R)-3-(5-methylpyrimidin-2-yl)butane-2-sulfonamide (Example 464.0, 0.2 g, 0.87 mmol) in ACN (8.72 mL) was added 2-isothiocyanato-1,3-dimethoxybenzene (Example 465.0, 0.170 g, 0.87 mmol), and cesium carbonate (0.369 g, 1.13 mmol). The resulting mixture was stirred at RT. After 24h, LCMS showed complete consumption of starting material and conversion to the thiourea intermediate. To this white slurry was added benzo[d]isoxazole-3-carbohydrazide (Example 77.1, 0.155 g, 0.872 mmol) followed by silver(I) nitrate (0.296 g, 1.74 mmol) and the reaction was stirred at RT. After 15 min, the mixture had turned brown and LCMS indicated conversion to product. The mixture was loaded directly onto silica gel and purified using a gradient of 30-100% EtOAc:EtOH (3:1) in heptanes to yield Example 77.01 (0.3 g, 0.53 mmol, 61% yield) as a white solid. LCMS-ESI (pos.) m/z: 568.2 (M+H)$^+$.

(2S,3R)-N-(5-(Benzo[d]isoxazol-3-yl)-4-(2,6-dimethoxyphenyl)-4H-1,2,4-triazol-3-yl)-3-(5-methylpyrimidin-2-yl)butane-2-sulfonamide. To a solution of Example 77.01 (0.3 g, 0.529 mmol) in IPA (1.76 mL)/water (0.881 mL) was added sodium hydroxide (1.0 N, 0.661 mL, 0.661 mmol). The reaction was then heated to 80° C. After 12h, the LCMS indicated approximately 50% conversion to product and so the reaction was heated for a further 24h after which LCMS indicated 80% conversion to product. The reaction was then neutralized to pH 7.0 by addition of 1.0 M HCl. The mixture was then diluted with water, extracted with DCM and the combined organic layers were dried over Na$_2$SO$_4$. The mixture was then concentrated in vacuo and purified by silica gel chromatography using a gradient of 0-100% EtOAc:EtOH (3:1) in heptanes to yield Example 77.0 (0.08 g, 0.146 mmol, 28% yield) as a white solid. $^1$H NMR (400 MHz, DMSO-d$_6$) δ 14.03 (s, 1H) 8.59 (s, 2H) 8.17 (d, J=7.7 Hz, 1H) 7.72-7.88 (m, 2H) 7.43-7.62 (m, 2H) 6.83 (dd, J=8.4, 2.7 Hz, 2H) 3.60-3.74 (m, 8H) 2.23 (s, 3H) 1.25 (d, J=6.9 Hz, 3H) 1.13 (d, J=6.9 Hz, 3H). LCMS-ESI (pos.) m/z: 550.2 (M+H)$^+$.

The compounds set forth in the following table were synthesized following the procedure in Example 77.0 using the known starting material as described.

TABLE 4

| Example | Reagents | Structure, Name and and Data |
|---|---|---|
| 83.0 | Benzo[d]isoxazole-3-carbohydrazide (Example 77.1), isothiocyanato-1,3-dimethoxybenzene (Example 465.0), and (1R,2S)-1-(5-chloropyrimidin-2-yl)-1-methoxypropane-2-sulfonamide (Example 466.3). | (1R,2S)-N-(5-(benzo[d]isoxazol-3-yl)-4-(2,6-dimethoxyphenyl)-4H-1,2,4-triazol-3-yl)-1-(5-chloropyrimidin-2-yl)-1-methoxypropane-2-sulfonamide. $^1$H NMR (400 MHz, DMSO-d$_6$) δ 8.92-8.95 (m, 2H) 8.13-8.21 (m, 1H) 7.81-7.87 (m, 1H) 7.74-7.80 (m, 1H) 7.54-7.61 (m, 1H) 7.46-7.53 (m, 1H) 6.82-6.87 (m, 2H) 4.81-4.86 (m, 1H) 4.06-4.14 (m, 1H) 3.65-3.70 (m, 6H) 3.17-3.18 (m, 3H) 1.18- 1.21 (m, 3H). LCMS-ESI (pos.) m/z: 586.2 (M + H)$^+$. |

TABLE 4-continued

| Example | Reagents | Structure, Name and and Data |
|---|---|---|
| 84.0 | Benzo[d]isoxazole-3-carbohydrazide (Example 77.1), 4-isothiocyanatotetrahydro-2H-pyran (Comercially avilable from Matrix Scientific), and (2S,3R)-3-(5-methylpyrimidin-2-yl)butane-2-sulfonamide (Example 464.0). | 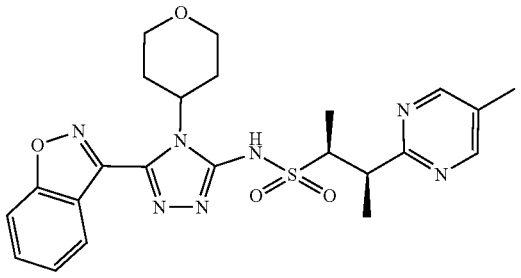 [SMILES: Cc1cnc([C@@H](C)[C@H](C)S(=O)(=O)Nc2nnc(-c3noc4ccccc34)n2C2CCOCC2)nc1]<br>(2S,3R)-N-(5-(benzo[d]isoxazol-3-yl)-4-(tetrahydro-2H-pyran-4-yl)-4H-1,2,4-triazol-3-yl)-3-(5-methylpyrimidin-2-yl)butane-2-sulfonamide.<br>$^1$H NMR (500 MHz, CDCl$_3$) δ 11.55-11.85 (m, 1H) 8.54-8.58 (m, 2H) 8.21-8.27 (m, 1H) 7.68-7.76 (m, 2H) 7.47-7.52 (m, 1H) 5.36-5.46 (m, 1H) 4.09-4.16 (m, 2H) 3.95-4.02 (m, 1H) 3.77-3.85 (m, 1H) 3.50-3.58 (m, 2H) 2.95-3.08 (m, 2H) 2.30-2.34 (m, 3H) 1.73-1.83 (m, 2H) 1.48- 1.53 (m, 6H) 1.29-1.33 (m, 1H). LCMS-ESI (pos.) m/z: 498.2 (M + H)$^+$. |
| 87.0 | Benzo[d]isoxazole-3-carbohydrazide (Example 77.1), isothiocyanato-1,3-dimethoxybenzene (Example 465.0), and (1R,2S)-1-methoxy-1-(5-methylpyrimidin-2-yl)propane-2-sulfonamide (Example 466.0). | 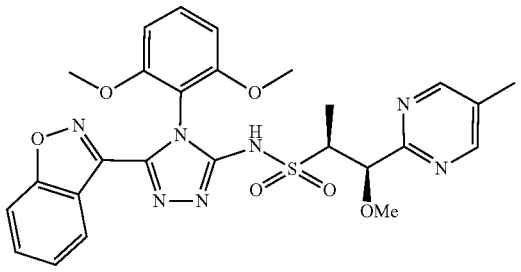 [SMILES: COc1cccc(OC)c1-n1c(NS(=O)(=O)[C@@H](C)[C@H](OC)c2ncc(C)cn2)nnc1-c1noc2ccccc12]<br>(1R,2S)-N-(5-(benzo[d]isoxazol-3-yl)-4-(2,6-dimethoxyphenyl)-4H-1,2,4-triazol-3-yl)-1-methoxy-1-(5-methylpyrimidin-2-yl)propane-2-sulfonamide.<br>$^1$H NMR (500 MHz, DMSO-d$_6$) δ 13.90 (br d, J = 0.6 Hz, 1H) 8.49-8.56 (m, 2H) 8.41-8.45 (m, 1H) 8.15-8.21 (m, 1H) 7.82-7.86 (m, 1H) 7.75-7.80 (m, 1H) 7.56-7.61 (m, 1H) 7.48-7.53 (m, 1H) 6.84-6.87 (m, 1H) 4.87-4.91 (m, 1H) 3.66-3.70 (m, 6H) 3.39-3.48 (m, 1H) 3.33-3.34 (m, 3H) 3.18-3.22 (m, 3H) 1.07-1.11 (m, 3H). LCMS-ESI (pos.) m/z: 566.2 (M +H)$^+$. |
| 88.0 | Benzo[d]isoxazole-3-carbohydrazide (Example 77.1), 5-isothiocyanato-4,6-dimethoxypyrimidine (Example 465.1), and (2S,3R)-3-(5-methylpyrimidin-2-yl)butane-2-sulfonamide (Example 464.0). | 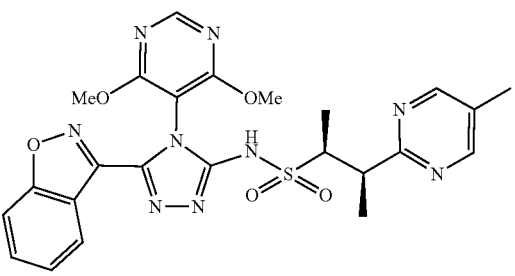 [SMILES: COc1ncnc(OC)c1-n1c(NS(=O)(=O)[C@@H](C)[C@H](C)c2ncc(C)cn2)nnc1-c1noc2ccccc12]<br>(2S,3R)-N-(5-(benzo[d]isoxazol-3-yl)-4-(4,6-dimethoxypyrimidin-5-yl)-4H-1,2,4-triazol-3-yl)-3-(5-methylpyrimidin-2-yl)butane-2-sulfonamide.<br>$^1$H NMR (400 MHz, DMSO-d$_6$) δ 13.77-14.43 (m, 1H) 8.66-8.78 (m, 1H) 8.55-8.65 (m, 2 H) 8.17-8.26 (m, 1H) 7.85-7.90 (m, 1H) 7.77-7.84 (m, 1H) 7.57-7.64 (m, 1H) 3.86-3.89 (m, 6H) 3.65-3.73 (m, 2H) 2.22-2.26 (m, 3 H) 1.25-1.28 (m, 3H) 1.13-1.16 (m, 3H). LCMS-ESI (pos.) m/z: 552.2 (M + H)$^+$. |

TABLE 4-continued

| Example | Reagents | Structure, Name and and Data |
|---|---|---|
| 90.0 | isoxazole-3-carbohydrazide (comercially avilable from Frontier Scientific Services Inc), isothiocyanato-1,3-dimethoxybenzene (Example 465.0), and (1R,2S)-1-methoxy-1-(5-methylpyrimidin-2-yl)propane-2-sulfonamide (Example 466.0). | 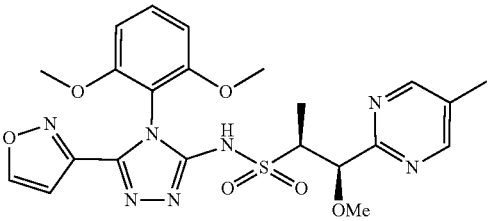 [SMILES: COc1cccc(OC)c1-n1c(NS(=O)(=O)[C@@H](C)[C@H](OC)c2ncc(C)cn2)nnc1-c1ccon1] (1R,2S)-N-(4-(2,6-dimethoxyphenyl)-5-(isoxazol-3-yl)-4H-1,2,4-triazol-3-yl)-1-methoxy-1-(5-methylpyrimidin-2-yl)propane-2-sulfonamide. $^1$H NMR (500 MHz, CDCl$_3$) δ 11.10-11.35 (m, 1H) 8.51-8.53 (m, 1H) 8.41-8.45 (m, 2H) 7.41-7.47 (m, 1H) 6.69-6.72 (m, 1H) 6.63-6.69 (m, 2H) 5.03-5.06 (m, 1H) 3.72-3.78 (m, 6H) 3.51-3.59 (m, 1H) 3.31-3.35 (m, 3H) 2.57-2.60 (m, 3H) 1.25-1.28 (m, 3H). LCMS-ESI (pos.) m/z: 516.1 (M + H)$^+$. |

Example 136.0. Preparation of 2-(4-chlorophenyl)-N-(4-(2,6-dimethoxyphenyl)-5-(thiazol-2-yl)-4H-1,2,4-triazol-3-yl)ethanesulfonamide

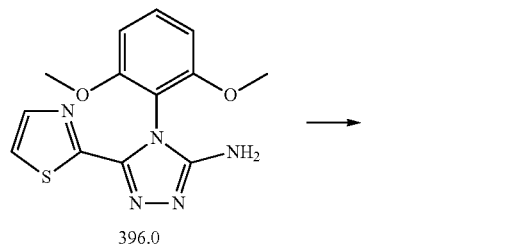

396.0

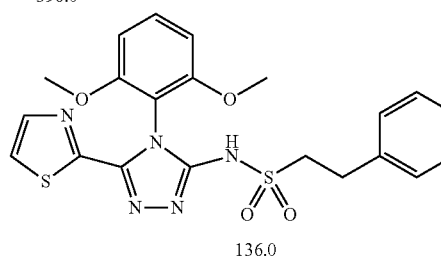

136.0

2-(4-Chlorophenyl)-N-(4-(2,6-dimethoxyphenyl)-5-(thiazol-2-yl)-4H-1,2,4-triazol-3-yl)ethanesulfonamide, Example 136.0. To a solution of 396.0 (57.5 mg, 0.19 mmol) and TEA (105 μL, 0.76 mmol) in DCM (2.0 mL) was added 2-(4-chlorophenyl)ethanesulfonyl chloride (Synchem Inc., 68 mg, 0.28 mmol). The resulting yellow solution was stirred at RT for 1.5 h. The reaction was then quenched with water (5 mL) and extracted with DCM (3×). The combined organic layers were dried over anhydrous sodium sulfate and concentrated in vacuo. The residue was purified by reverse phase preparatory HPLC (Sunfire 5 μM C18 column, eluent: 30-80% ACN in water over a 35 min period where both solvents contain 0.1% TFA) to provide 136.0 (49 mg, 51% yield) as a white solid. $^1$H NMR (500 MHz, DMSO-d$_6$) δ 13.60 (s, 1H), 7.93 (s, 1H), 7.85 (s, 1H), 7.50 (t, J=8.6 Hz, 1H), 7.33 (d, J=7.8 Hz, 2H), 7.23 (d, J=7.9 Hz, 2H), 6.85 (d, J=8.6 Hz, 2H), 3.67 (s, 3H), 3.67 (s, 3H), 3.21-3.28 (m, 2H), 2.85-2.95 (m, 2H). LCMS-ESI (pos.) m/z: 506.0 (M+H)$^+$.

The compounds set forth in the following table were synthesized following the procedure in Example 136.0 using the starting material as described.

TABLE 5

| Example | Reagents | Structure, Name and Data |
|---|---|---|
| 137.0 | 4-(2,6-dimethoxyphenyl)-5-(thiazol-5-yl)-4H-1,2,4-triazol-3-amine (Example 397.0). | 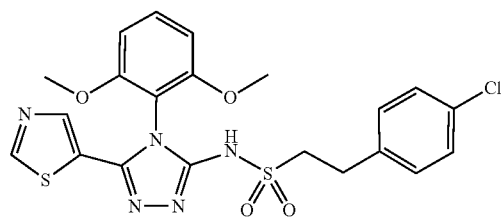 [SMILES: COc1cccc(OC)c1-n1c(NS(=O)(=O)CCc2ccc(Cl)cc2)nnc1-c1cncs1] 2-(4-chlorophenyl)-N-(4-(2,6-dimethoxyphenyl)-5-(thiazol-5-yl)-4H-1,2,4-triazol-3-yl)ethanesulfonamide. $^1$H NMR (400 MHz, DMSO-d$_6$) δ 13.51 (s, 1H), 9.18 (d, J = 1.0 Hz, 1H), 7.80 (d, J = 01.0 H, 1H), 7.57-7.64 (m, 1H), 7.30-7.37 (m, 2H), 7.22 (d, J = 7.1 Hz, 2H), 6.92 (dd, J = 8.7, 1.6 Hz, 2H), 3.73 (s, 3H), 3.72 (s, 3H), 3.17-3.23 (m, 2H), 2.85-2.92 (m, 2H). LCMS-ESI (pos.) m/z: 506.2 (M + H)$^+$. |

TABLE 5-continued

| Example | Reagents | Structure, Name and Data |
|---|---|---|
| 138.0 | 4-(2,6-dimethoxyphenyl)-5-(oxazol-5-yl)-4H-1,2,4-triazol-3-amine (Example 397.1). | 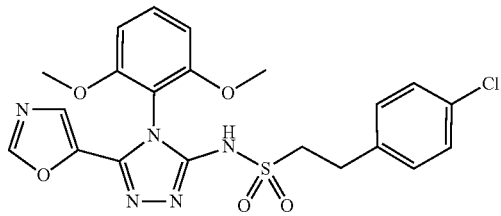 [SMILES: COc1cccc(OC)c1-n1c(NS(=O)(=O)CCc2ccc(Cl)cc2)nnc1-c1cnco1] 2-(4-chlorophenyl)-N-(4-(2,6-dimethoxyphenyl)-5-(oxazol-5-yl)-4H-1,2,4-triazol-3-yl)ethanesulfonamide. $^1$H NMR (400 MHz, CD$_3$OD) δ 8.29 (s, 1H), 7.59 (t, J = 8.5 Hz, 1H), 7.25-7.31 (m, 2H), 7.15-7.21 (m, 2H), 6.88 (d, J = 8.61 Hz, 2H), 6.73 (s, 1H), 3.78 (s, 3H), 3.78 (s, 3H), 3.22-3.28 (m, 2H), 2.98-3.04 (m, 2H). LCMS-ESI (pos.) m/z: 490.2 (M + H)$^+$. |
| 139.0 | 4-(2,6-dimethoxyphenyl)-5-(oxazol-4-yl)-4H-1,2,4-triazol-3-amine (Example 397.2). | 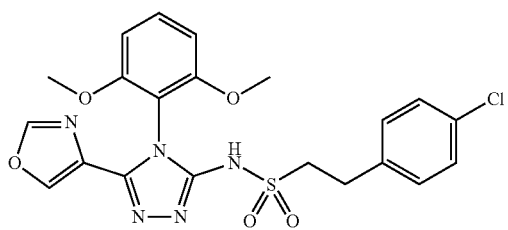 [SMILES: COc1cccc(OC)c1-n1c(NS(=O)(=O)CCc2ccc(Cl)cc2)nnc1-c1cocn1] 2-(4-chlorophenyl)-N-(4-(2,6-dimethoxyphenyl)-5-(oxazol-4-yl)-4H-1,2,4-triazol-3-yl)ethanesulfonamide. $^1$H NMR (400 MHz, DMSO-d$_6$) δ 13.37 (s, 1H), 8.46 (d, J = 1.0 Hz, 1H), 7.92 (d, J = 1.0 Hz, 1H), 7.52 (t, J = 8.5 Hz, 1H), 7.33 (d, J = 8.4 Hz, 2H), 7.22 (d, J = 8.2 Hz, 2H), 6.85 (d, J = 8.6 Hz, 2H), 3.70 (s, 3H), 3.70 (s, 3H), 3.15-3.22 (m, 2H), 2.85-2.92 (m, 2H). LCMS-ESI (pos.) m/z: 490.0 (M + H)$^+$. |
| 141.0 | 4-(2,6-dimethoxyphenyl)-5-(thiophen-3-yl)-4H-1,2,4-triazol-3-amine (Example 397.3). | 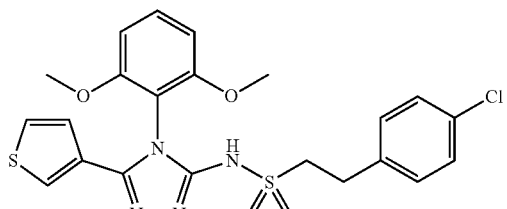 2-(4-chlorophenyl)-N-(4-(2,6-dimethoxyphenyl)-5-(thiophen-3-yl)-4H-1,2,4-triazol-3-yl)ethanesulfonamide. $^1$H NMR (400 MHz, DMSO-d$_6$) δ 13.23 (s, 1H), 7.61 (dd, J = 5.9, 2.9 Hz, 1H), 7.56 (t, J = 8.5 Hz, 1H), 7.33 (d, J = 8.4 Hz, 2H), 7.29 (dd, J = 2.8, 1.3 Hz, 1H), 7.22 (d, J = 8.6 Hz, 2H), 7.14 (dd, J = 5.1, 1.9 Hz, 1H), 6.89 (d, J = 8.6 Hz, 2H), 3.71 (s, 3H), 3.71 (s, 3H), 3.14-3.20 (m, 2H), 2.85-2.92 (m, 2H). LCMS-ESI (pos.) m/z: 505.0 (M + H)$^+$. |

TABLE 5-continued

| Example | Reagents | Structure, Name and Data |
|---|---|---|
| 142.0 | 4-(2,6-dimethoxyphenyl)-5-(4-methylthiazol-2-yl)-4H-1,2,4-triazol-3-amine (Example 397.4). | 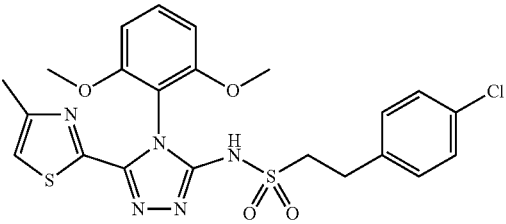 [SMILES: COc1cccc(OC)c1-n1c(NS(=O)(=O)CCc2ccc(Cl)cc2)nnc1-c1nc(C)cs1]2-(4-chlorophenyl)-N-(4-(2,6-dimethoxyphenyl)-5-(4-methylthiazol-2-yl)-4H-1,2,4-triazol-3-yl)ethanesulfonamide.<br>$^1$H NMR (400 MHz, DMSO-d$_6$) δ 13.56 (s, 1H), 7.53 (t, J = 8.5 Hz, 1H), 7.45 (d, J = 1.0 Hz, 1H), 7.31-7.36 (m, 2H), 7.20-7.25 (m, 2H), 6.85 (d, J = 8.6 Hz, 2H), 3.68 (s, 3H), 3.68 (s, 3H), 3.18-3.24 (m, 2H), 2.87-2.93 (m, 2H), 2.25 (d, J = 1.0 Hz, 3H). LCMS-ESI (pos.) m/z: 520.0 (M + H)$^+$. |
| 143.0 | 4-(2,6-dimethoxyphenyl)-5-(5-methylthiazol-2-yl)-4H-1,2,4-triazol-3-amine (Example 397.5). | 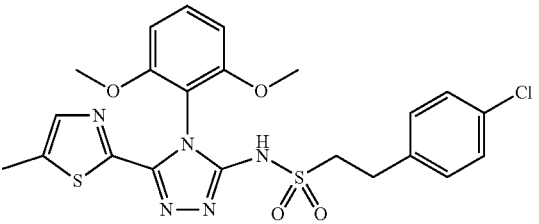 [SMILES: COc1cccc(OC)c1-n1c(NS(=O)(=O)CCc2ccc(Cl)cc2)nnc1-c1ncc(C)s1]2-(4-chlorophenyl)-N-(4-(2,6-dimethoxyphenyl)-5-(5-methylthiazol-2-yl)-4H-1,2,4-triazol-3-yl)ethanesulfonamide.<br>$^1$H NMR (500 MHz, DMSO-d$_6$) δ 13.53 (s, 1H), 7.52 (s, 1H), 7.49 (t, J = 8.4 Hz, 1H), 7.33 (d, J = 7.8 Hz, 2H), 7.22 (d, J = 8.1 Hz, 2H), 6.83 (d, J = 8.6 Hz, 2H), 3.67 (s, 3H), 3.67 (s, 3H), 3.16-3.22 (m, 2H), 2.86-2.92 (m, 2H), 2.43 (s, 3H). LCMS-ESI (pos.) m/z: 520.0 (M + H)$^+$. |
| 144.0 | 5-(5-chlorothiazol-2-yl)-4-(2,6-dimethoxyphenyl)-4H-1,2,4-triazol-3-amine (Example 397.6). | 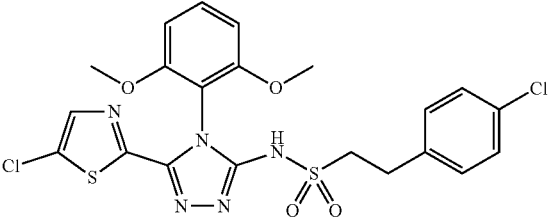 [SMILES: COc1cccc(OC)c1-n1c(NS(=O)(=O)CCc2ccc(Cl)cc2)nnc1-c1ncc(Cl)s1]2-(4-chlorophenyl)-N-(5-(5-chlorothiazol-2-yl)-4-(2,6-dimethoxyphenyl)-4H-1,2,4-triazol-3-yl)ethanesulfonamide.<br>$^1$H NMR (500 MHz, DMSO-d$_6$) δ 13.72 (s, 1H), 7.91 (s, 1H), 7.51 (t, J = 8.6 Hz, 1H), 7.33 (d, J = 8.6 Hz, 2H), 7.22 (d, J = 8.3 Hz, 2H), 6.84 (d, J = 8.6 Hz, 2H), 3.69 (s, 3H), 3.69 (s, 3H), 3.18-3.24 (m, 2H), 2.86-2.92 (m, 2H). LCMS-ESI (pos.) m/z: 540.0 (M + H)$^+$. |

TABLE 5-continued

| Example | Reagents | Structure, Name and Data |
|---|---|---|
| 145.0 | 4-(2,6-dimethoxyphenyl)-5-(5-methylisoxazol-3-yl)-4H-1,2,4-triazol-3-amine (Example 397.7). | 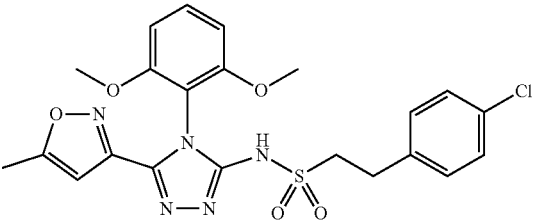 [SMILES: COc1cccc(OC)c1-n1c(NS(=O)(=O)CCc2ccc(Cl)cc2)nnc1-c1cc(C)on1]<br>2-(4-chlorophenyl)-N-(4-(2,6-dimethoxyphenyl)-5-(5-methylisoxazol-3-yl)-4H-1,2,4-triazol-3-yl)ethanesulfonamide.<br>$^1$H NMR (500 MHz, DMSO-$d_6$) δ 13.66 (s, 1H), 7.49 (t, J = 8.4 Hz, 1H), 7.33 (d, J = 8.6 Hz, 2H), 7.22 (d, J = 8.6 Hz, 2H), 6.83 (d, J = 8.6 Hz, 2H), 6.52 (d, J = 1.0 Hz, 1H), 3.69 (s, 3H), 3.69 (s, 3H), 3.16-3.23 (m, 2H), 2.86-2.92 (m, 2H), 2.40 (d, J = 0.7 Hz, 3H). LCMS-ESI (pos.) m/z: 504.0 (M + H)$^+$. |
| 146.0 | 4-(2,6-dimethoxyphenyl)-5-(2-(methoxymethyl)thiazol-4-yl)-4H-1,2,4-triazol-3-amine (Example 397.8). | 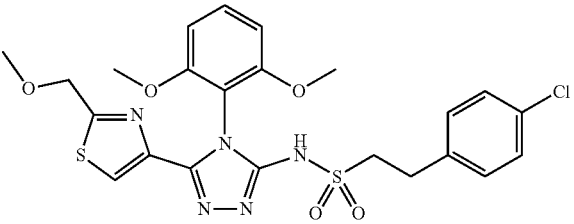 [SMILES: COCc1nc(-c2nnc(NS(=O)(=O)CCc3ccc(Cl)cc3)n2-c2c(OC)cccc2OC)cs1]<br>2-(4-chlorophenyl)-N-(4-(2,6-dimethoxyphenyl)-5-(2-(methoxymethypthiazol-4-yl)-4H-1,2,4-triazol-3-yl)ethanesulfonamide.<br>$^1$H NMR (500 MHz, CD$_3$OD) 67.52 (td, J = 8.4, 3.3 Hz, 1H), 7.43 (d, J = 3.4 Hz, 1H), 7.28 (dd, J = 8.3, 3.2 Hz 2H), 7.18 (dd, J = 8.3, 2.9 Hz, 2H), 6.81 (dd, J = 8.4, 3.3 Hz, 2H), 4.61 (d, J = 3.42 Hz, 2H), 3.75 (s, 3H), 3.74 (s, 3H), 3.39 (d, J = 3.4 Hz, 3H), 3.32-.27 (m, 2H), 2.98-3.04 (m, 2H). LCMS-ESI (pos.) m/z: 550.0 (M + H)$^+$. |
| 149.0 | 4-(2,6-dimethoxyphenyl)-5-(2-methylthiazol-4-yl)-4H-1,2,4-triazol-3-amine (Example 397.9). | 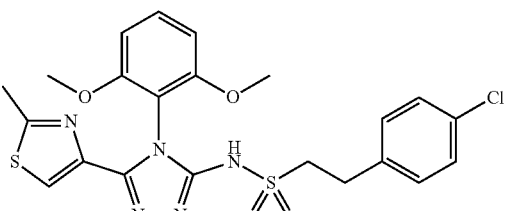<br>2-(4-chlorophenyl)-N-(4-(2,6-dimethoxyphenyl)-5-(2-methylthiazol-4-yl)-4H-1,2,4-triazol-3-yl)ethanesulfonamide.<br>$^1$H NMR (400 MHz, CD$_3$OD) δ 7.52 (td, J = 8.4, 1.8 Hz, 1H), 7.25-7.32 (m, 2H), 7.14-7.21 (m, 3H), 6.82 (dd, J = 8.4, 2.0 Hz, 2H), 3.75 (s, 3H), 3.74 (s, 3H), 3.21-3.28 (m, 2H), 2.98-3.05 (m, 2H), 2.62 (d, J = 1.7 HZ, 3H). LCMS-ESI (pos.) m/z: 520.0 (M + H)$^+$. |

TABLE 5-continued

| Example | Reagents | Structure, Name and Data |
|---|---|---|
| 150.0 | 4-(2,6-dimethoxyphenyl)-5-(4-isopropylthiazol-2-yl)-4H-1,2,4-triazol-3-amine (Example 397.10). | 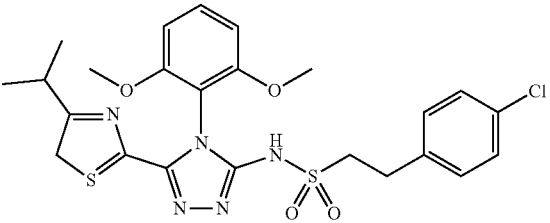 2-(4-chlorophenyl)-N-(4-(2,6-dimethoxyphenyl)-5-(4-isopropylthiazol-2-yl)-4H-1,2,4-triazol-3-yl)ethanesulfonamide. $^1$H NMR (400 MHz, DMSO-d$_6$) δ 13.53 (s, 1H), 7.50 (t, J = 8.5 Hz, 1H), 7.44 (s, 1H), 7.31-7.36 (m, 2H), 7.20-7.26 (m, 2H), 6.83 (d, J = 8.6 Hz, 2H), 3.66 (s, 3H), 3.66 (s, 3H), 3.16-3.24 (m, 2H), 2.87-2.93 (m, 2H), 2.82 (dt, J = 13.6, 6.7 Hz, 1H), 0.98 (d, J = 6.8 Hz, 3H), 0.98 (d, J = 6.8 Hz, 3H). LCMS-ESI (pos.) m/z: 548.0 (M + H)$^+$. |
| 152.0 | 4-(2,6-dimethoxyphenyl)-5-(4-ethylthiazol-2-yl)-4H-1,2,4-triazol-3-amine (Example 398.0). | 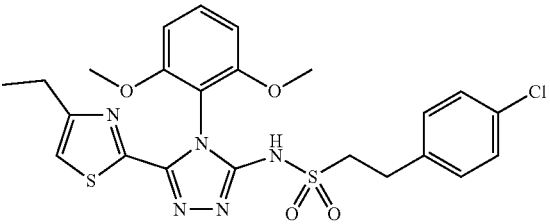 [SMILES: CCc1csc(-c2nnc(NS(=O)(=O)CCc3ccc(Cl)cc3)n2-c2c(OC)cccc2OC)n1] 2-(4-chlorophenyl)-N-(4-(2,6-dimethoxyphenyl)-5-(4-ethylthiazol-2-yl)-4H-1,2,4-triazol-3-yl)ethanesulfonamide. $^1$H NMR (500 MHz, DMSO-d$_6$) δ 13.55 (s, 1H), 7.51 (td, J = 8.6, 2.0 Hz, 1H), 7.46 (d, J = 0.7 Hz, 1H), 7.34 (dd, J = 8.3, 2.0 Hz, 2H), 7.21-7.26 (m, 2H), 6.84 (dd, J = 8.6, 1.7 Hz, 2H), 3.67 (s, 3H), 3.67 (s, 3H), 3.17-3.24 (m, 2H), 2.87-2.94 (m, 2H), 2.52-2.58 (m, 2H), 0.98 (td, J = 7.5, 2.1 Hz, 3H). LCMS-ESI (pos.) m/z: 534.0 (M + H)$^+$. |
| 91.0 | 4-(2,6-dimethoxyphenyl)-5-(thiazol-4-yl)-4H-1,2,4-triazol-3-amine (Example 397.12). | 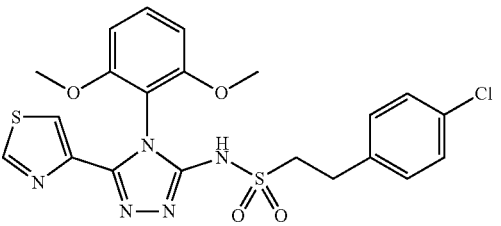 [SMILES: COc1cccc(OC)c1-n1c(NS(=O)(=O)CCc2ccc(Cl)cc2)nnc1-c1cscn1] 2-(4-chlorophenyl)-N-(4-(2,6-dimethoxyphenyl)-5-(thiazol-4-yl)-4H-1,2,4-triazol-3-yl)ethanesulfonamide. $^1$H NMR (500 MHz, DMSO-d$_6$) δ 13.34 (s, 1H), 9.05 (d, J = 2.0 Hz, 1H), 7.84 (s, 1H), 7.47 (t, J = 8.6 Hz, 1H), 7.32-7.37 (m, 2H), 7.22 (d, J = 8.6 Hz, 2H), 6.82 (d, J = 8.6 Hz, 2H), 3.66 (s, 3H), 3.66 (s, 3H), 3.16-3.21 (m, 2H), 2.87-2.92 (m, 2H). LCMS-ESI (pos.) m/z: 506.0 (M + H)$^+$. |

TABLE 5-continued

| Example | Reagents | Structure, Name and Data |
|---|---|---|
| 92.0 | 4-(2,6-dimethoxyphenyl)-5-(oxazol-2-yl)-4H-1,2,4-triazol-3-amine (Example 397.13). | 2-(4-chlorophenyl)-N-(4-(2,6-dimethoxyphenyl)-5-(oxazol-2-yl)-4H-1,2,4-triazol-3-yl)ethanesulfonamide. $^1$H NMR (400 MHz, CD$_3$OD) δ 8.01 (d, J = 0.8 Hz, 1H), 7.52 (t, J = 8.5 Hz, 1H), 7.36-7.35 (m, 2H), 7.14-7.26 (m, 3H), 6.82 (d, J = 8.4 Hz, 2H) 3.77 (s, 3H), 3.77 (s, 3H), 3.22-3.28 (m, 2H), 2.98-3.04 (m, 2H). LCMS-ESI (pos.) m/z: 490.1 (M + H)$^+$. |
| 93.0 | 4-(2,6-dimethoxyphenyl)-5-(1-methyl-1H-imidazol-5-yl)-4H-1,2,4-triazol-3-amine (Example 397.14). | 2-(4-chlorophenyl)-N-(4-(2,6-dimethoxyphenyl)-5-(1-methyl-1H-imidazol-5-yl)-4H-1,2,4-triazol-3-yl)ethanesulfonamide. $^1$H NMR (400 MHz, CD$_3$OD) δ 8.69 (s, 1H), 7.57 (t, J = 8.5 Hz, 1H) 7.25-7.31 (m, 2H), 7.18 (d, J = 8.4 Hz, 2H), 6.93 (d, J = 1.2 Hz, 1H), 6.86 (d, J = 8.6 Hz, 2H), 4.06 (s, 3H), 3.79 (s, 3H), 3.79 (s, 3H), 3.23-3.29 (m, 2H), 2.98-3.04 (m, 2H). LCMS-ESI (pos.) m/z: 503.0 (M + H)$^+$. |

Example 147.0. Preparation of 2-(2-cyano-4-fluorophenyl)-N-(4-(2,6-dimethoxyphenyl)-5-(4-methylthiazol-2-yl)-4H-1,2,4-triazol-3-_yl)ethanesulfonamide

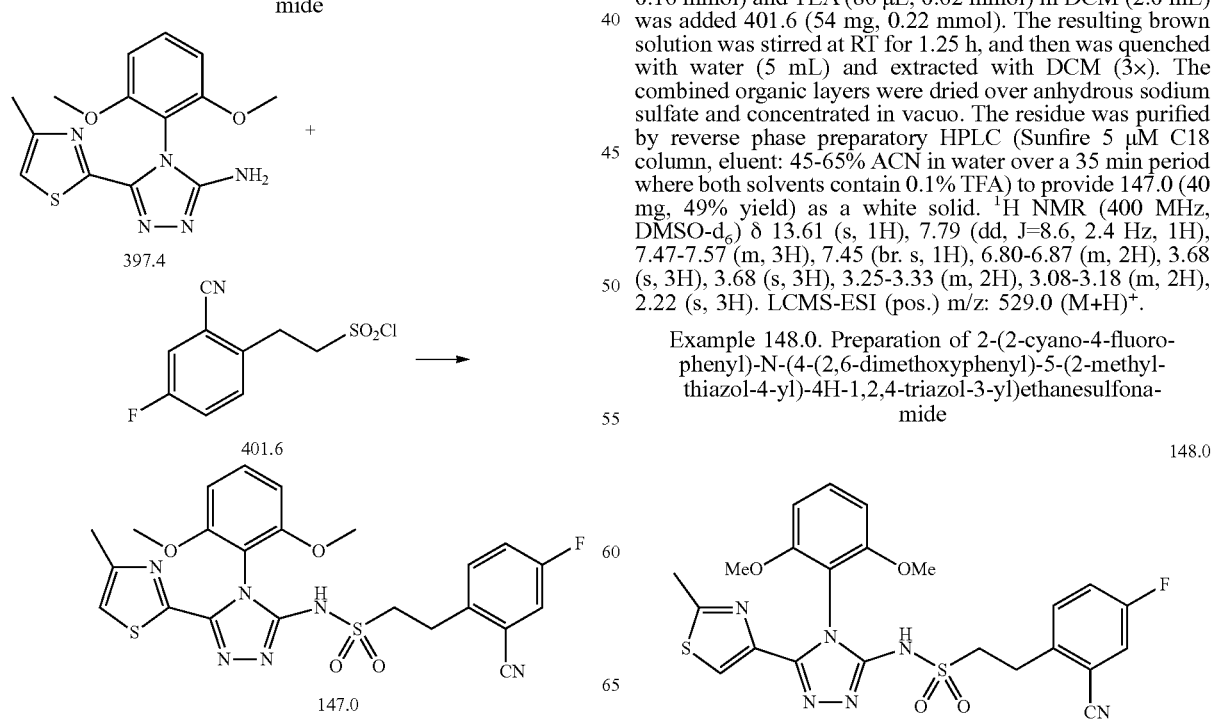

2-(2-Cyano-4-fluorophenyl)-N-(4-(2,6-dimethoxyphenyl)-5-(4-methylthiazol-2-yl)-4H-1,2,4-triazol-3-yl)ethanesulfonamide, Example 147.0. To a solution of 397.4 (49 mg, 0.16 mmol) and TEA (86 μL, 0.62 mmol) in DCM (2.0 mL) was added 401.6 (54 mg, 0.22 mmol). The resulting brown solution was stirred at RT for 1.25 h, and then was quenched with water (5 mL) and extracted with DCM (3×). The combined organic layers were dried over anhydrous sodium sulfate and concentrated in vacuo. The residue was purified by reverse phase preparatory HPLC (Sunfire 5 μM C18 column, eluent: 45-65% ACN in water over a 35 min period where both solvents contain 0.1% TFA) to provide 147.0 (40 mg, 49% yield) as a white solid. $^1$H NMR (400 MHz, DMSO-d$_6$) δ 13.61 (s, 1H), 7.79 (dd, J=8.6, 2.4 Hz, 1H), 7.47-7.57 (m, 3H), 7.45 (br. s, 1H), 6.80-6.87 (m, 2H), 3.68 (s, 3H), 3.68 (s, 3H), 3.25-3.33 (m, 2H), 3.08-3.18 (m, 2H), 2.22 (s, 3H). LCMS-ESI (pos.) m/z: 529.0 (M+H)$^+$.

Example 148.0. Preparation of 2-(2-cyano-4-fluorophenyl)-N-(4-(2,6-dimethoxyphenyl)-5-(2-methylthiazol-4-yl)-4H-1,2,4-triazol-3-yl)ethanesulfonamide 2-(2-Cyano-4-fluorophenyl)-N-(4-(2,6-dimethoxyphenyl)-5-(2-methylthiazol-4-yl)-4H-1,2,4-triazol-3-yl)ethanesulfonamide, Example 148.0. To a solution of 4-(2,6-dimethoxyphenyl)-5-(2-methylthiazol-4-yl)-4H-1,2,4-triazol-3-amine (Example 397.9, 34 mg, 0.11 mmol) in DCM (2.2 mL) was added TEA (60 µL, 0.43 mmol) via syringe followed by 2-(2-cyano-4-fluorophenyl)ethanesulfonyl chloride (Example 401.6, 38 mg, 0.15 mmol) directly. The resulting orange solution was stirred at RT for 4.25 h and then was partitioned between water and DCM (3×). The combined organic layers were dried over anhydrous sodium sulfate and concentrated in vacuo. The residue was purified by reverse phase preparatory HPLC (eluent: 40% ACN in water grading to 70% ACN in water over a 35 min period where both solvents contain 0.1% TFA) to provide Example 148.0 (18 mg, 32% yield) as an off-white solid. $^1$H NMR (500 MHz, DMSO-$d_6$) δ 13.35 (s, 1H), 7.79 (dd, J=2.69, 8.56 Hz, 1H), 7.45-7.56 (m, 3H), 7.39 (s, 1H), 6.82 (d, J=8.56 Hz, 2H), 3.69 (s, 3H), 3.69 (s, 3H), 3.23-3.29 (m, 2H), 3.08-3.15 (m, 2H), 2.54 (s, 3H). LCMS-ESI (pos.) m/z: 529.0 (M+H)$^+$.

The compounds set forth in the following table were synthesized following the procedure in Example 147.0 using the starting material as described.

TABLE 6

| Example | Reagents | Structure, Name and Data |
|---|---|---|
| 151.0 | 4-(2,6-dimethoxyphenyl)-5-(4-isopropylthiazol-2-yl)-4H-1,2,4-triazol-3-amine (Example 397.10). | 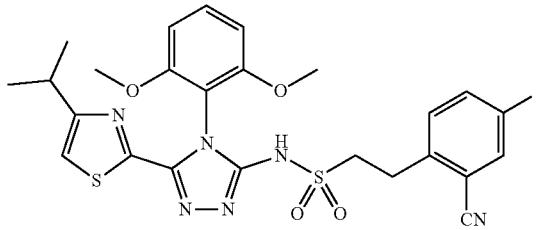<br>2-(2-cyano-4-fluorophenyl)-N-(4-(2,6-dimethoxyphenyl)-5-(4-isopropylthiazol-2-yl)-4H-1,2,4-triazol-3-yl)ethanesulfonamide.<br>$^1$H NMR (500 MHz, DMSO-$d_6$) δ 13.59 (s, 1H), 7.79 (dd, J = 8.6, 2.7 Hz, 1H), 7.47-7.55 (m, 3H), 7.44 (s, 1H), 6.82 (d, J = 8.6 Hz, 2H), 3.66 (s, 3H), 3.66 (s, 3H), 3.26-3.32 (m, 2H), 3.09-3.15 (m, 2H), 2.81 (dt, J = 13.5, 6.8 Hz, 1H), 0.98 (d, J = 6.9 Hz, 3H), 0.98 (d, J = 6.9 Hz, 3H). LCMS-ESI (pos.) m/z: 557.0 (M + H)$^+$. |
| 153.0 | 4-(2,6-dimethoxyphenyl)-5-(4-ethylthiazol-2-yl)-4H-1,2,4-triazol-3-amine (Example 398.0). | 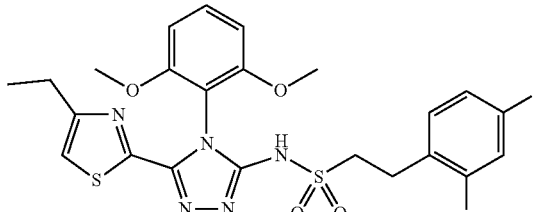<br>2-(2-cyano-4-fluorophenyl)-N-(4-(2,6-dimethoxyphenyl)-5-(4-ethylthiazol-2-yl)-4H-1,2,4-triazol-3-yl)ethanesulfonamide.<br>$^1$H NMR (400 MHz, DMSO-$d_6$) δ 13.60 (s, 1H), 7.79 (dd, J = 8.7, 2.5 Hz, 1H), 7.44-7.55 (m, 4H), 6.82 (d, J = 8.6 Hz, 2H), 3.67 (s, 3H), 3.67 (s, 3H), 3.26-3.32 (m, 2H), 3.09-3.17 (m, 2H), 2.50-2.58 (m, 2H), 0.98 (t, J = 7.4 Hz, 3H). LCMS-ESI (pos.) m/z: 543.0 (M + H)$^+$. |
| 154.0 | 4-(2,6-dimethoxyphenyl)-5-(2-ethylthiazol-4-yl)-4H-1,2,4-triazol-3-amine (Example 397.11). | 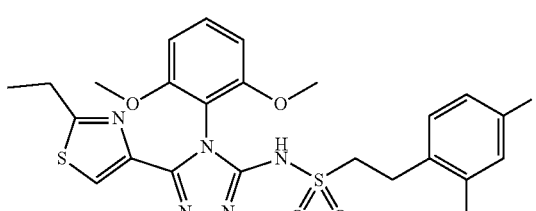<br>2-(2-cyano-4-fluorophenyl)-N-(4-(2,6-dimethoxyphenyl)-5-(2-ethylthiazol-4-yl)-4H-1,2,4-triazol-3-yl)ethanesulfonamide.<br>$^1$H NMR (500 MHz, DMSO-$d_6$) δ 13.35 (s, 1H), 7.79 (dd, J = 8.6, 2.7 Hz, 1H), 7.61 (d, J = 0.7 Hz, 1H) 7.45-7.56 (m, 3H), 6.81 (d, J = 8.6 Hz, 2H), 3.67 (s, 3H), 3.67 (s, 3H), 3.23-3.29 (m, 2H), 3.08-3.15 (m, 2H), 2.84 (q, J = 7. Hz, 2H), 1.08 (t, J = 7.5 Hz, 3H). LCMS-ESI (pos.) m/z: 543.0 (M + H)$^+$. |

TABLE 6-continued

| Example | Reagents | Structure, Name and Data |
|---|---|---|
| 155.0 | 5-(4-cyclopropylthiazol-2-dimethoxyphenyl)-4H-1,2,4-triazol-3-amine (Example 398.6). | 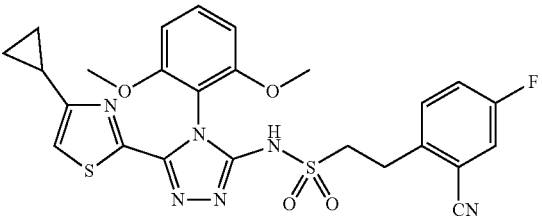 [SMILES: COc1cccc(OC)c1-n1c(NS(=O)(=O)CCc2ccc(F)cc2C#N)nnc1-c1nc(C2CC2)cs1] 2-(2-cyano-4-fluorophenyl)-N-(5-(4-cyclopropylthiazol-2-yl)-4-(2,6-dimethoxyphenyl)-4H-1,2,4-triazol-3-yl)ethanesulfonamide. $^1$H NMR (400 MHz, DMSO-d$_6$) δ 13.58 (s, 1H), 7.79 (dd, J = 8.4, 2.2 Hz, 1H), 7.46-7.57 (m, 4H), 6.82 (d, J = 8.6 Hz, 2H), 3.66 (s, 3H), 3.66 (s, 3H), 3.25-3.33 (m, 2H), 3.07-3.15 (m, 2H), 1.88-1.98 (m, 1H), 0.68-0.75 (m, 2H), 0.26-0.33 (m, 2H). LCMS-ESI (pos.) m/z: 555.0 (M + H)$^+$. |

Example 140.0. Preparation of 2-(2-bromo-4-fluorophenyl)-N-(4-(2,6-dimethoxyphenyl)-5-(thiazol-2-yl)-4H-1,2,4-triazol-3-yl)ethanesulfonamide Example 94.0. Preparation of N-(4-(2,6-dimethoxyphenyl)-5-(4-methylthiazol-2-yl)-4H-1,2,4-triazol-3-yl)-2-(5-fluoropyrimidin-2-yl)ethanesulfonamide

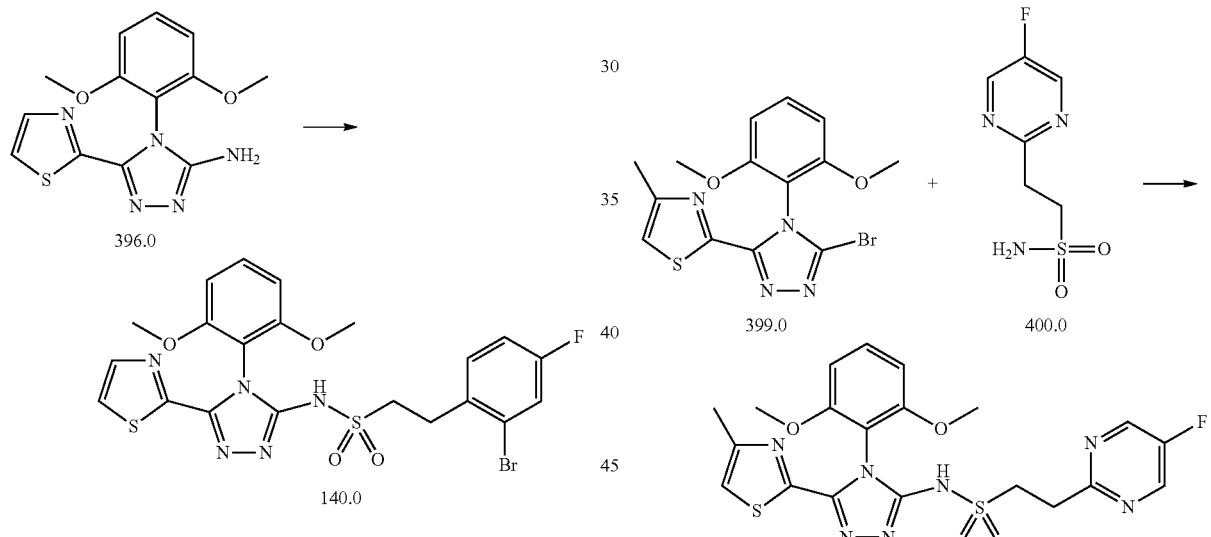

2-(2-Bromo-4-fluorophenyl)-N-(4-(2,6-dimethoxyphenyl)-5-(thiazol-2-yl)-4H-1,2,4-triazol-3-yl)ethanesulfonamide, Example 140.0. To a solution of 396.0 (204 mg, 0.67 mmol) and TEA (374 µL, 2.7 mmol) in DCM (5 mL) was added 2-(2-bromo-4-fluorophenyl)ethanesulfonyl chloride (Synchem, 304 mg, 1.0 mmol). The resulting orange solution was stirred at RT for 2.5 and then was quenched with water (10 mL) and extracted with DCM (3×). The combined organic layers were dried over anhydrous sodium sulfate and concentrated. The residue was purified by reverse phase preparatory HPLC (Sunfire 5 µM C18 column, eluent: 50-75% ACN in water over a 35 min period where both solvents contain 0.1% TFA) to provide 140.0 (148 mg, 39% yield) as a white solid. $^1$H NMR (500 MHz, DMSO-d$_6$) δ 13.67 (s, 1H), 7.92 (d, J=2.9 Hz, 1H), 7.84 (d, J=3.2 Hz, 1H), 7.55 (dd, J=8.6, 2.7 Hz, 1H), 7.49 (t, J=8.4 Hz, 1H), 7.36 (dd, J=8.6, 6.4 Hz, 1H), 7.21 (td, J=8.6, 2.7 Hz, 1H), 6.83 (d, J=8.6 Hz, 2H), 3.67 (s, 3H), 3.67 (s, 3H), 3.14-3.21 (m, 2H), 2.97-3.03 (m, 2H). LCMS-ESI (pos.) m/z: 568.0 (M+H)$^+$.

N-(4-(2,6-Dimethoxyphenyl)-5-(4-methylthiazol-2-yl)-4H-1,2,4-triazol-3-yl)-2-(5-fluoropyrimidin-2-yl)ethanesulfonamide, Example 94.0. A microwave vial containing 399.0 (112 mg, 0.29 mmol), 400.0 (60 mg, 0.29 mmol), copper (I) iodide (56 mg, 0.29 mmol), trans-N,N-dimethyl-1,2-cyclohexanediamine (93 µL, 0.59 mmol), and cesium carbonate (479 mg, 1.50 mmol) was degassed and then backfilled with argon. Evacuation and backfilling were repeated three times. 1,4-Dioxane (2.9 mL) was added and the dark blue-green slurry was heated in the microwave at 100° C. for 3 h. The reaction was partitioned between 1:1 saturated aqueous sodium bicarbonate:brine (10 mL) and extracted with EtOAc (3×). The combined organic layers were dried over anhydrous magnesium sulfate and concentrated in vacuo. The residue was purified by reverse phase preparatory HPLC (Sunfire 5 µM C18 column, eluent:

20-80% ACN in water over a 25 min period where both solvents contain 0.1% TFA) to provide 94.0 (29 mg, 19% yield) as a light yellow solid. $^1$H NMR (400 MHz, CDCl$_3$) δ 8.52 (s, 2H), 7.46 (t, J=8.5 Hz, 1H), 6.92 (d, J=1.0 Hz, 1H), 6.65 (d, J=8.4 Hz, 2H), 3.74 (s, 3H), 3.74 (s, 3H), 3.57-3.63 (m, 2H), 3.43-3.50 (m, 2H), 2.39 (d, J=0.8 Hz, 3H). LCMS-ESI (pos.) m/z: 506.0 (M+H)$^+$.

Example 95.0. Preparation of N-(4-(2,6-dimethoxyphenyl)-5-(4-methyl-1,3-thiazol-2-yl)-4H-1,2,4-triazol-3-yl)-2-((2R)-2-methyl-6-oxo-1-piperidinyl)ethanesulfonamide and N-(4-(2,6-dimethoxyphenyl)-5-(4-methyl-1,3-thiazol-2-yl)-4H-1,2,4-triazol-3-yl)-2-((2S)-2-methyl-6-oxo-1-piperidinyl)ethanesulfonamide

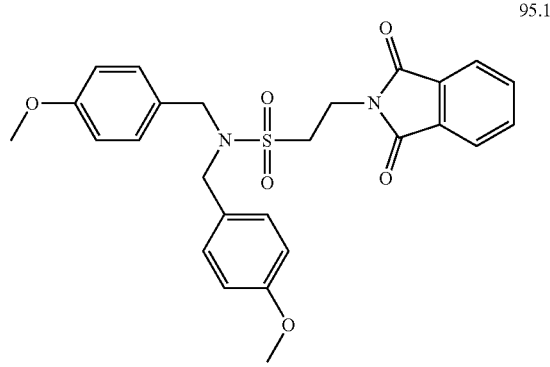 [SMILES: COc1ccc(CN(Cc2ccc(OC)cc2)S(=O)(=O)CCN2C(=O)c3ccccc3C2=O)cc1]

95.1

2-(1,3-Dioxoisoindolin-2-yl)-N,N-bis(4-methoxybenzyl)ethanesulfonamide, Example 95.1. To bis(4-methoxybenzyl)amine (Example 406.01, 3.37 g, 13.10 mmol) and TEA (5.46 mL, 39.3 mmol) in DCM (109 mL) at 0° C. was added 2-phthalimidoethanesulfonyl chloride (3.94 g, 14.41 mmol, commercially available from Matrix Scientific) slowly. The reaction was stirred at RT until complete by LCMS analysis. The reaction was diluted with a saturated solution of NaCl and extracted with DCM, dried over MgSO$_4$, filtered and concentrated in vacuo. Purification of the residue by flash chromatography on a Versapak Spherical pre-packed silica gel column (Sigma-Aldrich, St. Louis, Mo., eluent: 10-55% EtOAc/hexanes, gradient elution) provided Example 95.1 (4.04 g, 62%) as a white solid after evaporation. The product was used directly in the next step without further purification.

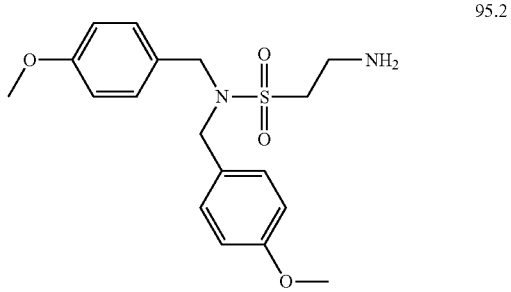 [SMILES: COc1ccc(CN(Cc2ccc(OC)cc2)S(=O)(=O)CCN)cc1]

95.2

2-Amino-N,N-bis(4-methoxybenzyl)ethanesulfonamide, Example 95.2. To a refluxing solution of Example 95.1 (755 mg, 1.53 mmol) in EtOH (7.6 mL) was added hydrazine hydrate (80%, 178 µL, 4.58 mmol). The reaction was heated at 80° C. for 3h until complete by LCMS analysis. The solution was filtered and concentrated in vacuo to provide Example 95.2 as a glassy semi-crystalline solid. The product was used directly in the next step without purification. LCMS-ESI (pos.) m/z: 365.1 (M+H)$^+$.

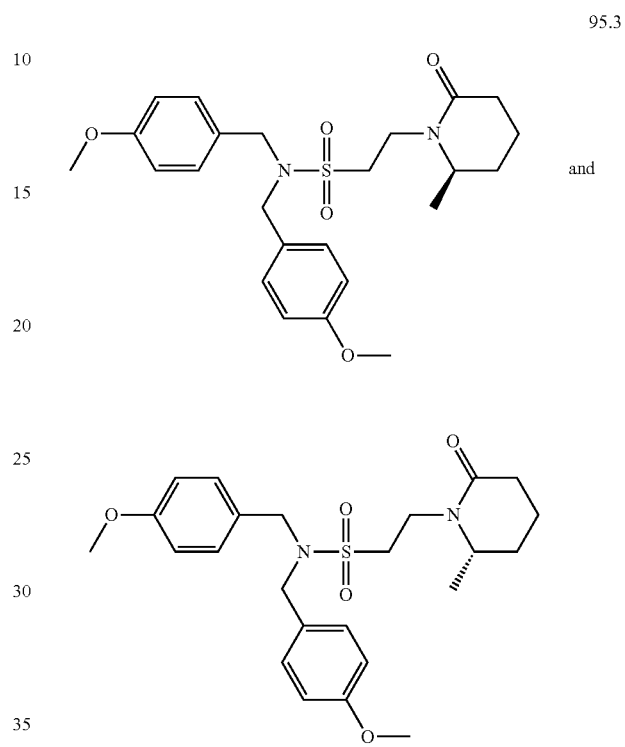

(R)-N,N-Bis(4-methoxybenzyl)-2-(2-methyl-6-oxopiperidin-1-yl)ethanesulfonamide and (S)-N,N-bis(4-methoxybenzyl)-2-(2-methyl-6-oxopiperidin-1-yl)ethanesulfonamide, Example 95.3. A solution of Example 95.2 (590 mg, 1.619 mmol) and 4-acetylbutyric acid (0.251 mL, 2.10 mmol) in 1,2-dichloroethane (16.2 mL) was stirred for 1 h at RT, to this mixture was added sodium triacetoxyborohydride (686 mg, 3.24 mmol) slowly. The reaction was stirred overnight after which LCMS analysis showed the title product formed. The reaction mixture was diluted with a saturated solution of NaCl and sodium bicarbonate. The solution was extracted with DCM. The organic layers were dried over Na$_2$SO$_4$, filtered and concentrated in vacuo. Purification of the residue by flash chromatography on a Redisep Gold pre-packed spherical silica gel column (eluent: 60-100% EtOAc/hexanes) provided Example 95.3 (575 mg, 77%). LCMS-ESI (pos.) m/z: 461.0 (M+H)$^+$.

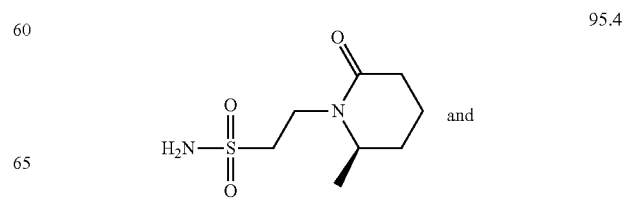

95.4

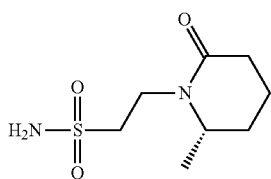

(R)-2-(2-Methyl-6-oxopiperidin-1-yl)ethanesulfonamide and (S)-2-(2-methyl-6-oxopiperidin-1-yl)ethanesulfonamide, Example 95.4. To Example 95.3 (575 mg, 1.248 mmol) was added TFA (12.5 mL) at RT. The reaction was stirred at RT until complete as determined by LCMS, after which the reaction was concentrated in vacuo. Purification by flash chromatography on a Redisep Gold pre-packed spherical silica gel column (eluent: 0-100% EtOAc/hexanes, followed by 0-10% MeOH/DCM) provided Example 95.4 (270 mg, 98%) as a clear, colorless glass. LCMS-ESI (pos.) m/z: 221.0 (M+H)$^+$.

95.0

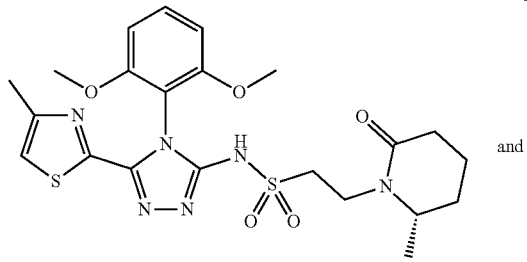

and

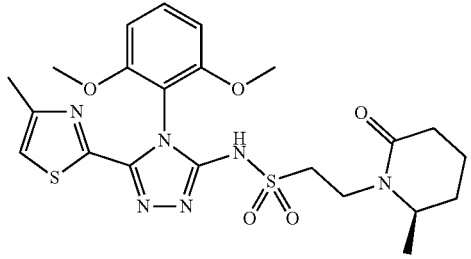

N-(4-(2,6-Dimethoxyphenyl)-5-(4-methyl-1,3-thiazol-2-yl)-4H-1,2,4-triazol-3-yl)-2-((2R)-2-methyl-6-oxo-1-piperidinyl)ethanesulfonamide and N-(4-(2,6-dimethoxyphenyl)-5-(4-methyl-1,3-thiazol-2-yl)-4H-1,2,4-triazol-3-yl)-2-((2S)-2-methyl-6-oxo-1-piperidinyl)ethanesulfonamide, Example 95.0. The title compound was prepared following the general procedure described in Example 101.0 employing Example 399.0 and Example 95.4. Purification of the initial product was conducted via preparatory RP-HPLC (10 to 65% ACN, water, 0.1% TFA, gradient elution) over 30 min using Sunfire™ Prep C18 OBD column, 10 μm, 30×150 mm (Waters, Milford, Mass.) at 30 mL/min provided Example 95.0 (45 mg, 33%). $^1$H NMR (400 MHz, CDCl$_3$) δ 7.48 (t, J=8.5 Hz, 1H) 6.94 (d, J=0.8 Hz, 1H) 6.68 (d, J=8.6 Hz, 2H) 3.99 (dd, J=11.4, 6.6 Hz, 1H) 3.71-3.84 (m, 7H) 3.43-3.60 (m, 2H) 3.21-3.32 (m, 1H) 2.30-2.49 (m, 5H) 1.80-1.98 (m, 2H) 1.66-1.78 (m, 1H) 1.54-1.66 (m, 1H) 1.24 (d, J=6.5 Hz, 3H). LCMS-ESI (pos.) m/z: 521.2 (M+H)$^+$.

The compounds set forth in the following table were synthesized following the procedure in Example 94.0 using the starting materials as described.

TABLE 7

| Example | Reagents | Structure, Name and Data |
|---|---|---|
| 97.0 | 2-(5-bromo-4-(2,6-dimethoxyphenyl)-4H-1,2,4-triazol-3-yl)-4-ethylthiazole (Example 399.1), and 2-(5-fluoropyrimidin-2-yl)ethanesulfonamide, Example 400.0. | N-(4-(2,6-dimethoxyphenyl)-5-(4-ethylthiazol-2-yl)-4H-1,2,4-triazol-3-yl)-2-(5-fluoropyrimidin-2-yl)ethanesulfonamide. $^1$H NMR (400 MHz, CDCl$_3$) δ 8.54 (s, 2H), 7.44 (t, J = 8.5 Hz, 1H), 6.93 (s, 1H), 6.64 (d, J = 8.6 Hz, 2H), 3.73 (s, 3H), 3.73 (s, 3H), 3.59-3.65 (m, 2H), 3.43-3.51 (m, 2H), 2.70 (q, J = 7.4 Hz, 2H), 1.13 (t, J = 7.5 Hz, 3H). LCMS-ESI (pos.) m/z: 520.1 (M + H)$^+$. |
| 96.0 | 2-(5-bromo-4-(2,6-dimethoxyphenyl)-4H-1,2,4-triazol-3-yl)-4-isopropylthiazole (Example 399.3), and 2-(5-fluoropyrimidin-2-yl)ethanesulfonamide, Example 400.0. | N-(4-(2,6-dimethoxyphenyl)-5-(4-isopropylthiazol-2-yl)-4H-1,2,4-triazol-3-yl)-2-(5-fluoropyrimidin-2-yl)ethanesulfonamide. $^1$H NMR (400 MHz, CDCl$_3$) δ 8.53 (s, 2H), 7.41 (t, J = 8.5 Hz, 1H), 6.92 (d, J = 0.8 Hz, 1H), 6.63 (d, J = 8.6 Hz, 2H), 3.72 (s, 3H), 3.72 (s, 3H), 3.58-3.65 (m, 2H), 3.44-3.51 (m, 2H), 2.92 (dt, J = 13.6, 6.7 Hz, 1H), 1.09 (d, J = 6.9 Hz, 3H), 1.09 (d, J = 6.9 Hz, 3H). LCMS-ESI (pos.) m/z: 534.0 (M + H)$^+$. |

TABLE 7-continued

| Example | Reagents | Structure, Name and Data |
|---|---|---|
| 99.0 | 4-(5-bromo-4-(2,6-dimethoxyphenyl)-4H-1,2,4-triazol-3-yl)-2-ethylthiazole (Example 399.4), and 2-(5-fluoropyrimidin-2-yl)ethanesulfonamide, Example 400.0. | 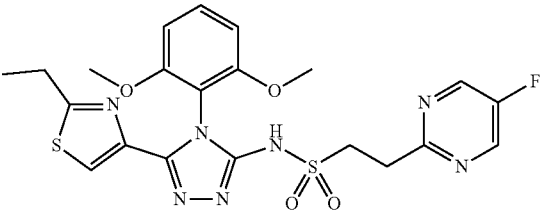 N-(4-(2,6-dimethoxyphenyl)-5-(2-ethylthiazol-4-yl)-4H-1,2,4-triazol-3-yl)-2-(5-fluoropyrimidin-2-yl)ethanesulfonamide. $^1$H NMR (400 MHz, CDCl$_3$) δ 8.52 (s, 2H), 7.44 (t, J = 8.5 Hz, 1H), 6.94 (s, 1H), 6.66 (d, J = 8.6 Hz, 2H), 3.74 (s, 3H), 3.74 (s, 3H), 3.55-3.61 (m, 2H), 3.42-3.49 (m, 2H), 3.00 (q, J = 7.6 Hz, 2H), 1.31 (t, J = 7.6 Hz, 3H). LCMS-ESI (pos.) m/z: 520.1 (M + H)$^+$. |

Example 101.0. Preparation of (R)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or(S)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide 101.0

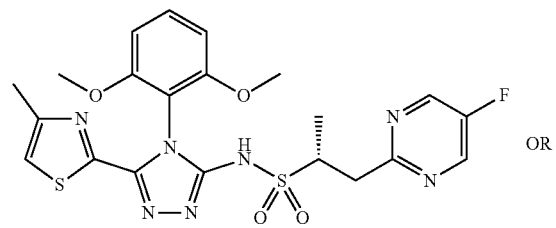

OR

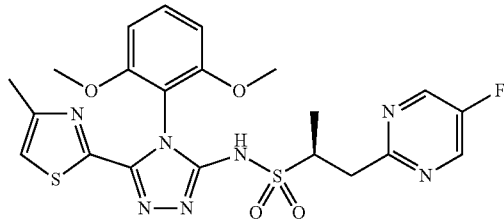

(R)-N-(4-(2,6-Dimethoxyphenyl)-5-(4-methylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide, Example 101.0. A vial containing Example 399.0 (100 mg, 0.26 mmol), Example 402.0 (115 mg, 0.53 mmol), copper(I) iodide (25 mg, 0.13 mmol), trans-N,N-dimethyl-1,2-cyclohexanediamine (81 L, 0.53 mmol) and cesium carbonate (214 mg, 0.66 mmol) was degassed and then backfilled with argon. Evacuation and backfilling were repeated three times. 1,4-Dioxane (525 L) was added and the vial was capped and heated at 90° C. for 14 h. The reaction was filtered through Celite® brand filter aid and the filtrate was partitioned between a saturated aqueous ammonium chloride solution and EtOAc (3×). The combined organic layers were dried over anhydrous sodium sulfate and concentrated in vacuo. The residue was purified by reverse phase preparatory HPLC (Sunfire 5 µM C18 column, eluent: 20-50% ACN in water over a 25 min period where both solvents contain 0.1% TFA) to provide the racemic product (88 mg, 65% yield) as a tan sold. The racemate was separated by preparative SFC (Column: 2×25 cm Chiralpak AD-H, 70% of a 2:1 mixture of MeOH and ACN (containing NH$_4$OH)/ CO$_2$, 100 bar, 60 mL/min, 220 nm, Inj vol.: 0.5 mL of a 5.0 mg/mL solution of sample in MeOH). The initial eluting peak was Example 101.0. $^1$H NMR (400 MHz, CDCl$_3$) δ 8.53 (s, 2H), 7.46 (t, J=8.5 Hz, 1H), 6.90 (s, 1H), 6.65 (dd, J=8.6, 1.6 Hz, 2H), 3.78-3.87 (m, 1H), 3.75 (s, 3H), 3.73 (s, 3H), 3.65-3.74 (m, 1H), 3.09 (dd, J=14.8, 9.9 Hz, 1H), 2.39 (s, 3H), 1.31 (d, J=6.9 Hz, 3H). LCMS-ESI (pos.) m/z: 520.1 (M+H)$^+$.

Example 102.0. Preparation of (R)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide 102.0

(R)-N-(4-(2,6-Dimethoxyphenyl)-5-(4-methylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide, Example 102.0. Further elution under the conditions described in Example 101.0 yielded the second eluting peak, Example 102.0 (38 mg). $^1$H NMR (400 MHz, CDCl$_3$) δ 8.53 (s, 2H), 7.46 (t, J=8.5 Hz, 1H), 6.91 (s, 1H), 6.66 (dd, J=8.6, 1.8 Hz, 2H), 3.78-3.86 (m, 1H), 3.75 (s, 3H), 3.73 (s, 3H), 3.65-3.74 (m, 1H), 3.09 (dd, J=14.8, 9.9 Hz, 1H), 2.40 (d, J=0.8 Hz, 3H), 1.32 (d, J=6.7 Hz, 3H). LCMS-ESI (pos.) m/z: 520.1 (M+H)$^+$.

The compounds set forth in the following table were synthesized following the procedures described in Example 101.0 and 102.0 using the starting materials as described.

TABLE 8

| Example | Reagents | Structure, Name and Data |
|---|---|---|
| 105.0 | 2-(5-bromo-4-(2,6-dimethoxyphenyl)-4H-1,2,4-triazol-3-yl)-4-ethylthiazole (Example 399.1), (S)-1-(5-fluoropyrimidin-2-yl)propane-2-sulfonamide and (R)-1-(5-fluoropyrimidin-2-yl)propane-2-sulfonamide (Example 402.0). Preparative SFC method: Column: 250 × 21 mm Chiralpak IA, 19 g/min MeOH + 55 g/min $CO_2$, 100 bar, 297 nm, Inj vol.: 0.3 mL of a 7 mg/mL solution of sample in 5:1 MeOH/DCM. | First eluting peak:<br>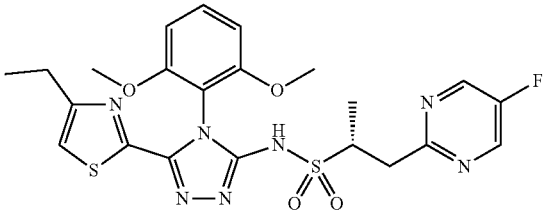<br>OR<br>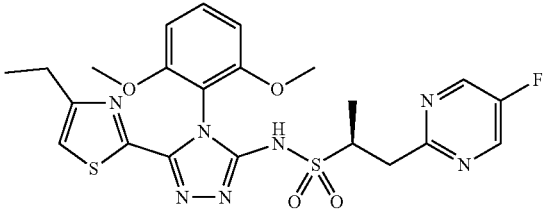<br>(R)-N-(4-(2,6-dimethoxyphenyl)-5-(4-ethylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-ethylthiazol-2-yl)-4H-1,2,4-triazol-3-yl)-1-(5-fluoropyrimidin-2-yl)propane-2-sulfonamide.<br>$^1$H NMR (400 M,Hz, $CDCl_3$) δ 11.19 (br. s, 1H), 8.53 (s, 2H), 7.44 (t, J = 8.4 Hz, 1H), 6.92 (s, 1H), 6.64 (dd, J = 8.5, 1.7 Hz, 2H), 3.77-3.86 (m, 1H), 3.74 (s, 3H), 3.72 (s, 3H), 3.66-3.72 (m, 1H), 3.09 (dd, J = 14.8, 9.7 Hz, 1H), 2.70 (qd, J = 7.5, 0.9 Hz, 2H), 1.32 (d, J = 6.6 104.0 Hz, 3H), 1.13 (t, J = 7.5 Hz, 3H). LCMS-ESI (pos.) m/z: 534.0 (M + H)$^+$. |
| 104.0 | | Second eluting peak:<br>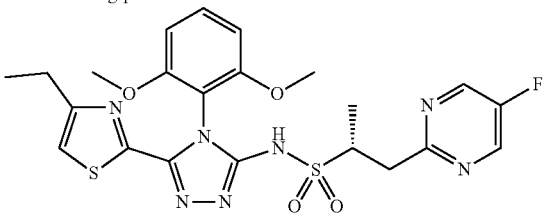<br>OR<br>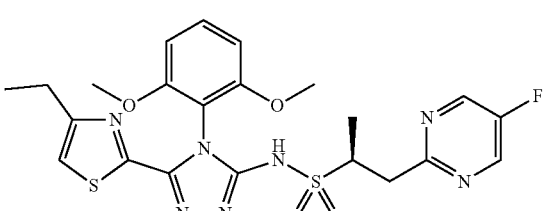<br>(R)-N-(4-(2,6-dimethoxyphenyl)-5-(4-ethylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-ethylthiazol-2-yl)-4H-1,2,4-triazol-3-yl)-1-(5-fluoropyrimidin-2-yl)propane-2-sulfonamide.<br>$^1$H NMR (400 M,Hz, $CDCl_3$) δ 11.20 (br. s, 1H), 8.53 (s, 2H), 7.44 (t, J = 8.4 Hz, 1H), 6.92 (s, 1H), 6.64 (dd, J = 8.5, 1.7 Hz, 2H), 3.77-3.86 (m, 1H), 3.74 (s, 3H), 3.72 (s, 3H), 3.66-3.73 (m, 1H), 3.09 (dd, J = 14.9, 9.8 Hz, 1H), 2.70 (q, J = 7 .6 Hz, 2H), 1.32 (d, J = 6.7 Hz, 3H), 1.13 (t, J = 7.5 Hz, 3H). LCMS-ESI (pos.) m/z: 534.0 (M + H)$^+$. |

TABLE 8-continued

| Example | Reagents | Structure, Name and Data |
|---|---|---|
| 159.0 | 2-(5-bromo-4-(2,6-dimethoxyphenyl)-4H-1,2,4-triazol-3-yl)-4-cyclopropylthiazole (Example 399.2), and (S)-1-(5-fluoropyrimidin-2-yl)propane-2-sulfonamide and (R)-1-(5-fluoropyrimidin-2-yl)propane-2-sulfonamide (Example 402.0). Preparative SFC method: Column: 2 × 15 cm Chiralpak IA, 20% MeOH/CO$_2$, 100 bar, 70 mL/min, 220 nm, Inj vol.: 1.0 mL of a 3.2 mg/mL solution of sample in MeOH. | First eluting peak:<br>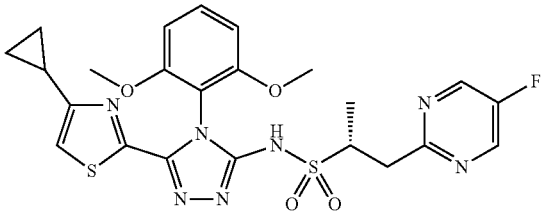<br>OR<br>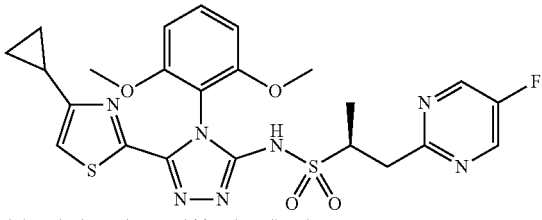<br>(R)-N-(5-(4-cyclopropylthiazol-2-yl)-4-(2,6-dimethoxyphenyl)-4H-1,2,4-triazol-3-yl)-1-(5-fluoropyrimidin-2-yl)propane-2-sulfonamide or (S)-N-(5-(4-cyclopropylthiazol-2-yl)-4-(2,6-dimethoxyphenyl)-4H-1,2,4-triazol-3-yl)-1-(5-fluoropyrimidin-2-yl)propane-2-sulfonamide.<br>$^1$H NMR (400 M,Hz, CDCl$_3$) δ 11.11 (br. s, 1H), 8.52 (s, 2H), 7.42 (t, J = 8.5 Hz, 1H), 6.92 (s, 1H), 6.63 (d, J = 8.6 Hz, 2H), 3.75-3.87 (m, 1H), 3.73 (s, 3H), 3.70 (s, 3H), 3.64-3.72 (m, 1H), 3.09 (dd, J = 14.6, 10.1 Hz, 1H), 1.87 (br. s, 1H), 1.31 (d, J = 6.7 Hz, 3H), 0.71-0.82 (m, 2H), 0.47 (br. s, 2H). LCMS-ESI (pos.) m/z: 546.2 (M + H)$^+$. |
| 160.0 | | Second eluting peak:<br>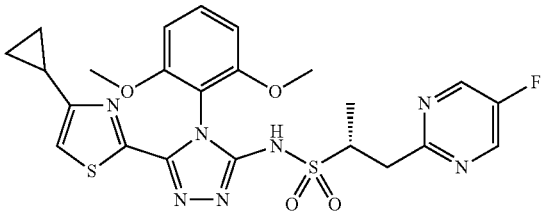<br>OR<br>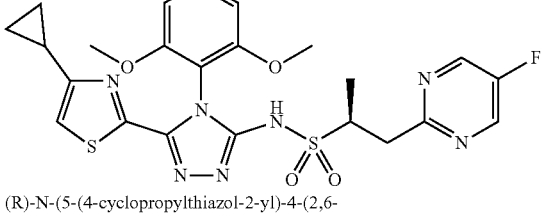<br>(R)-N-(5-(4-cyclopropylthiazol-2-yl)-4-(2,6-dimethoxyphenyl)-4H-1,2,4-triazol-3-yl)-1-(5-fluoropyrimidin-2-yl)propane-2-sulfonamide or (S)-N-(5-(4-cyclopropylthiazol-2-yl)-4-(2,6-dimethoxyphenyl)-4H-1,2,4-triazol-3-yl)-1-(5-fluoropyrimidin-2-yl)propane-2-sulfonamide.<br>$^1$H NMR (400 M,Hz, CDCl$_3$) δ 11.12 (br. s, 1H), 8.53 (s, 2H), 7.42 (t, J = 8.4 Hz, 1H), 6.92 (s, 1H), 6.63 (d, J = 8.6 Hz, 2H), 3.77-3.86 (m, 1H), 3.73 (s, 3H), 3.70 (s, 3H), 3.65-3.72 (m, 1H), 3.09 (dd, J = 14.7, 9.8 Hz, 1H), 1.87 (br. s, 1H), 1.31 (d, J = 6.9 Hz, 3H), 0.72-0.81 (m, 2H), 0.44-0.52 (m, 2H). LCMS-ESI (pos.) m/z: 546.2 (M + H)$^+$. |

TABLE 8-continued

| Example | Reagents | Structure, Name and Data |
|---|---|---|
| 157.0 | 2-(5-bromo-4-(2,6-dimethoxyphenyl)-4H-1,2,4-triazol-3-yl)-4-isopropylthiazole (Example 399.3), and (S)-1-(5-fluoropyrimidin-2-yl)propane-2-sulfonamide and (R)-1-(5-fluoropyrimidin-2-yl)propane-2-sulfonamide (Example 402.0). Preparative SFC method: Column: 250 × 20 mm Chiralpak IA, 30 g/min MeOH + 70 g/min $CO_2$, 100 bar, 220 nm, Inj vol.: 1.4 mL of a 3.6 mg/mL solution of sample in 2:1 MeOH/DCM. | First eluting peak:<br>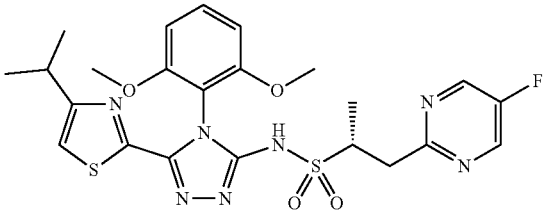<br>OR<br>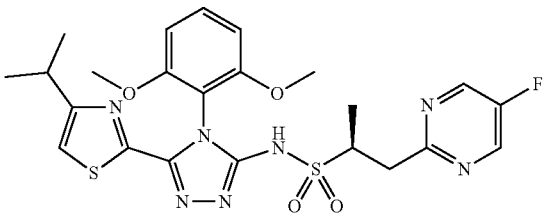<br>(R)-N-(4-(2,6-dimethoxyphenyl)-5-(4-isopropylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-isopropylthiazol-2-yl)-4H-1,2,4-triazol-3-yl)-1-(5-fluoropyrimidin-2-yl)propane-2-sulfonamide.<br>$^1$H NMR (400 M,Hz, $CDCl_3$) δ 11.17 (br. s, 1H), 8.53 (s, 2H), 7.41 (t, J = 8.4 Hz, 1H), 6.91 (s, 1H), 6.63 (dd, J = 8.4, 1.8 Hz, 2H), 3.77-3.88 (m, 1H), 3.73 (s, 3H), 3.70 (s, 3H), 3.67-3.71 (m, 1H), 3.10 (dd, J = 14.9, 9.8 Hz, 1H), 2.88-2.97 (m, 1H), 1.32 (d, J = 6.9 Hz, 3H), 1.10 (d, J = 6.9 Hz, 3H), 1.10 (d, J = 6.9 Hz, 3H). LCMS-ESI (pos.) m/z: 548.2 $(M + H)^+$. |
| 158.0 | | Second eluting peak:<br>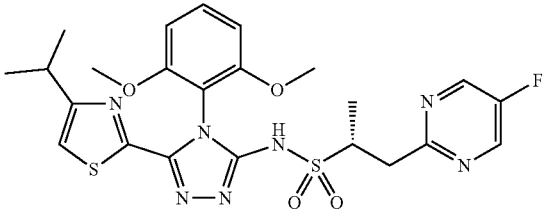<br>OR<br>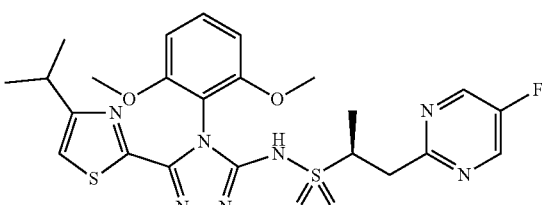<br>(R)-N-(4-(2,6-dimethoxyphenyl)-5-(4-isopropylthiazol-2-yl)-4H-1,2,4-triazol-3-yl)-1-(5-fluoropyrimidin-2-yl)propane-2-sulfonamide or (S)-N-(4-(2,6-dimethoxyphenyl)-5-(4-isopropylthiazol-2-yl)-4H-1,2,4-triazol-3-yl)-1-(5-fluoropyrimidin-2-yl)propane-2-sulfonamide.<br>$^1$H NMR (400 M,Hz, $CDCl_3$) δ 11.15 (br. s, 1H), 8.53 (s, 2H), 7.41 (t, J = 8.4 Hz, 1H), 6.91 (s, 1H), 6.63 (dd, J = 8.6, 1.7 Hz, 2H), 3.77-3.87 (m, 1H), 3.72 (s, 3H), 3.70 (s, 3H), 3.67-3.71 (m, 1H), 3.10 (dd, J = 14.8, 9.9 Hz, 1H), 2.87-2.97 (m, 1H), 1.32 (d, J = 6.6 Hz, 3H), 1.09 (d, J = 6.9 Hz, 3H), 1.10 (d, J = 6.9 Hz, 3H). LCMS-ESI (pos.) m/z: 548.2 $(M + H)^+$. |

TABLE 8-continued

| Example | Reagents | Structure, Name and Data |
|---|---|---|
| 162.0 | 2-(5-bromo-4-(2,6-dimethoxyphenyl)-4H-1,2,4-triazol-3-yl)-4-methylthiazole (Example 399.0), and (S)-1-(5-fluoropyrimidin-2-yl)butane-2-sulfonamide and (R)-1-(5-fluoropyrimidin-2-yl)butane-2-sulfonamide (Example 407.0). Preparative SFC method: Column: 2 × 15 cm Chiralpak AD-H, 34% i-PrOH (containing 0.1% NH$_4$OH)/CO$_2$, 100 bar, 65 mL/min, 220 nm, Inj vol.: 0.5 mL of a 4.1 mg/mL solution of sample in 1:1 MeOH/DCM. | First eluting peak:<br>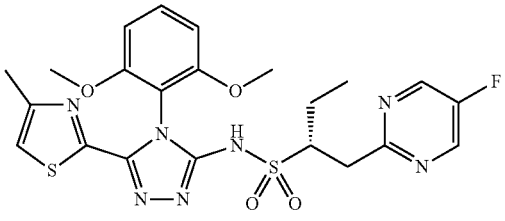<br>OR<br>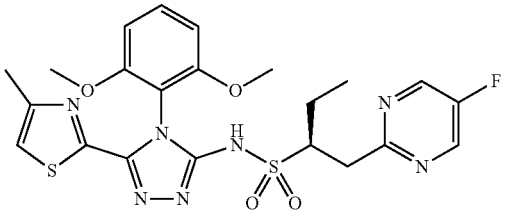<br>(R)-N-(4-(2,6-dimethoxyphenyl)-5-(4-methylthiazol-2-yl)-4H-1,2,4-triazol-3-yl)-1-(5-fluoropyrimidin-2-yl)butane-2-sulfonamide or (S)-N-(4-(2,6-dimethoxyphenyl)-5-(4-methylthiazol-2-yl)-4H-1,2,4-triazol-3-yl)-1-(5-fluoropyrimidin-2-yl)butane-2-sulfonamide.<br>$^1$H NMR (400 M,Hz, CDCl$_3$) δ 11.30 (br. s, 1H), 8.52 (s, 2H), 7.46 (t, J = 8.4 Hz, 1H), 6.91 (s, 1H), 6.65 (d, J = 8.6 Hz, 2H), 3.75 (s, 3H), 3.71 (s, 3H), 3.59 (dd, J = 15.1, 5.9 Hz, 1H), 3.22 (dd, J = 15.3, 7.6 Hz, 1H), 2.39 (s, 3H), 1.95-2.08 (m, 1H), 1.64-1.76 (m, 2H), 0.95 (t, J = 7.5 Hz, 3H). LCMS-ESI (pos.) m/z: 534.0 (M + H)$^+$. |
| 163.0 | | Second eluting peak:<br>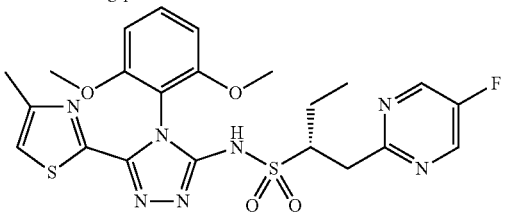<br>OR<br>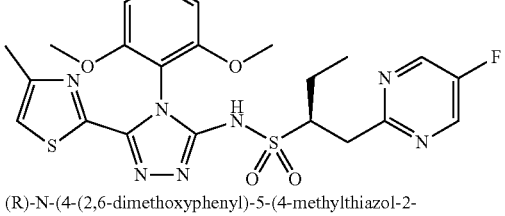<br>(R)-N-(4-(2,6-dimethoxyphenyl)-5-(4-methylthiazol-2-yl)-4H-1,2,4-triazol-3-yl)-1-(5-fluoropyrimidin-2-yl)butane-2-sulfonamide or (S)-N-(4-(2,6-dimethoxyphenyl)-5-(4-methylthiazol-2-yl)-4H-1,2,4-triazol-3-yl)-1-(5-fluoropyrimidin-2-yl)butane-2-sulfonamide.<br>$^1$H NMR (400 M,Hz, CDCl$_3$) δ 11.31 (br. s, 1H), 8.53 (s, 2H), 7.46 (t, J = 8.5 Hz, 1H), 6.91 (s, 1H), 6.65 (d, J = 8.4 Hz, 2H), 3.75 (s, 3H), 3.71 (s, 3H), 3.58 (dd, J = 15.2, 6.0 Hz, 1H), 3.22 (dd, J = 15.3, 7.6 Hz, 1H), 2.39 (s, 3H), 1.95-2.08 (m, 1H), 1.63-1.76 (m, 2H), 0.95 (t, J = 7.5 Hz, 3H). LCMS-ESI (pos.) m/z: 534.0 (M + H)$^+$. |

TABLE 8-continued

| Example | Reagents | Structure, Name and Data |
|---|---|---|
| 107.0 | 2-(5-bromo-4-(2,6-dimethoxyphenyl)-4H-1,2,4-triazol-3-yl)-4-methylthiazole (Example 399.0), and (1R,2S)-N-(2,4-dimethoxybenzyl)-2-(5-fluoropyrimidin-2-yl)cyclopentane-1-sulfonamide and (1S,2R)-N-(2,4-dimethoxybenzyl)-2-(5-fluoropyrimidin-2-yl)cyclopentane-1-sulfonamide (Example 408.1). Preparative SFC method: Column: 250 × 30 mm Phenomenex Lux-2 Cell, 60 mL/min MeOH + 60 g/min $CO_2$, 100 bar, 215 nm, Inj vol.: 3.0 mL of a 4.2 mg/mL solution of sample in 3:1 MeOH/DCM. | First eluting peak:<br>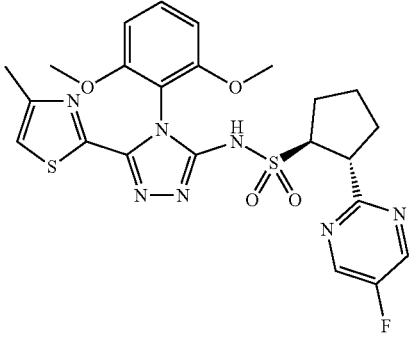<br>OR<br>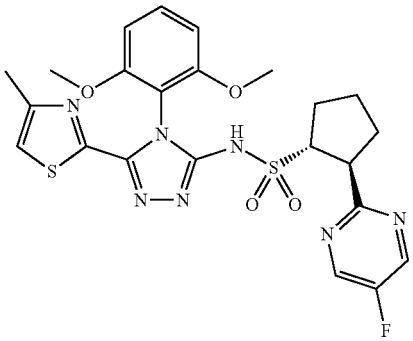<br>(1S,2R)-N-(4-(2,6-dimethoxyphenyl)-5-(4-methylthiazol-2-yl)-4H-1,2,4-triazol-3-yl)-2-(5-fluoropyrimidin-2-yp cyclopentane-1-sulfonamide or (1R,2S)-N-(4-(2,6-dimethoxyphenyl)-5-(4-methylthiazol-2-yl)-4H-1,2,4-triazol-3-yl)-2-(5-fluoropyrimidin-2-yl)cyclopentane-1-sulfonamide.<br><br>$^1$H NMR (500 MHz, $CDCl_3$) δ 8.51 (s, 2H), 7.46 (t, J = 8.6 Hz, 1H), 6.91 (s, 1H), 6.65 (d, J = 8.6 Hz, 2H), 4.21 (q, J = 8.1 Hz, 1H), 3.87 (q, J = 8.2 Hz, 1H), 3.74 (s, 3H), 3.73 (s, 3H), 2.39 (d, J = 0.7 Hz, 3H), 2.17-2.31 (m, 3H), 1.77-1.89 (m, 3H). LCMS-ESI (pos.) m/z: 546.0 $(M + H)^+$. |

| Example Reagents | Structure, Name and Data |
|---|---|
| 108.0 | Second eluting peak:<br>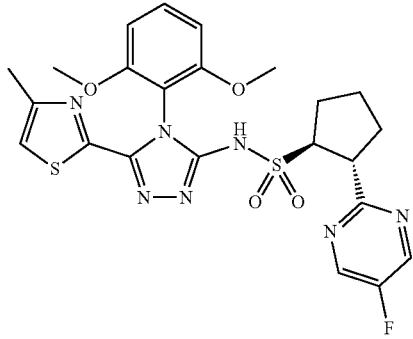<br>OR<br>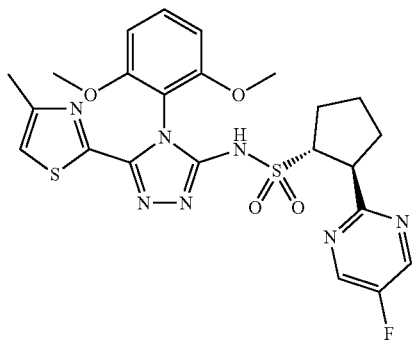<br>(1S,2R)-N-(4-(2,6-dimethoxyphenyl)-5-(4-methylthiazol-2-yl)-4H-1,2,4-triazol-3-yl)-2-(5-fluoropyrimidin-2-yl)cyclopentane-1-sulfonamide or (1R,2S)-N-(4-(2,6-dimethoxyphenyl)-5-(4-methylthiazol-2-yl)-4H-1,2,4-triazol-3-yl)-2-(5-fluoropyrimidin-2-ypcyclopentane-1-sulfonamide.<br><br>$^1$H NMR (500 MHz, CDCl$_3$) δ 8.52 (s, 2H), 7.46 (t, J = 8.4 Hz, 1H), 6.91 (s, 1H), 6.65 (d, J = 8.6 Hz, 2H), 4.21 (q, J = 8.1 Hz, 1H), 3.88 (q, J = 8.0 Hz, 1H), 3.74 (s, 3H), 3.74 (s, 3H), 2.39 (s, 3H), 2.18-2.31 (m, 3H), 1.78-1.90 (m, 3H). LCMS-ESI (pos.) m/z: 546.0 (M + H)$^+$. |

TABLE 8-continued

| Example | Reagents | Structure, Name and Data |
|---|---|---|
| 122.0 | 2-(5-bromo-4-(2,6-dimethoxyphenyl)-4H-1,2,4-triazol-3-yl)-4-methylthiazole (Example 399.0), and (1R,2S)-1-(5-fluoropyrimidin-2-yl)-1-hydroxypropane-2-sulfonamide and (1S,2R)-1-(5-fluoropyrimidin-2-yl)-1-hydroxypropane-2-sulfonamide (Example 404.6). Preparative SFC method, Stage 1: Column: 500 × 30 mm Chiralpak IC, 35 g/min MeOH + 35 g/min $CO_2$, 100 bar, 300 nm, Inj vol.: 0.5 mL of a 5.3 mg/mL solution of sample in 2:1 MeOH/DCM. Stage 2: Column: 250 × 21 mm Chiralpak IC, 23 g/min MeOH + 27 g/min $CO_2$, 100 bar, 300 nm, Inj vol.: 0.6 mL of a 3.8 mg/mL solution of sample in MeOH. | First eluting peak:<br>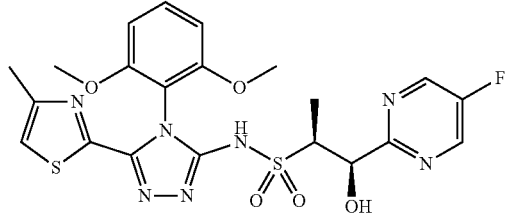<br>OR<br>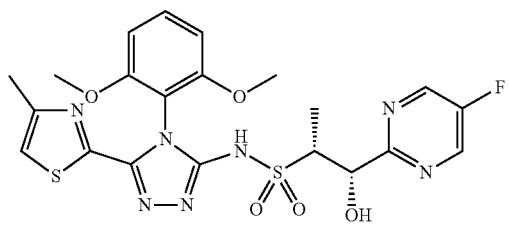<br>(1R,2S)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide or (1S,2R)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide.<br><br>$^1$H NMR (500 MHz, CDCl$_3$) δ 11.17 (br. s, 1H), 8.62 (s, 2H), 7.46 (br. s, 1H), 6.92 (s, 1H), 6.66 (dd, J = 13.9, 7.6 Hz, 2H), 5.61 (br. s, 1H), 3.84 (br. s, 1H), 3.76 (s, 3H), 3.73 (s, 3H), 2.38 (s, 3H), 1.25 (br. s, 3H). LCMS-ESI (pos.) m/z: 536.0 (M + H)$^+$. |

TABLE 8-continued

| Example Reagents | Structure, Name and Data |
|---|---|
| 123.0 | Second eluting peak:<br><br>OR<br>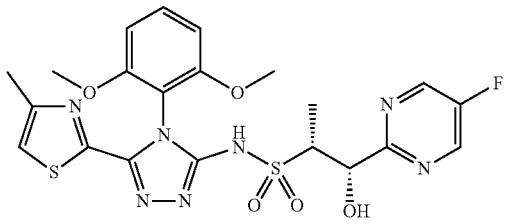<br>(1R,2S)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide or (1S,2R)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide.<br><br>$^1$H NMR (500 MHz, CDCl$_3$) δ 11.07 (br. s, 1H), 8.61 (s, 2H), 7.46 (t, J = 8.6 Hz, 1H), 6.93 (d, J = 0.7 Hz, 1H), 6.67 (dd, J = 14.8, 8.2 Hz, 2H), 5.62 (s, 1H), 3.81-3.87 (m, 1H), 3.76 (s, 3H), 3.74 (s, 3H), 2.39 (s, 3H), 1.23 (d, J = 7.1 Hz, 3H). LCMS-ESI (pos.) m/z: 536.2 (M + H)$^+$. |

TABLE 8-continued

| Example | Reagents | Structure, Name and Data |
|---|---|---|
| 111.0 | 2-(5-bromo-4-(2,6-dimethoxyphenyl)-4H-1,2,4-triazol-3-yl)-4-methylthiazole (Example 399.0), and (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide (Example 404.5). Preparative SFC method: Column: 250 × 30 mm Chiralpak AD-H, 40 g/min EtOH + 40 g/min CO$_2$, 100 bar, 299 nm, Inj volume: 1.0 mL of a 7.5 mg/mL solution of sample in EtOH. | First eluting peak:<br />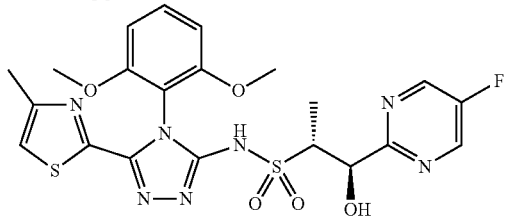<br />OR<br />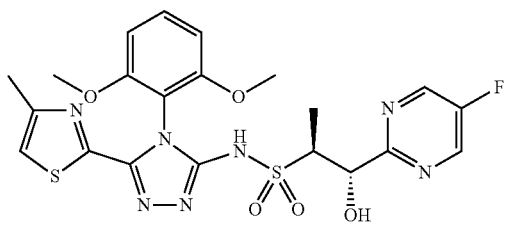<br />(1R,2R)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide or (1S,2S)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide.<br /><br />$^1$H NMR (500 MHz, CDCl$_3$) δ 11.10 (br. s, 1H), 8.58 (s, 2H), 7.48 (t, J = 8.6 Hz, 1H), 6.93 (s, 1H), 6.67 (dd, J = 8.4, 3.8 Hz, 2H), 5.07 (d, J = 6.3 Hz, 1H), 3.77-3.82 (m, 1H), 3.77 (s, 3H), 3.77 (s, 3H), 2.39 (s, 3H), 1.30 (d, J = 6.9 Hz, 3H). LCMS-ESI (pos.) m/z: 536.2 (M + H)$^+$. |

TABLE 8-continued

| Example Reagents | Structure, Name and Data |
|---|---|
| 112.0 | Second eluting peak:<br>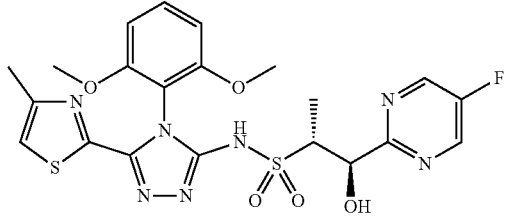<br>OR<br>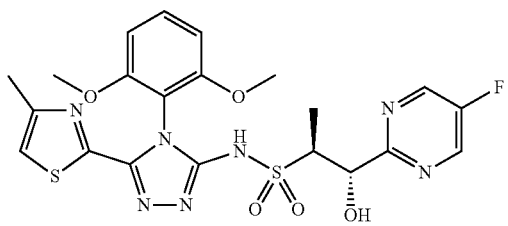<br>(1R,2R)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide or (1S,2S)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide.<br><br>$^1$H NMR (500 MHz, CDCl$_3$) δ 11.04 (br. s, 1H), 8.59 (s, 2H), 7.48 (t, J = 8.6 Hz, 1H), 6.93 (d, J = 0.7 Hz, 1H), 6.68 (dd, J = 8.4, 4.0 Hz, 2H), 5.07 (d, J = 6.4 Hz, 1H), 3.77-3.82 (m, 1H), 3.78 (s, 3H), 3.77 (s, 3H), 2.40 (s, 3H), 1.31 (d, J = 7.1 Hz, 3H). LCMS-ESI (pos.) m/z: 536.0 (M + H)$^+$. |

TABLE 8-continued

| Example | Reagents | Structure, Name and Data |
|---|---|---|
| 117.0 | 3-bromo-4-(2,6-dimethoxyphenyl)-5-(1-methyl-1H-pyrazol-3-yl)-4H-1,2,4-triazole (Example 399.5), and (1R,2S)-1-(5-fluoropyrimidin-2-yl)-1-methoxypropane-2-sulfonamide and (1S,2R)-1-(5-fluoropyrimidin-2-yl)-1-methoxypropane-2-sulfonamide (Example 409.0). Preparative SFC method: 30 × 150 + 30 × 250 mm Chiralpak IC columns in series, 36 mL/min MeOH 39 g/min CO$_2$, 100 bar, 253 nm, Inj vol.: 0.4 mL of a 8.5 mg/mL solution of sample in 2:1 MeOH/DCM. | First eluting peak:<br><br>OR<br>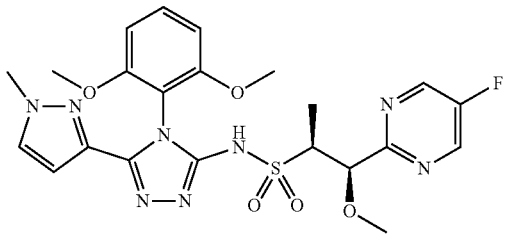<br>(1S,2R)-N-(4-(2,6-dimethoxyphenyl)-5-(1-methyl-1H-pyrazol-3-yl)-4H-1,2,4-triazol-3-yl)-1-(5-fluoropyrimidin-2-yl)-1-methoxypropane-2-sulfonamide or (1R,2S)-N-(4-(2,6-dimethoxyphenyl)-5-(1-methyl-1H-pyrazol-3-yl)-4H-1,2,4-triazol-3-yl)-1-(5-fluoropyrimidin-2-yl)-1-methoxypropane-2-sulfonamide.<br><br>$^1$H NMR (400 MHz, CDCl$_3$) δ 10.99 (br. s, 1H), 8.60 (s, 2H), 7.41 (t, J = 8.5 Hz, 1H), 7.22 (d, J = 2.3 Hz, 1H), 6.63 (d, J = 8.4 Hz, 2H), 5.88 (d, J = 2.3 Hz, 1H), 4.97 (d, J = 4.9 Hz, 1H), 3.86 (s, 3H), 3.68-3.77 (m, 1H), 3.74 (s, 3H), 3.72 (s, 3H), 3.32 (s, 3H), 1.38 (d, J = 7.0 Hz, 3H). LCMS-ESI (pos.) m/z: 533.2 (M + H)$^+$. |

| Example Reagents | Structure, Name and Data |
|---|---|
| 118.0 | Second eluting peak: 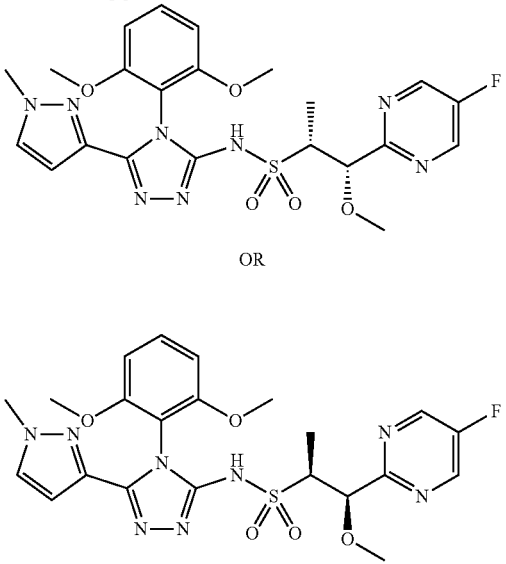 [SMILES: COc1cccc(OC)c1-n1c(NS(=O)(=O)[C@H](C)[C@@H](OC)c2ncc(F)cn2)nnc1-c1ccn(C)n1 ; COc1cccc(OC)c1-n1c(NS(=O)(=O)[C@@H](C)[C@H](OC)c2ncc(F)cn2)nnc1-c1ccn(C)n1]

OR (1S,2R)-N-(4-(2,6-dimethoxyphenyl)-5-(1-methyl-1H-pyrazol-3-yl)-4H-1,2,4-triazol-3-yl)-1-(5-fluoropyrimidin-2-yl)-1-methoxypropane-2-sulfonamide or (1R,2S)-N-(4-(2,6-dimethoxyphenyl)-5-(1-methyl-1H-pyrazol-3-yl)-4H-1,2,4-triazol-3-yl)-1-(5-fluoropyrimidin-2-yl)-1-methoxypropane-2-sulfonamide.

$^1$H NMR (400 MHz, CDCl$_3$) δ 10.85 (br. s, 1H), 8.60 (s, 2H), 7.41 (t, J = 8.5 Hz, 1H), 7.23 (d, J = 2.2 Hz, 1H), 6.63 (d, J = 8.4 Hz, 2H), 5.88 (d, J = 2.2 Hz, 1H), 4.97 (d, J = 4.9 Hz, 1H), 3.86 (s, 3H), 3.68-3.77 (m, 1H), 3.74 (s, 3H), 3.72 (s, 3H), 3.32 (s, 3H), 1.38 (d, J = 7.0 Hz, 3H). LCMS-ESI (pos.) m/z: 533.2 (M + H)$^+$. |

TABLE 8-continued

| Example | Reagents | Structure, Name and Data |
|---|---|---|
| 170.0 | 2-(5-bromo-4-(2,6-dimethoxyphenyl)-4H-1,2,4-triazol-3-yl)-4-methylthiazole (Example 399.0), and (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide (Example 405.0). Preparative SFC method: Column: 2 × 15 cm Chiralpak AD-H, 60 mL/min of 25% MeOH/CO$_2$, 100 bar, 220 mm, Inj vol.: 0.5 mL of a 9.0 mg/mL solution of sample in MeOH. | First eluting peak:<br /><br />OR<br />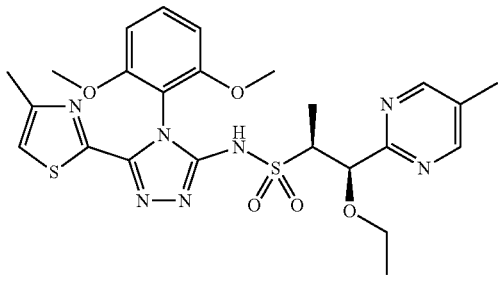<br />(1S,2R)-N-(4-(2,6-dimethoxyphenyl)-5-(4-methylthiazol-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(4-methylthiazol-2-yl)-4H-1,2,4-triazol-3-yl)-1-ethoxy-1-(5-methylpyrimidin-2-yl)propane-2-sulfonamide.<br /><br />$^1$H NMR (400 MHz, CDCl$_3$) δ 11.50 (br. s, 1H), 8.61 (s, 2H), 7.45 (t, J = 8.5 Hz, 1H), 6.91 (d, J = 1.0 Hz, 1H), 6.65 (d, J = 8.6 Hz, 2H), 4.97 (d, J = 6.1 Hz, 1H), 3.77-3.86 (m, 1H), 3.75 (s, 3H), 3.73 (s, 3H), 3.44-3.58 (m, 2H), 2.40 (d, J = 0.8 Hz, 3H), 2.33 (s, 3H), 1.45 (d, J = 7.0 Hz, 3H), 1.14 (t, J = 7.0 Hz, 3H). LCMS-ESI (pos.) m/z: 560.0 (M + H)$^+$. |

TABLE 8-continued

| Example Reagents | Structure, Name and Data |
|---|---|
| 171.0 | Second eluting peak:<br>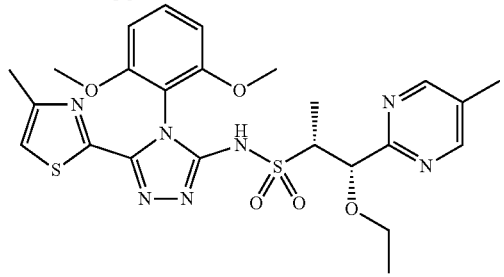<br>OR<br>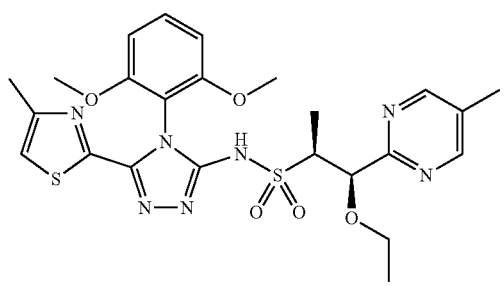<br>(1S,2R)-N-(4-(2,6-dimethoxyphenyl)-5-(4-methylthiazol-2-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(4-methylthiazol-2-yl)-4H-1,2,4-triazol-3-yl)-1-ethoxy-1-(5-methylpyrimidin-2-yppropane-2-sulfonamide.<br><br>$^1$H NMR (400 MHz, CDCl$_3$) δ 11.50 (br. s, 1H), 8.61 (s, 2H), 7.45 (t, J = 8.5 Hz, 1H), 6.90 (d, J = 0.8 Hz, 1H), 6.65 (d, J = 8.8 Hz, 2H), 4.97 (d, J = 5.9 Hz, 1H), 3.77-3.86 (m, 1H), 3.75 (s, 3H), 3.73 (s, 3H), 3.44-3.58 (m, 2H), 2.40 (d, J = 0.8 Hz, 3H), 2.33 (s, 3H), 1.45 (d, J = 7.0 Hz, 3H), 1.14 (t, J = 7.0 Hz, 3H). LCMS-ESI (pos.) m/z 560.0 (M + H)$^+$. |

TABLE 8-continued

| Example | Reagents | Structure, Name and Data |
|---|---|---|
| 172.0 | 3-bromo-4-(2,6-dimethoxyphenyl)-5-(1-methyl-1H-pyrazol-3-yl)-4H-1,2,4-triazole (Example 399.5), and (1S,2R)-1-ethoxy-1-(5-methylpyrimidin-2-yl)propane-2842933-sulfonamide and (1R,2S)-1-ethoxy-1-(5-methylpyrimidin-2-yl)propane-2-sulfonamide (Example 405.0). Preparative SFC method: Column: 250 × 21 mm Chiralpak AD-H, 70 mL/min 35% EtOH/CO$_2$, 206 bar, 220 nm. | First eluting peak:<br>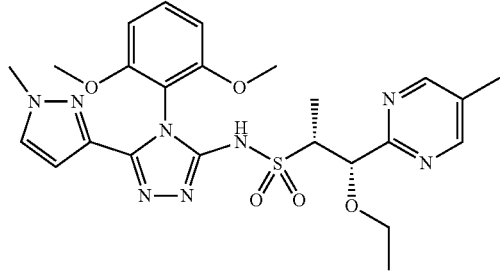<br>OR<br>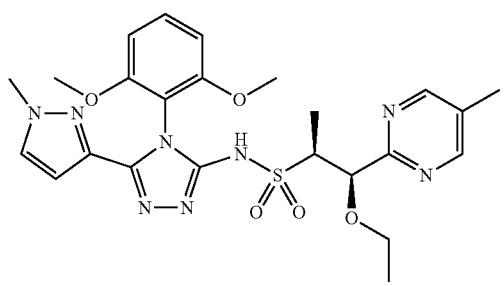<br><br>(1S,2R)-N-(4-(2,6-dimethoxyphenyl)-5-(1-methyl-1H-pyrazol-3-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(1-methyl-1H-pyrazol-3-yl)-4H-1,2,4-triazol-3-yl)-1-ethoxy-1-(5-methylpyrimidin-2-yl)propane-2-sulfonamide.<br><br>$^1$H NMR (400 M,Hz, CDCl$_3$) δ 8.65 (s, 2H), 7.41 (t, J = 8.4 Hz, 1H), 7.22 (d, J = 2.4 Hz, 1H), 6.64 (d, J = 8.4 Hz, 2H), 5.89 (d, J = 2.4 Hz, 1H), 5.01 (d, J = 5.9 Hz, 1H), 3.87 (s, 3H), 3.78-3.86 (m, 1H), 3.75 (s, 3H), 3.73 (s, 3H), 3.44-3.58 (m, 2H), 2.34 (s, 3H), 1.45 (d, J = 7.0 Hz, 3H), 1.15 (t, J = 7.0 Hz, 3H). LCMS-ESI (pos.) m/z: 543.0 (M + H)+. |

TABLE 8-continued

| Example | Reagents | Structure, Name and Data |
|---|---|---|
| 173.0 | | Second eluting peak:<br>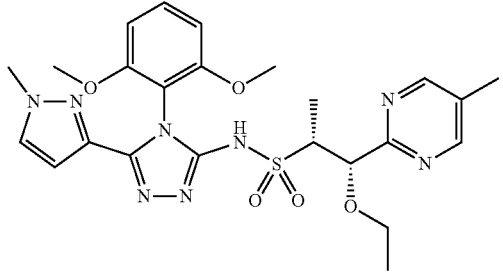<br>OR<br>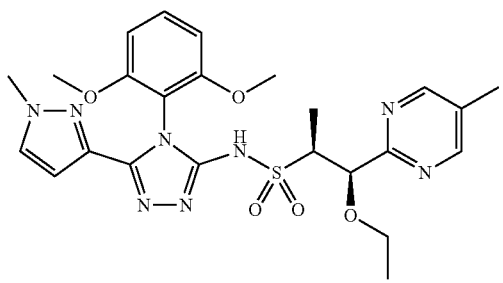<br>(1S,2R)-N-(4-(2,6-dimethoxyphenyl)-5-(1-methyl-1H-pyrazol-3-yl)-4H-1,2,4-triazol-3-yl)-1-ethoxy-1-(5-methylpyrimidin-2-yl)propane-2-sulfonamide or (1R,2S)-N-(4-(2,6-dimethoxyphenyl)-5-(1-methyl-1H-pyrazol-3-yl)-4H-1,2,4-triazol-3-yl)-1-ethoxy-1-(5-methylpyrimidin-2-yl)propane-2-sulfonamide.<br>$^1$H NMR (400 M,Hz, CDCl$_3$) δ 8.61 (s, 2H), 7.41 (t, J = 8.5 Hz, 1H), 7.22 (d, J = 2.4 Hz, 1H), 6.64 (d, J = 8.6 Hz, 2H), 5.88 (d, J = 2.2 Hz, 1H), 4.99 (d, J = 6.1 Hz, 1H), 3.87 (s, 3H), 3.77-3.86 (m, 1H), 3.75 (s, 3H), 3.73 (s, 3H), 3.44-3.59 (m, 2H), 2.33 (s, 3H), 1.45 (d, J = 7.0 Hz, 3H), 1.15 (t, J = 6.9 Hz, 3H). LCMS-ESI (pos.) m/z: 543.0 (M + H)$^+$. |
| 119.0 | 2-(5-bromo-4-(2,6-dimethoxyphenyl)-4H-1,2,4-triazol-3-yl)-4-methylthiazole (Example 399.0), and (2S,3R)-3-(5-fluoropyrimidin-2-yl)butane-2-sulfonamide and (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide (Example 403.0). Preparative SFC method, Stage 1: Column: 2x25 cm Chiralpak AD-H, 60 mL/min of 20% EtOH (containing 0.1% NH$_3$)/CO$_2$, 100 bar, 220 | First eluting peak from Stage 1 separation:<br>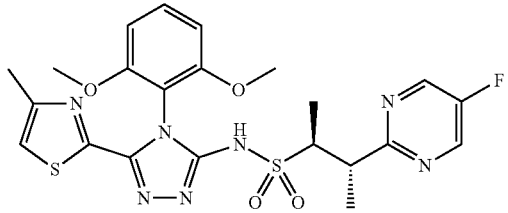 [SMILES: COc1cccc(OC)c1-n1c(NS(=O)(=O)[C@@H](C)[C@@H](C)c2ncc(F)cn2)nnc1-c1nc(C)cs1]<br>(2S,3S)-N-(4-(2,6-dimethoxyphenyl)-5-(4-methylthiazol-2-yl)-4H-1,2,4-triazol-3-yl)-3-(5-fluoropyrimidin-2-yl)butane-2-sulfonamide.<br>$^1$H NMR (500 MHz, CDCl$_3$) δ 11.36 (s, 1H), 8.53 (s, 2H), 7.46 (t, J = 8.4 Hz, 1H), 6.91 (s, 1H), 6.66 (d, J = 8.6 Hz, 2H), 3.75 (s, 3H), 3.75 (s, 3H), 3.62-3.69 (m, 1H), 3.54-3.61 (m, 1H), 2.40 (s, 3H), 1.50 (d, J = 7.1 Hz, 3H), 1.26 (d, J = 7.1 Hz, 3H). LCMS-ESI (pos.) m/z: 534.0 (M + H)$^+$. |

TABLE 8-continued

| Example | Reagents | Structure, Name and Data |
|---|---|---|
| 165.0 | nm, Inj vol.: 0.5 mL of a 4.0 mg/mL solution of sample in 1:1 MeOH/DCM. Stage 2 for separation of peak #2: Column: 250 × 21 mm Chiralpak AD-H, 20 g/min i-PrOH (containing 20 mM NH₃) + 30 g/min CO₂, 100 bar, 300 nm, Inj vol.: 0.8 mL of a 3.7 mg/mL solution of sample in 1:1 MeOH/DCM. | Second eluting peak from Stage 1 separation/first eluting peak from Stage 2 separation: 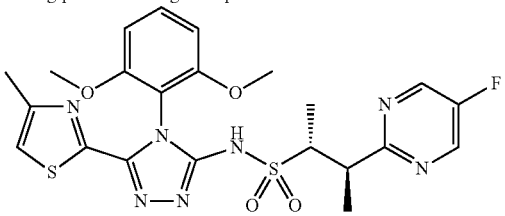 (2R,3R)-N-(4-(2,6-dimethoxyphenyl)-5-(4-methylthiazol-2-yl)-4H-1,2,4-triazol-3-yl)-3-(5-fluoropyrimidin-2-yl)butane-2-sulfonamide. $^1$H NMR (500 MHz, CDCl₃) δ 11.37 (s, 1H), 8.53 (s, 2H), 7.46 (t, J = 8.6 Hz, 1H), 6.91 (s, 1H), 6.66 (d, J = 8.6 Hz, 2H), 3.75 (s, 3H), 3.75 (s, 3H), 3.62-3.69 (m, 1H), 3.54-3.61 (m, 1H), 2.40 (s, 3H), 1.50 (d, J = 6.9 Hz, 3H), 1.26 (d, J = 7.1 Hz, 3H). LCMS-ESI (pos.) m/z: 534.0 (M + H)⁺. |
| 120.0 | | Second eluting peak from Stage 1 separation/second eluting peak from Stage 2 separation: 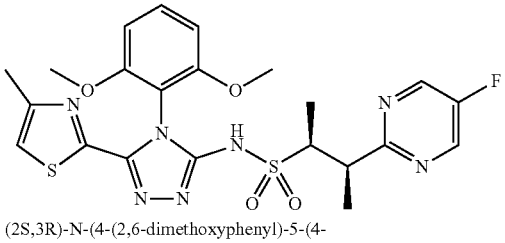 (2S,3R)-N-(4-(2,6-dimethoxyphenyl)-5-(4-methylthiazol-2-yl)-4H-1,2,4-triazol-3-yl)-3-(5-fluoropyrimidin-2-yl)butane-2-sulfonamide. $^1$H NMR (400 MHz, CDCl₃) δ 11.15 (br. s, 1H), 8.54 (s, 2H), 7.46 (t, J = 8.5 Hz, 1H), 6.92 (s, 1H), 6.65 (dd, J = 8.5, 4.8 Hz, 2H), 3.79-3.90 (m, 2H), 3.74 (s, 3H), 3.72 (s, 3H), 2.39 (s, 3H), 1.37 (d, J = 6.3 Hz, 3H), 1.36 (d, J = 6.8 Hz, 3H). LCMS-ESI (pos.) m/z: 534.0 (M + H)⁺. |
| 121.0 | | Third eluting peak from Stage 1 separation: 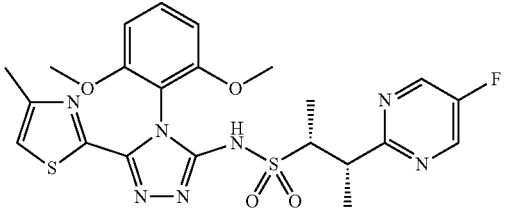 [SMILES: COc1cccc(OC)c1-n1c(NS(=O)(=O)[C@H](C)[C@@H](C)c2ncc(F)cn2)nnc1-c1nc(C)cs1] (2R,3S)-N-(4-(2,6-dimethoxyphenyl)-5-(4-methylthiazol-2-yl)-4H-1,2,4-triazol-3-yl)-3-(5-fluoropyrimidin-2-yl)butane-2-sulfonamide. $^1$H NMR (400 MHz, CDCl₃) δ 11.10 (br. s, 1H), 8.54 (s, 2H), 7.46 (t, J = 8.5 Hz, 1H), 6.91 (s, 1H), 6.65 (dd, J = 8.5, 4.8 Hz, 2H), 3.78-3.90 (m, 2H), 3.74 (s, 3H), 3.72 (s, 3H), 2.39 (s, 3H), 1.37 (d, J = 6.3 Hz, 3H), 1.36 (d, J = 6.8 Hz, 3H). LCMS-ESI (pos.) m/z: 534.2 (M + H)⁺. |

TABLE 8-continued

| Example | Reagents | Structure, Name and Data |
|---|---|---|
| 116.0 | 3-bromo-4-(2,6-dimethoxyphenyl)-5-(1-methyl-1H-pyrazol-3-yl)-4H-1,2,4-triazole (Example 399.5), and (R)-2-(2,4-difluorophenyl)-2-hydroxyethanesulfonamide and (S)-2-(2,4-difluorophenyl)-2-hydroxyethanesulfonamide (Example 406.0). The racemic mixture was not separated. | 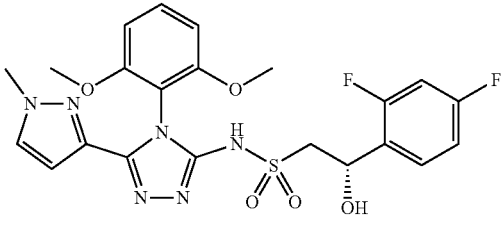 AND 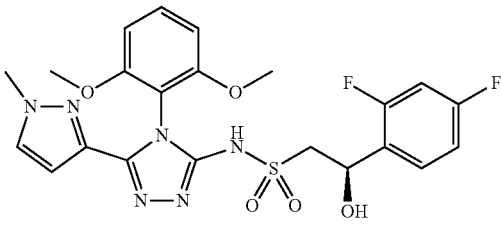 (S)-2-(2,4-difluorophenyl)-N-(4-(2,6-dimethoxyphenyl)-5-(1-methyl-1H-pyrazol-3-yl)-4H-1,2,4-triazol-3-yl)-2-hydroxyethanesulfonamide and (R)-2-(2,4-difluorophenyl)-N-(4-(2,6-dimethoxyphenyl)-5-(1-methyl-1H-pyrazol-3-yl)-4H-1,2,4-triazol-3-yl)-2-hydroxyethanesulfonamide. $^1$H NMR (400 MHz, CDCl$_3$) δ 10.84 (br. s, 1H), 7.41-7.53 (m, 2H), 7.25 (d, J = 2.4 Hz, 1H), 6.87 (td, J = 8.2, 1.9 Hz, 1H), 6.77 (ddd, J = 10.7, 8.7, 2.4 Hz, 1H), 5.96 (d, J = 2.4 Hz, 1H), 5.43 (dd, J = 8.2, 3.3 Hz, 1H), 3.87 (s, 3H), 3.79 (s, 3H), 3.74 (s, 3H), 3.25-3.36 (m, 2H). LCMS-ESI (pos.) m/z: 521.0 (M + H)$^+$. |

Example 113.0. Preparation of (1R,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide or (1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide

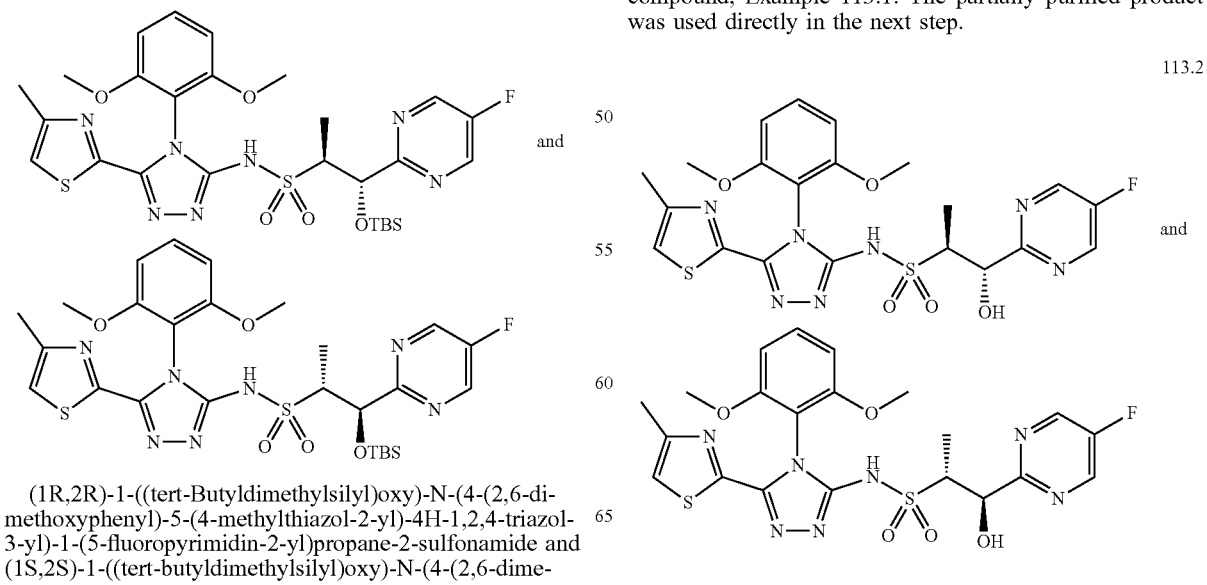

(1R,2R)-1-((tert-Butyldimethylsilyl)oxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide and (1S,2S)-1-((tert-butyldimethylsilyl)oxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide, Example 113.1. The title compound was prepared following the procedure described in Example 101.0 employing Example 399.0 and (1R,2R)-1-((tert-butyldimethylsilyl)oxy)-1-(5-fluoropyrimidin-2-yl)propane-2-sulfonamide and (1S,2S)-1-((tert-butyldimethylsilyl)oxy)-1-(5-fluoropyrimidin-2-yl)propane-2-sulfonamide (prepared in an anlogous fashion to that of Example 466.6) to provide the title compound, Example 113.1. The partially purified product was used directly in the next step.

(1R,2R)-N-(4-(2,6-Dimethoxyphenyl)-5-(4-methylthi-azol-2-yl)-4H-1,2,4-triazol-3-yl)-1-(5-fluoropyrimidin-2-yl)-1-hydroxypropane-2-sulfonamide and (1S,2S)-N-(4-(2,6-dimethoxyphenyl)-5-(4-methylthiazol-2-yl)-4H-1,2,4-triazol-3-yl)-1-(5-fluoropyrimidin-2-yl)-1-hydroxypropane-2-sulfonamide. To Example 113.1 in EtOH (3.7 mL) was added 10 equivalents of concentrated HCl. The reaction was stirred at RT for 8 h. The reaction was then concentrated in vacuo and extracted with DCM. The organic layers were dried over MgSO$_4$, filtered and dry loaded onto silica gel. Purification by flash chromatography on a 40 g Redisep Gold pre-packed spherical silica gel column (eluent: 40-70% EtOAc in hexanes, gradient elution) provided the title product as a white solid. LCMS-ESI (pos.) m/z: 536.0 (M+H)$^+$.

113.3

(1R,2R)-N-(4-(2,6-Dimethoxyphenyl)-5-(4-methyl-1,3-thiazol-2-yl)-4H-1,2,4-triazol-3-yl)-1-(5-fluoro-2-pyrimidi-nyl)-1-methoxy-2-propanesulfonamide and (1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide, Example 113.3. To a 10 mL vial containing Example 113.2 (70 mg, 0.131 mmol) in THF (1.3 mL) was added NaH (60% w/w in mineral oil, 26.1 mg, 0.654 mmol) followed by 1 equivalent of MeI in THF. The reaction was stirred overnight at RT. Water was added to the reaction and the mixture was extracted with EtOAc. The organic layers were dried over MgSO$_4$, filtered, and concentrated in vacuo. Purification of the residue by flash chromatography on a 24 g Redisep Gold pre-packed spherical silica gel column (eluent: 0-10% IPA in DCM, gradient elution) provided Example 113.3 (36 mg, 50%). $^1$H NMR (500 MHz, CDCl$_3$) δ 11.5 (br s, 1H), 8.62 (s, 2H) 7.46 (t, J=8.6 Hz, 1H) 6.90 (s, 1H) 6.66 (t, J=8.1 Hz, 2H) 4.79 (d, J=6.4 Hz, 1H) 3.71-3.80 (m, 7H) 3.23 (s, 3H) 2.40 (s, 3H) 1.25 (d, J=7.1 Hz, 3H). LCMS-ESI (pos.), m/z: 560.1 (M+H)$^+$.

113.0

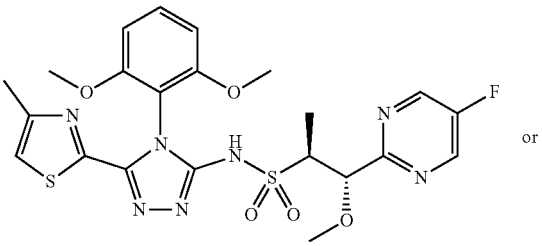

or

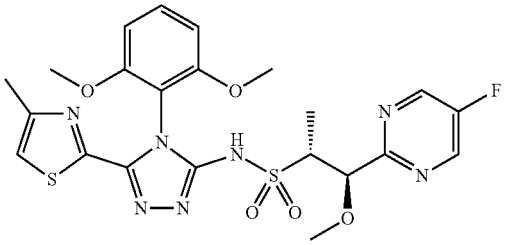

(1R,2R)-N-(4-(2,6-Dimethoxyphenyl)-5-(4-methyl-1,3-thiazol-2-yl)-4H-1,2,4-triazol-3-yl)-1-(5-fluoro-2-pyrimidi-nyl)-1-methoxy-2-propanesulfonamide or (1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide, Example 113.0. Example 113.3 was purified by chiral purification (36 mg): Run on Thar 80 SFC with a 250×30 mm CC4 column with 40 g/min MeOH (neat)+33 g/min CO$_2$, 50% co-solvent at 80 g/min. Temp.=27° C., Outlet pressure=100 bar, Wavelength=215 nm. Injected 0.5 mL of 36 mg sample dissolved in 4 mL of MeOH, c=9 mg/mL i.e. 4.5 mg per injection. Cycle time 8.0 min, run time=18 min. The title compound was the first peak to elute under the conditions described. $^1$H NMR (500 MHz, CDCl$_3$) δ 11.51 (br. s, 1H) 8.62 (s, 2H) 7.46 (t, J=8.4 Hz, 1H) 6.90 (d, J=1.0 Hz, 1H) 6.66 (t, J=7.7 Hz, 2H) 4.80 (d, J=6.1 Hz, 1H) 3.69-3.70 (m, 1H) 3.68-3.85 (m, 7H) 3.24 (s, 3H) 2.41 (s, 3H) 1.25-1.28 (m, 3H). LCMS-ESI (pos.) m/z: 550.1 (M+H)$^+$.

Example 114.0. Preparation of (1R,2R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide or (1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide 114.0

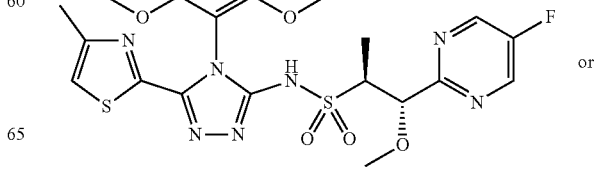

or

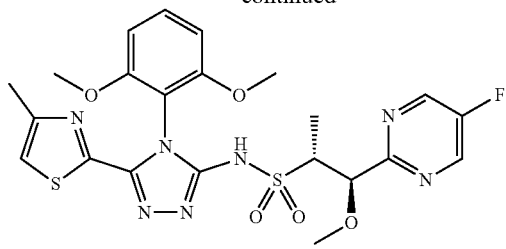

(1R,2R)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide or (1S,2S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-1-methoxy-2-propanesulfonamide, Example 114.0. Further elution under the conditions described in Example 113.0 delivered the second eluting peak. ¹H NMR (500 MHz, CDCl₃) δ 11.52 (br. s, 1H) 8.64 (s, 2H) 7.48 (t, J=8.6 Hz, 1H) 6.92 (d, J=0.7 Hz, 1H) 6.68 (t, J=7.7 Hz, 2H) 4.82 (d, J=6.1 Hz, 1H) 3.74-3.85 (m, 7H) 3.26 (s, 3H) 2.42 (d, J=0.7 Hz, 3H) 1.28 (d, J=7.1 Hz, 3H). LCMS-ESI (pos.) m/z: 550.1 (M+H)⁺.

Example 124.0. Preparation of P-2-(4-chlorophenyl)-N-(4-(2-methoxy-6-methylphenyl)-5-(thiophen-2-yl)-4H-1,2,4-triazol-3-yl)ethanesulfonamide and M-2-(4-chlorophenyl)-N-(4-(2-methoxy-6-methylphenyl)-5-(thiophen-2-yl)-4H-1,2,4-triazol-3-yl)ethanesulfonamide

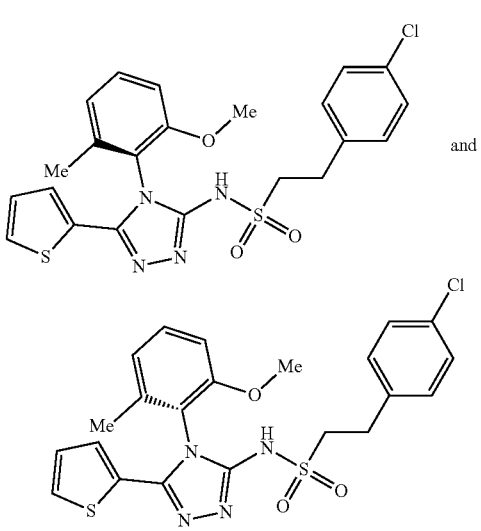

P-2-(4-Chlorophenyl)-N-(4-(2-methoxy-6-methylphenyl)-5-(thiophen-2-yl)-4H-1,2,4-triazol-3-yl)ethanesulfonamide and M-2-(4-chlorophenyl)-N-(4-(2-methoxy-6-methylphenyl)-5-(thiophen-2-yl)-4H-1,2,4-triazol-3-yl) ethanesulfonamide, Example 124.0. To a 5 mL vial, containing 4-(2-methoxy-6-methylphenyl)-5-(thiophen-2-yl)-4H-1,2,4-triazol-3-amine (prepared in an analogous fashion to that described in Example 234.03 employing 2-methoxy-6-methylaniline, 100.0 mg, 0.35 mmol) in DCM (6984 µL) at 0° C. was added TEA (195 µL, 1.4 mmol) followed by 2-(4-chlorophenyl)ethanesulfonyl chloride (92 mg, 0.384 mmol). The reaction was stirred for 48 h after which LCMS analysis indicated the formation of product and the consumption of starting material. The solution was diluted with EtOAc, washed with H₂O and brine, dried over Na₂SO₄, filtered, and concentrated under reduced pressure. The residue was loaded on a prepacked silica gel cartridge eluting with a solvent gradient of 1-3% MeOH/DCM to provide Example 124.0 (130.0 mg, 0.27 mmol, 76% yield) as an off-white solid. LCMS-ESI (pos.) m/z: 489.0 (M+H)⁺.

Example 125.0. Preparation of 2-(4-chlorophenyl)-N-(4-(2-methoxy-5-(2-oxo-1-pyrrolidinyl)phenyl)-5-(2-thiophenyl)-4H-1,2,4-triazol-3-yl)ethanesulfonamide

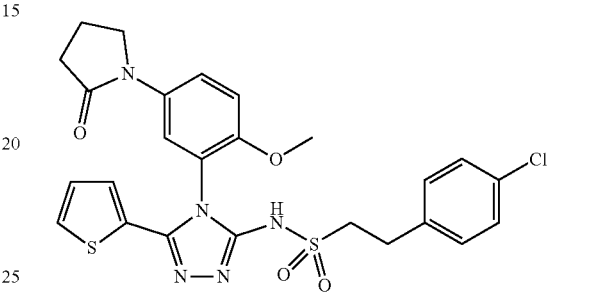

2-(4-Chlorophenyl)-N-(4-(2-methoxy-5-(2-oxo-1-pyrrolidinyl)phenyl)-5-(2-thiophenyl)-4H-1,2,4-triazol-3-yl)ethanesulfonamide, Example 125.0. Example 133.0 (30 mg, 0.054 mmol), pyrrolidin-2-one (16.6 µL, 0.22 mmol), N,N'-dimethylethan-1,2-diamine (14.6 uL, 0.22 mmol), copper (I) iodide (12.9 mg, 0.068 mmol), potassium carbonate (18.7 mg, 0.14 mmol) and toluene (0.54 mL) were combined in a 5 mL vial and sparged with dry nitrogen for 2 min. The resulting mixture was then heated at 110° C. until LCMS analysis showed that the reaction was complete. Thereafter, the mixture was cooled to RT, concentrated in vacuo, and purified on a 24 g silica gel column, employing a gradient of 1-7% MeOH in DCM, to afford Example 125.0 (12.5 mg, 0.022 mmol, 41%) as an off-white amorphous solid. ¹H NMR (400 MHz, DMSO-d₆) δ 13.30 (s, 1H) 7.93 (s, 1H) 7.90 (d, J=8.80 Hz, 1H) 7.72 (d, J=5.87 Hz, 1H) 7.31-7.37 (m, 3H) 7.22-7.29 (m, 2H) 7.02-7.09 (m, 1H) 6.93 (br. s, 1H) 3.75-3.84 (m, 2H) 3.69 (s, 3H) 3.19-3.28 (m, 2H) 2.92 (t, J=8.31 Hz, 2H) 2.46-2.54 (m, 2H) 1.99-2.09 (m, 2H). LCMS-ESI (pos.), m/z: 558.0 (M+H)⁺.

Example 126.0. Preparation of 2-(4-chlorophenyl)-N-(4-(2-methoxy-5-(2-oxo-1-azetidinyl)phenyl)-5-(2-thiophenyl)-4H-1,2,4-triazol-3-yl)ethanesulfonamide

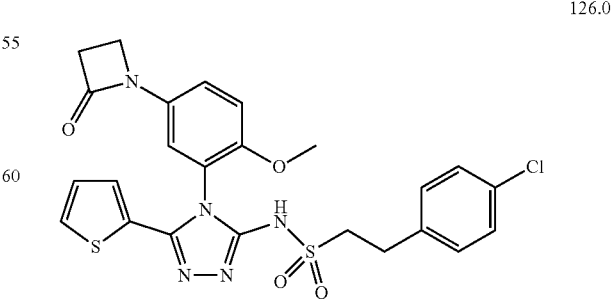

2-(4-Chlorophenyl)-N-(4-(2-methoxy-5-(2-oxo-1-azetidinyl)phenyl)-5-(2-thiophenyl)-4H-1,2,4-triazol-3-yl)ethanesulfonamide, Example 126.0. The title compound was prepared employing azetidin-2-one (commercially available from Matrix Scientific, Columbia, S.C., USA) and the procedure described in Example 125.0, to yield Example 126.0 (30 mg, 0.014 mmol, 26%) as an off-white amorphous solid. $^1$H NMR (400 MHz, DMSO-$d_6$) δ 13.30 (s, 1H) 7.71 (d, J=3.72 Hz, 1H) 7.59 (d, J=6.85 Hz, 2H) 7.30-7.36 (m, 3H) 7.24-7.29 (m, 2H) 7.03-7.08 (m, 1H) 6.92 (br. s, 1H) 3.67 (s, 3H) 3.61 (d, J=2.35 Hz, 2H) 3.18-3.27 (m, 2H) 3.08 (t, J=4.50 Hz, 2H) 2.92 (t, J=8.12 Hz, 2H). LCMS-ESI (pos.), m/z: 544.1 (M+H)$^+$.

Example 127.0. Preparation of 2-(4-chlorophenyl)-N-(4-(2-methoxy-5-(2-oxo-1-pyrrolidinyl)phenyl)-5-(2-thiophenyl)-4H-1,2,4-triazol-3-yl)ethanesulfonamide

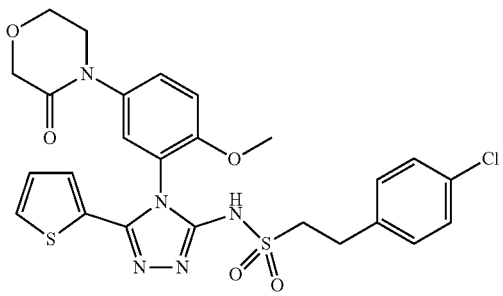

127.0

2-(4-Chlorophenyl)-N-(4-(2-methoxy-5-(3-oxo-4-morpholinyl)phenyl)-5-(2-thiophenyl)-4H-1,2,4-triazol-3-yl) ethanesulfonamide, Example 127.0. The title compound was prepared employing morpholin-3-one (commercially available from CombiBlocks, San Diego, Calif., USA) and the procedure described for the synthesis of Example 125.0 to yield Example 127.0 (20 mg, 0.035 mmol, 64%) as an off-white amorphous solid. $^1$H NMR (400 MHz, DMSO-$d_6$) δ 13.30 (s, 1H) 7.64-7.76 (m, 3H) 7.30-7.38 (m, 3H) 7.22-7.30 (m, 2H) 7.01-7.08 (m, 1H) 6.94 (dd, J=3.81, 1.08 Hz, 1H) 4.13-4.25 (m, 2H) 3.91-3.98 (m, 2H) 3.74-3.82 (m, 1H) 3.70-3.74 (m, 3H) 3.61-3.70 (m, 1H) 3.14-3.31 (m, 2H) 2.93 (t, J=8.31 Hz, 2H). LCMS-ESI (pos.), m/z: 574.1 (M+H)$^+$.

Example 128.0. Preparation of P-2-(4-chlorophenyl)-N-(4-(2-methoxy-6-methylphenyl)-5-(thiophen-2-yl)-4H-1,2,4-triazol-3-yl)ethanesulfonamide or M-2-(4-chlorophenyl)-N-(4-(2-methoxy-6-methylphenyl)-5-(thiophen-2-yl)-4H-1,2,4-triazol-3-yl)ethanesulfonamide

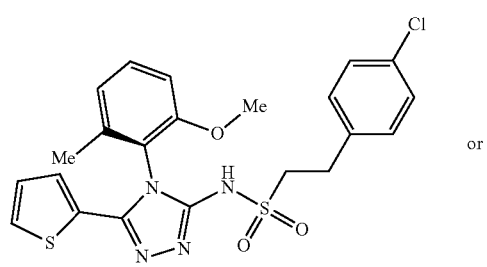

128.0

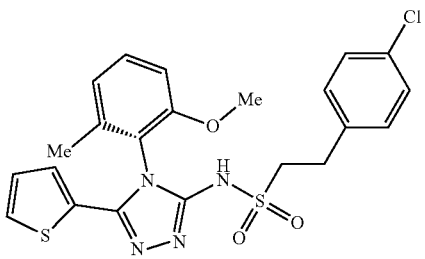

P-2-(4-Chlorophenyl)-N-(4-(2-methoxy-6-methylphenyl)-5-(thiophen-2-yl)-4H-1,2,4-triazol-3-yl)ethanesulfonamide or M-2-(4-chlorophenyl)-N-(4-(2-methoxy-6-methylphenyl)-5-(thiophen-2-yl)-4H-1,2,4-triazol-3-yl) ethanesulfonamide, Example 128.0. Example 124.0 was purified by chiral purification (103 mg) on a 250×30 mm OJ column yielded (7 min run) to yield peak one as the title compound (36.8 mg, retention time 1.78 min, 99% ee). Specific Optical Rotation: [α]=−38.3 (c=1.545 g/100 mL, CHCl$_3$, ee=99%). LCMS-ESI (pos.), m/z: 489.0 (M+H)$^+$.

Example 129.0. Preparation of P-2-(4-chlorophenyl)-N-(4-(2-methoxy-6-methylphenyl)-5-(thiophen-2-yl)-4H-1,2,4-triazol-3-yl)ethanesulfonamide or M-2-(4-chlorophenyl)-N-(4-(2-methoxy-6-methylphenyl)-5-(thiophen-2-yl)-4H-1,2,4-triazol-3-yl) ethanesulfonamide 129.0

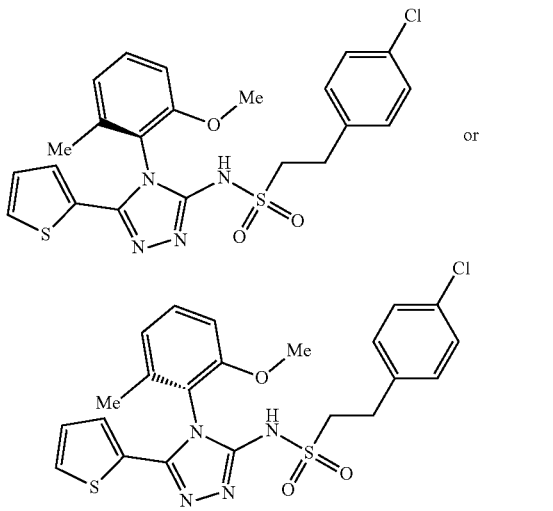

P-2-(4-Chlorophenyl)-N-(4-(2-methoxy-6-methylphenyl)-5-(thiophen-2-yl)-4H-1,2,4-triazol-3-yl)ethanesulfonamide or M-2-(4-chlorophenyl)-N-(4-(2-methoxy-6-methylphenyl)-5-(thiophen-2-yl)-4H-1,2,4-triazol-3-yl) ethanesulfonamide, Example 129.0. Example 124.0 was purified by chiral purification (103 mg) on a 250×30 mm OJ column yielded (7 min run). To yield peak one as the title compound (36.8 mg, retention time 2.35 min, 99% ee). Specific Optical Rotation: [α]=+37.2 (c=1.295 g/100 mL, CHCl$_3$, ee=99%). LCMS-ESI (pos.), m/z: 489.0 (M+H)$^+$.

Example 130.0. Preparation of 2-(4-fluorophenyl)-N-(4-(2-methoxy-5-(2-oxo-1-azetidinyl)phenyl)-5-(2-thiophenyl)-4H-1,2,4-triazol-3-yl)ethanesulfonamide

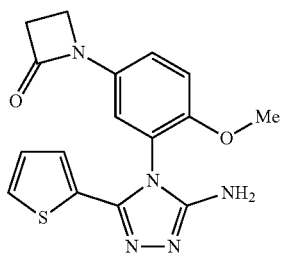

130.1

1-(3-(3-Amino-5-(thiophen-2-yl)-4H-1,2,4-triazol-4-yl)-4-methoxyphenyl)azetidin-2-one, Example 130.1. To a 20 mL vial containing 4-(5-bromo-2-methoxyphenyl)-5-(thiophen-2-yl)-4H-1,2,4-triazol-3-amine (Example 133.01, 3.14 g, 8.95 mmol), and toluene (90 mL) at RT was added potassium carbonate (3.09 g, 22.38 mmol) and azetidin-2-one (1.91 g, 26.9 mmol). A steady stream of dry nitrogen was passed through the mixture for 5 min. After which, N,N'-dimethylethane-1,2-diamine (2.41 mL, 22.38 mmol) was added to the contents and the mixture was heated to 110° C. After 24 h, LCMS analysis indicated the consumption of starting material and the formation of product. EtOAc and a saturated aqueous solution of NH$_4$Cl were added. The aqueous phase was extracted with EtOAc and the combined organic phase was dried over Na$_2$SO$_4$. The organic phase was filtered and concentrated under reduced pressure. The residue was taken up in DCM and concentrated onto silica gel. The mixture was purified on a 40 g prepacked silica gel column using a combiflash and eluting with 0.5-10% MeOH/DCM gradient containing 1% NH$_3$ (aq). The product containing fractions were collected and concentrated to give the title compound (0.31 g, 0.92 mmol, 10% yield) as an off-white solid. LCMS-ESI (pos.), m/z: 341.9 (M+H)$^+$.

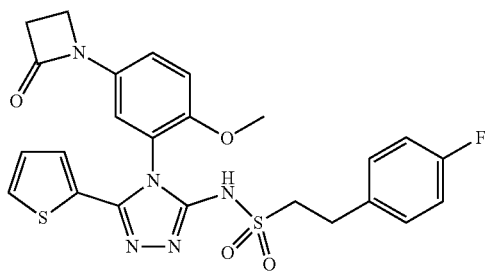

130.0

2-(4-Fluorophenyl)-N-(4-(2-methoxy-5-(2-oxo-1-azetidinyl)phenyl)-5-(2-thiophenyl)-4H-1,2,4-triazol-3-yl)ethanesulfonamide, Example 130.0. To a 5 mL vial containing Example 130.1 (20 mg, 0.059 mmol), DCM (1.2 mL) and TEA (32.7 μL, 0.23 mmol) at 0° C. was added 2-(4-fluorophenyl)ethanesulfonyl chloride (Oakwood, 16.96 mg, 0.076 mmol). The mixture was allowed to warm to RT and was stirred for 1 day. LCMS analysis indicated the consumption of starting material and the formation of product. The mixture was diluted with EtOAc and the organic phase was washed with a saturated NaHCO$_3$ solution, H$_2$O and brine. The organic layer was then dried over Na$_2$SO$_4$, filtered and concentrated under reduced pressure. The residue was loaded on a prepacked 5 g silica gel cartridge and purified on a 12 g prepacked silica gel column using combiflash and eluting with 0.5-7% MeOH/DCM to provide the title compound (14 mg, 0.026 mmol, 45% yield) as an off-white amorphous solid. LCMS-ESI (pos.), m/z: 527.9 (M+H)$^+$.

Example 131.0. Preparation of 2-(2-bromo-4-fluorophenyl)-N-(4-(2-methoxy-5-(2-oxoazetidin-1-yl)phenyl)-5-(thiophen-2-yl)-4H-1,2,4-triazol-3-yl)ethanesulfonamide

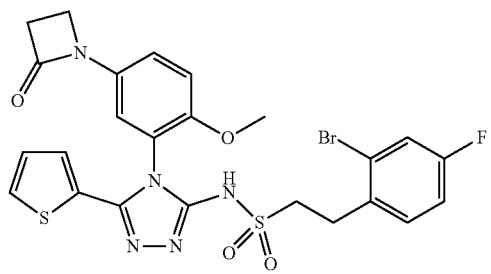

131.0

2-(2-Bromo-4-fluorophenyl)-N-(4-(2-methoxy-5-(2-oxoazetidin-1-yl)phenyl)-5-(thiophen-2-yl)-4H-1,2,4-triazol-3-yl)ethanesulfonamide, Example 131.0. To a 5 mL vial containing Example 130.1 (290 mg, 0.849 mmol), DCM (1.7 mL) and TEA (474 μL, 3.40 mmol) at 0° C. was added 2-(2-bromo-4-fluorophenyl)ethanesulfonyl chloride (333 mg, 1.10 mmol). The mixture was allowed to warm to RT and was stirred for 1 h. LCMS analysis indicated the consumption of starting material and formation of product. The mixture was diluted with EtOAc, and the organic phase was washed with a saturated NaHCO$_3$ solution, H$_2$O and brine. The organic layer was then dried over Na$_2$SO$_4$, filtered and concentrated under reduced pressure. The residue was loaded on a prepacked 5 g silica gel cartridge and purified on a 12 g prepacked silica gel column using combiflash and eluting with 0.5-7% MeOH/DCM to provide Example 131.0 (261.4 mg, 0.431 mmol, 51% yield) as an off-white amorphous solid. LCMS-ESI (pos.), m/z: 608.0 (M+H)$^+$.

Example 132.0. Preparation of 2-(2-cyano-4-fluorophenyl)-N-(4-(2-methoxy-5-(2-oxoazetidin-1-yl)phenyl)-5-(thiophen-2-yl)-4H-1,2,4-triazol-3-yl)ethanesulfonamide

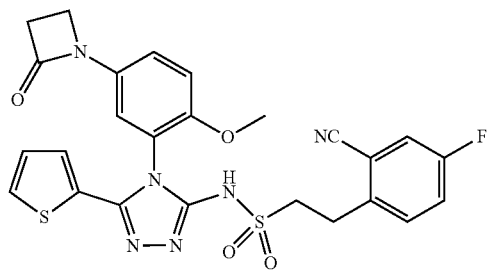

132.0

2-(2-Cyano-4-fluorophenyl)-N-(4-(2-methoxy-5-(2-oxoazetidin-1-yl)phenyl)-5-(thiophen-2-yl)-4H-1,2,4-triazol-3-yl)ethanesulfonamide, Example 132.0. To a 5 mL vial containing Example 131.0 (51.6 mg, 0.085 mmol) and DMF (850 µL) at RT was added copper(I) cyanide (76 mg, 0.850 mmol). The mixture was heated to 130° C. and stirred for 21 h. LCMS analysis indicated the consumption of starting material and formation of product. The mixture was diluted with EtOAc, and the organic phase was washed with NaHCO₃ solution, H₂O and brine. The organic layer was then dried over Na₂SO₄, filtered and concentrated in vacuo. The residue was purified on a 12 g prepacked silica gel column using combiflash and eluting with 0.5-7% MeOH/DCM; further purification was accomplished by reverse phase HPLC using 10%-90% ACN/H₂O containing 0.5% TFA to provide the title compound (18.2 mg, 0.033 mmol, 39% yield) as an off-white amorphous solid. LCMS-ESI (pos.), m/z: 553.1 (M+H)⁺.

Example 168.0. Preparation of (1S,2R)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or (1R,2S)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide L, 0.04 mmol) was added via syringe. After an additional 1.5 h, the reaction was quenched with water (7 mL) and extracted with EtOAc (4×). After solvent removal, the residue was purified by silica gel chromatography (eluent: 0-7% MeOH in DCM) to provide the racemic product (13.2 mg, 16% yield) as a white solid. The racemate was separated by preparative SFC (Column: 250×21 mm Chiralpak AS-H, 13.75 g/min MeOH+41.2 g/min CO₂, 100 bar, 300 nm, Inj vol.: 0.3 mL of a 4.3 mg/mL solution of sample in MeOH.) to deliver the first eluting peak, Example 168.0 (5.0 mg). ¹H NMR (400 MHz, CDCl₃) δ 11.13 (br. s, 1H), 8.60 (s, 2H), 7.46 (t, J=8.5 Hz, 1H), 6.91 (d, J=1.0 Hz, 1H), 6.65 (dd, J=8.6, 1.6 Hz, 2H), 5.82 (ddt, J=17.3, 10.4, 5.7, 5.7 Hz, 1H), 5.17-5.24 (m, 1H), 5.06-5.12 (m, 2H), 4.00-4.07 (m, 1H), 3.91-3.98 (m, 1H), 3.77-3.86 (m, 1H), 3.74 (s, 3H), 3.72 (s, 3H), 2.39 (d, J=1.0 Hz, 3H), 1.45 (d, J=7.0 Hz, 3H). LCMS-ESI (pos.) m/z: 575.9 (M+H)⁺.

Example 169.0. Preparation of (1S,2R)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or (1R,2S)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide

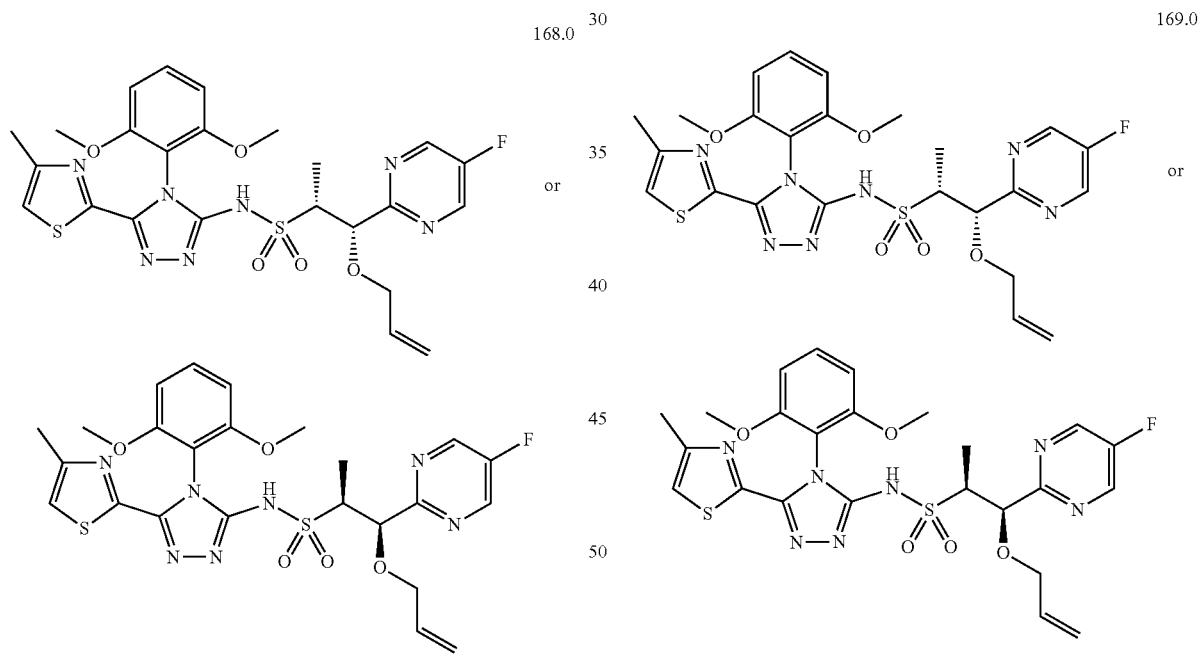

(1S,2R)-1-(Allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or (1R,2S)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide, Example 168.0. A mixture of 122.0 and 123.0 (76.5 mg, 0.14 mmol) was suspended in THF (4 mL) and treated with sodium hydride (60% dispersion in mineral oil, 25.7 mg, 0.64 mmol). After 5 min, a solution of allyl iodide in THF (1.0 M, 186 L, 0.19 mmol) was added via syringe. The resulting light yellow slurry was stirred at RT for 22 h and then more allyl iodide in THF (1.0 M, 36

(1S,2R)-1-(Allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide or (1R,2S)-1-(allyloxy)-N-(4-(2,6-dimethoxyphenyl)-5-(4-methylthiazol-2-yl)-4H-1,2,4-triazol-3-yl)-1-(5-fluoropyrimidin-2-yl)propane-2-sulfonamide, Example 169.0. Further elution under the conditions described in Example 168.0, provide the second eluting peak (2.0 mg). ¹H NMR (400 MHz, CDCl₃) δ 11.12 (br. s, 1H), 8.60 (s, 2H), 7.46 (t, J=8.5 Hz, 1H), 6.91 (d, J=1.0 Hz, 1H), 6.65 (dd, J=8.6, 1.6 Hz, 2H), 5.82 (ddt, J=17.2, 10.4, 5.8, 5.8 Hz, 1H), 5.21 (dq, J=17.2, 1.6 Hz, 1H), 5.05-5.12 (m, 2H), 4.00-4.08 (m, 1H), 3.91-

3.98 (m, 1H), 3.77-3.86 (m, 1H), 3.74 (s, 3H), 3.72 (s, 3H), 2.39 (d, J=1.0 Hz, 3H), 1.45 (d, J=7.0 Hz, 3H). LCMS-ESI (pos.) m/z: 575.9 (M+H)+.

The compounds set forth in the following table were synthesized following the procedure in Example 168.0 and 169.0 using the starting materials as described.

TABLE 9

| Example | Reagents | Structure, Name and Data |
|---|---|---|
| 166.0 | Methyl iodide was used instead of allyl iodide. Preparative SFC method: Column: 2 × 25 cm Chiralpak AD-H, 60 mL/min of 25% MeOH/CO$_2$, 100 bar, 220 nm, Inj vol.: 1.0 mL of a 4.0 mg/mL solution of sample in MeOH. | First eluting peak:<br>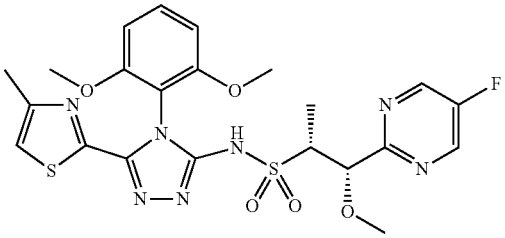<br>OR<br>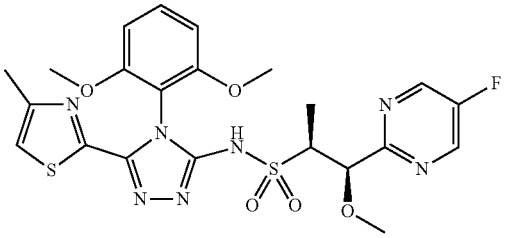<br>(1S,2R)-N-(4-(2,6-dimethoxyphenyl)-5-(4-methylthiazol-2-yl)-4H-1,2,4-triazol-3-yl)-1-(5-fluoropyrimidin-2-yl)-1-methoxypropane-2-sulfonamide or (1R,2S)-N-(4-(2,6-dimethoxyphenyl)-5-(4-methylthiazol-2-yl)-4H-1,2,4-triazol-3-yl)-1-(5-fluoropyrimidin-2-yl)-1-methoxypropane-2-sulfonamide.<br>$^1$H NMR (400 MHz, CDCl$_3$) δ 8.60 (s, 2H), 7.45 (t, J = 8.5 Hz, 1H), 6.90 (br. s, 1H), 6.65 (d, J = 8.6 Hz, 2H), 4.97 (d, J = 4.7 Hz, 1H), 3.73 (s, 3H), 3.71 (s, 3H), 3.32 (s, 3H), 2.91-3.08 (m, 1H), 2.39 (s, 3H), 1.38 (d, J = 6.5 Hz, 3H). LCMS-ESI (pos.) m/z: 550.1 (M + H)+. |
| 167.0 | | Second eluting peak:<br>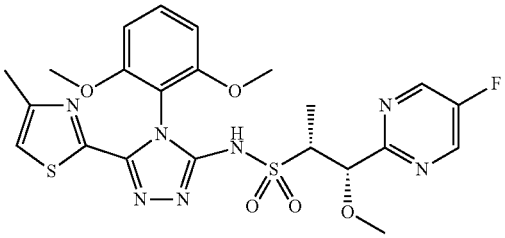<br>OR<br>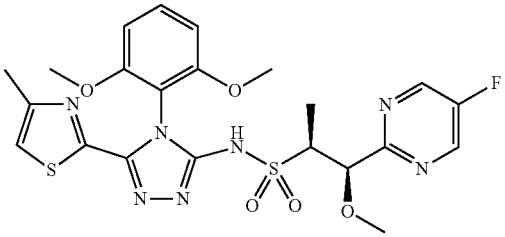<br>(1S,2R)-N-(4-(2,6-dimethoxyphenyl)-5-(4-methylthiazol-2-yl)-4H-1,2,4-triazol-3-yl)-1-(5-fluoropyrimidin-2-yl)-1-methoxypropane-2-sulfonamide or (1R,2S)-N-(4-(2,6-dimethoxyphenyl)-5-(4-methylthiazol-2-yl)-4H-1,2,4-triazol-3-yl)-1-(5-fluoropyrimidin-2-yl)-1-methoxypropane-2-sulfonamide.<br>$^1$H NMR (400 MHz, CDCl$_3$) δ 8.59 (s, 2H), 7.44 (t, J = 8.4 Hz, 1H), 6.87 (br. s, 1H), 6.65 (d, J = 8.6 Hz, 2H), 4.97 (br. s, 1H), 3.73 (s, 3H), 3.71 (s, 3H), 3.33 (s, 3H), 2.92-3.07 (m, 1H), 2.40 (s, 3H), 1.37 (d, J = 6.5 Hz, 3H). LCMS-ESI (pos.) m/z: 550.1 (M + H)+. |

Example 98.0. Preparation of (R)-3-cyclopentyl-N-(4-(2,6-dimethoxyphenyl)-5-(4-methylthiazol-2-yl)-4H-1,2,4-triazol-3-yl)-3-hydroxypropane-1-sulfonamide and (S)-3-cyclopentyl-N-(4-(2,6-dimethoxyphenyl)-5-(4-methylthiazol-2-yl)-4H-1,2,4-triazol-3-yl)-3-hydroxypropane-1-sulfonamide

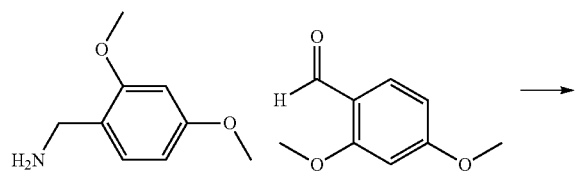

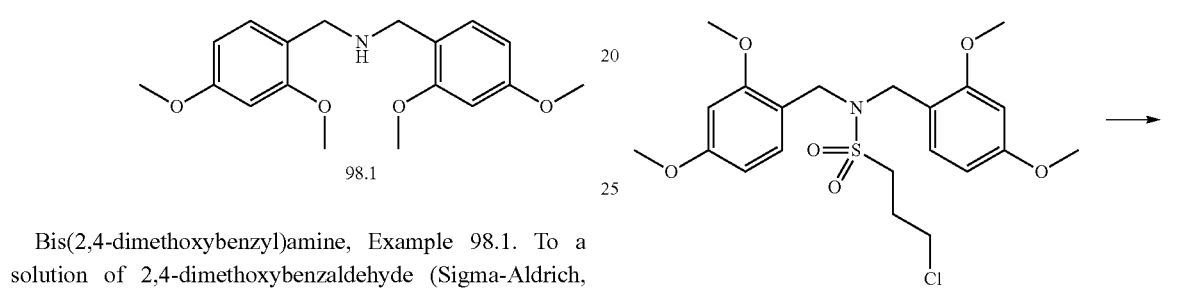

Bis(2,4-dimethoxybenzyl)amine, Example 98.1. To a solution of 2,4-dimethoxybenzaldehyde (Sigma-Aldrich, 5.00 g, 30.1 mmol) in MeOH (100 mL) was added 2,4-dimethoxybenzylamine (Sigma-Aldrich, 5.53 mL, 33.1 mmol). The resulting mixture was stirred at RT for 1 h and then sodium borohydride (1.30 g, 34.3 mmol) was added slowly. Gas evolution was observed. After stirring at RT overnight, the reaction was quenched with water and then partially concentrated to remove MeOH in vacuo. The residue was extracted with EtOAc (3×). The combined organic layers were washed with brine (1×), dried over anhydrous magnesium sulfate and concentrated in vacuo to afford 98.1 as a colorless oil. The product was used directly in the next step. LCMS-ESI (pos.) m/z: 318.2 (M+H)$^+$.

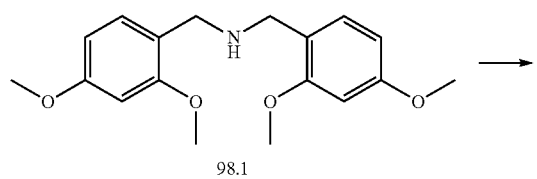

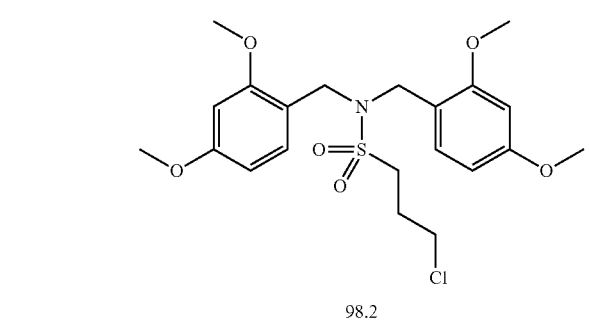

3-Chloro-N,N-bis(2,4-dimethoxybenzyl)propane-1-sulfonamide, Example 98.2. To an ice-cooled solution of 98.1 (2.32 g, 7.3 mmol) and TEA (3.06 mL, 21.9 mmol) in DCM (36.5 mL) was added 3-chloropropanesulfonyl chloride (Sigma-Aldrich, 978 µL, 8.0 mmol) dropwise via syringe. The reaction was warmed to RT and stirred until completion. The reaction mixture was quenched with brine and extracted with DCM (3×). The combined organic layers were washed with brine (1×), dried over anhydrous magnesium sulfate and concentrated in vacuo. The residue was purified by silica gel chromatography (eluent: 0-60% EtOAc in hexanes) to provide 98.2 (1.86 g, 56% yield). LCMS-ESI (pos.) m/z: 480.2 (M+Na)$^+$.

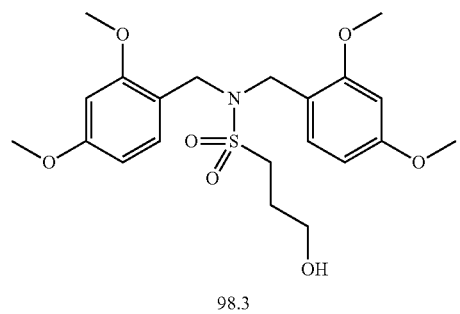

N,N-Bis(2,4-dimethoxybenzyl)-3-hydroxypropane-1-sulfonamide, Example 98.3. To a solution of 98.2 (2.55 g, 5.7 mmol) in DMF (10.2 mL) was added potassium acetate (1.20 g, 12.2 mmol). The reaction was heated at 100° C. and stirred until completion. The reaction mixture was cooled and partitioned between a 1:1 mixture of saturated aqueous sodium bicarbonate/brine and extracted with EtOAc (3×). The combined organic layers were washed with brine (1×), dried over anhydrous magnesium sulfate and concentrated. The residue was dissolved in THF (40 mL) and a 1.0 M aqueous solution of LiOH (12.2 mL, 12.2 mmol) was added via syringe. The reaction was stirred at RT until completion, as observed by LCMS, and was partially concentrated in vacuo to remove the THF. The residue was diluted with a 1:1 mixture of saturated aqueous sodium bicarbonate/brine and extracted with EtOAc (3×). The combined organic layers were washed with brine (1×), dried over anhydrous magnesium sulfate and concentrated in vacuo to afford 98.3 (2.15 g, 89% yield). The product was used directly in the next step. LCMS-ESI (pos.) m/z: 462.0 (M+Na)⁺.

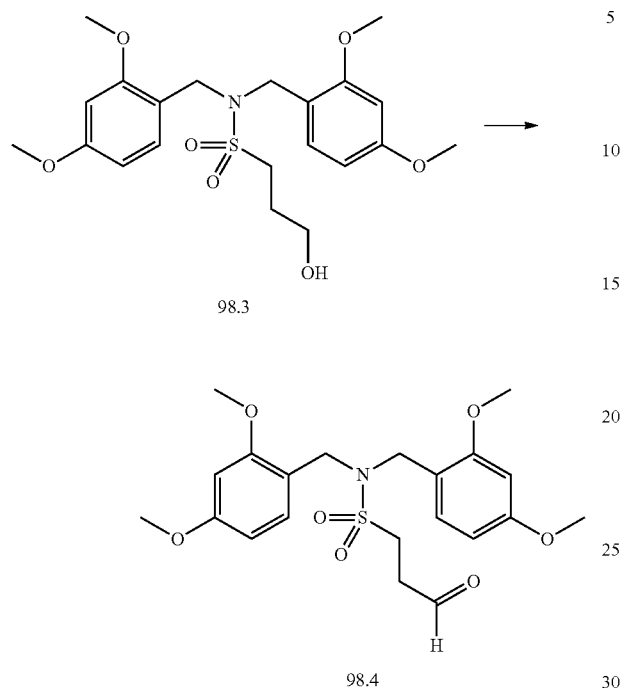

98.3

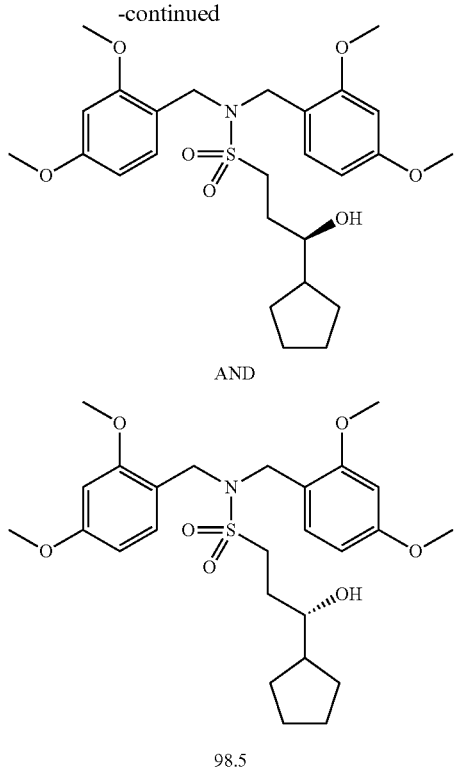

98.4

N,N-Bis(2,4-dimethoxybenzyl)-3-oxopropane-1-sulfonamide, Example 98.4. To an ice-cooled solution of 98.3 (2.15 g, 4.9 mmol) in DCM (49 mL) was added water (88 µL, 4.9 mmol) and Dess-Martin periodinane (2.70 g, 6.4 mmol). The reaction mixture was stirred at 0° C. overnight and then pyridine (1.2 mL, 14.7 mmol) was added via syringe followed by additional Dess-Martin periodinane (2.07 g, 4.9 mmol) directly. The reaction mixture was warmed to RT and sonicated until completion. The solids were filtered off, and the filtrate was partitioned between a 1:1 mixture of saturated aqueous sodium bicarbonate/brine and extracted with DCM (3×). The combined organic layers were washed with brine (1×), dried over anhydrous magnesium sulfate and concentrated. The residue was purified by silica gel chromatography (eluent: 25-75% EtOAc in hexanes) to provide 98.4 (970 mg, 45% yield). LCMS-ESI (pos.) m/z: 460.2 (M+Na)⁺.

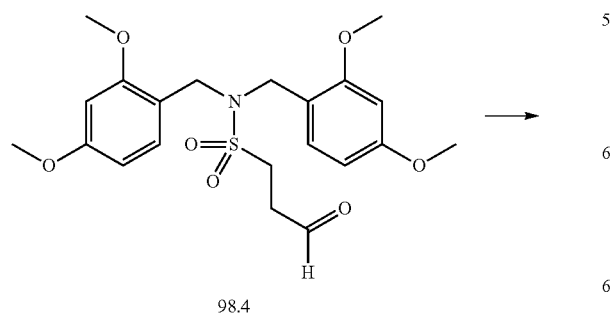

98.4

(R)-3-Cyclopentyl-N,N-bis(2,4-dimethoxybenzyl)-3-hydroxypropane-1-sulfonamide and (S)-3-cyclopentyl-N,N-bis(2,4-dimethoxybenzyl)-3-hydroxypropane-1-sulfonamide, Example 98.5. To a −78° C. solution of 98.4 (485 mg, 1.1 mmol) in THF (11 mL) was added cyclopentyl magnesium bromide (2.0 M solution in diethyl ether, 1.66 mL, 3.3 mmol) slowly via syringe. The reaction mixture was allowed to warm to RT over a 3 h period and then was quenched with 1.0 N HCl solution. A small amount of saturated aqueous ammonium chloride was added and the mixture was extracted with DCM (3×). The combined organic layers were dried over anhydrous magnesium sulfate and concentrated in vacuo. The residue was purified by silica gel chromatography (eluent: 25-75% EtOAc in hexanes) to provide 98.5 (172 mg, 31% yield) as a white solid. LCMS-ESI (pos.) m/z: 530.2 (M+H)⁺.

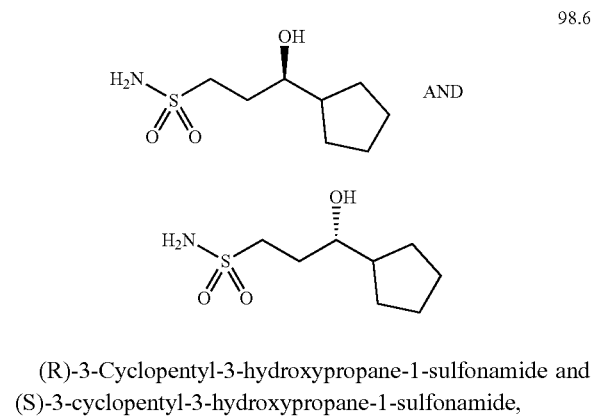

(R)-3-Cyclopentyl-3-hydroxypropane-1-sulfonamide and (S)-3-cyclopentyl-3-hydroxypropane-1-sulfonamide, Example 98.6. To a solution of 98.5 (170 mg, 0.34 mmol) in TFA (3.5 mL) was added anisole (109 μL, 1.0 mmol) via syringe. The reaction was stirred at RT until completion, as observed by LCMS analysis, and then was concentrated in vacuo. The residue was purified by silica gel chromatography (eluent: 0-100% EtOAc in hexanes) to provide 98.6 (27 mg, 39% yield) as a white solid. LCMS-ESI (pos.) m/z: 230.1 (M+Na)+.

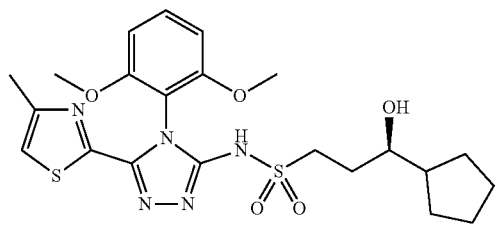

and

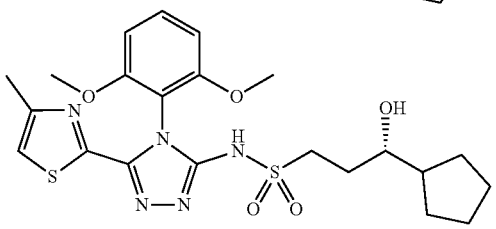

(R)-3-Cyclopentyl-N-(4-(2,6-dimethoxyphenyl)-5-(4-methylthiazol-2-yl)-4H-1,2,4-triazol-3-yl)-3-hydroxypropane-1-sulfonamide and (S)-3-cyclopentyl-N-(4-(2,6-dimethoxyphenyl)-5-(4-methylthiazol-2-yl)-4H-1,2,4-triazol-3-yl)-3-hydroxypropane-1-sulfonamide, Example 98.0. A microwave vial containing 399.0 (99 mg, 0.26 mmol), 98.6 (27 mg, 0.13 mmol), copper(I) iodide (20 mg, 0.10 mmol), trans-N,N-dimethyl-1,2-cyclohexanediamine (40 μL, 0.26 mmol) and cesium carbonate (170 mg, 0.52 mmol) was degassed and then backfilled with argon. Evacuation and backfilling were repeated three times. 1,4-Dioxane (1.3 mL) was added and the vial was capped and heated at 115° C. in the microwave for 3 h. The reaction was treated sequentially with brine, EtOAc and 10% aqueous ammonium hydroxide solution. The resulting mixture was stirred at RT for 30 min and then was filtered through Celite® brand filter aid. The layers were separated and the aqueous layer was extracted with EtOAc (3×). The combined organic layers were dried over anhydrous magnesium sulfate and concentrated in vacuo. The residue was purified by reverse phase preparatory HPLC (Sunfire 5 μM C18 column, eluent: 25-60% ACN in water over a 25 min period where both solvents contain 0.1% TFA) to provide 98.0 (6.9 mg, 10% yield) as an off-white sold. $^1$H NMR (400 MHz, CDCl$_3$) δ 11.00 (br. s, 1H), 7.46 (t, J=8.5 Hz, 1H), 6.91 (d, J=0.8 Hz, 1H), 6.66 (dd, J=8.6 Hz, 2H), 3.75 (s, 3H), 3.75 (s, 3H), 3.46-3.59 (m, 1H), 3.15-3.28 (m, 2H), 2.38 (d, J=0.8 Hz, 3H), 2.00-2.16 (m, 1H), 1.71-1.87 (m, 3H), 1.47-1.70 (m, 7H). LCMS-ESI (pos.) m/z: 508.1 (M+H)+.

Example 133.0. Preparation of N-(4-(5-bromo-2-methoxyphenyl)-5-(2-thiophenyl)-4H-1,2,4-triazol-3-yl)-2-(4-chlorophenyl)ethanesulfonamide

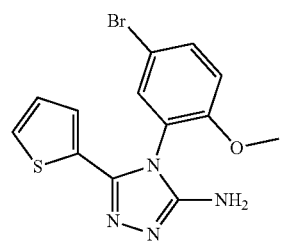

4-(2-Bromo-6-methoxyphenyl)-5-cyclopentyl-4H-1,2,4-triazol-3-amine, Example 133.01. Example 133.01 was prepared from 5-bromo-2-methoxyaniline instead of o-anisidine using procedures described in Example 234.03. LCMS-ESI (pos.), m/z: 350.9 (M+H)+.

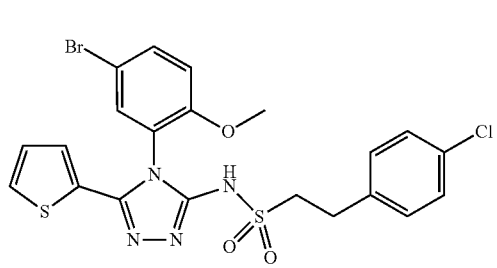

N-(4-(5-Bromo-2-methoxyphenyl)-5-(thiophen-2-yl)-4H-1,2,4-triazol-3-yl)-2-(4-chlorophenyl)ethanesulfonamide, Example 133.0. Example 133.0 was prepared from Example 133.01 using the procedure described in Example 236.0. $^1$H NMR (400 MHz, DMSO-d$_6$) δ 13.33 (s, 1H), 7.87 (d, J=2.5 Hz, 1H), 7.81 (dd, J=8.9, 2.6 Hz, 1H), 7.73 (dd, J=5.0, 1.1 Hz, 1H), 7.31-7.37 (m, 2H), 7.24-7.31 (m, 3H), 7.08 (dd, J=5.0, 3.8 Hz, 1H), 6.94 (dd, J=3.7, 1.2 Hz, 1H), 3.67-3.74 (m, 3H), 3.15-3.32 (m, 2H), 2.86-3.00 (m, 2H). LCMS-ESI (pos.), m/z: 552.8 (M+H)+.

Example 134.0. Preparation of (1R,2S)-N-(4-(2,6-dimethoxyphenyl)-5-(1-ethyl-1H-pyrazol-3-yl)-4H-1,2,4-triazol-3-yl)-1-(5-fluoro-2-pyrimidinyl)-1-methoxy-2-propanesulfonamide

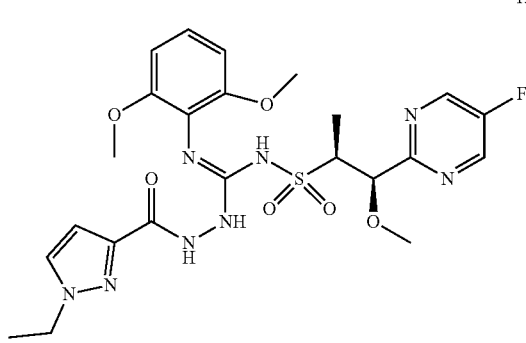

(Z)-N'-(2,6-Dimethoxyphenyl)-2-(1-ethyl-1H-pyrazole-3-carbonyl)-N-(((1R,2S)-1-(5-fluoropyrimidin-2-yl)-1-methoxypropan-2-yl)sulfonyl)hydrazinecarboximidamide, Example 134.1. To a solution of (1R,2S)-1-(5-fluoropyrimidin-2-yl)-1-methoxypropane-2-sulfonamide (63.9 mg, 0.231 mmol, Example 466.2 and ACN (3 mL) was added 2-isothiocyanato-1,3-dimethoxybenzene (Example 465.0) (49 mg, 0.251 mmol) and cesium carbonate (100 mg, 0.307 mmol). The reaction was stirred at RT. After 16 h, the reaction was cooled in an ice bath and then treated with 1-ethyl-1H-pyrazole-3-carbohydrazide (37.4 mg, 0.231 mmol, ChemBridge Corporation) and silver nitrate (78 mg, 0.461 mmol). After 45 min, the reaction was diluted with brine (10 mL) and CHCl₃ (10 mL). The reaction was stirred for 30 min and then filtered through a pad of Celite® brand filter aid. The pad was rinsed with CHCl₃:IPA (9:1, 2×20 mL). The filtrate was partitioned, and the organic layer was washed with brine (20 mL). The organic layers were dried over MgSO₄ and concentrated in vacuo to give the title compound as an off-white solid. The material was carried on without any further purification. LC-MS ESI (pos.) m/z=565.3 [M+H]⁺.

134.0

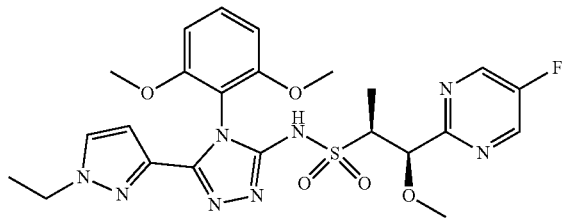

(1R,2S)-N-(4-(2,6-Dimethoxyphenyl)-5-(1-ethyl-1H-pyrazol-3-yl)-4H-1,2,4-triazol-3-yl)-1-(5-fluoro-2-pyrimidinyl)-1-methoxy-2-propanesulfonamide, Example 134.0. To a solution of Example 134.1 (130 mg, 0.230 mmol) and ACN (5 mL) was added methanesulfonic acid (0.05 mL, 0.771 mmol). The reaction was heated at 60° C. for 3 d and then cooled to RT and diluted with DCM (20 mL). The organic layers were washed with water and concentrated in vacuo. The product was adsorbed onto a plug of silica gel and chromatographed through a Redi-Sep® pre-packed silica gel column (40 g), eluting with 0-40% EtOAc:EtOH (3:1) in heptanes. The desired fractions were concentrated in vacuo, and the resulting white solid was suspended in heptanes (10 mL). The solids were filtered, washed with heptanes (5 mL), and dried in the funnel to provide the title compound (26.4 mg, 0.048 mmol, 21% yield) as a white solid. ¹H NMR (300 MHz, CDCl₃) δ: 10.98 (br. s, 1H), 8.62 (s, 2H), 7.42 (t, J=8.3 Hz, 1H), 7.27 (d, J=2.3 Hz, 1H), 6.64 (d, J=8.6 Hz, 2H), 5.99 (d, J=2.3 Hz, 1H), 4.99 (d, J=5.1 Hz, 1H), 4.12 (q, J=7.3 Hz, 2H), 3.69-3.79 (m, 7H), 3.35 (s, 3H), 1.37-1.43 (m, 6H). LC-MS ESI (pos.) m/z=547.2 [M+H]⁺.

Example 135.0. Preparation of (1R,2S)-N-(4-(2,6-dimethoxyphenyl)-5-(1-methyl-1H-pyrazol-3-yl)-4H-1,2,4-triazol-3-yl)-1-ethoxy-1-(5-fluoro-2-pyrimidinyl)-2-propanesulfonamide 135.0

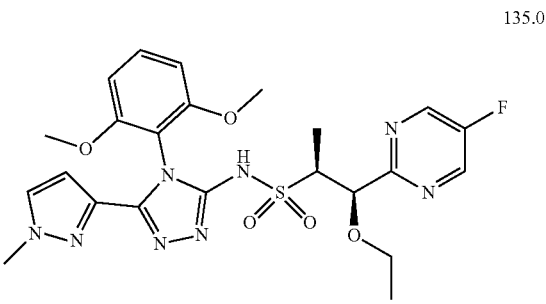 [SMILES: CCO[C@H](c1ncc(F)cn1)[C@H](C)S(=O)(=O)Nc1nnc(-c2ccn(C)n2)n1-c1c(OC)cccc1OC]

(1R,2S)-N-(4-(2,6-Dimethoxyphenyl)-5-(1-methyl-1H-pyrazol-3-yl)-4H-1,2,4-triazol-3-yl)-1-ethoxy-1-(5-fluoro-2-pyrimidinyl)-2-propanesulfonamide, Example 135.0. To a Chemglass 20 mL vial with pressure relief cap was added (1R,2S)-1-ethoxy-1-(5-fluoropyrimidin-2-yl)propane-2-sulfonamide (81 mg, 0.308 mmol, Example 466.5), 3-bromo-4-(2,6-dimethoxyphenyl)-5-(1-methyl-H-pyrazol-3-yl)-4H-1,2,4-triazole (150.1 mg, 0.412 mmol, Example 399.5), cesium carbonate (251 mg, 0.769 mmol), copper (I) iodide (37.4 mg, 0.196 mmol), and 1,4-dioxane (3 mL). The suspension was treated with trans-N,N'-dimethylcyclohexane-1,2-diamine (0.097 mL, 0.615 mmol) and was then sparged with Ar for 10 min. The suspension was then stirred at 80° C. for 20 h. LC-MS suggested about 80% conversion. The reaction was continued at the same temperature for a further 3 d. The reaction was then cooled to RT and filtered through a plug of Celite® brand filter aid and the plug was rinsed with CHCl₃:IPA (9:1, 3×12 mL). The filtrate was concentrated in vacuo and purified by reverse-phase preparative HPLC on a Phenomenex Luna column (5 micron, Phenyl-hexyl, 100 Å, 100×30 mm) eluting at 45 mL/min with a linear gradient of 30% to 60% ACN (0.1% TFA) in water (0.1% TFA) over 20 min to afford the title compound (36.7 mg, 0.067 mmol, 22% yield) as a white solid after lyopholization. ¹H NMR (300 MHz, CDCl₃) δ: 8.62 (s, 2H), 7.43 (t, J=8.5 Hz, 1H), 7.24 (d, J=2.3 Hz, 1H), 6.65 (d, J=8.7 Hz, 2H), 5.90 (d, J=2.3 Hz, 1H), 5.01 (d, J=6.1 Hz, 1H), 3.88 (s, 3H), 3.72-3.82 (m, 7H), 3.46-3.56 (m, 2H), 1.45 (d, J=7.0 Hz, 3H), 1.15 (t, J=7.0 Hz, 3H). LC-MS ESI (pos.) m/z=547.2 [M+H]⁺.

The compounds set forth in the following table were synthesized following the procedure in Example 350.1 using the known starting material as described.

TABLE 10

| Example | Reagents | Structure, Name and Data |
|---|---|---|
| 174.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and 1-(difluoromethyl)-1H-pyrazole-3-carbohydrazide (Princeton BioMolecular Research, Inc.). | 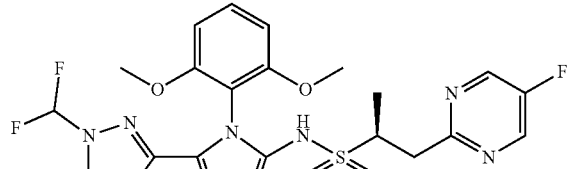<br>AND<br>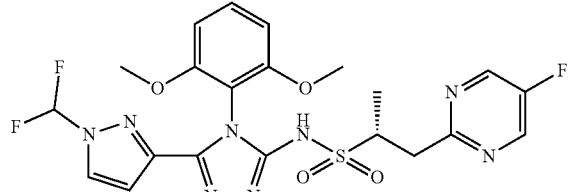<br>(2S)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide and (2R)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide.<br>LCMS-ESI (pos.) m/z: 539.2 (M + H)$^+$. |
| 175.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and oxazole-2-carboxylic acid hydrazide (J & W PharmLab, LLC). | 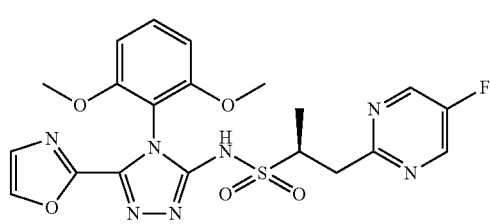<br>AND<br>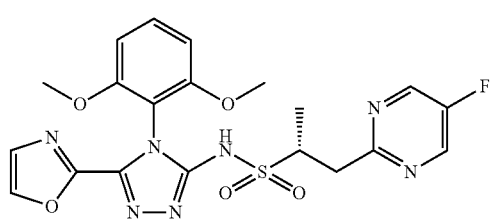<br>(2S)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide and (2R)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide.<br>LCMS-ESI (pos.) m/z: 489.8 (M + H)$^+$. |
| 176.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and 3-methyl-1H-pyrazole-5-carbohydrazide (Maybridge Chemical Co., Ltd.). | 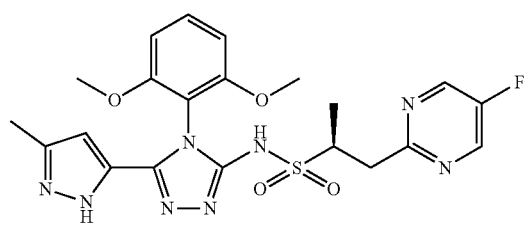<br>AND |

| Example | Reagents | Structure, Name and Data |
|---|---|---|
| | | 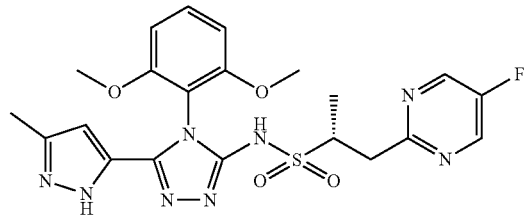<br>(S)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide and (R)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide.<br>LCMS-ESI (pos.) m/z: 502.7 (M + H)$^+$. |
| 177.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and 6-methoxypyrazine-2-carbohydrazide (Example 395.24) | 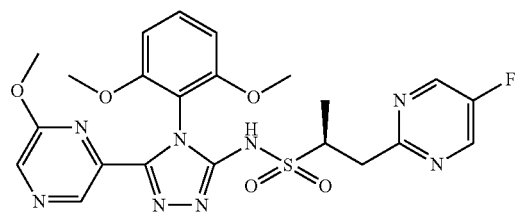<br>AND<br>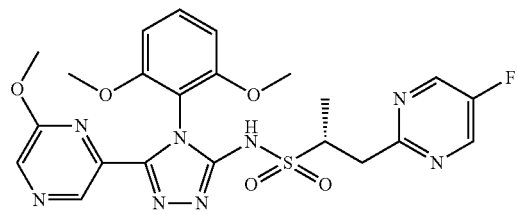<br>(2S)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide and (2R)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide.<br>LCMS-ESI (pos.) m/z: 530.8 (M + H)$^+$. |
| 178.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and 2-methyloxazole-4-carbohydrazide (Frontier Scientific Services). | 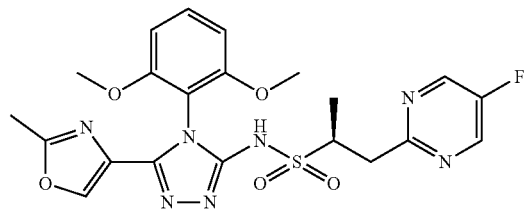<br>AND<br>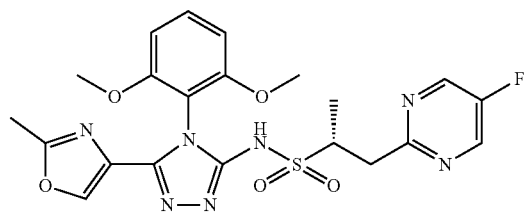<br>(2S)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide and (2R)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide.<br>LCMS-ESI (pos.) m/z: 503.8 (M + H)$^+$ |

TABLE 10-continued

| Example | Reagents | Structure, Name and Data |
|---|---|---|
| 179.0 | The racemic compound (Example 174.0) was separated by SFC (2 × 15 cm IA column with 70 mL/min 15% MeOH/CO$_2$. Outlet pressure = 100 bar; wavelength = 220 nm; injection volume = 1 mL, 5 mg/mL MeOH). Two enantiomers were obtained. This was the first isomer to elute under these conditions. | 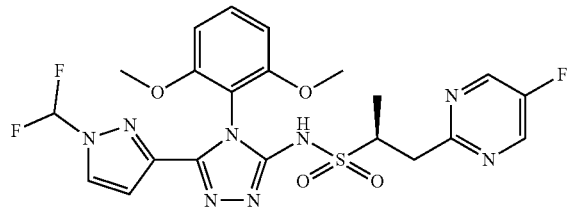<br>OR<br>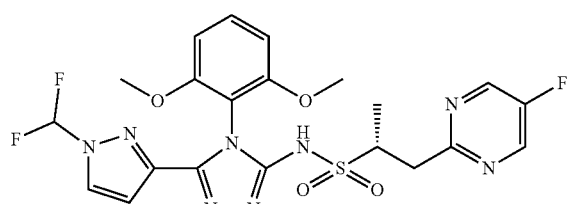<br>(2S)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide or (2R)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide.<br>$^1$H NMR (400 MHz, CDCl$_3$) δ 11.17 (br. s, 1H), 8.53 (s, 2H), 7.74 (d, J = 2.74 Hz, 1H), 7.42 (t, J = 8.51 Hz, 1H), 6.78-7.20 (m, 1 H), 6.63 (dd, J = 8.61, 1.76 Hz, 2H), 6.42 (d, J = 2.54 Hz, 1H), 3.77-3.85 (m, 1 H), 3.74 (s, 3 H), 3.72 (s, 3 H), 3.68 (d, J = 3.52 Hz, 1 H), 3.09 (dd, J = 14.77, 9.88 Hz, 1 H), 1.32 (d, J = 6.85 Hz, 3 H). LCMS-ESI (pos.) m/z: 539.2 (M + H)$^+$. |
| 180.0 | The racemic compound (Example 174.0) was separated by SFC (2 × 15 cm IA column with 70 mL/min 15% MeOH/CO$_2$. Outlet pressure = 100 bar; wavelength = 220 nm; injection volume = 1 mL, 5 mg/mL MeOH). Two enantiomers were obtained. This was the second isomer to elute under these conditions. | 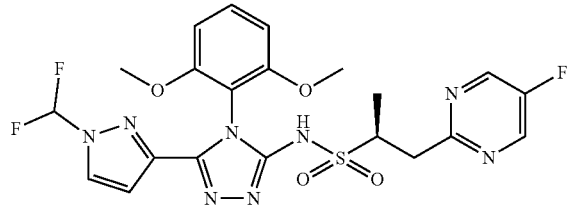<br>OR<br>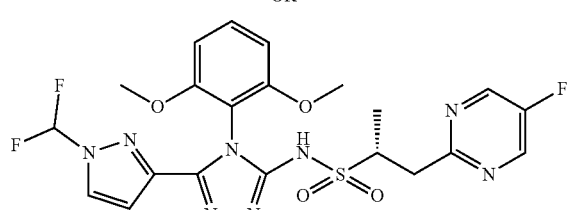<br>(2S)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide or (2R)-N-(5-(1-(difluoromethyl)-1H-pyrazol-3-yl)-4-(2,6-dimethoxyphenyl)-4H-1,2,4-triazol-3-yl)-1-(5-fluoro-2-pyrimidinyl)-2-propanesulfonamide.<br>$^1$H NMR (400 MHz, CDCl$_3$) δ 11.17 (br. s, 1H), 8.53 (s, 2 H), 7.74 (d, J = 2.74 Hz, 1H), 7.42 (t, J = 8.41 Hz, 1H), 6.84-7.18 (m, 1H), 6.63 (dd, J = 8.61, 1.76 Hz, 2 H), 6.42 (d, J = 2.54 Hz, 1H), 3.77-3.86 (m, 1 H), 3.74 (s, 3H), 3.72 (s, 3H), 3.68 (br. s, 1 H), 3.09 (dd, J = 14.77, 9.88 Hz, 1 H), 1.31 (d, J = 6.85 Hz, 3 H). LCMS-ESI (pos.) m/z: 539.2 (M + H)$^+$. |

TABLE 10-continued

| Example | Reagents | Structure, Name and Data |
|---|---|---|
| 181.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and 2-methyl-2H-1,2,3-triazole-4-carbohydrazide (Example 395.25). | 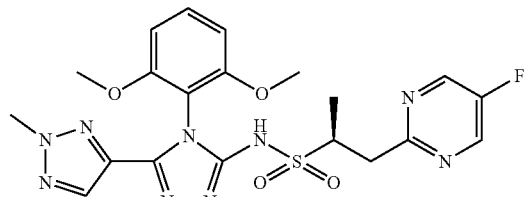<br>AND<br>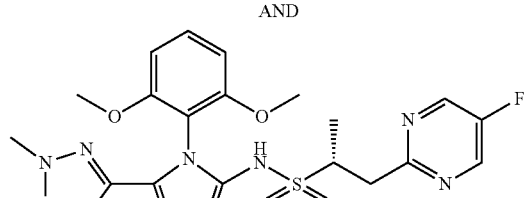<br>(2S)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide and (2R)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide.<br>LCMS-ESI (pos.) m/z: 503.8 (M + H)⁺. |
| 182.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and pyrazine-2-carbohydrazide (Frontier Scientific Services). | 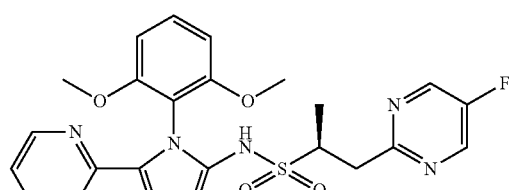<br>AND<br>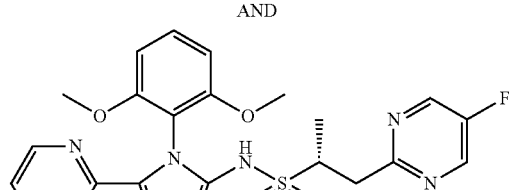<br>(2S)-N-(4-(2,6-dimethoxyphenyl)-5-(2-pyrazinyl)-4H-1,2,4-triazol-3-yl)-1-(5-fluoro-2-pyrimidinyl)-2-propanesulfonamide and (2R)-N-(4-(2,6-dimethoxyphenyl)-5-(2-pyrazinyl)-4H-1,2,4-triazol-3-yl)-1-(5-fluoro-2-pyrimidinyl)-2-propanesulfonamide.<br>¹H NMR (500 MHz, CDCl₃) δ 9.06 (d, J = 1.22 Hz, 1H), 8.56 (s, 3H), 8.36 (dd, J = 1.71, 2.45 Hz, 1H), 8.05 (s, 1H), 7.40 (t, J = 8.56 Hz, 1H), 6.62 (dd, J = 1.96, 8.56 Hz, 2H), 3.80-3.89 (m, 2H), 3.74 (s, 3H), 3.72 (s, 3H), 3.13 (dd, J = 9.66, 14.79 Hz, 1H), 1.35 (d, J = 6.85 Hz, 3H). LCMS-ESI (pos.) m/z: 500.8 (M + H)⁺. |
| 183.0 | The racemic compound (Example 175.0) was separated by SFC (2 × 15 cm IA column with 60 mL/min 22% MeOH/CO₂. Outlet pressure = 100 bar; wavelength = 220 nm; injection volume = 1 mL, 4 mg/mL 1:1 DCM:MeOH). Two enantiomers were obtained. This the first isomer to elute under these conditions. | 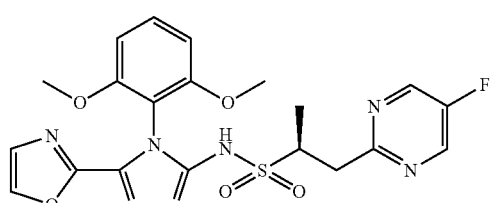<br>OR |

TABLE 10-continued

| Example | Reagents | Structure, Name and Data |
|---|---|---|
| | | 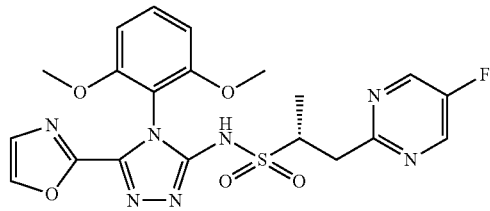<br>(2S)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide or (2R)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide.<br>$^1$H NMR (400 MHz, CDCl$_3$) δ 8.53 (s, 2H), 7.69 (d, J = 0.78 Hz, 1H), 7.44 (t, J = 8.51 Hz, 1H), 7.15 (s, 1H), 6.66 (dd, J = 8.61, 1.57 Hz, 2H), 3.79-3.85 (m, 1H), 3.76 (s, 3H), 3.73 (s, 3H), 3.69 (dd, J = 14.87, 4.70 Hz, 1H), 3.05-3.15 (m, 1H), 1.32 (d, J = 6.85 Hz, 3H).<br>LCMS-ESI (pos.) m/z: 489.8 (M + H)$^+$. |
| 184.0 | The racemic compound (Example 175.0) was separated by SFC (2 × 15 cm IA column with 60 mL/min 22% MeOH/CO$_2$. Outlet pressure = 100 bar; wavelength = 220 nm; injection volume = 1 mL, 4 mg/mL 1:1 DCM:MeOH). Two enantiomers were obtained. This was the second isomer to elute under these conditions. | 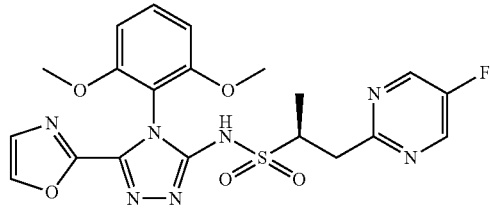<br>OR<br>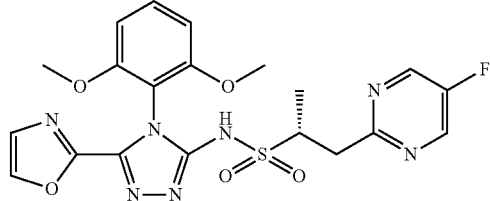<br>(2S)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide or (2R)-N-(4-(2,6-dimethoxyphenyl)-5-(1,3-oxazol-2-yl)-4H-1,2,4-triazol-3-yl)-1-(5-fluoro-2-pyrimidinyl)-2-propanesulfonamide.<br>$^1$H NMR (400 MHz, CDCl$_3$) δ 8.54 (s, 2 H), 7.69 (d, J = 0.78 Hz, 1 H), 7.44 (t, J = 8.51 Hz, 1 H), 7.16 (s, 1 H), 6.66 (dd, J = 8.51, 1.47 Hz, 2 H), 3.82 (ddd, J = 9.68, 6.75, 4.69 Hz, 1 H), 3.76 (s, 3 H), 3.74 (s, 3H), 3.69 (dd, J = 15.16, 4.60 Hz, 1H), 3.10 (dd, J = 14.87, 9.59 Hz, 1H), 1.33 (d, J = 6.85 Hz, 3H).<br>LCMS-ESI (pos.) m/z: 489.8 (M + H)$^+$. |
| 185.0 | The racemic compound (Example 176.0) was separated by SFC (2 × 15 cm IA column with 60 mL/min 22% MeOH/CO$_2$. Outlet pressure = 100 bar; wavelength = 220 nm; injection volume = 0.5 mL, 4 mg/mL MeOH). Two enantiomers were obtained. This was the first isomer to elute under these conditions. | 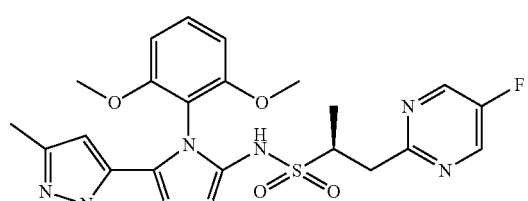<br>OR |

TABLE 10-continued

| Example | Reagents | Structure, Name and Data |
|---|---|---|
| | | 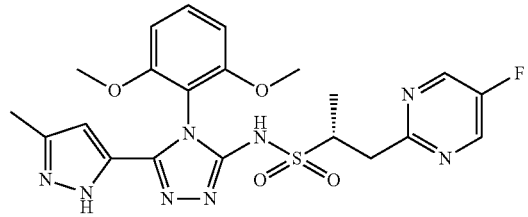<br>(S)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide or (R)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide.<br>$^1$H NMR (400 MHz, CDCl$_3$) δ 8.53 (s, 2H), 7.44 (t, J = 8.51 Hz, 1H), 6.66 (dd, J = 8.41, 2.15 Hz, 2H), 5.77 (s, 1H), 3.82 (ddd, J = 9.88, 6.75, 4.30 Hz, 1 H), 3.75 (s, 3H), 3.73 (s, 3H), 3.69 (d, J = 4.30 Hz, 1H), 3.12 (dd, J = 14.67, 9.98 Hz, 1H), 2.22 (s, 3 H), 1.31 (d, J = 6.65 Hz, 3H). LCMS-ESI (pos.) m/z: 502.7 (M + H)$^+$. |
| 186.0 | The racemic compound (Example 176.0) was separated by SFC (2 × 15 cm IA column with 60 mL/min 22% MeOH/CO$_2$. Outlet pressure = 100 bar; wavelength = 220 nm; injection volume = 0.5 mL, 4 mg/mL MeOH). Two enantiomers were obtained. This was the second isomer to elute under these conditions. | 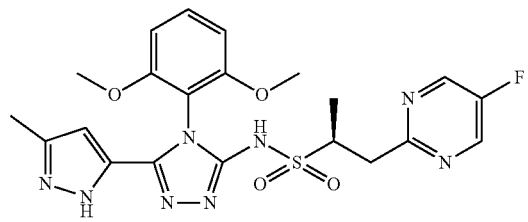<br>OR<br>(S)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide or (R)-N-(4-(2,6-dimethoxyphenyl)-5-(3-methyl-1H-pyrazol-5-yl)-4H-1,2,4-triazol-3-yl)-1-(5-fluoropyrimidin-2-yl)propane-2-sulfonamide.<br>$^1$H NMR (400 MHz, CDCl$_3$) δ 8.55 (s, 2H), 7.46 (t, J = 8.51 Hz, 1H), 6.68 (dd, J = 8.51, 2.25 Hz, 2H), 5.81 (s, 1H), 3.80-3.87 (m, 1H), 3.77 (s, 3H), 3.75 (s, 3H), 3.71 (d, J = 3.91 Hz, 1H), 3.14 (dd, J = 14.77, 9.88 Hz, 1H), 2.25 (s, 3H), 1.33 (d, J = 6.85 Hz, 3H). LCMS-ESI (pos.) m/z: 502.7 (M + H)$^+$. |
| 187.0 | (S)-1-(5-fluoropyrimidin-2-yl)propane-2-sulfonamide and (R)-1-(5-fluoropyrimidin-2-yl)propane-2-sulfonamide (Example 402.0), 2-isothiocyanato-1,3-dimethoxybenzene (Example 465.0), and oxazole-4-carbohydrazide (Frontier Scientific Services). | 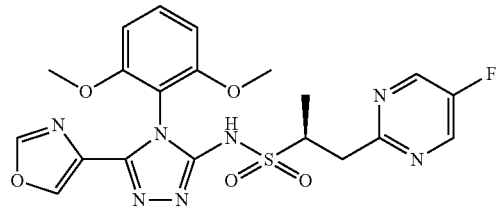<br>AND |

TABLE 10-continued

| Example | Reagents | Structure, Name and Data |
|---|---|---|
| | | 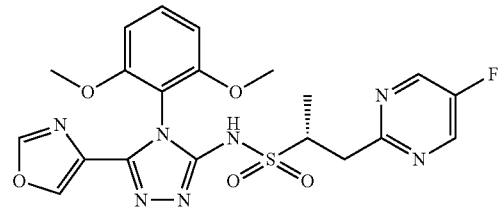<br>(2S)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide and (2R)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide.<br>LCMS-ESI (pos.) m/z: 490.1 (M + H)$^+$. |
| 188.0 | The racemic compound (Example 177.0) was separated by SFC (2 × 15 cm IA column with 65 mL/min 25% MeOH (0.1% NH$_4$OH)/CO$_2$. Outlet pressure = 100 bar; wavelength = 220 nm; injection volume = 0.75 mL, 6 mg/mL MeOH). Two enantiomers were obtained. This was the second isomer to elute under these conditions. | 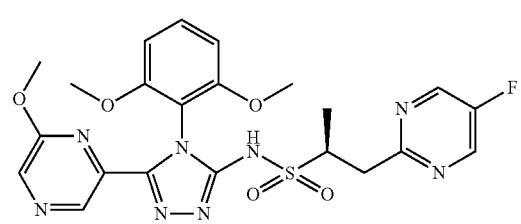<br>OR<br>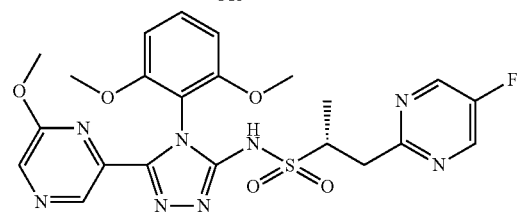<br>(2S)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide or (2R)-N-(4-(2,6-dimethoxyphenyl)-5-(6-methoxy-2-pyrazinyl)-4H-1,2,4-triazol-3-yl)-1-(5-fluoro-2-pyrimidinyl)-2-propanesulfonamide.<br>$^1$H NMR (400 MHz, CDCl$_3$) δ 8.78 (s, 1H), 8.53 (s, 2H), 8.18 (s, 1H), 7.34 (t, J = 8.51 Hz, 1H), 6.61 (dd, J = 8.51, 1.47 Hz, 2H), 3.81 (ddd, J = 9.88, 6.85, 4.40 Hz, 1H), 3.73 (s, 3 H), 3.71 (s, 3 H), 3.68 (d, J = 4.89 Hz, 1 H), 3.27 (s, 3H), 3.09 (dd, J = 14.67, 9.98 Hz, 1H), 1.32 (d, J = 6.85 Hz, 3H). LCMS-ESI (pos.) m/z: 530.8 (M + H)$^+$. |
| 189.0 | The racemic compound (Example 178.0) was separated by SFC (2 × 15 cm IA column with 60 mL/min 25% 2:1 ACN:IPA (0.1% NH$_4$OH)/CO$_2$. Outlet pressure = 100 bar; wavelength = 220 nm; injection volume = 0.4 mL, 4 mg/mL 1:3 DCM:MeOH). Two enantiomers were obtained. This was the first isomer to elute under these conditions. | 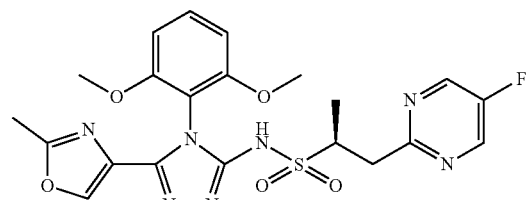<br>OR<br>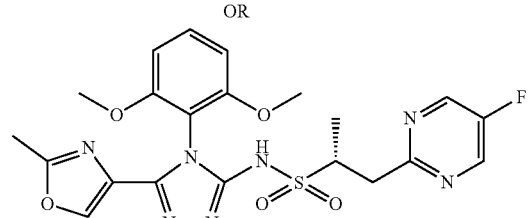<br>(2S)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide or (2R)-N-(4- |

| Example | Reagents | Structure, Name and Data |
|---|---|---|
| | | (2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide.<br>$^1$H NMR (400 MHz, CDCl$_3$) δ 11.18 (br. s, 1H), 8.53 (s, 2H), 7.48 (t, J = 8.51 Hz, 1H), 6.84 (s, 1H), 6.69 (dd, J = 8.51, 2.05 Hz, 2H), 3.78-3.86 (m, 1H), 3.77 (s, 3H), 3.75 (s, 3H), 3.63-3.71 (m, 1H), 3.08 (dd, J = 14.67, 9.78 Hz, 1H), 2.46 (s, 3H), 1.30 (d, J = 6.65 Hz, 3H). LCMS-ESI (pos.) m/z: 503.8 (M + H)$^+$. |
| 190.0 | The racemic compound (Example 178.0) was separated by SFC (2 × 15 cm IA column with 60 mL/min 25% 2:1 ACN:IPA (0.1% NH$_4$OH)/CO$_2$. Outlet pressure = 100 bar; wavelength = 220 nm; injection volume = 0.4 mL, 4 mg/mL 1:3 DCM:MeOH). Two enantiomers were obtained. This was the second isomer to elute under these conditions. | 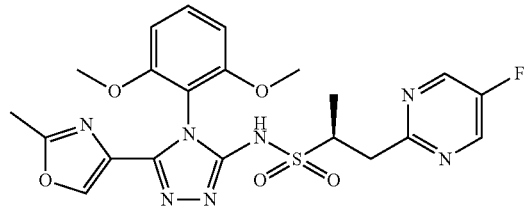<br>OR<br>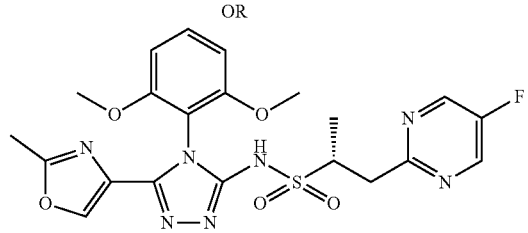<br>(2S)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide or (2R)-N-(4-(2,6-dimethoxyphenyl)-5-(2-methyl-1,3-oxazol-4-yl)-4H-1,2,4-triazol-3-yl)-1-(5-fluoro-2-pyrimidinyl)-2-propanesulfonamide.<br>$^1$H NMR (400 MHz, CDCl$_3$) δ 11.19 (br. s, 1H), 8.53 (s, 2H), 7.48 (t, J = 8.51 Hz, 1H), 6.84 (s, 1H), 6.69 (dd, J = 8.61, 2.15 Hz, 2H), 3.80 (m, J = 2.93 Hz, 1H), 3.77 (s, 3H), 3.75 (s, 3H), 3.63-3.71 (m, 1H), 3.07 (dd, J = 14.67, 9.78 Hz, 1H), 2.46 (s, 3H), 1.29 (d, J = 6.85 Hz, 3H). LCMS-ESI (pos.) m/z: 503.8 (M + H)$^+$. |
| 192.0 | The racemic compound (Example 181.0) was separated by SFC (2 × 15 cm IA column with 60 mL/min 25% MeOH/CO$_2$. Outlet pressure = 100 bar; wavelength = 220 nm; injection volume = 0.5 mL, 5 mg/mL 1:1 DCM:MeOH). Two enantiomers were obtained. This was the first isomer to elute under these conditions. | 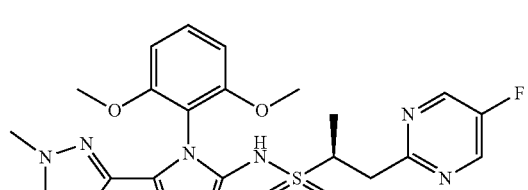<br>OR<br>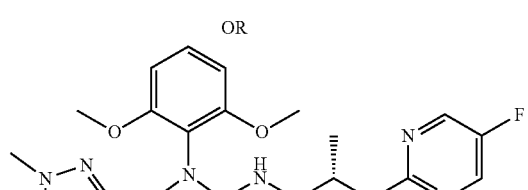<br>(2S)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide or (2R)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide.<br>$^1$H NMR (400 MHz, CDCl$_3$) δ 8.53 (s, 2H), 7.44 (t, J = 8.61 Hz, 1H), 7.22 (s, 1H), 6.66 (dd, J = 8.51, 1.47 Hz, 2H), 4.16 (s, 3H), 3.81 (ddd, J = 9.88, 6.75, 4.50 Hz, 1H), 3.75 (s, 3H), 3.73 (s, 3H), 3.69 (dd, J = 15.36, |

TABLE 10-continued

| Example | Reagents | Structure, Name and Data |
|---|---|---|
| | | 4.21 Hz, 1H), 3.09 (dd, J = 14.77, 9.88 Hz, 1H), 1.31 (d, J = 6.85 Hz, 3H). LCMS-ESI (pos.) m/z: 503.8 (M + H)⁺. |
| 193.0 | The racemic compound (Example 181.0) was separated by SFC (2 × 15 cm IA column with 60 mL/min 25% MeOH/CO₂. Outlet pressure = 100 bar; wavelength = 220 nm; injection volume = 0.5 mL, 5 mg/mL 1:1 DCM:MeOH). Two enantiomers were obtained. This was the second isomer to elute under these conditions. | 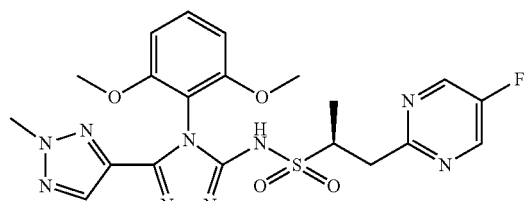<br>OR<br>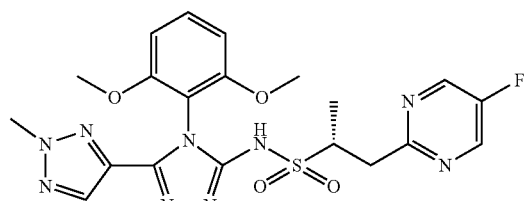<br>(2S)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide or (2R)-N-(4-(2,6-dimethoxyphenyl)-5-(2-methyl-2H-1,2,3-triazol-4-yl)-4H-1,2,4-triazol-3-yl)-1-(5-fluoro-2-pyrimidinyl)-2-propanesulfonamide.<br>¹H NMR (400 MHz, CDCl₃) δ 8.53 (s, 2H), 7.44 (t, J = 8.51 Hz, 1H), 7.22 (s, 1H), 6.66 (dd, J = 8.41, 1.56 Hz, 2H), 4.16 (s, 3H), 3.81 (ddd, J = 9.83, 6.80, 4.50 Hz, 1H), 3.75 (s, 3H), 3.73 (s, 3H), 3.69 (dd, J = 15.16, 4.21 Hz, 1H), 3.09 (dd, J = 14.77, 9.88 Hz, 1H), 1.31 (d, J = 6.65 Hz, 3H). LCMS-ESI (pos.) m/z: 503.8 (M + H)⁺. |
| 195.0 | The racemic compound (Example 187.0) was separated by SFC (400 × 21 mm IA column on Thar 80 with 14 g/min MeOH + 41 g/min CO₂, 26% co-solvent at 55 g/min. Temperature = 21° C.; outlet pressure = 100 bar; wavelength = 251 nm; injection volume = 0.30 mL of 38 mg sample dissolved in 5 mL of MeOH:DCM 1:1). Two enantiomers were obtained. This was the first isomer to elute under these conditions. | 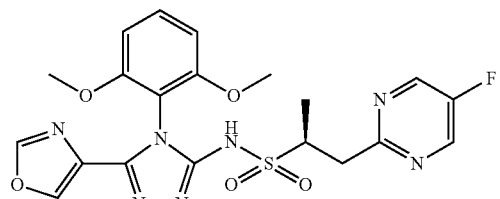<br>OR<br>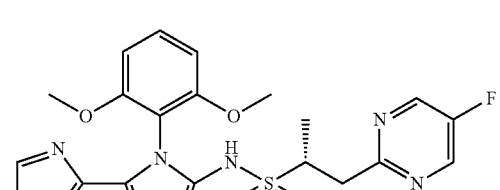<br>(2S)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide or (2R)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide.<br>¹H NMR (400 MHz, CDCl₃) δ 11.16 (br. s, 1 H), 8.53 (s, 2H), 7.89 (d, J = 0.78 Hz, 1H), 7.48 (t, J = 8.51 Hz, 1H), 7.20 (d, J = 0.78 Hz, 1H), 6.69 (dd, J = 8.61, 1.96 Hz, 2H), 3.82 (m, J = 6.99, 2.08, 2.08 Hz, 1H), 3.78 (s, 3H), 3.76 (s, 3H), 3.69 (dd, J = 14.09, 4.30 Hz, 1H), 3.08 (dd, J = 14.67, 9.78 Hz, 1H), 1.31 (d, J = 6.65 Hz, 3H). LCMS-ESI (pos.) m/z: 490.1 (M + H)⁺. |

TABLE 10-continued

| Example | Reagents | Structure, Name and Data |
|---|---|---|
| 196.0 | The racemic compound (Example 187.0) was separated by SFC (400 × 21 mm IA column on Thar 80 with 14 g/min MeOH + 41 g/min $CO_2$, 26% co-solvent at 55 g/min. Temperature = 21° C.; outlet pressure = 100 bar; wavelength = 251 nm; injection volume = 0.30 mL of 38 mg sample dissolved in 5 mL of MeOH:DCM 1:1). Two enantiomers were obtained. This was the second isomer to elute under these conditions. | (2S)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide or (2R)-N-(4-(2,6-dimethoxyphenyl)-5-(1,3-oxazol-4-yl)-4H-1,2,4-triazol-3-yl)-1-(5-fluoro-2-pyrimidinyl)-2-propanesulfonamide.<br><br>$^1$H NMR (400 MHz, CDCl$_3$) δ 11.16 (br. s, 1 H), 8.53 (s, 2H), 7.89 (d, J = 0.78 Hz, 1H), 7.48 (t, J = 8.51 Hz, 1H), 7.20 (d, J = 0.78 Hz, 1H), 6.69 (dd, J = 8.61, 1.96 Hz, 2H), 3.81 (m, J = 2.15 Hz, 1H), 3.78 (s, 3H), 3.76 (s, 3H), 3.69 (dd, J = 14.67, 4.50 Hz, 1H), 2.96-3.18 (m, 1H), 1.31 (d, J = 6.85 Hz, 3H). LCMS-ESI (pos.) m/z: 490.1 (M + H)$^+$. |

The compounds set forth in the following table were synthesized following the procedure in Example 134.0 using the known starting material as described.

TABLE 11

| Example | Reagents | Structure, Name and Data |
|---|---|---|
| 191.0 | (2S,3R)-3-(5-fluoropyrimidin-2-yl)butane-2-sulfonamide (Example 464.1), 2-isothiocyanato-1,3-dimethoxybenzene (Example 465.0), and 1-ethyl-1H-pyrazole-3-carbohydrazide (ChemBridge Corporation). | (2S,3R)-N-(4-(2,6-dimethoxyphenyl)-5-(1-ethyl-1H-pyrazol-3-yl)-4H-1,2,4-triazol-3-yl)-3-(5-fluoro-2-pyrimidinyl)-2-butanesulfonamide.<br><br>$^1$H NMR (400 MHz, CDCl$_3$) δ 10.96 (s, 1H), 8.53 (s, 2H), 7.40 (t, J = 8.51 Hz, 1H), 7.26 (d, J = 2.35 Hz, 1H), 6.52-6.73 (m, 2 H), 5.97 (d, J = 2.35 Hz, 1H), 4.11 (q, J = 7.43 Hz, 2H), 3.77-3.93 (m, 2H), 3.73 (s, 3H), 3.71 (s, 3H), 1.36-1.41 (m, 6H), 1.34 (d, J = 6.85 Hz, 3H). LCMS-ESI (pos.) m/z: 530.8 (M + H)$^+$. |

TABLE 11-continued

| Example | Reagents | Structure, Name and Data |
|---|---|---|
| 194.0 | (2S,3R)-3-(5-fluoropyrimidin-2-yl)butane-2-sulfonamide (Example 464.1), 2-isothiocyanato-1,3-dimethoxybenzene (Example 465.0), and 1-(difluoromethyl)-1H-pyrazole-3-carbohydrazide (Princeton BioMolecular Research, Inc.). | 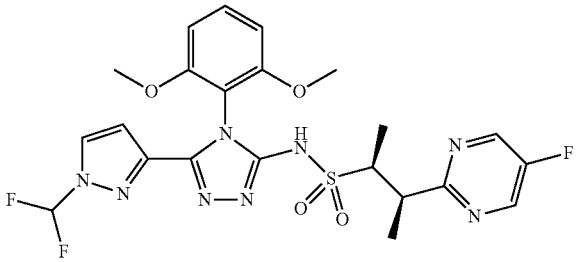 [SMILES: COc1cccc(OC)c1-n1c(NS(=O)(=O)[C@@H](C)[C@H](C)c2ncc(F)cn2)nnc1-c1ccn(C(F)F)n1]<br>(2S,3R)-N-(5-(1-(difluoromethyl)-1H-pyrazol-3-yl)-4-(2,6-dimethoxyphenyl)-4H-1,2,4-triazol-3-yl)-3-(5-fluoro-2-pyrimidinyl)-2-butanesulfonamide.<br>$^1$H NMR (400 MHz, CDCl$_3$) δ 11.09 (br. s, 1H), 8.55 (s, 2H), 7.76 (d, J = 2.74 Hz, 1H), 7.44 (t, J = 8.51 Hz, 1H), 6.84-7.22 (m, 1H), 6.62-6.68 (m, 2H), 6.43 (d, J = 2.74 Hz, 1H), 3.87 (dt, J = 15.01, 6.19 Hz, 2H), 3.75 (s, 3H), 3.73 (s, 3H), 1.39 (m, 6H). LCMS-ESI (pos.) m/z: 552.7 (M + H)$^+$. |
| 197.0 | (2S,3R)-3-(5-fluoropyrimidin-2-yl)butane-2-sulfonamide (Example 464.1), 2-isothiocyanato-1,3-dimethoxybenzene (Example 465.0), and 2-methoxypyrimidine-4-cathohydrazide (Example 395.26). | 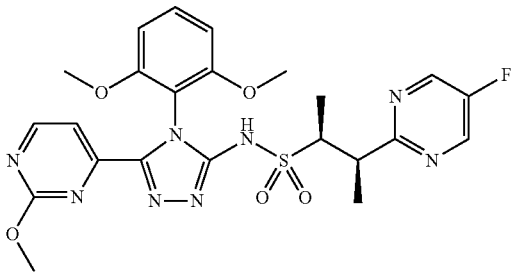 [SMILES: COc1nccc(-c2nnc(NS(=O)(=O)[C@@H](C)[C@H](C)c3ncc(F)cn3)n2-c2c(OC)cccc2OC)n1]<br>(2S,3R)-N-(4-(2,6-dimethoxyphenyl)-5-(2-methoxy-4-pyrimidinyl)-4H-1,2,4-triazol-3-yl)-3-(5-fluoro-2-pyrimidinyl)-2-butanesulfonamide.<br>$^1$H NMR (500 MHz, CDCl$_3$) δ 11.28 (br. s, 1 H), 8.63 (d, J = 4.89 Hz, 1 H), 8.55 (s, 2 H), 7.60 (d, J = 5.14 Hz, 1 H), 7.37 (t, J = 8.56 Hz, 1 H), 6.63 (t, J = 8.19 Hz, 2 H), 3.81 (d, J = 5.38 Hz, 2 H), 3.75 (s, 3 H), 3.72 (s, 3 H), 3.30 (s, 3 H), 1.38 (d, J = 6.85 Hz, 3 H), 1.37 (d, J = 6.85 Hz, 3 H). LCMS-ESI (pos.) m/z: 545.2 (M + H)$^+$. |
| 198.0 | (2S,3R)-3-(5-methylpyrimidin-2-yl)butane-2-sulfonamide (Example 464.0), 2-isothiocyanato-1,3-dimethoxybenzene (Example 465.0), and 1-(difluoromethyl)-1H-pyrazole-3-carbohydrazide (Princeton BioMolecular Research, Inc.). | 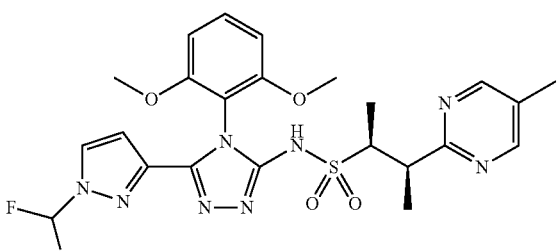<br>(2S,3R)-N-(5-(1-(difluoromethyl)-1H-pyrazol-3-yl)-4-(2,6-dimethoxyphenyl)-4H-1,2,4-triazol-3-yl)-3-(5-methyl-2-pyrimidinyl)-2-butanesulfonamide.<br>$^1$H NMR (500 MHz, CDCl$_3$) δ 11.41 (br. s, 1 H), 8.54 (s, 2 H), 7.74 (d, J = 2.69 Hz, 1 H), 7.41 (t, J = 8.56 Hz, 1 H), 6.88-7.16 (m, 1 H), 6.60-6.65 (m, 2 H), 6.38 (d, J = 2.69 Hz, 1 H), 3.80-3.87 (m, 1 H), 3.76 (s, 1 H), 3.73 (s, 3 H), 3.71 (s, 3 H), 2.30 (s, 3 H), 1.38 (d, J = 7.09 Hz, 3 H), 1.36 (d, J = 6.85 Hz, 3 H). LCMS-ESI (pos.) m/z: 548.9 (M + H)$^+$. |

TABLE 11-continued

| Example | Reagents | Structure, Name and Data |
|---|---|---|
| 199.0 | (1R,2S)-1-ethoxy-1-(5-methylpyrimidin-2-yl)propane-2-sulfonamide (Example 466.9), 2-isothiocyanato-1,3-dimethoxybenzene (Example 465.0), and 1-(difluoromethyl)-1H-pyrazole-3-carbohydrazide (Princeton BioMolecular Research, Inc.). | 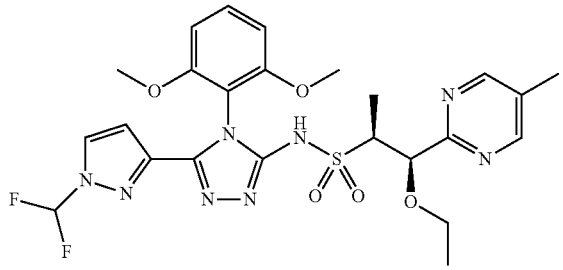 [SMILES: CCO[C@H](c1ncc(C)cn1)[C@H](C)S(=O)(=O)Nc1nnc(-c2ccn(C(F)F)n2)n1-c1c(OC)cccc1OC]<br>(1R,2S)-N-(5-(1-(difluoromethyl)-1H-pyrazol-3-yl)-4-(2,6-dimethoxyphenyl)-4H-1,2,4-triazol-3-yl)-1-ethoxy-1-(5-methyl-2-pyrimidinyl)-2-propanesulfonamide.<br>$^1$H NMR (500 MHz, CDCl$_3$) δ 11.34 (br. s, 1 H), 8.54 (d, J = 0.73 Hz, 2 H), 7.66 (d, J = 2.93 Hz, 1 H), 7.34 (t, J = 8.44 Hz, 1 H), 6.81-7.09 (m, 1 H), 6.55 dd, J = 8.44, 1.10 Hz, 2 H), 6.30 (d, J = 2.69 Hz, 1 H), 4.91 (d, J = 5.87 Hz, 1 H), 3.71-3.75 (m, 1 H), 3.67 (s, 3 H), 3.64 (s, 3 H), 3.38-3.48 (m, 2 H), 2.25 (s, 3 H), 1.37 (d, J = 7.09 Hz, 3 H), 1.07 (t, J = 6.97 Hz, 3 H). LCMS-ESI (pos.) m/z: 578.9 (M + H)$^+$. |
| 200.0 | (1R,2S)-1-methoxy-1-(5-methylpyrimidin-2-yl)propane-2-sulfonamide (Example 466.0), 2-isothiocyanato-1,3-dimethoxybenzene (Example 465.0), and 1-methyl-1h-pyrazole-3-cathohydrazide (ChemBridge Corporation). | 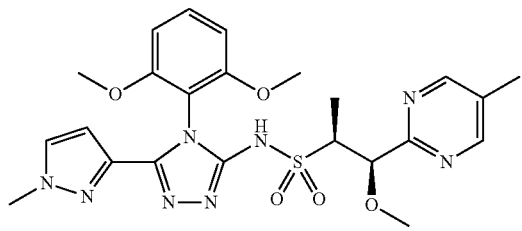<br>(1R,2S)-N-(4-(2,6-dimethoxyphenyl)-5-(1-methyl-1H-pyrazol-3-yl)-4H-1,2,4-triazol-3-yl)-1-methoxy-1-(5-methyl-2-pyrimidinyl)-2-propanesulfonamide.<br>$^1$H NMR (500 MHz, CDCl$_3$) δ 11.17 (br. s, 1 H), 8.60 (d, J = 0.73 Hz, 2 H), 7.41 (t, J = 8.56 Hz, 1 H), 7.22 (d, J = 2.20 Hz, 1 H), 6.60-6.66 (m, 2 H), 5.86 (d, J = 2.45 Hz, 1 H), 4.96 (d, J = 4.89 Hz, 1 H), 3.88 (s, 3 H), 3.75-3.79 (m, 1 H), 3.75 (s, 3 H), 3.73 (s, 3 H), 3.34 (s, 3 H), 2.32 (s, 3 H), 1.39 (d, J = 7.09 Hz, 3 H). LCMS-ESI (pos.) m/z: 529.3 (M + H)$^+$. |
| 201.0 | (2S,3R)-3-(5-methylpyrimidin-2-yl)butane-2-sulfonamide (Example 464.0), 2-isothiocyanato-1,3-dimethoxybenzene (Example 465.0), and 1-methyl-1h-pyrazole-3-cathohydrazide (ChemBridge Corporation). | 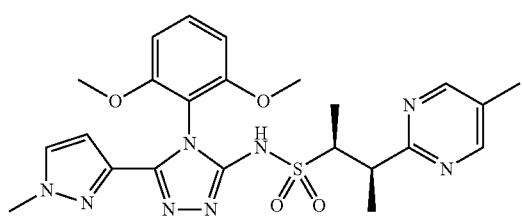<br>(2S,3R)-N-(4-(2,6-dimethoxyphenyl)-5-(1-methyl-1H-pyrazol-3-yl)-4H-1,2,4-triazol-3-yl)-3-(5-methyl-2-pyrimidinyl)-2-butanesulfonamide.<br>$^1$H NMR (500 MHz, CDCl$_3$) δ 8.55 (s, 2 H), 7.41 (t, J = 8.56 Hz, 1 H), 7.22 (d, J = 2.20 Hz, 1 H), 6.63 (dd, J = 8.56, 3.91 Hz, 2 H), 5.87 (d, J = 2.20 Hz, 1 H), 3.89-3.93 (m, 1 H), 3.88 (s, 3 H), 3.74-3.82 (m, 1 H), 3.73 (s, 3 H), 3.72 (s, 3 H), 2.30 (s, 3 H), 1.37-1.41 (m, 3 H), 1.36 (d, J = 6.85 Hz, 3 H). LCMS-ESI (pos.) m/z: 513.3 (M + H)$^+$. |

TABLE 11-continued

| Example | Reagents | Structure, Name and Data |
|---|---|---|
| 202.0 | (2S,3R)-3-(5-methylpyrimidin-2-yl)butane-2-sulfonamide (Example 464.0), 2-isothiocyanato-1,3-dimethoxybenzene (Example 465.0), and 2-methoxypyrimidine-4-cathohydrazide (Example 395.24). | 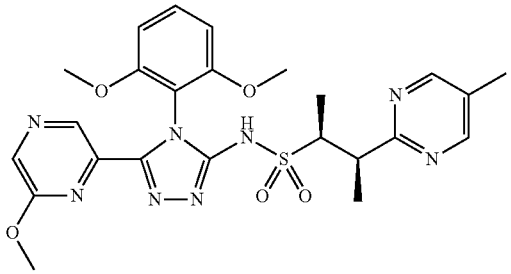 [SMILES: COc1cncc(-c2nnc(NS(=O)(=O)[C@@H](C)[C@H](C)c3ncc(C)cn3)n2-c2c(OC)cccc2OC)n1]<br>(2S,3R)-N-(4-(2,6-dimethoxyphenyl)-5-(6-methoxy-2-pyrazinyl)-4H-1,2,4-triazol-3-yl)-3-(5-methyl-2-pyrimidinyl)-2-butanesulfonamide.<br>$^1$H NMR (500 MHz, CDCl$_3$) δ 11.43 (br. s, 1 H), 8.78 (s, 1 H), 8.53 (s, 2 H), 8.17 (s, 1 H), 7.33 (t, J = 8.44 Hz, 1 H), 6.56-6.63 (m, 2 H), 3.87-3.91 (m, 1 H), 3.74-3.79 (m, 1 H), 3.72 (s, 3 H), 3.69 (s, 3 H), 3.26 (s, 3 H), 2.29 (s, 3 H), 1.37 (d, J = 7.09 Hz, 3 H), 1.35 (d, J = 7.09 Hz, 3 H). LCMS-ESI (pos.) m/z: 541.3 (M + H)$^+$. |
| 203.0 | (1R,2S)-1-methoxy-1-(5-methylpyrimidin-2-yl)propane-2-sulfonamide (Example 466.0), 2-isothiocyanato-1,3-dimethoxybenzene (Example 465.0), and 1-(difluoromethyl)-1H-pyrazole-3-carbohydrazide (Princeton BioMolecular Research, Inc.). | 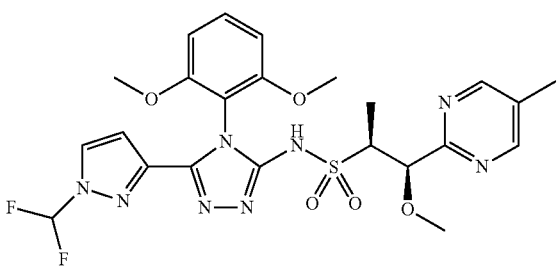 [SMILES: COc1cccc(OC)c1-n1c(NS(=O)(=O)[C@@H](C)[C@H](OC)c2ncc(C)cn2)nnc1-c1ccn(C(F)F)n1]<br>(1R,2S)-N-(5-(1-(difluoromethyl)-1H-pyrazol-3-yl)-4-(2,6-dimethoxyphenyl)-4H-1,2,4-triazol-3-yl)-1-methoxy-1-(5-methyl-2-pyrimidinyl)-2-propanesulfonamide.<br>$^1$H NMR (500 MHz, CDCl$_3$) δ 11.31 (br. s, 1 H), 8.60 (s, 2 H), 7.74 (d, J = 2.69 Hz, 1 H), 7.41 (t, J = 8.44 Hz, 1 H), 6.89-7.16 (m, 1 H), 6.63 (d, J = 8.80 Hz, 2 H), 6.38 (d, J = 2.69 Hz, 1 H), 4.96 (d, J = 4.65 Hz, 1 H), 3.74-3.77 (m, 1 H), 3.74 (s, 3 H), 3.72 (s, 3 H), 3.33 (s, 3 H), 2.32 (s, 3 H), 1.39 (d, J = 7.09 Hz, 3 H). LCMS-ESI (pos.) m/z: 565.1 (M + H)$^+$. |
| 204.0 | (1R,2S)-1-methoxy-1-(5-methylpyrimidin-2-yl)propane-2-sulfonamide (Example 466.0), 2-isothiocyanato-1,3-dimethoxybenzene (Example 465.0), and 1-methyl-1H-1,2,4-triazole-3-carbohydrazide (Example 395.27). | 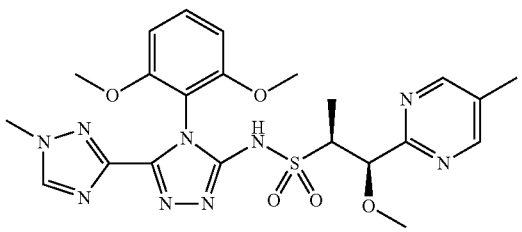<br>(1R,2S)-N-(4'-(2,6-dimethoxyphenyl)-1-methyl-1H,4'H-3,3'-bi-1,2,4-triazol-5'-yl)-1-methoxy-1-(5-methyl-2-pyrimidinyl)-2-propanesulfonamide.<br>$^1$H NMR (500 MHz, CDCl$_3$) δ 8.69 (s, 2 H), 8.03 (s, 1 H), 7.40 (t, J = 8.44 Hz, 1 H), 6.62 (dd, J = 8.56, 3.42 Hz, 2 H), 4.99 (d, J = 4.65 Hz, 1 H), 4.02 (s, 1 H), 3.87 (s, 3 H), 3.74 (s, 3 H), 3.73 (s, 3 H), 3.30 (s, 3 H), 2.37 (s, 3 H), 1.36 (d, J = 6.85 Hz, 3 H). LCMS-ESI (pos.) m/z: 530.2 (M + H)$^+$. |

TABLE 11-continued

| Example | Reagents | Structure, Name and Data |
|---|---|---|
| 205.0 | (1R,2S)-1-methoxy-1-(5-methylpyrimidin-2-yl)propane-2-sulfonamide (Example 466.0), 2-isothiocyanato-1,3-dimethoxybenzene (Example 465.0), and 5,6-dihydro-4H-pyrrolo[1,2-b]pyrazole-2-carbohydrazide (Example 395.28). | 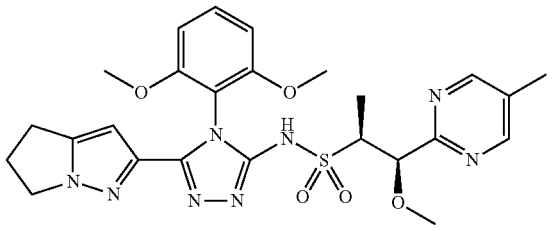 [SMILES: COc1cccc(OC)c1-n1c(NS(=O)(=O)[C@@H](C)[C@H](OC)c2ncc(C)cn2)nnc1-c1cc2n(n1)CCC2]<br>(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-1-(5-methyl-2-pyrimidinyl)-2-propanesulfonamide.<br>$^1$H NMR (500 MHz, CDCl$_3$) δ 8.62 (d, J = 0.73 Hz, 2 H), 7.42 (t, J = 8.44 Hz, 1 H), 6.65 (dd, J = 8.44, 3.55 Hz, 2 H), 5.57 (s, 1 H), 4.96 (d, J = 4.65 Hz, 1 H), 4.08-4.13 (m, 2 H), 3.76 (s, 3 H), 3.74 (s, 3 H), 3.74 (br. s, 1 H), 3.33 (s, 3 H), 2.80 (t, J = 7.21 Hz, 2 H), 2.51-2.60 (m, 2 H), 2.33 (s, 3 H), 1.37 (d, J = 6.85 Hz, 3 H). LCMS-ESI (pos.) m/z: 555.0 (M + H)$^+$. |
| 206.0 | (1R,2S)-1-methoxy-1-(5-methylpyrimidin-2-yl)propane-2-sulfonamide (Example 466.0), 2-isothiocyanato-1,3-dimethoxybenzene (Example 465.0), and 5H-pyrrolo[2,3-b]pyrazine-2-carbohydrazide (Example 395.29). | 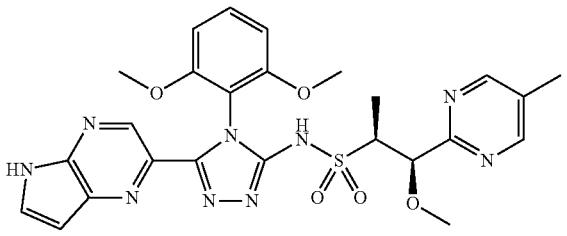 [SMILES: COc1cccc(OC)c1-n1c(NS(=O)(=O)[C@@H](C)[C@H](OC)c2ncc(C)cn2)nnc1-c1cnc2[nH]ccc2n1]<br>(1R,2S)-N-(4-(2,6-dimethoxyphenyl)-5-(5H-pyrrolo[2,3-b]pyrazin-2-yl)-4H-1,2,4-triazol-3-yl)-1-methoxy-1-(5-methyl-2-pyrimidinyl)-2-propanesulfonamide.\<br>$^1$H NMR (CDCl$_3$) δ 12.27 (br. s, 1H), 9.90 (br. s, 1H), 8.82 (s, 1H), 8.58 (s, 2H), 7.57-7.63 (m, 1H), 7.34 (t, J = 8.4 Hz, 1H), 6.58 (dd, J = 8.2, 4.8 Hz, 2H), 6.45 (d, J = 2.2 Hz, 1H), 5.04 (d, J = 4.4 Hz, 1H), 3.77 (dd, J = 7.0, 4.5 Hz, 1H), 3.70 (s, 3H), 3.70 (s, 3H), 3.35 (s, 3H), 2.28 (s, 3H), 1.41 (d, J = 6.8 Hz, 3H). LCMS-ESI (pos.) m/z: 566.0 (M + H)$^+$. |
| 207.0 | (1R,2S)-1-(5-chloropyrimidin-2-yl)-1-methoxypropane-2-sulfonamide (Example 466.3), 2-isothiocyanato-1,3-dimethoxybenzene (Example 465.0), and 1-(difluoromethyl)-1H-pyrazole-3-carbohydrazide (Princeton BioMolecular Research, Inc.). | 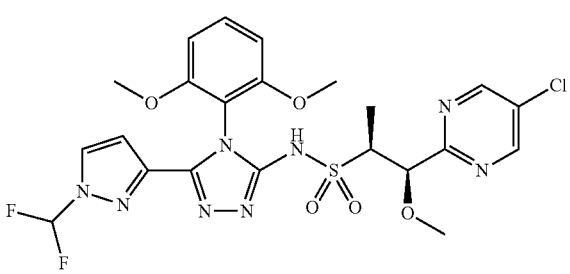 [SMILES: COc1cccc(OC)c1-n1c(NS(=O)(=O)[C@@H](C)[C@H](OC)c2ncc(Cl)cn2)nnc1-c1ccn(C(F)F)n1]<br>(1R,2S)-1-(5-chloro-2-pyrimidinyl)-N-(5-(1-(difluoromethyl)-1H-pyrazol-3-yl)-4-(2,6-dimethoxyphenyl)-4H-1,2,4-triazol-3-yl)-1-methoxy-2-propanesulfonamide.<br>$^1$H NMR (CDCl$_3$) δ 10.92-11.39 (m, 1H), 8.71 (s, 2H), 7.74 (d, J = 2.7 Hz, 1H), 7.42 (t, J = 8.6 Hz, 1H), 6.81-7.18 (m, 1H), 6.63 (d, J = 8.6 Hz, 2H), 6.41 (d, J = 2.7 Hz, 1H), 4.97 (d, J = 4.9 Hz, 1H), 3.73 (s, 3H), 3.72-3.73 (m, 1H), 3.71 (s, 3H), 3.33 (s, 3H), 1.38 (d, J = 7.1 Hz, 3H). LCMS-ESI (pos.) m/z: 585.0 (M + H)$^+$. |

TABLE 11-continued

| Example | Reagents | Structure, Name and Data |
|---|---|---|
| 208.0 | (2S,3R)-3-(5-fluoropyrimidin-2-yl)butane-2-sulfonamide (Example 464.1), 2-isothiocyanato-1,3-dimethoxybenzene (Example 465.0), and 5,6-dihydro-4H-pyrrolo[1,2-b]pyrazole-2-carbohydrazide (Example 395.28). | 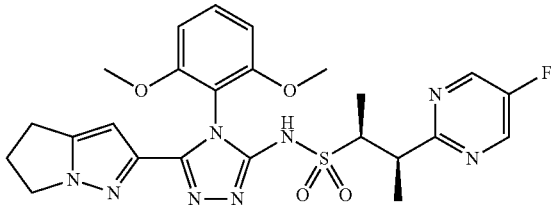 [SMILES: COc1cccc(OC)c1-n1c(NS(=O)(=O)[C@@H](C)[C@H](C)c2ncc(F)cn2)nnc1-c1cc2n(n1)CCC2]<br>(2S,3R)-N-(5-(5,6-dihydro-4H-pyrrolo[1,2-b]pyrazol-2-yl)-4-(2,6-dimethoxyphenyl)-4H-1,2,4-triazol-3-yl)-3-(5-fluoro-2-pyrimidinyl)-2-butanesulfonamide.<br>$^1$H NMR (CDCl$_3$) δ 11.00 (br. s, 1H), 8.53 (s, 2H), 7.42 (t, J = 8.6 Hz, 1H), 6.61-6.66(m, 2H), 5.57 (s, 1H), 4.07-4.13 (m, 2H), 3.80-3.85 (m, 2H), 3.74 (s, 3H), 3.72 (s, 3H), 2.80 (t, J = 7.3 Hz, 2H), 2.51-2.61 (m, 2H), 1.36 (d, J = 6.8 Hz, 3H), 1.33 (d, J = 6.6 Hz, 3H). LCMS-ESI (pos.) m/z: 543.0 (M + H)$^+$. |
| 209.0 | (2S,3R)-3-(5-fluoropyrimidin-2-yl)butane-2-sulfonamide (Example 464.1), 2-isothiocyanato-1,3-dimethoxybenzene (Example 465.0), and 6-methylpyrazine-2-carbohydrazide (Accel Pharmtech). | 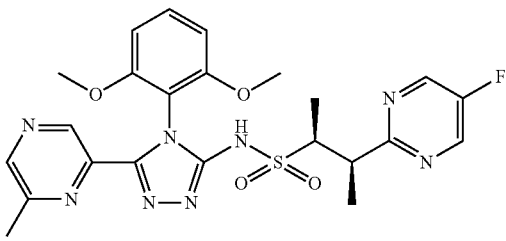 [SMILES: COc1cccc(OC)c1-n1c(NS(=O)(=O)[C@@H](C)[C@H](C)c2ncc(F)cn2)nnc1-c1cncc(C)n1]<br>(2S,3R)-N-(4-(2,6-dimethoxyphenyl)-5-(6-methyl-2-pyrazinyl)-4H-1,2,4-triazol-3-yl)-3-(5-fluoro-2-pyrimidinyl)-2-butanesulfonamide.<br>$^1$H NMR (CDCl$_3$) δ 11.23 (br. s, 1H), 8.80 (s, 1H), 8.54 (s, 2H), 8.40 (s, 1H), 7.38 (t, J = 8.6 Hz, 1H), 6.55-6.62 (m, 2H), 3.81-3.88 (m, 2H), 3.71 (s, 3H), 3.68 (s, 3H), 2.29 (s, 3H), 1.37 (m, 6H). LCMS-ESI (pos.) m/z: 529.1 (M + H)$^+$. |
| 210.0 | (1R,2S)-1-(5-chloropyrimidin-2-yl)-1-methoxypropane-2-sulfonamide (Example 466.3), 2-dimethoxybenzene (Example 465.0), and 5,6-dihydro-4H-pyrrolo[1,2-b]pyrazole-2-carbohydrazide (Example 395.28). | 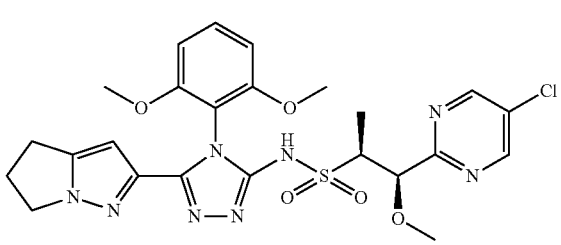 [SMILES: COc1cccc(OC)c1-n1c(NS(=O)(=O)[C@@H](C)[C@H](OC)c2ncc(Cl)cn2)nnc1-c1cc2n(n1)CCC2]<br>(1R,2S)-1-(5-chloro-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-2-propanesulfonamide.<br>$^1$H NMR (CDCl$_3$) δ 10.98 (br. s, 1H), 8.71 (s, 2H), 7.42 (t, J = 8.4 Hz, 1H), 6.64 (d, J = 8.6 Hz, 2H), 5.57 (s, 1H), 4.95 (d, J = 4.9 Hz, 1H), 4.07-4.13 (m, 2H), 3.75 (s, 3H), 3.73 (s, 3H), 3.67-3.72 (m, 1H), 3.33 (s, 3H), 2.79 (t, J = 7.3 Hz, 2H), 2.48-2.62 (m, 2H), 1.37 (d, J = 7.1 Hz, 3H). LCMS-ESI (pos.) m/z: 575.0 (M + H)$^+$. |

TABLE 11-continued

| Example | Reagents | Structure, Name and Data |
|---|---|---|
| 211.0 | (2S,3R)-3-(5-fluoropyrimidin-2-yl)butane-2-sulfonamide (Example 464.1), 2-isothiocyanato-1,3-dimethoxybenzene (Example 465.0), and 1-methyl-1H-pyrazole-5-cathohydrazide (ChemBridge Corporation). | 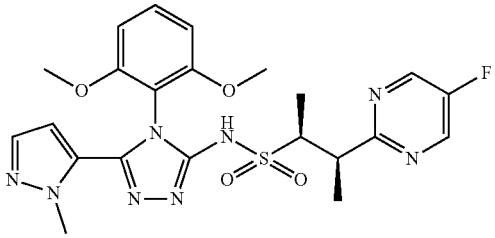 [SMILES: COc1cccc(OC)c1-n1c(NS(=O)(=O)[C@@H](C)[C@H](C)c2ncc(F)cn2)nnc1-c1ccnn1C]<br>(2S,3R)-N-(4-(2,6-dimethoxyphenyl)-5-(1-methyl-1H-pyrazol-4-yl)-4H-1,2,4-triazol-3-yl)-3-(5-fluoro-2-pyrimidinyl)-2-butanesulfonamide.<br>$^1$H NMR (CDCl$_3$) δ 8.54 (s, 2H), 7.46 (t, J = 8.6 Hz, 1H), 7.38 (br. s, 1H), 7.26 (s, 1H), 6.63-6.70 (m, 2H), 3.85-3.88 (m, 1H), 3.84 (s, 3H), 3.80-3.84 (m, 1H), 3.75 (s, 3H), 3.74 (s, 3H), 1.37 (d, J = 6.8 Hz, 3H), 1.35 (d, J = 6.8 Hz, 3H). LCMS-ESI (pos.) m/z: 517.1 (M + H)$^+$. |
| 212.0 | (2S,3R)-3-(5-fluoropyrimidin-2-yl)butane-2-sulfonamide (Example 464.1), 2-isothiocyanato-1,3-dimethoxybenzene (Example 465.0), and 1-methyl-1H-pyrazole-4-calbohydrazide (Example 395.30). | 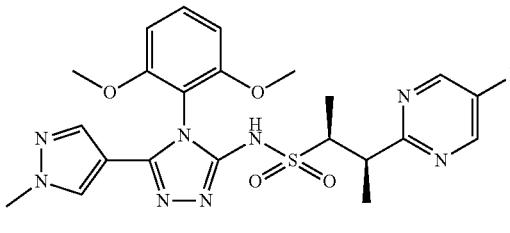<br>(2S,3R)-N-(4-(2,6-dimethoxyphenyl)-5-(1-methyl-1H-pyrazol-4-yl)-4H-1,2,4-triazol-3-yl)-3-(5-fluoro-2-pyrimidinyl)-2-butanesulfonamide.<br>$^1$H NMR (CDCl$_3$) δ 8.54 (s, 2H), 7.46 (t, J = 8.6 Hz, 1H), 7.38 (br. s, 1H), 7.26 (s, 1H), 6.63-6.70 (m, 2H), 3.85-3.88 (m, 1H), 3.84 (s, 3H), 3.80-3.84 (m, 1H), 3.75 (s, 3H), 3.74 (s, 3H), 1.37 (d, J = 6.8 Hz, 3H), 1.35 (d, J = 6.8 Hz, 3H). LCMS-ESI (pos.) m/z: 517.1 (M + H)$^+$. |
| 214.0 | (1R,2S)-1-(5-chloropyrimidin-2-yl)-1-methoxypropane-2-sulfonamide (Example 466.3), 2-isothiocyanato-1,3-dimethoxybenzene (Example 465.0), and 6-methylpyrazine-2-carbohydrazide (Accel Pharmtech). | 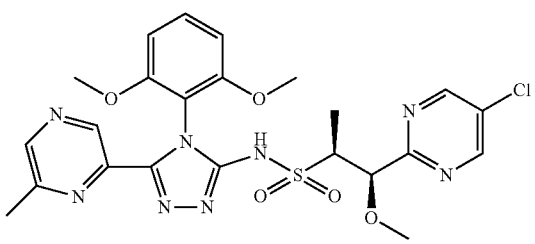 [SMILES: COc1cccc(OC)c1-n1c(NS(=O)(=O)[C@@H](C)[C@H](OC)c2ncc(Cl)cn2)nnc1-c1cncc(C)n1]<br>(1R,2S)-1-(5-chloro-2-pyrimidinyl)-N-(4-(2,6-dimethoxyphenyl)-5-(6-methyl-2-pyrazinyl)-4H-1,2,4-triazol-3-yl)-1-methoxy-2-propanesulfonamide.<br>$^1$H NMR (CDCl$_3$) δ 8.84 (s, 1H), 8.75 (s, 2H), 8.42 (s, 1H), 7.39 (t, J = 8.6 Hz, 1H), 6.60 (d, J = 8.6 Hz, 2H), 4.99 (d, J = 4.6 Hz, 1H), 3.74-3.78 (m, 1H), 3.72 (s, 3H), 3.71 (s, 3H), 3.33 (s, 3H), 2.30 (s, 3H), 1.38 (d, J = 7.1 Hz, 3H). LCMS-ESI (pos.) m/z: 561.3 (M + H)$^+$. |

TABLE 11-continued

| Example | Reagents | Structure, Name and Data |
|---|---|---|
| 215.0 | (2S,3R)-3-(5-methylpyrimidin-2-yl)butane-2-sulfonamide (Example 464.0), 2-isothiocyanato-1,3-dimethoxybenzene (Example 465.0), and 6-methylpyrazine-2-carbohydrazide (Accel Pharmtech). | 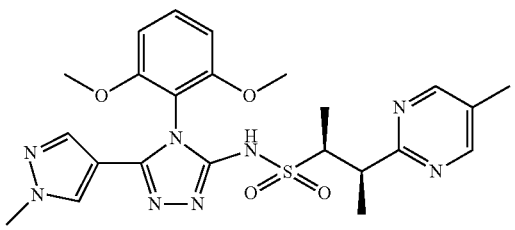<br>(2S,3R)-N-(4-(2,6-dimethoxyphenyl)-5-(1-methyl-1H-pyrazol-4-yl)-4H-1,2,4-triazol-3-yl)-3-(5-methyl-2-pyrimidinyl)-2-butanesulfonamide.<br>$^1$H NMR (CDCl$_3$) δ 11.11 (br. s, 1H), 8.53 (s, 2H), 7.45 (t, J = 8.6 Hz, 1H), 7.37 (s, 1H), 6.62-6.70 (m, 2H), 3.90 (quin, J = 6.7 Hz, 1H), 3.84 (s, 3H), 3.75-3.79 (m, 1H), 3.75 (s, 3H), 3.73 (s, 3H), 2.29 (s, 3H), 1.38 (d, J = 7.1 Hz, 3H), 1.35 (d, J = 6.8 Hz, 3H). LCMS-ESI (pos.) m/z: 513.3 (M + H)$^+$. |
| 216.0 | (1R,2S)-1-methoxy-1-(5-methylpyrazin-2-yl)propane-2-sulfonamide (Example 466.1), 2-isothiocyanato-1,3-dimethoxybenzene (Example 465.0), and 5,6-dihydro-4H-pyrrolo[1,2-b]pyrazole-2-carbohydrazide (Example 395.28). | 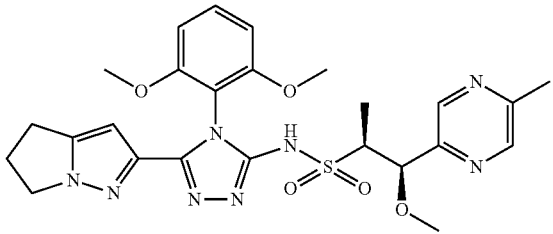 [SMILES: COc1cccc(OC)c1-n1c(NS(=O)(=O)[C@@H](C)[C@H](OC)c2cnc(C)cn2)nnc1-c1cc2n(n1)CCC2]<br>(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-methoxy-1-(5-methyl-2-pyrazinyl)-2-propanesulfonamide.<br>$^1$H NMR (500 MHz, DMSO-d$_6$) δ 8.47-8.56 (m, 2H), 8.42 (s, 1H), 7.46 (t, J = 8.43 Hz, 1H), 6.80 (d, J = 8.30 Hz, 2H), 5.84 (s, 1H), 4.84 (d, J = 2.53 Hz, 1H), 3.96 (t, J = 7.20 Hz, 2H), 3.68 (s, 3H), 3.66 (s, 3H), 3.18 (s, 3H), 2.76 (t, J = 7.23 Hz, 2H), 2.54 (s, 3H), 2.41-2.48 (m, 2H), 1.05 (d, J = 7.01 Hz, 3H). LCMS-ESI (pos.) m/z: 555.2 (M + H)$^+$. |
| 217.0 | (1R,2S)-1-ethoxy-1-(5-methylpyrimidin-2-yl)propane-2-sulfonamide (Example 466.9), 2-isothiocyanato-1,3-dimethoxybenzene (Example 465.0), and 5,6-dihydro-4H-pyrrolo[1,2-b]pyrazole-2-carbohydrazide (Example 395.28). | 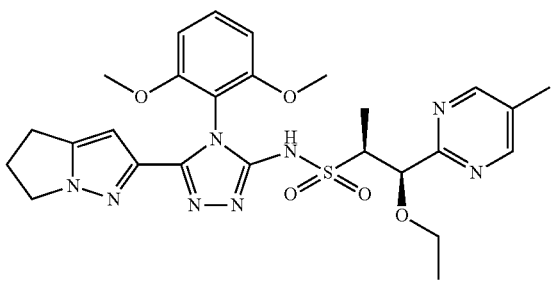 [SMILES: CCO[C@H](c1ncc(C)cn1)[C@H](C)S(=O)(=O)Nc1nnc(-c2cc3n(n2)CCC3)n1-c1c(OC)cccc1OC]<br>(1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-ethoxy-1-(5-methyl-2-pyrimidinyl)-2-propanesulfonamide.<br>$^1$H NMR (500 MHz, DMSO-d$_6$) δ 12.91 (br s, 1H), 8.59-8.67 (m, 2H), 7.46 (t, J = 8.50 Hz, 1H), 6.80 (d, J = 8.56 Hz, 2H), 6.64-6.75 (m, 1H), 5.84 (s, 1H), 4.85-4.96(m, 1H), 3.96 (t, J = 7.27 Hz, 2H), 3.68 (s, 3H), 3.66 (s, 3H), 3.39-3.46 (m, 2H), 2.75 (t, J = 7.20 Hz, 2H), 2.43-2.48 (m, 2H), 2.26 (s, 3H), 1.16 (d, J = 7.01 Hz, 3H), 0.99 (t, J = 6.94 Hz, 3H). LCMS-ESI (pos.) m/z: 569.2 (M + H)$^+$. |

TABLE 11-continued

| Example | Reagents | Structure, Name and Data |
|---|---|---|
| 218.0 | (1R,2S)-1-((tert-butyldimethylsilyl)oxy)-1-(5-methylpyrimidin-2-yl)propane-2-sulfonamide (Example 349.01), 2-isothiocyanato-1,3-dimethoxybenzene (Example 465.0), and 1-(difluoromethyl)-1H-pyrazole-3-carbohydrazide (Princeton BioMolecular Research, Inc.). | 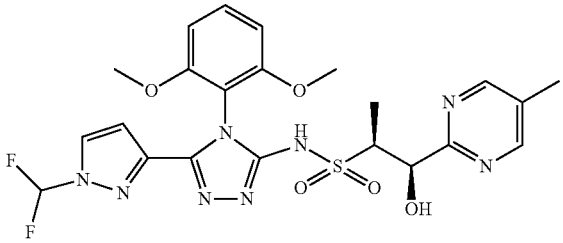 [SMILES: COc1cccc(OC)c1-n1c(NS(=O)(=O)[C@@H](C)[C@H](O)c2ncc(C)cn2)nnc1-c1ccn(C(F)F)n1](1R,2S)-N-(5-(1-(difluoromethyl)-1H-pyrazol-3-yl)-4-(2,6-dimethoxyphenyl)-4H-1,2,4-triazol-3-yl)-1-hydroxy-1-(5-methyl-2-pyrimidinyl)-2-propanesulfonamide.<br>$^1$H NMR (500 MHz, DMSO-$d_6$) δ 8.63 (s, 2H), 8.24 (d, J = 2.53 Hz, 1H), 7.66 (t, J = 58.84 Hz, 1H), 7.46 (t, J = 8.50 Hz, 1H), 6.79 (d, J = 8.50 Hz, 2H), 6.43 (d, J = 2.40 Hz, 1H), 5.18 (d, J = 2.79 Hz, 1H), 3.99 (s, 1H), 3.65 (m, 6H), 3.60 (d, J = 3.50 Hz, 1H), 2.71 (d, J = 7.20 Hz, 1H), 2.26 (s, 3H), 1.09 (d, J = 6.94 Hz, 3H). LCMS-ESI (pos.) m/z: 551.2 (M + H)$^+$. |
| 219.0 | (2S,3R)-3-(5-methylpyrimidin-2-yl)butane-2-sulfonamide (Example 464.0), 2-isothiocyanato-1,3-dimethoxybenzene (Example 465.0), and 5,6-dihydro-4H-pyrrolo[1,2-b]pyrazole-2-carbohydrazide (Example 395.28). | 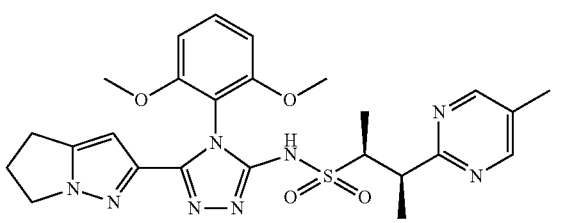 [SMILES: COc1cccc(OC)c1-n1c(NS(=O)(=O)[C@@H](C)[C@H](C)c2ncc(C)cn2)nnc1-c1cc2n(n1)CCC2](2S,3R)-N-(5-(5,6-dihydro-4H-pyrrolo[1,2-b]pyrazol-2-yl)-4-(2,6-dimethoxyphenyl)-4H-1,2,4-triazol-3-yl)-3-(5-methyl-2-pyrimidinyl)-2-butanesulfonamide.<br>$^1$H NMR (400 MHz, CDCl$_3$) δ 11.25 (br s, 1H), 8.51 (s, 2H), 7.28-7.43 (m, 1H), 6.62 (dd, J = 4.07, 8.47 Hz, 2H), 5.56 (s, 1H), 4.01-4.17 (m, 2H), 3.82-3.92 (m, 1H), 3.74-3.81 (m, 1H), 3.72 (s, 3H), 3.70 (s, 3H), 2.78 (t, J = 7.28 Hz, 2H), 2.43-2.66 (m, 2H), 2.27 (s, 3H), 1.34 (m, 6H). LCMS-ESI (pos.) m/z: 539.2 (M + H)$^+$. |
| 220.0 | (1R,2S)-1-((tert-butyldimethylsilyl)oxy)-1-(5-methylpyrimidin-2-yl)propane-2-sulfonamide (Example 349.01), 2-isothiocyanato-1,3-dimethoxybenzene (Example 465.0), and 5,6-dihydro-4H-pyrrolo[1,2-b]pyrazole-2-carbohydrazide (Example 395.28). | 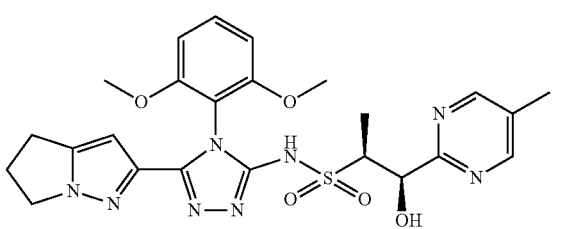 [SMILES: COc1cccc(OC)c1-n1c(NS(=O)(=O)[C@@H](C)[C@H](O)c2ncc(C)cn2)nnc1-c1cc2n(n1)CCC2](1R,2S)-N-(5-(5,6-dihydro-4H-pyrrolo[1,2-b]pyrazol-2-yl)-4-(2,6-dimethoxyphenyl)-4H-1,2,4-triazol-3-yl)-1-hydroxy-1-(5-methyl-2-pyrimidinyl)-2-propanesulfonamide.<br>$^1$H NMR (400 MHz, CDCl$_3$) δ 11.01 (br s, 1H), 8.56 (s, 2H), 7.28-7.47 (m, 1H), 6.64 (dd, J = 8.58, 10.55 Hz, 2H), 5.60 (s, 1H), 5.56 (s, 1H), 4.09 (t, J = 7.31 Hz, 2H), 3.78-3.94 (m, 2H), 3.75 (s, 3H), 3.73 (s, 3H), 2.70-2.90 (m, 2H), 2.50-2.59 (m, 2H), 2.31 (s, 3H), 1.19 (d, J = 7.00 Hz, 3H). LCMS-ESI (pos.) m/z: 541.2 (M + H)$^+$. |

TABLE 11-continued

| Example | Reagents | Structure, Name and Data |
|---|---|---|
| 221.0 | (2S,3R)-3-(5-chloropyrimidin-2-yl)butane-2-sulfonamide (Example 464.4), 2-isothiocyanato-1,3-dimethoxybenzene (Example 465.0), and 5,6-dihydro-4H-pyrrolo[1,2-b]pyrazole-2-carbohydrazide (Example 395.28). | (2S,3R)-3-(5-chloro-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-2-butanesulfonamide.<br>$^1$H NMR (500 MHz, DMSO-d$_6$) δ 12.98 (s, 1H), 8.85 (s, 2H), 7.46 (t, J = 8.50 Hz, 1H), 6.80 (dd, J = 3.67, 8.47 Hz, 2H), 5.86 (s, 1H), 3.96 (t, J = 7.27 Hz, 2H), 3.67 (m, 6H), 3.61-3.66 (m, 1H), 3.52-3.60 (m, 1H), 2.76 (t, J = 7.23 Hz, 2H), 2.43-2.48 (m, 2H), 1.24 (d, J = 7.07 Hz, 3H), 1.11 (d, J = 6.94 Hz, 3H). LCMS-ESI (pos.) m/z: 559.2 (M + H)$^+$. |
| 222.0 | (2S,3R)-3-(5-chloropyrimidin-2-yl)butane-2-sulfonamide (Example 464.4), 2-isothiocyanato-1,3-dimethoxybenzene (Example 465.0), and 1-(difluoromethyl)-1H-pyrazole-3-carbohydrazide (Princeton BioMolecular Research, Inc.). | (2S,3R)-3-(5-chloro-2-pyrimidinyl)-N-(5-(1-(difluoromethyl)-1H-pyrazol-3-yl)-4-(2,6-dimethoxyphenyl)-4H-1,2,4-triazol-3-yl)-2-butanesulfonamide.<br>$^1$H NMR (500 MHz, DMSO-d$_6$) δ 13.27 (s, 1H), 8.86 (s, 2H), 8.27 (d, J = 2.59 Hz, 1H), 7.67 (t, J = 58.84 Hz, 1H), 7.48 (t, J = 8.50 Hz, 1H), 6.81 (dd, J = 3.60, 8.47 Hz, 2H), 6.46 (d, J = 2.66 Hz, 1H), 3.67 (m, 7H), 3.58 (dd, J = 4.35, 6.81 Hz, 1H), 1.25 (d, J = 7.07 Hz, 3H), 1.13 (d, J = 6.94 Hz, 3H). LCMS-ESI (pos.) m/z: 569.2 (M + H)$^+$. |
| 223.0 | (1R,2S)-1-methoxy-1-(5-methylpyrazin-2-yl)propane-2-sulfonamide (Example 466.1), 2-isothiocyanato-1,3-dimethoxybenzene (Example 465.0), and 1-(difluoromethyl)-1H-pyrazole-3-carbohydrazide (Princeton BioMolecular Research, Inc.). | (1R,2S)-N-(5-(1-(difluoromethyl)-1H-pyrazol-3-yl)-4-(2,6-dimethoxyphenyl)-4H-1,2,4-triazol-3-yl)-1-methoxy-1-(5-methyl-2-pyrazinyl)-2-propanesulfonamide.<br>$^1$H NMR (500 MHz, DMSO-d$_6$) δ 8.51 (s, 1H), 8.43 (s, 1H), 8.26 (d, J = 2.60 Hz, 1H), 7.67 (t, J = 58.84 Hz, 1H), 7.48 (t, J = 8.47 Hz, 1H), 6.81 (d, J = 8.43 Hz, 2H), 6.44 (d, J = 2.53 Hz, 1H), 4.86 (d, J = 2.47 Hz, 1H), 3.67 (s, 3H), 3.66 (s, 3H), 2.54 (m, 7H), 1.07 (d, J = 7.01 Hz, 3H). LCMS-ESI (pos.) m/z: 565.2 (M + H)$^+$. |

Example 213.0. Preparation of (1R,2S)-1-(5-cyano-pyrimidin-2-yl)-N-(4-(2,6-dimethoxyphenyl)-5-(1-methyl-1H-pyrazol-3-yl)-4H-1,2,4-triazol-3-yl)-1-methoxypropane-2-sulfonamide

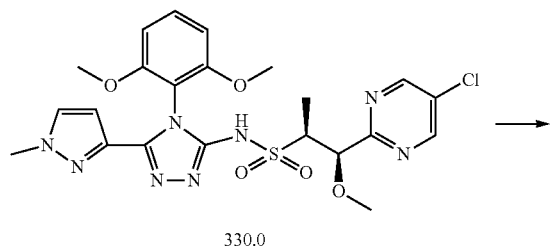

330.0

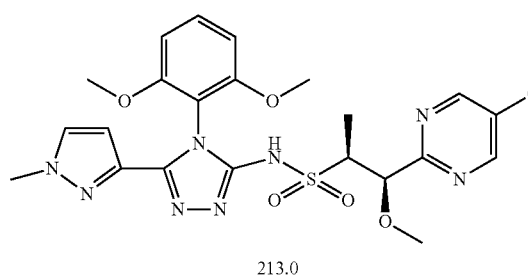

213.0

(1R,2S)-1-(5-Cyanopyrimidin-2-yl)-N-(4-(2,6-dimethoxyphenyl)-5-(1-methyl-1H-pyrazol-3-yl)-4H-1,2,4-triazol-3-yl)-1-methoxypropane-2-sulfonamide, Example 213.0. A reaction vessel was charged with Example 330.0 (0.067 g, 0.122 mmol), tris(dibenzylideneacetone)dipalladium (0) (Sigma Aldrich, 0.011 g, 0.012 mmol), 2-(dicyclohexylphosphino)-2',4',6'-tri-i-propyl-1,1'-biphenyl (X-phos, Sigma Aldrich, 0.012 g, 0.024 mmol) and zinc cyanide (Sigma Aldrich, 0.010 g, 0.085 mmol) in DMA (0.5 mL). The reaction mixture was stirred and heated at 100° C. for 4 h. The material thus obtained was absorbed onto a plug of silica gel and purified by chromatography through a Redi-Sep pre-packed silica gel column (4 g), eluting with a gradient of 0% to 75% (3:1 EtOAc:EtOH) in heptanes then re-purified by reverse-phase preparative HPLC using a Capcell Pak column, 5 micron, C18(2), 100 Å, 150×30 mm, 0.1% TFA in ACN/H$_2$O, gradient 10% to 95% over 25 min. The product was collected and dried using a lyophilizer to provide the title compound (0.013 g, 0.024 mmol, 20% yield) as a white powder. $^1$H NMR (CDCl$_3$) δ 9.02 (s, 2H), 7.45 (t, J=8.4 Hz, 1H), 7.25 (d, J=2.4 Hz, 1H), 6.66 (d, J=8.6 Hz, 2H), 5.90 (d, J=2.2 Hz, 1H), 4.99 (d, J=5.4 Hz, 1H), 3.89 (s, 3H), 3.80 (dd, J=6.8, 5.6 Hz, 1H), 3.76 (s, 3H), 3.75 (s, 3H), 3.37 (s, 3H), 1.40 (d, J=7.1 Hz, 3H). LCMS-ESI (pos.) m/z: 540.1 (M+H)$^+$.

The compounds set forth in the following table were synthesized following the procedure in Example 213.0 using the known starting material as described.

TABLE 12

| Example | Reagents | Structure, Name and Data |
| --- | --- | --- |
| 224.0 | (2S,3R)-3-(5-chloro-2-pyrimidinyl)-N-(5-(1-(difluoromethyl)-1H-pyrazol-3-yl)-4-(2,6-dimethoxyphenyl)-4H-1,2,4-triazol-3-yl)-2-butanesulfonamide (Example 222.0). | 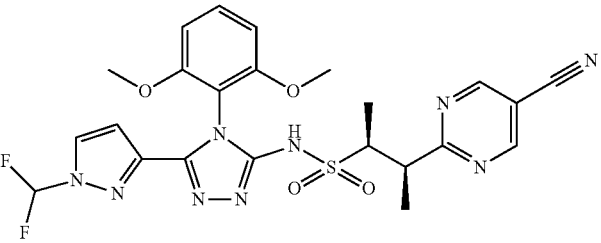 [SMILES: COc1cccc(OC)c1-n1c(NS(=O)(=O)[C@@H](C)[C@H](C)c2ncc(C#N)cn2)nnc1-c1ccn(C(F)F)n1]<br><br>(2S,3R)-3-(5-cyano-2-pyrimidinyl)-N-(5-(1-(difluoromethyl)-1H-pyrazol-3-yl)-4-(2,6-dimethoxyphenyl)-4H-1,2,4-triazol-3-yl)-2-butanesulfonamide.<br><br>$^1$H NMR (400 MHz, CDCl$_3$) δ 11.02 (br s, 1 H) 8.93 (s, 2 H) 7.75 (d, J = 2.80 Hz, 1 H) 7.43 (t, J = 8.50 Hz, 1 H) 7.01 (t, J = 60.23 Hz, 1 H) 6.61-6.70 (m, 2 H) 6.44 (d, J = 2.80 Hz, 1 H) 3.90 (quin, J = 7.02 Hz, 1 H) 3.80 (quin, J = 7.05 Hz, 1 H) 3.74 (s, 3 H) 3.73 (s, 3 H) 1.39-1.43 (m, 3 H) 1.37 (s, 3 H). LCMS-ESI (pos.) m/z: 560.2 (M + H)$^+$. |

TABLE 12-continued

| Example | Reagents | Structure, Name and Data |
|---|---|---|
| 225.0 | (2S,3R)-3-(5-chloro-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-2-butanesulfonamide (Example 221.0). | 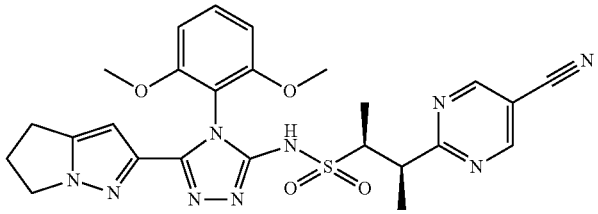 [SMILES: COc1cccc(OC)c1-n1c(NS(=O)(=O)[C@@H](C)[C@H](C)c2ncc(C#N)cn2)nnc1-c1cc2n(n1)CCC2]<br><br>(2S,3R)-3-(5-cyano-2-pyrimidinyl)-N-(5-(5,6-dihydro-4H-pyrrolo[1,2-b]pyrazol-2-yl)-4-(2,6-dimethoxyphenyl)-4H-1,2,4-triazol-3-yl)-2-butanesulfonamide.<br><br>$^1$H NMR (400 MHz, CDCl$_3$) δ 8.92 (s, 2H), 7.43 (t, J = 8.50 Hz, 1H), 6.65 (dd, J = 3.63, 8.50 Hz, 2H), 5.58 (s, 1H), 4.12 (t, J = 7.31 Hz, 2H), 3.84-3.94 (m, 1H), 3.77-3.83 (m, 1H), 3.74 (s, 3H), 3.73 (s, 3H), 2.81 (t, J = 7.31 Hz, 2H), 2.57 (quin, J = 7.32 Hz, 2H), 1.37 (m, 6H). LCMS-ESI (pos.) m/z: 550.2 (M + H)$^+$. |

The compounds set forth in the following table were synthesized following the procedure in Example 77.0 using the known starting material as described.

TABLE 13

| Example | Reagents | Structure, Name and Data |
|---|---|---|
| 226.0 | (2S,3R)-3-(5-methylpyrimidin-2-yl)butane-2-sulfonamide (Example 464.0), 1,3-difluoro-2-isothiocyanatobenzene (Sigma Aldrich), and 1-methyl-1H-pyrazole-3-carbohydrazide (ChemBridge Corporation). | 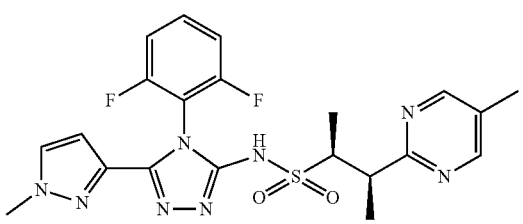<br><br>(2S,3R)-N-(4-(2,6-difluorophenyl)-5-(1-methyl-1H-pyrazol-3-yl)-4H-1,2,4-triazol-3-yl)-3-(5-methyl-2-pyrimidinyl)-2-butanesulfonamide.<br><br>$^1$H NMR (400 MHz, CDCl$_3$) δ 11.46 (br s, 1 H) 8.52 (d, J = 0.73 Hz, 2 H) 7.47 (11, J = 8.59, 6.13 Hz, 1 H) 7.32 (d, J = 2.28 Hz, 1 H) 6.98-7.08 (m, 2 H) 6.53 (d, J = 2.38 Hz, 1 H) 3.90 (quin, J = 6.79 Hz, 1 H) 3.74 (s, 3 H) 3.67-3.73 (m, 1 H) 2.28 (s, 3 H) 1.39 (d, J = 2.38 Hz, 3 H) 1.37 (d, J = 2.28 Hz, 3 H). LCMS-ESI (pos.) m/z: 489.2 (M + H)$^+$. |

TABLE 13-continued

| Example | Reagents | Structure, Name and Data |
|---|---|---|
| 227.0 | (1S,2S)-1-isopropoxy-1-(5-methylpyrimidin-2-yl)propane-2-sulfonamide (Example 468.0), and 1,3-difluoro-2-isothiocyanatobenzene (Sigma Aldrich), 1-methyl-1H-pyrazole-3-carbohydrazide (ChemBridge Corporation). | (1S,2S)-N-(4-(2,6-difluorophenyl)-5-(1-methyl-1H-pyrazol-3-yl)-4H-1,2,4-triazol-3-yl)-1-(1-methylethoxy)-1-(5-methyl-2-pyrimidinyl)-2-propanesulfonamide.<br>$^1$H NMR (500 MHz, CDCl$_3$) δ 13.10 (br s, 1 H) 8.65 (s, 2 H) 7.41-7.52 (m, 1 H) 7.32 (d, J = 2.34 Hz, 1 H) 6.95-7.14 (m, 2 H) 6.44 (d, J = 2.21 Hz, 1 H) 4.88 (d, J = 3.37 Hz, 1 H) 3.77 (s, 3 H) 3.70-3.76 (m, 1 H) 3.53-3.62 (m, 1 H) 2.35 (s, 3 H) 1.56 (d, J = 7.01 Hz, 3 H) 1.10 (d, J = 5.97 Hz, 3 H) 0.98 (d, J = 6.10 Hz, 3 H). LCMS-ESI (pos.) m/z: 533.2 (M + H)$^+$. |
| 228.0 | (2S,3R)-3-(5-chloropyrimidin-2-yl)butane-2-sulfonamide (Example 464.4), 1,3-difluoro-2-isothiocyanatobenzene (Sigma Aldrich), and 1-methyl-1H-pyrazole-3-carbohydrazide (ChemBridge Corporation). | (2S,3R)-3-(5-chloro-2-pyrimidinyl)-N-(4-(2,6-difluorophenyl)-5-(1-methyl-1H-pyrazol-3-yl)-4H-1,2,4-triazol-3-yl)-2-butanesulfonamide.<br>$^1$H NMR (500 MHz, CDCl$_3$) δ 11.02 (br s, 1 H) 8.63 (s, 2 H) 7.44-7.54 (m, 1 H) 7.33 (d, J = 2.08 Hz, 1 H) 7.00-7.10 (m, 2 H) 6.54 (d, J = 2.34 Hz, 1 H) 3.89 (quin, J = 6.78 Hz, 1 H) 3.76-3.81 (m, 1 H) 3.75 (s, 3 H) 1.38 (app dd, J = 7.01, 2.21 Hz, 6 H). LCMS-ESI (pos.) m/z: 509.0 (M + H)$^+$. |
| 229.0 | (1R,2S)-1-(5-chloropyrimidin-2-yl)-1-methoxypropane-2-sulfonamide (Example 466.3), 1,3-difluoro-2-isothiocyanatobenzene (Sigma Aldrich), and 1-methyl-1h-pyrazole-3-carbohydrazide (ChemBridge Corporation). | (1R,2S)-1-(5-chloro-2-pyrimidinyl)-N-(4-(2,6-difluorophenyl)-5-(1-methyl-1H-pyrazol-3-yl)-4H-1,2,4-triazol-3-yl)-1-methoxy-2-propanesulfonamide.<br>$^1$H NMR (500 MHz, CDCl$_3$) δ 10.99 (br s, 1 H) 8.72 (s, 2 H) 7.44-7.53 (m, 1 H) 7.33 (d, J = 2.21 Hz, 1 H) 7.06 (t, J = 8.17 Hz, 2 H) 6.54 (d, J = 2.34 Hz, 1 H) 4.99 (d, J = 4.54 Hz, 1 H) 3.75 (s, 3 H) 3.67-3.74 (m, 1 H) 3.35 (s, 3 H) 1.39 (d, J = 7.01 Hz, 3 H). LCMS-ESI (pos.) m/z: 525.0 (M + H)$^+$. |

TABLE 13-continued

| Example | Reagents | Structure, Name and Data |
|---|---|---|
| 230.0 | (2S,3R)-3-(5-methoxypyrazin-2-yl)butane-2-sulfonamide (Example 464.5). 1,3-difluoro-2-isothiocyanatobenzene (Sigma Aldrich), and 1-methyl-1H-pyrazole-3-carbohydrazide (ChemBridge Corporation). | 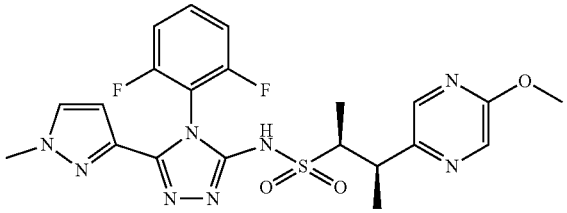<br>(2S,3R)-N-(4-(2,6-difluorophenyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (500 MHz, CDCl$_3$) δ 10.92 (br s, 1 H) 8.16 (s, 1 H) 7.96 (s, 1 H) 7.44-7.55 (m, 1 H) 7.33 (d, J = 2.08 Hz, 1 H) 7.05 (t, J = 8.30 Hz, 2 H) 6.55 (d, J = 2.08 Hz, 1 H) 3.94 (s, 3 H) 3.75-3.82 (m, 1 H) 3.74 (s, 3 H) 3.49-3.57 (m, 1 H) 1.36 (app t, J = 6.68 Hz, 6 H). LCMS-ESI (pos.) m/z: 505.2 (M + H)$^+$. |
| 231.0 | (2S,3R)-3-(5-methylpyrazin-2-yl)butane-2-sulfonamide (Example 464.2), 1,3-difluoro-2-sothiocyanatobenzene (Sigma Aldrich), and 1-methyl-1H-pyrazole-3-carbohydrazide (ChemBridge Corporation). | 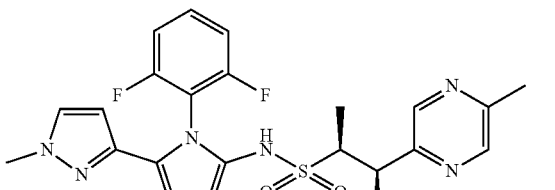<br>(2S,3R)-N-(4-(2,6-difluorophenyl)-5-(1-methyl-1H-pyrazol-3-yl)-4H-1,2,4-triazol-3-yl)-3-(5-methyl-2-pyrazinyl)-2-butanesulfonamide.<br>$^1$H NMR (500 MHz, CDCl$_3$) δ 10.93 (br s, 1 H) 8.38 (s, 1 H) 8.35 (s, 1 H) 7.44-7.55 (m, 1 H) 7.33 (d, J = 2.08 Hz, 1 H) 7.06 (t, J = 8.24 Hz, 2 H) 6.55 (d, J = 2.21 Hz, 1 H) 3.75-3.80 (m, 1 H) 3.74 (s, 3 H) 3.52-3.63 (m, 1 H) 2.54 (s, 3 H) 1.38 (m, 6 H). LCMS-ESI (pos.) m/z: 489.2 (M + H)$^+$. |
| 232.0 | (1R,2S)-1-methoxy-1-(5-methylpyrazin-2-yl)propane-2-sulfonamide (Example 466.1), 1,3-difluoro-2-sothiocyanatobenzene (Sigma Aldrich), and 1-methyl-1H-pyrazole-3-carbohydrazide (ChemBridge Corporation). | 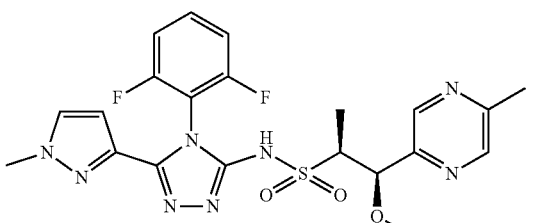<br>(1R,2S)-N-(4-(2,6-difluorophenyl)-5-(1-methyl-1H-pyrazol-3-yl)-4H-1,2,4-triazol-3-yl)-1-methoxy-1-(5-methyl-2-pyrazinyl)-2-propanesulfonamide.<br>$^1$H NMR (500 MHz, CDCl$_3$) δ 11.06 (br s, 1 H) 8.53 (s, 1 H) 8.46 (s, 1 H) 7.50 (tt, J = 8.53, 6.13 Hz, 1 H) 7.34 (d, J = 2.34 Hz, 1 H) 7.07 (ddd, J = 8.60, 7.23, 1.43 Hz, 2 H) 6.55 (d, J = 2.34 Hz, 1 H) 5.06 (d, J = 2.98 Hz, 1 H) 3.75 (s, 3 H) 3.54 (qd, J = 7.05, 2.98 Hz, 1 H) 3.34 (s, 3 H) 2.59 (s, 3 H) 1.27 (d, J = 7.01 Hz, 3 H). LCMS-ESI (pos.) m/z: 505.2 (M + H)$^+$. |

TABLE 13-continued

| Example | Reagents | Structure, Name and Data |
|---|---|---|
| 233.0 | (1R,2S)-1-methoxy-1-(5-methylpyrimidin-2-yl)propane-2-sulfonamide (Example 466.0), 1,3-difluoro-2-sothiocyanatobenzene (Sigma Aldrich), and 1-methyl-1H-pyrazole-3-carbohydrazide (ChemBridge Corporation). | 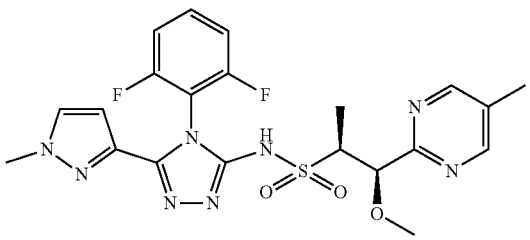<br>(1R,2S)-N-(4-(2,6-difluorophenyl)-5-(1-methyl-1H-pyrazol-3-yl)-4H-1,2,4-triazol-3-yl)-1-methoxy-1-(5-methyl-2-pyrimidinyl)-2-propanesulfonamide.<br>$^1$H NMR (500 MHz, CDCl$_3$) δ 11.23 (br s, 1 H) 8.61 (s, 2 H) 7.44-7.54 (m, 1 H) 7.33 (d, J = 2.34 Hz, 1 H) 7.05 (t, J = 8.11 Hz, 2 H) 6.51 (d, J = 2.34 Hz, 1 H) 4.98 (d, J = 4.41 Hz, 1 H) 3.75 (s, 3 H) 3.70-3.75 (m, 1 H) 3.34 (s, 3 H) 2.33 (s, 3 H) 1.39 (d, J = 7.01 Hz, 3 H). LCMS-ESI (pos.) m/z: 505.2 (M + H)$^+$. |

Example 234.0 1-(4-chlorophenyl)-N-(4-(2-methoxyphenyl)-5-(2-thiophenyl)-4H-1,2,4-triazol-3-yl)methanesulfonamide

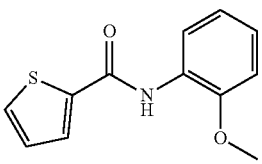

234.01

N-(2-Methoxyphenyl)thiophene-2-carboxamide, Example 234.01. To a 500 mL RBF was added o-anisidine (4.77 mL, 42.3 mmol) and TEA (11.77 mL, 85 mmol) in DCM (141 mL). At 0° C., thiophene-2-carbonyl chloride (4.97 mL, 46.5 mmol) was added dropwise via syringe. The reaction mixture was stirred at 0° C. to RT for the weekend. The reaction mixture was diluted with water and extracted with EtOAc. The organic extract was washed with brine and dried over Na$_2$SO$_4$. The solution was filtered and concentrated in vacuo to give Example 234.01 (9.9 g, 42.4 mmol, 100% yield) as a white powder, which was used directly in the next step without purification. LCMS-ESI (pos.), m/z: 234.1 (M+H)$^+$.

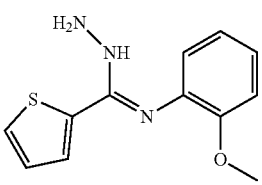

234.02

N-(2-Methoxyphenyl)thiophene-2-carbohydrazonamide, Example 234.02. To a 500 mL RBF was added Example 234.01 (9.9 g, 42.4 mmol) and thionyl chloride (30 mL, 411 mmol). The reaction mixture was stirred at 80° C. for 16 h. The reaction mixture was then concentrated in vacuo to give a tan oil. To a 500 mL RBF was added hydrazine (anhydrous, 33.3 mL, 1061 mmol) in benzene (100 mL). To this solution, at 0° C., was added (Z)-N-(2-methoxyphenyl)thiophene-2-carbimidoyl chloride in benzene (100 mL) dropwise. The reaction mixture was stirred at RT for 20 h. The reaction mixture was then diluted with water and extracted with Et$_2$O. The organic extract was washed with a saturated solution of NaHCO$_3$ and brine, and dried over Na$_2$SO$_4$. The solution was filtered and concentrated in vacuo to give Example 234.02 (10.45 g, 42.3 mmol, 100% yield) as a tan oil, which was used in the next step without purification. LCMS-ESI (pos.), m/z: 266.0 (M+H)$^+$.

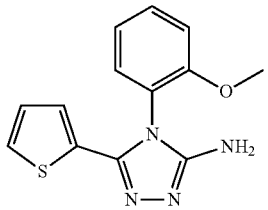

234.03

4-(2-Methoxyphenyl)-5-(thiophen-2-yl)-4H-1,2,4-triazol-3-amine, Example 234.03. To a 250 mL RBF was added Example 234.02 (3.58 g, 14.48 mmol) and cyanogen bromide (2.90 mL, 14.48 mmol) in MeOH (65.8 mL). The reaction mixture was stirred at 90° C. for 18 h. LCMS analysis indicated the reaction was complete. The solution was allowed to cool and concentrated in vacuo to give a tan oil. The residual mixture was diluted with a saturated solution of NaHCO$_3$ and extracted with DCM. The organic extract was washed with brine and dried over Na$_2$SO$_4$. The solution was filtered and concentrated in vacuo to give a tan glass. The material was absorbed onto a plug of silica gel and purified by chromatography through a Redi-Sep prepacked silica gel column (24 g, gold), eluting with a gradient of 60% to 100% EtOAc in DCM, to provide Example 234.03 (3.2 g, 11.75 mmol, 81% yield) as a light-yellow powder. LCMS-ESI (pos.), m/z: 273.0 (M+H)$^+$.

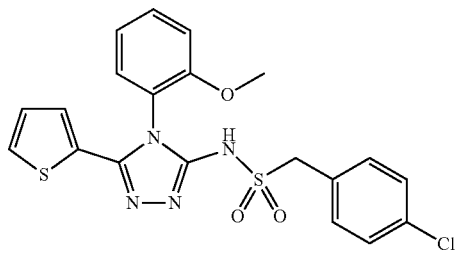

234.0

1-(4-Chlorophenyl)-N-(4-(2-methoxyphenyl)-5-(2-thiophenyl)-4H-1,2,4-triazol-3-yl)methanesulfonamide, Example 234.0. To a flask was added Example 234.03 (68 mg, 0.25 mmol) and (4-chloro-phenyl)-methanesulfonyl chloride (61.8 mg, 0.275 mmol) in pyridine (1 mL, 12.26 mmol). The reaction mixture was stirred at 50° C. for 14 h. LCMS analysis showed title product formed but the reaction was not complete. Additional (4-chloro-phenyl)-methanesulfonyl chloride (30 mg) was added and the reaction mixture was stirred at 80° C. for another 6 h. The reaction mixture was then concentrated in vacuo, diluted with DCM, washed with brine, and dried over Na$_2$SO$_4$. The solution was filtered and concentrated in vacuo to give a light-yellow oil. The material was purified by silica gel chromatography (10% to 80% EtOAc in DCM with 0.5 v/v % MeOH and 0.5 v/v % saturated NH$_3$—H$_2$O in EtOAc) and then reverse phase prep HPLC, to provide the title compound (62 mg, 60% yield) as a light yellow solid. $^1$H NMR (400 MHz, CDCl$_3$) δ 7.56-7.64 (m, 1H) 7.37 (dd, J=4.99, 1.27 Hz, 1H) 7.26-7.34 (m, 5H) 7.17 (td, J=7.63, 1.17 Hz, 1H) 7.10 (dd, J=8.41, 1.17 Hz, 1H) 6.86-6.99 (m, 2H) 4.23 (s, 2H) 3.76 (s, 3H). LCMS-ESI (pos.) m/z: 458.9 (M+H)$^+$.

Example 235.0. Preparation of 1-(4-chlorophenyl)-N-(5-(5-fluoro-2-thiophenyl)-4-(2-methoxyphenyl)-4H-1,2,4-triazol-3-yl)methanesulfonamide

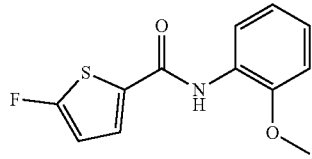

235.01

5-Fluoro-N-(2-methoxyphenyl)thiophene-2-carboxamide, Example 235.01. To a 500 mL RBF was added 5-fluorothiophene-2-carboxylic acid (commercially available from Aces Pharma, NJ, USA, 3.1 g, 20 mmol) and oxalyl chloride (8.9 mL, 100 mmol) in DCM (40 mL). The reaction mixture was stirred at RT for 4 h and 3 drops of DMF was added. The reaction mixture was stirred at RT for another 30 min. The reaction mixture was concentrated in vacuo to give the material as a tan oil (3.3 g). To the above product in DCM (40 mL) was added o-anisidine (2.3 mL, 20 mmol) and TEA (4.2 mL, 30 mmol). The reaction mixture was stirred at RT for 16 h. LCMS analysis showed the reaction was complete. The reaction mixture was diluted with 1.0 N HCl and extracted with DCM. The organic extract was washed with brine and dried over Na$_2$SO$_4$. The solution was filtered and concentrated in vacuo to give the material as an orange oil. The material was absorbed onto a plug of silica gel and purified by chromatography through a Redi-Sep pre-packed silica gel column (120 g), eluting with a gradient of 0% to 60% EtOAc in hexanes, to provide the title compound, Example 235.01 (4.6 g, 18.3 mmol, 91% yield), as a light-yellow oil. LCMS-ESI (pos.) m/z: 252.1 (M+H)$^+$.

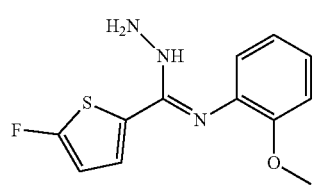

235.02

(Z)-5-Fluoro-N'-(2-methoxyphenyl)thiophene-2-carboximidhydrazide, Example 235.02. To a 500 mL RBF was added Example 235.01 (4.6 g, 18.3 mmol) and thionyl chloride (26.7 mL, 366 mmol). The reaction mixture was stirred at 60° C. for 20 h. The reaction mixture was concentrated in vacuo to give an orange oil (4.9 g). To the above product in toluene (100 mL), was added hydrazine (11.5 mL, 366 mmol) with stirring at RT. The reaction mixture was stirred at RT for 3 h. LCMS analysis showed the reaction was complete. The reaction mixture was diluted with water and extracted with Et$_2$O. The organic extract was washed with brine and dried over Na$_2$SO$_4$. The solution was filtered and concentrated in vacuo to give the title compound Example 235.02 as an orange glass. The material was used directly in the next step without purification. LCMS-ESI (pos.) m/z: 266.0 (M+H)$^+$.

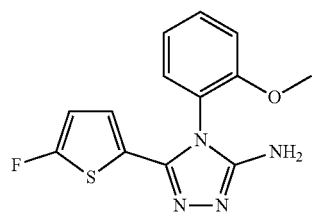

235.03

5-(5-Fluorothiophen-2-yl)-4-(2-methoxyphenyl)-4H-1,2,4-triazol-3-amine, Example 235.03. To a 500 mL RBF was added Example 235.02 (4.9 g, 18.3 mmol) and cyanogen bromide (5.0 M in ACN, 3.7 mL, 18.3 mmol) in MeOH (100 mL). The reaction mixture was stirred at 90° C. for 20 h. LCMS analysis showed formation of the title product. The reaction mixture was concentrated in vacuo to give the material as a tan oil. The reaction mixture was then diluted with a saturated solution of NaHCO$_3$ and extracted with DCM. The organic extract was washed with brine and dried over Na$_2$SO$_4$. The solution was filtered and concentrated in vacuo to give the title compound, Example 235.03 (5.3 g, 18.3 mmol, 100% yield), as an orange solid. The material was used directly in the next step without purification. LCMS-ESI (pos.) m/z: 291.0 (M+H)$^+$.

235.0

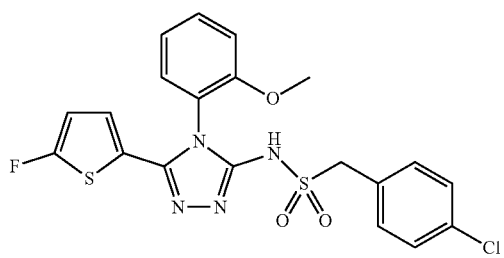

1-(4-Chlorophenyl)-N-(5-(5-fluoro-2-thiophenyl)-4-(2-methoxyphenyl)-4H-1,2,4-triazol-3-yl)methanesulfonamide, Example 235.0. Example 235.0 was prepared from Example 235.03 using the procedure described in Example 234.0. $^1$H NMR (400 MHz, CDCl$_3$) δ 7.51 (t, J=7.82 Hz, 1H) 7.15-7.22 (m, 5H) 7.07 (t, J=7.70 Hz, 1H) 7.01 (d, J=8.53 Hz, 1H) 6.41 (t, J=4.12 Hz, 1H) 6.23 (dd, J=4.30, 1.76 Hz, 1H) 4.12 (s, 2H) 3.70 (s, 3H). LCMS-ESI (pos.) m/z: 479.0 (M+H)$^+$.

Example 236.0. Preparation of 2-(4-chlorophenyl)-N-(4-(2-methoxyphenyl)-5-(thiophen-2-yl)-4H-1,2,4-triazol-3-yl)ethanesulfonamide 236.0

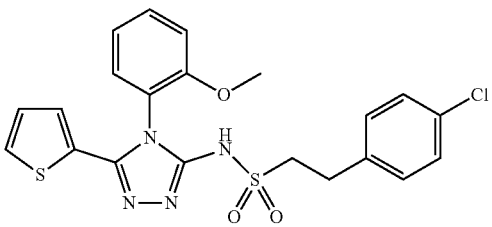

2-(4-Chlorophenyl)-N-(4-(2-methoxyphenyl)-5-(thiophen-2-yl)-4H-1,2,4-triazol-3-yl)ethanesulfonamide, Example 236.0. To a 10 mL RBF was added Example 234.03 (0.118 g, 0.433 mmol) and TEA (0.121 mL, 0.867 mmol) in DCM (4.33 mL). 2-(4-chlorophenyl)ethanesulfonyl chloride (commercially available from Oakwood Products, Inc., SC, USA, 0.124 g, 0.520 mmol). The reaction mixture was stirred at RT for 16 h. LCMS analysis showed formation of the title product. The reaction mixture was then diluted with water and extracted with DCM. The organic extract was washed with brine and dried over Na$_2$SO$_4$. The solution was filtered and concentrated in vacuo to give the material as a light-yellow glass. The material was absorbed onto a plug of silica gel and purified by chromatography through a Redi-Sep pre-packed silica gel column (12 g), eluting with a gradient of 0% to 40% EtOAc in hexanes, to provide Example 236.0 (0.08 g, 0.168 mmol, 39% yield) as a white solid. $^1$H NMR (400 MHz, CDCl$_3$) δ 10.88 (br. s, 1H), 7.58 (t, J=7.9 Hz, 1H), 7.35-7.39 (m, 1H), 7.23-7.35 (m, 3H), 7.05-7.18 (m, 4H), 6.90-6.99 (m, 2H), 3.71 (s, 3H), 3.21-3.37 (m, 2H), 3.04-3.15 (m, 2H). LCMS-ESI (pos.), m/z: 475.0 (M+H)$^+$.

Example 237.0. Preparation of 1-(4-chlorophenyl)-N-(4-(2-(difluoromethoxy)phenyl)-5-(2-thiophenyl)-4H-1,2,4-triazol-3-yl)methanesulfonamide 237.01

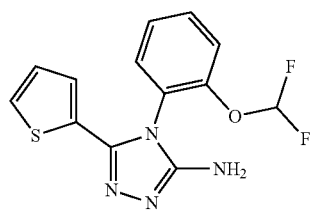

4-(2-(Difluoromethoxy)phenyl)-5-(thiophen-2-yl)-4H-1,2,4-triazol-3-amine, Example 237.01. Example 237.01 was prepared from 2-(difluoromethoxy)aniline (commercially available from Oakwood Products, Inc., SC, USA) instead of o-anisidine using the procedure described in Example 234.03. LCMS-ESI (pos.), m/z: 309.0 (M+H)$^+$.

237.0

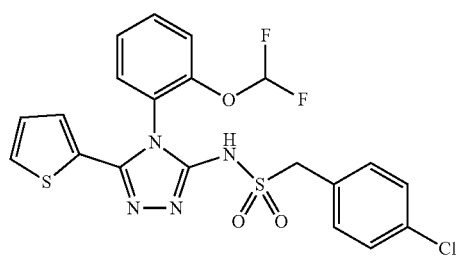

1-(4-Chlorophenyl)-N-(4-(2-(difluoromethoxy)phenyl)-5-(2-thiophenyl)-4H-1,2,4-triazol-3-yl)methanesulfonamide, Example 237.0. Example 237.0 was prepared from Example 237.01 using the procedure described in Example 235.0. $^1$H NMR (400 MHz, CDCl$_3$) δ 10.47 (br. s, 1H) 7.67 (td, J=7.92, 1.76 Hz, 1H) 7.34-7.50 (m, 4H) 7.30 (s, 2H) 7.03 (s, 1H) 6.96 (dd, J=5.09, 3.91 Hz, 1H) 6.89 (dd, J=3.91, 1.17 Hz, 1H) 6.38 (t, J=72 Hz, 1H) 4.23 (s, 2H). LCMS-ESI (pos.) m/z: 496.9 (M+H)$^+$.

Example 238.0. Preparation of N-(4-(2-methoxyphenyl)-5-(2-thiophenyl)-4H-1,2,4-triazol-3-yl)-2-phenylethanesulfonamide 238.0

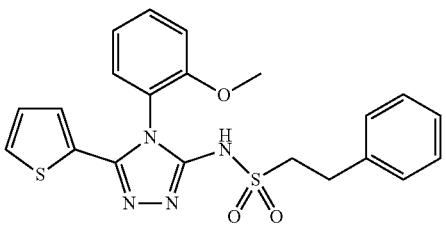

N-(4-(2-Methoxyphenyl)-5-(2-thiophenyl)-4H-1,2,4-triazol-3-yl)-2-phenylethanesulfonamide, Example 238.0. Example 238.0. was prepared from Example 234.03 and 2-phenyl-ethanesulfonyl chloride (commercially available from Oakwood Products, Inc., SC, USA) using the procedure described in Example 236.0. $^1$H NMR (400 MHz, CDCl$_3$) δ 10.90 (br. s, 1H) 7.58 (t, J=8.01 Hz, 1H) 7.37-7.40 (m, 1H) 7.17-7.33 (m, 6H) 7.14 (td, J=7.63, 1.17 Hz, 1H) 7.08 (dd, J=8.41, 1.17 Hz, 1H) 6.94-6.97 (m, 2H) 3.72 (s, 3H) 3.30-3.37 (m, 2H) 3.08-3.16 (m, 2H). LCMS-ESI (pos.) m/z: 441.0 (M+H)$^+$.

Example 239.0. Preparation of 2-(4-chlorophenyl)-N-(5-(5-fluorothiophen-2-yl)-4-(2-methoxyphenyl)-4H-1,2,4-triazol-3-yl)ethanesulfonamide

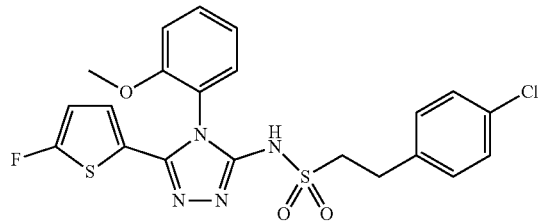

239.0

2-(4-Chlorophenyl)-N-(5-(5-fluorothiophen-2-yl)-4-(2-methoxyphenyl)-4H-1,2,4-triazol-3-yl)ethanesulfonamide, Example 239.0. To a 10 mL vial was added Example 235.03 (92 mg, 0.31 mmol) and TEA (88 µL, 0.63 mmol) in DCM (3 mL). 2-(4-Chlorophenyl)ethanesulfonyl chloride (commercially available from Oakwood Products, Inc., SC, USA, 83 mg, 0.35 mmol) was added with stirring at RT. The reaction mixture was stirred at RT for 4 d. LCMS analysis showed title product was formed and the starting material was consumed. The reaction mixture was then diluted with water and extracted with DCM. The organic extract was washed with brine and dried over Na$_2$SO$_4$. The solution was filtered and concentrated in vacuo to give the material as a tan oil. The material was absorbed onto a plug of silica gel and purified by silica gel chromatography (0% to 100% EtOAc in hexanes) to provide the title compound Example 239.0 (20 mg, 0.041 mmol, 13% yield) as a light-yellow solid. $^1$H NMR (400 MHz, CDCl$_3$) δ 7.36-7.59 (m, 1H), 7.11-7.25 (m, 4H), 6.92-7.11 (m, 3H), 6.43 (t, J=4.0 Hz, 1H), 6.24 (dd, J=4.3, 1.6 Hz, 1H), 3.64 (s, 3H), 3.26-3.12 (m, 2H), 3.03-2.92 (m, 2H). LCMS-ESI (pos.) m/z: 493.0 (M+H)$^+$.

Example 240.0. Preparation of 2-(4-chlorophenyl)-N-(4-(2-(difluoromethoxy)phenyl)-5-(thiophen-2-yl)-4H-1,2,4-triazol-3-yl)ethanesulfonamide

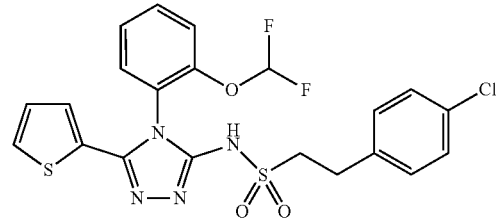

240.0

2-(4-Chlorophenyl)-N-(4-(2-(difluoromethoxy)phenyl)-5-(thiophen-2-yl)-4H-1,2,4-triazol-3-yl)ethanesulfonamide, Example 240.0. Example 240.0 was prepared from Example 237.01 using the procedure described in Example 236.0. $^1$H NMR (400 MHz, CDCl$_3$) δ 7.50-7.60 (m, 1H), 7.25-7.40 (m, 4H), 7.13-7.23 (m, 2H), 7.02 (d, J=8.4 Hz, 2H), 6.87 (dd, J=5.1, 3.9 Hz, 1H), 6.81 (dd, J=3.7, 1.2 Hz, 1H), 6.32 (t, J=71.8 Hz, 1H), 3.15-3.23 (m, 2H), 2.95-3.04 (m, 2H). LCMS-ESI (pos.), m/z: 511.0 (M+H)$^+$.

Example 241.0. Preparation of (P)-N-(4-(5-bromo-2-methoxyphenyl)-5-(2-thiophenyl)-4H-1,2,4-triazol-3-yl)-2-(4-chlorophenyl)-N-methylethanesulfonamide and (M)-N-(4-(5-bromo-2-methoxyphenyl)-5-(2-thiophenyl)-4H-1,2,4-triazol-3-yl)-2-(4-chlorophenyl)-N-methylethanesulfonamide

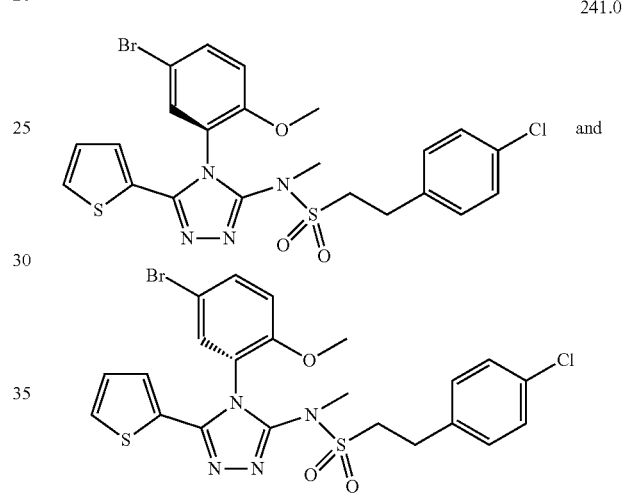

241.0 and (P)-N-(4-(5-Bromo-2-methoxyphenyl)-5-(2-thiophenyl)-4H-1,2,4-triazol-3-yl)-2-(4-chlorophenyl)-N-methylethanesulfonamide and (M)-N-(4-(5-bromo-2-methoxyphenyl)-5-(2-thiophenyl)-4H-1,2,4-triazol-3-yl)-2-(4-chlorophenyl)-N-methylethanesulfonamide, Example 241.0. To a 10 mL vial was added Example 133.0 (106 mg, 0.191 mmol) and cesium carbonate (187 mg, 0.574 mmol) in DMF (3 mL). Methyl iodide (0.024 mL, 0.383 mmol) was then added at RT. The reaction mixture was stirred at RT for 2 h. The reaction mixture was diluted with water and extracted with EtOAc. The organic extract was washed with brine and dried over Na$_2$SO$_4$. The solution was filtered and concentrated in vacuo to give the material as a light-yellow solid. The material was absorbed onto a plug of silica gel and purified by chromatography through a Redi-Sep pre-packed silica gel column (12 g), eluting with a gradient of 0% to 100% EtOAc in DCM, to provide Example 241.0 (80 mg, 0.141 mmol, 74% yield). $^1$H NMR (400 MHz, CDCl$_3$) δ 2.76-2.89 (m, 1H) 3.01-3.09 (m, 1H) 3.09-3.20 (m, 1H) 3.50-3.73 (m, 1H) 3.13 (s, 1.5H) 3.61 (s, 1.5H) 3.65 (s, 1.5H) 3.98 (s, 1.5H) 6.80-7.05 (m, 4H) 7.13-7.18 (m, 2H) 7.20-7.27 (m, 1H) 7.30 (ddd, J=10.76, 4.99, 1.27 Hz, 1H) 7.45-7.55 (m, 1H) 7.60 (ddd, J=8.90, 6.46, 2.45 Hz, 1H). LCMS-ESI (pos.), m/z: 566.9 (M+H)$^+$.

Example 242.0. Preparation of (1R,2S)-2-(4-chlorophenyl)-N-(4-(2-methoxyphenyl)-5-(thiophen-2-yl)-4H-1,2,4-triazol-3-yl)cyclopropane-1-sulfonamide and (1S,2R)-2-(4-chlorophenyl)-N-(4-(2-methoxyphenyl)-5-(thiophen-2-yl)-4H-1,2,4-triazol-3-yl)cyclopropane-1-sulfonamide

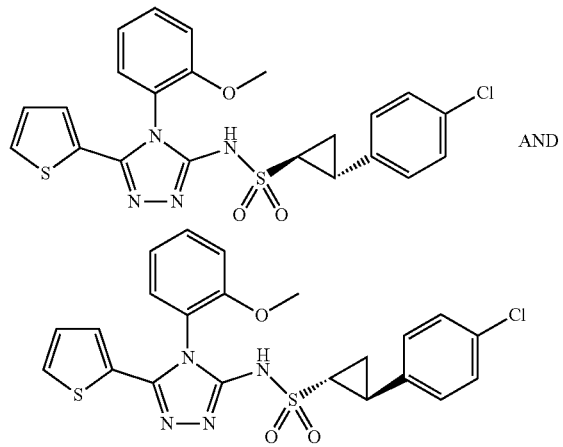

242.0

(1R,2S)-2-(4-Chlorophenyl)-N-(4-(2-methoxyphenyl)-5-(thiophen-2-yl)-4H-1,2,4-triazol-3-yl)cyclopropane-1-sulfonamide and (1S,2R)-2-(4-chlorophenyl)-N-(4-(2-methoxyphenyl)-5-(thiophen-2-yl)-4H-1,2,4-triazol-3-yl)cyclopropane-1-sulfonamide, Example 242.0. Example 242.0 was prepared from Example 234.0 and racemic trans-2-(4-chlorophenyl)cyclopropane-1-sulfonyl chloride (commercially available from Chemizon, a division of OptoMagic Co., Ltd, Seongnam Si, South Korea) using the procedure described in Example 236.0. $^1$H NMR (400 MHz, CDCl$_3$) δ 7.55 (t, J=7.88 Hz, 1H) 7.32-7.42 (m, 2H) 7.25 (d, J=8.22 Hz, 2H) 7.09-7.19 (m, 3H) 7.01-7.09 (m, 2H) 6.96 (dd, J=4.99, 3.81 Hz, 1H) 3.63 (d, J=17.22 Hz, 3H) 3.01-3.16 (m, 2H) 2.03-2.17 (m, 1H) 1.59-1.70 (m, 1H). LCMS-ESI (pos.) m/z: 487.0 (M+H)$^+$.

Example 243.0. Preparation of (1R,2S)-N-(4-(5-bromo-2-methoxyphenyl)-5-(2-thiophenyl)-4H-1,2,4-triazol-3-yl)-2-(4-chlorophenyl)cyclopropanesulfonamide and (1S,2R)-N-(4-(5-bromo-2-methoxyphenyl)-5-(2-thiophenyl)-4H-1,2,4-triazol-3-yl)-2-(4-chlorophenyl)cyclopropanesulfonamide 243.0

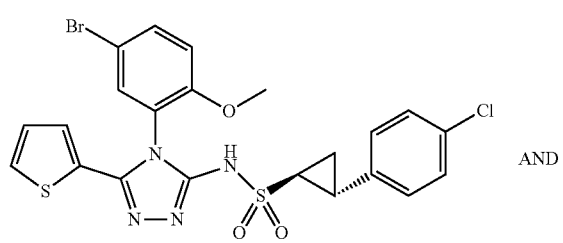

AND

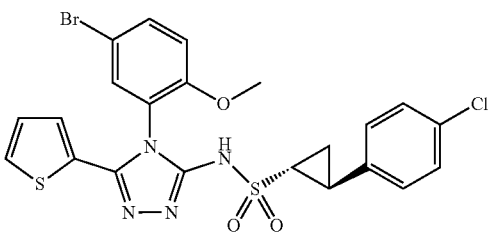

(1R,2S)-N-(4-(5-Bromo-2-methoxyphenyl)-5-(2-thiophenyl)-4H-1,2,4-triazol-3-yl)-2-(4-chlorophenyl)cyclopropanesulfonamide and (1S,2R)-N-(4-(5-bromo-2-methoxyphenyl)-5-(2-thiophenyl)-4H-1,2,4-triazol-3-yl)-2-(4-chlorophenyl)cyclopropanesulfonamide, Example 243.0. Example 243.0 was prepared from Example 133.01 and (1) trans-2-(4-chlorophenyl)cyclopropane-1-sulfonyl chloride (commercially available from Chemizon, a division of OptoMagic Co., Ltd, Seongnam Si, South Korea) using the procedure described in Example 236.0. $^1$H NMR (400 MHz, CDCl$_3$) δ 7.64 (dd, J=8.90, 2.45 Hz, 1H) 7.48 (dd, J=4.11, 2.54 Hz, 1H) 7.44 (dt, J=4.99, 1.03 Hz, 1H) 7.22-7.29 (m, 2H) 7.09-7.16 (m, 2H) 7.07 (dd, J=3.91, 1.17 Hz, 1H) 6.99 (dd, J=4.99, 3.81 Hz, 1H) 6.94 (dd, J=8.80, 2.54 Hz, 1H) 3.59-3.68 (m, 3H) 2.97-3.16 (m, 2H) 2.02-2.14 (m, 1H) 1.59-1.74 (m, 1H). LCMS-ESI (pos.) m/z: 565.0 (M+H)$^+$.

Example 244.0. Preparation of 2-(4-chlorophenyl)-N-(4-(2-(difluoromethoxy)phenyl)-5-(5-fluoro-2-thiophenyl)-4H-1,2,4-triazol-3-yl)ethanesulfonamide 244.0

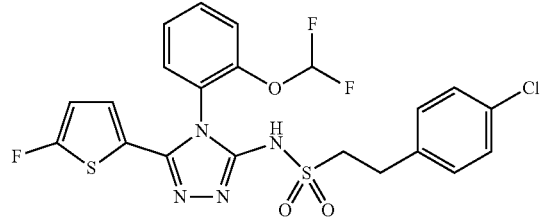

2-(4-Chlorophenyl)-N-(4-(2-(difluoromethoxy)phenyl)-5-(5-fluoro-2-thiophenyl)-4H-1,2,4-triazol-3-yl)ethanesulfonamide, Example 244.0. Example 244.0 was prepared from Example 237.01 using the procedure described in Example 236.0. $^1$H NMR (400 MHz, CDCl$_3$) δ 10.90 (br. s, 1H) 7.61-7.73 (m, 1H) 7.35-7.52 (m, 3H) 7.21-7.34 (m, 3H) 7.11 (d, J=8.22 Hz, 2H) 6.47 (t, J=4.21, 72 Hz, 1H) 6.42-6.54 (m, 1H) 6.36 (dd, J=4.21, 1.27 Hz, 1H) 3.21-3.39 (m, 2H) 2.98-3.18 (m, 2H). LCMS-ESI (pos.), m/z: 529.0 (M+H)$^+$.

Example 245.0. Preparation of 3-(3-(2-(4-chlorophenyl)ethylsulfonamido)-5-(thiophen-2-yl)-4H-1,2,4-triazol-4-yl)-4-methoxybenzoic acid

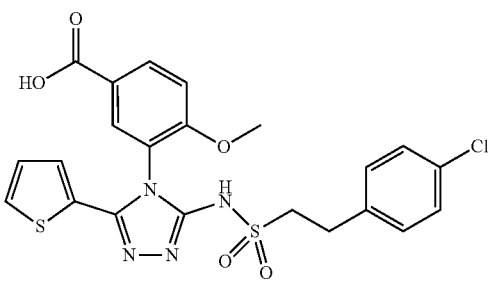

245.0

3-(3-(2-(4-Chlorophenyl)ethylsulfonamido)-5-(thiophen-2-yl)-4H-1,2,4-triazol-4-yl)-4-methoxybenzoic acid, Example 245.0. To a 50 mL vial was added Example 28.0 (80 mg, 0.146 mmol) and sodium hydroxide (2.5M, 175 µL, 0.439 mmol) in EtOH (487 µL, 0.146 mmol). The reaction mixture was stirred at RT for 4 h. LCMS analysis indicated the reaction was complete. The reaction mixture was diluted with water, acidified with AcOH and extracted with DCM. The organic extract was washed with brine and dried over $Na_2SO_4$. The solution was filtered and concentrated in vacuo to give the material as a tan oil. The material was absorbed onto a plug of silica gel and purified by chromatography through a Redi-Sep pre-packed silica gel column (4 g), eluting with a gradient of 0% to 40% MeOH in DCM, followed by reverse-phase preparative HPLC using a Phenomenex Gemini column, 10 micron, C18, 100 Å, 150×30 mm, 0.1% TFA in $ACN/H_2O$, gradient 5% to 95% over 30 min, to provide the title compound, Example 245.0 (5 mg, 9.63 gmol, 6.59% yield), as a white solid. $^1$H NMR (400 MHz, DMSO-$d_6$) δ 13.30 (br. s, 1H) 13.06 (br. s, 1H) 8.19 (dd, J=8.80, 2.15 Hz, 1H) 8.15 (s, 1H) 7.71 (d, J=4.7 Hz, 1H) 7.41 (d, J=8.80 Hz, 1H) 7.22-7.37 (m, 4H) 7.05 (dd, J=4.99, 3.81 Hz, 1H) 6.89 (d, J=3.13 Hz, 1H) 3.70-3.90 (m, 3H) 3.14-3.30 (m, 2H) 2.85-2.98 (m, 2H). LCMS-ESI (pos.), m/z: 519.0 (M+H)$^+$.

Example 246.0. Preparation of N-(4-(2-(difluoromethoxy)phenyl)-5-(5-fluoro-2-thiophenyl)-4H-1,2,4-triazol-3-yl)-2-phenylethanesulfonamide

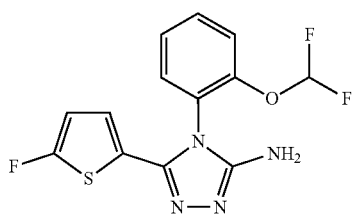

246.01

4-(2-(Difluoromethoxy)phenyl)-5-(5-fluorothiophen-2-yl)-4H-1,2,4-triazol-3-amine, Example 246.01. Example 246.01 was prepared from 2-(difluoromethoxy)aniline (commercially available from Oakwood Products, Inc., SC, USA) and 5-fluorothiophene-2-carboxylic acid (commercially available from Aces Pharma, NJ, USA) using the procedure described in Example 234.03. LCMS-ESI (pos.), m/z: 337.0 (M+H)$^+$.

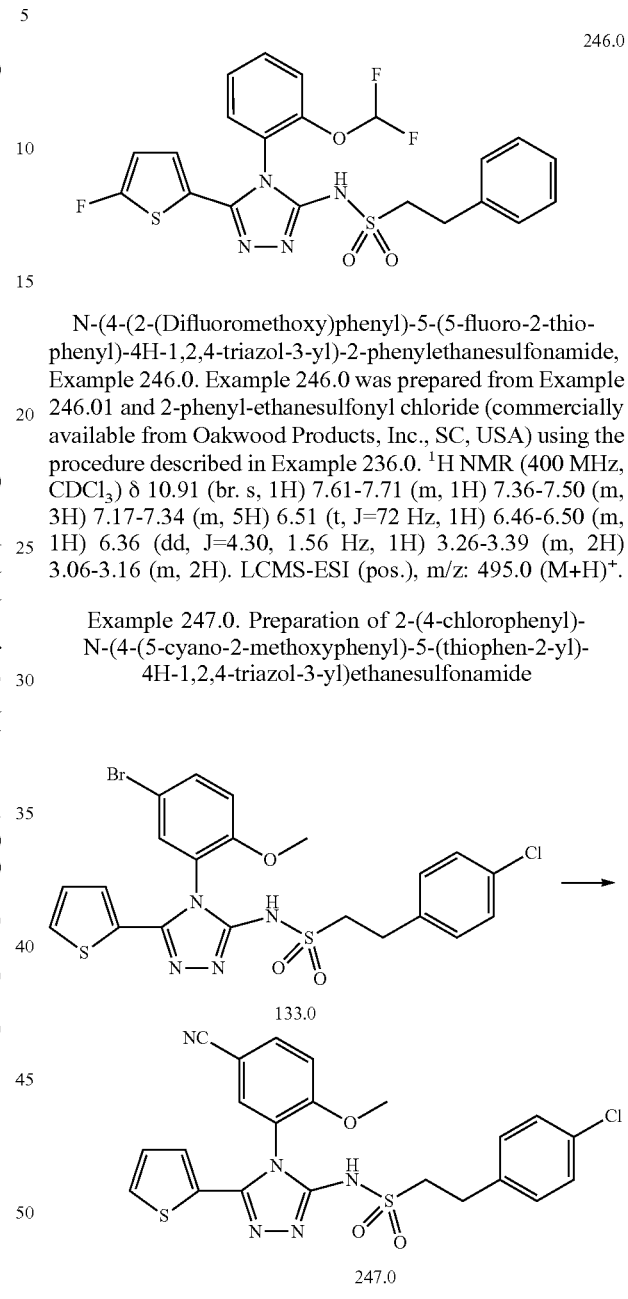

N-(4-(2-(Difluoromethoxy)phenyl)-5-(5-fluoro-2-thiophenyl)-4H-1,2,4-triazol-3-yl)-2-phenylethanesulfonamide, Example 246.0. Example 246.0 was prepared from Example 246.01 and 2-phenyl-ethanesulfonyl chloride (commercially available from Oakwood Products, Inc., SC, USA) using the procedure described in Example 236.0. $^1$H NMR (400 MHz, CDCl$_3$) δ 10.91 (br. s, 1H) 7.61-7.71 (m, 1H) 7.36-7.50 (m, 3H) 7.17-7.34 (m, 5H) 6.51 (t, J=72 Hz, 1H) 6.46-6.50 (m, 1H) 6.36 (dd, J=4.30, 1.56 Hz, 1H) 3.26-3.39 (m, 2H) 3.06-3.16 (m, 2H). LCMS-ESI (pos.), m/z: 495.0 (M+H)$^+$.

Example 247.0. Preparation of 2-(4-chlorophenyl)-N-(4-(5-cyano-2-methoxyphenyl)-5-(thiophen-2-yl)-4H-1,2,4-triazol-3-yl)ethanesulfonamide 2-(4-Chlorophenyl)-N-(4-(5-cyano-2-methoxyphenyl)-5-(thiophen-2-yl)-4H-1,2,4-triazol-3-yl)ethanesulfonamide, Example 247.0. A mixture of Example 133.0 (35 mg, 0.063 mmol), zinc cyanide (9 mg, 0.076 mmol) and tetrakis(triphenylphosphine)palladium (4 mg, 3.2 µmol) in DMF (0.6 mL) was combined in a 5 mL vial. The mixture was heated at 110° C. for 48 h. The mixture was partitioned between EtOAc and water resulting in an emulsion. The emulsion layer was removed and filtered through a coarse fritted funnel and worked up separately. The organic layers were combined, washed with brine, and evaporated to give a black solid. The material thus obtained was absorbed onto a plug of silica gel and purified by chromatography through a Redi-Sep pre-packed silica gel column (4 g), eluting with a gradient of 0% to 100% EtOAc in DCM, to provide the title compound, Example 247.0 (19 mg, 0.038 mmol, 60% yield), as an off-white solid. $^1$H NMR (400 MHz, CDCl$_3$) δ 10.87 (br. s, 1H) 7.88 (dd, J=8.71, 2.05 Hz, 1H) 7.52-7.56 (m, 1H) 7.43 (dd, J=3.52, 2.74 Hz, 1H) 7.25-7.34 (m, 3H) 7.13-7.16 (m, 2H) 6.99-7.05 (m, 2H) 3.79 (s, 3H) 3.27-3.38 (m, 2H) 3.06-3.18 (m, 2H). LCMS-ESI (pos.), m/z: 551.0 (M+H)$^+$.

Example 248.0. Preparation of 2-(4-chlorophenyl)-N-(4-(5-(3,6-dihydro-2H-thiopyran-4-yl)-2-methoxyphenyl)-5-(thiophen-2-yl)-4H-1,2,4-triazol-3-yl)ethanesulfonamide

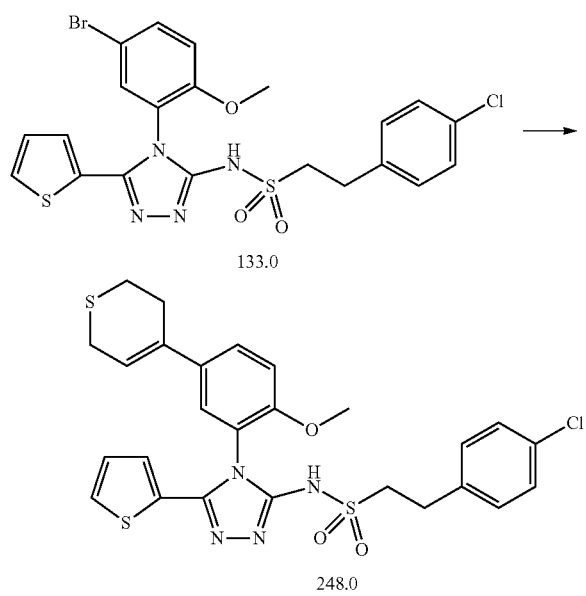

2-(4-Chlorophenyl)-N-(4-(5-(3,6-dihydro-2H-thiopyran-4-yl)-2-methoxyphenyl)-5-(thiophen-2-yl)-4H-1,2,4-triazol-3-yl)ethanesulfonamide, Example 248.0. A mixture Example 133.0 (268 mg, 0.484 mmol), 2-(3,6-dihydro-2H-thiopyran-4-yl)-4,4,5,5-tetramethyl-1,3,2-dioxaborolane (commercially available from Combiblocks, CA, USA) (131 mg, 0.58 mmol), 2-dicyclohexylphosphino-2',6'-dimethoxy-1'1'-biphenyl (40 mg, 0.1 mmol), palladium (II) acetate (10.9 mg, 0.048 mmol) and potassium phosphate (154 mg, 0.73 mmol) in dioxane (6 mL) was combined in a 30 mL vial. The mixture was heated at 100° C. for 18 h. The mixture was partitioned between EtOAc and water resulting in an emulsion. The emulsion layer was removed and filtered through a pad of Celite® brand filter aid. The combined organic layers were washed with brine and evaporated to give a black solid. The material thus obtained was absorbed onto a plug of silica gel and purified by chromatography through a Redi-Sep pre-packed silica gel column (24 g), eluting with a gradient of 0% to 100% EtOAc in DCM, to provide the title compound, Example 248.0 (70 mg, 0.122 mmol, 25.2% yield), as tan solid. $^1$H NMR (400 MHz, DMSO-d$_6$) δ 13.28 (s, 1H) 7.71 (dd, J=5.09, 1.17 Hz, 1H) 7.62-7.69 (m, 2H) 7.34 (d, J=7.49 Hz, 2H) 7.26 (d, J=7.63 Hz, 3H) 7.05 (dd, J=4.99, 3.81 Hz, 1H) 6.91 (dd, J=3.72, 1.17 Hz, 1H) 6.29 (t, J=5.28 Hz, 1H) 3.71 (s, 3H) 3.12-3.29 (m, 4H) 2.92 (t, J=8.12 Hz, 2H) 2.75-2.84 (m, 2H) 2.60 (br.s, 2H). LCMS-ESI (pos.), m/z: 573.0 (M+H)$^+$.

Example 249.0. Preparation of 2-(4-chlorophenyl)-N-(4-(2-methoxy-5-(2-oxooxazolidin-3-yl)phenyl)-5-(thiophen-2-yl)-4H-1,2,4-triazol-3-yl)ethanesulfonamide

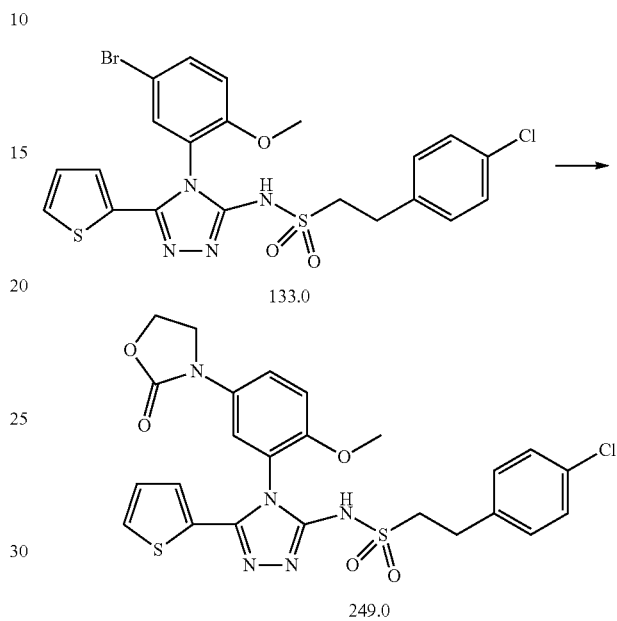

2-(4-Chlorophenyl)-N-(4-(2-methoxy-5-(2-oxooxazolidin-3-yl)phenyl)-5-(thiophen-2-yl)-4H-1,2,4-triazol-3-yl)ethanesulfonamide, Example 249.0. A mixture of Example 133.0 (168 mg, 0.303 mmol), potassium phosphate (129 mg, 0.607 mmol), 2-oxazolidinone (40 mg, 0.455 mmol), N,N'-dimethylethylenediamine (49 μL, 0.455 mmol) and copper (I) iodide (58 mg, 0.303 mmol) in dioxane (6 mL) was combined in a 10 mL vial. The mixture was heated at 110° C. for 15 h. The mixture was partitioned between EtOAc and water resulting in an emulsion. The emulsion layer was removed and filtered through a coarse fritted funnel and worked up separately. The organic layers were combined, washed with brine and evaporated to give a black solid. The material thus obtained was absorbed onto a plug of silica gel and purified by chromatography through a Redi-Sep pre-packed silica gel column (12 g), eluting with a gradient of 0% to 30% MeOH in DCM, to provide product enriched material, which was further purified by reverse-phase preparative HPLC using a Phenomenex Luna column, 5 micron, C18(2), 100 Å, 150×30 mm, 0.1% TFA in ACN/H$_2$O, gradient 5% to 100% over 35 min to provide Example 249.0 (55 mg, 0.098 mmol, 32% yield) as a white solid. $^1$H NMR (400 MHz, CDCl$_3$) δ 7.66 (dd, J=9.10, 2.84 Hz, 1H) 7.54 (d, J=2.74 Hz, 1H) 7.30 (dd, J=4.99, 1.08 Hz, 1H) 7.14-7.18 (m, 2H) 7.04 (d, J=8.41 Hz, 2H) 6.98 (d, J=9.00 Hz, 1H) 6.92 (dd, J=3.81, 1.08 Hz, 1H) 6.87 (dd, J=5.09, 3.72 Hz, 1H) 4.39-4.49 (m, 2H) 3.90-4.06 (m, 2H) 3.61 (s, 3H) 3.15-3.25 (m, 2H) 2.95-3.05 (m, 2H). LCMS-ESI (pos.), m/z: 560.0 (M+H)$^+$.

Example 250.0. Preparation of 2-(4-chlorophenyl)-N-(4-(5-(1,1-dioxido-3,6-dihydro-2H-thiopyran-4-yl)-2-methoxyphenyl)-5-(2-thiophenyl)-4H-1,2,4-triazol-3-yl)ethanesulfonamide

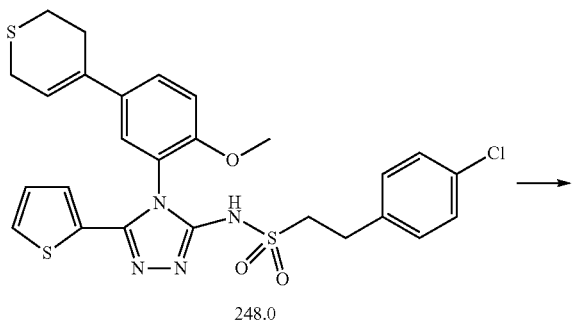

248.0

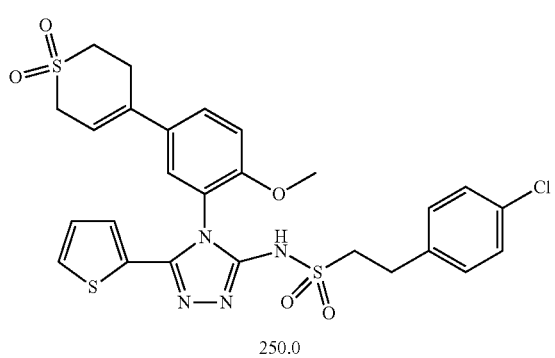

250.0

2-(4-Chlorophenyl)-N-(4-(5-(1,1-dioxido-3,6-dihydro-2H-thiopyran-4-yl)-2-methoxyphenyl)-5-(2-thiophenyl)-4H-1,2,4-triazol-3-yl)ethanesulfonamide, Example 250.0. To a 250 mL RBF was added Example 248.0 (170 mg, 0.297 mmol) in DCM (6 mL). At 0° C., 3-chloroperoxybenzoic acid (<77%) (166 mg, 0.74 mmol) was added. The reaction mixture was stirred at 0° C. for 40 min. LCMS analysis indicated the reaction was complete. The reaction mixture was then diluted with a saturated solution of $Na_2S_2O_3$ and extracted with DCM. The organic extract was washed with brine and dried over $Na_2SO_4$. The solution was filtered and concentrated in vacuo to give the material as a yellow glass. The material was absorbed onto a plug of silica gel and purified by chromatography through a Redi-Sep pre-packed silica gel column (4 g), eluting with a gradient of 0% to 100% EtOAc in DCM, to provide the title compound, Example 250.0 (35 mg, 0.058 mmol, 20% yield), as a yellow solid. Less pure fractions afforded another batch of the title compound, Example 250.0 (80 mg, 0.132 mmol, 44.6% yield), as a light yellow solid. $^1$H NMR (500 MHz, $CD_2Cl_2$) δ 10.80 (br. s, 1H) 7.54 (dd, J=8.80, 2.45 Hz, 1H) 7.32 (dd, J=4.89, 1.22 Hz, 1H) 7.26 (d, J=2.45 Hz, 1H) 7.14-7.21 (m, 2H) 6.98-7.07 (m, 3H) 6.83-6.92 (m, 2H) 5.78-5.87 (m, 1H) 3.66-3.72 (m, 2H) 3.61-3.66 (m, 3H) 3.09-3.18 (m, 4H) 3.00-3.09 (m, 2H) 2.91-2.98 (m, 2H). LCMS-ESI (pos.), m/z: 605.2 (M+H)$^+$.

Example 251.0. Preparation of 2-(4-chlorophenyl)-N-(4-(5-((2-hydroxyethyl)amino)-2-methoxyphenyl)-5-(2-thiophenyl)-4H-1,2,4-triazol-3-yl)ethanesulfonamide

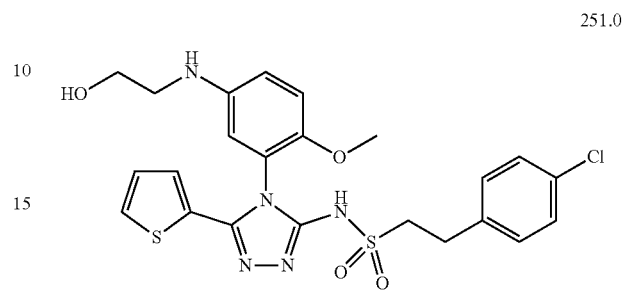

251.0

2-(4-Chlorophenyl)-N-(4-(5-((2-hydroxyethyl)amino)-2-methoxyphenyl)-5-(2-thiophenyl)-4H-1,2,4-triazol-3-yl)ethanesulfonamide, Example 251.0. Example 251.0 was obtained as a side-product in the preparation of Example 249.0. $^1$H NMR (400 MHz, $CD_3OD$) δ 7.56 (dd, J=4.99, 1.08 Hz, 1H) 7.25-7.34 (m, 2H) 7.19-7.25 (m, 2H) 7.16 (s, 2H) 6.99-7.07 (m, 2H) 6.96 (br. s, 1H) 3.71-3.81 (m, 2H) 3.68 (s, 3H) 3.26-3.34 (m, 4H) 3.02-3.11 (m, 2H). LCMS-ESI (pos.), m/z: 534.0 (M+H)$^+$.

Example 252.0. Preparation of 2-(4-chlorophenyl)-N-(4-(5-(dimethylamino)-2-methoxyphenyl)-5-(2-thiophenyl)-4H-1,2,4-triazol-3-yl)ethanesulfonamide

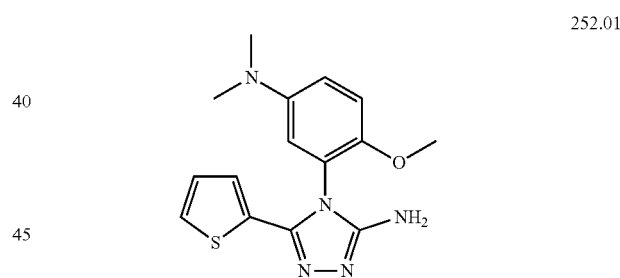

252.01

4-(5-(Dimethylamino)-2-methoxyphenyl)-5-(thiophen-2-yl)-4H-1,2,4-triazol-3-amine, Example 252.01. In the preparation of Example 303.0, a by-product, Example 252.01 (160 mg), was isolated as a tan solid. LCMS-ESI (pos.) m/z: 316.1 (M+H)$^+$.

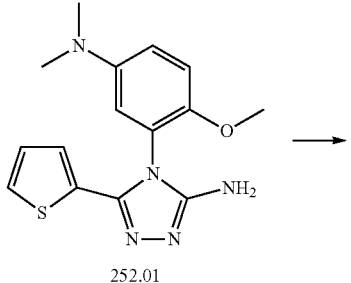

252.01

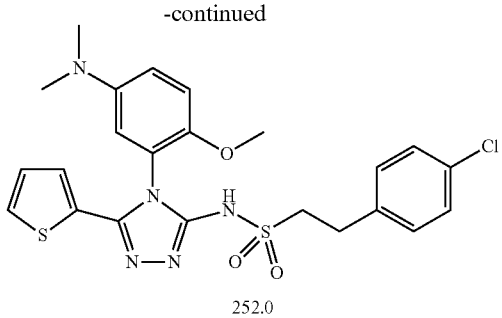

252.0

2-(4-Chlorophenyl)-N-(4-(5-(dimethylamino)-2-methoxyphenyl)-5-(2-thiophenyl)-4H-1,2,4-triazol-3-yl)ethanesulfonamide, Example 252.0. Example 252.0 was prepared from Example 252.01 using the procedure described in Example 236.0. $^1$H NMR (500 MHz, DMSO-$d_6$) δ 13.24 (br. s, 1H) 7.70 (dd, J=5.01, 1.10 Hz, 1H) 7.33 (d, J=7.81 Hz, 2H) 7.25 (d, J=7.89 Hz, 2H) 7.16 (d, J=9.05 Hz, 1H) 6.98-7.06 (m, 3H) 6.90 (dd, J=3.67, 1.22 Hz, 1H) 3.54-3.62 (s, 3H) 3.16-3.29 (m, 2H) 2.92 (t, J=8.19 Hz, 2H) 2.86 (m, 6H). LCMS-ESI (pos.) m/z: 515.0 (M+H)$^+$.

Example 253.0. Preparation of (3R,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3R,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide

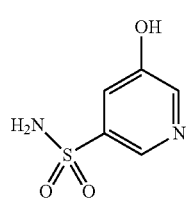

253.01

5-Hydroxypyridine-3-sulfonamide, Example 253.01. To a 100 mL RBF was added 5-bromopyridine-3-sulfonamide (commercially available from Enamine, KIEV, Ukraine, 0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.164 mmol) and Pd$_2$(dba)$_3$ (Sigma-Aldrich Chemical Company, Inc.) (0.038 g, 0.041 mmol). The flask was placed under vacuum and filled with a potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was allowed to cool to RT and then was diluted with 1.0 N HCl and extracted with Et$_2$O. An insoluble white solid was removed by filtration, the aqueous phase was concentrated in vacuo to afford the title compound Example 253.01 (0.387 g) as a white solid, which was directly used in the next step. LCMS-ESI (pos.), m/z: 175.1 (M+H)$^+$.

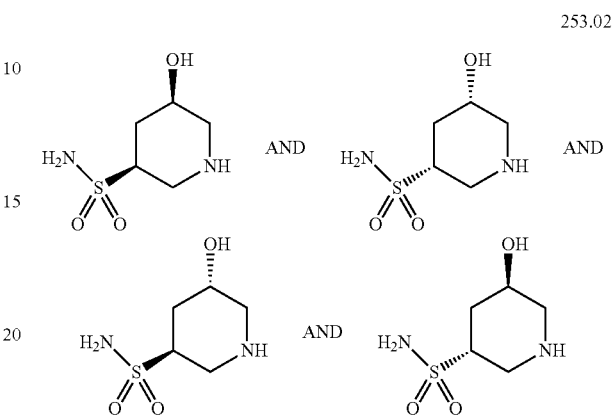

253.02

(3R,5R)-5-Hydroxypiperidine-3-sulfonamide and (3S,5R)-5-hydroxypiperidine-3-sulfonamide and (3R,5S)-5-hydroxypiperidine-3-sulfonamide and (3S,5S)-5-hydroxypiperidine-3-sulfonamide, Example 253.02. To a 1-L hydrogenation flask was added Example 253.01 (6.46 g, 37.1 mmol) and AcOH (250 mL, 4330 mmol). Water (20 mL) was added as a co-solvent. The mixture was sparged with N$_2$ for 2 min before platinum (IV) oxide hydrate (8.42 g, 37.1 mmol) was added under an atmosphere of N$_2$. The flask was set up on a shaker, placed under vacuum and back-filled with N$_2$ twice, and then evacuated and back-filled with hydrogen gas. The reaction mixture was stirred at RT under 50 psi of hydrogen gas for 24 h. LCMS analysis indicated the reaction was complete. Celite® brand filter aid (20 g) was added to the mixture with stirring. The solid was removed by filtration after 10 min of stirring. The cake was rinsed with MeOH. The combined organics were concentrated in vacuo to afford Example 253.02 (8.91 g, 100% yield) as a light-yellow oil which was directly used in the next step without purification. LCMS-ESI (pos.) m/z: 181.1 (M+H)$^+$.

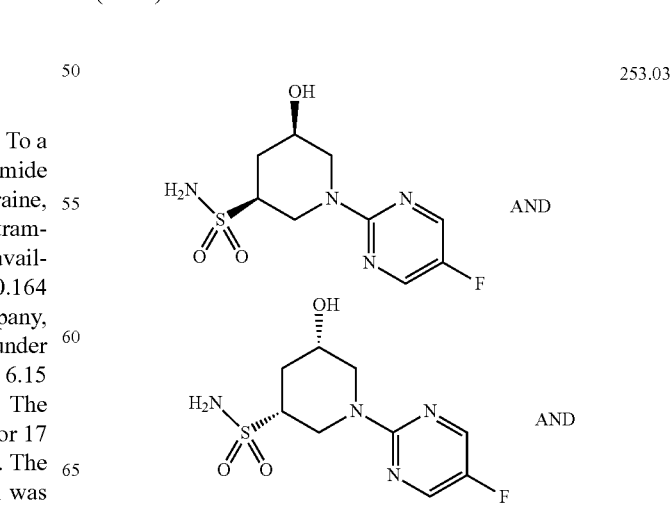

253.03

341

-continued

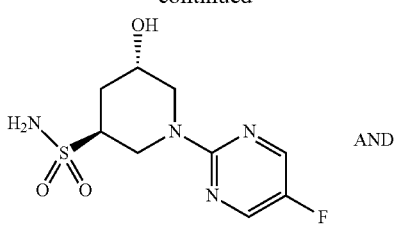

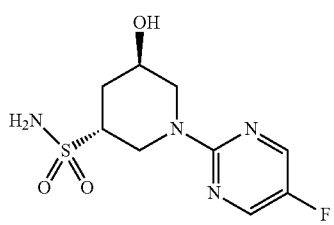

(3R,5R)-1-(5-Fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3S,5S)-1-(5-fluoropyrimidin-2-yl)-5-hydroxypiperidine-3-sulfonamide, Example 253.03. To a 500 mL RBF was added Example 253.02 (8.91 g, 37.1 mmol) and Hunig's base (32.3 mL, 185 mmol) in DMF (80 mL). 2-Chloro-5-fluoro-pyrimidine (18.32 mL, 148 mmol) was added with stirring. The reaction mixture was stirred at 120° C. for 18 h. LCMS analysis indicated the reaction was complete. The reaction mixture was then allowed to cool to RT. The reaction mixture was diluted with water and extracted with DCM. The organic extract was washed with brine and dried over Na$_2$SO$_4$. The solution was filtered and concentrated in vacuo to give an orange oil. The material was purified by silica gel chromatography (a gradient of 0% to 100% EtOAc in DCM), to provide Example 253.03 (3.7 g, 10.93 mmol, 36% yield) as a light-yellow solid. LCMS-ESI (pos.) m/z: 277.0 (M+H)$^+$.

253.0

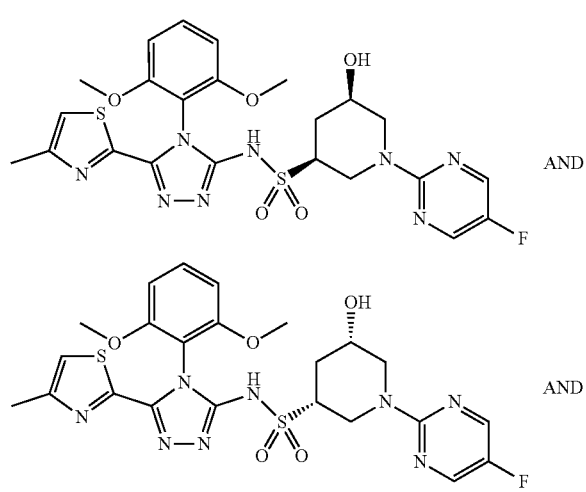

342

-continued

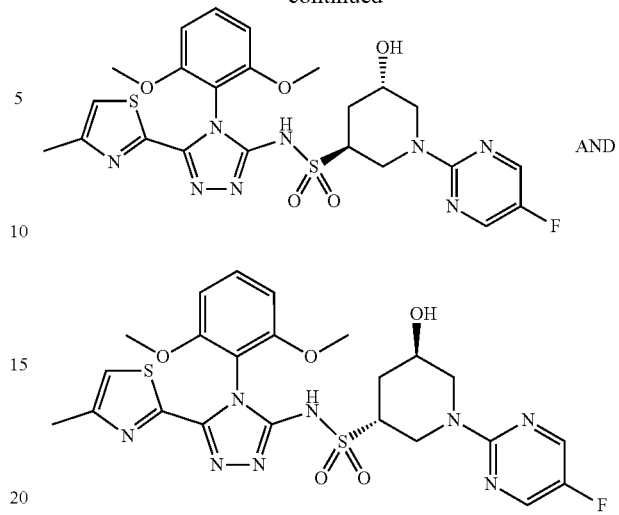

(3R,5R)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide and (3R,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide, Example 253.0. Example 253.0 was prepared from Example 399.0 and Example 253.03 using the procedure described in Example 135.0. The title compound Example 253.0 was isolated as an off-white solid as a mixture of four isomers. LCMS-ESI (pos.), m/z: 577.1 (M+H)$^+$. The mixture was purified by SFC chiral separation and four isomers were obtained. The SFC chiral separation was carried on in the following three stages to obtain four pure enantiomers. First purification step: Run on Thar 80 SFC with 250×30 mm AS-H column with 48 g/min EtOH (neat)+32 g/min CO$_2$, 60% co-solvent at 80 g/min. Outlet pressure=100 bar; Temp.=25° C.; Wavelength=215 nm. Used 1.5 mL injections of 38.0 mg sample dissolved in 3.0 mL of MeOH, 2.0 mL of DCM c=7.6 mg/mL, resulting in 11.4 mg/injection. Second Purification step: Run on Thar 80 SFC with 250×30 mm AS-H column with 32 g/min EtOH (neat)+48 g/min CO$_2$, 40% co-solvent at 80 g/min. Outlet pressure=100 bar; Temp.=21° C.; Wavelength=215 nm. Used 0.6-1.2 mL injections of 18.0 mg sample dissolved in 3.0 mL of MeOH, 1.0 mL of DCM c=4.5 mg/mL, resulting in 2.7-3.2 mg/injection. Third purification step: Run on Thar 80 SFC with 250×30 mm OJ-H column with 16 g/min EtOH (neat)+64 g/min CO$_2$, 20% co-solvent at 80 g/min. Outlet pressure=100 bar; Temp.=22° C.; Wavelength=215 nm. Used 0.6 mL injections of 8.0 mg sample dissolved in 4.0 mL of MeOH, c=2.0 mg/mL, resulting in 1.2 mg/injection. Cycle time 5.5 min, run time 12 min.

Example 254.0. Preparation of (3R,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide

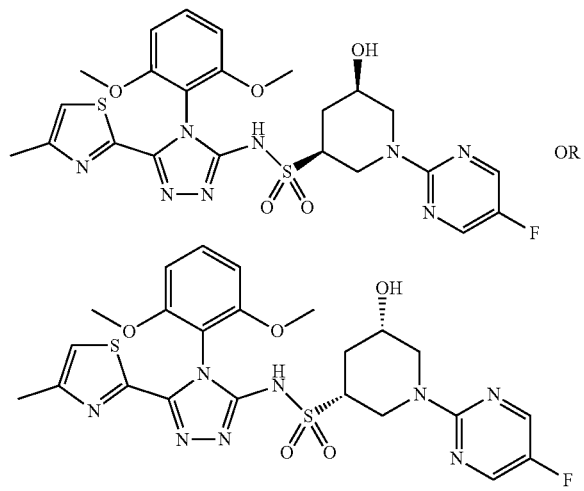

254.0

(3R,5S)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide, Example 254.0. Example 254.0 was prepared from SFC chiral separation of Example 253.0. Example 254.0 was the earlier cis isomer to elute from an AS-H column under the conditions described in Example 253.0. $^1$H NMR (500 MHz, CD$_2$Cl$_2$) δ 8.23 (s, 2H) 7.53 (t, J=8.56 Hz, 1H) 7.01 (s, 1H) 6.72 (dd, J=8.56, 2.93 Hz, 2H) 4.70 (dd, J=13.20, 3.18 Hz, 1H) 4.44 (d, J=10.27 Hz, 1H) 3.68-3.82 (m, 7H) 3.42 (dd, J=13.20, 9.54 Hz, 1H) 3.10-3.21 (m, 1H) 3.05 (dd, J=12.72, 9.05 Hz, 1H) 2.47 (d, J=12.23 Hz, 1H) 2.35 (s, 3H) 1.84-1.99 (m, 1H). LCMS-ESI (pos.), m/z: 577.1 (M+H)$^+$.

Example 255.0. Preparation of (3R,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide 255.0

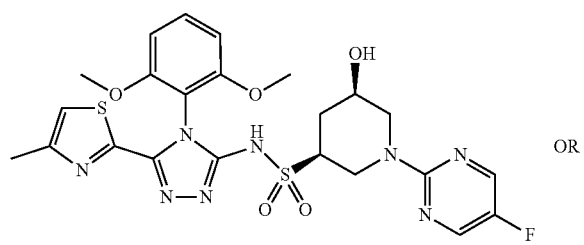

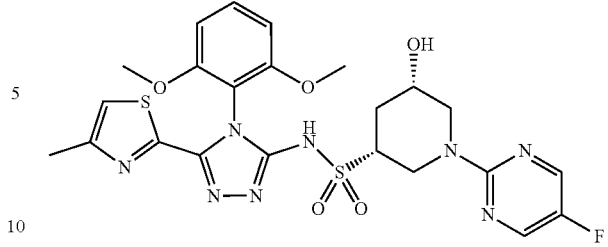

(3R,5S)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide, Example 255.0. Example 255.0 is the enantiomer of Example 254.0. Example 255.0 was the later (second) cis isomer to elute from an AS column under the conditions described in Example 253.0. $^1$H NMR (500 MHz, CD$_2$Cl$_2$) δ 8.23 (s, 2H) 7.53 (t, J=8.56 Hz, 1H) 7.01 (s, 1H) 6.72 (dd, J=8.56, 2.93 Hz, 2H) 4.70 (dd, J=13.20, 3.18 Hz, 1H) 4.44 (d, J=10.27 Hz, 1H) 3.68-3.82 (m, 7H) 3.42 (dd, J=13.20, 9.54 Hz, 1H) 3.10-3.21 (m, 1H) 3.05 (dd, J=12.72, 9.05 Hz, 1H) 2.47 (d, J=12.23 Hz, 1H) 2.35 (s, 3H) 1.84-1.99 (m, 1H). LCMS-ESI (pos.) m/z: 577.1 (M+H)$^+$.

Example 256.0. Preparation of (3R,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide 256.0

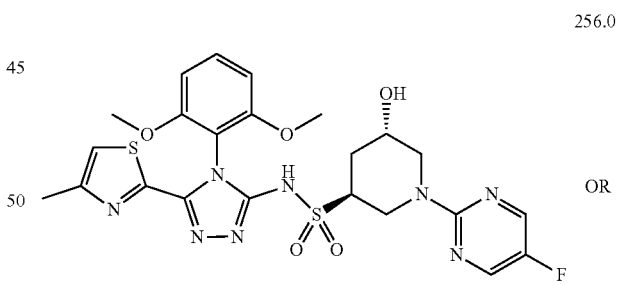

(3R,5R)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide, Example 256.0. Example 256.0 was prepared from SFC chiral separation of Example 253.0. Example 256.0 was the earlier trans isomer to elute from an AS column under the conditions described in Example 253.0. $^1$H NMR (500 MHz, CD$_3$OD) δ 8.25 (s, 2H) 7.55 (t, J=8.56 Hz, 1H) 7.23 (s, 1H) 6.83 (dd, J=8.56, 3.18 Hz, 2H) 4.96-5.04 (m, 1H) 4.59 (d, J=12.23 Hz, 1H) 4.14 (br. s, 1H) 3.79 (s, 3H) 3.78 (s, 3H) 3.51 (t, J=11.00 Hz, 1H) 3.17 (dd, J=12.96, 10.51 Hz, 1H) 3.05-3.13 (m, 1H) 2.33 (s, 3H) 2.28 (d, J=13.45 Hz, 1H) 1.91-2.04 (m, 1H). LCMS-ESI (pos.), m/z: 577.1 (M+H)$^+$.

Example 257.0. Preparation of (3R,5R)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide

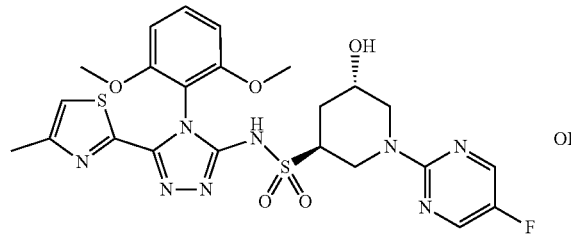

257.0

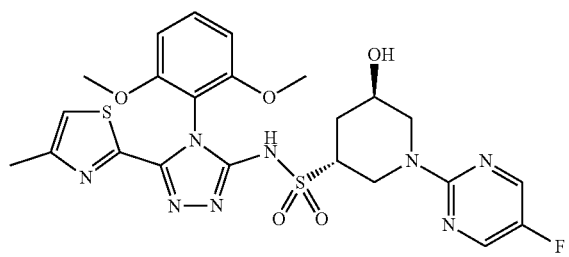

(3R,5R)-N-(4-(2,6-Dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide or (3S,5S)-N-(4-(2,6-dimethoxyphenyl)-5-(4-methyl-1,3-thiazol-2-yl)-4H-1,2,4-triazol-3-yl)-1-(5-fluoro-2-pyrimidinyl)-5-hydroxy-3-piperidinesulfonamide, Example 257.0. Example 257.0 is the enantiomer of Example 256.0. Example 257.0 was the later (second) trans isomer to elute from an AS column under the conditions described in Example 253.0. $^1$H NMR (500 MHz, CD$_3$OD) δ 8.25 (s, 2H) 7.55 (t, J=8.56 Hz, 1H) 7.23 (s, 1H) 6.83 (dd, J=8.56, 3.18 Hz, 2H) 4.96-5.04 (m, 1H) 4.59 (d, J=12.23 Hz, 1H) 4.14 (br. s, 1H) 3.79 (s, 3H) 3.78 (s, 3H) 3.51 (t, J=11.0 Hz, 1H) 3.17 (dd, J=12.96, 10.51 Hz, 1H) 3.05-3.13 (m, 1H) 2.33 (s, 3H) 2.28 (d, J=13.45 Hz, 1H) 1.91-2.04 (m, 1H). LCMS-ESI (pos.), m/z: 577.1 (M+H)$^+$.

Example 258.0. Preparation of (3R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide and (3S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide 258.0

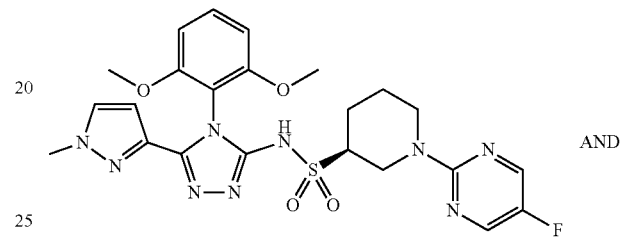

AND

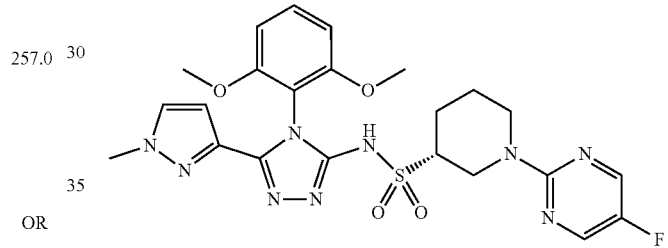

(3R)-N-(4-(2,6-Dimethoxyphenyl)-5-(1-methyl-1H-pyrazol-3-yl)-4H-1,2,4-triazol-3-yl)-1-(5-fluoro-2-pyrimidinyl)-3-piperidinesulfonamide and (3S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide, Example 258.0. To a 50 mL RBF was added Example 263.0 (0.68 g, 0.363 mmol), 2-chloro-5-fluoropyrimidine carboxylate (commercially available from Combi-Blocks Inc., CA, USA, 0.224 mL, 1.82 mmol) and N,N-diisopropylethylamine (0.63 mL, 3.63 mmol) in DMSO (3 mL). The reaction mixture was stirred at 100° C. for 1.5 h. The reaction mixture was then allowed to cool to RT. The reaction mixture was diluted with water and extracted with DCM. The organic extract was washed with brine and dried over Na$_2$SO$_4$. The solution was filtered and concentrated in vacuo to give a brown oil, which was purified by silica gel chromatography (a gradient of 0% to 100% EtOAc in DCM) to provide the title compound, Example 258.0, as a white solid. $^1$H NMR (500 MHz, CD$_2$Cl$_2$) δ 10.99 (br. s, 1H) 8.20-8.27 (m, 2H) 7.48-7.56 (m, 1H) 7.22-7.36 (m, 1H) 6.70-6.78 (m, 2H) 6.11 (d, J=2.20 Hz, 1H) 5.00-5.11 (m, 1H) 4.65 (dd, J=13.20, 1.47 Hz, 1H) 3.83 (s, 3H) 3.76-3.81 (m, 6H) 2.95-3.13 (m, 2H) 2.83 (td, J=12.78, 2.81 Hz, 1H) 2.19-2.34 (m, 1H) 1.74-1.93 (m, 2H) 1.67 (br. s, 1H) 1.40-1.59 (m, 1H). LCMS-ESI (pos.), m/z: 544.3 (M+H)$^+$.

Example 259.0. Preparation of (3R,5S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide and (3S,5R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide 259.0

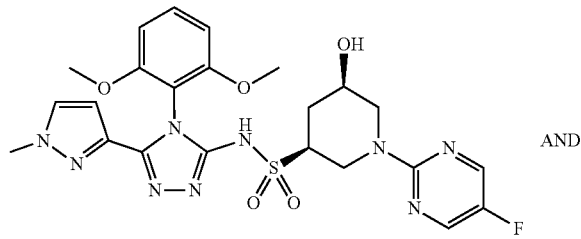

AND

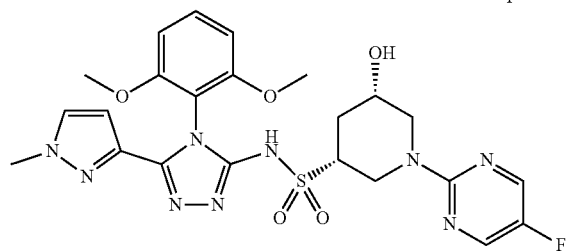

(3R,5S)-N-(4-(2,6-Dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide and (3S,5R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide, Example 259.0. Example 259.0 was prepared from Example 253.03, 2-isothiocyanato-1,3-dimethoxybenzene, Example 465.0, and 1-methyl-H-pyrazole-3-carbohydrazide (commercially available from ChemBridge Corporation, CA, USA) using the procedure described in Example 350.1. The title compound was isolated as the major isomer. $^1$H NMR (500 MHz, CD$_3$OD) δ 8.29 (s, 2H) 7.49-7.53 (m, 2H) 6.77-6.83 (m, 2H) 6.06 (s, 1H) 5.07-5.13 (m, 1H) 4.83 (dd, J=12.47, 4.65 Hz, 1H) 3.82 (s, 3H) 3.76-3.81 (m, 6H) 3.56-3.63 (m, 1H) 3.07-3.16 (m, 1H) 2.87 (dd, J=12.84, 11.62 Hz, 1H) 2.49-2.58 (m, 2H) 1.67 (q, J=12.15 Hz, 1H). LCMS-ESI (pos.), m/z: 560.2 (M+H)$^+$.

Example 260.0. Preparation of N-(4-(2,6-dimethoxyphenyl)-5-(1-methyl-1H-pyrazol-3-yl)-4H-1,2,4-triazol-3-yl)methanesulfonamide 260.0

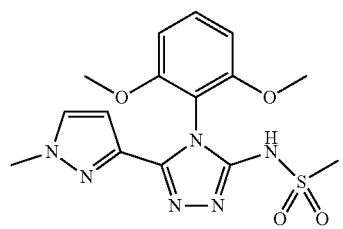

N-(4-(2,6-Dimethoxyphenyl)-5-(1-methyl-1H-pyrazol-3-yl)-4H-1,2,4-triazol-3-yl)methanesulfonamide, Example 260.0. Example 260.0 was prepared from methyl sulfonamide (Aldrich), Example 465.0.0, and 1-methyl-H-pyrazole-3-carbohydrazide (commercially available from ChemBridge Corporation, CA, USA) using the procedure described in Example 350.1. $^1$H NMR (400 MHz, DMSO-d$_6$) δ 13.13 (s, 1H) 7.69 (d, J=2.35 Hz, 1H) 7.49 (t, J=8.51 Hz, 1H) 6.83 (d, J=8.61 Hz, 2H) 6.09 (d, J=2.35 Hz, 1H) 3.74 (s, 3H) 3.72 (m, 6H) 2.82 (s, 3H). LCMS-ESI (pos.), m/z: 393.2 (M+H)$^+$.

Example 261.0. Preparation of (3R)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide or (3S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide 261.0

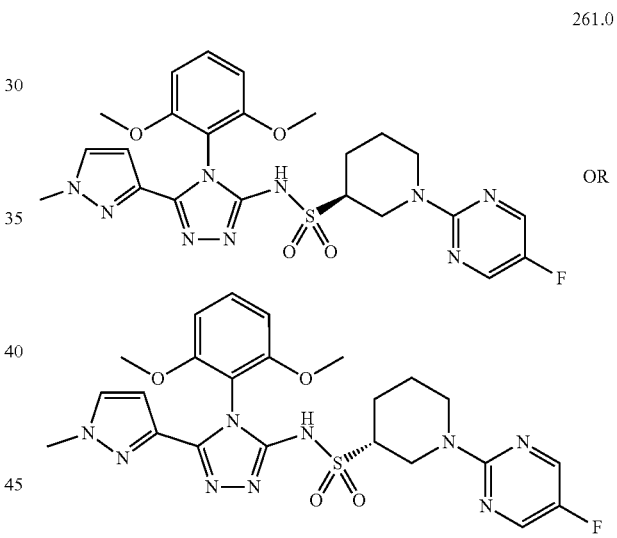

(3R)-N-(4-(2,6-Dimethoxyphenyl)-5-(1-methyl-1H-pyrazol-3-yl)-4H-1,2,4-triazol-3-yl)-1-(5-fluoro-2-pyrimidinyl)-3-piperidinesulfonamide or (3S)-N-(4-(2,6-dimethoxyphenyl)-5-(1-methyl-1H-pyrazol-3-yl)-4H-1,2,4-triazol-3-yl)-1-(5-fluoro-2-pyrimidinyl)-3-piperidinesulfonamide, Example 261.0. Example 261.0 was the first isomer to elute from an AS column on subjecting Example 258.0 to the following SFC conditions: AS-H (2×25 cm), 35% MeOH/CO$_2$, 100 bar, 65 mL/min, 220 nm. Injection vol.: 1 mL, 3 mg/mL 1:1 DCM:MeOH solution of Example 258.0. $^1$H NMR (500 MHz, CD$_3$OD) δ 8.27 (s, 2H) 7.49-7.54 (m, 2H) 6.79-6.83 (m, 2H) 6.07 (d, J=2.20 Hz, 1H) 5.07 (d, J=12.23 Hz, 1H) 4.64 (d, J=13.45 Hz, 1H) 3.83 (s, 3H) 3.78 (s, 3H) 3.77 (s, 3H) 2.98-3.10 (m, 2H) 2.82 (td, J=12.84, 2.69 Hz, 1H) 2.27 (d, J=12.96 Hz, 1H) 1.74-1.88 (m, 2H) 1.47-1.57 (m, 1H). LCMS-ESI (pos.), m/z: 544.3 (M+H)$^+$.

Example 262.0. Preparation of (3R)-N-(4-(2,6-di-
methoxyphenyl)-5-(1-methyl-1H-pyrazol-3-yl)-4H-
1,2,4-triazol-3-yl)-1-(5-fluoro-2-pyrimidinyl)-3-pip-
eridinesulfonamide or (3S)-N-(4-(2,6-
dimethoxyphenyl)-5-(1-methyl-1H-pyrazol-3-yl)-
4H-1,2,4-triazol-3-yl)-1-(5-fluoro-2-pyrimidinyl)-3-
piperidinesulfonamide

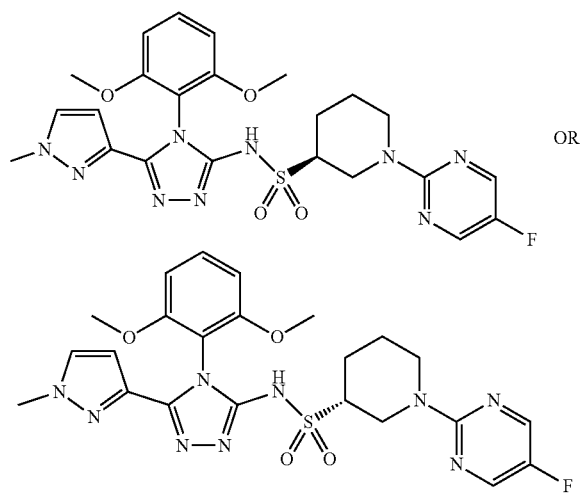

262.0

OR (3R)-N-(4-(2,6-Dimethoxyphenyl)-5-(1-methyl-1H-pyra-
zol-3-yl)-4H-1,2,4-triazol-3-yl)-1-(5-fluoro-2-pyrimidinyl)-
3-piperidinesulfonamide or (3S)-N-(4-(2,6-dimethoxyphe-
nyl)-5-(1-methyl-1H-pyrazol-3-yl)-4H-1,2,4-triazol-3-yl)-
1-(5-fluoro-2-pyrimidinyl)-3-piperidinesulfonamide,
Example 262.0. Example 262.0 is the enantiomer of
Example 261.0. Example 262.0 was the second isomer to
elute from an AS column on subjecting Example 258.0
under the SFC conditions described in Example 261.0. $^1$H
NMR (500 MHz, CD$_3$OD) δ 8.27 (s, 2H) 7.49-7.54 (m, 2H)
6.79-6.83 (m, 2H) 6.07 (d, J=2.20 Hz, 1H) 5.07 (d, J=12.23
Hz, 1H) 4.64 (d, J=13.45 Hz, 1H) 3.83 (s, 3H) 3.78 (s, 3H)
3.77 (s, 3H) 2.98-3.10 (m, 2H) 2.82 (td, J=12.84, 2.69 Hz,
1H) 2.27 (d, J=12.96 Hz, 1H) 1.74-1.88 (m, 2H) 1.47-1.57
(m, 1H). LCMS-ESI (pos.), m/z: 544.3 (M+H)$^+$.

Example 263.0. Preparation of (3R)-N-(4-(2,6-di-
methoxyphenyl)-5-(1-methyl-1H-pyrazol-3-yl)-4H-
1,2,4-triazol-3-yl)-3-piperidinesulfonamide and
(3S)-N-(4-(2,6-dimethoxyphenyl)-5-(1-methyl-1H-
pyrazol-3-yl)-4H-1,2,4-triazol-3-yl)-3-piperidine-
sulfonamide 263.01

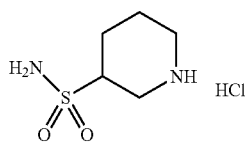

Piperidine-3-sulfonamide hydrochloride, Example
263.01. To a 100 mL RBF was added 4-chloro-3-pyridine-
sulfonamide (commercially available from Alfa Aesar, A Johnson Matthey Company, 0.56 g, 2.91 mmol) in AcOH
(25 mL). The resulting mixture was sparged with N$_2$ for 5
min before platinum (IV) oxide (commercially available
from Sigma-Aldrich, USA, 0.330 g, 1.454 mmol) was added
under N$_2$ flow. The flask was then sealed with a septum and
evacuated. Hydrogen gas was back-filled from a balloon.
The reaction mixture was stirred at RT under hydrogen gas
for 3 d. Next, 20 g of Celite® brand filter aid was added to
the reaction mixture with stirring. The solution was filtered
through a short pad of Celite® brand filter aid. The pad was
rinsed with MeOH. The combine organics was concentrated
in vacuo to give the material as a light-yellow glass. The
residue was triturated with DCM to afford the title com-
pound, Example 263.01 (0.6 g, 2.99 mmol, 103% yield), as
a light yellow solid. LCMS-ESI (pos.), m/z: 165.2 (M+H)$^+$.

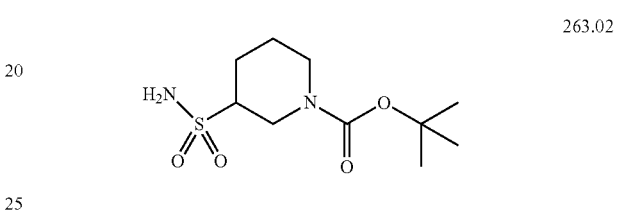

263.02 tert-Butyl 3-sulfamoylpiperidine-1-carboxylate, Example
263.02. A solution of di-tert-butyl dicarbonate (13.31 g, 61.0
mmol) in DCM (60.0 mL) was injected into a mixture of
Example 263.01 (10.2 g, 50.8 mmol) and TEA (35.4 mL,
254 mmol) in DCM (180 mL) in a 500 mL RBF. The
reaction mixture was stirred at RT for 24 h and was then
washed with 0.2 M HCl (2×200 mL) followed by water
(3×200 mL), The organic layer was then dried over Na$_2$SO$_4$.
The solution was filtered and concentrated in vacuo to give
the initial product which was purified by silica gel chroma-
tography (a gradient of 0% to 100% EtOAc in DCM) to
provide Example 263.02 (6.98 g, 26.4 mmol, 52.0% yield)
as a white powder. LCMS-ESI (pos.), m/z: 265.0 (M+H)$^+$.

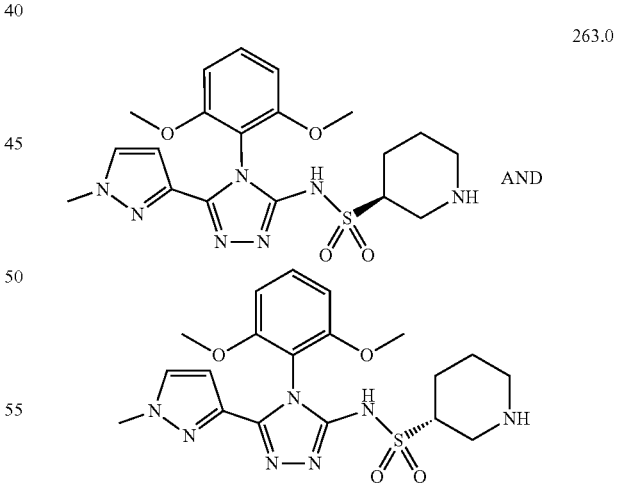

263.0

AND (3R)-N-(4-(2,6-Dimethoxyphenyl)-5-(1-methyl-1H-pyra-
zol-3-yl)-4H-1,2,4-triazol-3-yl)-3-piperidinesulfonamide
and (3S)-N-(4-(2,6-dimethoxyphenyl)-5-(1-methyl-1H-
pyrazol-3-yl)-4H-1,2,4-triazol-3-yl)-3-piperidinesulfona-
mide, Example 263.0. Example 263.0 was prepared from
Example 263.02, 2-isothiocyanato-1,3-dimethoxybenzene
Example 465.0, and 1-methyl-1H-pyrazole-3-carbohydraz-
ide (commercially available from ChemBridge Corporation, CA, USA) using the procedure described in Example 134.0 using TFA instead of methyl sulfonic acid (MSA). During the reaction, the Boc group was removed under the reaction conditions and the title compound Example 263.0 was isolated as a white solid as the TFA salt. $^1$H NMR (500 MHz, CD$_3$OD) δ 7.52-7.56 (m, 2H) 6.84 (d, J=8.63 Hz, 2H) 6.11 (d, J=2.61 Hz, 1H) 3.82 (s, 3H) 3.80 (s, 3H) 3.80 (s, 3H) 3.63 (dd, J=12.47, 4.16 Hz, 1H) 3.29-3.37 (m, 2H) 3.10 (dd, J=12.72, 10.76 Hz, 1H) 2.93 (td, J=12.17, 3.30 Hz, 1H) 2.23-2.29 (m, 1H) 2.11 (dt, J=14.43, 4.03 Hz, 1H) 1.80-1.88 (m, 1H) 1.69-1.78 (m, 1H). LCMS-ESI (pos.), m/z: 448.3 (M+H)$^+$.

Example 264.0. Preparation of (1S,2R)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide and (1R,2S)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide

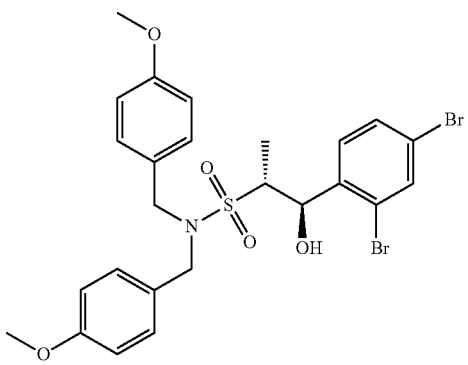

(1R,2R)-1-(2,4-Dibromophenyl)-1-hydroxy-N,N-bis(4-methoxybenzyl)propane-2-sulfonamide and (1R,2S)-1-(2,4-dibromophenyl)-1-hydroxy-N,N-bis(4-methoxybenzyl)propane-2-sulfonamide and (1S,2R)-1-(2,4-dibromophenyl)-1-hydroxy-N,N-bis(4-methoxybenzyl)propane-2-sulfonamide and (1S,2S)-1-(2,4-dibromophenyl)-1-hydroxy-N,N-bis(4-methoxybenzyl)propane-2-sulfonamide, Example 264.01. To a 250 mL RBF was added Example 467.0 (3.06 g, 8.76 mmol) in 2-methyltetrahydrofuran (21.89 mL). n-Butyllithium (2.5 M solution in hexanes, 4.20 mL, 10.51 mmol) was then added under N$_2$ at −78° C. with stirring. The reaction mixture was stirred at −78° C. for 10 min and then left at RT with stirring for 20 min. 2,4-Dibromobenzaldehyde (2.54 g, 9.63 mmol) in 2-methyltetrahydrofuran (21.89 mL) was added dropwise under N$_2$ at −78° C. with stirring. The reaction mixture was stirred at −78° C. for 1 h. LCMS analysis indicated formation of the title product. The reaction was quenched with a saturated aqueous solution of NH$_4$Cl and extracted with EtOAc. The organic extract was washed with brine and dried over Na$_2$SO$_4$. The solution was filtered and concentrated in vacuo to give the material as a light-yellow solid which was purified by silica gel chromatography (a gradient of 0% to 100% EtOAc in DCM), to provide Example 264.01 (4.9 g, 7.99 mmol, 91% yield) as a white solid, which was a mixture of diastereomers. LCMS-ESI (pos.), m/z: 634.0 (M+Na)$^+$.

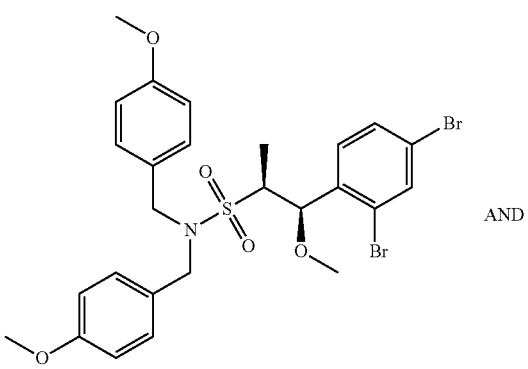

-continued

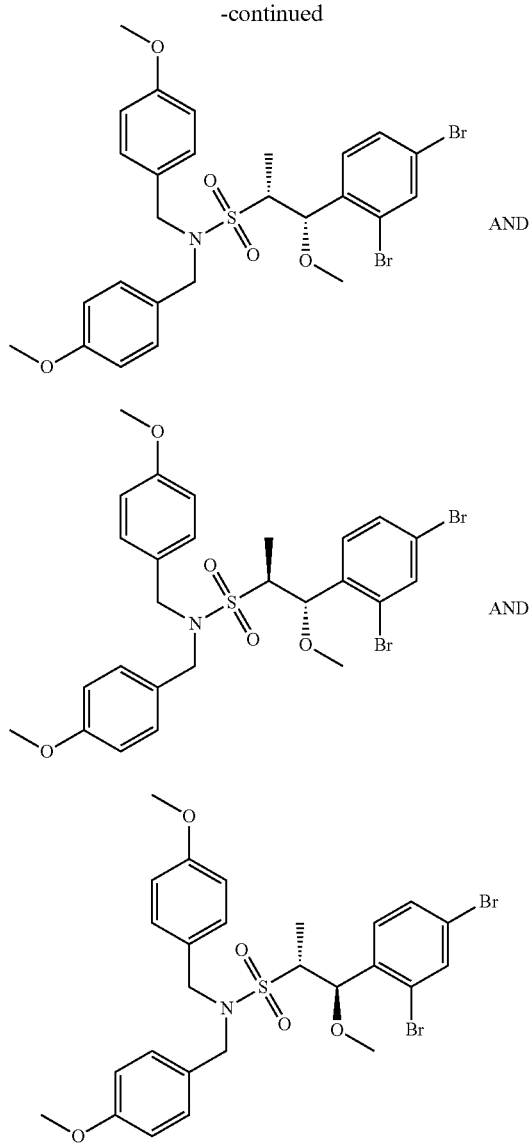

(1R,2R)-1-(2,4-Dibromophenyl)-1-methoxy-N,N-bis(4-methoxybenzyl)propane-2-sulfonamide and (1R,2S)-1-(2,4-dibromophenyl)-1-methoxy-N,N-bis(4-methoxybenzyl)propane-2-sulfonamide and (1S,2R)-1-(2,4-dibromophenyl)-1-methoxy-N,N-bis(4-methoxybenzyl)propane-2-sulfonamide and (1S,2S)-1-(2,4-dibromophenyl)-1-methoxy-N,N-bis(4-methoxybenzyl)propane-2-sulfonamide, Example 264.02. To a 250 mL RBF was added Example 264.01 (4.9 g, 7.99 mmol) in 2-methyltetrahydrofuran (53.3 mL). Potassium bis(trimethylsilyl)amide, (1.0 M in THF, 8.79 mL, 8.79 mmol) was added under N₂ at −78° C. with stirring. The reaction mixture was stirred at −78° C. for 10 min and then left at RT with stirring for 5 min. Iodomethane (stabilized, 0.546 mL, 8.79 mmol) was added dropwise under N₂ at −78° C. with stirring. The reaction mixture was then stirred at −78° C. for 30 min and then the dry ice-acetone bath was removed and the reaction was left at RT with stirring for 10 min. LCMS analysis indicated formation of the title product, but the reaction was not complete. The reaction mixture was stirred at RT for 16 h. The reaction mixture was then cooled to −78° C. again and quenched with a saturated aqueous solution of NaHCO₃. The reaction mixture was diluted with water and extracted with EtOAc. The organic extract was washed with brine and dried over Na₂SO₄. The solution was filtered and concentrated in vacuo to give the material as a light-yellow oil which was purified by silica gel chromatography (0% to 100% EtOAc in hexanes) to provide the title compound Example 264.02 (5.0 g, 7.97 mmol, 100% yield) as a white solid which was a mixture of diastereomers. LCMS-ESI (pos.), m/z: 626.0 (M+H)⁺.

264.03

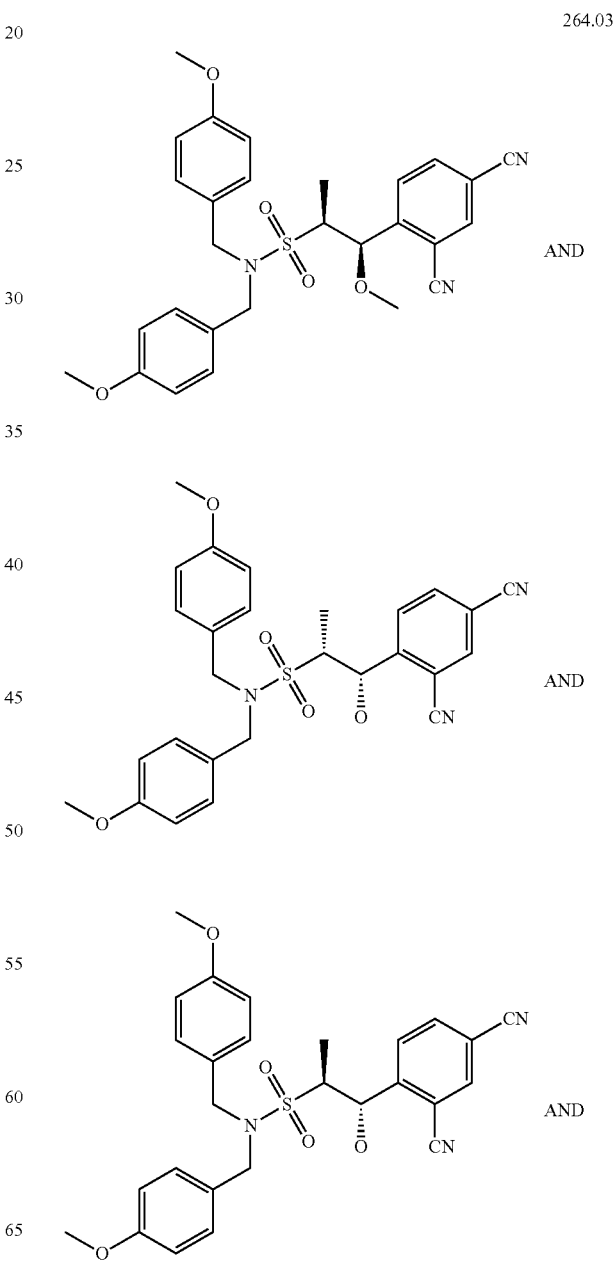

-continued

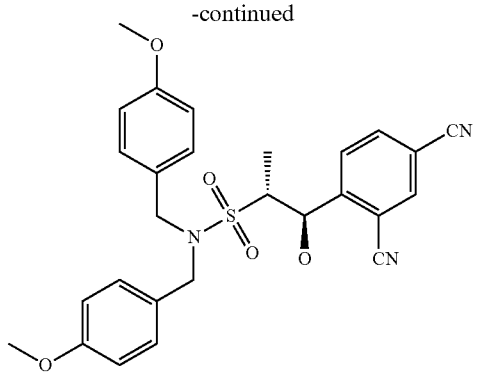

(1R,2R)-1-(2,4-Dicyanophenyl)-1-methoxy-N,N-bis(4-methoxybenzyl)propane-2-sulfonamide and (1R,2S)-1-(2,4-dicyanophenyl)-1-methoxy-N,N-bis(4-methoxybenzyl)propane-2-sulfonamide and (1S,2R)-1-(2,4-dicyanophenyl)-1-methoxy-N,N-bis(4-methoxybenzyl)propane-2-sulfonamide and (1S,2S)-1-(2,4-dicyanophenyl)-1-methoxy-N,N-bis(4-methoxybenzyl)propane-2-sulfonamide, Example 264.03. To a 250 mL RBF was added Example 264.02 (5.0 g, 7.97 mmol) in DMA (53.1 mL). Under $N_2$, zinc cyanide (2.059 g, 17.53 mmol) and bis(tri-tert-butylphosphine)palladium (0) (0.815 g, 1.594 mmol) were added. The reaction mixture was stirred at 100° C. for 15 h. The reaction mixture was then cooled and filtered. The solution was concentrated in vacuo at 75° C. The material was purified by silica gel chromatography (a gradient of 0% to 100% EtOAc in DCM) to provide Example 264.03 (4 g, 7.70 mmol, 97% yield) as a white solid which was a mixture of diastereomers. LCMS-ESI (pos.), m/z: 542.2 (M+Na)$^+$.

264.04

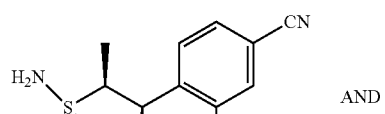
AND
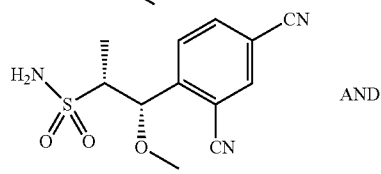
AND
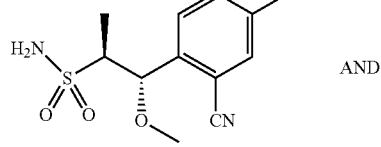
AND (1R,2R)-1-(2,4-Dicyanophenyl)-1-methoxypropane-2-sulfonamide and (1R,2S)-1-(2,4-dicyanophenyl)-1-methoxypropane-2-sulfonamide and (1S,2R)-1-(2,4-dicyanophenyl)-1-methoxypropane-2-sulfonamide and (1S,2S)-1-(2,4-dicyanophenyl)-1-methoxypropane-2-sulfonamide, Example 264.04. To a 250 mL RBF was added Example 264.03 (4 g, 7.70 mmol) and anisole (4.18 mL, 38.5 mmol) in TFA (42.8 mL, 7.70 mmol). The reaction mixture was stirred at RT for 15 h. The reaction mixture was concentrated in vacuo. The material was purified by silica gel chromatography (a gradient of 0% to 100% EtOAc in DCM), to provide Example 264.04 (1.6 g, 5.73 mmol, 74% yield) as a white solid which was a mixture of diastereomers. LCMS-ESI (pos.), m/z: 302.1 (M+Na)$^+$.

264.0

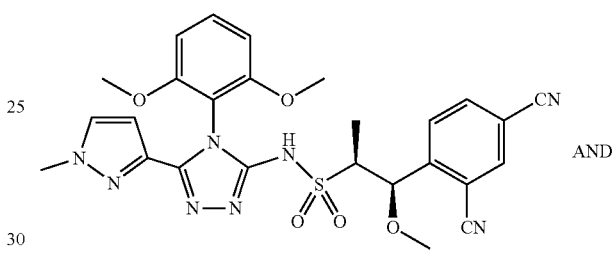
AND
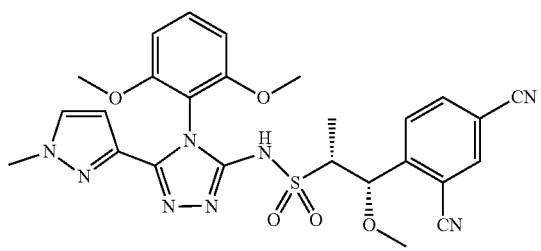

(1S,2R)-1-(2,4-Dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide and (1R,2S)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide, Example 264.0. Example 264.0 was prepared from Example 264.04, 2-isothiocyanato-1,3-dimethoxybenzene (Example 465.0), and 1-methyl-1H-pyrazole-3-carbohydrazide (commercially available from ChemBridge Corporation, CA, USA) using the procedure described in Example 350.1. The title compound Example 264.0 was isolated as the major product from the reaction by silica gel chromatography (30-100% of EtOAc in hexanes). $^1$H NMR (400 MHz, CD$_3$OD) δ 8.20 (d, J=1.57 Hz, 1H) 8.01 (dd, J=8.12, 1.66 Hz, 1H) 7.66 (d, J=8.22 Hz, 1H) 7.49-7.57 (m, 2H) 6.82 (d, J=8.27 Hz, 2H) 6.08 (d, J=2.35 Hz, 1H) 5.15 (d, J=4.11 Hz, 1H) 4.87 (s, 7H) 3.89-4.03 (m, 1H) 3.76-3.85 (m, 9H) 3.37-3.47 (m, 1H) 3.34 (dt, J=3.18, 1.64 Hz, 8H) 3.20 (s, 3H) 3.16-3.24 (m, 3H) 1.27 (d, J=7.04 Hz, 3H) 1.18 (d, J=6.06 Hz, 3H). LCMS-ESI (pos.), m/z: 563.2 (M+H)$^+$.

Example 265.0. Preparation of (1S,2R)-1-(2,4-di-
cyanophenyl)-N-(4-(2,6-dimethoxyphenyl)-5-(1-
methyl-1H-pyrazol-3-yl)-4H-1,2,4-triazol-3-yl)-1-
methoxy-2-propanesulfonamide or (1R,2S)-1-(2,4-
dicyanophenyl)-N-(4-(2,6-dimethoxyphenyl)-5-(1-
methyl-1H-pyrazol-3-yl)-4H-1,2,4-triazol-3-yl)-1-
methoxy-2-propanesulfonamide

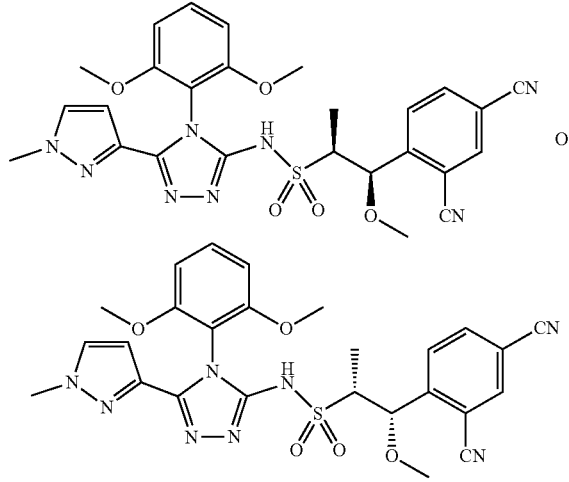

(1S,2R)-1-(2,4-Dicyanophenyl)-N-(4-(2,6-dimethoxy-phenyl)-5-(1-methyl-1H-pyrazol-3-yl)-4H-1,2,4-triazol-3-yl)-1-methoxy-2-propanesulfonamide or (1R,2S)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide, Example 265.0. Example 265.0 was the first isomer to elute from an AD-H column on subjecting Example 264.0 to the following SFC conditions: Run on Thar 80 SFC with 250×30 mm AD-H column with 40 g/min EtOH (with 20 mM $NH_3$)+40 g/min $CO_2$, 50% co-solvent at 80 g/min. Temp.=22° C., Outlet pressure=100 bar, Wavelength=220 nm. Injected 0.5 mL of 180 mg sample dissolved in 15 mL MeOH; c=12 mg/mL and 6 mg per injection. Cycle time 11.0 min, run time=19 min. $^1$H NMR (500 MHz, $CD_3OD$) δ 8.19 (d, J=1.47 Hz, 1H) 8.01 (dd, J=8.19, 1.59 Hz, 1H) 7.66 (d, J=8.31 Hz, 1H) 7.48-7.56 (m, 2H) 6.81 (dd, J=8.56, 3.18 Hz, 2H) 6.07 (d, J=2.20 Hz, 1H) 5.15 (d, J=3.91 Hz, 1H) 3.83 (s, 3H) 3.80 (s, 3H) 3.77 (s, 3H) 3.36-3.45 (m, 1H) 3.20 (s, 3H) 1.27 (d, J=6.85 Hz, 3H). LCMS-ESI (pos.), m/z: 563.2 $(M+H)^+$.

Example 266.0. Preparation of (1S,2R)-1-(2,4-di-
cyanophenyl)-N-(4-(2,6-dimethoxyphenyl)-5-(1-
methyl-1H-pyrazol-3-yl)-4H-1,2,4-triazol-3-yl)-1-
methoxy-2-propanesulfonamide or (1R,2S)-1-(2,4-
dicyanophenyl)-N-(4-(2,6-dimethoxyphenyl)-5-(1-
methyl-H-pyrazol-3-yl)-4H-1,2,4-triazol-3-yl)-1-
methoxy-2-propanesulfonamide

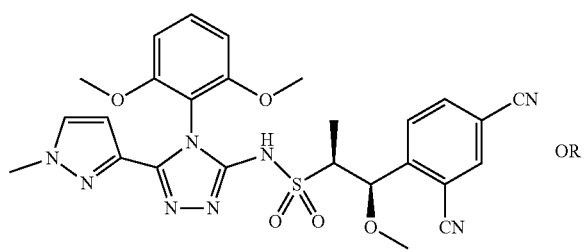

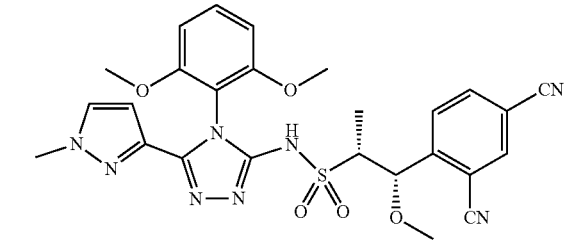

(1S,2R)-1-(2,4-Dicyanophenyl)-N-(4-(2,6-dimethoxy-phenyl)-5-(1-methyl-1H-pyrazol-3-yl)-4H-1,2,4-triazol-3-yl)-1-methoxy-2-propanesulfonamide or (1R,2S)-1-(2,4-dicyanophenyl)-N-(4-(2,6-dimethoxyphenyl)-5-(1-methyl-1H-pyrazol-3-yl)-4H-1,2,4-triazol-3-yl)-1-methoxy-2-propanesulfonamide, Example 265.0. Example 266.0 is the enantiomer of Example 265.0. Example 266.0 was the second isomer to elute from the AD-H column on subjecting Example 264.0 under the SFC conditions described in Example 265.0. $^1$H NMR (400 MHz, $CD_3OD$) δ 8.20 (d, J=1.57 Hz, 1H) 8.01 (dd, J=8.12, 1.66 Hz, 1H) 7.66 (d, J=8.22 Hz, 1H) 7.48-7.57 (m, 2H) 6.82 (dd, J=8.61, 1.96 Hz, 2H) 6.08 (d, J=2.35 Hz, 1H) 5.15 (d, J=4.11 Hz, 1H) 3.83 (s, 3H) 3.80 (s, 3H) 3.78 (s, 3H) 3.41 (qd, J=6.91, 4.30 Hz, 1H) 3.20 (s, 3H) 1.27 (d, J=7.04 Hz, 3H). LCMS-ESI (pos.), m/z: 563.2 $(M+H)^+$.

Example 267.0. Preparation of N-(4-(2,6-dime-
thoxyphenyl)-5-(1-methyl-1H-pyrazol-3-yl)-4H-1,2,
4-triazol-3-yl)ethanesulfonamide

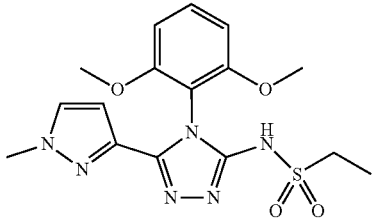

N-(4-(2,6-Dimethoxyphenyl)-5-(1-methyl-1H-pyrazol-3-yl)-4H-1,2,4-triazol-3-yl)ethanesulfonamide, Example 267.0. Example 267.0 was prepared from ethyl sulfonamide (commercially available from Accela ChemBio Inc., CA, USA), 2-isothiocyanato-1,3-dimethoxybenzene, Example 465.0, and 1-methyl-1H-pyrazole-3-carbohydrazide (commercially available from ChemBridge Corporation, CA, USA) using the procedure described in Example 350.1. $^1$H NMR (400 MHz, DMSO-$d_6$) δ 13.05 (s, 1H) 7.69 (d, J=2.15 Hz, 1H) 7.49 (t, J=8.51 Hz, 1H) 6.83 (d, J=8.61 Hz, 2H) 6.08 (d, J=2.35 Hz, 1H) 3.74 (s, 3H) 3.72 (s, 6H) 2.89 (q, J=7.43 Hz, 2H) 1.14 (t, J=7.34 Hz, 3H). LCMS-ESI (pos.), m/z: 393.2 $(M+H)^+$.

The compounds set forth in the following table were synthesized following the procedure in Example 264.04 using the known starting material as described.

TABLE 14

| Example | Reagents | Structure, name and data |
|---|---|---|
| 271.1 | 5-chloropicolinaldehyde (Matrix Scientific). | 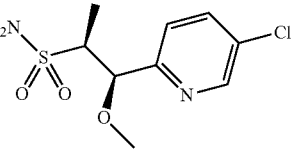 AND 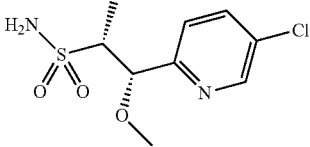<br>(1R,2S)-1-(5-chloropyridin-2-yl)-1-methoxypropane-2-sulfonamide and (1S,2R)-1-(5-chloropyridin-2-yl)-1-methoxypropane-2-sulfonamide.<br>LCMS-ESI (pos.) m/z: 265.1 (M + H)$^+$. |
| 275.1 | 5-chlorothiazole-2-carbaldehyde (Acros Organics). | 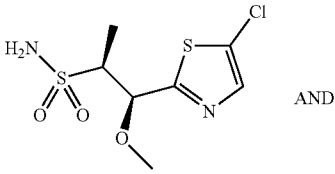 AND 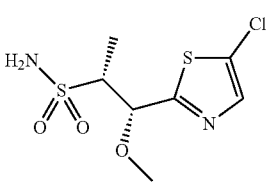<br>(1R,2R)-1-(5-chlorothiazol-2-yl)-1-methoxypropane-2-sulfonamide and (1S,2 S)-1-(5-chlorothiazol-2-yl)-1-methoxypropane-2-sulfonamide.<br>LCMS-ESI (pos.) m/z: 271.0 (M + H)$^+$. |
| 282.1 | 5-methoxypyrazine-2-carbaldehyde (Frontier Scientific, Inc.). | 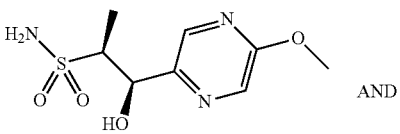 AND 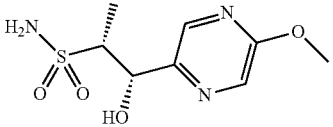<br>(1R,2S)-1-hydroxy-1-(5-methoxypyrazin-2-yl)propane-2-sulfonamide and (1S,2R)-1-hydroxy-1-(5-methoxypyrazin-2-yl)propane-2-sulfonamide.<br>LCMS-ESI (pos.) m/z: 270.0 (M + Na)$^+$. |

TABLE 14-continued

| Example | Reagents | Structure, name and data |
|---|---|---|
| 307.1 | 5-methoxypyrazine-2-carbaldehyde (Frontier Scientific, Inc.). | 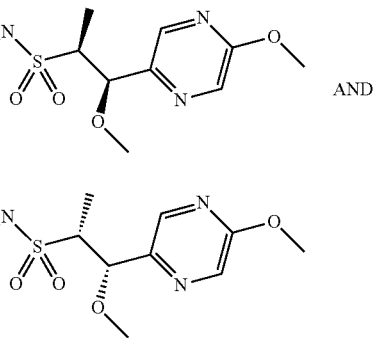 AND<br><br>(1R,2S)-1-methoxy-1-(5-methoxypyrazin-2-yl)propane-2-sulfonamide and (1S,2R)-1-methoxy-1-(5-methoxypyrazin-2-yl)propane-2-sulfonamide.<br>LCMS-ESI (pos.) m/z: 262.2 (M + H)+. |

The compounds set forth in the following table were synthesized following the procedure in Example 134.0 using the known starting material as described.

TABLE 15

| Example | Reagents | Structure, name and data |
|---|---|---|
| 268.0 | 2-isothiocyanato-1,3-dimethoxybenzene (Example 465.0), 5-methyl-1H-pyrazole-3-carbohydrazide (commercially available from Frontier Scientific Services, Inc., Newark, DE), and (2S,3R)-3-(5-fluoropyrimidin-2-yl)butane-2-sulfonamide (Example 464.1). | 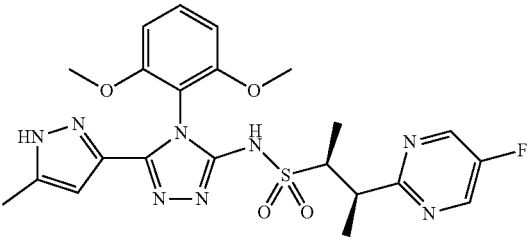 [SMILES: COc1cccc(OC)c1-n1c(NS(=O)(=O)[C@@H](C)[C@H](C)c2ncc(F)cn2)nnc1-c1cc(C)[nH]n1]<br><br>(2S,3R)-N-(4-(2,6-dimethoxyphenyl)-5-(5-methyl-1H-pyrazol-3-yl)-4H-1,2,4-triazol-3-yl)-3-(5-fluoro-2-pyrimidinyl)-2-butanesulfonamide.<br>1H NMR (500 MHz, CD3OD) δ 8.66 (d, J = 0.73 Hz, 2 H) 7.50 (br t, J = 8.19 Hz, 1 H) 6.79 (br d, J = 5.38 Hz, 2H) 5.82 (br s, 1 H) 3.76-3.83 (m, 2 H) 3.75 (s, 3 H) 3.75 (s, 3 H) 2.20 (br s, 3 H) 1.33-1.39 (m, 3 H) 1.27-1.33 (m, 3 H). LCMS-ESI (pos.) m/z: 517.1 (M + H)+. |
| 269.0 | isothiocyanato-2-methoxybenzene (Sigma Aldrich), (2S,3R)-3-(5-fluoropyrimidin-2-yl)butane-2-sulfonamide (Example 464.1), and 1-methyl-1H-pyrazole-3-carbohydrazide (Bellen). | 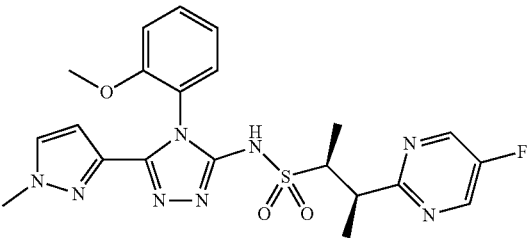 [SMILES: COc1ccccc1-n1c(NS(=O)(=O)[C@@H](C)[C@H](C)c2ncc(F)cn2)nnc1-c1ccn(C)n1]<br><br>(2S,3R)-3-(5-fluoro-2-pyrimidinyl)-N-(4-(2-methoxyphenyl)-5-(1-methyl-1H-pyrazol-3-yl)-4H-1,2,4-triazol-3-yl)-2-butanesulfonamide.<br>1H NMR (500 MHz, CDCl3) δ 10.78-11.37 (m, 1 H) 8.53 (s, 2 H) 7.50 (td, J = 7.95, 1.71 Hz, 1 H) 7.28-7.37 (m, 1 H) 7.25 (t, J = 1.96 Hz, 1 H) 7.07 (tdd, J = 7.64, 7.64, 4.77, 1.22 Hz, 1 H) 7.02 (ddd, J = 8.31, 4.40, 0.98 Hz, 1 H) 5.88 (dd, J = 4.52, 2.32 Hz, 1 H) 3.87 (d, J = 0.98 Hz, 3 H) 3.77-3.86 (m, 2 H) 3.71 (d, J = 5.87 Hz, 3 H) 1.31-1.42 (m, 6 H). LCMS-ESI (pos.) m/z: 487.1 (M + H)+. |

TABLE 15-continued

| Example | Reagents | Structure, name and data |
|---|---|---|
| 270.0 | 2-isothiocyanato-1,3-dimethoxybenzene (Example 465.0), 5-methyl-1H-pyrazole-3-carbohydrazide (commercially available from Frontier Scientific Services, Inc., Newark, DE), (1R,2S)-1-(5-chloropyridin-2-yl)-1-methoxypropane-2-sulfonamide and (1S,2R)-1-(5-chloropyridin-2-yl)-1-methoxypropane-2-sulfonamide (Example 271.1). | 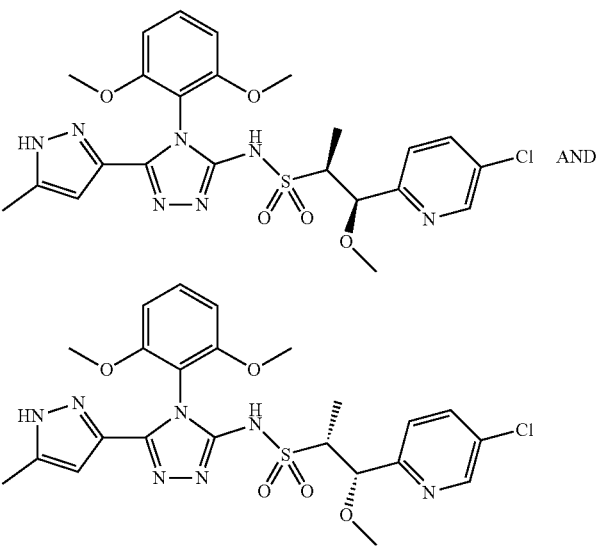 [SMILES: COc1cccc(OC)c1-n1c(NS(=O)(=O)[C@@H](C)[C@H](OC)c2ccc(Cl)cn2)nnc1-c1cc(C)[nH]n1 ; COc1cccc(OC)c1-n1c(NS(=O)(=O)[C@H](C)[C@@H](OC)c2ccc(Cl)cn2)nnc1-c1cc(C)[nH]n1] (1R,2S)-1-(5-chloro-2-pyridinyl)-N-(4-(2,6-dimethoxyphenyl)-5-(5-methyl-1H-pyrazol-3-yl)-4H-1,2,4-triazol-3-yl)-1-methoxy-2-propanesulfonamide and (1S,2R)-1-(5-chloro-2-pyridinyl)-N-(4-(2,6-dimethoxyphenyl)-5-(5-methyl-1H-pyrazol-3-yl)-4H-1,2,4-triazol-3-yl)-1-methoxy-2-propanesulfonamide.<br><br>$^1$H NMR (500 MHz, CDCl$_3$) δ 8.55 (d, J = 1.96 Hz, 1 H) 7.70 (dd, J = 8.44, 2.32 Hz, 1 H) 7.46 (t, J = 8.56 Hz, 1 H) 7.40 (d, J = 8.31 Hz, 1 H) 6.67 (t, J = 7.83 Hz, 2 H) 5.75 (s, 1 H) 5.06 (d, J = 2.45 Hz, 1 H) 3.74 (s, 3 H) 3.74 (s, 3 H )3.53 (qd, J = 6.93, 2.69 Hz, 1 H) 3.31 (s, 3 H) 2.25 (s, 3 H) 1.22 (d, J = 7.09 Hz, 3 H). LCMS-ESI (pos.) m/z: 548.0 (M + H)$^+$. |

TABLE 15-continued

| Example | Reagents | Structure, name and data |
|---|---|---|
| 271.0 | 2-isothiocyanato-1,3-dimethoxybenzene (Example 465.0), 1-methyl-1H-pyrazole-3-carbohydrazide (Bellen), (1R,2S)-1-(5-chloropyridin-2-yl)-1-methoxypropane-2-sulfonamide and (1S,2R)-1-(5-chloropyridin-2-yl)-1-methoxypropane-2-sulfonamide (Example 271.1). | 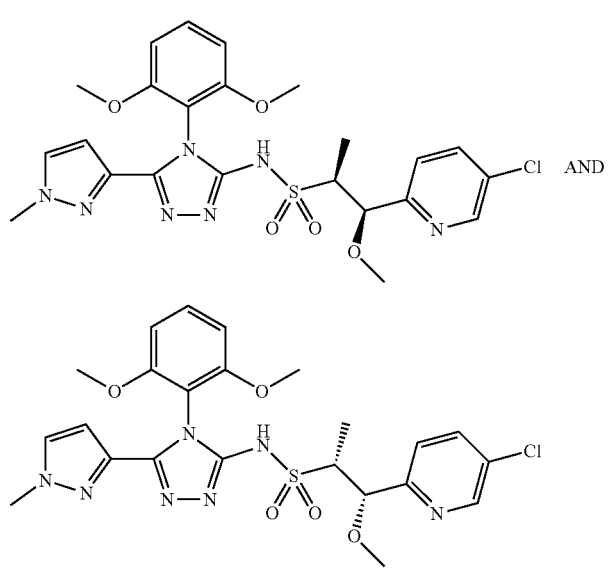 [SMILES: COc1cccc(OC)c1-n1c(NS(=O)(=O)[C@@H](C)[C@H](OC)c2ccc(Cl)cn2)nnc1-c1ccn(C)n1 ; COc1cccc(OC)c1-n1c(NS(=O)(=O)[C@H](C)[C@@H](OC)c2ccc(Cl)cn2)nnc1-c1ccn(C)n1]<br>(1R,2S)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide and (1S,2R)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide.<br>$^1$H NMR (500 MHz, CDCl$_3$) δ 8.73 (d, J = 2.20 Hz, 1 H) 7.90 (dd, J = 8.44, 2.32 Hz, 1 H) 7.56 (d, J = 8.56 Hz, 1 H) 7.44 (t, J = 8.44 Hz, 1 H) 7.25 (d, J = 2.20 Hz, 1 H) 6.61-6.69 (m, 2 H) 5.91 (d, J = 2.45 Hz, 1 H) 5.02 (d, J = 3.91 Hz, 1 H) 3.86 (s, 3 H) 3.72 (s, 3 H) 3.72 (s, 3 H) 3.56 (qd, J = 6.97, 4.03 Hz, 1 H) 3.32 (s, 3 H) 1.28 (d, J = 7.09 Hz, 3 H). LCMS-ESI (pos.) m/z: 548.0 (M + H)$^+$. |
| 272.0 | This was the first enantiomer to elute from an AS-H column by SFC chiral separation of Example 271.0 under the following condition: Run on Thar 200 SFC with 30 × 250 mm AS-H column with 42 mL/min IPA (20 mM NH$_3$) + 98 g/min CO$_2$, 30% co-solvent at 140 g/min. Temp. = 30° C., Outlet pressure = 100 bar, Wavelength = 256 nm. Injected 1.0 mL of 146 mg sample dissolved in 10 mL MeOH; c = 14.6 mg/mL, i.e. 14.6 mg per injection. Cycle time = 11 min, nm time 13 min. (Avoiding collection of TFA.). | 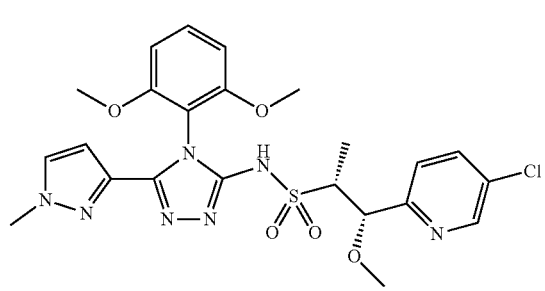 [SMILES: COc1cccc(OC)c1-n1c(NS(=O)(=O)[C@H](C)[C@@H](OC)c2ccc(Cl)cn2)nnc1-c1ccn(C)n1]<br>(1S,2R)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide.<br>$^1$H NMR (500 MHz, CD$_3$OD) δ 8.56 (d, J = 1.96 Hz, 1 H) 7.88 (dd, J = 8.31, 2.45 Hz, 1 H) 7.47-7.56 (m, 2 H) 7.45 (d, J = 8.31 Hz, 1 H) 6.80 (d, J = 8.56 Hz, 2 H) 6.06 (d, J = 2.45 Hz, 1 H) 5.01 (d, J = 2.69 Hz, 1 H) 3.83 (s, 3 H) 3.77 (s, 3 H) 3.74 (s, 3 H) 3.43 (qd, J = 7.05, 2.57 Hz, 1 H) 3.28 (s, 3 H) 1.15 (d, J = 7.09 Hz, 3 H). LCMS-ESI (pos.) m/z: 548.0 (M + H)$^+$. |

TABLE 15-continued

| Example | Reagents | Structure, name and data |
|---|---|---|
| 273.0 | This was the second enantiomer to elute from the SFC chiral separation of Example 271.0 under the condition described in Example 272.0. | 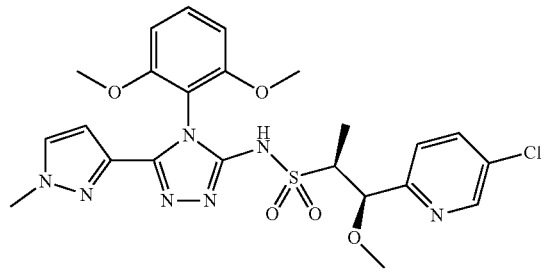 [SMILES: COc1cccc(OC)c1-n1c(NS(=O)(=O)[C@@H](C)[C@H](OC)c2ccc(Cl)cn2)nnc1-c1ccn(C)n1]<br>(1R,2S)-1-(5-chloro-2-pyridinyl)-N-(4-(2,6-dimethoxyphenyl)-5-(1-methyl-1H-pyrazol-3-yl)-4H-1,2,4-triazol-3-yl)-1-methoxy-2-propanesulfonamide.<br>$^1$H NMR (400 MHz, CDCl$_3$) δ 8.56 (d, J = 2.45 Hz, 1 H) 7.88 (dd, J = 8.31, 2.45 Hz, 1 H) 7.47-7.57 (m, 2 H) 7.45 (d, J = 8.31 Hz, 1 H) 6.80 (d, J = 8.56 Hz, 2 H) 6.06 (d, J = 2.45 Hz, 1 H) 5.01 (d, J = 2.45 Hz, 1 H) 3.83 (s, 3 H) 3.77 (s, 3 H) 3.74 (s, 3 H) 3.43 (qd, J = 7.05, 2.57 Hz, 1 H) 3.28 (s, 3 H) 1.15 (d, J = 6.85 Hz, 3 H). LCMS-ESI (pos.) m/z: 548.0 (M + H)$^+$. |
| 274.0 | This was the first enantiomer to elute from an IC-H column by SFC chiral separation of Example 270.0 under the following condition: Run on Thar 80 SFC with 250 × 21 mm and 150 × 21 mm IC-H columns in series with 22.0 mL/min MeOH (+20 mM NH$_3$) + 33.0 g/min CO$_2$, 40% co-solvent at 55.0 g/min. Temp. = 28° C., Outlet pressure = 100 bar, Wavelength = 256 nm. Injected 1.0 mL of 140 mg sample dissolved in 15 mL of MeOH/DCM (2:1); c = 9.33 mg/mL and 9.33 mg per injection. Cycle time 15.0 min, run time 27.0 min. | 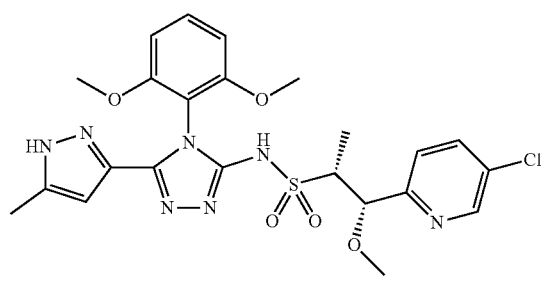 [SMILES: COc1cccc(OC)c1-n1c(NS(=O)(=O)[C@H](C)[C@@H](OC)c2ccc(Cl)cn2)nnc1-c1cc(C)[nH]n1]<br>(1S,2R)-1-(5-chloro-2-pyridinyl)-N-(4-(2,6-dimthoxyphenyl)-5-(5-methyl-1H-pyrazol-3-yl)-4H-1,2,4-triazol-3-yl)-1-methoxy-2-propanesulfonamide.<br>$^1$H NMR (400 MHz, CD$_2$Cl$_2$) 68.55 (d, J = 1.96 Hz, 1 H) 7.88 (dd, J = 8.56, 2.45 Hz, 1 H) 7.50 (br t, J = 8.19 Hz, 1 H) 7.44 (d, J = 8.56 Hz, 1 H) 6.80 (br d, J = 8.31 Hz, 2 H) 5.83 (br s, 1 H) 5.00 (d, J = 2.45 Hz, 1 H) 3.77 (s, 3 H) 3.74 (s, 3 H) 3.44 (br d, J = 6.11 Hz, 1 H) 3.28 (s, 3 H) 2.21 (br s, 3 H) 1.15 (d, J = 6.85 Hz, 3 H). LCMS-ESI (pos.) m/z: 548.0 (M + H)$^+$. |

TABLE 15-continued

| Example | Reagents | Structure, name and data |
|---|---|---|
| 275.0 | 2-isothiocyanato-1,3-dimethoxybenzene (Example 465.0), 5-methyl-1H-pyrazole-3-carbohydrazide (commercially available from Frontier Scientific Services, Inc., Newark, DE), and (1R,2R)-1-(5-chlorothiazol-2-yl)-1-methoxypropane-2-sulfonamide and (1S,2S)-1-(5-corothiazol-2-yl)-1-methoxypropane-2-sulfonamide (Example 275.1). | 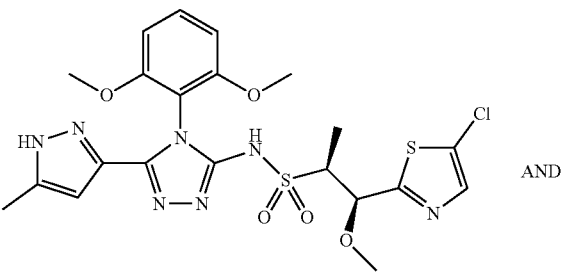<br>(1R,2R)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide and (1S,2 S)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide.<br>$^1$H NMR (400 MHz, CD$_3$OD) δ 7.66 (s, 1 H) 7.50 (t, J = 8.56 Hz, 1 H) 6.76-6.83 (m, 2 H) 5.80 (d, J = 0.73 Hz, 1 H) 5.15 (d, J = 1.96 Hz, 1 H) 3.75 (m, 7 H) 3.53 (qd, J = 7.01, 2.20 Hz, 1 H) 3.40 (s, 3 H) 2.20 (s, 3 H) 1.22 (d, J = 7.09 Hz, 3 H). LCMS-ESI (pos.) m/z: 554.2 (M + H)$^+$ .. |
| 276.0 | This was the second enantiomer to elute from the IC-H column by SFC chiral separation of Example 270.0 under the condition described in Example 274.0. | 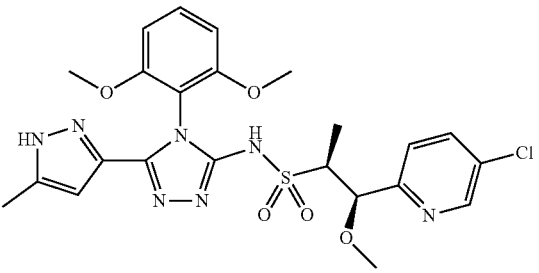 [SMILES: COc1cccc(OC)c1-n1c(NS(=O)(=O)[C@@H](C)[C@H](OC)c2ccc(Cl)cn2)nnc1-c1cc(C)[nH]n1]<br>(1R,2S)-1-(5-chloro-2-pyridinyl)-N-(4-(2,6-dimethoxyphenyl)-5-(5-methyl-1H-pyrazol-3-yl)-4H-1,2,4-triazol-3-yl)-1-methoxy-2-propanesulfonamide.<br>$^1$H NMR (500 MHz, CD$_3$OD) δ 8.55 (d, J = 2.45 Hz, 1 H) 7.88 (dd, J = 8.56, 2.45 Hz, 1 H) 7.50 (br t, J = 8.19 Hz, 1 H) 7.44 (d, J = 8.56 Hz, 1 H) 6.80 (br d, J = 8.31 Hz, 2 H) 5.83 (br s, 1 H) 5.00 (d, J = 2.45 Hz, 1 H) 3.77 (s, 3 H) 3.74 (s, 3 H) 3.39-3.49 (m, 1 H) 3.28 (s, 3 H) 2.21 (br s, 3 H) 1.15 (d, J = 7.09 Hz, 3 H). LCMS-ESI (pos.) m/z: 548.0 (M + H)$^+$ . |

TABLE 15-continued

| Example | Reagents | Structure, name and data |
|---|---|---|
| 277.0 | This was the first enantiomer to elute from and IA column by SFC chiral separation of Example 275.0 under the following condition: Run on Thar 200 SFC with 21 × 250 + 21 × 150 mm IA columns in series with 17.5 mL/min MeOH (20 mM NH$_3$) + 33 g/min CO$_2$, 35% co-solvent at 50 g/min. Temp. = 30° C., Outlet pressure = 100 bar, Wavelength = 249 nm. Injected 0.8 mL of 193 mg sample dissolved in 15 mL 13:2 MeOH:DCM; c = 12.9 mg/mL, i.e. 10.3 mg per injection. Cycle time 9 min, run time 20 min. | 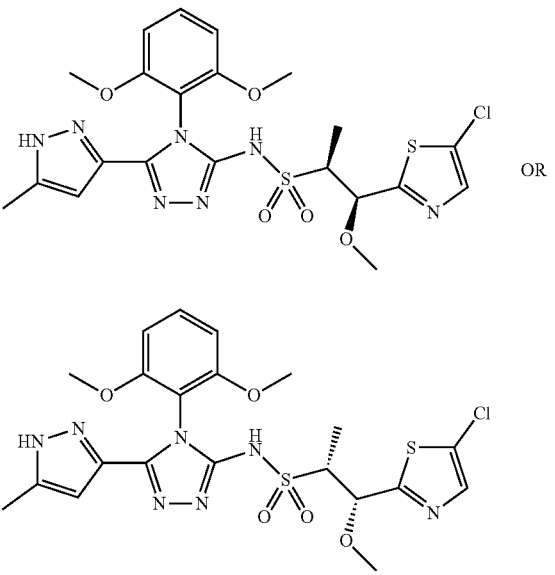 [SMILES: COc1cccc(OC)c1-n1c(NS(=O)(=O)[C@@H](C)[C@H](OC)c2ncc(Cl)s2)nnc1-c1cc(C)[nH]n1 ; COc1cccc(OC)c1-n1c(NS(=O)(=O)[C@H](C)[C@@H](OC)c2ncc(Cl)s2)nnc1-c1cc(C)[nH]n1] (1R,2R)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide or (1S,2S)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide.<br><br>$^1$H NMR (500 MHz, CD$_3$OD) δ 7.66 (s, 1 H) 7.50 (br t, J = 8.44 Hz, 1 H) 6.76-6.88 (m, 2 H) 5.84 (br s, 1 H) 5.15 (d, J = 1.96 Hz, 1 H) 3.76 (s, 3 H) 3.76 (s, 3 H) 3.49-3.59 (m, 1 H) 3.41 (s, 3 H) 2.22 (s, 3 H). LCMS-ESI (pos.) m/z: 554.2 (M + H)$^+$. |

TABLE 15-continued

| Example | Reagents | Structure, name and data |
|---|---|---|
| 278.0 | This was the second enantiomer to elute from an IA column by SFC chiral separation of Example 275.0 under the following condition described in Example 277.0. | 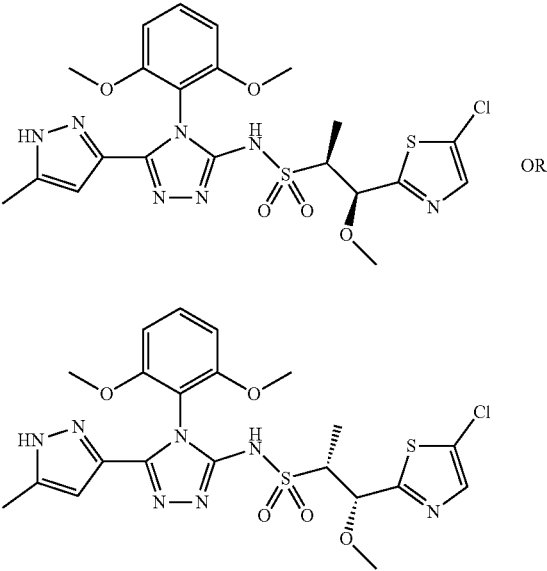 [SMILES: COc1cccc(OC)c1-n1c(NS(=O)(=O)[C@@H](C)[C@H](OC)c2ncc(Cl)s2)nnc1-c1cc(C)[nH]n1 ; COc1cccc(OC)c1-n1c(NS(=O)(=O)[C@H](C)[C@@H](OC)c2ncc(Cl)s2)nnc1-c1cc(C)[nH]n1] OR<br><br>(1R,2R)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide or (1S,2S)-1-(5-chloro-1,3-thiazol-2-yl)-N-(4-(2,6-dimethoxyphenyl)-5-(5-methyl-1H-pyrazol-3-yl)-4H-1,2,4-triazol-3-yl)-1-methoxy-2-propanesulfonamide.<br>$^1$H NMR (500 MHz, CD$_3$OD) δ 7.66 (s, 1 H) 7.50 (br t, J = 8.31 Hz, 1 H) 6.74-6.87 (m, 2 H) 5.80-5.91 (m, 1 H) 5.15 (d, J = 1.96 Hz, 1 H) 3.76 (s, 7 H) 3.49-3.58 (m, 1 H) 3.41 (s, 3 H) 2.18-2.27 (m, 3 H) 1.22 (d, J = 7.09 Hz, 3 H). LCMS-ESI (pos.) m/z: 554.2 (M + H)$^+$. |
| 279.0 | 2-isothiocyanato-1,3-dimethoxybenzene (Example 465.0), 1-methyl-1H-pyrazole-3-carbohydrazide (Bellen), and (2R,3S)-3-(5-methylpyrazin-2-yl)butane-2-sulfonamide and (2S,3R)-3-(5-methylpyrazin-2-yl)butane-2-sulfonamide (Example 464.9). | 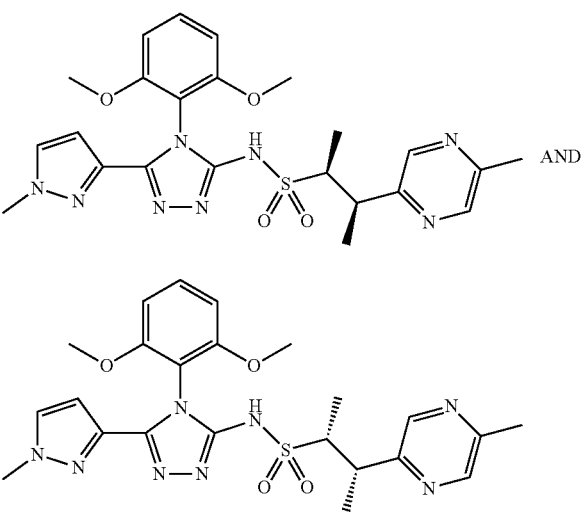 AND<br><br>(2R,3S)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide and (2S,3R)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide.<br>$^1$H NMR (500 MHz, CDCl$_3$) δ 8.38 (d, J = 0.73 Hz, 1 H) 8.34 (d, J = 1.47 Hz, 1 H) 7.44 (t, J = 8.44 Hz, 1 H) 7.24 (d, J = 2.45 Hz, 1 H) 6.60-6.70 (m, 2 H) 5.90 (d, J = 2.45 Hz, 1 H) 3.88 (s, 3 H) 3.74-3.83 (m, 1 H) 3.73 (s, 3 H) 3.73 (s, 3 H) 3.54 (qd, J = 7.01, 4.40 Hz, 1 H) 2.54 (s, 3 H) 1.37 (d, J = 7.09 Hz, 3 H) 1.34 (d, J = 7.09 Hz, 3 H). LCMS-ESI (pos.) m/z: 513.2 (M + H)$^+$. |

TABLE 15-continued

| Example | Reagents | Structure, name and data |
|---|---|---|
| 280.0 | 2-isothiocyanato-1,3-dimethoxybenzene (Example 465.0), 1-methyl-1H-pyrazole-3-carbohydrazide (Bellen), and 5-methyl-2-((2R,3S)-3-sulfamoylbutan-2-yl)pyrazine 1-oxide and 5-methyl-2-((2S,3R)-3-sulfamoylbutan-2-yl)pyrazine 1-oxide (Example 464.4). | 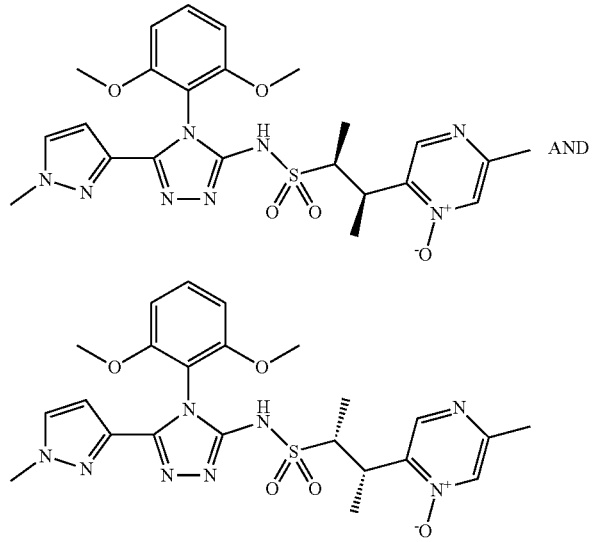<br>(2R,3S)-N-(4-(2,6-dimethoxyphenyl)-5-(1-methyl-1H-pyrazol-3-yl)-4H-1,2,4-triazol-3-yl)-3-(5-methyl-1-oxido-2-pyrazinyl)-2-butanesulfonamide and (2S,3R)-N-(4-(2,6-dimethoxyphenyl)-5-(1-methyl-1H-pyrazol-3-yl)-4H-1,2,4-triazol-3-yl)-3-(5-methyl-1-oxido-2-pyrazinyl)-2-butanesulfonamide.<br>$^1$H NMR (400 MHz, CDCl$_3$) δ 8.41 (s, 1 H) 8.00 (s, 1 H) 7.46 (t, J = 8.44 Hz, 1 H) 7.25 (d, J = 2.20 Hz, 1 H) 6.62-6.73 (m, 2 H) 5.91 (d, J = 2.45 Hz, 1 H) 3.89 (s, 3 H) 3.75 (s, 3 H) 3.75 (s, 3 H) 3.36-3.48 (m, 1 H) 2.45 (s, 3 H) 1.35-1.40 (m, 1 H) 1.34 (m, 6H). LCMS-ESI (pos.) m/z: 529.2 (M + H)$^+$. |
| 281.0 | This was the second enantiomer to elute from an AS column by SFC chiral separation of Example 279.0 under the following conditions: Run on Thar 80 SFC with two 250 × 30 mm AS-H columns in series with 24.0 mL/min IPA (+20 mM NH$_3$) + 56.0 g/min CO$_2$, 30% co-solvent at 80.0 g/min. Temp. = 29° C., Outlet pressure = 100 bar, Wavelength = 270 nm. Injected 0.8 mL of 290 mg sample dissolved in 33.0 mL of MeOH:DCM 2:1; c = 8.7 mg/mL and 7.03 mg per injection. Cycle time 9.7 min, run time 25.0 min. | 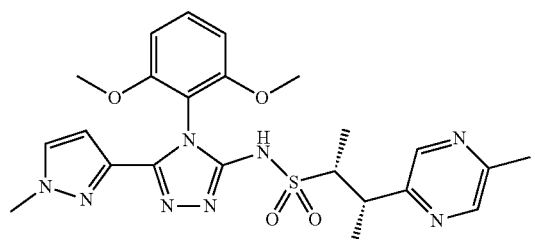<br>(2R,3S)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide.<br>$^1$H NMR (500 MHz, CDCl$_3$) δ 10.91 (br s, 1 H) 8.41 (s, 1 H) 8.31 (s, 1 H) 7.45 (t, J = 8.44 Hz, 1 H) 7.24 (d, J = 2.20 Hz, 1 H) 6.63-6.70 (m, 2 H) 5.90 (d, J = 2.20 Hz, 1 H) 3.89 (s, 3 H) 3.74 (s, 3 H) 3.74 (s, 3 H) 3.55 (qd, J = 7.01, 4.40 Hz, 1 H) 2.57 (s, 3 H) 1.37 (app dd, J = 8.44, 7.21 Hz, 6 H). LCMS-ESI (pos.) m/z: 513.2 (M + H)$^+$. |

TABLE 15-continued

| Example | Reagents | Structure, name and data |
|---|---|---|
| 282.0 | 2-isothiocyanato-1,3-dimethoxybenzene (Example 465.0), 1-methyl-1H-pyrazole-3-carbohydrazide (Bellen), and (1R,2S)-1-hydroxy-1-(5-methoxypyrazin-2-yl)propane-2-sulfonamide and (1S,2R)-1-hydroxy-1-(5-methoxypyrazin-2-yl)propane-2-sulfonamide (Example 282.1). | 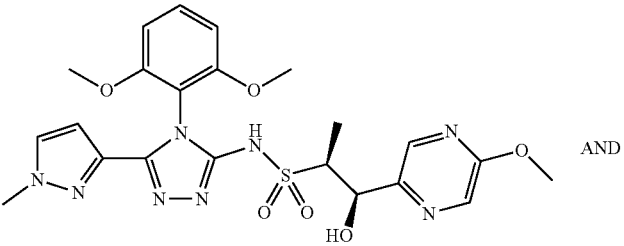 AND<br>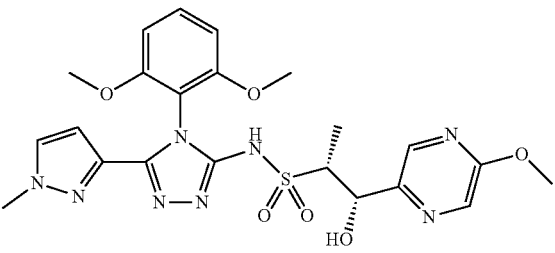<br>(1R,2S)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide and (1S,2R)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide.<br>$^1$H NMR (400 MHz, CD$_3$OD) δ 8.16-8.22 (m, 1 H) 8.13 (d, J = 1.35 Hz, 1 H) 7.45-7.54 (m, 2 H) 6.74-6.84 (m, 2 H) 6.07 (d, J = 2.38 Hz, 1 H) 5.33 (dd, J = 2.38, 0.83 Hz, 1 H) 3.95 (s, 3 H) 3.80 (s, 3 H) 3.76 (s, 3 H) 3.73 (s, 3 H) 3.56 (qd, J = 6.98, 2.38 Hz, 1 H) 1.14 (d, J = 7.05 Hz, 3 H). LCMS-ESI (pos.) m/z: 531.0 (M + H)$^+$. |
| 283.0 | This was the first enantiomer to elute from a Lux column by SFC chiral separation of Example 282.0 under the following conditions: Run on Thar 80 SFC with 250 × 30 mm Lux column with 44.0 mL/min MeOH (+20 mM NH$_3$) + 36.0 g/min CO$_2$, 55% co-solvent at 80.0 g/min. Temp. = 29° C., Outlet pressure = 100 bar, Wavelength = 222 nm. Injected 1.0 mL of 122 mg sample dissolved in 16.0 mL of MeOH:DCM 5:3; c = 7.625 mg/mL and 7.625 mg per injection. Cycle time 8.5 min, run time 11.0 min. | 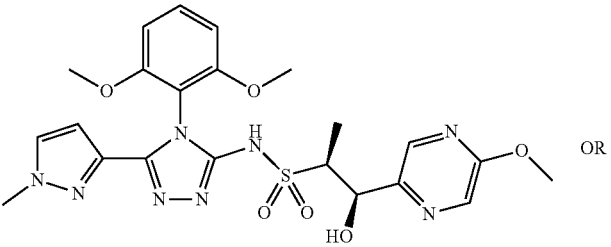 OR<br>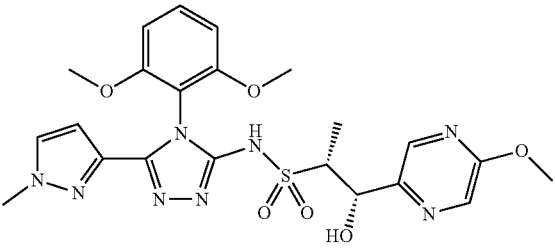<br>(1R,2S)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide or (1S,2R)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide.<br>$^1$H NMR (400 MHz, CDCl$_3$) δ 1.15 (d, J = 7.00 Hz, 3 H) 3.66-3.69 (m, 1 H) 3.73 (s, 3 H) 3.81 (s, 3 H) 3.87 (s, 3 H) 3.97 (s, 3 H) 5.52 (s, 1 H) 5.98 (d, J = 2.18 Hz, 1 H) 6.66 (br d, J = 8.55 Hz, 1 H) 6.69 (br d, J = 8.50 Hz, 1 H) 7.46 (t, J = 8.30 Hz, 1 H) 8.14 (s, 1 H) 8.27 (s, 1 H) 11.04 (br s, 1 H). LCMS-ESI (pos.) m/z: 531.0 (M + H)$^+$. |

TABLE 15-continued

| Example | Reagents | Structure, name and data |
|---|---|---|
| 284.0 | This was the second enantiomer to elute from a Lux column by SFC chiral separation of Example 282.0 under the condition described in Example 283.0. | (1R,2S)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide or (1S,2R)-N-(4-(2,6-dimethoxyphenyl)-5-(1-methyl-1H-pyrazol-3-yl)-4H-1,2,4-triazol-3-yl)-1-hydroxy-1-(5-methoxy-2-pyrazinyl)-2-propanesulfonamide.<br>$^1$H NMR (400 MHz, CDCl$_3$) δ 11.02 (br s, 1 H) 8.25 (s, 1 H) 8.12 (s, 1 H) 7.44 (t, J = 8.50 Hz, 1 H) 7.25 (d, J = 2.28 Hz, 1 H) 6.65 (ddd, J = 14.51, 8.55, 0.78 Hz, 2 H) 5.96 (d, J = 2.38 Hz, 1 H) 5.50 (s, 1 H) 3.95 (s, 3 H) 3.85 (s, 3 H) 3.79 (s, 3 H) 3.71 (s, 3 H) 3.64-3.70 (m, 1 H) 1.13 (d, J = 6.95 Hz, 3 H). LCMS-ESI (pos.) m/z: 531.0 (M + H)$^+$. |
| 285.0 | 3-isothiocyanato-2,4-dimethoxypyridine (Example 465.5), 1-methyl-1H-pyrazole-3-carbohydrazide (Bellen), and (2S,3R)-3-(5-chloropyrimidin-2-yl)butane sulfonamide (Example 464.4)<br>The title compound was a side-product obtained from the reaction to prepare Example 286.0. | (P,2S,3R)-3-(5-chloro-2-pyrimidinyl)-N-(4-(4-methoxy-2-oxo-1,2-dihydro-3-pyridinyl)-5-(1-methyl-1H-pyrazol-3-yl)-4H-1,2,4-triazol-3-yl)-2-butanesulfonamide and (M,2S,3R)-3-(5-chloro-2-pyrimidinyl)-N-(4-(4-methoxy-2-oxo-1,2-dihydro-3-pyridinyl)-5-(1-methyl-1H-pyrazol-3-yl)-4H-1,2,4-triazol-3-yl)-2-butanesulfonamide.<br>$^1$H NMR (400 MHz, CDCl$_3$) δ 8.71 (s, 2 H) 7.62-7.65 (m, 1 H) 7.57 (d, J = 2.38 Hz, 1 H) 6.54 (d, J = 2.38 Hz, 1 H) 6.49 (dd, J = 7.62, 1.09 Hz, 1 H) 3.86 (d, J = 2.59 Hz, 3 H) 3.74-3.84 (m, 5 H) 1.29-1.39 (m, 6 H). LCMS-ESI (pos.) m/z: 520.1 (M + H)$^+$. |

| Example | Reagents | Structure, name and data |
|---|---|---|
| 286.0 | 3-isothiocyanato-2,4-dimethoxypyridine (Example 465.5), 1-methyl-1H-pyrazole-3-carbohydrazide (Bellen), and (2S,3R)-3-(5-chloropyrimidin-2-yl)butane-2-sulfonamide (Example 464.4). | 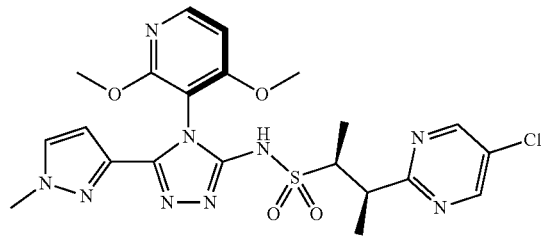<br>AND<br>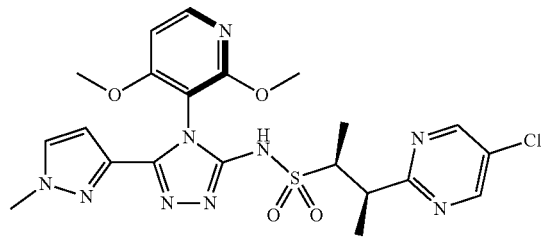<br>(P,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide and (M,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide.<br>$^1$H NMR (400 MHz, CD$_3$OD) δ 8.73 (s, 2 H) 8.21 (d, J = 6.12 Hz, 1 H) 7.56 (d, J = 2.38 Hz, 1 H) 6.90 (dd, J = 6.12, 1.97 Hz, 1 H) 6.42 (d, J = 2.38 Hz, 1 H) 3.82-3.88 (m, 6 H) 3.67-3.82 (m, 5 H) 1.35 (dd, J = 7.05, 3.32 Hz, 3 H) 1.31 (dd, J = 6.89, 1.61 Hz, 3 H). LCMS-ESI (pos.) m/z: 534.2 (M + H)$^+$. |
| 287.0 | 2-isothiocyanato-1,3-dimethoxybenzene (Example 465.0), 1-methyl-1H-pyrazole-3-carbohydrazide (Bellen), and (2S,3R)-3-(5-methoxypyrazin-2-yl)butane-2-sulfonamide (Example 464.5). | 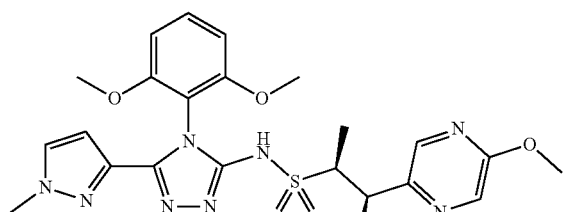<br>(2S,3R)-N-(4-(2,6-dimethoxyphenyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (500 MHz, CDCl$_3$) δ 1.32 (d, J = 7.01 Hz, 3 H) 1.35 (d, J = 7.14 Hz, 3 H) 3.47-3.53 (m, 1 H) 3.72 (s, 3 H) 3.72 (s, 3 H) 3.87 (s, 3 H) 3.95 (s, 3 H) 5.87 (d, J = 2.34 Hz, 1 H) 6.63 (dd, J = 8.43, 4.41 Hz, 2 H) 7.20-7.26 (m, 1 H) 7.42 (t, J = 8.50 Hz, 1 H) 7.96 (s, 1 H) 8.15 (d, J = 1.17 Hz, 1 H) 10.90 (br s, 1 H). LCMS-ESI (pos.) m/z: 529.2 (M + H)$^+$. |

TABLE 15-continued

| Example | Reagents | Structure, name and data |
|---|---|---|
| 288.0 | 5-isothiocyanato-4,6-dimethoxypyrimidine (Example 465.1), 1-methyl-1H-pyrazole-3-carbohydrazide (Bellen), and (1R,2S)-1-(5-chloropyridin-2-yl)-1-methoxypropane-2-sulfonamide (was obtained by SFC chiral separation of Example 271.1. The compound above was the second peak to elute from a Chiralpak AD-H column with 15% EtOH. | 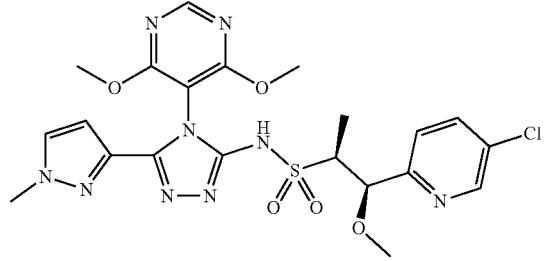 [SMILES: COc1ncnc(OC)c1-n1c(NS(=O)(=O)[C@@H](C)[C@H](OC)c2ccc(Cl)cn2)nnc1-c1ccn(C)n1]<br>(1R,2S)-1-(5-chloro-2-pyridinyl)-N-(4-(4,6-dimethoxy-5-pyrimidinyl)-5-(1-methyl-1H-pyrazol-3-yl)-4H-1,2,4-triazol-3-yl)-1-methoxy-2-propanesulfonamide.<br>$^1$H NMR (400 MHz, CDCl$_3$) δ 1.27 (d, J = 7.00 Hz, 3 H) 3.32 (s, 3 H) 3.50 (dd, J = 7.05, 3.21 Hz, 1 H) 3.77 (s, 3 H) 3.93 (s, 3 H) 3.93 (s, 3 H) 5.06 (d, J = 3.16 Hz, 1 H) 6.57 (d, J = 2.38 Hz, 1 H) 7.34 (d, J = 2.33 Hz, 1 H) 7.48 (d, J = 8.40 Hz, 1 H) 7.82 (dd, J = 8.40, 2.33 Hz, 1 H) 8.53 (s, 1 H) 8.64 (d, J = 2.28 Hz, 1 H). LCMS-ESI (pos.) m/z: 550.1 (M + H)$^+$. |
| 289.0 | 5-isothiocyanato-4,6-dimethoxypyrimidine (Example 465.1), 1-methyl-1H-pyrazole-3-carbohydrazide (Bellen), and (2S,3R)-3-(5-chloropyrimidin-2-yl)butane-2-sulfonamide and (2R,3S)-3-(5-chloropyrimidin-2-yl)butane-2-sulfonamide (isolated from the mother liquor of re-crystallization of Example 464.4). | 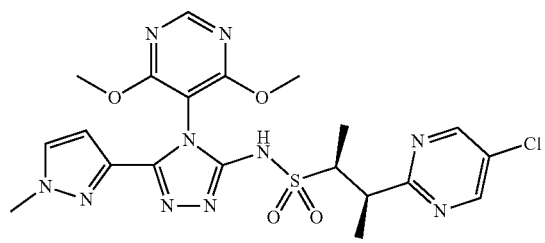<br>AND<br>(2R,3S)-3-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-2-butanesulfonamide and (2S,3R)-3-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-2-butanesulfonamide.<br>$^1$H NMR (400 MHz, DMSO-d$_6$) δ ppm 13.27 (s, 1 H) 8.86 (s, 2 H) 8.66 (s, 1 H) 7.78 (d, J = 2.28 Hz, 1 H) 6.61 (d, J = 2.28 Hz, 1 H) 3.88-3.95 (m, 1 H) 3.86 (s, 3 H) 3.86 (s, 3 H) 3.67 (s, 3 H) 3.52-3.66 (m, 1 H) 1.25 (d, J = 7.15 Hz, 3 H) 1.14 (d, J = 6.95 Hz, 3 H). LCMS-ESI (pos.) m/z: 535.1 (M + H)$^+$. |

| Example | Reagents | Structure, name and data |
|---|---|---|
| 290.0 | This was the first atropisomer to elute from a Chiralpak AD-H column by SFC chiral separation of Example 286.0 with 45% IPA. | 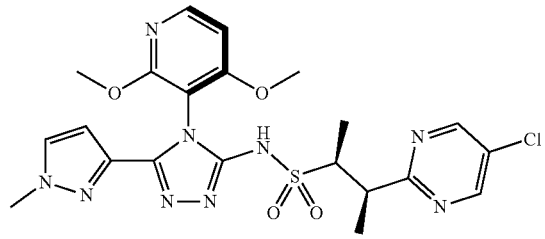<br>OR<br>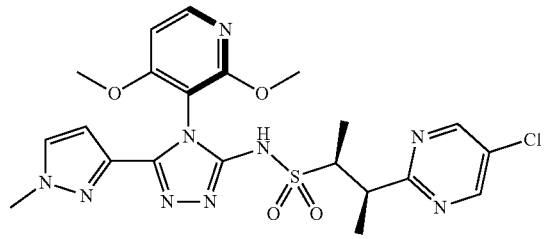<br><br>(P,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide or (M,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide.<br>$^1$H NMR (400 MHz, CD$_3$OD) δ 8.74 (s, 2 H) 8.22 (d, J = 6.01 Hz, 1 H) 7.58 (d, J = 2.28 Hz, 1 H) 6.91 (d, J = 6.12 Hz, 1 H) 6.43 (d, J = 2.38 Hz, 1 H) 3.86 (s, 3 H) 3.86 (s, 3 H) 3.68-3.83 (m, 5 H) 1.37 (d, J = 7.05 Hz, 3 H) 1.32 (d, J = 6.95 Hz, 3 H). LCMS-ESI (pos.) m/z: 534.0 (M + H)$^+$. |
| 291.0 | This was the second atropisomer to elute from a Chiralpak AD-H column by SFC chiral separation of Example 286.0 with 45% IPA. | 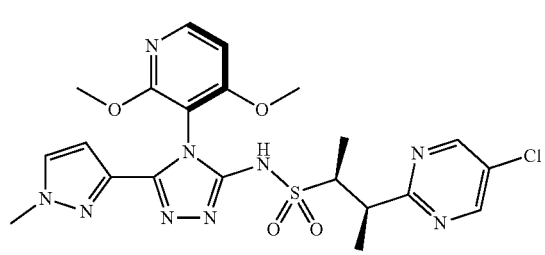<br>OR<br>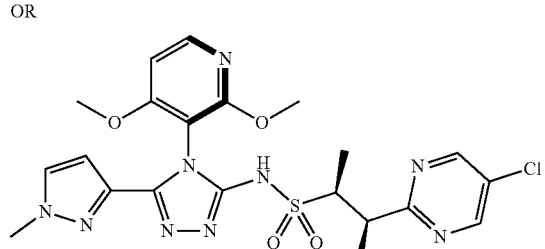<br><br>(P,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide or (M,2S,3R)-3-(5-chloro-2-pyrimidinyl)-N-(4-(2,4-dimethoxy-3-pyridinyl)-5-(1-methyl-1H-pyrazol-3-yl)-4H-1,2,4-triazol-3-yl)-2-butanesulfonamide.<br>$^1$H NMR (400 MHz, CDCl$_3$) δ 8.74 (s, 2 H) 8.22 (d, J = 6.01 Hz, 1 H) 7.57 (d, J = 2.28 Hz, 1 H) 6.91 (d, J = 6.12 Hz, 1 H) 6.43 (d, J = 2.38 Hz, 1 H) 3.86 (s, 3 H) 3.85 (s, 3 H) 3.68-3.83 (m, 5 H) 1.36 (d, J = 7.05 Hz, 3 H) 1.32 (d, J = 6.95 Hz, 3 H). LCMS-ESI (pos.) m/z: 534.2 (M + H)$^+$. |

TABLE 15-continued

| Example | Reagents | Structure, name and data |
|---|---|---|
| 292.0 | 5-isothiocyanato-4,6-dimethoxypyrimidine (Example 465.1), 1-methyl-1H-pyrazole-3-carbohydrazide (Bellen), and (2S,3R)-3-(5-methoxypyrazin-2-yl)butane-2-sulfonamide (Example 464.5). | 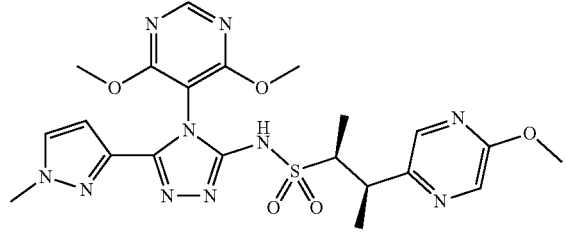<br>(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (400 MHz, CD$_2$Cl$_2$) δ 8.55 (s, 1 H) 8.16 (d, J = 1.35 Hz, 1 H) 7.98 (d, J = 1.35 Hz, 1 H) 7.38 (d, J = 2.28 Hz, 1 H) 6.62 (d, J = 2.28 Hz, 1 H) 3.96 (s, 3 H) 3.94 (s, 3 H) 3.94 (s, 3 H) 3.74 (s, 3 H) 3.68 (qd, J = 7.15, 4.35 Hz, 1 H) 3.51 (qd, J = 7.01, 4.25 Hz, 1 H) 1.37 (d, J = 7.15 Hz, 3 H) 1.30 (d, J = 7.05 Hz, 3 H). LCMS-ESI (pos.) m/z: 531.2 (M + H)$^+$. |
| 293.0 | 5-isothiocyanato-4,6-dimethoxypyrimidine (Example 465.1), 1-methyl-1H-pyrazole-3-carbohydrazide (Bellen), and (2S,3R)-3-(5-methoxypyrazin-2-yl)butane-2-sulfonamide (Example 464.5). This was the side-product obtained in the reaction to prepare Example 292.0. | 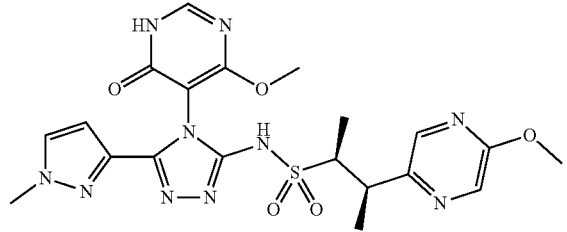<br>AND<br><br>(M,2S,3R)-N-(4-(4-methoxy-6-oxo-1,6-dihydro-5-pyrimidinyl)-5-(1-methyl-1H-pyrazol-3-yl)-4H-1,2,4-triazol-3-yl)-3-(5-methoxy-2-pyrazinyl)-2-butanesulfonamide and (P,2S,3R)-N-(4-(4-methoxy-6-oxo-1,6-dihydro-5-pyrimidinyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (400 MHz, CDCl$_3$) δ 8.15-8.21 (m, 2 H) 8.05 (dd, J = 6.32, 1.04 Hz, 1 H) 7.41 (dd, J = 2.23, 1.19 Hz, 1H) 6.64-6.70 (m, 1 H) 3.93-3.99 (m, 6 H) 3.80 (s, 3 H) 3.68-3.78 (m, 1 H) 3.46-3.56 (m, 1 H) 1.38 (dd, J = 7.10, 5.96 Hz, 3 H) 1.34 (dd, J = 7.05, 1.14 Hz, 3 H). LCMS-ESI (pos.) m/z: 517.2 (M + H)$^+$. |

TABLE 15-continued

| Example | Reagents | Structure, name and data |
|---|---|---|
| 294.0 | 5-isothiocyanato-4,6-dimethoxypyrimidine (Example 465.1), 1-methyl-1H-pyrazole-3-carbohydrazide (Bellen), and (2S,3R)-3-(5-chloropyrimidin-2-yl)butane-2-sulfonamide (Example 464.4). | 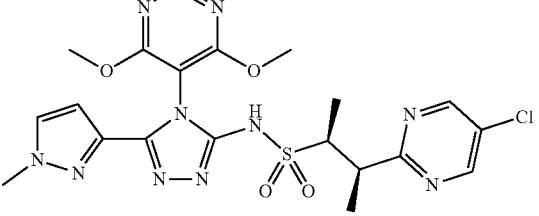<br>(2S,3R)-3-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-2-butanesulfonamide.<br>$^1$H NMR (400 MHz, CD$_2$Cl$_2$) δ 10.84-11.05 (m, 1 H) 8.67 (s, 2 H) 8.55 (s, 1 H) 7.39 (s, 1 H) 6.62 (d, J = 2.18 Hz, 1 H) 3.95 (s, 3 H) 3.94 (s, 3 H) 3.67-3.84 (m, 5 H) 1.37 (d, J = 7.05 Hz, 3 H) 1.34 (d, J = 6.95 Hz, 3 H). LCMS-ESI (pos.) m/z: 535.3 (M + H)$^+$. |
| 295.0 | 2-isothiocyanato-1,3-dimethoxybenzene (Example 465.0), 1-methyl-1H-pyrazole-3-carbohydrazide (Bellen), and (2S,3R)-3-(5-methoxypyrimidin-2-yl)butane-2-sulfonamide (Example 471.0). | 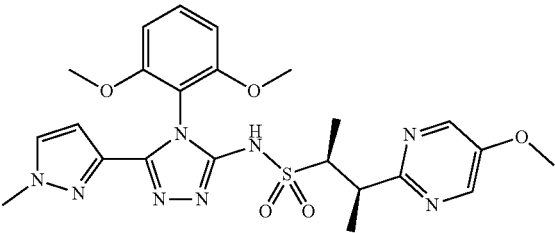<br>(2S,3R)-N-(4-(2,6-dimethoxyphenyl)-5-(1-methyl-1H-pyrazol-3-yl)-4H-1,2,4-triazol-3-yl)-3-(5-methoxy-2-pyrimidinyl)-2-butanesulfonamide.<br>$^1$H NMR (400 MHz, CDCl$_3$) δ 8.35 (s, 2 H) 7.39 (t, J = 8.50 Hz, 1 H) 7.22 (d, J = 2.28 Hz, 1 H) 6.57-6.66 (m, 2 H) 5.86 (d, J = 2.38 Hz, 1 H) 3.88 (s, 3 H) 3.85 (s, 3 H) 3.73-3.84 (m, 2 H) 3.70 (s, 3 H) 3.69 (s, 3 H) 1.36 (d, J = 6.95 Hz, 3 H) 1.32 (d, J = 6.84 Hz, 3 H). LCMS-ESI (pos.) m/z: 529.1 (M + H)$^+$. |
| 296.0 | 5-isothiocyanato-4,6-dimethoxypyrimidine (Example 465.1), 1-methyl-1H-pyrazole-3-carbohydrazide (Bellen), and (2S,3R)-3-(5-methoxypyrimidin-2-yl)butane-2-sulfonamide (Example 471.0). | 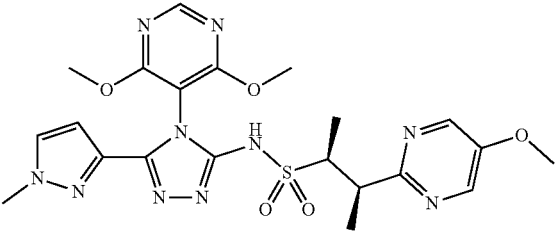<br>(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyrimidinyl)-2-butanesulfonamide.<br>$^1$H NMR (400 MHz, CDCl$_3$) δ 11.23 (br s, 1 H) 8.51 (s, 1 H) 8.37 (s, 2 H) 7.32 (d, J = 2.38 Hz, 1 H) 6.53 (d, J = 2.28 Hz, 1 H) 3.93 (s, 3 H) 3.91 (s, 3 H) 3.90 (s, 3 H) 3.74-3.90 (m, 5 H) 1.40 (d, J = 7.05 Hz, 3 H) 1.37 (d, J = 6.95 Hz, 3 H). LCMS-ESI (pos.) m/z: 531.2 (M + H)$^+$. |

TABLE 15-continued

| Example | Reagents | Structure, name and data |
|---|---|---|
| 299.0 | 2-isothiocyanato-1,3-difluorobenzene (Sigma Aldrich), 1-methyl-1H-pyrazole-3-carbohydrazide (Bellen), and (3R,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide (Example 474.0). This was the first enantiomer to elute from a Chiralpak AS-H column by SFC chiral separation with 35% MeOH. | 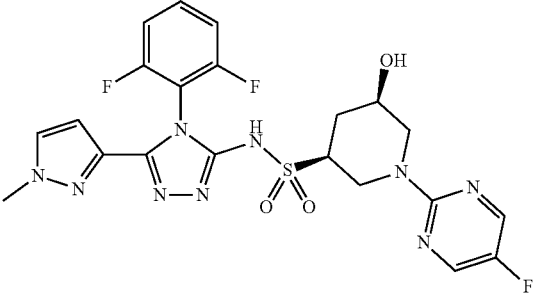<br>OR<br>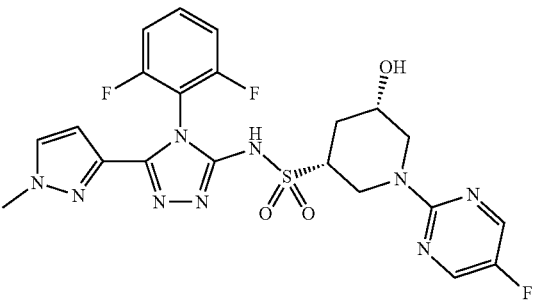<br>(3R,5S)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide or (3S,5R)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide.<br><br>$^1$H NMR (400 MHz, CD$_3$OD) δ 8.28 (d, J = 0.73 Hz, 2 H) 7.57-7.72 (m, 2 H) 7.18-7.28 (m, 2 H) 6.65 (d, J = 2.38 Hz, 1 H) 5.05-5.14 (m, 1 H) 4.77-4.85 (m, 1 H) 3.72 (s, 3 H) 3.53-3.63 (m, 1 H) 3.07-3.19 (m, 1 H) 2.88 (dd, J = 12.96, 11.30 Hz, 1 H) 2.45-2.59 (m, 2 H) 1.59-1.73 (m, 1 H). LCMS-ESI (pos.) m/z: 536.0 (M + H)$^+$. |

TABLE 15-continued

| Example | Reagents | Structure, name and data |
|---|---|---|
| 300.0 | 2-isothiocyanato-1,3-difluorobenzene (Sigma Aldrich), 1-methyl-1H-pyrazole-3-carbohydrazide (Bellen), and (3R,5R)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide (Example 474.0). This was the second enantiomer to elute from a Chiralpak AS-H column by SFC chiral separation with 35% MeOH. | 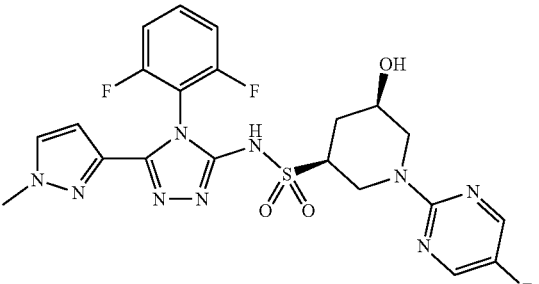<br><br>OR<br><br>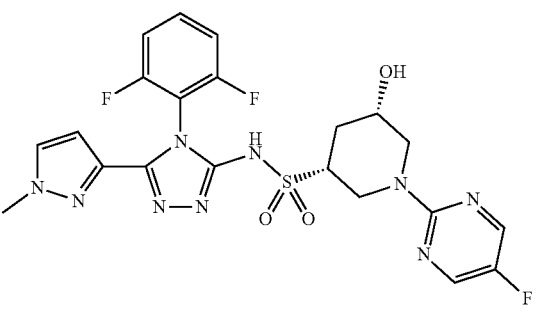<br><br>(3R,5R)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide or (3S,5R)-N-(4-(2,6-difluorophenyl)-5-(1-methyl-1H-pyrazol-3-yl)-4H-1,2,4-triazol-3-yl)-1-(5-fluoro-2-pyrimidinyl)-5-hydroxy-3-piperidinesulfonamide.<br>$^1$H NMR (400 MHz, CD$_3$OD) δ 8.28 (d, J = 0.73 Hz, 2 H) 7.63-7.72 (m, 1 H) 7.59-7.63 (m, 1 H) 7.19-7.27 (m, 2 H) 6.65 (d, J = 2.38 Hz, 1 H) 5.05-5.15 (m, 1 H) 4.83 (br s, 1 H) 3.72 (s, 3 H) 3.53-3.64 (m, 1 H) 3.07-3.19 (m, 1 H) 2.87 (dd, J = 13.01, 11.35 Hz, 1 H) 2.44-2.60 (m, 2 H) 1.60-1.74 (m, 1 H). LCMS-ESI (pos.) m/z: 536.0 (M + H)$^+$. |
| 301.0 | 2-isothiocyanato-1,3-dimethoxybenzene (Example 465.0), 1-methyl-1H-pyrazole-3-carbohydrazide (Bellen), and (2S,3R)-3-(5-methoxypyrazin-2-yl)butane-2-sulfonamide (Example 464.5). | 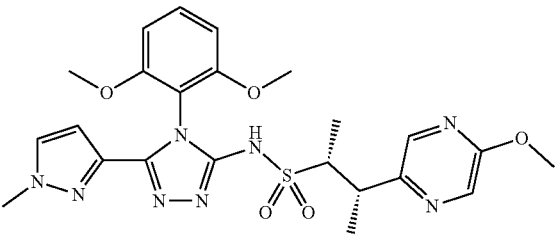<br><br>(2R,3S)-N-(4-(2,6-dimethoxyphenyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (400 MHz, CDCl$_3$) δ 8.13 (d, J = 1.14 Hz, 1 H) 7.93 (d, J = 1.04 Hz, 1 H) 7.41 (t, J = 8.50 Hz, 1 H) 7.23 (d, J = 2.28 Hz, 1 H) 6.62 (dd, J = 8.50, 3.11 Hz, 2 H) 5.88 (d, J = 2.38 Hz, 1 H) 3.93 (s, 3 H) 3.85 (s, 3 H) 3.70 (m, 7 H) 3.48 (qd, J = 6.98, 3.94 Hz, 1 H) 1.33 (d, J = 7.15 Hz, 3 H) 1.30 (d, J = 7.05 Hz, 3 H). LCMS-ESI (pos.) m/z: 529.3 (M + H)$^+$. |

Example 302.0. Preparation of N-(4-(5-bromo-2-methoxyphenyl)-5-(2-thiophenyl)-4H-1,2,4-triazol-3-yl)-2-(4-fluorophenyl)ethanesulfonamide

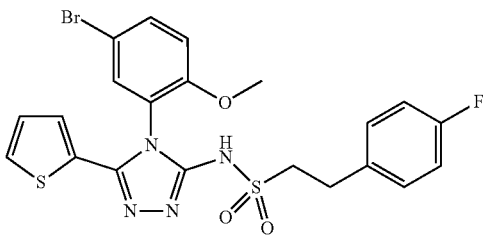

302.0

N-(4-(5-Bromo-2-methoxyphenyl)-5-(2-thiophenyl)-4H-1,2,4-triazol-3-yl)-2-(4-fluorophenyl)ethanesulfonamide, Example 302.0. Example 302.0 was prepared from Example 133.01 and 2-(4-fluorophenyl)-ethanesulfonyl chloride (SynChem, IL) using the procedure described in Example 236.0. $^1$H NMR (400 MHz, DMSO-$d_6$) δ 13.33 (s, 1H), 7.87 (d, J=2.5 Hz, 1H), 7.81 (dd, J=8.9, 2.6 Hz, 1H), 7.73 (dd, J=5.0, 1.1 Hz, 1H), 7.31-7.37 (m, 2H), 7.24-7.31 (m, 3H), 7.08 (dd, J=5.0, 3.8 Hz, 1H), 6.94 (dd, J=3.7, 1.2 Hz, 1H), 3.67-3.74 (m, 3H), 3.15-3.32 (m, 2H), 2.86-3.00 (m, 2H). LCMS-ESI (pos.), m/z: 537.0 (M+H)$^+$.

Example 303.0. Preparation of N-(4-(5-(dimethylamino)-2-methoxyphenyl)-5-(2-thiophenyl)-4H-1,2,4-triazol-3-yl)-2-(4-fluorophenyl)ethanesulfonamide

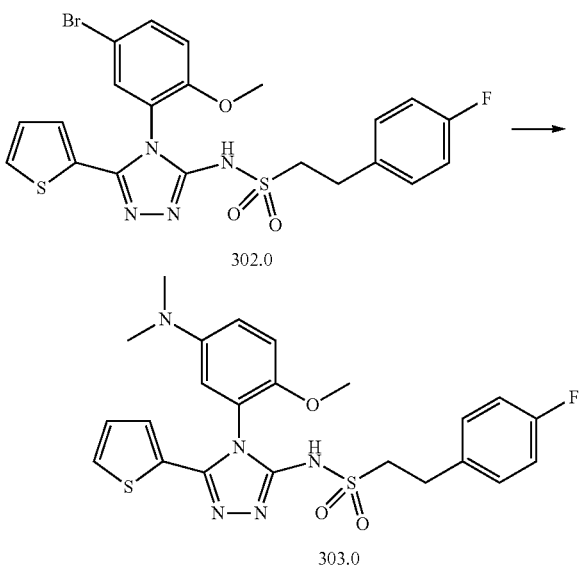

N-(4-(5-(Dimethylamino)-2-methoxyphenyl)-5-(2-thiophenyl)-4H-1,2,4-triazol-3-yl)-2-(4-fluorophenyl)ethanesulfonamide, Example 303.0. A mixture of Example 302.0 (116 mg, 0.216 mmol), Xantphos (24.98 mg, 0.043 mmol), Pd$_2$(dba)$_3$ (19.77 mg, 0.022 mmol) and sodium 2-methylpropan-2-olate (72.6 mg, 0.755 mmol) in dioxane (1.4 mL) was sparged with nitrogen gas for a min. Dimethylamine (2.0 M) in THF (324 µL, 0.648 mmol) was added and the reaction mixture was sparged with nitrogen gas for 10 seconds. The mixture was then heated at 100° C. for 9 h. The reaction mixture was filtered through a 5 mL Chem Elute extraction cartridge and rinsed with DCM (20 mL). The solution was concentrated in vacuo. The material thus obtained was separated by preparative HPLC on a C-18 reverse phase column (CAPCELL PAK, UG120, 5 um, 30×250 mm) eluting with (10-90% ACN with 0.1% TFA/water with 0.1% TFA), the fractions were lyophilized to provide Example 303.0 (36 mg, 0.058 mmol, 27% yield) as a white powder. $^1$H NMR (500 MHz, CD$_3$OD) δ 7.57 (dd, J=5.01, 1.10 Hz, 1H) 7.53 (dd, J=9.05, 2.93 Hz, 1H) 7.45 (d, J=2.93 Hz, 1H) 7.31 (d, J=9.05 Hz, 1H) 7.23 (dd, J=8.56, 5.38 Hz, 2H) 7.06 (dd, J=3.91, 1.22 Hz, 1H) 6.99-7.04 (m, 3H) 3.74 (s, 3H) 3.26-3.32 (m, 2H) 3.15 (m, 6H) 3.02-3.08 (m, 2H). LCMS-ESI (pos.), m/z: 502.1 (M+H)$^+$.

Example 304.0. Preparation of (2R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide and (2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide

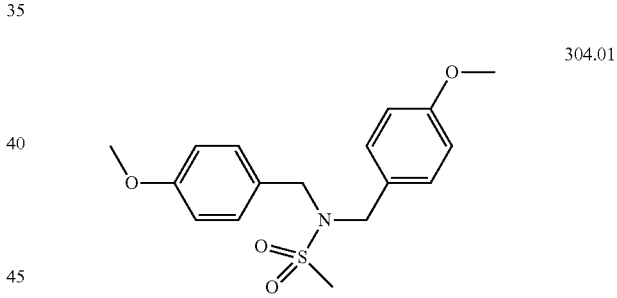

304.01

N,N-Bis(4-methoxybenzyl)methanesulfonamide, Example 304.01. To a 1 L RBF was added Example 406.01 (48.9 g, 190 mmol) and TEA (anhydrous (31.7 mL, 228 mmol)) in DCM (317 mL). The solution was cooled to −5° C. with an ice-salt bath and then methanesulfonyl chloride (16.17 mL, 209 mmol) in DCM (158 mL) was added dropwise with stirring at −5° C. Upon completion of the addition, the reaction mixture was stirred at −5° C. to RT for 15 h. A white solid was isolated by filtration. The cake was rinsed with DCM (100 mL). The combined organic layers were washed with 1.0 N HCl (150 mL×4) and brine and dried over Na$_2$SO$_4$. The solution was filtered and concentrated in vacuo. The material thus obtained was purified by silica gel chromatography (a gradient of 0% to 50% EtOAc in hexanes) to provide Example 304.01 (52 g, 155 mmol, 82% yield) as a white solid. LCMS-ESI (pos.) m/z: 358.1 (M+Na)$^+$.

304.02

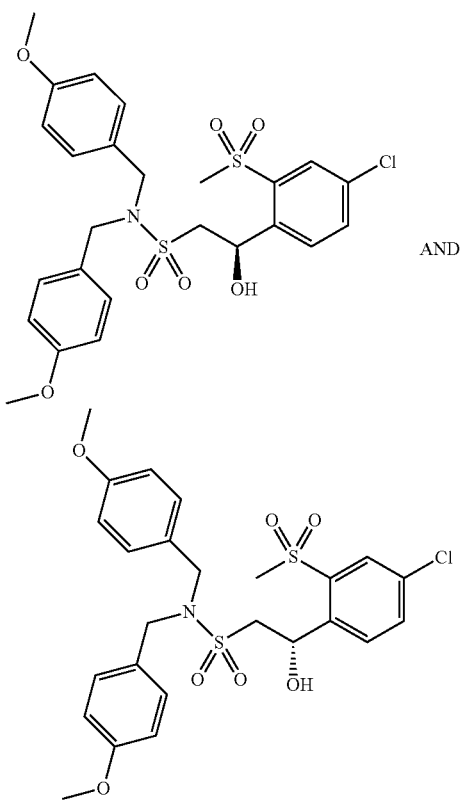

AND (R)-2-(4-Chloro-2-(methylsulfonyl)phenyl)-2-hydroxy-N,N-bis(4-methoxybenzyl)ethanesulfonamide and (S)-2-(4-chloro-2-(methylsulfonyl)phenyl)-2-hydroxy-N,N-bis(4-methoxybenzyl)ethanesulfonamide, Example 304.02. To a 250 mL RBF was added N,N-bis(4-methoxybenzyl)methanesulfonamide (Example 304.01, 1.52 g, 4.53 mmol) in 2-methyltetrahydrofuran (25 mL). To this mixture was added n-butyllithium (2.5 M in hexanes, 2.18 mL, 5.44 mmol) dropwise under N₂ at −78° C. The resulting solution was stirred at −78° C. for 10 min and then 4-chloro-2-(methylsulfonyl)benzaldehyde (1.090 g, 4.98 mmol) in 2-methyltetrahydrofuran (25 mL) was added dropwise via syringe under N₂ at −78° C. with stirring. The reaction mixture was stirred at −78° C. for 10 min before the dry-ice bath was removed. The reaction mixture was stirred at −78° C. to RT for 60 min in total before being quenched with a saturated solution of NH₄Cl. The reaction mixture was diluted with water and extracted with EtOAc. The organic extract was washed with brine and dried over Na₂SO₄. The solution was filtered and concentrated in vacuo. The material thus obtained was purified by silica gel chromatography (a gradient of 0% to 100% EtOAc in hexanes) to provide Example 304.02 (806 mg, 1.46 mmol, 32% yield) as a white solid. LCMS-ESI (pos.), m/z: 576.0 (M+Na)⁺.

304.03

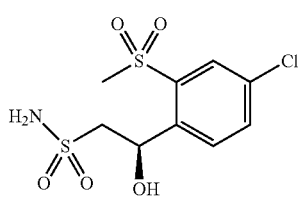

AND

-continued

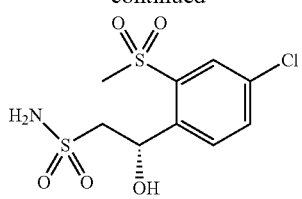

(R)-2-(4-Chloro-2-(methylsulfonyl)phenyl)-2-hydroxyethanesulfonamide and (S)-2-(4-chloro-2-(methylsulfonyl)phenyl)-2-hydroxyethanesulfonamide, Example 304.03. To a 250 mL RBF was added Example 304.02 (806 mg, 1.46 mmol) and anisole (0.632 mL, 5.82 mmol) in TFA (14.5 mL, 1.45 mmol). The reaction mixture was stirred at RT for 72 h. The mixture was concentrated in vacuo and purified by silica gel chromatography (a gradient of 0% to 100% EtOAc in DCM) to provide Example 304.03 (360 mg, 1.147 mmol, 79% yield) as a white solid. LCMS-ESI (pos.), m/z: 336.0 (M+Na)⁺.

304.0

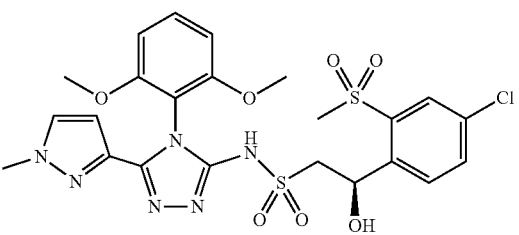

AND

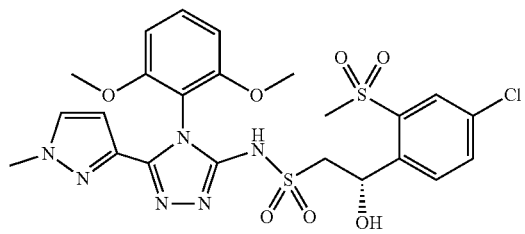

(2R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide and (2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide, Example 304.0. Example 304.0 was prepared from Example 304.03 using the procedure as described in Example 6.0. ¹H NMR (500 MHz, CD₂Cl₂) δ 7.92 (d, J=2.20 Hz, 1H) 7.66 (d, J=8.31 Hz, 1H) 7.55 (dd, J=8.56, 2.20 Hz, 1H) 7.40 (t, J=8.56 Hz, 1H) 7.21 (d, J=2.20 Hz, 1H) 6.62 (dd, J=8.44, 1.10 Hz, 2H) 6.01 (d, J=2.20 Hz, 1H) 5.82 (d, J=7.83 Hz, 1H) 3.72 (s, 3H) 3.69 (s, 3H) 3.66 (s, 3H) 3.35 (dd, J=13.94, 1.96 Hz, 1H) 3.20 (dd, J=13.94, 9.54 Hz, 1H) 3.02 (s, 3H). LCMS-ESI (pos.), m/z: 597.0 (M+H)⁺.

Example 305.0. Preparation of (2R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide and (2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide

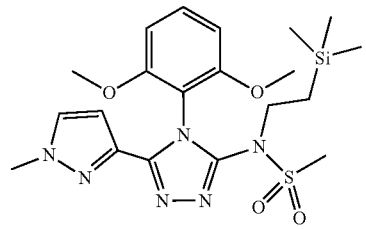

Example 305.01

N-(4-(2,6-Dimethoxyphenyl)-5-(1-methyl-1H-pyrazol-3-yl)-4H-1,2,4-triazol-3-yl)-N-(2-(trimethylsilyl)ethyl)methanesulfonamide, Example 305.02. Example 260.0 (4.87 g, 12.87 mmol) was azeotroped with toluene and then suspended in toluene (18 mL). To the mixture was added 2-(trimethylsilyl)ethanol (3.69 mL, 25.7 mmol), and then the mixture was sparged with nitrogen gas for 3 min. To the mixture was added cyanomethylenetributyl-phosphorane (5.59 mL, 23.2 mmol), and the resulting mixture was sparged with nitrogen again for 2 min. The reaction was heated at 90° C. for 45 min. The reaction was then cooled to RT. The solution was absorbed onto a plug of silica gel and purified by chromatography through a Redi-Sep pre-packed silica gel column (220 g) eluting with a gradient of 0% to 100% EtOAc in hexanes. The fractions were concentrated and then triturated with ethyl ether to provide the title compound, Example 305.1 (5.65 g, 11.8 mmol, 92% yield), as a white solid. $^1$H NMR (400 MHz, CD$_2$Cl$_2$) δ 7.45 (t, J=8.6 Hz, 1H), 7.25 (d, J=2.3 Hz, 1H), 6.67 (d, J=8.4 Hz, 2H), 5.93 (d, J=2.3 Hz, 1H), 4.26-4.33 (m, 2H), 3.82 (s, 3H), 3.75 (m, 6H), 2.68 (s, 3H), 1.28-1.35 (m, 2H), 0.08-0.12 (m, 9H). LCMS-ESI (pos.) m/z: 479.1 (M+H)$^+$.

305.02

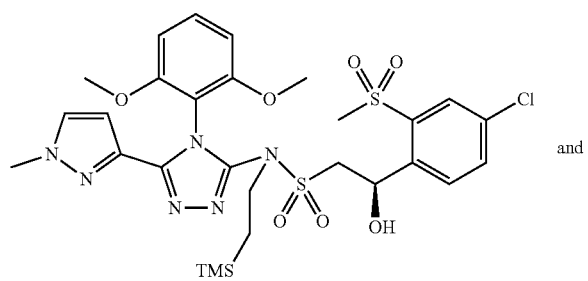

and

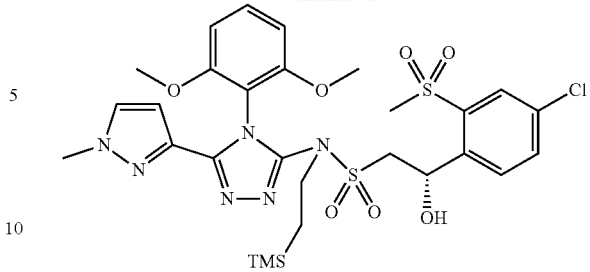

(S)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide and (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide, Example 305.02. Example 305.02 was prepared from Example 305.01 and 4-chloro-2-(methylsulfonyl)benzaldehyde using the procedure described in Example 351.4. LCMS-ESI (pos.), m/z: 697.1 (M+H)$^+$.

305.03

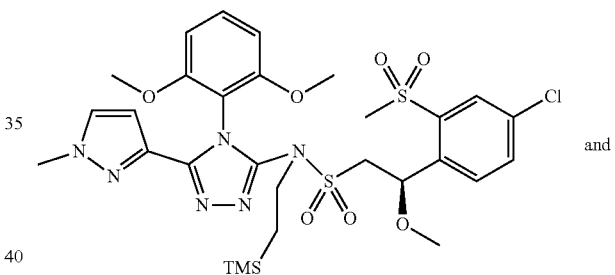

and

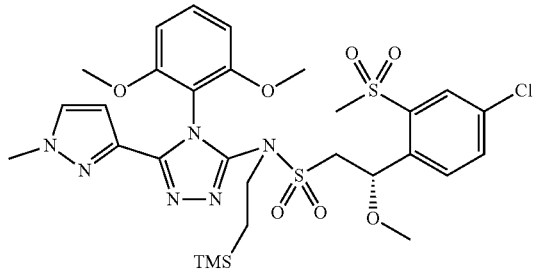

(S)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxy-N-(2-(trimethylsilyl)ethyl)ethanesulfonamide and (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxy-N-(2-(trimethylsilyl)ethyl)ethanesulfonamide, Example 305.03. Example 305.03 was prepared from Example 305.02 and iodomethane using the procedure described in Example 264.01. LCMS-ESI (pos.), m/z: 711.2 (M+H)$^+$.

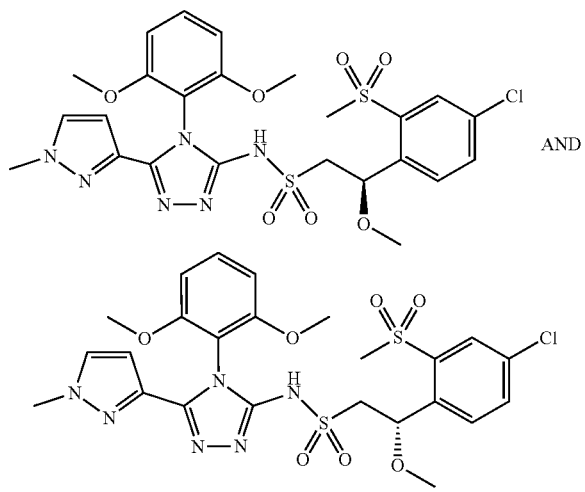

(2R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide and (2S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide, Example 305.0. Example 305.0 was prepared from Example 305.03 using the procedure described in Example 350.0. $^1$H NMR (500 MHz, CD$_3$OD) δ 8.04 (d, J=2.20 Hz, 1H) 7.61-7.72 (m, 2H) 7.49 (t, J=8.56 Hz, 1H) 7.27 (br. s, 1H) 6.74 (d, J=8.07 Hz, 1H) 6.66 (d, J=8.07 Hz, 1H) 5.94 (s, 1H) 5.73 (t, J=6.24 Hz, 1H) 3.89 (s, 3H) 3.81 (s, 3H) 3.74 (s, 3H) 3.59 (dd, J=14.31, 6.97 Hz, 1H) 3.47 (dd, J=14.31, 5.75 Hz, 1H) 3.24 (s, 3H) 3.05 (s, 3H). LCMS-ESI (pos.), m/z: 611.2 (M+H)$^+$.

The compounds set forth in the following table were synthesized following the procedure in Example 134.0 using the known starting material as described.

TABLE 16

| Example | Reagents | Structure, name and data |
|---|---|---|
| 306.0 | This was the second enantiomer to elute from an AS-H column by SFC chiral separation of Example 279.0 under the condition described in Example 281.0. | (2S,3R)-N-(4-(2,6-dimethoxyphenyl)-5-(1-methyl-1H-pyrazol-3-yl)-4H-1,2,4-triazol-3-yl)-3-(5-methyl-2-pyrazinyl)-2-butanesulfonamide. $^1$H NMR (400 MHz, CDCl$_3$) δ 10.91 (br s, 1 H) 8.41 (s, 1 H) 8.32 (s, 1 H) 7.45 (t, J = 8.44 Hz, 1 H) 7.24 (d, J = 2.45 Hz, 1 H) 6.62-6.71 (m, 2 H) 5.90 (d, J = 2.45 Hz, 1 H) 3.89 (s, 3 H) 3.74 (m, 7 H) 3.55 (qd, J = 6.97, 4.52 Hz, 1 H) 2.57 (s, 3 H) 1.37 (app dd, J = 8.19, 7.21 Hz, 6 H). LCMS-ESI (pos.) m/z: 528.2 (M + H)$^+$. |
| 307.0 | 2-isothiocyanato-1,3-dimethoxybenzene (Example 465.0), 1-methyl-1H-pyrazole-3-carbohydrazide (Bellen), and (1R,2S)-1-methoxy-1-(5-methoxypyrazin-2-yl)propane-2-sulfonamide and (1S,2R)-1-methoxy-1-(5-methoxypyrazin-2-yl)propane-2-sulfonamide (Example 307.1). | AND |

TABLE 16-continued

| Example | Reagents | Structure, name and data |
|---|---|---|

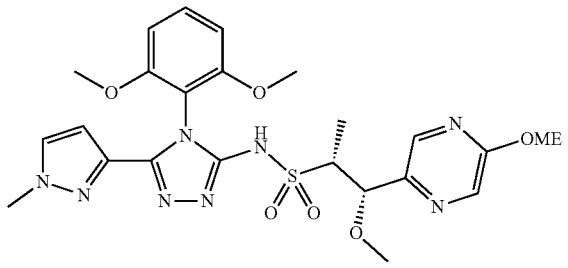

(1R,2S)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide and
(1S,2R)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide.
$^1$H NMR (400 MHz, CDCl$_3$) δ 1.24 (d, J = 3.0 Hz, 3 H) 3.27 (s, 3 H) 3.46 (qd, J = 7.03, 3.06 Hz, 1 H) 3.87 (s, 3 H) 3.88 (s, 3 H) 3.92 (s, 3 H) 4.95 (d, J = 3.01 Hz, 1 H) 7.28-7.31 (m, 1 H) 7.71 (dt, J = 8.02, 1.95 Hz, 1 H) 8.08 (s, 1 H) 8.14 (d, J = 1.30 Hz, 1 H) 8.42 (s, 1 H) 8.58 (d, J = 1.76 Hz, 1 H) 8.63 (dd, J = 4.87, 1.61 Hz, 1 H) 11.11 (s, 1 H). LCMS-ESI (pos.) m/z: 544.1 (M+ H)$^+$.

308.0  This was the first enantiomer to elute from a Lux column by SFC chiral separation of Example 307.0 under the following condition: Run on Thar 80 SFC with 250 × 30 mm Lux column with 44.0 mL/min MeOH (+20 mM NH$_3$) + 36.0 g/min CO$_2$, 55% co-solvent at 80.0 g/min. Temp. = 29° C., Outlet pressure = 100 bar, Wavelength = 222 nm. Injected 1.0 mL of 122 mg sample dissolved in 16.0 mL of MeOH:DCM 5:3; c = 7.625 mg/mL and 7.625 mg per injection. Cycle time 8.5 min, run time 11.0 min.

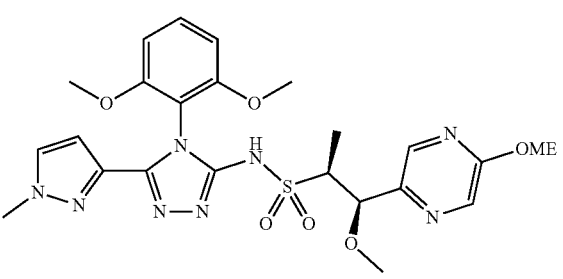

(1R,2S)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide or
(1S,2R)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide.
$^1$H NMR (400 MHz, CDCl$_3$) δ 1.24 (d, J = 3.0 Hz, 3 H) 3.27 (s, 3 H) 3.46 (m, 1 H) 3.87 (s, 3 H) 3.88 (s, 3 H) 3.92 (s, 3 H) 4.95 (d, J = 3.01 Hz, 1 H) 7.28-7.31 (m, 1 H) 7.71 (dt, J = 8.02, 1.95 Hz, 1 H) 8.08 (s, 1 H) 8.14 (d, J = 1.3 Hz, 1 H) 8.42 (s, 1 H) 8.58 (d, J = 1.76 Hz, 1 H) 8.63 (dd, J = 4.87, 1.61 Hz, 1 H) 11.11 (s, 1 H). LCMS-ESI (pos.) m/z: 544.1 (M+ H)$^+$.

or

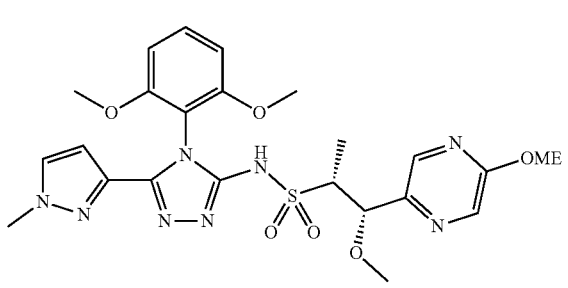

TABLE 16-continued

| Example | Reagents | Structure, name and data |
|---|---|---|
| 309.0 | This was the second enantiomer to elute from a Lux column by SFC chiral separation of Example 307.0 under thecondition as described in Example 308.0. | 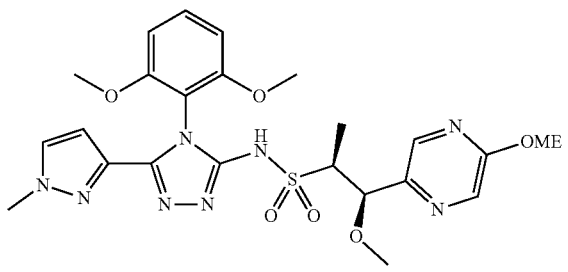<br>(1R,2S)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide or (1S,2R)-N-(4-(2,6-dimethoxyphenyl)-5-(1-methyl-1H-pyrazol-3-yl)-4H-1,2,4-triazol-3-yl)-1-methoxy-1-(5-methoxy-2-pyrazinyl)-2-propanesulfonamide.<br>$^1$H NMR (400 MHz, CDCl$_3$) δ δ 1.24 (d, J = 3.0 Hz, 3 H) 3.27 (s, 3 H) 3.46 (m, 1 H) 3.87 (s, 3 H) 3.88 (s, 3 H) 3.92 (s, 3 H) 4.95 (d, J = 3.01 Hz, 1 H) 7.28-7.31 (m, 1 H) 7.71 (dt, J = 8.02, 1.95 Hz, 1 H) 8.08 (s, 1 H) 8.14 (d, J = 1.3 Hz, 1 H) 8.42 (s, 1 H) 8.58 (d, J = 1.76 Hz, 1 H) 8.63 (dd, J = 4.87, 1.61 Hz, 1 H) 11.11 (s, 1 H). LCMS-ESI (pos.) m/z: 544.1 (M+ H)$^+$.<br>or<br>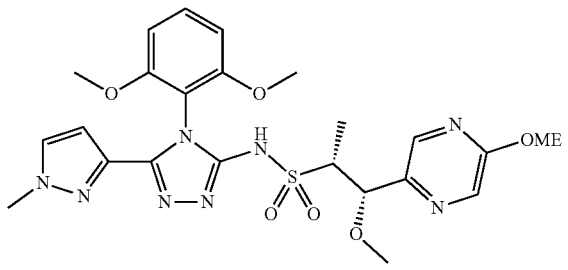 |

Example 310.0. Preparation of 2-(4-chlorophenyl)-N-(4-(4-methoxybiphenyl-3-yl)-5-(thiophen-2-yl)-4H-1,2,4-triazol-3-yl)ethanesulfonamide

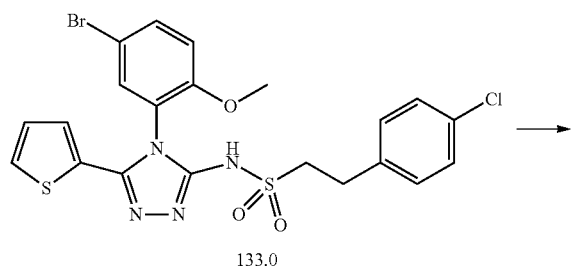

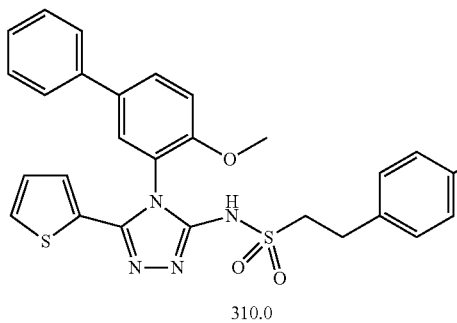

3-(3-(2-(4-Chlorophenyl)ethylsulfonamido)-5-(thiophen-2-yl)-4H-1,2,4-triazol-4-yl)-4-methoxybenzoic acid, Example 310.0. A glass microwave reaction vessel was charged with Example 133.0 (34 mg, 0.061 mmol), phenylboronic acid (14.97 mg, 0.12 mmol), cesium fluoride (4.53 µL, 0.12 mmol) and tetrakis(triphenylphosphine)palladium (3.55 mg, 3.07 µmol) in dioxane (1.2 mL). The reaction mixture was stirred and heated in a Discover model microwave reactor (CEM, Matthews, N.C.) at 100° C. for 5 h. LCMS analysis showed title product. The mixture was partitioned between EtOAc and water resulting in an emulsion. The emulsion layer was filtered through a coarse fritted funnel. The organic layers were combined, washed with brine and evaporated to give a tan solid. The material thus obtained was absorbed onto a plug of silica gel and purified by chromatography through a Redi-Sep pre-packed silica gel column (4 g) eluting with a gradient of 0% to 100% EtOAc in hexanes, to provide the title compound, Example 310.0 (7 mg, 0.013 mmol, 21%), as a light-yellow solid. $^1$H NMR (400 MHz, CDCl$_3$) δ 10.94 (br. s, 1H) 7.81 (dd, J=8.61, 2.35 Hz, 1H) 7.52-7.61 (m, 3H) 7.43-7.49 (m, 2H) 7.36-7.43 (m, 2H) 7.21-7.27 (m, 2H) 7.03-7.18 (m, 4H) 6.92-7.00 (m, 1H) 3.76 (s, 3H) 3.25-3.35 (m, 2H) 3.10 (dd, J=11.15, 5.28 Hz, 2H). LCMS-ESI (pos.) m/z: 551.0 (M+H)$^+$.

Example 311.0. 2-(4-chlorophenyl)-N-(4-(2,6-dimethoxyphenyl)-5-(thiophen-2-yl)-4H-1,2,4-triazol-3-yl)ethanesulfonamide

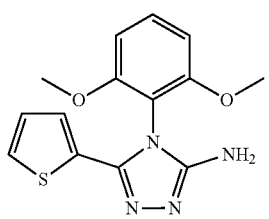

311.01

4-(2,6-Dimethoxyphenyl)-5-(thiophen-2-yl)-4H-1,2,4-triazol-3-amine, Example 311.01. Example 311.01 was prepared from 2,6-dimethoxyaniline (commercially available from Oakwood Products, Inc., SC, USA) instead of o-anisidine using the procedure described in Example 234.03. LCMS-ESI (pos.) m/z: 303.2 (M+H)$^+$.

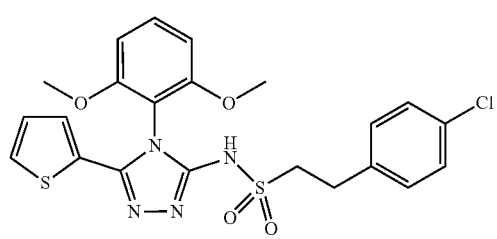

311.0

2-(4-Chlorophenyl)-N-(4-(2,6-dimethoxyphenyl)-5-(thiophen-2-yl)-4H-1,2,4-triazol-3-yl)ethanesulfonamide, Example 311.0. Example 311.0 was prepared from Example 311.01 using the procedure described in Example 236.0. $^1$H NMR (400 MHz, CD$_2$Cl$_2$) δ 10.87 (br. s, 1H), 7.55 (t, J=8.5 Hz, 1H), 7.38 (dd, J=5.1, 1.2 Hz, 1H), 7.23-7.30 (m, 2H), 7.05-7.16 (m, 3H), 6.96 (dd, J=5.1, 3.9 Hz, 1H), 6.72-6.77 (m, J=8.4 Hz, 2H), 3.75 (m, 6H), 3.15-3.29 (m, 2H), 2.97-3.09 (m, 2H). LCMS-ESI (pos.) m/z: 505.1 (M+H)$^+$.

Example 312.0. Preparation of 2-(4-chlorophenyl)-N-(4-(2-methoxy-5-(methylsulfonyl)phenyl)-5-(thiophen-2-yl)-4H-1,2,4-triazol-3-yl)ethanesulfonamide

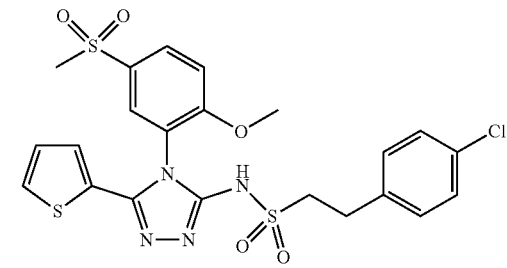

312.0

2-(4-Chlorophenyl)-N-(4-(2-methoxy-5-(methylsulfonyl)phenyl)-5-(thiophen-2-yl)-4H-1,2,4-triazol-3-yl)ethanesulfonamide, Example 312.0. A mixture of Example 133.0 (31 mg, 0.056 mmol), copper(II) triflate (4.1 mg, 0.011 mmol), sodium methanesulfinate (9 mg, 0.084 mmol) and N,N'-dimethylethylenediamine (3 μL, 0.03 mmol) in DMSO (0.6 mL) was combined in a 5 mL vial. A small amount of CuI was added, and the resulting mixture was heated at 100° C. for 2 d. The mixture was partitioned between EtOAc and water resulting in an emulsion. The emulsion layer was removed and filtered through a coarse fritted funnel and worked up separately. The organics were combined, washed with brine and evaporated to give black solid. The material thus obtained was absorbed onto a plug of silica gel and purified by chromatography though a Redi-Sep pre-packed silica gel column (4 g) eluting with a gradient of 0% to 100% EtOAc in DCM, to provide Example 312.0 (5 mg, 16%) as a white solid. $^1$H NMR (400 MHz, CD$_3$OD) δ 8.21 (dd, J=8.80, 2.35 Hz, 1H) 8.05 (d, J=2.35 Hz, 1H) 7.58 (dd, J=5.09, 1.17 Hz, 1H) 7.47 (d, J=8.80 Hz, 1H) 7.18-7.37 (m, 4H) 7.00-7.11 (m, 2H) 3.85 (s, 3H) 3.30-3.38 (m, 2H) 3.18 (s, 3H) 3.03-3.14 (m, 2H). LCMS-ESI (pos.) m/z: 553.0 (M+H)$^+$.

The compounds set forth in the following table were synthesized following the procedures described in Example 101.0 and 102.0 using the starting materials as described.

TABLE 17

| Example | Reagents | Structure, Name and Data |
|---|---|---|
| 313.0 | 2-(5-bromo-4-(2,6-dimethoxyphenyl)-4H-1,2,4-triazol-3-yl)-4-methylthiazole, Example 399.0, and (1S,2S)-1-methoxy-1-(5-methylpyrimidin-2-yl)propane-2-sulfonamide and (1R,2R)-1-methoxy-1-(5-methylpyrimidin-2-yl)propane-2-sulfonamide (prepared in an analogous fashion to the procedure described in Example 466.0 employing (Z)-5-methyl-2-(prop-1-en-1-yl)pyrimidine). Chiral separation conditions: Run on Thar 80 SFC with 250 × 21 mm IA column with 15 g/min MeOH (neat) + 35 g/min CO$_2$, 30% co-solvent at 50 g/min. Outlet pressure = 100 bar; Temp. = 23° C.; Wavelength = 299 nm. Injected 0.3 mL of a solution from 18 mg sample dissolved in 6.0 mL of MeOH:DCM, 5:1, c = 3.0 mg/mL; 0.9 mg per injection. Cycle time 8 min, run time 11 min to deliver peak 2 as the title compound. | (1S,2S)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide or (1R,2R)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide. $^1$H NMR (400 MHz, CD$_3$OD) δ 8.68 (s, 2 H) 7.54 (t, J = 8.51 Hz, 1 H) 7.22 (s, 1 H) 6.82 (d, J = 8.08 Hz, 2 H) 4.62-4.69 (m, 1 H) 4.59 (s, 1 H) 3.81 (s, 3 H) 3.77 (s, 3 H) 3.69 (m, 1 H) 3.13 (s, 3 H) 2.37 (s, 3 H) 2.34 (s, 3 H) 1.05 (d, J = 7.04 Hz, 3 H). LCMS-ESI (pos.) m/z: 546.0 (M + H)$^+$. |
| 314.0 | 2-(5-bromo-4-(2,6-dimethoxyphenyl)-4H-1,2,4-triazol-3-yl)-4-methylthiazole, Example 399.0, and (1R,2R)-1-hydroxy-1-(5-methylpyrimidin-2-yl)propane-2-sulfonamide and (1S,2S)-1-hydroxy-1-(5-methylpyrimidin-2-yl)propane-2-sulfonamide (prepared in an analogous fashion to the procedure described in Example 466.0 employing (Z)-5-methyl-2-(prop-1-en-1-yl)pyrimidine) Chiral separation conditions of the racemic mixture (32 mg): 250 × 30 mm CC4 column with 60 mL/min MeOH (neat) + 60 g/min CO$_2$ on Thar 350 SFC, 50% co-solvent at 120 g/min. Outlet pressure = 100 bar; Temp. = 20° C.; Wavelength = 293 nm. Used 0.6 mL injections of 32 mg sample dissolved in 10 mL MeOH (3.2 mg/mL), resulting in 1.9 mg/injection. Cycle time = 7.5 min run time = 23 min delivered the title compound as peak 1. | |

| Example | Reagents | Structure, Name and Data |
|---|---|---|
| | | (1R,2R)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide or (1S,2S)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide.<br>$^1$H NMR (500 MHz, CD$_3$OD) δ 8.66 (s, 2 H) 7.54 (t, J = 8.56 Hz, 1 H) 7.21-7.28 (m, 1 H) 6.81 (d, J = 8.56 Hz, 2 H) 5.42 (d, J = 2.69 Hz, 1 H) 3.73-3.76 (m, 7 H) 2.35 (s, 3 H) 2.32 (s, 3 H) 2.30-2.33 (m, 1 H) 1.20 (d, J = 7.09 Hz, 3 H). LCMS-ESI (pos.) m/z: 532.0 (M + H)$^+$. |
| 315.0 | 2-(5-bromo-4-(2,6-dimethoxyphenyl)-4H-1,2,4-triazol-3-yl)-4-methylthiazole, Example 399.0, and (1R,2R)-1-hydroxy-1-(5-methylpyrimidin-2-yl)propane-2-sulfonamide and (1S,2S)-1-hydroxy-1-(5-methylpyrimidin-2-yl)propane-2-sulfonamide (prepared in an analogous fashion to the procedure described in Example 466.0 employing (Z)-5-methyl-2-(prop-1-en-1-yl)pyrimidine) Chiral separation conditions of the racemic mixture (32 mg): 250 × 30 mm CC4 column with 60 mL/min MeOH (neat) + 60 g/min CO$_2$ on Thar 350 SFC, 50% co-solvent at 120 g/min. Outlet pressure = 100 bar; Temp. = 20° C.; Wavelength = 293 nm. Used 0.6 mL injections of 32 mg sample dissolved in 10 mL MeOH (3.2 mg/mL), resulting in 1.9 mg/injection. Cycle time = 7.5 min run time = 23 min delivered the title compound as peak 2. | (1R,2R)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide or (1S,2S)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide.<br>$^1$H NMR (500 MHz, CD$_3$OD) δ 8.66 (s, 2 H) 7.55 (t, J = 8.52 Hz, 1 H) 7.25 (d, J = 0.98 Hz, 1 H) 6.82 (d, J = 10.12 Hz, 2 H) 5.42 (d, J = 2.69 Hz, 1 H) 3.76 (s, 3 H) 3.75 (s, 3 H) 3.74 (d, J = 2.69 Hz, 1 H) 2.35 (s, 3 H) 2.32 (s, 3 H) 1.20 (d, J = 6.85 Hz, 3 H). LCMS-ESI (pos.) m/z: 532.0 (M + H)$^+$. |

TABLE 17-continued

| Example | Reagents | Structure, Name and Data |
|---|---|---|
| 316.0 | 2-(5-bromo-4-(2,6-dimethoxyphenyl)-4H-1,2,4-triazol-3-yl)-4-methylthiazole, Example 399.0, and (1R,2S)-1-hydroxy-1-(5-methylpyrimidin-2-yl)propane-2-sulfonamide and (1S,2R)-1-hydroxy-1-(5-methylpyrimidin-2-yl)propane-2-sulfonamide (prepared in an analogous fashion to the procedure described in Example 466.0 employing (E)-5-methyl-2-(prop-1-en-1-yl)pyrimidine). Chiral separation conditions of the racemic mixture: Run on Thar 80 SFC with 250 × 30 mm AD column with 46.5 mL/min EtOH (neat) + 28.5 g/min CO₂, 62% co-solvent at 75 g/min. Outlet pressure = 100 bar; Temp. = 24° C.; Wavelength = 300 nm. Injected 0.30 mL of a solution from 44 mg sample dissolved in 10.0 mL of MeOH, c = 4.4 mg/mL; 1.32 mg per injection. Cycle time 9 min, run time 12 min delivered the title compound as peak 1. | 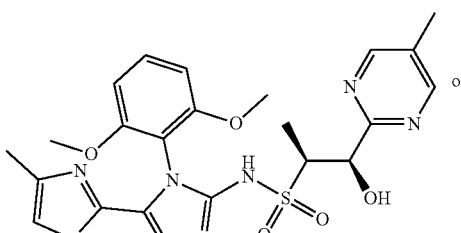<br>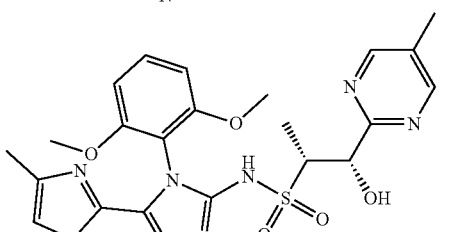<br>(1R,2R)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide or (1S,2S)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide.<br>$^{1}$H NMR (400 MHz, CD₃OD) δ 8.65 (s, 2 H) 7.55 (t, J = 8.41 Hz, 1 H) 7.26 (s, 1 H) 6.83 (d, J = 8.61 Hz, 2 H) 4.97 (d, J = 7.43 Hz, 2 H) 3.81 (s, 3 H) 3.80 (s, 3 H) 3.64 (td, J = 6.80, 2.64 Hz, 2 H) 2.36 (s, 3 H) 2.33 (s, 3 H) 1.13 (d, J = 6.58 Hz, 3 H). LCMS-ESI (pos.) m/z: 532.0 (M + H)⁺. |
| 317.0 | 2-(5-bromo-4-(2,6-dimethoxyphenyl)-4H-1,2,4-triazol-3-yl)-4-methylthiazole, Example 399.0, and (1R,2S)-1-hydroxy-1-(5-methylpyrimidin-2-yl)propane-2-sulfonamide and (1S,2R)-1-hydroxy-1-(5-methylpyrimidin-2-yl)propane-2-sulfonamide (prepared in an analogous fashion to the procedure described in Example 466.0 employing (E)-5-methyl-2-(prop-1-en-1-yl)pyrimidine) Chiral separation conditions of the racemic mixture: Run on Thar 80 SFC with 250 × 30 mm AD column with 46.5 mL/min EtOH (neat) + 28.5 g/min CO₂, 62% co-solvent at 75 g/min. Outlet pressure = 100 bar; Temp. = 24° C.; Wavelength = 300 nm. Injected 0.30 mL of a solution from 44 mg sample dissolved in 10.0 mL of MeOH, c = 4.4 mg/mL; 1.32 mg per injection. Cycle time 9 min, run time 12 min delivered the title compound as peak 2. | 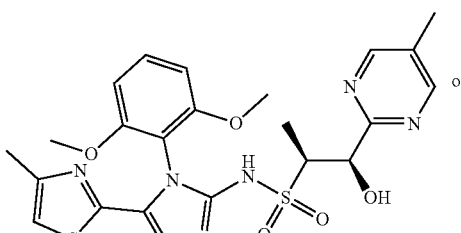<br>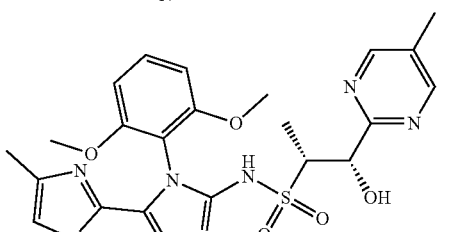 |

| Example | Reagents | Structure, Name and Data |
|---|---|---|
| | | (1R,2R)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide or (1S,2S)-N-(4-(2,6-dimethoxyphenyl)-5-(4-methylthiazol-2-yl)-4H-1,2,4-triazol-3-yl)-1-hydroxy-1-(5-methylpyrimidin-2-yl)propane-2-sulfonamide.<br>$^1$H NMR (400 MHz, CD$_3$OD) δ 8.65 (s, 2 H) 7.56 (t, J = 8.41 Hz, 1 H) 7.26 (s, 1 H) 6.84 (d, J = 8.41 Hz, 2 H) 4.97 (d, J = 7.43 Hz, 1 H) 3.82 (s, 3 H) 3.80 (s, 3 H) 3.55-3.73 (m, 2 H) 2.36 (s, 3 H) 2.33 (s, 3 H) 1.14 (d, J = 7.04 Hz, 3 H). LCMS-ESI (pos.) m/z: 532.0 (M + H)$^+$. |
| 318.0 | 2-(5-bromo-4-(2,6-dimethoxyphenyl)-4H-1,2,4-triazol-3-yl)-4-methylthiazole, Example 399.0, and (1R,2S)-1-methoxy-1-(5-methylpyrimidin-2-yl)propane-2-sulfonamide and (1S,2R)-1-methoxy-1-(5-methylpyrimidin-2-yl)propane-2-sulfonamide (prepared in an analogous fashion to the procedure described in Example 466.0 employing (Z)-5-methyl-2-(prop-1-en-1-yl)pyrimidine) Chiral separation conditions of the racemic mixture: Run on Thar 80 SFC with 250 × 21 mm IA column with 15 g/min MeOH (neat) + 35 g/min CO$_2$, 30% co-solvent at 50 g/min. Outlet pressure = 100 bar; Temp. = 23° C.; Wavelength = 299 nm. Injected 0.3 mL of a solution from 18 mg sample dissolved in 6.0 mL of MeOH:DCM, 5:1, c = 3.0 mg/mL; 0.9 mg per injection. Cycle time 8 min, run time 11 min delivered the title compound as peak 1. | 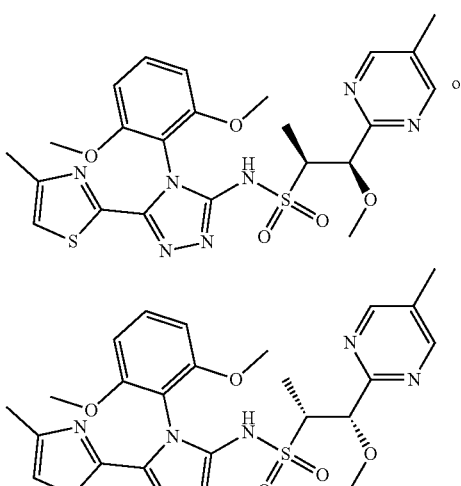<br>(1S,2R)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide or (1R,2S)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide.<br>$^1$H NMR (400 MHz, CD$_3$OD) δ 8.66 (s, 2 H) 7.54 (t, J = 8.51 Hz, 1 H) 7.25 (s, 1 H) 6.82 (d, J = 8.61 Hz, 2 H) 5.02 (d, J = 3.52 Hz, 1 H) 3.78 (s, 3 H) 3.75 (s, 3 H) 3.54-3.65 (m, 1 H) 3.37 (s, 2 H) 3.29 (s, 3 H) 2.36 (s, 3 H) 2.33 (s, 3 H) 1.27 (d, J = 7.04 Hz, 3 H). LCMS-ESI (pos.) m/z: 546.0 (M + H)$^+$. |
| 323.0 | 3-bromo-4-(2,6-dimethoxyphenyl)-5-(1-methyl-1H-pyrazol-3-yl)-4H-1,2,4-triazole, Example 399.5, and (1R,2S)-1-methoxy-1-(5-methylpyrazin-2-yl)propane-2-sulfonamide (Example 466.1). | 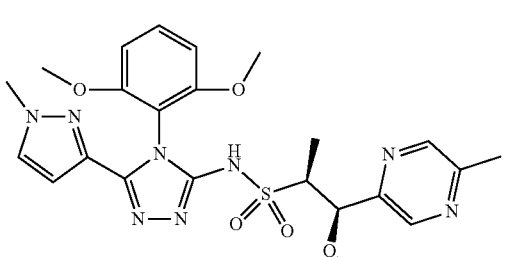<br>(1R,2S)-N-(4-(2,6-dimethoxyphenyl)-5-(1-methyl-1H-pyrazol-3-yl)-4H-1,2,4-triazol-3-yl)-1-methoxy-1-(5-methyl-2-pyrazinyl)-2-propanesulfonamide.<br>$^1$H NMR (500 MHz, CDCl$_3$) δ 11.07 (br s, 1H), 8.5 (s, 1H), 8.41 (br s, 1H), 7.4 (dd, J = 8.4, 8.4 Hz, 1H), 7.22 (br s, 1H), 6.61-6.64 (m, 2H), 5.85 (s, 1H), 5.52 (d, J = 2.9 Hz, 1H), 3.84 (s, 3H), 3.70 (s, 3H), 3.69 (s, 3H), 3.45-3.49 (m, 1H), 3.29 (s, 3H), 2.54 (s, 3H), 1.22 (d, J = 7.1 Hz, 3H). LCMS-ESI (pos.) m/z: 529.3 (M + H)$^+$. |

TABLE 17-continued

| Example | Reagents | Structure, Name and Data |
|---|---|---|
| 324.0 | 3-bromo-4-(2,6-dimethoxyphenyl)-5-(1-methyl-1H-pyrazol-3-yl)-4H-1,2,4-triazole, Example 399.5, and (1S,2S)-1-(5-chloropyrimidin-2-yl)-1-methoxypropane-2-sulfonamide and (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide and (1R,2R)-1-(5-chloropyrimidin-2-yl)-1-methoxypropane-2-sulfonamide (prepared in an analogous fashion to the described in Example 264.0 employing 5-chloropyrimidine-2-carbaldehyde). Preparative chiral separation conditions of racemic material (125 mg), step 1: Run on Thar 350 SFC with 250 × 30 mm AD-H column with 45 mL/min EtOH (neat) + 55 g/min CO$_2$, 45% co-solvent at 100 g/min. Temp. = 20° C., Outlet pressure = 97 bar, Wavelength = 253 nm. Injected 1.0 mL of 125 mg sample dissolved in 12 mL (10 + 2) MeOH:DCM; c = 10.4 mg/mL, 10.4 mg per injection. Cycle time 14.5 min, run time 16 min. Further preparative chiral SFC separation of the mixture from step1 (68 mg). Run on Thar 200 SFC with 250 × 30 mm AS-H column with 25 mL/min EtOH (neat) + 75 g/min CO$_2$, 25% co-solvent at 100 g/min. Temp. = 29° C., Outlet pressure = 100 bar, Wavelength = 253 nm. Injected 0.5 mL of 68 mg sample dissolved in 10 mL MeOH:DCM, 7:3; c = 6.8 mg/mL and 3.4 mg per injection. Cycle time 7.5 min, run time 15 min. To deliver the title compound as peak 1. | 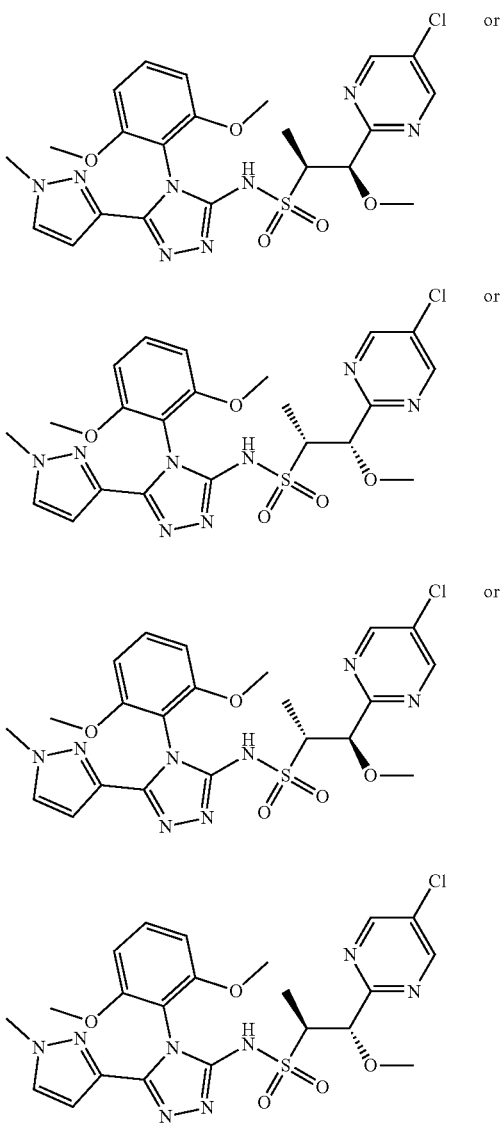 [SMILES: COc1cccc(OC)c1-n1c(NS(=O)(=O)[C@@H](C)[C@H](OC)c2ncc(Cl)cn2)nnc1-c1ccn(C)n1 ; COc1cccc(OC)c1-n1c(NS(=O)(=O)[C@H](C)[C@@H](OC)c2ncc(Cl)cn2)nnc1-c1ccn(C)n1 ; COc1cccc(OC)c1-n1c(NS(=O)(=O)[C@H](C)[C@H](OC)c2ncc(Cl)cn2)nnc1-c1ccn(C)n1 ; COc1cccc(OC)c1-n1c(NS(=O)(=O)[C@@H](C)[C@@H](OC)c2ncc(Cl)cn2)nnc1-c1ccn(C)n1] (1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide.<br><br>$^1$H NMR (500 MHz, CDCl$_3$) δ 8.70 (s, 2H), 7.42 (dd, J = 8.6, 8.6 Hz, 1H), 7.23 (d, J = 2.2 Hz, 1H), 6.63 (d, J = 8.6 Hz, 2H), 5.86 (d, J = 2.4 Hz, 1H), 4.96 (d, J = 4.9 Hz, 1H), 3.87 (s, 3H), 3.73 (s, 3H), 3.71 (s, 3H), 3.71 (obscured m, 1H), 3.33 (s, 3H), 1.37 (d, J = 6.8 Hz, 3H). LCMS-ESI (pos.) m/z: 549.2 (M + H)$^+$ |

TABLE 17-continued

| Example | Reagents | Structure, Name and Data |
|---|---|---|
| 325.0 | 3-bromo-4-(2,6-dimethoxyphenyl)-5-(1-methyl-1H-pyrazol-3-yl)-4H-1,2,4-triazole, Example 399.5, and (1S,2S)-1-(5-chloropyrimidin-2-yl)-1-methoxypropane-2-sulfonamide and (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide and (1R,2R)-1-(5-chloropyrimidin-2-yl)-1-methoxypropane-2-sulfonamide (prepared in an analogous fashion to the described in Example 264.0 employing 5-chloropyrimidine-2-carbaldehyde). Preparative chiral separation conditions of racemic material (125 mg), step 1: Run on Thar 350 SFC with 250 × 30 mm AD-H column with 45 mL/min EtOH (neat) + 55 g/min CO$_2$, 45% co-solvent at 100 g/min. Temp. = 20° C., Outlet pressure = 97 bar, Wavelength = 253 nm. Injected 1.0 mL of 125 mg sample dissolved in 12 mL, (10 + 2) MeOH:DCM; c = 10.4 mg/mL, 10.4 mg per injection. Cycle time 14.5 min, run time 16 min. To deliver the title compound as peak 2. | (1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide. <br><br> $^1$H NMR (500 MHz, CDCl$_3$) δ 8.74 (s, 2H), 7.43 (dd, J = 8.6, 8.6 Hz, 1H), 7.23 (d, J = 2.2 Hz, 1H), 6.63-6.66 (m,, 2H), 5.85 (d, J = 2.4 Hz, 1H), 4.78 (d, J = 6.4 Hz, 1H), 3.88 (s, 3H), 3.79 (s, 3H), 3.78 (obscured m, 1H), 3.73 (s, 3H), 3.25 (s, 3H), 1.26 (d, J = 7.1 Hz, 3H). LCMS-ESI (pos.) m/z: 549.2 (M + H)$^+$. |

TABLE 17-continued

| Example | Reagents | Structure, Name and Data |
|---|---|---|
| 326.0 | 3-bromo-4-(2,6-dimethoxyphenyl)-5-(1-methyl-1H-pyrazol-3-yl)-4H-1,2,4-triazole, Example 399.5, and (1S,2S)-1-(5-chloropyrimidin-2-yl)-1-methoxypropane-2-sulfonamide and (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide and (1R,2R)-1-(5-chloropyrimidin-2-yl)-1-methoxypropane-2-sulfonamide (prepared in an analogous fashion to the described in Example 264.0 employing 5-chloropyrimidine-2-carbaldehyde). Preparative chiral separation conditions of racemic material (125 mg), step 1: Run on Thar 350 SFC with 250 × 30 mm AD-H column with 45 mL/min EtOH (neat) + 55 g/min $CO_2$, 45% co-solvent at 100 g/min. Temp. = 20° C., Outlet pressure = 97 bar, Wavelength = 253 nm. Injected 1.0 mL of 125 mg sample dissolved in 12 mL (10 + 2) MeOH:DCM; c = 10.4 mg/mL, 10.4 mg per injection. Cycle time 14.5 min, run time 16 min. Further preparative chiral SFC separation of the mixture from step1 (68 mg). Run on Thar 200 SFC with 250 × 30 mm AS-H column with 25 mL/min EtOH (neat) + 75 g/min $CO_2$, 25% co-solvent at 100 g/min. Temp. = 29° C., Outlet pressure = 100 bar, Wavelength = 253 nm. Injected 0.5 mL of 68 mg sample dissolved in 10 mL MeOH:DCM, 7:3; c = 6.8 mg/mL and 3.4 mg per injection. Cycle time 7.5 min, run time 15 min. To deliver the title compound as peak 3. | 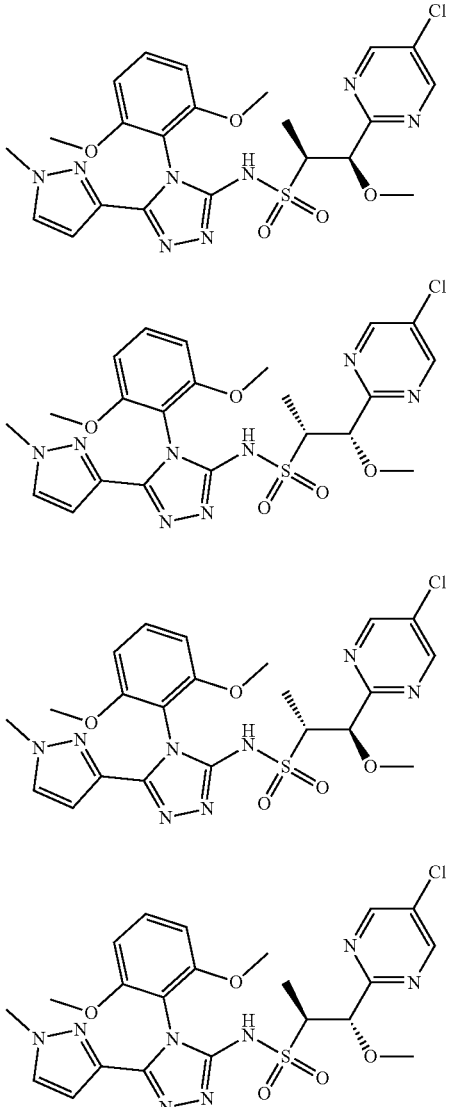 |

(1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1S,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide or (1R,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-methoxy-2-propanesulfonamide.

$^1$H NMR (500 MHz, $CDCl_3$) δ 8.72 (s, 2H), 7.42 (dd, J = 8.2, 8.2 Hz, 1H), 7.22 (d, J = 2.2 Hz, 1H), 6.65 (dd, J = 7.9, 6.5 Hz, 2H), 5.83 (d, J = 2.2 Hz, 1H), 4.77 (d, J = 6.4 Hz, 1H), 3.87 (s, 3H), 3.79 (s, 3H), 3.75 (obscured m, 1H), 3.73 (s, 3H), 3.24 (s, 3H), 1.24 (d, J = 7.1 Hz, 3H). LCMS-ESI (pos.) m/z: 549.2 (M + H)$^+$.

Example 319.0. Preparation of (2R,3S)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide or (2R,3R)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide or (2S,3S)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide or (2S,3R)-3-(5-cyano-2-pyrimidinyl)-N-(4-(2,6-dimethoxyphenyl)-5-(4-methyl-1,3-thiazol-2-yl)-4H-1,2,4-triazol-3-yl)-3-fluoro-2-butanesulfonamide 319.1

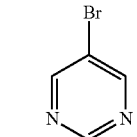

1-(5-Bromopyrimidin-2-yl)ethanone, Example 319.1. At 0° C., methylmagnesium bromide (1.4 M solution in toluene/THF (75:25, 21.35 mL, 29.9 mmol) was added to a THF (54.3 mL) solution containing 5-bromo-2-cyanopyrimidine (5 g, 27.2 mmol). The resulting mixture was stirred for 2 h at 0° C. Next, a saturated aqueous ammonium chloride solution was added followed by 3.0 N HCl to adjust the pH to 1. This solution was allowed to stir overnight. The pH was then adjusted to 7-8 with a saturated aqueous solution of $K_2CO_3$ and the material was extracted with EtOAc and concentrated in vacuo. The product thus obtained was purified on silica gel eluting with a hexanes/EtOAc gradient (0-100%). Desired fractions were then pooled and concentrated in vacuo to provide the title compound. LCMS-ESI (pos.) m/z: 200.9 (M+H)+.

319.2

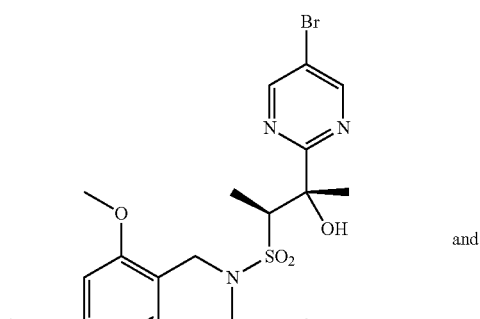

and

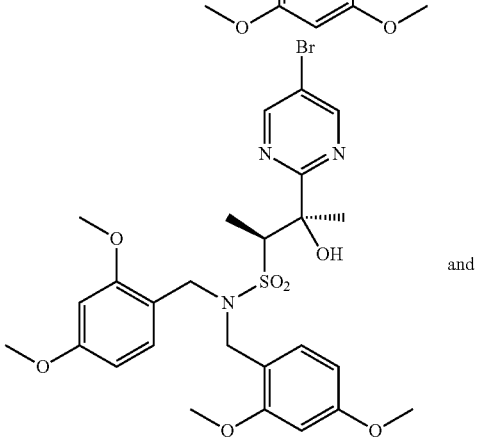

and

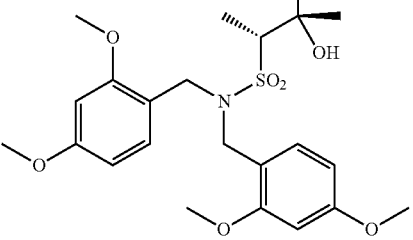

and

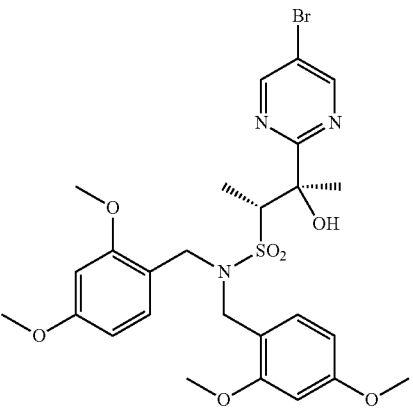

(2R,3S)-3-(5-Bromopyrimidin-2-yl)-N,N-bis(2,4-dimethoxybenzyl)-3-hydroxybutane-2-sulfonamide and (2R,3R)-3-(5-bromopyrimidin-2-yl)-N,N-bis(2,4-dimethoxybenzyl)-3-hydroxybutane-2-sulfonamide and (2S,3S)-3-(5-bromopyrimidin-2-yl)-N,N-bis(2,4-dimethoxybenzyl)-3-hydroxybutane-2-sulfonamide and (2S,3S)-3-(5-bromopyrimidin-2-yl)-N,N-bis(2,4-dimethoxybenzyl)-3-hydroxybutane-2-sulfonamide, Example 319.2. At −78° C., n-butyllithium (2.5 M, 4.38 mL, 10.94 mmol) was added to a THF (99 mL) solution containing N,N-bis(2,4-dimethoxybenzyl)ethanesulfonamide (4.07 g, 9.95 mmol, prepared following the procedure described in Example 467.0 employing 2,4-methoxybenzylamine and 2,4-methoxybenzaldehyde). The resulting mixture was stirred for 30 min at −78° C. Next, a THF solution of 1-(5-bromopyrimidin-2-yl)ethanone (2.0 g, 9.95 mmol) was added at −78° C. Stirring was continued at −78°, and then the reaction was allowed to slowly warm to RT and stirred overnight. The reaction was then quenched with a saturated aqueous ammonium chloride solution and extracted with EtOAc (3×100 mL). After concentration, the product thus obtained was purified on silica eluting with a hexanes/EtOAc gradient (0-100%). Desired fractions were then pooled and concentrated in vacuo to give the title compound. LCMS-ESI (pos.) m/z: 629.9 (M+H₂O)+.

319.3

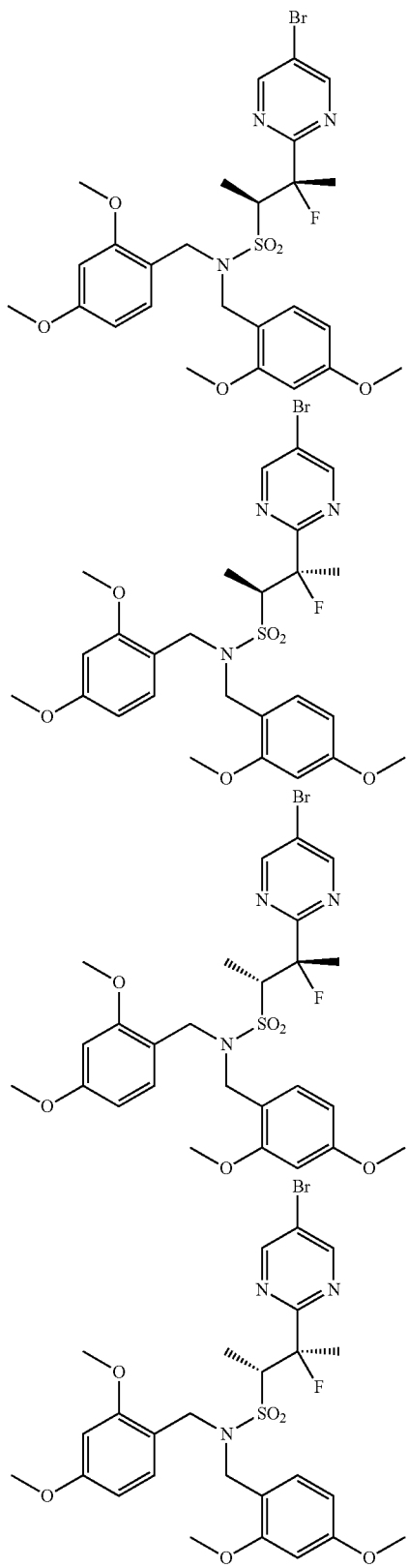

(2R,3S)-3-(5-Bromopyrimidin-2-yl)-N,N-bis(2,4-dimethoxybenzyl)-3-fluorobutane-2-sulfonamide and (2S,3S)-3-(5-bromopyrimidin-2-yl)-N,N-bis(2,4-dimethoxybenzyl)-3-fluorobutane-2-sulfonamide and (2R,3R)-3-(5-bromopyrimidin-2-yl)-N,N-bis(2,4-dimethoxybenzyl)-3-fluorobutane-2-sulfonamide and (2S,3R)-3-(5-bromopyrimidin-2-yl)-N,N-bis(2,4-dimethoxybenzyl)-3-fluorobutane-2-sulfonamide, Example 319.3. At 23° C., DAST (2.052 mL, 15.53 mmol) was added to a DCM (38.8 mL) solution containing Example 319.2 (4.74 g, 7.76 mmol). The resulting mixture was stirred for 1 h at 23° C. TLC indicated the reaction was complete. MeOH (1.0 mL) was then added to the reaction mixture, and the mixture was concentrated in vacuo. The reaction was purified on silica eluting with a hexanes/EtOAc gradient (0-100%). Desired fractions were then pooled and concentrated in vacuo to give the title compound.

319.4

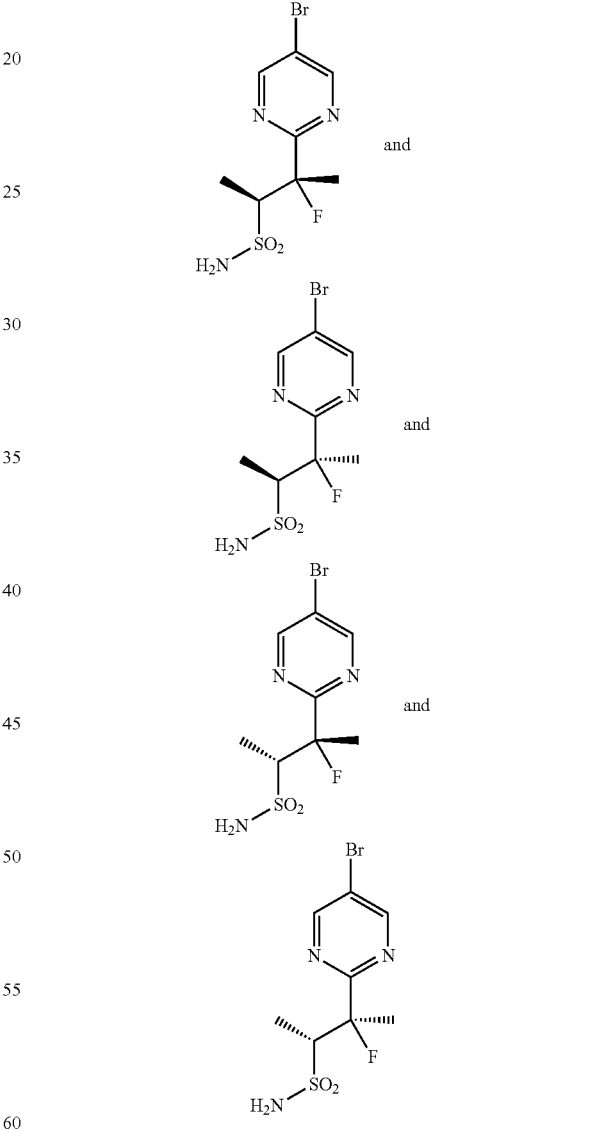

(2R,3S)-3-(5-Bromopyrimidin-2-yl)-3-fluorobutane-2-sulfonamide and (2S,3S)-3-(5-bromopyrimidin-2-yl)-3-fluorobutane-2-sulfonamide and (2R,3R)-3-(5-bromopyrimidin-2-yl)-3-fluorobutane-2-sulfonamide and (2S,3R)-3-(5-bromopyrimidin-2-yl)-3-fluorobutane-2-sulfonamide, Example 319.4. At 0° C., TFA (1.26 mL, 16.33 mmol) was added to a flask containing triethylsilane (2.61 mL, 16.33 mmol) and Example 319.3 (1 g, 1.633 mmol). The resulting mixture was stirred for 3 h at 0° C. The reaction was then partitioned with a saturated aqueous sodium bicarbonate solution and DCM. The organics were dried and concentrated in vacuo. The reaction was purified on silica gel eluting with a MeOH/DCM using a stepwise gradient (0-20%). Desired fractions were then pooled and concentrated in vacuo to give the title compound. LCMS-ESI (pos.) m/z: 311.9 (M+H)$^+$.

Example 13.0 employing Example 319.4, Example 465.0 and 4-methyl-1,3-thiazole-2-carbohydrazide. The reaction was purified via reverse phase HPLC (Phenomenex Gemini-C18 column, 50×250 mm, 10 m, 10-70% water/ACN gradient over 30 min., with 0.1% TFA, flow rate 100 mL/min). Desired fractions were pooled and lyophilized to give pure product. LCMS-ESI (pos.) m/z: 611.9 (M+H)$^+$.

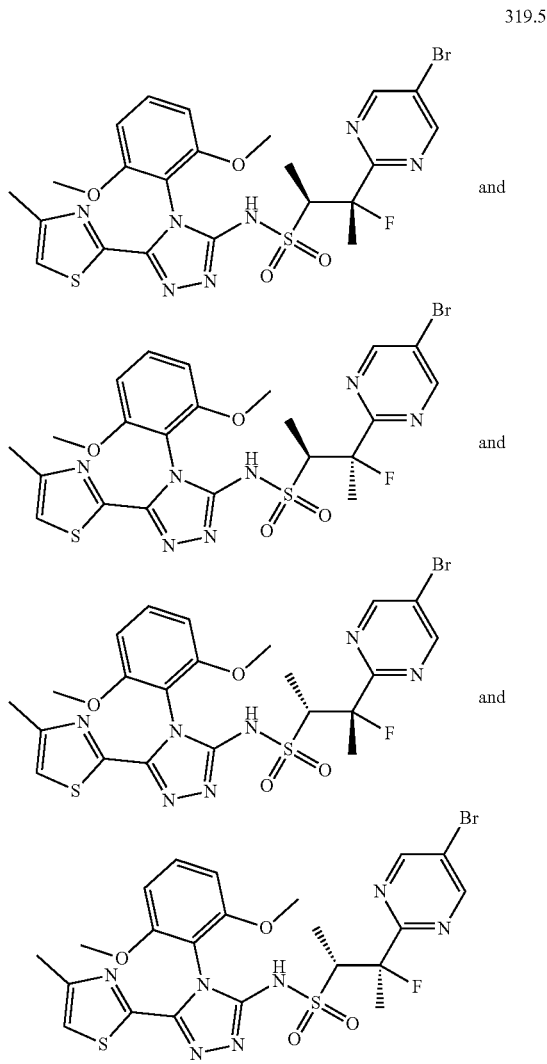

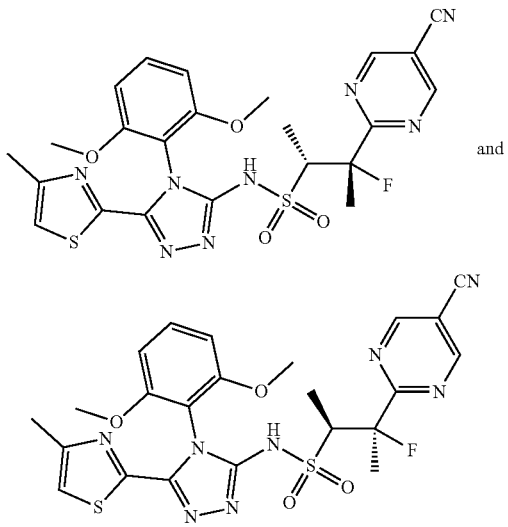

(2S,3S)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2R,3R)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 319.6. A glass microwave reaction vessel was charged with Example 319.5 (200 mg, 0.327 mmol), zinc cyanide (0.104 mL, 1.633 mmol), and tetrakis(triphenylphosphine)palladium (37.7 mg, 0.033 mmol). The reaction mixture was stirred and heated in a Discover model microwave reactor (CEM, Matthews, N.C.) at 120° C. for 30 min. The reaction was purified via reverse phase HPLC (Agilent SB-C8 column, 30×250 mm, 5 m, 10-95% water/ACN gradient over 25 min., with 0.1% TFA, flow rate 50 mL/min). Desired fractions were pooled and lyophilized to give the title compound as peak 1. LCMS-ESI (pos.) m/z: 542.0 (M+H)$^+$.

(2S,3S)-3-(5-Bromopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2R,3S)-3-(5-bromopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2R,3R)-3-(5-bromopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3R)-3-(5-bromopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 319.5. Example 319.5 was prepared following the procedure described in

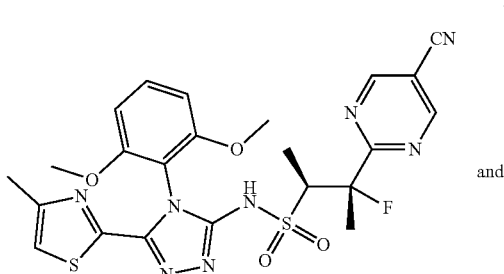

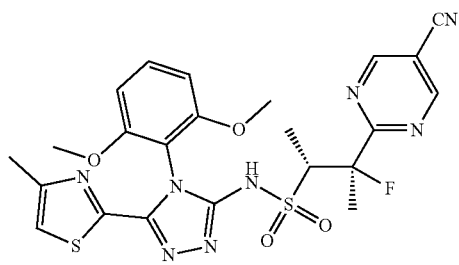

319.0

(2R,3S)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 319.7. Further elution under the conditions described in Example 319.6 delivered Example 319.7 as peak 2. LCMS-ESI (pos.) m/z: 542.0 (M+H)+.

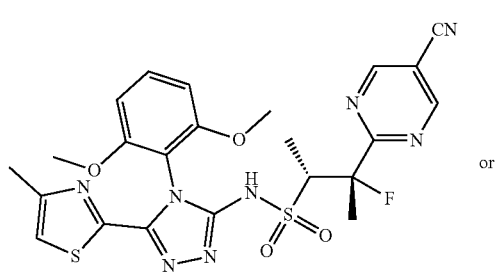

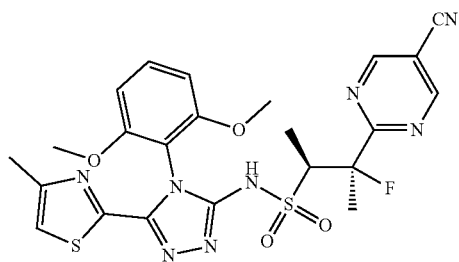

(2R,3S)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 319.0. The title compound was isolated using chiral separation of Example 319.6 by preparative SFC Run on Thar 200 with a 400×30 mm OD-H column with 12 g/min MeOH and 68 g/min CO$_2$, 15% co-solvent at 80 g/min. Wavelength 215 nm. Injected 3 mL of a solution of 20 mg sample dissolved in 4 mL solvent 50% DCM/50% MeOH); c=5 mg/mL, collected manually, run time 90 min, to provide the title compound as peak 1. $^1$H NMR (400 MHz, CD$_3$OD) δ 9.16 (s, 2H) 7.55 (t, J=8.61 Hz, 1H) 7.23 (s, 1H) 6.83 (dd, J=8.61 Hz, 2H) 4.38 (m, 1H) 3.79 (s, 3H) 3.78 (s, 3H) 2.33 (s, 3H) 1.99 (d, J=24.2 Hz, 3H) 1.49 (d, J=7.04 Hz, 3H). LCMS-ESI (pos.) m/z: 558.9 (M+H)+.

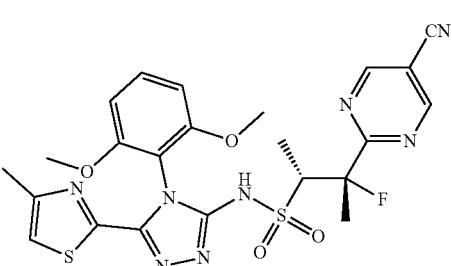

320.0

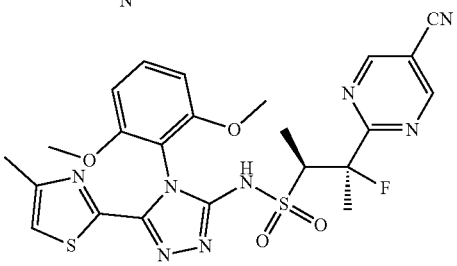

(2R,3S)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 320.0. The title compound was isolated using chiral separation of Example 319.6 as described in Example 319.0, to provide the title compound as peak 2. $^1$H NMR (400 MHz, CD$_3$OD) δ 9.16 (s, 2H) 7.55 (t, J=8.61 Hz, 1H) 7.23 (s, 1H) 6.83 (d, J=8.41 Hz, 2H) 4.38 (m, 1H) 3.79 (s, 3H) 3.78 (s, 3H) 3.37 (s, 1H) 2.33 (s, 3H) 1.99 (d, J=24.2 Hz, 3H) 1.49 (d, J=6.65 Hz, 3H). LCMS-ESI (pos.) m/z: 558.9 (M+H)+.

321.0

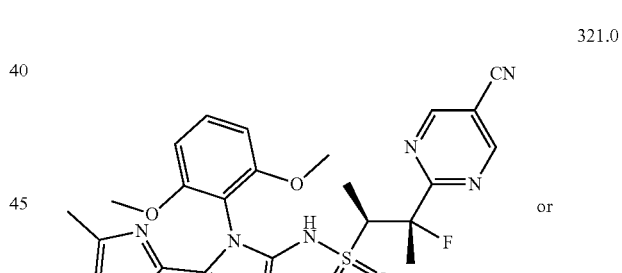

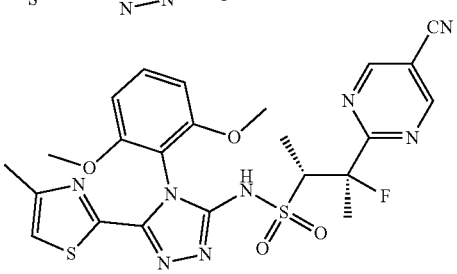

(2R,3R)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3S)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 321.0. The title compound was isolated using chiral separation of Example 319.7 by preparative SFC Run on Thar 200 with a 400×30 mm OD-H column with 12 g/min MeOH (Neat) and 68 g/min CO$_2$, 15% co-solvent at 80 g/min. Wavelength 215 nm. Injected 3 mL of a solution of 20 mg sample dissolved in 4 mL solvent 50% DCM/50% MeOH); c=5 mg/mL, collected manually, run time 90 min, to provide the title compound as peak 1. $^1$H NMR (400 MHz, CD$_3$OD) δ 9.16 (s, 2H) 7.56 (t, J=8.51 Hz, 1H) 7.25 (s, 1H) 6.84 (d, J=8.61 Hz, 2H) 4.38 (m, 1H) 4.38 (d, J=3.91 Hz, 1H) 3.80 (s, 3H) 3.78 (s, 3H) 2.32 (d, J=0.78 Hz, 3H) 1.92 (s, 2H) 1.89 (d, J=24.1 Hz, 3H) 1.49 (dd, J=6.94, 0.88 Hz, 3H). LCMS-ESI (pos.) m/z: 558.9 (M+H)$^+$.

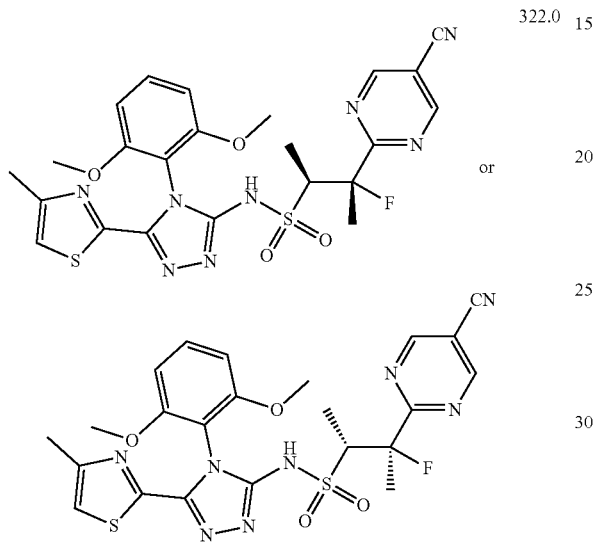

322.0

(2R,3R)-3-(5-Cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide and (2S,3S)-3-(5-cyanopyrimidin-2-yl)-N-(4-(2,6-dimethoxyphenyl)-5-(4-methylthiazol-2-yl)-4H-1,2,4-triazol-3-yl)-3-fluorobutane-2-sulfonamide, Example 322.0. The title compound was isolated using chiral separation of Example 319.7 as described in Example 321.0, to provide the title compound as peak 2. $^1$H NMR (400 MHz, CD$_3$OD) δ 9.16 (s, 2H) 7.56 (t, J=8.51 Hz, 1H) 7.24 (s, 1H) 6.83 (d, J=8.61 Hz, 2H) 4.38 (m, 1H) 3.80 (s, 3H) 3.78 (s, 3H) 2.33 (d, J=0.78 Hz, 3H) 1.89 (d, J=24.1 Hz, 2H) 1.49 (dd, J=7.04, 0.78 Hz, 3H). LCMS-ESI (pos.) m/z: 558.9 (M+H)$^+$.

Example 329.0. Preparation of (1R,2S)-N-(4-(2,6-dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide

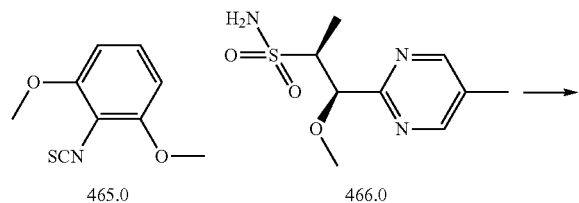

465.0      466.0

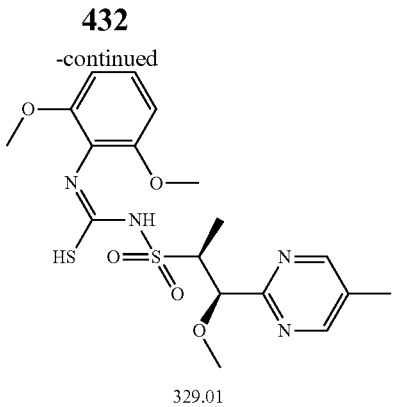

329.01

(E)-N'-(2,6-Dimethoxyphenyl)-N-(((1R,2S)-1-methoxy-1-(5-methylpyrimidin-2-yl)propan-2-yl)sulfonyl)carbamimidothioic acid, Example 329.01. In a 20 mL scintillation vial, Example 466.0 (0.203 g, 0.83 mmol) was suspended in ACN (8 mL). The vial was warmed in a warm water bath to give a clear solution. To the solution at RT was added Example 465.0 (0.168 g, 0.86 mmol) followed by portion-wise addition of cesium carbonate (0.367 g, 1.13 mmol). The slightly cloudy mixture was stirred at RT for 15 h to obtain a suspension. LCMS (pos.) m/z: 440.9 (M+H)$^+$. This suspension of 329.01 was used as 0.1 M stock solution in the next step.

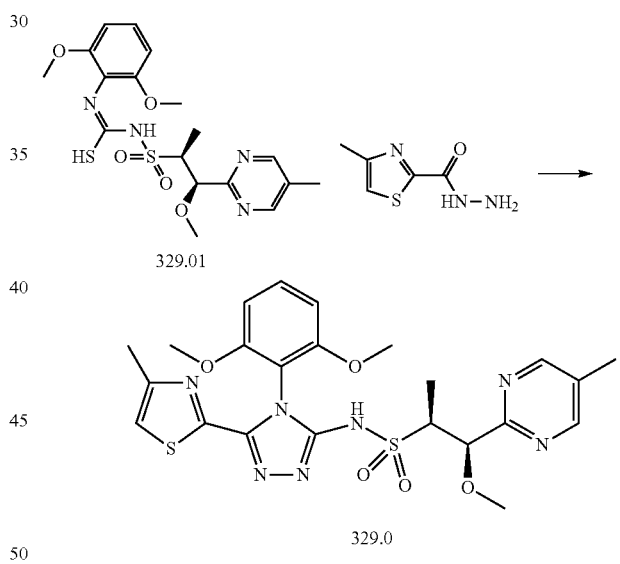

(1R,2S)-N-(4-(2,6-Dimethoxyphenyl)-5-(4-methyl-1,3-thiazol-2-yl)-4H-1,2,4-triazol-3-yl)-1-methoxy-1-(5-methyl-2-pyrimidinyl)-2-propanesulfonamide, Example 329.0. Example 329.01 (2.50 mL, 0.250 mmol) and 4-methyl-1,3-thiazole-2-carbohydrazide (0.040 g, 0.25 mmol, Allichem LLC, Baltimore, Md.) were mixed in a 20 mL scintillation vial. The mixture was cooled in an ice-water bath and silver(I) nitrate (0.0878 g, 0.517 mmol) was added at once. The cold bath was then removed, and the brown mixture was stirred at RT. After 15 min, the mixture was filtered through a pad of diatomeceous earth and flushed with ACN. The filtrate was concentrated in GeneVac into a 20 mL scintillation vial. Dioxane (2 mL) was added to the yellow residue followed by methanesulfonic acid (0.073 g, 0.76 mmol). The mixture was stirred at 80° C. overnight. The reaction mixture was then allowed to cool to RT and concentrated in vacuo. MeOH (2 mL) was added to the residue, and the mixture was passed through a PS-carbonate column eluting with MeOH. The filtrate was concentrated and the product thus obtained was purified by mass-triggered HPLC to afford Example 329.0 (0.0320 g, 19%). ¹H NMR (400 MHz, CDCl₃) δ 8.64 (s, 2H), 7.46 (t, J=8.41 Hz, 1H), 6.91 (s, 1H), 6.66 (d, J=8.61 Hz, 2H), 4.96 (d, J=4.69 Hz, 1H), 3.76 (m, 1H), 3.75 (s, 3H), 3.73 (s, 3H), 3.32 (s, 3H), 2.40 (s, 3H), 2.34 (s, 3H), 1.38 (d, J=6.85 Hz, 3H). LCMS (pos.) m/z: 545.8 (M+H)⁺.

Example 331.0. Preparation of (1R,2S)-N-(4-(2,6-dimethoxyphenyl)-5-(5-methyl-1,3-thiazol-2-yl)-4H-1,2,4-triazol-3-yl)-1-methoxy-1-(5-methyl-2-pyrimidinyl)-2-propanesulfonamide

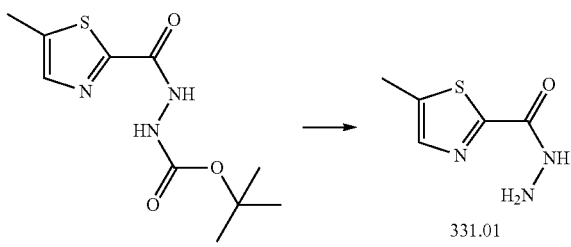

331.01

5-Methylthiazole-2-carbohydrazide, Example 331.01. tert-Butyl 2-(5-methylthiazole-2-carbonyl)hydrazinecarboxylate (0.464 g, 1.80 mmol, JPM², Wayland, Mass.) and hydrochloric acid (4.0 M in 1,4-dioxane, 0.90 mL, 3.60 mmol) were mixed into 1,4-dioxane (6 mL) in a 20 mL scintillation vial. The mixture was then stirred at RT. After 25 h, hydrochloric acid (4.0 M in 1,4-dioxane, 0.90 mL, 3.60 mmol) was added, and the mixture was stirred at RT overnight. The mixture was then slowly added to a stirred solution of saturated NaHCO₃ (~50 mL). The aqueous phase was extracted with CHCl₃ (3×20 mL). The aqueous phase was saturated with solid NaCl and was extracted with 5% IPA/CHCl₃ (2×20 mL). The combined organic phases were dried over sodium sulfate, filtered, and concentrated in vacuo to afford Example 331.01 (0.263 g, 1.68 mmol, 93%) as a light brown solid. ¹H NMR (300 MHz, CDCl₃) δ 8.25 (br. s, 1H), 7.52 (d, J=1.2 Hz, 1H), 4.04 (d, J=3.5 Hz, 2H), 2.55 (d, J=1.0 Hz, 3H). LCMS (pos.) m/z: 158.0 (M+H)⁺.

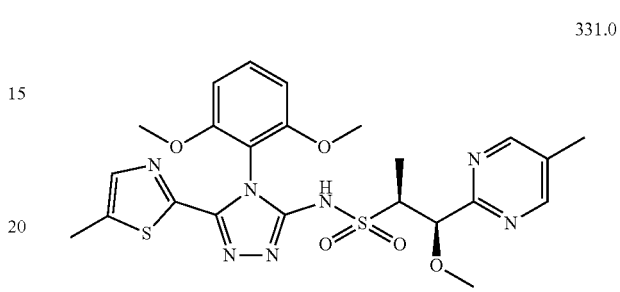

331.0

(1R,2S)-N-(4-(2,6-Dimethoxyphenyl)-5-(5-methyl-1,3-thiazol-2-yl)-4H-1,2,4-triazol-3-yl)-1-methoxy-1-(5-methyl-2-pyrimidinyl)-2-propanesulfonamide, Example 331.0. The title compound was prepared following the procedure in Example 329.0 using 331.01 and 329.01. ¹H NMR (300 MHz, CD₃OD) δ 8.64 (s, 2H), 7.38-7.58 (m, 2H), 6.78 (d, J=8.48 Hz, 2H), 4.98 (d, J=3.65 Hz, 1H), 3.76 (s, 3H), 3.73 (s, 3H), 3.49-3.62 (m, 1H), 3.26 (s, 3H), 2.45 (d, J=1.17 Hz, 3H), 2.34 (s, 3H), 1.24 (d, J=7.02 Hz, 3H). LCMS (pos.) m/z: 546.1 (M+H)⁺.

The compounds set forth in the following table were synthesized following the procedure in Example 329.0 using the known starting material as described.

TABLE 18

| Example | Reagents | Structure, Name and and Data |
|---|---|---|
| 332.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 5-methylthiophene-2-carbohydrazide (commercially available from Frontier Scientific Services, Inc., Newark, DE). | (1R,2S)-N-(4-(2,6-dimethoxyphenyl)-5-(5-methyl-2-thiophenyl)-4H-1,2,4-triazol-3-yl)-1-methoxy-1-(5-methyl-2-pyrimidinyl)-2-propanesulfonamide.<br><br>¹H NMR (500 MHz, DMSO-d₆) δ 13.05 (s, 1H), 8.64 (s, 2H), 7.56 (t, J = 8.5 Hz, 1H), 6.88 (d, J = 8.0 Hz, 2H), 6.76-6.71 (m, 2H), 4.81 (d, J = 3.5 Hz, 1H), 3.71 (s, 3H), 3.70 (s, 3H), 3.40 (d, J = 3.6 Hz, 1H), 3.15 (s, 3H), 2.38 (s, 3H), 2.26 (s, 3H), 1.13 (d, J = 6.9 Hz, 3H). LCMS (pos.) m/z: 545.0 (M + H)⁺. |

TABLE 18-continued

| Example | Reagents | Structure, Name and and Data |
|---|---|---|
| 333.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 5-methyl-1H-pyrazole-3-carbohydrazide (commercially available from Frontier Scientific Services, Inc., Newark, DE). | 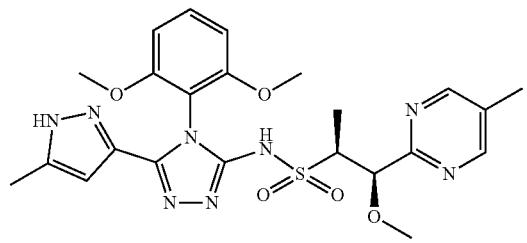<br>(1R,2S)-N-(4-(2,6-dimethoxyphenyl)-5-(5-methyl-1H-pyrazol-3-yl)-4H-1,2,4-triazol-3-yl)-1-methoxy-1-(5-methyl-2-pyrimidinyl)-2-propanesulfonamide.<br>$^1$H NMR (300 MHz, CDCl$_3$) δ 11.33 (br. s, 1H), 8.59 (s, 2H), 7.43 (t, J = 8.5 Hz, 1H), 6.65 (d, J = 8.6 Hz, 2H), 5.85 (s, 1H), 4.97 (d, J = 4.7 Hz, 1H), 3.75 (m, 7H), 3.33 (s, 3H), 2.31 (s, 3H), 2.23 (s, 3H), 1.38 (d, J = 7.0 Hz, 3H). LCMS (pos.) m/z: 529.2 (M + H)$^+$. |
| 334.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 5-(1R,2S)-N-(5-(5-chloro-2-thiophenyl)-4-chlorothiophene-2-carbohydrazide (commercially available from Frontier Scientific Services, Inc., Newark, DE). | 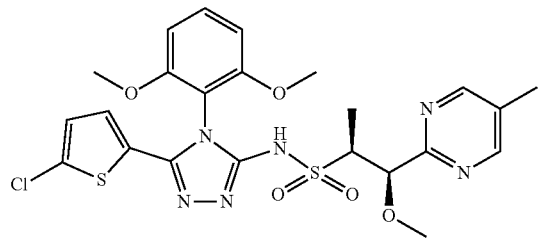 [SMILES: COc1cccc(OC)c1-n1c(NS(=O)(=O)[C@@H](C)[C@H](OC)c2ncc(C)cn2)nnc1-c1ccc(Cl)s1]<br>(2,6-dimethoxyphenyl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 13.24 (s, 1H), 8.64 (s, 2H), 7.59 (t, J = 8.53 Hz, 1H), 7.10 (d, J = 4.09 Hz, 1H), 6.84-6.94 (m, 3H), 4.81 (d, J = 3.44 Hz, 1H), 3.73 (s, 3H), 3.72 (s, 3H), 3.40-3.44 (m, 1H), 3.15 (s, 3H), 2.26 (s, 3H), 1.13 (d, J = 7.01 Hz, 3H). LCMS (pos.) m/z: 565.0 (M + H)$^+$. |
| 335.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 4,5,6,7-tetrahydro-1H-indazole-3-carbohydrazide (commercially available from Frontier Scientific Services, Inc., Newark, DE). | 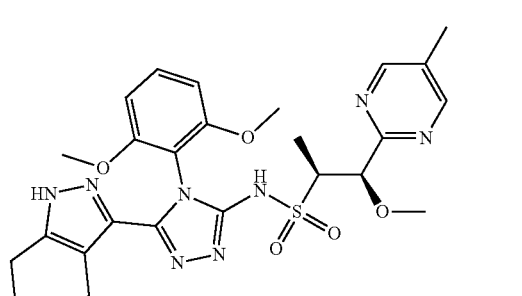<br>(1R,2S)-N-(4-(2,6-dimethoxyphenyl)-5-(4,5,6,7-tetrahydro-1H-indazol-3-yl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 12.84 (br. s, 1H), 8.56 (s, 2H), 7.30 (t, J = 8.47 Hz, 1H), 6.66 (d, J = 8.50 Hz, 2H), 4.73 (d, J = 3.57 Hz, 1H), 3.56 (s, 3H), 3.54 (s, 3H), 3.33 (dd, J = 3.70, 7.01 Hz, 1H), 3.08 (s, 3H), 2.42 (m, 4H), 2.18 (s, 3H), 1.61 (d, J = 4.41 Hz, 4H), 1.04 (d, J = 7.01 Hz, 3H). LCMS (pos.) m/z: 565.0 (M + H)$^+$. |

TABLE 18-continued

| Example | Reagents | Structure, Name and and Data |
|---|---|---|
| 336.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 5-methoxy-1H-indole-2-carbohydrazide (commercially available from Frontier Scientific Services, Inc., Newark, DE). | 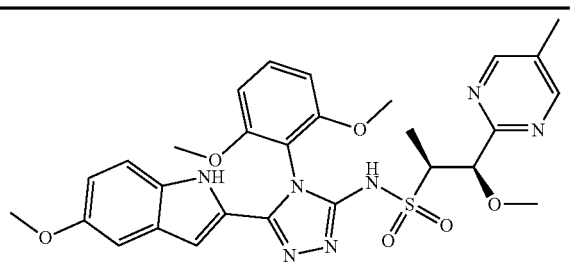<br>(1R,2S)-N-(4-(2,6-dimethoxyphenyl)-5-(5-methoxy-1H-indol-2-yl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 13.25 (s, 1H), 11.80 (s, 1H), 8.65 (s, 2H), 7.61 (t, J = 8.5 Hz, 1H), 7.28 (d, J = 8.8 Hz, 1H), 6.93 (d, J = 8.6 Hz, 2H), 6.86 (d, J = 2.0 Hz, 1H), 6.79 (dd, J = 2.3, 8.9 Hz, 1H), 5.66 (d, J = 1.5 Hz, 1H), 4.85 (d, J = 3.4 Hz, 1H), 3.71 (s, 3H), 3.70 (s, 3H), 3.67 (s, 3H), 3.17 (s, 3H), 2.26(s, 3H), 1.15 (d, J = 6.9 Hz, 3H). One proton was obscured under the water peak. LCMS (pos.) m/z: 594.1 (M + H)$^+$. |
| 337.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and pyrazine-2-carbohydrazide (commercially available from Frontier Scientific Services, Inc., Newark, DE). | 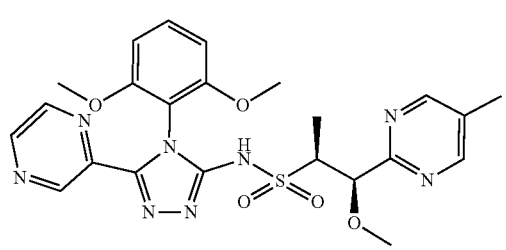 [SMILES: COc1cccc(OC)c1-n1c(NS(=O)(=O)[C@@H](C)[C@H](OC)c2ncc(C)cn2)nnc1-c1cnccn1]<br>(1R,2S)-N-(4-(2,6-dimethoxyphenyl)-5-(2-pyrazinyl)-4H-1,2,4-triazol-3-yl)-1-methoxy-1-(5-methyl-2-pyrimidinyl)-2-propanesulfonamide.<br>$^1$H NMR (500 MHz, DMSO-d$_6$) δ 13.46 (br. s, 1H), 9.04 (d, J = 1.2 Hz, 1H), 8.67 (d, J = 2.4 Hz, 1H), 8.64 (s, 2H), 8.45-8.40 (m, 1H), 7.42 (t, J = 8.5 Hz, 1H), 6.76 (d, J = 8.6 Hz, 2H), 4.83 (d, J = 3.6 Hz, 1H), 3.64 (s, 3H), 3.62 (s, 3H), 3.45 (dd, J = 3.7, 6.9 Hz, 1H), 3.16 (s, 3H), 2.26 (s, 3H), 1.16 (d, J = 7.0 Hz, 3H). LCMS (pos.) m/z: 527.1 (M + H)$^+$. |
| 338.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 2-methylthiazole-4-cathohydrazide (commercially available from Oakwood Products, Inc., Estill, SC). | 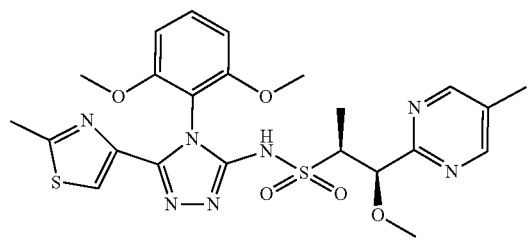<br>(1R,2S)-N-(4-(2,6-dimethoxyphenyl)-5-(2-methyl-1,3-thiazol-4-yl)-4H-1,2,4-triazol-3-yl)-1-methoxy-1-(5-methyl-2-pyrimidinyl)-2-propanesulfonamide.<br>$^1$H NMR (300 MHz, CDCl$_3$) δ 11.24 (s, 1H), 8.59 (s, 2H), 7.45 (t, J = 8.5 Hz, 1H), 6.75 (s, 1H), 6.67 (d, J = 8.5 Hz, 2H), 4.94 (d, J = 4.8 Hz, 1H), 3.75 (m, 7H), 3.33 (s, 3H), 2.71 (s, 3H), 2.32 (s, 3H), 1.39 (d, J = 7.0 Hz, 3H). LCMS (pos.) m/z: 545.9 (M + H)$^+$. |

TABLE 18-continued

| Example | Reagents | Structure, Name and and Data |
|---|---|---|
| 339.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 2-methyloxazole-4-carbohydrazide (commercially available from Frontier Scientific Services, Inc., Newark, DE). | 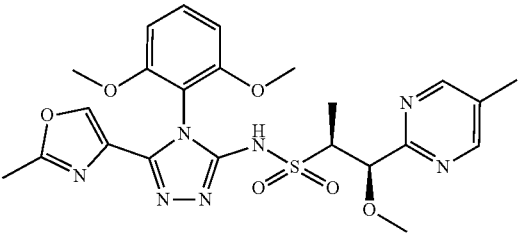<br>(1R,2S)-N-(4-(2,6-dimethoxyphenyl)-5-(2-methyl-1,3-oxazol-4-yl)-4H-1,2,4-triazol-3-yl)-1-methoxy-1-(5-methyl-2-pyrimidinyl)-2-propanesulfonamide.<br>$^1$H NMR (500 MHz, DMSO-$d_6$) δ 13.15 (br. s, 1H), 8.64 (s, 2H), 7.53 (t, J = 8.5 Hz, 1H), 7.42 (s, 1H), 6.85 (d, J = 8.6 Hz, 2H), 4.82 (d, J = 3.4 Hz, 1H), 3.71 (s, 3H), 3.69 (s, 3H), 3.42 (dd, J = 3.5, 7.0 Hz, 1H), 3.15 (s, 3H), 2.37 (s, 3H), 2.26 (s, 3H), 1.13 (d, J = 7.0 Hz, 3H). LCMS (pos.) m/z: 530.1 (M + H)$^+$. |
| 340.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 4-cyclopropylthiazole-2-carbohydrazide (commercially available from Frontier Scientific Services, Inc., Newark, DE). | 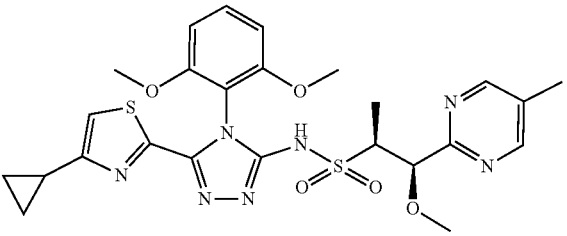 [SMILES: COc1cccc(OC)c1-n1c(NS(=O)(=O)[C@@H](C)[C@H](OC)c2ncc(C)cn2)nnc1-c1nc(C2CC2)cs1]<br>(1R,2S)-N-(5-(4-cyclopropyl-1,3-thiazol-2-yl)-4-(2,6-dimethoxyphenyl)-4H-1,2,4-triazol-3-yl)-1-methoxy-1-(5-methyl-2-pyrimidinyl)-2-propanesulfonamide.<br>$^1$H NMR (500 MHz, DMSO-$d_6$) δ 13.36 (br. s, 1H), 8.64 (s, 2H), 7.50 (t, J = 8.5 Hz, 1H), 7.46 (s, 1H), 6.81 (dd, J = 1.5, 8.5 Hz, 2H), 4.83 (d, J = 3.4 Hz, 1H), 3.67 (s, 3H), 3.65 (s, 3H), 3.43 (dd, J = 3.5, 6.9 Hz, 1H), 3.15 (s, 3H), 2.26 (s, 3H), 1.97-1.89 (m, 1H), 1.14 (d, J = 6.9 Hz, 3H), 0.72 (dd, J = 2.4, 8.1 Hz, 2H), 0.30 (d, J = 2.3 Hz, 2H). LCMS (pos.) m/z: 572.0 (M + H)$^+$. |
| 341.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and thiazole-2-carbohydrazide (commercially available from Frontier Scientific Services, Inc., Newark, DE). propanesulfonamide. | 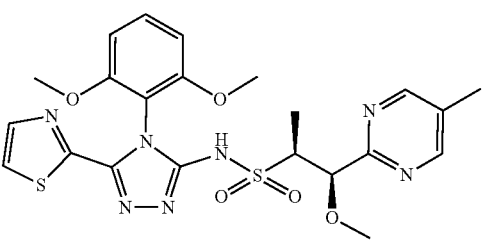 [SMILES: COc1cccc(OC)c1-n1c(NS(=O)(=O)[C@@H](C)[C@H](OC)c2ncc(C)cn2)nnc1-c1nccs1]<br>(1R,2S)-N-(4-(2,6-dimethoxyphenyl)-5-(1,3-thiazol-2-yl)-4H-1,2,4-triazol-3-yl)-1-methoxy-1-(5-methyl-2-pyrimidinyl)-2-<br>$^1$H NMR (500 MHz, DMSO-$d_6$) δ 13.43 (br. s, 1H), 8.65 (s, 2H), 7.94-7.80 (m, 2H), 7.48 (t, J = 8.5 Hz, 1H), 6.82 (d, J = 8.6 Hz, 2H), 4.83 (d, J = 3.5 Hz, 1H), 3.67 (s, 3H), 3.65 (s, 3H), 3.44 (dd, J = 3.6, 7.0 Hz, 1H), 3.16 (s, 3H), 2.26 (s, 3H), 1.15 (d, J = 7.0 Hz, 3H). LCMS (pos.) m/z: 532.0 (M + H)$^+$. |

TABLE 18-continued

| Example | Reagents | Structure, Name and Data |
|---|---|---|
| 342.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and thiazole-4-carbohydrazide (commercially available from Frontier Scientific Services, Inc., Newark, DE). | 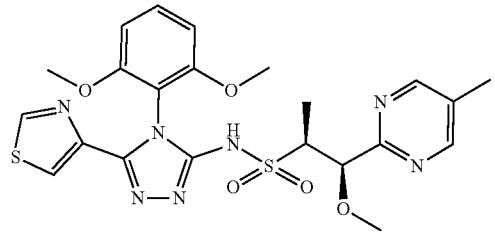 [SMILES: COc1cccc(OC)c1-n1c(NS(=O)(=O)[C@@H](C)[C@H](OC)c2ncc(C)cn2)nnc1-c1cscn1]<br>(1R,2S)-N-(4-(2,6-dimethoxyphenyl)-5-(1,3-thiazol-4-yl)-4H-1,2,4-triazol-3-yl)-1-methoxy-1-(5-methyl-2-pyrimidinyl)-2-propanesulfonamide.<br><br>$^1$H NMR (500 MHz, DMSO-d$_6$) δ 13.17 (br. s, 1H), 9.05 (d, J = 1.8 Hz, 1H), 8.65 (s, 2H), 7.82 (d, J = 1.8 Hz, 1H), 7.46 (t, J = 8.5 Hz, 1H), 6.80 (d, J = 8.6 Hz, 2H), 4.83 (d, J = 3.6 Hz, 1H), 3.67 (s, 3H), 3.65 (s, 3H), 3.43 (dd, J = 3.6, 7.0 Hz, 1H), 3.16 (s, 3H), 2.26 (s, 3H), 1.15 (d, J = 7.0 Hz, 3H). LCMS (pos.) m/z: 532.0 (M + H)$^+$. |
| 343.0 | (E)-N'-(2,6-dimethoxyphenyl)-N-(((1R,2S)-1-methoxy-1-(5-methylpyrimidin-2-yl)propan-2-yl)sulfonyl)carbamimidothioic acid, Example 329.01, and 6-methoxypyrazine-2-carbohydrazide, Example 395.24. | 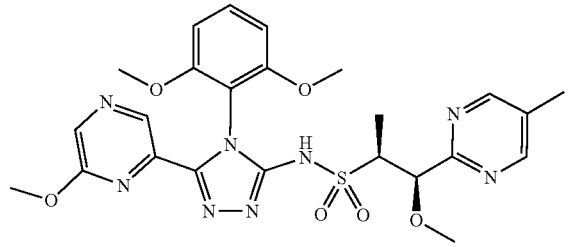<br>(1R,2S)-N-(4-(2,6-dimethoxyphenyl)-5-(6-methoxy-2-pyrazinyl)-4H-1,2,4-triazol-3-yl)-1-methoxy-1-(5-methyl-2-pyrimidinyl)-2-propanesulfonamide.<br><br>$^1$H NMR (300 MHz, CDCl$_3$) δ 11.34 (br. s, 1H), 8.78 (s, 1H), 8.60 (s, 2H), 8.17 (s, 1H), 7.33 (t, J = 8.5 Hz, 1H), 6.60 (d, J = 8.5 Hz, 2H), 4.96 (d, J = 4.7 Hz, 1H), 3.77-3.74 (m, 1H), 3.73 (s, 3H), 3.71 (s, 3H), 3.33 (s, 3H), 3.27 (s, 3H), 2.32 (s, 3H), 1.39 (d, J = 7.0 Hz, 3H). LCMS (pos.) m/z: 557.0 (M + H)$^+$. |

The compounds set forth in the following table were synthesized following the procedure in Example 134.0 using the known starting material as described.

TABLE 19

| Example | Reagents | Structure, Name and and Data |
|---|---|---|
| 327.0 | (1R,2S)-1-methoxy-1-(5-methylpyrazin-2-yl)propane-2-sulfonamide, Example 466.1, 2-isothiocyanato-1,3-dimethoxybenzene (Example 465.0), and 6-methoxypyrazine-2-carbohydrazide, Example 395.24. | 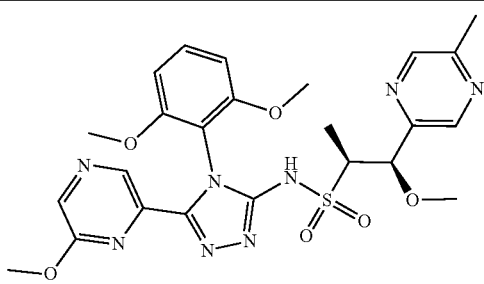<br>(1R,2S)-N-(4-(2,6-dimethoxyphenyl)-5-(6-methoxy-2-pyrazinyl)-4H-1,2,4-triazol-3-yl)-1-methoxy-1-(5-methyl-2-pyrazinyl)-2-propanesulfonamide.<br>$^1$H NMR (500 MHz, CDCl$_3$) δ 8.79 (s, 1H), 8.60 (s, 1H), 8.5 (d, J = 1.0 Hz, 1H), 8.19 (s, 1H), 5.0 (d, J = 3.4 Hz, 1H), 4.05 (d, J = 3.9 Hz, 1H), 3.73 (s, 3H), 3.73 (s, 3H), 3.54-3.59 (m, 1H), 3.30 (s, 3H), 3.08 (s, 3H), 2.65 (s, 3H), 1.27 (d, J = 6.8 Hz, 3H). LCMS-ESI (pos.) ink: 557.3 (M + H)$^+$. |
| 328.0 | (1R,2S)-1-methoxy-1-(5-methylpyrazin-2-yl)propane-2-sulfonamide, Example 466.1, 2-isothiocyanato-1,3-dimethoxybenzene (Example 465.0), and 1-ethyl-1H-pyrazole-3-carbohydrazide (ChemBridge). | 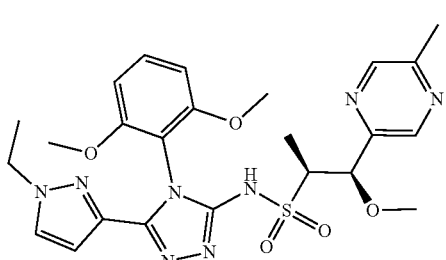<br>(1R,2S)-N-(4-(2,6-dimethoxyphenyl)-5-(1-ethyl-1H-pyrazol-3-yl)-4H-1,2,4-triazol-3-yl)-1-methoxy-1-(5-methyl-2-pyrazinyl)-2-propanesulfonamide.<br>$^1$H NMR (500 MHz, CDCl$_3$) δ 1.27 (d, J = 7.09 Hz, 3 H) 1.39 (t, J = 7.34 Hz, 3 H) 2.67 (s, 3 H) 3.31 (s, 3 H) 3.55 (dd, J = 6.97, 3.55 Hz, 1 H) 3.73 (s, 3 H) 3.74 (s, 3 H) 4.12 (q, J = 7.34 Hz, 2 H) 5.01 (d, J = 3.42 Hz, 1 H) 5.98 (d, J = 2.45 Hz, 1 H) 6.66 (d, J = 8.56 Hz, 2 H) 7.43 (t, J = 8.35 Hz, 1 H) 8.49 (s, 1 H) 8.60 (s, 1 H). LCMS-ESI (pos.) m/z: 540.1 (M + H)$^+$. |
| 330.0 | (1R,2S)-1-(5-chloropyrimidin-2-yl)-1-methoxypropane-2-sulfonamide (Example 466.3), 1-methyl-1H-pyrazole-3-carbohydrazide, Example 395.13, and 2-isothiocyanato-1,3-dimethoxybenzene (Example 465.0). | 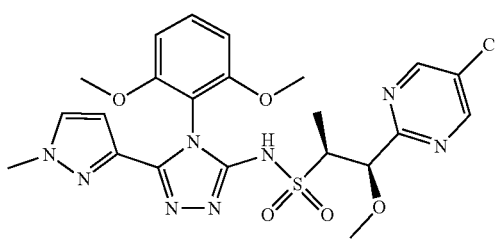<br>(1R,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-methoxypropane-2-sulfonamide.<br>$^1$H NMR (500 MHz, DMSO-d$_6$) δ 13.05 (s, 1H), 8.97-8.87 (m, 2H), 7.68 (d, J = 2.2 Hz, 1H), 7.52-7.45 (m, 1H), 6.81 (d, J = 8.6 Hz, 2H), 6.05 (d, J = 2.2 Hz, 1H), 4.79 (d, J = 4.4 Hz, 1H), 3.73 (s, 3H), 3.69 (s, 3H), 3.67 (s, 3H), 3.46-3.40 (m, 1H), 3.15 (s, 3H), 1.15 (d, J = 6.8 Hz, 3H). MS (pos.) m/e: 549.2 (M + H)$^+$. |

TABLE 19-continued

| Example | Reagents | Structure, Name and and Data |
|---|---|---|
| 344.0 | (1R,2S)-1-(5-chloropyrimidin-2-yl)-1-methoxypropane-2-sulfonamide (Example 466.3), isothiocyanato-1,3-dimethoxybenzene (Example 465.0), and 5-methyl-1H-pyrazole-3-carbohydrazide (commercially available from Frontier Scientific Services, Inc., Newark, DE). | 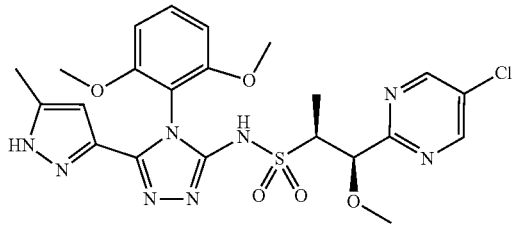 [SMILES: COc1cccc(OC)c1-n1c(NS(=O)(=O)[C@@H](C)[C@H](OC)c2ncc(Cl)cn2)nnc1-c1cc(C)[nH]n1]<br>(1R,2S)-1-(5-chloro-2-pyrimidinyl)-N-(4-(2,6-dimethoxyphenyl)-5-(5-methyl-1H-pyrazol-3-yl)-4H-1,2,4-triazol-3-yl)-1-methoxy-2-propanesulfonamide.<br>$^1$H NMR (300 MHz, CDCl$_3$) δ 11.08 (br. s, 1H), 8.71 (s, 2H), 7.44 (t, J = 8.5 Hz, 1H), 6.66 (d, J = 8.6 Hz, 2H), 5.90 (s, 1H), 4.96 (d, J = 5.0 Hz, 1H), 3.75 (m, 7H), 3.34 (s, 3H), 2.24 (s, 3H), 1.38 (d, J = 7.0 Hz, 3H). LCMS (pos.) m/z: 548.6 (M + H)$^+$. |
| 345.0 | (1R,2S)-1-(5-fluoropyrimidin-2-yl)-1-methoxypropane-2-sulfonamide, Example 466.2, 2-isothiocyanato-1,3-dimethoxybenzene (Example 465.0), and 5-methyl-1H-pyrazole-3-carbohydrazide (commercially available from Frontier Scientific Services, Inc., Newark, DE). | 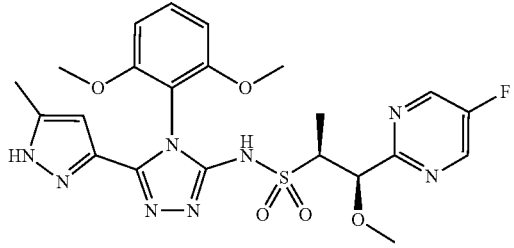 [SMILES: COc1cccc(OC)c1-n1c(NS(=O)(=O)[C@@H](C)[C@H](OC)c2ncc(F)cn2)nnc1-c1cc(C)[nH]n1]<br>(1R,2S)-N-(4-(2,6-dimethoxyphenyl)-5-(5-methyl-1H-pyrazol-3-yl)-4H-1,2,4-triazol-3-yl)-1-(5-fluoro-2-pyrimidinyl)-1-methoxy-2-propanesulfonamide.<br>$^1$H NMR (300 MHz, CDCl$_3$) δ 11.14 (br. s, 1H), 8.61 (s, 2H), 7.44 (t, J = 8.5 Hz, 1H), 6.66 (d, J = 8.6 Hz, 2H), 5.87 (s, 1H), 4.98 (d, J = 5.0 Hz, 1H), 3.76 (s, 3H), 3.74 (s, 3H), 3.73-3.69 (m, 1H), 3.33 (s, 3H), 2.24 (s, 3H), 1.39 (d, J = 7.0 Hz, 3H). LCMS (pos.) m/z: 532.9 (M + H)$^+$. |
| 346.0 | (2S,3R)-3-(5-methylpyrimidin-2-yl)butane-2-sulfonamide Example 464.0, 2-isothiocyanato-1,3-dimethoxybenzene (Example 465.0), and 5-methyl-1H-pyrazole-3-carbohydrazide (commercially available from Frontier Scientific Services, Inc., Newark, DE). | 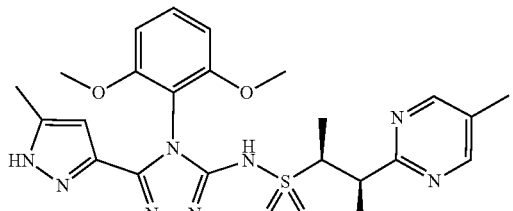<br>(2S,3R)-N-(4-(2,6-dimethoxyphenyl)-5-(5-methyl-1H-pyrazol-3-yl)-4H-1,2,4-triazol-3-yl)-3-(5-methyl-2-pyrimidinyl)-2-butanesulfonamide.<br>$^1$H NMR (300 MHz, CDCl$_3$) δ 11.89-11.15 (m, 1H), 8.51 (s, 2H), 7.42 (t, J = 8.5 Hz, 1H), 6.64 (dd, J = 3.7, 8.5 Hz, 2H), 5.78 (s, 1H), 3.93-3.85 (m, 1H), 3.84-3.78 (m, 1H), 3.74 (s, 3H), 3.71 (s, 3H), 2.26 (s, 3H), 2.22 (s, 3H), 1.37 (d, J = 7.0 Hz, 3H), 1.34 (d, J = 7.0 Hz, 3H). LCMS (pos.) m/z: 513.0 (M + H)$^+$. |

US 11,046,680 B1

447    448

TABLE 19-continued

| Example | Reagents | Structure, Name and and Data |
|---|---|---|
| 348.0 | (1R,2 S)-1-methoxy-1-(5-methylpyrazin-2-yl)propane-2-sulfonamide, Example 466.1, 2-isothiocyanato-1,3-dimethoxybenzene (Example 465.0), and 5-methyl-1H-pyrazole-3-carbohydrazide (commercially available from Frontier Scientific Services, Inc., Newark, DE). | (1R,2S)-N-(4-(2,6-dimethoxyphenyl)-5-(5-methyl-1H-pyrazol-3-yl)-4H-1,2,4-triazol-3-yl)-1-methoxy-1-(5-methyl-2-pyrazinyl)-2-propanesulfonamide.<br>$^1$H NMR (300 MHz, CDCl$_3$) δ 11.24 (br. s, 1H), 8.51 (d, J = 1.2 Hz, 1H), 8.42 (d, J = 1.0 Hz, 1H), 7.44 (t, J = 8.6 Hz, 1H), 6.66 (dd, J = 3.6, 8.6 Hz, 2H), 5.86 (s, 1H), 5.04 (d, J = 3.1 Hz, 1H), 3.74 (s, 3H), 3.74 (s, 3H), 3.58-3.47 (m, 1H), 3.31 (s, 3H), 2.56 (s, 3H), 2.24 (s, 3H), 1.26 (d, J = 7.0 Hz, 3H). LCMS (pos.) m/z: 529.0 (M + H)$^+$. |
| 355.0 | (1S,2S)-1-isopropoxy-1-(5-methylpyrimidin-2-yl)propane-2-sulfonamide (Example 468.0), 1-methyl-1H-pyrazole-3-carbohydrazide, Example 395.13, and 2-isothiocyanato-1,3-dimethoxybenzene (Example 465.0). | (1S,2S)-N-(4-(2,6-dimethoxyphenyl)-5-(1-methyl-1H-pyrazol-3-yl)-4H-1,2,4-triazol-3-yl)-1-isopropoxy-1-(5-methylpyrimidin-2-yl)propane-2-sulfonamide.<br>$^1$H NMR (400 MHz, DMSO-d$_6$) δ 13.03 (s, 1H), 8.73-8.61 (m, 2H), 7.69 (d, J = 2.3 Hz, 1H), 7.47 (t, J = 8.4 Hz, 1H), 6.85-6.78 (m, 2H), 6.03 (d, J = 2.3 Hz, 1H), 4.70 (d, J = 7.5 Hz, 1H), 3.73 (s, 3H), 3.71 (s, 3H), 3.69 (s, 3H), 3.46-3.37 (m, 2H), 2.33-2.25 (m, 3H), 0.98 (d, J = 6.0 Hz, 3H), 0.92 (d, J = 7.0 Hz, 3H), 0.84-0.75 (m, 3H). MS (pos.) m/e: 557.0 (M + H)$^+$. |

Example 347.0. Preparation of (1R,2S)-N-(4-(2,6-dimethoxyphenyl)-5-(5-methyl-1H-pyrazol-3-yl)-4H-1,2,4-triazol-3-yl)-1-hydroxy-1-(5-methyl-2-pyrazinyl)-2-propanesulfonamide

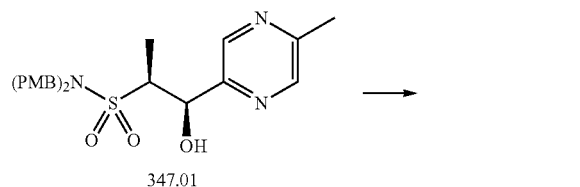

347.01

347.02

(1R,2S)-1-((tert-Butyldimethylsilyl)oxy)-N,N-bis(4-methoxybenzyl)-1-(5-methylpyrazin-2-yl)propane-2-sulfonamide, Example 347.02. A 250 mL RBF was charged with (1R,2S)-1-hydroxy-N,N-bis(4-methoxybenzyl)-1-(5-methylpyrazin-2-yl)propane-2-sulfonamide (Example 347.01, prepared in an analogous fashion to the procedure described in Example 264.0 employing 5-methylpyrazine-2-carbaldehyde, followed by isolation of the major diastereomer. Chiral SFC purification Method: 25% MeOH (20 mM NH$_3$) on an IC column delivered peak 2, 4.28 g, 9.08 mmol), TEA (1.50 mL, 10.76 mmol) and DCM (30 mL). The mixture was cooled in an ice-water bath. TBSOTf (2.30 mL, 10.01 mmol) was then added slowly over 13 min. The mixture was stirred at that temperature for 15 min and then the cold bath was removed and the mixture was stirred at RT. After 1.5 h, the reaction mixture was washed with saturated NaCl (2×50 mL). The organic phase was dried by passing through a Chem Elute extraction cartridge eluting with DCM (2×20 mL). The organic layer was concentrated and the product was purified by silica gel column chromatography (50 g, eluent: EtOAc in hexanes 0%-50%) to afford 347.02 (5.24 g, 8.94 mmol, 98%) as a thick syrup. $^1$H NMR (300 MHz, CDCl$_3$) δ 8.64 (d, J=1.02 Hz, 1H), 8.39 (d, J=1.02 Hz, 1H), 7.16 (d, J=8.62 Hz, 4H), 6.84 (d, J=8.77 Hz, 4H), 5.61 (d, J=2.19 Hz, 1H), 4.49 (d, J=15.20 Hz, 2H), 4.04-4.12 (m, 2H), 3.80 (m, 6H), 3.43 (dq, J=2.27, 6.94 Hz, 1H), 2.59 (s, 3H), 1.19 (d, J=7.02 Hz, 3H), 0.93-1.01 (m, 9H), 0.26 (s, 3H), −0.07 (s, 3H). LCMS (pos.) m/z: 586.0 (M+H)$^+$.

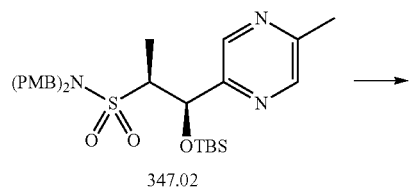

347.02

(1R,2S)-1-((tert-Butyldimethylsilyl)oxy)-1-(5-methylpyrazin-2-yl)propane-2-sulfonamide, Example 347.03. A 500 mL RBF was charged with (1R,2S)-1-((tert-butyldimethylsilyl)oxy)-N,N-bis(4-methoxybenzyl)-1-(5-methylpyrazin-2-yl)propane-2-sulfonamide (5.24 g, 8.94 mmol, Example 347.02), anisole (4.0 mL, 36.6 mmol) and DCM (20 mL). TFA (21 mL, 273 mmol) was added, and the mixture was stirred at RT for 35 h. Toluene (10 mL) was then added to the mixture, and the mixture was concentrated in vacuo to 20 mL and then partitioned between saturated aqueous NaHCO$_3$ (20 mL) and EtOAc (20 mL). The organic phase was washed with a saturated aqueous sodium chloride solution (20 mL). The organic phase was dried by passing through a Chem Elute extraction cartridge eluting with EtOAc (2×20 mL). The organics were then concentrated in vacuo, and the product was purified by column chromatography (100 g, eluent: (3:1 EtOAc/EtOH) in hexanes 0%-60%). The mixed fraction were re-purified (50 g, eluent: EtOAc/hexanes 20%-80%). The corresponding fractions were combined and concentrated to give 347.03 (2.82 g, 8.17 mmol, 91% yield) as a white solid. $^1$H NMR (300 MHz, CDCl$_3$) δ 8.63 (d, J=1.17 Hz, 1H), 8.39 (s, 1H), 5.52 (d, J=2.78 Hz, 1H), 4.66 (s, 2H), 3.50 (dq, J=2.92, 6.97 Hz, 1H), 2.59 (s, 3H), 1.35 (d, J=6.87 Hz, 3H), 0.97 (s, 9H), 0.19 (s, 3H), −0.15 (s, 3H). LCMS (pos.) m/z: 346.0 (M+H)$^+$.

347.0

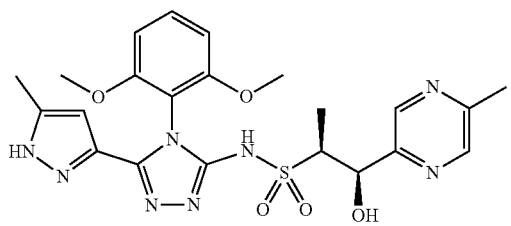

(1R,2S)-N-(4-(2,6-Dimethoxyphenyl)-5-(5-methyl-1H-pyrazol-3-yl)-4H-1,2,4-triazol-3-yl)-1-hydroxy-1-(5-methyl-2-pyrazinyl)-2-propanesulfonamide, Example 347.0. The title compound was prepared following the procedure in Example 134.0 using Example 347.03, Example 465.0 and 5-methyl-1H-pyrazole-3-carbohydrazide (ChemImpex, Wood Dale, Ill.). $^1$H NMR (300 MHz, CDCl$_3$) δ 11.59-10.56 (m, 1H), 8.66 (s, 1H), 8.37 (d, J=0.9 Hz, 1H), 7.49 (t, J=8.5 Hz, 1H), 6.70 (dd, J=8.6, 12.7 Hz, 2H), 5.96 (s, 1H), 5.54 (s, 1H), 4.06 (br. s, 1H), 3.82 (s, 3H), 3.75 (s, 3H), 3.72 (d, J=1.5 Hz, 1H), 2.56 (s, 3H), 2.26 (s, 3H), 1.13 (d, J=7.0 Hz, 3H). LCMS (pos.) m/z: 515.0 (M+H)$^+$.

Example 349.0. Preparation of (1R,2S)-N-(4-(2,6-dimethoxyphenyl)-5-(3-methyl-1H-pyrazol-5-yl)-4H-1,2,4-triazol-3-yl)-1-hydroxy-1-(5-methylpyrimidin-2-yl)propane-2-sulfonamide

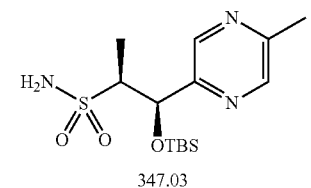

469.0

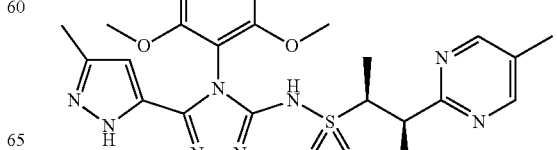

349.01

(1R,2S)-1-((tert-Butyldimethylsilyl)oxy)-1-(5-methylpyrimidin-2-yl)propane-2-sulfonamide, Example 349.01. A 250 mL RBF was charged with (1R,2S)-1-((tert-butyldimethylsilyl)oxy)-N,N-bis(4-methoxybenzyl)-1-(5-methylpyrimidin-2-yl)propane-2-sulfonamide (6.60 g, 9.85 mmol, Example 469.0) and DCM (30 mL). Anisole (5.00 mL, 45.8 mmol) was added, and the mixture was cooled in an ice-water bath. TFA (26.0 mL, 337 mmol) was added slowly over 2 min and the cold bath was removed. The light brown mixture was stirred at RT for 48 h. TFA (10 mL, 130 mmol) was then added and the mixture was further stirred at RT for 24 h. Toluene (10 mL) was added, and the mixture was concentrated in vacuo. The product was purified by a silica gel column chromatography (100 g, eluent, EtOAc in hexanes 10%-60%) to afford (1R,2S)-1-((tert-butyldimethylsilyl)oxy)-1-(5-methylpyrimidin-2-yl)propane-2-sulfonamide, 349.02 (3.06 g, 8.96 mmol, 90%) as a pale yellow paste. $^1$H NMR (300 MHz, CDCl$_3$) δ 8.57 (s, 2H), 5.28 (d, J=4.1 Hz, 1H), 4.97 (s, 2H), 3.70 (qd, J=7.1, 4.2 Hz, 1H), 2.34 (s, 3H), 1.48 (d, J=7.0 Hz, 3H), 0.88-0.94 (m, 9H), 0.07 (s, 3H), −0.13 (s, 3H). LCMS (pos.) m/z: 346.0 (M+H)$^+$.

349.0

(1R,2S)-N-(4-(2,6-Dimethoxyphenyl)-5-(3-methyl-1H-pyrazol-5-yl)-4H-1,2,4-triazol-3-yl)-1-hydroxy-1-(5-methylpyrimidin-2-yl)propane-2-sulfonamide, Example 349.0. The title compound was prepared following the procedure in Example 134.0 using 349.01, 465.0, and 5-methyl-H-pyrazole-3-carbohydrazide (Chemlmpex, Wood Dale, Ill.). $^1$H NMR (300 MHz, CDCl$_3$) δ 11.15 (br. s, 1H), 10.49-9.82 (m, 1H), 8.57 (s, 2H), 7.43 (t, J=8.5 Hz, 1H), 6.66 (t, J=7.5 Hz, 2H), 5.90 (s, 1H), 5.58 (s, 1H), 4.05 (d, J=2.9 Hz, 1H), 3.85 (dd, J=1.7, 6.9 Hz, 1H), 3.76 (s, 3H), 3.74 (s, 3H), 2.32 (s, 3H), 2.24 (s, 3H), 1.20 (d, J=7.0 Hz, 3H). LCMS (pos.) m/z: 515.0 (M+H)$^+$.

Example 350.0. Preparation of (1R,2S)-N-(4-(2,6-dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide or (1S,2R)-N-(4-(2,6-dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide

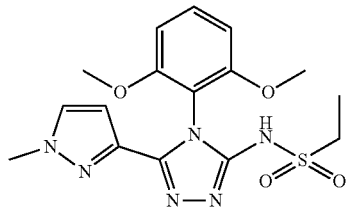

350.1

N-(4-(2,6-Dimethoxyphenyl)-5-(1-methyl-1H-pyrazol-3-yl)-4H-1,2,4-triazol-3-yl)ethanesulfonamide, Example 350.1. To a solution of 2-isothiocyanato-1,3-dimethoxybenzene (Example 465.0, 1.97 g, 10.1 mmol) and ethanesulfonamide (1 g, 9.2 mmol) in ACN (18 mL), was added cesium carbonate (3.88 g, 11.9 mmol). The reaction was stirred at RT for 16 h. To the reaction mixture was added silver(I) nitrate (3.11 g, 18.3 mmol) and then 1-methyl-1H-pyrazole-3-carbohydrazide (1.28 g, 9.2 mmol). Stirring was continued for 10 min at RT. The reaction was then filtered through a plug of silica gel and concentrated in vacuo to give (Z)-N'-(2,6-dimethoxyphenyl)-N-(ethylsulfonyl)-2-(1-methyl-1H-pyrazole-3-carbonyl)hydrazinecarboximidamide (3.76 g, 100% yield). To a solution of (Z)-N'-(2,6-dimethoxyphenyl)-N-(ethylsulfonyl)-2-(1-methyl-1H-pyrazole-3-carbonyl)hydrazinecarboximidamide (3.76 g, 9.2) in 1,4-dioxane (92 mL) was added TFA (4.23 mL, 55.0 mmol). The reaction was stirred at 90° C. for 16h. The reaction was concentrated in vacuo, neutralised with an aqueous solution of sodium bicarbonate, and then extracted with EtOAc. After concentration in vacuo, the residue was purified on silica gel (0-50%) EtOAc/EtOH (3/1) in heptanes to give Example 350.1 (2 g, 56% yield). MS (pos.) m/z: 393.2 (M+H)$^+$.

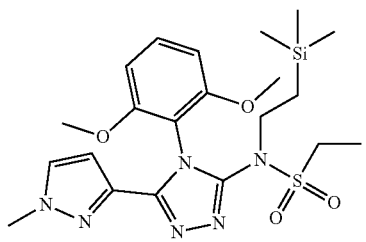

350.2

N-(4-(2,6-Dimethoxyphenyl)-5-(1-methyl-1H-pyrazol-3-yl)-4H-1,2,4-triazol-3-yl)-N-(2-(trimethylsilyl)ethyl)ethanesulfonamide, Example 350.2. To a vial containing Example 350.1 (473 mg, 1.20 mmol) in toluene (6 mL), was added 2-(trimethylsilyl)ethanol (0.35 mL, 2.44 mmol) and then cyanomethylenetri-n-butylphosphorane (0.63 mL, 2.40 mmol) separately dropwise by syringe. The heterogeneous mixture was heated to 90° C. and monitored with LCMS. After 0.5 h, the mixture was concentrated under reduced pressure. The mixture was purified on silica gel eluting with (0-70% EtOAc in heptanes) to afford a colorless film that solidified into a white solid as Example 350.2 (397.0 mg, 67% yield) that was used without further purification. MS (pos.) m/z: 493.1 (M+H)$^+$.

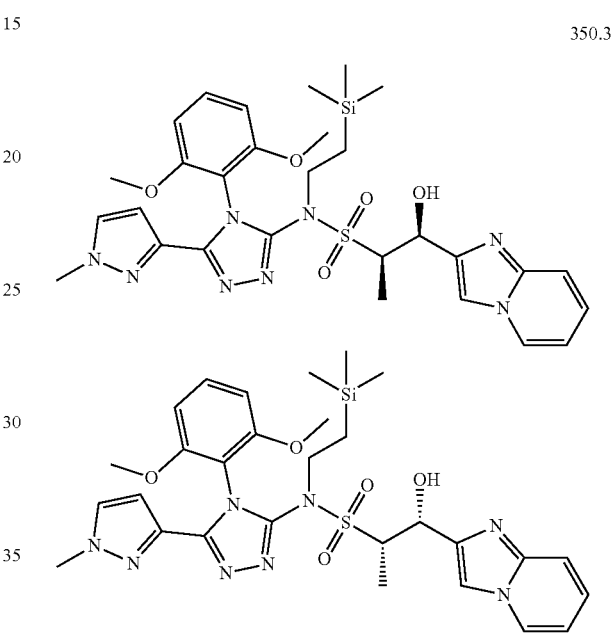

350.3

(1S,2R)-N-(4-(2,6-Dimethoxyphenyl)-5-(1-methyl-1H-pyrazol-3-yl)-4H-1,2,4-triazol-3-yl)-1-hydroxy-1-(imidazo[1,2-a]pyridin-2-yl)-N-(2-(trimethylsilyl)ethyl)propane-2-sulfonamide and (1R,2S)-N-(4-(2,6-dimethoxyphenyl)-5-(1-methyl-1H-pyrazol-3-yl)-4H-1,2,4-triazol-3-yl)-1-hydroxy-1-(imidazo[1,2-a]pyridin-2-yl)-N-(2-(trimethylsilyl)ethyl)propane-2-sulfonamide, Example 350.3. To a vial containing Example 350.2 (397 mg, 0.81 mmol) was added toluene. The mixture was concentrated in vacuo. The residue was further dried on HVAC. Anhydrous THF (3 mL) was then added to the flask. Upon complete addition of THF, argon was sparged through the solution for 15 min. The flask was then cooled in an acetone-dry ice bath. After 20 min, n-butyllithium, (2.5M solution in hexanes, 0.5 mL, 1.25 mmol) was carefully added dropwise to the cold solution. After 20 min, a solution of imidazo[1,2-a]pyridine-2-carbaldehyde (180 mg, 1.23 mmol) in anhydrous THF (2 mL) was added dropwise over 5 min. Upon complete addition, the reaction was warmed to RT and monitored with LC-MS. After 2 h, the reaction was transferred to an ice-water bath and then carefully quenched with saturated aqueous ammonium chloride solution. After extracting three times with CHCl$_3$, the organics were pooled and then dried over anhydrous MgSO$_4$. After filtration and concentration under reduced pressure, the dark brown residue was purified on silica gel eluting with 0-95% of (3:1 EtOAc:EtOH) in heptanes to afford the first eluting isomer, Example 350.3 (36.7 mg, 0.057 mmol, 7.13% yield as a light yellow film), that was used without further purification. MS (pos.) m/z: 639.2 (M+H)$^+$.

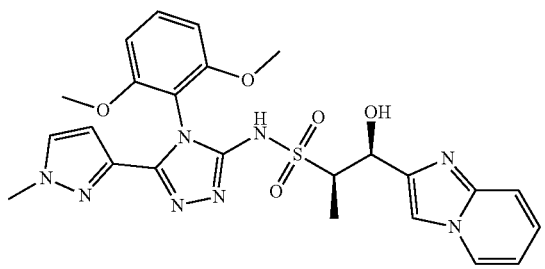

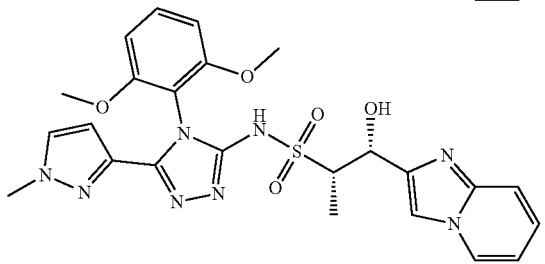

(1R,2S)-N-(4-(2,6-Dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide or (1S,2R)-N-(4-(2,6-dimethoxyphenyl)-5-(1-methyl-1H-pyrazol-3-yl)-4H-1,2,4-triazol-3-yl)-1-hydroxy-1-imidazo[1,2-a]pyridin-2-yl-2-propanesulfonamide, Example 350.0. To a vial containing Example 350.3 was added tris(dimethylamino)sulfonium difluorotrimethylsilicate (TASF, 50 mg, 0.18 mmol) followed by dropwise addition of anhydrous DMF (0.3 mL). The mixture was carefully heated to 60° C. and monitored with LC-MS. After 19 h, the mixture was cooled to RT and then purified on silica gel eluting with 20-95% of (3:1 EtOAc:EtOH) in heptanes to afford a light yellow liquid that was further purified with reverse-phase HPLC (10-65% of premixed 0.1% TFA in ACN in 0.1% TFA in water). Fractions containing the title product were combined and then concentrated under reduced pressure. The residue was treated with a saturated aqueous solution of NaHCO₃. After extracting three times with DCM, the organics were pooled and then dried over anhydrous MgSO₄. Filtration and concentration in vacuo afforded, Example 350.0 as an off-white solid. $^1$H NMR (400 MHz, DMSO-d₆) δ 8.49 (d, J=6.8 Hz, 1H), 7.74 (s, 1H), 7.44-7.53 (m, 2H), 7.33 (t, J=8.4 Hz, 1H), 7.12-7.19 (m, 1H), 6.81 (td, J=6.7, 1.2 Hz, 1H), 6.72 (dd, J=8.4, 1.8 Hz, 2H), 6.33 (d, J=2.0 Hz, 1H), 5.87 (d, J=2.2 Hz, 1H), 5.48 (s, 1H), 3.68-3.73 (m, 4H), 3.63 (s, 3H), 3.61 (s, 3H), 0.90 (d, J=7.2 Hz, 3H). MS (pos.) m/z: 539.2 (M+H)⁺.

Example 351.0. Preparation (1S,2R)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide or (1R,2S)-1-(5-chloro-2-pyrimidinyl)-N-(4-(2,6-dimethoxyphenyl)-5-(1-methyl-1H-pyrazol-3-yl)-4H-1,2,4-triazol-3-yl)-1-ethoxy-2-propanesulfonamide

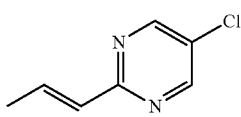

(E)-5-Chloro-2-(prop-1-en-1-yl)pyrimidine, Example 351.1. To a 1 L flask was added 2,5-dichloropyrimidine (10 g, 67 mmol), potassium (E)-trifluoro(prop-1-en-1-yl)borate (12.9 g, 87 mmol), potassium phosphate (43 g, 203 mmol), 1,1-bis[(di-t-butyl-p-methylaminophenyl]palladium(II) chloride (9.5 g, 13.42 mmol), 1,4-dioxane (200 mL), and water (20 mL). The resulting mixture was sparged with Ar for 5 min and then a condensor was attached and the mixture was heated at 85° C. under nitrogen overnight. The reaction was cooled to RT and partitioned between EtOAc (100 mL) and water (60 mL). The aqueous layer was extracted with EtOAc (50 mL). The combined organic layers were dried over MgSO₄, filtered, and concentrated in vacuo. The product was purified on silica gel eluting with hexanes:acetone=97%:3% to afford Example 351.1 (7.5 g, 72%) as a yellow solid. $^1$H NMR (300 MHz, CDCl₃) δ 8.66-8.52 (m, 2H), 7.17 (qd, J=6.9, 15.5 Hz, 1H), 6.56 (qd, J=1.7, 15.5 Hz, 1H), 2.07-1.91 (m, 3H).

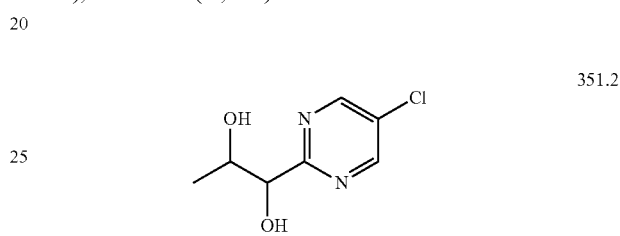

1-(5-Chloropyrimidin-2-yl)propane-1,2-diol, Example 351.2. To a 500 mL flask was added (Example 351.1 (7.5 g, 48.5 mmol), 4-methylmorpholine-4-oxide (8.5 g, 72.6 mmol), acetone (140 mL), water (14.0 mL), and osmium tetroxide (4 wt. %, in water, 3.0 mL, 0.49 mmol). The resulting mixture was stirred at RT under N₂. After 3.5 h, solvent was removed under reduced pressure. The residue was partitioned between EtOAc (150 mL) and water (10 mL). The aqueous layer was extracted with 10% IPA in CHCl₃ (3×60 mL). The combined organic layers were dried over MgSO₄, filtered, and concentrated in vacuo. The product was purified by column chromatography (330 g of silica, 15 to 40% acetone in hexanes) to afford Example 351.2 (6.0 g, 66%) as a white solid. $^1$H NMR (400 MHz, CDCl₃) δ 8.85-8.53 (m, 2H), 4.79-4.54 (m, 1H), 4.22 (m, 1H), 4.03 (d, J=5.7 Hz, 1H), 2.46 (d, J=8.0 Hz, 1H), 1.47-1.09 (m, 3H).

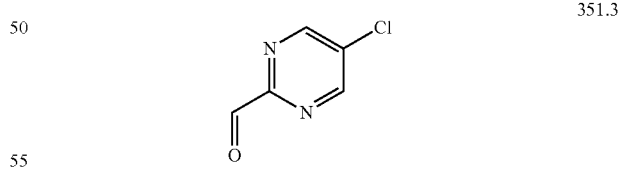

5-Chloropyrimidine-2-carbaldehyde, Example 351.3. At 23° C., sodium periodate (14.9 g, 70 mmol) was added to a 1,4-dioxane/water solution containing Example 351.2 (6.48 g, 34.4 mmol). The resulting mixture was stirred for 1.5 h. DCM (300 mL) was added, and then the reaction was filtered through a pad of magnesium sulfate and concentrated. The reaction was purified on silica eluting with a DCM/EtOAc gradient (0-100%). Desired fractions were then pooled and concentrated under reduced pressure to afford Example 351.3. MS (pos.) m/z: 143.1 (M+H)⁺.

455

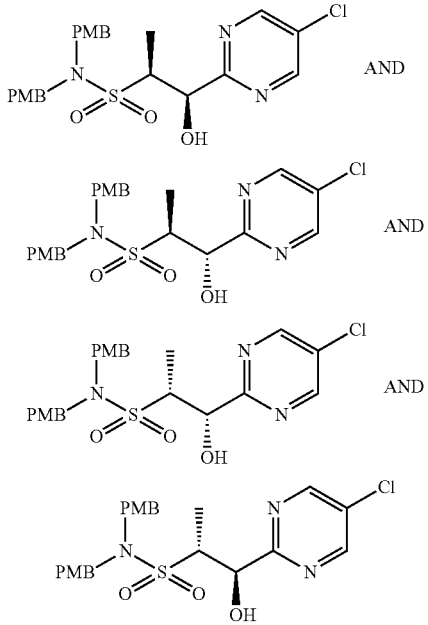

(1R,2S)-1-(5-Chloropyrimidin-2-yl)-1-hydroxy-N,N-bis(4-methoxybenzyl)propane-2-sulfonamide and (1S,2R)-1-(5-chloropyrimidin-2-yl)-1-hydroxy-N,N-bis(4-methoxybenzyl)propane-2-sulfonamide and (1R,2R)-1-(5-chloropyrimidin-2-yl)-1-hydroxy-N,N-bis(4-methoxybenzyl)propane-2-sulfonamide and (1S,2S)-1-(5-chloropyrimidin-2-yl)-1-hydroxy-N,N-bis(4-methoxybenzyl)propane-2-sulfonamide, Example 351.4. At −78° C., n-butyllithium (2.5 M, 29.0 mL, 72.5 mmol) was added to a 2-methyltetrahydrofuran (440 mL) solution containing Example 467.0 (25.3 g, 72.5 mmol). The resulting mixture was stirred for 15 min at −78° C. and then a 2-methyltetrahydrofuran solution containing Example 351.3 (9.4 g, 65.9 mmol) was added. The reaction was allowed to slowly warm to room temp and then stirred overnight. The reaction was partitioned with EtOAc/water, washed with brine, dried over sodium sulfate, and concentrated in vacuo. The residue was purified on silica eluting with a hexanes/EtOAc gradient (0-100%). Desired fractions were then pooled and concentrated to afford Example 351.4 (16.2 g, 50% yield). MS (pos.) m/z: 514.1 (M+Na)⁺.

351.5

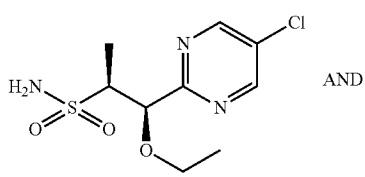

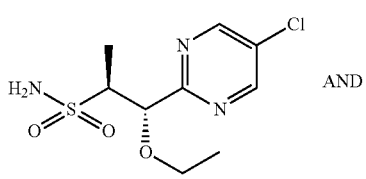

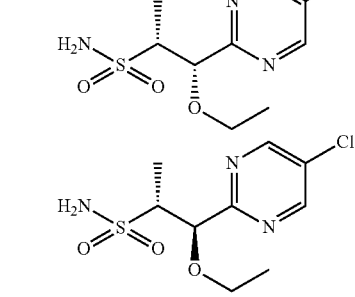

(1R,2S)-1-(5-Chloropyrimidin-2-yl)-1-ethoxypropane-2-sulfonamide and (1S,2R)-1-(5-chloropyrimidin-2-yl)-1-ethoxypropane-2-sulfonamide and (1R,2R)-1-(5-chloropyrimidin-2-yl)-1-ethoxypropane-2-sulfonamide and (1S,2S)-1-(5-chloropyrimidin-2-yl)-1-ethoxypropane-2-sulfonamide, Example 351.5. At −78° C., KHMDS (1.0 M, 10 mL, 10 mmol) was added to a 2-methyltetrahydrofuran (75 mL) solution containing Example 351.4 (4.49 g, 9.13 mmol). The resulting mixture was stirred for 5 min at −78° C. and then EtOTf (1.63 g, 9.13 mmol) was added. After 45 min, a saturated solution of ammonium chloride was added at −78° C. The reaction was then warmed to RT. The reaction was partitioned with EtOAc/water, washed with brine, dried over sodium sulfate, and concentrated in vacuo. The residue was purified on silica eluting with a hexanes/EtOAc gradient (0-100%). Desired fractions were then pooled and concentrated in vacuo. The residue was placed in anisole (2 mL) and DCM (10 mL) and then treated with TFA (10 mL). After stirring at RT overnight, the reaction was concentrated in vacuo. The residue was purified on silica eluting with a MeOH/DCM stepwise gradient (0-20%). Desired fractions were then pooled and concentrated in vacuo to afford Example 351.5 (720 mg, 2.6 mmol). MS (pos.) m/z: 280.0 (M+H)⁺.

351.6

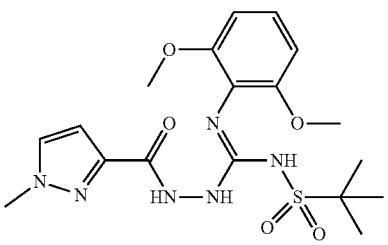

(Z)-N-(tert-Butylsulfonyl)-N'-(2,6-dimethoxyphenyl)-2-(1-methyl-1H-pyrazole-3-carbonyl)hydrazine-1-carboximidamide, Example 351.6. To a solution of 2-isothiocyanato-1,3-dimethoxybenzene (Example 465.0, 60 g, 0.31 mol) and tert-butylsulfonamide (44.3 g, 0.32 mol) in ACN (1.2 L), was added cesium carbonate (130 g, 0.4 mol) in portions. The mixture was stirred overnight at RT. To the heterogeneous mixture were successively added 1-methyl-H-pyrazole-3-carbohydrazide (45 g, 0.32 mol) and silver nitrate (104 g, 0.61 mol) in portions (Note: the addition was mildly exothermic ~10° raise in temperature). After 1 h, Celite® brand filter aid was added to the reaction, and the mixture was stirred for 15 min. The reaction mixture was then filtered through a pad of Celite® brand filter aid. After rinsing the pad with DCM and 10% MeOH in DCM, the mixture was concentrated under reduced pressure to afford a black residue which was purified by column chromatography (silica gel, 60-120 mesh) using DCM and MeOH as eluent to provide Example 351.6 (130 g, 96%) as a white solid. MS (pos.) m/z: 439.4 (M+H)⁺.

351.7

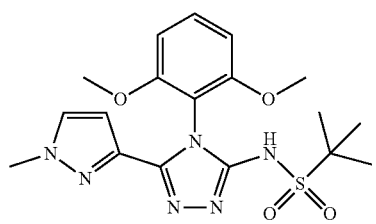

N-(4-(2,6-Dimethoxyphenyl)-5-(1-methyl-1H-pyrazol-3-yl)-4H-1,2,4-triazol-3-yl)-2-methylpropane-2-sulfonamide, Example 351.7. To a solution of Example 351.6 (130 g, 0.3 mol) in dioxane (515 mL), was added TFA (113 mL, 1.48 mol). The reaction was then heated at reflux at 100° C. over 20 h. The reaction was then concentrated in vacuo and the material was carried on to the next step without further purification. MS (pos.) m/z: 421.2 (M+H)⁺.

351.8

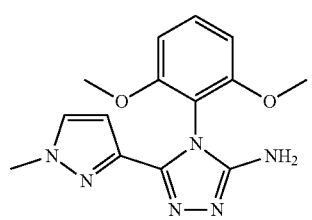

4-(2,6-Dimethoxyphenyl)-5-(1-methyl-1H-pyrazol-3-yl)-4H-1,2,4-triazol-3-amine, Example 351.8. To a solution of Example 351.7 (160 g, 0.38 mol) in TFA (530 mL, 5 v/w) was added anisole (125 mL, 1.1 mol). The resulting mixture was then heated for 20 h at 100° C. After completion of the reaction, TFA was removed using a high vacuum. The residue was added to a small amount of ice and brought to a pH of 8-9 using a 10% NaHCO₃ aqueous solution. The resulting solids were filtered off, and washed with water, and petroleum ether, diethyl ether and then dried to obtain Example 351.8 (53 g, 60% for two steps) as a beige solid. MS (pos.) m/z: 301.2 (M+H)⁺.

351.9

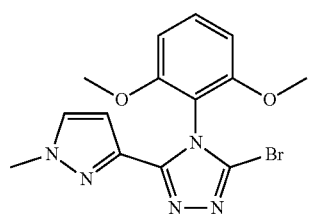

3-Bromo-4-(2,6-dimethoxyphenyl)-5-(1-methyl-1H-pyrazol-3-yl)-4H-1,2,4-triazole, Example 351.9. To a stirred solution of Example 351.8 (53 g, 0.18 mol, 1.0 equiv.) in dibromomethane (2.0 L) was added benzyltriethyl ammonium bromide (144 g, 0.53 mol) and sodium nitrite (244 g, 3.5 mol, 20 equiv.) at RT. Dichloroacetic acid (29.3 mL, 0.35 mol, 2.0 equiv.) was added dropwise at 0° C. (internal temperature), and the resulting solution was stirred at RT for 18 h. The reaction mixture was concentrated in vacuo and the residue thus obtained was purified by column chromatography (silica gel, 60-120 mesh) using 1.0% MeOH in DCM) to yield a pale yellow solid. The solid obtained was taken into a minimal amount of ether (2 v/w) and stirred for 15 min and filtered to obtain Example 351.9. (20 g, 31%) as a pale yellow solid. MS (pos.) m/z: 364.2 (M+H)⁺.

351.9

(1S,2R)-1-(5-Chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide and (1R,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide and (1S,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide and (1R,2R)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide, Example 351.9. To a vial containing Example 351.5 (537 mg, 1.48 mmol), copper (I) iodide (115 mg, 0.60 mmol), cesium carbonate (938 mg, 2.88 mmol), and trans-N,N'-dimethyl-1,2-cyclohexanediamine (0.37 mL, 2.34 mmol), was added degassed, anhydrous 1,4-dioxane (2.5 mL). Argon was sparged through the reaction solution. After 15 min, the dark blue heterogeneous solution was heated on a pre-heated stirplate at 80° C. After 17 h, LCMS showed the reaction was complete. The reaction was cooled to RT and then an aqueous solution of sodium thiosulfate was carefully added to the mixture. After extracting three times with DCM, the organics were pooled and then dried over anhydrous magnesium sulfate. After filtration and concentration, the residue was purified via reverse-phase HPLC (Phenomenex Gemini-C18 column, 30×250 mm, 10 m, 10-95% water/ACN gradient over 25 min., with 0.1% TFA, flow rate 50 mL/min). Desired fractions were pooled and lyophilized to give Example 351.9. MS (pos.) m/z: 563.3 (M+H)$^+$.

The compounds set forth in the following table were synthesized following the procedure in Example 94.0 using the known starting material as described.

TABLE 20

| Example | Reagents | Structure, Name and and Data |
|---|---|---|
| 351.0 | Example 351.9 was purified by preparative SFC using the following methodology: methodology: Column: AS-H (2 × 15 cm) Mobile Phase: 80:15 (A:B) A: Liquid CO$_2$, B: MeOH, Flow Rate: 60 mL/min, 220 nm, 100 bar inlet pressure to deliver peak 1. | 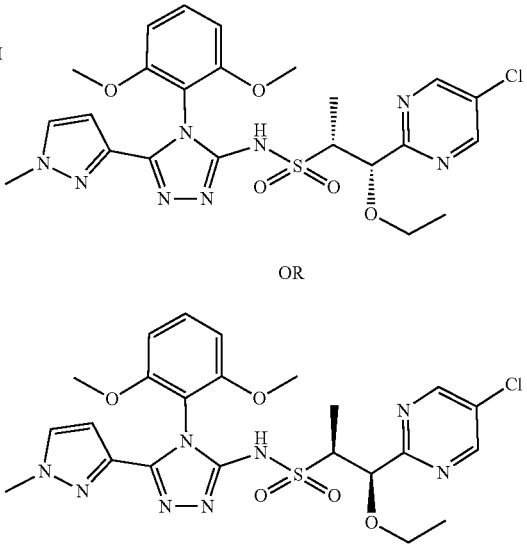 [SMILES: CCO[C@@H](c1ncc(Cl)cn1)[C@@H](C)S(=O)(=O)Nc1nnc(-c2ccn(C)n2)n1-c1c(OC)cccc1OC ; CCO[C@H](c1ncc(Cl)cn1)[C@H](C)S(=O)(=O)Nc1nnc(-c2ccn(C)n2)n1-c1c(OC)cccc1OC] OR (1S,2R)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide or (1R,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide. $^1$H NMR (500 MHz, DMSO-d$_6$) δ 13.02 (br. s, 1H), 8.95-8.90 (m, 2H), 7.67 (s, 1H), 7.48 (t, J = 8.6 Hz, 1H), 6.81 (d, J = 8.6 Hz, 2H), 6.04 (s, 1H), 4.88 (d, J = 4.6 Hz, 1H), 3.72 (s, 3H), 3.69 (s, 3H), 3.66 (s, 3H), 3.49-3.37 (m, 2H), 3.36-3.29(m, 1H), 1.18 (d, J = 6.8 Hz, 3H), 1.03-0.96 (m, 3H). MS (pos.) m/z: 563.3 (M + H)$^+$. |

TABLE 20-continued

| Example | Reagents | Structure, Name and and Data |
|---|---|---|
| 352.0 | Example 351.9 was purified by preparative SFC using the following methodology: Column: AS-H (2 × 15 cm) Mobile Phase: 80:15 (A:B) A: Liquid $CO_2$, B: MeOH, Flow Rate: 60 mL/min, 220 nm, 100 bar inlet pressure to deliver peak 2. | 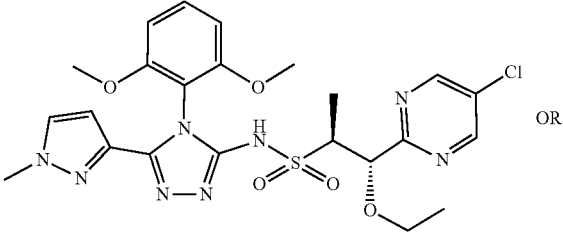 (1S,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide.<br><br>$^1$H NMR (500 MHz, DMSO-$d_6$) δ 12.96 (s, 1H), 8.94 (s, 2H), 7.67 (br. s, 1H), 7.48 (t, J = 8.4 Hz, 1H), 6.82 (d, J = 8.3 Hz, 2H), 6.03 (br. s, 1H), 4.69 (d, J = 7.1 Hz, 1H), 3.77-3.62 (m, 9H), 3.51-3.40 (m, 1H), 3.31-3.24 (m, 1H), 3.22-3.14 (m, 1H), 0.96 (d, J = 7.1 Hz, 3H), 0.93-0.84 (m, 3H). MS (pos.) m/z: 563.3 (M + H)$^+$. |

TABLE 20-continued

| Example | Reagents | Structure, Name and and Data |
|---|---|---|
| 353.0 | Example 351.9 was purified by preparative SFC using the following methodology: Column: AS-H (2 × 15 cm) Mobile Phase: 80:15 (A:B) A: Liquid $CO_2$, B: MeOH, Flow Rate: 60 mL/min, 220 nm, 100 bar inlet pressure to deliver peak 3. | 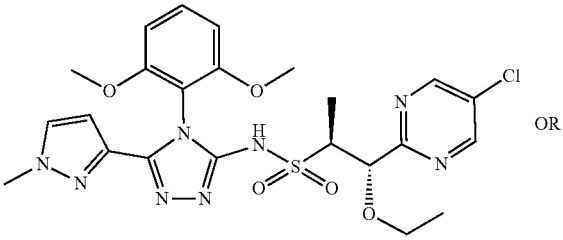 OR 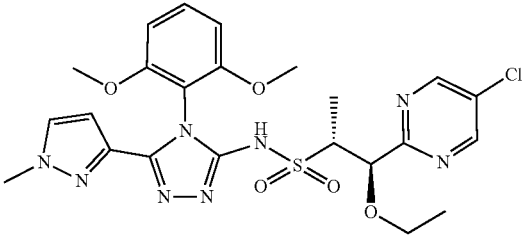 (1S,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide or (1R,2R)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide. $^1$H NMR (500 MHz, DMSO-$d_6$) δ 12.96 (s, 1H), 8.94(s, 2H), 7.67 (d, J = 1.7 Hz, 1H), 7.48 (t, J = 8.4 Hz, 1H), 6.82 (dd, J = 2.8, 8.4 Hz, 2H), 6.03 (d, J = 1.5 Hz, 1H), 4.69 (d, J = 7.3 Hz, 1H), 3.78-3.63 (m, 9H), 3.52-3.40 (m, 1H), 3.32-3.27 (m, 1H), 3.22-3.14 (m, 1H), 0.96 (d, J = 7.1 Hz, 3H), 0.91 (t, J = 7.0 Hz, 3H). MS (pos.) m/z: 563.3 (M + H)$^+$. |

| Example | Reagents | Structure, Name and and Data |
|---|---|---|
| 354.0 | Example 351.9 was purified by preparative SFC using the following methodology: Column: AS-H (2 × 15 cm) Mobile Phase: 80:15 (A:B) A: Liquid CO$_2$, B: MeOH, Flow Rate: 60 mL/min, 220 nm, 100 bar inlet pressure to deliver peak 4. | (1S,2R)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide or (1R,2S)-1-(5-chloropyrimidin-2-yl)-N-(4-(2,6-dimethoxyphenyl)-5-(1-methyl-1H-pyrazol-3-yl)-4H-1,2,4-triazol-3-yl)-1-ethoxypropane-2-sulfonamide. <br> $^1$H NMR (500 MHz, DMSO-d$_6$) δ 13.02 (s, 1H), 8.95-8.89 (m, 2H), 7.67 (d, J = 2.0 Hz, 1H), 7.48 (t, J = 8.4 Hz, 1H), 6.81 (d, J = 8.6 Hz, 2H), 6.04 (d, J = 2.0 Hz, 1H), 4.88 (d, J = 4.9 Hz, 1H), 3.73 (s, 3H), 3.69 (s, 3H), 3.66 (s, 3H), 3.52-3.27 (m, 3H), 1.18 (d, J = 7.1 Hz, 3H), 0.99 (t, J = 7.0 Hz, 3H). MS (pos.) m/z: 563.3 (M + H)$^+$. |

Example 356.0. Preparation of 1-(4-Chlorophenyl)-N-(5-(thiophen-2-yl)-4-(2-(trifluoromethyl)phenyl)-4H-1,2,4-triazol-3-yl)methanesulfonamide

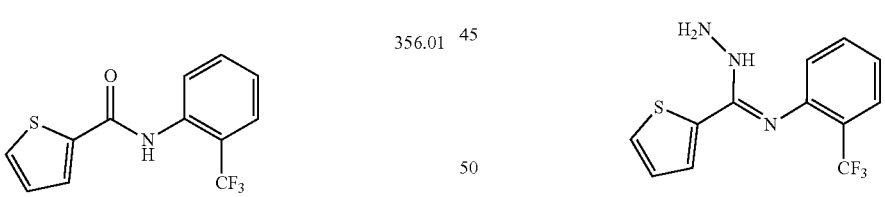

356.01

356.02

N-(2-(Trifluoromethyl)phenyl)thiophene-2-carboxamide, Example 356.01. Thiophen-2-yl magnesium bromide (28.6 mL, 28.6 mmol) was injected dropwise into a solution of 2-(trifluoromethyl)phenyl isocyanate (4.86 g, 26.0 mmol) in THF (100 mL) at −78° C. The reaction was stirred at −78° C. for 30 min. The reaction mixture was then quenched with a saturated solution of NH$_4$Cl (100 mL) and extracted with EtOAc (3×100 mL). The organic layers were combined, dried over MgSO$_4$, filtered and concentrated in vacuo. The product was purified on a silica gel column (0%-20% EtOAc in DCM) to provide Example 356.01 (2.73 g, 10.1 mmol, 38.7% yield). $^1$H NMR (400 MHz, DMSO-d$_6$) δ 10.14 (s, 1H) 7.96 (dd, J=3.72, 1.17 Hz, 1H) 7.86 (dd, J=4.99, 1.08 Hz, 1H) 7.80 (d, J=8.02 Hz, 1H) 7.71-7.77 (m, 1H) 7.52-7.58 (m, 2H) 7.23 (dd, J=4.99, 3.81 Hz, 1H). LCMS-ESI (pos.) m/z: 272.0 (M+H)$^+$.

(Z)-N'''-(2-(Trifluoromethyl)phenyl)thiophene-2-carboximidhydrazide, Example 356.02. To a 250 mL round bottom flask was added Example 356.01 (2.71 g, 9.99 mmol) and thionyl chloride (14.6 mL, 200 mmol). The reaction mixture was then stirred at 60° C. for 24 h and then concentrated in vacuo to give a material as a light brown solid which was then dissolved in toluene (10 mL). The resulting solution was injected dropwise into a mixture of hydrazine (6.27 mL, 200 mmol) in toluene (40 mL). The reaction was stirred at RT for 6 h. The reaction mixture was diluted with water (100 mL) and extracted with Et$_2$O (3×100 mL). The organic extract was washed with brine (100 mL) and dried over Na$_2$SO$_4$. The solution was filtered and concentrated in vacuo to give Example 356.02 (3.03 g) as a light brown oil, which was used directly in the next step without further purification. LCMS-ESI (pos.) m/z: 286.1 (M+H)$^+$.

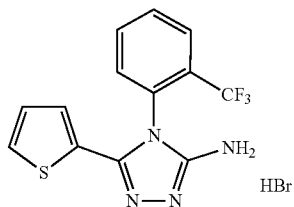

5-(Thiophen-2-yl)-4-(2-(trifluoromethyl)phenyl)-4H-1,2,4-triazol-3-amine hydrobromide, Example 356.03. To a solution of (Z)-N'-(2-(trifluoromethyl)phenyl)thiophene-2-carboximidhydrazide (2.85 g, 9.99 mmol) in MeOH, was added cyanogen bromide (5.0 M solution in ACN, 2.00 mL, 10.0 mmol) dropwise. The mixture was heated at 80° C. for 6 h and then cooled to RT overnight. The solvent was removed under vacuum. The residue was triturated with DCM (100 mL), and filtered and rinsed with DCM to provide Example 356.03 (3.17 g, 8.10 mmol, 81% yield) as an off-white powder. $^1$H NMR (400 MHz, DMSO-d$_6$) δ 8.38 (br. s, 2H) 7.98-8.13 (m, 4H) 7.74 (dd, J=5.09, 1.17 Hz, 1H) 7.03 (dd, J=5.09, 3.72 Hz, 1H) 6.70 (dd, J=3.81, 1.08 Hz, 1H). LCMS-ESI (pos.) m/z: 311.0 (M+H)$^+$.

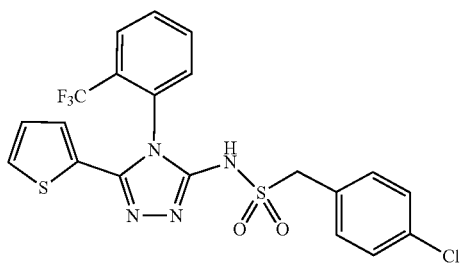

1-(4-Chlorophenyl)-N-(5-(thiophen-2-yl)-4-(2-(trifluoromethyl)phenyl)-4H-1,2,4-triazol-3-yl)methanesulfonamide, Example 356.0. The title compound was synthesized following the same procedure as described in Example 239.0 starting from Example 356.03 (130 mg, 0.33 mmol) and (4-chlorophenyl)methanesulfonyl chloride (commercially available from Oakwood Products, Inc., Columbia, S.C., USA, 150 mg, 0.67 mmol). $^1$H NMR (400 MHz, DMSO-d$_6$) δ 13.38 (s, 1H), 8.06-7.99 (m, 2H), 7.96-7.89 (m, 2H), 7.71 (dd, J=5.1, 1.2 Hz, 1H), 7.35-7.32 (m, 2H), 7.31-7.27 (m, 2H), 7.01 (dd, J=5.0, 3.8 Hz, 1H), 6.65 (d, J=4.1 Hz, 1H), 4.26-4.17 (m, 2H). LCMS-ESI (pos.) m/z: 499.0 (M+H)$^+$.

Example 357.0. Preparation of 2-(4-Chlorophenyl)-N-(5-(thiophen-2-yl)-4-(2-(trifluoromethyl)phenyl)-4H-1,2,4-triazol-3-yl)ethanesulfonamide

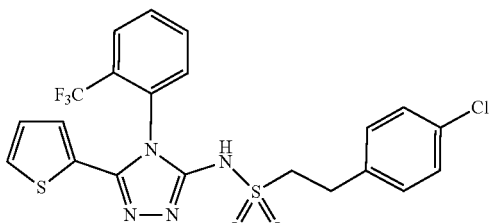

2-(4-Chlorophenyl)-N-(5-(thiophen-2-yl)-4-(2-(trifluoromethyl)phenyl)-4H-1,2,4-triazol-3-yl)ethanesulfonamide, Example 357.0. The title compound was synthesized following the same procedure as described in Example 239.0 starting from Example 356.03 (130 mg, 0.33 mmol) and 2-(4-chlorophenyl)ethanesulfonyl chloride (commercially available from Oakwood Products, Inc., Columbia, S.C., USA, 87 mg, 0.37 mmol) to obtain Example 357.0 (48 mg, 0.094 mmol, 28% yield) as a white powder. $^1$H NMR (400 MHz, DMSO-d$_6$) δ 13.41 (s, 1H), 8.06-7.89 (m, 4H), 7.70 (dd, J=5.1, 1.0 Hz, 1H), 7.39-7.28 (m, 2H), 7.23 (d, J=7.5 Hz, 2H), 7.01 (dd, J=5.0, 3.8 Hz, 1H), 6.65 (dd, J=3.8, 1.1 Hz, 1H), 3.26-3.12 (m, 2H), 2.93-2.84 (m, 2H). LCMS-ESI (pos.) m/z: 513.0 (M+H)$^+$.

Example 358.0. Preparation of 2-(4-Fluorophenyl)-N-(4-(2-methoxy-5-(methylsulfonyl)phenyl)-5-(thiophen-2-yl)-4H-1,2,4-triazol-3-yl)ethanesulfonamide 2-(4-Fluorophenyl)-N-(4-(2-methoxy-5-(methylsulfonyl)phenyl)-5-(thiophen-2-yl)-4H-1,2,4-triazol-3-yl)ethanesulfonamide, Example 358.0. The title compound was synthesized following the procedures described in Example 312.0 employing Example 302.0 (46 mg, 0.086 mmol) to obtain Example 358.0 (15 mg, 0.028 mmol, 33% yield) as a white powder. $^1$H NMR (400 MHz, DMSO-d$_6$) δ 13.33 (s, 1H), 8.27 (d, J=2.3 Hz, 1H), 8.18 (dd, J=8.9, 2.4 Hz, 1H), 7.71 (dd, J=5.0, 1.1 Hz, 1H), 7.54 (d, J=8.8 Hz, 1H), 7.24-7.29 (m, 2H), 7.04-7.12 (m, 3H), 6.93 (dd, J=3.8, 1.1 Hz, 1H), 3.81 (s, 3H), 3.16-3.27 (m, 5H), 2.86-2.96 (m, 2H). LCMS-ESI (pos.) m/z: 537.0 (M+H)$^+$.

Example 359.0. Preparation of 2-(4-fluorophenyl)-N-(4-(2-methoxyphenyl)-5-(thiophen-2-yl)-4H-1,2,4-triazol-3-yl)ethanesulfonamide 2-(4-Fluorophenyl)-N-(4-(2-methoxyphenyl)-5-(thiophen-2-yl)-4H-1,2,4-triazol-3-yl)ethanesulfonamide, Example 359.0. The title compound (12 mg, 19% yield, white solid) was obtained as a by-product from the procedure of preparing Example 303.0. ¹H NMR (400 MHz, DMSO-d₆) δ 13.27 (s, 1H), 7.69 (dd, J=5.1, 1.0 Hz, 1H), 7.61 (t, J=7.9 Hz, 1H), 7.53 (d, J=7.5 Hz, 1H), 7.21-7.31 (m, 3H), 7.16 (dt, J=7.6, 1.0 Hz, 1H), 7.06-7.13 (m, 2H), 7.02 (dd, J=5.0, 3.8 Hz, 1H), 6.83 (dd, J=3.7, 1.0 Hz, 1H), 3.69 (s, 3H), 3.13-3.24 (m, 2H), 2.90 (t, J=8.2 Hz, 2H). LCMS-ESI (pos.), m/z: 459.0 (M+H)⁺.

Example 360.0. Preparation of N-(4-(5-chloro-2-methoxyphenyl)-5-(thiophen-2-yl)-4H-1,2,4-triazol-3-yl)-2-(4-fluorophenyl)ethanesulfonamide

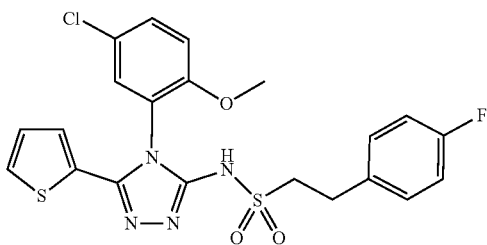

360.0

N-(4-(5-Chloro-2-methoxyphenyl)-5-(thiophen-2-yl)-4H-1,2,4-triazol-3-yl)-2-(4-fluorophenyl)ethanesulfonamide, Example 360.0. A mixture of Example 302.0 (75 mg, 0.14 mmol) and copper(II) chloride (155 mg, 1.15 mmol) in DMF was sparged with N₂ for 1 min. The mixture was then heated at 180° C. for 2 h in a microwave. The reaction mixture was then cooled to RT and partitioned between EtOAc (15 mL) and water (15 mL). The organic layer was washed with brine (4×15 mL), dried over Na₂SO₄, filtered, and concentrated in vacuo. The product was purified by on a silica gel column (0%-100% EtOAc in hexanes) followed by further purification using preparative HPLC (Gemini 5u C-18 column, 100×30 mm, 5 micron) (10%-90% ACN with 0.1% TFA/water with 0.1% TFA) to provide the title compound (11 mg, 16% yield). ¹H NMR (400 MHz, DMSO-d₆) δ 13.32 (s, 1H), 7.77 (d, J=2.7 Hz, 1H), 7.72 (dd, J=5.0, 1.1 Hz, 1H), 7.68 (dd, J=9.0, 2.7 Hz, 1H), 7.33 (d, J=9.2 Hz, 1H), 7.23-7.29 (m, 2H), 7.05-7.13 (m, 3H), 6.92 (dd, J=3.7, 1.2 Hz, 1H), 3.70 (s, 3H), 3.16-3.27 (m, 2H), 2.90 (t, J=8.2 Hz, 2H). LCMS-ESI (pos.) m/z: 493.0 (M+H)⁺.

Example 361.0. Preparation of N-(4-(2,6-dimethoxyphenyl)-5-(thiophen-2-yl)-4H-1,2,4-triazol-3-yl)-3-oxo-3-(pyrrolidin-1-yl)propane-1-sulfonamide

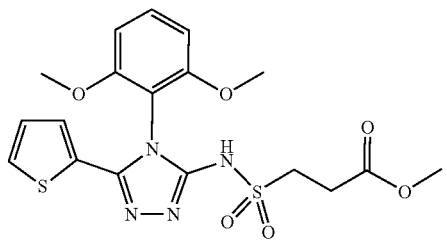

361.01

Methyl 3-(N-(4-(2,6-dimethoxyphenyl)-5-(thiophen-2-yl)-4H-1,2,4-triazol-3-yl)sulfamoyl)propanoate, Example 361.01. To a suspension of Example 311.01 (1.02 g, 3.37 mmol) in DCM (18 mL) in a 250 mL RBF at RT, was added TEA (2.35 mL, 16.9 mmol). To the mixture was added a solution of 3-chlorosulfonyl-propionic acid methyl ester (0.755 g, 4.05 mmol) in DCM (4 mL). The reaction mixture was stirred at RT for 3 h. Additional 3-chlorosulfonyl-propionic acid methyl ester (0.378 g, 2.02 mmol) was added to the reaction mixture, and stirring was continued at RT for 16 h. Another portion of 3-chlorosulfonyl-propionic acid methyl ester (0.378 g, 2.02 mmol) was then added, and the reaction was stirred for a further 24 h. The reaction mixture was then washed with 1.0 N HCl (aq), and then with saturated brine. The organic layer was then dried over Na₂SO₄, filtered, and concentrated in vacuo. The residue was triturated with MeOH/DCM/EtOAc/hexanes (5:2:2:91, 100 mL) and decanted. The solid was then further washed with 10% DCM/Et₂O (200 mL) and dried under vacuum to provide the title compound, Example 361.01 (1.13 g, 74% yield), as a tan powder which was used in the next step without further purification. LCMS-ESI (pos.) m/z: 452.9 (M+H)⁺.

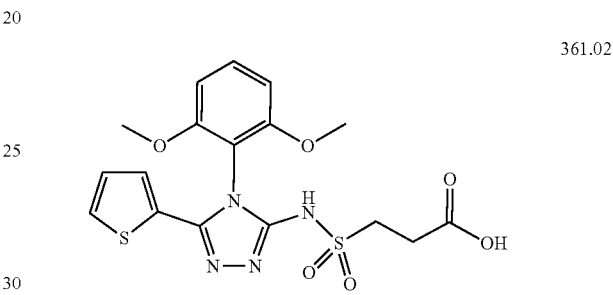

361.02

3-(N-(4-(2,6-Dimethoxyphenyl)-5-(thiophen-2-yl)-4H-1,2,4-triazol-3-yl)sulfamoyl)propanoic acid, Example 361.02. To a suspension of Example 361.01 (522 mg, 1.15 mmol) in THF (4 mL)/Water (2.0 mL) in a 25 mL RBF, was added lithium hydroxide (138 mg, 5.77 mmol). The reaction mixture was sonicated to form a clear solution and then stirred at RT for 3 h. The solvents were evaporated in vacuo. The residue was re-dissolved in 10 mL water and acidified by adding 1.0 N HCl (aq) dropwise to give a pH of 2. An off-white precipitate was collected by filtration which was then rinsed with water and then 5% EtOAc/hexanes and dried under high vacuum to provide the title compound Example 361.02 (458 mg, 91% yield). LCMS-ESI (pos.) m/z: 439.0 (M+H)⁺.

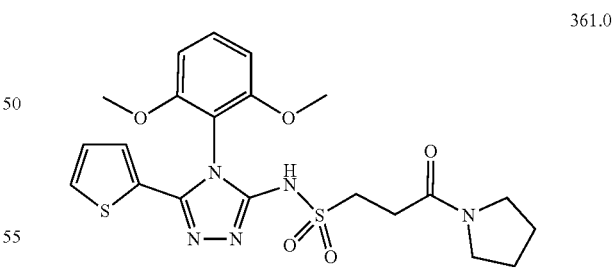

361.0

N-(4-(2,6-Dimethoxyphenyl)-5-(thiophen-2-yl)-4H-1,2,4-triazol-3-yl)-3-oxo-3-(pyrrolidin-1-yl)propane-1-sulfonamide, Example 361.0. To a solution of Example 361.02 (81.5 mg, 0.19 mmol), pyrrolidine (17.1 µL, 0.204 mmol, commercially available from ALFA AESAR), N-ethyl-N-isopropylpropan-2-amine (35.6 µL, 0.204 mmol) and DMF (310 µL) in a 2-dram vial, was added HATU (78.0 mg, 0.204 mmol). The reaction mixture was stirred at RT for 6 h. The reaction was then diluted with 0.1N HCl(aq) (10 mL) and sonicated. An off-white precipitate was collected by filtration, and rinsed with water and 5% EtOAc/hexanes, and then dried under high vacuum. The compound was dissolved in 1% TFA/DCM and purified twice on a silica gel column (0%-100% EtOAc/10% MeOH in DCM) to provide the title compound, Example 361.0 (69 mg, 0.140 mmol, 76%), as a tan powder. $^1$H NMR (400 MHz, CD$_2$Cl$_2$) δ 11.58 (br. s, 1H) 7.53 (t, J=8.61 Hz, 1H) 7.38 (dd, J=5.09, 1.17 Hz, 1H) 7.07 (dd, J=3.72, 1.17 Hz, 1H) 6.96 (dd, J=5.09, 3.72 Hz, 1H) 6.73 (d, J=8.41 Hz, 2H) 3.76 (m, 6H) 3.44 (t, J=6.85 Hz, 2H) 3.40 (t, J=6.75 Hz, 2H) 3.35 (t, J=7.34 Hz, 2H) 2.70 (t, J=7.34 Hz, 2H) 1.91-1.99 (m, 2H) 1.81-1.90 (m, 2H). LCMS-ESI (pos.) m/z: 492.0 (M+H)$^+$.

Example 362.0. Preparation of (R)-3-cyclopentyl-N-(4-(2,6-dimethoxyphenyl)-5-(thiophen-2-yl)-4H-1,2,4-triazol-3-yl)-3-hydroxypropane-1-sulfonamide and (S)-3-cyclopentyl-N-(4-(2,6-dimethoxyphenyl)-5-(thiophen-2-yl)-4H-1,2,4-triazol-3-yl)-3-hydroxypropane-1-sulfonamide 362.02

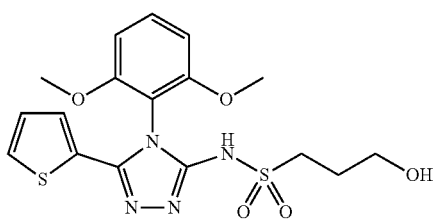

N-(4-(2,6-Dimethoxyphenyl)-5-(thiophen-2-yl)-4H-1,2,4-triazol-3-yl)-3-hydroxypropane-1-sulfonamide, Example 362.02. To a 100 mL RBF was added Example 361.01 (600 mg, 1.33 mmol) in THF (2 mL). At 0° C., under N$_2$, lithium borohydride, (2.0 M solution in THF, 3.33 mL, 6.66 mmol) was added with stirring. The reaction mixture was stirred at 0-RT for 14 h. LCMS analysis indicated the reaction was complete. The reaction mixture was then diluted with a saturated solution of NH$_4$Cl and 2.0 N HCl, and extracted with DCM. The organic extract was washed with brine and dried over Na$_2$SO$_4$. The solution was filtered and concentrated in vacuo to give the material as a white solid. The material was triturated with ether, to provide Example 362.02 (396 mg, 0.933 mmol, 70%). LCMS-ESI (pos.) m/z: 425.0 (M+H)$^+$.

362.03

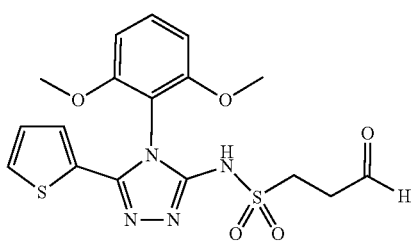

N-(4-(2,6-Dimethoxyphenyl)-5-(thiophen-2-yl)-4H-1,2,4-triazol-3-yl)-3-oxopropane-1-sulfonamide, Example 362.03. To a 250 mL RBF was added Example 362.02 (231 mg, 0.54 mmol) in DCM (33 mL) and water (0.036 mL). At 0° C., Dess-Martin periodinane (257 mg, 0.61 mmol) was added. The reaction mixture was then stirred at 0° C. for 30 min and then at RT for 2 h. Another batch of Dess-Martin periodinane (257 mg, 0.61 mmol) was added. After 2 h, LCMS analysis indicated formation of the title product but starting material still remained. Thus, another batch of Dess-Martin periodinane (257 mg, 0.61 mmol) was added and the reaction mixture was stirred at RT for another 15 h. The white solid was removed by filtration. The solution was diluted with water and extracted with DCM. The organic extract was washed with brine and dried over Na$_2$SO$_4$. The solution was filtered and concentrated in vacuo to give Example 362.03 (162 mg, 0.383 mmol, 71%) as a light-yellow solid. The material was used without purification in the next step. LCMS-ESI (pos.) m/z: 422.9 (M+H)$^+$.

362.0

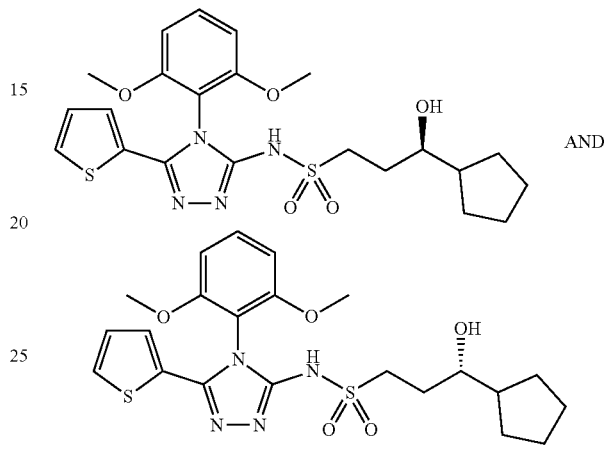

(R)-3-Cyclopentyl-N-(4-(2,6-dimethoxyphenyl)-5-(thiophen-2-yl)-4H-1,2,4-triazol-3-yl)-3-hydroxypropane-1-sulfonamide and (S)-3-cyclopentyl-N-(4-(2,6-dimethoxyphenyl)-5-(thiophen-2-yl)-4H-1,2,4-triazol-3-yl)-3-hydroxypropane-1-sulfonamide, Example 362.0. The title compound was prepared from Example 362.03 (154 mg, 0.364 mmol) using the procedure described in Example 98.5 to obtain Example 362.0 (95 mg, 0.19 mmol, 53% yield) as a white solid. $^1$H NMR (400 MHz, CD$_2$Cl$_2$) δ 10.87 (br. s, 1H) 7.53 (t, J=8.51 Hz, 1H) 7.38 (dd, J=5.09, 1.17 Hz, 1H) 7.06 (dd, J=3.91, 1.17 Hz, 1H) 6.96 (dd, J=5.09, 3.72 Hz, 1H) 6.74 (d, J=8.41 Hz, 2H) 3.76-3.78 (m, 6H) 3.42-3.49 (m, 1H) 3.05-3.20 (m, 2H) 1.93-2.03 (m, 1H) 1.69-1.80 (m, 3H) 1.53-1.61 (m, 5H) 1.31 (td, J=7.68, 3.23 Hz, 1H) 1.11-1.19 (m, 1H). LCMS-ESI (pos.), m/z: 493.0 (M+H)$^+$.

Example 363.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide 363.01

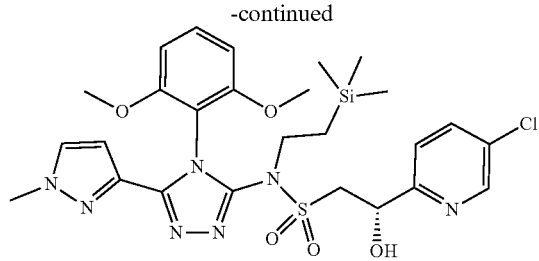

(R)-2-(5-Chloropyridin-2-yl)-N-(4-(2,6-dimethoxyphenyl)-5-(1-methyl-H-pyrazol-3-yl)-4H-1,2,4-triazol-3-yl)-2-hydroxy-N-(2-(trimethylsilyl)ethyl)ethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide, Example 363.01. Example 305.01 (0.495 g, 1.03 mmol) was azeotroped with toluene in a 250 mL RBF and then dissolved in THF (5 mL). The solution was cooled to −78° C. and an n-butyllithium solution, (2.5 M in hexanes, 0.496 mL, 1.24 mmol) was added. The reaction mixture was stirred for 15 min at −78° C. A solution of 5-chloro-2-formylpyridine (0.176 g, 1.24 mmol) in THF (2.0 mL) was then added dropwise at −78° C. After addition, the cold bath was removed and the reaction was warmed to RT for 1 h. The reaction was quenched with a saturated aqueous solution of NH$_4$Cl (10 mL), diluted with water (10 mL) and extracted with DCM (2×20 mL). The organic extract was dried over Na$_2$SO$_4$. The solution was filtered and concentrated in vacuo to give an orange gum. The material thus obtained was absorbed onto a plug of silica gel and purified by chromatography through a Redi-Sep pre-packed silica gel column (24 g), eluting with a gradient of 0% to 100% EtOAc in hexanes, to provide the title compound, Example 363.01 (0.356 g, 56%), as a yellow solid. LCMS-ESI (pos.) m/z: 620.2 (M+H)$^+$.

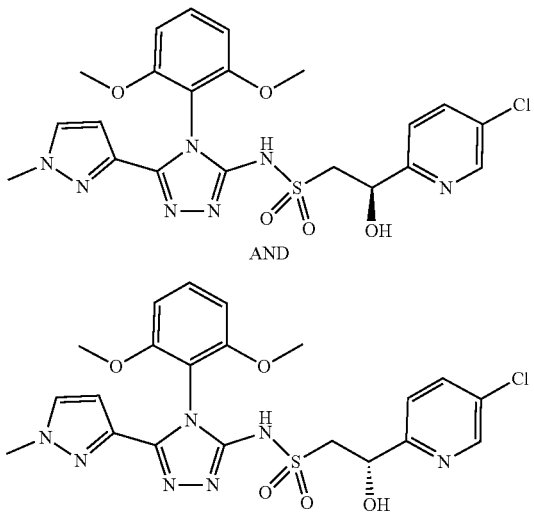

(R)-2-(5-Chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide, Example 363.0. The title compound was prepared from Example 363.01 (148 mg, 0.239 mmol) and tris(dimethylamino)sulfonium difluorotrimethylsilicate (IV) (197 mg, 0.716 mmol) using the procedure described in Example 350.0, to obtain Example 363.0 (92 mg, 74% yield) as a white solid. $^1$H NMR (400 MHz, DMSO-d$_6$) δ 13.19 (br. s, 1H) 8.54 (dd, J=2.54, 0.59 Hz, 1H) 7.91 (dd, J=8.61, 2.54 Hz, 1H) 7.68 (d, J=2.35 Hz, 1H) 7.45-7.52 (m, 2H) 6.81 (d, J=8.61 Hz, 2H) 6.07 (d, J=2.35 Hz, 1H) 5.54 (br. s, 1H) 4.96-5.02 (m, 1H) 3.73 (s, 3H) 3.68 (s, 3H) 3.66 (s, 3H) 3.51 (dd, J=14.18, 3.42 Hz, 1H) 3.19 (dd, J=14.09, 8.61 Hz, 1H). LCMS-ESI (pos.) m/z: 520.1 (M+H)$^+$.

Example 364.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide and (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide

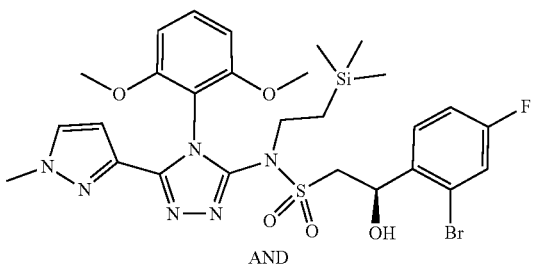

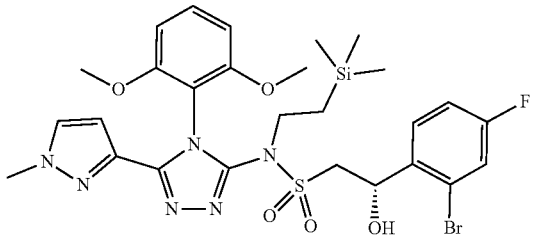

(R)-2-(2-Bromo-4-fluorophenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide and (S)-2-(2-bromo-4-fluorophenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide, Example 364.01. The title compound was prepared from Example 305.01 (1.49 g, 3.11 mmol) and 2-bromo-4-fluorobenzaldehyde (0.695 g, 3.42 mmol) using the procedure described in Example 363.0, to obtain Example 364.01 (1.57 g, 74% yield) as a white solid. LCMS-ESI (pos.), m/z: 681.0 (M+H)$^+$.

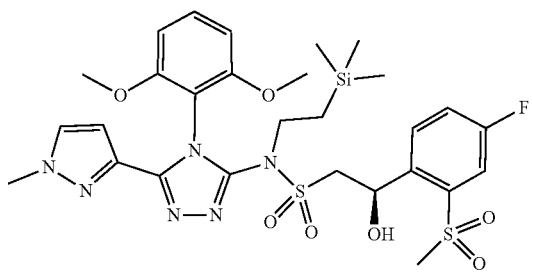

-continued

AND

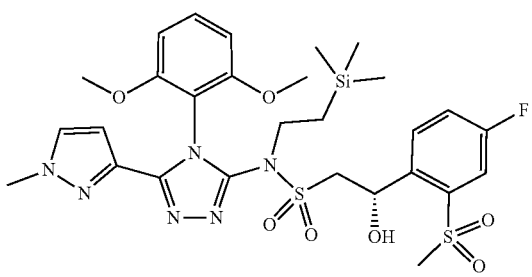

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-hydroxy-N-(2-(trimethylsilyl)ethyl)ethanesulfonamide and (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxy-N-(2-(trimethylsilyl)ethyl)ethanesulfonamide, Example 364.02. Sodium methanesulfinate (404 mg, 3.95 mmol), copper(I) iodide (75 mg, 0.395 mmol) and N,N'-dimethylethylenediamine (0.085 mL, 0.79 mmol) were mixed in DMSO (3.5 mL) in a 40 mL-vial. The mixture was sparged with N₂ for 2 min. To the mixture was then added a solution of Example 364.01 (539 mg, 0.791 mmol) in DMSO (3.50 mL). The reaction was further sparged with N₂. The reaction mixture was then heated at 110° C. using a heating block for 12 h. The reaction was cooled to RT, diluted with EtOAc (150 mL), washed with a saturated aqueous solution of NH₄Cl (3×150 mL) and brine (150 mL). The organic extract was dried over Na₂SO₄, filtered, and concentrated in vacuo to give the material as brown film. The material thus obtained was absorbed onto a plug of silica gel and purified by chromatography through a Redi-Sep pre-packed silica gel column eluting with a gradient of 0% to 100% EtOAc in hexanes to provide Example 364.02 (341 mg, 0.501 mmol, 63% yield). LCMS-ESI (pos.), m/z: 681.2 (M+H)⁺.

364.0

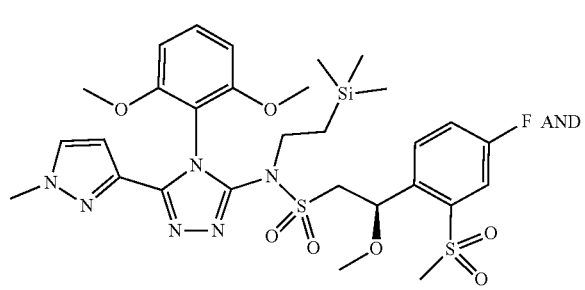

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide and (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide, Example 364.0. The title compound was prepared from Example 364.02 (138 mg, 0.203 mmol) and tris(dimethylamino)sulfonium difluorotrimethylsilicate(IV) (168 mg, 0.608 mmol), using the procedure described in Example 350.0 to obtain Example 364.0 (77 mg, 0.13 mmol, 65% yield) as a white solid. ¹H NMR (400 MHz, DMSO-d₆) δ 13.22 (s, 1H) 7.85 (dd, J=8.31, 5.38 Hz, 1H) 7.68 (d, J=2.35 Hz, 1H) 7.56-7.62 (m, 2H) 7.48 (t, J=8.51 Hz, 1H) 6.78-6.84 (m, 2H) 6.07 (d, J=2.35 Hz, 1H) 5.84 (dd, J=7.04, 5.09 Hz, 1H) 5.50 (br. s, 1H) 3.73 (s, 3H) 3.71 (s, 3H) 3.67 (s, 3H) 3.35-3.40 (m, 2H) 3.19 (s, 3H). LCMS-ESI (pos.), m/z: 581.2 (M+H)⁺.

Example 365.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide and (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide 365.01

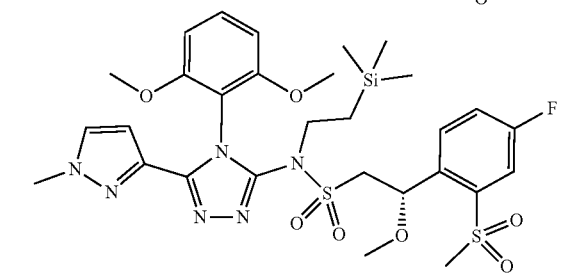

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-methoxy-N-(2-(trimethylsilyl)ethyl)ethanesulfonamide and (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxy-N-(2-(trimethylsilyl)ethyl)ethanesulfonamide, Example 365.01. The title compound was prepared from Example 364.02 (198 mg, 0.291 mmol) using the procedure described in Example 369.01 to obtain the title compound, Example 365-1 (153 mg, 0.220 mmol, 76% yield), as a white solid. LCMS-ESI (pos.), m/z: 695.2 (M+H)⁺.

365.0

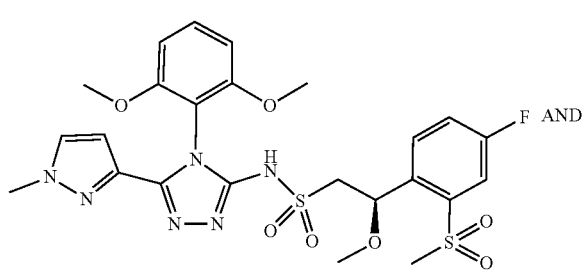

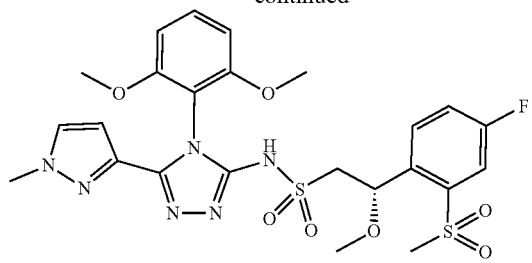

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide and (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide, Example 365.0. The title compound was prepared using Example 365.01 (148 mg, 0.213 mmol) and tris(dimethylamino)sulfonium difluorotrimethylsilicate(IV) (176 mg, 0.639 mmol) using the procedure described in Example 350.0, to obtain the title compound, Example 365.0 (75 mg, 0.13 mmol, 59% yield), as a white solid. $^1$H NMR (400 MHz, DMSO-d$_6$) δ 13.18 (s, 1H) 7.78 (dd, J=8.61, 5.48 Hz, 1H) 7.60-7.69 (m, 3H) 7.49 (t, J=8.41 Hz, 1H) 6.82 (dd, J=5.04 Hz, 2H) 6.04 (d, J=2.35 Hz, 1H) 5.52 (dd, J=7.34, 4.79 Hz, 1H) 3.73 (s, 3H) 3.70 (s, 3H) 3.69 (s, 3H) 3.47 (dd, J=14.48, 7.43 Hz, 1H) 3.32-3.37 (m, 1H) 3.19 (s, 3H) 3.04 (s, 3H). LCMS-ESI (pos.), m/z: 595.1 (M+H)$^+$.

Example 366.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide

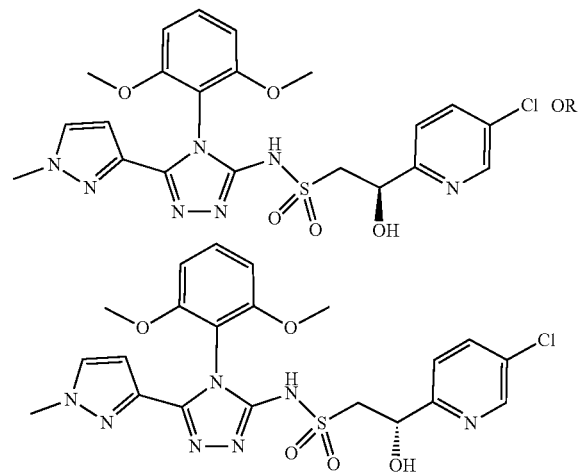

366.0

(R)-2-(5-Chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide, Example 366.0. The title compound Example 366.0 was the first isomer to elute under the following SFC conditions: Run on 2×15 cm AD-H column with 65 mL/min 40% MeOH/CO$_2$, Outlet pressure=100 bar, Wavelength=220 nm. Injection volume=(1.25 mL, 7 mg/mL) of a solution of Example 363.0 in 1:1 MeOH:DCM. $^1$H NMR (400 MHz, DMSO-d$_6$) δ 13.20 (br. s, 1H) 8.54 (dd, J=2.45, 0.49 Hz, 1H) 7.91 (dd, J=8.51, 2.45 Hz, 1H) 7.67 (d, J=2.35 Hz, 1H) 7.44-7.54 (m, 2H) 6.80 (d, J=8.41 Hz, 2H) 6.05 (d, J=2.35 Hz, 1H) 5.56 (br. s, 1H) 4.99 (dd, J=8.61, 3.33 Hz, 1H) 3.73 (s, 3H) 3.68 (s, 3H) 3.66 (s, 3H) 3.51 (dd, J=14.09, 3.33 Hz, 1H) 3.19 (dd, J=13.99, 8.51 Hz, 1H). LCMS-ESI (pos.), m/z: 520.1 (M+H)$^+$.

Example 367.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide

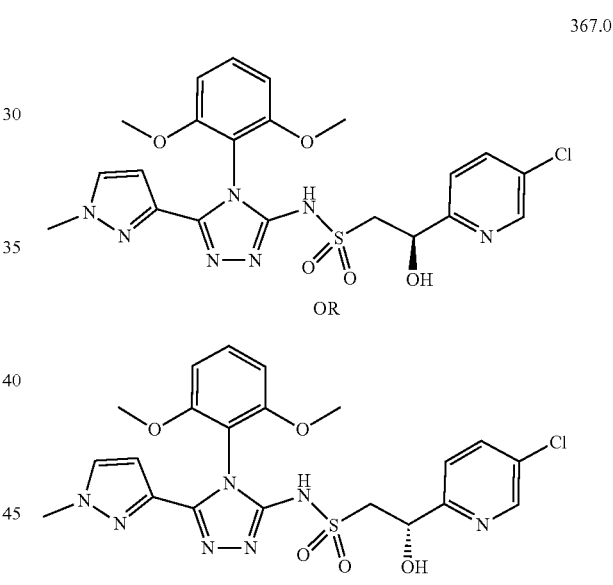

367.0

(R)-2-(5-Chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-hydroxyethanesulfonamide, Example 367.0. Example 367.0 is the enantiomer of Example 366.0. Example 367.0 was the second isomer to elute from an AD-H column on subjecting Example 363.0 to the SFC conditions described in Example 366.0. $^1$H NMR (400 MHz, DMSO-d$_6$) δ 13.20 (br. s, 1H) 8.54 (dd, J=2.45, 0.49 Hz, 1H) 7.91 (dd, J=8.41, 2.54 Hz, 1H) 7.67 (d, J=2.35 Hz, 1H) 7.44-7.53 (m, 2H) 6.80 (d, J=8.61 Hz, 2H) 6.05 (d, J=2.15 Hz, 1H) 5.59 (br. s, 1H) 4.99 (dd, J=8.61, 3.33 Hz, 1H) 3.73 (s, 3H) 3.68 (s, 3H) 3.66 (s, 3H) 3.51 (dd, J=13.99, 3.42 Hz, 1H) 3.19 (dd, J=13.99, 8.51 Hz, 1H). LCMS-ESI (pos.), m/z: 520.1 (M+H)$^+$.

Example 368.0. Preparation of (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide and (S)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide

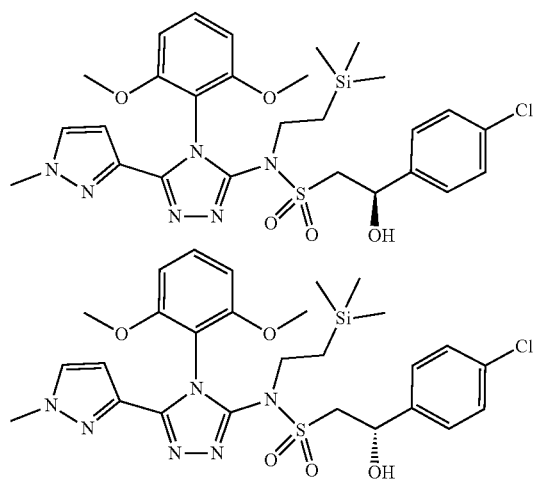

(R)-2-(4-Chlorophenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide and (S)-2-(4-chlorophenyl)-N-(4-(2,6-dimethoxyphenyl)-5-(1-methyl-1H-pyrazol-3-yl)-4H-1,2,4-triazol-3-yl)-2-hydroxy-N-(2-(trimethylsilyl)ethyl)ethanesulfonamide, Example 368.01. The title compound was prepared from Example 350.01 (503 mg, 1.05 mmol) and 4-chlorobenzaldehyde (162 mg, 1.16 mmol) using the procedure described in Example 350.02 to obtain the title compound Example 368.01 (532 mg, 0.859 mmol, 82%) as a white solid. LCMS-ESI (pos.), m/z: 619.3 (M+H)+.

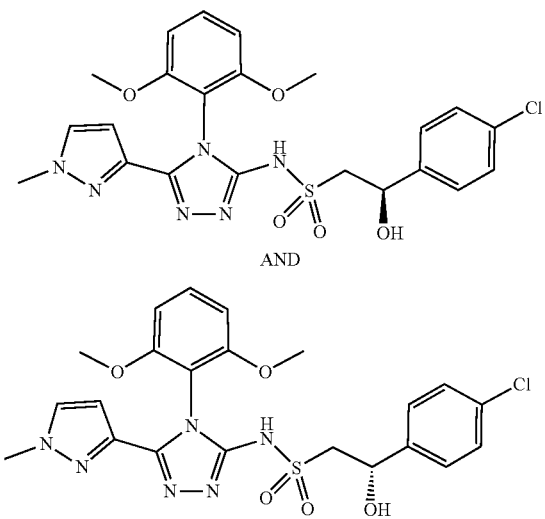

(R)-2-(4-Chlorophenyl)-N-(4-(2,6-dimethoxyphenyl)-5-(1-methyl-1H-pyrazol-3-yl)-4H-1,2,4-triazol-3-yl)-2-hydroxyethanesulfonamide and (S)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide, Example 368.0. The title compound was prepared from Example 368.01 (191 mg, 0.308 mmol) and tris(dimethylamino)sulfonium difluorotrimethylsilicate(IV) (255 mg, 0.925 mmol) using the procedure described in Example 350.0 to obtain the title compound, Example 368.0 (105 mg, 0.202 mmol, 66% yield), as a white solid. $^1$H NMR (400 MHz, DMSO-$d_6$) δ 13.21 (s, 1H) 7.68 (d, J=2.35 Hz, 1H) 7.50 (t, J=8.41 Hz, 1H) 7.33-7.38 (m, 2H) 7.26-7.32 (m, 2H) 6.83 (dd, J=8.61, 1.17 Hz, 2H) 6.07 (d, J=2.15 Hz, 1H) 5.36 (br. s, 1H) 4.93 (dd, J=7.43, 4.11 Hz, 1H) 3.73 (s, 3H) 3.69 (m, 6H) 3.27 (dd, J=14.09, 7.63 Hz, 1H) 3.16 (dd, J=14.09, 4.11 Hz, 1H). LCMS-ESI (pos.), m/z: 519.1 (M+H)+.

Example 369.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide

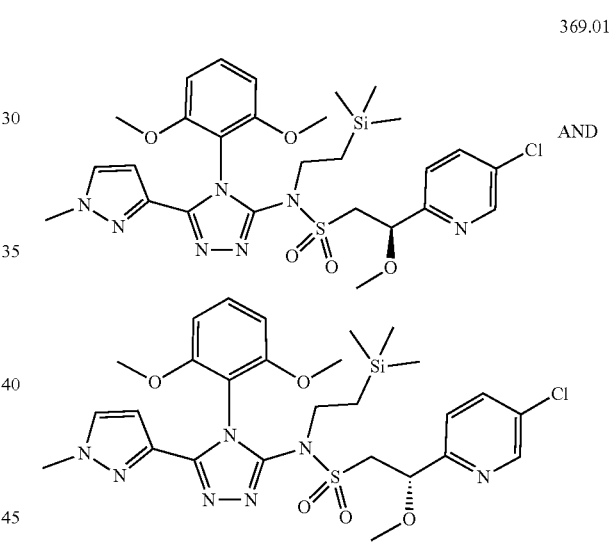

(R)-2-(5-Chloropyridin-2-yl)-N-(4-(2,6-dimethoxyphenyl)-5-(1-methyl-1H-pyrazol-3-yl)-4H-1,2,4-triazol-3-yl)-2-methoxy-N-(2-(trimethylsilyl)ethyl)ethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxy-N-(2-(trimethylsilyl)ethyl)ethanesulfonamide, Example 369.01. To a solution of Example 368.01 (262 mg, 0.422 mmol) in DMF (3 mL) at 0° C. was added sodium hydride (60% dispersion in mineral oil, 20.28 mg, 0.507 mmol) in one portion. The mixture was warmed to RT for 15 min. The reaction was then cooled to 0° C. A solution of iodomethane (stabilized, 0.034 mL, 0.549 mmol) in DMF (0.750 mL) was injected dropwise. The reaction was then stirred at 0° C. for 1 h and 45 min. The reaction was quenched with a saturated aqueous solution of NH$_4$Cl (10 mL), and diluted with water (10 mL) and EtOAc (50 mL). The organic layer was washed with brine (3×50 mL), dried over Na$_2$SO$_4$, filtered, and concentrated in vacuo. The material thus obtained was absorbed onto a plug of silica gel and purified by chromatography through a silica gel column (24 g) eluting with a gradient of 0% to 100% EtOAc in hexanes to provide the title compound, Example 369.01 (205 mg, 77% yield), as a white foam. LCMS-ESI (pos.), m/z: 634.3 (M+H)+.

369.0

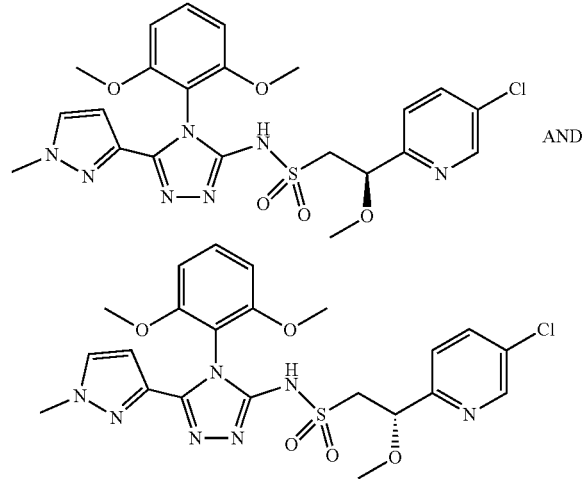

(R)-2-(5-Chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide and (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide, Example 369.0. The title compound was prepared from Example 369.01 (200 mg, 0.315 mmol) and tris(dimethylamino)sulfonium difluorotrimethylsilicate(IV) (261 mg, 0.946 mmol) using the procedure described in Example 350.0 to obtain the title compound Example 369.0 (142 mg, 84% yield) as a white solid. $^1$H NMR (400 MHz, DMSO-$d_6$) δ 13.12 (s, 1H) 8.59 (dd, J=2.54, 0.59 Hz, 1H) 7.94 (dd, J=8.41, 2.54 Hz, 1H) 7.68 (d, J=2.15 Hz, 1H) 7.48 (t, J=8.51 Hz, 1H) 7.43 (d, J=8.22 Hz, 1H) 6.82 (dd, J=8.61, 0.78 Hz, 2H) 6.05 (d, J=2.15 Hz, 1H) 4.66 (t, J=5.97 Hz, 1H) 3.73 (s, 3H) 3.69 (m, 6H) 3.36 (d, J=5.87 Hz, 2H) 3.10 (s, 3H). LCMS-ESI (pos.), m/z: 534.2 (M+H)+.

Example 370.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide 370.0

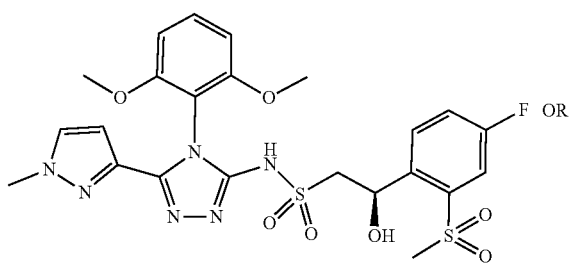

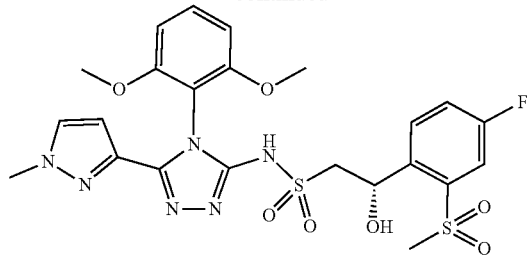

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide, Example 370.0. The title compound Example 370.0 was the first isomer to elute under the following SFC conditions: Run on Thar 80 SFC with 250×21 mm+150×21 mm AD-H columns with 15 g/min EtOH (+20 mM NH$_3$)+35 g/min CO$_2$, 30% co-solvent at 50 g/min. Temp.=22° C., Outlet pressure=100 bar, Wavelength=220 nm. Injected a 0.3 mL solution of Example 364.0 in MeOH; c=10 mg/mL and 3 mg per injection. Cycle time 8.7 min, run time=26 min. $^1$H NMR (400 MHz, DMSO-$d_6$) δ 13.18 (br. s, 1H) 7.85 (dd, J=8.41, 5.48 Hz, 1H) 7.68 (d, J=2.35 Hz, 1H) 7.56-7.63 (m, 2H) 7.48 (t, J=8.51 Hz, 1H) 6.78-6.84 (m, 2H) 6.06 (d, J=2.35 Hz, 1H) 5.84 (dd, J=6.94, 5.18 Hz, 1H) 5.51 (br. s, 1H) 3.73 (s, 3H) 3.70 (s, 3H) 3.67 (s, 3H) 3.34-3.44 (m, 2H) 3.19 (s, 3H). LCMS-ESI (pos.), m/z: 581.2 (M+H)+.

Example 371.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide or (S)-N-(4-(2,6-dimethoxyphenyl)-5-(1-methyl-H-pyrazol-3-yl)-4H-1,2,4-triazol-3-yl)-2-(4-fluoro-2-(methylsulfonyl)phenyl)-2-hydroxyethanesulfonamide 371.0

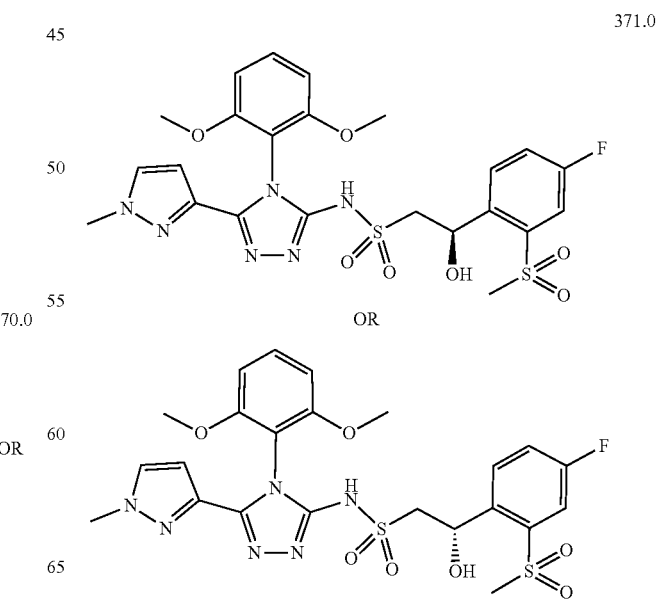

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-hydroxyethanesulfonamide, Example 371.0.0. Example 371.0 is the enantiomer of Example 370.0. Example 371.0 was the second isomer to elute from an AD-H column on subjecting Example 364.0 to the SFC conditions described in Example 370.0. $^1$H NMR (400 MHz, DMSO-$d_6$) δ 13.21 (br. s, 1H) 7.85 (dd, J=8.41, 5.48 Hz, 1H) 7.66 (d, J=2.15 Hz, 1H) 7.56-7.63 (m, 2H) 7.46 (t, J=8.51 Hz, 1H) 6.77-6.83 (m, 2H) 6.04 (d, J=2.15 Hz, 1H) 5.85 (dd, J=7.43, 4.69 Hz, 1H) 5.57 (br. s, 1H) 3.73 (s, 3H) 3.70 (s, 3H) 3.67 (s, 3H) 3.33-3.45 (m, 2H) 3.20 (s, 3H). LCMS-ESI (pos.), m/z: 581.2 (M+H)$^+$.

Example 372.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide or (S)-N-(4-(2,6-dimethoxyphenyl)-5-(1-methyl-H-pyrazol-3-yl)-4H-1,2,4-triazol-3-yl)-2-(4-fluoro-2-(methylsulfonyl)phenyl)-2-methoxyethanesulfonamide

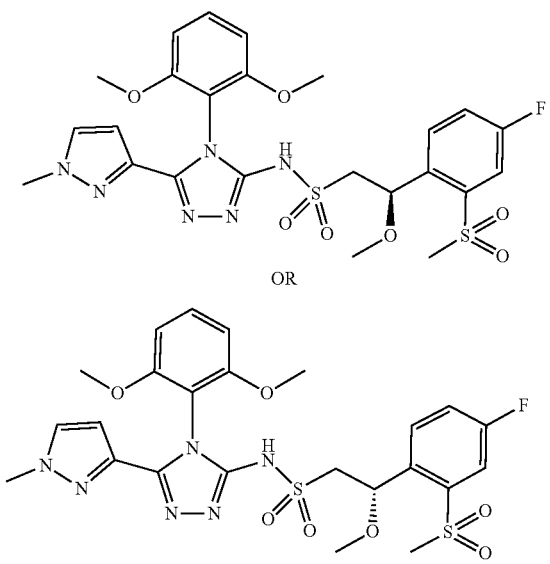

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide, Example 372.0. The title compound Example 372.0 was the first isomer to elute under the following SFC conditions: Run on Thar 80 SFC with 250×21 mm IA column with 24 g/min MeOH+36 g/min CO$_2$, 40% co-solvent at 60 g/min. Temp.=24° C., Outlet pressure=100 bar, Wavelength=250 nm. Injected a 0.5 mL solution of Example 365.0 in (1:1) MeOH:DCM; c=5.9 mg/mL, i.e. 3.0 mg per injection. Cycle time 5.0 min, run time=8.5 min. $^1$H NMR (400 MHz, DMSO-$d_6$) δ 13.17 (br. s, 1H) 7.78 (dd, J=8.51, 5.38 Hz, 1H) 7.60-7.69 (m, 3H) 7.48 (t, J=8.51 Hz, 1H) 6.82 (dd, J=8.51, 2.64 Hz, 2H) 6.03 (d, J=1.96 Hz, 1H) 5.52 (dd, J=7.14, 4.99 Hz, 1H) 3.73 (s, 3H) 3.70 (s, 3H) 3.69 (s, 3H) 3.49 (dd, J=14.28, 7.24 Hz, 1H) 3.33-3.39 (m, 1H) 3.19 (s, 3H) 3.04 (s, 3H). LCMS-ESI (pos.), m/z: 595.1 (M+H)$^+$.

Example 373.0. Preparation of (R)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide

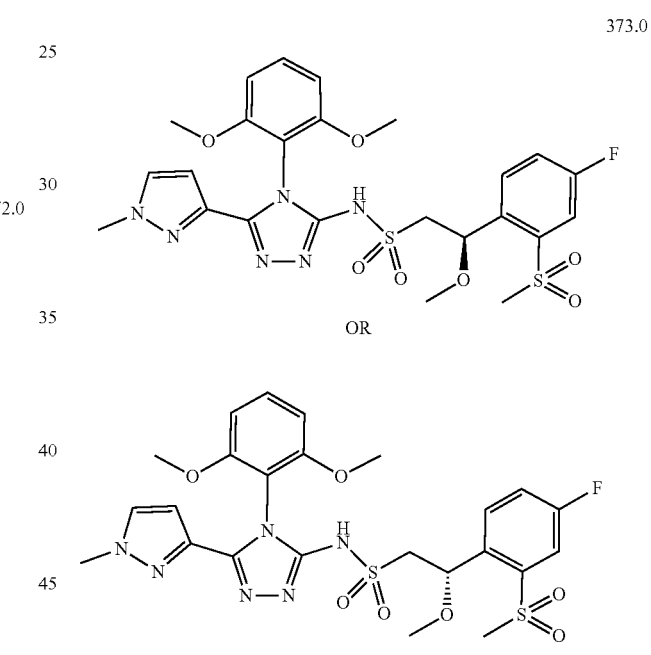

(R)-N-(4-(2,6-Dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide or (S)-N-(4-(2,6-dimethoxyphenyl)-5-(1-methyl-1H-pyrazol-3-yl)-4H-1,2,4-triazol-3-yl)-2-(4-fluoro-2-(methylsulfonyl)phenyl)-2-methoxyethanesulfonamide, Example 373.0. Example 373.0 is the enantiomer of Example 372.0. Example 373.0 was the second isomer to elute from an IA column on subjecting Example 365.0 to the SFC conditions described in Example 372.0. $^1$H NMR (400 MHz, DMSO-$d_6$) δ 13.16 (br. s, 1H) 7.78 (dd, J=8.61, 5.48 Hz, 1H) 7.60-7.68 (m, 3H) 7.48 (t, J=8.51 Hz, 1H) 6.81 (dd, J=8.41, 2.74 Hz, 2H) 6.03 (d, J=2.15 Hz, 1H) 5.52 (dd, J=7.14, 4.99 Hz, 1H) 3.73 (s, 3H) 3.70 (s, 3H) 3.69 (s, 3H) 3.50 (dd, J=14.28, 7.24 Hz, 1H) 3.33-3.39 (m, 1H) 3.19 (s, 3H) 3.04 (s, 3H). LCMS-ESI (pos.), m/z: 595.1 (M+H)$^+$.

Example 374.0. Preparation of (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide or (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide 374.0

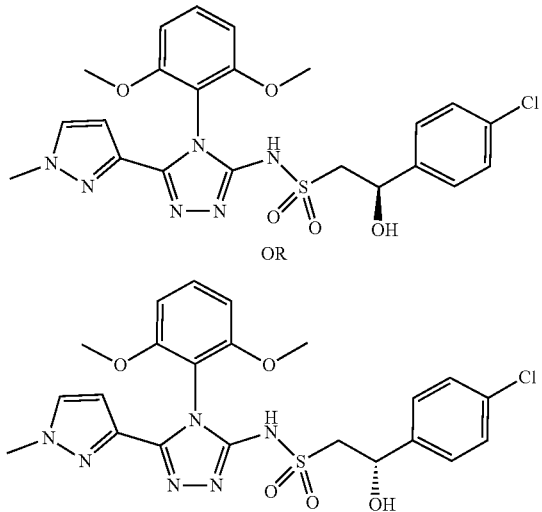

OR (R)-2-(4-Chlorophenyl)-N-(4-(2,6-dimethoxyphenyl)-5-(1-methyl-1H-pyrazol-3-yl)-4H-1,2,4-triazol-3-yl)-2-hydroxyethanesulfonamide or (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide, Example 374.0. The title compound Example 374.0 was the first isomer to elute under the following SFC conditions: Run on AD column with 60 mL/min 50% MeOH/CO$_2$, Outlet pressure=100 bar, Wavelength=220 nm. Injection volume=(0.5 mL, 7 mg/mL) of a solution of Example 368.0 in MeOH. $^1$H NMR (400 MHz, CD$_2$Cl$_2$) δ 7.49 (t, J=8.51 Hz, 1H) 7.27-7.34 (m, 5H) 6.71 (dd, J=8.61, 1.96 Hz, 2H) 6.11 (d, J=2.35 Hz, 1H) 5.13 (dd, J=7.83, 3.91 Hz, 1H) 3.80 (s, 3H) 3.78 (s, 3H) 3.74 (s, 3H) 3.19-3.24 (m, 2H). LCMS-ESI (pos.) m/z: 519.1 (M+H)$^+$.

Example 375.0. Preparation of (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide or (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide 375.0

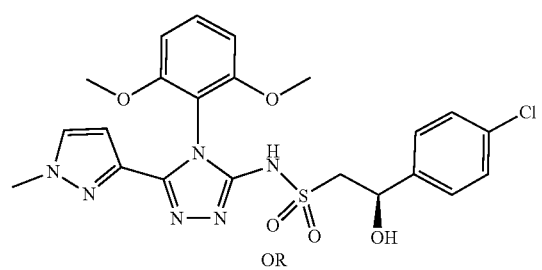

OR

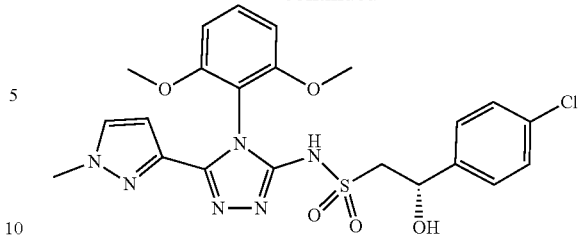

(R)-2-(4-Chlorophenyl)-N-(4-(2,6-dimethoxyphenyl)-5-(1-methyl-1H-pyrazol-3-yl)-4H-1,2,4-triazol-3-yl)-2-hydroxyethanesulfonamide or (R)-2-(4-chlorophenyl)-N-(4-(2,6-dimethoxyphenyl)-5-(1-methyl-1H-pyrazol-3-yl)-4H-1,2,4-triazol-3-yl)-2-hydroxyethanesulfonamide, Example 375.0. Example 375.0 is the enantiomer of Example 374.0. Example 375.0 was the second isomer to elute from an AD column on subjecting Example 368.0 to the SFC conditions described in Example 374.0. $^1$H NMR (400 MHz, CD$_2$Cl$_2$) δ 7.48 (t, J=8.51 Hz, 1H) 7.26-7.34 (m, 5H) 6.71 (dd, J=8.51, 1.86 Hz, 2H) 6.07 (br. s, 1H) 5.13 (dd, J=8.31, 3.03 Hz, 1H) 3.80 (s, 3H) 3.77 (s, 3H) 3.74 (s, 3H) 3.16-3.24 (m, 2H). LCMS-ESI (pos.), m/z: 519.1 (M+H)$^+$.

Example 376.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide 376.0

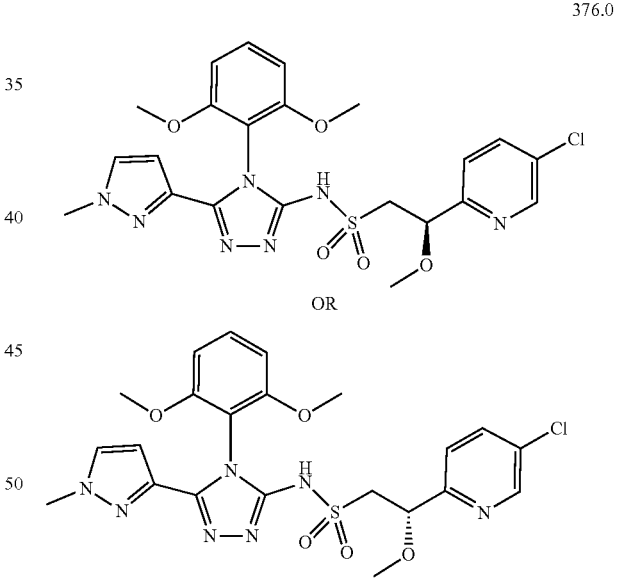

OR (R)-2-(5-Chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide, Example 376.0. The title compound, Example 376.0, was the first isomer to elute under the following SFC conditions: Run on 2×25 cm ID column with 60 mL/min 40% MeOH/CO$_2$, Outlet pressure=100 bar, Wavelength=220 nm. Injection volume=(0.5 mL, 12 mg/mL) of a solution of Example 369.0 in MeOH. $^1$H NMR (400 MHz, DMSO-d$_6$) δ 13.12 (br. s, 1H) 8.59 (dd, J=2.35, 0.59 Hz, 1H) 7.94 (dd, J=8.41, 2.54 Hz, 1H) 7.67 (d, J=2.15 Hz, 1H) 7.48 (t, J=8.29 Hz, 1H) 7.43 (d, J=8.41 Hz, 1H) 6.82 (dd, J=8.51, 0.88 Hz, 2H) 6.05

(d, J=2.35 Hz, 1H) 4.66 (t, J=5.97 Hz, 1H) 3.73 (s, 3H) 3.68-3.70 (m, 6H) 3.36 (d, J=5.87 Hz, 2H) 3.10 (s, 3H). LCMS-ESI (pos.), m/z: 534.2 (M+H)+.

Example 377.0. Preparation of (R)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide 377.0

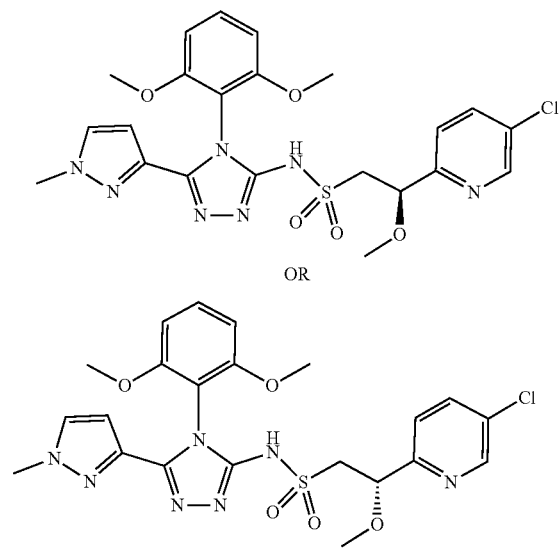

OR (R)-2-(5-Chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(5-chloropyridin-2-yl)-N-(4-(2,6-dimethoxyphenyl)-5-(1-methyl-1H-pyrazol-3-yl)-4H-1,2,4-triazol-3-yl)-2-methoxyethanesulfonamide, Example 377.0. Example 377.0 is the enantiomer of Example 376.0. Example 377.0 was the second isomer to elute from an ID column on subjecting Example 369.0 to the SFC conditions described in Example 376.0. $^1$H NMR (400 MHz, DMSO-$d_6$) δ 13.12 (br. s, 1H) 8.59 (dd, J=2.54, 0.59 Hz, 1H) 7.94 (dd, J=8.41, 2.54 Hz, 1H) 7.67 (d, J=2.35 Hz, 1H) 7.48 (t, J=8.35 Hz, 1H) 7.43 (d, J=8.22 Hz, 1H) 6.82 (dd, J=8.61, 0.78 Hz, 2H) 6.05 (d, J=2.35 Hz, 1H) 4.66 (t, J=5.97 Hz, 1H) 3.73 (s, 3H) 3.68-3.70 (m, 6H) 3.36 (d, J=5.87 Hz, 2H) 3.10 (s, 3H). LCMS-ESI (pos.) m/z: 534.2 (M+H)+.

Example 378.0. Preparation of (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide 378.0

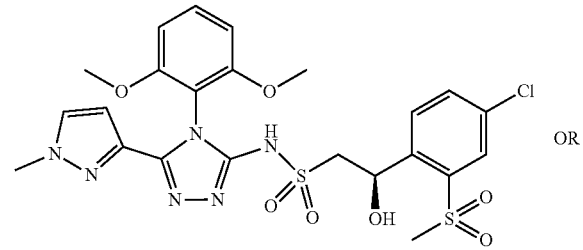

OR

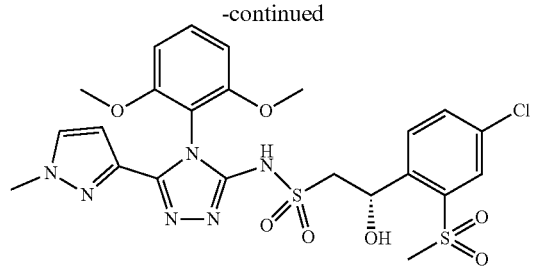

-continued (R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide, Example 378.0. The title compound was the first isomer to elute under the following SFC conditions: Run on 2×25 cm OD-H column with 30% methanol/$CO_2$, Outlet pressure=100 bar, Wavelength=220 nm. Injection volume=0.5 mL solution of Example 304.0 in (5:1) MeOH:DCM; c=10 mg/mL. $^1$H NMR (400 MHz, DMSO-$d_6$) δ 13.22 (br. s, 1H) 7.77-7.84 (m, 3H) 7.67 (d, J=2.15 Hz, 1H) 7.48 (t, J=8.41 Hz, 1H) 6.78-6.84 (m, 2H) 6.06 (d, J=2.35 Hz, 1H) 5.83 (t, J=6.06 Hz, 1H) 5.57 (br. s, 1H) 3.73 (s, 3H) 3.71 (s, 3H) 3.68 (s, 3H) 3.35-3.41 (m, 2H) 3.20 (s, 3H). LCMS-ESI (pos.), m/z: 597.0 (M+H)+.

Example 379.0. Preparation of (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide 379.0

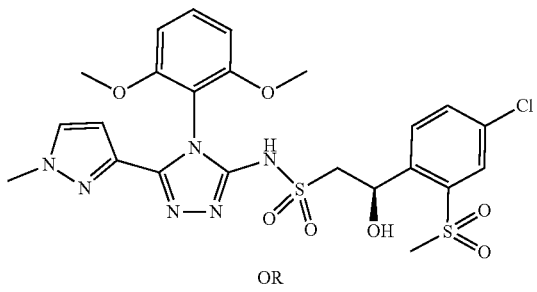

OR

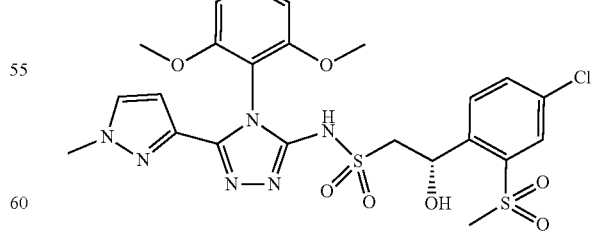

(R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-hydroxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4- triazol-3-yl)-2-hydroxyethanesulfonamide, Example 379.0. Example 379.0 is the enantiomer of Example 378.0. Example 379.0 was the second isomer to elute from an OD-H column on subjecting Example 304.0 to the SFC conditions described in Example 378.0. $^1$H NMR (400 MHz, DMSO-d$_6$) δ 13.22 (br. s, 1H) 7.77-7.84 (m, 3H) 7.67 (d, J=2.15 Hz, 1H) 7.48 (t, J=8.51 Hz, 1H) 6.78-6.84 (m, 2H) 6.06 (d, J=2.35 Hz, 1H) 5.84 (t, J=6.06 Hz, 1H) 5.58 (br.s, 1H) 3.73 (s, 3H) 3.70 (s, 3H) 3.68 (s, 3H) 3.35-3.41 (m, 2H) 3.20 (s, 3H). LCMS-ESI (pos.), m/z: 597.0 (M+H)$^+$.

Example 380.0. Preparation of (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide 380.0

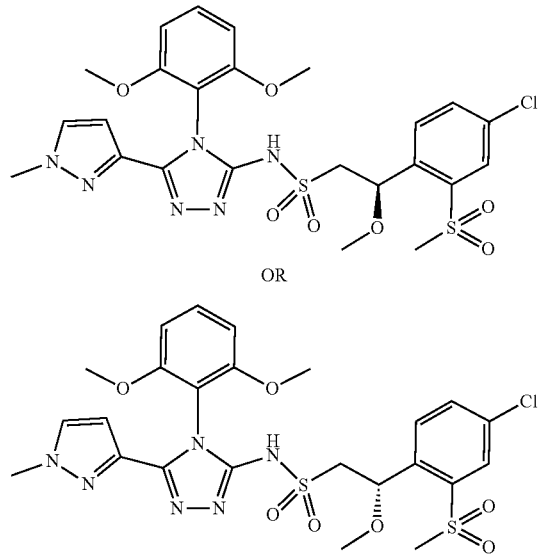

OR (R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide, Example 380.0. The title compound Example 380.0 was the first isomer to elute under the following SFC conditions: Run on Thar 200 SFC with an 250×30 mm IA column with 60.0 g/min MeOH (neat)+40.0 g/min CO$_2$, 40% co-solvent at 100 g/min. Temp.=26° C., Outlet pressure=100 bar, Wavelength=223 nm. Injected 0.6 mL solution of Example 305.0 in MeOH: DCM 4:3, c=16 mg/mL and 6.4 mg per injection. Cycle time 7 min, run time=15 min. $^1$H NMR (400 MHz, DMSO-d$_6$) δ 13.18 (s, 1H) 7.86 (d, J=2.15 Hz, 1H) 7.81-7.85 (m, 1H) 7.75 (d, J=8.05 Hz, 1H) 7.67 (d, J=2.35 Hz, 1H) 7.49 (t, J=8.51 Hz, 1H) 6.82 (dd, J=5.05 Hz, 2H) 6.04 (d, J=2.35 Hz, 1H) 5.51 (dd, J=7.43, 4.89 Hz, 1H) 3.73 (s, 3H) 3.71 (s, 3H) 3.70 (s, 3H) 3.44-3.51 (m, 1H) 3.28-3.34 (m, 1H) 3.20 (s, 3H) 3.04 (s, 3H). LCMS-ESI (pos.) m/z: 611.2 (M+H)$^+$.

Exmple 381.0. Preparation of (R)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide 381.0

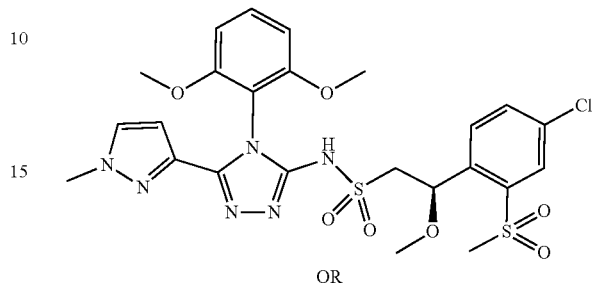

OR

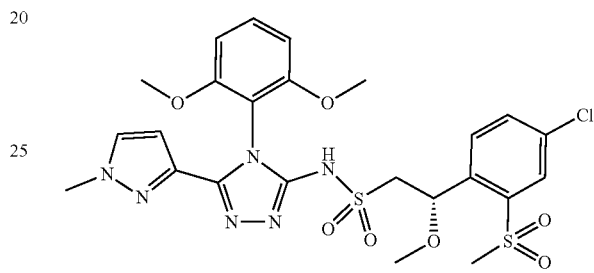

(R)-2-(4-Chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide or (S)-2-(4-chloro-2-(methylsulfonyl)phenyl)-N-(4-(2,6-dimethoxyphenyl)-5-(1-methyl-1H-pyrazol-3-yl)-4H-1,2,4-triazol-3-yl)-2-methoxyethanesulfonamide, Example 381.0. Example 381.0 is the enantiomer of Example 380.0. Example 381.0 was the second isomer to elute from an IA column on subjecting Example 305.0 to the SFC conditions described in Example 380.0. $^1$H NMR (400 MHz, DMSO-d$_6$) δ 13.18 (br. s, 1H) 7.86 (d, J=2.15 Hz, 1H) 7.81-7.85 (m, 1H) 7.75 (d, J=8.52 Hz, 1H) 7.67 (d, J=2.15 Hz, 1H) 7.49 (t, J=8.51 Hz, 1H) 6.82 (d, J=8.30 Hz, 2H) 6.04 (d, J=2.35 Hz, 1H) 5.51 (dd, J=7.24, 4.89 Hz, 1H) 3.73 (s, 3H) 3.70 (s, 3H) 3.70 (s, 3H) 3.48 (dd, J=14.38, 7.34 Hz, 1H) 3.28-3.34 (m, 1H) 3.20 (s, 3H) 3.04 (s, 3H). LCMS-ESI (pos.) m/z: 611.2 (M+H)$^+$.

Example 382.0. Preparation of N-(5-(5-((R)-(4-chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)ethanesulfonamide and N-(5-(5-((S)-(4-chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)ethanesulfonamide 382.01

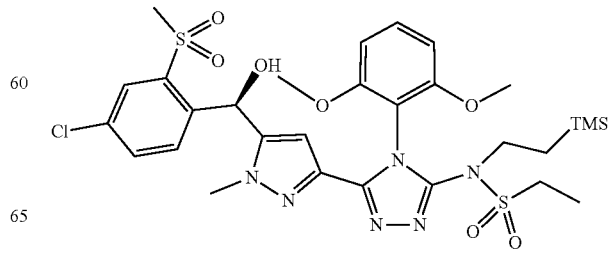

-continued

AND

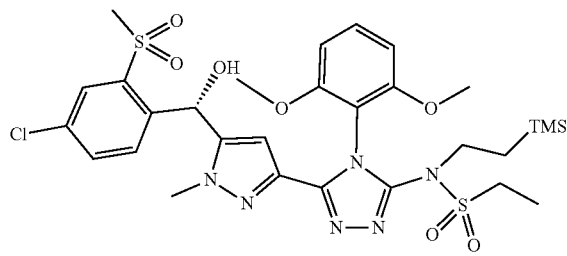

(R)-N-(5-(5-((4-Chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)-N-(2-(trimethylsilyl)ethyl)ethanesulfonamide and (S)-N-(5-(5-((4-chloro-2-(methylsulfonyl)phenyl)(hydroxy)methyl)-1-methyl-H-pyrazol-3-yl)-4-(2,6-dimethoxyphenyl)-4H-1,2,4-triazol-3-yl)-N-(2-(trimethylsilyl)ethyl)ethanesulfonamide, Example 382.01. The title compound was prepared from Example 267.0 using the procedure described in Example 305.02. LCMS-ESI (pos.), m/z: 711.2 (M+H)⁺.

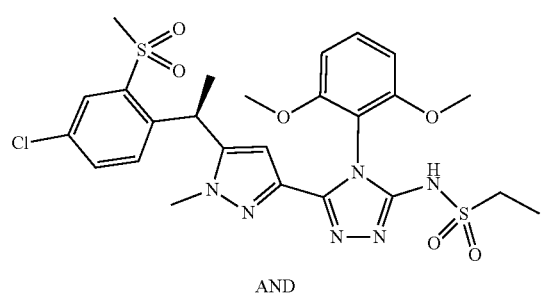

AND

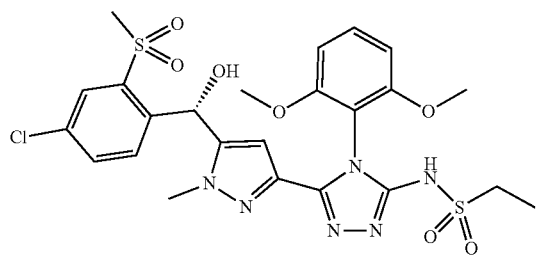

N-(5-(5-((R)-(4-Chloro-2-(methylsulfonyl)phenyl)(hydroxy)methyl)-1-methyl-1H-pyrazol-3-yl)-4-(2,6-dimethoxyphenyl)-4H-1,2,4-triazol-3-yl)ethanesulfonamide and N-(5-(5-((S)-(4-chloro-2-(methylsulfonyl)phenyl)(hydroxy)methyl)-1-methyl-H-pyrazol-3-yl)-4-(2,6-dimethoxyphenyl)-4H-1,2,4-triazol-3-yl)ethanesulfonamide, Example 382.0. The title compound was prepared from Example 267.0 using the procedure described in Example 305.02. ¹H NMR (500 MHz, DMSO-d₆) δ 13.05 (s, 1H) 7.87-7.94 (m, 2H) 7.74-7.81 (m, 1H) 7.40 (t, J=8.44 Hz, 1H) 6.61-6.73 (m, 2H) 6.55 (d, J=5.62 Hz, 1H) 6.50 (d, J=5.87 Hz, 1H) 3.79 (s, 3H) 3.66 (s, 3H) 3.58 (s, 3H) 3.34 (s, 4H) 2.97-3.08 (m, 3H) 2.85 (q, J=7.34 Hz, 2H) 1.10 (t, J=7.34 Hz, 3H). LCMS-ESI (pos.), m/z: 611.1 (M+H)⁺.

Example 383.0. Preparation of N-(4-(5-bromo-2-methoxyphenyl)-5-(thiophen-2-yl)-4H-1,2,4-triazol-3-yl)-1-(4-chlorophenyl)methanesulfonamide

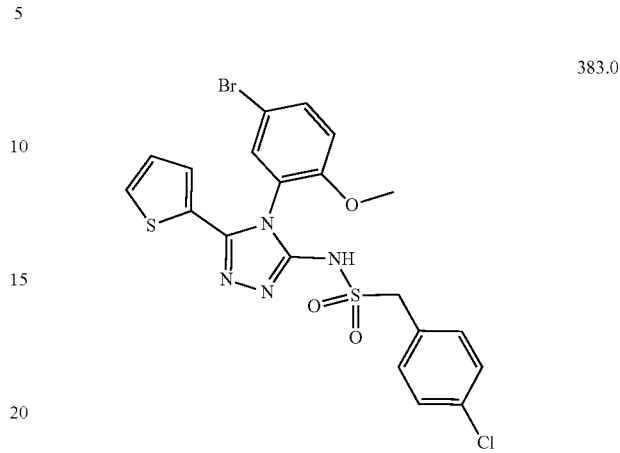

N-(4-(5-Bromo-2-methoxyphenyl)-5-(thiophen-2-yl)-4H-1,2,4-triazol-3-yl)-1-(4-chlorophenyl)methanesulfonamide, Example 383.0. Example 133.01 (200 mg, 0.57 mmol) was dissolved in pyridine (2.8 mL) and (4-chlorophenyl)methanesulfonyl chloride (385 mg, 1.71 mmol) was added slowly. The reaction mixture was stirred at 80° C. for 18 h. Next, the reaction was acidified with 10% HCl and extracted with EtOAc. The combined organic layers were washed with a saturated NaHCO₃ solution and brine and then dried over Na₂SO₄. The organic solution was filtered and concentrated in vacuo. The material thus obtained was purified by preparative HPLC using a C-18 column (Gemini AXIA, 5 um, C18, 100×30 mm) (5%-95% ACN with 0.1% TFA/water with 0.1% TFA) to obtain the title compound. ¹H NMR (400 MHz, CD₃OD) δ 7.75 (1H, dd, J=9.0, 2.5 Hz), 7.51-7.61 (2H, m), 7.28-7.37 (4H, m), 7.26-7.27 (1H, m), 6.98-7.05 (2H, m), 4.60 (1H, s), 4.31 (2H, d, J=2.2 Hz), 3.75 (3H, s). LCMS (ESI) m/z 540 (M+H)⁺.

Example 384.0. Preparation of 3-(3-((4-chlorophenyl)methylsulfonamido)-5-(thiophen-2-yl)-4H-1,2,4-triazol-4-yl)-4-methoxybenzoic acid

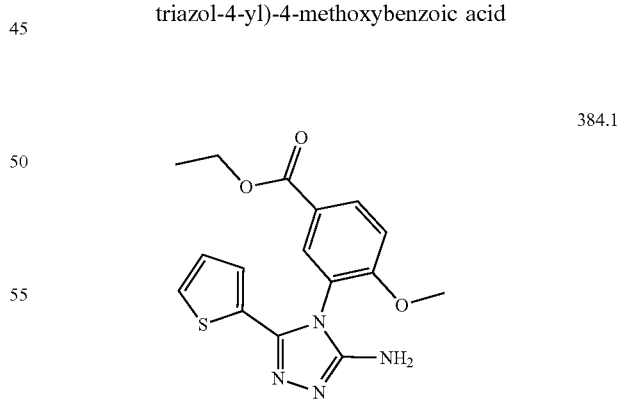

Ethyl 3-(3-Amino-5-(thiophen-2-yl)-4H-1,2,4-triazol-4-yl)-4-methoxybenzoate, Example 384.1. A mixture of Example 133.01 (1.0 g, 2.85 mmol), TEA (0.792 mL, 5.69 mmol), and 1,1'-bis(diphenylphosphino)ferrocene-palladium dichloride (0.116 g, 0.142 mmol) in N-methyl-2-pyrrolidinone (28.5 mL) and EtOH (28.5 mL) were combined in a flask. The flask was evacuated with stirring and placed under an atmosphere of CO. The mixture was heated at 80° C. overnight. Next, the reaction was quenched with water and extracted with EtOAc (×3). The organic layer was washed with brine, dried over MgSO₄, filtered, and concentrated in vacuo. The material thus obtained was dry loaded onto silica gel and purified eluting with 5% MeOH in DCM to provide the title compound (0.71 g, 72%). LCMS (ESI) m/z=345.0 [M+H]⁺.

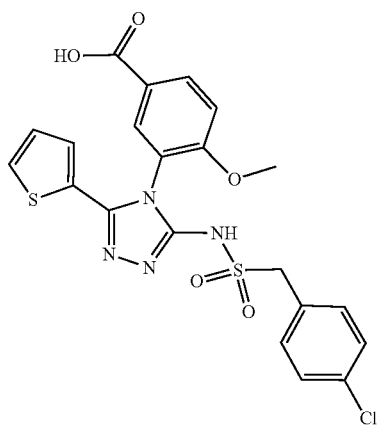

384.0

3-(3-((4-Chlorophenyl)methylsulfonamido)-5-(thiophen-2-yl)-4H-1,2,4-triazol-4-yl)-4-methoxybenzoic acid, Example 384.0. To a 1 dram vial was added Example 384.1 (200 mg, 0.58 mmol) in pyridine (2904 μL). (4-Chlorophenyl)methanesulfonyl chloride (392 mg, 1.74 mmol) was added and the reaction mixture was stirred at 70° C. for 18 h. Next, the reaction was concentrated in vacuo, redissolved in THF, and a 15% NaOH solution in water was added. The mixture was then stirred for 2 h at 70° C. Next, the reaction was made acidic with 10% HCl and extracted with EtOAc. The combined organic layers were concentrated, and the material thus obtained was pre-loaded on silica and purified with flash chromatography on a silica gel column eluting with a gradient of 0%-5% MeOH in DCM followed by preparative HPLC using C-18 column (Gemini AXIA, 5 um, C18, 100×30 mm) (5%-95% ACN with 0.1% TFA/water with 0.1% TFA) yielding the title compound. ¹H NMR (400 MHz, CD₃OD) δ 8.28 (1H, dd, J=8.8, 2.0 Hz), 8.17 (1H, d, J=2.2 Hz), 7.79 (2H, d, J=8.6 Hz), 7.58-7.63 (1H, m), 7.47 (2H, d, J=8.4 Hz), 7.34 (1H, d, J=8.8 Hz), 7.17 (1H, dd, J=3.7, 1.0 Hz), 7.07 (1H, dd, J=5.1, 3.9 Hz), 4.60 (1H, s), 4.31 (2H, d, J=2.2 Hz), 3.84 (3H, s). LCMS (ESI) m/e=505 [M+H]⁺.

Example 385.0. Preparation of 1-(4-chlorophenyl)-N-(4-(2-methoxyphenyl)-5-(thiophen-2-yl)-4H-1,2,4-triazol-3-yl)methanesulfonamide

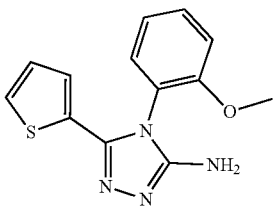

385.1

4-(2-Methoxyphenyl)-5-(thiophen-2-yl)-4H-1,2,4-triazol-3-amine, Example 385.1. To a 200 mL flask containing Example 133.01 (5.0 g, 14.24 mmol) and EtOH (30 mL) was added palladium on carbon (10% wt., 0.151 g, 1.42 mmol). The flask was placed under an atmosphere of H₂ and the mixture was stirred at RT for 48 h. The solution was then filtered through Celite® brand filter aid (Celpure P300, USP-NF, Pharmaceutical Grade) and concentrated in vacuo providing the title compound as a white powder. LCMS (ESI) m/z=273 [M+H]⁺.

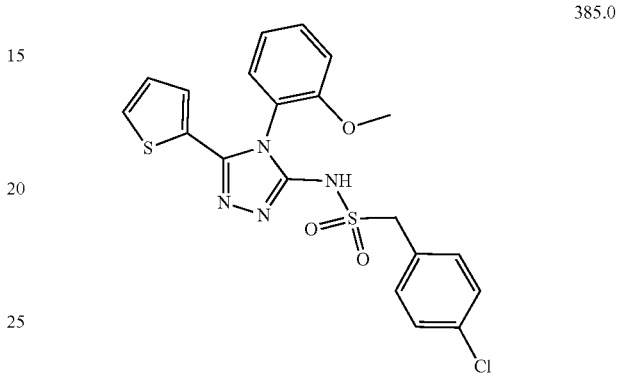

385.0

1-(4-Chlorophenyl)-N-(4-(2-methoxyphenyl)-5-(thiophen-2-yl)-4H-1,2,4-triazol-3-yl)methanesulfonamide, Example 385.0. Example 385.1 (50 mg, 0.093 mmol) was dissolved in EtOH. Pd/C (10%) was added, and the reaction was stirred for 3 h under an atmosphere of H₂ at RT. The reaction mixture was filtered through a pad of Celite® brand filter aid (Celpure P300, USP-NF, Pharmaceutical Grade) and concentrated in vacuo yielding the title compound. LCMS (ESI) m/z 475 [M+H]⁺.

Example 386.0. Preparation of 3,3,3-trifluoro-N-(4-(2-methoxyphenyl)-5-(2-thiophenyl)-4H-1,2,4-triazol-3-yl)-1-propanesulfonamide

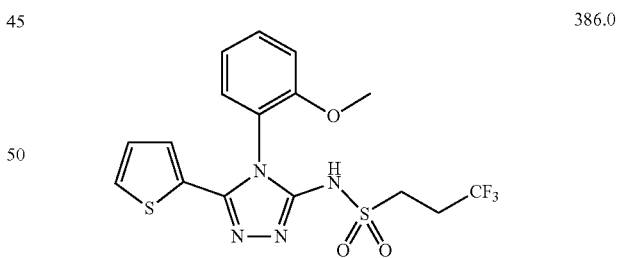

386.0

3,3,3-Trifluoro-N-(4-(2-methoxyphenyl)-5-(2-thiophenyl)-4H-1,2,4-triazol-3-yl)-1-propanesulfonamide, Example 386.0. The title compound was prepared employing Example 133.01 and 3,3,3-trifluoropropane-1-sulfonyl chloride (commercially available from Matrix Scientific, Columbia, S.C., USA) following the procedure described in Example 383.0. ¹H NMR (400 MHz, DMSO-d₆) δ 13.43 (s, 1H) 7.69 (d, J=5.28 Hz, 1H) 7.58-7.64 (m, 1H) 7.56 (d, J=8.02 Hz, 1H) 7.29 (d, J=7.83 Hz, 1H) 7.16 (t, J=7.14 Hz, 1H) 7.00-7.04 (m, 1H) 6.83 (br. s, 1H) 3.71 (s, 3H) 3.14-3.21 (m, 2H) 2.53-2.62 (m, 2H). LCMS-ESI (pos.) m/z: 433.0 (M+H)⁺.

Example 387.0. Preparation of (1R,2S)-N-(4-(2,6-dimethoxyphenyl)-5-(1-ethyl-1H-pyrazol-3-yl)-4H-1,2,4-triazol-3-yl)-1-methoxy-1-(5-methylpyrimidin-2-yl)propane-2-sulfonamide

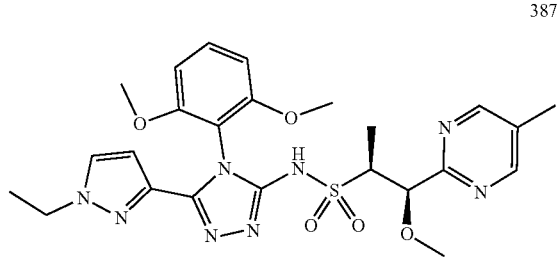

387.0

(1R,2S)-N-(4-(2,6-Dimethoxyphenyl)-5-(1-ethyl-1H-pyrazol-3-yl)-4H-1,2,4-triazol-3-yl)-1-methoxy-1-(5-methylpyrimidin-2-yl)propane-2-sulfonamide, Example 387.0. Following the general procedure described in Example 134.0, Example 387.0 was obtained employing (1R,2S)-1-methoxy-1-(5-methylpyrimidin-2-yl)propane-2-sulfonamide (Example 466.0), isothiocyanato-1,3-dimethoxybenzene (Example 465.0), and 1-ethyl-1H-pyrazole-3-carbohydrazide (ChemBridge). $^1$H NMR (300 MHz, CDCl$_3$) δ 1.39 (m, 6H) 2.32 (s, 3H) 3.34 (s, 3H) 3.58-3.82 (m, 7H) 4.00-4.24 (m, 2H) 4.88-5.03 (m, 1H) 5.87-6.05 (m, 1H) 6.58-6.71 (m, 2H) 7.25 (d, J=2.48 Hz, 1H) 7.40 (t, J=8.48 Hz, 1H) 8.47-8.67 (m, 2H) 11.14 (s, 1H). MS-ESI (pos.) m/z: 543.0 (M+H)$^+$.

Example 388.0. Preparation of (1R,2S)-N-(4-(2,6-dimethoxyphenyl)-5-(1-ethyl-1H-pyrazol-3-yl)-4H-1,2,4-triazol-3-yl)-1-hydroxy-1-(5-methylpyrimidin-2-yl)propane-2-sulfonamide

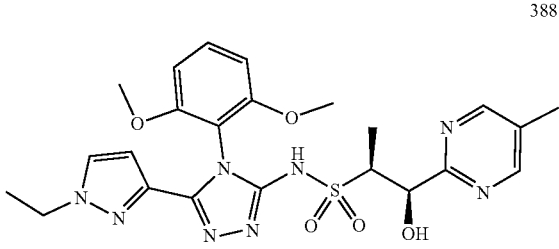

388.0

(1R,2S)-N-(4-(2,6-Dimethoxyphenyl)-5-(1-ethyl-1H-pyrazol-3-yl)-4H-1,2,4-triazol-3-yl)-1-hydroxy-1-(5-methylpyrimidin-2-yl)propane-2-sulfonamide, Example 388.0. Following the general procedure described in Example 134.0, Example 388.0 was obtained employing (1R,2S)-1-hydroxy-1-(5-methylpyrimidin-2-yl)propane-2-sulfonamide (prepared Example 469.8 and following the procedure described in Example 390.2), isothiocyanato-1,3-dimethoxybenzene (Example 465.0) and 1-ethyl-1H-pyrazole-3-carbohydrazide (ChemBridge).

Example 389.0. Preparation of (2S,3R)-N-(4-(2,6-dimethoxyphenyl)-5-(1-ethyl-1H-pyrazol-3-yl)-4H-1,2,4-triazol-3-yl)-3-(5-methylpyrimidin-2-yl)butane-2-sulfonamide

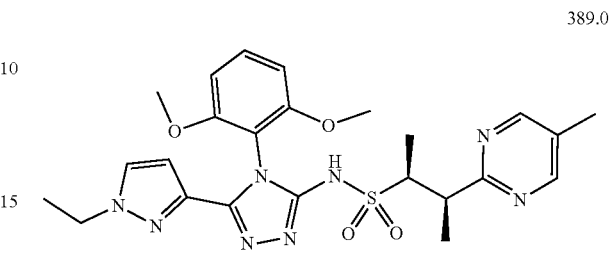

389.0

(2S,3R)-N-(4-(2,6-Dimethoxyphenyl)-5-(1-ethyl-1H-pyrazol-3-yl)-4H-1,2,4-triazol-3-yl)-3-(5-methylpyrimidin-2-yl)butane-2-sulfonamide, Example 389.0. Following the general procedure described in Example 134.0, Example 389.0 was obtained employing (2S,3R)-3-(5-methylpyrimidin-2-yl)butane-2-sulfonamide (Example 464.0), isothiocyanato-1,3-dimethoxybenzene (Example 465.0), and 1-ethyl-1H-pyrazole-3-carbohydrazide (ChemBridge). $^1$H NMR (300 MHz, CDCl$_3$) δ 1.31-1.44 (m, 9H) 2.28 (s, 3H) 3.69-3.73 (m, 6H) 3.74-3.83 (m, 1H) 3.83-3.94 (m, 1H) 4.11 (q, J=7.31 Hz, 2H) 5.96 (d, J=2.34 Hz, 1H) 6.62 (dd, J=8.55, 3.14 Hz, 2H) 7.25 (d, J=2.34 Hz, 1H) 7.40 (t, J=8.48 Hz, 1H) 8.52 (s, 2H) 11.21 (s, 1H). LCMS-ESI (pos.) m/z: 527.2 (M+H)$^+$.

Example 390.0. Preparation of (2S,3R)-N-(4-(2,6-dimethoxyphenyl)-5-(1-ethyl-1H-pyrazol-3-yl)-4H-1,2,4-triazol-3-yl)-4,4,4-trifluoro-3-hydroxy-3-(5-methylpyrimidin-2-yl)butane-2-sulfonamide and (2S,3S)-N-(4-(2,6-dimethoxyphenyl)-5-(1-ethyl-1H-pyrazol-3-yl)-4H-1,2,4-triazol-3-yl)-4,4,4-trifluoro-3-hydroxy-3-(5-methylpyrimidin-2-yl)butane-2-sulfonamide

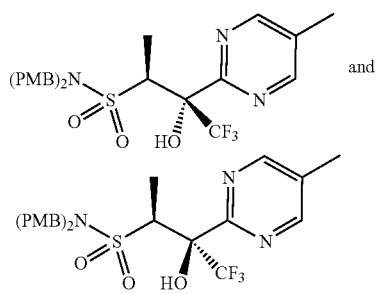

390.1

(2S,3R)-4,4,4-Trifluoro-3-hydroxy-N,N-bis(4-methoxybenzyl)-3-(5-methylpyrimidin-2-yl)butane-2-sulfonamide and (2S,3S)-4,4,4-trifluoro-3-hydroxy-N,N-bis(4-methoxybenzyl)-3-(5-methylpyrimidin-2-yl)butane-2-sulfonamide, Example 390.1. To a stirred solution of (S)-N,N-bis(4-methoxybenzyl)-1-(5-methylpyrimidin-2-yl)-1-oxopropane-2-sulfonamide (0.200 g, 0.426 mmol) in 1,2-dimethoxyethane (3 mL) at 0° C. was added trimethyl(trifluoromethyl)silane (0.270 mL, 1.7 mmol, Aldrich, St. Louis, Mo.) followed by cesium fluoride (5.0 mg, 0.033 mmol, Aldrich, St. Louis, Mo.). After the addition, the ice bath was removed. The reaction mixture was then warmed to RT and stirred for 20 h. The reaction was then partitioned between water (15 mL) and DCM (30 mL). The aqueous layer was extracted with 10% IPA in CHCl$_3$ (2×20 mL). The combined organic layers were dried over MgSO$_4$, filtered, and concentrated. The residue was redissolved in THF (3 mL) and treated with TBAF (0.340 mL, 1.3 mmol, Aldrich, St. Louis, Mo.). The resulting mixture was stirred at RT under N$_2$ for 5 h. The reaction mixture was partitioned between water (15 mL) and DCM (20 mL). The aqueous layer was extracted with 10% IPA in CHCl$_3$ (2×20 mL). The combined organic layers were dried over MgSO$_4$, filtered, and concentrated. The product was purified by column chromatography (40 g of silica, 5 to 40% EtOAc in hexanes) and provided the title compound as a light brown paste (0.080 g). $^1$H NMR (300 MHz, CDCl$_3$) δ 1.74 (dd, J=7.02, 1.61 Hz, 3H) 2.38 (s, 3H) 3.76-3.86 (m, 6H) 3.98 (d, J=15.35 Hz, 2H) 4.35 (d, J=15.20 Hz, 2H) 4.68 (q, J=6.97 Hz, 1H) 6.02 (s, 1H) 6.75-6.92 (m, 4H) 7.03-7.17 (m, 4H) 8.53-8.71 (m, 2H). MS-ESI (pos.) m/z: 539.9 (M+H)$^+$.

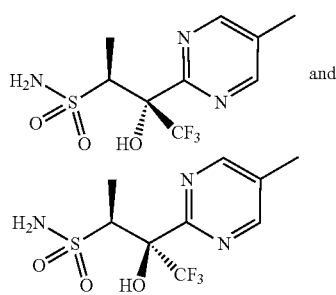

390.2

(2S,3R)-4,4,4-Trifluoro-3-hydroxy-3-(5-methylpyrimidin-2-yl)butane-2-sulfonamide and (2S,3S)-4,4,4-trifluoro-3-hydroxy-3-(5-methylpyrimidin-2-yl)butane-2-sulfonamide, Example 390.2. To a 20 mL scintillation vial which contained Example 390.1 (0.075 g, 0.139 mmol), was added anisole (0.070 mL, 0.644 mmol, Aldrich, St. Louis, Mo.) and TFA (1.0 mL). The vial was capped, and the mixture was stirred for 20 h. The reaction mixture was then concentrated. The product thus obtained was purified by column chromatography (12 g of silica, 5 to 50% acetone in hexanes) and provided the title compound as a white foam (0.028 g). $^1$H NMR (300 MHz, CDCl$_3$) δ 1.84 (d, J=6.87 Hz, 3H) 2.40 (s, 3H) 4.37-4.91 (m, 3H) 6.30 (br. s, 1H) 8.64 (s, 2H). MS-ESI (pos.) m/z: 299.9 (M+H)$^+$.

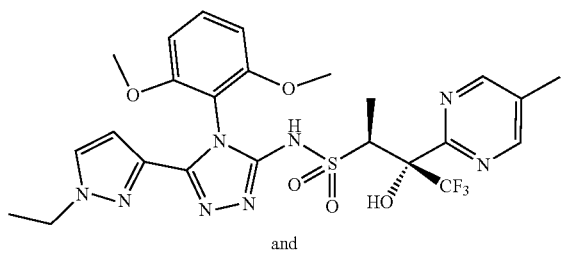

390.0

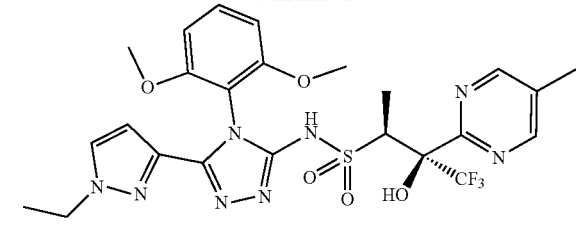

(2S,3R)-N-(4-(2,6-Dimethoxyphenyl)-5-(1-ethyl-1H-pyrazol-3-yl)-4H-1,2,4-triazol-3-yl)-4,4,4-trifluoro-3-hydroxy-3-(5-methylpyrimidin-2-yl)butane-2-sulfonamide and (2S,3S)-N-(4-(2,6-dimethoxyphenyl)-5-(1-ethyl-H-pyrazol-3-yl)-4H-1,2,4-triazol-3-yl)-4,4,4-trifluoro-3-hydroxy-3-(5-methylpyrimidin-2-yl)butane-2-sulfonamide, Example 390.0. Following the general procedure described in Example 134.0, Example 390.0 was obtained employing Example 390.2, 1-ethyl-1H-pyrazole-3-carbohydrazide (ChemBridge), and isothiocyanato-1,3-dimethoxybenzene (Example 465.0). $^1$H NMR (300 MHz, CDCl$_3$) δ 1.41 (t, J=7.31 Hz, 3H) 1.70 (dd, J=7.02, 1.46 Hz, 3H) 2.37 (s, 3H) 3.69-3.81 (m, 6H) 4.06-4.18 (m, 2H) 4.45 (q, J=6.92 Hz, 1H) 5.66 (s, 1H) 5.96 (d, J=2.34 Hz, 1H) 6.64 (d, J=8.48 Hz, 2H) 7.24-7.26 (m, 1H) 7.26 (br. s, 1H) 7.42 (t, J=8.55 Hz, 1H) 8.51-8.72 (m, 2H) 10.64 (br. s, 1H). MS-ESI (pos.) m/z: 596.9 (M+H)$^+$.

Example 391.0. Preparation of (1R,2S)-1-(5-chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide 391.0

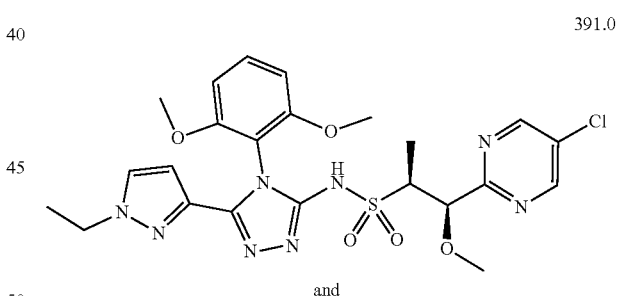

and

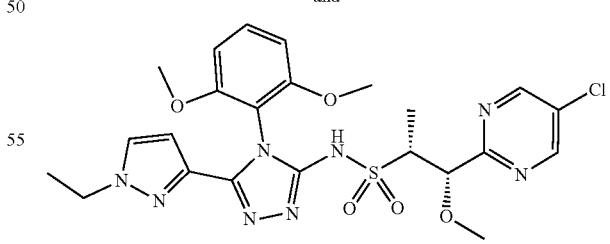

(1R,2S)-1-(5-Chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide and (1S,2R)-1-(5-chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide, Example 391.0. Following the general procedure described in Example 134.0, Example 391.0 was obtained employing (1R,2S)-1-(5-chloropyrimidin-2-yl)-1-methoxypropane-2-sulfonamide and (1S,2R)-1-(5-chloropyrimidin-2-yl)-1-methoxypropane-2-sulfonamide (prepared in an analogous fashion to the described in Example 264.0 employing 5-chloropyrimidine-2-carbaldehyde and isolating the major isomers), 1-ethyl-1H-pyrazole-3-carbohydrazide (ChemBridge), and isothiocyanato-1,3-dimethoxybenzene (Example 465.0). $^1$H NMR (300 MHz, CDCl$_3$) δ 1.32-1.45 (m, 6H) 3.34 (s, 3H) 3.61-3.80 (m, 7H) 4.04-4.18 (m, 2H) 4.88-5.02 (m, 1H) 5.91-6.03 (m, 1H) 6.63 (d, J=8.48 Hz, 2H) 7.26 (d, J=2.48 Hz, 1H) 7.33-7.47 (m, 1H) 8.71 (s, 2H) 10.96 (br. s, 1H). LCMS-ESI (pos.) m/z: 562.9 (M+H)$^+$.

Example 392.0. Preparation of (1R,2S)-1-(5-chloropyrimidin-2-yl)-N-(4-(2,6-dimethoxyphenyl)-5-(3-methyl-1H-pyrazol-5-yl)-4H-1,2,4-triazol-3-yl)-1-ethoxypropane-2-sulfonamide

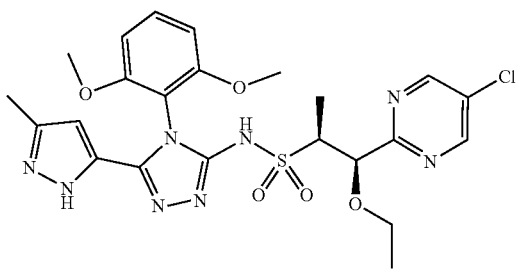

392.0

(1R,2S)-1-(5-Chloropyrimidin-2-yl)-N-(4-(2,6-dimethoxyphenyl)-5-(3-methyl-1H-pyrazol-5-yl)-4H-1,2,4-triazol-3-yl)-1-ethoxypropane-2-sulfonamide, Example 392.0. Following the general procedure described in Example 134.0, Example 392.0 was obtained employing (1R,2S)-1-(5-chloropyrimidin-2-yl)-1-ethoxypropane-2-sulfonamide (Example 466.7), isothiocyanato-1,3-dimethoxybenzene (Example 465.0), and 3-methyl-1H-pyrazole-5-carbohydrazide (Maybridge Chemical Co., Ltd.). $^1$H NMR (400 MHz, CDCl$_3$) δ 1.05-1.21 (m, 3H) 1.38-1.48 (m, 3H) 2.14-2.30 (m, 3H) 3.37-3.58 (m, 2H) 3.66-3.83 (m, 7H) 4.89-5.05 (m, 1H) 5.74-5.92 (m, 1H) 6.55-6.74 (m, 2H) 7.44 (t, J=8.51 Hz, 1H) 8.59-8.76 (m, 2H) 11.19 (br. s, 1H). One exchangeable proton was not observed. LCMS-ESI (pos.) m/z: 562.9 (M+H)$^+$.

Example 393.0. Preparation of (1R,2S)-1-(5-chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide

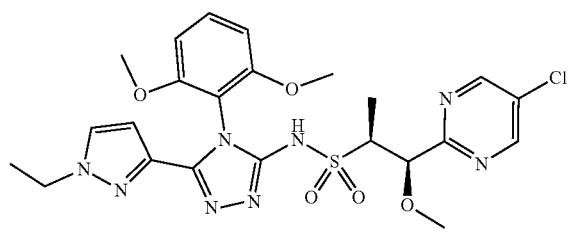

393.0

(1R,2S)-1-(5-Chloropyrimidin-2-yl)-N-(4-(2,6-dimethoxyphenyl)-5-(1-ethyl-1H-pyrazol-3-yl)-4H-1,2,4-triazol-3-yl)-1-methoxypropane-2-sulfonamide, Example 393.0. Following the general procedure described in Example 134.0, Example 393.0 was obtained employing (1R,2S)-1-(5-chloropyrimidin-2-yl)-1-methoxypropane-2-sulfonamide (Example 466.3), 1-ethyl-1H-pyrazole-3-carbohydrazide (ChemBridge), and isothiocyanato-1,3-dimethoxybenzene (Example 465.0). $^1$H NMR (400 MHz, CDCl$_3$) δ 1.31-1.47 (m, 6H) 3.23-3.43 (m, 3H) 3.59-3.81 (m, 7H) 4.11 (q, J=7.24 Hz, 2H) 4.96 (d, J=5.09 Hz, 1H) 5.88-6.05 (m, 1H) 6.63 (d, J=8.41 Hz, 2H) 7.41 (t, J=8.51 Hz, 1H) 8.71 (s, 2H) 10.96 (br. s, 1H). One exchangeable proton was not observed. LCMS-ESI (pos.) m/z: 562.9 (M+H)$^+$.

Example 394.0. Preparation of (1R,2S)-1-(5-chloropyrimidin-2-yl)-N-(4-(2,6-dimethoxyphenyl)-5-(1-ethyl-1H-pyrazol-3-yl)-4H-1,2,4-triazol-3-yl)-1-ethoxypropane-2-sulfonamide

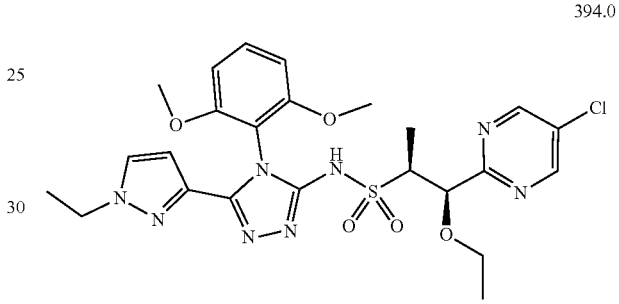

394.0

(1R,2S)-1-(5-Chloropyrimidin-2-yl)-N-(4-(2,6-dimethoxyphenyl)-5-(1-ethyl-1H-pyrazol-3-yl)-4H-1,2,4-triazol-3-yl)-1-ethoxypropane-2-sulfonamide, Example 394.0. Following the general procedure described in Example 134.0, Example 394.0 was obtained employing (1R,2S)-1-(5-chloropyrimidin-2-yl)-1-ethoxypropane-2-sulfonamide (Example 466.7), 1-ethyl-H-pyrazole-3-carbohydrazide (ChemBridge), and isothiocyanato-1,3-dimethoxybenzene (Example 465.0). $^1$H NMR (400 MHz, CDCl$_3$) δ 1.09-1.18 (m, 3H) 1.35-1.41 (m, 3H) 1.44 (d, J=7.04 Hz, 3H) 3.44-3.56 (m, 2H) 3.68-3.75 (m, 6H) 3.75-3.83 (m, 1H) 4.06-4.15 (m, 2H) 4.98 (d, J=6.06 Hz, 1H) 5.95-6.00 (m, 1H) 6.63 (dd, J=8.41, 2.15 Hz, 2H) 7.26 (d, J=2.35 Hz, 1H) 7.37-7.45 (m, 1H) 8.67-8.73 (m, 2H) 10.96 (s, 1H). MS-ESI (pos.) m/z: 576.9 (M+H)$^+$.

Example 395.2. Preparation of 3-(hydrazinecarbonyl)-N-methyl-1H-pyrazole-1-carboxamide

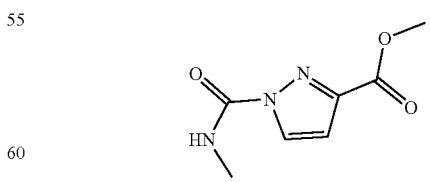

395.1

Methyl 1-(methylcarbamoyl)-1H-pyrazole-3-carboxylate, Example 395.1. To a mixture of 1H-pyrazole-3-methyl carboxylate (0.53 mL, 5.35 mmol) and N,N-diisopropylethylamine (2.8 mL, 16.0 mmol) in DCM (10.7 mL) was added dropwise a solution of methylaminoformyl chloride (1.0 g, 11 mmol) in DCM (5 mL) at −78° C. The resulting mixture was warmed to RT and stirred for 18 h. The mixture was concentrated in vacuo and the residue was directly absorbed onto a plug of silica gel and purified by chromatography through a Redi-Sep pre-packed silica gel column (40 g), eluting with a gradient of 0% to 70% EtOAc in hexanes to give Example 395.1 (943 mg, 5.15 mmol, 96%). $^1$H NMR (400 MHz, CDCl$_3$) δ 8.23 (d, J=2.54 Hz, 1H), 7.26 (br. s, 1H), 6.82 (d, J=2.54 Hz, 1H), 3.90 (s, 3H), 2.99 (d, J=4.89 Hz, 3H).

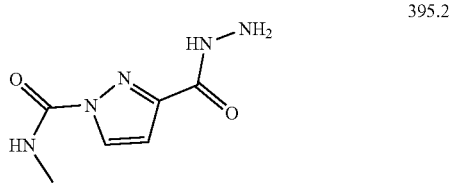

395.2

3-(Hydrazinecarbonyl)-N-methyl-1H-pyrazole-1-carboxamide, Example 395.2. To a solution of methyl 1-(methylcarbamoyl)-1H-pyrazole-3-carboxylate, Example 395.1 (0.943 g, 5.15 mmol) in MeOH (10 mL, 247 mmol), was added hydrazine (0.236 mL, 10.30 mmol) at RT. The resulting mixture was stirred at RT for 24 h. The mixture was then concentrated in vacuo and the residue was dissolved in water (100 mL). The aqueous solution was lyophilized to give the title compound (943 mg). LCMS-ESI (pos.): 184.1 (M+H)$^+$.

Example 395.3. Preparation of isobutyl pyridazine-3-carboxylate

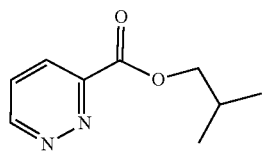

395.3

Isobutyl pyridazine-3-carboxylate, Example 395.3. To a mixture of pyridazine-3-carboxylic acid (1.07 mL, 12.09 mmol) and TEA (anhydrous, 3.36 mL, 24.17 mmol) in THF (60.4 mL) was added isobutyl chloroformate (1.88 mL, 14.50 mmol) at 0° C. The resulting mixture was stirred at the same temperature for 6.5 h. Next, water (50 mL) was added to the mixture, and the resulting mixture was extracted with CHCl$_3$ (70 mL×4). The combined extracts were dried with anhydrous sodium sulfate and concentrated in vacuo. The residue was purified by CombiFlash on a 125 g silica gel column using 0-100% EtOAc gradient in hexanes as the eluent to give Example 395.3 (1.24 g). LCMS-ESI (pos.): 139.1 (M+H)$^+$.

Example 395.4. Preparation of methyl 1-methyl-1H-pyrrole-3-carboxylate

395.4

Methyl 1-methyl-1H-pyrrole-3-carboxylate, Example 395.4. To a mixture of 1H-pyrrole-3-carboxylic acid (1.0 g, 9.00 mmol) and cesium carbonate (1.58 mL, 19.80 mmol) in ACN (20 mL) cooled in an ice bath, was added iodomethane (1.68 mL, 27.0 mmol). The resulting mixture was stirred at RT. The mixture was then filtered, and the solid was washed with EtOAc. The filtrate was concentrated and dried under reduced pressure to give methyl 1-methyl-1H-pyrrole-3-carboxylate (577 mg). LCMS-ESI (pos.): 140.1 (M+H)$^+$.

Following the procedure described in Example 395.4, the following examples were synthesized using the reagents described.

TABLE 21

| Example | Reagents | Structure, Name and data |
|---|---|---|
| 395.5 | 1-methyl-1H-pyrazole-3-carboxylic acid | Methyl 1-methyl-1H-pyrazole-3-calboxylate. LCMS-ESI (pos.): 141.1 (M + H)$^+$. |
| 395.6 | pyrimidine-4-carboxylic acid | Methyl pyrimidine-4-carboxylate. LCMS-ESI (pos.): 139.1 (M + H)$^+$. |
| 395.7 | 1-methyl-1H-pyrazole-4-carboxylic acid | Methyl 1-methyl-1H-pyrazole-4-calboxylate. LCMS-ESI (pos.): 141.1 (M + H)$^+$. |
| 395.8 | pyrimidine-2-carboxylic acid | Methyl pyrimidine-2-carboxylate. LCMS-ESI (pos.): 139.1 (M + H)$^+$. |
| 395.9 | 3-methylisoxazole-5-carboxylic acid | Methyl 3-methylisoxazole-5-carboxylate. LCMS-ESI (pos.): 142.1 (M + H)$^+$. |

Following the procedure described in Example 395.2, the following examples were synthesized using the reagents described.

TABLE 22

| Example | Reagents | Structure and Name and Data |
|---|---|---|
| 395.10 | Isobutyl pyridazine-3-carboxylate, Example 395.3. | 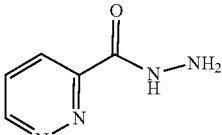<br>pyridazine-3-carbohydrazide.<br>LCMS-ESI (pos.) m/z: 139.1 (M + H)$^+$. |
| 395.11 | methyl pyrazine-2-carboxylate (Sigma-Aldrich Chemical Company, Inc.). | 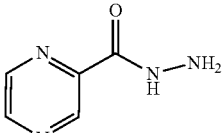<br>pyrazine-2-carbohydrazide.<br>LCMS-ESI (pos.) m/z: 139.1 (M + H)$^+$. |
| 395.12 | Methyl 1-methyl-1H-pyrrole-3-carboxylate, Example 395.4. | 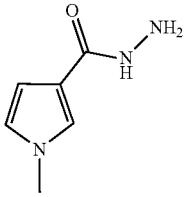<br>1-methyl-1H-pyrrole-3-carbohydrazide.<br>LCMS-ESI (pos.) m/z: 140.1 (M + H)$^+$. |
| 395.13 | Methyl 1-methyl-1H-pyrazole-3-carboxylate, Example 395.5. | 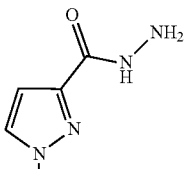<br>1-methyl-1H-pyrazole-3-carbohydrazide.<br>LCMS-ESI (pos.) m/z: 141.1 (M + H)$^+$. |
| 395.14 | methyl pyrimidine-4-carboxylate, Example 395.6. | 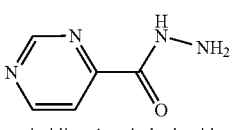<br>pyrimidine-4-carbohydrazide.<br>LCMS-ESI (pos.) m/z: (M + H)$^+$. |
| 395.15 | 1-methyl-1H-pyrazole-4-carboxylic acid, Example 395.7. | 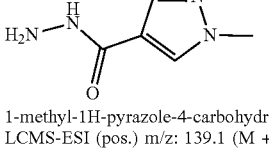<br>1-methyl-1H-pyrazole-4-carbohydrazide.<br>LCMS-ESI (pos.) m/z: 139.1 (M + H)$^+$. |
| 395.16 | ethyl pyrimidine-5-carboxylate (Acros Organics). | 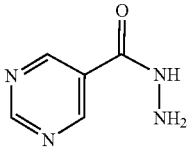<br>pyrimidine-5-carbohydrazide.<br>LCMS-ESI (pos.) m/z: 139.3 (M + H)$^+$. |
| 395.17 | Ethyl 5-methyl-1,3,4-oxadiazole-2-carboxylate (J & W PharmLab, LLC). | 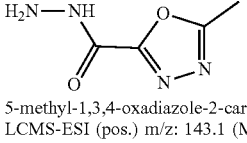<br>5-methyl-1,3,4-oxadiazole-2-carbohydrazide.<br>LCMS-ESI (pos.) m/z: 143.1 (M + H)$^+$. |

TABLE 22-continued

| Example | Reagents | Structure and Name and Data |
|---|---|---|
| 395.18 | Methyl pyridazine-4-carboxylate (Sigma-Aldrich Chemical Company, Inc.). | 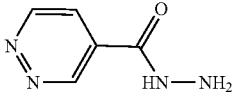 pyridazine-4-carbohydrazide. LCMS-ESI (pos.) m/z: 139.1 (M + H)$^+$. |
| 395.19 | Methyl 1,5-dimethyl-1H-pyrazole-3-carboxylate (Sigma-Aldrich Chemical Company, Inc.). | 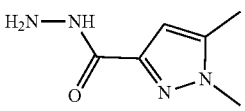 1,5-dimethyl-1H-pyrazole-3-carbohydrazide. LCMS-ESI (pos.) m/z: 155.1 (M + H)$^+$. |
| 395.20 | pyrimidine-2-carboxylic acid, Example 395.8. | 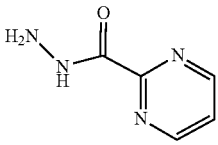 pyrimidine-2-carbohydrazide. LCMS-ESI (pos.) m/z: 139.1 (M + H)$^+$. |
| 395.21 | Methyl 1-methyl-1H-1,2,3-triazole-4-carboxylate (Princeton Bio). | 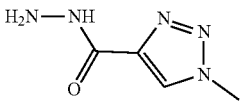 1-methyl-1H-1,2,3-triazole-4-carbohydrazide LCMS-ESI (pos.) m/z: 142.1 (M + H)$^+$. |
| 395.22 | Methyl 3-methylisoxazole-5-carboxylate, Example 395.9. | 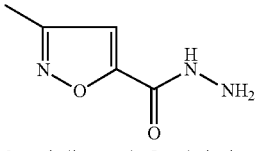 3-methylisoxazole-5-carbohydrazide. LCMS-ESI (pos.) m/z: 142.1 (M + H)$^+$. |
| 395.23 | ethyl 3-methylisoxazole-4-carboxylate (Lancaster Synthesis Ltd.). | 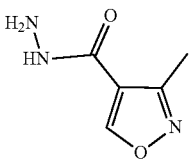 3-methylisoxazole-4-carbohydrazide. LCMS-ESI (pos.) m/z: 142.1 (M + H)$^+$. |
| 395.24 | methyl 6-methoxypyrazine-2-carboxylate (Parkway Scientific LLC). | 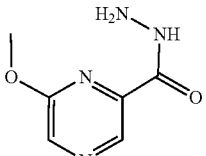 6-methoxypyrazine-2-carbohydrazide. LCMS-ESI (pos.) m/z: 168.9 (M + H)$^+$. |
| 395.25 | Methyl 2-methyl-2H-1,2,3-triazole-4-carboxylate (AccelaChemBio Inc.). | 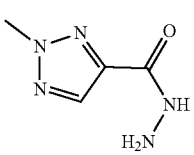 2-methyl-2H-1,2,3-triazole-4-carbohydrazide. LCMS-ESI (pos.) m/z: 142.1 (M + H)$^+$. |

TABLE 22-continued

| Example | Reagents | Structure and Name and Data |
|---|---|---|
| 395.26 | Methyl 2-methoxypyrimidine-4-carboxylate (Ark Pharm, Inc.). | 2-methoxypyrimidine-4-carbohydrazide. $^1$H NMR (500 MHz, CDCl$_3$) δ 8.85 (br. s, 1H), 8.73-8.79 (m, 1H), 7.70-7.74 (m, 1H), 4.08-4.20 (m, 2H), 4.07 (s, 3H). |
| 395.27 | Methyl 1-methyl-1H-1,2,4-triazole-3-carboxylate (Matrix Scientific). | 1-methyl-1H-1,2,4-triazole-3-carbohydrazide. $^1$H NMR (500 MHz, DMSO-d$_6$) δ 9.65 (s, 1H), 8.55 (s, 1H), 4.48 (s, 2H), 3.91 (s, 3H). |
| 395.28 | Ethyl 5,6-dihydro-4H-pyrrolo[1,2-b]pyrazole-2-carboxylate (Ark Pharm, Inc.). | 5,6-dihydro-4H-pyrrolo[1,2-b]pyrazole-2-carbohydrazide. $^1$H NMR (500 MHz, CD$_3$OD) 66.44 (s, 1H), 4.12-4.15 (m, 2H), 2.91 (t, J = 7.34 Hz, 2H), 2.59-2.67 (m, 2H). |
| 395.29 | methyl 5H-pyrrolo[2,3-b]pyrazine-2-carboxylate (Molbridge LLC). | 5H-pyrrolo[2,3-b]pyrazine-2-carbohydrazide. $^1$H NMR (DMSO-d$_6$) δ 12.37 (br. s, 1H), 9.88 (s, 1H), 8.83 (s, 1H), 8.04 (d, J = 1.7 Hz, 1H), 6.70 (d, J = 3.4 Hz, 1H), 4.59 (br. s, 2H). |
| 395.30 | methyl 1-methyl-1H-pyrazole-4-carboxylate (Combi-Blocks). | 1-methyl-1H-pyrazole-4-carbohydrazide. LCMS-ESI (pos.) m/z: 141.2 (M + H)$^+$. |

Example 396.0. Preparation of 4-(2,6-dimethoxyphenyl)-5-(thiazol-2-yl)-4H-1,2,4-triazol-3-amine

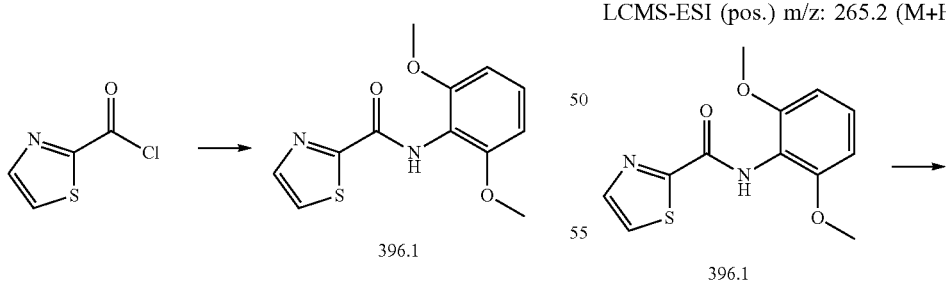

N-(2,6-Dimethoxyphenyl)thiazole-2-carboxamide, Example 396.1. To an ice-cooled solution of 2,6-dimethoxyaniline (Amfinecom Inc., 1.2 g, 7.8 mmol) in DCM (20 mL) was added N,N-diisopropylethylamine (2.73 mL, 15.7 mmol) via syringe followed by a solution of 1,3-thiazole-2-carbonyl chloride (Maybridge, 1.16 g, 7.9 mmol) in DCM (27 mL) slowly via cannula. The resulting brown solution was allowed to warm to RT and stirred for 19 h. The reaction was then partitioned between water (80 mL) and DCM (2×). The combined organic layers were washed with brine (2×), dried over anhydrous sodium sulfate, filtered, and concentrated in vacuo. The residue was purified by silica gel chromatography (eluent: 10-100% EtOAc in hexanes) to provide 396.1 (1.30 g, 63% yield) as alight yellow solid. LCMS-ESI (pos.) m/z: 265.2 (M+H)$^+$.

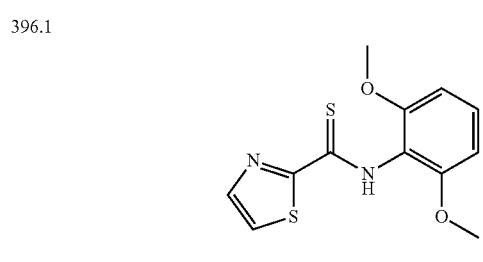

N-(2,6-Dimethoxyphenyl)thiazole-2-carbothioamide, Example 396.2. To a suspension of 396.1 (1.25 g, 4.7 mmol) in toluene (37 mL) was added Lawesson's reagent (1.53 g, 3.8 mmol). The resulting light yellow slurry was heated at reflux for 2.5 h and was then allowed to cool to RT. The reaction was quenched with water (40 mL) and extracted with EtOAc (3×). The combined organic layers were washed with brine (1×), dried over anhydrous sodium sulfate, and concentrated in vacuo. The residue was purified by silica gel chromatography (eluent: 5-60% EtOAc in hexanes) to provide 396.2 (1.26 g, 95% yield) as a bright yellow solid. LCMS-ESI (pos.) m/z: 281.2 (M+H)⁺.

N-(2,6-Dimethoxyphenyl)thiazole-2-carbohydrazonamide, Example 396.3. To a solution of 396.2 (130 mg, 0.46 mmol) in THF (4.5 mL) was added hydrazine hydrate (80%, 283 µL, 4.7 mmol). The resulting yellow solution was heated at 50° C. for 45 min and was then cooled to RT. The reaction was quenched with a saturated aqueous sodium bicarbonate (10 mL) and extracted with EtOAc (3×). The organic layer was washed with brine (1×), dried over anhydrous sodium sulfate, and concentrated in vacuo. The residue was triturated with Et₂O to provide 396.3 (86.5 mg, 67% yield) as a light yellow solid. LCMS-ESI (pos.) m/z: 279.2 (M+H)⁺.

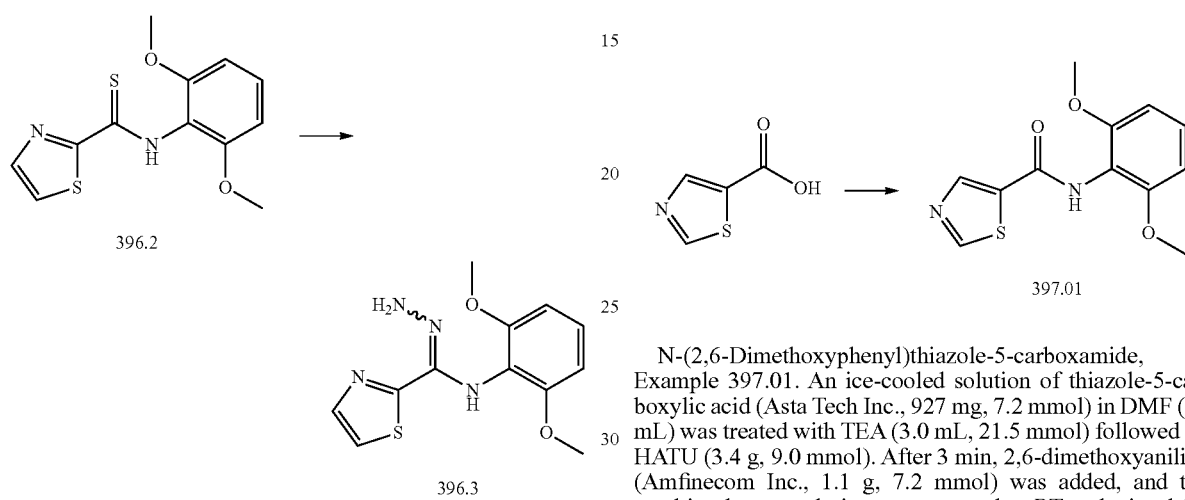

4-(2,6-Dimethoxyphenyl)-5-(thiazol-2-yl)-4H-1,2,4-triazol-3-amine, Example 396.0. To a slurry of 396.3 (86.5 mg, 0.31 mmol) in EtOH (4 mL) was added cyanogen bromide (5.0 M solution in ACN, 155 µL, 0.78 mmol) slowly via syringe over 4 min. The resulting yellow slurry was heated at 60° C. for 19 h and was then cooled to RT. The reaction was quenched with water (2 mL) and concentrated in vacuo. The residue was purified by reverse phase preparatory HPLC (Sunfire 5 µM C18 column, eluent: 35-75% ACN in water over a 35 min period where both solvents contain 0.1% TFA) to provide 396.0 (61 mg, 65% yield) as a white solid. LCMS-ESI (pos.) m/z: 304.2 (M+H)⁺.

Example 397.0. Preparation of 4-(2,6-dimethoxyphenyl)-5-(thiazol-5-yl)-4H-1,2,4-triazol-3-amine N-(2,6-Dimethoxyphenyl)thiazole-5-carboxamide, Example 397.01. An ice-cooled solution of thiazole-5-carboxylic acid (Asta Tech Inc., 927 mg, 7.2 mmol) in DMF (20 mL) was treated with TEA (3.0 mL, 21.5 mmol) followed by HATU (3.4 g, 9.0 mmol). After 3 min, 2,6-dimethoxyaniline (Amfinecom Inc., 1.1 g, 7.2 mmol) was added, and the resulting brown solution was warmed to RT and stirred for 60 min. Next, the reaction was partitioned between brine (125 mL) and EtOAc (2×). The combined organic layers were washed with water (1×) and brine (1×), dried over anhydrous sodium sulfate, and concentrated in vacuo. The residue was purified by silica gel chromatography (eluent: 10-100% EtOAc in hexanes) to provide 397.01 (1.79 g, 94% yield) as a light orange solid. LCMS-ESI (pos.) m/z: 265.2 (M+H)⁺.

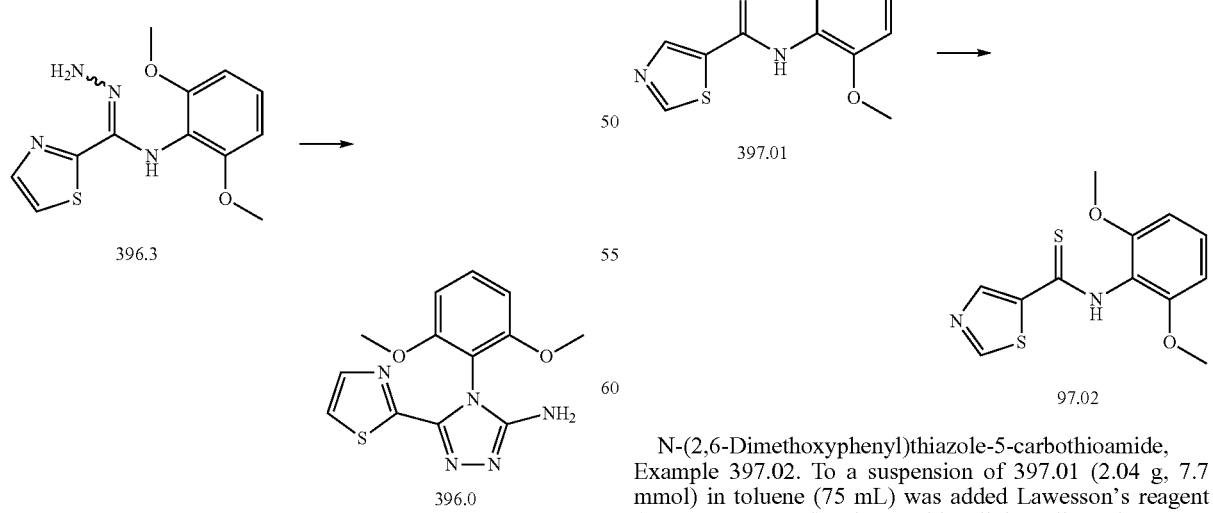

N-(2,6-Dimethoxyphenyl)thiazole-5-carbothioamide, Example 397.02. To a suspension of 397.01 (2.04 g, 7.7 mmol) in toluene (75 mL) was added Lawesson's reagent (2.50 g, 6.2 mmol). The resulting light yellow slurry was heated at reflux for 2.5 h and was then cooled to RT. The reaction was quenched with water (60 mL) and extracted with EtOAc (2×). The combined organic layers were washed with brine (1×), dried over anhydrous sodium sulfate, and concentrated in vacuo. The residue was purified by silica gel chromatography (eluent: 2-95% EtOAc in hexanes) to provide 397.02 (1.59 g, 74% yield) as a bright yellow solid. LCMS-ESI (pos.) m/z: 281.2 (M+H)⁺.

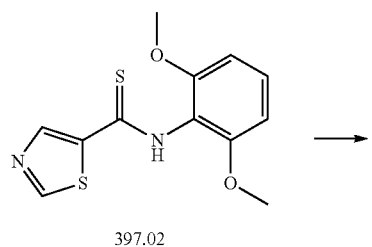

397.02

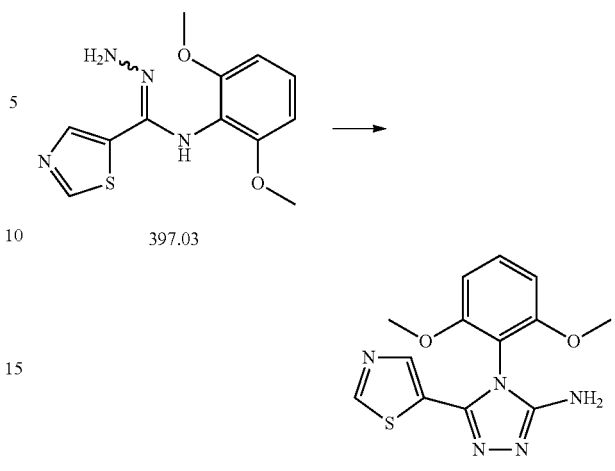

397.03

N-(2,6-Dimethoxyphenyl)thiazole-5-carbohydrazonamide, Example 397.03. To a solution of 397.02 (228 mg, 0.81 mmol) in THF (7.5 mL) was added hydrazine hydrate (80%, 493 mL, 8.1 mmol). The resulting yellow slurry was heated at 50° C. for 35 min and then it was cooled to RT. The reaction was quenched with a saturated aqueous sodium bicarbonate solution (20 mL) and extracted with EtOAc (3×). The organic layer was washed with brine (1×), dried over anhydrous sodium sulfate, and concentrated in vacuo. The residue was triturated with ethyl ether to provide 397.03 (120 mg, 53% yield) as a yellow solid. LCMS-ESI (pos.) m/z: 279.2 (M+H)⁺.

4-(2,6-Dimethoxyphenyl)-5-(thiazol-5-yl)-4H-1,2,4-triazol-3-amine, Example 397.0. To a slurry of 397.03 (120 mg, 0.43 mmol) in EtOH (6.5 mL) was added cyanogen bromide (5.0 M solution in ACN, 224 μL, 1.12 mmol) slowly via syringe over 5 min. The resulting yellow slurry was heated at 60° C. for 19 h and then was cooled to RT. The reaction was quenched with water (2.5 mL) and concentrated. The residue was purified by reverse phase preparatory HPLC (Sunfire 5 μM C18 column, eluent: 10-45% ACN in water over a 35 min period where both solvents contain 0.1% TFA) to provide 397.0 (52.5 mg, 40% yield) as alight yellow solid. LCMS-ESI (pos.) m/z: 304.2 (M+H)⁺.

The compounds set forth in the following table were synthesized following the procedure in Example 397.0 using the known starting material as described.

TABLE 23

| Example | Reagents | Structure, Name and Data |
|---|---|---|
| 397.1 | oxazole-5-caiboxylic acid (Combi-Blocks). | 4-(2,6-dimethoxyphenyl)-5-(oxazol-5-yl)-4H-1,2,4-triazol-3-amine. LCMS-ESI (pos.) m/z: 288.2 (M + H)⁺. |
| 397.2 | oxazole-4-caiboxylic acid (Acros). | 4-(2,6-dimethoxyphenyl)-5-(oxazol-4-yl)-4H-1,2,4-triazol-3-amine. LCMS-ESI (pos.) m/z: 288.2 (M + H)⁺. |

TABLE 23-continued

| Example | Reagents | Structure, Name and Data |
|---|---|---|
| 397.3 | 3-thiophenecarboxylic acid (Sigma-Aldrich). | 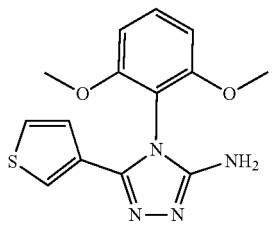 [SMILES: COc1cccc(OC)c1-n1c(N)nnc1-c1ccsc1]<br>4-(2,6-dimethoxyphenyl)-5-(thiophen-3-yl)-4H-1,2,4-triazol-3-amine.<br>LCMS-ESI (pos.) m/z: 303.2 (M + H)+. |
| 397.4 | 4-methyl-1,3-thiazole-2-carboxylic acid (Acros). | 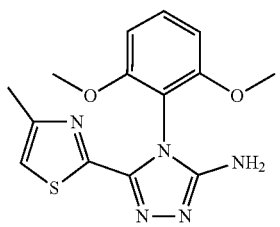<br>4-(2,6-dimethoxyphenyl)-5-(4-methylthiazol-2-yl)-4H-1,2,4-triazol-3-amine.<br>LCMS-ESI (pos.) m/z: 318.2 (M + H)+. |
| 397.5 | 5-methyl-thiazole-2-carboxylic acid (APAC Pharmaceutical). | 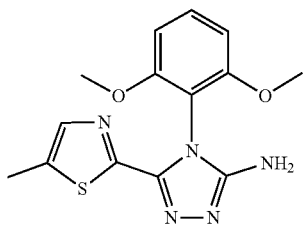<br>4-(2,6-dimethoxyphenyl)-5-(5-methylthiazol-2-yl)-4H-1,2,4-triazol-3-amine.<br>LCMS-ESI (pos.) m/z: 318.2 (M + H)+. |
| 397.6 | 5-chloro-thiazole-2-carboxylic acid (Hande Sciences). | 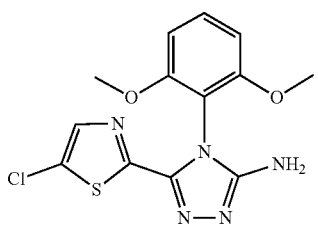 [SMILES: COc1cccc(OC)c1-n1c(N)nnc1-c1ncc(Cl)s1]<br>5-(5-chlorothiazol-2-yl)-4-(2,6-dimethoxyphenyl)-4H-1,2,4-triazol-3-amine. LCMS-ESI (pos.) m/z: 338.0 (M + H)+. |
| 397.7 | 5-methylisoxazole-3-carboxylic acid (Sigma-Aldrich). | 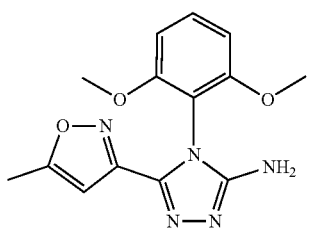<br>4-(2,6-dimethoxyphenyl)-5-(5-methylisoxazol-3-yl)-4H-1,2,4-triazol-3-amine.<br>LCMS-ESI (pos.) m/z: 302.2 (M + H)+. |

TABLE 23-continued

| Example | Reagents | Structure, Name and Data |
|---|---|---|
| 397.8 | 2-methoxymethyl-1,3-thiazole-4-carboxylic acid (Enamine). | 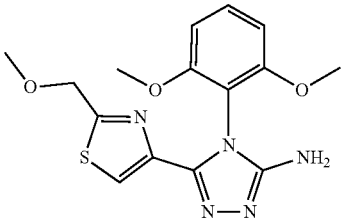 4-(2,6-dimethoxyphenyl)-5-(2-(methoxymethyl)thiazol-4-yl)-4H-1,2,4-triazol-3-amine. LCMS-ESI (pos.) m/z: 348.2 (M + H)$^+$. |
| 397.9 | 2-methyl-1,3-thiazole-4-carboxylic acid (Sigma-Aldrich). | 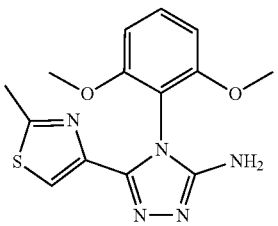 4-(2,6-dimethoxyphenyl)-5-(2-methylthiazol-4-yl)-4H-1,2,4-triazol-3-amine. LCMS-ESI (pos.) m/z: 318.2 (M + H)$^+$. |
| 397.10 | potassium 4-isopropylthiazole-2-carboxylate (2.10 g, 10.03 mmol) (Chembridge). | 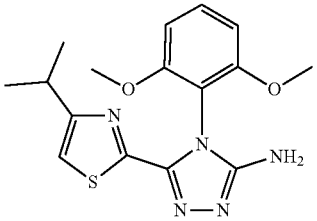 [SMILES: COc1cccc(OC)c1-n1c(N)nnc1-c1nc(C(C)C)cs1] 4-(2,6-dimethoxyphenyl)-5-(4-isopropylthiazol-2-yl)-4H-1,2,4-triazol-3-amine. LCMS-ESI (pos.) m/z: 346.1 (M + H)$^+$. |
| 397.11 | 2-ethylthiazole-4-carboxylic acid (Acros). | 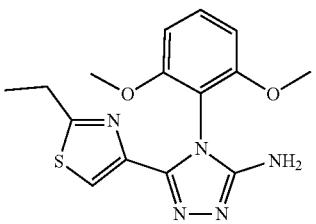 [SMILES: CCc1nc(-c2nnc(N)n2-c2c(OC)cccc2OC)cs1] 4-(2,6-dimethoxyphenyl)-5-(2-ethylthiazol-4-yl)-4H-1,2,4-triazol-3-amine.\ LCMS-ESI (pos.) m/z: 332.1 (M + H)$^+$. |
| 397.12 | 4-thiazolecarboxylic acid (Sigma-Aldrich). | 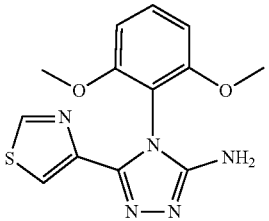 [SMILES: COc1cccc(OC)c1-n1c(N)nnc1-c1cscn1] 4-(2,6-dimethoxyphenyl)-5-(thiazol-4-yl)-4H-1,2,4-triazol-3-amine. LCMS-ESI (pos.) m/z: 304.1 (M + H)$^+$. |

TABLE 23-continued

| Example | Reagents | Structure, Name and Data |
|---|---|---|
| 397.13 | 1,3-oxazole-2-carboxylic acid (Princeton Biomolecular Research Inc.). | 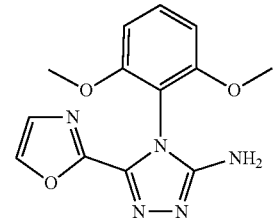 [SMILES: COc1cccc(OC)c1-n1c(N)nnc1-c1ncco1]<br>4-(2,6-dimethoxyphenyl)-5-(oxazol-2-yl)-4H-1,2,4-triazol-3-amine.<br>LCMS-ESI (pos.) m/z: 288.0 (M + H)$^+$. |
| 397.14 | 1-methyl-1H-imidazole-5-carboxylic acid (Maybridge). | 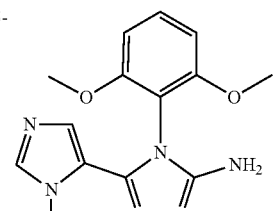<br>4-(2,6-dimethoxyphenyl)-5-(1-methyl-1H-imidazol-5-yl)-4H-1,2,4-triazol-3-amine.<br>LCMS-ESI (pos.) m/z: 301.2 (M + H)$^+$. |
| 397.15 | 1-methyl-1H-pyrazole-3-carboxylic acid (Sigma Aldrich). | 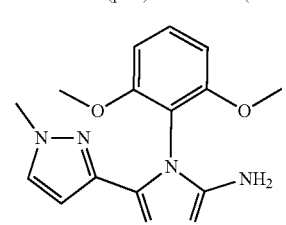<br>4-(2,6-dimethoxyphenyl)-5-(1-methyl-1H-pyrazol-3-yl)-4H-1,2,4-triazol-3-amine.<br>LCMS-ESI (pos.) m/z: 301.1 (M + H)$^+$. |

Example 398.0. Preparation of 4-(2,6-dimethoxyphenyl)-5-(4-ethylthiazol-2-yl)-4H-1,2,4-triazol-3-amine

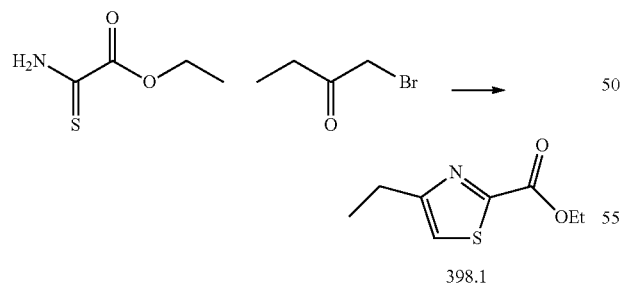

398.1

Ethyl 4-ethylthiazole-2-carboxylate, Example 398.1. A suspension of ethyl 2-thiooxamate (Sigma-Aldrich, 5.05 g, 37.9 mmol) in EtOH (32 mL) was heated to reflux. Once all of the solids dissolved, 1-bromo-2-butanone (Sigma-Aldrich, 3.9 mL, 37.2 mmol) was added slowly via syringe to the refluxing solution over a 10 min period. The resulting orange solution was heated at reflux for an additional 1.25 h and then was cooled to RT. The reaction mixture was poured into a beaker of ice water and then treated with ammonium hydroxide until strongly basic. The mixture was extracted with EtOAc (1×) and the organic layer was washed with brine (1×), dried over anhydrous sodium sulfate, and concentrated in vacuo. The residue was purified by fractional distillation under vacuum (bp=140° C.-145° C. @ 1 mm Hg) to provide Example 398.1 (5.31 g, 77% yield) as a light yellow oil. LCMS-ESI (pos.) m/z: 186.2 (M+H)$^+$.

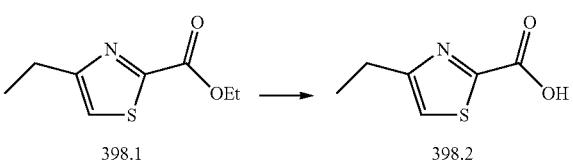

4-Ethylthiazole-2-carboxylic acid, Example 398.2. A slurry of 398.1 (5.31 g, 28.7 mmol) and potassium hydroxide (3.06 g, 54.5 mmol) in water (20.5 mL) was heated at reflux for 1.25 h. The reaction was allowed to cool to RT and then 3 N HCl was added until the pH was 2. The mixture was extracted with EtOAc (4×). The combined organic layers were dried over anhydrous sodium sulfate and concentrated to afford 398.2 (3.76 g, 83% yield) as a light yellow oil. Note that 398.2 contains 35% of the corresponding decarboxylation byproduct 4-ethylthiazole. This mixture was used in the subsequent step. LCMS-ESI (pos.) m/z: 158.2 (M+H)$^+$.

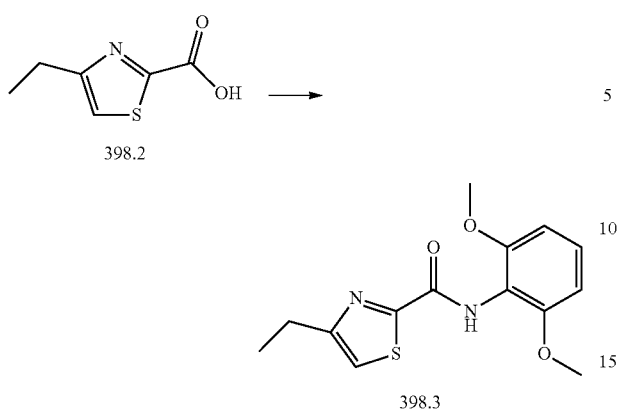

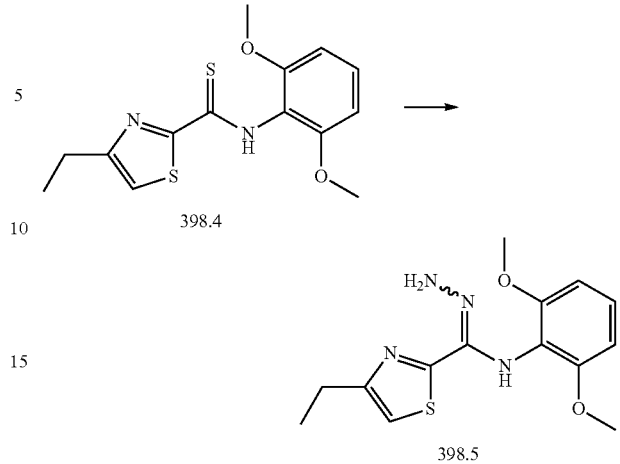

N-(2,6-Dimethoxyphenyl)-4-ethylthiazole-2-carboxamide, Example 398.3. An ice-cooled solution of 398.2 (3.70 g, 65% pure, 15.3 mmol) in DMF (55 mL) was treated with TEA (5.95 mL, 42.8 mmol) followed by HATU (7.0 g, 18.4 mmol) directly. After 5 min, 2,6-dimethoxyaniline (Amfinecom Inc., 2.3 g, 15.3 mmol) was added. The resulting brown solution was warmed to RT and stirred for 1.75 h. The reaction was then partitioned between water (275 mL) and EtOAc (2×). The combined organic layers were washed with water (1×) and brine (1×), dried over anhydrous sodium sulfate, and concentrated in vacuo. The residue was purified by silica gel chromatography (eluent: 10-100% EtOAc in hexanes) to provide Example 398.3 (2.54 g, 57% yield) as a light yellow solid. LCMS-ESI (pos.) m/z: 293.0 (M+H)$^+$.

N-(2,6-dimethoxyphenyl)-4-ethylthiazole-2-carbohydrazonamide, Example 398.5. To a solution of 398.4 (1.13 g, 3.7 mmol) in THF (43 mL) was added hydrazine hydrate (80%, 2.2 mL, 36.5 mmol). The resulting yellow solution was heated at 50° C. for 3.75 h and then was allowed to cool to RT. The reaction was quenched with saturated aqueous NaHCO$_3$ (140 mL) and extracted with EtOAc (1×). The organic layer was washed with brine (1×), dried over anhydrous sodium sulfate, and concentrated in vacuo. The residue was purified by chromatography on basic alumina (eluent: 0-3.5% MeOH in DCM) to provide 398.5 (726 mg, 65% yield) as a bright yellow oil. LCMS-ESI (pos.) m/z: 307.1 (M+H)$^+$.

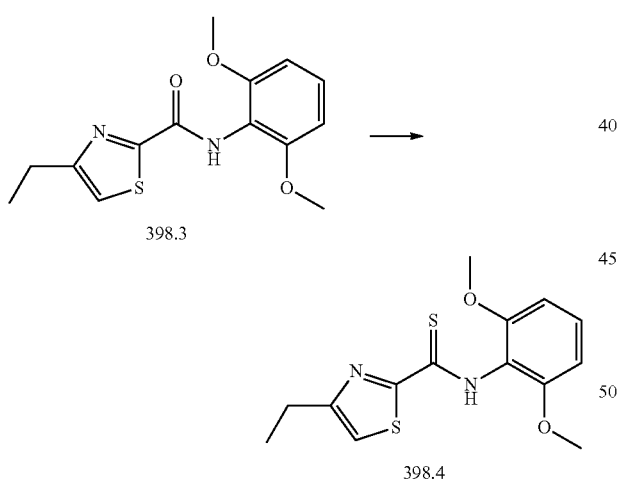

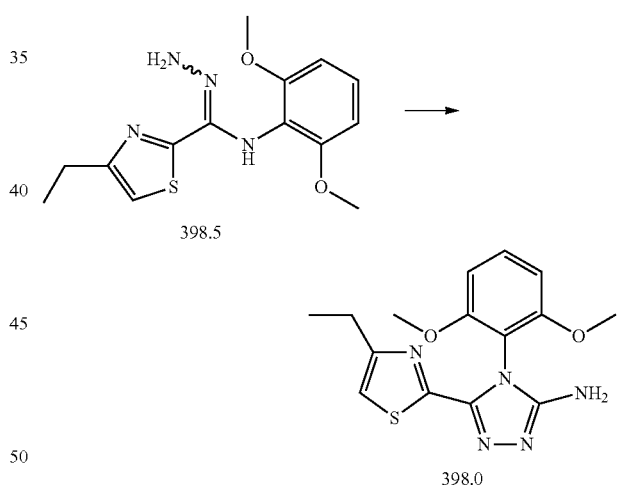

N-(2,6-Dimethoxyphenyl)-4-ethylthiazole-2-carbothioamide, Example 398.4. To a suspension of 398.3 (2.54 g, 8.7 mmol) in toluene (87 mL) was added Lawesson's reagent (1.93 g, 4.8 mmol). The resulting light yellow slurry was heated at reflux for 4 h and then was cooled to RT. The reaction was quenched with water (135 mL) and extracted with EtOAc (2×). The combined organic layers were washed with brine (1×), dried over anhydrous sodium sulfate, and concentrated in vacuo. The residue was purified by silica gel chromatography (eluent: 5-95% EtOAc in hexanes) to provide 398.4 (1.13 g, 42% yield) as a bright yellow solid. LCMS-ESI (pos.) m/z: 309.0 (M+H)$^+$.

4-(2,6-Dimethoxyphenyl)-5-(4-ethylthiazol-2-yl)-4H-1,2,4-triazol-3-amine, Example 398.0. To a slurry of 3.05 (726 mg, 2.4 mmol) in EtOH (30 mL) was added cyanogen bromide (5.0 M solution in ACN, 4.27 mL, 21.3 mmol) slowly via syringe over 5 min. The resulting yellow slurry was heated at 60° C. for 23.75 h, then was allowed to cool to RT. The reaction was quenched with water (2.5 mL) and concentrated in vacuo. The residue was purified in two batches by reverse phase preparatory HPLC (Sunfire 5 μM C18 column, eluent: 15-45% ACN in water over a 35 min period where both solvents contain 0.1% TFA) to provide 398.0 (722 mg, 92% yield) as a tan solid. LCMS-ESI (pos.) m/z: 332.1 (M+H)$^+$.

The compounds set forth in the following table were synthesized following the procedure in Example 398.0 using the known starting material as described.

TABLE 24

| Example | Reagents | Structure, Name and Data |
|---|---|---|
| 398.6 | 2-bromo-1-cyclopropyethanone (Accela Chembio Inc.). | 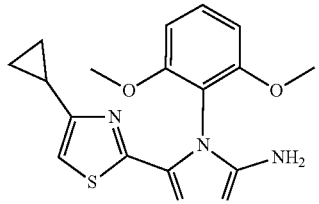<br>5-(4-cyclopropylthiazol-2-yl)-4-(2,6-dimethoxyphenyl)-4H-1,2,4-triazol-3-amine.<br>LCMS-ESI (pos.) m/z: 344.1 (M + H)⁺. |

Example 399.0. Preparation of 2-(5-bromo-4-(2,6-dimethoxyphenyl)-4H-1,2,4-triazol-3-yl)-4-methylthiazole

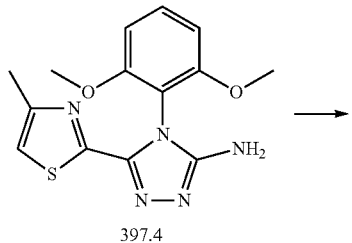

397.4

→

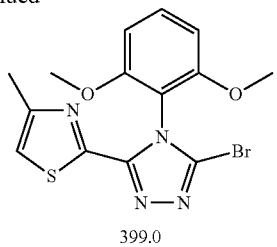

399.0

2-(5-Bromo-4-(2,6-dimethoxyphenyl)-4H-1,2,4-triazol-3-yl)-4-methylthiazole, Example 399.0. To a slurry of 397.4 (1.0 g, 3.2 mmol) in dibromomethane (31.5 mL) was added benzyltriethylammonium bromide (2.57 g, 9.5 mmol) and sodium nitrite (4.4 g, 63 mmol) directly followed by 2,2-dichloroacetic acid (520 µL, 6.3 mmol) slowly via syringe. The resulting dark orange slurry was stirred at RT for 3 h and then was loaded directly onto a silica gel column and purified by silica gel chromatography (eluent: 1-4% MeOH in DCM) to provide 399.0 (645 mg, 54% yield) as an orange solid. LCMS-ESI (pos.) m/z: 381.0 (M+H)⁺.

The compounds set forth in the following table were synthesized following the procedure in Example 399.0 using the starting material as described.

TABLE 25

| Example | Reagents | Structure, Name and Data |
|---|---|---|
| 399.1 | 4-(2,6-dimethoxyphenyl)-5-(4-ethylthiazol-2-yl)-4H-1,2,4-triazol-3-amine (Example 398.0). | 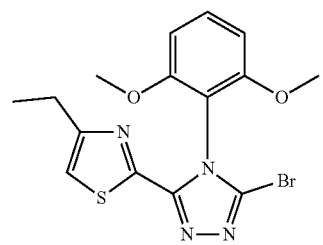 [SMILES: CCc1csc(-c2nnc(Br)n2-c2c(OC)cccc2OC)n1]<br>2-(5-bromo-4-(2,6-dimethoxyphenyl)-4H-1,2,4-triazol-3-yl)-4-ethylthiazole.<br>LCMS-ESI (pos.) m/z: 395.0 (M + H)⁺. |
| 399.2 | 5-(4-cyclopropylthiazol-dimethoxyphenyl)-4H-1,2,4-triazol-3-amine (Example 398.6). | 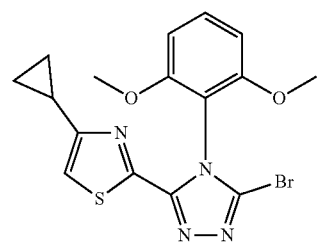 [SMILES: COc1cccc(OC)c1-n1c(Br)nnc1-c1nc(C2CC2)cs1]<br>2-(5-bromo-4-(2,6-dimethoxyphenyl)-4H-1,2,4-triazol-3-yl)-4-cyclopropylthiazole.<br>LCMS-ESI (pos.) m/z: 407.0 (M + H)⁺. |

TABLE 25-continued

| Example | Reagents | Structure, Name and Data |
|---|---|---|
| 399.3 | 4-(2,6-dimethoxyphenyl)-5-(4-isopropylthiazol-2-yl)-4H-1,2,4-triazol-3-amine (Example 397.10). | 2-(5-bromo-4-(2,6-dimethoxyphenyl)-4H-1,2,4-triazol-3-yl)-4-isopropylthiazole. LCMS-ESI (pos.) m/z: 409.0 (M + H)+. |
| 399.4 | 4-(2,6-dimethoxyphenyl)-5-(2-ethylthiazol-4-yl)-4H-1,2,4-triazol-3-amine (Example 397.11). | 4-(5-bromo-4-(2,6-dimethoxyphenyl)-4H-1,2,4-triazol-3-yl)-2-ethylthiazole. LCMS-ESI (pos.) m/z: 395.0 (M + H)+. |
| 399.5 | 4-(2,6-dimethoxyphenyl)-5-(1-methyl-/H-pyrazol-3-yl)-4H-1,2,4-triazol-3-amine (Example 397.15). | 3-bromo-4-(2,6-dimethoxyphenyl)-5-(1-methyl-1H-pyrazol-3-yl)-4H-1,2,4-triazole. LCMS-ESI (pos.) m/z: 364.1 (M + H)+. |

Example 400.0. Preparation of 2-(5-fluoropyrimidin-2-yl)ethanesulfonamide

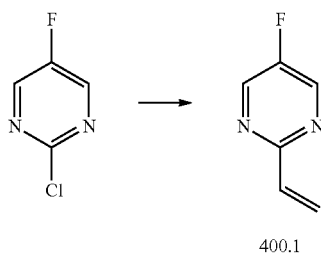

400.1

5-Fluoro-2-vinylpyrimidine, Example 400.1. To a solution of 2-chloro-5-fluoropyrimidine (10.0 g, 75.46 mmol, Sigma Aldrich) in DMF (100 mL) was added tributyl(vinyl) tin (31.1 g, 98.09 mmol) at RT. The reaction mixture was purged with N₂ for 5 min and Pd(PPh₃)₄ (2.62 g, 2.26 mmol) was added. The reaction mixture was further degassed with N₂ for 5 min and stirred at 100° C. for 24 h. After completion of the reaction (monitored by TLC), the reaction mixture was cooled to RT and quenched with water (100 mL). The aqueous layer was extracted with diethyl ether (2×100 mL) and the combined organic layers were washed with brine (100 mL), dried over anhydrous Na₂SO₄, and concentrated in vacuo to obtain the initial product which was purified by silica gel chromatography (eluent: 6% EtOAc in hexanes) to provide 400.1 (8.0 g, 85% yield) as an oil. $^1$H NMR (400 MHz, CDCl₃) δ 8.58-8.49 (m, 2H), 6.86 (dd, J=17.4, 10.6 Hz, 1H), 6.53 (d, J=17.3 Hz, 1H), 5.70 (d, J=10.6 Hz, 1H). LCMS-ESI (pos.) m/z: =125.1.

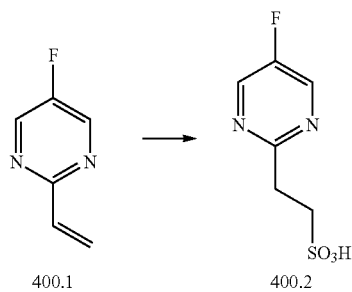

400.1             400.2

2-(5-Fluoropyrimidin-2-yl) ethanesulfonic acid, Example 400.2. A solution of 400.1 (20.0 g, 16.12 mmol) in a saturated aqueous solution of NaHSO₃ (80 mL) was stirred at RT for 12h. After completion of the reaction (monitored by TLC), the reaction mixture was concentrated under reduced pressure and the residue was purified by silica gel chromatography (eluent: 4-10% H₂O in ACN) to provide 400.2 (16.0 g, 48% yield) as white solid. ¹H NMR (400 MHz, DMSO-d₆) δ 8.89-8.73 (m, 2H), 3.17 (t, J=8.2 Hz, 2H), 2.85 (t, J=8.2 Hz, 2H).

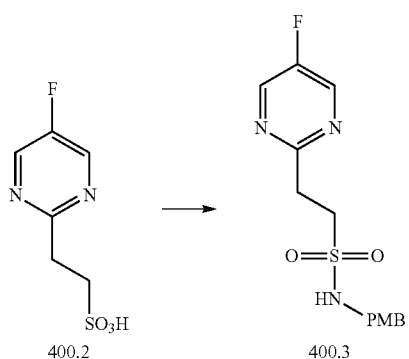

2-(5-Fluoropyrimidin-2-yl)-N-(4-methoxybenzyl)ethanesulfonamide, Example 400.3. To a suspension of 400.2 (16.0 g, 77.30 mmol) in DCM (385 mL) was added oxalyl chloride (29.4 g, 231.8 mmol) followed by DMF (1 mL) at 0° C. The reaction mixture was stirred at RT for 1 h and concentrated in vacuo. The reaction mixture was azeotroped with cyclopentylmethylether to remove the traces of oxalyl chloride. The reaction mixture was diluted with DCM (385 mL), cooled to 0° C., and 4-methoxybenzylamine (31.8 g, 231.88 mmol) followed by TEA (39.1 g, 386.4 mmol) were added. The reaction mixture was stirred at RT for 12 h. After completion of the reaction (monitored by TLC), the reaction mixture was quenched with water (500 mL). The aqueous layer was extracted with DCM (2×400 mL). The organic layers were combined and washed with brine (1000 mL), dried over anhydrous Na₂SO₄, and concentrated in vacuo to obtain the initial material which was purified by silica gel chromatography (eluent: 55% EtOAc in hexanes) to provide 400.3 (13.5 g, 54% yield) as an off yellow solid. LCMS-ESI (pos.) m/z: 326.1.

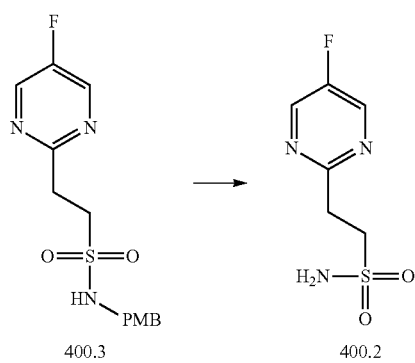

2-(5-Fluoropyrimidin-2-yl)ethanesulfonamide, Example 400.0. To a suspension of 400.3 (13.5 g, 41.41 mmol) in DCM (46 mL) was added TFA (207 mL) at 0° C. The reaction mixture was stirred at RT for 12 h. After completion of the reaction (monitored by TLC), the reaction mixture was concentrated in vacuo providing a residue which was purified by silica gel chromatography (eluent: 65% EtOAc in hexanes) to provide 400.0 (5.3 g, 63% yield) as an off yellow solid. ¹H NMR (400 MHz, DMSO-d₆) δ 8.77 (s, 2H), 6.92 (s, 2H), 3.54-3.48 (m, 2H), 3.24-3.20 (s, 2H). LCMS-ESI (pos.) m/z: 206.0.

Example 401.0. Preparation of 2-(2-cyano-4-fluorophenyl)ethanesulfonamide

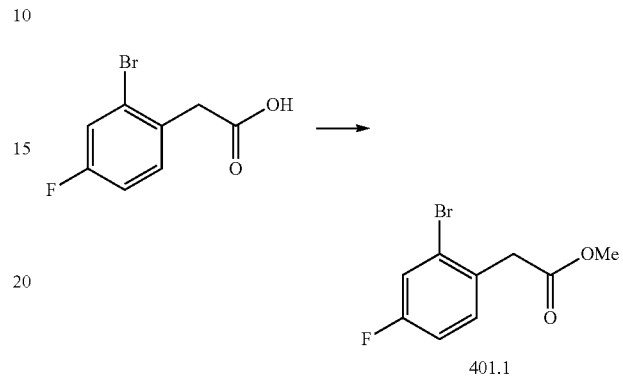

Methyl 2-(2-bromo-4-fluorophenyl) acetate, Example 401.1. To a solution of 2-bromo-4-fluorophenyl acetic acid (commercially available from Combi-Blocks Inc., San Diego, Calif., USA) (25.0 g, 0.11 mol) in MeOH (100 mL) was added thionyl chloride (23.5 mL, 0.32 mol) dropwise at 0° C. The resulting mixture was then heated at 80° C. for 16 h. The mixture was cooled to RT and the volatiles were removed under vacuum. The material thus obtained was diluted with DCM and washed with an aqueous solution of sodium bicarbonate and water. The organic layers were dried over sodium sulfate, filtered, and concentrated in vacuo to afford 401.1 (26 g, 100% yield), which was used as such in the next step. ¹H NMR (400 MHz, DMSO-d₆) δ 7.59 (dd, J=8.6, 2.6 Hz, 1H), 7.47 (dd, J=8.5, 6.2 Hz, 1H), 7.25 (td, J=8.5, 2.7 Hz, 1H), 3.82 (s, 2H), 3.63 (s, 3H).

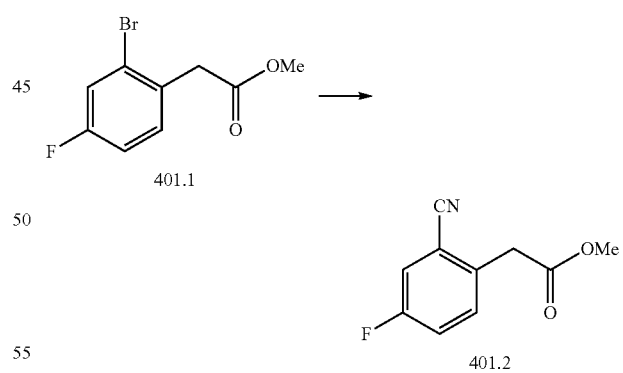

Methyl 2-(2-cyano-4-fluorophenyl) acetate, Example 401.2. To a solution of 401.1 (8.0 g, 0.032 mol) in DMA (60 mL) was added zinc cyanide (5.7 g, 0.049 mol). The flask was then degassed with argon and bis-(tri-tert-butylphosphine)palladium (1.7 g, 0.003 mol) was added. The resulting mixture was heated at 110° C. for 18 h in a sealed tube. Thereafter, the reaction mixture was cooled to RT, diluted with water and extracted with EtOAc. The combined organic layers were dried over sodium sulfate and concentrated in vacuo. The residue was purified by silica gel chromatography (eluent: 20-25% EtOAc in hexanes) to obtain 401.2 (5.4 g, 86% yield) as a light brown liquid. $^1$H NMR (400 MHz, DMSO-$d_6$) δ 7.91-7.81 (m, 1H), 7.68-7.51 (m, 2H), 3.95 (s, 2H), 3.65 (s, 3H). LCMS-ESI (neg.) m/z: 192.2 (M–H)$^-$.

purification. $^1$H NMR (400 MHz, DMSO-$d_6$) δ 7.81-7.84 (dd, J=2.4 Hz, 8.8 Hz, 1H), 7.56-7.66 (m, 2H), 3.90-3.94 (t, J=6.8 Hz, 13.6 Hz, 2H), 3.22-3.25 (t, J=6.8 Hz, 13.2 Hz, 2H). LCMS-ESI (neg.) m/z: 182.0 (M–H)$^-$.

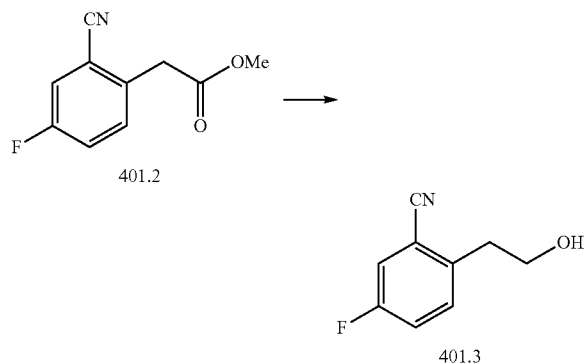

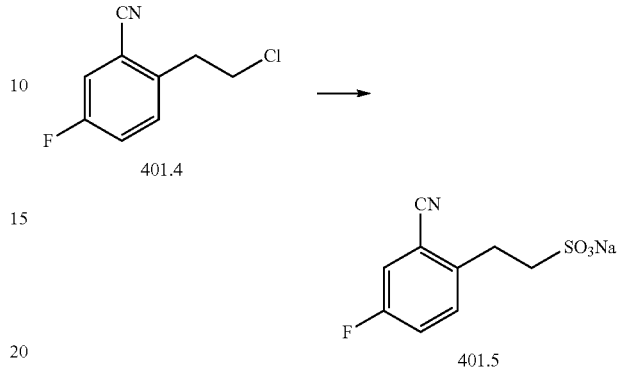

5-Fluoro-2-(2-hydroxyethyl)benzonitrile, Example 401.3. To a solution of 401.2 (5.3 g, 0.027 mol) in THF (60 mL) at 0° C. was added LiBH$_4$ (1.20 g, 0.055 mol) portion-wise. The resulting mixture was stirred at RT for 5 h. After completion of the reaction (monitored by TLC), the reaction mixture was cooled to 0° C. and quenched with water. The solvent was evaporated to obtain the initial material which was further diluted with water and extracted with EtOAc. The combined organic layers were dried over anhydrous sodium sulfate, filtered, and concentrated in vacuo. The residue was purified by silica gel chromatography (eluent: 15-20% EtOAc in hexanes) to obtain 401.3 (3.1 g, 67% yield) as a light brown liquid. $^1$H NMR (400 MHz, DMSO-$d_6$) δ 7.81-7.73 (m, 1H), 7.52 (dd, J=10.6, 8.0 Hz, 2H), 4.82 (t, J=5.2 Hz, 1H), 3.64 (dd, J=11.9, 6.5 Hz, 2H), 2.91 (t, J=6.6 Hz, 2H).

Sodium 2-(2-cyano-4-fluorophenyl)ethanesulfonate, Example 401.5. To a solution of 401.4 (3.0 g, 0.016 mol) in H$_2$O (50 mL) at RT was added sodium sulfite (3.1 g, 0.024 mol). The reaction mixture was heated at reflux for 18 h. After completion of the reaction (monitored by TLC), the reaction mixture was concentrated in vacuo to obtain the initial material which was further stirred with EtOAc and filtered to obtain 401.5 (5.8 g) as an off-white solid which was used for the next reaction without further purification. $^1$H NMR (400 MHz, DMSO-$d_6$) δ 7.74-7.76 (dd, J=2 Hz, 8.4 Hz, 1H), 7.47-7.55 (m, 2H), 3.05-3.09 (t, J=8 Hz, 16.4 Hz, 2H), 2.69-2.74 (t, J=8.4 Hz, 16.4 Hz, 2H). LCMS-ESI (neg.) m/z: 228.0 (M–H)$^-$.

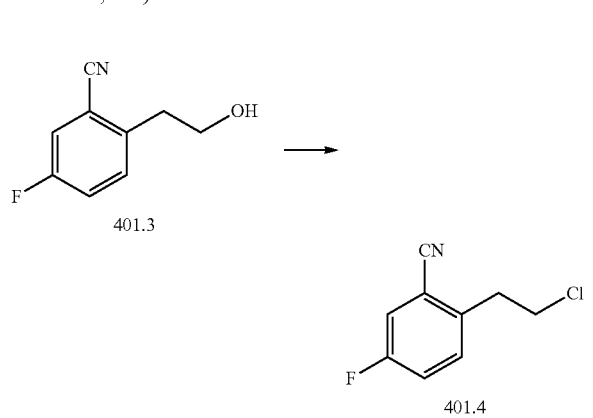

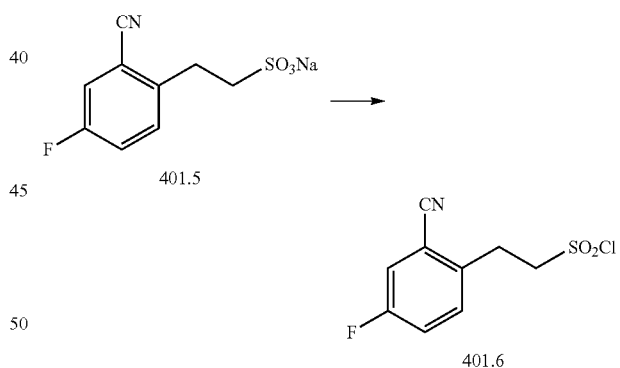

2-(2-Chloroethyl)-5-fluorobenzonitrile, Example 401.4. To a solution of 401.3 (3.0 g, 0.018 mol) in DCM (50 mL) was added thionyl chloride (6.6 mL, 0.091 mol) dropwise followed by DMF (4 drops) at 0° C. The resulting mixture was heated at 55° C. for 7 h. After completion of the reaction (monitored by TLC), the reaction mixture was concentrated in vacuo to obtain the initial product, which was diluted with water and extracted with EtOAc. The combined organic layers were dried over anhydrous sodium sulfate and concentrated in vacuo to obtain 401.4 (3.0 g, 90% yield) as a brown liquid which was used in the next step without further 2-(2-Cyano-4-fluorophenyl)ethanesulfonyl chloride, Example 401.6. To a solution of 401.5 (5.8 g) in benzene (50 mL) was added thionyl chloride (2.5 mL, 0.035 mol) dropwise followed by DMF (3 drops) at 0° C. The resulting mixture was heated to reflux for 16 h. After completion of the reaction (monitored by TLC), the mixture was cooled to RT, poured into ice water, and extracted with EtOAc. The EtOAc layer was dried over anhydrous sodium sulfate and concentrated in vacuo to obtain 401.6 (3.4 g, 84% yield over two steps) as a brown solid. $^1$H NMR (400 MHz, CDCl$_3$) δ 7.47-7.38 (m, 2H), 7.33 (td, J=8.2, 2.7 Hz, 1H), 3.98 (dd, J=8.7, 6.7 Hz, 2H), 3.56-3.53 (m, 2H). LCMS-ESI (neg.) m/z: 245.9 (M–H)$^-$.

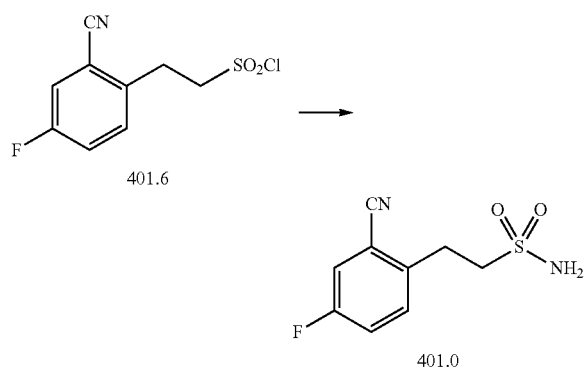

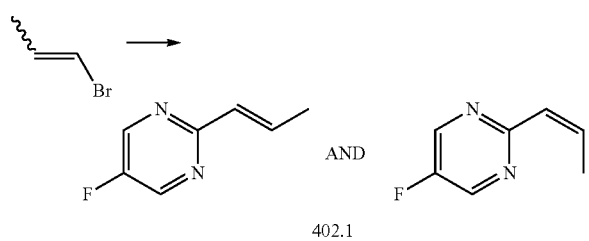

2-(2-Cyano-4-fluorophenyl)ethanesulfonamide, Example 401.0. To a mixture of aqueous ammonia (10 mL, 77 mmol) and DCM (30 mL, 468 mmol) was added 401.6 (1.42 g, 5.73 mmol) in portions at RT. The reaction mixture was stirred at RT for 2 h. LCMS analysis indicated the reaction was complete. The mixture was neutralized by adding concentrated HCl solution and then extracted with DCM. The extract was washed with water and a saturated NaHCO$_3$ solution twice, dried over anhydrous sodium sulfate and concentrated in vacuo to provide Example 401.0 (1.1 g, 84% yield) as a white solid. LCMS-ESI (pos.), m/z: 229.1 (M+H)$^+$.

Example 402.0. Preparation of (S)-1-(5-fluoropyrimidin-2-yl)propane-2-sulfonamide and (R)-1-(5-fluoropyrimidin-2-yl)propane-2-sulfonamide

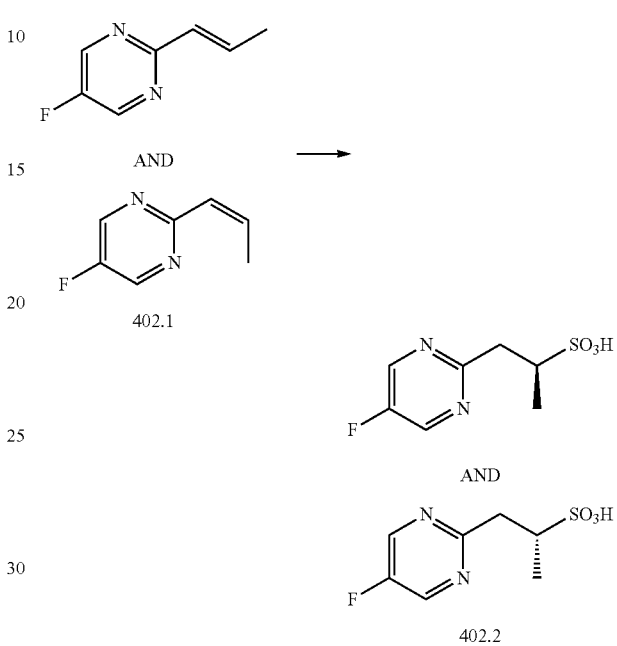

(E)-5-Fluoro-2-(prop-1-en-1-yl)pyrimidine and (Z)-5-fluoro-2-(prop-1-en-1-yl)pyrimidine, Example 402.1. To magnesium turnings (9.0 g, 371.9 mmol) was added 1-2 crystals of iodine under anhydrous conditions. The mixture was heated at 60° C. for 5 min under reduced pressure to activate the magnesium. The flask was then cooled to RT and THF (370 mL) was added. The resulting mixture was heated to 65° C. and then (Z/E)-1-bromo-1-propene (45 g, 371.9 mmol) was added dropwise. The mixture was then stirred at 65° C. for 2 h under a nitrogen atmosphere. Thereafter, the mixture was cooled to RT and cooled in an ice bath. Zinc chloride (1.0 M in diethyl ether, 283 mL, 283 mmol) was then added dropwise over 10 min. The internal temperature of the reaction was kept at 10-15° C. during the addition. The resulting organozinc reagent was stirred at RT for 45 min. In a separate RBF, a solution of 2-chloro-5-fluoropyrimidine (commercially available from Novochemy, Jupiter, Fla., USA) (25 g, 189 mmol), S-phos (7.7 g, 18.8 mmol) and palladium (II) acetate (2.1 g, 9.4 mmol) in THF (38 mL) were degassed with nitrogen gas for 5 min. The organozinc reagent was then added dropwise. The resulting mixture was heated at 60° C. for 12 h. After completion of reaction (monitored by TLC), the reaction mixture was quenched with water (50 mL) and acidified with 1.0 N HCl (700 mL, pH 2). The mixture was then extracted with diethyl ether (2×500 mL). The combined organic layers were washed with brine (200 mL), dried over sodium sulfate, and concentrated under reduced pressure at 20° C. to a volume of approximately 50 mL containing 402.1, which was used as such in the next step.

(S)-1-(5-Fluoropyrimidin-2-yl)propane-2-sulfonic acid and (R)-1-(5-fluoropyrimidin-2-yl)propane-2-sulfonic acid, Example 402.2. To a solution of 402.1 (188.6 mmol) in THF (50 mL) was added an aqueous solution of sodium bisulfite (19.6 g, 188.6 mmol in 100 mL of H$_2$O). The reaction mixture was stirred at RT for 20 h. Once the reaction was complete (monitored by TLC), the mixture was brought to a pH of about 1 with concentrated HCl (10 mL). The aqueous layer was then concentrated under reduced pressure to furnish the initial product which was suspended in EtOH (250 mL). The product thus obtained was heated to reflux, filtered hot, and rinsed with hot EtOH (100 mL). The filtrate was concentrated under reduced pressure to give a brown solid which was recrystallized from IPA (50 mL) to afford 402.2 (20 g, 48% yield) as a brown solid. $^1$H NMR (400 MHz, D$_2$O) δ 8.69 (s, 2H), 3.47 (td, J=9.8, 8.2, 4.0 Hz, 2H), 3.06 (dd, J=16.1, 10.2 Hz, 1H), 1.24 (d, J=6.5 Hz, 3H). LCMS-ESI (neg.) m/z: 118.9 (M−H)$^-$.

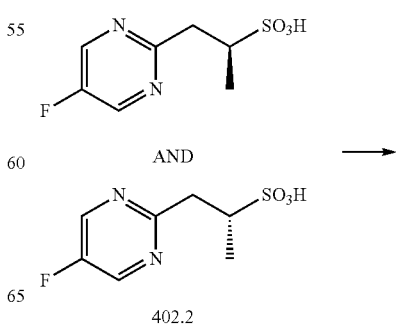

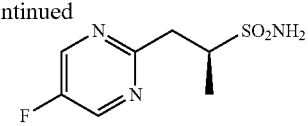

AND

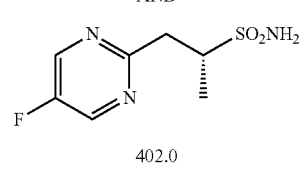

402.0

(S)-1-(5-Fluoropyrimidin-2-yl)propane-2-sulfonamide and (R)-1-(5-fluoropyrimidin-2-yl)propane-2-sulfonamide, Example 402.0. A solution of 402.2 (80 g, 360 mmol) in thionyl chloride (268 mL, 3600 mmol) was heated at 60° C. for 3 h. The reaction was concentrated under reduced pressure to afford the sulfonyl chloride compound which was azeotroped with toluene (3×300 mL). The residue was diluted with DCM (1.0 L) and ammonia gas was sparged through the solution for 15 min at −78° C. The mixture was then stirred at RT for 1 h. Thereafter, the reaction mixture was filtered through Celite® brand filter aid rinsing with DCM (100 mL) and EtOAc (100 mL). The combined filtrate was then concentrated under reduced pressure to obtain a residue which was purified by column chromatography (silica gel, elution 0-60% EtOAc in hexanes) to provide 402.0 (43 g, 54% yield) as a white solid. $^1$H NMR (400 MHz, DMSO-$d_6$) δ 8.86 (d, J=1.1 Hz, 2H), 6.90 (s, 2H), 3.57-3.51 (m, 2H), 2.93 (dd, J=15.4, 11.1 Hz, 1H), 1.19 (d, J=6.5 Hz, 3H). LCMS-ESI (pos.) m/z: 220.0 (M+H)$^+$.

Example 403.0. Preparation of (2S,3R)-3-(5-fluoropyrimidin-2-yl)butane-2-sulfonamide and (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide

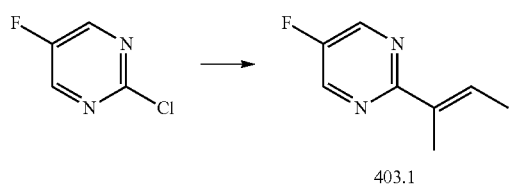

403.1

(E)-2-(But-2-en-2-yl)-5-fluoropyrimidine, Example 403.1. A large microwave vial was charged with potassium (2Z)-2-buten-2-yltrifluoroborate (Sigma-Aldrich, 900 mg, 5.6 mmol), potassium phosphate (3.54 g, 16.7 mmol) and 2-chloro-5-fluoro-pyrimidine (686 µL, 5.6 mmol). DMF (10 mL) and water (2 mL) were added and the mixture was deoxygenated with an Ar stream. Tetrakis(triphenylphosphine)palladium (642 mg, 0.56 mmol) was added, and the slurry was again deoxygentaed with an Ar stream. The vial was then capped and heated in the microwave at 95° C. for 12 h. The reaction mixture was then partitioned between water (60 mL) and diethyl ether (2×). The combined organic layers were washed with water (1×) and brine (1×), dried over anhydrous sodium sulfate, and concentrated in vacuo. The residue was purified by silica gel chromatography (eluent: pure DCM) to provide 403.1 (476 mg, 56% yield) as a light yellow oil. LCMS-ESI (pos.) m/z: 153.2 (M+H)$^+$.

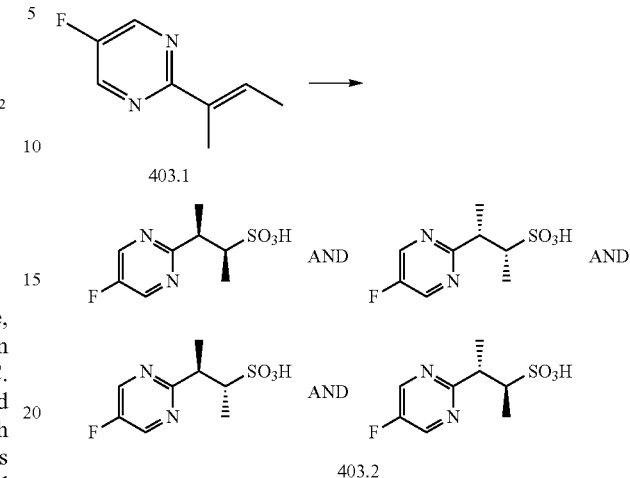

403.2

(2S,3R)-3-(5-Fluoropyrimidin-2-yl)butane-2-sulfonic acid and (2R,3S)-3-(5-fluoropyrimidin-2-yl)butane-2-sulfonic acid and (2R,3R)-3-(5-fluoropyrimidin-2-yl)butane-2-sulfonic acid and (2S,3S)-3-(5-fluoropyrimidin-2-yl)butane-2-sulfonic acid, Example 402.2. To a solution of 403.1 (1.10 g, 7.2 mmol) in THF (12 mL) was added a solution of sodium bisulfite (2.26 g, 21.7 mmol) in water (4 mL). The mixture was heated at 60° C. for 3 d and then was concentrated in vacuo. The residue was purified in batches by reverse phase preparatory HPLC (Sunfire 5 µM C18 column, eluent: 0-40% ACN in water over a 40 min period where both solvents contain 0.1% TFA) to provide 403.2 (1.03 g, 61% yield) as a white solid. LCMS-ESI (pos.) m/z: 235.1 (M+H)$^+$.

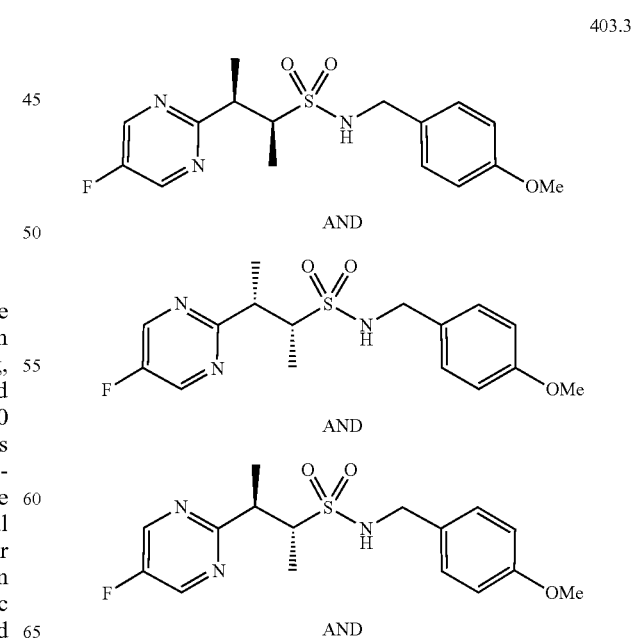

403.3

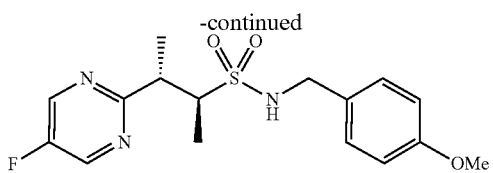

(2S,3R)-3-(5-Fluoropyrimidin-2-yl)-N-(4-methoxybenzyl)butane-2-sulfonamide and (2R,3S)-3-(5-fluoropyrimidin-2-yl)-N-(4-methoxybenzyl)butane-2-sulfonamide and (2R,3R)-3-(5-fluoropyrimidin-2-yl)-N-(4-methoxybenzyl)butane-2-sulfonamide and (2S,3S)-3-(5-fluoropyrimidin-2-yl)-N-(4-methoxybenzyl)butane-2-sulfonamide, Example 403.3. To a suspension of 403.2 (49.2 mg, 0.21 mmol) in DCM (2.5 mL) was added oxalyl chloride (37 µL, 0.42 mmol) via syringe followed by a catalytic amount of DMF. Vigorous bubbling was observed. The resulting white slurry was stirred at RT for 2.5 h and then was concentrated in vacuo. The residue was azeotroped to dryness with benzene and then was suspended in DCM (2.5 mL). 4-Methoxybenzylamine (60 µL, 0.46 mmol) and TEA (102 µL, 0.74 mmol) were added sequentially via syringe. The resulting light yellow slurry was stirred at RT overnight. The reaction mixture was partitioned between water and DCM (3×). The combined organic layers were dried over anhydrous magnesium sulfate and concentrated in vacuo. The residue was purified by reverse phase preparatory HPLC (Sunfire 5 µM C18 column, eluent: 30%-70% ACN in water over a 35 min period where both solvents contain 0.1% TFA) to provide 403.3 (16.2 mg, 22% yield) as a light yellow oil. LCMS-ESI (pos.) m/z: 376.1 (M+Na)⁺.

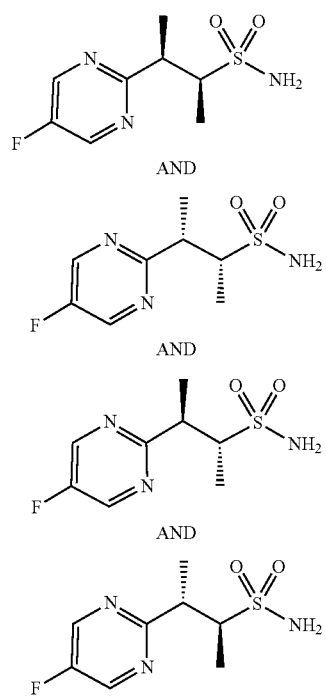

(2S,3R)-3-(5-Fluoropyrimidin-2-yl)butane-2-sulfonamide and (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide, Example 403.0. A flask was charged with 403.3 (84 mg, 0.21 mmol) and treated with TFA (4.0 mL, 54 mmol) via syringe. The resulting red solution was stirred for 20 h and then was directly concentrated in vacuo. The residue was purified by silica gel chromatography (eluent: 0-3% MeOH in DCM) to provide 403.0 (112 mg, 65% yield) as a yellow solid. LCMS-ESI (pos.) m/z: 234.1 (M+H)⁺.

Example 404.5. Preparation of (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide

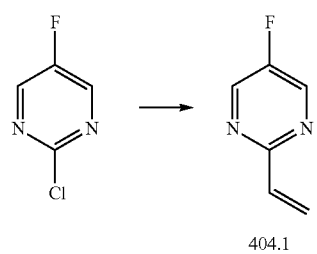

5-Fluoro-2-vinylpyrimidine, Example 404.1. To a solution of 2-chloro-5-fluoropyrimidine (10.0 g, 75.46 mmol, Sigma Aldrich) in DMF (100 mL) was added tributyl(vinyl)tin (31.1 g, 98.09 mmol) at RT. The reaction mixture was purged with $N_2$ for 5 min and Pd(PPh₃)₄ (2.62 g, 2.26 mmol) was added. The reaction mixture was further degassed with $N_2$ for 5 min and stirred at 100° C. for 24 h. After completion of the reaction (monitored by TLC), the reaction mixture was cooled to RT and quenched with water (100 mL). The aqueous layer was extracted with diethyl ether (2×100 mL) and the combined organic layers were washed with brine (100 mL), dried over anhydrous Na₂SO₄, and concentrated in vacuo to obtain the initial product which was purified by silica gel column chromatography (eluent: 6% EtOAc in hexanes) to provide 404.1 (8.0 g, 85% yield) as a yellow oil. LCMS-ESI (pos.) m/z: 125.1 (M+H)⁺.

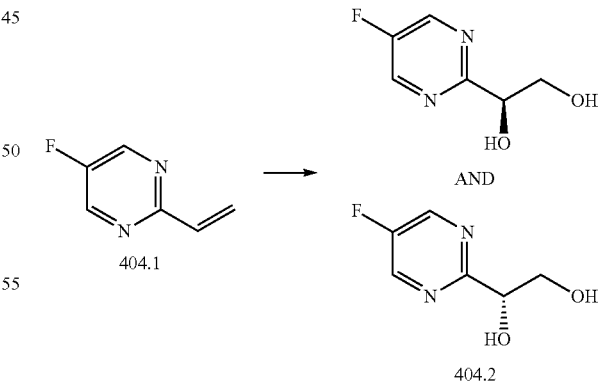

(S)-1-(5-Fluoropyrimidin-2-yl)ethane-1,2-diol and (R)-1-(5-fluoropyrimidin-2-yl)ethane-1,2-diol, Example 404.2. To a solution of 404.1 (2.68 g, 21.6 mmol) in a mixture of acetone (200 mL) and water (60 mL) was added a catalytic amount of osmium tetroxide followed by 4-methylmorpholine-N-oxide (8.85 g, 76 mmol). The resulting dark brown solution was stirred at RT for 24 h and then was partially concentrated in vacuo to remove acetone. The residue was diluted with brine (30 mL) and extracted with DCM (6×). The combined organic layers were dried over anhydrous sodium sulfate and concentrated. The residue was purified by silica gel chromatography (eluent: 2-50% MeOH in DCM) to provide 404.2 (899 mg, 26% yield) as a brown oil. LCMS-ESI (pos.) m/z: 159.2 (M+H)+.

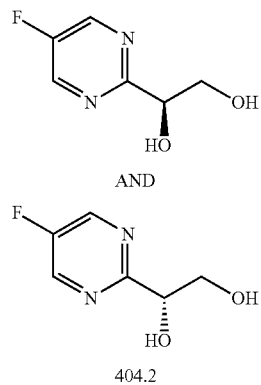

404.2

5-Fluoropyrimidine-2-carbaldehyde, Example 404.3. To a solution of 404.2 (899 mg, 5.69 mmol) in a mixture of THF (43 mL) and water (15 mL) was added sodium periodate (3.41 g, 15.9 mmol). The resulting thick orange slurry was stirred at RT for 2 h and then was filtered. The filtrate was partially concentrated on a rotary evaporator to remove THF. The residue was partitioned between water (15 mL) and DCM (3×). The combined organic layers were dried over anhydrous sodium sulfate and concentrated in vacuo to provide 404.3 (512 mg, 75% yield) as an orange oil. The aldehyde was used without purification. LCMS-ESI (pos.) m/z: 127.1 (M+H)+.

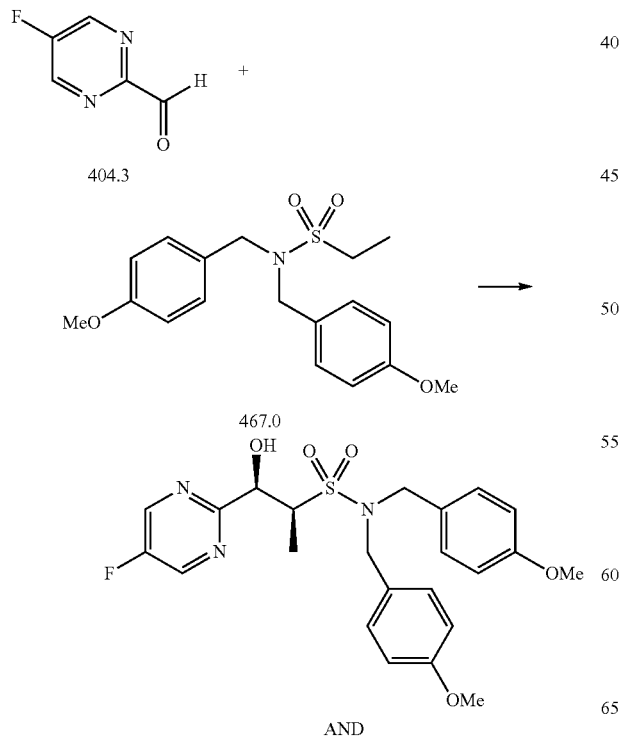

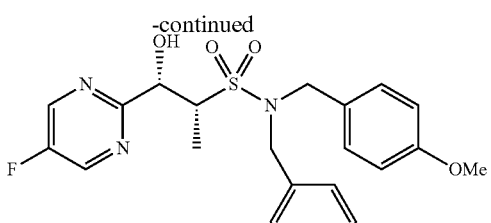

AND

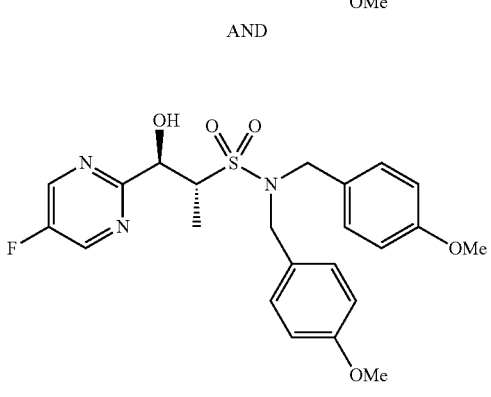

AND

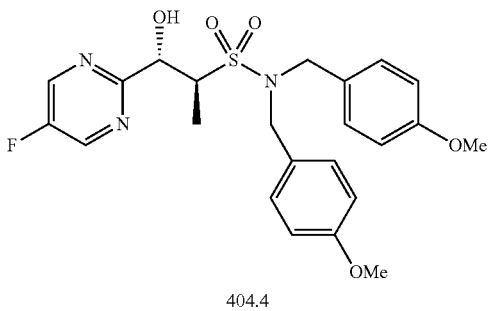

404.4

(1R,2S)-1-(5-fluoropyrimidin-2-yl)-1-hydroxy-N,N-bis(4-methoxybenzyl)propane-2-sulfonamide and (1S,2R)-1-(5-fluoropyrimidin-2-yl)-1-hydroxy-N,N-bis(4-methoxybenzyl)propane-2-sulfonamide and (1R,2R)-1-(5-fluoropyrimidin-2-yl)-1-hydroxy-N,N-bis(4-methoxybenzyl)propane-2-sulfonamide and (1S,2S)-1-(5-fluoropyrimidin-2-yl)-1-hydroxy-N,N-bis(4-methoxybenzyl)propane-2-sulfonamide, Example 404.4. To a −60° C. solution of Example 467.0 (2.20 g, 6.3 mmol) in THF (13 mL) was added n-butyllithium (2.5 M solution in hexanes, 2.72 mL, 6.8 mmol) slowly via syringe. After 10 min, a solution of 404.3 (660 mg, 5.2 mmol) in THF (5 mL) was added dropwise via cannula at −60° C. The resulting mixture was stirred at −60° C. for 15 min. The mixture was then warmed to RT and stirred overnight. The reaction was quenched with a saturated aqueous ammonium chloride solution and extracted with EtOAc (3×). The combined organic layers were dried over anhydrous sodium sulfate and concentrated in vacuo. The residue was purified by silica gel chromatography (eluent: 20-70% EtOAc in hexanes) to provide 404.4 (547 mg, 22% yield) as a red solid. LCMS-ESI (pos.) m/z: 498.0 (M+Na)+.

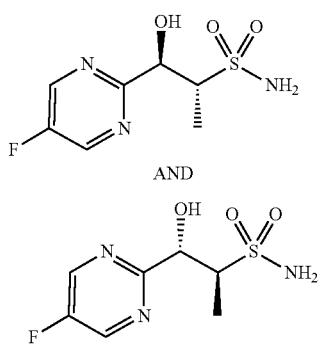

404.5

AND (1R,2R)-1-(5-Fluoropyrimidin-2-yl)-1-hydroxypropane-2-sulfonamide and (1S,2S)-1-(5-fluoropyrimidin-2-yl)-1-hydroxypropane-2-sulfonamide, Example 404.5. A flask was charged with 404.4 (545 mg, 1.15 mmol) and was treated with TFA (11.5 mL, 155 mmol) and anisole (501 L, 4.6 mmol). The resulting red solution was stirred overnight. The mixture was then directly concentrated in vacuo. The residue was purified twice by silica gel chromatography (eluent: 1-6% MeOH in DCM) to provide 404.5 (trans diastereomer, 69 mg, 51% yield) as a pink solid as the first-eluting peak. LCMS-ESI (pos.) m/z: 236.2 (M+Na)⁺.

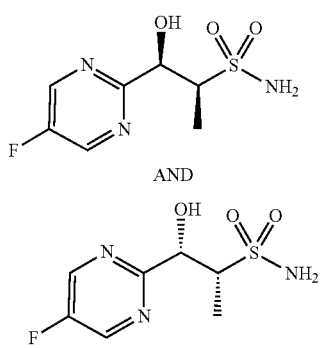

404.6

AND (1R,2S)-1-(5-fluoropyrimidin-2-yl)-1-hydroxypropane-2-sulfonamide and (1S,2R)-1-(5-fluoropyrimidin-2-yl)-1-hydroxypropane-2-sulfonamide, Example 404.6. Further elution under the conditions described in Example 404.5 delivered 404.6 (cis diastereomer, 66 mg, 49% yield) as the second-eluting peak. The product is a pink solid. LCMS-ESI (pos.) m/z: 236.2 (M+Na)⁺.

Example 405.0. Preparation of (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamidesulfonamide

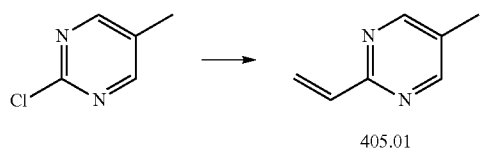

405.01

5-Methyl-2-vinylpyrimidine, Example 405.01. A 3-necked 3 L RBF was fitted with a reflux condenser, a temperature controller and a septum and was charged with 2-chloro-5-methylpyrimidine (81 mL, 778 mmol), potassium vinyltrifluoroborate (156 g, 1167 mmol), triphenylphosphine (18.02 mL, 78 mmol), and cesium carbonate (156 mL, 1945 mmol). Water (1565 mL) was added, and the mixture was stirred for 2 min and then THF (244 mL) was added. Argon was sparged through the mixture for 5 min and then palladium (II) chloride (1.72 g, 38.9 mmol) was added. The reaction was further sparged with argon for 5 min. The temperature was raised to 62° C. and stirring was continued until completion. The reaction was cooled to RT and filtered through two Whatman GF/F filter cups, rinsing with diethyl ether. The mixture was transferred to a separatory funnel and the layers were separated. The aqueous layer was further extracted with diethyl ether (4×). The combined organic layers were dried over anhydrous magnesium sulfate and partially concentrated in vacuo at 20° C. and 115 torr for an extended period of time to give an orange liquid. The initial product was purified by Kugelrohr distillation to provide 405.01 (65.4 g, 70% yield) as a light yellow oil. LCMS-ESI (pos.) m/z: 121.1 (M+H)⁺.

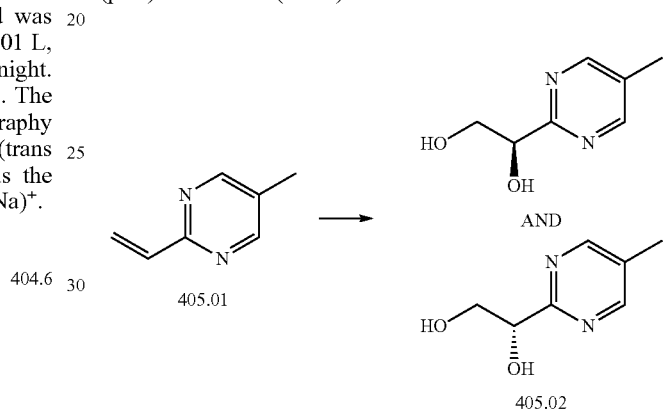

405.01

AND 405.02

(R)-1-(5-Methylpyrimidin-2-yl)ethane-1,2-diol and (S)-1-(5-methylpyrimidin-2-yl)ethane-1,2-diol, Example 405.02. To a 2 L RBF was added 405.01 (64.5 g, 537 mmol), osmium tetroxide (0.204 mL, 3.93 mmol), 1,4-dioxane (537 mL, 537 mmol), 4-methylmorpholine-n-oxide, 50% wt. in water (40 mL, 341 mmol) and 4-methylmorpholine-4-oxide (94 g, 805 mmol). The resulting mixture was stirred for 2 d after which the solvent was removed in vacuo. The residue was purified by silica gel chromatography (eluent: 0-100% EtOAc/EtOH mixture (3:1) in hexanes). The title product was isolated and was triturated with 40% EtOAc in hexanes. The solid was filtered, washed with 20% EtOAc in hexanes and dried to provide 405.02 (67.3 g, 81% yield). ¹H NMR (400 MHz, CDCl₃) δ 8.59 (s, 2H), 4.81-4.98 (m, 1H), 3.88-4.19 (m, 2H), 2.36 (s, 3H).

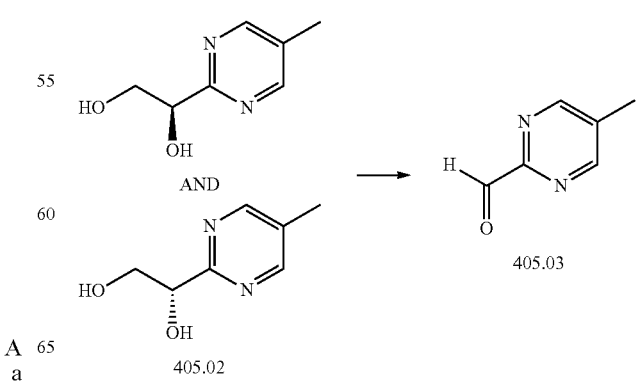

405.02

405.03

5-Methylpyrimidine-2-carbaldehyde, Example 405.03. A 5 L RBF was equipped with a mechanical stirrer and charged with 405.02 (64.3 g, 417 mmol), 1,4-dioxane (1.04 L), and water (261 mL). The reaction mixture was cooled to 0° C. Sodium periodate (223 g, 1043 mmol) was added and the reaction was allowed to gradually warm to RT. After an additional 2.3 h at RT, DCM (2 L) was added. The resulting solution was filtered through a plug of anhydrous $MgSO_4$ (700 g), and the plug was washed with additional DCM (7 L). The solvent was concentrated in vacuo, and the residue was azeotroped with toluene to provide 405.03 (44 g, 86% yield) as a white solid. LCMS-ESI (pos.) m/z: 122.8 $(M+H)^+$.

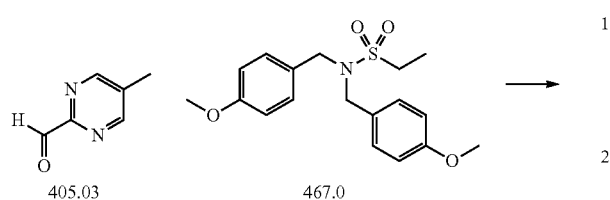

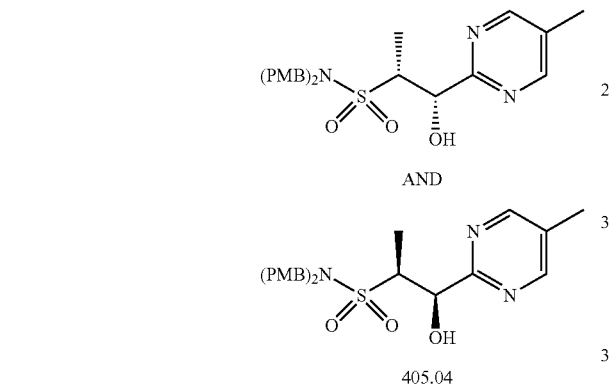

(1R,2S)-1-Hydroxy-N,N-bis(4-methoxybenzyl)-1-(5-methylpyrimidin-2-yl)propane-2-sulfonamide and (1S,2S)-1-hydroxy-N,N-bis(4-methoxybenzyl)-1-(5-methylpyrimidin-2-yl)propane-2-sulfonamide, Example 405.04. A 3 L 3-necked RBF was charged with 467.0 (151 g, 432 mmol) and THF (1.2 L) under nitrogen. A pre-dried addition funnel was attached and the flask was cooled to a −78° C. n-Butyllithium (1.6 M solution in hexanes, 270 mL, 432 mmol) was added via the addition funnel, and the reaction was stirred for 10 min. A solution of 405.03 (44 g, 360 mmol) in THF (300 mL) was then added via cannula. The resulting mixture was stirred at −78° C. for 45 min and then was warmed to RT and stirred for an additional 2.2 h. The reaction was quenched with saturated aqueous ammonium chloride and extracted with EtOAc. The organic layer was dried over anhydrous sodium sulfate and concentrated. The residue was purified by silica gel chromatography (eluent: 0-50% EtOAc in DCM) to provide the cis diastereomer 405.04 (cis diastereomer, 56.4 g, 33% yield) as the first-eluting peak. LCMS-ESI (pos.) m/z: 472.1 $(M+H)^+$.

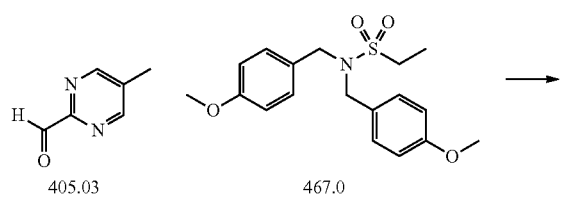

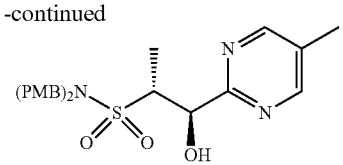

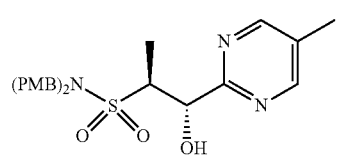

(1R,2R)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide, Example 405.05. Further elution under the conditions described in Example 405.04, delivered 405.05 (trans diastereomer) as the second-eluting peak. LCMS-ESI (pos.) m/z: 472.1 $(M+H)^+$.

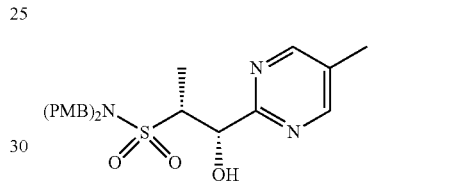

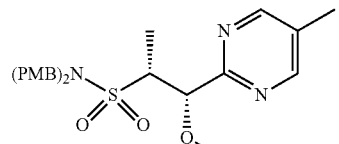

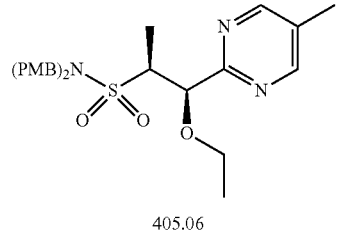

(1R,2S)-1-Ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 405.06. To a −78° C. solution of 405.04 (1.62 g, 3.4 mmol) in THF (70 mL) was added potassium bis(trimethylsilyl)amide (1.0 M solution in THF, 10.6 mL, 10.6 mmol) slowly via syringe.

After 1.25 h, EtOTf (1.4 mL, 10.6 mmol) was added slowly. The resulting orange solution was stirred at −78° C. for 45 min after which it was quenched with a 2:1 mixture of a saturated aqueous ammonium chloride solution and water (75 mL). The resulting mixture was extracted with EtOAc (4×). The combined organic layers were dried over anhydrous sodium sulfate and concentrated. The residue was purified by silica gel chromatography (eluent: 10-65% EtOAc in hexanes) to provide 405.06 (1.02 g, 60% yield) as a light yellow oil. LCMS-ESI (pos.) m/z: 500.1 (M+H)⁺.

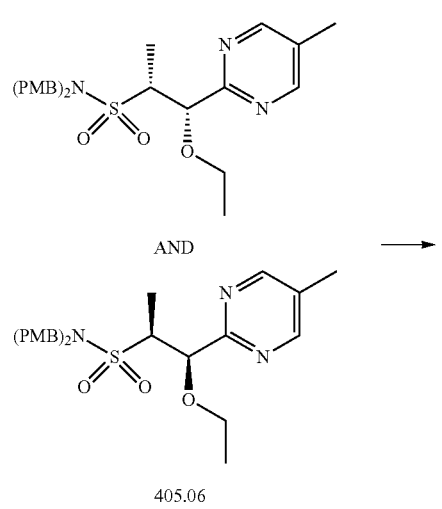

405.06

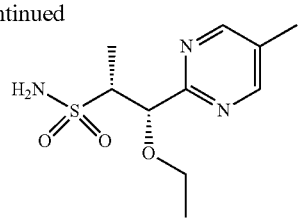

AND

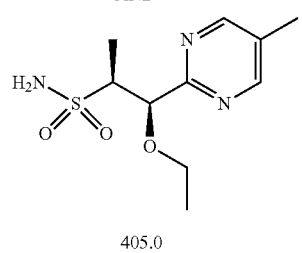

405.0

(1S,2R)-1-Ethoxy-1-(5-methylpyrimidin-2-yl)propane-2-sulfonamide and (1R,2S)-1-ethoxy-1-(5-methylpyrimidin-2-yl)propane-2-sulfonamide, Example 405.0. Example 405.06 (1.02 g, 2.0 mmol) was dissolved in TFA (14 mL). Anisole (466 μL, 4.3 mmol) was added via syringe. The resulting orange solution was stirred at RT for 16.5 h and then was concentrated in vacuo. The residue was purified by silica gel chromatography (eluent: 0-4.5% MeOH in DCM over a 45 min period) to provide the title compound 405.0 (495 mg, 93% yield) as a white solid. LCMS-ESI (pos.) m/z: 260.0 (M+H)⁺.

The compounds set forth in the following table were synthesized following the procedure in Example 405.0 as described above.

TABLE 26

| Example | Reagents | Structure, Name and Data |
|---------|----------|--------------------------|
| 405.1 | Material was prepared in an anlogous manner to that of Example 405.0 employing Example 405.05. | (1S,2S)-1-ethoxy-1-(5-methylpyrimidin-2-yl)propane-2-sulfonamide and (1R,2R)-1-ethoxy-1-(5-methylpyrimidin-2-yl)propane-2-sulfonamide. LCMS-ESI (pos.) m/z: 260.0 (M + H)⁺. |

Example 406.0. Preparation of (R)-2-(2,4-difluorophenyl)-2-hydroxyethanesulfonamide and (S)-2-(2,4-difluorophenyl)-2-hydroxyethanesulfonamide

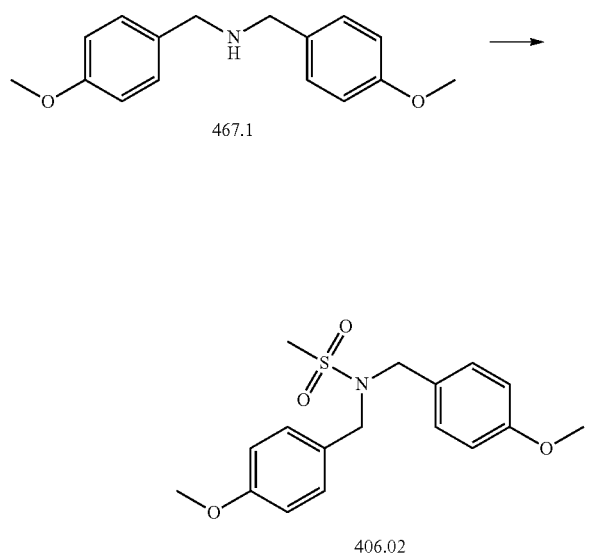

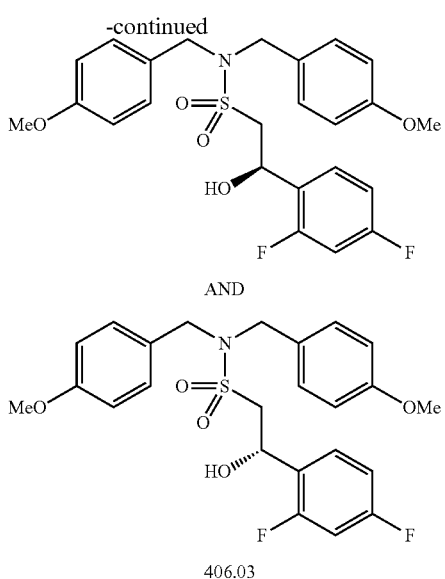

N,N-Bis(4-methoxybenzyl)methanesulfonamide, Example 406.02. To an ice-cooled solution of 467.1 (38.8 g, 151 mmol) in DCM (300 mL) was added TEA (27.3 mL, 196 mmol) via syringe followed by methanesulfonyl chloride (14.0 mL, 181 mmol) slowly via syringe. The reaction was warmed to RT and stirred until completion. The reaction was quenched with 1.0 N HCl solution and extracted with DCM. The organic layer was washed with brine (1×), dried over anhydrous sodium sulfate, and concentrated in vacuo. The residue was suspended in 20% EtOAc/hexanes and filtered to provide 406.02 (38 g, 75% yield) as a white solid. LCMS-ESI (pos.) m/z: 358.2 (M+Na)⁺.

(R)-2-(2,5-Difluorophenyl)-N,N-bis(4-methoxybenzyl)-2-hydroxyethanesulfonamide and (S)-2-(2,5-difluorophenyl)-N,N-bis(4-methoxybenzyl)-2-hydroxyethanesulfonamide, Example 406.03. To a −78° C. solution of 406.02 (2.62 g, 7.8 mmol) in THF (15.6 mL) was added n-butyllithium (1.6 M solution in hexanes, 7.32 mL, 11.7 mmol) slowly via syringe. The reaction was stirred at −78° C. for 30 min, warmed to RT and stirred for 5 min, and then recooled to −78° C. A solution of 2,4-difluorobenzaldehyde (Acros Organics, 1.66 g, 11.7 mmol) in THF (5 mL) was then added slowly via cannula. The resulting mixture was allowed to warm to RT and stirred overnight. The reaction was quenched with a saturated aqueous ammonium chloride and extracted with EtOAc (3×). The combined organic layers were dried over anhydrous sodium sulfate and concentrated in vacuo. The residue was purified by silica gel chromatography (eluent: 0-100% EtOAc in hexanes) to provide 406.03 (2.86 g, 77% yield) as a white solid. LCMS-ESI (pos.) m/z: 500.0 (M+Na)⁺.

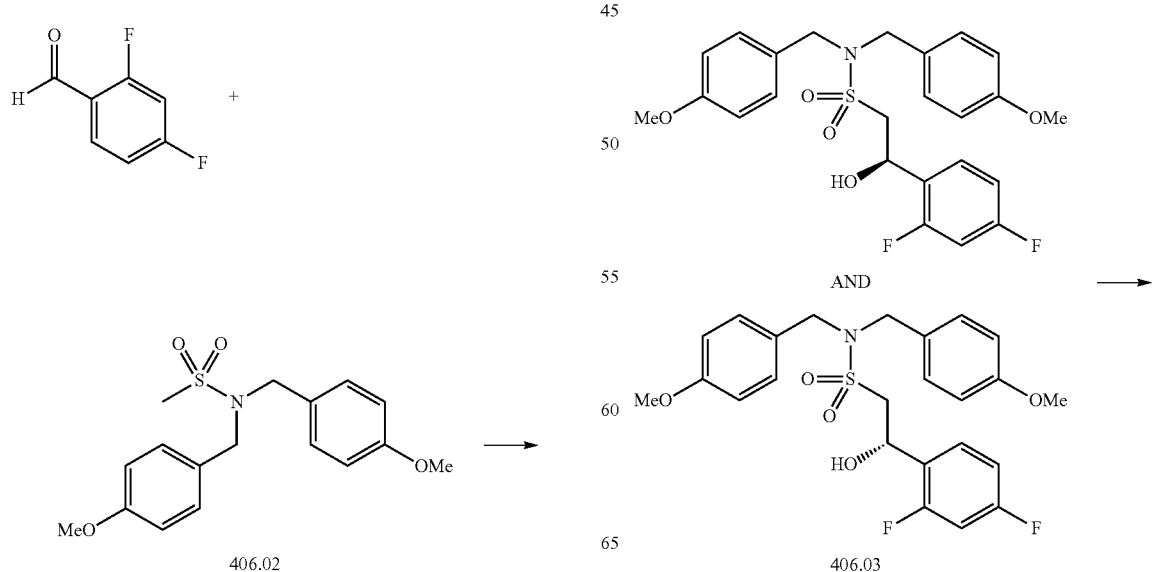

-continued

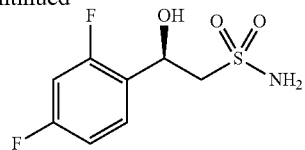

AND

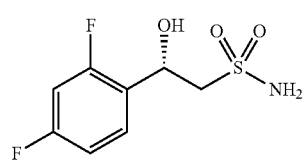

406.0

(R)-2-(2,4-Difluorophenyl)-2-hydroxyethanesulfonamide and (S)-2-(2,4-difluorophenyl)-2-hydroxyethanesulfonamide, Example 406.0. A flask was charged with 406.03 (2.65 g, 5.6 mmol) and treated with TFA (428 μL, 5.6 mmol) and anisole (2.43 mL, 22.2 mmol). The resulting solution was stirred overnight and then was directly concentrated in vacuo. The residue was purified twice by silica gel chromatography (eluent: 0-100% EtOAc in hexanes) to provide 406.0 (807 mg, 61% yield) as a white solid. LCMS-ESI (pos.) m/z: 260.0 (M+Na)+.

Example 407.0. Preparation of (S)-1-(5-fluoropyrimidin-2-yl)butane-2-sulfonamide and (R)-1-(5-fluoropyrimidin-2-yl)butane-2-sulfonamide

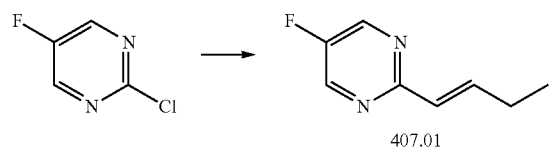

(E)-2-(But-1-en-1-yl)-5-fluoropyrimidine, Example 407.01. A slurry of (E)-but-1-en-1-ylboronic acid (Matrix Scientific, 488 mg, 4.9 mmol), potassium carbonate (1.35 g, 9.8 mmol) and 2-chloro-5-fluoro-pyrimidine (603 μL, 4.9 mmol) in ACN (5 mL) and water (2.5 mL) in a microwave vial was deoxygenated with an Ar stream. Tetrakis(triphenylphosphine)palladium (564 mg, 0.49 mmol) was added, and the yellow slurry was again deoxygentaed with an Ar stream. The reaction was sealed and heated in the microwave at at 100° C. for 10 h. The reaction mixture was diluted with water (75 mL) and extracted with ethyl ether (2×). The combined organic layers were washed with water (1×) and brine (1×), and then dried over anhydrous sodium sulfate and partially concentrated on a rotary evaporator at 200 torr. The remaining solution was purified by silica gel chromatography (eluent: pure DCM) to provide 407.01 (656 mg, 88% yield) as alight yellow oil. LCMS-ESI (pos.) m/z: 153.2 (M+H)+.

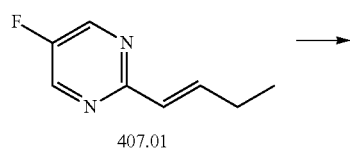

-continued

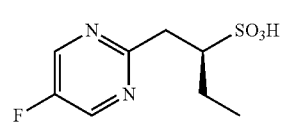

AND

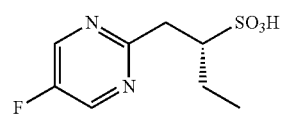

407.02

(S)-1-(5-Fluoropyrimidin-2-yl)butane-2-sulfonic acid and (R)-1-(5-fluoropyrimidin-2-yl)butane-2-sulfonic acid, Example 407.02. To a solution of 407.01 (650 mg, 4.3 mmol) in THF (6 mL) was added an aqueous solution of sodium bisulfite (1.33 g, 12.8 mmol in 2 mL of H₂O). The yellow slurry was heated at 60° C. for 19 h and then was concentrated. The residue was purified by reverse phase preparatory HPLC (Sunfire 5 μM C18 column, eluent: 0-40% ACN in water over a 40 min period where both solvents contain 0.1% TFA) to provide 407.02 (426 mg, 43% yield) as a white solid. LCMS-ESI (pos.) m/z: 235.1 (M+H)+.

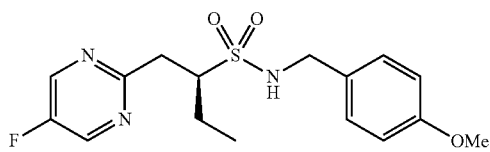

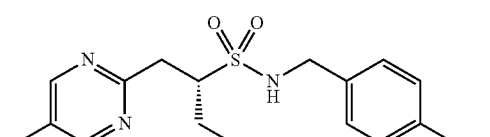

(S)-1-(5-Fluoropyrimidin-2-yl)-N-(4-methoxybenzyl)butane-2-sulfonamide and (R)-1-(5-fluoropyrimidin-2-yl)-N-(4-methoxybenzyl)butane-2-sulfonamide, Example 407.03. To an ice-cooled suspension of 407.02 (426 mg, 1.8 mmol) in DCM (18 mL) was added oxalyl chloride (323 μL, 3.6 mmol) via syringe followed by a catalytic amount of DMF via syringe. Vigorous bubbling was observed. The resulting white slurry was warmed to RT and stirred for 2.25 h. The reaction mixture was then concentrated. The residue was azeotroped to dryness with benzene (2×) and then was suspended in DCM (18 mL) and cooled to 0° C. 4-Methoxybenzylamine (519 L, 4.0 mmol) and TEA (885 µL, 6.4 mmol) were then added sequentially via syringe. The resulting yellow slurry was stirred at 0° C. for 15 min and then was warmed to RT and stirred for an additional 20 h. The reaction mixture was partitioned between water (30 mL) and DCM (3×). The combined organic layers were dried over anhydrous sodium sulfate and concentrated in vacuo. The residue was purified by reverse phase preparatory HPLC (Sunfire 5 µM C18 column, eluent: 30-75% ACN in water over a 35 min period where both solvents contain 0.1% TFA) to provide 407.03 (490 mg, 76% yield) as a light yellow oil. LCMS-ESI (pos.) m/z: 376.1 (M+Na)$^+$.

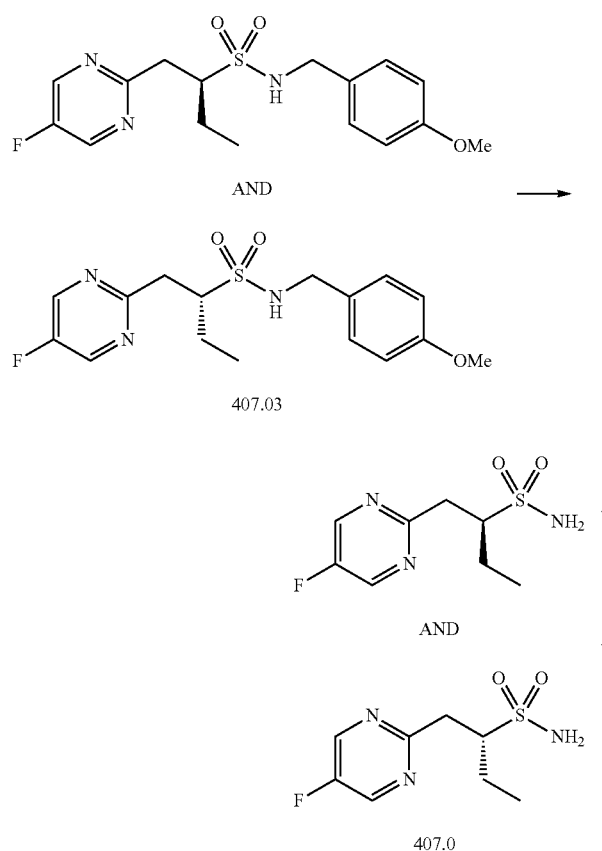

407.03

407.0

(S)-1-(5-Fluoropyrimidin-2-yl)butane-2-sulfonamide and (R)-1-(5-fluoropyrimidin-2-yl)butane-2-sulfonamide, Example 407.0. An ice-cooled flask containing 407.03 (489 mg, 1.4 mmol) was treated with TFA (5 mL, 67.3 mmol) via syringe. The resulting yellow solution was warmed to RT and stirred for 16 h and then was concentrated in vacuo. The residue was purified by reverse phase preparatory HPLC (Sunfire 5 µM C18 column, eluent: 5-45% ACN in water over a 35 min period where both solvents contain 0.1% TFA) to provide 407.0 (264 mg, 82% yield) as a white solid. LCMS-ESI (pos.) m/z: 234.1 (M+H)$^+$.

Example 408.0. Preparation of (1S,2S)-N-(2,4-dimethoxybenzyl)-2-(5-fluoropyrimidin-2-yl)cyclopentane-1-sulfonamide and (1R,2R)-N-(2,4-dimethoxybenzyl)-2-(5-fluoropyrimidin-2-yl)cyclopentane-1-sulfonamide

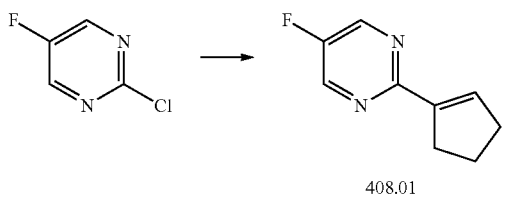 [SMILES: Fc1cnc(Cl)nc1 ; Fc1cnc(C2=CCCC2)nc1]

408.01

2-(Cyclopent-1-en-1-yl)-5-fluoropyrimidine, Example 408.01. A slurry of cyclopentene-1-boronic acid (Combi-Blocks, 2.05 g, 18.3 mmol), sodium carbonate (3.88 g, 36.6 mmol) and 2-chloro-5-fluoro-pyrimidine (2.26 mL, 18.3 mmol) in a mixture of THF (24 mL) and water (12 mL) was deoxygenated with an Ar stream. Tetrakis(triphenylphosphine)palladium (2.12 g, 1.8 mmol) was added, and the slurry was again deoxygentaed with an Ar stream. The reaction was heated under Ar at 100° C. for 3 d. The reaction mixture was then extracted with DCM (3×). The combined organic layers were dried over anhydrous magnesium sulfate and concentrated. The residue was purified by silica gel chromatography (eluent: pure DCM) to provide 408.01 (2.6 g, 86% yield) as a colorless oil. LCMS-ESI (pos.) m/z: 165.2 (M+H)$^+$.

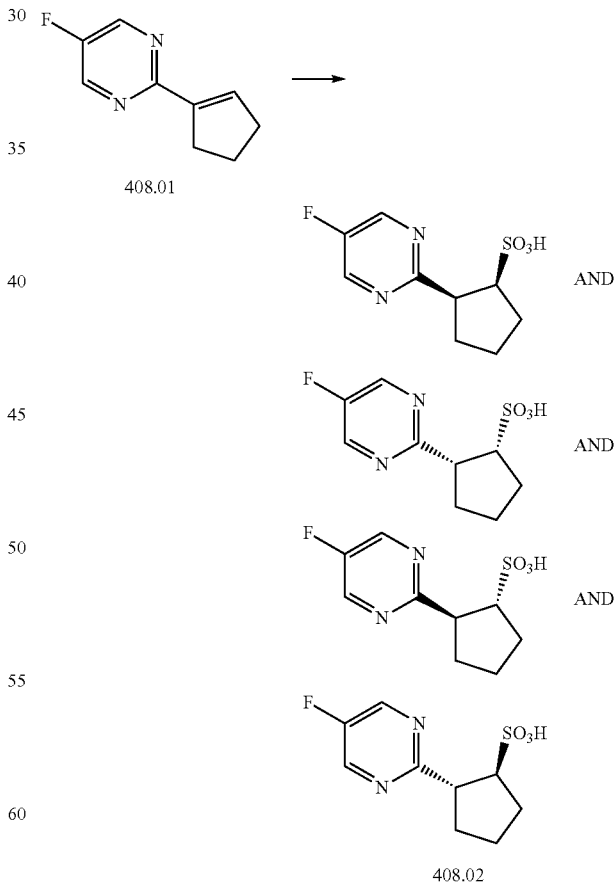

408.02

(1S,2S)-2-(5-Fluoropyrimidin-2-yl)cyclopentane-1-sulfonic acid and (1R,2R)-2-(5-fluoropyrimidin-2-yl)cyclopentane-1-sulfonic acid and (1R,2S)-2-(5-fluoropyrimidin-2-yl)cyclopentane-1-sulfonic acid and (1S,2R)-2-(5- fluoropyrimidin-2-yl)cyclopentane-1-sulfonic acid, Example 408.02. To a microwave vial containing a suspension of 408.01 (2.6 g, 15.8 mmol) in 4.0 M aqeuous sodium bisulfite solution (3.76 mL, 15.0 mmol) was added EtOH (4 mL). The vial was sealed, and the resulting slurry was heated at 90° C. in the microwave for 12 h. The reaction was filtered and the filtrate was directly purified by reverse phase preparatory HPLC (Sunfire 5 µM C18 column, eluent: 0-40% ACN in water over a 15 min period where both solvents contain 0.1% TFA) to provide 408.02 (3.09 g, 79% yield). LCMS-ESI (pos.) m/z: 247.2 (M+H)$^+$.

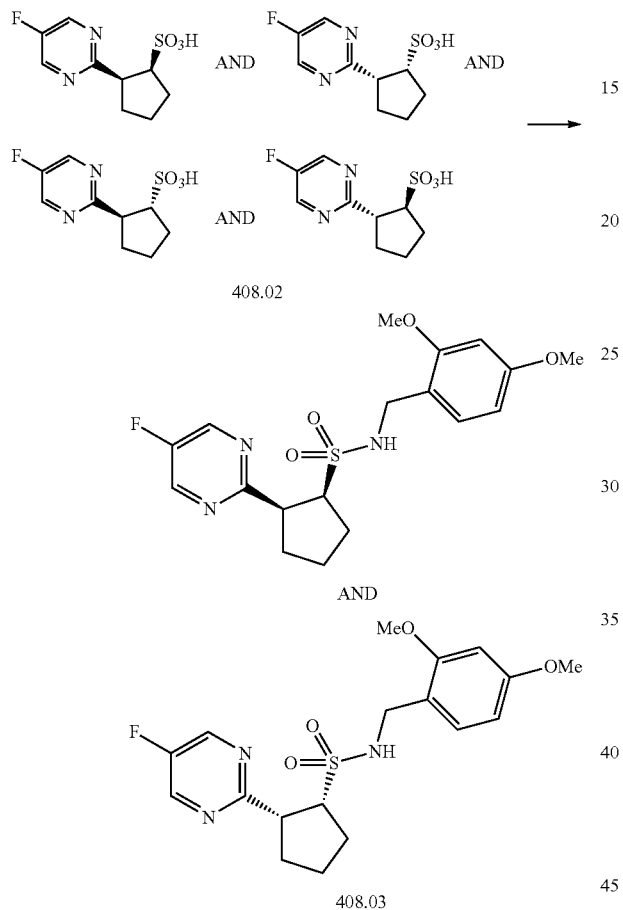

408.02

(1S,2S)-N-(2,4-Dimethoxybenzyl)-2-(5-fluoropyrimidin-2-yl)cyclopentane-1-sulfonamide and (1R,2R)-N-(2,4-dimethoxybenzyl)-2-(5-fluoropyrimidin-2-yl)cyclopentane-1-sulfonamide, Example 408.03. To a suspension of 408.02 (1.24 g, 5.0 mmol) in DCM (50 mL) was added oxalyl chloride (1.34 mL, 15.1 mmol) via syringe followed by a catalytic amount of DMF via syringe. Vigorous bubbling was observed. The resulting white slurry was stirred at RT for 2 h and was concentrated in vacuo. The residue was azeotroped to dryness with cyclopentylmethylether and then was suspended in DCM (50 mL). 2,4-Dimethoxybenzylamine (2.53 mL, 15.1 mmol) and TEA (3.51 mL, 25.2 mmol) were added sequentially via syringe. The resulting slurry was stirred at RT overnight. The reaction mixture was then partitioned between water and DCM (3×). The combined organic layers were dried over anhydrous magnesium sulfate and concentrated. The residue was purified by silica gel chromatography (eluent: 10-40% EtOAc in hexanes over a 30 min period) to provide 408.03 (cis diastereomer, 408 mg, 21% yield, colorless oil) as the first-eluting peak. LCMS-ESI (pos.) m/z: 418.2 (M+Na)$^+$.

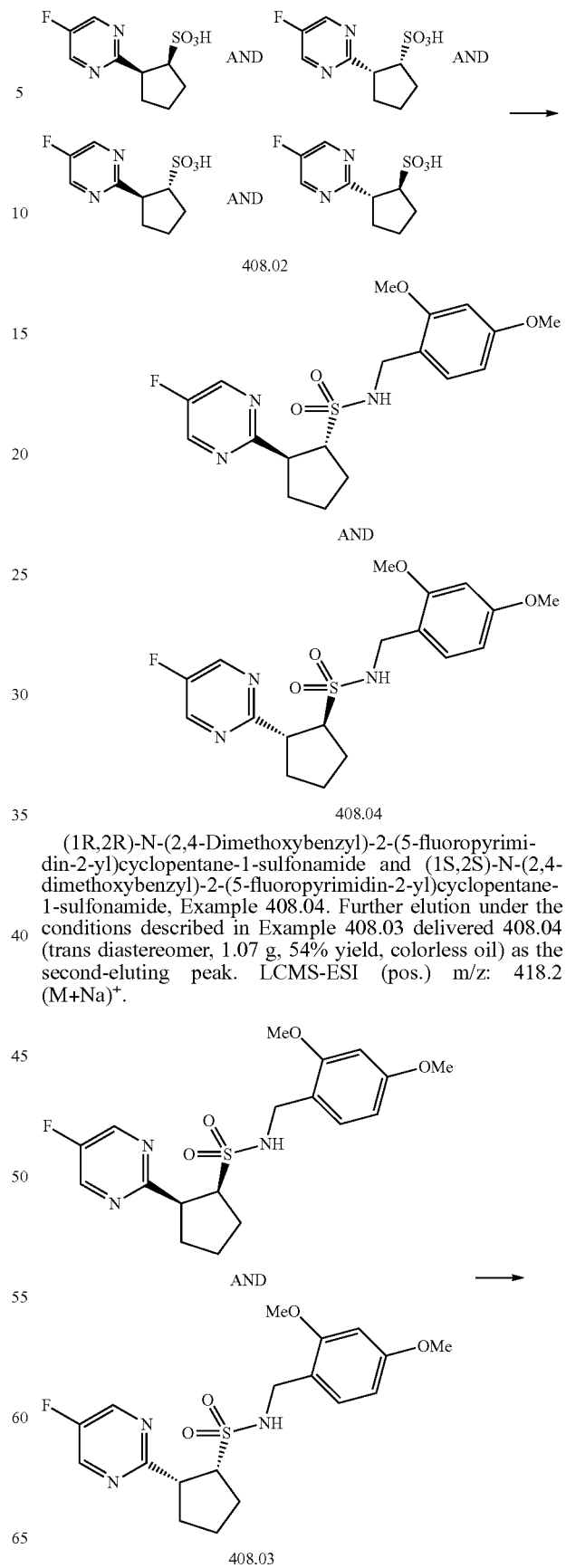

(1R,2R)-N-(2,4-Dimethoxybenzyl)-2-(5-fluoropyrimidin-2-yl)cyclopentane-1-sulfonamide and (1S,2S)-N-(2,4-dimethoxybenzyl)-2-(5-fluoropyrimidin-2-yl)cyclopentane-1-sulfonamide, Example 408.04. Further elution under the conditions described in Example 408.03 delivered 408.04 (trans diastereomer, 1.07 g, 54% yield, colorless oil) as the second-eluting peak. LCMS-ESI (pos.) m/z: 418.2 (M+Na)$^+$.

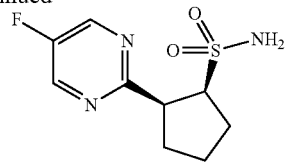

AND

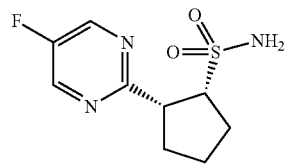

408.0

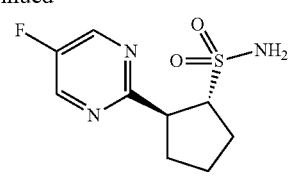

AND

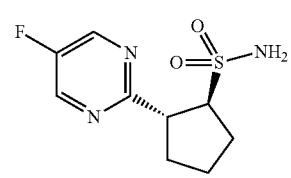

408.1

(1S,2S)-N-(2,4-Dimethoxybenzyl)-2-(5-fluoropyrimidin-2-yl)cyclopentane-1-sulfonamide and (1R,2R)-N-(2,4-dimethoxybenzyl)-2-(5-fluoropyrimidin-2-yl)cyclopentane-1-sulfonamide, Example 408.0. An ice-cooled solution of 408.03 (408 mg, 1.0 mmol) in DCM (5 mL) was treated sequentially with anisole (336 µL, 3.1 mmol) via syringe and TFA (767 µL, 10.3 mmol) via syringe. The resulting solution was stirred at 0° C. for 30 min and then was warmed to RT and stirred for an additional 3 h. The reaction was directly concentrated and the residue was purified by silica gel chromatography (eluent: 30-100% EtOAc in hexanes) to provide 408.0 (60 mg, 24% yield) as a white solid. LCMS-ESI (pos.) m/z: 246.2 (M+H)$^+$.

Example 408.1. Preparation of (1R,2S)-N-(2,4-dimethoxybenzyl)-2-(5-fluoropyrimidin-2-yl)cyclopentane-1-sulfonamide and (1S,2R)-N-(2,4-dimethoxybenzyl)-2-(5-fluoropyrimidin-2-yl)cyclopentane-1-sulfonamide (1R,2S)-N-(2,4-Dimethoxybenzyl)-2-(5-fluoropyrimidin-2-yl)cyclopentane-1-sulfonamide and (1S,2R)-N-(2,4-dimethoxybenzyl)-2-(5-fluoropyrimidin-2-yl)cyclopentane-1-sulfonamide, Example 408.1. An ice-cooled solution of 408.04 (1.09 g, 2.7 mmol) in DCM (14 mL) was treated sequentially with anisole (899 µL, 8.3 mmol) and TFA (2.05 mL, 27.6 mmol) via syringe. The resulting solution was stirred at 0° C. for 30 min and then was warmed to RT and stirred for an additional 3 h. The reaction was directly concentrated and the residue was purified by silica gel chromatography (eluent: 30-100% EtOAc in hexanes) to provide 408.1 (540 mg, 80% yield) as a white solid. LCMS-ESI (pos.) m/z: 246.1 (M+H)$^+$.

Example 409.0. Preparation of (1R,2R)-1-(5-fluoropyrimidin-2-yl)-1-methoxypropane-2-sulfonamide and (1S,2S)-1-(5-fluoropyrimidin-2-yl)-1-methoxypropane-2-sulfonamide

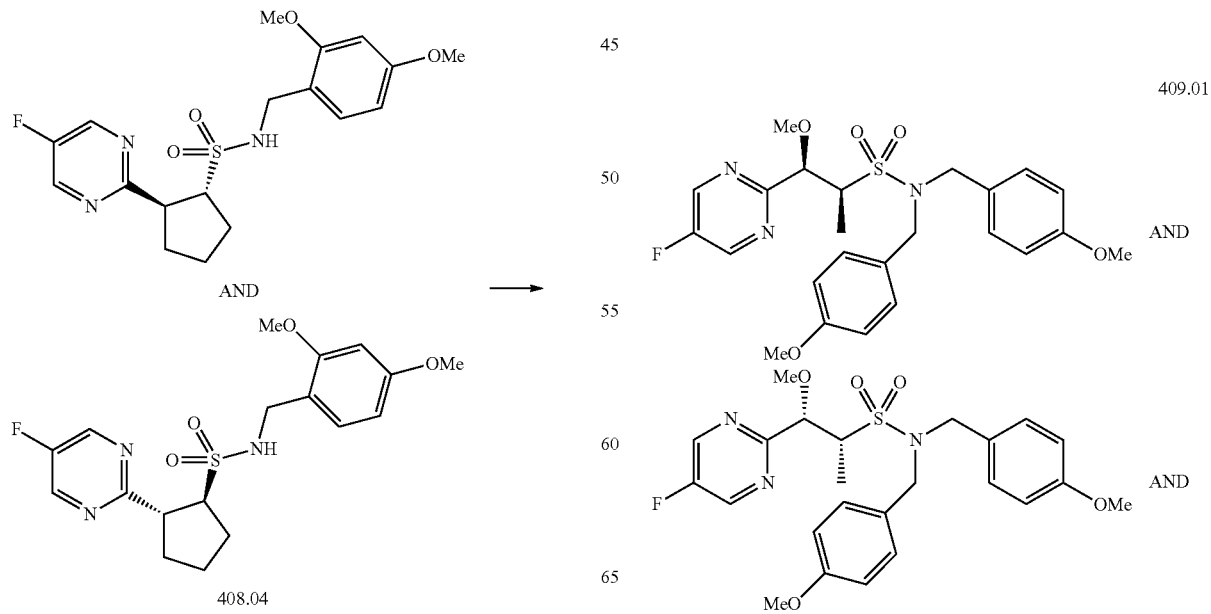

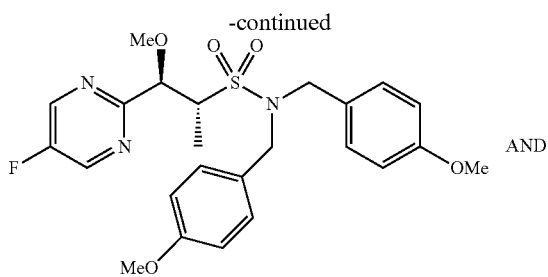

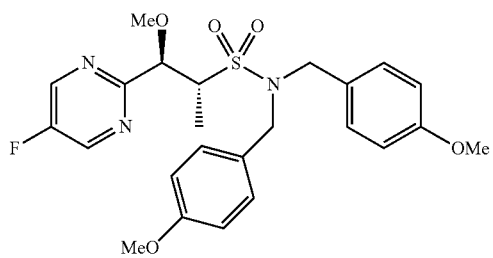

((1R,2S)-1-(5-Fluoropyrimidin-2-yl)-1-methoxy-N,N-bis(4-methoxybenzyl)propane-2-sulfonamide and ((1S,2R)-1-(5-fluoropyrimidin-2-yl)-1-methoxy-N,N-bis(4-methoxybenzyl)propane-2-sulfonamide and (1R,2R)-1-(5-fluoropyrimidin-2-yl)-1-methoxy-N,N-bis(4-methoxybenzyl)propane-2-sulfonamide and (1S,2S)-1-(5-fluoropyrimidin-2-yl)-1-methoxy-N,N-bis(4-methoxybenzyl)propane-2-sulfonamide, Example 409.01. To an ice-cooled solution of 404.4 (274 mg, 0.58 mmol) in DMF (8 mL) was added sodium hydride (60% dispersion in mineral oil, 81 mg, 2.0 mmol). The ice bath was removed and the resulting orange slurry was stirred at RT for 15 min. Iodomethane (179 µL, 2.9 mmol) was then added slowly via syringe. After an additional 25 min at RT, the reaction was quenched with water (90 mL) and extracted with EtOAc (2×). The combined organic layers were dried over anhydrous sodium sulfate and concentrated. The residue was purified by silica gel chromatography (eluent: 10-65% EtOAc in hexanes) to provide 409.01 (183 mg, 65% yield) as a white solid. LCMS-ESI (pos.) m/z: 512.2 (M+Na)⁺.

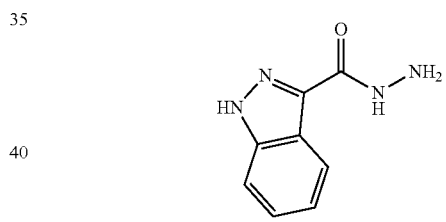

(1R,2S)-1-(5-Fluoropyrimidin-2-yl)-1-methoxypropane-2-sulfonamide and (1S,2R)-1-(5-fluoropyrimidin-2-yl)-1-methoxypropane-2-sulfonamide, Example 409.0. A flask was charged with 409.01 (175 mg, 0.36 mmol) and was treated with TFA (5.5 mL, 74 mmol) and anisole (194 µL, 1.8 mmol) via syringe. The resulting yellow solution was stirred for 20 h and then was directly concentrated in vacuo. The residue was purified by silica gel chromatography (eluent: 0.8-6% MeOH in DCM) to provide 409.0 (cis diastereomer, 31 mg, 35% yield, white solid) as the first-eluting peak. LCMS-ESI (pos.) m/z: 250.1 (M+H)⁺.

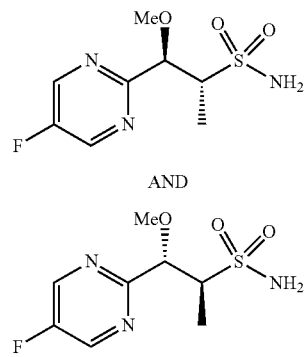

Example 409.1. Preparation of (1R,2R)-1-(5-fluoropyrimidin-2-yl)-1-methoxypropane-2-sulfonamide and (1S,2S)-1-(5-fluoropyrimidin-2-yl)-1-methoxypropane-2-sulfonamide. Further elution under the conditions described in Example 409.0 delivered 409.1 (trans diastereomer, 56 mg, 63% yield, white solid) as the second-eluting peak. LCMS-ESI (pos.) m/z: 250.1 (M+H)⁺.

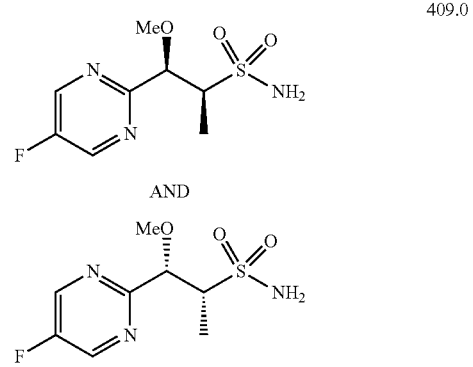 [SMILES: CO[C@H](c1ncc(F)cn1)[C@H](C)S(N)(=O)=O ; CO[C@@H](c1ncc(F)cn1)[C@@H](C)S(N)(=O)=O]

1H-Indazole-3-carbohydrazide, Example 395.31. To a solution of indazole-3-carboxylic acid (1.155 g, 7.12 mmol) in MeOH (14.24 mL) was added sulfuric acid (0.038 mL, 0.712 mmol), and the mixture was heated to reflux. After 4 h, LCMS indicated complete conversion to the methyl ester. As such, the mixture was concentrated in vacuo, dissolved in DCM and washed with NaHCO₃. It was then dried over Na₂SO₄ and concentrated in vacuo to yield the initial methyl 1H-indazole-3-carboxylate. The material was then dissolved in MeOH (11.53 mL) and hydrazine monohydrate (1.019 mL, 13.62 mmol) was added. The mixture was heated at 80° C. for 6 h after which a white solid precipitated formed. The precipitate was filtered and washed with heptanes:EtOAc (1:1) (50 mL) and dried under vacuum to yield 1H-indazole-3-carbohydrazide (0.85 g, 4.82 mmol, 67% yield). The initial material was carried forward directly without further purification.

The compounds set forth in the following table were synthesized following the procedure in Example 395.31 using the known starting material as described.

TABLE 27

| Example | Reagents | Structure, Name and Data |
|---|---|---|
| 395.31 | Indazole-3-carboxylic acid (commercially available from Matrix Scientific). | 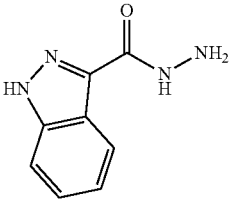 [SMILES: NNC(=O)c1n[nH]c2ccccc12]<br>1H-indazole-3-carbohydrazide.<br>LCMS-ESI (pos.) m/z: 177.2 (M + H)+. |
| 395.32 | 5-chloro-3-(1H)indazole carboxylic acid (commercially available from Chem-Impex International, Inc.). | 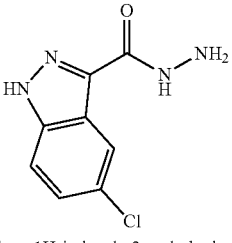<br>5-chloro-1H-indazole-3-carbohydrazide.<br>LCMS-ESI (pos.) m/z: 211.0 (M + H)+. |
| 395.33 | 1H-pyrrolo [2,3-b]pyridine-3-carboxylic acid, methyl ester (commercially available from Alfa Aesar). | 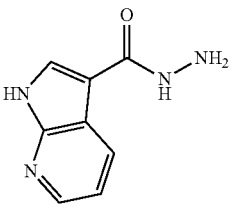 [SMILES: NNC(=O)c1c[nH]c2ncccc12]<br>1H-pyrrolo [2,3-b]pyridine-3-carbohydrazide.<br>LCMS-ESI (pos.) m/z: 177.0 (M + H)+. |
| 395.34 | methyl 5-bromobenzo[d]isoxazole-3-carboxylate (commercially available from J&W Pharma). | 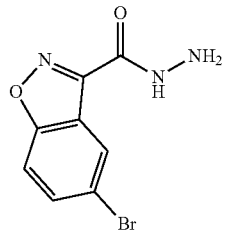 [SMILES: NNC(=O)c1noc2ccc(Br)cc12]<br>5-bromobenzo[d]isoxazole-3-carbohydrazide<br>LCMS-ESI (pos.) m/z: 256.0 (M + H)+. |
| 395.35 | pyrazolo[1,5-a]pyridine-3-carboxylic acid (commercially available from Synthonix Inc.). | 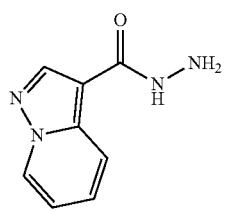 [SMILES: NNC(=O)c1cnn2ccccc12]<br>pyrazolo[1,5-a]pyridine-3-carbohydrazide.<br>LCMS-ESI (pos.) m/z: 177.2 (M + H)+. |

TABLE 27-continued

| Example | Reagents | Structure, Name and Data |
|---|---|---|
| 395.36 | 5-methylpyrazolo [1,5-a]pyridine-3-carboxylic acid (commercially available from Enamine). | 5-methylpyrazolo [1,5-a]pyridine-3-carbohydrazide. LCMS-ESI (pos.) m/z: 191.2 (M + H)+. |
| 395.37 | 5-methylpyrazolo[1,5-a]pyridine-3-carboxylic acid (commercially available from Ark Pharm, Inc.). | 5-methyl-1H-indazole-3-cathohydrazide. LCMS-ESI (pos.) m/z: 191.2 (M + H)+. |
| 395.38 | 1,5-dimethyl-1H-indazole-3-carboxylic acid (commercially available from Matrix Scientific). | 1,5-dimethyl-1H-indazole-3-carbohydrazide. LCMS-ESI (pos.) m/z: 205.0 (M + H)+. |
| 395.39 | 7h-pyrrolo[2,3-d]pyrimidine-4-carboxylic acid (commercially available from Advance Fine Chemicals LLC). | 5H-pyrrolo[3,2-d]pyrimidine-4-carbohydrazide. LCMS-ESI (pos.) m/z: 178.2 (M + H)+. |
| 395.40 | 1-methylindazole-3-carboxylic acid (commercially available from Accela ChemBio Inc.). | 1-methyl-1H-indazole-3-cathohydrazide. LCMS-ESI (pos.) m/z: 191.2 (M + H)+. |

TABLE 27-continued

| Example | Reagents | Structure, Name and Data |
|---|---|---|
| 395.41 | 5-fluoro-1H-indazole-3-carboxylic acid (commercially available from Accela ChemBio Inc.). | 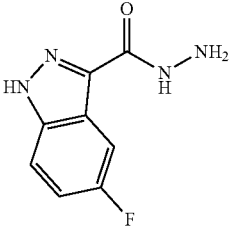 [SMILES: NNC(=O)c1n[nH]c2ccc(F)cc12]<br>5-fluoro-1H-indazole-3-carbohydrazide.<br>LCMS-ESI (pos.) m/z: 195.0 (M + H)$^+$. |
| 395.42 | methyl 4,5,6,7-tetrahydrobenzo[d]isoxazole-3-carboxylate (commercially available from Frontier Scientific Services Inc.). | 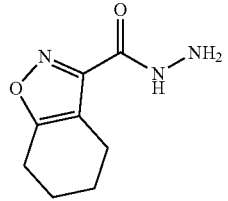 [SMILES: NNC(=O)c1noc2c1CCCC2]<br>4,5,6,7-tetrahydrobenzo[d]isoxazole-3-carbohydrazide.<br>LCMS-ESI (pos.) m/z: 182.0 (M + H)$^+$. |
| 395.43 | 4H,5H,6H-pyrrolo[1,2-b]pyrazole-3-carboxylic acid (commercially available from Ark Pharm, Inc.). | 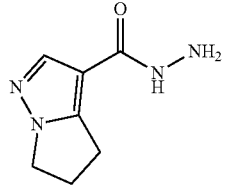 [SMILES: NNC(=O)c1cnn2c1CCC2]<br>5,6-dihydro-4H-pyrrolo[1,2-b]pyrazole-3-carbohydrazide. LCMS-ESI (pos.) m/z: 167.0 (M + H)$^+$. |

The compounds set forth in the following table were synthesized following the procedure in Example 77.0 using the known starting material as described.

TABLE 28

| Example | Reagents | Structure, Name and Data |
|---|---|---|
| 410.0 | 2-methylimidazo[1,2-a]pyridine-3-carbohydrazide (Frontier Scientific Services Inc.), isothiocyanato-1,3-dimethoxybenzene (Example 465.0), and (1R,2S)-1-methoxy-1-(5-methylpyrimidin-2-yl)propane-2-sulfonamide (Example 466.0). | 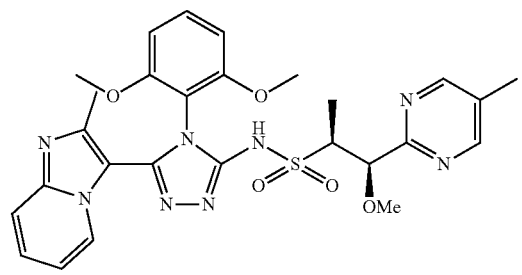 [SMILES: COc1cccc(OC)c1-n1c(NS(=O)(=O)[C@@H](C)[C@H](OC)c2ncc(C)cn2)nnc1-c1c(C)nc2ccccn12]<br>(1R,2S)-N-(4-(2,6-dimethoxyphenyl)-5-(2-methylimidazo[1,2-a]pyridin-3-yl)-4H-1,2,4-triazol-3-yl)-1-methoxy-1-(5-methylpyrimidin-2-yl)propane-2-sulfonamide.<br>$^1$H NMR (500 MHz, DMSO-d$_6$) δ 13.58-13.76 (m, 1H) 8.51-8.58 (m, 1H) 8.40-8.48 (m, 1H) 8.27-8.37 (m, 1H) 7.61-7.67 (m, 1H) 7.51-7.60 (m, 1H) 7.30-7.40 (m, 1H) 7.13-7.22 (m, 1H) 6.63-6.73 (m, 2H) 4.86-4.95 (m, 1H) 3.57-3.63 (m, 6 H) 3.28-3.35 (m, 4H) 3.23-3.26 (m, 3H) 2.05-2.16 (m, 3H) 1.09-1.18 (m, 3H). LCMS-ESI (pos.) m/z: 579.2 (M + H)$^+$. |

TABLE 28-continued

| Example | Reagents | Structure, Name and Data |
|---|---|---|
| 411.0 | 1H-indazole-3-carbohydrazide (Example 395.31), isothiocyanato-1,3-dimethoxybenzene (Example 465.0), and (1R,2S)-1-methoxy-1-(5-methylpyrimidin-2-yl)propane-2-sulfonamide (Example 466.0). | 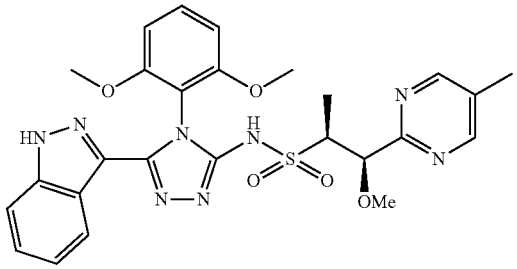 [SMILES: COc1cccc(OC)c1-n1c(NS(=O)(=O)[C@@H](C)[C@H](OC)c2ncc(C)cn2)nnc1-c1n[nH]c2ccccc12]<br>(1R,2S)-N-(4-(2,6-dimethoxyphenyl)-5-(1H-indazol-3-yl)-4H-1,2,4-triazol-3-yl)-1-methoxy-1-(5-methylpyrimidin-2-yppropane-2-sulfonamide.<br>$^1$H NMR (500 MHz, DMSO-$d_6$) δ 13.41-13.59 (m, 1H) 13.21-13.35 (m, 1H) 8.48-8.56 (m, 1H) 8.39-8.45 (m, 1H) 8.08-8.16 (m, 1H) 7.51-7.58 (m, 1H) 7.41-7.48 (m, 2H) 7.25-7.33 (m, 1H) 6.77-6.85 (m, 2H) 4.82-4.90 (m, 1H) 3.59-3.68 (m, 6 H) 3.40-3.45 (m, 3H) 3.29-3.31 (m, 1H) 3.18-3.22 (m, 3H) 1.03-1.11 (m, 3H). LCMS-ESI (pos.) m/z: 565.2 (M + H)$^+$. |
| 412.0 | 5-chloro-1H-indazole-3-carbohydrazide (Example 395.32). isothiocyanato-1,3-dimethoxybenzene (Example 465.0), and (1R,2S)-1-methoxy-1-(5-methylpyrimidin-2-yl)propane-2-sulfonamide (Example 466.0). | 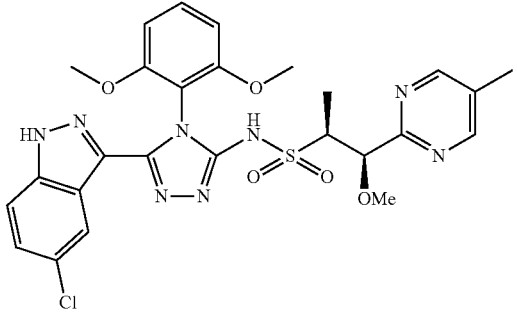 [SMILES: COc1cccc(OC)c1-n1c(NS(=O)(=O)[C@@H](C)[C@H](OC)c2ncc(C)cn2)nnc1-c1n[nH]c2ccc(Cl)cc12]<br>(1R,2S)-N-(5-(5-chloro-1H-indazol-3-yl)-4-(2,6-dimethoxyphenyl)-4H-1,2,4-triazol-3-yl)-1-methoxy-1-(5-methylpyrimidin-2-yl)propane-2-sulfonamide.<br>$^1$H NMR (400 MHz, DMSO-$d_6$) δ 13.61-13.80 (m, 1H) 13.23-13.41 (m, 1H) 8.50-8.53 (m, 1H) 8.41-8.45 (m, 1H) 8.08-8.12 (m, 1H) 7.57-7.63 (m, 1H) 7.42-7.50 (m, 2H) 6.77-6.84 (m, 2H) 4.81-4.89 (m, 1H) 3.61-3.67 (m, 6 H) 3.31-3.33 (m, 3H) 3.25-3.30 (m, 1H) 3.18-3.22 (m, 3H) 1.05-1.10 (m, 3H). LCMS-ESI (pos.) m/z: 599.1 (M + H)$^+$. |
| 413.0 | 1H-pyrrolo[2,3-b]pyridine-3-carbohydrazide (Example 395.33), isothiocyanato-1,3-dimethoxybenzene (Example 465.0), and (1R,2S)-1-methoxy-1-(5-methylpyrimidin-2-yl)propane-2-sulfonamide (Example 466.0). | 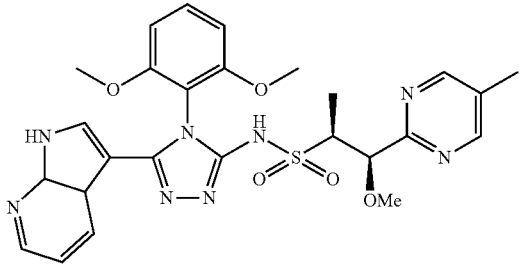 [SMILES: COc1cccc(OC)c1-n1c(NS(=O)(=O)[C@@H](C)[C@H](OC)c2ncc(C)cn2)nnc1C1=CNC2N=CC=CC12]<br>(1R,2S)-N-(4-(2,6-dimethoxyphenyl)-5-(1H-pyrrolo[2,3-b]pyridin-3-yl)-4H-1,2,4-triazol-3-yl)-1-methoxy-1-(5-methylpyrimidin-2-yl)propane-2-sulfonamide.<br>$^1$H NMR (400 MHz, DMSO-$d_6$) δ 12.93-13.13 (m, 1H) 11.90-12.10 (m, 1H) 8.50-8.53 (m, 1H) 8.39-8.45 (m, 2H) 8.32-8.35 (m, 1H) 7.56-7.63 (m, 1H) 7.22-7.28 (m, 1H) 6.90-6.95 (m, 2H) 6.57-6.60 (m, 1H) 4.31-4.37 (m, 1H) 3.66-3.72 (m, 6 H) 3.31-3.32 (m, 3H) 3.27 (br d, J = 3.0 Hz, 1H) 3.18-3.21 (m, 3H) 1.01-1.06 (m, 3H). LCMS-ESI (pos.) m/z: 565.2 (M + H)$^+$. |

TABLE 28-continued

| Example | Reagents | Structure, Name and Data |
|---|---|---|
| 414.0 | 5-bromobenzo[d]isoxazole-3-carbohydrazide (Example 395.34.), isothiocyanato-1,3-dimethoxybenzene (Example 465.0), and (1R,2S)-1-methoxy-1-(5-methylpyrimidin-2-yl)propane-2-sulfonamide (Example 466.0). | 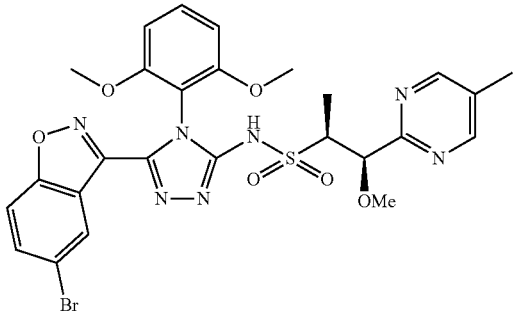 [SMILES: COc1cccc(OC)c1-n1c(NS(=O)(=O)[C@@H](C)[C@H](OC)c2ncc(C)cn2)nnc1-c1noc2ccc(Br)cc12]<br>(1R,2S)-N-(5-(5-bromobenzo[d]isoxazol-3-yl)-4-(2,6-dimethoxyphenyl)-4H-1,2,4-triazol-3-yl)-1-methoxy-1-(5-methylpyrimidin-2-yppropane-2-sulfonamide.<br><sup>1</sup>H NMR (400 MHz, DMSO-d<sub>6</sub>) δ 13.81-14.03 (m, 1H) 8.54-8.56 (m, 1H) 8.49-8.55 (m, 1H) 8.40-8.46 (m, 1H) 8.15-8.35 (m, 1H) 7.90-7.97 (m, 1H) 7.82-7.90 (m, 1H) 7.47-7.55 (m, 1H) 6.80-6.88 (m, 1H) 4.84-4.91 (m, 1H) 3.63-3.70 (m, 6 H) 3.38 (dd, J = 7.1, 3.0 Hz, 1H) 3.17-3.22 (m, 3H) 1.13-1.18 (m, 3H) 1.06-1.12 (m, 3H). LCMS-ESI (pos.) m/z: 646.2 (M + H)<sup>+</sup>. |
| 415.0 | pyrazolo [1,5-a]pyridine-3-carbohydrazide (Example 395.35), isothiocyanato-1,3-dimethoxybenzene (Example 465.0), and (1R,2S)-1-methoxy-1-(5-methylpyrimidin-2-yl)propane-2-sulfonamide (Example 466.0). | 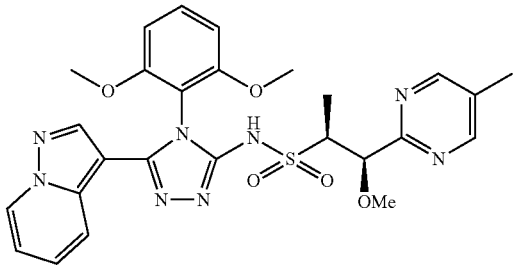 [SMILES: COc1cccc(OC)c1-n1c(NS(=O)(=O)[C@@H](C)[C@H](OC)c2ncc(C)cn2)nnc1-c1cnn2ccccc12]<br>(1R,2S)-N-(4-(2,6-dimethoxyphenyl)-5-(pyrazolo[1,5-a]pyridin-3-yl)-4H-1,2,4-triazol-3-yl)-1-methoxy-1-(5-methylpyrimidin-2-yl)propane-2-sulfonamide.<br><sup>1</sup>H NMR (500 MHz, DMSO-d<sub>6</sub>) δ 13.04-13.19 (m, 1H) 8.75-8.81 (m, 1H) 8.50-8.54 (m, 1H) 8.40-8.45 (m, 1H) 8.09-8.15 (m, 1H) 7.54-7.63 (m, 2H) 7.10-7.15 (m, 1H) 7.05-7.09 (m, 1H) 6.89-6.94 (m, 2H) 4.84-4.90 (m, 1H) 3.66-3.72 (m, 6 H) 3.31-3.33 (m, 3H) 3.27-3.30 (m, 1H) 3.20 (s, 3H) 1.04-1.09 (m, 3H). LCMS-ESI (pos.) m/z: 565.2 (M + H)<sup>+</sup>. |
| 416.0 | 5-methylpyrazolo [1,5-a]pyridine-3-carbohydrazide (Example 395.36), isothiocyanato-1,3-dimethoxybenzene (Example 465.0), and (1R,2S)-1-methoxy-1-(5-methylpyrimidin-2-yl)propane-2-sulfonamide (Example 466.0). | 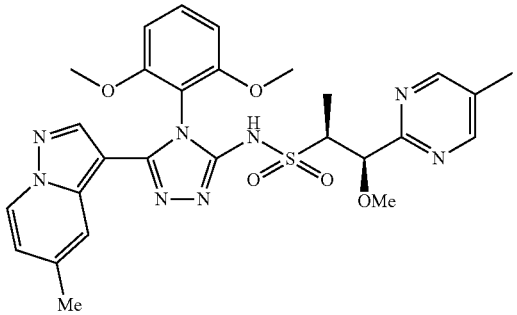 [SMILES: COc1cccc(OC)c1-n1c(NS(=O)(=O)[C@@H](C)[C@H](OC)c2ncc(C)cn2)nnc1-c1cnn2ccc(C)cc12]<br>(1R,2S)-N-(4-(2,6-dimethoxyphenyl)-5-(5-methylpyrazolo[1,5-a]pyridin-3-yl)-4H-1,2,4-triazol-3-yl)-1-methoxy-1-(5-methylpyrimidin-2-yl)propane-2-sulfonamide.<br><sup>1</sup>H NMR (400 MHz, DMSO-d<sub>6</sub>) δ 12.99-13.13 (m, 1H) 8.63-8.68 (m, 1H) 8.50-8.54 (m, 1H) 8.41-8.44 (m, 1H) 7.85-7.88 (m, 1H) 7.55-7.62 (m, 1H) 7.01-7.04 (m, 1H) 6.95-6.99 (m, 1H) 6.88-6.93 (m, 2H) 4.85-4.89 (m, 1H) 3.65-3.72 (m, 6 H) 3.30-3.33 (m, 3H) 3.27-3.30 (m, 1H) 3.18-3.22 (m, 3H) 2.42-2.46 (m, 3H) 1.04-1.09 (m, 3H). LCMS-ESI (pos.) m/z: 579.2 (M + H)<sup>+</sup>. |

TABLE 28-continued

| Example | Reagents | Structure, Name and Data |
|---|---|---|
| 417.0 | Quinoline-4-carbohydrazide (Frontier Scientific Services Inc.), isothiocyanato-1,3-dimethoxybenzene (Example 465.0), and (1R,2S)-1-methoxy-1-(5-methylpyrimidin-2-yl)propane-2-sulfonamide (Example 466.0). | 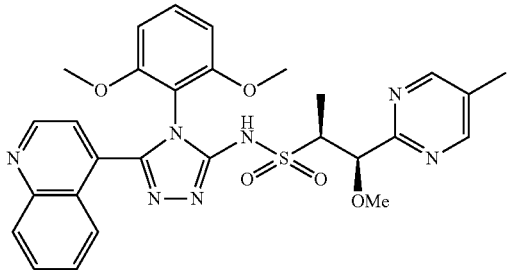 [SMILES: COc1cccc(OC)c1-n1c(NS(=O)(=O)[C@@H](C)[C@H](OC)c2ncc(C)cn2)nnc1-c1ccnc2ccccc12]<br>(1R,2S)-N-(4-(2,6-dimethoxyphenyl)-5-(quinolin-4-yl)-4H-1,2,4-triazol-3-yl)-1-methoxy-1-(5-methylpyrimidin-2-yppropane-2-sulfonamide.<br>$^1$H NMR (500 MHz, DMSO-d$_6$) δ 13.47-13.69 (m, 1H) 8.86-8.92 (m, 1H) 8.51-8.57 (m, 1H) 8.43-8.49 (m, 1H) 7.99-8.09 (m, 2H) 7.79-7.86 (m, 1H) 7.67-7.74 (m, 1H) 7.26-7.34 (m, 2H) 6.59-6.67 (m, 2H) 4.88-4.93 (m, 1H) 3.59 (d, J = 6.1 Hz, 6 H) 3.40-3.43 (m, 3H) 3.31-3.35 (m, 1H) 3.24 (s, 3H) 1.07-1.17 (m, 3H). LCMS-ESI (pos.) m/z: 576.2 (M + H)$^+$. |
| 418.0 | 5-chloro-1H-indazole-3-carbohydrazide (Example 395.37). isothiocyanato-1,3-dimethoxybenzene (Example 465.0), and (1R,2S)-1-(5-chloropyrimidin-2-yl)-1-methoxypropane-2-sulfonamide (Example 466.3). | 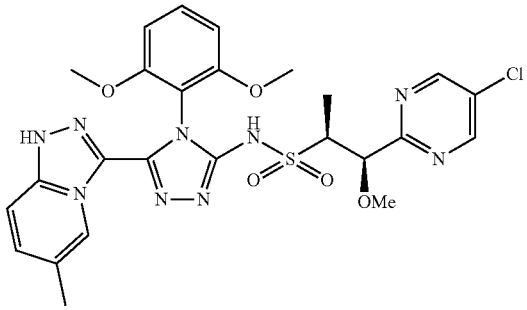<br>(1R,2S)-1-(5-chloropyrimidin-2-yl)-N-(4-(2,6-dimethoxyphenyl)-5-(5-methyl-1H-indazol-3-yl)-4H-1,2,4-triazol-3-yl)-1-methoxypropane-2-sulfonamide.<br>$^1$H NMR (500 MHz, DMSO-d$_6$) δ 13.29-13.47 (m, 1H) 13.09-13.27 (m, 1H) 8.78-9.01 (m, 2H) 7.83-7.93 (m, 1H) 7.37-7.50 (m, 2H) 7.21-7.34 (m, 1H) 6.75-6.86 (m, 2H) 4.73-4.89 (m, 1H) 3.59-3.67 (m, 6 H) 3.43-3.51 (m, 1H) 3.13-3.20 (m, 3H) 2.43-2.47 (m, 3H) 1.11-1.20(m, 3H). LCMS-ESI (pos.) m/z: 599.2 (M + H)$^+$. |
| 419.0 | 1H-pyrrolo[2,3-b]pyridine-3-carbohydrazide (Example 395.33), isothiocyanato-1,3-dimethoxybenzene (Example 465.0), and (1R,2S)-1-(5-chloropyrimidin-2-yl)-1-methoxypropane-2-sulfonamide (Example 466.3). | 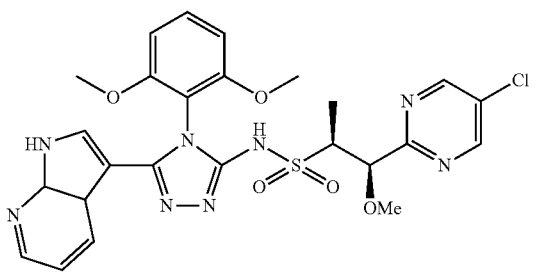 [SMILES: COc1cccc(OC)c1-n1c(NS(=O)(=O)[C@@H](C)[C@H](OC)c2ncc(Cl)cn2)nnc1C1=CNC2N=CC=CC12]<br>(1R,2S)-1-(5-chloropyrimidin-2-yl)-N-(4-(2,6-dimethoxyphenyl)-5-(1H-pyrrolo[2,3-b]pyridin-3-yl)-4H-1,2,4-triazol-3-yl)-1-methoxypropane-2-sulfonamide.<br>$^1$H NMR (500 MHz, DMSO-d$_6$) δ 12.92-13.06 (m, 1H) 11.96-12.10 (m, 1H) 8.90-9.00 (m, 2H) 8.40-8.44 (m, 1H) 8.32-8.35 (m, 1H) 7.56-7.62 (m, 1H) 7.24-7.28 (m, 1H) 6.90-6.95 (m, 2H) 6.54-6.60 (m, 1H) 4.78-4.83 (m, 1H) 3.68-3.74 (m, 7H) 3.14-3.18 (m, 3H) 1.17 (d, J = 7.0 Hz, 3H). LCMS-ESI (pos.) m/z: 585.2 (M + H)$^+$. |

TABLE 28-continued

| Example | Reagents | Structure, Name and Data |
|---|---|---|
| 420.0 | Benzo[d]isoxazole-3-carbohydrazide (Example 77.1), 5-isothiocyanato-4,6-dimethoxypyrimidine (Example 465.1), and (1R,2S)-1-methoxy-1-(5-chloropyrimidin-2-yl)propane-2-sulfonamide (Example 466.3). | 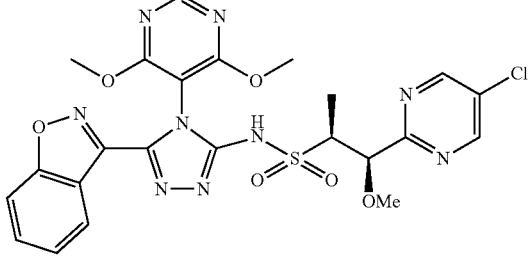<br>(1R,2S)-N-(5-(benzo[d]isoxazol-3-yl)-4-(4,6-dimethoxypyrimidin-5-yl)-4H-1,2,4-triazol-3-yl)-1-(5-chloropyrimidin-2-yl)-1-methoxypropane-2-sulfonamide.<br>$^1$H NMR (500 MHz, DMSO-d$_6$) δ 14.04-14.10 (m, 1H) 8.93-8.97 (m, 2H) 8.71-8.75 (m, 1H) 8.19-8.23 (m, 1H) 7.86-7.90 (m, 1H) 7.79-7.84 (m, 1H) 7.59-7.64 (m, 1H) 4.83-4.88 (m, 1H) 3.90-3.95 (m, 6 H) 3.50-3.56 (m, 1H) 3.17 (s, 3H) 1.20 (br s, 3H). LCMS-ESI (pos.) m/z: 588.0 (M + H)$^+$. |
| 421.0 | 1H-indazole-3-carbohydrazide (Example 395.31). isothiocyanato-1,3-dimethoxybenzene (Example 465.0), and (1R,2S)-1-(5-chloropyrimidin-2-yl)-1-methoxypropane-2-sulfonamide (Example 466.3). | 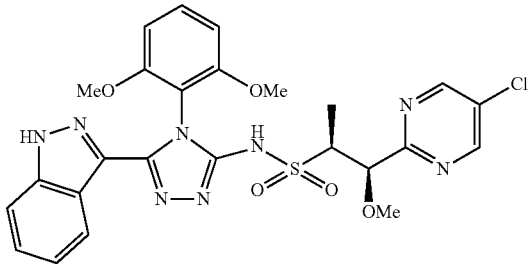 [SMILES: COc1cccc(OC)c1-n1c(NS(=O)(=O)[C@@H](C)[C@H](OC)c2ncc(Cl)cn2)nnc1-c1n[nH]c2ccccc12]<br>(1R,2S)-1-(5-chloropyrimidin-2-yl)-N-(4-(2,6-dimethoxyphenyl)-5-(1H-indazol-3-yl)-4H-1,2,4-triazol-3-yl)-1-methoxypropane-2-sulfonamide.<br>$^1$H NMR (500 MHz, DMSO-d$_6$) δ 13.45-13.53 (m, 1H) 13.20-13.27 (m, 1H) 8.87-8.97 (m, 2H) 8.06-8.17 (m, 1H) 7.51-7.57 (m, 1H) 7.40-7.48 (m, 2H) 7.25-7.33 (m, 1H) 6.77-6.84 (m, 2H) 4.79-4.84 (m, 1H) 3.60-3.68 (m, 6 H) 3.45-3.50 (m, 1H) 3.15-3.19 (m, 3H) 1.16-1.21 (m, 3H). LCMS-ESI (pos.) m/z: 585.2 (M + H)$^+$. |
| 422.0 | 5-chloro-1H-indazole-3-carbohydrazide (Example 395.32), isothiocyanato-1,3-dimethoxybenzene (Example 465.0), and (1R,2S)-1-(5-chloropyrimidin-2-yl)-1-methoxypropane-2-sulfonamide (Example 466.3). | 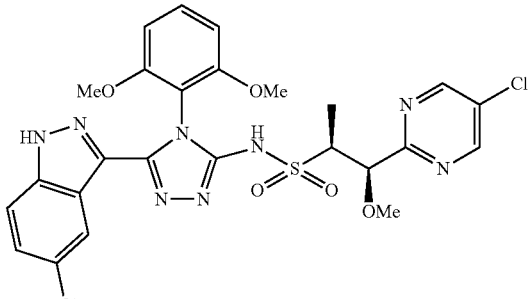<br>(1R,2S)-N-(5-(5-chloro-1H-indazol-3-yl)-4-(2,6-dimethoxyphenyl)-4H-1,2,4-triazol-3-yl)-1-(5-chloropyrimidin-2-yl)-1-methoxypropane-2-sulfonamide.<br>$^1$H NMR (500 MHz, DMSO-d$_6$) δ 13.63-13.76 (m, 1H) 13.24-13.34 (m, 1H) 8.87-8.98 (m, 2H) 8.01-8.15 (m, 1H) 7.51-7.66 (m, 1H) 7.39-7.51 (m, 2H) 6.76-6.86 (m, 2H) 4.76-4.87 (m, 1H) 3.61-3.69 (m, 6 H) 3.44-3.50 (m, 1H) 3.16-3.19 (m, 3H) 1.15-1.20 (m, 3H). LCMS-ESI (pos.) m/z: 619.2 (M + H)$^+$. |

TABLE 28-continued

| Example | Reagents | Structure, Name and Data |
|---|---|---|
| 423.0 | Pyrazolo [1,5-a]pyridine-3-carbohydrazide (Example 395.35), isothiocyanato-1,3-dimethoxybenzene (Example 465.0), and (1R,2S)-1-(5-chloropyrimidin-2-yl)-1-methoxypropane-2-sulfonamide (Example 466.3). | 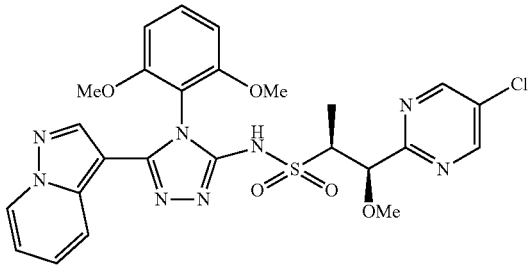 [SMILES: COc1cccc(OC)c1-n1c(NS(=O)(=O)[C@@H](C)[C@H](OC)c2ncc(Cl)cn2)nnc1-c1cnn2ccccc12]<br>(1R,2S)-1-(5-chloropyrimidin-2-yl)-N-(4-(2,6-dimethoxyphenyl)-5-(pyrazolo [1,5-a]pyridin-3-yl)-4H-1,2,4-triazol-3-yl)-1-methoxypropane-2-sulfonamide .<br>$^1$H NMR (500 MHz, DMSO-d$_6$) δ 12.96-13.17 (m, 1H) 8.88-8.97 (m, 2H) 8.73-8.84 (m, 1H) 8.05-8.16 (m, 1H) 7.44-7.71 (m, 2H) 7.02-7.17 (m, 2H) 6.86-6.97 (m, 2H) 4.67-4.86 (m, 1H) 3.70 (d, J = 9.2 Hz, 6 H) 3.41-3.48 (m, 1H) 3.14-3.19 (m, 3H) 1.13-1.19 (m, 3H). LCMS-ESI (pos.) m/z: 585.2 (M + H)$^+$. |
| 424.0 | 5-cyclopropylisoxazole-3-carbohydrazide (Frontier Scientific Services Inc.), isothiocyanato-1,3-dimethoxybenzene (Example 465.0), and (1R,2S)-1-(5-methylpyrimidin-2-yl)-1-methoxypropane-2-sulfonamide (Example 466.methoxy-1-(5-methylpyrimidin-2-yl)propane-2-0). | 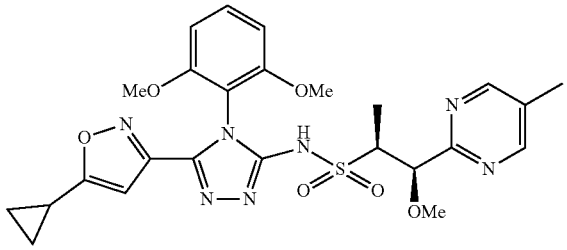 [SMILES: COc1cccc(OC)c1-n1c(NS(=O)(=O)[C@@H](C)[C@H](OC)c2ncc(C)cn2)nnc1-c1cc(C2CC2)on1]<br>(1R,2S)-N-(5-(5-cyclopropylisoxazol-3-yl)-4-(2,6-dimethoxyphenyl)-4H-1,2,4-triazol-3-yl)-1-methoxy-1-(5-methylpyrimidin-2-yl)propane-2-sulfonamide.<br>1H NMR (400 MHz, DMSO-d$_6$) δ 13.49-13.63 (m, 1H) 8.45-8.56 (m, 1H) 8.37-8.45 (m, 1H) 7.42-7.54 (m, 1H) 6.76-6.88 (m, 2H) 6.49-6.58 (m, 1H) 4.81-4.88 (m, 1H) 3.66-3.69 (m, 6 H) 3.26-3.28 (m, 1H) 3.17 (s, 3H) 2.45 (br d, J = 4.0 Hz, 3H) 2.10-2.19 (m, 1H) 1.05-1.07 (m, 3H) 1.04-1.09 (m, 5 H) 0.88-0.94 (m, 2H). LCMS-ESI (pos.) m/z: 556.2 (M + H)$^+$. |
| 425.0 | 5-methylisoxazole-3-carbohydrazide (Frontier Scientific Services Inc.). isothiocyanato-1,3-dimethoxybenzene (Example 465.0), and (1R,2S)-1-(5-methylpyrimidin-2-yl)-1-methoxypropane-2-sulfonamide (Example 466.0). | 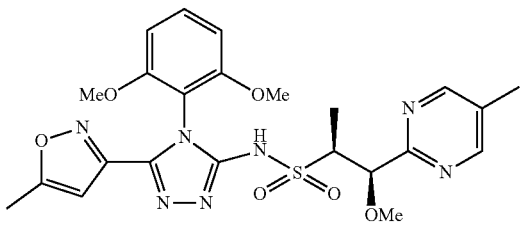<br>(1R,2S)-N-(4-(2,6-dimethoxyphenyl)-5-(5-methylisoxazol-3-yl)-4H-1,2,4-triazol-3-yl)-1-sulfonamide.<br>$^1$H NMR (400 MHz, DMSO-d$_6$) δ 13.46-13.68 (m, 1H) 8.48-8.57 (m, 1H) 8.38-8.45 (m, 1H) 7.40-7.54 (m, 1H) 6.79-6.86 (m, 2H) 6.47-6.54 (m, 1H) 4.82-4.88 (m, 1H) 3.64-3.74 (m, 6 H) 3.42-3.49 (m, 3 H) 3.25-3.29 (m, 1H) 3.16-3.19 (m, 3H) 2.38-2.42 (m, 3H) 1.04-1.08 (m, 3H). LCMS-ESI (pos.) m/z: 530.2 (M + H)$^+$. |

TABLE 28-continued

| Example | Reagents | Structure, Name and Data |
|---|---|---|
| 426.0 | 1H-indazole-3-carbohydrazide (Example 395.31), 5-isothiocyanato-4,6-dimethoxypyrimidine (Example 465.1), and (2S,3R)-3-(5-chloropyrimidin-2-yl)butane-2-sulfonamide (Example 464.4). | 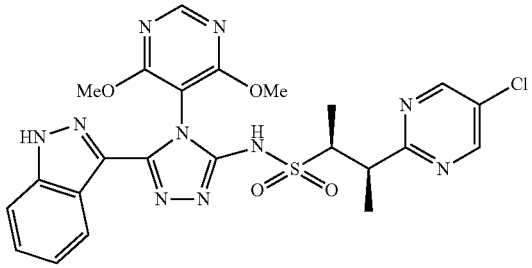 [SMILES: COc1ncnc(OC)c1-n1c(NS(=O)(=O)[C@@H](C)[C@H](C)c2ncc(Cl)cn2)nnc1-c1n[nH]c2ccccc12]<br>(2S,3R)-3-(5-chloropyrimidin-2-yl)-N-(4-(4,6-dimethoxypyrimidin-5-yl)-5-(1H-indazol-3-yl)-4H-1,2,4-triazol-3-yl)butane-2-sulfonamide.<br>$^1$H NMR (500 MHz, DMSO-d$_6$) δ 13.58-13.68 (m, 1H) 13.39-13.55 (m, 1H) 8.80-8.91 (m, 2H) 8.63-8.73 (m, 1H) 8.08-8.18 (m, 1H) 7.54-7.63 (m, 1H) 7.44-7.51 (m, 1H) 7.30-7.38 (m, 1H) 3.81-3.91 (m, 6 H) 3.55-3.73 (m, 2H) 1.24-1.33 (m, 3H) 1.12-1.22 (m, 3H). LCMS-ESI (pos.) m/z: 571.0 (M + H)$^+$. |
| 427.0 | 1H-indazole-3-carbohydrazide (Example 395.31), 5-isothiocyanato-4,6-dimethoxypyrimidine (Example 465.1), and (2S,3R)-3-(5-methylpyrimidin-2-yl)butane-2-sulfonamide (Example 464.0). | 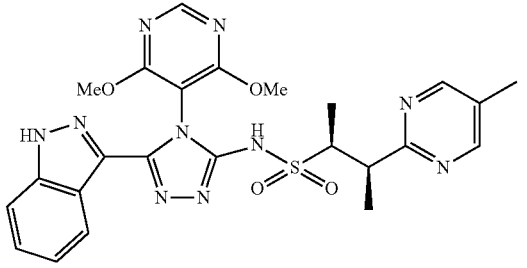 [SMILES: COc1ncnc(OC)c1-n1c(NS(=O)(=O)[C@@H](C)[C@H](C)c2ncc(C)cn2)nnc1-c1n[nH]c2ccccc12]<br>(2S,3R)-N-(4-(4,6-dimethoxypyrimidin-5-yl)-5-(1H-indazol-3-yl)-4H-1,2,4-triazol-3-yl)-3-(5-methylpyrimidin-2-yl)butane-2-sulfonamide.<br>$^1$H NMR (500 MHz, DMSO-d$_6$) δ 13.56-13.71 (m, 1H) 13.38-13.56 (m, 1H) 8.66-8.74 (m, 1H) 8.53-8.66 (m, 2H) 8.06-8.19 (m, 1H) 7.54-7.64 (m, 1H) 7.43-7.53 (m, 1H) 7.27-7.39 (m, 1H) 3.80-3.89 (m, 6 H) 3.66-3.72 (m, 2H) 2.17-2.27 (m, 3H) 1.20-1.32 (m, 3H) 1.06-1.19 (m, 3H). LCMS-ESI (pos.) m/z: 551.2 (M + H)$^+$. |
| 428.0 | 2-methylimidazo[1,2-a]pyridine-3-carbohydrazide (Frontier Scientific Services Inc.), isothiocyanato-1,3-dimethoxybenzene (Example 465.0), and (1R,2S)-1-(5-chloropyrimidin-2-yl)-1-methoxypropane-2-sulfonamide (Example 466.3). | 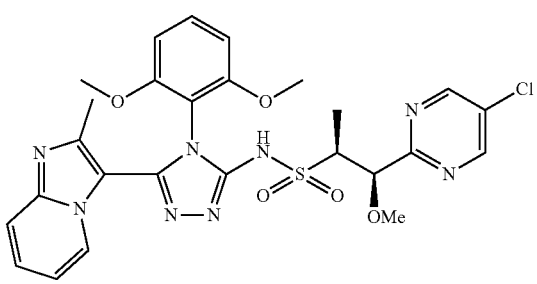 [SMILES: COc1cccc(OC)c1-n1c(NS(=O)(=O)[C@@H](C)[C@H](OC)c2ncc(Cl)cn2)nnc1-c1c(C)nc2ccccn12]<br>(1R,2S)-1-(5-chloropyrimidin-2-yl)-N-(4-(2,6-dimethoxyphenyl)-5-(2-methylimidazo[1,2-a]pyridin-3-yl)-4H-1,2,4-triazol-3-yl)-1-methoxypropane-2-sulfonamide.<br>$^1$H NMR (500 MHz, DMSO-d$_6$) δ 13.53-13.66 (m, 1H) 8.88-8.98 (m, 2H) 8.24-8.37 (m, 1H) 7.62-7.67 (m, 1H) 7.52-7.60 (m, 1H) 7.32-7.39 (m, 1H) 7.15-7.21 (m, 1H) 6.65-6.71 (m, 2H) 4.82-4.88 (m, 1H) 3.60-3.61 (m, 7 H) 3.20 (s, 3H) 2.10 (s, 3H) 1.19-1.24 (m, 3H). LCMS-ESI (pos.) m/z: 599.2 (M + H)$^+$. |

TABLE 28-continued

| Example | Reagents | Structure, Name and Data |
|---|---|---|
| 429.0 | 1H-indazole-3-carbohydrazide (Example 395.31), isothiocyanato-1,3-dimethoxybenzene (Example 465.0), and (2S,3R)-3-(5-chloropyrimidin-2-yl)butane-2-sulfonamide (Example 464.4). | 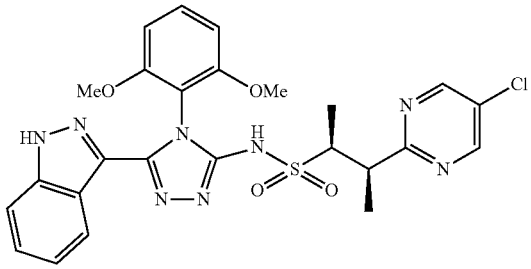 [SMILES: COc1cccc(OC)c1-n1c(NS(=O)(=O)[C@@H](C)[C@H](C)c2ncc(Cl)cn2)nnc1-c1n[nH]c2ccccc12]<br>(2S,3R)-3-(5-chloropyrimidin-2-yl)-N-(4-(4,6-dimethoxypyrimidin-5-yl)-5-(1H-indazol-3-yl)-4H-1,2,4-triazol-3-yl)butane-2-sulfonamide.<br>$^1$H NMR (500 MHz, DMSO-d$_6$) δ 13.39-13.59 (m, 1H) 13.09-13.35 (m, 1H) 8.79-8.90 (m, 2H) 8.06-8.18 (m, 1H) 7.50-7.57 (m, 1H) 7.39-7.49 (m, 2H) 7.24-7.34 (m, 1H) 6.74-6.87 (m, 2H) 3.66-3.73 (m, 1H) 3.54-3.66 (m, 7 H) 1.22-1.30 (m, 3H) 1.10-1.20 (m, 3H). LCMS-ESI (pos.) m/z: 569.2 (M + H)$^+$. |
| 430.0 | 1H-indazole-3-carbohydrazide (Example 395.31), isothiocyanato-1,3-dimethoxybenzene (Example 465.0), and (2R,3S)-3-(5-chloropyrimidin-2-yl)butane-2-sulfonamide (Example 464.7.0). | 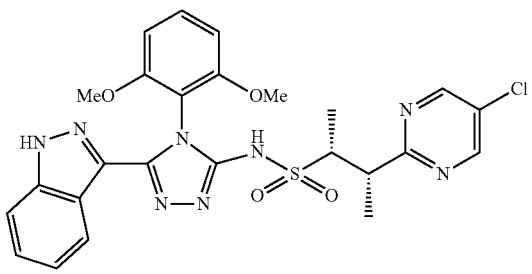 [SMILES: COc1cccc(OC)c1-n1c(NS(=O)(=O)[C@H](C)[C@@H](C)c2ncc(Cl)cn2)nnc1-c1n[nH]c2ccccc12]<br>(2R,3S)-3-(5-chloropyrimidin-2-yl)-N-(4-(4,6-dimethoxypyrimidin-5-yl)-5-(1H-indazol-3-yl)-4H-1,2,4-triazol-3-yl)butane-2-sulfonamide.<br>$^1$H NMR (500 MHz, DMSO-d$_6$) δ 13.39-13.59 (m, 1H) 13.09-13.35 (m, 1H) 8.79-8.90 (m, 2H) 8.06-8.18 (m, 1H) 7.50-7.57 (m, 1H) 7.39-7.49 (m, 2H) 7.24-7.34 (m, 1H) 6.74-6.87 (m, 2H) 3.66-3.73 (m, 1H) 3.54-3.66 (m, 7 H) 1.22-1.30 (m, 3H) 1.10-1.20 (m, 3H). LCMS-ESI (pos.) m/z: 569.2 (M + H)$^+$. |
| 431.0 | 1H-indazole-3-carbohydrazide (Example 395.31), isothiocyanato-1,3-dimethoxybenzene (Example 465.0), and (2R,3S)-3-(5-methyllpyrimidin-2-yl)butane-2-sulfonamide (Example 464.8.0). | 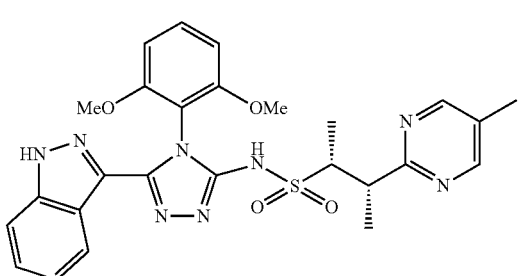<br>(2R,3S)-N-(4-(2,6-dimethoxyphenyl)-5-(1H-indazol-3-yl)-4H-1,2,4-triazol-3-yl)-3-(5-methylpyrimidin-2-yl)butane-2-sulfonamide.<br>$^1$H NMR (400 MHz, DMSO-d$_6$) δ 13.42-13.57 (m, 1H) 13.18-13.35 (m, 1H) 8.47-8.68 (m, 2H) 8.06-8.22 (m, 1H) 7.48-7.62 (m, 1H) 7.42-7.49 (m, 2H) 7.25-7.34 (m, 1H) 6.74-6.84 (m, 2H) 3.68-3.77 (m, 1H) 3.56-3.64 (m, 7 H) 2.19-2.30 (m, 3H) 1.22-1.30 (m, 3H) 1.09-1.16 (m, 3H). LCMS-ESI (pos.) m/z: 549.2 (M + H)$^+$. |

TABLE 28-continued

| Example | Reagents | Structure, Name and Data |
|---|---|---|
| 432.0 | 1,5-dimethyl-1H-inclazole-3-carbohydrazide (Example 395.38), isothiocyanato-1,3-dimethoxybenzene (Example 465.0), and (2S,3R)-3-(5-chloropyrimidin-2-yl)butane-2-sulfonamide (Example 464.4). | 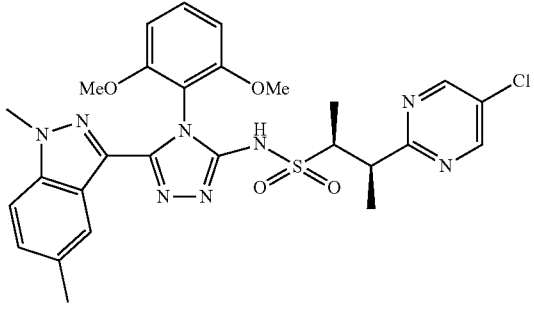<br>(2S,3R)-3-(5-chloropyrimidin-2-yl)-N-(4-(2,6-dimethoxyphenyl)-5-(1,5-dimethyl-1H-indazol-3-yl)-4H-1,2,4-triazol-3-yl)butane-2-sulfonamide.<br>$^1$H NMR (500 MHz, DMSO-d$_6$) δ 13.14-13.23 (m, 1H) 8.84-9.01 (m, 2H) 7.76-7.89 (m, 1H) 7.54-7.63 (m, 1H) 7.43-7.51 (m, 1H) 7.27-7.35 (m, 1H) 6.77-6.85 (m, 2H) 4.80-4.86 (m, 1H) 3.75-3.82 (m, 3H) 3.61-3.70 (m, 6 H) 3.41-3.51 (m, 1H) 3.13-3.23 (m, 3H) 2.42-2.48 (m, 3H) 1.14-1.26 (m, 3H). LCMS-ESI (pos.) m/z: 613.2 (M + H)$^+$. |
| 433.0 | 1,5-dimethyl-1H-inclazole-3-carbohydrazide (Example 395.38), 5-isothiocyanato-4,6-dimethoxypyrimidine (Example 465.1), and (2S,3R)-3-(5-chloropyrimidin-2-yl)butane-2-sulfonamide (Example 464.4). | 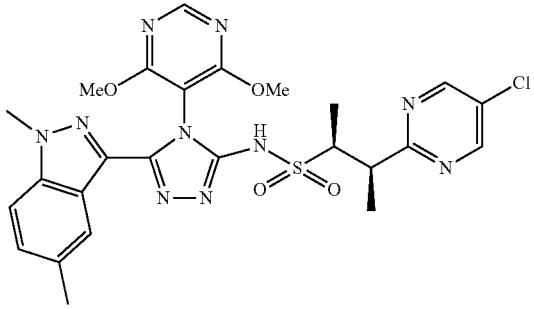 [SMILES: COc1ncnc(OC)c1-n1c(NS(=O)(=O)[C@@H](C)[C@H](C)c2ncc(Cl)cn2)nnc1-c1nn(C)c2ccc(C)cc12]<br>(2S,3R)-3-(5-chloropyrimidin-2-yl)-N-(4-(4,6-dimethoxypyrimidin-5-yl)-5-(1,5-dimethyl-1H-indazol-3-yl)-4H-1,2,4-triazol-3-yl)butane-2-sulfonamide.<br>$^1$H NMR (500 MHz, DMSO-d$_6$) δ 13.37-13.54 (m, 1H) 8.79-8.91 (m, 2H) 8.64-8.75 (m, 1H) 7.79-7.93 (m, 1H) 7.55-7.67 (m, 1H) 7.28-7.41 (m, 1H) 3.81-3.88 (m, 9 H) 3.58-3.72 (m, 2H) 2.40-2.53 (m, 3H) 1.22-1.31 (m, 3H) 1.09-1.22 (m, 3H). LCMS-ESI (pos.) m/z: 599.2 (M + H)$^+$. |
| 434.0 | 5H-pyrrolo[3,2-d]pyrimidine-4-carbohydrazide (Example 395.39), isothiocyanato-1,3-dimethoxybenzene (Example 465.0), and (1R,2S)-1-(5-chloropyrimidin-2-yl)-1-methoxypropane-2-sulfonamide (Example 466.3). | 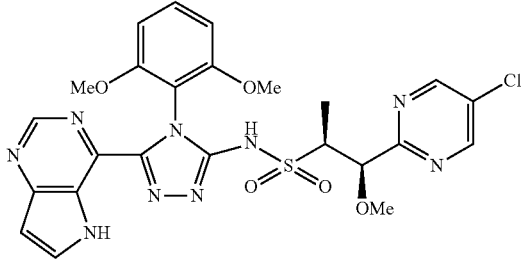 [SMILES: COc1cccc(OC)c1-n1c(NS(=O)(=O)[C@@H](C)[C@H](OC)c2ncc(Cl)cn2)nnc1-c1ncnc2cc[nH]c12]<br>(1R,2S)-1-(5-chloropyrimidin-2-yl)-N-(4-(2,6-dimethoxyphenyl)-5-(5H-pyrrolo[3,2-d]pyrimidin-4-yl)-4H-1,2,4-triazol-3-yl)-1-methoxypropane-2-sulfonamide.<br>$^1$H NMR (500 MHz, DMSO-d$_6$) δ 13.41-13.56 (m, 1H) 12.32-12.47 (m, 1H) 8.90-9.00 (m, 2H) 8.35-8.49 (m, 1H) 7.69-7.78 (m, 1H) 7.36-7.47 (m, 1H) 6.86-6.94 (m, 1H) 6.72-6.81 (m, 2H) 4.77-4.86 (m, 1H) 3.58-3.63 (m, 6 H) 3.46-3.52 (m, 1H) 3.13-3.20 (m, 3H) 1.16-1.22 (m, 3H). LCMS-ESI (pos.) m/z: 586.0 (M + H)$^+$. |

TABLE 28-continued

| Example | Reagents | Structure, Name and Data |
|---|---|---|
| 435.0 | 5H-pyrrolo[3,2-d]pyrimidine-4-carbohydrazide (Example 395.39), isothiocyanato-1,3-dimethoxybenzene (Example 465.0), and (1R,2S)-1-(5-methylpyrimidin-2-yl)-1-methoxypropane-2-sulfonamide (Example 466.0). | 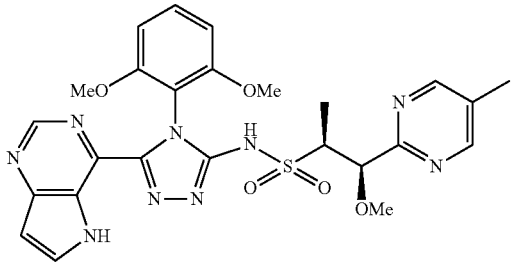 [SMILES: COc1cccc(OC)c1-n1c(NS(=O)(=O)[C@@H](C)[C@H](OC)c2ncc(C)cn2)nnc1-c1ncnc2cc[nH]c12]<br>(1R,2S)-N-(4-(2,6-dimethoxyphenyl)-5-(5H-pyrrolo[3,2-d]pyrimidin-4-yl)-4H-1,2,4-triazol-3-yl)-1-methoxy-1-(5-methylpyrimidin-2-yl)propane-2-sulfonamide.<br>$^1$H NMR (500 MHz, DMSO-d$_6$) δ 13.49-13.65 (m, 1H) 12.28-12.49 (m, 1H) 8.47-8.55 (m, 1H) 8.37-8.47 (m, 2H) 7.69-7.78 (m, 1H) 7.38-7.47 (m, 1H) 6.87-6.95 (m, 1H) 6.72-6.82 (m, 2H) 4.81-4.94 (m, 1H) 3.55-3.64 (m, 6 H) 3.28-3.31 (m, 1H) 3.18* 3.22 (m, 3H) 2.47-2.49 (m, 3H) 1.07-1.11 (m, 3H). LCMS-ESI (pos.) m/z: 566.2 (M + H)$^+$. |
| 436.0 | 1-methyl-1H-indazole-3-carbohydrazide (Example 395.40), isothiocyanato-1,3-dimethoxybenzene (Example 465.0), and (1R,2S)-1-(5-methylpyrimidin-2-yl)-1-methoxypropane-2-sulfonamide (Example 466.0). | 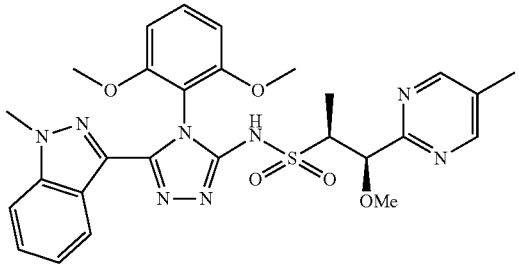<br>(1R,2S)-N-(4-(2,6-dimethoxyphenyl)-5-(1-methyl-1H-indazol-3-yl)-4H-1,2,4-triazol-3-yl)-1-methoxy-1-(5-methylpyrimidin-2-yl)propane-2-sulfonamide.<br>$^1$H NMR (400 MHz, DMSO-d$_6$) δ 13.17-13.43 (m, 1H) 8.49-8.58 (m, 1H) 8.39-8.47 (m, 1H) 7.96-8.13 (m, 1H) 7.60-7.77 (m, 1H) 7.44-7.56 (m, 2H) 7.28-7.38 (m, 1H) 6.76-6.86 (m, 2H) 4.82-4.93 (m, 1H) 3.80-3.85 (m, 3H) 3.60-3.67 (m, 6 H) 3.26-3.35 (m, 4H) 3.18-3.23 (m, 3H) 1.05-1.12 (m, 3H). LCMS-ESI (pos.) m/z: 579.2 (M + H)$^+$. |
| 437.0 | 5-fluoro-1H-indazole-3-carbohydrazide (Example 395.41), isothiocyanato-1,3-dimethoxybenzene (Example 465.0), and (1R,2S)-1-(5-methylpyrimidin-2-yl)-1-methoxypropane-2-sulfonamide (Example 466.0). | 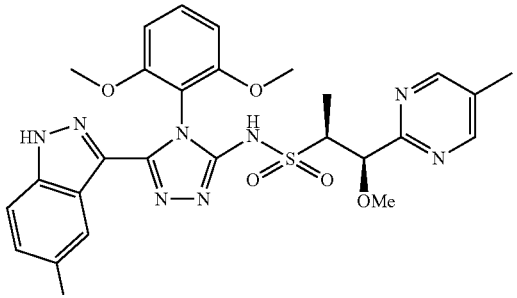<br>(1R,2S)-N-(4-(2,6-dimethoxyphenyl)-5-(5-fluoro-1H-indazol-3-yl)-4H-1,2,4-triazol-3-yl)-1-methoxy-1-(5-methylpyrimidin-2-yl)propane-2-sulfonamide.<br>$^1$H NMR (500 MHz, DMSO-d$_6$) δ 13.55-13.75 (m, 1H) 13.19-13.44 (m, 1H) 8.50-8.54 (m, 1H) 8.40-8.46 (m, 1H) 7.72-7.79 (m, 1H) 7.57-7.64 (m, 1H) 7.41-7.48 (m, 1H) 7.32-7.39 (m, 1H) 6.77-6.84 (m, 2H) 4.85-4.89 (m, 1H) 3.59-3.67 (m, 6 H) 3.28-3.31 (m, 1H) 3.17-3.23 (m, 3H) 2.48-2.49(m, 3 H) 1.06-1.10 (m, 3H). LCMS-ESI (pos.) m/z: 583.2 (M + H)$^+$. |

TABLE 28-continued

| Example | Reagents | Structure, Name and Data |
|---|---|---|
| 438.0 | 4,5,6,7-tetrahydro-1H-indazole-3-carbohydrazide carbohydrazide (commercially available from Frontier Scientific Services, Inc., Newark, DE), isothiocyanato-1,3-dimethoxybenzene (Example 465.0), and (2S,3R)-3-(5-chloropyrimidin-2-yl)butane-2-sulfonamide (Example 464.4). | 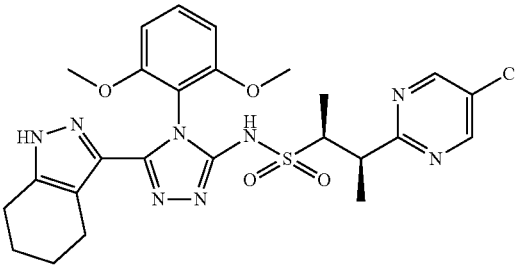<br>(2S,3R)-3-(5-chloropyrimidin-2-yl)-N-(4-(2,6-dimethoxyphenyl)-5-(4,5,6,7-tetrahydro-1H-indazol-3-yl)-4H-1,2,4-triazol-3-yl)butane-2-sulfonamide.<br>$^1$H NMR (500 MHz, DMSO-d$_6$) δ 12.88-13.01 (m, 1H) 12.54-12.69 (m, 1H) 8.76-8.90 (m, 2H) 7.29-7.44 (m, 1H) 6.72-6.78 (m, 2H) 3.63-3.69 (m, 7 H) 3.52-3.58 (m, 1H) 2.56-2.62 (m, 3H) 1.65-1.74 (m, 5 H) 1.22-1.25 (m, 3H) 1.08-1.12 (m, 3H). LCMS-ESI (pos.) m/z: 573.2 (M + H)$^+$. |
| 439.0 | Pyrazolo[1,5-a]pyridine-3-carbohydrazide (Example 395.35), isothiocyanato-4,6-dimethoxypyrimidine (Example 465.1), and (1R,2S)-1-(5-chloropyrimidin-2-yl)-1-methoxypropane-2-sulfonamide (Example 466.3). | 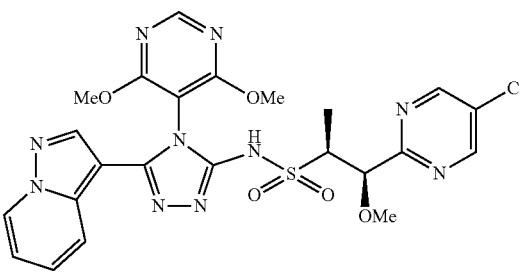<br>(1R,2S)-1-(5-chloropyrimidin-2-yl)-N-(4-(4,6-dimethoxypyrimidin-5-yl)-5-(pyrazolo[1,5-a]pyridin-3-yl)-4H-1,2,4-triazol-3-yl)-1-methoxypropane-2-sulfonamide.<br>$^1$H NMR (400 MHz, DMSO-d$_6$) δ 13.20-13.39 (m, 1H) 8.91-8.97 (m, 2H) 8.81-8.87 (m, 1H) 8.73-8.78 (m, 1H) 8.04-8.10 (m, 1H) 7.55-7.62 (m, 1H) 7.51-7.54 (m, 1H) 7.13-7.19 (m, 1H) 4.78-4.83 (m, 1H) 3.89-3.96 (m, 6 H) 3.41-3.48 (m, 1H) 3.14-3.18 (m, 3H) 1.15-1.18 (m, 3H). LCMS-ESI (pos.) m/z: 587.2 (M + H)$^+$. |
| 440.0 | Pyrazolo[1,5-a]pyridine-3-carbohydrazide (Example 395.35), isothiocyanato-4,6-dimethoxypyrimidine (Example 465.1), and (2S,3R)-3-(5-chloropyrimidin-2-yl)butane-2-sulfonamide (Example 464.4). | 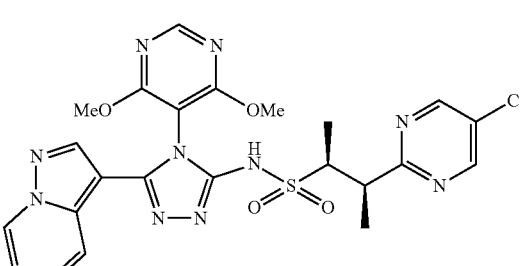<br>(2S,3R)-3-(5-chloropyrimidin-2-yl)-N-(4-(4,6-dimethoxypyrimidin-5-yl)-5-(pyrazolo[1,5-a]pyridin-3-yl)-4H-1,2,4-triazol-3-yl)butane-2-sulfonamide.<br>$^1$H NMR (500 MHz, DMSO-d$_6$) δ 13.24-13.38 (m, 1H) 8.81-8.90 (m, 3H) 8.73-8.77 (m, 1H) 8.05-8.10 (m, 1H) 7.55-7.63 (m, 1H) 7.49-7.55 (m, 1H) 7.13-7.19 (m, 1H) 3.89-3.93 (m, 6 H) 3.56-3.69 (m, 2H) 1.25-1.28 (m, 3H) 1.13-1.16 (m, 3H). LCMS-ESI (pos.) m/z: 571.2 (M + H)$^+$. |

TABLE 28-continued

| Example | Reagents | Structure, Name and Data |
|---------|----------|--------------------------|
| 441.0 | 4,5,6,7-tetrahydrobenzo[d]isoxazole-3-carbohydrazide (Example 395.42). isothiocyanato-1,3-dimethoxybenzene (Example 465.0), and (2S,3R)-3-(5-chloropyrimidin-2-yl)butane-2-sulfonamide (Example 464.4). | 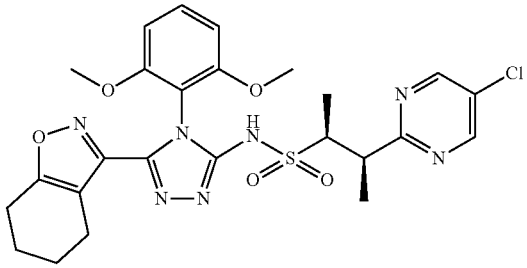 [SMILES: COc1cccc(OC)c1-n1c(NS(=O)(=O)[C@@H](C)[C@H](C)c2ncc(Cl)cn2)nnc1-c1noc2c1CCCC2] (2S,3R)-3-(5-chloropyrimidin-2-yl)-N-(4-(2,6-dimethoxyphenyl)-5-(4,5,6,7-tetrahydrobenzo[d]isoxazol-3-yl)-4H-1,2,4-triazol-3-yl)butane-2-sulfonamide. $^1$H NMR (400 MHz, DMSO-$d_6$) δ 13.41-13.57 (m, 1H) 8.76-8.91 (m, 2H) 7.38-7.53 (m, 1H) 6.74-6.83 (m, 2H) 3.63-3.69 (m, 7 H) 3.54-3.61 (m, 1H) 2.65-2.71 (m, 2H) 2.54-2.60 (m, 2H) 1.76-1.84 (m, 2H) 1.69-1.75 (m, 2H) 1.21-1.26 (m, 3H) 1.09-1.14 (m, 3H). LCMS-ESI (pos.) m/z: 574.0 (M + H)$^+$. |
| 442.0 | Pyrazolo [1,5-a]pyridine-3-carbohydrazide (Example 395.35). (1R,2r,3S)-2-isothiocyanato-1,3-dimethoxycyclohexane (Example 476.3), and (2S,3R)-3-(5-chloropyrimidin-2-yl)butane-2-sulfonamide (Example 464.4). | 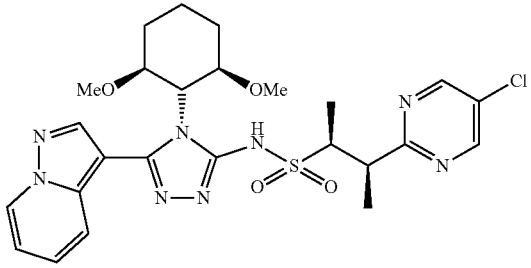 (2S,3R)-3-(5-chloropyrimidin-2-yl)-N-(4-((1r,2R,6S)-2,6-dimethoxycyclohexyl)-5-(pyrazolo[1,5-a]pyridin-3-yl)-4H-1,2,4-triazol-3-yl)butane-2-sulfonamide. $^1$H NMR (400 MHz, CDCl$_3$) δ 11.23 (br s, 1H) 8.63-8.67 (m, 2H) 8.53-8.57 (m, 1H) 8.40-8.44 (m, 1H) 7.86-7.94 (m, 1H) 7.29-7.35 (m, 1H) 6.87-6.95 (m, 1H) 4.25-4.35 (m, 2H) 3.87-3.96 (m, 2H) 3.25-3.30 (m, 6 H) 2.19-2.29 (m, 2H) 1.73-1.85 (m, 1 H) 1.43-1.52 (m, 6 H) 1.25-1.33 (m, 2H) 0.98-1.13 (m, 2H). LCMS-ESI (pos.) m/z: 575.2 (M + H)$^+$. |
| 443.0 | 1-methyl-1H-pyrazole-3-carbohydrazide (ChemBridge Corporation), isothiocyanato-1,3-dimethoxybenzene (Example 465.0), and (2R,3S)-3-(5-chloropyrimidin-2-yl)butane-2-sulfonamide (Example 464.7). | 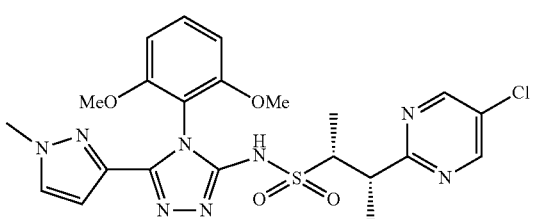 (2R,3S)-3-(5-chloropyrimidin-2-yl)-N-(4-(2,6-dimethoxyphenyl)-5-(1-methyl-1H-pyrazol-3-yl)-4H-1,2,4-triazol-3-yl)butane-2-sulfonamide. $^1$H NMR (400 MHz, DMSO-$d_6$) δ 12.93-13.11 (m, 1H) 8.77-8.94 (m, 2H) 7.63-7.75 (m, 1H) 7.43-7.57 (m, 1H) 6.72-6.88 (m, 2H) 6.04-6.13 (m, 1H) 3.71-3.76 (m, 3H) 3.64-3.70 (m, 7 H) 3.52-3.62 (m, 1H) 1.21-1.28 (m, 3H) 1.06-1.15 (m, 3H). LCMS-ESI (pos.) m/z: 533.2 (M + H)$^+$. |

TABLE 28-continued

| Example | Reagents | Structure, Name and Data |
|---|---|---|
| 444.0 | 5,6-dihydro-4H-pyrrolo[1,2-b]pyrazole-3-carbohydrazide (Example 395.43). isothiocyanato-1,3-dimethoxybenzene (Example 465.0), and (1R,2S)-1-(5-methylpyrimidin-2-yl)-1-methoxypropane-2-sulfonamide (Example 466.0). | 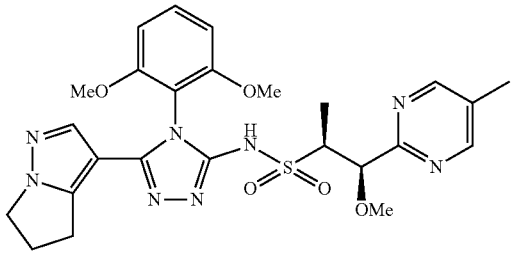 [SMILES: COc1cccc(OC)c1-n1c(NS(=O)(=O)[C@@H](C)[C@H](OC)c2ncc(C)cn2)nnc1-c1cnn2c1CCC2]<br>(1R,2S)-N-(5-(5,6-dihydro-4H-pyrrolo[1,2-b]pyrazol-3-yl)-4-(2,6-dimethoxyphenyl)-4H-1,2,4-triazol-3-yl)-1-methoxy-1-(5-methylpyrimidin-2-yl)propane-2-sulfonamide.<br>$^1$H NMR (400 MHz, DMSO-$d_6$) δ 12.75-13.08 (m, 1H) 8.48-8.58 (m, 1H) 8.33-8.46 (m, 1H) 7.43-7.66 (m, 1H) 6.85-6.95 (m, 2H) 6.67-6.78 (m, 1H) 4.81-4.88 (m, 1H) 3.94-4.13 (m, 2H) 3.65-3.73 (m, 6 H) 3.22-3.29 (m, 1H) 3.16-3.20 (m, 3H) 2.70-2.79 (m, 2H) 2.51-2.57 (m, 2H) 2.41-2.49 (m, 3H) 1.03-1.07 (m, 3H). LCMS-ESI (pos.) m/z: 555.2 (M + H)$^+$. |
| 445.0 | 5,6-dihydro-4H-pyrrolo[1,2-b]pyrazole-3-carbohydrazide (Example 395.43). isothiocyanato-1,3-dimethoxybenzene (Example 465.0), and (2S,3R)-3-(5-chloropyrimidin-2-yl)butane-2-sulfonamide (Example 464.4). | 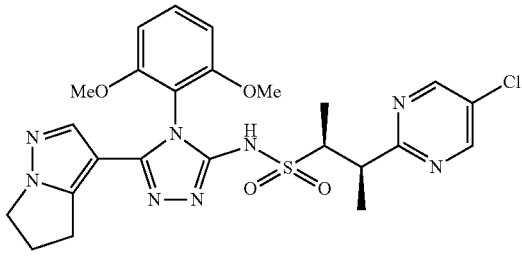 [SMILES: COc1cccc(OC)c1-n1c(NS(=O)(=O)[C@@H](C)[C@H](C)c2ncc(Cl)cn2)nnc1-c1cnn2c1CCC2]<br>(2S,3R)-3-(5-chloropyrimidin-2-yl)-N-(5-(5,6-dihydro-4H-pyrrolo[1,2-b]pyrazol-3-yl)-4-(2,6-dimethoxyphenyl)-4H-1,2,4-triazol-3-yl)butane-2-sulfonamide.<br>$^1$H NMR (500 MHz, DMSO-$d_6$) δ 12.29-13.22 (m, 1H) 8.71-8.91 (m, 2H) 7.46-7.63 (m, 1H) 6.81-6.95 (m, 2H) 6.65-6.80 (m, 1H) 3.97-4.10 (m, 2H) 3.62-3.73 (m, 7 H) 3.50-3.60 (m, 1H) 2.71-2.78 (m, 2H) 2.51-2.56 (m, 2H) 1.20-1.26 (m, 3H) 1.08-1.14 (m, 3H). LCMS-ESI (pos.) m/z: 559.2 (M + H)$^+$. |
| 446.0 | 5,6-dihydro-4H-pyrrolo[1,2-b]pyrazole-3-carbohydrazide (Example 395.43). isothiocyanato-1,3-dimethoxybenzene (Example 465.0), and (1S,2S)-1-isopropoxy-1-(5-methylpyrimidin-2-yl)propane-2-sulfonamide (Example 468.0). | 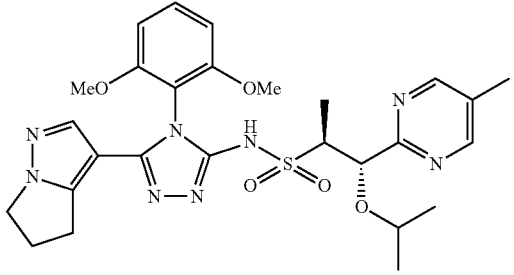 [SMILES: COc1cccc(OC)c1-n1c(NS(=O)(=O)[C@@H](C)[C@@H](OC(C)C)c2ncc(C)cn2)nnc1-c1cnn2c1CCC2]<br>(1S,2S)-N-(5-(5,6-dihydro-4H-pyrrolo[1,2-b]pyrazol-3-yl)-4-(2,6-dimethoxyphenyl)-4H-1,2,4-triazol-3-yl)-1-isopropoxy-1-(5-methylpyrimidin-2-yl)propane-2-sulfonamide.<br>$^1$H NMR (500 MHz, DMSO-$d_6$) δ 12.79-12.93 (m, 1H) 8.31-8.54 (m, 2H) 7.47-7.64 (m, 1H) 6.82-6.97 (m, 2H) 6.66-6.80 (m, 1H) 4.71-4.81 (m, 1H) 3.97-4.12 (m, 2H) 3.67-3.76 (m, 6 H) 3.36-3.45 (m, 2H) 2.70-2.77 (m, 2H) 2.51-2.56 (m, 2H) 2.47 (s, 3H) 1.01-1.05 (m, 3H) 0.97-1.01 (m, 3H) 0.84-0.88 (m, 3H). LCMS-ESI (pos.) m/z: 583.2 (M + H)$^+$. |

TABLE 28-continued

| Example | Reagents | Structure, Name and Data |
|---|---|---|
| 447.0 | 5,6-dihydro-4H-pyrrolo[1,2-b]pyrazole-3-carbohydrazide (Example 395.43). isothiocyanato-1,3-dimethoxybenzene (Example 465.0), and (1S,2S)-1-(5-chloropyrimidin-2-yl)-1-isopropoxypropane-2-sulfonamide (Example 468.1). | 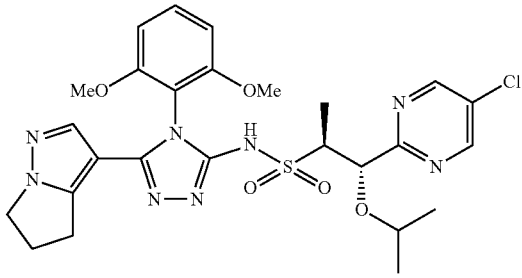 [SMILES: COc1cccc(OC)c1-n1c(NS(=O)(=O)[C@@H](C)[C@@H](OC(C)C)c2ncc(Cl)cn2)nnc1-c1cnn2c1CCC2]<br>(1S,2S)-1-(5-chloropyrimidin-2-yl)-N-(5-(5,6-dihydro-4H-pyrrolo[1,2-b]pyrazol-3-yl)-4-(2,6-dimethoxyphenyl)-4H-1,2,4-triazol-3-yl)-1-isopropoxypropane-2-sulfonamide.<br>$^1$H NMR (500 MHz, DMSO-$d_6$) δ 12.67-12.86 (m, 1H) 8.80-9.01 (m, 2H) 7.45-7.60 (m, 1H) 6.84-6.94 (m, 2H) 6.67-6.81 (m, 1H) 4.69-4.85 (m, 1H) 3.97-4.11 (m, 3H) 3.67-3.85 (m, 6 H) 3.35-3.50 (m, 2H) 3.28-3.33 (m, 3H) 2.68-2.78 (m, 2H) 2.51-2.56 (m, 1H) 0.94-1.03 (m, 6 H) 0.80-0.85 (m, 3H). LCMS-ESI (pos.) m/z: 603.2 (M + H)$^+$. |
| 448.0 | 1,5-dimethyl-1H-indazole-3-carbohydrazide (Example 395.38), 2-isothiocyanato-1,3-dimethoxypropane (Example 452.1), and (2S,3R)-3-(5-chloropyrimidin-2-yl)butane-2-sulfonamide (Example 464.4). | 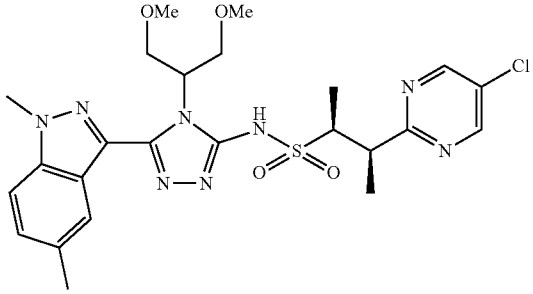 [SMILES: COCC(COC)n1c(NS(=O)(=O)[C@@H](C)[C@H](C)c2ncc(Cl)cn2)nnc1-c1nn(C)c2ccc(C)cc12]<br>(2S,3R)-3-(5-chloropyrimidin-2-yl)-N-(4-(1,3-dimethoxypropan-2-yl)-5-(1,5-dimethyl-1H-indazol-3-yl)-4H-1,2,4-triazol-3-yl)butane-2-sulfonamide.<br>$^1$H NMR (500 MHz, DMSO-$d_6$) δ 12.99-13.18 (m, 1H) 8.78-8.93 (m, 2H) 7.79-7.94 (m, 1H) 7.59-7.78 (m, 1H) 7.34-7.46 (m, 1H) 4.08-4.16 (m, 5 H) 3.60-3.83 (m, 5 H) 3.19-3.21 (m, 3H) 2.48-2.52 (m, 3H) 2.43-2.47 (m, 3H) 1.38 (br d, J = 7.0 Hz, 3H) 1.24-1.31 (m, 3H). LCMS-ESI (pos.) m/z: 563.2 (M + H)$^+$. |
| 449.0 | 1-methyl-1H-indazole-3-carbohydrazide (Example 395.40), 2-isothiocyanato-1,3-dimethoxypropane (Example 452.1), and (2S,3R)-3-(5-chloropyrimidin-2-yl)butane-2-sulfonamide (Example 464.4). | 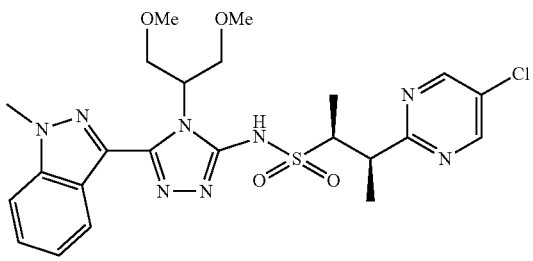 [SMILES: COCC(COC)n1c(NS(=O)(=O)[C@@H](C)[C@H](C)c2ncc(Cl)cn2)nnc1-c1nn(C)c2ccccc12]<br>(2S,3R)-3-(5-chloropyrimidin-2-yl)-N-(4-(1,3-dimethoxypropan-2-yl)-5-(1-methyl-1H-indazol-3-yl)-4H-1,2,4-triazol-3-yl)butane-2-sulfonamide.<br>$^1$H NMR (500 MHz, DMSO-$d_6$) δ 13.12-13.24 (m, 1H) 8.78-9.01 (m, 2H) 8.05-8.20 (m, 1H) 7.74-7.86 (m, 1H) 7.51-7.62 (m, 1H) 7.29-7.42 (m, 1H) 5.62-6.12 (m, 1H) 4.09-4.25 (m, 5 H) 3.76-3.82 (m, 1H) 3.70-3.76 (m, 1H) 3.63-3.70 (m, 2H) 3.15-3.24 (m, 6H) 1.35-1.43 (m, 3H) 1.25-1.33 (m, 3H). LCMS-ESI (pos.) m/z: 549.2 (M + H)$^+$. |

Example 451.1. Preparation of 1-isothiocyanato-1-(methoxymethyl)cyclopropane

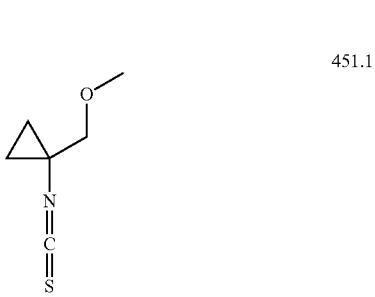

451.1

1-Isothiocyanato-1-(methoxymethyl)cyclopropane, Example 451.1. To a dry 200 mL RBF was added 1-(methoxymethyl)cyclopropanamine hydrochloride (commercially available from J&W Pharm Lab, 2.06 g, 14.97 mmol) and di(2-pyridyl) thionocarbonate (3.65 g, 15.72 mmol) in DCM (49.9 mL). Hunig's base (2.86 mL, 16.5 mmol) in DCM (15 mL) was then added dropwise via an addition funnel over 5 min at RT with stirring. The reaction mixture was stirred at RT for 3.5 h. The reaction mixture was then concentrated in vacuo. The material thus obtained was absorbed onto a plug of silica gel and purified by chromatography through a Redi-Sep pre-packed silica gel column (24 g) eluting with a gradient of 0% to 50% EtOAc in heptanes to provide the title compound, Example 451.1 (1.88 g, 13.13 mmol, 88% yield), as a colorless oil. $^1$H NMR (400 MHz, CDCl$_3$) δ 3.47 (s, 2H), 3.43 (s, 3H), 1.06-1.16 (m, 2H), 0.81-0.94 (m, 2H).

Example 452.1. Preparation of 2-isothiocyanato-1,3-dimethoxypropane 452.1

2-Isothiocyanato-1,3-dimethoxypropane, Example 452.1. To a dry 200 mL RBF was added di(2-pyridyl) thionocarbonate (5.34 g, 23.00 mmol) in DCM (73.0 mL). 2-Amino-1,3-dimethoxypropane (commercially available from Combi-Blocks Inc., 2.61 g, 21.90 mmol) in DCM (15 mL) was added dropwise via an addition funnel over 5 min at RT with stirring. The reaction mixture was stirred at RT for 3.5 h. The reaction mixture was then concentrated in vacuo. The material thus obtained was absorbed onto a plug of silica gel and purified by chromatography through a Redi-Sep pre-packed silica gel column (40 g) eluting with a gradient of 0% to 50% EtOAc in heptanes to provide the title compound, Example 452.1 (3.28 g, 20.34 mmol, 93% yield), as a colorless oil. $^1$H NMR (400 MHz, CDCl$_3$) δ 3.95 (quin, J=5.49 Hz, 1H) 3.50-3.60 (m, 4H) 3.41 (m, 6H). MS (pos.) m/z: 162.2 (M+H)$^+$.

The compounds set forth in the following table were synthesized following the procedure in Example 77.0 using the known starting material as described.

TABLE 29

| Example | Reagents | Structure, Name and Data |
|---|---|---|
| 450.0 | 5-isothiocyanato-4,6-dimethoxypyrimidine (Example 465.1), 1-methyl-1H-pyrazole-3-carbohydrazide (ChemBridge Corporation), and (1R,2S)-1-(5-chloropyrimidin-2-yl)-1-methoxypropane-2-sulfonamide (Example 466.3). | 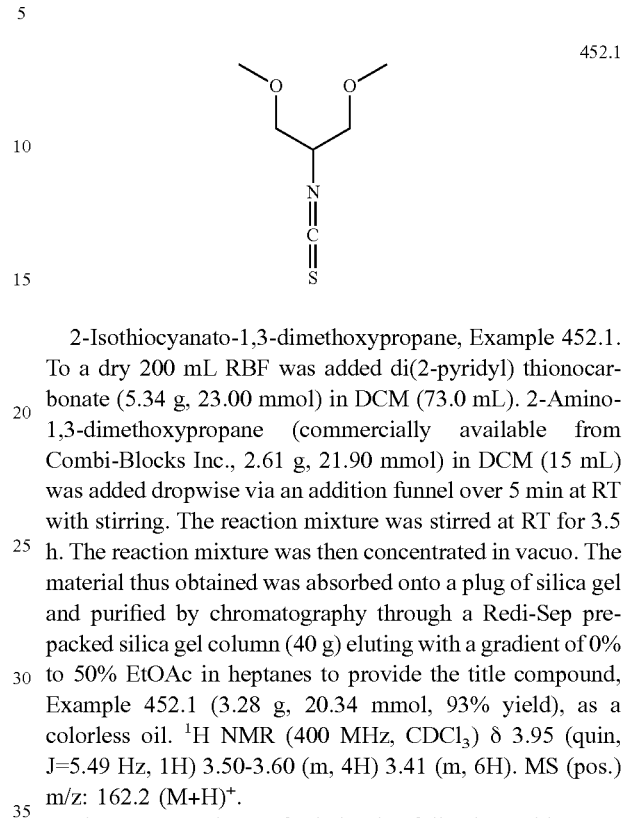<br>(1R,2S)-1-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-1-methoxy-2-propanesulfonamide.<br><br>$^1$H NMR (500 MHz, DMSO-d$_6$) δ 13.25 (s, 1 H) 8.93 (s, 2 H) 8.66 (s, 1 H) 7.78 (d, J = 2.34 Hz, 1 H) 6.61 (d, J = 2.08 Hz, 1 H) 4.81 (br d, J = 3.89 Hz, 2 H) 3.89 (br s, 3 H) 3.87 (br s, 3 H) 3.68 (s, 3 H) 3.38-3.49 (m, 2 H) 3.10-3.23 (m, 3 H) 1.17 (br d, J = 6.75 Hz, 3 H). LCMS-ESI (pos.) m/z: 551.1 (M + H)$^+$. |

TABLE 29-continued

| Example | Reagents | Structure, Name and Data |
|---|---|---|
| 451.0 | 1-isothiocyanato-1-(methoxymethyl)cyclopropane, (Example 451.1), 1-methyl-1H-pyrazole-3-carbohydrazide (ChemBridge Corporation), and (1R,2S)-1-(5-chloropyrimidin-2-yl)-1-methoxypropane-2-sulfonamide (Example 466.3). | 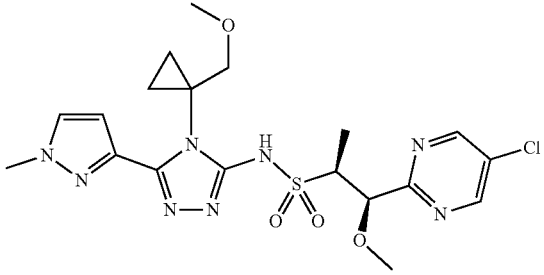 [SMILES: COCC1(n2c(NS(=O)(=O)[C@@H](C)[C@H](OC)c3ncc(Cl)cn3)nnc2-c2ccn(C)n2)CC1]<br>(2S,3R)-N-(4-(1,3-dimethoxy-2-propanyl)-5-(1-methyl-1H-pyrazol-3-yl)-4H-1,2,4-triazol-3-yl)-3-(5-methyl-2-pyrazinyl)-2-butanesulfonamide.<br>$^1$H NMR (500 MHz, DMSO-d$_6$) δ 12.86 (br s, 1 H) 8.94 (s, 2 H) 7.85 (d, J = 2.08 Hz, 1 H) 6.82 (d, J = 2.08 Hz, 1 H) 4.98 (br d, J = 3.63 Hz, 1 H) 4.07 (br s, 1 H) 3.93 (s, 3 H) 3.65 (br s, 1 H) 3.49 (br s, 1 H) 3.29 (s, 3 H) 3.17 (br s,2 H) 2.93-3.14 (m, 3 H) 1.30 (br d, J = 7.01 Hz, 3 H) 1.04 (br s, 4 H). LCMS-ESI (pos.) m/z: 497.2 (M + H)$^+$. |
| 452.0 | 2-isothiocyanato-1,3-dimethoxypropane (Example 452.1), 1-methyl-1H-pyrazole-3-carbohydrazide (ChemBridge Corporation), and (2S,3R)-3-(5-methylpyrazin-2-yl)butane-2-sulfonamide (Example 464.2). | 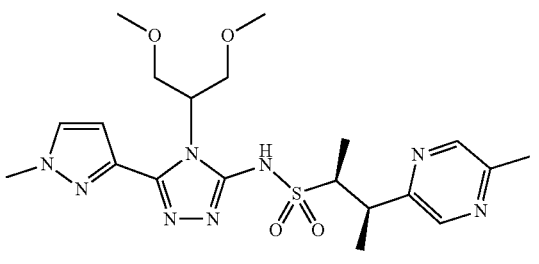<br>(1R,2S)-N-(5-(5-chloro-1H-indazol-3-yl)-4-(2,6-dimethoxyphenyl)-4H-1,2,4-triazol-3-yl)-1-methoxy-1-(5-methylpyrimidin-2-yl)propane-2-sulfonamide.<br>$^1$H NMR (400 MHz, CDCl$_3$) δ 10.97 (br s, 1 H) 8.43 (d, J = 1.45 Hz, 1 H) 8.38-8.40 (m, 1 H) 7.44 (d, J = 2.28 Hz, 1 H) 6.78 (d, J = 2.28 Hz, 1 H) 5.55-5.62 (m, 1 H) 4.14 (ddd, J = 10.11, 8.45, 5.91 Hz, 2 H) 3.99 (s, 3 H) 3.79-3.85 (m, 1 H) 3.72 (ddd, J = 10.11, 5.96, 3.84 Hz, 2 H) 3.65 (qd, J = 7.01, 4.66 Hz, 1 H) 3.31 (s, 3 H) 3.30 (s, 3 H) 2.55 (s, 3 H) 1.47 (d, J = 7.26 Hz, 3 H) 1.41 (d, J = 7.05 Hz, 3 H). LCMS-ESI (pos.) m/z: 479.2 (M + H)$^+$. |
| 453.0 | 2-isothiocyanato-1,3-dimethoxypropane (Example 452.1), 1-methyl-1H-pyrazole-3-carbohydrazide (ChemBridge Corporation), and (2S,3R)-3-(5-methoxypyrazin-2-yl)butane-2-sulfonamide (Example 464.5). | 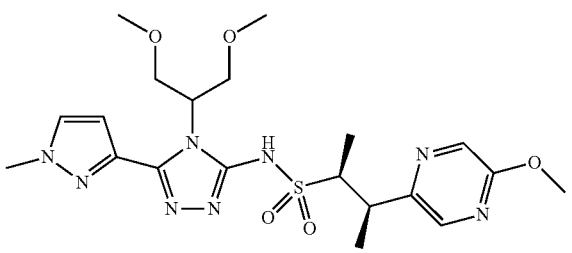<br>(2S,3R)-N-(4-(1,3-dimethoxy-2-propanyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (400 MHz, CDCl$_3$) δ 10.99 (br s, 1 H) 8.16 (d, J = 1.24 Hz, 1 H) 8.03 (d, J = 1.24 Hz, 1 H) 7.43 (d, J = 2.28 Hz, 1 H) 6.78 (d, J = 2.28 Hz, 1 H) 5.54-5.62 (m, 1 H) 4.13 (dt, J = 10.11, 8.11 Hz, 2 H) 3.98 (s, 3 H) 3.94 (s, 3 H) 3.75-3.83 (m, 1 H) 3.72 (ddd, J = 10.21, 5.65, 4.66 Hz, 2 H) 3.61 (qd, J = 7.05, 4.35 Hz, 1 H) 3.30 (s, 3 H) 3.29 (s, 3 H) 1.45 (d, J = 7.05 Hz, 3 H) 1.38 (d, J = 7.05 Hz, 3 H). LCMS-ESI (pos.) m/z: 495.2 (M + H)$^+$. |

TABLE 29-continued

| Example | Reagents | Structure, Name and Data |
|---|---|---|
| 454.0 | 1-isothiocyanato-1-(methoxymethyl)cyclopropane, (Example 451.1), 1-methyl-1H-pyrazole-3-carbohydrazide (ChemBridge Corporation), and (2S,3R)-3-(5-methoxypyrazin-2-yl)butane-2-sulfonamide (Example 464.5). | 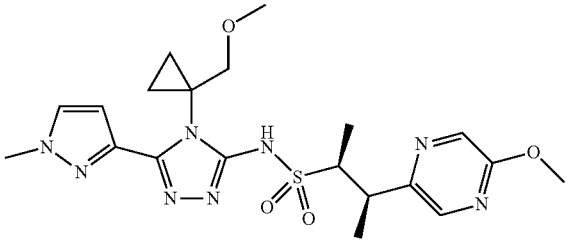<br>(2S,3R)-N-(4-(1-(methoxymethyl)cyclopropyl)-5-(1-methyl-1H-pyrazol-3-yl)-4H-1,2,4-triazol-3-yl)-3-(5-methoxy-2-pyrazinyl)-2-butanesulfonamide.<br>$^1$H NMR (400 MHz, CDCl$_3$) δ 10.71-10.97 (br s, 1 H) 8.17 (d, J = 1.24 Hz, 1 H) 8.05 (d, J = 1.04 Hz, 1 H) 7.45 (d, J = 2.28 Hz, 1 H) 7.04 (d, J = 2.28 Hz, 1 H) 4.00 (s, 3 H) 3.96 (s, 3 H) 3.79-3.90 (m, 2 H) 3.59-3.66 (m, 2 H) 3.35 (s, 3 H) 1.48 (d, J = 7.05 Hz, 3 H) 1.40 (d, J = 7.05 Hz, 3 H) 0.80-1.25 (m, 4 H). m/z: 477.2 (M + H)$^+$. |

Example 455.0. Preparation of (1R,2S)-N-(4-(4,6-dimethoxy-5-pyrimidinyl)-5-(1-methyl-1H-pyrazol-3-yl)-4H-1,2,4-triazol-3-yl)-1-methoxy-1-(5-methoxy-2-pyridinyl)-2-propanesulfonamide

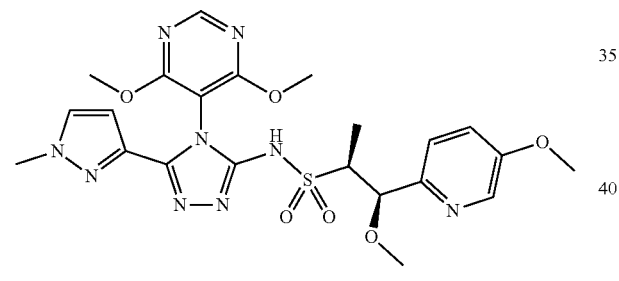

455.0

(1R,2S)-N-(4-(4,6-Dimethoxy-5-pyrimidinyl)-5-(1-methyl-1H-pyrazol-3-yl)-4H-1,2,4-triazol-3-yl)-1-methoxy-1-(5-methoxy-2-pyridinyl)-2-propanesulfonamide, Example 455.0. A suspension of Example 288.0 (253 mg, 0.460 mmol), tBu-Brettphos (commercially available from Strem Chemicals, Inc., 11.15 mg, 0.023 mmol) and tBu-Brettphos-Pd-G3 (commercially available from Sigma-Aldrich Chemical Company, Inc., 19.65 mg, 0.023 mmol) in toluene (1150 μL) was sparged with argon gas for 2 min before sodium methoxide (0.5 M solution in MeOH, 218 μL, 1.380 mmol) was added under argon stream. The reaction mixture was stirred at 80° C. for 24 h. LCMS indicated formation of the title product. The reaction mixture was allowed to cool to RT. The reaction mixture was then diluted with a saturated aqueous solution of NH$_4$Cl and extracted with DCM. The organic extract was concentrated in vacuo to give the initial material as a light-yellow solid which was absorbed onto a plug of silica gel and purified by chromatography through a Redi-Sep pre-packed silica gel column (12 g), eluting with a gradient of 20% to 100% 1/3 EtOH/EA in heptanes, to provide the title compound Example 455.0 (192 mg, 76% yield) as white solid. $^1$H NMR (400 MHz, CDCl$_3$) δ 11.00-11.33 (m, 1H) 8.51 (s, 1H) 8.29 (d, J=2.90 Hz, 1H) 7.29-7.34 (m, 2H) 7.28 (s, 1H) 7.21 (dd, J=8.71, 2.90 Hz, 1H) 6.54 (d, J=2.28 Hz, 1H) 5.01 (d, J=2.90 Hz, 1H) 3.92 (m, 6H) 3.87 (s, 3H) 3.77 (s, 3H) 3.53 (dd, J=7.05, 2.90 Hz, 1H) 3.31 (s, 3H) 1.25 (d, J=7.26 Hz, 3H). LCMS-ESI (pos.) m/z: 546.2 (M+H)$^+$.

Example 458.1. Preparation of (2S,3R)-3-(5-methoxypyridin-2-yl)butane-2-sulfonamide

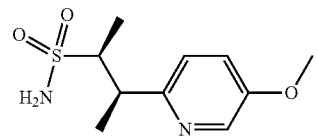

458.1

(2S,3R)-3-(5-methoxypyridin-2-yl)butane-2-sulfonamide, Example 458.1. A suspension of (2S,3R)-3-(5-chloropyridin-2-yl)butane-2-sulfonamide Example 477.0 (360 mg, 1.447 mmol), tBu-Brettphos (17.54 mg, 0.036 mmol) and tBu-Brettphos-Pd-G3 (30.9 mg, 0.036 mmol) in toluene (3618 μL) was sparged with argon gas for 2 min before sodium methoxide (0.5 M solution in MeOH, 685 μL, 4.34 mmol) was added under argon stream. The reaction mixture was stirred at 40° C. for 14 h. LCMS indicated no formation of the title compound. The reaction mixture was stirred at 80° C. for a further 8 h. The reaction mixture was then allowed to cool to RT. The reaction mixture was diluted with a saturated solution of NH$_4$Cl and extracted with DCM. The organic extract was concentrated in vacuo to give the initial material as a light-yellow solid, which was absorbed onto a plug of silica gel and purified by chromatography through a Redi-Sep pre-packed silica gel column (12 g) eluting with a gradient of 0% to 100% EtOAc in heptanes, to provide the title compound Example 458.1 (316 mg, 89% yield) as a white solid. MS (pos.) m/z: 245.1 (M+H)$^+$.

The compounds set forth in the following table were synthesized following the procedure in Example 77.0 using the known starting material as described.

TABLE 30

| Example | Reagents | Structure, Name and Data |
|---|---|---|
| 456.0 | 5-isothiocyanato-4,6-dimethoxypyrimidine (Example 465.1), 1-methyl-1H-pyrazole-3-carbohydrazide (ChemBridge Corporation), and (1S,2S)-1-(5-chloropyrimidin-2-yl)-1-isopropoxypropane-2-sulfonamide (Example 468.1). | 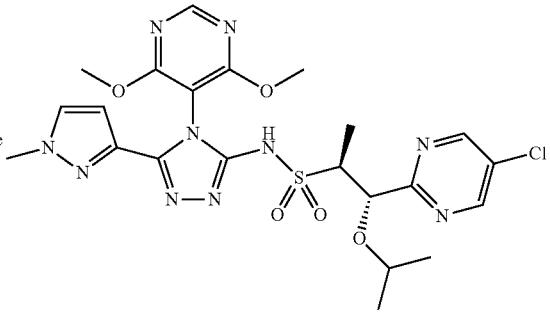<br>(1S,2S)-1-(5-chloro-2-pyrimidinyl)-N-(4-(4,6-dimethoxy-5-pyrimidinyl)-5-(1-methyl-1H-pyrazol-3-yl)-4H-1,2,4-triazol-3-yl)-1-(1-methylethoxy)-2-propanesulfonamide.<br>$^1$H NMR (400 MHz, CDCl$_3$) δ 11.53-12.31 (m, 1 H) 8.75 (s, 2 H) 8.50 (s, 1 H) 7.32 (d, J = 2.28 Hz, 1 H) 6.49 (d, J = 2.49 Hz, 1 H) 4.93 (d, J = 4.15 Hz, 1 H) 3.99 (s, 3 H) 3.89 (s, 3 H) 3.74-3.81 (m, 4 H) 3.55-3.63 (m, 1 H) 1.46 (d, J = 7.05 Hz, 3 H) 1.13 (d, J = 6.01 Hz, 3 H) 1.00 (d, J = 6.01 Hz, 3 H). LCMS-ESI (pos.) m/z: 579.0 (M + H)$^+$. |
| 458.0 | 5-isothiocyanato-4,6-dimethoxypyrimidine (Example 465.1), 1-methyl-1H-pyrazole-3-carbohydrazide (ChemBridge Corporation), and (2S,3R)-3-(5-methoxypyridin-2-yl)butane-2-sulfonamide Example 458.1. | 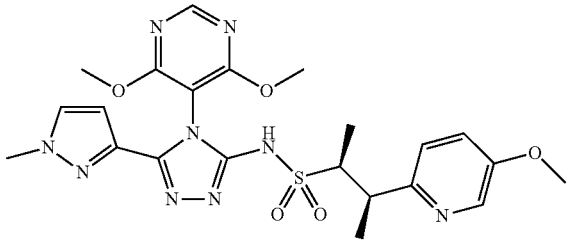<br>(2S,3R)-N-(4-(4,6-dimethoxy-5-pyrimidinyl)-5-(1-methyl-1H-pyrazol-3-yl)-4H-1,2,4-triazol-3-yl)-3-(5-methoxy-2-pyridinyl)-2-butanesulfonamide.<br>$^1$H NMR (400 MHz, CDCl$_3$) δ 10.86-11.63 (m, 1 H) 8.49 (s, 1 H) 8.24 (d, J = 2.28 Hz, 1 H) 7.32 (d, J = 2.28 Hz, 1 H) 7.15-7.22 (m, 2 H) 6.56 (d, J = 2.28 Hz, 1 H) 3.89 (s, 3 H) 3.89 (s, 3 H) 3.84 (s, 3 H) 3.66-3.78 (m, 5 H) 1.39 (d, J = 7.05 Hz, 3 H) 1.32 (d, J = 6.84 Hz, 3 H). LCMS-ESI (pos.) m/z: 530.0 (M + H)$^+$. |
| 459.0 | 2-isothiocyanato-1,3-dimethoxybenzene (Example 465.0), 1-methyl-1H-pyrazole-3-carbohydrazide (ChemBridge Corporation), and (2S,3R)-3-(5-methoxypyridin-2-yl)butane-2-sulfonamide Example 458.1. | 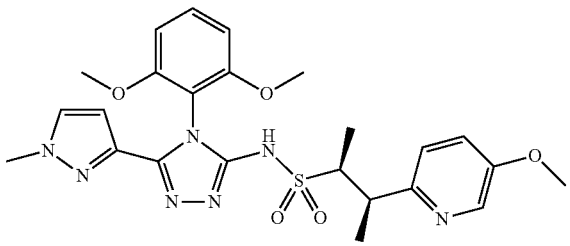<br>(2S,3R)-N-(4-(2,6-dimethoxyphenyl)-5-(1-methyl-1H-pyrazol-3-yl)-4H-1,2,4-triazol-3-yl)-3-(5-methoxy-2-pyridinyl)-2-butanesulfonamide.<br>$^1$H NMR (400 MHz, CDCl$_3$) δ 8.56 (br s, 1 H) 7.64-7.70 (m, 1 H) 7.54-7.61 (m, 1 H) 7.44 (t, J = 8.40 Hz, 1 H) 7.28 (s, 2 H) 7.24 (d, J = 2.07 Hz, 1 H) 6.65 (dd, J = 7.98, 6.53 Hz, 2 H) 5.94 (d, J = 2.49 Hz, 1 H) 3.97 (s, 3 H) 3.86 (s, 3 H) 3.75 (s, 3 H) 3.74 (s, 3 H) 3.57-3.66 (m, 2 H) 1.50 (br d, J = 6.43 Hz, 3 H) 1.44 (br d, J = 6.01 Hz, 3 H). LCMS-ESI (pos.) m/z: 528.2 (M + H)$^+$. |

TABLE 30-continued

| Example | Reagents | Structure, Name and Data |
|---|---|---|
| 460.0 | 5-isothiocyanato-4,6-dimethoxypyrimidine (Example 465.1), 1-methyl-1H-pyrazole-3-carbohydrazide (ChemBridge Corporation), and (1R,2S)-1-methoxy-1-(5-methoxypyrazin-2-yl)propane-2-sulfonamide (Example 460.1) was obtained by SFC chiral separation of Example 307.1 and it was the second enantiomer to elute from a Chiralpak AS column with 10% MeOH and 0.2% DEA. | 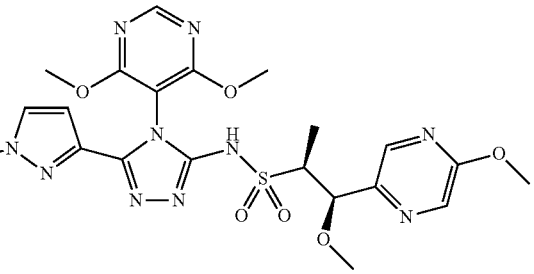<br><br>(1R,2S)-N-(4-(4,6-dimethoxy-5-pyrimidinyl)-5-(1-methyl-1H-pyrazol-3-yl)-4H-1,2,4-triazol-3-yl)-1-methoxy-1-(5-methoxy-2-pyrazinyl)-2-propanesulfonamide.<br><br>$^1$H NMR (400 Hz, CDCl$_3$) δ 11.20 (br s, 1 H) 8.49 (s, 1 H) 8.17 (d, J = 1.45 Hz, 1 H) 8.11-8.12 (m, 1 H) 7.32 (d, J = 2.28 Hz, 1 H) 6.59 (d, J = 2.28 Hz, 1 H) 5.00 (d, J = 2.90 Hz, 1 H) 3.94 (s, 3 H) 3.90 (s, 3 H) 3.90 (s, 3 H) 3.73 (s, 3 H) 3.49 (qd, J = 7.08, 3.01 Hz, 1 H) 3.29 (s, 3 H) 1.26 (d, J = 7.05 Hz, 3 H). LCMS-ESI (pos.) m/z: 547.2 (M + H)$^+$. |
| 461.0 | 5-isothiocyanato-4,6-dimethoxypyrimidine (Example 465.1), 1-methyl-1H-pyrazole-3-carbohydrazide (ChemBridge Corporation), and (1S,2S)-1-isopropoxy-1-(5-methylpyrazin-2-yl)propane-2-sulfonamide (Example 468.6). | 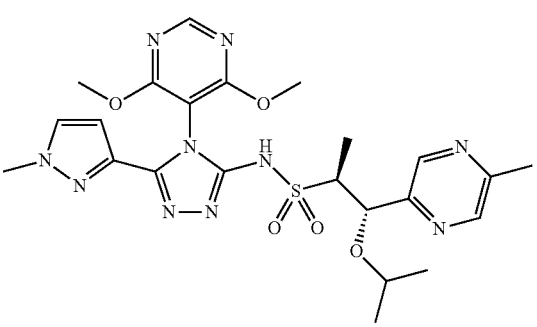<br><br>(1S,2S)-N-(4-(4,6-dimethoxy-5-pyrimidinyl)-5-(1-methyl-1H-pyrazol-3-yl)-4H-1,2,4-triazol-3-yl)-1-(5-methyl-2-pyrazinyl)-1-(2-propanyloxy)-2-propanesulfonamide.<br><br>$^1$H NMR (400 MHz, CD$_2$Cl$_2$) δ 11.48 (br s, 1 H) 8.59 (d, J = 1.24 Hz, 1 H) 8.55 (s, 1 H) 8.40-8.43 (m, 1 H) 7.38 (d, J = 2.28 Hz, 1 H) 6.62 (d, J = 2.49 Hz, 1 H) 4.91 (d, J = 5.39 Hz, 1 H) 3.98 (s, 3 H) 3.95 (s, 3 H) 3.75 (s, 3 H) 3.52-3.62 (m, 2 H) 2.57 (s, 3 H) 1.21-1.26 (m, 4 H) 1.15 (d, J = 6.01 Hz, 3 H) 1.02 (d, J = 6.01 Hz, 3 H). LCMS-ESI (pos.) m/z: 559.2 (M+ H)$^+$. |

TABLE 30-continued

| Example | Reagents | Structure, Name and Data |
|---|---|---|
| 462.0 | 1-isothiocyanato-1-(methoxymethyl)cyclopropane (Example 451.1), 1-methyl-1H-pyrazole-3-carbohydrazide (ChemBridge Corporation), and (1S,2 S)-1-isopropoxy-1-(5-methylpyrimidin-2-yl)propane-2-sulfonamide (Example 468.0). | 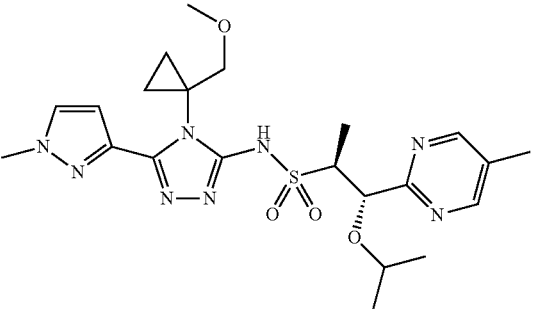<br>(1S,2S)-N-(4-(1-(methoxymethyl)cyclopropyl)-5-(1-methyl-1H-pyrazol-3-yl)-4H-1,2,4-triazol-3-yl)-1-(5-methyl-2-pyrimidinyl)-1-(2-propanyloxy)-2-propanesulfonamide.<br>$^1$H NMR (400 MHz, CDCl$_3$) δ 12.40 (br s, 1 H) 8.58 (s, 2 H) 7.43 (d, J = 1.87 Hz, 1 H) 7.08 (d, J = 2.07 Hz, 1 H) 4.88 (d, J = 4.15 Hz, 1 H) 3.97 (s, 3 H) 3.72-3.87 (m, 1 H) 3.48 (dt, J = 11.77, 5.83 Hz, 2 H) 3.30-3.40 (m, 4 H) 2.31 (s, 3 H) 1.54 (br d, J = 7.05 Hz, 3 H) 1.08-1.17 (m, 4 H) 1.04 (d, J = 6.01 Hz, 3 H) 0.78-0.87 (m, 3 H). LCMS-ESI (pos.) m/z: 505.2 (M+ H)$^+$. |
| 463.0 | 2-isothiocyanato-1,3-dimethoxypropane (Example 452.1), 1-methyl-1H-pyrazole-3-carbohydrazide (ChemBridge Corporation), and (1R,2S)-1-(5-chloropyrimidin-2-yl)-1-methoxypropane-2-sulfonamide (Example 466.3). | 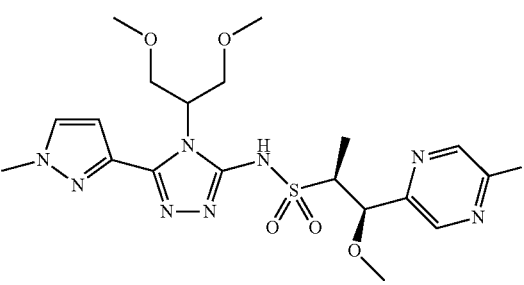<br>(1R,2S)-1-(5-chloro-2-pyrimidinyl)-N-(4-(1,3-dimethoxy-2-propanyl)-5-(1-methyl-1H-pyrazol-3-yl)-4H-1,2,4-triazol-3-yl)-1-methoxy-2-propanesulfonamide.<br>$^1$H NMR (400 MHz, CDCl$_3$) δ 11.04 (s, 1 H) 8.73 (s, 2 H) 7.44 (d, J = 2.28 Hz, 1 H) 6.79 (d, J = 2.28 Hz, 1 H) 5.56-5.63 (m, 1 H) 5.05 (d, J = 4.56 Hz, 1 H) 4.15-4.23 (m, 2 H) 3.98 (s, 3 H) 3.71-3.79 (m, 3 H) 3.37 (s, 3 H) 3.33 (s, 3 H) 3.31 (s, 3 H) 1.44 (d, J = 7.05 Hz, 3 H). LCMS-ESI (pos.) m/z: 515.2 (M+ H)$^+$. |

Example 457.0. Preparation of (2R,3S)-N-(4-(2,6-dimethoxyphenyl)-5-(1-methyl-1H-pyrazol-3-yl)-4H-1,2,4-triazol-3-yl)-3-(5-methoxy-2-pyrimidinyl)-2-butanesulfonamide

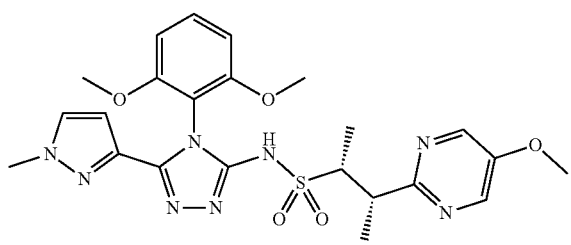

457.0

(2R,3S)-N-(4-(2,6-Dimethoxyphenyl)-5-(1-methyl-1H-pyrazol-3-yl)-4H-1,2,4-triazol-3-yl)-3-(5-methoxy-2-pyrimidinyl)-2-butanesulfonamide, Example 457.0. To a solution of Example 67.0 (218 mg, 0.422 mmol) in MeOH (2.1 mL) was added potassium carbonate (175 mg, 1.27 mmol). The reaction was stirred at 80° C. for 17 h. The reaction mixture was then allowed to cool to RT. The reaction mixture was diluted with a saturated aqueous solution of NH$_4$Cl and extracted with DCM. The material obtained after solvent removal was absorbed onto a plug of silica gel and purified by chromatography through a Redi-Sep pre-packed silica gel column eluting with a gradient of 10% to 100% of 1/3 EtOH/EtOAc in heptanes, to provide the title compound (196 mg, 88% yield) as white solid. $^1$H NMR (400 MHz, CDCl$_3$) δ 11.11 (br s, 1H) 8.34 (s, 2H) 7.39 (t, J=8.50 Hz, 1H) 7.22 (d, J=2.49 Hz, 1H) 6.61 (dd, J=8.50, 4.77 Hz, 2H) 5.86 (d, J=2.49 Hz, 1H) 3.88 (s, 3H) 3.72-3.87 (m, 5H) 3.70 (s, 3H) 3.69 (s, 3H) 1.35 (d, J=7.05 Hz, 3H) 1.30-1.33 (m, 3H). LCMS-ESI (pos.) m/z: 529.2 (M+H)$^+$.

Example 464.0. Preparation of (2S,3R)-3-(5-methylpyrimidin-2-yl)butane-2-sulfonamide

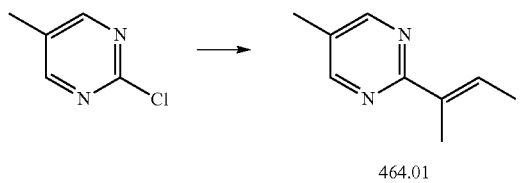

464.01

(E)-2-(But-2-en-2-yl)-5-methylpyrimidine, Example 464.01. 2-Chloro-5-methyl-pyrimidine (18 mL, 151 mmol), potassium (Z)-but-2-en-2-yltrifluoroborate (Sigma Aldrich, 31 g, 191 mmol), tricyclohexylphosphine (8.5 g, 30.2 mmol), and $Pd_2(dba)_3$ (13.82 g, 15.09 mmol) were added to a flask which was then degassed and backfilled with nitrogen. To the flask was added 1,4-dioxane (252 mL) and aqueous potassium phosphate tribasic (37.5 mL, 453 mmol). The resulting reaction mixture was heated at 100° C. for 16 h. The reaction was then cooled to RT. The residue was filtered through a plug of silica gel and was then loaded onto silica gel and purified (0-20% EtOAc in heptanes) to afford (E)-2-(but-2-en-2-yl)-5-methylpyrimidine 464.01 (19 g, 125 mmol, 83% yield).

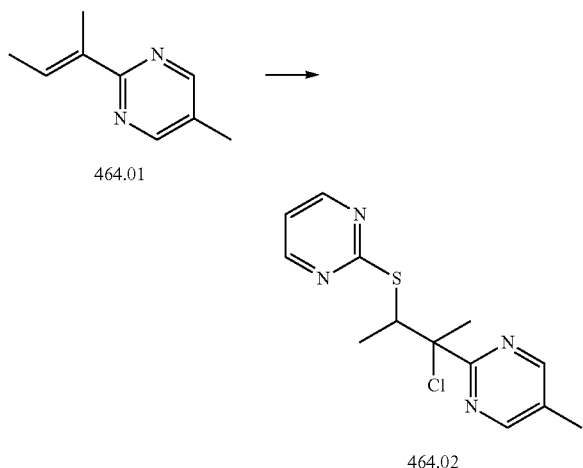

2-(2-Chloro-3-(pyrimidin-2-ylthio)butan-2-yl)-5-methylpyrimidine, Example 464.02. To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at RT. To the cloudy reaction mixture was added (E)-2-(but-2-en-2-yl)-5-methylpyrimidine 464.01 (20 g, 132 mmol) dropwise and the mixture was further stirred for 2 h. The reaction mixture was then concentrated in vacuo. Aqueous sodium bicarbonate solution was added to neutralize the reaction mixture. The reaction was then extracted with EtOAc and concentrated in vacuo. The residue was purified on silica gel with 0-25% EtOAc in hexanes to give the title product 2-(2-chloro-3-(pyrimidin-2-ylthio)butan-2-yl)-5-methylpyrimidine 464.02 (30 g, 76% yield).

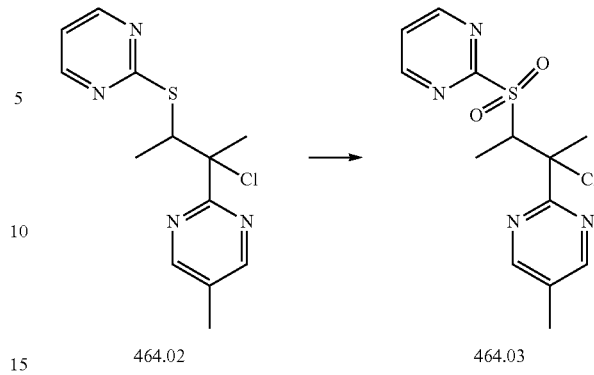

2-(2-Chloro-3-(pyrimidin-2-ylsulfonyl)butan-2-yl)-5-methylpyrimidine, Example 464.03. To a solution of 2-(2-chloro-3-(pyrimidin-2-ylthio)butan-2-yl)-5-methylpyrimidine 464.02 (30 g, 100 mmol) in DCM (201 mL) was added meta-chloroperoxybenzoic acid (45.0 g, 201 mmol). The reaction was stirred at RT for 1 d. The reaction was concentrated in vacuo and aqueous sodium bicarbonate and sodium thiosulfate solutions were added. The mixture was extracted with EtOAc and concentrated in vacuo to give the title product 2-(2-chloro-3-(pyrimidin-2-ylsulfonyl)butan-2-yl)-5-methylpyrimidine 464.03 (33.2 g, 100 mmol, 100% yield).

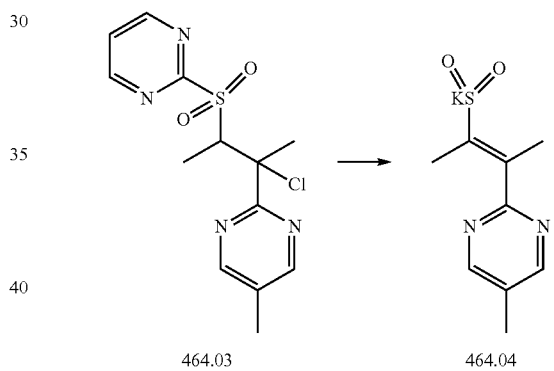

Potassium (E)-3-(5-methylpyrimidin-2-yl)but-2-ene-2-sulfinate, Example 464.04. To a solution of 2-(2-chloro-3-(pyrimidin-2-ylsulfonyl)butan-2-yl)-5-methylpyrimidine 464.03 (33 g, 100 mmol) in MeOH (249 mL) was added potassium carbonate (27.6 g, 200 mmol). The reaction was stirred at RT for 16 h. The reaction was then concentrated in vacuo to give the title product potassium (E)-3-(5-methylpyrimidin-2-yl)but-2-ene-2-sulfinate 464.04 (21.57 g, 100% yield) which was used without further purification.

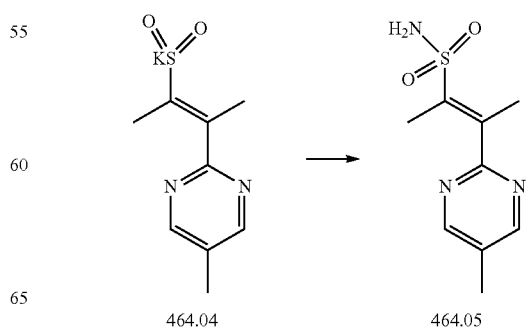

(E)-3-(5-Methylpyrimidin-2-yl)but-2-ene-2-sulfonamide, Example 464.05. To a solution of potassium (E)-3-(5-methylpyrimidin-2-yl)but-2-ene-2-sulfinate (Example 464.04, 21.57 g, 85 mmol) in water (424 mL, 85 mmol) was added potassium acetate (5.30 mL, 85 mmol) followed by amidoperoxymonosulfuric acid (19.18 g, 170 mmol). The reaction was stirred at RT for 24 h. The reaction was then extracted with EtOAc and concentrated in vacuo. The product thus obtained was purified on silica gel eluting with 0-50% EtOAc in hexanes to give the title product (E)-3-(5-methylpyrimidin-2-yl)but-2-ene-2-sulfonamide, 464.05 (12 g, 61.2% yield).

(2S,3R)-3-(5-Methylpyrimidin-2-yl)butane-2-sulfonamide, Example 464.0. A 900 mL pressure reactor was charged under nitrogen flow with (E)-3-(5-methylpyrimidin-2-yl)but-2-ene-2-sulfonamide, Example 464.05 (40.00 g, 0.1760 mol, 1 equiv.), zinc trifluoromethane sulfonate (12.79 g, 0.0352 mol, 0.2 equiv, Aldrich), bis(1,5-cyclooctadiene)rhodium(I) tetrafluoroborate (1.43 g, 0.00352 mol, 0.02 equiv, Strem Chemicals, Inc.), (S)-1-[(R)-2-(di-1-naphthylphosphino)ferrocenyl]-ethyl-di-tert-butylphosphine (2.60 g, 0.00405 mol, 0.023 equiv, Solvias), and MeOH (520 mL). The mixture was purged with nitrogen and then with hydrogen and the media was stirred under 3-4 bars of hydrogen for 20 h. The reaction was monitored by HPLC and showed a complete conversion. The reactor was then purged with nitrogen and the resulting suspension was concentrated at 35° C. under industrial vacuum to give the initial product as an orange solid. The product thus obtained was mixed with EtOH (742 mL), and the resulting suspension was stirred at 20-25° C. for 40 min. The solid was filtered, washed with EtOH (2 7×97 mL) and dried at 40° C. under vacuum to give the title compound as a white powder (85.2% yield, 99% ee). $^1$H NMR (400 MHz, DMSO-$d_6$): δ8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). LCMS (ESI, positive ion) m/z; 230.1 (M+H)$^+$.

The compounds in the following table were synthesized following the procedure in Example 464.0 using the known starting material as described.

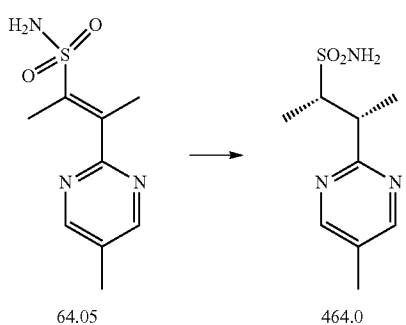

TABLE 31

| Example | Reagents | Structure, Name and Data |
|---|---|---|
| 464.1 | 2-chloro-5-fluoropyrimidine. | (2S,3R)-3-(5-fluoropyrimidin-2-yl)butane-2-sulfonamide. LCMS ESI (pos.) m/z: 234.2 (M + H)$^+$. |
| 464.2 | 2-bromo-5-methylpyrazine. The title compound was the first isomer to elute under the following SFC conditions: Run on Thar 200 SFC with 250 × 30 mm AD-H column with 20 mL/min MeOH (+20 mM NH$_3$) + 80 g/min CO$_2$, 20% co-solvent at 100 g/min. Temperature. = 29 ° C., Outlet pressure = 100 bar, Wavelength = 271 mm Injected 1.0 mL of 550 mg of the enantiomerically enriched product dissolved in 20 mL MeOH:DCM, 15:5; c = 27.5 mg/mL and 27.5 mg per injection. Cycle time 5.0 min, run time 13 mm. | (2S,3R)-3-(5-methylpyrazin-2-yl)butane-2-sulfonamide. $^1$H NMR (400 MHz, DMSO-$d_6$) δ 8.46 (d, J = 6.5 Hz, 2H), 6.84 (s, 2H), 3.63 (qd, J = 7.0, 4.3 Hz, 1H), 3.44 (qd, J = 7.0, 4.3 Hz, 1H), 2.47 (s, 3H), 1.31 (d, J = 7.0 Hz, 3H), 1.23 (d, J = 7.0 Hz, 3H). LCMS (ESI, pos.) m/z: 230.0 (M + H)$^+$. |

TABLE 31-continued

| Example | Reagents | Structure, Name and Data |
|---|---|---|
| 464.3 | 2-bromo-5-methylpyrazine. The title compound is the enantiomer of Example 464.2. Example 464.2 was the second isomer to elute from AD-H column on subjecting the enantiomerically enriched product to the SFC conditions described in Example 464.2. | 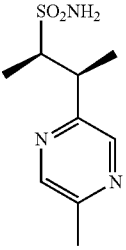<br>(2R,3S)-3-(5-methylpyrazin-2-yl)butane-2-sulfonamide.<br>LCMS-ESI (pos.) m/z: 230.0 (M + H)⁺. |
| 464.4 | 2-chloro-5-chloro-pyrimidine. Recrystallization: Example 464.4 (38 g, 90% ee) was dissolved in IPA (400 mL) at 70 ° C.. | 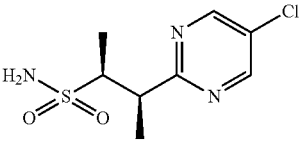<br>(2S,3R)-3-(5-chloropyrimidin-2-yl)butane-2-sulfonamide.<br>$^1$H NMR (400 Hz, DMSO-$d_6$) δ 8.93-8.85 (m, 2H), 6.86 (d, J = 4.0 Hz, 2H), 3.73-3.59 (m, 2H), 1.31 (dt, J = 7.3, 2.4 Hz, 3H), 1.25-1.19 (m, 3H). LCMS (ESI pos.) m/z: 250.2 (M + H)⁺. |
| 464.5 | 2-bromo-5-methoxypyrazine. | 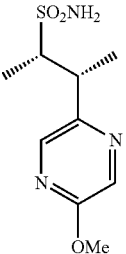 [SMILES: COc1cnc([C@@H](C)[C@H](C)S(N)(=O)=O)cn1]<br>(2S,3R)-3-(5-methoxypyrazin-2-yl)butane-2-sulfonamide.<br>$^1$H NMR (400 MHz, DMSO-$d_6$) δ 8.26 (d, J = 1.4 Hz, 1H), 8.12 (d, J = 1.4 Hz, 1H), 6.84 (s, 2H), 3.90 (d, J = 1.5 Hz, 3H), 3.62 (dd, J = 7.1, 4.3 Hz, 1H), 3.42-3.38 (m, 1H), 1.32 (d, J = 1.5 Hz, 3H), 1.23-1.21 (m, 3H). LCMS (ESI pos.) m/z: 246.2 (M + H)⁺. |
| 464.6 | By-product from Example 464.2. | 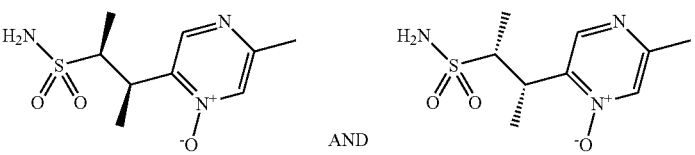<br>5-methyl-2-((2R,3S)-3-sulfamoylbutan-2-yl)pyrazine 1-oxide and 5-methyl-2-((2S,3R)-3-sulfamoylbutan-2-yl)pyrazine 1-oxide. |

TABLE 31-continued

| Example | Reagents | Structure, Name and Data |
|---|---|---|
| 464.7 | Mother liquors from recrystalisation of Example 464.4. The mother liquors were purified by chiral SFC, following the method described: Sample Preparation: Sample dissolved in 150 mL 2:1 MeOH:DCM (~73 mg/mL). Instrument: Prep SFC-4, Column: Chirapak AD-H 3 × 25 cm. Mobile Phase: 45% MeOH, Flowrate: 140 mL/min, Pressure Drop: 150 bar, BPR: 100 bar, UV Detector Wavelength: 220 nm, Injection Volume: 3.0 mL, Cycle Time: 7.0 min. Sample separated by SFC using a Chirapal AD-H, 45% MeOH. Under these conditions this was the first peak to elute. | 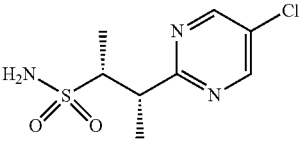 (2R,3S)-3-(5-chloropyrimidin-2-yl)butane-2-sulfonamide. $^1$H NMR (400 MHz, DMSO-d$_6$) δ 8.93-8.85 (m, 2H), 6.86 (d, J = 4.0 Hz, 2H), 3.73-3.59 (m, 2H), 1.31 (dt, J = 7.3, 2.4 Hz, 3H), 1.25-1.19 (m, 3H). LCMS (ESI pos.) m/z: 250.2 (M + H)$^+$. |
| 464.8 | Mother liquors from reciystalisation of Example 464.0. The mother liquors were purified by chiral SFC following the method described: Column: Chiralpak AD-H, 5 × 15 cm, Modifier and Percentage: 25% MeOH w/ 0.2% DEA Flowrate (mL/min): 350 Pressure Drop (bar): 104 BPR (bar): 100, Detection (nm): 215 Sample Dissolution: 150 mL MeOH and 150 mL DCM, sonication for 5 mm to generate clear solution. Sample processing: Volume: (mL): 3 Cycle Time (min): 3.0 Sample separated by SFC using a Chirapal AD-H, 25% MeOH w/ 0.2% DEA. Under these conditions this was the first peak to elute. | 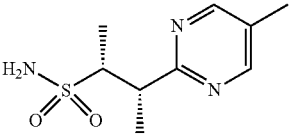 (2S,3R)-3-(5-Methylpyrimidin-2-yl)butane-2-sulfonamide. $^1$H NMR (400 MHz, DMSO-d$_6$): δ8.61 (s, 2H), 6.84 (s, 2H), 3.69 (tt, J = 12.4, 4.5 Hz, 2H), 2.25 (s, 3H), 1.32 (d, J = 6.9 Hz, 3H), 1.20 (d, J = 7.0 Hz, 3H). LCMS (ESI, positive ion) m/z; 230.1 (M + H)$^+$. |
| 464.9 | Example 464.2. | 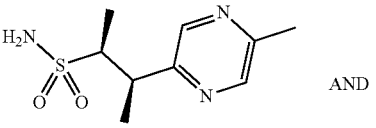 AND 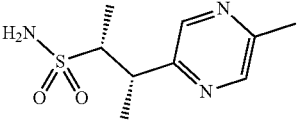 (2R,3S)-3-(5-methylpyrazin-2-yl)butane-2-sulfonamide and (2S,3R)-3-(5-methylpyrazin-2-yl)butane-2-sulfonamide. LCMS (ESI, pos.) m/z; 230.0 (M + H)$^+$. |

Example 465.0. Preparation of 2-isothiocyanato-1,3-dimethoxybenzene

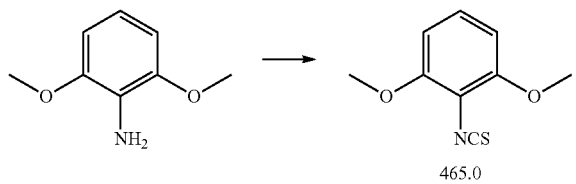

465.0

2-Isothiocyanato-1,3-dimethoxybenzene, Example 465.0. To a solution of 2,6-dimethoxyaniline (500 g, 3.25 mol, 1 eq) in DCM (5.0 L) was added 2,6-lutidine (1.5 L, 13.0 mol, 4 eq). The reaction mixture was cooled to 0° C. (internal temperature) and $CSCl_2$ (374 mL, 4.88 mol, 1.5 eq) was added dropwise. The reaction mixture was then stirred for 2 h. The solvent was evaporated under reduced pressure, and the material thus obtained was purified by silica column to provide the title compound, 2-isothiocyanato-1,3-dimethoxybenzene, Example 465.0 as a white solid (1.06 g, 2.80 mol, 86%). $^1$H NMR (400 MHz, $CDCl_3$) δ 7.16 (t, J=8.48 Hz, 1H), 6.55 (d, J=8.48 Hz, 2H), 3.90 (m, 6H). LCMS (ESI pos. ion) m/z: $(M+H)^+$ 196.

The compounds set forth in the following table were synthesized following the procedure in Example 465.0 using the known starting material as described.

TABLE 32

| Example | Reagents | Structure, Name and Data |
|---|---|---|
| 465.1 | 4,6-dimethoxypyrimidin-5-amine (D-L Chiral chemicals). | 5-isothiocyanato-4,6-dimethoxypyrimidine. LCMS-ESI (pos.) m/z: 198.1 (M + H)$^+$. |
| 465.2 | 2-methoxyaniline (Aldrich). | 1-isothiocyanato-2-methoxybenzene. $^1$H NMR (400 MHz, DMSO-$d_6$) δ 3.89 (s, 3H), 6.96 (td, J = 7.68, 1.27 Hz, 1H), 7.16 (dd, J = 8.31, 1.27 Hz, 1H), 7.30 (dd, J = 7.92, 1.66 Hz, 1H), 7.31-7.37 (m, 1H). |
| 465.3 | 3,5-difluoropyridin-4-amine (commercially available from Ark Pharm Inc, Libertyville, IL). | 3,5-difluoro-4-isothiocyanatopyridine. LCMS-ESI (pos.) m/z: 173.0 (M + H)$^+$. |

Example 466.0. Preparation of (1R,2S)-1-methoxy-1-(5-methylpyrimidin-2-yl)propane-2-sulfonamide

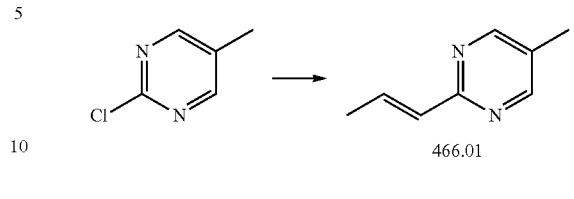

466.01

(E)-5-Methyl-2-(prop-1-en-1-yl)pyrimidine, Example 466.01. To a 500 mL RBF was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with $N_2$ (5×) and then 1,4-dioxane (200 mL) and water (20 mL) were added. The resulting yellow suspension was sparged with Ar for 15 min and then 1,1-bis[(di-t-butyl-p-methylaminophenyl]palladium(II) chloride (Amphos, commercially available from Strem, 2.64 g, 3.73 mmol) was added, a reflux condenser was attached, and the reaction was warmed to 90° C. in an oil bath and stirred under $N_2$ for 16.5 h. The reaction was then cooled to RT. The reaction was diluted with water (250 mL) and extracted with EtOAc (2×250 mL). The organic layers were combined, dried ($MgSO_4$), and concentrated. The residue was purified by flash chromatography on silica gel eluting with 0-20% EtOAc/hexanes) to afford (E)-5-methyl-2-(prop-1-en-1-yl)pyrimidine 466.01 (12.96 g, 97 mmol, 100% yield) as a yellow/orange oily solid. $^1$H NMR (300 MHz, $CDCl_3$) δ 8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). LCMS (ESI pos.) m/z: 135.2 $(M+H)^+$.

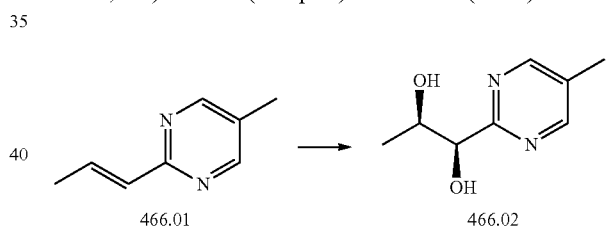

466.01                    466.02

(1R,2R)-1-(5-Methylpyrimidin-2-yl)propane-1,2-diol, Example 466.02. Racemic conditions. To a solution of (E)-5-methyl-2-(prop-1-en-1-yl)pyrimidine, 466.01 (5.75 g, 42.9 mmol) and 4-methylmorpholine-4-oxide (7.53 g, 64.3 mmol) in acetone (60 mL) and water (6 mL) was added osmium tetroxide, 4 wt. %, in water (0.681 mL, 0.111 mmol). The resulting reaction mixture was stirred at RT under $N_2$ for 21.5 h. LCMS showed complete conversion to a product corresponding to the mass of the title compound $(M+H)^+$=169. The reaction was then passed through a Varian Chem-Elut cartridge to remove water and concentrated in vacuo. Water was still present. The residue was dissolved in DCM, dried ($MgSO_4$), and concentrated. The residue was purified by flash chromatography (120 g $SiO_2$, 0-10% MeOH/DCM) to give the racemic syn-diol (1S,2S)-1-(5-methylpyrimidin-2-yl)propane-1,2-diol and (2R,2R)-1-(5-methylpyrimidin-2-yl)propane-1,2-diol (5.85 g, 34.8 mmol, 81% yield) as a light yellow solid. $^1$H NMR (300 MHz, $CDCl_3$) δ 8.59 (s, 2H), 4.67 (br. s, 1H), 4.33 (br. s, 1H), 4.09-4.25 (m, 1H), 2.86 (d, J=7.2 Hz, 1H), 2.36 (s, 3H), 1.30 (d, J=6.6 Hz, 3H). LCMS (ESI pos.) m/z: 169.2 $(M+H)^+$. Chiral conditions. A batch of AD-mix-beta was prepared from: (26 mg, 0.07 mmol) $K_2OsO_2(OH)_4$; (16.4 g, 49.9 mmol) K$_3$Fe(CN)$_6$; (6.89 g, 49.9 mmol) K$_2$CO$_3$; (125 mg, 0.16 mmol) (DHQD)$_2$PHAL. In a 50 mL RBF was added t-BuOH (5 mL), water (5.00 mL), and 1.4 g of AD-mix-beta (prepared above) and methanesulfonamide (95 mg, 1.00 mmol). The mixture was stirred at RT until clear, and was then cooled to 0° C. (E)-5-methyl-2-(prop-1-en-1-yl)pyrimidine (intermediate 11.1 168 mg, 1 mmol) in t-BuOH (1 mL) was added and the slurry was stirred at 0° C. for 2 h. LCMS (1.5 h) shows 10% conversion. The reaction was then allowed to warm slowly to RT as the ice bath melted and stirred an additional 22 h. LCMS showed 90% conversion. The reaction was quenched with saturated aqueous sodium sulfite (10 mL), and extracted with EtOAc (2×20 mL). The combined organic layers were washed with 2 N NaOH (10 mL), dried (MgSO$_4$), and concentrated. The aqueous layer was extracted with DCM (2×50 mL), EtOAc (2×50 mL), and 10% IPA in CHCl$_3$ (2×50 mL). The combined organic layers were concentrated and the residue purified by flash column chromatography (12 g SiO$_2$, 5-100% 3:1 EtOAc:EtOH/heptanes) to give (1R,2R)-1-(5-methylpyrimidin-2-yl)propane-1,2-diol (Example 466.02, 88.6 mg, 0.527 mmol, 52.7% yield) as a clear, colorless oil. Chiral Analysis: SFC Chiral Analysis showed the % ee to be 94.8% using an AS-H (100×2.1 mm, 3 um), 10% organic modifier (IPA with 20 mM ammonia), 90% carbon dioxide. F=1.0 mL/min, column temperature=RT, BRP=105 bar.

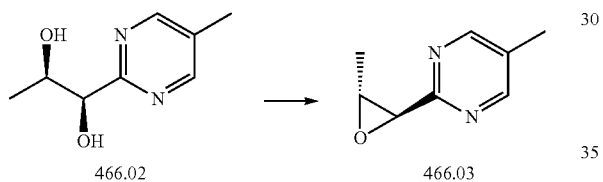

5-Methyl-2-((2R,3R)-3-methyloxiran-2-yl)pyrimidine, Example 466.03. To a solution of syn-diol (1R,2R)-1-(5-methylpyrimidin-2-yl)propane-1,2-diol 466.02 (1.46 g, 8.68 mmol) in DCM (25 mL) (cooled with a RT water bath) was added 1,1,1-trimethoxyethane (2.50 mL, 2.29 mmol). Chlorotrimethylsilane (TMSCl, 2.50 mL, 19.7 mmol) was then added in 2 portions 5 min apart. The reaction had a small exotherm on the first portion of addition of TMSCl (23-28° C.). The reaction was stirred at RT under N$_2$ 23 h. LCMS indicated incomplete conversion. Thus, an additional 1.25 equiv. of 1,1,1-trimethoxyethane (1.25 mL, 9.95 mmol) and chlorotrimethylsilane (1.25 mL, 9.85 mmol) were added, and the reaction was stirred for an additional 24 h. LCMS indicated the reaction was complete and the reaction mixture was concentrated in vacuo. The residue was dissolved in MeOH (20 mL) and potassium carbonate (1.50 g, 10.85 mmol) was added, and the reaction was stirred at RT for 4 h. LCMS showed complete conversion to product corresponding to the title epoxide (LCMS; ((M+H)$^+$=151)). The reaction was filtered, and the filter cake was washed with DCM (5 mL). The filtrates were combined and concentrated in vacuo. The residue was purified by flash column chromatography on silica gel eluting with 0-100% EtOAc/hexanes) to afford 5-methyl-2-((2R,3R)-3-methyloxiran-2-yl)pyrimidine (466.03 (1.00 g, 6.6 mmol, 77%)) as a clear, light yellow oil. $^1$H NMR (300 MHz, CDCl$_3$) δ 8.54 (s, 2H), 3.81 (d, J=1.9 Hz, 1H), 3.32-3.53 (m, 1H), 2.31 (s, 3H), 1.50 (d, J=5.1 Hz, 3H). LCMS (ESI pos.) m/z: 151.2 (M+H)$^+$.

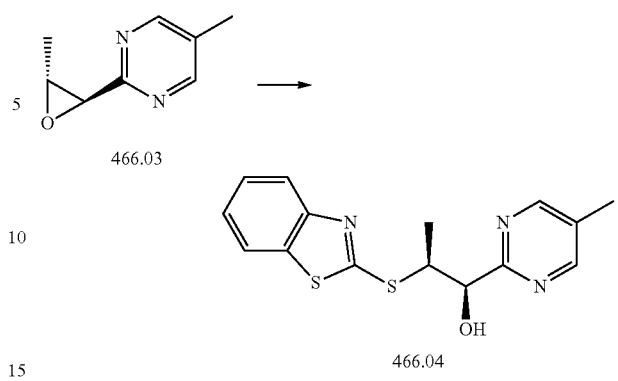

(1R,2S)-2-(Benzo[d]thiazol-2-ylthio)-1-(5-methylpyrimidin-2-yl)propan-1-ol, Example 466.04. To a solution of 5-methyl-2-((2R,3R)-3-methyloxiran-2-yl)pyrimidine 466.03 (250 mg, 1.33 mmol) in DCM (5 mL) was added benzo[d]thiazole-2-thiol (245 mg, 1.465 mmol) followed by tris(((trifluoromethyl)sulfonyl)oxy)ytterbium (83 mg, 0.133 mmol). The suspension was heated in a 35° C. heating block for 17 h and showed 100% conversion to the title product. The reaction was cooled to RT, loaded on a plug of silica, and purified by flash chromatography (12 g SiO$_2$, 5-100% 3:1 EtOAc:EtOH/heptanes) to afford 466.04 (428 mg, 1.35 mmol, 100% yield) as a clear colorless oil. $^1$H NMR (300 MHz, CDCl$_3$) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). LCMS (ESI pos.) m/z: 318.2 (M+H)$^+$.

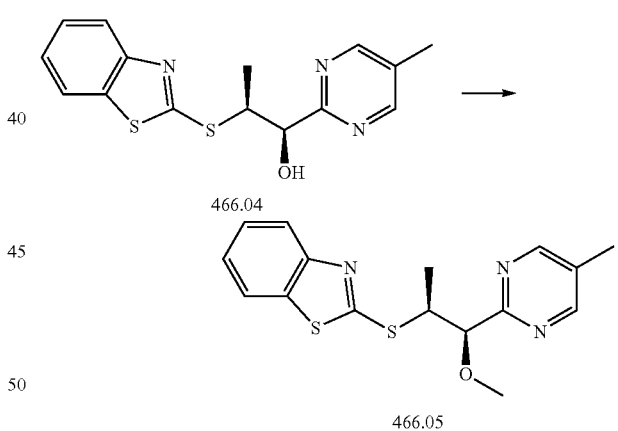

2-(((1R,2S)-1-Methoxy-1-(5-methylpyrimidin-2-yl)propan-2-yl)thio)benzo[d]thiazole, Example 466.05. A 50 mL flask equipped with a magnetic stirrer was charged with 466.04 (350 mg, 1.103 mmol) in 2-methyltetrahydrofuran (1.1 mL). The reaction mixture was cooled to −78° C. and potassium bis(trimethylsilyl)amide (1.0 M solution in THF, 1.32 μL, 1.32 mmol)) was added dropwise (total addition time was 2 min). The resulting mixture was stirred for 1 h and then MeOTf (374 μL, 3.31 mmol) was added dropwise. The reaction mixture was then stirred at −78° C. for 15 min. LCMS showed complete conversion to the product. The reaction mixture was quenched with a saturated aqueous NH$_4$Cl solution (30 mL) at −78° C. The reaction was allowed to warm to RT and the aqueous layer was back extracted with EtOAc (3×75 mL). The combined organic layers were washed with brine, dried (Na$_2$SO$_4$), and concentrated in vacuo. The material thus obtained was purified by chromatography through a Biotage 50 g ultra silica gel column, eluting with a gradient of 0-25% EtOAc in hexanes, to provide 2-(((1R,2S))-1-methoxy-1-(5-methylpyrimidin-2-yl)propan-2-yl)thio)benzo[d]thiazole (466.05 (0.32 g, 75% for two runs)) as a light-yellow oil.

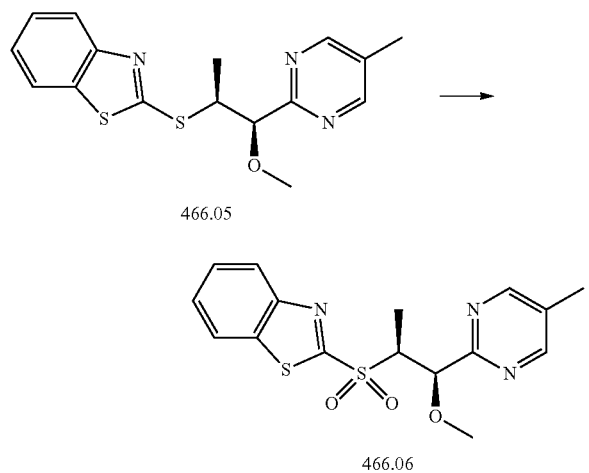

466.05

466.06

2-(((1R,2S)-1-Methoxy-1-(5-methylpyrimidin-2-yl)propan-2-yl)sulfonyl)benzo[d]thiazole, Example, Example 466.06. A solution of 2-(((1R,2S)-1-methoxy-1-(5-methylpyrimidin-2-yl)propan-2-yl)thio)benzo[d]thiazole 466.05 (313 mg, 0.94 mmol) in DCM (2.8 mL) at 0° C. was treated with 3-chloroperoxybenzoic acid, 77% max. (476 mg, 2.13 mmol). The reaction was stirred at 0° C. for 1 h before the ice bath was removed. LCMS showed the title sulfoxide compound and the presumed sulfoxide/sulfone. The mixture was allowed to warm to RT and stirred for an additional 40 h. The reaction was then quenched with saturated aqueous sodium bisulfite (6 mL) and saturated aqueous sodium bicarbonate (5 mL). The mixture was then stirred for 10 min. The reaction was extracted with EtOAc (2×20 mL) and the organic layers were combined, washed with saturated aqueous NaHCO$_3$ (10 mL), brine (10 mL), dried (MgSO$_4$), and filtered. Iodide/starch strip indicator showed no peroxide was present. The filtrates were concentrated to give a clear, colorless oil (360 mg). Purification of the residue by flash chromatography (40 g SiO$_2$, 0-100% 3:1 EtOAc:EtOH/heptanes) gave 466.06 (285 mg, 0.78 mmol, 83% yield, 77% purity) as a white foam. $^1$H NMR (300 MHz, CDCl$_3$) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). LCMS (ESI pos.) m/z: 364.0 (M+H)$^+$.

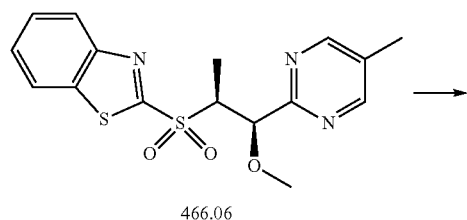

466.06

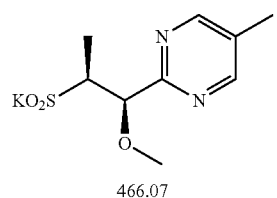

466.07

Potassium (1R,2S)-1-methoxy-1-(5-methylpyrimidin-2-yl)propane-2-sulfinate, Example 466.07. To a solution of 466.06 (268 mg, 0.74 mmol) in MeOH (1843 µL) was added potassium carbonate (204 mg, 1.48 mmol). The reaction was stirred at RT for 17 h. LCMS showed title compound formation as the sulfinic acid 466.07. LCMS ((M+H)*=231.1). The reaction was concentrated in vacuo (yellow solid) and used directly in the following step. Epimerization occurred in this reaction (~15%).

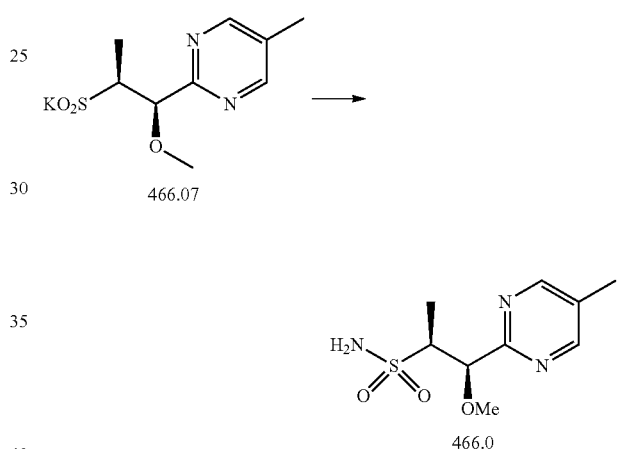

466.07

466.0

(1R,2S)-1-Methoxy-1-(5-methylpyrimidin-2-yl)propane-2-sulfonamide, Example 466.0. To a suspension of potassium (1R,2S)-1-methoxy-1-(5-methylpyrimidin-2-yl)propane-2-sulfinate (Example 466.07, 198 mg, 0.74 mmol) in water (3.7 mL) was added potassium acetate (72.4 mg, 0.74 mmol) followed by hydroxylamine-o-sulfonic acid, 97% (167 mg, 1.476 mmol). The reaction mixture was stirred at RT for 4.5 h. LCMS showed title compound formation plus a small peak that corresponded to the stereoisomer. The reaction mixture was extracted with EtOAc (2×) and the organic layers were combined, dried (Na$_2$SO$_4$), and concentrated in vacuo. The residue was loaded onto a silica gel column eluting with 0-30% (3:1 EtOAc:EtOH)/DCM to afford 466.0 (114 mg, 0.465 mmol, 63.0% yield) as a white solid. (contained ~15% other diastereomer, which could be removed by recrystalisation). $^1$H NMR (300 MHz, CDCl$_3$) δ 8.63 (s, 2H), 5.10 (d, J=3.3 Hz, 1H), 4.78 (br. s, 2H), 3.74 (qd, J=7.1, 3.3 Hz, 1H), 3.51 (s, 3H), 2.36 (s, 3H), 1.33 (d, J=7.1 Hz, 3H). LCMS (ESI pos.) m/z: 246.1 (M+H)$^+$.

The compounds set forth in the following table were synthesized following the procedure in Example 466.0 using the known starting material as described.

TABLE 33

| Example | Reagents | Structure, Name and Data |
|---|---|---|
| 466.1 | 2-bromo-5-methyl pyrazine (NOWA pharmaceuticals). | (1R,2S)-1-methoxy-1-(5-methylpyrazin-2-yl)propane-2-sulfonamide.<br>LCMS-ESI (pos.) m/z: 246.2 (M + H)⁺. |
| 466.2 | 2-chloro-5-fluoropyrimidine (Oakwood). | (1R,2S)-1-(5-fluoropyrimidin-2-yl)-1-methoxypropane-2-sulfonamide.<br>LCMS-ESI (pos.) m/z: 250.1 (M + H)⁺. |
| 466.3 | 2,5-dichloropyrimidine (Oakwood). | (1R,2S)-1-(5-chloropyrimidin-2-yl)-1-methoxypropane-2-sulfonamide. LCMS-ESI (pos.) m/z: 265.9 (M + H)⁺. |
| 466.4 | 2-chloropyrimidine (Acros Organics). | (1R,2S)-1-methoxy-1-(pyrimidin-2-yl)propane-2-sulfonamide.<br>LCMS-ESI (pos.) m/z: 232.0 (M + H)⁺. |
| 466.5 | 2-chloro-5-fluoropyrimidine (Oakwood).<br>EtOTf used in place of MeOTf. | (1R,2S)-1-ethoxy-1-(5-fluoropyrimidin-2-yl)propane-2-sulfonamide.<br>LCMS-ESI (pos.) m/z: 264.0 (M + H)⁺. |
| 466.6 | 2-chloro-5-fluoropyrimidine (Oakwood).<br>TBSOTf used in place of MeOTf. | (1R,2S)-1-((tert-butyldimethylsilyloxy)-1-(5-fluoropyrimidin-2-yl)propane-2-sulfonamide.<br>LCMS-ESI (pos.) m/z: 350.1 (M + H)⁺. |

-continued
TABLE 33

| Example | Reagents | Structure, Name and Data |
|---|---|---|
| 466.7 | 2,5-dichloropyrimidine (Oakwood). EtOTf used in place of MeOTf. | 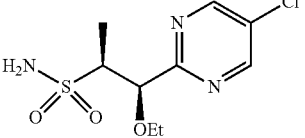<br>(1R,2S)-1-(5-chloropyrimidin-2-yl)-1-ethoxypropane-2-sulfonamide.<br>LCMS-ESI (pos.) m/z: 279.9. |
| 466.9 | 2-chloro-5-methylpyrimidine (Oakwood). EtOTf used in place of MeOTf | 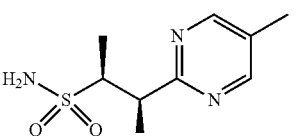<br>(1R,2S)-1-ethoxy-1-(5-methylpyrimidin-2-yl)propane-2-sulfonamide.<br>LCMS-ESI (pos.) m/z: 260.1. |

Example 466.8: Preparation of Example (1R,2S)-1-methoxy-1-(5-methoxypyrimidin-2-yl)propane-2-sulfonamide

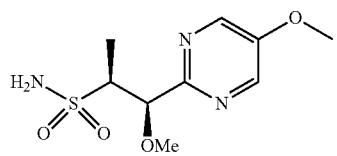

466.8

(1R,2S)-1-Methoxy-1-(5-methoxypyrimidin-2-yl)propane-2-sulfonamide, Example 466.8. The title compound was obtained as a by-product of the synthesis of (1R,2S)-1-methoxy-1-(5-fluoropyrimidin-2-yl)propane-2-sulfonamide (Example 466.2) during step 466.07 and isolated in the final step of the synthesis of Example 466.2 to give the title compound 466.8 (240 mg, 10.2% yield) as a white solid. $^1$H NMR (CDCl$_3$) δ: 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (pos.) m/z: 284.1 (M+Na)$^+$.

Example 467.0. Preparation of N,N-bis(4-methoxybenzyl)ethanesulfonamide

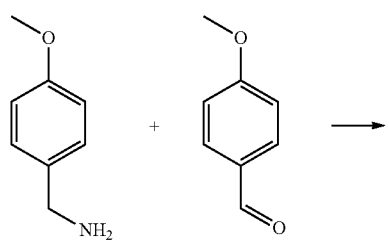

-continued

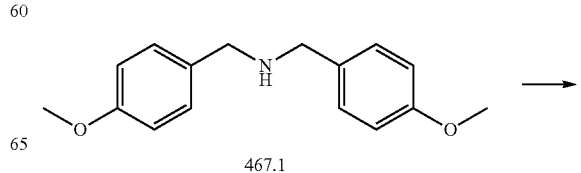

467.1

Bis(4-methoxybenzyl)amine, Example 467.1. 4-Methoxybenzylamine (neat, 600 g, 4.37 mol, 1 eq)and 4-methoxybenzaldehyde (532 mL, 4.37 mol, 1 eq) were added to a 10 L RBF at RT with stirring. The reaction spontaneously warmed and a white precipitate was observed. The mixture was stirred for 1 h. To the above mixture was added anhydrous EtOH (4.8 L) and stirring was continued at RT for 15-30 min. This was followed by the addition of sodium borohydride granules (99 g, 2.62 mol, 0.6 eq) portionwise over ~2 h (Note: During the addition of NaBH$_4$, the internal temperature of the reaction rose up to 42° C.). The resulting mixture was then stirred at RT overnight. The reaction was quenched slowly with water (600 mL). The mixture was then concentrated on a rotary evaporator at 50° C. The residue was partitioned between water (4 L) and DCM (4 L). The aqueous layer was extracted with more DCM (2×2 L). The combined organic layers were dried over Na$_2$SO$_4$, filtered and concentrated in vacuo to give bis(4-methoxybenzyl)amine 467.1 (1112 g, 99% yield) as a semi-solid. The material was used directly in the next step without further purification. $^1$H-NMR (400 MHz, CDCl$_3$) δ 7.28 (t, J=7.12 Hz, 4H), 6.89 (d, J=8.60 Hz, 4H), 3.83 (m, 6H), 3.76 (s, 4H) (—NH proton not observed). LCMS (ESI pos.) m/z: 258.4 (M+H)$^+$.

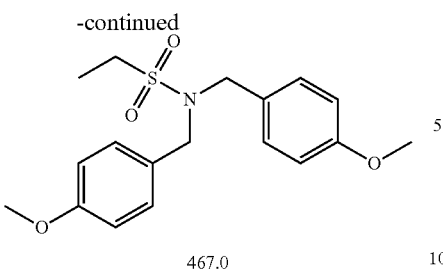

467.0

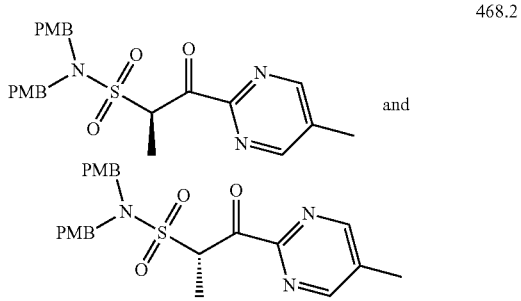

468.2

N,N-Bis(4-methoxybenzyl)ethanesulfonamide, Example 467.0. To a solution of bis(4-methoxybenzyl)amine 467.1 (900 g, 3.49 mol, 1 eq) in DCM (9 L) was added TEA (634 mL, 4.55 mol, 1.3 eq) followed by dropwise addition of ethanesulfonyl chloride (399 mL, 4.19 mol, 1.2 eq). The internal temperature was kept between 5-10° C. during the addition of the ethanesulfonyl chloride. Once addition was complete, the cooling bath was removed. After 1.5 h, TLC showed complete loss of starting material. The reaction was quenched by addition of water (4 L) to the reaction mixture. The layers were separated and the aqueous layer was extracted with DCM (2×2 L). The combined organic layers were washed with brine (2×1 L), dried over $Na_2SO_4$, and concentrated in vacuo. The material thus obtained was adsorbed onto a plug of silica gel and purified by chromatography (silica gel (60-120 mesh) eluting with a gradient of 10-80% EtOAc in hexanes) to provide the title compound 467.0 (1125 g, 3.22 mol, 92%) as a white solid. $^1$H-NMR (400 MHz, $CDCl_3$) δ 7.23 (dd, J=2.08, 6.62 Hz, 4H), 6.90 (dd, J=2.12, 6.60 Hz, 4H), 4.29 (s, 4H), 3.83 (m, 6H), 2.92 (q, J=7.40 Hz, 2H), 1.33 (t, J=7.40 Hz, 3H). GC-LCMS (ESI pos.) m/z: =372.2 $(M+Na)^+$.

Example 468.0. Preparation of (1S,2S)-1-isopropoxy-1-(5-methylpyrimidin-2-yl)propane-2-sulfonamide

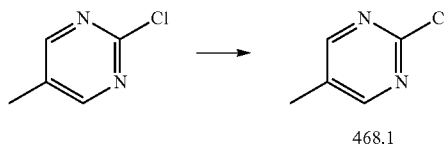

468.1

5-Methylpyrimidine-2-carbonitrile, Example 468.1. A solution of 2-chloro-5-methylpyrimidine (500 g, 3889 mmol, 1.0 equiv.) in DMF (5 L) was degassed with $N_2$ for 20 min and dppf (108 g, 194 mmol, 0.05 equiv.) and $Pd_2(dba)_3$ (178 g, 194 mmol, 0.05 equiv.) were added to the reaction mixture. $Zn(CN)_2$ (685 g, 5834 mmol, 1.5 equiv.) was then added, and the reaction mixture was heated at 100° C. for 16h. The reaction was quenched with water (5 L) and stirred for 10 min. The reaction mixture was then filtered through a pad of Celite® brand filter agent. The filtrate was diluted with water (4 L) and extracted with EtOAc (2×4 L). The combined organic layers were washed with brine (4 L), dried over $Na_2SO_4$, filtered and concentrated under reduced pressure to give the initial product which was further purified by column chromatography using silica gel (60-120 mesh) and 0-10% EtOAc in hexanes to obtain Example 468.1 (330 g, 71%) as an off white solid. $^1$H NMR (400 MHz, DMSO-$d_6$) δ 8.89 (s, 2H), 2.39 (s, 3H).

(R)-N,N-Bis(4-methoxybenzyl)-1-(5-methylpyrimidin-2-yl)-1-oxopropane-2-sulfonamide and (S)-N,N-bis(4-methoxybenzyl)-1-(5-methylpyrimidin-2-yl)-1-oxopropane-2-sulfonamide, Example 468.2. To a solution of Example 467.0 (293 g, 839 mmol, 2.0 equiv.) in THF (2000 mL) was added isopropylmagnesium chloride (420 mL, 839 mmol, 2.0 equiv, 2.0 M in diethyl ether) at 0° C. The resulting reaction mixture was stirred at 25° C. for 3 h. To that reaction mixture was added 5-methylpyrimidine-2-carbonitrile (50 g, 420 mmol, 1.0 equiv.) in THF (100 mL) at 0° C., and the resulting mixture was stirred at RT for 2h. The reaction was then quenched with 1.5 N HCl (500 mL) and water (2 L) and stirred for 10 min. The mixture was extracted with EtOAc (2×1 L) and the combined organic layers were washed with brine (500 mL), dried over $Na_2SO_4$ and filtered. The organic layer was concentrated under reduced pressure to give the initial compound which was purified by column chromatography using silica gel (100-200 mesh) and 0-50% EtOAc in hexanes as eluent to obtain Example 468.2 (60 g, 30% yield) as a brown liquid. $^1$H NMR (400 MHz, DMSO-$d_6$) δ 8.90 (s, 2H), 7.15-7.09 (m, 4H), 6.85-6.80 (m, 4H), 4.34-4.18 (m, 5H), 3.71 (m, 6H), 2.39 (s, 3H), 1.50 (d, J=6.9 Hz, 3H). LCMS (ESI pos.) m/z: $(M+H)^+$: 470.0.

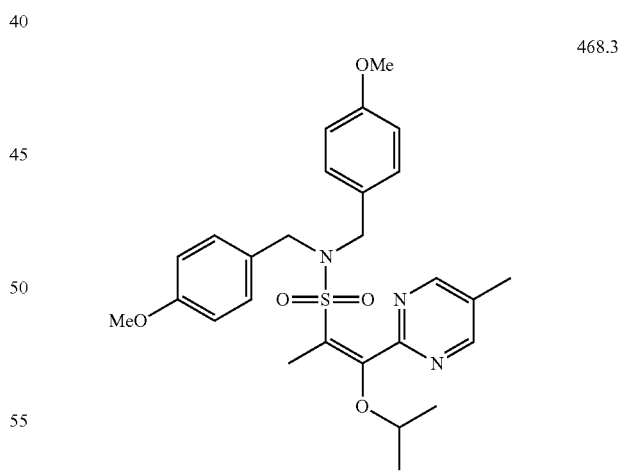

468.3

(E)-1-Isopropoxy-N,N-bis(4-methoxybenzyl)-1-(5-methylpyrimidin-2-yl)prop-1-ene-2-sulfonamide, Example 468.3. To a solution of Example 468.2 (120 g, 256 mmol, 1.0 equiv.) in DMF (1.2 L) was added 2-iodopropane (129 mL, 1278 mmol, 5.0 equiv.) and potassium carbonate (70.6 g, 511 mmol, 2.0 equiv.). The reaction mixture was stirred at 60° C. for 14 h. The reaction was then quenched with water (1 L), stirred for 10 min, and extracted with EtOAc (2×1 L). The combined organic layers were washed with brine (1 L), dried over Na₂SO₄, filtered, and concentrated under reduced pressure to give the initial material. The product thus obtained was purified by column chromatography using silica gel (100-200 mesh) and 0-50% EtOAc in hexanes as eluent to obtain Example 468.3 (75 g, 57.4% yield) as an off white solid. ¹H NMR (400 MHz, DMSO-d₆) δ 8.72 (s, 2H), 7.09 (d, J=8.3 Hz, 4H), 6.86 (d, J=8.3 Hz, 4H), 4.16 (s, 4H), 3.73 (s, 3H), 3.73 (s, 3H), 3.71-3.67 (m, 1H), 2.31 (s, 3H), 1.87 (s, 3H), 1.19-1.16 (m, 6H). LCMS (ESI pos.) m/z: (M+H)⁺: 512.1.

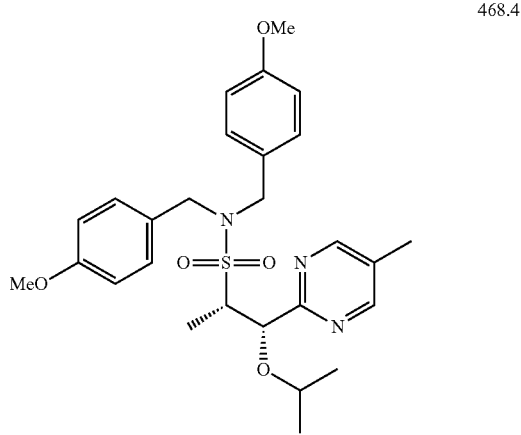 [SMILES: COc1ccc(CN(Cc2ccc(OC)cc2)S(=O)(=O)[C@@H](C)[C@@H](OC(C)C)c2ncc(C)cn2)cc1]

468.4

(1S,2S)-1-Isopropoxy-N,N-bis(4-methoxybenzyl)-1-(5-methylpyrimidin-2-yl)propane-2-sulfonamide, Example 468.4. To a solution of Example 468.3 (180 g, 352 mmol, 1.0 equiv.) in MeOH (1.8 L) was added zinc triflate (256 g, 704 mmol, 2.0 equiv.) and (S)-RuCl[(p-cymene(BINAP)]Cl (6.54 g, 7.04 mmol, 0.02 equiv.). The resulting mixture was then heated at 60° C. under H₂ pressure (60 psi) for 16h. The reaction mixture was concentrated under reduced pressure to obtain the initial product which was further purified by column chromatography using silica gel (60-120 mesh) and 0-50% EtOAc in DCM as eluent to obtain Example 468.4 (140 g, 77%, 92% ee) as an off white solid. ¹H NMR (400 MHz, DMSO-d₆) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (m, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). LCMS (ESI pos.) m/z: (M+H)⁺: 514.2.

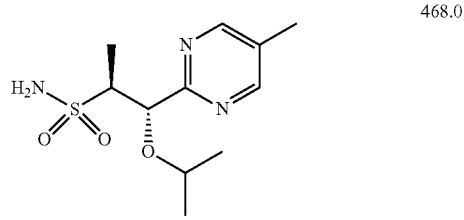 [SMILES: Cc1cnc([C@H](OC(C)C)[C@H](C)S(N)(=O)=O)nc1]

468.0

(1S,2S)-1-Isopropoxy-1-(5-methylpyrimidin-2-yl)propane-2-sulfonamide, Example 468.0. To a solution of Example 468.4 (140.0 g, 273 mmol, 1.0 equiv.) in DCM (500 mL) was added TFA (250 mL) at 0° C. The reaction mixture was then allowed to stir at RT for 16 h. The reaction mixture was concentrated under reduced pressure to obtain the initial product which was dissolved in DCM (1 L) and washed with saturated aqueous NaHCO₃ solution (1 L). The organic layer was dried over Na₂SO₄, filtered, and concentrated under reduced pressure to obtain the initial material which was further purified by column chromatography using silica gel (60-120 mesh) and 0-2% MeOH in DCM to obtain Example 468.0 (72 g, 97% yield, 90% ee) as an off white solid. Example 468.0 (72 g, 90% ee) was suspended in IPA (500 mL) and heated to 70° C. until the mixture became homogeneous. Once the solution became homogeneous, the mixture was cooled to RT overnight. The white solid thus obtained was filtered and dried under vacuum to obtain Example 468 (30 g, >99% ee). The mother liquor was concentrated, and the solid obtained was recrystallized again following the same procedure. ¹H NMR (400 MHz, DMSO-d₆) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). LCMS (ESI pos.) m/z: (M+H)⁺: 274.1.

The compounds in the following table were synthesized following the procedure in Example 468.0 using the known starting material as described.

TABLE 34

| Example | Reagents | Structure, Name and Data |
|---|---|---|
| 468.1 | 2-chloro-5-chloro-pyrimidine. | 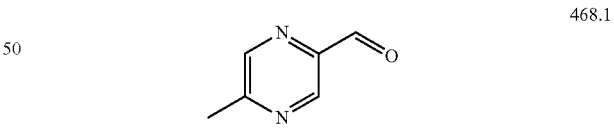<br>(1S,2S)-1-(5-chloropyrimidin-2-yl)-1-isopropoxypropane-2-sulfonamide.<br>LCMS ESI (pos.) m/z: 234.2 (M + H)⁺. |

Example 468.0. Preparation of (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide 468.1

5-Methylpyrazine-2-carbaldehyde, Example 468.1. A solution of LAH (164.0 mL, 0.164 mol, 1.0 M in THF, 0.5 equivalents) was added to a suspension of methyl 5-methylpyrazine-2-carboxylate (50 g, 0.328 mol, 1.0 equiv.) in anhydrous THF (750 mL) at −78° C. (The internal temperature was kept below −72° C. during the addition of LAH). Upon completion of addition, the reaction mixture was left to stir at −78° C. for a further 20 min and then quenched with glacial AcOH (50.0 mL) at the same temperature. The resulting mixture was warmed to RT and the volatiles were removed in vacuo. The residue was dissolved in hydrochloric acid (1.5 N, 500 mL) and extracted with DCM (2×2 L). The extracts were combined, washed with a saturated aqueous NaHCO$_3$ solution (2×500 mL), dried over anhydrous Na$_2$SO$_4$, and concentrated in vacuo, to yield the product as a brown oil. The residue was purified by column chromatography (silica gel 60-120 mesh) eluting with a gradient of 10% EtOAc in petroleum ether to provide the title compound as a pale yellow liquid (21.3 g, 53%). TLC Info: (9.0/1.0 Petroleum ether/EtOAc). $^1$H NMR (400 MHz, CDCl$_3$) δ 10.14 (s, 1H), 9.07 (d, J=1.5 Hz, 1H), 8.63 (d, J=1.4 Hz, 1H), and 2.70 (s, 3H). LCMS (ESI positive ion) m/z: 123 (M+H)$^+$.

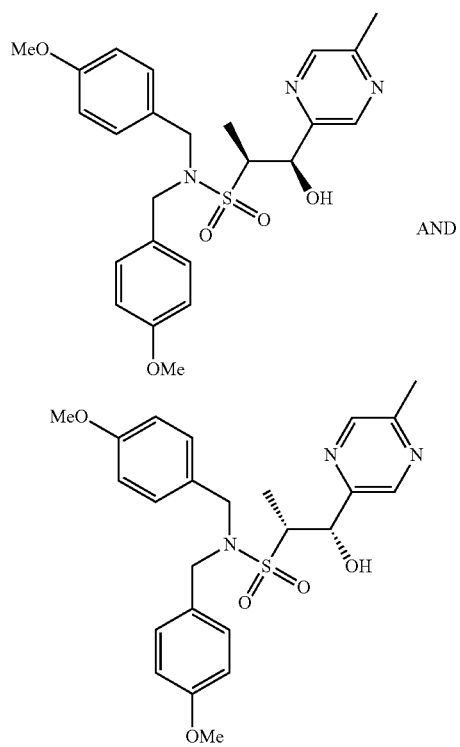

(1R,2S)-1-Hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide, Example 468.2. To a solution of N,N-bis(4-methoxybenzyl)ethanesulfonamide (Example 467.0, 73.13 g, 0.209 mol, 1.2 equiv.) in anhydrous THF (600 mL) at −78° C. was slowly added n-butyllithium (83.71 mL, 0.209 mol, 2.5 M solution in hexanes, 1.2 equiv.) via additional funnel. The resulting mixture was then stirred for 10 min. Next, a solution of 5-methylpyrazine-2-carbaldehyde (Example 468.1, 21.3 g, 0.174 mol, 1.0 equiv.) in anhydrous THF (150 mL) was added, and the resulting mixture was stirred at the same temperature for 45 min and then allowed to warm to RT for 2 h. The reaction mixture was quenched by addition of an aqueous ammonium chloride solution (200 mL) and extracted with EtOAc (2×2 L). The combined organic layers were washed with brine (2×500 mL). After drying over anhydrous Na$_2$SO$_4$, the filtrate was concentrated in vacuo affording the initial product as an oil. The oil was purified by flash column chromatography (silica gel, 230-400 mesh) to afford the two isomers. The faster moving isomer (32 g as a white solid) was obtained from the column with a gradient of 10% to 30% EtOAc in petroleum ether. $^1$H NMR (400 MHz, DMSO-d$_6$) δ 8.61 (d, J=1.5 Hz, 1H), 8.51 (d, J=1.5 Hz, 1H), 7.22-7.11 (m, 4H), 6.90-6.80 (m, 4H), 6.10 (d, J=5.9 Hz, 1H), 5.29 (dd, J=5.9, 2.2 Hz, 1H), 4.36-4.16 (m, 4H), 3.73 (m, 6H), 3.70-3.66 (m, 1H) 2.50 (merged with solvent peak, 3H) and 1.10 (d, J=7.0 Hz, 3H). LCMS (ESI positive ion) m/z: 472.4 (M+H)$^+$.

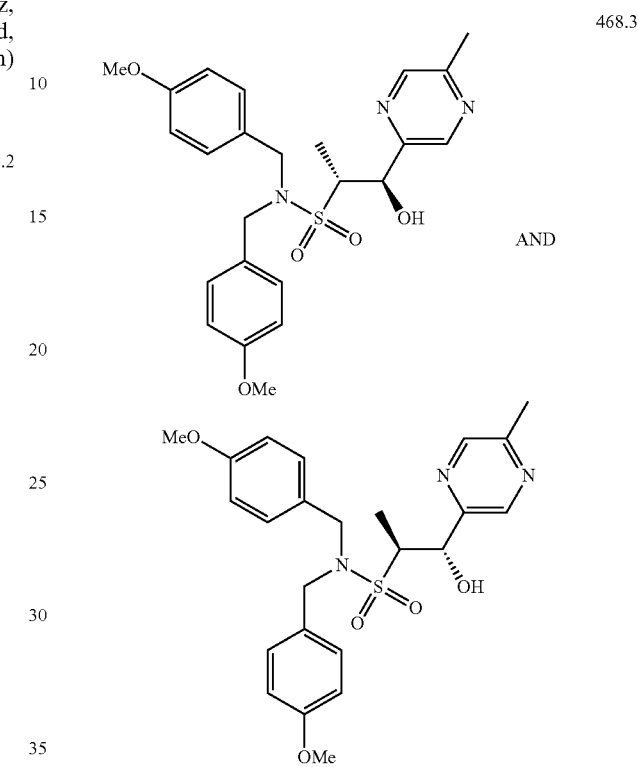

(1S,2S)-1-Hydroxy-N,N-bis(4-methoxybenzyl)-1-(5-methyl-pyrazin-2-yl)propane-2-sulfonamide and (1R,2R)-1-hydroxy-N,N-bis(4-methoxybenzyl)-1-(5-methyl-pyrazin-2-yl)propane-2-sulfonamide, Example 28.3. Further elution of the mixture with a gradient of 30% to 35% EtOAc in petroleum ether yielded Example 468.3 (16 g, pale yellow gummy liquid). $^1$H NMR (400 MHz, CDCl$_3$) δ 8.62 (d, J=1.6 Hz, 1H), 8.44 (d, J=1.5 Hz, 1H), 7.25-7.12 (m, 4H), 6.93-6.82 (m, 4H), 5.17 (d, J=7.1 Hz, 1H), 4.47 (d, J=15.2 Hz, 3H), 4.14 (d, J=15.4 Hz, 2H), 3.82 (s, 3H), 3.82 (s, 3H), 3.66-3.61 (m, 1H), 2.60 (d, J=2.0 Hz, 3H), and 1.08 (dd, J=7.2, 2.1 Hz, 3H). LCMS (ESI pos.) m/z: 472.4 (M+H)$^+$.

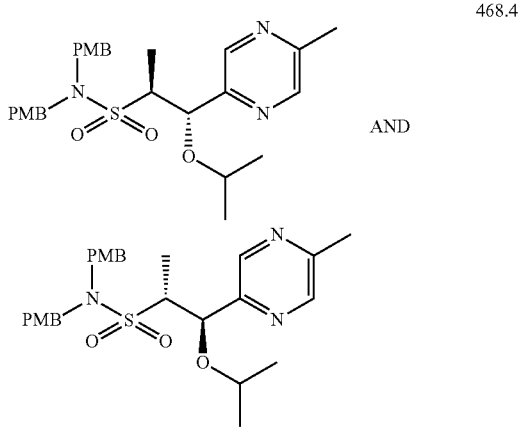

(1S,2S)-1-Isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methylpyrazin-2-yl)propane-2-sulfonamide, Example 468.4. To a flask containing (1S,2S)-1-hydroxy-N,N-bis(4-methoxybenzyl)-1-(5-methylpyrazin-2-yl)propane-2-sulfonamide and (1R,2R)-1-hydroxy-N,N-bis(4-methoxybenzyl)-1-(5-methylpyrazin-2-yl)propane-2-sulfonamide (Example 468.3, 4.16 g, 8.81 mmol) and isopropyl iodide (12.3 mL, 123 mmol) in anhydrous toluene (35 mL), was added silver(I) oxide (4.17 g, 18.0 mmol) carefully in portions. Upon complete addition of silver oxide, the reaction was protected from light and heated to an internal temperature of 72° C. After 60 h, the mixture was cooled to RT and then filtered through a Chemglass disposable filter that was rinsed with EtOAc. The filtrate was concentrated under reduced pressure. The resulting dark brown residue was loaded onto a silica gel column (10-55% EtOAc in heptanes). Fractions containing the product were combined and then concentrated in vacuo to afford Example 468.4 (1.52 g, 2.97 mmol, 34% yield) which was used without further purification. $^1$H NMR (400 MHz, DMSO-d$_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). LCMS (ESI pos.) m/z: 514.0 (M+H)$^+$.

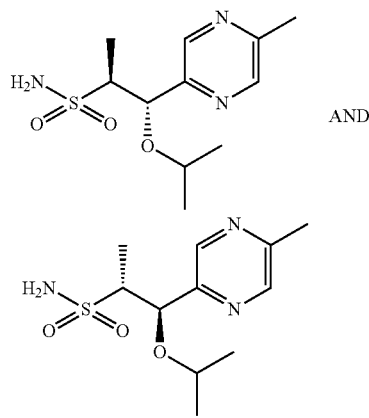

(1R,2R)-1-Isopropoxy-1-(5-methylpyrazin-2-yl)propane-2-sulfonamide and (1S,2S)-1-isopropoxy-1-(5-methylpyrazin-2-yl)propane-2-sulfonamide (Example 468.0), Example 468.5. Anisole (1.3 mL, 11.9 mmol) was added to a flask containing Example 468.4 (1.5 g, 3 mmol) and DCM (7.5 mL). The homogeneous solution was cooled in an ice-water bath. After 15 min, TFA (7.6 mL, 99 mmol) was added dropwise to the reaction solution. Upon complete addition of TFA, the reaction was allowed to warm to RT. After 20 h, the brownish reaction solution was concentrated under reduced pressure. The residue was loaded onto a silica gel column (15-85% EtOAc in heptanes). Fractions containing the product were concentrated under reduced pressure to afford Example 468.5 (714 mg, 2.6 mmol, 88% yield) as an off white solid. LCMS (ESI pos.) m/z: 274.0 (M+H)$^+$.

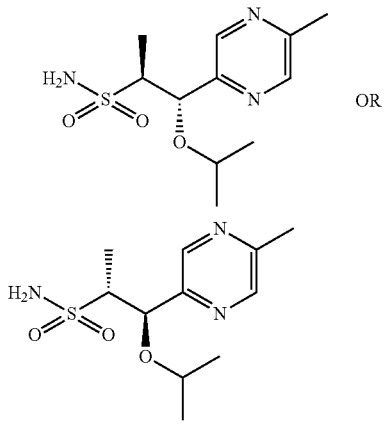

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide, Example 468.6. Example 468.5 (714 mg, 2.6 mmol) was purified by preparative SFC method: Column: IC (2×25 cm) Mobile Phase: 70:30 (A:B) A: Liquid CO$_2$, B: IPA to afford peak 1 as Example 468.6 (293 mg, 1.07 mmol, 36% yield). $^1$H NMR (400 MHz, DMSO-d$_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured CH$_3$ in DMSO peak). LCMS (ESI pos.) m/z: 274.2 (M+H)$^+$.

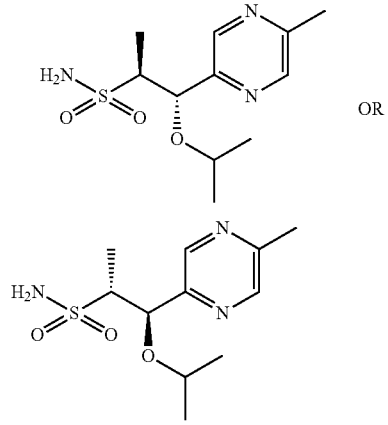

(1R,2R)-1-Isopropoxy-1-(5-methylpyrazin-2-yl)propane-2-sulfonamide or (1S,2S)-1-isopropoxy-1-(5-methylpyrazin-2-yl)propane-2-sulfonamide Example 468.0. Further elution under the conditions described in Example 468.6 delivered the second eluting peak as Example 468.0 (303 mg, 1.11 mmol, 37% yield). $^1$H NMR (400 MHz, DMSO-d$_6$) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured CH$_3$ in DMSO peak). LCMS (ESI pos.) m/z: 274.2 (M+H)$^+$.

Example 469.0. Preparation of (1R,2S)-1-((tert-butyldimethylsilyl)oxy)-N,N-bis(4-methoxybenzyl)-1-(5-methylpyrimidin-2-yl)propane-2-sulfonamide

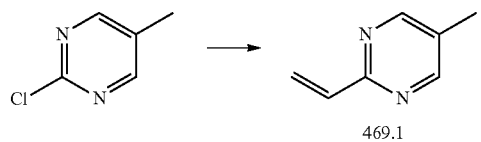

469.1

5-Methyl-2-vinylpyrimidine, Example 469.1. A 3 L 3-neck RBF was fitted with a reflux condenser, a temperature controller and a septum, and was charged with 2-chloro-5-methylpyrimidine (81 mL, 778 mmol), potassium vinyltrifluoroborate (156 g, 1167 mmol), triphenylphosphine (18.02 mL, 78 mmol), cesium carbonate (156 mL, 1945 mmol), and a large stir bar. Water (1565 mL) was added, and the mixture was stirred for several min before THF (244 mL) was added. Argon was sparged through the mixture for 5 min and then palladium (II) chloride (1.72 g, 38.9 mmol) was added. The reaction was further sparged with argon for 5 min. The temperature was then raised to 62° C. and stirring was continued to completion. The reaction was then cooled to RT and filtered through two Whatman GF/F filter cups, rinsing with ether. The mixture was transferred to a separatory funnel and the layers were separated. The aqueous layer was further extracted with diethyl ether (4×200 mL). The organic layers were combined, dried over anhydrous MgSO$_4$, and then filtered. The mixture was partially concentrated in vacuo at 20° C. and 115 torr for an extended period of time to give an orange liquid. The material was further purified by Kugelrohr distillation to isolate the title compound (65.4 g, 70%) as a light yellow oil. $^1$H NMR (400 MHz, CDCl$_3$) δ 2.31 (s, 3H), 5.68 (d, J=10.56 Hz, 1H), 6.55 (d, J=17.22 Hz, 1H), 6.86 (dd, J=17.41, 10.56 Hz, 1H), 8.54 (s, 2H). LCMS-ESI (pos.) m/z: 121.1 (M+H)$^+$.

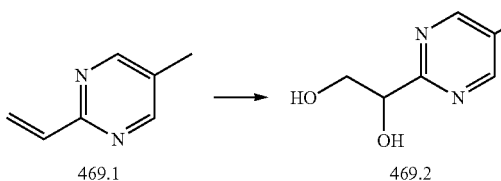

469.1     469.2

1-(5-Methylpyrimidin-2-yl)ethane-1,2-diol, Example 469.2. To a 2 L RBF was added 5-methyl-2-vinylpyrimidine (64.5 g, 537 mmol), osmium tetroxide (0.204 mL, 3.93 mmol), 1,4-dioxane (537 mL, 537 mmol), 4-methylmorpholine-n-oxide, 50% wt. in water (40 mL, 341 mmol) and 4-methylmorpholine-4-oxide (94 g, 805 mmol). The reaction mixture was stirred over 2 d. LCMS showed that the reaction was complete and the solvent was then removed in vacuo. The compound was purified by silica gel chromatography. The gradient was 100% heptanes for 3CV's, then 0-100% EtOAc-EtOH (3:1) in heptanes for 6 CV's, then 100% EtOAc:EtOH (3:1) for 5 CV's. The title compound was collected and concentrated in vacuo. The material was triturated with 40% EtOAc in hexanes to give a solid which was filtered. The solid was washed with 20% EtOAc in hexanes several times and then dried to give the title compound (67.3 g). $^1$H NMR (400 MHz, CDCl$_3$) δ 8.59 (s, 2H), 4.81-4.98 (m, 1H), 3.88-4.19 (m, 2H), 2.36 (s, 3H).

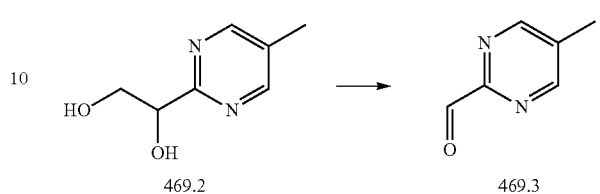

469.2     469.3

5-Methylpyrimidine-2-carbaldehyde, Example 469.3. A 5 L flask equipped with a mechanical stirrer was charged with 1-(5-methylpyrimidin-2-yl)ethane-1,2-diol (64.3 g, 417 mmol), 1,4-dioxane (1043 mL), and water (261 mL). The reaction was cooled in an ice-water bath. Sodium periodate (223 g, 1043 mmol) was then added and the internal temperature was monitored until it returned to RT. The reaction was further stirred at RT for 2 hr and 20 min. DCM (2 L) was then added. The resulting solution was filtered through a plug of dried MgSO$_4$ (700 g). The plug was washed with DCM (7 L). The solvent was concentrated in vacuo, and the aldehyde was azeotroped with toluene to deliver the title compound (44 g) as a white solid. LCMS-ESI (pos.) m/z: 122.8 (M+H)$^+$.

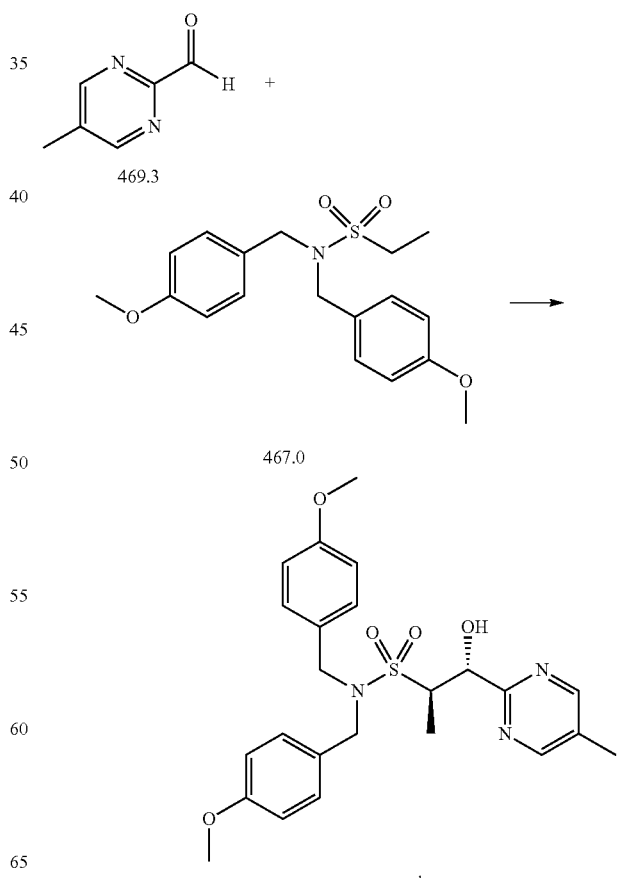

and

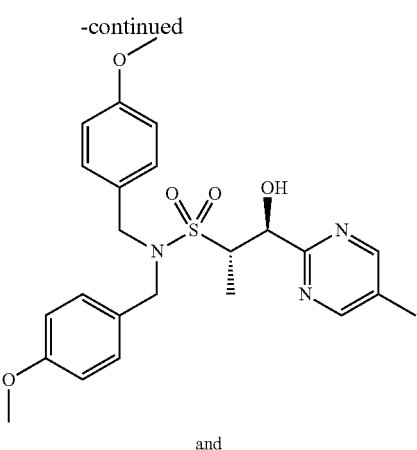

and

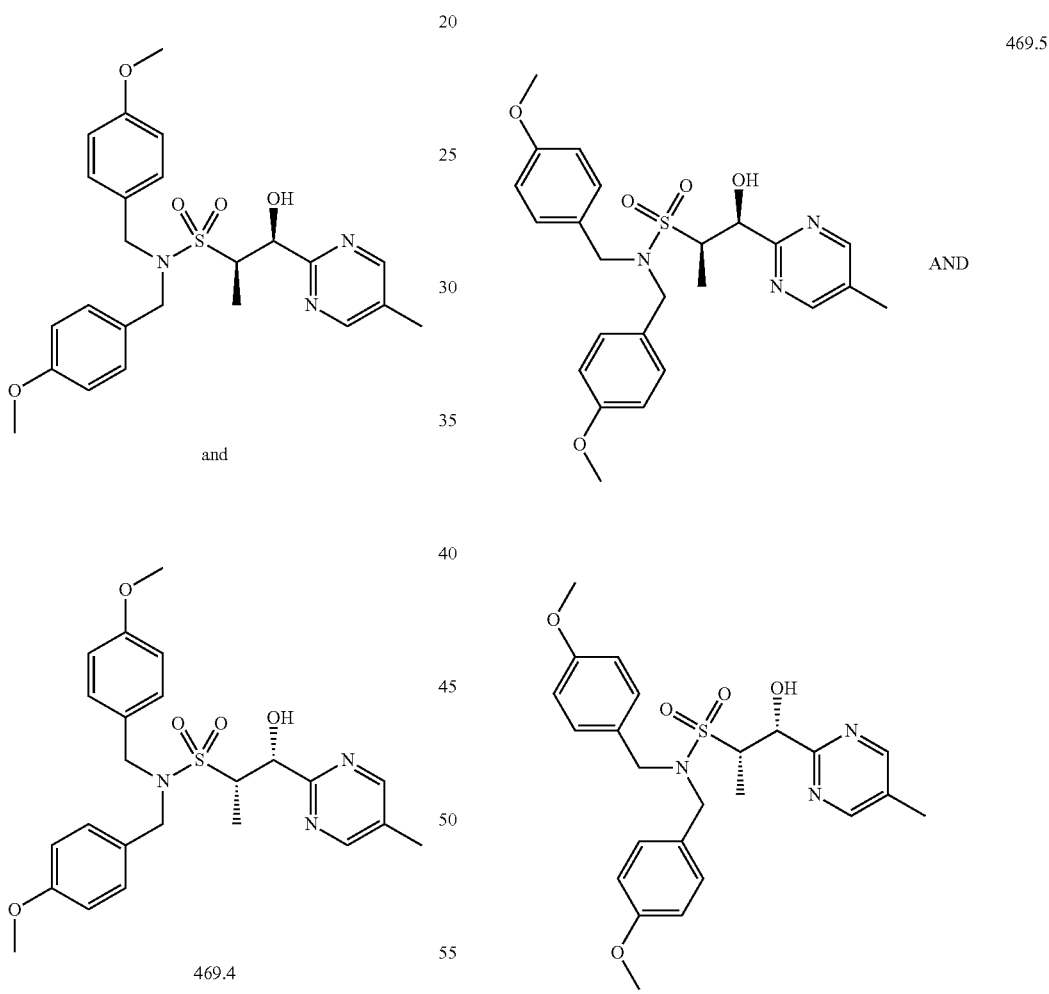

469.4

(1R,2S)-1-Hydroxy-N,N-bis(4-methoxybenzyl)-1-(5-methylpyrimidin-2-yl)propane-2-sulfonamide and (1S,2S)-1-hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide Example 469.4. A 3 L flask was charged with N,N-bis(4-methoxybenzyl)ethanesulfonamide (Example 467.0, 151 g, 432 mmol) and anhydrous THF (1200 mL) under nitrogen and then equipped with a pre-dried addition funnel under nitrogen. The flask was cooled in a dry ice-acetone bath. n-Butyllithium (1.6 M, 270 mL, 432 mmol) was first cannulated into the additional funnel and was then added slowly into the reaction flask which was stirred for 10 min. 5-Methylpyrimidine-2-carbaldehyde (469.3, 44 g, 360 mmol) in THF (300 mL) was next cannulated into the reaction. The reaction was stirred at −78° C. for 45 min and then was warmed to RT and stirred for 2 h and 10 min. A saturated solution of ammonium chloride was added to quench the reaction, and the mixture was extracted with EtOAc and concentrated in vacuo to give the product.

(1R,2S)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide, Example 469.5. The mixture of diastereomers of Example 469.4 was separated and purified on silica gel eluting with 0-50% EtOAc gradient in DCM to give the title compound (56.4 g). LCMS-ESI (pos.) m/z: 472.1 (M+H)$^+$.

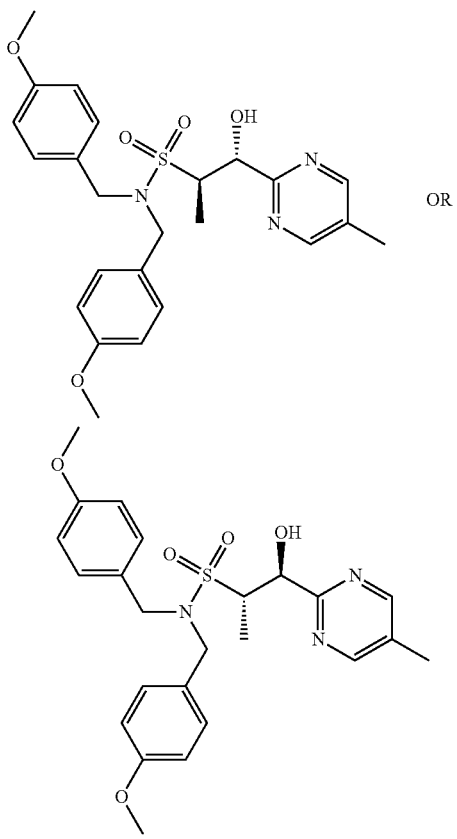

(1S,2S)-1-Hydroxy-N,N-bis(4-methoxybenzyl)-1-(5-methylpyrimidin-2-yl)propane-2-sulfonamide and (1R,2R)-1-hydroxy-N,N-bis(4-methoxybenzyl)-1-(5-methylpyrimidin-2-yl)propane-2-sulfonamide, Example 469.6. Further elution under the conditions described in Example 469.5 delivered the title compound. LCMS-ESI (pos.) m/z: 472.1 (M+H)$^+$.

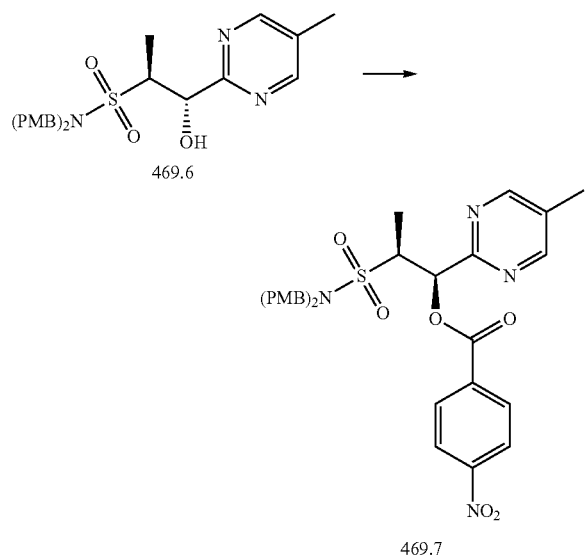

(1R,2S)-2-(N,N-Bis(4-methoxybenzyl)sulfamoyl)-1-(5-methylpyrimidin-2-yl)propyl 4-nitrobenzoate, Example 469.7. To a stirred solution of (1S,2S)-1-hydroxy-N,N-bis(4-methoxybenzyl)-1-(5-methylpyrimidin-2-yl)propane-2-sulfonamide (22.7 g, 48.1 mmol) in toluene (241 mL) was added 4-nitrobenzoic acid (12.07 g, 72.2 mmol) and triphenylphosphine (18.94 g, 72.2 mmol) followed by dropwise addition of (E)-diisopropyl diazene-1,2-dicarboxylate (14.22 mL, 72.2 mmol). The mixture was stirred at RT overnight. The reaction was then concentrated in vacuo and purified on silica gel eluting with 0-50% EtOAc/hexanes to give the title compound, Example 469.7 (29.9 g, 48.1 mmol, 100% yield). LCMS-ESI (pos.) m/z: 621.3 (M+H)$^+$.

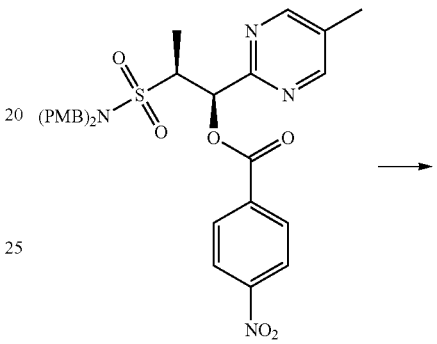

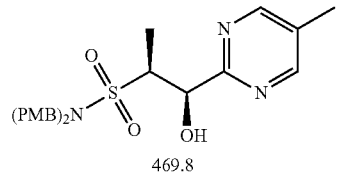

(1R,2S)-2-(N,N-Bis(4-methoxybenzyl)sulfamoyl)-1-(5-methylpyrimidin-2-yl)propyl 4-nitrobenzoate, Example 469.9. To a stirred solution of 469.8 (76 g, 122 mmol) in MeOH (612 mL) at 0° C. was added potassium carbonate (16.92 g, 122 mmol). The mixture was allowed to warm to RT over 1 h and showed the title product by LCMS. The reaction was then concentrated in vacuo and purified on silica gel eluting with 0-40% EtOAc in hexanes to give the title compound. LCMS-ESI (pos.) m/z: 472.0 (M+H)$^+$.

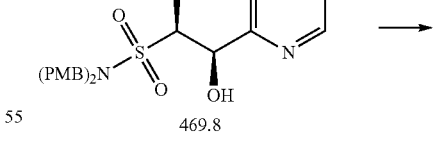

(1R,2S)-1-((tert-Butyldimethylsilyl)oxy)-N,N-bis(4-methoxybenzyl)-1-(5-methylpyrimidin-2-yl)propane-2-sulfonamide, Example 469.0. To a stirred solution of (1R, 2S)-1-hydroxy-N,N-bis(4-methoxybenzyl)-1-(5-methylpyrimidin-2-yl)propane-2-sulfonamide (469.8, 28 g, 59.4 mmol) in DCM (297 mL, 59.4 mmol) at 0° C. was added TBSOTf (15.00 mL, 65.3 mmol), followed by TEA (9.12 mL, 65.3 mmol). The mixture was allowed to warm to RT over 1 h. The reaction mixture was then concentrated in vacuo and purified on silica gel eluting with 0-30% EtOAc in hexanes to give the title compound, (1R,2S)-1-((tert-butyldimethylsilyl)oxy)-N,N-bis(4-methoxybenzyl)-1-(5-methylpyrimidin-2-yl)propane-2-sulfonamide (15 g, 25.6 mmol, 43.1% yield). LCMS-ESI (pos.) m/z: 586.0 (M+H)$^+$.

Example 470.0. Preparation of (2R,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)-N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)-N-(4-(2,6-dimethoxyphenyl)-5-(3-pyridinyl)-4H-1,2,4-triazol-3-yl)-3-(5-methoxy-2-pyrazinyl)-2-butanesulfonamide

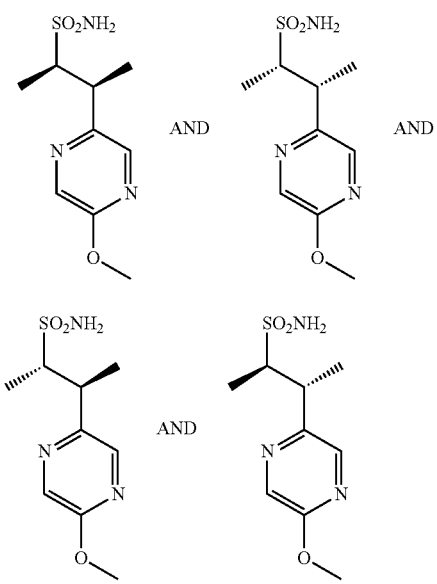

470.0

(2R,3R)-3-(5-Methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 470.0. Example 470.0 was synthesized following the procedure in Example 477.0 using 2-bromo-5-methoxypyrazine (commercially available from Ark Pharm, Inc.). LCMS-ESI (pos.) m/z: 246.2 (M+H)$^+$.

Example 471.0. Preparation of (2S,3R)-3-(5-methoxypyrimidin-2-yl)butane-2-sulfonamide

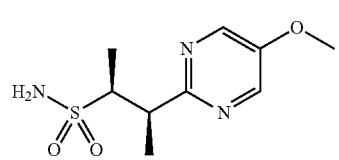

471.0

(2S,3R)-3-(5-Methoxypyrimidin-2-yl)butane-2-sulfonamide, Example 471.0. A RBF was charged with (2S,3R)-3-(5-fluoropyrimidin-2-yl)butane-2-sulfonamide (Example 464.1, 575 mg, 2.47 mmol), MeOH (7 mL), and potassium carbonate (679 mg, 4.91 mmol). The reaction was stirred at RT. After 48 h, the reaction was heated to 50° C. and stirred for 24 h and then the temperature was raised to 65° C. and the reaction was stirred for 48 h. LCMS-ESI showed the reaction was 75% complete. The reaction was then allowed to cool to RT and filtered. The solids were rinsed with MeOH (2×5 mL). The filtrate was concentrated in vacuo and adsorbed onto a plug of silica gel and chromatographed through a RediSep® pre-packed silica gel column, eluting with 0-40% EtOAc:EtOH (3:1) in heptanes. The organic layers from several fractions were concentrated in vacuo to give a mixture of starting material and the title compound (56 mg, 0.23 mmol, 9% yield) as an off-white solid. Water was found to be present in the chromatography solvents and some fractions contained water. The fractions containing water were combined and the aqueous layer was saturated with NaCl and extracted with CHCl$_3$:IPA (9:1, 3×15 mL). The combined organic layers were dried over MgSO$_4$ and concentrated in vacuo to give more title compound (114 mg). The material was carried forward without further purification. LCMS-ESI (pos.) m/z: 246.1 (M+H)$^+$.

Example 472.4. Preparation of (3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide

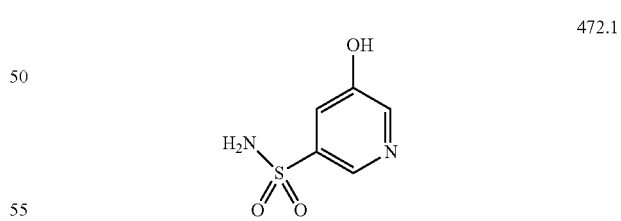

472.1

5-Hydroxypyridine-3-sulfonamide, Example 472.1. To a 100 mL RBF was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.16 mmol), and Pd$_2$(dba)$_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was then allowed to cool to RT. The reaction mixture was diluted with 1.0 N HCl and washed with Et$_2$O. The aqueous phase was concentrated in vacuo to afford the title compound 472.1 (0.387 g, 2.22 mmol, 100% yield) as a white solid which was directly used in the next step without further purification. LCMS-ESI (pos.), m/z: 175.1 (M+H)$^+$.

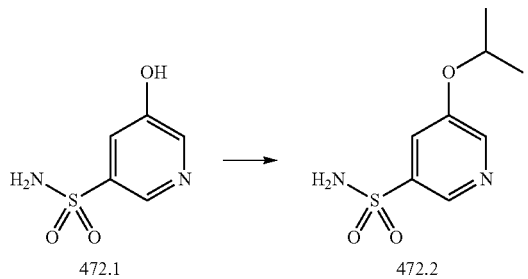

5-Isopropoxypyridine-3-sulfonamide, Example 472.2. To a suspension of 5-hydroxypyridine-3-sulfonamide, Example 472.1 (1.1 g, 6.32 mmol), in THF (16 mL) and IPA (16 mL), was added triphenylphosphine (1.99 g, 7.58 mmol). The mixture was sparged with argon for 3 min before diisopropyl azodicarboxylate (1.49 mL, 7.58 mmol) was added dropwise at 0° C. under a N$_2$ stream. The reaction was then stirred at 0° C. to RT for 15 h. The reaction mixture was concentrated in vacuo. The material thus obtained was absorbed onto a plug of silica gel and purified by chromatography through a RediSep pre-packed silica gel column (40 g), eluting with a gradient of 0% to 100% EtOAc in heptanes to provide the enriched product fractions which were combined and extracted with 1N HCl. The title compound was enriched in acidic aqueous solution, which was then modified by saturated aqueous NaHCO$_3$ to a pH of greater than 8. The basic aqueous solution was then extracted with DCM. The organic extract was washed with brine and dried over Na$_2$SO$_4$. The solution was filtered and concentrated in vacuo to give 5-isopropoxypyridine-3-sulfonamide, Example 472.2, (0.95 g, 70% yield) as a white solid. LCMS-ESI (pos.), m/z: 217.2 (M+H)$^+$.

472.3

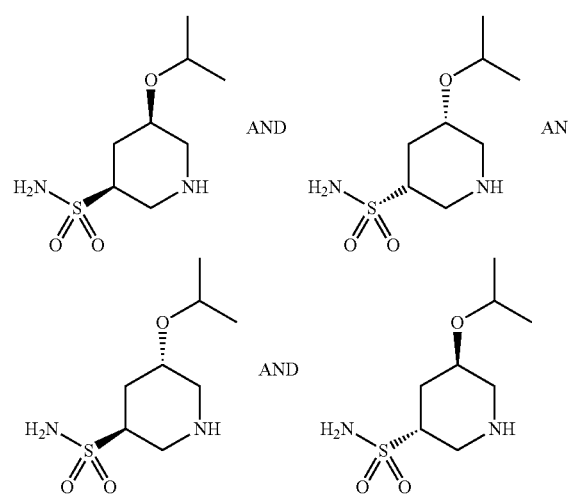

(3S,5R)-5-Isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide, Example 472.3. A solution of Example 472.2 (1.8 g, 8.32 mmol) in AcOH (41.6 mL) was sparged with argon gas for 2 min before platinum (IV) oxide (1.89 g, 8.32 mmol) was added under an argon stream. The above reaction mixture was stirred at RT under 45 psi of hydrogen gas for 2 d. Next, Celite® brand filter agent (5 g) was added to the reaction mixture, and the resulting mixture was stirred at RT for 10 min. The mixture was then filtered and the solution was concentrated in vacuo to give the initial product mixture as a light yellow oil, which was used as such in the next step. LCMS-ESI (pos.), m/z: 223.3 (M+H)$^+$.

472.4

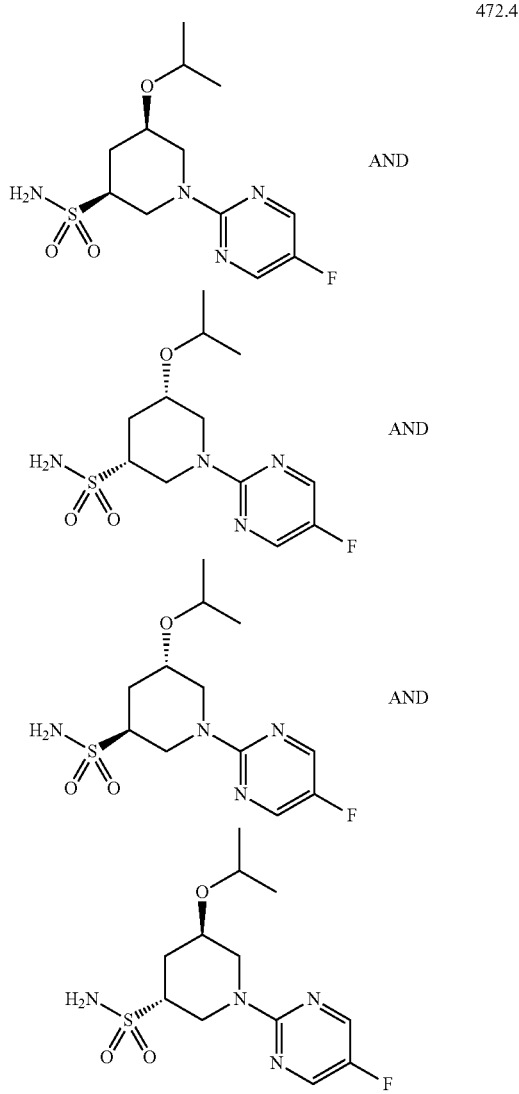

(3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 472.4. To a 40 mL vial (with pressure release septa) was added Example 472.3 (3S,5R)-5-isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide (2.0 g, 4.96 mmol), and 2-chloro-5-fluoropyrimidine (3.29 g, 24.79 mmol). The reaction mixture was stirred at 90° C. for 21 h. LCMS indicated the reaction was complete. Next, the reaction mixture was concentrated in vacuo. The material thus obtained was absorbed onto a plug of silica gel and purified by chromatography through a RediSep pre-packed silica gel column (40 g), eluting with a gradient of 0% to 100% EtOAc in heptanes to provide Example 472.4 as a mixture of diastereomers (0.5 g, 1.6 mmol, 32% yield) as an off-white solid. LCMS-ESI (pos.), m/z: 319.2 (M+H)+.

472.5

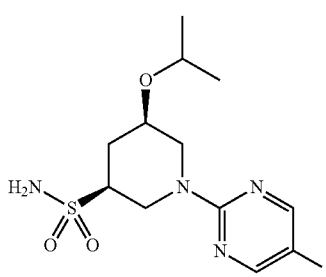

OR

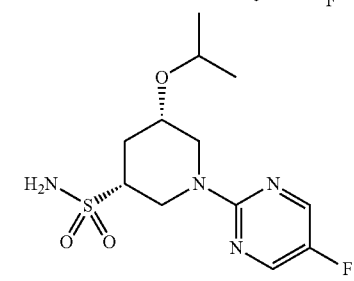

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 472.5. Example 472.4 was separated by SFC on a Chiralpak AS-H column using 15% MeOH/CO$_2$. Example 472.5 and Example 472.6 are a pair of enantiomers. Example 472.5 was the second peak among 4 isomers (earlier peak vs. its opposite enantiomer) on the AS-H column. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)+.

472.6

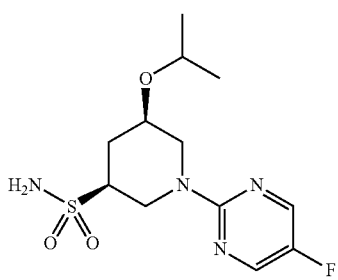

OR

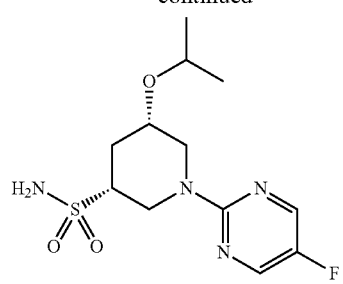

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 472.6. Further elution under the conditions described in Example 472.5 gave Example 472.6 as the third peak. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)+.

472.7

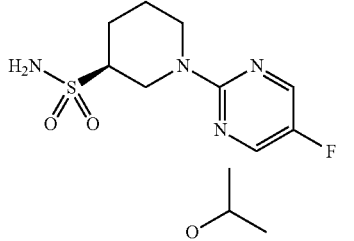

OR

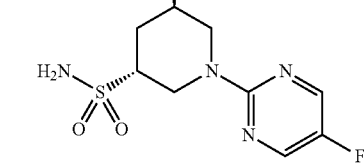

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 472.7. Examples 472.7 and 472.8 are a pair of enantiomers. Example 472.7 was the first peak among 4 isomers (earlier peak vs. its opposite enantiomer) on an AS-H column under conditions described in Example 472.5. $^1$H NMR (400 MHz, CD$_3$OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)+.

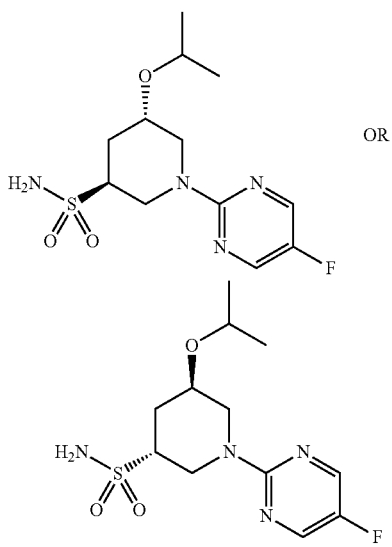

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 472.8. Further elution under the conditions described in Example 472.5 gave Example 472.8 as the fourth peak. $^1$H NMR (400 MHz, CD$_3$OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)$^+$.

Example 473.0. Preparation of (S)-tert-butyl 3-sulfamoylpiperidine-1-carboxylate and (R)-tert-butyl 3-sulfamoylpiperidine-1-carboxylate

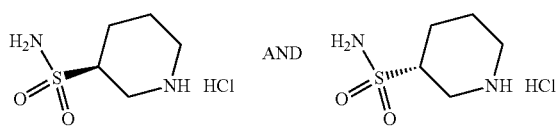

(S)-Piperidine-3-sulfonamide hydrochloride and (R)-piperidine-3-sulfonamide hydrochloride, Example 473.1. A solution of 4-chloropyridine-3-sulfonamide (5.0 g, 25.9 mmol) in AcOH (150 mL) was placed in a Parr bottle. The mixture was sparged with nitrogen gas for 5 min. To this solution was added a suspension of platinum (IV) oxide (5.9 g, 25.9 mmol) in AcOH (30 mL). The reaction was stirred under an atmosphere of hydrogen (50 psi) for 72 h. The reaction mixture was then filtered through a pad of Celite® brand filter agent and the pad was washed with MeOH (2×50 mL). The combined filtrate was concentrated under reduced pressure to provide Example 473.1 (6.0 g) as an oil which was used in the next step without further purification. LCMS-ESI (pos.) m/z: 165 (M+H)$^+$.

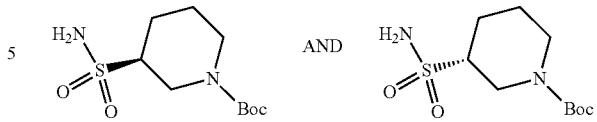

(S)-tert-Butyl 3-sulfamoylpiperidine-1-carboxylate and (R)-tert-butyl 3-sulfamoylpiperidine-1-carboxylate, Example 473.0. To a mixture of 473.1 (12.0 g, 59.8 mmol) and TEA (41.6 mL, 299 mmol) in DCM (215 mL) was added a solution of di-tert-butyl dicarbonate (15.7 mL, 71.8 mmol) in DCM (70 mL) at RT. The reaction mixture was stirred for 16 h at RT. The reaction mixture was then washed with water (2×200 mL). The combined organic layers were washed with brine (100 mL), dried over sodium sulfate, and evaporated under reduced pressure to obtain the initial product which was purified by column chromatography (silica: 100-200 mesh; elution: 0-30% EtOAc in DCM) to provide 473.0 (4.6 g, 34%, over two steps) as a white solid. $^1$H NMR (400 MHz, CD$_3$CN) δ 5.30 (s, 2H), 4.36 (d, J=11.8 Hz, 1H), 3.94 (d, J=13.3 Hz, 1H), 3.01-2.84 (m, 2H), 2.64-2.58 (s, 1H), 2.20 (d, J=13.3 Hz, 1H), 1.78 (d, J=13.5 Hz, 1H), 1.74-1.57 (m, 2H), 1.43 (s, 9H). LCMS-ESI (pos.) m/z: 263 (M–H)$^+$.

Example 474.0. Preparation of (3S,5S)-1-(5-fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide

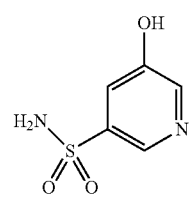

5-Hydroxypyridine-3-sulfonamide, Example 474.1. To a 100 mL RBF was added 5-bromopyridine-3-sulfonamide (commercially available from Enamine, KIEV, Ukraine) (0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.16 mmol) and Pd$_2$(dba)$_3$ (Sigma-Aldrich Chemical Company, Inc., 0.038 g, 0.041 mmol). The flask was placed under vacuum and back-filled with potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was allowed to cool to RT. The reaction mixture was diluted with 1.0 N HCl and washed with Et$_2$O. The aqueous phase was concentrated in vacuo to afford the title compound 474.1 (0.387 g, 2.22 mmol, 100% yield) as a white solid, which was directly used in the next step without further purification. LCMS-ESI (pos.), m/z: 175.1 (M+H)$^+$.

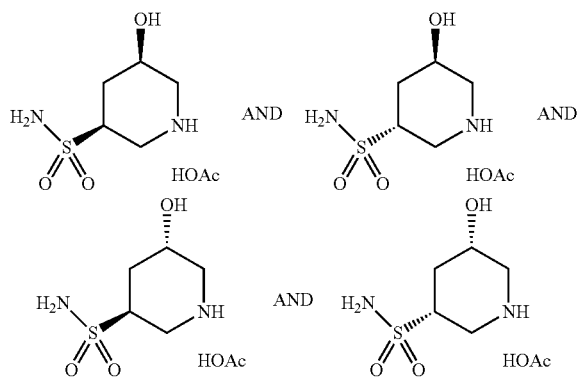

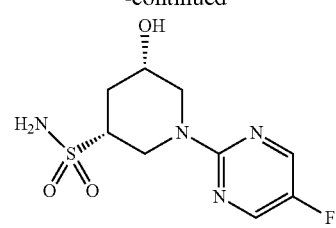

(3R,5R)-5-Hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 474.2. To a 1-L hydrogenation flask was added 474.1 (6.46 g, 37.1 mmol) and AcOH (250 mL, 4330 mmol). Water (20 mL) was added as co-solvent. The mixture was sparged with $N_2$ for 2 min before platinum (IV) oxide hydrate (8.42 g, 37.1 mmol) was added under $N_2$ flow. The flask was set up on a Parr shaker, vacuumed and back-filled with $N_2$ two times, and then placed under vacuum and back-filled with hydrogen gas. The reaction mixture was stirred at RT under 50 psi of hydrogen gas for 24 h. LCMS analysis indicated that the reaction was complete. Celite® brand filter agent (20 g) was then added to the mixture with stirring. The solid was removed by filtration after 10 min of stirring. The filter cake was rinsed with MeOH. The combined organic layers were concentrated in vacuo to afford 474.2 (8.91 g, 100% yield) as a light-yellow oil, which was directly used in the next step without purification. LCMS-ESI (pos.) m/z: 181.1 (M+H)$^+$.

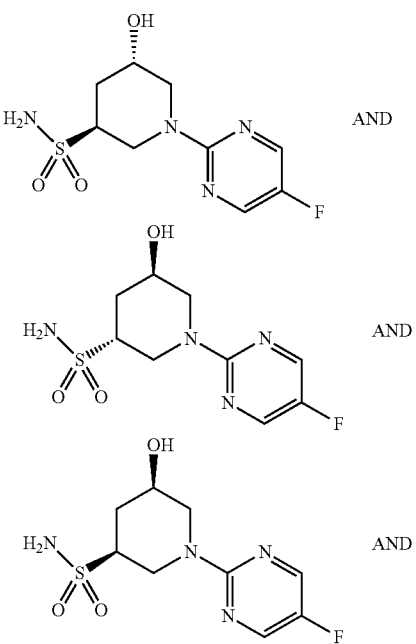

(3S,5S)-1-(5-Fluoropyrimidin-2-yl)-5-hydroxypiperidine-3-sulfonamide and (3S,5R)-1-(5-fluoropyrimidin-2-yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 474.0. To a 500 mL RBF was added 474.2 (8.91 g, 37.1 mmol) and Hunig's base (32.3 mL, 185 mmol) in DMF (80 mL). 2-Chloro-5-fluoro-pyrimidine (18.32 mL, 148 mmol) was then added with stirring. The reaction mixture was stirred at 120° C. for 18 h. LCMS analysis indicated the reaction was complete. The reaction mixture was allowed to cool to RT and then was diluted with water and extracted with DCM. The organic layers were washed with brine and dried over $Na_2SO_4$. The solution was filtered and concentrated in vacuo to give the initial material as an orange oil. The material thus obtained was purified by silica gel chromatography (a gradient of 0-100% EtOAc in DCM), to provide 474.0 (3.7 g, 10.93 mmol, 36% yield) as a light-yellow solid. LCMS-ESI (pos.), m/z: 277.0 (M+H)$^+$.

Example 475.3. Preparation of (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide

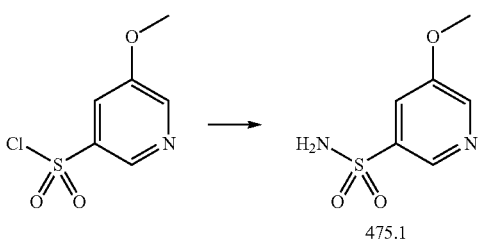

5-Methoxypyridine-3-sulfonamide, Example 475.1. A reaction mixture of 5-methoxypyridine-3-sulfonyl chloride (commercially available from Enamine, KIEV, Ukraine) (1.0 g, 4.82 mmol) and ammonia, (0.5 M solution in 1,4-dioxane, 96 mL, 48.2 mmol) was stirred at 0° C. to RT for 30 min. LCMS indicated the reaction was complete. The reaction was then filtered and the filter cake was rinsed with dioxane. The combined solution was concentrated in vacuo to give the title compound (0.91 g, 100% yield) as a light yellow foam which was used as such in the next step without purification. LCMS-ESI (pos.) m/z: 189.2 (M+H)$^+$.

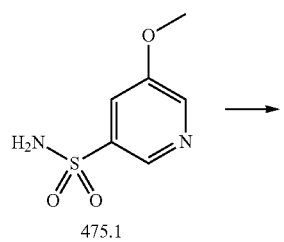

475.1

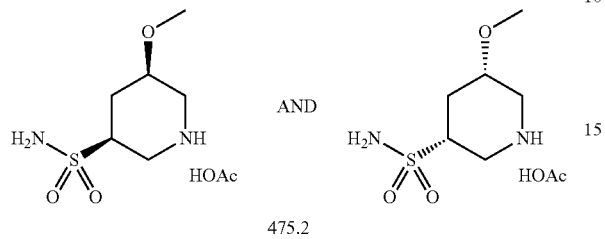

475.2

(3S,5R)-5-Methoxypiperidine-3-sulfonamide acetate and (3R,5S)-5-methoxypiperidine-3-sulfonamide acetate, Example 475.2. A solution of 5-methoxypyridine-3-sulfonamide (0.9 g, 4.78 mmol) in AcOH (31.9 mL) was sparged with argon gas for 2 min before platinum (IV) oxide ((1.09 g, 4.78 mmol) was added under an argon stream. The reaction mixture was stirred at RT under 45 psi of hydrogen gas for 38 h. The mixture was then filtered and the filtrate was concentrated in vacuo to give the title compound (1.22 g, 100% yield) as a light yellow foam which was used as such in the next step. LCMS-ESI (pos.) m/z: 195.2 (M+H)$^+$.

475.3

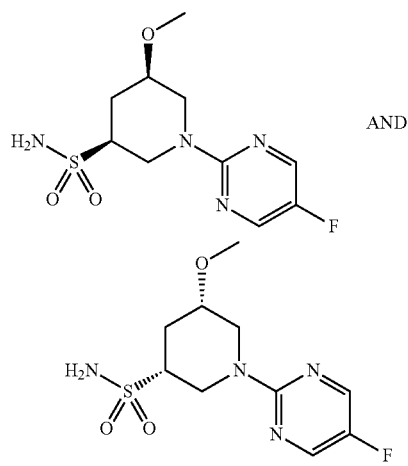

(3S,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide, Example 475.3. To a 40 mL vial (w/ pressure release septa) was added 5-methoxypiperidine-3-sulfonamide acetate (475.2, 2.45 g, 9.62 mmol), N-ethyl-N-isopropylpropan-2-amine (16.75 mL, 96 mmol), and 2-chloro-5-fluoropyrimidine (6.37 g, 48.1 mmol) in DMSO (48 mL). The reaction mixture was stirred at 100° C. for 23 h. LCMS indicated formation of the title product. The reaction mixture was then diluted with water and extracted with DCM. The organic extract was washed with saturated aqueous NaCl, brine, and dried over Na$_2$SO$_4$. The resulting solution was filtered and concentrated in vacuo to give the initial product as an orange oil. The material thus obtained was absorbed onto a plug of silica gel and purified by chromatography through RediSep pre-packed silica gel column (40 g), eluting with a gradient of 0% to 100% 1/3 EtOH/EtOAc in heptanes to provide the title compound, 475.3 (0.51 g, 18% yield), as a white solid. LCMS-ESI (pos.) m/z: 291.0 (M+H)$^+$.

475.4

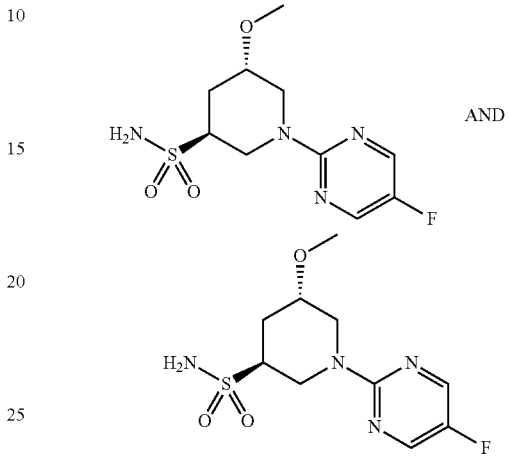

(3S,5S)-1-(5-Fluoropyrimidin-2-yl)-5-methoxypiperidine-3-sulfonamide and (3R,5R)-1-(5-fluoropyrimidin-2-yl)-5-methoxypiperidine-3-sulfonamide, Example 475.4. Further elution under the conditions described in Example 475.3 delivered 475.4 (0.24 g, 0.832 mmol, 8.65% yield) as light yellow solid. LCMS-ESI (pos.) m/z: 291.0 (M+H)$^+$.

475.5

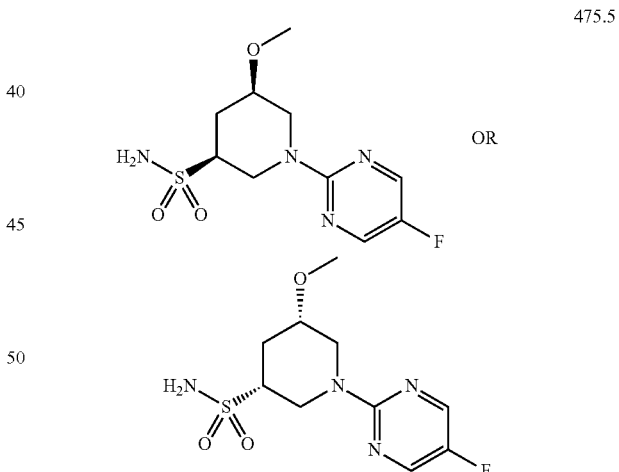

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 475.5. Example 475.5 was obtained by chiral separation of 475.3 using SFC: Chiralpak AD-H, 30% MeOH/CO$_2$, with 0.2% DEA. Example 475.5 was the earlier peak to elute on the Chiralpak AD-H column. $^1$H NMR (400 MHz, CD$_3$OD) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (pos.) m/z: 291.0 (M+H)$^+$.

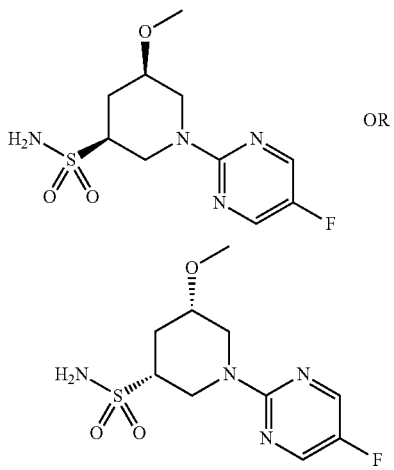

475.6

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 475.6. Further elution under the conditions described in Example 475.5 delivered Example 475.6. $^1$H NMR (400 MHz, CD$_3$OD) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45 (s, 3H) 4.97 (ddt, 1H) 5.17 (ddt, 1H) 8.32 (s, 2H). LCMS-ESI (pos.) m/z: 291.0 (M+H)$^+$.

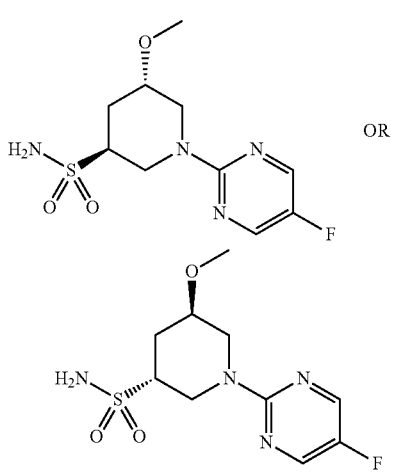

475.7

(3S,5S)-1-(5-Fluoropyrimidin-2-yl)-5-methoxypiperidine-3-sulfonamide or (3R,5R)-1-(5-fluoropyrimidin-2-yl)-5-methoxypiperidine-3-sulfonamide, Example 475.7. Example 475.7 was obtained by chiral separation of 475.3 using SFC: Chiralpak AD-H, 25% MeOH/CO$_2$, with 0.2% DEA. 475.7 was the earlier peak to elute on the Chiralpak AD-H column. $^1$H NMR (400 MHz, CD$_3$OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H) LCMS-ESI (pos.) m/z: 291.0 (M+H)$^+$.

475.8

(3R,5R)-1-(5-Fluoropyrimidin-2-yl)-5-methoxypiperidine-3-sulfonamide or (3S,5S)-1-(5-fluoropyrimidin-2-yl)-5-methoxypiperidine-3-sulfonamide, Example 475.8. Further elution under the conditions described in Example 475.7 delivered Example 475.8. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 291.0 (M+H)$^+$.

Example 468.3. Preparation of (1R,2R)-1-hydroxy-N,N-bis(4-methoxybenzyl)-1-(5-methylpyrimidin-2-yl)propane-2-sulfonamide 142.1

N-Methoxy-N,5-dimethylpyrimidine-2-carboxamide, Example 142.1. To a solution of 5-methylpyrimidine-2-carboxylic acid (1 g, 7.24 mmol) in DMF (72.4 mL) was added 5-methylpyrimidine-2-carboxylic acid (1 g, 7.24 mmol), and N,O-dimethylhydroxylamine hydrochloride (0.777 g, 7.96 mmol). The mixture was cooled to 0° C. and 1-propanephosphonic acid cyclic anhydride (50 wt. % solution in EtOAc, 9.21 mL, 14.48 mmol) was added dropwise. The mixture was allowed to warm to RT overnight. LCMS indicated complete conversion to product. The mixture was then diluted with water, extracted with CHCl$_3$:IPA (3:1), and washed with brine and NaHCO$_3$. The mixture was dried over Na$_2$SO$_4$, concentrated in vacuo, and purified by silica gel chromatography (0-100% heptanes:EtOAc) to yield N-methoxy-N,5-dimethylpyrimidine-2-carboxamide (0.7 g, 3.86 mmol, 53.4% yield), Example 142.1. H NMR (500 MHz, CDCl$_3$) δ8.61-8.69 (m, 2H) 3.61-3.79 (m, 3H) 3.27-3.47 (m, 3H) 2.34-2.45 (m, 3H). LCMS-ESI (pos.) m/z: 182.2 (M+H)$^+$.

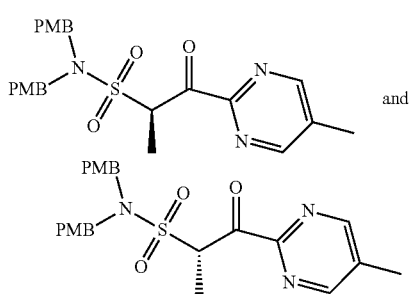

468.2 and (R)-N,N-Bis(4-methoxybenzyl)-1-(5-methylpyrimidin-2-yl)-1-oxopropane-2-sulfonamide and (S)-N,N-bis(4-methoxybenzyl)-1-(5-methylpyrimidin-2-yl)-1-oxopropane-2-sulfonamide, Example 468.2. A solution of N,N-bis(4-methoxybenzyl)ethanesulfonamide (azeotroped three times with toluene before use) (Example 467.0, 0.771 g, 2.21 mmol) was dissolved in THF (3.68 mL) and then cooled to −78° C. using a dry ice acetone bath. To this was added a solution of n-butyllithium (0.883 mL, 2.21 mmol, 2.5 M in hexanes). The reaction turned pink immediately and then slowly faded to yellow upon stirring at −78° C. for 30 min. This solution was then added quickly to a solution of N-methoxy-N,5-dimethylpyrimidine-2-carboxamide (Example 142.1, 0.2 g, 1.104 mmol) in THF (0.5 mL) at RT. The reaction was stirred at RT for 20 min after which LCMS indicated complete consumption of Weinreb amide and conversion to product. The reaction was quenched by addition to a separatory funnel that contained 1.0 M HCl (15 mL). The mixture was extracted with DCM, (aqueous layer was checked for product by LCMS), dried over $Na_2SO_4$ and concentrated in vacuo. The mixture was purified by silica gel chromatography 0-100% EtOAc:heptanes to yield N,N-bis(4-methoxybenzyl)-1-(5-methylpyrimidin-2-yl)-1-oxopropane-2-sulfonamide (0.36 g, 0.767 mmol, 69.5% yield), Example 468.2. $^1$H NMR (500 MHz, DMSO-$d_6$) δ 8.86-8.93 (m, 2H) 7.06-7.15 (m, 4H) 6.79-6.87 (m, 4H) 5.87-5.95 (m, 1H) 4.20-4.34 (m, 4H) 3.67-3.73 (m, 6H) 2.38-2.42 (m, 3H) 1.46-1.55 (m, 3H). LCMS-ESI (pos.) m/z: 470.0 (M+H)$^+$.

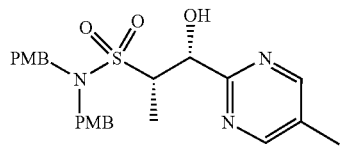

468.3

(1R,2R)-1-Hydroxy-N,N-bis(4-methoxybenzyl)-1-(5-methylpyrimidin-2-yl)propane-2-sulfonamide, Example 468.3. To a solution of Example 468.2 (1.0 g, 2.13 mmol) in DMF (22.18 mL) was added (N-((1S,2S)-1,2-diphenyl-2-((3-phenylpropyl)amino)ethyl)-4-methylphenylsulfonamido)ruthenium(II) chloride (9.91 mg, 0.016 mmol). The mixture was then degassed by placing under vacuum and backfilling with $N_2$ three times. To this mixture was added a solution of HCOOH:TEA (5:2 v/v) (0.55 mL), and the reaction was stirred at RT for 12 h after which LCMS indicated complete conversion to product and 7:1 d.r. (syn: anti). The mixture was then washed with 5% LiCl (aq) and then extracted with DCM and then with $CHCl_3$:IPA (3:1). The organic layers were combined and dried over $Na_2SO_4$ and concentrated in vacuo. The mixture was loaded directly onto a silica gel column and purified using a gradient of 0-100% heptanes:EtOAc to yield the title compound (0.77 g, 1.63 mmol, 77% yield) as an off white solid. $^1$H NMR (500 MHz, DMSO-$d_6$) δ 8.85-8.93 (m, 2H) 7.08-7.15 (m, 4H) 6.78-6.86 (m, 4H) 5.86-5.96 (m, 1H) 4.20-4.35 (m, 4H) 3.68-3.75 (m, 6H) 3.28-3.34 (m, 2H) 2.37-2.42 (m, 3H) 1.47-1.54 (m, 3H) LCMS-ESI (pos.) m/z: 572.2 (M+H)$^+$.

Example 476.0. Preparation of (2S,3R)-N-(4-((1r,2R,6S)-2,6-dimethoxycyclohexyl)-5-phenyl-4H-1,2,4-triazol-3-yl)-3-(5-methyl-2-pyrimidinyl)-2-butanesulfonamide

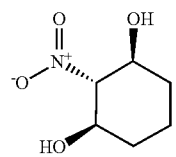

476.1

(1R,2r,3S)-2-Nitrocyclohexane-1,3-diol, Example 476.1. A 500 mL RBF was charged with glutaric dialdehyde (12.5 g, 50 mL, 25% aqueous solution, 125 mmol) and diluted with nitromethane (27.6 mL, 512 mmol) and a 1:1 solution of MeOH (69.3 mL) and water (69.3 mL). The solution was cooled to 0° C. and sodium carbonate (48.4 g, 457 mmol) in water (69.3 mL) was added. The resulting mixture was warmed to RT and stirred for 4 h. Carefully, AcOH (32.3 mL, 570 mmol) was added, and the solution was concentrated in vacuo to remove all organics (bath temp 30-35° C.). Next the water solution was partitioned with ether (5×200 mL), dried over sodium sulfate, filtered and concentrated to dryness. The material was then recrystallized with EtOAc to obtain the desired product (1R,2r,3S)-2-nitrocyclohexane-1,3-diol (7.5 g, 37%), Example 476.1.

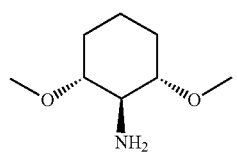

476.2

(1r,2R,6S)-2,6-Dimethoxycyclohexanamine, Example 476.2. Silver(I) oxide (6.15 mL, 192 mmol) was added to a DMF (96 mL) solution containing iodomethane (30.0 mL, 479 mmol) and (1R,2r,3S)-2-nitrocyclohexane-1,3-diol (7.72 g, 47.9 mmol). The resulting mixture was stirred overnight at RT. The reaction was then filtered and the filtrate was partitioned with EtOAc/water, washed with brine, dried over sodium sulfate, and concentrated. Next, the residue was dissolved in EtOH and Raney 2400 nickel (0.316 mL, 47.9 mmol) was added. The reaction was shaken in a Parr hydrogenator at 50 psi overnight. The reaction was then carefully filtered and concentrated in vacuo to provide the title compound.

476.3

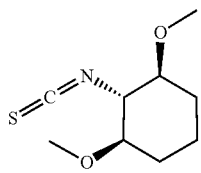

(1R,2r,3S)-2-Isothiocyanato-1,3-dimethoxycyclohexane, Example 476.3. 1,1"-Thiocarbonyldi-2(1H)-pyridone (0.802 g, 3.45 mmol) was added to a DCM (15.70 mL) solution containing (1r,2R,6S)-2,6-dimethoxycyclohexanamine (0.5 g, 3.14 mmol). The resulting mixture was stirred overnight at RT. The reaction was concentrated and purified on silica eluting with a hexanes/EtOAc gradient (0-100%). Desired fractions were then pooled and concentrated to yield the title compound (0.45 g, 71%).

Example 477.0. Preparation of (2S,3R)-3-(5-chloro-pyridin-2-yl)butane-2-sulfonamide

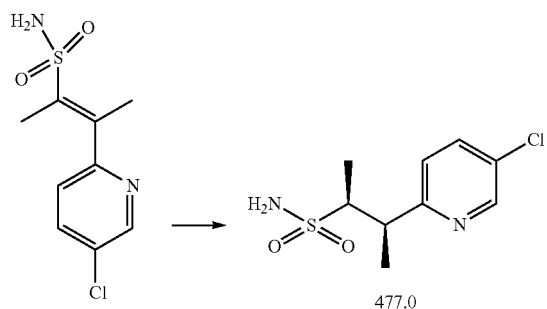

477.0

(2S,3R)-3-(5-Chloropyridin-2-yl)butane-2-sulfonamide, Example 477.0. To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1,5-cyclooctadiene)rhodium(I) tetrafluroborate (0.329 g, 0.811 mmol) and (S)-1-[(R)-2-(di-1-naphthylphosphino)ferrocenyl]-ethyl-di-tert-butylphosphine (0.651 g, 1.013 mmol). The reaction mixture was degassed with argon and hydrogen three times and then hydrogen was added (50 Psi). The resulting mixture in a 200 mL Mini-clave, was stirred at RT for 16 h followed by heating at 65° C. for 16 h. TLC indicated completion of reaction and that starting material was completely absent. The reaction was concentrated under reduced pressure providing the initial product which was purified by column chromatography (silica gel 60-120 mesh) using 40-45% of EtOAc in petroleum ether as eluent to obtain the title product, (2S,3R)-3-(5-chloropyridin-2-yl)butane-2-sulfonamide (Example 477.0) (9 g, 36.2 mmol, 89%), as a brownish solid in 82% ee. Recrystallization from i-PrOH yielded >97% ee material. $^1$H NMR (400 MHz, DMSO-d6) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (pos.) m/z: 249.0 (M+H)$^+$.

The compounds set forth in the following table were synthesized following the procedure in Example 395.31 using the known starting material as described.

TABLE 35

| Example | Reagents | Structure, Name and Data |
|---|---|---|
| 478.1 | 4h,5h,6h-pyrrolo[1,2-b]pyrazole-3-carboxylic acid (commercially available from Ark Pharm, Inc.). | 5,6-dihydro-4H-pyrrolo[1,2-b]pyrazole-3-carbohydrazidecarbohydrazide. LCMS-ESI (pos.) m/z: 167.0 (M + H)$^+$. |
| 489.1 | 1,4,5,6-tetrahydrocyclopenta[c]pyrazole-3-carbxylic acid (commercially available from Ark Pharm, Inc.). | 1,4,5,6-tetrahydrocyclopenta[c]pyrazole-3-carbohydrazide. LCMS-ESI (pos.) m/z: 167.0 (M + H)$^+$. |

TABLE 35-continued

| Example | Reagents | Structure, Name and Data |
|---|---|---|
| 499.1 | 1,5-dimethyl-1H-pyrazole-4-carboxylic acid (commercially available from Frontier Scientific Services, Inc.). | 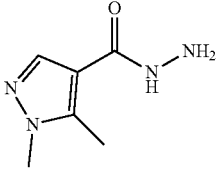<br>1,5-dimethyl-1H-pyrazole-4-carbohydrazide.<br>LCMS-ESI (pos.) m/z: 155.2 (M + H)+. |
| 501.1 | 5-isopropyl-1-methyl-1H-pyrazole-4-carboxylic acid (commercially available from Frontier Scientific Services, Inc.). | 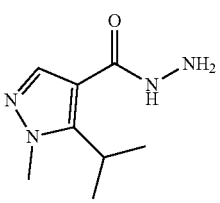<br>5-isopropyl-1-methyl-1H-pyrazole-4-carbohydrazide.<br>LCMS-ESI (pos.) m/z: 183.2 (M + H)+. |
| 512.1 | 1-methyl-4,5,6,7-tetrahydro-1H-indazole-3-carboxylic acid (commercially available from Frontier Scientific Services, Inc.). | 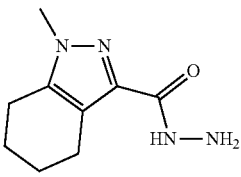<br>1-methyl-4,5,6,7-tetrahydro-1H-indazole-3-carbohydrazide.<br>LCMS-ESI (pos.) m/z: 195.2 (M + H)+. |
| 515.1 | 4,5-dimethylisoxazole-3-carboxylic acid (commercially available from Asta Tech Inc.) | 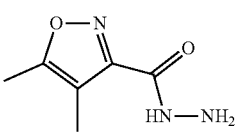<br>4,5-dimethylisoxazole-3-carbohydrazide.<br>LCMS-ESI (pos.) m/z: 156.2 (M + H)+. |
| 519.1 | 5-ethyl-4-methyl-1,2-oxazole-3-carboxylic acid (commercially available from Matrix Scientific Inc.). | 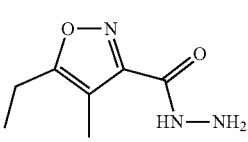<br>5-ethyl-4-methylisoxazole-3-carbohydrazide.<br>LCMS-ESI (pos.) m/z: 170.2 (M + H)+. |

The compounds set forth in the following table were synthesized following the procedure in Example 77.0 using the known starting material as described.

TABLE 36

478.0 5,6-dihydro-4H-pyrrolo[1,2-b]pyrazole-3-carbohydrazide (Example 478.1), isothiocyanatocyclopropane (commercially available from Aldrich), and (1R,2S)-1-methoxy-1-(5-chloropyrimidin-2-yl)propane-2-sulfonamide (Example 466.3).

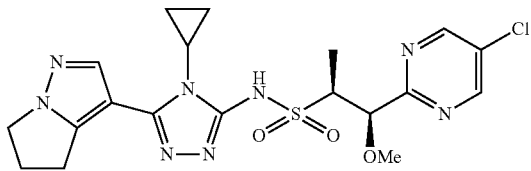 [SMILES: CO[C@H](c1ncc(Cl)cn1)[C@H](C)S(=O)(=O)Nc1nnc(-c2cnn3c2CCC3)n1C1CC1]

(1R,2S)-1-(5-chloropyrimidin-2-yl)-N-(4-cyclopropyl-5-(5,6-dihydro-4H-pyrrolo[1,2-b]pyrazol-3-yl)-4H-1,2,4-triazol-3-yl)-1-methoxypropane-2-sulfonamide.
$^1$H NMR (500 MHz, DMSO-d$_6$) δ 12.54-12.82 (m, 1 H) 8.84-8.97 (m, 2 H) 7.86-8.04 (m, 1 H) 4.87 (d, J = 4.5 Hz, 1 H) 4.08-4.24 (m, 2 H) 3.45-3.57 (m, 1 H) 3.09-3.14 (m, 3 H) 3.03-3.09 (m, 1 H) 2.96-3.01 (m, 2 H) 2.57-2.65 (m, 2 H) 1.28-1.32 (m, 3 H) 1.02-1.08 (m, 2 H) 0.85-0.91 (m, 1 H) 0.74-0.80 (m, 1 H). LCMS-ESI (pos.) m/z: 479.2 (M + H)$^+$.

479.0 5,6-dihydro-4H-pyrrolo[1,2-b]pyrazole-3-carbohydrazide (Example 478.1), isothiocyanato-1,3-dimethoxybenzene (Example 10.0), and (2S,3R)-3-(5-fluoropyrimidin-2-yl)butane-2-sulfonamide (Example 464.1).

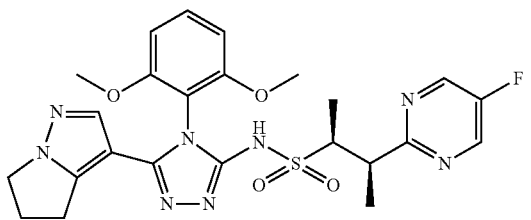 [SMILES: COc1cccc(OC)c1-n1c(NS(=O)(=O)[C@@H](C)[C@H](C)c2ncc(F)cn2)nnc1-c1cnn2c1CCC2]

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-fluoropyrimidin-2-yl)butane-2-sulfonamide.
$^1$H NMR (500 MHz, DMSO-d$_6$) δ 12.79-12.96 (m, 1 H) 8.76-8.84 (m, 2 H) 7.47-7.59 (m, 1 H) 6.83-6.95 (m, 2 H) 6.68-6.78 (m, 1 H) 3.99-4.08 (m, 2 H) 3.66-3.73 (m, 7 H) 3.49-3.59 (m, 1 H) 2.72-2.79 (m, 2 H) 2.51-2.57 (m, 2 H) 1.21-1.26 (m, 3 H) 1.07-1.12 (m, 3 H). LCMS-ESI (pos.) m/z: 543.2 (M + H)$^+$.

480.0 5,6-dihydro-4H-pyrrolo[1,2-b]pyrazole-3-carbohydrazide (Example 478.1), 5-isothiocyanato-4,6-dimethoxypyrimidine (Example 465.1), and (2S,3R)-3-(5-fluoropyrimidin-2-yl)butane-2-sulfonamide (Example 464.1).

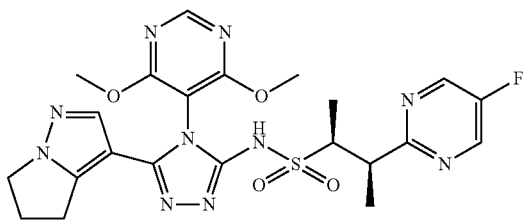 [SMILES: COc1ncnc(OC)c1-n1c(NS(=O)(=O)[C@@H](C)[C@H](C)c2ncc(F)cn2)nnc1-c1cnn2c1CCC2]

(2S,3R)-N-(5-(5,6-dihydro-4H-pyrrolo[1,2-b]pyrazol-3-yl)-4-(4,6-dimethoxypyrimidin-5-yl)-4H-1,2,4-triazol-3-yl)-3-(5-fluoropyrimidin-2-yl)butane-2-sulfonamide.
$^1$H NMR (500 MHz, DMSO-d$_6$) δ 13.02-13.23 (m, 1 H) 8.81-8.84 (m, 2 H) 8.71-8.75 (m, 1 H) 7.01-7.15 (m, 1 H) 4.03-4.14 (m, 2 H) 3.91 (s, 3 H) 3.90 (s, 3 H) 3.64-3.72 (m, 1 H) 3.55 (br dd, J = 6.9, 4.0 Hz, 1 H) 2.70-2.76 (m, 2 H) 2.52-2.59 (m, 2 H) 1.24 (d, J = 7.1 Hz, 3 H) 1.08-1.13 (m, 3 H). LCMS-ESI (pos.) m/z: 545.2 (M + H)$^+$.

TABLE 36-continued

| 481.0 | 5,6-dihydro-4H-pyrrolo[1,2-b]pyrazole-3-carbohydrazide (Example 478.1), 2-isothiocyanato-1,3-dimethoxypropane (Example 452.1), and (1R,2S)-1-methoxy-1-(5-chloropyrimidin-2-yl)propane-2-sulfonamide (Example 466.3). | 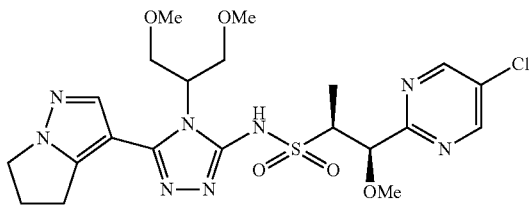 [SMILES: COCC(COC)n1c(NS(=O)(=O)[C@@H](C)[C@H](OC)c2ncc(Cl)cn2)nnc1-c1cnn2c1CCC2]<br>(2S,3R)-N-(5-(5,6-dihydro-4H-pyrrolo[1,2-b]pyrazol-3-yl)-4-(4,6-dimethoxypyrimidin-5-yl)-4H-1,2,4-triazol-3-yl)-3-(5-fluoropyrimidin-2-yl)butane-2-sulfonamide.<br>1H NMR (500 MHz, DMSO-$d_6$) δ 12.77-12.92 (m, 1 H) 8.90-8.99 (m, 2 H) 7.68-7.78 (m, 1 H) 4.95 (d, J = 3.9 Hz, 1 H) 4.44 (br d, J = 4.4 Hz, 1 H) 4.13-4.19 (m, 2 H) 4.04-4.12 (m, 2 H) 3.52-3.59 (m, 2 H) 3.44-3.51 (m, 1 H) 3.20-3.23 (m, 3 H) 3.18-3.20 (m, 3 H) 3.16-3.18 (m, 3 H) 2.89-2.94 (m, 2 H) 2.56-2.62 (m, 2 H) 1.25-1.29 (m, 3 H). LCMS-ESI (pos.) m/z: 541.2 (M + H)$^+$. |
| 482.0 | 5,6-dihydro-4H-pyrrolo[1,2-b]pyrazole-3-carbohydrazide (Example 478.1), isothiocyanato-1,3-dimethoxybenzene (Example 10.0),and (1S,2S)-1-(5-fluoropyrimidin-2-yl)-1-isopropoxypropane-2-sulfonamide (Example 482.1). | 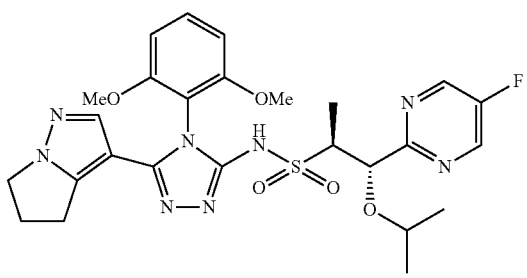 [SMILES: COc1cccc(OC)c1-n1c(NS(=O)(=O)[C@@H](C)[C@@H](OC(C)C)c2ncc(F)cn2)nnc1-c1cnn2c1CCC2]<br>(1S,2S)-N-(5-(5,6-dihydro-4H-pyrrolo[1,2-b]pyrazol-3-yl)-4-(2,6-dimethoxyphenyl)-4H-1,2,4-triazol-3-yl)-1-(5-fluoropyrimidin-2-yl)-1-isopropoxypropane-2-sulfonamide.<br>$^1$H NMR (400 MHz, DMSO-$d_6$) δ 12.74-12.85 (m, 1 H) 8.83-8.91 (m, 2 H) 7.46-7.65 (m, 1 H) 6.84-6.94 (m, 2 H) 6.71-6.79 (m, 1 H) 5.69-5.78 (m, 1 H) 4.76-4.82 (m, 1 H) 4.01-4.10 (m, 2 H) 3.74-3.75 (m, 3 H) 3.72-3.74 (m, 3 H) 3.36-3.46 (m, 2 H) 2.70-2.76 (m, 2 H) 0.98-1.02 (m, 3 H) 0.93-0.98 (m, 3 H) 0.81 (d, J = 6.1 Hz, 3 H). LCMS-ESI (pos.) m/z: 587.2 (M + H)$^+$. |
| 483.0 | 5,6-dihydro-4H-pyrrolo[1,2-b]pyrazole-3-carbohydrazide (Example 478.1), 1,3-difluoro-2-isothiocyanatobenzene (commercially available from Sigma Aldrich), and (2S,3R)-3-(5-methylpyrimidin-2-yl)butane-2-sulfonamide (Example 464.0). | 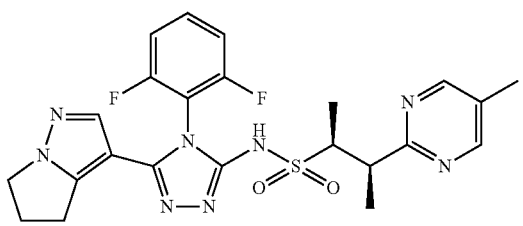 [SMILES: Cc1cnc([C@@H](C)[C@H](C)S(=O)(=O)Nc2nnc(-c3cnn4c3CCC4)n2-c2c(F)cccc2F)nc1]<br>(2S,3R)-N-(4-(2,6-difluorophenyl)-5-(5,6-dihydro-4H-pyrrolo[1,2-b]pyrazol-3-yl)-4H-1,2,4-triazol-3-yl)-3-(5-methylpyrimidin-2-yl)butane-2-sulfonamide.<br>$^1$H NMR (500 MHz, DMSO-$d_6$) δ 13.26-13.42 (m, 1 H) 8.56-8.57 (m, 2 H) 7.70-7.87 (m, 1 H) 7.43-7.53 (m, 2 H) 6.92-7.01 (m, 1 H) 5.70-5.78 (m, 1 H) 4.03-4.11 (m, 3 H) 3.59-3.67 (m, 2 H) 2.68-2.73 (m, 2 H) 2.51-2.55 (m, 2 H) 2.22-2.23 (m, 3 H) 1.20-1.23 (m, 3 H) 1.07-1.11 (m, 3 H). LCMS-ESI (pos.) m/z: 515.2 (M + H)$^+$. |

TABLE 36-continued 484.0  5,6-dihydro-4H-pyrrolo[1,2-b]pyrazole-3-carbohydrazide (Example 478.1), 1,3-difluoro-2-isothiocyanatobenzene (commercially available Sigma Aldrich), and (1S,2S)-1-isopropoxy-1-(5-methylpyrazin-2-yl)propane-2-sulfonamide (Example 468.6).

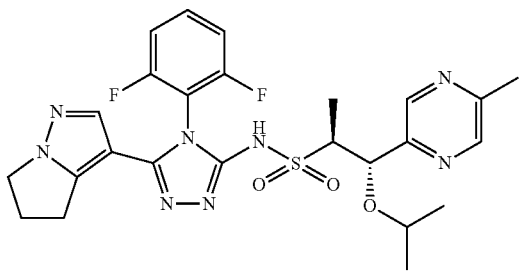 [SMILES: Cc1cnc([C@H](OC(C)C)[C@H](C)S(=O)(=O)Nc2nnc(-c3cnn4c3CCC4)n2-c2c(F)cccc2F)cn1]

(1S,2S)-N-(4-(2,6-difluorophenyl)-5-(5,6-dihydro-4H-pyrrolo[1,2-b]pyrazol-3-yl)-4H-1,2,4-triazol-3-yl)-1-isopropoxy-1-(5-methylpyrazin-2-yl)propane-2-sulfonamide.
$^1$H NMR (500 MHz, DMSO-d$_6$) δ 13.14-13.30 (m, 1 H) 8.38-8.50 (m, 2 H) 7.76-7.88 (m, 1 H) 7.45-7.55 (m, 2 H) 6.92-7.03 (m, 1 H) 4.73-4.79 (m, 1 H) 4.07-4.11 (m, 2 H) 3.44-3.51 (m, 1 H) 3.34-3.40 (m, 1 H) 2.67-2.72 (m, 2 H) 2.51-2.57 (m, 2 H) 2.47-2.49 (m, 3 H) 1.02-1.05 (m, 4 H) 0.97-1.01 (m, 3 H) 0.82-0.85 (m, 3 H). LCMS-ESI (pos.) m/z: 559.2 (M + H)$^+$.

485.0  5,6-dihydro-4H-pyrrolo[1,2-b]pyrazole-3-carbohydrazide (Example 478.1), isothiocyanato-1,3-dimethoxybenzene (Example 10.0), and (2S,3R)-3-(5-methoxypyrimidin-2-yl)butane-2-sulfonamide (Example 471.0).

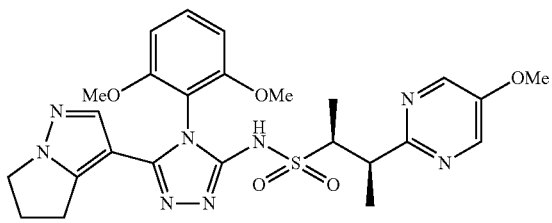 [SMILES: COc1cnc([C@@H](C)[C@H](C)S(=O)(=O)Nc2nnc(-c3cnn4c3CCC4)n2-c2c(OC)cccc2OC)nc1]

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methoxypyrimidin-2-yl)butane-2-sulfonamide.
$^1$H NMR (500 MHz, DMSO-d$_6$) δ 12.81-12.96 (m, 1 H) 8.43-8.53 (m, 2 H) 7.48-7.61 (m, 1 H) 6.79-6.91 (m, 2 H) 6.68-6.78 (m, 1 H) 4.00-4.09 (m, 2 H) 3.86-3.90 (m, 3 H) 3.67-3.71 (m, 6 H) 3.63-3.67 (m, 1 H) 3.50-3.57 (m, 1 H) 2.72-2.77 (m, 2 H) 2.51-2.56 (m, 2 H) 1.21-1.25 (m, 3 H) 1.05-1.09 (m, 3 H). LCMS-ESI (pos.) m/z: 555.2 (M + H)$^+$.

486.0  5,6-dihydro-4H-pyrrolo[1,2-b]pyrazole-3-carbohydrazide (Example 478.1), isothiocyanato-1,3-dimethoxybenzene (Example 10.0), and (2S,3R)-3-(5-methoxypyrazin-2-yl)butane-2-sulfonamide (Example 464.5).

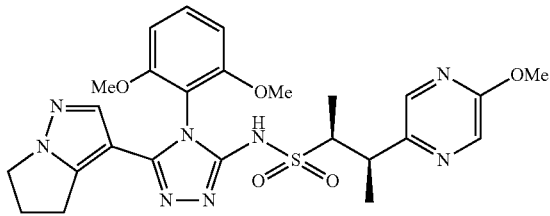 [SMILES: COc1cnc([C@@H](C)[C@H](C)S(=O)(=O)Nc2nnc(-c3cnn4c3CCC4)n2-c2c(OC)cccc2OC)cn1]

(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methoxypyrazin-2-yl)butane-2-sulfonamide.
$^1$H NMR (500 MHz, DMSO-d$_6$) δ 12.84-12.98 (m, 1 H) 8.16-8.28 (m, 1 H) 7.94-8.06 (m, 1 H) 7.50-7.66 (m, 1 H) 6.85-6.98 (m, 2 H) 6.68-6.79 (m, 1 H) 3.98-4.12 (m, 2 H) 3.85-3.90 (m, 3 H) 3.69-3.71 (m, 3 H) 3.67-3.69 (m, 3 H) 3.51-3.60 (m, 1 H) 3.23-3.27 (m, 1 H) 2.72-2.77 (m, 2 H) 2.51-2.57 (m, 2H) 1.19-1.25 (m, 3 H) 1.07-1.11 (m, 3 H). LCMS-ESI (pos.) m/z: 555.2 (M + H)$^+$.

TABLE 36-continued

| | | |
|---|---|---|
| 487.0 | 5,6-dihydro-4H-pyrrolo[1,2-b]pyrazole-3-carbohydrazide (Example 478.1), isothiocyanato-1,3-dimethoxybenzene (Example 10.0), and (2S,3R)-3-(5-methylpyrimidin-2-yl)butane-2-sulfonamide (Example 464.0). | 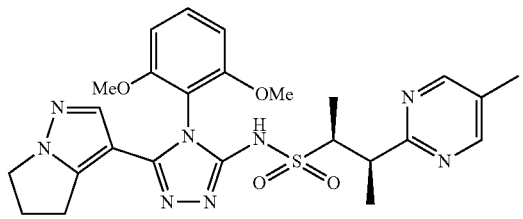 [SMILES: COc1cccc(OC)c1-n1c(NS(=O)(=O)[C@@H](C)[C@H](C)c2ncc(C)cn2)nnc1-c1cnn2c1CCC2]<br>(2S,3R)-N-(5-(5,6-dihydro-4H-pyrrolo[1,2-b]pyrazol-3-yl)-4-(2,6-dimethoxyphenyl)-4H-1,2,4-triazol-3-yl)-3-(5-methylpyrimidin-2-yl)butane-2-sulfonamide.<br>$^1$H NMR (500 MHz, DMSO-d$_6$) δ 12.81-12.94 (m, 1 H) 8.55-8.61 (m, 2 H) 7.49-7.61 (m, 1 H) 6.81-6.91 (m, 2 H) 6.71-6.75 (m, 1 H) 4.04 (t, J = 7.3 Hz, 2 H) 3.65-3.70 (m, 7 H) 3.54-3.62 (m, 1 H) 2.71-2.78 (m, 2 H) 2.51-2.57 (m, 2 H) 2.20-2.25 (m, 3 H) 1.21-1.24 (m, 3 H) 1.06-1.11 (m, 3 H). LCMS-ESI (pos. m/z: 539.2 (M + H)$^+$. |
| 488.0 | 5,6-dihydro-4H-pyrrolo[1,2-b]pyrazole-3-carbohydrazide (Example 478.1), isothiocyanato-1,3-dimethoxybenzene (Example 10.0), and (1R,2S)-1-methoxy-1-(5-chloropyrimidin-2-yl)propane-2-sulfonamide (Example 466.3). | 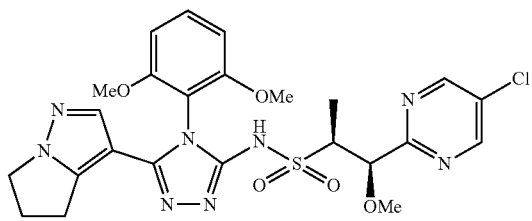 [SMILES: COc1cccc(OC)c1-n1c(NS(=O)(=O)[C@@H](C)[C@H](OC)c2ncc(Cl)cn2)nnc1-c1cnn2c1CCC2]<br>(1R,2S)-1-(5-chloropyrimidin-2-yl)-N-(5-(5,6-dihydro-4H-pyrrolo[1,2-b]pyrazol-3-yl)-4-(2,6-dimethoxyphenyl)-4H-1,2,4-triazol-3-yl)-1-methoxypropane-2-sulfonamide.<br>$^1$H NMR (500 MHz, DMSO-d$_6$) δ 12.77-12.90 (m, 1 H) 8.87-8.98 (m, 2 H) 7.45-7.66 (m, 1 H) 6.84-6.94 (m, 2 H) 6.68-6.78 (m, 1 H) 4.70-4.82 (m, 1 H) 4.01-4.08 (m, 2 H) 3.70-3.74 (m, 3 H) 3.68-3.70 (m, 3 H) 3.39-3.49 (m, 1 H) 3.15-3.18 (m, 3 H) 2.71-2.77 (m, 2 H) 2.51-2.56 (m, 2 H) 1.12-1.16 (m, 3 H). LCMS-ESI (pos. m/z: 575.0 (M + H)$^+$. |
| 489.0 | 1,4,5,6-tetrahydrocyclopenta[c]pyrazole-3-carbohydrazide (Example 489.1), 1-isothiocyanato-1-(methoxymethyl)cyclobutane (Example 489.2), and (1R,2S)-1-methoxy-1-(5-chloropyrimidin-2-yl)propane-2-sulfonamide (Example 466.3). | 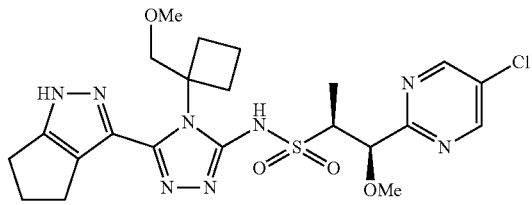 [SMILES: COCC1(n2c(NS(=O)(=O)[C@@H](C)[C@H](OC)c3ncc(Cl)cn3)nnc2-c2n[nH]c3c2CCC3)CCC1]<br>(1R,2S)-1-(5-chloropyrimidin-2-yl)-1-methoxy-N-(4-(1-(methoxymethyl)cyclobutyl)-5-(1,4,5,6-tetrahydrocyclopenta[c]pyrazol-3-yl)-4H-1,2,4-triazol-3-yl)propane-2-sulfonamide.<br>$^1$H NMR (500 MHz, CDCl$_3$) δ 8.68-8.85 (m, 2 H) 5.03-5.08 (m, 1 H) 3.97-4.02 (m, 2 H) 3.74-3.82 (m, 1 H) 3.40-3.44 (m, 3 H) 3.38-3.40 (m, 3 H) 3.04-3.12 (m, 2 H) 2.75-2.83 (m, 2 H) 2.56-2.71 (m, 6 H) 1.89 (br d, J = 1.8 Hz, 1 H) 1.81 (br dd, J = 12.5, 2.3 Hz, 1 H) 1.44-1.48 (m, 3 H). LCMS-ESI (pos. m/z: 537.2 (M + H)$^+$. |

TABLE 36-continued

| 490.0 | 1,4,5,6-tetrahydrocyclopenta[c]pyrazole-3-carbohydrazide (Example 489.1), 1-isothiocyanato-1-methylcyclopropane (commercially available from Frontier Scientific Services, Inc.), and (1R,2S)-1-methoxy-1-(5-chloropyrimidin-2-yl)propane-2-sulfonamide (Example 466.3). | 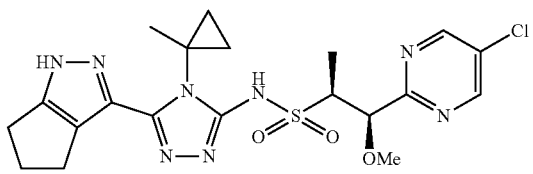 [SMILES: CO[C@H](c1ncc(Cl)cn1)[C@H](C)S(=O)(=O)Nc1nnc(-c2n[nH]c3c2CCC3)n1C1(C)CC1] (1R,2S)-1-(5-chloropyrimidin-2-yl)-1-methoxy-N-(4-(1-(methoxymethyl)cyclobutyl)-5-(1,4,5,6-tetrahydrocyclopenta[c]pyrazol-3-yl)-4H-1,2,4-triazol-3-yl)propane-2-sulfonamide. $^1$H NMR (500 MHz, DMSO-d$_6$) δ 12.90-13.09 (m, 1 H) 8.89-8.96 (m, 2 H) 4.91-5.00 (m, 1 H) 3.44-3.53 (m, 1 H) 3.07-3.10 (m, 3 H) 2.71-2.77 (m, 2 H) 2.60-2.66 (m, 2 H) 2.51-2.56 (m, 2 H) 1.52-1.59 (m, 3 H) 1.30 (d, J = 7.0 Hz, 3 H) 1.22-1.27 (m, 1 H) 0.84-0.92 (m, 3 H). LCMS-ESI (pos. m/z: 493.2 (M + H)$^+$. |
| --- | --- | --- |
| 491.0 | 4,5,6,7-tetrahydro-1H-indazole-3-carbohydrazide (commercially available from Frontier Scientific Services, Inc.), 1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 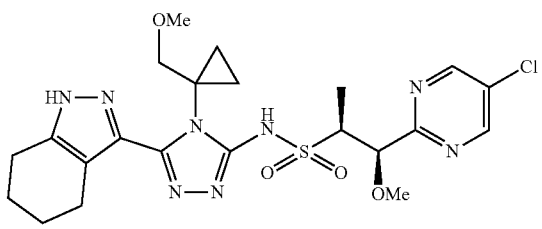 [SMILES: COCC1(n2c(NS(=O)(=O)[C@@H](C)[C@H](OC)c3ncc(Cl)cn3)nnc2-c2n[nH]c3c2CCCC3)CC1] (1R,2S)-1-(5-chloropyrimidin-2-yl)-1-methoxy-N-(4-(1-(methoxymethyl)cyclopropyl)-5-(4,5,6,7-tetrahydro-1H-indazol-3-yl)-4H-1,2,4-triazol-3-yl)propane-2-sulfonamide. $^1$H NMR (500 MHz, CDCl$_3$) δ 11.05-11.36 (m, 1 H) 8.65-8.84 (m, 2 H) 7.23-7.35 (m, 1 H) 5.08 (br d, J = 2.3 Hz, 1 H) 4.03 (br s, 1 H) 3.66-3.73 (m, 1 H) 3.60 (s, 3 H) 3.40 (br d, J = 14.3 Hz, 1 H) 3.32-3.37 (m, 3 H) 2.81 (br d, J = 7.1 Hz, 4 H) 2.53 (br s,5 H) 1.78-1.93 (m, 2 H) 1.38-1.44 (m, 3 H) 1.27 (br t, J = 7.0 Hz, 1 H) LCMS-ESI (pos. m/z: 537.2 (M + H)$^+$. |
| 492.0 | 1,4,5,6-tetrahydrocyclopenta[c]pyrazole-3-carbohydrazide (Example 489.1), 1-isothiocyanato-1-methylcyclobutane (commercially available from Ukrorgsyntez), and (1R,2S)-1-methoxy-1-(5-chloropyrimidin-2-yl)propane-2-sulfonamide (Example 466.3). | 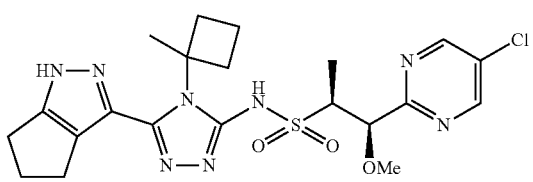 [SMILES: CO[C@H](c1ncc(Cl)cn1)[C@H](C)S(=O)(=O)Nc1nnc(-c2n[nH]c3c2CCC3)n1C1(C)CCC1] (1R,2S)-1-(5-chloropyrimidin-2-yl)-1-methoxy-N-(4-(1-methylcyclobutyl)-5-(1,4,5,6-tetrahydrocyclopenta[c]pyrazol-3-yl)-4H-1,2,4-triazol-3-yl)propane-2-sulfonamide. $^1$H NMR (500 MHz, DMSO-d$_6$) δ 12.59-13.05 (m, 2 H) 8.79-9.00 (m, 2 H) 4.83-5.00 (m, 1 H) 3.42-3.54 (m, 1 H) 3.09-3.17 (m, 3 H) 2.66-2.77 (m, 2 H) 2.58-2.65 (m, 2 H) 2.49-2.49 (m, 3 H) 2.18-2.31 (m, 2 H) 2.00-2.12 (m, 2 H) 1.71-1.75 (m, 3 H) 1.55-1.64 (m, 1 H) 1.25-1.31 (m, 3 H). LCMS-ESI (pos. m/z: 507.0 (M + H)$^+$. |

TABLE 36-continued

| | | |
|---|---|---|
| 493.0 | 1-methyl-1H-indazole-3-carbohydrazide (Example 395.40), 1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 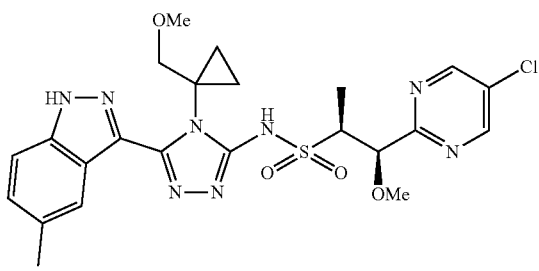 [SMILES: COCC1(n2c(NS(=O)(=O)[C@@H](C)[C@H](OC)c3ncc(Cl)cn3)nnc2-c2n[nH]c3ccc(C)cc23)CC1]<br>(1R,2S)-1-(5-chloropyrimidin-2-yl)-1-methoxy-N-(4-(1-(methoxymethyl)cyclopropyl)-5-(5-methyl-1H-indazol-3-yl)-4H-1,2,4-triazol-3-yl)propane-2-sulfonamide.<br>¹H NMR (500 MHz, DMSO-d₆) δ 13.60-13.75 (m, 1 H) 12.89-13.07 (m, 1 H) 8.91-8.99 (m, 2 H) 7.69-7.82 (m, 1 H) 7.46-7.63 (m, 1 H) 7.22-7.39 (m, 1 H) 4.97-5.03 (m, 1 H) 3.49-3.59 (m, 1 H) 3.30-3.32 (m, 3 H) 3.26-3.30 (m, 3 H) 3.15 (br s, 2 H) 2.41-2.46 (m, 3 H) 1.31-1.36(m, 3 H) 0.76-1.28 (m, 4 H). LCMS-ESI (pos. m/z: 547.0 (M + H)⁺. |
| 494.0 | 5-methyl-1H-indazole-3-carbohydrazide (Example 395.37), 1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 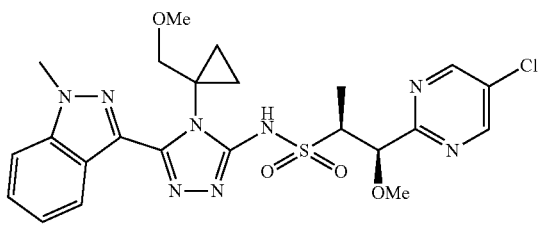 [SMILES: COCC1(n2c(NS(=O)(=O)[C@@H](C)[C@H](OC)c3ncc(Cl)cn3)nnc2-c2nn(C)c3ccccc23)CC1]<br>(1R,2S)-1-(5-chloropyrimidin-2-yl)-1-methoxy-N-(4-(1-(methoxymethyl)cyclopropyl)-5-(5-methyl-1H-indazol-3-yl)-4H-1,2,4-triazol-3-yl)propane-2-sulfonamide.<br>¹H NMR (500 MHz, DMSO-d₆) δ 12.96-13.15 (m, 1 H) 8.91-8.99 (m, 2 H) 8.00-8.08 (m, 1 H) 7.76-7.85 (m, 1 H) 7.44-7.58 (m, 1 H) 7.26-7.38 (m, 1 H) 4.96-5.04 (m, 1 H) 4.14-4.21 (m, 3 H) 3.54 (br s, 1 H) 3.29-3.34 (m, 6 H) 3.15 (br s,3 H) 1.29-1.34 (m, 3 H) 1.06-1.27 (m, 3 H). LCMS-ESI (pos. m/z: 547.0 (M + H)⁺. |
| 495.0 | 1H-indazole-3-carbohydrazide (Example 395.31), 1-1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 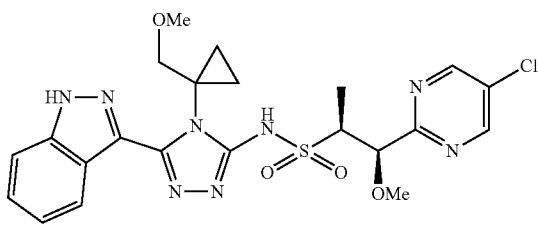 [SMILES: COCC1(n2c(NS(=O)(=O)[C@@H](C)[C@H](OC)c3ncc(Cl)cn3)nnc2-c2n[nH]c3ccccc23)CC1]<br>(1R,2S)-1-(5-chloro-2-pyrimidinyl)-N-(5-(1H-indazol-3-yl)-4-(1-(methoxymethyl)cyclopropyl)-4H-1,2,4-triazol-3-yl)-1-methoxy-2-propanesulfonamide.<br>¹H NMR (500 MHz, DMSO-d₆) δ 12.96-13.15 (m, 1 H) 8.91-8.99 (m, 2 H) 8.00-8.08 (m, 1 H) 7.76-7.85 (m, 1 H) 7.44-7.58 (m, 1 H) 7.26-7.38 (m, 1 H) 4.96-5.04 (m, 1 H) 4.14-4.21 (m, 3 H) 3.54 (br s, 1 H) 3.29-3.34 (m, 3 H) 3.15 (br s,3 H) 1.29-1.34 (m, 3 H) 1.06-1.27 (m, 3 H) LCMS-ESI (pos. m/z: 533.0 (M + H)⁺. |

| | | |
|---|---|---|
| 496.0 | 5-methylisoxazole-3-carbohydrazide (Frontier Scientific Services Inc.), isothiocyanato-1,3-dimethoxybenzene (Example 10.0), and (1R,2S)-1-methoxy-1-(5-chloropyrimidin-2-yl)propane-2-sulfonamide (Example 466.3). | 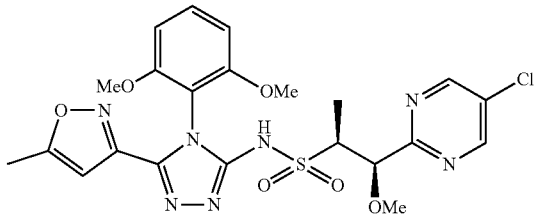 [SMILES: COc1cccc(OC)c1-n1c(NS(=O)(=O)[C@@H](C)[C@H](OC)c2ncc(Cl)cn2)nnc1-c1cc(C)on1] |
| | (1R,2S)-1-(5-chloropyrimidin-2-yl)-N-(4-(2,6-dimethoxyphenyl)-5-(5-methylisoxazol-3-yl)-4H-1,2,4-triazol-3-yl)-1-methoxypropane-2-sulfonamide. $^1$H NMR (500 MHz, DMSO-d$_6$) δ 13.43-13.62 (m, 1 H) 8.90-8.98 (m, 2 H) 7.37-7.56 (m, 1 H) 6.75-6.90 (m, 2 H) 6.44-6.65 (m, 1 H) 4.73-4.83 (m, 1 H) 3.69-3.72 (m, 3 H) 3.67-3.69 (m, 3 H) 3.39-3.48 (m, 1 H) 3.13-3.16 (m, 3 H) 2.38-2.41 (m, 3 H) 1.13-1.18 (m, 3 H). LCMS-ESI (pos. m/z: 550.0 (M + H)$^+$. | |
| 497.0 | 5-methylisoxazole-3-carbohydrazide (commercially available Frontier Scientific Services Inc.), isothiocyanato-1,3-dimethoxybenzene (Example 10.0), and (1S,2S)-1-isopropoxy-1-(5-methylpyrazin-2-yl)propane-2-sulfonamide (Example 468.6). | 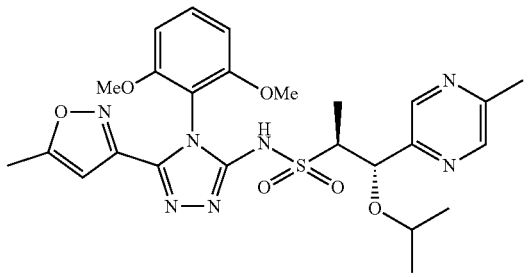 |
| | (1S,2S)-N-(4-(2,6-dimethoxyphenyl)-5-(5-methylisoxazol-3-yl)-4H-1,2,4-triazol-3-yl)-1-isopropoxy-1-(5-methylpyrazin-2-yl)propane-2-sulfonamide. $^1$H NMR (500 MHz, DMSO-d$_6$) δ 13.44-13.54 (m, 1 H) 8.38-8.53 (m, 2 H) 7.42-7.58 (m, 1 H) 6.76-6.90 (m, 2 H) 6.48-6.54 (m, 1 H) 4.68-4.81 (m, 1 H) 3.68-3.74 (m, 6 H) 3.35-3.51 (m, 2 H) 2.47-2.48 (m, 3 H) 2.39-2.43 (m, 3 H) 0.97-1.04 (m, 6 H) 0.82-0.88 (m, 3 H). LCMS-ESI (pos. m/z: 558.2 (M + H)$^+$. | |
| 498.0 | 5-methylisoxazole-3-carbohydrazide (commercially available from Frontier Scientific Services Inc.), isothiocyanato-1,3-dimethoxybenzene (Example 10.0), and (2S,3R)-3-(5-chloropyrimidin-2-yl)butane-2-sulfonamide (Example 464.4). | 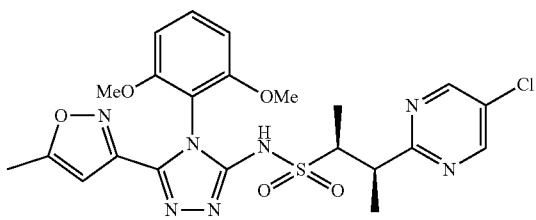 [SMILES: COc1cccc(OC)c1-n1c(NS(=O)(=O)[C@@H](C)[C@H](C)c2ncc(Cl)cn2)nnc1-c1cc(C)on1] |
| | (2S,3R)-3-(5-chloropyrimidin-2-yl)-N-(4-(2,6-dimethoxyphenyl)-5-(5-methylisoxazol-3-yl)-4H-1,2,4-triazol-3-yl)butane-2-sulfonamide. $^1$H NMR (600 MHz, DMSO-d$_6$) δ 13.38-13.74 (m, 1 H) 8.42-9.21 (m, 2 H) 7.28-7.60 (m, 1 H) 6.71-6.97 (m, 2 H) 6.42-6.65 (m, 1 H) 3.66-3.71 (m, 6 H) 3.61-3.66 (m, 1 H) 3.52-3.61 (m, 1 H) 2.37-2.42 (m, 3 H) 1.15-1.27 (m, 3 H) 1.07-1.14 (m, 3 H). LCMS-ESI (pos.) m/z: 534.2 (M + H)$^+$. | |

TABLE 36-continued

| 499.0 | 1,5-dimethyl-1H-pyrazole-4-carbohydrazide (Example 499.1), isothiocyanato-1,3-dimethoxybenzene (Example 10.0), and (1R,2S)-1-methoxy-1-(5-chloropyrimidin-2-yl)propane-2-sulfonamide (Example 466.3). | 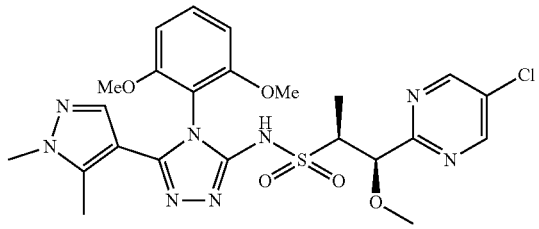 [SMILES: COc1cccc(OC)c1-n1c(NS(=O)(=O)[C@@H](C)[C@H](OC)c2ncc(Cl)cn2)nnc1-c1cnn(C)c1C] |

(1R,2S)-1-(5-chloropyrimidin-2-yl)-N-(4-(2,6-dimethoxyphenyl)-5-(1,5-dimethyl-1H-pyrazol-4-yl)-4H-1,2,4-triazol-3-yl)-1-methoxypropane-2-sulfonamide
$^1$H NMR (600 MHz, DMSO-d$_6$) δ 12.92-13.05 (m, 1 H) 8.88-8.95 (m, 2 H) 7.40-7.57 (m, 1 H) 6.79-6.92 (m, 2 H) 6.53-6.61 (m, 1 H) 4.76-4.82 (m, 1 H) 3.70-3.73 (m, 6 H) 3.68-3.70 (m, 3 H) 3.39-3.44 (m, 1 H) 3.13-3.16 (m, 3 H) 2.40-2.44 (m, 3 H) 1.11-1.16 (m, 3 H). LCMS-ESI (pos. m/z: 562.2 (M + H)$^+$.

| 501.0 | 5-isopropyl-1-methyl-1H-pyrazole-4-carbohydrazide (Example 501.1) isothiocyanato-1,3-dimethoxybenzene (Example 10.0), and (1R,2S)-1-methoxy-1-(5-chloropyrimidin-2-yl)propane-2-sulfonamide (Example 466.3). | 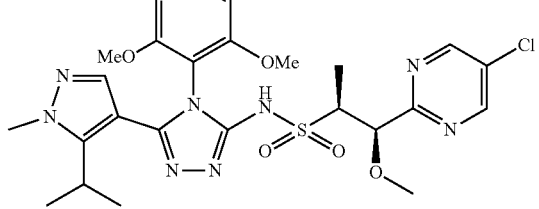 |

(1R,2S)-1-(5-chloropyrimidin-2-yl)-N-(4-(2,6-dimethoxyphenyl)-5-(5-isopropyl-1-methyl-1H-pyrazol-4-yl)-4H-1,2,4-triazol-3-yl)-1-methoxypropane-2-sulfonamide.
$^1$H NMR (500 MHz, DMSO-d$_6$) δ 12.82-13.03 (m, 1 H) 8.84-8.99 (m, 2 H) 7.35-7.48 (m, 1 H) 6.86-6.96 (m, 1 H) 6.73-6.83 (m, 2 H) 4.71-4.87 (m, 1 H) 3.75-3.79 (m, 3 H) 3.71-3.74 (m, 3 H) 3.69-3.71 (m, 3 H) 3.39-3.45 (m, 1 H) 3.26-3.31 (m, 1 H) 3.14-3.18 (m, 3 H) 1.20-1.26 (m, 6 H) 1.12-1.17 (m, 3 H). LCMS-ESI (pos. m/z: 591.2 (M + H)$^+$.

| 505.0 | benzo[d]isoxazole-3-carbohydrazide (Example 77.1), 1-1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 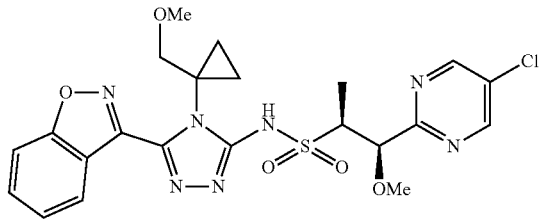 |

(1R,2S)-N-(5-(1,2-benzoxazol-3-yl)-4-(1-(methoxymethyl)cyclopropyl)-4H-1,2,4-triazol-3-yl)-1-(5-chloro-2-pyrimidinyl)-1-methoxy-2-propanesulfonamide.
$^1$H NMR (500 MHz, DMSO-d$_6$) δ 13.41-13.67 (m, 1 H) 8.93-8.99 (m, 2 H) 8.09-8.15 (m, 1 H) 7.93 (d, J = 8.6 Hz, 1 H) 7.76-7.83 (m, 1 H) 7.57 (t, J = 7.6 Hz, 1 H) 4.98-5.03 (m, 1 H) 3.69-3.83 (m, 1 H) 3.59-3.69 (m, 1 H) 3.53-3.59 (m, 1 H) 3.23-3.27 (m, 3 H) 3.11-3.20 (m, 3 H) 1.32-1.38 (m, 3 H) 1.18-1.32 (m, 4 H). LCMS-ESI (pos.) m/z: 534.0 (M + H)$^+$.

TABLE 36-continued

| 506.0 | benzo[d]isoxazole-3-carbohydrazide (Example 77.1), isothiocyanatocyclopropane (commercially available from Sigma Aldrich), and (1R,2S)-1-methoxy-1-(5-chloropyrimidin-2-yl)propane-2-sulfonamide (Example 466.3). | 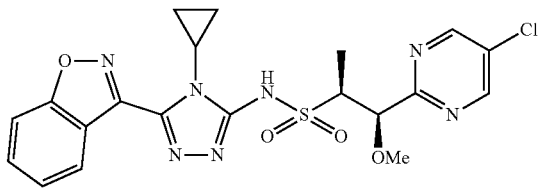 [SMILES: CO[C@H](c1ncc(Cl)cn1)[C@H](C)S(=O)(=O)Nc1nnc(-c2noc3ccccc23)n1C1CC1] |
|---|---|---|

(1R,2S)-N-(5-(benzo[d]isoxazol-3-yl)-4-cyclopropyl-4H-1,2,4-triazol-3-yl)-1-(5-chloropyrimidin-2-yl)-1-methoxypropane-2-sulfonamide.
$^1$H NMR (500 MHz, DMSO-d$_6$) δ 13.43-13.59 (m, 1 H) 8.82-8.97 (m, 2 H) 8.07-8.22 (m, 1 H) 7.89-8.00 (m, 1 H) 7.76-7.87 (m, 1 H) 7.50-7.60 (m, 1 H) 4.88-5.00 (m, 1 H) 3.53-3.68 (m, 1 H) 3.13-3.19 (m, 4H) 1.31-1.39 (m, 3 H) 1.05 (br d, J = 6.7 Hz, 4 H). LCMS-ESI (pos.) m/z: 490.2 (M + H)$^+$.

| 507.0 | pyrazolo[1,5-a]pyridine-3-carbohydrazide (Example 395.35), isothiocyanatocyclopropane (commercially available from Sigma Aldrich), and (1R,2S)-1-methoxy-1-(5-chloropyrimidin-2-yl)propane-2-sulfonamide (Example 466.3). | 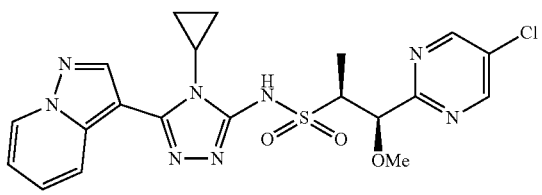 [SMILES: CO[C@H](c1ncc(Cl)cn1)[C@H](C)S(=O)(=O)Nc1nnc(-c2cnn3ccccc23)n1C1CC1] |
|---|---|---|

(1R,2S)-1-(5-chloropyrimidin-2-yl)-N-(4-cyclopropyl-5-(pyrazolo[1,5-a]pyridin-3-yl)-4H-1,2,4-triazol-3-yl)-1-methoxypropane-2-sulfonamide.
$^1$H NMR (500 MHz, DMSO-d$_6$) δ 12.74-12.89 (m, 1 H) 8.90-8.97 (m, 2 H) 8.85-8.90 (m, 1 H) 8.64-8.70 (m, 1 H) 8.04 (d, J = 8.8 Hz, 1 H) 7.48-7.56 (m, 1 H) 7.09-7.16 (m, 1 H) 4.87-4.93 (m, 1 H) 3.56 (dd, J = 6.9, 4.6 Hz, 1 H) 3.18-3.25 (m, 1 H) 3.11-3.16 (m, 3 H) 1.31-1.37 (m, 3 H) 1.04-1.14 (m, 2 H) 0.88-0.95 (m, 1 H) 0.75-0.81 (m, 1 H). LCMS-ESI (pos.) m/z: 489.0 (M + H)$^+$.

| 508.0 | pyrazolo[1,5-a]pyridine-3-carbohydrazide (Example 395.35), 1-isothiocyanato-1-(methoxymethyl)cyclobutane (Example 489.2), and (1R,2S)-1-methoxy-1-(5-chloropyrimidin-2-yl)propane-2-sulfonamide (Example 466.3). | 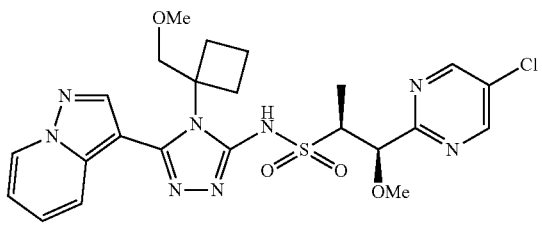 [SMILES: COCC1(n2c(NS(=O)(=O)[C@@H](C)[C@H](OC)c3ncc(Cl)cn3)nnc2-c2cnn3ccccc23)CCC1] |
|---|---|---|

(1R,2S)-1-(5-chloropyrimidin-2-yl)-1-methoxy-N-(4-(1-(methoxymethyl)cyclobutyl)-5-(pyrazolo[1,5-a]pyridin-3-yl)-4H-1,2,4-triazol-3-yl)propane-2-sulfonamide.
$^1$H NMR (500 MHz, DMSO-d$_6$) δ 12.82-13.09 (m, 1 H) 8.94-9.04 (m, 2 H) 8.74-8.90 (m, 1 H) 8.43 (s, 1 H) 7.71-7.81 (m, 1 H) 7.37-7.49 (m, 1 H) 6.98-7.09 (m, 1 H) 4.90-5.02 (m, 1 H) 3.86-3.99 (m, 2 H) 3.41-3.49 (m, 4 H) 3.16-3.20 (m, 3 H) 2.06-2.35 (m, 4 H) 1.70-1.82 (m, 1 H) 1.52-1.67 (m, 1 H) 1.29 (d, J = 7.0 Hz, 3 H). LCMS-ESI (pos.) m/z: 547.2 (M + H)$^+$.

TABLE 36-continued 509.0 pyrazolo[1,5-a]pyridine-3-carbohydrazide (Example 395.35), 1-1-isothiocyanato-1-(methoxymethyl)cyclopropane (Example 451.1), and (1R,2S)-1-methoxy-1-(5-chloropyrimidin-2-yl)propane-2-sulfonamide (Example 466.3).

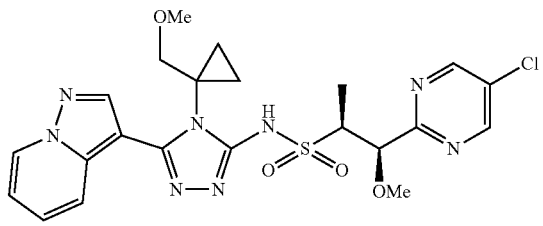 [SMILES: COCC1(n2c(NS(=O)(=O)[C@@H](C)[C@H](OC)c3ncc(Cl)cn3)nnc2-c2cnn3ccccc23)CC1]

(1R,2S)-1-(5-chloropyrimidin-2-yl)-1-methoxy-N-(4-(1-(methoxymethyl)cyclopropyl)-5-(pyrazolo[1,5-a]pyridin-3-yl)-4H-1,2,4-triazol-3-yl)propane-2-sulfonamide.
$^1$H NMR (500 MHz, DMSO-d$_6$) δ 12.77-13.03 (m, 1 H) 8.92-8.98 (m, 2 H) 8.80-8.86 (m, 2 H) 7.95-8.03 (m, 1 H) 7.45-7.53 (m, 1 H) 7.06-7.13 (m, 1 H) 4.97-5.03 (m, 1 H) 4.05-4.28 (m, 1 H) 3.42-3.53 (m, 1 H) 3.31 (m, 6 H) 3.04-3.28 (m, 4 H) 1.27-1.35 (m, 3 H) 0.86-0.93 (m, 1 H). LCMS-ESI (pos.) m/z: 533.2 (M + H)$^+$.

511.0 benzo[d]isoxazole-3-carbohydrazide (Example 77.1) isothiocyanatocyclopropane (commercially available from Sigma Aldrich), and (1R,2S)-1-methoxy-1-(5-chloropyrimidin-2-yl)propane-2-sulfonamide (Example 466.3).

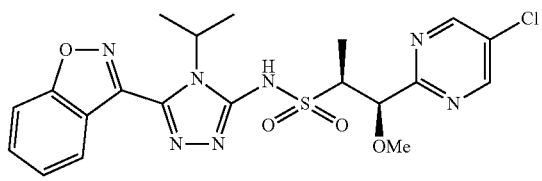 [SMILES: CO[C@H](c1ncc(Cl)cn1)[C@H](C)S(=O)(=O)Nc1nnc(-c2noc3ccccc23)n1C(C)C]

(1R,2S)-N-(5-(benzo[d]isoxazol-3-yl)-4-isopropyl-4H-1,2,4-triazol-3-yl)-1-(5-chloropyrimidin-2-yl)-1-methoxypropane-2-sulfonamide.
$^1$H NMR (600 MHz, DMSO-d$_6$) δ 13.34-13.80 (m, 1 H) 8.85-9.10 (m, 2 H) 8.11-8.25 (m, 1 H) 7.91-8.02 (m, 1 H) 7.78-7.86 (m, 1 H) 7.53-7.59 (m, 1 H) 5.18-5.35 (m, 1 H) 4.92-5.03 (m, 1 H) 3.52-3.67 (m, 1 H) 3.12-3.17 (m, 3 H) 1.52-1.59 (m, 6 H) 1.29-1.33 (m, 3 H). LCMS-ESI (pos.) m/z: 492.2 (M + H)$^+$.

512.0 1-methyl-4,5,6,7-tetrahydro-1H-indazole-3-carbohydrazide (Example 512.1) isothiocyanatocyclopropane (commercial available from Sigma Aldrich), and (1R,2S)-1-methoxy-1-(5-chloropyrimidin-2-yl)propane-2-sulfonamide (Example 466.3).

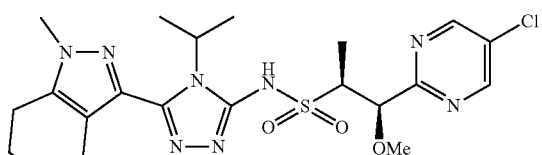

(1R,2S)-1-(5-chloropyrimidin-2-yl)-N-(4-isopropyl-5-(1-methyl-4,5,6,7-tetrahydro-1H-indazol-3-yl)-4H-1,2,4-triazol-3-yl)-1-methoxypropane-2-sulfonamide.
$^1$H NMR (400 MHz, DMSO-d$_6$) δ 12.70-12.99 (m, 1 H) 8.85-8.98 (m, 2 H) 5.09-5.33 (m, 1 H) 4.85-4.97 (m, 1 H) 3.70-3.81 (m, 3 H) 3.43-3.55 (m, 1 H) 3.09-3.17 (m, 3 H) 2.59-2.66 (m, 2 H) 2.52-2.58 (m, 2 H) 1.71-1.81 (m, 2 H) 1.62-1.71 (m, 2 H) 1.44-1.50 (m, 6H) 1.26-1.31 (m, 3 H). LCMS-ESI (pos.) m/z: 509.2 (M + H)$^+$.

TABLE 36-continued

| 513.0 | 1-methyl-4,5,6,7-tetrahydro-1H-indazole-3-carbohydrazide (Example 512.1) 1-1-isothiocyanato-1-(methoxymethyl)cyclopropane (Example 451.1), and (1R,2S)-1-methoxy-1-(5-chloropyrimidin-2-yl)propane-2-sulfonamide (Example 466.3). | 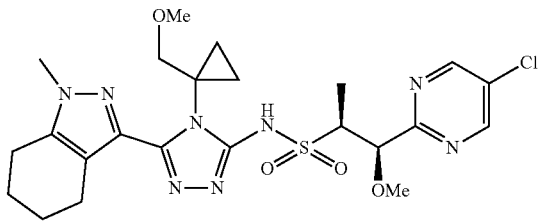 [SMILES: COCC1(n2c(NS(=O)(=O)[C@@H](C)[C@H](OC)c3ncc(Cl)cn3)nnc2-c2nn(C)c3c2CCCC3)CC1] |

(1R,2S)-1-(5-chloropyrimidin-2-yl)-1-methoxy-N-(4-(1-(methoxymethyl)cyclopropyl)-5-(1-methyl-4,5,6,7-tetrahydro-1H-indazol-3-yl)-4H-1,2,4-triazol-3-yl)propane-2-sulfonamide.
$^1$H NMR (400 MHz, DMSO-d$_6$) δ 12.67-12.91 (m, 1 H) 8.78-9.02 (m, 2 H) 5.69-5.80 (m, 1 H) 4.92-5.00 (m, 1 H) 3.74-3.79 (m, 3 H) 3.45-3.55 (m, 1 H) 3.31-3.34 (m, 3 H) 3.27-3.30 (m, 3 H) 3.05-3.18 (m, 3 H) 2.59-2.66 (m, 2 H) 1.71-1.80 (m, 2 H) 1.62-1.71 (m, 2 H) 1.25-1.32 (m, 3 H) 1.13-1.20 (m, 1 H) 0.89-1.13 (m, 3 H). LCMS-ESI (pos.) m/z: 551.2 (M + H)$^+$.

| 514.0 | 1-methyl-4,5,6,7-tetrahydro-1H-indazole-3-carbohydrazide (Example 512.1), 1-1-isothiocyanatocyclopropane (commercially available from Sigma Aldrich), and (1R,2S)-1-methoxy-1-(5-chloropyrimidin-2-yl)propane-2-sulfonamide (Example 466.3). | 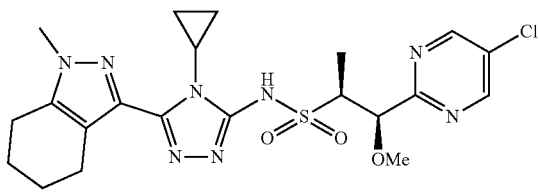 [SMILES: CO[C@H](c1ncc(Cl)cn1)[C@H](C)S(=O)(=O)Nc1nnc(-c2nn(C)c3c2CCCC3)n1C1CC1] |

(1R,2S)-1-(5-chloropyrimidin-2-yl)-N-(4-cyclopropyl-5-(1-methyl-4,5,6,7-tetrahydro-1H-indazol-3-yl)-4H-1,2,4-triazol-3-yl)-1-methoxypropane-2-sulfonamide.
$^1$H NMR (500 MHz, DMSO-d$_6$) δ 12.68-12.97 (m, 1 H) 8.84-9.03 (m, 2 H) 4.88 (d, J = 4.5 Hz, 1 H) 3.72-3.80 (m, 3 H) 3.46-3.57 (m, 1 H) 3.06-3.12 (m, 3 H) 3.00-3.06 (m, 1 H) 2.59-2.67 (m, 2 H) 2.51-2.55 (m, 2 H) 1.72-1.82 (m, 2 H) 1.61-1.72 (m, 2 H) 1.26-1.33 (m, 3 H) 0.82-1.00 (m, 3 H) 0.70-0.80 (m, 1 H). LCMS-ESI (pos.) m/z: 507.2 (M + H)$^+$.

| 515.0 | 4,5-dimethylisoxazole-3-carbohydrazide (Example 515.1), isothiocyanato-1,3-dimethoxybenzene (Example 10.0), and (1R,2S)-1-methoxy-1-(5-chloropydin-2-yl)propane-2-sulfonamide (Example 466.3). | 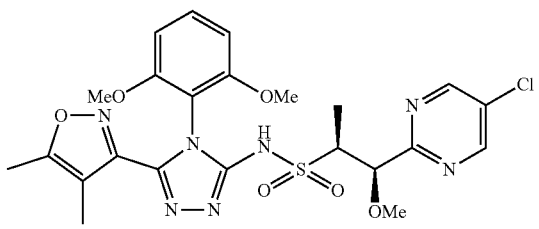 [SMILES: COc1cccc(OC)c1-n1c(NS(=O)(=O)[C@@H](C)[C@H](OC)c2ncc(Cl)cn2)nnc1-c1noc(C)c1C] |

(1R,2S)-1-(5-chloropyrimidin-2-yl)-N-(4-(2,6-dimethoxyphenyl)-5-(4,5-dimethylisoxazol-3-yl)-4H-1,2,4-triazol-3-yl)-1-methoxypropane-2-sulfonamide.
$^1$H NMR (500 MHz, DMSO-d$_6$) δ 13.43-13.52 (m, 1 H) 8.81-9.00 (m, 2 H) 7.32-7.53 (m, 1 H) 6.70-6.84 (m, 2 H) 4.73-4.92 (m, 1 H) 3.67-3.70 (m, 3 H) 3.66-3.67 (m, 3 H) 3.37-3.47 (m, 1 H) 3.13-3.17 (m, 3 H) 2.32-2.34 (m, 3 H) 2.05-2.09 (m, 3 H) 1.13-1.18 (m, 3 H). LCMS-ESI (pos.) m/z: 564.0 (M + H)$^+$.

TABLE 36-continued 516.0 4,5-dimethylisoxazole-3-carbohydrazide (Example 515.1), isothiocyanato-1,3-dimethoxybenzene (Example 10.0), and (1R,2S)-1-methoxy-1-(5-methylpyrimidin-2-yl) propane-2-sulfonamide (Example 466.0).

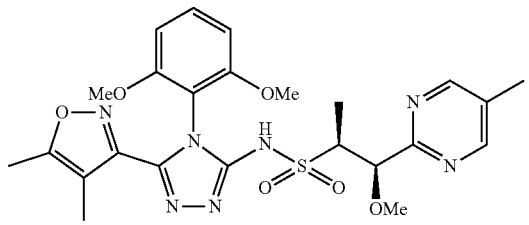

(1R,2S)-1-(5-chloropyrimidin-2-yl)-N-(4-(2,6-dimethoxyphenyl)-5-(4,5-dimethylisoxazol-3-yl)-4H-1,2,4-triazol-3-yl)-1-methoxypropane-2-sulfonamide.
$^1$H NMR (500 MHz, DMSO-$d_6$) δ 13.46-13.65 (m, 1 H) 8.45-8.58 (m, 1 H) 8.35-8.45 (m, 1 H) 7.35-7.49 (m, 1 H) 6.65-6.84 (m, 2 H) 4.76-4.93 (m, 1 H) 3.66-3.68 (m, 3 H) 3.64-3.66 (m, 3 H) 3.25-3.30 (m, 1 H) 3.17-3.20 (m, 3 H) 2.50-2.52 (m, 3 H) 2.31-2.35 (m, 3 H) 2.04-2.10 (m, 3 H) 1.03-1.09 (m, 3 H). LCMS-ESI (pos.) m/z: 544.2 (M + H)$^+$.

517.0 4,5-dimethylisoxazole-3-carbohydrazide (Example 515.1), isothiocyanato-1,3-dimethoxybenzene (Example 10.0), and (1S,2S)-1-isopropoxy-1-(5-methylpyrimidin-2-yl)propane-2-sulfonamide (Example 468.0).

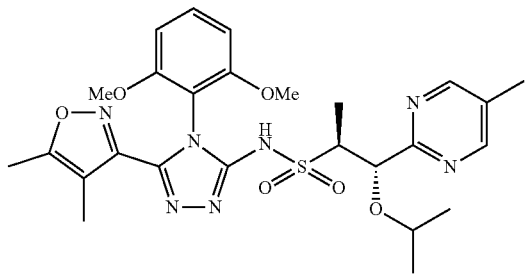

(1S,2S)-N-(4-(2,6-dimethoxyphenyl)-5-(4,5-dimethylisoxazol-3-yl)-4H-1,2,4-triazol-3-yl)-1-isopropoxy-1-(5-methylpyrimidin-2-yl)propane-2-sulfonamide.
$^1$H NMR (500 MHz, DMSO-$d_6$) δ 13.38-13.54 (m, 1 H) 8.60-8.75 (m, 2 H) 7.34-7.51 (m, 1 H) 6.71-6.88 (m, 2 H) 4.61-4.74 (m, 1 H) 3.64-3.74 (m, 6 H) 3.35-3.50 (m, 2 H) 2.31-2.36(m, 3 H) 2.22-2.31 (m, 3 H) 2.04-2.09 (m, 3 H) 1.95-2.01 (m, 1 H) 0.96-1.00 (m, 3 H) 0.91-0.96 (m, 3 H) 0.75-0.82 (m, 3 H). LCMS-ESI (pos.) m/z: 572.2 (M + H)$^+$.

518.0 1-methyl-4,5,6,7-tetrahydro-1H-indazole-3-carbohydrazide (Example 512.1), 1-1-1-isothiocyanato-1-(methoxymethyl)cyclobutane (Example 489.2), and (1R,2S)-1-methoxy-1-(5-chloropyrimidin-2-yl)propane-2-sulfonamide (Example 466.3).

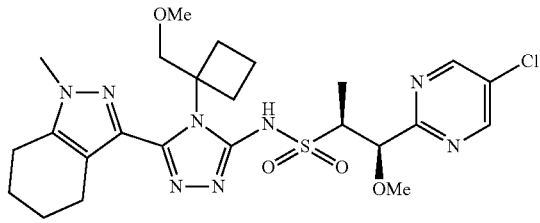 [SMILES: COCC1(n2c(NS(=O)(=O)[C@@H](C)[C@H](OC)c3ncc(Cl)cn3)nnc2-c2nn(C)c3c2CCCC3)CCC1]

(1R,2S)-1-(5-chloropyrimidin-2-yl)-1-methoxy-N-(4-(1-(methoxymethyp)cyclobutyl)-5-(1-methyl-4,5,6,7-tetrahydro-1H-indazol-3-yl)-4H-1,2,4-triazol-3-yl)propane-2-sulfonamide.
$^1$H NMR (500 MHz, DMSO-$d_6$) δ 12.79-12.87 (m, 1 H) 8.89-8.95 (m, 2 H) 4.89-4.98 (m, 1 H) 3.81-3.93 (m, 2 H) 3.68-3.80 (m, 3 H) 3.34-3.36 (m, 3 H) 3.13-3.17 (m, 3 H) 2.59-2.63 (m, 2 H) 2.51-2.54 (m, 2 H) 2.12-2.33 (m, 4 H) 1.54-1.80 (m, 7 H) 1.26-1.30 (m, 3 H). LCMS-ESI (pos.) m/z: 565.1 (M + H)$^+$.

TABLE 36-continued

| 519.0 | 5-ethyl-4-methylisoxazole-3-carbohydrazide (Example 519.1), isothiocyanato-1,3-dimethoxybenzene (Example 10.0), and (1R,2S)-1-methoxy-1-(5-chloropyrimidin-2-yl)propane-2-sulfonamide (Example 466.3). | 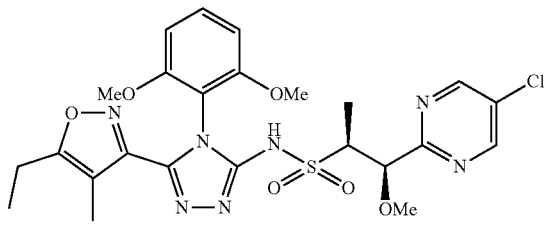 [SMILES: CCc1onc(-c2nnc(NS(=O)(=O)[C@@H](C)[C@H](OC)c3ncc(Cl)cn3)n2-c2c(OC)cccc2OC)c1C] |
|---|---|---|
| | (1R,2S)-1-(5-chloropyrimidin-2-yl)-N-(4-(2,6-dimethoxyphenyl)-5-(4,5-dimethylisoxazol-3-yl)-4H-1,2,4-triazol-3-yl)-1-methoxypropane-2-sulfonamide. $^1$H NMR (500 MHz, DMSO-$d_6$) δ 13.40-13.56 (m, 1 H) 8.86-8.98 (m, 2 H) 7.38-7.50 (m, 1 H) 6.71-6.84 (m, 2 H) 4.75-4.82 (m, 1 H) 3.67-3.69 (m, 3 H) 3.64-3.67 (m, 3 H) 3.40-3.47 (m, 1 H) 3.12-3.16 (m, 3 H) 2.69-2.77 (m, 2 H) 2.06-2.11 (m, 3 H) 1.11-1.18 (m, 6H). LCMS-ESI (pos.) m/z: 578.0 (M + H)$^+$. | |
| 523.0 | 4,5-dimethylisoxazole-3-carbohydrazide (Example 523.1), isothiocyanato-1,3-dimethoxybenzene (Example 10.0), and (1R,2S)-1-methoxy-1-(5-chloropyrimidin-2-yl)propane-2-sulfonamide (Example 466.3). | 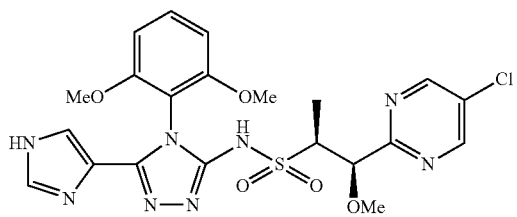 [SMILES: COc1cccc(OC)c1-n1c(NS(=O)(=O)[C@@H](C)[C@H](OC)c2ncc(Cl)cn2)nnc1-c1c[nH]cn1] |
| | (1R,2S)-1-(5-chloropyrimidin-2-yl)-N-(4-(2,6-dimethoxyphenyl)-5-(1H-imidazol-4-yl)-4H-1,2,4-triazol-3-yl)-1-methoxypropane-2-sulfonamide. $^1$H NMR (500 MHz, DMSO-$d_6$) δ 13.43-13.52 (m, 1 H) 8.81-9.00 (m, 4 H) 7.32-7.53 (m, 1 H) 6.70-6.84 (m, 2 H) 4.73-4.92 (m, 1 H) 3.67-3.70 (m, 3 H) 3.66-3.67 (m, 3 H) 3.37-3.47 (m, 1 H) 3.13-3.17 (m, 3 H) 1.13-1.18 (m, 3 H). LCMS-ESI (pos.) m/z: 535.0 (M + H)$^+$. | |

The compounds set forth in the following table were synthesized following the procedure in Example 77.0 using the known starting material as described.

TABLE 37

| 531.0 | (R)-2-isothiocyanato-1-methoxypropane (Example 531.1), 1-methyl-1H-pyrazole-3-carbohydrazide (commercially available from ChemBridge Corporation), and (1R,2S)-1-(5-chloropyrimidin-2-yl)-1-methoxypropane-2-sulfonamide (Example 466.3). | 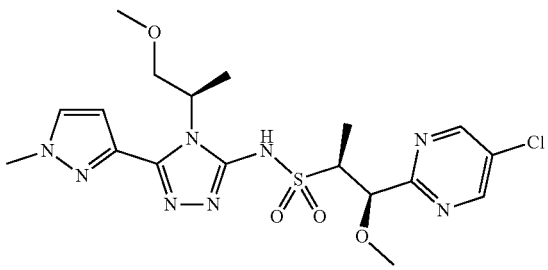 [SMILES: COC[C@@H](C)n1c(NS(=O)(=O)[C@@H](C)[C@H](OC)c2ncc(Cl)cn2)nnc1-c1ccn(C)n1] |
|---|---|---|
| | (1R,2S)-1-(5-chloro-2-pyrimidinyl)-1-methoxy-N-(4-((2R)-1-methoxy-2-propanyl)-5-(1-methyl-1H-pyrazol-3-yl)-4H-1,2,4-triazol-3-yl)-2-propanesulfonamide. $^1$H NMR (600 MHz, DMSO-$d_6$) δ 12.99 (s, 1H) 8.96 (s, 1H) 7.90 (d, J = 2.18 Hz, 1H), 6.69 (d, J = 2.26 Hz, 1H) 5.35 (br d, J = 0.70 Hz, 1H) 4.94 (d, J = 4.05 Hz, 1H) 4.11 (br t, J = 9.69 Hz, 1H) 3.94 (s, 3H), 3.48 (dd, J = 10.00, 5.10 Hz, 2H) 3.15 (d, J = 7.01 Hz, 6H) 1.45 (d, J = 7.01 Hz, 3H) 1.28 (d, J = 7.01 Hz, 3H). LCMS-ESI (pos.) m/z: 485.2 (M + H)$^+$. | |

TABLE 37-continued

| | | |
|---|---|---|
| 532.0 | cyclopropyl isothiocyanate (commercially available from Sigma Aldrich), 1-methyl-1H-pyrazole-3-carbohydrazide (commercially available from ChemBridge Corporation), and (1S,2S)-1-(5-chloropyrimidin-2-yl)-1-isopropoxypropane-2-sulfonamide (Example 468.1). | 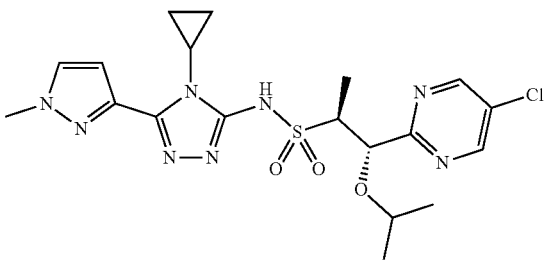 [SMILES: CC(C)O[C@@H](c1ncc(Cl)cn1)[C@H](C)S(=O)(=O)Nc1nnc(-c2ccn(C)n2)n1C1CC1] |

(1S,2S)-1-(5-chloro-2-pyrimidinyl)-N-(4-cyclopropyl-5-(1-methyl-1H-pyrazol-3-yl)-4H-1,2,4-triazol-3-yl)-1-(2-propanyloxy)-2-propanesulfonamide.
$^1$H NMR (600 MHz, DMSO-d$_6$) δ 12.69 (s, 1H) 8.96 (s, 2H) 7.89 (d, J = 2.18 Hz, 1H) 6.73 (d, J = 2.26 Hz, 1H) 4.87 (d, J = 7.40 Hz, 1H), 3.94 (s, 3H) 3.57 (quin, J = 7.18 Hz, 1H) 3.30 (dt, J = 12.20, 6.08 Hz, 1H) 3.06-3.12 (m, 1H) 1.07 (d, J = 7.16 Hz, 3H) 0.93-1.05 (m, 7 H) 0.67 (d, J = 6.15 Hz, 3H). LCMS-ESI (pos.) m/z: 481.2 (M + H)$^+$.

| | | |
|---|---|---|
| 533.0 | (S)-2-isothiocyanato-1-methoxypropane (Example 533.1), 1-methyl-1H-pyrazole-3-carbohydrazide (commercially available from ChemBridge Corporation), and (2S,3R)-3-(5-chloropyrimidin-2-yl)butane-2-sulfonamide (Example 464.4). | 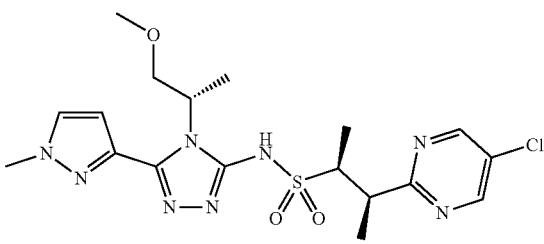 [SMILES: COC[C@H](C)n1c(NS(=O)(=O)[C@@H](C)[C@H](C)c2ncc(Cl)cn2)nnc1-c1ccn(C)n1] |

(2S,3R)-3-(5-chloro-2-pyrimidinyl)-N-(4-((2S)-1-methoxy-2-propanyl)-5-(1-methyl-1H-pyrazol-3-yl)-4H-1,2,4-triazol-3-yl)-2-butanesulfonamide.
$^1$H NMR (400 MHz, CDCl$_3$) δ 11.00 (br s, 1H) 8.64 (s, 2H) 7.45 (d, J = 2.18 Hz, 1H), 6.76 (d, J = 2.18 Hz, 1H) 5.34-5.48 (m, 1H) 4.25 (t, J = 9.59 Hz, 1H) 3.99 (s, 3H) 3.90 (quin, J = 6.76 Hz, 1H), 3.81 (quin, J = 6.82 Hz, 1H) 3.56 (dd, J = 10.00, 5.44 Hz, 1H), 3.28 (s, 3H) 1.56 (d, J = 6.95 Hz, 3H), 1.45 (app. d, J = 6.95 Hz, 6H). LCMS-ESI (pos.) m/z: 469.0 (M + H)$^+$.

| | | |
|---|---|---|
| 534.0 | 5-isothiocyanato-4,6-dimethoxypyrimidine (Example 465.1), 1-methyl-1H-pyrazole-3-carbohydrazide (commercially available from ChemBridge Corporation), and (2S,3R)-3-(5-chloropyridin-2-yl)butane-2-ulfonamide (Example 477.0). | 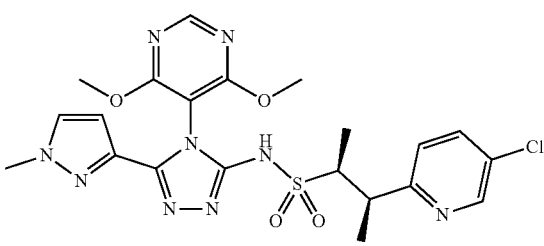 [SMILES: COc1ncnc(OC)c1-n1c(NS(=O)(=O)[C@@H](C)[C@H](C)c2ccc(Cl)cn2)nnc1-c1ccn(C)n1] |

(2S,3R)-3-(5-chloro-2-pyridinyl)-N-(4-(4,6-dimethoxy-5-pyrimidinyl)-5-(1-methyl-1H-pyrazol-3-yl)-4H-1,2,4-triazol-3-yl)-2-butanesulfonamide.
$^1$H NMR (600 MHz, DMSO-d$_6$) δ 13.35 (s, 1H) 8.67 (s, 1H) 8.55 (d, J = 2.26 Hz, 1H) 7.86 (dd, J = 8.45, 2.61 Hz, 1H) 7.79 (d, J = 2.26 Hz, 1H) 7.30 (d, J = 8.41 Hz, 1H) 6.62 (d, J = 2.34 Hz, 1H) 3.85 (s, 3H) 3.85 (s, 3H) 3.67 (s, 3H) 3.60 (qd, J = 7.06, 3.35 Hz, 1H) 3.38-3.45 (m, 1H) 1.23 (d, J = 7.16 Hz, 3H) 1.09 (d, J = 7.01 Hz, 3H). LCMS-ESI (pos.) m/z: 534.2 (M + H)$^+$.

TABLE 37-continued

| | | |
|---|---|---|
| 535.0 | 5-isothiocyanato-4,6-dimethoxypyrimidine (Example 465.1), 1-methyl-1H-pyrazole-4-carbohydrazide (commercially available from Enamine), and (2S,3R)-3-(5-chloropyridin-2-yl)butane-2-ulfonamide (Example 477.0). | 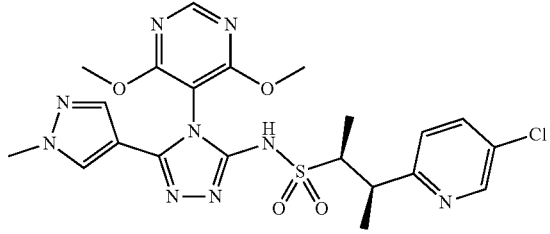 [SMILES: COc1ncnc(OC)c1-n1c(NS(=O)(=O)[C@@H](C)[C@H](C)c2ccc(Cl)cn2)nnc1-c1cnn(C)c1] |

(2S,3R)-3-(5-chloro-2-pyridinyl)-N-(4-(4,6-dimethoxy-5-pyrimidinyl)-5-(1-methyl-1H-pyrazol-4-yl)-4H-1,2,4-triazol-3-yl)-2-butanesulfonamide.
$^1$H NMR (600 MHz, DMSO-d$_6$) δ 13.24 (s, 1H) 8.74 (s, 1H) 8.55 (d, J = 2.34 Hz, 1H) 7.86 (dd, J = 8.41, 2.57 Hz, 1H) 7.82 (s, 1H) 7.47 (s, 1H) 7.29 (d, J = 8.41 Hz, 1H) 3.90 (s, 3H) 3.90 (s, 3H) 3.81 (s, 3H 3.57 (qd, J = 7.03, 3.43 Hz, 1H) 3.30-3.43 (m, 1H) 1.21 (d, J = 7.08 Hz, 3H) 1.07 (d, J = 7.08 Hz, 3H). LCMS-ESI (pos.) m/z: 534.0 (M + H)$^+$.

| | | |
|---|---|---|
| 536.0 | cyclopropyl isothiocyanate (commercially available from Sigma Aldrich), 1-methyl-1H-pyrazole-4-carbohydrazide (commercially available from Enamine), and (1S,2S)-1-(5-chloropyrimidin-2-yl)-1-isopropoxypropane-2-sulfonamide (Example 468.1). | 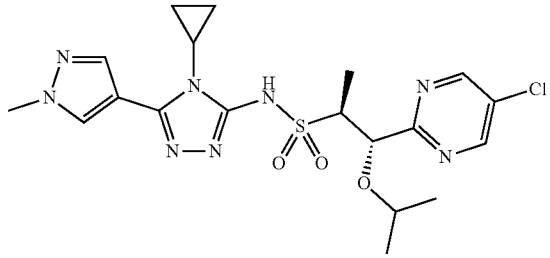 [SMILES: CC(C)O[C@@H](c1ncc(Cl)cn1)[C@H](C)S(=O)(=O)Nc1nnc(-c2cnn(C)c2)n1C1CC1] |

(1S,2S)-1-(5-chloro-2-pyrimidinyl)-N-(4-cyclopropyl-5-(1-methyl-1H-pyrazol-4-yl)-4H-1,2,4-triazol-3-yl)-1-(2-propanyloxy)-2-propanesulfonamide.
$^1$H NMR (600 MHz, DMSO-d$_6$) δ 12.53 (br s, 1H) 8.95 (s, 2H) 8.35 (s, 1H) 7.94 (s, 1H) 4.87 (d, J = 7.40 Hz, 1H) 3.93 (s, 3H) 3.52 -3.61 (m, 1H) 3.27-3.37 (m, 1H) 3.09 (tt, J = 7.01, 3.66 Hz, 1H) 1.01-1.17 (m, 7H) 0.98 (d, J = 6.07 Hz, 3H) 0.67 (d, J = 6.15 Hz, 3H). LCMS-ESI (pos.) m/z: 481.2 (M + H)$^+$.

| | | |
|---|---|---|
| 537.0 | 2-isothiocyanatopropane (commercially available from Sigma Aldrich), 1-methyl-1H-pyrazole-3-carbohydrazide (commercially available from ChemBridge Corporation), and (1S,2S)-1-(5-chloropyrimidin-2-yl)-1-isopropoxypropane-2-sulfonamide (Example 468.1). | 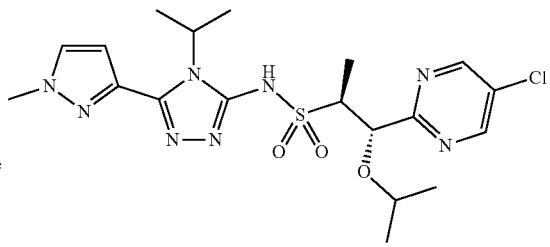 |

(1S,2S)-1-(5-chloro-2-pyrimidinyl)-N-(5-(1-methyl-1H-pyrazol-3-yl)-4-(2-propanyl)-4H-1,2,4-triazol-3-yl)-1-(2-propanyloxy)-2-propanesulfonamide.
$^1$H NMR (400 MHz, CDCl$_3$) δ 11.56 (s, 1H) 8.73 (s, 2H) 7.46 (d, J = 2.28 Hz, 1H) 6.71 (d, J = 2.28 Hz, 1H) 5.30 (m, 1H) 4.96 (d, J = 4.15 Hz, 1H) 4.01 (s, 3H) 3.85 (qd, J = 7.00, 4.30 Hz, 1H) 3.51-3.62 (m, 1H) 1.61 (d, J = 4.04 Hz, 3H) 1.59 (d, J = 3.94 Hz, 3H) 1.55 (d, J = 7.05 Hz, 3H) 1.10 (d, J = 6.01 Hz, 3H) 0.93 (d, J = 6.12 Hz, 3H). LCMS-ESI (pos.) m/z: 483.2 (M + H)$^+$.

TABLE 37-continued

| 538.0 | 1-isothiocyanato-1-methylcyclopropane (Example 465.1), 1-methyl-1H-pyrazole-3-carbohydrazide (commercially available from ChemBridge Corporation), and (1S,2S)-1-(5-chloropyrimidin-2-yl)-1-isopropoxypropane-2-sulfonamide (Example 468.1). | 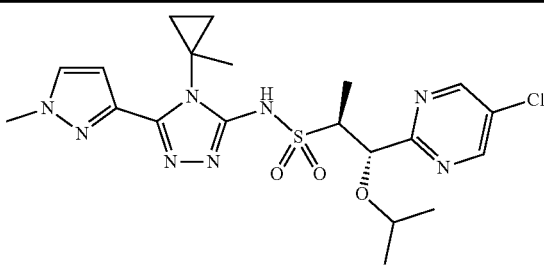<br>(1S,2S)-1-(5-chloro-2-pyrimidinyl)-N-(4-(1-methylcyclopropyl)-5-(1-methyl-1H-pyrazol-3-yl)-4H-1,2,4-triazol-3-yl)-1-(2-propanyloxy)-2-propanesulfonamide<br><br>$^1$H NMR (400 MHz, CDCl$_3$) δ 11.43 (br s, 1H) 8.72 (s, 2H) 7.48 (d, J = 2.28 Hz, 1H) 6.72 (d, J = 2.28 Hz, 1H) 4.95 (d, J = 4.46 Hz, 1H) 4.03 (s, 3H) 3.88 (qd, J = 7.03, 4.51 Hz, 1H) 3.46-3.59 (m, 1H) 1.67 (s, 3H) 1.53-1.63 (m, 7H) 1.08 (d, J = 6.01 Hz, 3H) 0.86 (d, J = 6.22 Hz, 3H). LCMS-ESI (pos.) m/z: 495.2 (M + H)$^+$. |

Example 531.1. Preparation of (R)-2-isothiocyanato-1-methoxypropane

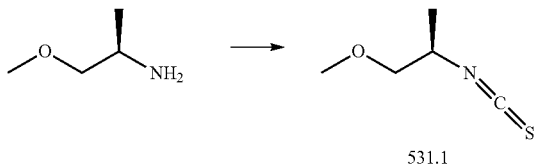

(R)-2-Isothiocyanato-1-methoxypropane, Example 531.1. This compound was prepared from (2R)-1-methoxy-2-propanamine (commercially available from Sigma Aldrich), using the procedure as described in Example 452.1. H NMR (400 MHz, CD$_3$CN) δ 4.03 (m, 1H) 3.39-3.50 (m, 2H) 3.37 (s, 3H) 1.30 (d, J=6.74 Hz, 3H).

Example 533.1. Preparation of (S)-2-isothiocyanato-1-methoxypropane

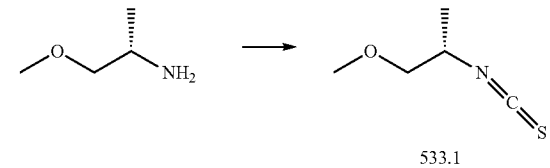

(S)-2-Isothiocyanato-1-methoxypropane, Example 533.1. This compound was prepared from (2S)-1-methoxy-2-propanamine (commercially available from Sigma Aldrich), using the procedure as described in Example 452.1. $^1$H NMR (400 MHz, CDCl$_3$) δ 3.93 (m, 1H) 3.36-3.46 (m, 5H) 1.33 (d, J=6.74 Hz, 3H).

The compounds set forth in the following table were synthesized following the procedure in Example 533.1 using the known starting material as described.

TABLE 38

| Example | Reagents | Structure, Name and Data |
|---|---|---|
| 489.2 | 1-(methoxymethyl)cyclobutanamine hydrochloride (commercially available from Enamine), Hunig's base (commercially available from Sigma-Aldrich Chemical Company, Inc.). | 1-isothiocyanato-1-(methoxymethyl)cyclobutane.<br>$^1$H NMR (400 MHz, CD$_3$CN) δ 1.73-1.97 (m, 2H) 2.18-2.26 (m, 2H) 2.31-2.40 (m, 2H) 3.40 (s, 3H) 3.52 (s, 2H). |

The compounds set forth in the following table were synthesized following the procedure in Example 468.0 using the known starting material as described.

TABLE 39

| Example | Reagents | Structure, Name and Data |
|---|---|---|
| 482.1 | 2-chloro-5-fluoropyrimidine (commercially available from Sigma-Aldrich Chemical Company, Inc.). | (1S,2S)-1-(5-fluoropyrimidin-2-yl)-1-isopropoxypropane-2-sulfonamide. $^1$H NMR (500 MHz, DMSO-d$_6$) δ 8.89-9.00 (m, 2H) 6.38-6.52 (m, 2H) 4.69-4.85 (m, 1H) 3.44-3.59 (m, 2H) 3.26-3.35 (m, 1H) 1.09- 1.19 (m, 3H) 0.95-1.04 (m, 3H) 0.86-0.94 (m, 3H) LCMS-ESI (pos.) m/z: 278.2 (M + H)$^+$. |

Biological Activity

[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in 9 μL assay buffer [20 mM HEPES, pH 7.5, 5 mM MgCl$_2$, 100 mM NaCl and 0.1% (w/v) BSA], 1 μL of diluted test compound (starting with 0.75 mM, 2-fold serial dilution with DMSO, total 22 points), 10 μL of 18 μM GDP (final concentration of 3 μM GDP), 20 μL of 0.25 μg/mL membrane protein expressing human APJ receptor captured with WGA PS beads (final concentration of 5 μg per well), and 20 μL of 0.3 nM [$^{35}$S]GTPγS (final concentration is 0.1 nM [$^{35}$S]GTPγS)(Perkin Elmer Life and Analytical Sciences, Waltham USA). One column of the plate was 1 μL of DMSO as background and another column of the plate was 1 μL of 180 μM Pyr-Apelin-13 which was used as control at a final concentration of 3 μM. Incubation was at RT for 90 min and the microplate was read using a ViewLux™ ultra HTS Microplate Imager (PerkinElmer, Inc.). All the results presented are means of several independent experiments and analyzed by non-linear regression methods using the commercially available program Prism (GraphPad, San Diego, Calif.) providing the EC$_{50}$ values detailed in Table 40.

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several h. A balloon was inserted into the left ventricle (LV) to measure dP/dt$_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects (Table 41). APJ agonists of the present invention showed improvement in cardiac contractility and relaxation when perfused into the heart as described above.

Evidence for Improvement in Cardiac Contractility In Vivo in Heart Failure Rat Model Based on the ex vivo findings in isolated heart assay, APJ agonists were dosed in vivo to investigate the translation of cardiac contractility in in vivo settings. Male Lewis rats (Charles River, USA) at 2-3 months of age were used for the study. Heart failure was induced by permanent ligation of the left descending coronary artery which results in injury to the heart with an ejection fraction of <35%. APJ agonists were administered dose dependently acutely for a period of 30 min. Administration of example compounds lead to an increase in cardiac contractility as measured by dP/dt$_{max}$ (derivative of left ventricular pressure) (Table 41).

The following table includes biological activity data obtained using the procedures and assays set forth above for the Example compounds described herein.

TABLE 40

Biological Activity Information for Example Compounds.

| Example(s) | Activity hAPJ SPA EC$_{50}$ IP (μM) |
|---|---|
| 1.0 | 0.00013 |
| 2.0 | 0.00032 |
| 3.0 | 0.0026 |
| 4.0 | 0.00092 |
| 5.0 | 0.0041 |
| 6.0 | 0.058 |
| 7.0 | 0.051 |
| 8.0 | 0.00075 |
| 9.0 | 0.011 |
| 10.0 | 0.0084 |
| 11.0 | 0.00080 |
| 12.0 | 0.0094 |
| 13.0 | 0.0029 |
| 14.0 | 0.0069 |
| 15.0 | 0.0061 |
| 16.0 | 0.0038 |
| 17.0 | 0.0052 |
| 18.0 | 0.014 |
| 19.0 | 0.0063 |
| 20.0 | 0.0011 |
| 21.0 | 0.090 |
| 22.0 | 0.015 |
| 23.0 | 0.0011 |

TABLE 40-continued

Biological Activity Information for Example Compounds.

| Example(s) | Activity hAPJ SPA EC$_{50}$ IP (μM) |
|---|---|
| 24.0 | 0.00018 |
| 25.0 | 0.015 |
| 26.0 | 0.00021 |
| 27.0 | 0.016 |
| 28.0 | 0.006 |
| 29.0 | 0.047 |
| 30.0 | 0.35 |
| 31.0 | 0.19 |
| 32.0 | 0.017 |
| 33.0 | 0.19 |
| 34.0 | 0.0045 |
| 35.0 | 0.027 |
| 36.0 | 0.021 |
| 37.0 | 0.0015 |
| 38.0 | 0.084 |
| 39.0 | 0.23 |
| 40.0 | 0.0052 |
| 41.0 | 0.037 |
| 42.0 | 0.068 |
| 43.0 | 0.046 |
| 44.0 | 0.0061 |
| 45.0 | 0.017 |
| 46.0 | 0.031 |
| 47.0 | 0.0058 |
| 48.0 | 0.15 |
| 49.0 | 0.023 |
| 50.0 | 0.13 |
| 51.0 | 0.30 |
| 52.0 | 0.059 |
| 53.0 | 0.0097 |
| 54.0 | 0.033 |
| 55.0 | 0.075 |
| 56.0 | 0.074 |
| 57.0 | 0.042 |
| 58.0 | 0.017 |
| 59.0 | 0.11 |
| 60.0 | 0.042 |
| 61.0 | 0.11 |
| 62.0 | 0.016 |
| 63.0 | 0.085 |
| 64.0 | 0.15 |
| 65.0 | 0.076 |
| 66.0 | 0.0024 |
| 67.0 | 0.077 |
| 68.0 | 0.00061 |
| 69.0 | 0.0015 |
| 70.0 | 0.0058 |
| 71.0 | 0.041 |
| 72.0 | 0.041 |
| 73.0 | 0.029 |
| 74.0 | 0.022 |
| 75.0 | 0.0095 |
| 76.0 | 0.055 |
| 77.0 | 0.0041 |
| 83.0 | 0.0019 |
| 84.0 | 0.26 |
| 87.0 | 0.082 |
| 88.0 | 0.050 |
| 90.0 | 0.033 |
| 91.0 | 0.026 |
| 92.0 | 0.071 |
| 93.0 | 0.020 |
| 94.0 | 0.0027 |
| 95.0 | >12.5 |
| 96.0 | 0.007 |
| 97.0 | 0.007 |
| 98.0 | 0.0053 |
| 99.0 | 0.013 |
| 100.0 | 0.003 |
| 101.0 | 0.00070 |
| 102.0 | 0.0041 |
| 103.0 | 0.0084 |
| 104.0 | 0.0046 |
| 105.0 | 0.0014 |
| 106.0 | 0.021 |
| 107.0 | 0.019 |
| 108.0 | 0.034 |
| 109.0 | 0.00072 |
| 110.0 | 0.0095 |
| 111.0 | 0.063 |
| 112.0 | 0.0030 |
| 113.0 | 0.0022 |
| 114.0 | 0.072 |
| 115.0 | 0.00078 |
| 116.0 | 0.0026 |
| 117.0 | 0.00069 |
| 118.0 | 0.10 |
| 119.0 | 0.0046 |
| 120.0 | 0.00017 |
| 121.0 | 0.012 |
| 122.0 | 0.011 |
| 123.0 | 0.00046 |
| 124.0 | 0.35 |
| 125.0 | 0.024 |
| 126.0 | 0.011 |
| 127.0 | 0.30 |
| 128.0 | 0.054 |
| 129.0 | 0.74 |
| 130.0 | 0.0035 |
| 131.0 | 0.0041 |
| 132.0 | 0.00024 |
| 133.0 | 0.363 |
| 134.0 | 0.0012 |
| 135.0 | 0.00088 |
| 136.0 | 0.035 |
| 137.0 | 0.030 |
| 138.0 | 0.586 |
| 139.0 | 0.118 |
| 140.0 | 0.0245 |
| 141.0 | 0.0094 |
| 142.0 | 0.017 |
| 143.0 | 0.236 |
| 144.0 | 0.33 |
| 145.0 | 0.071 |
| 146.0 | 0.097 |
| 147.0 | 0.0013 |
| 148.0 | 0.031 |
| 149.0 | 0.027 |
| 150.0 | 0.042 |
| 151.0 | 0.031 |
| 152.0 | >12.5 |
| 153.0 | 0.011 |
| 154.0 | 0.062 |
| 155.0 | 0.01 |
| 156.0 | 0.00032 |
| 157.0 | 0.058 |
| 158.0 | 0.0041 |
| 159.0 | 0.00061 |
| 160.0 | 0.0020 |
| 161.0 | 0.0038 |
| 162.0 | 0.0063 |
| 163.0 | 0.0040 |
| 164.0 | 0.026 |
| 165.0 | 0.11 |
| 166.0 | 0.029 |
| 167.0 | 0.00037 |
| 168.0 | 0.030 |
| 169.0 | 0.00046 |
| 170.0 | 0.034 |
| 171.0 | 0.00017 |
| 172.0 | 0.13 |
| 173.0 | 0.0018 |
| 174.0 | 0.0019 |
| 175.0 | 0.044 |
| 176.0 | 0.011 |
| 177.0 | 0.0045 |
| 178.0 | 0.017 |
| 179.0 | 0.0026 |
| 180.0 | 0.021 |
| 181.0 | 0.014 |

TABLE 40-continued

Biological Activity Information for Example Compounds.

| Example(s) | Activity hAPJ SPA EC$_{50}$ IP (μM) |
|---|---|
| 182.0 | 0.084 |
| 183.0 | 0.022 |
| 184.0 | 0.15 |
| 185.0 | 0.0042 |
| 186.0 | 0.011 |
| 187.0 | 0.028 |
| 188.0 | 0.015 |
| 189.0 | 0.0087 |
| 190.0 | 0.049 |
| 191.0 | 0.00063 |
| 192.0 | 0.0051 |
| 193.0 | 0.034 |
| 194.0 | 0.00048 |
| 195.0 | 0.011 |
| 196.0 | 0.14 |
| 197.0 | 0.0024 |
| 198.0 | 0.00020 |
| 199.0 | 0.00026 |
| 200.0 | 0.00079 |
| 201.0 | 0.00093 |
| 202.0 | 0.0029 |
| 203.0 | 0.0021 |
| 204.0 | 0.052 |
| 205.0 | 0.0030 |
| 206.0 | 0.096 |
| 207.0 | 0.00013 |
| 208.0 | 0.0025 |
| 209.0 | 0.0015 |
| 210.0 | 0.00083 |
| 211.0 | 0.014 |
| 212.0 | 0.00042 |
| 213.0 | 0.0012 |
| 214.0 | 0.00040 |
| 215.0 | 0.00042 |
| 216.0 | 0.0037 |
| 217.0 | 0.0028 |
| 218.0 | 0.00087 |
| 219.0 | 0.0017 |
| 220.0 | 0.0066 |
| 221.0 | 0.00032 |
| 222.0 | 0.00011 |
| 223.0 | 0.0029 |
| 224.0 | 0.00041 |
| 225.0 | 0.0020 |
| 226.0 | 0.011 |
| 227.0 | 0.0016 |
| 228.0 | 0.0040 |
| 229.0 | 0.0031 |
| 230.0 | 0.025 |
| 231.0 | 0.046 |
| 232.0 | 0.054 |
| 233.0 | 0.017 |
| 234.0 | 0.34 |
| 235.0 | >12.5 |
| 236.0 | 0.12 |
| 237.0 | >12.5 |
| 238.0 | 0.226 |
| 239.0 | 0.21 |
| 240.0 | 1.31 |
| 241.0 | 0.101 |
| 242.0 | >12.5 |
| 243.0 | >12.5 |
| 244.0 | 0.021 |
| 245.0 | 0.210 |
| 246.0 | 0.039 |
| 247.0 | 0.166 |
| 248.0 | 0.021 |
| 249.0 | 0.727 |
| 250.0 | 0.013 |
| 251.0 | 0.46 |
| 252.0 | 0.011 |
| 253.0 | 0.0025 |
| 254.0 | 0.0012 |
| 255.0 | 0.048 |
| 256.0 | 0.11 |
| 257.0 | 0.0039 |
| 258.0 | 0.0019 |
| 259.0 | 0.082 |
| 260.0 | 0.58 |
| 261.0 | 0.19 |
| 262.0 | 0.0048 |
| 263.0 | 0.18 |
| 264.0 | 0.00080 |
| 265.0 | 0.070 |
| 266.0 | 0.00040 |
| 267.0 | 0.082 |
| 268.0 | 0.00068 |
| 269.0 | 0.0087 |
| 270.0 | 0.0014 |
| 271.0 | 0.00013 |
| 272.0 | 0.012 |
| 273.0 | 0.00015 |
| 274.0 | 0.025 |
| 275.0 | 0.0031 |
| 276.0 | 0.00065 |
| 277.0 | 0.00059 |
| 278.0 | 0.0095 |
| 279.0 | 0.0028 |
| 280.0 | 0.0035 |
| 281.0 | 0.084 |
| 282.0 | 0.0010 |
| 283.0 | 0.027 |
| 284.0 | 0.00055 |
| 285.0 | 0.010 |
| 286.0 | 0.00026 |
| 287.0 | 0.00042 |
| 288.0 | 0.0013 |
| 289.0 | 0.00047 |
| 290.0 | 0.0029 |
| 291.0 | 0.00018 |
| 292.0 | 0.0012 |
| 293.0 | 0.037 |
| 294.0 | 0.00049 |
| 295.0 | 0.0004 |
| 296.0 | 0.0027 |
| 297.0 | 0.00014 |
| 298.0 | 0.0010 |
| 299.0 | 0.52 |
| 300.0 | 0.055 |
| 301.0 | 0.011 |
| 302.0 | 0.323 |
| 303.0 | 0.014 |
| 304.0 | 0.00064 |
| 305.0 | 0.00044 |
| 306.0 | 0.0025 |
| 307.0 | 0.0010 |
| 308.0 | 0.00058 |
| 309.0 | 0.034 |
| 310.0 | 0.014 |
| 311.0 | 0.0038 |
| 312.0 | 0.076 |
| 313.0 | 0.056 |
| 314.0 | 0.014 |
| 315.0 | 0.00068 |
| 316.0 | 0.081 |
| 317.0 | 0.0066 |
| 318.0 | 0.044 |
| 319.0 | 0.0025 |
| 320.0 | 0.068 |
| 321.0 | 0.0016 |
| 322.0 | 0.014 |
| 323.0 | 0.0011 |
| 324.0 | 0.035 |
| 325.0 | 0.0018 |
| 326.0 | 0.012 |
| 327.0 | 0.0040 |
| 328.0 | 0.0012 |
| 329.0 | 0.00020 |
| 330.0 | 0.00062 |
| 331.0 | 0.00098 |

TABLE 40-continued

Biological Activity Information for Example Compounds.

| Example(s) | Activity hAPJ SPA EC$_{50}$ IP (µM) |
|---|---|
| 332.0 | 0.00037 |
| 333.0 | 0.0015 |
| 334.0 | 0.00052 |
| 335.0 | 0.011 |
| 336.0 | 0.31 |
| 337.0 | 0.0068 |
| 338.0 | 0.00034 |
| 339.0 | 0.0021 |
| 340.0 | 0.00026 |
| 341.0 | 0.00073 |
| 342.0 | 0.00050 |
| 343.0 | 0.0026 |
| 344.0 | 0.00063 |
| 345.0 | 0.0081 |
| 346.0 | 0.0015 |
| 347.0 | 0.0038 |
| 348.0 | 0.0043 |
| 349.0 | 0.0021 |
| 350.0 | 0.0061 |
| 351.0 | 0.035 |
| 352.0 | 0.035 |
| 353.0 | 0.00022 |
| 354.0 | 0.00075 |
| 355.0 | 0.00047 |
| 356.0 | >12.5 |
| 357.0 | >12.5 |
| 358.0 | 0.034 |
| 359.0 | 0.143 |
| 360.0 | 0.194 |
| 361.0 | 0.034 |
| 362.0 | 0.003 |
| 363.0 | 0.0015 |
| 364.0 | 0.0019 |
| 365.0 | 0.00069 |
| 366.0 | 0.0047 |
| 367.0 | 0.0011 |
| 368.0 | 0.0084 |
| 369.0 | 0.0011 |
| 370.0 | 0.0031 |
| 371.0 | 0.0022 |
| 372.0 | 0.0014 |
| 373.0 | 0.0013 |
| 374.0 | 0.0070 |
| 375.0 | 0.0059 |
| 376.0 | 0.0017 |
| 377.0 | 0.00060 |
| 378.0 | 0.00041 |
| 379.0 | 0.00063 |
| 380.0 | 0.00040 |
| 381.0 | 0.00029 |
| 382.0 | 0.26 |
| 383.0 | >12.5 |
| 384.0 | >12.5 |
| 385.0 | >12.5 |
| 386.0 | >12.5 |
| 387.0 | 0.00055 |
| 388.0 | 0.00037 |
| 389.0 | 0.00034 |
| 390.0 | 0.073 |
| 391.0 | 0.00041 |
| 392.0 | 0.0010 |
| 393.0 | 0.00047 |
| 394.0 | 0.00054 |
| 410.0 | 0.94 |
| 411.0 | 0.058 |
| 412.0 | 0.14 |
| 413.0 | 0.030 |
| 414.0 | 0.21 |
| 415.0 | 0.0052 |
| 416.0 | 0.0084 |
| 417.0 | 0.51 |
| 418.0 | 0.0055 |
| 419.0 | 0.0024 |
| 420.0 | 0.027 |
| 421.0 | 0.0045 |
| 422.0 | 0.0062 |
| 423.0 | 0.00068 |
| 424.0 | 0.021 |
| 425.0 | 0.0081 |
| 426.0 | 0.014 |
| 427.0 | 0.021 |
| 428.0 | 0.12 |
| 429.0 | 0.0076 |
| 430.0 | 0.0028 |
| 431.0 | 0.014 |
| 432.0 | 0.00010 |
| 433.0 | 0.00084 |
| 434.0 | 0.0086 |
| 435.0 | 0.18 |
| 436.0 | 0.00081 |
| 437.0 | 0.19 |
| 438.0 | 0.0091 |
| 439.0 | 0.00082 |
| 440.0 | 0.00096 |
| 441.0 | 0.00033 |
| 442.0 | 0.19 |
| 443.0 | 0.0064 |
| 444.0 | 0.0012 |
| 445.0 | 0.000089 |
| 446.0 | 0.00074 |
| 447.0 | 0.00012 |
| 448.0 | 0.010 |
| 449.0 | 0.013 |
| 450.0 | 0.00081 |
| 451.0 | 0.0099 |
| 452.0 | 0.23 |
| 453.0 | 0.073 |
| 454.0 | 0.056 |
| 455.0 | 0.0057 |
| 456.0 | 0.00060 |
| 457.0 | 0.025 |
| 458.0 | 0.0028 |
| 459.0 | 0.00033 |
| 460.0 | 0.0026 |
| 461.0 | 0.0090 |
| 462.0 | 0.0041 |
| 463.0 | 0.016 |
| 478.0 | 0.011 |
| 479.0 | 0.00056 |
| 480.0 | 0.0044 |
| 481.0 | 0.0059 |
| 482.0 | 0.00038 |
| 483.0 | 0.0054 |
| 484.0 | 0.0092 |
| 485.0 | 0.00030 |
| 486.0 | 0.00029 |
| 487.0 | 0.00062 |
| 488.0 | 0.0002 |
| 489.0 | 0.0013 |
| 490.0 | 0.0074 |
| 491.0 | 0.015 |
| 492.0 | 0.034 |
| 493.0 | 0.043 |
| 494.0 | 0.00040 |
| 495.0 | 0.013 |
| 496.0 | 0.00062 |
| 497.0 | 0.015 |
| 498.0 | 0.00044 |
| 499.0 | 0.00050 |
| 501.0 | 0.0093 |
| 505.0 | 0.0085 |
| 506.0 | 0.26 |
| 507.0 | 0.038 |
| 508.0 | 0.062 |
| 509.0 | 0.0041 |
| 511.0 | 0.20 |
| 512.0 | 0.13 |
| 513.0 | 0.0031 |
| 514.0 | 0.019 |
| 515.0 | 0.00093 |

TABLE 40-continued

Biological Activity Information for Example Compounds.

| Example(s) | Activity hAPJ SPA $EC_{50}$ IP (µM) |
|---|---|
| 516.0 | 0.018 |
| 517.0 | 0.0030 |
| 518.0 | 0.092 |
| 519.0 | 0.00032 |
| 523.0 | 0.0032 |
| 531.0 | 0.050 |
| 532.0 | 0.022 |
| 533.0 | 0.11 |
| 534.0 | 0.00093 |
| 535.0 | 0.00066 |
| 536.0 | 0.070 |
| 537.0 | 0.027 |
| 538.0 | 0.020 |

The following table includes data obtained using the procedures and assays set forth above for the Example compounds described herein.

TABLE 41

Contractile Effects of Examples Observed in ex vivo (Isolated Heart Assay) and in vivo (MI Rat Model).

| | Isolated Heart Assay | | MI Rat Model |
|---|---|---|---|
| Example(s) | $dP/dt_{max}$ (%) | $dP/dt_{min}$ (%) | $dP/dt_{max}$ (%) |
| 3 | 12.7 | 14.8 | nd* |
| 68 | 12.1 | 15.3 | No effect |
| 135 | No effect | No effect | nd* |
| 201 | No effect | No effect | nd* |
| 207 | 10.8 | 15.6 | nd* |
| 210 | 2.01 | 4.68 | nd* |
| 226 | 2.1 | 7.83 | nd* |
| 276 | 6.08 | 2.12 | nd* |
| 284 | 6.33 | 0.3 | nd* |
| 287 | 22.6 | 25.7 | 25 |
| 294 | 18.6 | 23.1 | nd* |
| 296 | 4.05 | 3.62 | nd* |
| 306 | 8.9 | 5.0 | nd* |
| 330 | No effect | No effect | nd* |
| 333 | 13.5 | 26.2 | nd* |
| 354 | 9.28 | 6.47 | nd* |
| 355 | No effect | No effect | nd* |
| 393 | No effect | No effect | nd* |
| 457 | 7.2 | 8.3 | nd* |
| 463 | No effect | No effect | nd* |

*not determined

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun., 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction Between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15 k/well in a 96 well plate overnight. The next day, the culture medium was replaced with medium containing no serum for 4 h. The compound AngII at a range of concentrations (1 pM-10 μM) with or without different concentrations of APJ agonists were diluted in stimulation buffer and added to the cell plate. The plate was sealed and incubated for 1h. This was followed by addition of IP-d2 conjugate followed by europium cryptate antibody conjugate into the wells. The plate was sealed, followed with incubation for 2 h at RT. Time-resolved fluorescence resonance energy (TR-FRET) at 620 nm and 665 nm was measured after 2 h with an Envision reader. The signal ratios and delta F were calculated and the amount of IP1 produced was inversely proportional to the TR-FRET ratio, 665/620 nm.

Results

Figure 2:
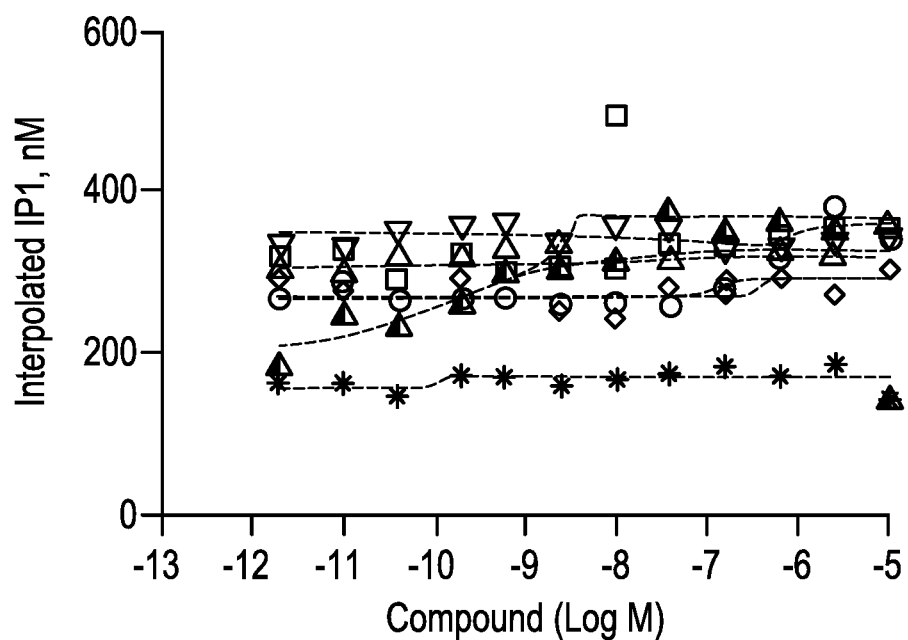
FIG. 2 is a graph plotting different concentrations of angiotensin (AngII) with fixed concentration of pyr apelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyr apelin-13 when the human APJ receptor is expressed alone.
Figure 3:
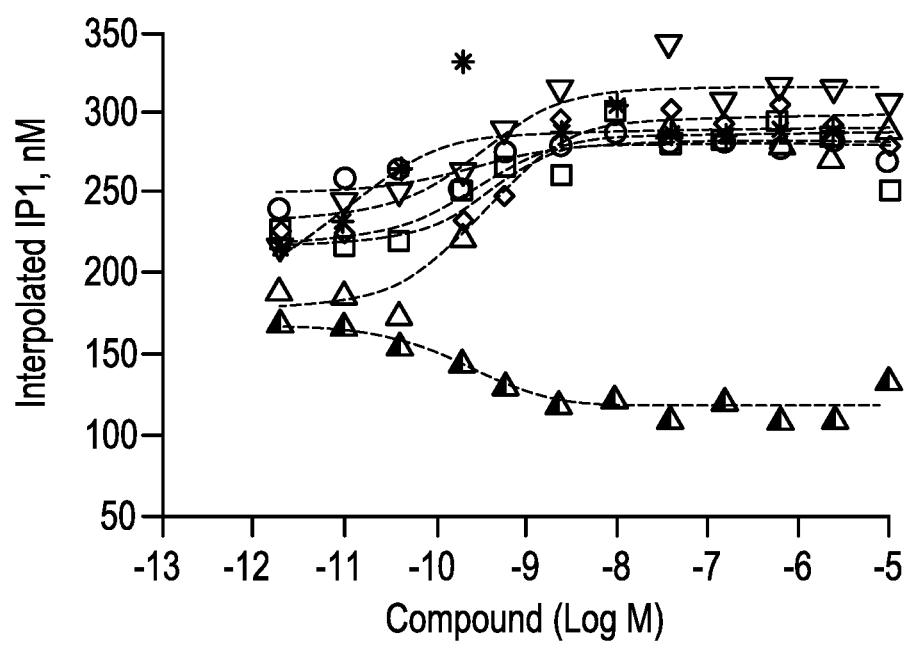
FIG. 3 is a graph plotting different concentrations of angiotensin (AngII) with fixed concentration of pyr apelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyr apelin-13 in the absence of APJ expression.

In cells expressing both APJ and the AT1R receptor, addition of APJ agonists at different concentrations increased the maximal response of AngII and also shifted the potency to the left. The increase in IP1 response reached a maximal effect both in potency and Emax indicating a ceiling effect which is a hallmark for allosteric cooperativity between the AT1R and APJ receptor (FIG. 1). However, this effect of cooperativity was not observed in either APJ or AT1R recombinant stable cell lines indicating that there is functional cross-talk between the two receptors through physical interaction or with downstream effectors (FIG. 2 and FIG. 3). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:
1. A compound of Formula I or Formula II:

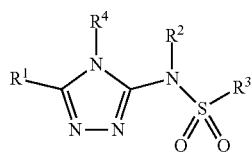

I

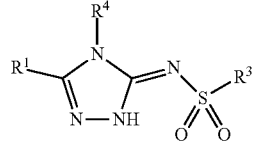

II or a pharmaceutically acceptable salt thereof, a tautomer thereof, a pharmaceutically acceptable salt of the tautomer, a stereoisomer of any of the foregoing, or a mixture thereof, wherein:

$R^{1a}$ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl $R^1$ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-

—O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{31}$ substituents, and further wherein the $C_3$-$C_8$ cycloalkyl of the —($C_3$-$C_8$ cycloalkyl)-Q group is unsubstituted or is substituted with 1 or 2 $R^{31}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^4$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or SO$_2$ moiety, and further wherein the heterocyclyl of the R$^4$ group may be further substituted with 1 oxo substituent; and R$^{4b}$ in each instance is selected from —F, —Cl, —Br, —I, —CN, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, or —S(=O)$_2$—(C$_1$-C$_6$ alkyl);

wherein if R$^1$ is a substituted or unsubstituted pyrimidine and R$^4$ is a substituted or unsubstituted alkyl and R$^3$ is -Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted C$_3$-C$_8$ cycloalkyl group or an unsubstituted or substituted 3 to 10 membered heterocyclyl group containing 1, 2, or 3 heteroatoms independently selected from N, O, or S;

wherein if R$^1$ is a substituted or unsubstituted pyrimidine and R$^4$ is a substituted or unsubstituted alkyl and R$^3$ is —CH$_2$-Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted C$_3$-C$_8$ cycloalkyl group or an unsubstituted or substituted 3 to 10 membered heterocyclyl group containing 1, 2, or 3 heteroatoms independently selected from N, O, or S;

and further wherein if R$^1$ is a substituted or unsubstituted pyrimidine and R$^3$ is -Q and Q is an unsubstituted or substituted phenyl, then R$^4$ is selected from an unsubstituted or substituted monocyclic or bicyclic C$_6$-C$_{10}$ aryl group, an unsubstituted or substituted monocyclic or bicyclic heteroaryl group with 5 to 10 ring members containing 1, 2, or 3 heteroatoms independently selected from N, O, or S, an unsubstituted or substituted monocyclic or bicyclic heterocyclyl group with 5 to 10 ring members containing 1, 2, 3, or 4 heteroatoms independently selected from N, O, or S, or an unsubstituted or substituted monocyclic 3-6 membered cycloalkyl group.

2. The compound of claim 1 or the pharmaceutically acceptable salt thereof, the tautomer thereof, the pharmaceutically acceptable salt of the tautomer, the stereoisomer of any of the foregoing, or the mixture thereof, wherein R$^1$ is selected from pyrazolyl, thiazolyl, imidazolyl, thienyl, pyrrolyl, 1,2,4-triazolyl, 1,2,3-triazolyl, oxazolyl, isoxazolyl, 1,3,4-oxadiazolyl, 1,3,4-thiadiazolyl, pyrazinyl, pyrimidinyl, or pyridazinyl any of which may unsubstituted or substituted with 1, 2, or 3 independently selected R$^{1a}$ substituents.

3. The compound of claim 2 or the pharmaceutically acceptable salt thereof, the tautomer thereof, the pharmaceutically acceptable salt of the tautomer, the stereoisomer of any of the foregoing, or the mixture thereof, wherein R$^1$ is unsubstituted or is substituted with 1 or 2 R$^{1a}$ substituents independently selected from —F, —Cl, —Br, —C$_1$-C$_6$ alkyl, —C$_1$-C$_6$ haloalkyl, —C$_1$-C$_6$ perhaloalkyl, —O—(C$_1$-C$_6$ alkyl), C$_3$-C$_8$ cycloalkyl, or —(C$_1$-C$_6$ alkyl)-O—(C$_1$-C$_6$ alkyl), or —C(=O)NH(C$_1$-C$_6$ alkyl).

4. The compound of claim 1 or the pharmaceutically acceptable salt thereof, the tautomer thereof, the pharmaceutically acceptable salt of the tautomer, the stereoisomer of any of the foregoing, or the mixture thereof, wherein R$^1$ is selected from

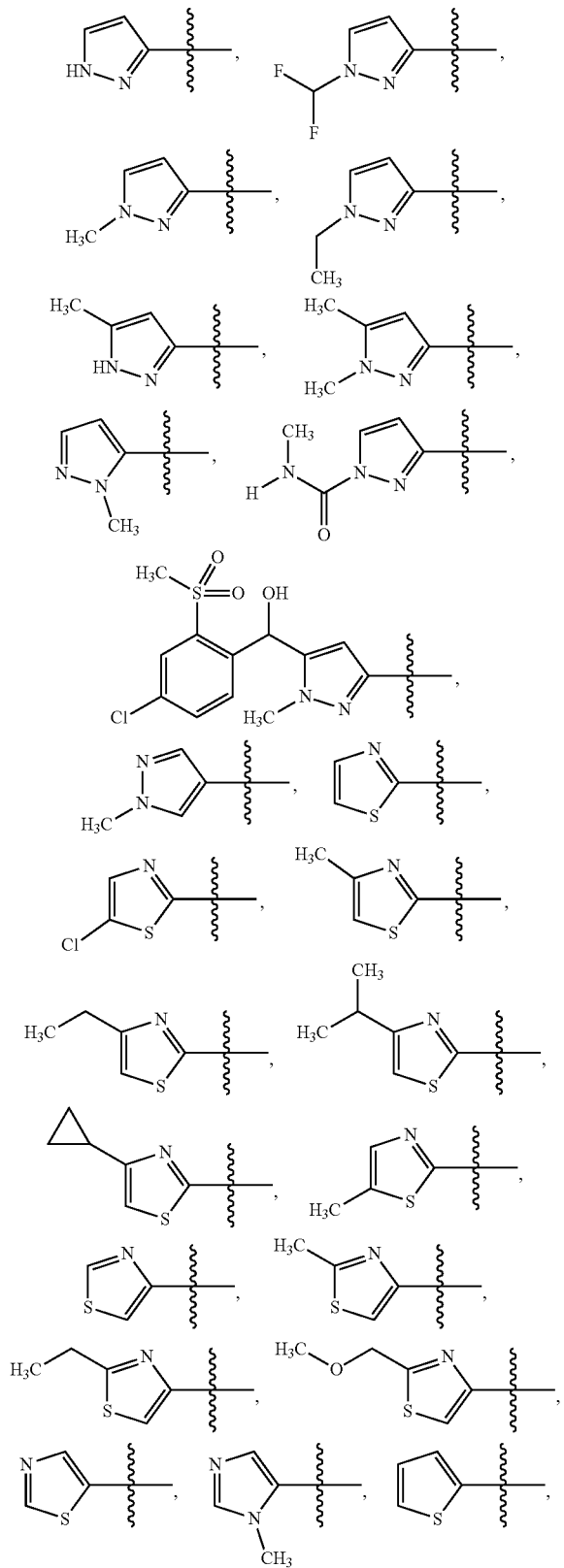

-continued

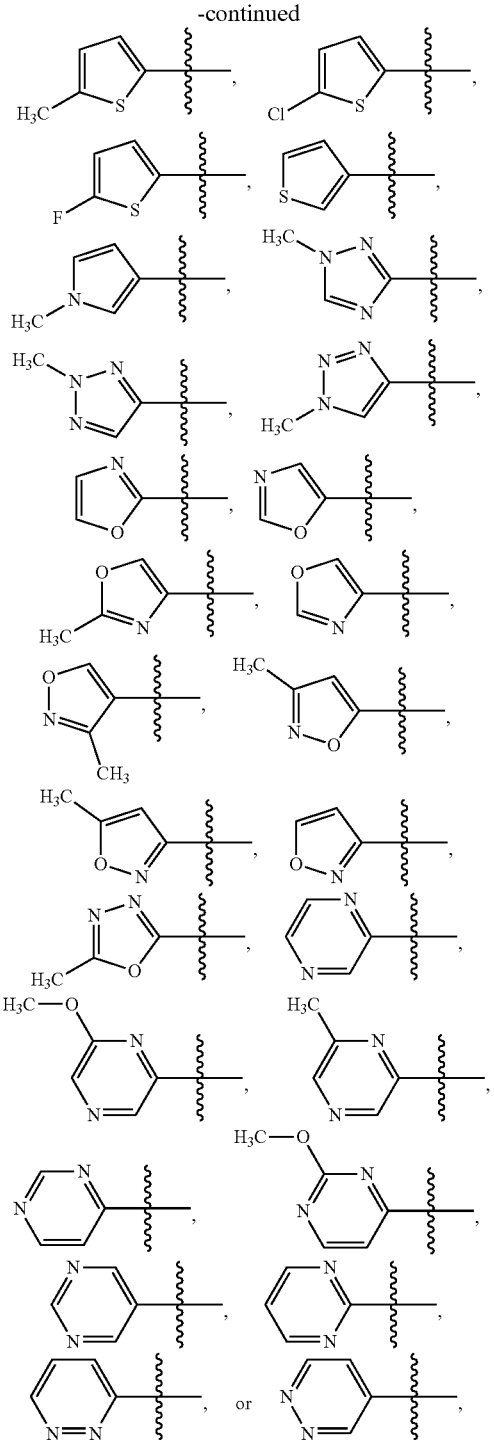

wherein the symbol

∼∼∼, when drawn across a bond, indicates the point of attachment to the rest of the molecule.

5. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from pyrrolo[2,3-b]pyrazinyl, 5,6-dihydro-4H-pyrrolo[1,2-b]pyrazolyl, 4,5,6,7-tetrahydro-1H-indazolyl, or indolyl any of which may unsubstituted or substituted with 1, 2, or 3 independently selected $R^{1a'}$ substituents.

6. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is selected from

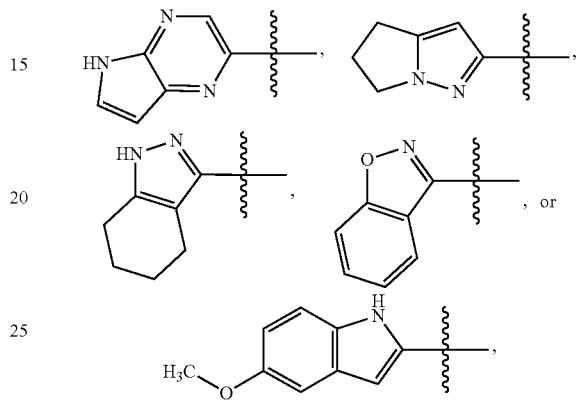

wherein the symbol

∼∼∼, when drawn across a bond, indicates the point of attachment to the rest of the molecule.

7. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, or pyrimidinyl, any of which may be unsubstituted or substituted with 1, 2, 3, or 4 $R^{4a}$ substituents.

9. The compound of claim 8 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —OH, —O—($C_1$-$C_6$ alkyl), —O—($C_1$-$C_6$ haloalkyl), —O—($C_1$-$C_6$ perhaloalkyl), —C(=O)OH, —C(=O)—O—($C_1$-$C_6$ alkyl), —$NH_2$, —NH($C_1$-$C_6$ alkyl), —N($C_1$-$C_6$ alkyl)$_2$, NH($C_1$-$C_6$ alkyl-OH), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), or heterocyclyl, wherein the heterocyclyl of the heterocyclyl $R^{4a}$ group is a 3-6 membered ring comprising 1 or 2 heteroatoms independently selected from N, O, or S and may be optionally substituted with 1 or 2 oxo groups.

10. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a monocyclic or bicyclic heteroaryl group with 5 to 10 ring members containing 1, 2, or 3 heteroatoms independently selected from N, O, or S, wherein the heteroaryl $R^4$ group is unsubstituted or is substituted with 1, 2, or 3 $R^{4a}$ substituents.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is selected from

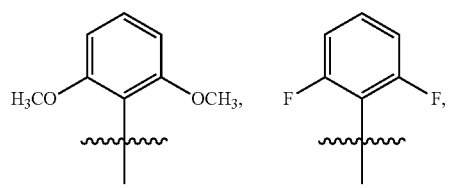
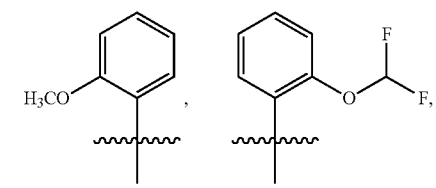
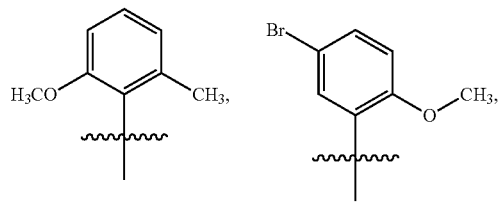
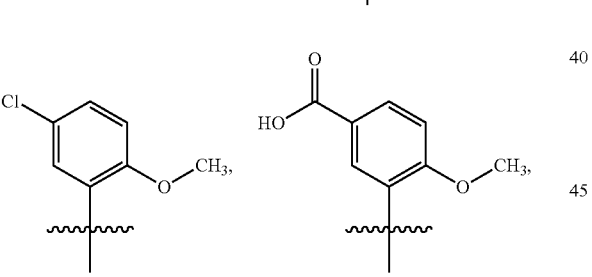
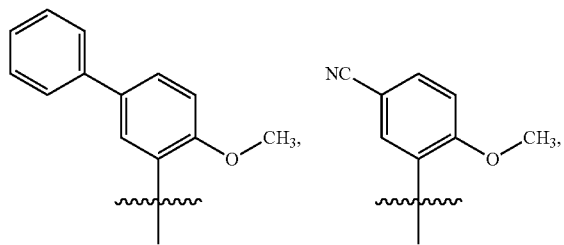

-continued

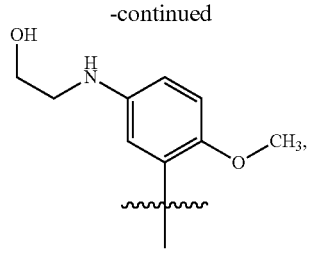
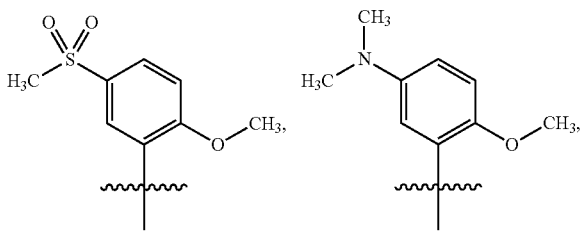
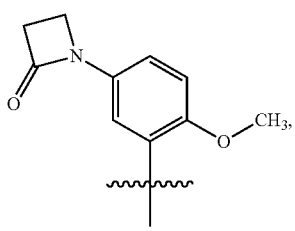
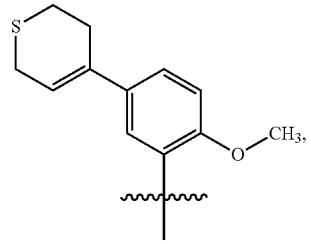
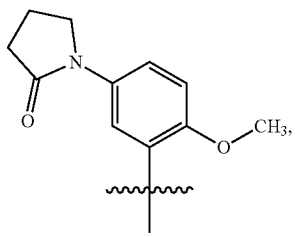
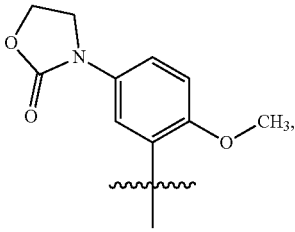
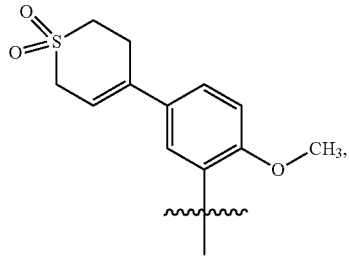

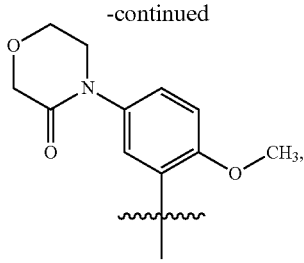

wherein the symbol

‍ⵯⵯⵯⵯ, when drawn across a bond, indicates the point of attachment to the rest of the molecule.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents.

13. The compound of claim 12 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

14. The compound of claim 12 or the pharmaceutically acceptable salt thereof, the tautomer thereof, the pharmaceutically acceptable salt of the tautomer, the stereoisomer of any of the foregoing, or the mixture thereof, wherein $R^4$ is

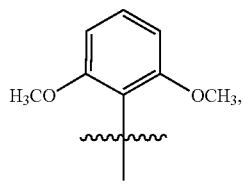 [SMILES: *c1c(OC)cccc1OC]

wherein the symbol

ⵯⵯⵯⵯ, when drawn across a bond, indicates the point of attachment to the rest of the molecule.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyrazine-1-oxide, pyradizinyl, pyridinyl, phenyl, oxazolyl, thiazolyl, imidazolyl, pyrazolyl, piperidinyl, piperidin-2-onyl, tetrahydropyrimidin-2(1H)-onyl, 1,3-oxazinan-2-onyl, pyrrolidin-2-onyl, pyrrolidinyl, cyclopentyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1 or 2 $R^Q$ substituents.

16. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

17. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^Q$ in each instance is independently selected from —F, —Cl, —Br, —CN, —$C_1$-$C_6$ alkyl, —$C_1$-$C_6$ haloalkyl, —$C_1$-$C_6$ perhaloalkyl, —O—($C_1$-$C_6$ alkyl), —O—($C_1$-$C_6$ haloalkyl), —O—($C_1$-$C_6$ perhaloalkyl), or —S(=O)$_2$—$C_1$-$C_6$ alkyl.

18. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

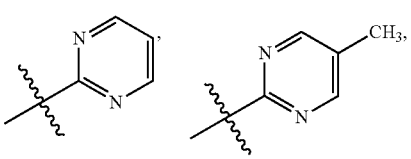

705
-continued

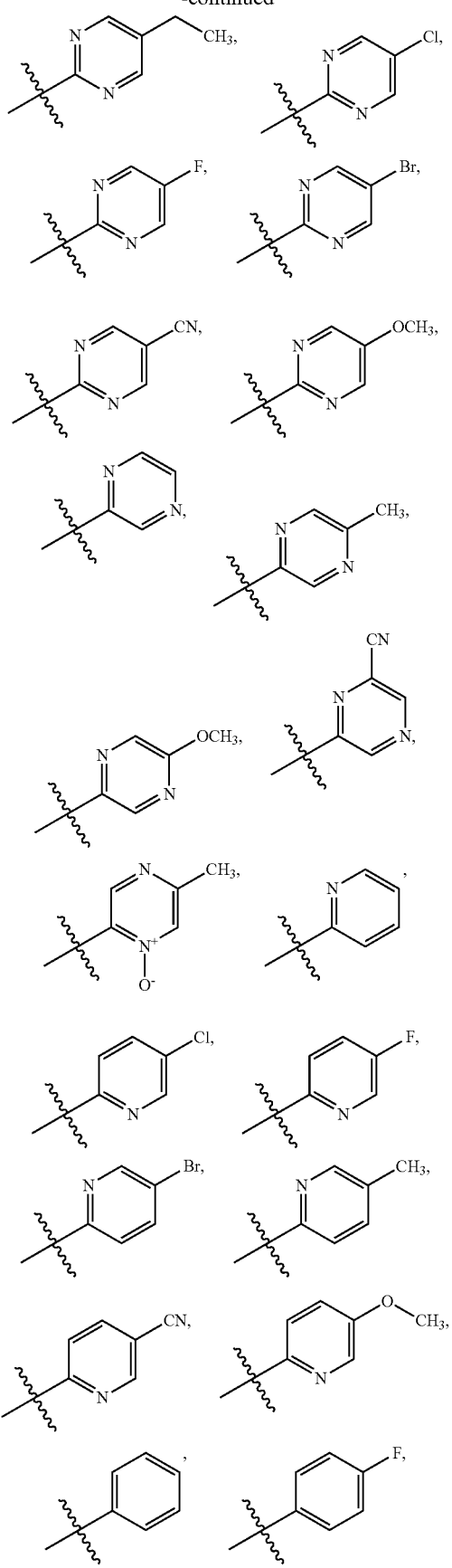

706
-continued

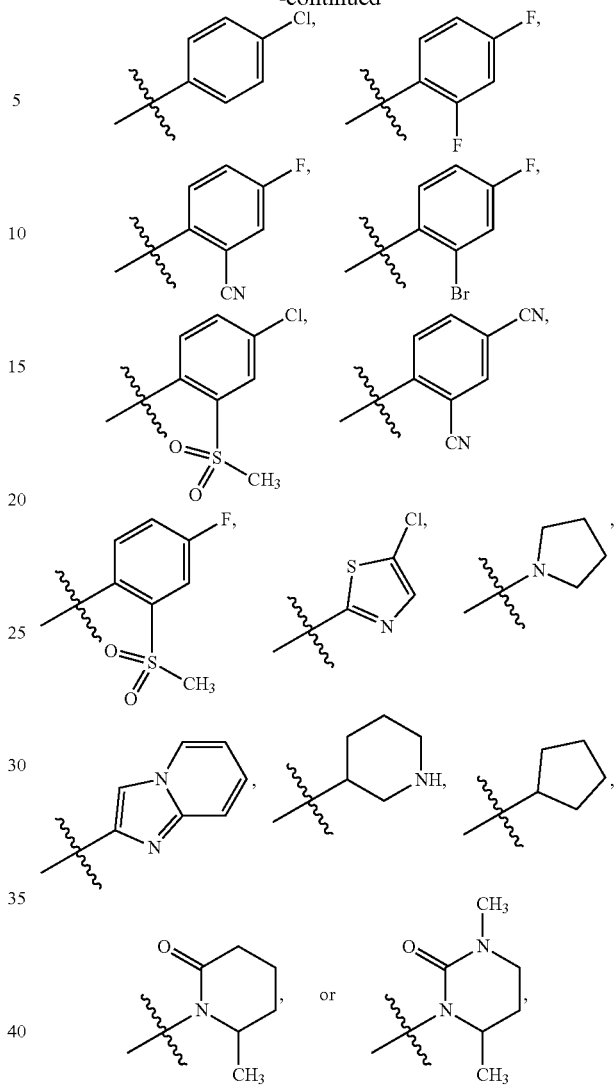

wherein the symbol

∼∼∼, when drawn across a bond, indicates the point of attachment to the rest of the molecule.

19. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —$(CR^{3b}R^{3c})$-Q, a group of formula —$(CR^{3d}R^{3e})$—$(CR^{3f}R^{3g})$-Q, a group of formula —$(CR^{3d}R^{3e})$—$(CR^{3f}R^{3g})$—C(=O)-Q, a group of formula —$(CR^{3d}R^{3e})$—$(CR^{3f}R^{3g})$—CH(OH)-Q, a group of formula —$(C_3-C_8$ cycloalkyl)-Q, a group of formula -(heterocyclyl)-Q, or -Q.

20. The compound of claim 19 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})(CR^{3f}R^{3g})$-Q.

21. The compound of claim 20 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, —($C_1$-$C_6$ alkyl)-O—($C_1$-$C_6$ alkyl), or —($C_1$-$C_6$ alkyl)-O—($C_1$-$C_6$ alkyl)-phenyl; and $R^{3f}$ and $R^{3g}$ are independently selected from —H, —F, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), or —O—($C_2$-$C_6$ alkenyl).

22. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from

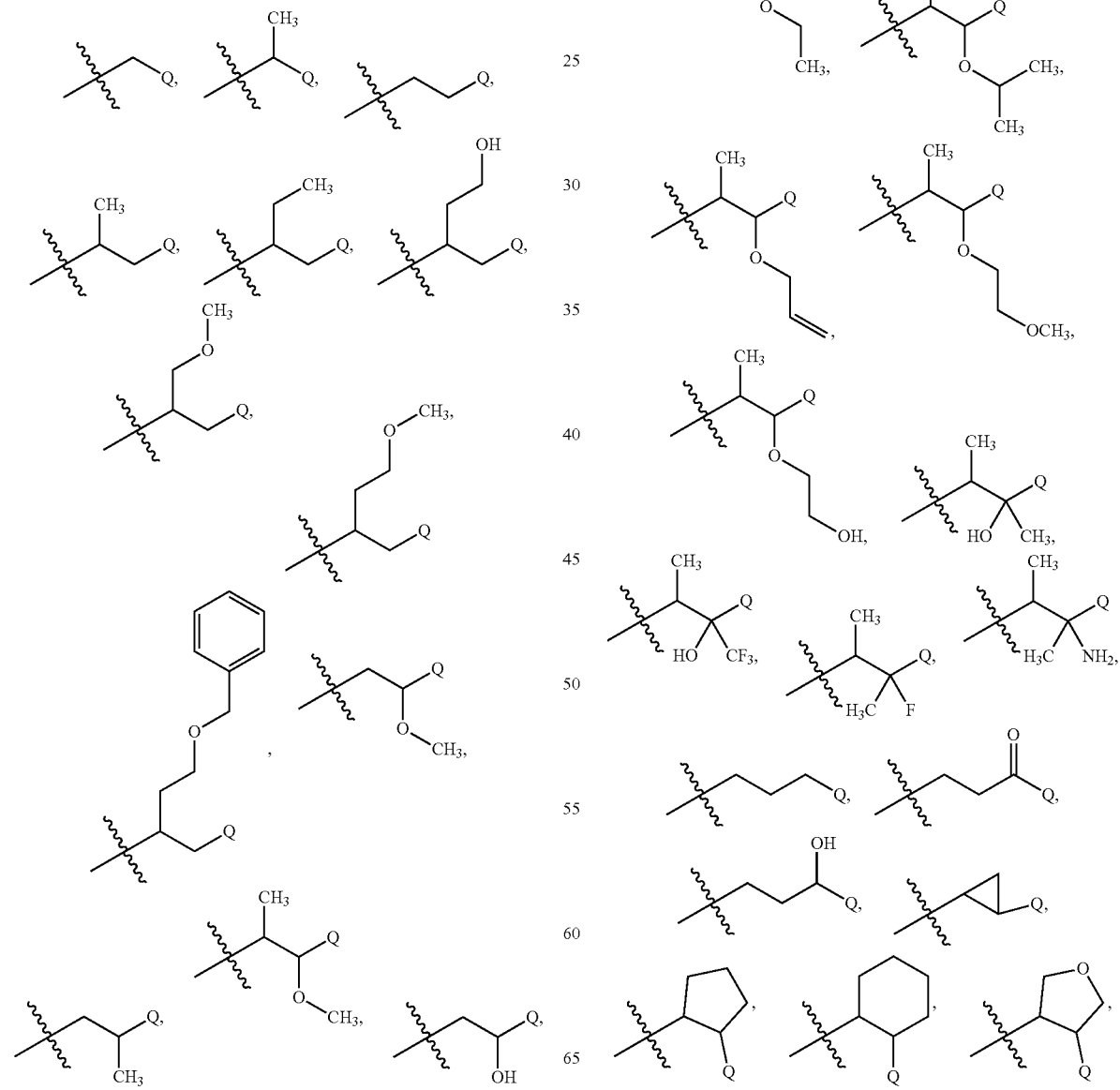

-continued
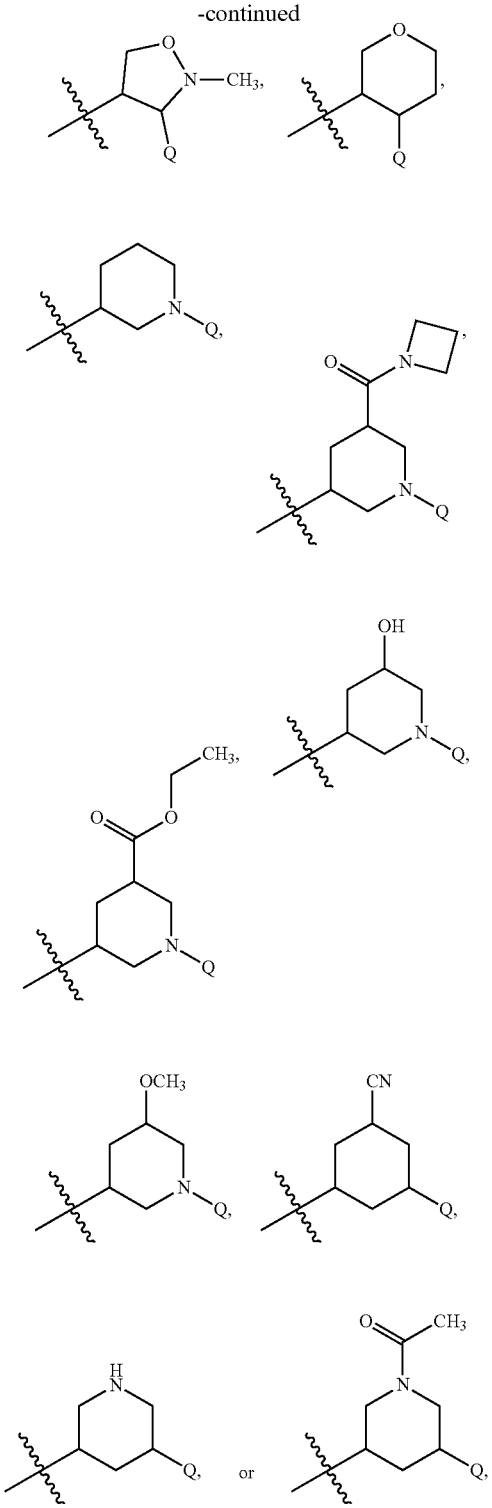
wherein the symbol
᭜᭜᭜,
when drawn across a bond, indicates the point of attachment to the rest of the molecule.
23. The compound of claim 1, wherein the compound is selected from
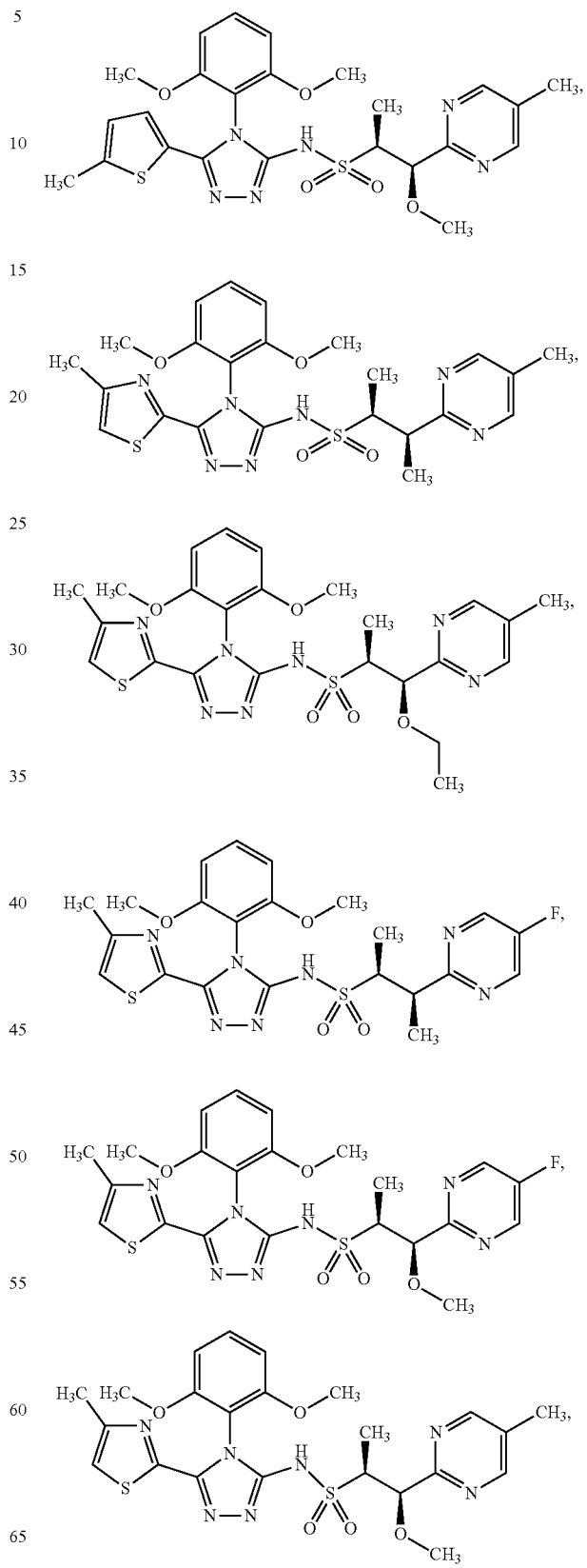

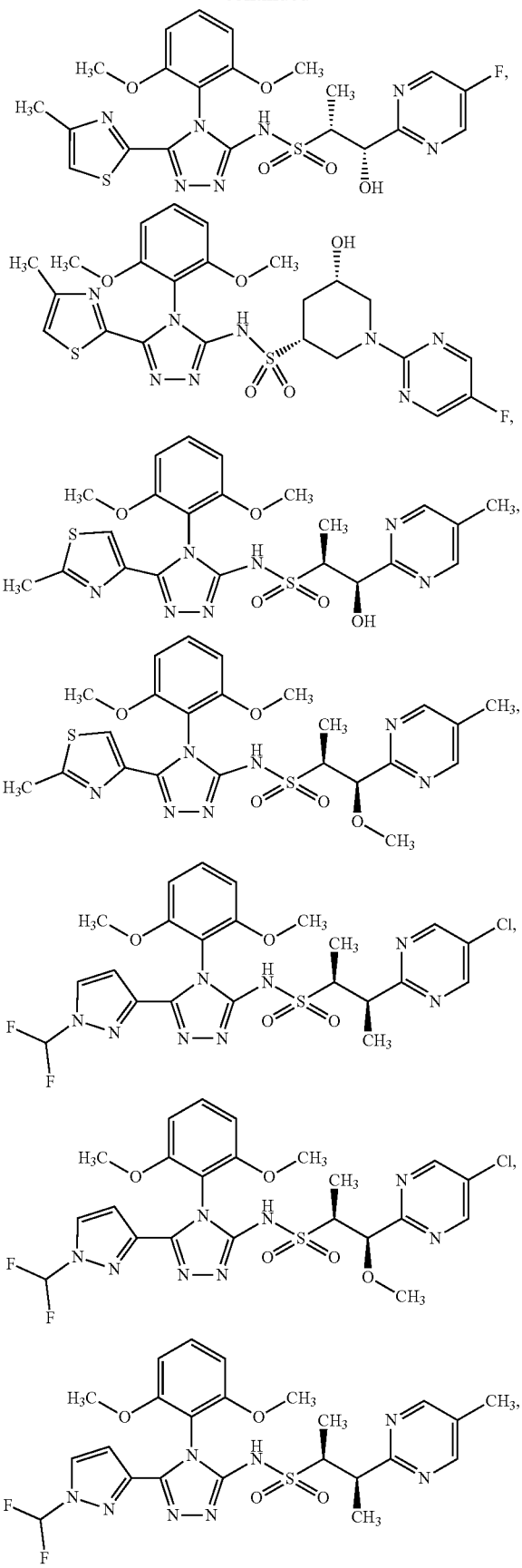
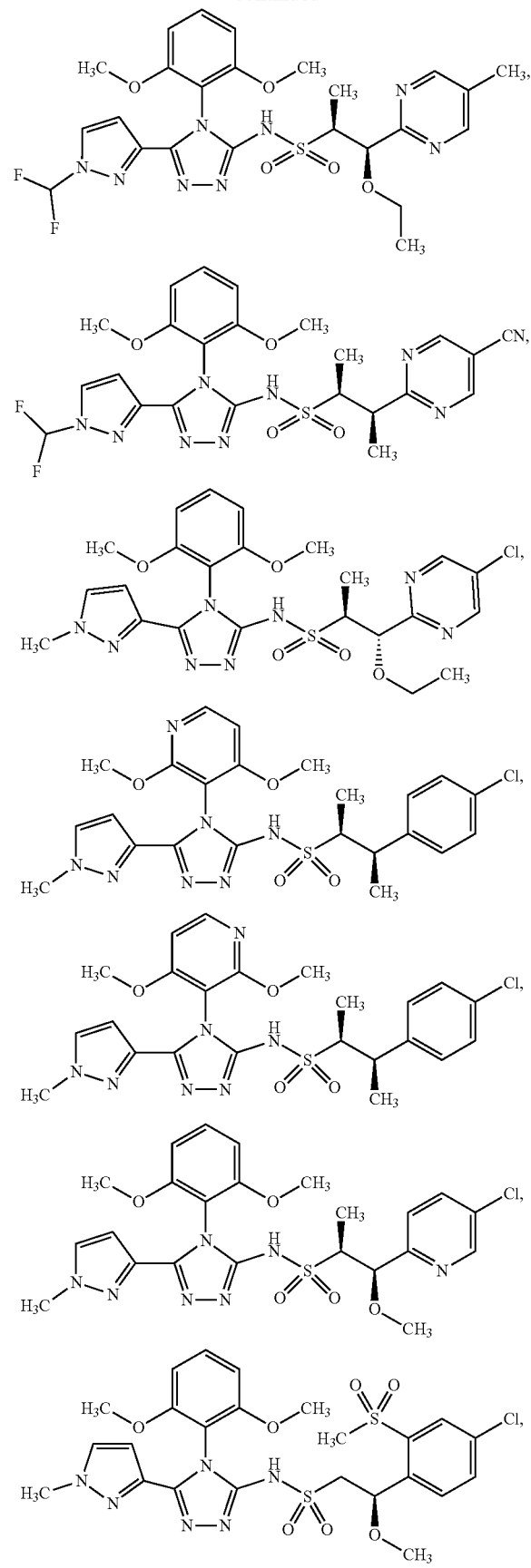

713
-continued
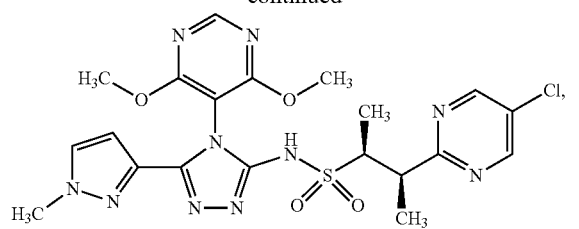
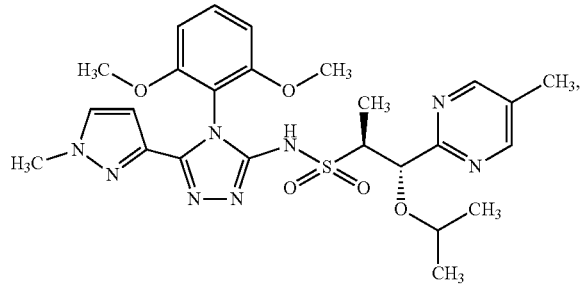
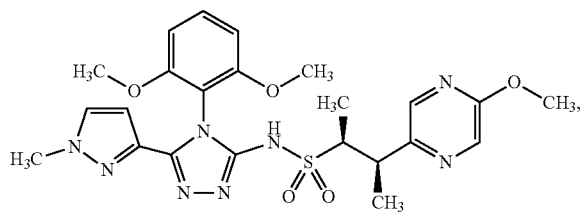
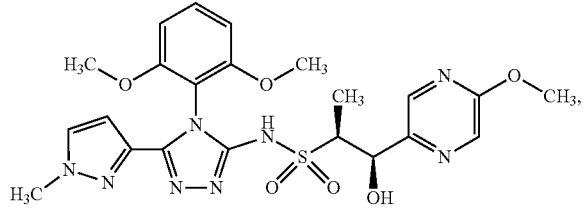
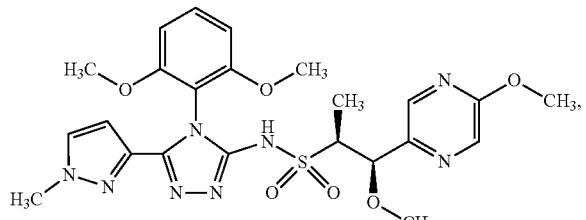
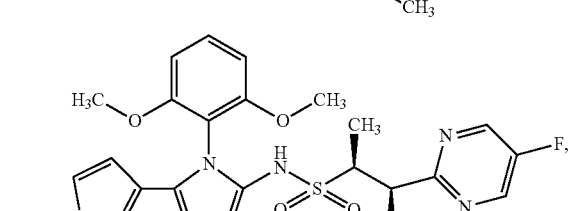
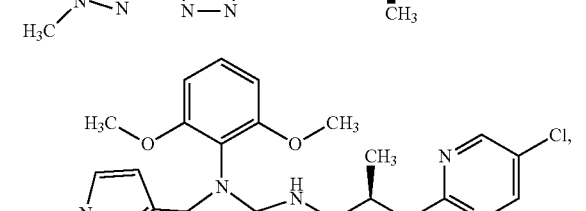
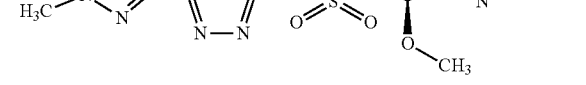
714
-continued
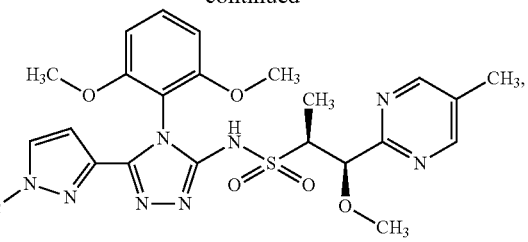
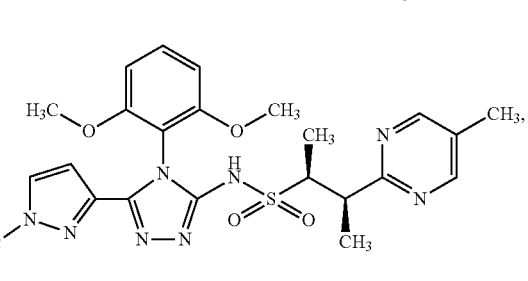
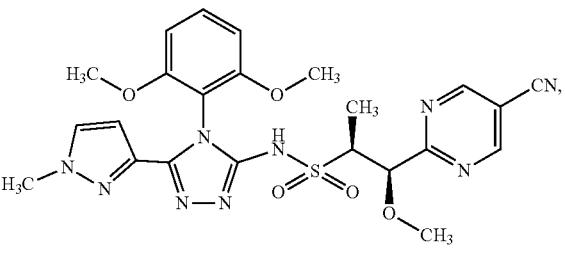
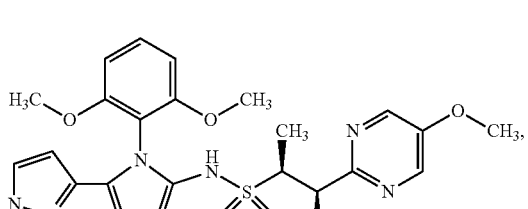
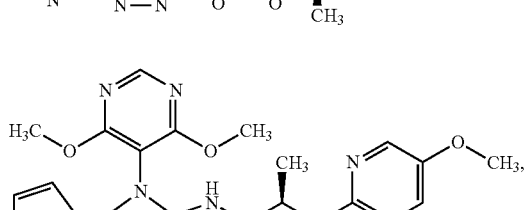
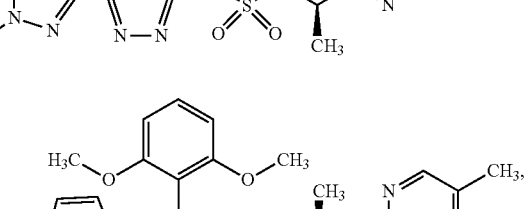
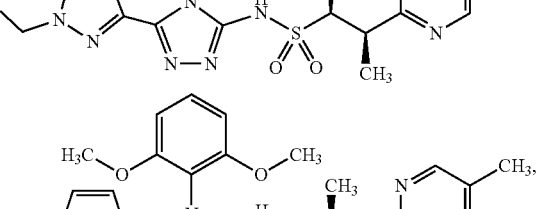
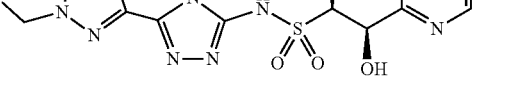

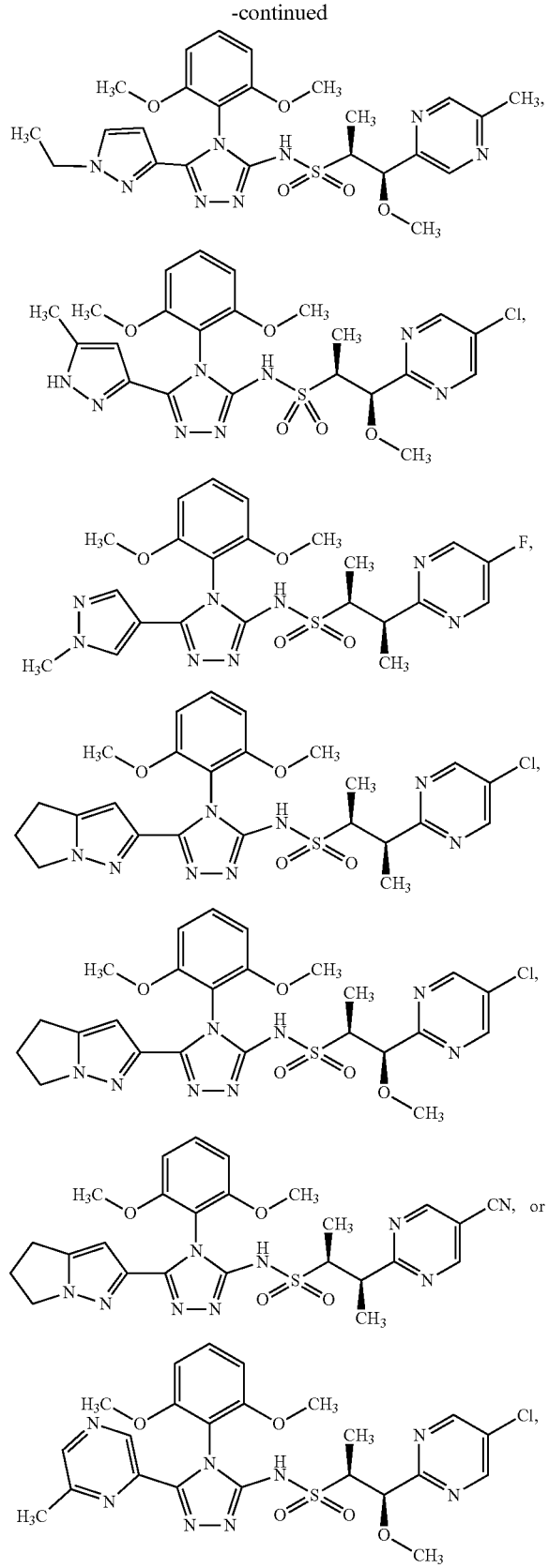

or the pharmaceutically acceptable salt thereof, or the mixture thereof.

24. The compound of claim 1, wherein the compound has the formula IA

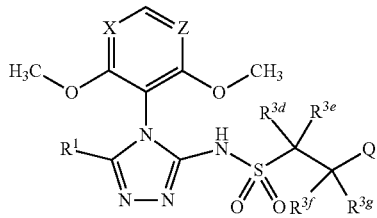

or is the pharmaceutically acceptable salt thereof, the tautomer thereof, the pharmaceutically acceptable salt of the tautomer, the stereoisomer of any of the foregoing, or the mixture thereof, wherein:

$R^1$ is as defined in claim 1;

X is selected from CH or N;

Z is selected from CH or N;

$R^{3d}$ and $R^{3e}$ are independently selected from —H, —$C_1$-$C_3$ alkyl, or —($C_1$-$C_3$ alkyl)-O—($C_1$-$C_3$ alkyl);

$R^{3f}$ and $R^{3g}$ are independently selected from —H, —F, —$CF_3$, —$C_1$-$C_3$ alkyl, —OH, —O—($C_1$-$C_4$ alkyl), or —O—($C_2$-$C_4$ alkenyl);

Q is a phenyl group or a monocyclic heteroaryl group with 6 ring members containing 1 or 2 N heteroatoms, wherein the phenyl and the monocyclic heteroaryl Q groups are unsubstituted or are substituted with 1 or 2 $R^Q$ substituent; and $R^Q$ is independently selected from —F, —Cl, —Br, —CN, —$C_1$-$C_6$ alkyl, —O—($C_1$-$C_6$ alkyl), or —S(=O)$_2$—($C_1$-$C_6$ alkyl).

25. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

26. A pharmaceutical composition, comprising the compound of claim 1 or the pharmaceutically acceptable salt thereof and at least one pharmaceutically acceptable excipient.

27. A method of treating a cardiovascular condition, the method comprising: administering to a subject an effective amount of the compound of claim 1 or the pharmaceutically acceptable salt thereof, the stereoisomer of any of the foregoing, or the mixture thereof.

28. The method of claim 27, wherein the cardiovascular condition is heart failure.

29. The method of claim 27, wherein the cardiovascular condition is heart failure with reduced ejection fraction.

30. The method of claim 27, wherein the cardiovascular condition is heart failure with preserved ejection fraction.

31. The method of claim 27, wherein the cardiovascular condition is chronic systolic heart failure or chronic diastolic heart failure.

32. The method of claim 27, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

33. A compound of Formula V, a salt thereof, a tautomer thereof, or a salt of the tautomer:

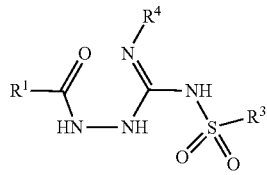

wherein:
R¹ is a 5- or 6-membered heteroaryl group that is unsubstituted or is substituted with 1, 2, or 3 $R^{1a}$ substituents, wherein the 5-membered heteroaryl group includes 1, 2, or 3 heteroatoms independently selected from N, O, and S and the 6-membered heteroaryl group includes 2 or 3 N heteroatoms; and further wherein if the 5-membered heteroaryl includes only 1 hetero atom, then it is selected from N or S;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), or —CH(OH)-phenyl, wherein the phenyl of the —CH(OH)-phenyl may optionally be substituted with one or two $R^{1b'}$ substituents; and further wherein two $R^{1a}$ substituents on adjacent carbon atoms or on an adjacent carbon atom and an adjacent N atom of the 5- or 6-membered heteroaryl R¹ group may join to form a 5 or 6 membered ring that may be saturated, partially saturated, or aromatic and may include 0, 1, 2, or 3 heteroatoms independently selected from N, O, and S and may further optionally be substituted with 1 or 2 $R^{1a'}$ substituent and may include an oxo substituent if the ring is not an aromatic ring;

$R^{1a'}$ is in each instance independently selected from —F, —Cl, —Br, —I, —$C_1$-$C_6$ alkyl, —$C_1$-$C_6$ haloalkyl, —$C_1$-$C_6$ perhaloalkyl, $C_3$-$C_8$ cycloalkyl —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$ or —S(=O)$_2$—($C_1$-$C_6$ alkyl);

$R^{1b'}$ is in each instance independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl);

R³ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{31}$ substituents, and further wherein the $C_3$-$C_8$ cycloalkyl of the —($C_3$-$C_8$ cycloalkyl)-Q group is unsubstituted or is substituted with 1 or 2 $R^{31}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —($C_1$-$C_6$ alkyl)-O—($C_1$-$C_6$ alkyl)-phenyl, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_2$-$C_6$ alkenyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, wherein the $C_6$-$C_{10}$ aryl, the heteroaryl, the cycloalkyl, and the heterocyclyl Q groups are unsubstituted or are substituted with 1, 2, 3, or 4 $R^Q$ substituents; and further wherein the Q heterocyclyl group may additionally be substituted with 1 or 2 oxo substituents, and the Q heteroaryl group may include an N-oxide if the heteroaryl includes a N heteroatom;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, and further wherein the heterocyclyl and the heterocyclyl of the —($C_1$-$C_6$ alkyl)heterocyclyl $R^Q$ groups may be further substituted with one or two oxo substituents and a substituent selected from, —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is saturated or partially unsaturated and is optionally substituted with 1 or 2 oxo substituents and may include an S=O or SO$_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl);

wherein if $R^1$ is a substituted or unsubstituted pyrimidine and $R^4$ is a substituted or unsubstituted alkyl and $R^3$ is -Q, then Q is selected from an unsubstituted or substituted monocyclic or bicyclic heteroaryl group with 5 to 10 ring members containing 1, 2, or 3 heteroatoms independently selected from N, O, or S; an unsubstituted or substituted $C_3$-$C_8$ cycloalkyl group or an unsubstituted or substituted 3 to 10 membered heterocyclyl group containing 1, 2, or 3 heteroatoms independently selected from N, O, or S.

\* \* \* \* \*

UNITED STATES PATENT AND TRADEMARK OFFICE
CERTIFICATE OF CORRECTION

PATENT NO. : 11,046,680 B1
APPLICATION NO. : 16/347910
DATED : June 29, 2021
INVENTOR(S) : Chen et al.

It is certified that error appears in the above-identified patent and that said Letters Patent is hereby corrected as shown below:

On the Title Page

Item [57], Column 2, Line 7, below "variables are provided herein." insert -- 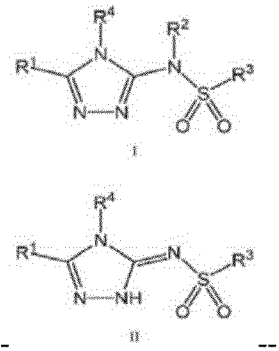 --.

In the Claims

Column 694, Claim 1, Line 14, delete "$R^{1a}$" and insert -- $R^1$ --, therefor.

Column 695, Claim 1, Line 24, delete "$R^{31}$" and insert -- $R^{3h}$ --, therefor.

Column 695, Claim 1, Line 27, delete "$R^{31}$" and insert -- $R^{3h}$ --, therefor.

Column 695, Claim 1, Line 53, delete "$(C_1–C_6$" and insert -- $(C_1-C_6$ --, therefor.

Column 696, Claim 1, Line 52, delete "$R^4$" and insert -- $R^{4b}$ --, therefor.

Column 704, Claim 17, Line 54, delete "alkyl." and insert -- alkyl). --, therefor.

Column 706, Claim 20, Line 67, delete "$(CR^{3d}R^{3e})(CR^{3f}R^{3g})$" and insert -- $(CR^{3d}R^{3e})-(CR^{3f}R^{3g})$ --, therefor.

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*

Column 707, Claim 21, Line 5, delete "$(CR^{3d}R^{3e})(CR^{3f}R^{3g})$" and insert -- $(CR^{3d}R^{3e})-(CR^{3f}R^{3g})$ --, therefor.

Column 711, Claim 23, Lines 25-27, delete "$\overset{\downarrow}{OH}$" and insert -- $\overset{\downarrow}{CH_3}$ --, therefor.

Column 718, Claim 33, Line 22, delete "$R^{31}$" and insert -- $R^{3h}$ --, therefor.

Column 718, Claim 33, Line 25, delete "$R^{31}$" and insert -- $R^{3h}$ --, therefor.